United States Patent
Tsou et al.

(10) Patent No.: US 7,713,994 B2
(45) Date of Patent: May 11, 2010

(54) SUBSTITUTED ISOQUINOLINE-1,3(2H,4H)-DIONES, 1-THIOXO,1,4-DIHYDRO-2H-ISOQUINOLINE-3-ONES AND 1,4-DIHYRO-3 (2H)-ISOQUINOLONES AND METHODS OF USE THEREOF

(75) Inventors: Hwei-Ru Tsou, New City, NY (US); Semiramis Ayral-Kaloustian, Tarrytown, NY (US); Gary Harold Birnberg, Tuxedo Park, NY (US); Middleton Brawner Floyd, Suffern, NY (US); Joshua Kaplan, Nyack, NY (US); Kristina M. Kutterer, Westwood, NJ (US); Xiaoxiang Liu, River Vale, NJ (US); Ramaswamy Nilakantan, Closter, NJ (US); Mercy Adufa Otteng, Pearl River, NY (US); Zhilian Tang, Edgewater, NJ (US); Arie Zask, New York, NY (US); Tritin Tran, King of Prussia, PA (US); Scott Christian Mayer, Bridgewater, NJ (US); Annette L. Banker, Plainsboro, NJ (US); Marvin Reich, Santa Fe, NM (US)

(73) Assignee: Wyeth LLC, Madison, NJ (US)

( * ) Notice: Subject to any disclaimer, the term of this patent is extended or adjusted under 35 U.S.C. 154(b) by 45 days.

(21) Appl. No.: 11/728,897

(22) Filed: Mar. 26, 2007

(65) Prior Publication Data
US 2008/0085890 A1 Apr. 10, 2008

Related U.S. Application Data

(63) Continuation-in-part of application No. PCT/US2006/048603, filed on Dec. 20, 2006.

(60) Provisional application No. 60/753,701, filed on Dec. 22, 2005.

(51) Int. Cl.
A61K 31/47 (2006.01)
C07D 217/08 (2006.01)

(52) U.S. Cl. ...................... 514/309; 546/142

(58) Field of Classification Search ........... None
See application file for complete search history.

(56) References Cited

FOREIGN PATENT DOCUMENTS

EP 0 549 348 A1 6/1993
WO WO 98/56392 12/1998

OTHER PUBLICATIONS

Patankar et al, Journal of Indian Council of Chemists (2002), 19(2), pp. 39-42.*
F.A. L'Eplattenier, et al., "Contributions to the Chemistry of Enamino Ketones; 12th Report. Formylation of Heterocyclic CH-acid Compounds with Orthocarboxylic Acid Trimesters and Aryl Amines," Synthesis, 8, 543-544 (1976). (English Translation).
O.S. Wolfbeis, et al., "2-Substituted PYRANO[2,3C]lsoquinoline-3,6-diones and Merocyanine Dyes from Homophthalic Acid Imides," Liebigs Ann. Chem., 811-818 (1981). (English Translation).
I.W. Elliot, Jr. and Y. Takekoshi, "Reduction of 4-arylidene-1,3-(2H,4H)isoquinolinediones", J. Heterocyclic Chem., 13, 597-599 (1976).
K. Higashiyama, et al., "Synthesis of 4-Hydroxymethylene-1,2(2H,4H)-isoquinolinediones and Related Compounds", Chem. Pharm. Bull., 34(7), 3014-3019 (1986).
V.F. Knyazeva, et al., "Acetals of lactams and acid amides. 34. Synthesis and properties of enamines of the isoquinoline series," Chemi. Heterocycl. Compd., 370-374 (1981).
V.F. Knyazeva, et al., "Synthesis and Pharmacological Properties of Some Amidines and Enamines of the Isoquinoline Series," Pharm. Chem. J., 15(5), 324-328 (1981).
D. Perez, et al., "Synthesis of antitumor Lycorine by intramolecular Diels-Alder reaction", J. Org. Chem., 61, 1650-1654 (1996).
Beilstein Institute for Organic Chemistry, Frankfurt-Main, DE, Abstract No. XP002448434, Beilstein Registry No. 24590.
Beilstein Institute for Organic Chemistry, Frankfurt-Main, DE, Abstract No. XP002448435, Beilstein Registry No. 5581728.
Beilstein Institute for Organic Chemistry, Frankfurt-Main, DE, Abstract No. XP002448436, Beilstein Registry No. 5827307.
Beilstein Institute for Organic Chemistry, Frankfurt-Main, DE, Abstract No. XP002448437, Beilstein Registry No. 1543679.
Perez, Dolores; Guitian, Enrique; Castedo, Luis; Journal of Organic Chemistry (1992), 57 (22), 5911-17.
Kobayashi, Goro; Matsuda, Yoshiro; Natsuki, Reiko; Ueno, Seiichi; Yakugaku Zasshi (1973), 93(3), 322-9; Japanese.
Beilstein Institute for Organic Chemistry, Frankfurt-Main, DE, Abstract No. XP002448434, Beilstein Registry No. 24590, 1957.
Beilstein Institute for Organic Chemistry, Frankfurt-Main, DE, Abstract No. XP002448435, Beilstein Registry No. 5581728, 1986.
Beilstein Institute for Organic Chemistry, Frankfurt-Main, DE, Abstract No. XP002448436, Beilstein Registry No. 5827307, 1992.
Beilstein Institute for Organic Chemistry, Frankfurt-Main, DE, Abstract No. XP002448437, Beilstein Registry No. 1543679, 1967.

* cited by examiner

*Primary Examiner*—Zinna N Davis
(74) *Attorney, Agent, or Firm*—Thomas C. McKenzie

(57) ABSTRACT

This invention provides compounds of Formula (I), having the structure

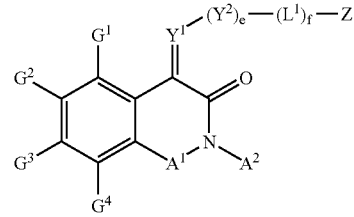

where $G^1$, $G^2$, $G^3$, $G^4$, $A^1$, $A^2$, $Y^1$, $Y^2$, $L^1$, Z, e and f are defined herein, or a pharmaceutically acceptable salt thereof, which are useful for treating or preventing cancer.

18 Claims, No Drawings

SUBSTITUTED ISOQUINOLINE-1,3(2H,4H)-DIONES, 1-THIOXO,1,4-DIHYDRO-2H-ISOQUINOLINE-3-ONES AND 1,4-DIHYDRO-3 (2H)-ISOQUINOLONES AND METHODS OF USE THEREOF

This is a continuation-in-part of International Patent Application No. PCT/US2006/048603 filed on Dec. 20, 2006, which claimed the benefit of the filing of U.S. Provisional Patent Application Ser. No. 60/753,701, filed on Dec. 22, 2005, now expired, the entire specification thereof of each is incorporated herein by reference.

FIELD OF THE INVENTION

The present invention relates to isoquinoline-1,3(2H,4H)-dione derivatives, 1-thioxo-1,4-dihydro-2H-isoquinoline-3-one derivatives and 1,4-dihydro-3(2H)-isoquinolone derivatives, methods of making thereof, compositions comprising an effective amount of a isoquinoline-1,3(2H,4H)-dione derivative, 1-thioxo-1,4-dihydro-2H-isoquinoline-3-one derivative or a 1,4-dihydro-3(2H)-isoquinolone derivative and methods for treating or preventing cancer, comprising administering to a subject in need thereof an effective amount of a isoquinoline-1,3(2H,4H)-dione derivative, 1-thioxo-1,4-dihydro-2H-isoquinoline-3-one derivative or a 1,4-dihydro-3(2H)-isoquinolone derivative.

BACKGROUND OF THE INVENTION

Protein kinases are a family of enzymes that catalyze the transfer of the terminal phosphate of ATP the hydroxyl group of specific tyrosine, serine, threonine, or histidine residues in protein. It is known that such phosphorylation plays a fundamental role in essentially all molecular aspects of cell life including metabolism, cell proliferation, cell differentiation, cell migration, and cell survival, and that protein kinases constitute major pharmacological targets [Schlessinger and Ullrich, *Neuron,* 9, 383 (1992); Cohen, P. *Nat. Rev. Drug Discov.* 1, 309-315 (2002); Scapin G., *Drug Discovery Today* 7(11): 601-611 (2002)].

Of the many different cellular functions in which the activity of protein kinases is known to be required, some processes represent attractive targets for therapeutic intervention for certain disease states. For example, specific protein kinases have been implicated as targets in cancer [Traxler, P. M., *Exp. Opin. Ther. Patents,* 8, 1599 (1998); Bridges, A. J., *Emerging Drugs,* 3, 279 (1998)], restenosis [Mattsson, E., *Trends Cardiovas. Med.* 5, 200 (1995); Shaw, *Trends Pharmacol. Sci.* 16, 401 (1995)], atherosclerosis [Raines, E. W., *Bioessays,* 18, 271 (1996)], blood vessel proliferative disorders such as angiogenesis [Shawver, L. K., *Drug Discovery Today,* 2, 50 (1997); Jackson et al *J. Pharm. Exp. Ther.* 284, 687 (1998); Folkman, J., *Nature Medicine,* 1, 27 (1995)], chronic obstructive pulmonary disease, bone disease such as osteoporosis [Boyce, *J. Clin. Invest.,* 90, 1622 (1992), Tanaka et al, *Nature,* 383, 528 (1996)], psoriasis [(Dvir, et al, *J. Cell Biol.* 113, 857 (1991)], inflammatory disorders such as arthritis [(Badger, *J. Pharm. Exp. Ther.* 279, 1453 (1996)], central nervous system disorders such as Alzheimer's [(Mandelkow, E. M., et al, *FEBS Lett,* 314, 315 (1992); Sengupta, A. et al, *Mol. Cell. Biochem.* 167, 99 (1997)], pain sesation [Yashpal, K., *J. Neurosci.* 15, 3263-72 (1995)], autoimmune diseases and transplant rejection [Bolen and Brugge, *Ann. Rev. Immunol.* 15, 371 (1997)], thrombosis [Salari, *FEBS,* 263, 104 (1990)], metabolic disorders such as diabetes [Borthwick, A. C. et al, *Biochem. Biopys. Res. Commun.* 210, 738 (1995)], and infectious diseases (Lum, R. T. PCT Int. Appl., WO 9805335A1 980212), and viral infections [Littler, E. *Nature,* 160, 358 (1992)].

A partial, non-limiting, list of such kinases includes CDK1, CDK2, CDK3, CDK4, CDK5, CDK6, CDK7, CDK8, CDK9, CDK11, PDK1, PDK2, cRaf1, c-src, abl, Araf, ATK, bcr-abl, Blk, Braf, Brk, Btk, cfms, c-fms, c-kit, c-met, CSF1R, CSK, EGFR, ErbB2, ErbB3, ErbB4, ERK, ERK1, ERK2, Fak, fes, FGFR1, FGFR2, EGFR3, EGFR4, EGFR5, Fgr, FLK-4, Fps, Frk, Fyn, GSK, gsk3a, gsk3b, Hck, IGF-1R, IKK1, IKK2, IKK3, INS-R, integrin-linked kinase, Jak, JAK1, JAK2, JAK3, JNK, Lck, Lyn, MEK, MEK1, MEK2, p38, PDGFR, PIK, PKB1, PKB2, PKB3, PKC, PLK1, Polo-like kinase, PYK2, tie1, tie2, TrkA, TrkB, TrkC, UL13, UL97, VEGF-R1, VEGF-R2, Yes, AKT, and Zap70.

As an example, in cancer cells, IGFR-1 plays a critical role because it contributes to the promotion of tumor growth by inhibition of the apoptosis, transformation, metastasis and induction of angiogenesis through the vascular endothelial growth factor.

In addition to tyrosine kinases, there are serine/threonine protein kinases, that phosphorylate serine and/or threonine residues on proteins. Among them, cyclin-dependent kinases (CDKs) play a key role in regulating the cell cycle machinery. These complexes consist of two components: a catalytic subunit (the kinase) and a regulatory subunit (the cyclin). To date, 13 CDKs have been identified along with 25 cyclin-box-containing proteins [Knockaert, M.; Greengard, P.; Meijer L. *Trends in Pharmacological Sciences* 23(9): 417-425.] Each kinase associates with a specific regulatory partner and together make up the active catalytic moiety. Each transition of the cell cycle is regulated by a particular CDK complex: G1/S by CDK2/cyclin E, CDK4/cyclin D1 and CDK6/cyclin D2; S/G2 by CDK2/cyclin A and CDK1/cyclin A; G2/M by CDK1/cyclin B, the coordinated activity of these kinases guides the individual cells through the replication process and ensures the vitality of each subsequent generation [*Science,* 274, 1643-1677 (1996); *Ann. Rev. Cell. Dev. Biol.,* 13, 261-291 (1997); Fischer, P. M. *Current Opinion in Drug Discovery and Development,* 4(5), 623-634 (2001); Draetta, *Trends Biochem. Sci.* 15:378-382 (1990); Sherr, *Cell* 73:1059-1065 (1993)].

An increasing body of evidence has shown a link between tumor development and CDK related malfunctions. Overexpression of the cyclin regulatory proteins and subsequent kinase hyperactivity have been linked to several types of human cancers [Senderowica, A. M., and Sausville, E. A., *J. Nat. Acad. Sci., U.S.A.* 96, 376-387 (2000); Garrett, M. D., *Current Opin. Genetics Devel.,* 9, 104 (1999); Webster, K. R., *Exp. Opin. Invest. Drugs,* 7, 865-887 (1998); Jiang, *Proc. Natl. Acad. Sci. USA* 90:9026-9030 (1993); Wang, *Nature* 343:555-557 (1990)]. More recently, endogenous, highly specific protein inhibitors of CDKs were found to have a major affect on cellular proliferation [Sherr, C. J., Roberts, J. M. *Genes Dev.* 13, 1501-1512 (1999); Kamb et al, *Science* 264:436-440; Beach *Nature* 336:701-704 (1993)]. These inhibitors include p16 (an inhibitor of CDK4/cyclin D1), p21 (a general CDK inhibitor) and p27 (an inhibitor of CDK2/cyclin E). A recent crystal structure of p27 bound to CDK2/cyclin A showed how these proteins effectively inhibit the kinase activity through multiple interactions with the CDK complex [Pavletich, *Nature* 382:325-331 (1996)]. These proteins help to regulate the cell cycle through specific interactions with their corresponding CDK complexes. Cells deficient in these inhibitors are prone to unregulated growth and tumor formation.

In addition to treating human cancers, CDK inhibitors could be useful in the treatment of other cell proliferative disorders such as familial adenomatosis polyposis, psoriasis, neuro-fibromatosis, fungal infections, endotoxic shock, vescular smooth cell proliferation associated with atherosclerosis, pulmonary fibrosis, glomerulonephritis, and post-surgical stenosis and testenosis [U.S. Pat. No. 6,114,365].

CDKs are also know to play an important role in apoptosis. Therefore, CDK inhibitors, could be useful in the prevention of AIDS development in HIV-infected patients; inflammatory bowel disease, and diabetes mellitus, dementia, Parkinson's disease, amyotrophic lateral sclerosis, retinitis pigmentosa, spinal muscular atrophy and cerebellar degeneration; myelodysplastic syndromes, aplastic anemia, ischemic injury associated with myocardial infarctions, stroke and reperfusion injury, arrhythmia, atherosclerosis, toxin-induced or alcohol related liver diseases, hematological diseases, for example, chronice anemia; degenerative diseases of the musculoskeletal system, for example, osteoporosis, aspirin-sensentive rhinosinusitis, cystic fibrosis, multiple sclerosis, kidney diseases and pain [U.S. Pat. No. 6,107,305].

Also, it has been discovered that some CDK inhibitors can be used in combination therapy with some other anticancer agents. For example, the cytotoxic activity of the CDK inhibitor, Flavopiridol, has been used with other anticancer agents in cancer combination therapy [Cancer Research 57:3375 (1997)].

In addition, a recent report showed that CDK5 is involved in the phosphorylation of tau protein, and therefore, CDK inhibitors may be useful in the treatment of Alzheimer's disease [J. Biochem., 117: 741-749 (1995)].

This increasing body of evidence has led to intense discovery efforts to search for small molecule inhibitors of the CDK family and their associated regulatory molecules (cyclins) as an approach to cancer chemotherapy [Sausville, E. A., Trends in Molecular Medicine 8(4), S32-S37 (2002); Malumbres, M, and Barbacid, M. Nat. Rev. Cancer 1, 222-231 (2001)].

More than 50 small molecule inhibitors of cyclin-dependent kinases have been identified. These CDK inhibitors all target the ATP-binding pocket of the catalytic site of the kinases. The effects of CDK inhibitors on the cell cycle and their potential value for the treatment of cancer, alopecia, neurodegenerative disorders (e.g. Alzheimer's disease, amyotrophic lateral sclerosis and stroke), cardiovascular disorders (e.g. atherosclerosis and restenosis), glomerulonephritis, viral infections (e.g. HCMV, HIV and HSV) and parasitic protozoa (Plasmodium sp. and Leishmania sp.) has been extensively studied [Knockaert, M. Greengard, P. Meijer L., Trends in Pharmacological Sciences 23 (9), 417-425 (2002); Malumbres, M, and Barbacid, M. Nat. Rev. Cancer 1, 222-231 (2001), Sielecki, T. M. J. Med. Chem. 43, 1-18 (2000)]. Three properties make CDK inhibitors attractive as potential anti-tumor agents. First, they are potent anti-proliferative agents, arresting cells in G1 [Soni, R. J. Natl. Cancer Inst. 21, 436-446 (2001)] or G2/M [Damiens, E. et al. Oncogene 20, 3786-3797 (2001)]. Second, they trigger apoptosis, alone or in combination with other treatments [Edamatsu, H. et al. Oncogene 19, 3059-3068 (2000)]. Third, in some instances, inhibition of CDKs contributes to cell differentiation [Matushansky, I. Et al. Proc. Natl. Acad. Sci. U.S.A. 97, 14317-14322 (2000)].

Despite the significant research efforts and resources which have been directed towards the development of novel anticancer agents and improved methods for treating cancer there remains a need in the art for novel compounds, compositions, and methods that are useful for treating cancer with improved therapeutic indices.

BRIEF SUMMARY OF THE INVENTION

This invention relates to isoquinoline-1,3(2H,4H)-diones, 1-thioxo-1,4-dihydro-2H-isoquinoline-3-ones, and 1,4-dihydro-3(2H)-isoquinolones containing compounds as well as their pharmaceutically acceptable salts having the structure of Formula I, wherein:

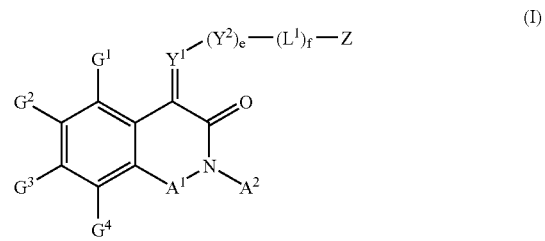

or a pharmaceutically acceptable salt thereof, $A^1$ is CO, C(S), NCOR$_{100}$, NH, or C(R$_1$)(R$_2$);

$A^2$ is H, OH, CH$_2$OH, C$_{1-6}$ alkyl, alkoxy, benzyloxy, arylalkyl, benzyl, aryl, acyl, —C(O)R, —OC(O)O-PEG, —CH$_2$OC(O)O-PEG, —OC(O)NH-PEG, —CH$_2$OC(O)NH-PEG, OC(O)OH, CH$_2$O(C(O)OH, OC(O)halogen, CH$_2$OC(O)halogen, OC(O)CH$_2$halogen, OC(O)CH$_2$S(CH$_2$)mO-PEG wherein the aryl or benzyl is optionally substituted with R$_4$;

PEG is —(OCH$_2$CH$_2$)$_r$OCH$_3$;

$Y^1$ is CR$_3$ or N, provided that when $Y^1$ is N, then $Y^2$ is NR$_1$;

$Y^2$ is NR$_1$, N(R$_1$)N(R$_1$), NHC(O) or NHNHC(O);

$L^1$ is C(R$_7$)(R$_8$);

R$_1$ and R$_2$ are each independently H, C$_{1-6}$ alkyl, aryl, or benzyl, or R$_1$ and R$_2$ when taken together with the carbon atom to which they are attached form a 3-6 membered spirocyclic ring;

R is C$_{1-6}$ alkyl, aryl, or pyridyl;

R$_3$ is H, aryl, C$_{1-6}$ alkyl, OR, NR$_{10}$R$_{11}$, or —O—, provided that when R$_3$ is OR or —NR$_{10}$R$_{11}$, that e and f are 0 when Z is H;

R$_4$, is selected from the group consisting of H, aryl, or C$_{1-6}$ alkyl, halogen, —CN, —OCF$_3$, —NO$_2$, —COOH, —CF$_3$, OH, SH, N$_3$, —C(O)H, heteroaryl, C$_{1-6}$alkoxy, heterocycloalkyl, C$_{2-6}$ alkenyl, C$_{2-6}$ alkynyl, —COR$_{100}$, —Oaryl, —OR$_{100}$, —NHaryl, —S(O)$_m$R$_{100}$, —C(O)Q, C(O)OR$_{100}$, —NR$_{100}$aryl, —OR$_{100}$aryl, —SR$_{100}$aryl, —NHR$_{102}$OH, —NHR$_{102}$OR$_{100}$, —NHR$_{102}$NHR$_{100}$, —NR$_{100}$R$_{102}$OH, —NHR$_{102}$Q, —NR$_{100}$R$_{102}$NH$_2$, —NR$_{100}$R$_{102}$NHR$_{100}$, —NR$_{100}$R$_{102}$OR$_{100}$, —NR$_{100}$R$_{102}$Q, —OR$_{102}$OH, —OR$_{102}$OR$_{100}$, —OR$_{102}$NH$_2$, —OR$_{102}$NHR$_{100}$, —OR$_{102}$Q, —OCOR$_{100}$, —OR$_{100}$COR$_{100}$, —NHCOR$_{100}$, —NHCONH$_2$, —NHCONHR$_{100}$, —NHR$_{100}$COR$_{100}$, —NHR$_{102}$NH$_2$, —NHOH, —NHOR$_{100}$, —CONR$_{10}$R$_{11}$, —NHSO$_2$R$_{100}$, NR$_{10}$R$_{11}$, —NHC(O)-heteroaryl, —NHC(O)R$_{102}$-heteroaryl, OC(O)CH$_2$halogen, —OC(O)CH$_2$S(CH)$_m$ O-PEG, OC(O)NH-PEG, —N(R$_{10}$)(R$_{11}$), —NHC(O)R$_{102}$-aryl, and —NHC(O)NH-heterocloalkyl that is optionally substituted with up to three C$_{1-3}$ alkyl groups;

wherein said aryl, said heteroaryl, and said heterocycloalkyl are each optionally substituted with up to four independently selected R$_{12}$ groups;

wherein said $C_{2-6}$ alkenyl, said $C_{1-6}$ alkyl, $C_{1-6}$alkoxy, and said $C_{2-6}$ alkynyl are each optionally substituted with up to three independently selected $R_{13}$ groups;

$R_5$ is selected from the group consisting of $C_{1-6}$ alkyl or alkenyl, wherein the alkyl or alkenyl are optionally substituted with OH, OR, $NR_{10}R_{11}$, $C_{1-6}$ alkyl;

$R_7$ and $R_8$ are selected from the group consisting of H, $C_{1-6}$ alkyl, $OR_{100}$, OH, C(O)H or COOH;

$R_{10}$ and $R_{11}$ are selected from the group consisting of H, $C_{1-6}$ alkyl, $C_{2-6}$alkenyl, $C_{1-6}$ acyl, —S(O)$_2$aryl, —C(O)$C_{2-6}$ alkenyl, $C_{2-6}$ alkynyl, aryl or heteroaryl, wherein said $C_{1-6}$ acyl is optionally substituted with a heteroaryl,
  wherein said $C_{1-6}$ alkyl is optionally substituted with up to three halogen atoms,
  wherein said aryl and said heteroaryl are optionally substituted with up to three $R_{12}$ groups, wherein $R_{10}$ and $R_{11}$ may be taken together with the N to which they are attached to form a 3-8 membered heterocylic ring, wherein said heterocyclic ring may contain additional atoms selected from the group N, O, and —S(O)$_m$ and said heterocyclic ring may be additionally substituted with 1 to 4 substituents selected from the group consisting of $C_{1-6}$alkyl, OH, —OC$_{1-6}$alkyl, —OC$_{3-6}$cycloalkyl, —(CH$_2$)$_n$OH, —(CH$_2$)$_n$OC$_{1-6}$alkyl, —(CH$_2$)$_n$OC$_{3-6}$cycloalkyl, —NR$_{10}$R$_{11}$, —(CH$_2$)$_n$NR$_{10}$R$_{11}$, and =O;

$R_{12}$ is independently selected from the group consisting of aryloxy, halogen, OH, —COOH, —C(O)H, —C(O)R, —C$_{1-3}$ perhaloalkyl, —OCF$_3$, C$_{1-6}$ acyl, —CN, —NO$_2$, aryl, heteroaryl, —S—C$_{1-6}$ alkyl, —NHCOC$_{1-6}$alkyl, —N(R$_{15}$)(R$_{16}$), C$_{1-3}$ perhaloalkoxy, C$_{1-6}$ alkyl, C$_{2-6}$ alkenyl, —CONH$_2$, —CF$_3$, SH, N$_3$, heterocycloalkyl, —C(O)R$_{100}$, —OR$_{100}$, —NHaryl, —S(O)$_m$R$_{100}$, —C(O)Q, C(O)OR$_{100}$, —C(O)NHR$_{100}$, —NR$_{100}$aryl, —N(R$_{100}$)R$_{102}$aryl, —OR$_{102}$aryl, —SR$_{102}$aryl, —NHS(O)$_2$—R$_{100}$, —NHR$_{102}$OH, —NHR$_{102}$OR$_{100}$, —NHR$_{102}$NHR$_{100}$, —N(R$_{100}$)R$_{102}$OH, —NHR$_{102}$Q, —N(R$_{100}$)R$_{102}$NH$_2$, —N(R$_{100}$)R$_{102}$NHR$_{100}$, —N(R$_{100}$)R$_{102}$OR$_{100}$, —N(R$_{100}$)R$_{102}$Q, —OR$_{102}$OH, —OR$_{102}$OR$_{100}$, —OR$_{102}$NH$_2$, —OR$_{102}$NHR$_{100}$, —OR$_{102}$Q, —OC(O)R$_{100}$, —OR$_{102}$C(O)R$_{100}$, —NHC(O)R$_{100}$, —NHCONH$_2$, —NHCONHR$_{100}$, —NHR$_{102}$C(O)R$_{100}$, —NHR$_{102}$NH$_2$, —NHS(O)$_2$-aryl, —NHOH, —NHC(O)aryl, —NHOR$_{100}$, —NHC(O)-heteroaryl, —NHC(O)R$_{102}$-heteroaryl, —C(O)N(R$_{10}$)(R$_{11}$), —N(R$_{10}$)(R$_{11}$), NHC(O)R$_{102}$aryl, and NHC(O)NH-heterocycloalkyl that is optionally substituted with up to three $C_{1-3}$ alkyl groups,
  wherein said $C_{2-6}$ alkenyl, said $C_{1-6}$ alkyl, and said $C_{2-6}$ alkynyl are each optionally substituted with up to three independently selected $R_{13}$ groups and —N(R$_{15}$)(R$_{16}$);

$R_{13}$ is independently selected from the group consisting of arylalkyl, aryl, heteroaryl, $C_{1-6}$ alkyl, $C_{3-6}$ cycloalkyl, heterocycle, heterocycloalkyl, heterocycloalkyloxy, CN, OH, $C_{1-6}$ alkoxy, halogen and —COOH, —SH, —COH, —COR$_{100}$, —CONH$_2$, —CONHR$_{100}$, —COQ, —OCOR$_{100}$, —OCONH$_2$, —OCONHR$_{100}$, —OCOQ, —OR$_{102}$OH, —OR$_{102}$NR$_{15}$R$_{16}$, and

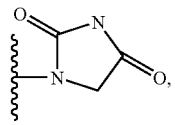

wherein said aryl, heteroaryl, and heterocycloalkyl are optionally substituted with up to three independently selected $R_{18}$ groups;

$R_{15}$ and $R_{16}$ are selected from the group consisting of H, $C_{1-6}$ alkyl, and $C_{1-6}$ acyl; and wherein said $R_{15}$ and $R_{16}$ groups taken together with the nitrogen to which they are attached may form a heterocylic ring of 3 to 8 atoms with 1 or 2 additional heteroatoms selected from the group N, O, and —S(O)$_m$, the heterocyclic ring may be substituted with groups consisting of OH, —OC$_{3-6}$cycloalkyl, —OC$_{1-6}$ alkyl, —(CH$_2$)$_n$OH, —(CH$_2$)$_n$OC$_{1-6}$alkyl, —NR$_{10}$R$_{11}$, —(CH$_2$)$_n$NR$_{10}$R$_{11}$, and —(CH$_2$)$_n$OC$_{3-6}$cycloalkyl;

$R_{18}$ is independently selected from the group consisting of OH, halogen, —NO$_2$, dialkylamino, —N(R$_{15}$)(R$_{16}$), —COOH, —S(O)$_2$NH$_2$, $C_{1-3}$ perhaloalkyl, —OCF$_3$, $C_{1-3}$ alkoxy, $C_{1-6}$ alkyl, CN, $C_{1-8}$ cyanoalkyl and $C_{4-8}$ cycloalkenyl, wherein said cycloalkenyl is optionally substituted with up to three groups independently selected from OH and $C_{1-3}$ alkoxy, and wherein said $C_{1-6}$ alkyl is optionally substituted with —N(R$_{15}$)(R$_{16}$);

$R_{20}$ is selected from the group consisting of $C_{1-6}$ alkyl, $C_{3-6}$ cycloalkyl and $C_{2-6}$ alkenyl, wherein said $C_{1-6}$ alkyl is optionally substituted with up to three halogen atoms or a group of formula —[(CH$_2$)(Q")]$_k$CH$_3$;

$R_{21}$ is selected from the group consisting of $C_{1-6}$ alkyl and cycloalkyl;

$R_{22}$ is selected from the group consisting of heteroaryl, aryl, arylalkyl and $C_{1-6}$ alkyl, wherein said $C_{1-6}$ alkyl is optionally substituted up to three halogen atoms;

$R_{23}$ is selected from the group consisting of aryl, heteroaryl and $C_{1-6}$ alkyl, wherein said aryl and said heteroaryl is optionally substituted with up to three $C_{1-3}$ alkyl groups, and said $C_{1-6}$ alkyl is optionally substituted with up to three halogen atoms;

$R_{24}$ is selected from the group consisting of H, —COOH, $C_{3-6}$ cycloalkyl, —OCHF$_2$, —OCHCl$_2$, $C_{1-3}$ perhaloalkyl, $C_{1-6}$ alkoxy, heteroaryl, heterocycloalkyl, $C_{2-6}$ alkynyl, $C_{1-6}$ alkyl, $C_{2-6}$ alkenyl, and aryl, wherein said $C_{1-6}$ alkyl is optionally substituted with up to three groups independently selected from halogen and $C_{3-6}$ cycloalkyl, said $C_{2-6}$ alkenyl optionally substituted with up to three groups independently selected from halogen and N(R$_{27}$)(R$_{28}$), said aryl is optionally substituted with up to three OH groups, and said heterocycloalkyl is optionally substituted with up to three independently selected $C_{1-6}$ alkyl groups, —(CH$_2$)$_m$cycloalkyl, —(CH$_2$)$_n$OH, —(CH$_2$)$_n$OR, —(CH)$_2$NR$_{10}$R$_{11}$, —COR$_5$, and Q;

$R_{25}$ is OH, or NR$_{10}$R$_{11}$;

$R_{27}$ and $R_{28}$ are independently selected from the group consisting of $C_{1-6}$ alkyl, $C_{3-6}$ cycloalkyl, heterocycloalkyl, $C_{2-6}$ alkenyl, H, aryl, Q, —C(O)C$_{3-6}$alkyl (cycloalkyl), —COalkyl, —COalkenyl, —COalkynyl, —COaryl, —COheteroaryl, —COcycloalkyl, $C_{1-6}$ acyl, —C(O)C(O)OH, halogen, —COC$_{1-6}$halogen, $C_{1-3}$alkoxy, and arylalkyl, wherein said $C_{1-6}$ alkyl, aryl, acyl, and heterocycloalkyl are optionally substituted with up to three $R_{52}$ groups; or $R_{27}$ and $R_{28}$ together with the nitrogen atom to which they are attached can form a 5 or 6 membered saturated heterocyclic ring that can include one additional O, N, or S ring atom, said saturated heterocyclic ring optionally substituted with a carboxylate or $C_{1-3}$ alkyl groups;

$R_{31}$ is selected from the group consisting of trialkylsilyl, $C_{1-6}$ alkoxycarbonyl, $C_{1-6}$ alkyl, $C_{2-6}$ alkenyl, heteroarylalkyl, heterocycloalkyl and arylalkyl, wherein said $C_{1-6}$ alkyl, said arylalkyl and said heteroarylalkyl are each optionally substituted with up to three independently selected $R_{53}$ groups, and said heterocycloalkyl is optionally substituted with up to three $C_{1-6}$ alkyl groups;

$R_{32}$ is selected from the group consisting of H, $C_{1-6}$ acyl, heteroaryl and $C_{1-6}$ alkyl, wherein said heteroaryl is optionally substituted with up to three $C_{1-3}$ alkyl groups, and said $C_{1-6}$ alkyl is optionally substituted with up to three heteroaryl or $R_{52}$ groups;

$R_{33}$ is selected from the group consisting of heterocycloalkyl, aryl, $C_{1-3}$ perhaloalkyl, —$N(R_{27})(R_{28})$ and $C_{1-6}$ alkyl, wherein said aryl, $C_{1-6}$ alkyl, heterocycloalkyl, are optionally substituted with up to three groups selected from halogen, $C_{1-6}$ alkyl, aryl, OH and —$N(R_{27})(R_{28})$;

$R_{34}$ is selected from the group consisting of aryloxy, $C_{1-6}$ alkyl, aryl and alkoxy, wherein said aryl is optionally substituted with COOH, and said alkoxy is optionally substituted with —$N(R_{27})(R_{28})$;

$R_{35}$ is selected from the group consisting of dialkylamino, or $C_{1-6}$ alkyl that is optionally substituted with —COOH or with —$N(R_{27})(R_{28})$;

$R_{41}$, is selected from the group consisting of —$R_{100}$, —$R_{102}R_{100}$, —$R_{102}OR_{100}$, —$R_{102}OH$, and —$R_{102}Q$;

$R_{50}$ is selected from the group consisting of heterocycloalkyl, (N=H), $NH_2$, —$NHCOC_{1-3}$ alkyl, $C_{1-3}$ alkyl, —$NHCOC_{1-3}$ cycloalkyl, —$NHCOC_{1-3}$ heterocycloalkyl, —OH, —CN, —COOH, —$N(R_{27})(R_{28})$, —$SO_2N(R_{27})(R_{28})$, halogen, heteroaryl and aryl, wherein said aryl, heteroaryl, or heterocycloalkyl are optionally substituted with a group selected from $C_{1-3}$ alkyl, C(O)H, $C_{1-4}$ alkoxy, and —$CONHN(R_{21})_2$, and up to three groups selected from halogen, and $NH_2$;

$R_{52}$ is independently selected from the group consisting of COH, OH, CN, $NH_2$, —$NHR_{21}$, —$N(R_{21})_2$, $C_{1-6}$ alkyl, aryl, —COaryl, heterocycloalkyl, halogen, $C_{1-3}$ perhaloalkyl, and —$C_{3-6}$ cycloalkyl, wherein the aryl can be substituted with COOH;

$R_{53}$ is selected from the group consisting of OH, $C_{1-6}$ alkyl, arylalkyloxy, heterocycloalkyl, $C_{1-3}$ alkoxy, halogen and $C_{3-6}$ cycloalkyl;

$R_{100}$ is selected from the group consisting of $C_{1-12}$alkyl, $C_{3-6}$ cycloalkyl aryl, heteroaryl, $C_{2-6}$alkenyl, and $C_{2-6}$alkynyl;

$R_{102}$ is a divalent $C_{1-6}$alkyl;

$R_{200}$ is selected from the group consisting of —$(CR_{201}R_{201})_qR_{203}$, —$N(R_{201})C(O)(CH_2)_qR_{203}$, $N(R_{201})(CH_2)_qR_{203}$ and —$NHC(O)NH-R_{203}$;

$R_{201}$ is selected from the group consisting of H and $C_{1-6}$ alkyl;

$R_{203}$ is selected from the group consisting of dialkylamino and a 5-7 membered heterocycloalkyl ring having up to three ring hetero atoms selected from O, N and S, said heterocycloalkyl ring being optionally substituted with up to three independently selected $R_{204}$ groups;

$R_{204}$ is selected from the group consisting of OH, COOH, $C_{1-6}$ alkyl, alkoxycarbonyl, arylalkyl, heteroarylalkyl, $C_{2-6}$ alkenyl, $C_{3-6}$ cycloalkyl, aryl, $C_{1-6}$ alkoxy, $C_{2-6}$ acyl, heterocycloalkyl, —$C(O)N(R_{300})(R_{300})$, —$NHC(O)R_{300}$, —$N(R_{201})(R_{201})$, and —$NHC(=O)N(R_{201})(R_{201})$, wherein said $C_{1-6}$ alkyl is optionally substituted with up to three independently selected $R_{207}$ groups, wherein said arylalkyl and said heteroarylalkyl are each optionally substituted with up to three independently selected $R_{206}$ groups, wherein said $C_{2-6}$ acyl may optionally contain one double bond, and may optionally be substituted with —$NR_{10}R_{11}$, wherein said heterocycloalkyl is optionally substituted with up to three independently selected $C_{1-6}$ alkyl groups;

$R_{206}$ is independently $C_{1-6}$ alkyl or $C(O)NH_2$;

$R_{207}$ is independently selected from the group consisting of CN, heterocycloalkyl, $C_{1-3}$ alkoxy, OH, $N(R_{27})(R_{28})$ and $C_{3-6}$ cycloalkyl;

$R_{209}$ is $R_{211}$, $R_{212}$—C≡C—, or $(R_{212})_2C$=$C(R_{212})$—;

$R_{210}$ is $C_{1-6}$ alkyl, or $C_{1-6}$ alkoxy;

$R_{211}$ is aryl and heteroaryl wherein said aryl and said heteroaryl, are each optionally substituted with up to four independently selected $R_{12}$ groups;

$R_{212}$ is $C_{1-6}$ alkyl, aryl, and heteroaryl, wherein said $C_{1-6}$ alkyl is optionally substituted with up to three independently selected $R_{13}$ groups wherein said aryl and said heteroaryl, are each optionally substituted with up to four independently selected $R_{12}$ groups;

$R_{214}$ is $R_{41}$, or $R_{211}$;

$R_{300}$ is selected from the group consisting of H, $C_{1-3}$ alkoxy and $C_{1-6}$ alkyl wherein said $C_{1-6}$ alkyl is optionally substituted with a dialkylamino group;

e is 0 or 1 provided that when $R_3$ is OR or NRR then e is 0;

f is 0-5;

k' is 1-6;

m is 0, 1, or 2;

n is 1-4;

q is 1-3;

r is 2-1800;

v is 1 or 2;

$G^1$, $G^2$, $G^3$ and $G^4$ are each independently selected from the group consisting of H, halogen, —CN, —$OCF_3$, —$NO_2$, —COOH, —$CONH_2$, —$CF_3$, OH, SH, $N_3$, —C(O)H, heteroaryl, $C_{1-6}$alkoxy, heterocycloalkyl, aryl, $C_{3-10}$cycloalkyl, $C_{1-12}$ alkyl, $C_{2-6}$ alkenyl, $C_{2-6}$ alkynyl, —$COR_{100}$, —$OC_{3-10}$cycloalkyl, —Oaryl, —$OR_{100}$, $R_{209}R_{211}$, Q, —$OS(O)_2NH_2$, $OS(O)_2R_{22}$, —$S(O)_mR_{100}$, —C(O)Q, $C(O)OR_{100}$, —$NHR_{100}$, —$NR_{100}$aryl, —$OR_{102}$aryl, —$SR_{102}$aryl, —$NHR_{102}OH$, —$NHR_{102}OR_{100}$, —$NHR_{102}NHR_{100}$, —$NR_{100}R_{102}OH$, —$NHR_{102}Q$, —$NR_{100}R_{102}NH_2$, —$NR_{100}R_{102}NHR_{100}$, —$NR_{100}R_{102}OR_{100}$, —$NR_{100}R_{102}Q$, —$OR_{102}OH$, —$OR_{102}OR_{100}$, —$OR_{102}NH_2$, —$OR_{102}NHR_{100}$, —$OR_{102}Q$, —$OCOR_{100}$, —$OR_{102}COR_{100}$, —NHCOR$_{110}$, —$NHCONH_2$, —$NHCONHR_{100}$, —$NHR_{102}COR_{100}$, —$NHR_{102}NH_2$, —NHOH, —$NHOR_{100}$, —$CONR_{10}R_{11}$, —$NHSO_2R_{100}$, —NHC(O)-heteroaryl, —NHC(O)R$_{102}$-heteroaryl, OC(O)CH$_2$halogen, OC(O)CH$_2$S(CH)$_m$O-PEG, OC(O)NH-PEG,

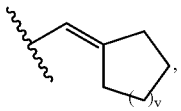

NHC(O)R$_{102}$-aryl, and NHC(O)NH-heterocycloalkyl optionally substituted with up to three C$_{1-3}$ alkyl groups;
  wherein said aryl, said heteroaryl, and said heterocycloalkyl are each optionally substituted with up to four independently selected R$_{12}$ groups;
  wherein said C$_{2-6}$ alkenyl, said C$_{1-6}$ alkyl, C$_{1-6}$alkoxy, and said C$_{2-6}$ alkynyl are each optionally substituted with up to three independently selected R$_{13}$ groups;
Q is —NR$_{100}$R$_{100}$ optionally the R$_{100}$ groups taken together with the nitrogen to which they are attached form a heterocylic ring of 3 to 8 atoms with 1 or 2 additional heteroatoms selected from the group N, O, and S, said heterocyclic ring may optionally be substituted with groups consisting of OH, OC$_{1-6}$ alkyl, (CH$_2$)$_n$OH, (CH$_2$)$_n$OC$_{1-6}$alkyl, NR$_{10}$R$_{11}$, (CH$_2$)$_n$NR$_{10}$R$_{11}$, and C$_{1-6}$alkyl;
Q" is selected from the group consisting of O, S, and NH;
Z may be absent or is selected from the group consisting of H, aryl, heteroaryl, cycloalkyl, dialkylamino, COOH, heterocycle, pyridone, pyrone, C$_{1-12}$ alkyl, wherein said alkyl is optionally substituted with up to 3 groups selected from an OH group, Q, NHQ, COOH, and a 5-10 member heteroaryl ring system having one or two rings with up to four ring heteroatoms independently selected from O, N and S,
  wherein said aryl, said pyridone, said pyrone, said cycloalkyl, said heteroaryl, and said heterocycle are each optionally substituted with up to five substituents independently selected from the group consisting of R$_{210}$, R$_{41}$, R$_{209}$, R$_{211}$, R$_{214}$, OR$_{41}$, (=O), OH, COOR$_{100}$, C$_{1-6}$ alkyl, C$_{1-6}$ alkoxy, C$_{1-3}$ perhaloalkyl, halogen, C$_{1-3}$ perhaloalkoxy, (=NH), NH$_2$, —NO$_2$, C(O)H, —C(O)OH, —C(O)NH$_2$, CN, Q, heterocycle, heteroaryl, S—C$_{1-3}$ alkyl, S—C$_{1-3}$ perhaloalkyl, S-heteroaryl, aryl, C$_{2-6}$ alkynyl, C(NH)NH$_2$, heterocycloalkyl, C$_{2-6}$ alkenyl, —O—C(O)—R$_{20}$, —O—C(O)OR$_{21}$, —NHS(O)$_2$R$_{22}$, —R$_{102}$NHS(O)$_2$R$_{23}$, —NHC(O)R$_{24}$, —R$_{102}$NHC(O)R$_{24}$, —NHC(O)(CH$_2$)$_m$R$_{25}$, —CH$_2$N(R$_{27}$)(R$_{28}$), —OC(O)N(R$_{27}$)(R$_{28}$), —N(R$_{27}$)(R$_{28}$), —OR$_{31}$, —S(O)$_2$NHR$_{32}$, —S(O)$_2$R$_{33}$, —C(O)R$_{34}$, —CH$_2$C(O)OH, —C(O)NHR$_{35}$, R$_{200}$, —CH$_2$NHS(O)$_2$R$_{21}$, OC(O)CH$_2$halogen, OC(O)R$_{100}$, —OC(O)CH$_2$S(CH$_2$)$_m$ O-PEG, —OC(O)NH-PEG, H, —CN, —OCF$_3$, —CF$_3$, SH, N$_3$, —C(O)H, —COR$_{100}$, —OR$_{100}$, —Saryl, —C(O)Q, C(O)OR$_{100}$, —C(O)NHR$_{100}$, —NR$_{100}$aryl, —OR$_{102}$aryl, —SR$_{102}$aryl, —NHS(O)$_2$—R$_{100}$, —NHR$_{102}$OH, —NHR$_{102}$OR$_{100}$, —NHR$_{102}$NHR$_{100}$, —NR$_{100}$R$_{102}$OH, —NHR$_{102}$Q, —NR$_{100}$R$_{102}$NH$_2$, —NR$_{100}$R$_{102}$NHR$_{100}$, —NR$_{100}$R$_{102}$OR$_{100}$, —NR$_{100}$R$_{102}$Q, —OR$_{102}$OH, —OR$_{102}$OR$_{100}$, —OR$_{102}$NH$_2$]—OR$_{102}$NHR$_{100}$, —OR$_{102}$Q, —OCOR$_{100}$, —OR$_{102}$COR$_{102}$OR$_{102}$COR$_{100}$, —OR$_{102}$COR$_{102}$OR$_{102}$OR$_{100}$, —NHCOR$_{100}$, —NHCONH$_2$, —NHCONHR$_{100}$, —NHR$_{102}$COR$_{100}$, —NHR$_{102}$NH$_2$, —NHS(O)$_2$-aryl, —NHOH, —NHC(O)aryl, —NHOR$_{100}$, —NHC(O)-heteroaryl, —NHC(O)R$_{102}$-heteroaryl, OC(O)CH$_2$halogen, OC(O)CH$_2$S(CH)$_m$O-PEG, OC(O)NH-PEG, OS(O)$_2$NH$_2$, OS(O)$_2$R$_{22}$, —N(R$_{10}$)(R$_{11}$), NHC(O)R$_{102}$-aryl, and NHC(O)NH-heterocycle that is optionally substituted with up to three C$_{1-3}$ alkyl groups,
  wherein said C$_{2-6}$ alkenyl, said C$_{1-6}$ alkyl, and said C$_{2-6}$ alkynyl are each optionally substituted with up to three independently selected R$_{13}$ groups,
  wherein said C$_{1-6}$ alkyl, said —S—C$_{1-6}$ alkyl, and C$_{1-6}$ alkoxy are each optionally substituted with up to three independently selected R$_{50}$ groups,
  wherein said aryl is optionally substituted with up to three groups independently selected from OH and NH$_2$,
  wherein said heteroaryl and said S-heteroaryl, heterocycle, and said heterocycloalkyl, are each optionally substituted with up to three independently selected R$_{12}$ groups,
  wherein said C$_{2-6}$ alkenyl is optionally substituted with COOH,
  wherein any two adjacent carbon atoms of said aryl, heteroaryl or heterocycloalkyl can optionally be joined together by a group of the formula —O—C(Ra)(Rb)—O— wherein R$_a$ and R$_b$ are independently H, C$_{1-3}$ alkyl, phenyl or alkoxycarbonyl; and C$_{1-3}$ alkoxy and C$_{1-3}$ perhaloalkyl, wherein said aryl can be substituted with COOH.

Among the embodiments of compounds of Formula (I) of this invention including pharmaceutically acceptable salts thereof are those in the embodiments below, wherein the other variables of Formula (I) in the embodiments are as defined above wherein:

In one embodiment, A$^1$ is CO or C(R$_1$)(R$_2$).
In another embodiment, e is 1; f is 0; Y$^1$ is CR$_3$; Y$^2$ is NR$_1$;
Z is selected from the group consisting of aryl, heteroaryl, bicyclic aryl, bicyclic heteroaryl, heterocycle, and a 5-10 member heteroaryl ring system having one or two rings, and having up to four ring heteroatoms selected from O, N and S,
  wherein said aryl, said heteroaryl, said bicyclic aryl, said bicyclic heteroaryl, and said heterocycle are each optionally substituted with up to five substituents independently selected from the group consisting of —CH$_2$N(R$_{27}$)(R$_{28}$), —NHR$_{102}$NHR$_{100}$, —NHR$_{102}$Q, —NR$_{100}$R$_{102}$NH$_2$, —NR$_{100}$R$_{102}$NHR$_{100}$, —NR$_{100}$R$_{102}$Q, —OR$_{102}$NH$_2$, —OR$_{102}$NHR$_{100}$, —OR$_{102}$Q, and —NHR$_{102}$NH$_2$.

In another embodiment, e is 1; f is 0; A$^1$ is C=O; A$^2$ is H; Y$^1$ is CR$_3$; Y$^2$ is NR$_1$;
Z is selected from the group consisting of aryl, heteroaryl, bicyclic aryl, bicyclic heteroaryl, heterocycle, and a 5-10 member heteroaryl ring system having one or two rings, and having up to four ring heteroatoms selected from O, N and S,
  wherein said aryl, said heteroaryl, said bicyclic aryl, said bicyclic heteroaryl, and said heterocycle are each optionally substituted with up to five substituents independently selected from the group consisting of —CH$_2$N(R$_{27}$)(R$_{28}$), —NHR$_{102}$NHR$_{100}$, —NHR$_{102}$Q, —NR$_{100}$R$_{102}$NH$_2$, —NR$_{100}$R$_{102}$NHR$_{100}$, —NR$_{100}$R$_{102}$Q, —OR$_{102}$NH$_2$, —OR$_{102}$NHR$_{100}$, —OR$_{102}$Q, and —NHR$_{102}$NH$_2$.

In one embodiment, e is 1; f is 0; A$^1$ is CH$_2$; A$^2$ is H; Y$^1$ is CR$_3$; Y$^2$ is NR$_1$;

Z is selected from the group consisting of aryl, heteroaryl, bicyclic aryl, bicyclic heteroaryl, heterocycle, and a 5-10 member heteroaryl ring system having one or two rings, having up to four ring heteroatoms selected from O, N and S, wherein said aryl, said heteroaryl, said bicyclic aryl, said bicyclic heteroaryl, and said heterocycle are each optionally substituted with up to five substituents independently selected from the group consisting of —CH$_2$N(R$_{27}$)(R$_{28}$), —NHR$_{102}$NHR$_{100}$, —NHR$_{102}$Q, —NR$_{100}$R$_{102}$NH$_2$, —NR$_{100}$R$_{102}$NHR$_{100}$—NR$_{100}$R$_{102}$Q, —OR$_{102}$NH$_2$, —OR$_{102}$NHR$_{100}$, —OR$_{102}$Q, and —NHR$_{102}$NH$_2$.

In another embodiment, e is 1; f is 0; A$^1$ is CR$_1$R$_2$; A$^2$ is H; Y$^1$ is CR$_3$; Y$^2$ is NR$_1$;

Z is selected from the group consisting of aryl, heteroaryl, bicyclic aryl, bicyclic heteroaryl, heterocycle, and a 5-10 member heteroaryl ring system having one or two rings, having up to four ring heteroatoms selected from O, N and S, wherein said aryl, said heteroaryl, said bicyclic aryl, said bicyclic heteroaryl, and said heterocycle are each optionally substituted with up to five substituents independently selected from the group consisting of —CH$_2$N(R$_{27}$)(R$_{28}$), —NHR$_{102}$NHR$_{100}$, —NHR$_{102}$Q, —NR$_{100}$R$_{102}$NH$_2$, —NR$_{100}$R$_{102}$NHR$_{100}$, —NR$_{100}$R$_{102}$Q, —OR$_{102}$NH$_2$, —OR$_{102}$NHR$_{100}$, —OR$_{102}$Q, and —NHR$_{102}$NH$_2$.

In further embodiments, Z is selected from a six membered aryl, heteroaryl or heterocyclic ring and further providing that the independently selected substituent on Z is at the para position of said six membered ring.

In one embodiment, e is 1; Y$^1$ is CR$_3$; Y$^2$ is NR$_1$;

Z is selected from the group consisting of aryl, heteroaryl, bicyclic aryl, bicyclic heteroaryl, heterocycle, and a 5-10 member heteroaryl ring system having one or two rings, having up to four ring heteroatoms selected from O, N and S, wherein said aryl, said heteroaryl, said bicyclic aryl, said bicyclic heteroaryl, and said heterocycle are each optionally substituted with up to five substituents independently selected from the group consisting of C$_{1-6}$ alkyl, C$_{1-6}$ alkoxy, S—C$_{1-3}$ alkyl, C$_{2-6}$ alkynyl, and C$_{2-6}$ alkenyl wherein said alkyl is substituted with OR$_{102}$NR$_{15}$R$_{16}$, NH$_2$ or N(R$_{27}$)(R$_{28}$), alkenyl and alkynyl are substituted with OR$_{102}$NR$_{15}$R$_{16}$ and wherein said S-alkyl and alkoxy are substituted with NH$_2$ or N(R$_{27}$)(R$_{28}$).

In another embodiment, e is 1; A$^1$ is C=O; A$^2$ is H; Y$^1$ is CR$_3$; Y$^2$ is NR$_1$;

Z is selected from the group consisting of aryl, heteroaryl, bicyclic aryl, bicyclic heteroaryl, heterocycle, and a 5-10 member heteroaryl ring system having one or two rings, and having up to four ring heteroatoms selected from O, N and S, wherein said aryl, said heteroaryl, said bicyclic aryl, said bicyclic heteroaryl, and said heterocycle are each optionally substituted with up to five substituents independently selected from the group consisting of C$_{1-6}$ alkyl, C$_{1-6}$ alkoxy, S—C$_{1-3}$ alkyl, C$_{2-6}$ alkynyl, and C$_{2-6}$ alkenyl wherein said alkyl is substituted with —OR$_{102}$NR$_{15}$R$_{16}$, NH$_2$ or —N(R$_{27}$)(R$_{28}$), alkenyl and alkynyl are substituted with —OR$_{102}$NR$_{15}$R$_{16}$ and wherein said S-alkyl and alkoxy are substituted with NH$_2$ or —N(R$_{27}$)(R$_{28}$).

In one embodiment, e is 1; A$^1$ is CH$_2$; A$^2$ is H; Y$^1$ is CR$_3$; Y$^2$ is NR$_1$;

Z is selected from the group consisting of aryl, heteroaryl, bicyclic aryl, bicyclic heteroaryl, heterocycle, and a 5-10 member heteroaryl ring system having one or two rings, and having up to four ring heteroatoms selected from O, N and S, wherein said aryl, said heteroaryl, said bicyclic aryl, said bicyclic heteroaryl, and said heterocycle are each optionally substituted with up to five substituents independently selected from the group consisting of C$_{1-6}$ alkyl, C$_{1-6}$ alkoxy, S—C$_{1-3}$ alkyl, C$_{2-6}$ alkynyl, and C$_{2-6}$ alkenyl wherein said alkyl is substituted with —OR$_{102}$NR$_{15}$R$_{16}$, NH$_2$ or —N(R$_{27}$)(R$_{28}$), alkenyl and alkynyl are substituted with —OR$_{102}$NR$_{15}$R$_{16}$ and wherein said S-alkyl and alkoxy are substituted with NH$_2$ or —N(R$_{27}$)(R$_{28}$).

In an embodiment of the invention, e is 1; A$^1$ is CR$_1$R$_2$; A$^2$ is H; Y$^1$ is CR$_3$; Y$^2$ is NR$_1$;

Z is selected from the group consisting of aryl, heteroaryl, bicyclic aryl, bicyclic heteroaryl, heterocycle, and a 5-10 member heteroaryl ring system having one or two rings, and having up to four ring heteroatoms selected from O, N and S, wherein said aryl, said heteroaryl, said bicyclic aryl, said bicyclic heteroaryl, and said heterocycle are each optionally substituted with up to five substituents independently selected from the group consisting of C$_{1-6}$ alkyl, C$_{1-6}$ alkoxy, S—C$_{1-3}$ alkyl, C$_{2-6}$ alkynyl, and C$_{2-6}$ alkenyl wherein said alkyl is substituted with OR$_{102}$NR$_{15}$R$_{16}$, NH$_2$ or N(R$_{27}$)(R$_{28}$), alkenyl and alkynyl are substituted with OR$_{102}$NR$_{15}$R$_{16}$ and wherein said S-alkyl and alkoxy are substituted with NH$_2$ or N(R$_{27}$)(R$_{28}$)—

In a further embodiment, e is 1; f is 0; Y$^1$ is N; Y$^2$ is NR$_1$;

Z is selected from the group consisting of aryl, heteroaryl, bicyclic aryl, bicyclic and heteroaryl, and a 5-10 member heteroaryl ring system having one or two rings, and having up to four ring heteroatoms selected from O, N and S, wherein said aryl, said heteroaryl, said bicyclic aryl, and said bicyclic heteroaryl, are each optionally substituted with up to five substituents independently selected from the group consisting of —CH$_2$N(R$_{27}$)(R$_{28}$), —NHR$_{102}$NHR$_{100}$, —NHR$_{102}$Q, —NR$_{100}$R$_{102}$NH$_2$, —NR$_{100}$R$_{102}$NHR$_{100}$, —NR$_{100}$R$_{102}$Q, —OR$_{102}$NH$_2$, —OR$_{102}$NHR$_{100}$, —OR$_{102}$Q, and —NHR$_{102}$NH$_2$.

In another embodiment, e is 1; f is 0; A$^1$ is C=O; A$^2$ is H; Y$^1$ is N; Y$^2$ is NR$_1$;

Z is selected from the group consisting of aryl, heteroaryl, bicyclic aryl, and bicyclic heteroaryl, and a 5-10 member heteroaryl ring system having one or two rings, and having up to four ring heteroatoms selected from O, N and S, wherein said aryl, said heteroaryl, said bicyclic aryl, and said bicyclic heteroaryl, are each optionally substituted with up to five substituents independently selected from the group consisting of —NHR$_{102}$NHR$_{100}$, —NHR$_{102}$Q, —NR$_{100}$R$_{102}$NH$_2$, —NR$_{100}$R$_{102}$NHR$_{100}$, —NR$_{100}$R$_{102}$Q, —OR$_{102}$NH$_2$, —OR$_{102}$NHR$_{100}$, —OR$_{102}$Q, and —NHR$_{102}$NH$_2$.

In an embodiment, e is 1; f is 0; A$^1$ is CH$_2$; A$^2$ is H; Y$^1$ is N; Y$^2$ is NR$_1$;

Z is selected from the group consisting of aryl, heteroaryl, bicyclic aryl, and bicyclic heteroaryl, and a 5-10 member heteroaryl ring system having one or two rings, and having up to four ring heteroatoms selected from O, N and S, wherein said aryl, said heteroaryl, said bicyclic aryl, and said bicyclic heteroaryl, are each optionally substituted with up to five substituents independently selected from the group consisting of —$NHR_{102}NHR_{100}$, —$NHR_{102}Q$, —$NR_{100}R_{102}NH_2$, —$NR_{100}R_{102}NHR_{100}$, —$NR_{100}R_{102}Q$, —$OR_{102}NH_2$, —$OR_{102}NHR_{100}$, —$OR_{102}Q$, and —$NHR_{102}NH_2$.

In another embodiment, e is 1; f is 0; $A^1$ is $CR_1R_2$; $A^2$ is H; $Y^1$ is N; $Y^2$ is $NR_1$;

Z is selected from the group consisting of aryl, heteroaryl, bicyclic aryl, and bicyclic heteroaryl, and a 5-10 member heteroaryl ring system having one or two rings, and having up to four ring heteroatoms selected from O, N and S, wherein said aryl, said heteroaryl, said bicyclic aryl, and said bicyclic heteroaryl, are each optionally substituted with up to five substituents independently selected from the group consisting of —$NHR_{102}NHR_{100}$, —$NHR_{102}Q$, —$NR_{100}R_{102}NH_2$, —$NR_{100}R_{102}NHR_{100}$, —$NR_{100}R_{102}Q$, —$OR_{102}NH_2$, —$OR_{102}NHR_{100}$, —$OR_{102}Q$, and —$NHR_{102}NH_2$.

In one embodiment, e is 1; f is 0; $Y^1$ is $CR_3$; $Y^2$ is $NR_1$;

Z is selected from the group consisting of aryl, or heteroaryl wherein said aryl, and said heteroaryl, are each optionally substituted with up to three substituents independently selected from the group consisting of $R_{210}$, $R_{41}$, $R_{209}$, $R_{211}$, $R_{214}$, $OR_{41}$, OH, $C_{1-6}$ alkyl, $C_{1-6}$ alkoxy, $C_{1-3}$ perhaloalkyl, halogen, $C_{1-3}$ perhaloalkoxy, $NH_2$, Q, heterocycle, heteroaryl, S—$C_{1-3}$ alkyl, S—$C_{1-3}$ perhaloalkyl, S-heteroaryl, aryl, —O—C(O)—$R_{20}$, —$NHC(O)R_{24}$, —$NHC(O)(CH_2)_mR_{25}$, —$OC(O)N(R_{27})(R_{28})$, —$N(R_{27})(R_{28})$, —$OR_{31}$, $R_{200}$, $OC(O)R_{100}$, —$OC(O)CH_2S(CH_2)_m$O-PEG, —OC(O)NH-PEG, —$OCF_3$, —$CF_3$, SH, —$OR_{100}$, —Saryl, $NR_{100}$aryl, —$OR_{102}$aryl, —$SR_{102}$aryl, —$NHR_{102}$OH, —$NHR_{102}OR_{100}$, —$NR_{100}R_{102}$OH, —$NHR_{102}Q$, —$NR_{100}R_{102}OR_{100}$, —$NR_{100}R_{102}Q$, —$OR_{102}$OH, —$OR_{102}OR_{100}$, —$OR_{102}Q$, —$OCOR_{100}$, $OR_{102}COR_{102}OR_{102}OR_{100}$, —NHC(O)aryl, —NHC(O)-heteroaryl, —$NHC(O)R_{102}$-heteroaryl, OC(O)CH$_2$S(CH)$_m$O-PEG, OC(O)NH-PEG, —$N(R_{10})(R_{11})$, and $NHC(O)R_{102}$-aryl.

In an embodiment, e is 1; f is 0; $A^1$ is C=O; $A^2$ is H; $Y^1$ is $CR_3$; $Y^2$ is $NR_1$;

Z is selected from the group consisting of aryl, or heteroaryl wherein said aryl, and said heteroaryl, are each optionally substituted with up to three substituents independently selected from the group consisting of $R_{210}$, $R_{41}$, $R_{209}$, $R_{211}$, $R_{214}$, $OR_{41}$, OH, $C_{1-6}$ alkyl, $C_{1-6}$ alkoxy, $C_{1-3}$ perhaloalkyl, halogen, $C_{1-3}$ perhaloalkoxy, $NH_2$, Q, heterocycle, heteroaryl, S—$C_{1-3}$ alkyl, S—$C_{1-3}$ perhaloalkyl, S-heteroaryl, aryl, —O—C(O)—$R_{20}$, —$NHC(O)R_{24}$, —$NHC(O)(CH_2)_mR_{25}$, —$OC(O)N(R_{27})(R_{28})$, —$N(R_{27})(R_{28})$, —$OR_{31}$, $R_{200}$, $OC(O)R_{100}$, —$OC(O)CH_2S(CH_2)_m$O-PEG, —OC(O)NH-PEG, —$OCF_3$, —$CF_3$, SH, —$OR_{100}$, —Saryl, $NR_{100}$aryl, —$OR_{102}$aryl, —$SR_{102}$aryl, —$NHR_{102}$OH, —$NHR_{102}OR_{100}$, —$NR_{100}R_{102}$OH, —$NHR_{102}Q$, —$NR_{100}R_{102}OR_{100}$, —$NR_{100}R_{102}Q$, —$OR_{102}$OH, —$OR_{102}OR_{100}$, —$OR_{102}Q$, —$OCOR_{100}$, $OR_{102}COR_{102}OR_{102}OR_{100}$, —NHC(O)aryl, —NHC(O)-heteroaryl, —$NHC(O)R_{102}$-heteroaryl, OC(O)CH$_2$S(CH)$_m$O-PEG, OC(O)NH-PEG, —$N(R_{10})(R_{11})$, and $NHC(O)R_{102}$-aryl.

In another embodiment, e is 1; f is 0; $A^1$ is $CH_2$; $A^2$ is H; $Y^1$ is $CR_3$; $Y^2$ is $NR_1$;

Z is selected from the group consisting of aryl, or heteroaryl wherein said aryl, and said heteroaryl, are each optionally substituted with up to three substituents independently selected from the group consisting of $R_{210}$, $R_{41}$, $R_{209}$, $R_{211}$, $R_{214}$, $OR_{41}$, OH, $C_{1-6}$ alkyl, $C_{1-6}$ alkoxy, $C_{1-3}$ perhaloalkyl, halogen, $C_{1-3}$ perhaloalkoxy, $NH_2$, Q, heterocycle, heteroaryl, S—$C_{1-3}$ alkyl, S—$C_{1-3}$ perhaloalkyl, S-heteroaryl, aryl, —O—C(O)—$R_{20}$, —$NHC(O)R_{24}$, —$NHC(O)(CH_2)_mR_{25}$, —$OC(O)N(R_{27})(R_{28})$, —$N(R_{27})(R_{28})$, —$OR_{31}$, $R_{200}$, $OC(O)R_{100}$, —$OC(O)CH_2S(CH_2)_m$O-PEG, —OC(O)NH-PEG, —$OCF_3$, —$CF_3$, SH, —$OR_{100}$, —Saryl, $NR_{100}$aryl, —$OR_{102}$aryl, —$SR_{102}$aryl, —$NHR_{102}$OH, —$NHR_{102}OR_{100}$, —$NR_{100}R_{102}$OH, —$NHR_{102}Q$, —$NR_{100}R_{102}OR_{100}$, —$NR_{100}R_{102}Q$, —$OR_{102}$OH, —$OR_{102}OR_{100}$, —$OR_{102}Q$, —$OCOR_{100}$, $OR_{102}COR_{102}OR_{102}OR_{100}$, —NHC(O)aryl, —NHC(O)-heteroaryl, —$NHC(O)R_{102}$-heteroaryl, OC(O)CH$_2$S(CH)$_m$O-PEG, OC(O)NH-PEG, —$N(R_{10})(R_{11})$, and $NHC(O)R_{102}$-aryl.

In one embodiment, e is 1; f is 0; $A^1$ is $CR_1R_2$; $A^2$ is H; $Y^1$ is $CR_3$; $Y^2$ is $NR_1$;

Z is selected from the group consisting of aryl, or heteroaryl wherein said aryl, and said heteroaryl, are each optionally substituted with up to three substituents independently selected from the group consisting of $R_{210}$, $R_{41}$, $R_{209}$, $R_{211}$, $R_{214}$, $OR_{41}$, OH, $C_{1-6}$ alkyl, $C_{1-6}$ alkoxy, $C_{1-3}$ perhaloalkyl, halogen, $C_{1-3}$ perhaloalkoxy, $NH_2$, Q, heterocycle, heteroaryl, S—$C_{1-3}$ alkyl, S—$C_{1-3}$ perhaloalkyl, S-heteroaryl, aryl, —O—C(O)—$R_{20}$, —$NHC(O)R_{24}$, —$NHC(O)(CH_2)_mR_{25}$, —$OC(O)N(R_{27})(R_{28})$, —$N(R_{27})(R_{28})$, —$OR_{31}$, $R_{200}$, $OC(O)R_{100}$, —$OC(O)CH_2S(CH_2)_m$O-PEG, —OC(O)NH-PEG, —$OCF_3$, —$CF_3$, SH, —$OR_{100}$, —Saryl, $NR_{100}$aryl, —$OR_{102}$aryl, —$SR_{102}$aryl, —$NHR_{102}$OH, —$NHR_{102}OR_{100}$, —$NR_{100}R_{102}$OH, —$NHR_{102}Q$, —$NR_{100}R_{102}OR_{100}$, —$NR_{100}R_{102}Q$, —$OR_{102}$OH, —$OR_{102}OR_{100}$, —$OR_{102}Q$, —$OCOR_{100}$, $OR_{102}COR_{102}OR_{102}OR_{100}$, —NHC(O)aryl, —NHC(O)-heteroaryl, —$NHC(O)R_{102}$-heteroaryl, OC(O)CH$_2$S(CH)$_m$O-PEG, OC(O)NH-PEG, —$N(R_{10})(R_{11})$, and $NHC(O)R_{102}$-aryl.

In one embodiment, Z is selected from moieties of the formulae substituents

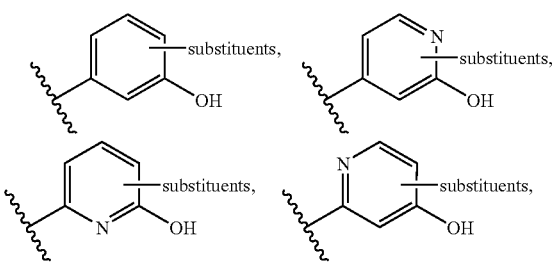

-continued

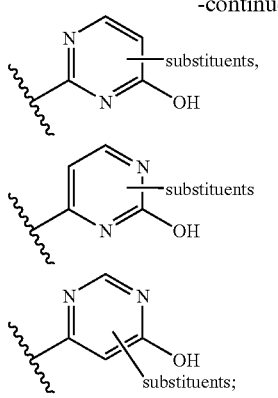

optionally substituted with up to 3 independently selected substituents.

In an embodiment, e is 1; f is 1; $Y^1$ is $CR_3$; $Y^2$ is $NR_1$;

Z is selected from a moiety of the formula

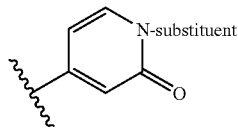

wherein said Z is optionally substituted with a substituent selected from the group consisting of $R_{41}$, $R_{211}$, $R_{214}$, $C_{1-6}$ alkyl, $C_{1-3}$ perhaloalkyl, heterocycle, heteroaryl, aryl, and heterocycloalkyl.

In one embodiment, e is 1; f is 1; $A^1$ is C=O; $A^2$ is H; $Y^1$ is $CR_3$; $Y^2$ is $NR_1$;

Z is selected from a moiety of the formula

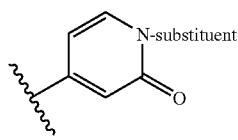

wherein said Z is optionally substituted with a substituent selected from the group consisting of $R_{41}$, $R_{211}$, $R_{214}$, $C_{1-6}$ alkyl, $C_{1-3}$ perhaloalkyl, heterocycle, heteroaryl, aryl, and heterocycloalkyl.

In another embodiment, e is 1; f is 1; $A^1$ is $CH_2$; $A^2$ is H; $Y^1$ is $CR_3$; $Y^2$ is $NR_1$;

Z is selected from a moiety of the formula

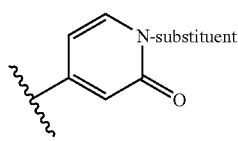

wherein said Z is optionally substituted with a substituent selected from the group consisting of $R_{41}$, $R_{211}$, $R_{214}$, $C_{1-6}$ alkyl, $C_{1-3}$ perhaloalkyl, heterocycle, heteroaryl, aryl, and heterocycloalkyl.

In another embodiment, e is 1; f is 1; $A^1$ is $CR_1R_2$; $A^2$ is H; $Y^1$ is $CR_3$; $Y^2$ is $NR_1$;

Z is selected from a moiety of the formula

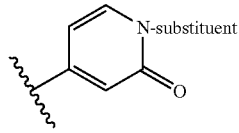

wherein said Z is optionally substituted with a substituent selected from the group consisting of $R_{210}$, $R_{41}$, $R_{211}$, $R_{214}$, $C_{1-6}$ alkyl, $C_{1-3}$ perhaloalkyl, heterocycle, heteroaryl, aryl, and heterocycloalkyl.

In one embodiment, e is 1; f is 1; $Y^1$ is $CR_3$; $Y^2$ is $NR_1$;

Z is selected from the group consisting of

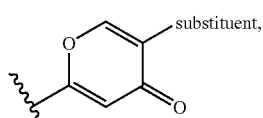

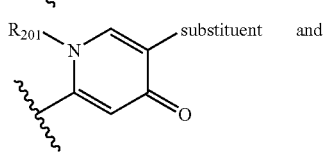

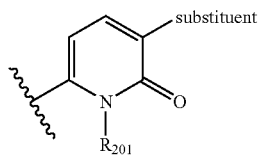

wherein said Z is optionally substituted with a substituent selected from the group consisting of $R_{211}$, $OR_{41}$, OH, $C_{1-6}$ alkoxy, $C_{1-3}$ perhaloalkoxy, heteroaryl, S—$C_{1-3}$ alkyl, S—$C_{1-3}$ perhaloalkyl, S-heteroaryl, aryl, —O—C(O)—$R_{20}$, —O—C(O)$OR_{21}$, OC(O)N($R_{27}$)($R_{28}$), —$OR_{31}$, OC(O)$R_{100}$, —OC(O)$CH_2S(CH_2)_m$O-PEG, —OC(O)NH-PEG, —$OCF_3$, —$OR_{100}$, —Saryl, —$OR_{102}$aryl, —$SR_{102}$aryl, —$OR_{102}$OH, —$OR_{102}OR_{100}$, —$OR_{102}$Q, —OCOR$_{100}$, $OR_{102}COR_{102}OR_{102}OR_{100}$, OC(O)$CH_2S(CH)_m$O-PEG, and OC(O)NH-PEG.

In another embodiment, e is 1; f is 1; $A^1$ is C=O; $A^2$ is H; $Y^1$ is $CR_3$; $Y^2$ is $NR_1$;

Z is selected from the group consisting of

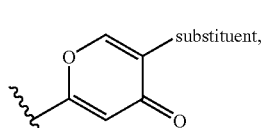

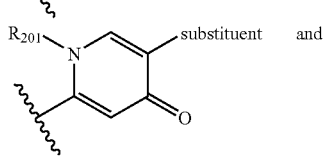

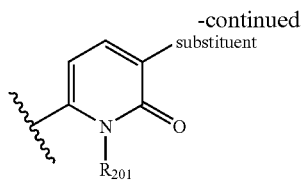

wherein said Z is optionally substituted with a substituent selected from the group consisting of $R_{211}$, $OR_{41}$, OH, $C_{1-6}$ alkoxy, $C_{1-3}$ perhaloalkoxy, heteroaryl, S—$C_{1-3}$ alkyl, S—$C_{1-3}$ perhaloalkyl, S-heteroaryl, aryl, —O—C(O)—$R_{20}$, —O—C(O)$OR_{21}$, OC(O)N($R_{27}$)($R_{28}$), —$OR_{31}$, OC(O)$R_{100}$, —OC(O)CH$_2$S(CH$_2$)$_m$O-PEG, —OC(O)NH-PEG, —OCF$_3$, —$OR_{100}$, —Saryl, —$OR_{102}$aryl, —$SR_{102}$aryl, —$OR_{102}$OH, —$OR_{102}OR_{100}$, —$OR_{102}$Q, —OCOR$_{100}$, $OR_{102}COR_{102}OR_{102}OR_{100}$, OC(O)CH$_2$S(CH)$_m$O-PEG, and OC(O)NH-PEG.

In another embodiment, e is 1; f is 1; $A^1$ is CH$_2$; $A^2$ is H; $Y^1$ is CR$_3$; $Y^2$ is NR$_1$;

Z is selected from the group consisting of

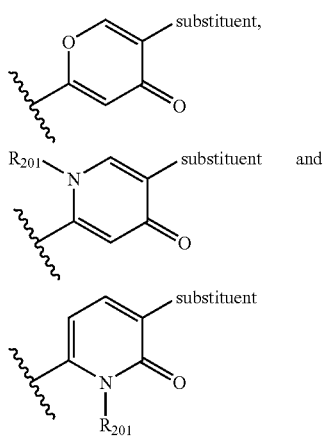

wherein said Z is optionally substituted with a substituent selected from the group consisting of $R_{211}$, $OR_{41}$, OH, $C_{1-6}$ alkoxy, $C_{1-3}$ perhaloalkoxy, heteroaryl, S—$C_{1-3}$ alkyl, S—$C_{1-3}$ perhaloalkyl, S-heteroaryl, aryl, —O—C(O)—$R_{20}$, —O—C(O)$OR_{21}$, OC(O)N($R_{27}$)($R_{28}$), —$OR_{31}$, OC(O)$R_{100}$, —OC(O)CH$_2$S(CH$_2$)$_m$O-PEG, —OC(O)NH-PEG, —OCF$_3$, —$OR_{100}$, —Saryl, —$OR_{102}$aryl, —$SR_{102}$aryl, —$OR_{102}$OH, —$OR_{102}OR_{100}$, —$OR_{102}$Q, —OCOR$_{100}$, $OR_{102}COR_{102}OR_{102}OR_{100}$, OC(O)CH$_2$S(CH)$_m$O-PEG, and OC(O)NH-PEG.

In one embodiment, e is 1; f is 1; $A^1$ is CR$_1$R$_2$; $A^2$ is H; $Y^1$ is CR$_3$; $Y^2$ is NR$_1$;

Z is selected from the group consisting of

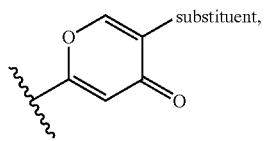

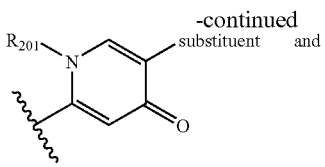

wherein said Z is optionally substituted with a substituent selected from the group consisting of $R_{211}$, $OR_{41}$, OH, $C_{1-6}$ alkoxy, $C_{1-3}$ perhaloalkoxy, heteroaryl, S—$C_{1-3}$ alkyl, S—$C_{1-3}$ perhaloalkyl, S-heteroaryl, aryl, —O—C(O)—$R_{20}$, —O—C(O)$OR_{21}$, OC(O)N($R_{27}$)($R_{28}$), —$OR_{31}$, OC(O)$R_{100}$, —OC(O)CH$_2$S(CH$_2$)$_m$O-PEG, —OC(O)NH-PEG, —OCF$_3$, —$OR_{100}$, —Saryl, —$OR_{102}$aryl, —$SR_{102}$aryl, —$OR_{102}$OH, —$OR_{102}OR_{100}$, —$OR_{102}$Q, —OCOR$_{100}$, $OR_{102}COR_{102}OR_{1020}R_{100}$, OC(O)CH$_2$S(CH)$_m$O-PEG, and OC(O)NH-PEG.

In another embodiment, $G^1$, $G^3$, and $G^4$=H; $G^2$ is selected from the group consisting of halogen, heteroaryl, heterocycloalkyl, aryl, $C_{3-10}$cycloalkyl, $C_{1-12}$ alkyl, $C_{2-6}$ alkenyl, $C_{2-6}$ alkynyl, —Oaryl, NHaryl, and

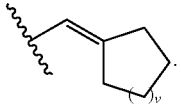

In some embodiments, $A^2$ or $R_3$ are not H.

In a further embodiment, are illustrative examples or pharmaceutically acceptable salts thereof of Formula (I) which include:

(4Z)-4-{[(4-Methoxyphenyl)amino]methylene}isoquinoline-1,3(2H,4H)-dione;

(4Z)-4-({[4-(4-Methyl-1-piperazinyl)phenyl]amino}methylene)-1,4-dihydro-3(2H)-isoquinolinone;

(4Z)-4-({[4-(1H-Imidazol-4-yl)phenyl]amino}methylene)-1,4-dihydro-3(2H)-isoquinolinone;

(4Z)-4-({[4-(4-Methylpiperazin-1-yl)phenyl]amino}methylene)isoquinoline 1,3(2H,4H)-dione;

(4Z)-4-({[4-(2-Pyrrolidin-1-ylethyl)phenyl]amino}methylene)isoquinoline-1,3(2H,4H)-dione;

(4Z)-4-{[(4-Morpholin-4-ylphenyl)amino]methylene}isoquinoline-1,3(2H,4H)-dione;

(4Z)-4-[(1H-Indazol-6-ylamino)methylene]isoquinoline-1,3(2H,4H)-dione;

(4Z)-4-[(Quinolin-6-ylamino)methylene]isoquinoline-1,3(2H,4H)-dione;

(4E)-4-[4-(dimethylamino)benzylidene]isoquinoline-1,3(2H,4H)-dione-(4Z)-4-[4-(dimethylamino)benzylidene]isoquinoline-1,3(2H,4H)-dione (1:1);

(4E)-4-(4-hydroxybenzylidene)isoquinoline-1,3(2H,4H)-dione;

(4Z)-4-({[4-(Piperidin-1-ylmethyl)phenyl]amino}methylene)isoquinoline-1,3(2H,4H)-dione;

(4Z-4-[{3-Chloro-4-[(1-methyl-1H-imidazole-2-uy)thio]phenyl}amino)methylene]isoquinoline-1,3(2H,4H)-dione;

(4Z)-4-[({3-Chloro-4-{(4-chlorobenzyl)oxy]phenyl}amino)methylene]isoquinoline-1,3(2H,4H)-dione;
(4Z)-4-({[3-(Piperidin-1-ylmethyl)phenyl]amino}methylene)isoquinoline-1,3(2H,4H)-dione) (1b);
(4Z)-4-({[3-(Azepan-1-ylmethyl)phenyl]amino}methylene)isoquinoline-1,3(2H,4H)-dione;
(4Z)-4-({[3-(Pyrrolidin-1-ylmethyl)phenyl]amino}methylene)isoquinoline-1,3(2H,4H)-dione) (1c);
(4Z)-4-({[4-(Morpholin-4-ylmethyl)phenyl]amino}methylene)isoquinoline-1,3(2H,4H)-dione (3);
(4Z)-4-[({4-[(4-Methylpiperazin-1-yl)methyl]phenylamino)mathylene]isoquilin-1,3(2H,4H)-dione (4);
(4Z)-4-[(1,1'-Biphenyl-4-ylamino)methylene]isoquinoline-1,3(2H,4H)-dione;
(4Z)-4-({[3-(2-Pyrrolidin-1-ylethyl)phenyl]amino}methylene)isoquinoline-1,3(2H,4H)-dione;
(4Z)-4-[({4-[(4-Hydroxypiperidin-1-yl)methyl]phenyl}amino)methylene]isoquinolin-1,3(2H,4H)-dione;
(4Z)-6-Bromo-4-{[(4-piperidin-1-ylmethyl)phenyl]amino}methyleneisoquinoline-1,3(2H,4H)-dione;
(4Z)-4-[({4-[(Dimethylamino)methyl]phenyl}amino}methylene]isoquinolin-1,3(2H,4H)-dione;
(4Z)-4-({[4-(Azepan-1-ylmethyl)phenyl]amino}methylene)isoquinoline-1,3(2H,4H)-dione) (1d);
(4Z)-6-Bromo-4-({[4-(4-methylpiperazin-1-yl)phenyl]amino}methylene)isoquinoline-1,3(2H,4H)-dione;
(4Z)-6-Bromo-4-{[(4-hydroxy-3-methoxybenzyl)amino]methylene}isoquinoline-1,3(2H,4H)-dione (3a);
N-(4-{[(Z)-(1,3-Dioxo-2,3-dihydroisoquinolin-4(1H)-ylidene)methyl]amino}phenyl)-1,3(2H,4H)-dione N-Methyl-2-piperidin-1-ylacetamide;
(4Z)-6-Bromo-4-{[(pyridin-3-ylmethyl)amino]methylene}isoquinoline-1,3(2H,4H)-dione;
(4Z)-6-Bromo-4-{[(pyridin-4-ylmethyl)amino]methylene}isoquinoline-1,3(2H,4H)-dione;
(4Z)-6-Nitro-4-({[4-(4-methylpiperazin-1-yl)phenyl]amino}methylene)isoquinoline-1,3(2H,4H)-dione;
tert-Butyl 4-(4-{[(Z)-1,3-dioxo-2,3-dihydroisoquinolin-4(1H)-ylidene)methyl]amino}piperazine-1-carboxylate;
(4Z)-6,7-Dimethoxy-4-({[4-(-methylpiperazin-1-yl)phenyl}amino)methylene]isoquinolin-1,3(2H,4H)-dione;
(4Z)-6-Bromo-4-{[(4-{[(2s)-2-(methoxymethyl)pyrrolidin-1-yl]methyl}phenyl)amino)methylene}isoquinoline-1,3(2H,4H)-dione;
(4Z)-6-Bromo-4-{[(4-{[(2R)-2-(methoxymethyl)pyrrolidin-1-yl]methyl}phenyl)amino)methylene}isoquinoline-1,3(2H,4H)-dione;
(4Z)-6-Bromo-4-{[(3,4-dihydroxybenzyl)amino]methylene}isoquinoline-1,3(2H,4H)-dione;
(4Z)-6-Bromo-4-({[2-(piperidin-1-ylmethyl)phenyl}amino]methylene]isoquinolin-1,3(2H,4H)-dione;
(4Z)-6-Nitro-4-{[(4-piperidin-1-ylmethyl)phenyl]amino}methyleneisoquinoline-1,3(2H,4H)-dione;
(4Z)-6-Bromo-4-({[2-(1H-indol-3-yl)ethyl]amino}methylene)isoquinoline-1,3(2H,4H)-dione;
(4Z)-7-Bromo-4-({[4-(Piperidin-1-ylmethyl)phenyl]amino}methylene)isoquinoline-1,3(2H,4H)-dione;
(4Z)-7-Bromo-4-({[4-(4-methylPiperzin-1-yl)phenyl]amino}methylene)isoquinoline-1,3(2H,4H)-dione;
(4Z)-6-Bromo-4-{[(3-hydroxybenzyl)amino]methylene}isoquinoline-1,3(2H,4-dione;
2-(Acetyloxy)-4-({[(Z)-(1,3-dioxo-2,3-dihydroisoquinolin-4(1H)-ylidene)methyl]amino}-methyl)phenyl acetate;
N-[(4Z)-1,3-Dioxo-4-({[4-piperidin-1-ylmethyl)phenyl]amino}methylene)-1,2,3,4-tetrahydroisoquinolin-6-yl]acetamide;
(4Z)-2-Methyl-4-{[(4-piperidin-1-ylmethyl)phenyl]amino}methyleneisoquinoline-1,3(2H,4H)-dione;
(4Z)-6-Bromo-4-{[(3-hydroxy-4-methoxybenzyl)amino]methylene}isoquinoline-1,3(2H,4H)-dione;
(4Z)-4-({[4-(4-Methylpiperazin-1-yl)phenyl]amino}methylene)-1,3-dioxo-1,2,3,4-tetrahydroisoquinoline-6-carboxylic acid;
(4Z)-4-{[(3-Aminobenzyl)amino]methylene}-6-bromoisoquinoline-1,3(2H,4H)-dione;
(4Z)-6-Bromo-4-{[(4-chlorobenzyl)amino]methylene}isoquinoline-1,3(2H,4H)-dione;
2-(Acetyloxy)-4-({[[(Z)-(6-bromo-1,3-dioxo-2,3-dihydroisoquinolin-4(1H)-ylidene)methyl]-amino}methyl)phenyl acetate;
(4Z)-6-Chloro-4-({[4-(piperidin-1-ylmethyl)phenyl]amino}methylene)isoquinoline-1,3(2H,4H)-dione;
4-({[[(Z)-(6-Bromo-1,3-dioxo-2,3-dihydroisoquinolin-4(1H)-ylidene)methyl]amino}methyl)benzenesulfonamide;
5-({[[(Z)-(6-Bromo-1,3-dioxo-2,3-dihydroisoquinolin-4(1H)-ylidene)methyl]amino}methyl)-2-methoxyphenyl acetate;
5-{[[(Z)-(6-Bromo-1,3-dioxo-2,3-dihydroisoquinolin-4(1H)-ylidene)methyl]amino}-2-hydroxybenzoic acid;
(4Z)-6-Bromo-4-({[4-(pyrrolidin-1-ylmethyl)phenyl]amino}methylene)isoquinoline-1,3(2H,4H)-dione;
(4Z)-4-({[4-(4-Methylpiperazin-1-yl)phenyl]amino}methylene)-6-(1H-pyrrol-1-yl)isoquinoline-1,3(2H,4H)-dione;
(4Z)-4-{[(4-Hydroxybenzyl)amino]methylene}isoquinoline-1,3(2H,4H)-dione;
(4Z)-6-Bromo-4-{[(4-hydroxybenzyl)amino]methylene}isoquinoline-1,3(2H,4H)-dione;
(4Z)-4-{[(3-Hydroxybenzyl)amino]methylene}isoquinoline-1,3(2H,4H)-dione;
(4Z)-6-Bromo-4-{[(3,5-dihydroxybenzyl)amino]methylene}isoquinoline-1,3(2H,4H)-dione;
(4Z)-N,N-Dimethyl-4-({[4-(4-methylpiperazin-1-yl)phenyl]amino}methylene)-1,3-dioxo-1,2,3,4-tetrahydroisoquinoline-6-carboxamide;
(4Z)-N,N-Dimethyl-1,3-dioxo-4-({[4-(piperidinylmethyl)phenyl]amino}methylene)-1,2,3,4-tetrahydroisoquinoline-6-carboxamide;
(4Z)-6-Chloro-4-{[(3-hydroxy-4-methoxybenzyl)amino]methylene}isoquinoline-1,3(2H,4H)-dione;
(4Z)-6-Fluoro-4-{[(3-hydroxy-4-methoxybenzyl)amino]methylene}isoquinoline-1,3(2H,4H)-dione;
Acetic acid 3-acetoxy-5-{[(6-bromo-1,3-dioxo-2,3-dihydro-1H-isoquinolin-4-ylidenemethyl)-amino]-methyl}-phenyl ester;
(4Z)-6-Fluoro-4-({[4-(4-methylPiperzin-1-yl)phenyl]amino}methylene)isoquinoline-1,3(2H,4H)-dione;
(4Z)-6-Fluoro-4-{[(3-hydroxy-4-methoxybenzyl)amino]methylene}-6-(1H-pyrrol-1-yl)isoquinoline-1,3(2H,4H-dione;
(4Z)-4-({[4-Pyrrolidin-1-ylmethyl)phenyl]amino}methylene)}-6-(1H-pyrrol-1-yl)isoquinoline-1,3(2H,4H)-dione;
(4Z)-6-Bromo-4-{[(4-{[(4-[(dimethylamino)methyl]methyl}phenyl)amino)methylene}isoquinoline-1,3(2H,4H)-dione;
(4Z)-4-({[4-Piperidin-1-ylmethyl)phenyl]amino}methylene)}-6-(1H-pyrrol-1-yl)isoquinoline-1,3(2H,4H)-dione;
(4Z)-6-Bromo-4-{[(4-[(4-hydroxypiperidin-1-yl)methyl]phenyl)amino)methylene}isoquinoline-1,3(2H,4H)-dione;

Carbonic acid 5-{[(6-bromo-1,3-dioxo-2,3-dihydro-1H-isoquinolin-4-ylidenemethyl)-amino]-methyl}-2-methoxy-carbonyloxy-phenyl ester methyl ester;

5-({[(Z)-(6-Bromo-1,3-dioxo-2,3-dihydroisoquinolin-4(1H)-ylidene)methyl]amino}methyl)-2,3-dimethoxyphenyl acetate;

(4Z)-6-Bromo-4-{[(3-hydroxy-4,5-dimethoxybenzyl)amino)methylene}isoquinoline-1,3(2H,4H-dione;

(4Z)-6-Bromo-4-{[(3,4,5-trihydroxybenzyl)amino)methylene}isoquinoline-1,3(2H,4H-dione;

(4Z)-6-Iodo-4-{[(3-hydroxy-4-methoxybenzyl)amino]methylene}isoquinoline-1,3(2H,4H)-dione (5c);

(4Z)-6-Iodo-4-({[4-(4-methylpiperazin-1-yl)phenyl]amino}methylene)isoquinoline-1,3(2H,4H)-dione (11c);

(4Z)-6-Iodo-4-({[4-(piperidin-1-ylmethyl)phenyl]amino}methylene)isoquinoline-1,3(2H,4H)-dione (11a);

5-({[(Z)-(6-Bromo-1,3-dioxo-2,3-dihydroisoquinolin-4(1H)-ylidene)methyl]amino}methyl)-2-methoxyphenyl methyl carbonate (8b);

(4Z)-5-Bromo-4-{[(3-hydroxy-4-methoxybenzyl)amino]methylene}isoquinoline-1,3(2H,4H) -dione;

(4Z)-4-{[(3-Hydroxy-4,5-dimethoxybenzyl)amino)methylene}-6-thien-3-ylisoquinoline-1,3(2H,4H-dione;

(4Z)-4-{[(3-Hydroxy-4,5-dimethoxybenzyl)amino)methylene}-6-phenylisoquinoline-1,3(2H,4H-dione;

(4Z)-6-(3-Furyl)-4-{[(3-hydroxy-4,5-dimethoxybenzyl)amino)methylene}isoquinoline-1,3(2H,4H-dione;

(4Z)-4-{[(3-Hydroxy-4-methoxybenzyl)amino]methylene}-6-thien-3-ylisoquinoline-1,3(2H,4H)-dione (5b);

(4Z)-6-Iodo-4-{[(3-hydroxy-4,5-dimethoxybenzyl)amino)methylene}isoquinoline-1,3(2H,4H)-dione;

4-[(3-Hydroxy-4-methoxy-benzylamino)-methylene]-6-methoxy-4H-isoquinoline-1,3-dione;

6-Methoxy-4-[(4-piperidin-1-ylmethyl-phenylamino)-methylene]-4H-isoquinoline-1,3-dione;

(4Z)-6-(3-Furyl)-4-{[(3-hydroxy-4-methoxybenzyl)amino)methylene}isoquinoline-1,3(2H,4H-dione;

(4Z)-6-(3-Furyl)-4-({[4-piperidin-1-ylmethyl)phenyl]amino}methylene)}isoquinoline-1,3(2H,4H)-dione;

(4Z)-6-Bromo-4-(3,5-dibromo-4-hydroxybenzylidene)isoquinoline-1,3(2H,4H)-dione;

(4Z)-6-Phenyl-4-({[4-piperidin-1-ylmethyl)phenyl]amino}methylene)}isoquinoline-1,3(2H,4H)-dione;

(4Z)-6-(3-Hydroxyphenyl)-4-({[4-(piperidin-1-ylmethyl)phenyl]amino}methylene)}isoquinoline-1,3(2H,4H)-dione;

3-[(4Z)-1,3-Dioxo-4-({[4-(piperidin-1-ylmethyl)phenyl]amino}methylene)-1,2,3,4-tetrahydroisoquinoline-6-yl]thiophene-2-carbaldehyde;

(4Z)-4-{[(3-Hydroxy-4-methoxybenzyl)amino]methylene}isoquinoline-1,3(2H,4H)-dione (3d);

5-({[(Z)-(6-Iodo-1,3-dioxo-2,3-dihydroisoquinolin-4(1H)-ylidene)methyl]amino}methyl)-2-methoxyphenyl diethylcarbamate;

(4Z)-6-(4-Phenoxyphenyl)-4-{[(3-hydroxy-4,5-dimethoxybenzyl)amino]methylene}isoquinoline-1,3(2H,4H)-dione;

(4Z)-6-(4-Phenoxyphenyl)-4-({[4-(piperidin-1-ylmethyl)phenyl]amino}methylene)}isoquinoline-1,3(2H,4H)-dione;

(4Z)-4-({[4-Piperidin-1-ylmethyl)phenyl]amino}methylene)-6-pyridin-3-ylisoquinoline-1,3(2H,4H)-dione;

(4Z)-6-(4-Hydroxyphenyl)-4-({[4-(piperidin-1-ylmethyl)phenyl]amino}methylene)}isoquinoline-1,3(2H,4H)-dione;

(4Z)-4-({[4-(Piperidin-1-ylmethyl)phenyl]amino}methylene)-6-thien-3-ylisoquinoline-1,3(2H,4H)-dione;

(4Z)-6-Bromo-4-{[4-(2-morpholin-4-ylethyl)piperazin-1-yl]methylene}isoquinoline-1,3(2H,4H)-dione;

(4Z)-6-Bromo-4-({4-[2-(dimethylamino)ethyl]piperazin-1-yl}methylene)isoquinoline-1,3(2H,4H)-dione;

(4Z)-4-({[4-(4-Methylpiperazin-1-yl)phenyl]amino}methylene)-6-thien-3-ylisoquinoline-1,3(2H,4H)-dione;

(4Z)-4-({[4-(4-Methylpiperazin-1-yl)phenyl]amino}methylene)-6-thien-3-ylisoquinoline-1,3(2H,4H)-dione;

(4Z)-4-{[(1,3-Benzodioxol-5-ylmethyl)amino]methylene}-6-bromoisoquinoline-1,3(2H,4H)-dione;

(4Z)-1,3-Dioxo-4-({[4-(piperidin-1-ylmethyl)phenyl]amino}methylene)1,2,3,4-tetrahydroisoquinoline-6-carbonitrile;

(4Z)-6-(4-Chlorophenyl)-4-({[4-(piperidin-1-ylmethyl)phenyl]amino}methylene)isoquinoline-1,3(2H,4H)-dione;

(4Z)-6-[(1E)-5-Chloropent-1-enyl]-4-({[4-(piperidin-1-ylmethyl)phenyl]amino}methylene)isoquinoline-1,3(2H,4H)-dione;

(4Z)-6-(4-Chlorophenyl)-4-{[(3-hydroxy-4,5-dimethoxybenzyl)amino]methylene}isoquinoline-1,3(2H,4H)-dione;

(4Z)-6-(4-methoxyphenyl)-4-({[4-(4-methylpiperazin-1-yl)phenyl]amino}methylene)-isoquinoline-1,3(2H,4H)-dione 4-[(4Z)-4-({[4-(4-Methylpiperazin-1-yl)phenyl]amino}methylene)-1,3-dioxo-1,2,3,4-tetra-hydroisoquinolin-6-yl]benzaldehyde;

(4Z)-6-(4-Methoxyphenyl)-4-({[4-(piperidin-1-ylmethyl)phenyl]amino}methylene)-isoquinoline-1,3(2H,4H)-dione;

(4Z)-6-(3-Methoxyphenyl)-4-({[4-(piperidin-1-ylmethyl)phenyl]amino}methylene)-isoquinoline-1,3(2H,4H)-dione;

(4Z)-6-Piperidin-1-yl-4-({[4-(piperidin-1-ylmethyl)phenyl]amino}methylene)isoquinoline-1,3(2H,4H)-dione;

(4Z)-6-Piperidin-1-yl-4-({[4-(methylPiperzin-1-yl)phenyl]amino}methylene)isoquinoline-1,3(2H,4H)-dione;

(4Z)-6-Morpholin-4-yl-4-({[4-(piperidin-1-ylmethyl)phenyl]amino}methylene)isoquinoline-1,3(2H,4H)-dione;

(4Z)-6-[(2R)-2-(Methoxymethyl)pyrrolidin-1-yl]-4-({[4-(piperidin-1-ylmethyl)phenyl]amino}methylene)isoquinoline-1,3(2H,4H)-dione;

(4Z)-4-{[(4-Amino-3-hydroxybenzyl)amino]methylene-6-iodoisoquinoline-1,3(2H,4H)-dione;

(4Z)-6-[(4-Methyl-piperazin-1-yl]-4-({[4-(piperidin-1-ylmethyl)phenyl]amino}methylene)isoquinoline-1,3(2H,4H)-dione;

5-[(4Z)-4-({[4-(4-Methylpiperazin-1-yl)phenyl]amino}methylene)-1,3-dioxo-1,2,3,4-tetrahydroisoquinolin-6-yl]-2-furaldehyde;

4Z)-6-Iodo-4-({[4-(pyrrolidin-1-ylmethyl)phenyl}amino)methyleneisoquinolin-1,3(2H,4H)-dione;

(4Z)-6-(4-Fluorophenyl)-4-({[4-(pyrrolidin-1-ylmethyl)phenyl]amino}methylene)isoquinoline-1,3(2H,4H)-dione;

(4Z)-6-Anilino-4-({[4-(piperidin-1-ylmethyl)phenyl]amino}methylene)isoquinoline-1,3(2H,4H)-dione;

(4Z)-6-Bromo-4-{[(1H-indol-6-ylmethyl)amino]methylene}isoquinoline-1,3(2H,4H)-dione;

(4Z)-6-Bromo-4-{[(3-hydroxy-4-propoxybenzyl)amino]methylene}isoquinoline-1,3(2H,4H)-dione;

(3Z)-3-(1-{[4-(4-Methylpiperazin-1-yl)phenyl]
  amino}ethylidene)piperidine-2,6-dione;
(4Z)-4-{[(4-Amino-3-hydroxybenzyl)amino]methylene}-
  6-(4 fluorophenyl)isoquinoline-1,3(2H,4H)-dione;
(4Z)-7-Bromo-4-{[(3-hydroxy-4-methoxybenzyl)amino]
  methylene}isoquinoline-1,3(2H,4H)-dione;
(4Z)-4-{[(3-Hydroxy-4-methoxybenzyl)amino]methylene}-
  6-(1H-pyrazol-4-yl)isoquinoline-1,3(2H,4H)-dione;
(4Z)-6-Bromo-4-{[(3-hydroxy-4-isopropoxybenzyl)amino]
  methylene}isoquinoline-1,3(2H,4H)-dione;
(4Z)-6-Iodo-4-[({4-[(2-methylpyrrolidin-1-yl)methyl]
  phenyl}amino)methylene]isoquinoline-1,3(2H,4H)-dione;
(4Z)-6-Bromo-4-({[3-hydroxy-4-(2-hydroxyethoxy)benzyl]
  amino}methylene)isoquinoline-1,3(2H,4H)-dione;
(3Z)-3-{1-[(3-hydroxy-4-methoxybenzyl)amino]eth-
  ylidene}-4-phenylpiperidine-2,6-dione;
2-(Acetylamino)-5-({[(Z)-(6-bromo-1,3-dioxo-2,3-dihy-
  droisoquinolin-4(1H)-'ylidene)methyl]amino}methyl)
  phenyl acetate;
N-[4-({[(Z)-(6-Bromo-1,3-dioxo-2,3-dihydroisoquinolin-4
  (1H)-ylidene)methyl]amino}methyl)-2-hydroxyphenyl]
  acetamide;
(4Z)-6-Bromo-4-({[3-hydroxy-4-(2-pyrrolidin-1-ylethoxy)
  benzyl]amino}methylene)isoquinoline-1,3(2H,4H)-dione;
6-Bromo-4-[(4-piperidin-1-ylmethyl-phenyl)-hydrazono]-
  4H-isoquinoline-1,3-dione Hydrochloride;
N-[4-({[(Z)-(1,3-Dioxo-6-thien-3-yl-2,3-dihydroisoquino-
  lin-4(1H)-'ylidene)methyl]amino}methyl)-2-hydrox-
  yphenyl]acetamide;
2-(Acetylamino)-5-({[(Z)-(6-iodo-1,3-dioxo-2,3-dihy-
  droisoquinolin-4(1H)-ylidene)methyl]amino}methyl)
  phenyl acetate;
(4Z)-4-({[4-(Benzyloxy)-3-hydroxybenzyl]
  amino}methylene)-6-bromoisoquinoline-1,3(2H,4H)-dione;
(4Z)-6-Bromo-4-{[(4-butoxy-3-hydroxybenzyl)amino]
  methylene}isoquinoline-1,3(2H,4H)-dione;
(4Z)-4-({[4-(Allyloxy)-3-hydroxybenzyl]
  amino}methylene)-6-bromoisoquinoline-1,3(2H,4H)-dione;
(4Z)-6-Bromo-4-({[4-(hexyloxy)-3-hydroxybenzyl]
  amino}methylene)isoquinoline-1,3(2H,4H)-dione;
N-[2-Hydroxy-4-({[[(Z)-(6-iodo-1,3-dioxo-2,3-dihydroiso-
  quinolin-4(1H)-'ylidene)methyl]amino}methyl)phenyl]
  acetamide;
4-[(4-Piperidin-1-ylmethyl-phenyl)-hydrazono]-6-thiophen-
  3-yl-4H-isoquinoline-1,3-dione;
4-(4-{[4-(4-Methyl-piperazin-1-yl)-phenylamino]-methyl-
  ene}-1,3-dioxo-1,2,3,4-tetrahydro-isoquinolin-6-yl)-ben-
  zonitrile;
6-(3-Fluoro-phenyl)-4-{[4-(4-methyl-piperazin-1-yl)-phe-
  nylamino]-methylene}-4H-isoquinoline-1,3-dione;
4-{[4-(4-Methyl-piperazin-1-yl)-phenylamino]-methyl-
  ene}-6-(2-morpholin-4-yl-ethoxy)-4H-isoquinoline-1,3-
  dione;
6-Furan-3-yl-4-[(4-piperidin-1-ylmethyl-phenyl)-hydra-
  zono]-4H-isoquinoline-1,3-dione;
(4Z)-4-{[(4-Methyl-3-hydroxybenzyl)amino]methylene)-6-
  iodoisoquinoline-'1,3(2H,4H)-dione;
(4Z)-6-Bromo-4-({[3-hydroxy-4-(2-ethoxyethoxy)benzyl]
  amino}methylene)isoquinoline-1,3(2H,4H)-dione;
(4Z)-4-[({4-[2-(Benzyloxy)ethoxy]-4-
  hydroxybenzyl}amino)methylene]-6-bromoisoquinoline-
  1,3(2H,4H)-dione;
4-[(3-Hydroxy-4-methoxy-benzylamino)-methylene]-1,4-
  dihydro-2H-isoquinoline-3-one;
(4Z)-4-({[4-(4-Methylpiperazin-1-yl)phenyl]
  amino}methylene)-6-[3-(tetrahydro-2H-pyran-2-yloxy)
  prop-1-ynyl]isoquinoline-1,3(2H,4H)-dione (7);
4-[(4-Piperidin-1-ylmethyl-phenylamino)-methylene]-1,4-
  dihydro-2H-isoquinolin-3-one;
(4Z)-6-Bromo-4-{[(3-hydroxy-4-methoxybenzyl)(methyl)
  amino]methylene}isoquinoline-1,3(2H,4H)-dione;
6-Bromo-4-{[4-(1H-imidazol-4-yl)-phenylamino]-methyl-
  ene}-4H-isoquinolin-1,3-dione;
(4Z)-4-{[(4-Chloro-3-hydroxybenzyl)amino]methylene}-6-
  iodoisoquinoline-1,3(2H,4H)-dione;
(4Z)-6-Bromo-4-{[(4-ethoxy-3-hydroxybenzyl)amino]
  methylene}isoquinoline-1,3(2H,4H)-dione;
(4Z)-1,2-Diacetyl-4-{[(3-hydroxy-4-methoxybenzyl)
  amino]methylene}-1,4-dihydrocinnolin-3(2H)-one;
6-Furan-2-yl-4-[(4-pyrrolidin-1-ylmethyl-phenylamino)-
  methylene]-4H-isoquinoline-1,3-dione;
4-{[4-(2-Pyrrolidin-1-yl-ethyl)-phenylamino]-methylene}-
  1,4-dihydro-2H-isoquinolin-3-one;
(4Z)-4-({[4-(4-Methylpiperazin-1-yl)phenyl]
  amino}methylene)-6-(phenylethynyl)-isoquinoline-1,3
  (2H,4H)-dione;
(4Z)-6-[(4-Methoxyphenyl)ethynyl]-4-({[4-(4-methylpiper-
  azin-1-yl)phenyl]amino}-methylene)isoquinoline-1,3
  (2H,4H)-dione;
(4Z)-6-Bromo-4-{[(2,5-dihydroxybenzyl)amino]
  methylene}isoquinoline-1,3(2H,4H)-dione;
(4Z)-6-Bromo-4-{[(2-hydroxybenzyl)amino]
  methylene}isoquinoline-1,3(2H,4H)-dione;
(4Z)}-6-Bromo-4-{[(2,3,4-trihydroxybenzyl)amino]
  methylene}isoquinoline-1,3(2H,4H)-dione;
6-Bromo-4-{[4-(2-pyrrolidin-1-yl-ethyl)-phenylamino]-me-
  thylene}-4H-isoquinolin-1,3-dione;
(4Z)-6-(3-Methoxyprop-1-ynyl)-4-({[4-(4-methylpiperazin-
  1-yl)phenyl]amino}-methylene)isoquinoline-1,3(2H,
  4H)-dione;
(4Z)-4-{[(3-Hydroxy-4-propoxybenzyl)amino]methylene}-
  6-iodoisoquinoline-1,3(2H,4H)-dione;
(4Z)-4-{[(3-Hydroxy-4-propoxybenzyl)amino]methylene}-
  6-iodoisoquinoline-1,3(2H,4H)-dione;
(Z)-Diethyl 5-(((6-bromo-1,3-dioxo-2,3-dihydroisoquino-
  lin-4(1H)-ylidene)methylamino)methyl)benzo[d][1,3]di-
  oxole-2,2-dicarboxylate;
(4Z)-6-Bromo-4-{[(4-difluoromethoxy-3-hydroxybenzyl)
  amino)methylene}isoquinoline-1,3(2H,4-dione;
(4Z)-6-Bromo-4-{[(3-fluoro-4-methoxybenzyl)amino]
  methylene}isoquinoline-1,3(2H,4H)-dione;
(4Z)-6-(2,2'-Bithien-5-yl)-4-({[4-(4-methylpiperazin-1-yl)
  phenyl]amino}methylene)-isoquinoline-1,3(2H,4H)-di-
  one;
(4Z)-4-{[(3-Hydroxy-4-propoxybenzyl)amino]methylene}-
  6-thiene-3-ylisoquinoline-1,3(2H,4H)-dione;
5-({[(Z)-(6-Bromo-1,3-dioxo-2,3-dihydroisoquinolin-4
  (1H)-'ylidene)methyl]amino}methyl)-2-[(methoxycarbo-
  nyl)amino]phenyl methyl carbonate;
5-({[(Z)-(6-Bromo-1,3-dioxo-2,3-dihydroisoquinolin-4
  (1H)-'cyclopropanecarboxylate 'ylidene)methyl]
  amino}methyl)-2-[(cyclopropylcarbonyl)amino]phenyl;
N-[(4Z)-4-({[4-(4-Methylpiperazin-1-yl)phenyl]
  amino}methylene)-1,3-dioxo-1,2,3,4-tetrahydroisoquino-
  lin-6-yl]acetamide;
(4Z)-4-({[4-(4-Methylpiperazin-1-yl)phenyl]
  amino}methylene)-6-(thien-3-ylethynyl)-isoquinoline-1,
  3(2H,4H)-dione;

1,2,3,4-Tetrahydroisoquinolin-6-yl]benzenesulfonamide'N-[(4Z)-4-({[4-(4-methylpiperazin-1-yl)phenyl]amino}methylene)-1,3-dioxo;
(4Z)-6-Bromo-4-({[1-(3-hydroxy-4-methoxyphenyl)ethyl]amino}methylene)isoquinoline-1,3(2H,4H)-dione;
5-({[(Z)-(6-Bromo-1,3-dioxo-2,3-dihydroisoquinolin-4(1H)-ylidene)methyl]amino}-methyl)-2-propoxyphenyl propionate;
5-({[(Z)-(6-Bromo-1,3-dioxo-2,3-dihydroisoquinolin-4(1H)-ylidene)methyl]amino}-methyl)-2-propoxyphenyl methyl carbonate;
(4Z)-6-(4-Fluorophenyl)-4-{[(3-hydroxy-4-propoxybenzyl)amino]methylene}-isoquinoline-1,3(2H,4H)-dione;
(4Z)-6-(3-Fluorophenyl)-4-{[(3-hydroxy-4-propoxybenzyl)amino]methylene}-isoquinoline-1,3(2H,4H)-dione;
(4Z)-6-(3,4-Difluorophenyl)-4-{[(3-hydroxy-4-propoxybenzyl)amino]methylene}-isoquinoline-1,3(2H,4H)-dione;
(4Z)}-6-Bromo-4-{[(3-hydroxy-5-propoxybenzyl)amino]methylene isoquinoline-1,3(2H,4H)-dione;
N-((4Z)-4-{[(3-Hydroxy-4-methoxybenzyl)amino]methylene}-1,3-dioxo-1,2,3,4-'tetrahydroisoquinolin-6-yl]benzenesulfonamide;
N-((4Z)-4-{[(3-Hydroxy-4-propoxybenzyl)amino]methylene}-1,3-dioxo-1,2,3,4-1,2,3,4-tetrahydroisoquinolin-6-yl]-2-thien-2-ylacetamide14;
1,2,3,4-Tetrahydroisoquinolin-6-yl]-2-thien-2-ylacetamide 'N-[(4Z)-4-({[4-(4-methylpiperazin-1-yl)phenyl]amino}methylene)-1,3-dioxo;
(4Z)-4-({[4-(Difluoromethoxy)-3-hydroxybenzyl]amino}methylene)-6-(3-furyl)isoquinoline-1,3(2H,4H)-dione;
(4Z)-4-({[4-(Difluoromethoxy)-3-hydroxybenzyl]amino}methylene)-6-thien-3-ylisoquinoline-1,3(2H,4H)-dione;
4Z)-6-Bromo-4-({[4-(3,5-dimethylpiperazin-1-yl)phenyl]amino}methylene)isoquinoline-1,3(2H,4H)-dione;
N'-[(Z)-(6-Bromo-1,3-dioxo-2,3-dihydroisoquinolin-4(1H)-ylidene)methyl]-3-hydroxy-4-methoxybenzohydrazide;
N-(4-Methylpiperazin-1-yl)-N'-[(4Z)-4-({[4-(4-methylpiperazin-1-'yl)phenyl]amino}methylene)-1,3-dioxo-1,2,3,4-tetrahydroisoquinolin-6-yl]urea;
(4Z)-4-{[(3-Amino-4,5-dihydroxybenzyl)amino]methylene}-6-bromoisoquinoline-1,3(2H,4H)-dione;
(4Z)-4-({[4-(3,5-Dimethylpiperazin-1-yl)phenyl]amino}methylene)-6-(4-fluorophenyl)-isoquinoline-1,3(2H,4H)-dione;
(4Z)-4-({[4-(3,5-Dimethylpiperazin-1-yl)phenyl]amino}methylene)-6-thien-3-ylisoquinoline-1,3(2H,4H)-dione;
(4Z)-4-({[4-(3,5-Dimethylpiperazin-1-yl)phenyl]amino}methylene)-6-(3-furyl)iso-quinoline-1,3(2H,4H)-dione;
(4Z)-6-(4-Fluorophenyl)-4-{[3-hydroxy-4-methoxybenzyl)amino]methylene}iso-quinoline-1,3(2H,4H)-dione;
(4Z)-6-(3-Fluorophenyl)-4-{[3-hydroxy-4-methoxybenzyl)amino]methylene}iso-quinoline-1,3(2H,4H)-dione;
(4Z)-6-Bromo-4-{[(3,5-dihydroxy-4-methoxybenzyl)amino]methylene}isoquinoline-1,3(2H,4H)-dione;
(4Z)-6-Bromo-4-{[(4-hydroxybutyl)amino]methylene}isoquinoline-1,3(2H,4H)-dione;
(4Z)-6-Bromo-4-{[(4-hydroxy-4,5-dipropoxybenzyl)amino]methylene}isoquinoline-1,3(2H,4H)-dione;
N-[5-({[(Z)-(6-Bromo-1,3-dioxo-2,3-dihydroisoquinolin-4(1H)-ylidene)methyl]-2,3-dihydroxyphenyl]acetamide;
(4Z)-6-Bromo-4-[(2,3-dihydro-1H-indol-5-ylamino)methylene]isoquinoline-1,3(2H,4H)-dione;

N-(4-{[(Z)-(6-Bromo-1,3-dioxo-2,3-dihydroisoquinolin-4(1H)-'ylidene)methyl]amino}phenyl)-4-methylpiperazine-1-carboxamide;
(4Z)-4-({[4-(3,5-Dimethylpiperazin-1-yl)phenyl]amino}methylene)-6-iodoisoquinoline-1,3(2H,4H)-dione (30);
N-(4-{[(Z)-(6-Bromo-1,3-dioxo-2,3-dihydroisoquinolin-4(1H)-'ylidene)methyl]amino}phenyl)-N'-(4-methylpiperazin-1-yl)urea;
N-[4-({[(Z)-(6-Bromo-1,3-dioxo-2,3-dihydroisoquinolin-4(1H)-'ylidene)methyl]amino}methyl)-2-hydroxyphenyl]-2,2,2-trifluoroacetamide;
(4Z)-6-Bromo-4-({[4-(cyclopropylmethoxy)-3-'hydroxybenzyl]amino}methylene)isoquinoline-1,3(2H,4H)-dione;
(4Z)-6-Bromo-2-(hydroxymethyl)-4-({[4-(4-methylpiperazin-1-yl)phenyl]amino}methylene)isoquinoline-1,3(2H,4H)-dione;
6-Iodo-4-{[4-(5-methyl-2,5-diaza-bicyclo[2.2.1]hept-2-yl)-phenylamino]-methylene}-4H-isoquinoline-1,3-dione;
(4Z)-6-Bromo-4-({[(2-methoxypyridin-4-yl)methyl]amino}methylene)isoquinoline-1,3(2H,4H)-dione;
(4Z)-6-Bromo-4-({[4-(4-methylpiperazin-1-yl)phenyl]amino}methylene)-1,4-dihydroisoquinolin-3(2H)-one;
(4Z)-6-Bromo-4-({[(7-hydroxy-2,2-dimethyl-1,3-benzodioxol-5-yl)methyl]amino}methylene)isoquinoline-1,3(2H,4H)-dione;
(4Z)-6-Bromo-4-({[(2-oxo-1,2-dihydropyridin-4-yl)methyl]amino}methylene)isoquinoline-1,3(2H,4H)-dione;
(4Z)-6-(2,5-Dimethyl-1H-pyrrol-1-yl)-4-({[4-(4-methylpiperazin-1-'yl)phenyl]amino}methylene)isoquinoline-1,3(2H,4H)-dione;
(4Z)-4-{[(4-Amino-3-hydroxybenzyl)amino]methylene}-6-bromoisoquinoline-1,3(2H,4H)-dione;
PEG5000thio-acetic acid 5-{[(6-bromo-1,3-dioxo-2,3-dihydro-1H-isoquinolin-4-ylidenemethyl)-amino]-methyl}-2-propoxy-phenyl ester;
(4Z)-6-Bromo-4-{[(4-{[2-(dimethylamino)ethyl]thio}phenyl)amino]methylene}isoquinoline-1,3(2H,4H)-dione;
2-Hydroxy-4-[(3-hydroxy-4-propoxy-benzylamino)-methylene]-4H-isoquinoline-1,3-dione;
(4Z)-6-Bromo-4-[({4-[[2-(dimethylamino)ethyl](methyl)amino]phenyl}-amino)methylene]isoquinoline-1,3(2H,4H)-dione;
(4Z)-6-Bromo-4-({[4-(4-methyl-1,4-diazepan-1-yl)phenyl]amino}methylene)isoquinoline-1,3(2H,4H)-dione;
(4Z)-6-Iodo-4-[({4-[(2S,5R)-2,4,5-trimethylpiperazin-1-yl]phenyl}amino)methylene]-isoquinoline-1,3(2H,4H)-dione;
(4Z)-6-Iodo-4-[({4-[(3R,5S)-3,4,5-trimethylpiperazin-1-yl]phenyl}amino)methylene]-isoquinoline-1,3(2H,4H)-dione;
(4Z)-4-({[4-(3,5-Dimethylpiperazin-1-yl)phenyl]amino}methylene)-6-nitroisoquinoline-1,3(2H,4H)-dione;
(4Z)-6-(3-Furyl)-4-({[4-(4-methylpiperazin-1-yl)phenyl]amino}methylene)isoquinoline-1,3(2H,4H)-dione (42);
(4Z)-6-Iodo-4-({[6-(4-methylpiperazin-1-yl)pyridin-3-'yl]amino}methylene)isoquinoline-1,3(2H,4H)-dione;
(4Z)-6-Bromo-4-[({4-[(2S,5R)-2,4,5-trimethylpiperazin-1-yl]phenyl}amino)methylene]-isoquinoline-1,3(2H,4H)-dione;
(4Z)-6-Iodo-4-({[4-(1-methylpiperidin-4-yl)phenyl]amino}methylene)isoquinoline-1,3(2H,4H)-dione;

(4Z)-6-Bromo-4-[({4-[(3R,5S)-3,4,5-trimethylpiperazin-1-yl]phenyl}amino)methylene]-isoquinoline-1,3(2H,4H)-dione;

(4Z)-6-(3-Furyl)-4-[({4-[(3R,5S)-3,4,5-trimethylpiperazin-1-yl]phenyl}amino)-methylene]isoquinoline-1,3(2H,4H)-dione;

6-Bromo-7-methoxy-4-{[4-(4-methyl-piperazin-1-yl)-phenylamino]-methylene}-4H-isoquinoline-1,3-dione;

(4Z)-6-Bromo-4-{[(4-{[2-(dimethylamino)ethyl]sulfonyl}phenyl)amino]methylene}isoquinoline-1,3(2H,4H)-dione;

(4Z)-6-Bromo-4-[({4-[(2-hydroxyethyl)(methyl)amino]phenyl}amino)methylene]isoquinoline-1,3(2H,4H)-dione;

(4Z)-6-Bromo-4-[({4-[methyl(1-methylpyrrolidin-3-yl)amino]phenyl}amino)methylene]isoquinoline-1,3(2H,4H)-dione;

6-Bromo-4-[(3-hydroxy-4-propoxy-benzylamino)-methylene]-7-methoxy-4H-isoquinoline-1,3-dione;

(4Z)-6-Iodo-4-({[4-(pyridin-2-ylmethoxy)phenyl]amin'methylene)isoquinoline1,3(2H,4H)-dione;

(4Z)-4-({[4-(3,4-Dimethylpiperazin-1-yl)phenyl]amino}methylene)-6-iodoisoquinoline-1,3(2H,4H)-dione;

(4Z)-6-(3-Furyl)-4-({[6-(4-methylpiperazin-1-yl)pyridin-3-'yl]amino}methylene)isoquinoline-1,3(2H,4H)-dione;

(4Z)-6-Bromo-4-({[6-(4-methylpiperazin-1-yl)pyridin-3-'yl]amino}methylene)isoquinoline-1,3(2H,4H)-dione;

(4Z)-6-(4-Fluorophenyl)-4-({[4-(piperidin-1-'ylmethyl)phenyl]amino}methylene)isoquinoline-1,3(2H,4H)-dione;

6-Bromo-7-methoxy-4-[(4-piperidin-1-ylmethyl-phenylamino)-methylene]-4H-isoquinoline-1,3-dione;

6-(4-Fluoro-phenyl)-7-methoxy-4-[(4-piperidin-1-ylmethyl-phenylamino)-methylene]-4H-isoquinoline-1,3-dione;

6-Furan-3-yl-7-methoxy-4-{[4-(4-methyl-piperazin-1-yl)-phenylamino]-methylene}-4H-isoquinoline-1,3-dione;

(4Z)-6-Bromo-4-[({4-[methyl(2-pyrrolidin-1-ylethyl)amino]phenyl}amino)methylene]isoquinoline-1,3(2H,4H)-dione;

(4Z)-6-Bromo-4-[({4-[methyl(2-piperidin-1-ylethyl)amino]phenyl}amino)methylene]isoquinoline-1,3(2H,4H)-dione;

(4Z)-6-Bromo-4-[({4-[{2-[butyl(methyl)amino]ethyl}(methyl)amino]phenyl}amino)methylene]isoquinoline-1,3(2H,4H)-dione;

(4Z)-6-Bromo-4-[({4-[2-(dimethylamino)ethoxy]phenyl}amino)methylene]isoquinoline-1,3(2H,4H)-dione;

(4Z)-6-Bromo-4-{[(2-methyl-2,3-dihydro-1H-isoindol-5-yl)amino]methylene}isoquinoline-1,3(2H,4H)-dione;

(4Z)-6-Bromo-4-({[4-(1H-imidazol-1-yl)phenyl]amino}methylene)isoquinoline-1,3(2H,4H)-dione;

(4Z)-6-Bromo-4-{[(4-{methyl[2-(4-methylpiperazin-1-yl)ethyl]amino}phenyl)amino]methylene}isoquinoline-1,3(2H,4H)-dione;

(4Z)-6-Bromo-4-[({4-[methyl(2-morpholin-4-ylethyl)amino]phenyl}amino)methylene]isoquinoline-1,3(2H,4H)-dione;

(4Z)-6-(4-Fluorophenyl)-4-({[4-(4-methylpiperazin-1-yl)phenyl]amino}methylene)-isoquinoline-1,3(2H,4H)-dione;

(4Z)-6-Iodo-4-{[(4-{[(3R)-3-methoxypyrrolidin-1-yl]methyl}phenyl)amino]methylene}isoquinoline-1,3(2H,4H)-dione;

(4Z)-6-(4-Fluorophenyl)-4-{[(4-{[(3S)-3-methoxypyrrolidin-1-yl]methyl}phenyl)amino]methylene}isoquinoline-1,3(2H,4H)-dione;

(4Z)-6-Bromo-4-{[(4-{[(3R)-3-methoxypyrrolidin-1-yl]methyl}phenyl)amino]methylene}isoquinoline-1,3(2H,4H)-dione;

(4Z)-6-Iodo-4-{[(4-difluoromethoxy-3-hydroxybenzyl)amino)methylene}isoquinoline-1,3(2H,4-dione;

6-({[[(Z)-(6-Bromo-1,3-dioxo-2,3-dihydroisoquinolin-4(1H)-ylidene)methyl]amino}methyl)-2,2-dimethyl-1,3-benzodioxol-4-yl acetate;

6-({[[(Z)-(6-Bromo-1,3-dioxo-2,3-dihydroisoquinolin-4(1H)-ylidene)methyl]amino}methyl)-2,2-dimethyl-1,3-benzodioxol-4-yl cyclopropanecarboxylate;

(4Z)-6-Bromo-4-[({4-[3-(dimethylamino)propyl]phenyl}amino)methylene]isoquinoline-1,3(2H,4H)-dione;

(4Z)-6-Bromo-4-[(quinolin-6-ylamino)methylene]isoquinoline-1,3(2H,4H)-dione;

(4Z)-6-Iodo-4-[(quinolin-6-ylamino)methylene]isoquinoline-1,3(2H,4H)-dione;

(4Z)-4-({[4-(1H-Imidazol-1-ylmethyl)phenyl]amino}methylene)-6-iodoisoquinoline-1,3(2H,4H)-dione;

(4Z)-6-Bromo-4-[({4-[3-(methoxyamino)propyl]phenyl}amino)methylene]isoquinoline-1,3(2H,4H)-dione;

(4Z)-6-Bromo-4-[({4-[[3-(dimethylamino)propyl](methyl)amino]phenyl}amino)methylene]isoquinoline-1,3(2H,4H)-dione;

(4Z)-6-Bromo-4-[({4-[(1-methylpyrrolidin-3-yl)oxy]phenyl}amino)methylene]isoquinoline-1,3(2H,4H)-dione;

2-Amino-2-{4-[(6-bromo-1,3-dioxo-2,3-dihydro-1H-isoquinolin-4-ylidenemethyl)-amino]-phenyl}-propionic acid;

4-[(3-Hydroxy-4-propoxy-benzylamino)-methylene]-6-pyrrol-1-yl-4H-isoquinoline-1,3-dione;

4-{[3-(4-Methyl-piperazin-1-yl)-propylamino]-methylene}-6-pyrrol-1-yl-4H-isoquinoline-1,3-dione;

4-{[(Z)-(6-Bromo-1,3-dioxo-2,3-dihydroisoquinolin-4(1H)-ylidene)methyl]amino}-N',N'-dimethylbenzohydrazide;

(4Z)-6-Bromo-4-({[4-(1,3-thiazolidin-3-ylmethyl)phenyl]amino}methylene)isoquinoline-1,3(2H,4H)-dione;

(4Z)-4-({[4-(Pyrrolidin-1-ylmethyl)phenyl]amino}methylene)-6-[4-(trifluoromethyl)phenyl]isoquinoline-1,3(2H,4H)-dione;

2-(4-{[(Z)-(6-Bromo-1,3-dioxo-2,3-dihydroisoquinolin-4(1H)-ylidene)methyl]amino}phenyl)-N',N'-dimethylacetohydrazide;

Diethyl [(4Z)-4-({[4-(4-methylpiperazin-1-yl)phenyl]amino}methylene)-1,3-dioxo-1,2,3,4-tetrahydroisoquinolin-6-yl]phosphonate;

(4Z)-6-Iodo-4-{[(4-{[(2S)-2-(methoxymethyl)pyrrolidin-1-yl]methyl}phenyl)amino]methylene}isoquinoline-1,3(2H,4H)-dione;

(4Z)-6-Bromo-4-({[4-(morpholin-4-ylmethyl)phenyl]amino}methylene)isoquinoline-1,3(2H,4H)-dione;

(4Z)-6-Bromo-4-[({4-[(2-methylpyrrolidin-1-yl)methyl]phenyl}amino)methylene]-isoquinoline-1,3(2H,4H)-dione (60);

(4Z)-6-Bromo-4-({[3-fluoro-4-(4-methylpiperazin-1-yl)phenyl]amino}methylene)-isoquinoline-1,3(2H,4H)-dione;

(4Z)-6-(4-Fluorophenyl)-4-[({4-[(2-methylpyrrolidin-1-yl)methyl]phenyl}amino)-methylene]isoquinoline-1,3(2H,4H)-dione;

(4Z)-4-({[3-Fluoro-4-(4-methylpiperazin-1-yl)phenyl]amino}methylene)-6-(4-fluorophenyl)isoquinoline-1,3(2H,4H)-dione;
(4Z)-6-(3-Furyl)-4-[({4-[(2-methylpyrrolidin-1-yl)methyl]phenyl}amino)methylene]-isoquinoline-1,3(2H,4H)-dione;
PEG5000thio-acetic acid 5-{[(6-iodo-1,3-dioxo-2,3-dihydro-1H-isoquinolin-4-ylidenemethyl)-amino]-methyl}-2-propoxy-phenyl ester;
5-({[(Z)-(6-Iodo-1,3-dioxo-2,3-dihydroisoquinolin-4(1H)-ylidene)methyl]amino}methyl)-2-propoxyphenyl chloroacetate;
tert-Butyl 4-(4-{[(Z)-(6-bromo-1,3-dioxo-2,3-dihydroisoquinolin-4(1H)-ylidene)methyl]amino}phenyl)piperazine-1-carboxylate;
(4Z)-4-({[3-Fluoro-4-(4-methylpiperazin-1-yl)phenyl]amino}methylene)-6-iodoisoquinoline-1,3(2H,4H)-dione;
(4Z)-6-Iodo-4-({[4-(morpholin-4-ylmethyl)phenyl]amino}methylene)isoquinoline-1,3(2H,4H)-dione;
(4Z)-4-({[3-Fluoro-4-(4-methylpiperazin-1-yl)phenyl]amino}methylene)-6-(3-furyl)isoquinoline-1,3(2H,4H)-dione;
(4Z)-4-({[4-(4-Methylpiperazin-1-yl)phenyl]amino}methylene)-6-[4-(trifluoromethoxy)phenyl]isoquinoline-1,3(2H,4H)-dione;
(4Z)-6-(4-Fluorophenyl)-4-{[(4-{[(2S)-2-(methoxymethyl)pyrrolidin-1-yl]methyl}phenyl)amino]methylene}isoquinoline-1,3(2H,4H)-dione;
(4Z)-6-(4-Isopropoxyphenyl)-4-{[(4-{[(2R)-2-(methoxymethyl)pyrrolidin-1-yl]methyl}phenyl)amino]methylene}isoquinoline-1,3(2H,4H)-dione;
N-[4-({[(Z)-(6-Bromo-1,3-dioxo-2,3-dihydroisoquinolin-4(1H)-ylidene)methyl]amino}methyl)-2-hydroxyphenyl]acrylamide;
N-[4-({[(Z)-(6-Bromo-1,3-dioxo-2,3-dihydroisoquinolin-4(1H)-ylidene)methyl]amino}methyl)phenyl]-2,2-dichloroacetamide;
(4Z)-4-[({4-Amino-3-[(triisopropylsilyl)oxy]benzyl}amino)methylene]-6-bromoisoquinoline-1,3(2H,4H)-dione;
(Z)-6-Bromo-4-((5-(dimethylamino)pentylamino)methylene)isoquinoline-1,3(2H,4H)-dione;
(Z)-6-Bromo-4-((4-(dimethylamino)butylamino)methylene)isoquinoline-1,3(2H,4H)-dione;
(Z)-6-Bromo-4-((3-(dimethylamino)propylamino)methylene)isoquinoline-1,3(2H,4H)-dione;
(Z)-6-Bromo-4-((2-(piperazin-1-yl)ethylamino)methylene)isoquinoline-1,3(2H,4H)-dione;
(Z)-6-Bromo-4-((4-(diethylamino)butylamino)methylene)isoquinoline-1,3(2H,4H)-dione;
(Z)-6-Bromo-4-((3-(pyrrolidin-1-yl)propylamino)methylene)isoquinoline-1,3(2H,4H)-dione;
(Z)-6-Bromo-4-((3-morpholinopropylamino)methylene)isoquinoline-1,3(2H,4H)-dione;
(Z)-6-Bromo-4-((3-(2-oxopyrrolidin-1-yl)propylamino)methylene)isoquinoline-1,3(2H,4H)-dione;
4-{[(5-Hydroxy-4-oxo-4H-pyran-2-ylmethyl)-amino]-methylene}-6-pyrrol-1-yl-4H-isoquinoline-1,3-dione;
6-Bromo-4-{[(5-hydroxy-4-oxo-4H-pyran-2-ylmethyl)-amino]-methylene}-4H-isoquinoline-1,3-dione;
(Z)-4-((6-Bromo-1,3-dioxo-2,3-dihydroisoquinolin-4(1H)-ylidene)methylamino)butanoic acid;
(Z)-4-((1,3-Dioxo-6-(1H-pyrrol-1-yl)-2,3-dihydroisoquinolin-4(1H)-ylidene)methylamino)butanoic acid;
6-Bromo-4-{[(5-methoxy-4-oxo-4H-pyran-2-ylmethyl)-amino]-methylene}-4H-isoquinoline-1,3-dione;
4-{[(5-Methoxy-4-oxo-4H-pyran-2-ylmethyl)-amino]-methylene}-6-pyrrol-1-yl-4H-isoquinoline-1,3-dione;
(4Z)-6-Bromo-4-[({4-[(3R,5S)-3,5-dimethylpiperazin-1-yl]-3-fluorophenyl}amino)methylene]isoquinoline-1,3(2H,4H)-dione;
(4Z)-4-[({4-[(3R,5S)-3,5-Dimethylpiperazin-1-yl]-3-fluorophenyl}amino)methylene]-6-iodoisoquinoline-1,3(2H,4H)-dione (75);
N-[4-({[(Z)-(6-Bromo-1,3-dioxo-2,3-dihydroisoquinolin-4(1H)-ylidene)methyl]amino}methyl)-2-hydroxyphenyl]-2,2-dichloroacetamide;
N-[4-({[(Z)-(6-Bromo-1,3-dioxo-2,3-dihydroisoquinolin-4(1H)-ylidene)methyl]amino}methyl)phenyl]propanamide;
N-[4-({[(Z)-(6-Bromo-1,3-dioxo-2,3-dihydroisoquinolin-4(1H)-ylidene)methyl]amino}methyl)phenyl]acrylamide;
(4Z)-4-[({4-Amino-3-[(triisopropylsilyl)oxy]benzyl}amino)methylene]-6-iodoisoquinoline-1,3(2H,4H)-dione;
(4Z)-4-[({4-[(3R,5S)-3,5-Dimethylpiperazin-1-yl]-3-fluorophenyl}amino)methylene]-6-(3-furyl)isoquinoline-1,3(2H,4H)-dione;
(4Z)-4-[({4-[(3R,5S)-3,5-Dimethylpiperazin-1-yl]-3-fluorophenyl}amino)methylene]-6-thien-3-ylisoquinoline-1,3(2H,4H)-dione;
(4Z)-4-[({4-[(3R,5S)-3,5-Dimethylpiperazin-1-yl]-3-fluorophenyl}amino)methylene]-6-(4-fluorophenyl)isoquinoline-1,3(2H,4H)-dione (78);
(4Z)-4-({[4-(1-Methylpiperidin-4-yl)phenyl]amino}methylene)-6-thien-3-ylisoquinoline-1,3(2H,4H)-dione;
(4Z)-4-({[3-Fluoro-4-(4-methylpiperazin-1-yl)phenyl]amino}methylene)-6-(1H-pyrrol-1-yl)isoquinoline-1,3(2H,4H)-dione;
6-Bromo-4-[(4-pyridin-4-yl-phenylamino)-methylene]-4H-isoquinoline-1,3-dione;
(4Z)-6-(3-Furyl)-4-{[(4-{[(2R)-2-(methoxymethyl)pyrrolidin-1-yl]methyl}phenyl)amino]methylene}isoquinoline-1,3(2H,4H)-dione;
(4Z)-4-{[(4-{[(2R)-2-(Methoxymethyl)pyrrolidin-1-yl]methyl}phenyl)amino]methylene}-6-thien-3-ylisoquinoline-1,3(2H,4H)-dione;
6-Bromo-4-{[(4-hydroxy-5-methoxy-pyridin-2-ylmethyl)-amino]-methylene}-4H-isoquinoline-1,3-dione;
4-[(3-Hydroxy-4-methoxy-benzylamino)-methylene]-6-pyrrol-1-yl-4H-isoquinoline-1,3-dione;
N-[2-Hydroxy-4-({[(Z)-(6-iodo-1,3-dioxo-2,3-dihydroisoquinolin-4(1H)-ylidene)methyl]amino}methyl)phenyl]benzamide;
N-[2-Hydroxy-4-({[(Z)-(6-iodo-1,3-dioxo-2,3-dihydroisoquinolin-4(1H)-ylidene)methyl]amino}methyl)phenyl]-2-methylpropanamide;
(2E)-N-[2-Hydroxy-4-({[(Z)-(6-iodo-1,3-dioxo-2,3-dihydroisoquinolin-4(1H)-ylidene)methyl]amino}methyl)phenyl]-2-methylbut-2-enamide;
(2Z)-3-Chloro-N-[2-hydroxy-4-({[(Z)-(6-iodo-1,3-dioxo-2,3-dihydroisoquinolin-4(1H)-ylidene)methyl]amino}methyl)phenyl]acrylamide;
2-[(Dimethylamino)methyl]-N-[2-hydroxy-4-({[(Z)-(6-iodo-1,3-dioxo-2,3-dihydroisoquinolin-4(1H)-ylidene)methyl]amino}methyl)phenyl]acrylamide;
N-[2-Hydroxy-4-({[(Z)-(6-iodo-1,3-dioxo-2,3-dihydroisoquinolin-4(1H)-ylidene)methyl]amino}methyl)phenyl]but-2-ynamide;
N-[2-Hydroxy-4-({[(Z)-(6-iodo-1,3-dioxo-2,3-dihydroisoquinolin-4(1H)-ylidene)methyl]amino}methyl)phenyl]prop-2-ynamide;

N-[2-Hydroxy-4-({[(Z)-(6-iodo-1,3-dioxo-2,3-dihydroiso-quinolin-4(1H)-ylidene)methyl]amino}methyl)phenyl] propanamide;

N-[2-Hydroxy-4-({[(Z)-(6-iodo-1,3-dioxo-2,3-dihydroiso-quinolin-4(1H)-ylidene)methyl]amino}methyl)phenyl] acrylamide;

2-[(2E)-But-2-enoylamino]-5-({[(Z)-(6-iodo-1,3-dioxo-2,3-dihydroisoquinolin-4(1H)-ylidene)methyl]amino}methyl)phenyl (2E)-but-2-enoate;

(4Z)-6-Bromo-4-({[4-(1-methylpiperidin-4-yl)phenyl]amino}methylene)isoquinoline-1,3(2H,4H)-dione;

(4Z)-4-[({4-[(3R,5S)-3,5-Dimethylpiperazin-1-yl]-3-fluorophenyl}amino)methylene]-6-(4-methoxyphenyl)isoquinoline-1,3(2H,4H)-dione;

(4Z)-4-[({5-[(3R,5S)-3,5-Dimethylpiperazin-1-yl]pyridin-3-yl}amino)methylene]-6-(3-furyl)isoquinoline-1,3(2H,4H)-dione;

(4Z)-4-({[4-(Dimethylamino)-3-hydroxybenzyl]amino}methylene)-6-iodoisoquinoline-1,3(2H,4H)-dione;

6-Bromo-4-{[4-(4-chloro-3,5-dimethyl-pyrazol-1-yl)-phenylamino]-methylene}-4H-isoquinoline-1,3-dione;

6-Bromo-4-[(4-pyridin-3-yl-phenylamino)-methylene]-4H-isoquinoline-1,3-dione: (4Z)-6-bromo-4-{[(3-hydroxy-4-propoxybenzyl)amino]methylene}isoquinoline-1,3(2H,4H)-dione;

(4Z)-6-Bromo-4-[({6-[(2R,6S)-2,6-dimethylpiperidin-4-yl]-5-methylpyridin-3-yl}amino)methylene]isoquinoline-1,3(2H,4H)-dione;

(4Z)-4-({[4-(1-Acetylpiperidin-4-yl)phenyl]amino}methylene)-6-(3-furyl)isoquinoline-1,3(2H,4H)-dione;

5-({[(Z)-(6-Bromo-1,3-dioxo-2,3-dihydroisoquinolin-4(1H)-ylidene)methyl]amino}methyl)-2-propoxybenzoic acid;

5-({[(Z)-(6-Bromo-1,3-dioxo-2,3-dihydroisoquinolin-4(1H)-ylidene)methyl]amino}methyl)-2-propoxybenzamide;

6-Iodo-4-{[4-(1-pyrrolidin-1-yl-ethyl)-phenylamino]-methylene}-4H-isoquinoline-1,3-dione;

(4Z)-4-[({6-[(3R,5S)-3,5-Dimethylpiperazin-1-yl]-5-methylpyridin-3-yl}amino)methylene]-6-(3-furyl)isoquinoline-1,3(2H,4H)-dione;

(4Z)-4-[({6-[(3R,5S)-3,5-Dimethylpiperazin-1-yl]-5-methylpyridin-3-yl}amino)methylene]-6-thien-3-ylisoquinoline-1,3(2H,4H)-dione;

(4Z)-4-[({6-[(3R,5S)-3,5-Dimethylpiperazin-1-yl]-5-methylpyridin-3-yl}amino)methylene]-6-(4-methoxyphenyl)isoquinoline-1,3(2H,4H)-dione;

(4Z)-6-(4-Methoxyphenyl)-4-[({4-[(2-methylpyrrolidin-1-yl)methyl]phenyl}amino)-methylene]-isoquinoline-1,3(2H,4H)-dione;

(2E)-4-(Dimethylamino)-N-[2-hydroxy-4-({[(Z)-(6-iodo-1,3-dioxo-2,3-dihydroisoquinolin-4(1H)-ylidene)methyl]amino}methyl)phenyl]but-2-enamide;

6-Iodo-4-{[4-(4-methyl-piperazin-1-yl)-cyclohexylamino]-methylene}-4H-isoquinoline-1,3-dione;

6-Iodo-4-{[4-(1-methyl-pyrrolidin-2-yl)-phenylamino]-methylene}-4H-isoquinoline-1,3-dione;

6-Iodo-4-{[(4-hydroxy-5-methoxy-pyridin-2-ylmethyl)-amino]-methylene}-4H-isoquinoline-1,3-dione;

4-{[(4-Hydroxy-5-propoxy-pyridin-2-ylmethyl)-amino]-methylene}-6-pyrrol-1-yl-4H-isoquinoline-1,3-dione;

4-{[(4-Hydroxy-5-propoxy-pyridin-2-ylmethyl)-amino]-methylene}-6-iodo-4H-isoquinoline-1,3-dione;

4-{[(4-Hydroxy-5-propoxy-pyridin-2-ylmethyl)-amino]-methylene)-6-bromo-4H-isoquinoline-1,3-dione;

(4Z)-4-({[3-Hydroxy-4-(propylamino)benzyl]amino}methylene)-6-iodoisoquinoline-1,3(2H,4H)-dione;

D-1-{4-[(6-Iodo-1,3-dioxo-2,3-dihydro-1H-isoquinolin-4-ylidenemethyl)-amino]-benzyl}-pyrrolidine-2-carboxylic acid methyl ester;

D-4-{[4-(2-Hydroxymethyl-pyrrolidin-1-ylmethyl)-phenylamino]-methylene}-6-iodo-4H-isoquinoline-1,3-dione;

D-4-({4-[2-(1-Hydroxy-1-methyl-ethyl)-pyrrolidin-1-ylmethyl]-phenylamino}-methylene)-6-iodo-4H-isoquinoline-1,3-dione;

(4Z)-6-Bromo-4-[({3,5-difluoro-4-[(8aS)-hexahydropyrrolo[1,2-a]pyrazin-2(1H)-yl]phenyl}amino)methylene]isoquinoline-1,3(2H,4H)-dione;

(4Z)-4-[({3,5-Difluoro-4-[(8aS)-hexahydropyrrolo[1,2-a]pyrazin-2(1H)-yl]phenyl}amino)-methylene]-6-thien-3-ylisoquinoline-1,3(2H,4H)-dione;

(4Z)-6-Bromo-4-({[4-[(3R,5S)-3,5-dimethylpiperazin-1-yl]-3-(trifluoromethyl)phenyl]amino}methylene)isoquinoline-1,3(2H,4H)-dione;

(4Z)-4-[({4-[(3R,5S)-4-(N,N-Dimethylglycyl)-3,5-dimethylpiperazin-1-yl]phenyl}amino)methylene]-6-(3-furyl)isoquinoline-1,3(2H,4H)-dione;

4-({4-[2-(1-Hydroxy-ethyl)-pyrrolidin-1-ylmethyl]-phenylamino}-methylene)-6-iodo-4H-isoquinoline-1,3-dione;

6-Iodo-4-({4-[2-(1-methoxy-ethyl)-pyrrolidin-1-ylmethyl]-phenylamino}-methylene)-4H-isoquinoline-1,3-dione;

L-4-{[4-(2-Hydroxymethyl-pyrrolidin-1-ylmethyl)-phenylamino]-methylene}-6-iodo-4H-isoquinoline-1,3-dione;

tert-Butyl 4-(4-{[(Z)-(6-iodo-1,3-dioxo-2,3-dihydroiso-quinolin-4(1H)-ylidene)methyl]amino}phenyl)piperazine-1-carboxylate;

(4Z)-6-Iodo-4-{[(4-piperazin-1-ylphenyl)amino]methylene}isoquinoline-1,3(2H,4H)-dione;

(Z)-4-(((6-Bromo-5-propoxypyridin-2-yl)methylamino)methylene)-6-iodoisoquinoline-1,3(2H,4H)-dione;

(4Z)-4-[({4-[(3R,5S)-4-(N,N-Dimethylglycyl)-3,5-dimethylpiperazin-1-yl]phenyl}amino)methylene]-6-thien-3-ylisoquinoline-1,3(2H,4H)-dione;

(4Z)-6-Bromo-4-[({4-[(3R,5S)-3,5-dimethylpiperazin-1-yl]-3,5-difluorophenyl}amino)-methylene]isoquinoline-1,3(2H,4H)-dione;

(4Z)-4-[({3-Fluoro-4-[(8aS)-hexahydropyrrolo[1,2-a]pyrazin-2(1H)-yl]phenyl}amino)-methylene]-6-thien-3-ylisoquinoline-1,3(2H,4H)-dione;

(4Z)-4-[({4-[(3R,5S)-3,5-Dimethylpiperazin-1-yl]-3,5-difluorophenyl}amino)methylene]-6-thien-3-ylisoquinoline-1,3(2H,4H)-dione (83);

N-[(4Z)-4-({[4-(4-Methylpiperazin-1-yl)phenyl]amino}methylene)-1,3-dioxo-1,2,3,4-tetrahydroisoquinolin-6-yl]acrylamide;

(4Z)-6-Iodo-4-({[4-(4-isopropylpiperazin-1-yl)phenyl]amino}methylene)isoquinoline-1,3(2H,4H)-dione;

(4Z)-6-Iodo-4-[({4-[4-(1-methylpiperidin-4-yl)piperazin-1-yl]phenyl}amino)methylene]isoquinoline-1,3(2H,4H)-dione;

(4Z)-6-Iodo-4-({[4-(4-propylpiperazin-1-yl)phenyl]amino}methylene)isoquinoline-1,3(2H,4H)-dione;

(4Z)-4-[({4-[4-(2-Furylmethyl)piperazin-1-yl]phenyl}amino)methylene]-6-iodoisoquinoline-1,3(2H,4H)-dione;

(4Z)-4-[({4-[4-(3-Furylmethyl)piperazin-1-yl]phenyl}amino)methylene]-6-iodoisoquinoline-1,3(2H,4H)-dione;

(4Z)-4-[({4-[4-(Cyclopropylmethyl)piperazin-1-yl]phenyl}amino)methylene]-6-iodoisoquinoline-1,3(2H,4H)-dione;

(4Z)-4-({[4-(4-Cyclobutylpiperazin-1-yl)phenyl]amino}methylene)-6-iodoisoquinoline-1,3(2H,4H)-dione;

(4Z)-4-({[4-(4-Ethylpiperazin-1-yl)phenyl]amino}methylene)-6-iodoisoquinoline-1,3(2H,4H)-dione;

(4Z)-6-Iodo-4-[({4-[(4-methoxypiperidin-1-yl)methyl]phenyl}amino)methylene]isoquinoline-1,3(2H,4H)-dione;

(4Z)-6-(4-Fluorophenyl)-4-[({4-[(4-methoxypiperidin-1-yl)methyl]phenyl}amino)methylene]isoquinoline-1,3(2H,4H)-dione;

(4Z)-4-({[6-(4-Methylpiperazin-1-yl)pyridin-3-yl]amino}methylene)-6-thien-3-ylisoquinoline-1,3(2H,4H)-dione;

(4Z)-6-Bromo-4-[({4-[(4-methoxypiperidin-1-yl)methyl]phenyl}amino)methylene]isoquinoline-1,3(2H,4H)-dione;

(4Z)-4-[({4-[4-(2-Hydroxy-1-methylethyl)piperazin-1-yl]phenyl}amino)methylene]-6-iodoisoquinoline-1,3(2H,4H)-dione;

(4Z)-4-({[4-(4-ethylpiperazin-1-yl)phenyl]amino}methylene)-6-iodoisoquinoline-1,3(2H,4H)-dione;

(4Z)-6-Iodo-4-[({4-[4-(2-methoxy-1-methylethyl)piperazin-1-yl]phenyl}amino)methylene]isoquinoline-1,3(2H,4H)-dione;

(4Z)-4-{[(4-{4-[2-(Dimethylamino)-1-methylethyl]piperazin-1-yl}phenyl)amino]methylene}-6-iodoisoquinoline-1,3(2H,4H)-dione;

(4Z)-4-[({4-[4-(2-Hydroxyethyl)piperazin-1-yl]phenyl}amino)methylene]-6-iodoisoquinoline-1,3(2H,4H)-dione;

4-({4-[1-(4-Dimethylamino-but-2-enoyl)-pyrrolidin-2-yl]-phenylamino}-methylene)-6-iodo-4H-isoquinoline-1,3-dione;

4-{[4-(4,5-Dihydro-3H-pyrrol-2-yl)-phenylamino]-methylene}-6-iodo-4H-isoquinoline-1,3-dione;

4-{[4-(1,2,3,6-Tetrahydro-pyridin-2-yl)-phenylamino]-methylene}-6-thiophen-3-yl-4H-isoquinoline-1,3-dione;

(4Z)-6-Bromo-4-({[3-fluoro-4-(4-pyrrolidin-1-ylpiperidin-1-yl)phenyl]amino}-methylene)-isoquinoline-1,3(2H,4H)-dione;

(4Z)-4-({[3-Fluoro-4-(4-pyrrolidin-1-ylpiperidin-1-yl)phenyl]amino}methylene)-6-thien-3-ylisoquinoline-1,3(2H,4H)-dione;

(4Z)-6-Bromo-4-({[6-(4-pyrrolidin-1-ylpiperidin-1-yl)pyridin-3-yl]amino}methylene)isoquinoline-1,3(2H,4H)-dione;

(4Z)-4-[({4-[(3R,5S)-4-(N,N-Dimethylglycyl)-3,5-dimethylpiperazin-1-yl]phenyl}amino)methylene]-6-thien-3-yl-isoquinoline-1,3(2H,4H)-dione;

tert-Butyl 4-(5-{[(Z)-(6-iodo-1,3-dioxo-2,3-dihydroisoquinolin-4(1H)-ylidene)methyl]amino}pyridin-2-yl)piperazine-1-carboxylate;

(4Z)-6-Iodo-4-{[(6-piperazin-1-ylpyridin-3-yl)amino]methylene}isoquinoline-1,3(2H,4H)-dione;

4-{[4-(2-Ethoxymethyl-pyrrolidin-1-ylmethyl)-phenylamino]-methylene}-6-iodo-4H-isoquinoline-1,3-dione;

4-{[4-(2-Dimethylaminomethyl-pyrrolidin-1-yl)-3-fluoro-phenylamino]-methylene}-6-iodo-4H-isoquinoline-1,3-dione;

(4Z)-6-Iodo-4-({[6-(4-isopropylpiperazin-1-yl)pyridin-3-yl]amino}methylene)isoquinoline-1,3(2H,4H)-dione;

(4Z)-4-({[6-(4-Ethylpiperazin-1-yl)pyridin-3-yl]amino}methylene)-6-iodoisoquinoline-1,3(2H,4H)-dione;

(4Z)-4-[({6-[4-(Cyclopropylmethyl)piperazin-1-yl]pyridin-3-yl}amino)methylene]-6-iodoisoquinoline-1,3(2H,4H)-dione;

(4Z)-4-({[6-(4-Ethylpiperazin-1-yl)pyridin-3-yl]amino}methylene)-6-(3-furyl)isoquinoline-1,3(2H,4H)-dione;

(4Z)-4-({[6-(4-Isopropylpiperazin-1-yl)pyridin-3-yl]amino}methylene)-6-(3-thienyl)isoquinoline-1,3(2H,4H)-dione;

(4Z)-4-[({6-[4-(Cyclopropylmethyl)piperazin-1-yl]pyridin-3-yl}amino)methylene]-6-(3-thienyl)isoquinoline-1,3(2H,4H)-dione;

4-{[4-(1-Allyl-pyrrolidin-2-yl)-phenylamino]-methylene-6-iodo-4H-isoquinoline-1,3-dione;

4-{[4-(1-Allyl-pyrrolidin-2-yl)-phenylamino]-methylene}-6-thiophen-3-yl-4H-isoquinoline-1,3-dione;

4-{[4-(2-Hydroxymethyl-pyrrolidin-1-ylmethyl)-phenylamino]-methylene}-6-thiophen-3-yl-4H-isoquinoline-1,3-dione;

(4Z)-4-{[(4-{[3-(Dimethylamino)pyrrolidin-1-yl]methyl}phenyl)amino]methylene}-6-iodoisoquinoline-1,3(2H,4H)-dione;

(4Z)-4-{[(4-{[3-(Dimethylamino)pyrrolidin-1-yl]methyl}phenyl)amino]methylene}-6-iodoisoquinoline-1,3(2H,4H)-dione;

4-{[(5-Amino-4-hydroxy-pyridin-2-ylmethyl)-amino]-methylene}-6-iodo-4H-isoquinoline-1,3-dione;

(4Z)-4-{[(4-{1-[3-(Dimethylamino)propyl]piperidin-4-yl}phenyl)amino]methylene}-6-iodoisoquinoline-1,3(2H,4H)-dione;

4-{[3-Fluoro-4-(2-hydroxymethyl-pyrrolidin-1-yl)-phenylamino]-methylene}-6-iodo-4H-isoquinoline-1,3-dione;

6-Iodo-4-{[(5-oxo-pyrrolidin-2-ylmethyl)-amino]-methylene}-4H-isoquinoline-1,3-dione;

N-(4-Hydroxy-6-{[(6-iodo-1,3-dioxo-2,3-dihydro-1H-isoquinolin-4-ylidenemethyl)-amino]-methyl}-pyridin-3-yl)-acrylamide;

1-(4-{[(Z)-(6-Iodo-1,3-dioxo-2,3-dihydroisoquinolin-4(1H)-ylidene)methyl]amino}phenyl)-N,N-dimethylpiperidine-4-carboxamide;

1-(4-{[(Z)-(6-Iodo-1,3-dioxo-2,3-dihydroisoquinolin-4(1H)-ylidene)methyl]amino}phenyl)piperidine-4-carboxamide;

1-(4-{[(Z)-(6-Iodo-1,3-dioxo-2,3-dihydroisoquinolin-4(1H)-ylidene)methyl]amino}phenyl)piperidine-4-carboxylic acid;

1-(4-{[(Z)-(6-Iodo-1,3-dioxo-2,3-dihydroisoquinolin-4(1H)-ylidene)methyl]amino}phenyl)-N-methoxy-N-methylpiperidine-4-carboxamide;

N-[2-(Dimethylamino)ethyl]-1-(4-{[(Z)-(6-iodo-1,3-dioxo-2,3-dihydroisoquinolin-4(1H)-ylidene)methyl]amino}phenyl)piperidine-4-carboxamide;

(4Z)-4-[({4-[4-(Hydroxymethyl)piperidin-1-yl]phenyl}amino)methylene]-6-iodoisoquinoline-1,3(2H,4H)-dione;

(4Z)-6-Iodo-4-[({4-[4-(methoxymethyl)piperidin-1-yl]phenyl}amino)methylene]isoquinoline-1,3(2H,4H)-dione;

4-{[4-(2-Ethyl-pyrrolidin-1-ylmethyl)-phenylamino]-methylene}-6-iodo-4H-isoquinoline-1,3-dione;

6-Bromo-4-{[4-(2-hydroxymethyl-pyrrolidin-1-ylmethyl)-phenylamino]-methylene}-4H-isoquinoline-1,3-dione;

4-{[4-(2-Hydroxymethyl-pyrrolidin-1-ylmethyl)-phenylamino]-methylene}-6-thiophen-2-yl-4H-isoquinoline-1,3-dione;

(4Z)-4-{[(4-{[2-(Hydroxymethyl)piperidin-1-yl]methyl}phenyl)amino]methylene}-6-iodoisoquinoline-1,3(2H,4H)-dione;

(4Z)-4-[({4-[(4-Hydroxypiperidin-1-yl)methyl]phenyl}amino)methylene]-6-iodoisoquinoline-1,3(2H,4H)-dione;

6-(5-Chloro-thiophen-2-yl)-4-{[4-(2-hydroxymethyl-pyrrolidin-1-ylmethyl)-phenylamino]-methylene}-4H-isoquinoline-1,3-dione;

(4Z)-6-Bromo-4-({[5-(4-methylpiperazin-1-yl)pyridin-2-yl]amino}methylene)isoquinoline-1,3(2H,4H)-dione;

(4Z)-6-(3-Furyl)-4-({[5-(4-methylpiperazin-1-yl)pyridin-2-yl]amino}methylene)isoquinoline-1,3(2H,4H)-dione;

(Z)-4-((5-Bromopyridin-2-ylamino)methylene)-6-(1H-pyrrol-1-yl)isoquinoline-1,3(2H,4H)-dione;

(4Z)-4-({[2-Fluoro-6-(4-methylpiperazin-1-yl)pyridin-3-yl]amino}methylene)-6-iodoisoquinoline-1,3(2H,4H)-dione;

(4Z)-4-[({4-[4-({[2-(Dimethylamino)ethyl]amino}methyl)piperidin-1-yl]phenyl}amino)methylene]-6-iodoisoquinoline-1,3(2H,4H)-dione;

(4Z)-4-({[2-Hydroxy-6-(4-methylpiperazin-1-yl)pyridin-3-yl]amino}methylene)-6-iodoisoquinoline-1,3(2H,4H)-dione;

4-[(4Z)-4-({[5-(4-Methylpiperazin-1-yl)pyridin-2-yl]amino}methylene)-1,3-dioxo-1,2,3,4-tetrahydroisoquinolin-6-yl]-2-furaldehyde;

(4Z)-4-({[5-(4-Methylpiperazin-1-yl)pyridin-2-yl]amino}methylene)-6-[5-(pyrrolidin-1-ylmethyl)-3-furyl]isoquinoline-1,3(2H,4H)-dione;

4-{[4-(1-Methyl-pyrrolidin-2-yl)-phenylamino]-methylene}-6-thiophen-2-yl-4H-isoquinoline-1,3-dione;

6-Furan-3-yl-4-{[4-(1-methyl-pyrrolidin-2-yl)-phenylamino]-methylene}-4H-isoquinoline-1,3-dione;

6-Bromo-1,1-dimethyl-4-{[4-(4-methyl-piperazin-1-yl)-phenylamino]-methylene}-1,4-dihydro-2H-isoquinolin-3-one;

(4Z)-6-Iodo-4-({[(1-methyl-2-oxo-1,2-dihydropyridin-4-yl)methyl]amino}methylene)isoquinoline-1,3(2H,4H)-dione;

(4Z)-4-{[(4-{4-[(Dimethylamino)methyl]piperidin-1-yl}phenyl)amino]methylene}-6-iodoisoquinoline-1,3(2H,4H)-dione;

(4Z)-6-Iodo-4-({[4-(4-{[methyl(1-methylpyrrolidin-3-yl)amino]methyl}piperidin-1-yl)phenyl]amino}methylene)isoquinoline-1,3(2H,4H)-dione;

(4Z)-4-{[(4-{4-[(Ethylamino)methyl]piperidin-1-yl}phenyl)amino]methylene}-6-iodoisoquinoline-1,3(2H,4H)-dione;

(4Z)-4-({[2-Fluoro-6-(4-methylpiperazin-1-yl)pyridin-3-yl]amino}methylene)-6-(3-furyl)isoquinoline-1,3(2H,4H)-dione;

6-Furan-3-yl-1,1-dimethyl-4-{[4-(4-methyl-piperazin-1-yl)-phenylamino]-methylene}-1,4-dihydro-2H-isoquinolin-3-one;

(Z)-4-((5-Bromopyridin-2-ylamino)methylene)-6-(1H-pyrrol-1-yl)isoquinoline-1,3(2H,4H)-dione;

(Z)-6-Iodo-4-((5-(1-methylpyrrolidin-2-yl)pyridin-2-ylamino)methylene)isoquinoline-1,3(2H,4H)-dione;

2-{4-[(6-Iodo-1,3-dioxo-2,3-dihydro-1H-isoquinolin-4-ylidenemethyl)-amino]-phenyl}-pyrrolidine-1-carboxylic acid tert-butyl ester;

6-Iodo-4-[(4-pyrrolidin-2-yl-phenylamino)-methylene]-4H-isoquinoline-1,3-dione;

6-Furan-3-yl-4-{[4-(2-hydroxymethyl-pyrrolidin-1-ylmethyl)-phenylamino]-methylene}-4H-isoquinoline-1,3-dione;

4-({4-[1-(2-Hydroxy-ethyl)-pyrrolidin-2-yl]-phenylamino}-methylene)-6-iodo-4H-isoquinoline-1,3-dione;

4-{[4-(1-Ethyl-pyrrolidin-2-yl)-phenylamino]-methylene-6-iodo-4H-isoquinoline-1,3-dione;

6-Furan-2-yl-4-{[4-(2-hydroxymethyl-pyrrolidin-1-ylmethyl)-phenylamino]-methylene}-4H-isoquinoline-1,3-dione;

(4Z)-6-(2-Furyl)-4-{[(4-{[(2S)-2-(methoxymethyl)pyrrolidin-1-yl]methyl}phenyl)amino]methylene}isoquinoline-1,3(2H,4H)-dione;

(4Z)-4-[({5-[(3R,5S)-3,5-Dimethylpiperazin-1-yl]pyridin-2-yl}amino)methylene]-6-(3-furyl)isoquinoline-1,3(2H,4H)-dione;

(4Z)-6-Bromo-4-[({5-[(3R,5S)-3,5-dimethylpiperazin-1-yl]pyridin-2-yl}amino)methylene]isoquinoline-1,3(2H,4H)-dione;

N-(4-Hydroxy-6-{[(6-iodo-1,3-dioxo-2,3-dihydro-1H-isoquinolin-4-ylidenemethyl)-amino]-methyl}-pyridin-3-yl)-propionamide;

6-Iodo-4-{[(1-methyl-4-oxo-5-propoxy-1,4-dihydro-pyridin-2-ylmethyl)-amino]-methylene}-4H-isoquinoline-1,3-dione;

4-{[4-(2-Hydroxymethyl-pyrrolidin-1-ylmethyl)-phenylamino]-methylene}-6-thiazol-2-yl-4H-isoquinoline-1,3-dione;

4-{[4-(1-Ethyl-pyrrolidin-2-yl)-phenylamino]-methylene}-6-furan-3-yl-4H-isoquinoline-1,3-dione;

(4Z)-4-({[6-(4-Methylpiperazin-1-yl)pyridin-3-yl]amino}methylene)-6-(1-methyl-1H-pyrrol-2-yl)isoquinoline-1,3(2H,4H)-dione;

(4Z)-6-Iodo-4-({[2-(4-methylpiperazin-1-yl)pyrimidin-5-yl]amino}methylene)isoquinoline-1,3(2H,4H)-dione;

(4Z)-6-(3-Furyl)-4-({[6-(4-methylpiperazin-1-yl)pyridazin-3-yl]amino}methylene)isoquinoline-1,3(2H,4H)-dione;

(4Z)-6-Bromo-4-({[6-(4-methylpiperazin-1-yl)pyridazin-3-yl]amino}methylene)isoquinoline-1,3(2H,4H)-dione;

(4Z)-6-Iodo-4-{[(5-{[(2S)-2-(methoxymethyl)pyrrolidin-1-yl]methyl}pyridin-2-yl)amino]methylene}isoquinoline-1,3(2H,4H)-dione;

4-{[(4-Hydroxy-5-methoxy-pyrimidin-2-ylmethyl)-amino]-methylene}-6-iodo-4H-isoquinoline-1,3-dione;

(4Z)-4-{[(4-{[4-(2-Hydroxyethyl)piperidin-1-yl]methyl}phenyl)amino]methylene}-6-iodoisoquinoline-1,3(2H,4H)-dione;

(4Z)-4-({[5-(4-Ethylpiperazin-1-yl)pyridin-2-yl]amino}methylene)-6-(3-furyl)isoquinoline-1,3(2H,4H)-dione;

(4Z)-6-(4-Fluorophenyl)-4-{[(4-{[4-(2-hydroxyethyl)piperidin-1-yl]methyl}phenyl)amino]methylene}isoquinoline-1,3(2H,4H)-dione;

4-{[4-(1,1-Dioxo-1-thiomorpholin-4-ylmethyl)-phenylamino]-methylene}-6-iodo-4H-isoquinoline-1,3-dione;

(4Z)-6-(3-Furyl)-4-({[2-(4-methylpiperazin-1-yl)pyrimidin-5-yl]amino}methylene)isoquinoline-1,3(2H,4H)-dione;

(4Z)-6-(3-Furyl)-4-{[(3-hydroxy-4-propoxybenzyl)amino]methylene}isoquinoline-1,3(2H,4H)-dione;

(4Z)-6-Bromo-4-({[5-(4-isopropylpiperazin-1-yl)pyridin-2-yl]amino}methylene)isoquinoline-1,3(2H,4H)-dione;

(4Z)-4-[({6-[(3R,5S)-3,5-Dimethylpiperazin-1-yl]pyridin-3-yl}amino)methylene]-6-[5-(hydroxymethyl)-2-furyl]isoquinoline-1,3(2H,4H)-dione;

(4Z)-6-(3-Furyl)-4-({[5-(4-isopropylpiperazin-1-yl)pyridin-2-yl]amino}methylene)isoquinoline-1,3(2H,4H)-dione;

(4Z)-6-Bromo-4-{[(4-{[4-(2-hydroxyethyl)piperidin-1-yl]methyl}phenyl)amino]methylene}isoquinoline-1,3(2H,4H)-dione 4-{[(2-Hydroxy-biphenyl-4-ylmethyl)-amino]-methylene}-6-iodo-4H-isoquinoline-1,3-dione;
(4Z)-6-(3-Furyl)-4-{[(4-{[4-(2-hydroxyethyl)piperidin-1-yl]methyl}phenyl)amino]methylene}isoquinoline-1,3(2H,4H)-dione;
5-[(4Z)-1,3-Dioxo-4-({[4-(piperidin-1-ylmethyl)phenyl]amino}methylene)-1,2,3,4-tetrahydroisoquinolin-6-yl]-2-furaldehyde;
(Z)-4-(((6-Bromo-5-propoxypyridin-2-yl)methylamino)methylene)-6-iodoisoquinoline-1,3(2H,4H)-dione;
6-Furan-3-yl-4-{[(2-hydroxy-biphenyl-4-ylmethyl)-amino]-methylene}-4H-isoquinoline-1,3-dione;
4-[(4-Butyl-3-hydroxy-benzylamino)-methylene]-6-iodo-4H-isoquinoline-1,3-dione;
4-[(5-Hydroxy-2-iodo-benzylamino)-methylene]-6-iodo-4H-isoquinoline-1,3-dione;
(4Z)-4-({[2-Fluoro-6-(4-methylpiperazin-1-yl)pyridin-3-yl]amino}methylene)-6-(3-furyl)isoquinoline-1,3(2H,4H)-dione;
4-[(2-Furan-2-yl-5-hydroxy-benzylamino)-methylene]-6-iodo-4H-isoquinoline-1,3-dione;
4-{[(4'-Fluoro-2-hydroxy-biphenyl-4-ylmethyl)-amino]-methylene}-6-iodo-4H-isoquinoline-1,3-dione;
4-{[(4'-Fluoro-2-hydroxy-biphenyl-4-ylmethyl)-amino]-methylene}-6-furan-2-yl-4H-isoquinoline-1,3-dione;
6-Furan-2-yl-4-{[(4-hydroxy-5-propoxy-pyridin-2-ylmethyl)-amino]-methylene}-4H-isoquinoline-1,3-dione;
6-Furan-2-yl-4-[(5-hydroxy-2-iodo-benzylamino)-methylene]-4H-isoquinoline-1,3-dione;
4-[(3-Hydroxy-4-iodo-benzylamino)-methylene]-6-iodo-4H-isoquinoline-1,3-dione;
4-[(4-Furan-2-yl-3-hydroxy-benzylamino)-methylene]-6-iodo-4H-isoquinoline-1,3-dione;
4-[(4-Furan-3-yl-3-hydroxy-benzylamino)-methylene]-6-iodo-4H-isoquinoline-1,3-dione;
(4Z)-6-Iodo-4-({[5-(4-methylpiperazin-1-yl)pyrazin-2-yl]amino}methylene)isoquinoline-1,3(2H,4H)-dione;
(4Z)-6-(3-Furyl)-4-({[5-(4-methylpiperazin-1-yl)pyrazin-2-yl]amino}methylene)isoquinoline-1,3(2H,4H)-dione;
4-[(3-Hydroxy-4-pyridin-2-yl-benzylamino)-methylene]-6-iodo-4H-isoquinoline-1,3-dione;
4-{[(6-Hydroxy-5-propoxy-pyridin-2-ylmethyl)-amino]-methylene}-6-iodo-4H-isoquinoline-1,3-dione;
4-[(3-Hydroxy-4-pyridin-4-yl-benzylamino)-methylene]-6-iodo-4H-isoquinoline-1,3-dione;
(4Z)-4-{[(4-{[3-(Dimethylamino)pyrrolidin-1-yl]methyl}phenyl)amino]methylene}-6-(4-fluorophenyl)isoquinoline-1,3(2H,4H)-dione;
(4Z)-4-{[(4-{[3-(Dimethylamino)pyrrolidin-1-yl]methyl}phenyl)amino]methylene}-6-(3-furyl)isoquinoline-1,3(2H,4H)-dione;
(4Z)-4-({[3-Hydroxy-4-(1H-pyrrol-1-yl)benzyl]amino}methylene)-6-iodoisoquinoline-1,3(2H,4H)-dione;
4-[(3-Hydroxy-4-pyridin-3-yl-benzylamino)-methylene]-6-iodo-4H-isoquinoline-1,3-dione;
N-[2-Hydroxy-4-({[(Z)-(6-iodo-1,3-dioxo-2,3-dihydroisoquinolin-4(1H)-ylidene)methyl]amino}methyl)phenyl]-2-furamide;
(4Z)-6-Iodo-4-({[(2-oxo-1-phenyl-1,2-dihydropyridin-4-yl)methyl]amino}methylene)isoquinoline-1,3(2H,4H)-dione;
(4Z)-6-Iodo-4-({[(2-oxo-1-phenyl-1,2-dihydropyridin-4-yl)methyl]amino}methylene)isoquinoline-1,3(2H,4H)-dione;
4-{[(3'-Dimethylaminomethyl-2-hydroxy-biphenyl-4-ylmethyl)-amino]-methylene}-6-iodo-4H-isoquinoline-1,3-dione;
4-[(2-Fluoro-4-furan-3-yl-5-hydroxy-benzylamino)-methylene]-6-iodo-4H-isoquinoline-1,3-dione;
(4Z)-4-({[3-Hydroxy-4-(4-methylpiperazin-1-yl)benzyl]amino}methylene)-6-iodoisoquinoline-1,3(2H,4H)-dione;
4-({[4-Hydroxy-5-(2-pyrrolidin-1-yl-ethoxy)-pyridin-2-ylmethyl]-amino}-methylene)-6-iodo-4H-isoquinoline-1,3-dione;
(4Z)-4-[({3-Hydroxy-4-[(2S)-2-(methoxymethyl)pyrrolidin-1-yl]benzyl}amino)methylene]-6-iodoisoquinoline-1,3(2H,4H)-dione;
(4Z)-{[(4-Hydroxy-5-phenyl-pyridin-2-ylmethyl)-amino]-methylene}-6-iodo-4H-isoquinoline-1,3-dione;
(4Z)-4-[({[1-(3-Furyl)-2-oxo-1,2-dihydropyridin-4-yl]methyl}amino)methylene]-6-iodoisoquinoline-1,3(2H,4H)-dione;
$N^1$-[2-Hydroxy-4-({[(Z)-(6-iodo-1,3-dioxo-2,3-dihydroisoquinolin-4(1H)-ylidene)methyl]amino}methyl)phenyl]-$N^2,N^2$-dimethylglycinamide;
(4Z)-{[(5-Furan-3-yl-4-hydroxy-pyridin-2-ylmethyl)-amino]-methylene}-6-iodo-4H-isoquinoline-1,3-dione;
6-tert-Butyl-4-[(2-furan-3-yl-5-hydroxy-benzylamino)-methylene]-4H-isoquinoline-1,3-dione;
6-tert-Butyl-4-[(4-furan-3-yl-3-hydroxy-benzylamino)-methylene]-4H-isoquinoline-1,3-dione;
(4Z)-6-Iodo-4-({[(1-butyl-2-oxo-1,2-dihydropyridin-4-yl)methyl]amino}methylene)isoquinoline-1,3(2H,4H)-dione;
6-tert-Butyl-4-{[(4-hydroxy-5-propoxy-pyridin-2-ylmethyl)-amino]-methylene}-4H-isoquinoline-1,3-dione;
6-tert-Butyl-4-{[(4-hydroxy-5-phenyl-pyridin-2-ylmethyl)-amino]-methylene}-4H-isoquinoline-1,3-dione;
6-tert-Butyl-4-{[(5-furan-3-yl-4-hydroxy-pyridin-2-ylmethyl)-amino]-methylene}-4H-isoquinoline-1,3-dione;
(4Z)-6-tert-Butyl-4-[({[1-(3-furyl)-2-oxo-1,2-dihydropyridin-4-yl]methyl}amino)methylene]isoquinoline-1,3(2H,4H)-dione;
6-tert-Butyl-4-[(2-fluoro-4-furan-3-yl-5-hydroxy-benzylamino)-methylene]-4H-isoquinoline-1,3-dione;
6-tert-Butyl-4-[(4-furan-3-yl-3-hydroxy-benzylamino)-methylene]-4H-isoquinoline-1,3-dione;
6-Cyclopentyl-4-[(4-furan-3-yl-3-hydroxy-benzylamino)-methylene]-4H-isoquinoline-1,3-dione;
6-Cyclopentyl-4-{[(5-furan-3-yl-4-hydroxy-pyridin-2-ylmethyl)-amino]-methylene}-4H-isoquinoline-1,3-dione;
6-Cyclopentyl-4-{[(4-hydroxy-5-propoxy-pyridin-2-ylmethyl)-amino]-methylene}-4H-isoquinoline-1,3-dione;
(4Z)-6-Iodo-4-[({[2-oxo-1-(3-thienyl)-1,2-dihydropyridin-4-yl]methyl}amino)methylene]isoquinoline-1,3(2H,4H)-dione;
(4Z)-6-Iodo-4-[({[2-oxo-1-(3-thienyl)-1,2-dihydropyridin-4-yl]methyl}amino)methylene]isoquinoline-1,3(2H,4H)-dione;
4-{[(1,3-Dioxo-2,3-dihydro-1H-isoquinolin-4-ylidenemethyl)-amino]-methyl}-benzenesulfonamide;
4-[(2-Trifluoromethoxy-phenylamino)-methylene]-4H-isoquinoline-1,3-dione;
3-[(1,3-Dioxo-2,3-dihydro-1H-isoquinolin-4-ylidenemethyl)-amino]-benzoic acid;
N-(2-Diethylamino-ethyl)-4-[(1,3-dioxo-2,3-dihydro-1H-isoquinolin-4-ylidenemethyl)-amino]-benzamide;
4-{[2-(3,4-Dihydroxy-phenyl)-ethylamino]-methylene-4H-isoquinoline-1,3-dione;

4-[(4-Amino-phenylamino)-methylene]-4H-isoquinoline-1,3-dione;
N-{4-[(1,3-Dioxo-2,3-dihydro-1H-isoquinolin-4-ylidenemethyl)-amino]-phenyl}-oxalamic acid;
4-[(1,3-Dioxo-2,3-dihydro-1H-isoquinolin-4-ylidenemethyl)-amino]-benzamidine;
{4-[(1,3-Dioxo-2,3-dihydro-1H-isoquinolin-4-ylidenemethyl)-amino]-phenylsulfanyl}-acetic acid;
4-[(1,3-Dioxo-2,3-dihydro-1H-isoquinolin-4-ylidenemethyl)-amino]-N-(5-methyl-[1,3,4]thiadiazol-2-yl)-benzenesulfonamide;
4-[(3,4-Dihydroxy-benzylamino)-methylene]-4H-isoquinoline-1,3-dione;
4-{[2-(1H-Benzoimidazol-2-yl)-phenylamino]-methylene}-4H-isoquinoline-1,3-dione;
3-[N'-(1,3-Dioxo-2,3-dihydro-1H-isoquinolin-4-ylidenemethyl)-hydrazino]-benzoic acid;
N-(4,5-Dimethyl-oxazol-2-yl)-4-[(1,3-dioxo-2,3-dihydro-1H-isoquinolin-4-ylidenemethyl)-amino]-benzenesulfonamide;
N-{4-[(1,3-Dioxo-2,3-dihydro-1H-isoquinolin-4-ylidenemethyl)-amino]-phenyl}-N-methyl-acetamide;
{4-[(1,3-Dioxo-2,3-dihydro-1H-isoquinolin-4-ylidenemethyl)-amino]-phenyl}-acetonitrile;
4-[(1,3-Dioxo-2,3-dihydro-1H-isoquinolin-4-ylidenemethyl)-amino]-N-(5-methyl-isoxazol-3-yl)-benzenesulfonamide;
3-{4-[(1,3-Dioxo-2,3-dihydro-1H-isoquinolin-4-ylidenemethyl)-amino]-phenyl}-acrylic acid;
4-{4-[(1,3-Dioxo-2,3-dihydro-1H-isoquinolin-4-ylidenemethyl)-amino]-phenyl}-butyric acid;
4-[(4-Hydroxy-phenylamino)-methylene]-4H-isoquinoline-1,3-dione;
4-[(1,3-Dioxo-2,3-dihydro-1H-isoquinolin-4-ylidenemethyl)-amino]-2-hydroxy-benzoic acid;
4-[(3-Hydroxy-4-methoxy-phenylamino)-methylene]-4H-isoquinoline-1,3-dione;
2-[(1,3-Dioxo-2,3-dihydro-1H-isoquinolin-4-ylidenemethyl)-amino]-5-hydroxy-benzoic acid;
5-[(1,3-Dioxo-2,3-dihydro-1H-isoquinolin-4-ylidenemethyl)-amino]-2-hydroxy-benzoic acid;
4-{[2-(3,4-Dihydroxy-phenyl)-2-hydroxy-ethylamino]-methylene}-4H-isoquinoline-1,3-dione;
4-[(2,6-Dihydroxy-phenylamino)-methylene]-4H-isoquinoline-1,3-dione;
3-(3,4-Dihydroxy-phenyl)-2-[(1,3-dioxo-2,3-dihydro-1H-isoquinolin-4-ylidenemethyl)-amino]-propionic acid;
3-(3,4-Dihydroxy-phenyl)-2-[(1,3-dioxo-2,3-dihydro-1H-isoquinolin-4-ylidenemethyl)-amino]-propionic acid;
4-[(2,4-Dihydroxy-phenylamino)-methylene]-4H-isoquinoline-1,3-dione;
4-[(8-Hydroxy-quinolin-5-ylamino)-methylene]-4H-isoquinoline-1,3-dione;
4-[(5-Chloro-2-hydroxy-4-nitro-phenylamino)-methylene]-4H-isoquinoline-1,3-dione;
4-({4-[4-(2-Morpholin-4-yl-ethyl)-piperazin-1-yl]-phenylamino}-methylene)-4H-isoquinoline-1,3-dione;
4-({4-[4-(2-Pyrrolidin-1-yl-ethyl)-piperazin-1-yl]-phenylamino}-methylene)-4H-isoquinoline-1,3-dione;
4-[(3-Amino-benzylamino)-methylene]-4H-isoquinoline-1,3-dione;
4-[(4-Diethylaminomethyl-phenylamino)-methylene]-4H-isoquinoline-1,3-dione;
4-({4-[(Cyclopropylmethyl-propyl-amino)-methyl]-phenylamino}-methylene)-4H-isoquinoline-1,3-dione;
4-[(4-Pyrrolidin-1-ylmethyl-phenylamino)-methylene]-4H-isoquinoline-1,3-dione;
4-({4-[(Cyclohexyl-methyl-amino)-methyl]-phenylamino}-methylene)-4H-isoquinoline-1,3-dione;
4-[(3-Aminomethyl-benzylamino)-methylene]-4H-isoquinoline-1,3-dione;
Thiophene-2-sulfonic acid (3-{[(1,3-dioxo-2,3-dihydro-1H-isoquinolin-4-ylidenemethyl)-amino]-methyl}-phenyl)-amide;
Propane-2-sulfonic acid (3-{[(1,3-dioxo-2,3-dihydro-1H-isoquinolin-4-ylidenemethyl)-amino]-methyl}-phenyl)-amide;
N-(3-{[(1,3-Dioxo-2,3-dihydro-1H-isoquinolin-4-ylidenemethyl)-amino]-methyl}-phenyl)-methanesulfonamide;
2,2,2-Trifluoro-ethanesulfonic acid (3-{[(1,3-dioxo-2,3-dihydro-1H-isoquinolin-4-ylidenemethyl)-amino]-methyl}-phenyl)-amide;
Ethanesulfonic acid (3-{[(1,3-dioxo-2,3-dihydro-1H-isoquinolin-4-ylidenemethyl)-amino]-methyl}-phenyl)-amide;
Propane-1-sulfonic acid (3-{[(1,3-dioxo-2,3-dihydro-1H-isoquinolin-4-ylidenemethyl)-amino]-methyl}-phenyl)-amide;
N-(3-{[(1,3-Dioxo-2,3-dihydro-1H-isoquinolin-4-ylidenemethyl)-amino]-methyl}-phenyl)-acetamide;
Cyclopropanecarboxylic acid (3-{[(1,3-dioxo-2,3-dihydro-1H-isoquinolin-4-ylidenemethyl)-amino]-methyl}-phenyl)-amide;
Cyclobutanecarboxylic acid (3-{[(1,3-dioxo-2,3-dihydro-1H-isoquinolin-4-ylidenemethyl)-amino]-methyl}-phenyl)-amide;
Thiophene-2-sulfonic acid (4-{[(1,3-dioxo-2,3-dihydro-1H-isoquinolin-4-ylidenemethyl)-amino]-methyl}-phenyl)-amide;
N-(4-[(1,3-Dioxo-2,3-dihydro-1H-isoquinolin-4-ylidenemethyl)-amino]-methyl}-phenyl)-methanesulfonamide;
N-(4{[(1,3-Dioxo-2,3-dihydro-1H-isoquinolin-4-ylidenemethyl)-amino]-methyl}-phenyl)-C-phenyl-methanesulfonamide;
2,2,2-Trifluoro-ethanesulfonic acid (4{[(1,3-dioxo-2,3-dihydro-1H-isoquinolin-4-ylidenemethyl)-amino]-methyl}-phenyl)-amide;
Propane-1-sulfonic acid (4{[(1,3-dioxo-2,3-dihydro-1H-isoquinolin-4-ylidenemethyl)-amino]-methyl}-phenyl)-amide;
N-(4{[(1,3-Dioxo-2,3-dihydro-1H-isoquinolin-4-ylidenemethyl)-amino]-methyl}-phenyl)-3-methyl-butyramide;
4-[(3,4-Dihydroxy-phenylamino)-methylene]-4H-isoquinoline-1,3-dione;
4-{[4-(4-Ethyl-piperazin-1-yl)-phenylamino]-methylene}-4H-isoquinoline-1,3-dione;
(4-{4-[(1,3-Dioxo-2,3-dihydro-1H-isoquinolin-4-ylidenemethyl)-amino]-phenyl}-piperazin-1-yl)-acetonitrile;
4-{[4-(4-Allyl-piperazin-1-yl)-phenylamino]-methylene}-4H-isoquinoline-1,3-dione;
4-({4-[4-(2-Hydroxy-ethyl)-piperazin-1-yl]-phenylamino}-methylene)-4H-isoquinoline-1,3-dione;
4-({4-[4-(2-Diethylamino-ethyl)-piperazin-1-yl]-phenylamino}-methylene)-4H-isoquinoline-1,3-dione;
4-{[4-(4-Isopropyl-piperazin-1-yl)-phenylamino]-methylene}-4H-isoquinoline-1,3-dione;
4-{[4-(4-Cyclopentyl-piperazin-1-yl)-phenylamino]-methylene}-4H-isoquinoline-1,3-dione;
4-{[4-(4-Cyclobutylmethyl-piperazin-1-yl)-phenylamino]-methylene}-4H-isoquinoline-1,3-dione;
4-{[3-(2,2,2-Trifluoro-ethylamino)-benzylamino]-methylene}-4H-isoquinoline-1,3-dione;
4-[(4-Methylamino-benzylamino)-methylene]-4H-isoquinoline-1,3-dione;

2,2,2-Trifluoro-ethanesulfonic acid 4-[(1,3-dioxo-2,3-dihydro-1H-isoquinolin-4-ylidenemethyl)-amino]-benzylamide;

4-{[(1,3-Dioxo-2,3-dihydro-1H-isoquinolin-4-ylidenemethyl)-amino]-methyl}-N-ethyl-benzenesulfonamide;

4-{[(1,3-Dioxo-2,3-dihydro-1H-isoquinolin-4-ylidenemethyl)-amino]-methyl}-N-pyridin-3-ylmethyl-benzenesulfonamide;

6-Diethylamino-4-[(3,4-dihydroxy-benzylamino)-methylene]-4H-isoquinoline-1,3-dione;

6-(1,3-Dihydro-isoindol-2-yl)-4-[(3,4-dihydroxy-benzylamino)-methylene]-4H-isoquinoline-1,3-dione;

6-[Bis-(3,3,3-trifluoro-propyl)-amino]-4-[(3,4-dihydroxy-benzylamino)-methylene]-4H-isoquinoline-1,3-dione;

N-{4-[(1,3-Dioxo-2,3-dihydro-1H-isoquinolin-4-ylidenemethyl)-amino]-benzyl}-methanesulfonamide;

Ethanesulfonic acid 4-[(1,3-dioxo-2,3-dihydro-1H-isoquinolin-4-ylidenemethyl)-amino]-benzylamide;

4-[(4-Dipropylaminomethyl-phenylamino)-methylene]-4H-isoquinoline-1,3-dione;

4-{[4-(3-Hydroxy-piperidin-1-ylmethyl)-phenylamino]-methylene}-4H-isoquinoline-1,3-dione;

4-[(4-{[(2-Methoxy-ethyl)-methyl-amino]-methyl}-phenylamino)-methylene]-4H-isoquinoline-1,3-dione;

4-{[4-(2-Methyl-pyrrolidin-1-ylmethyl)-phenylamino]-methylene}-4H-isoquinoline-1,3-dione;

4-(Pyridin-4-ylaminomethylene)-4H-isoquinoline-1,3-dione;

4-[(5-Hydroxy-naphthalen-1-ylamino)-methylene]-4H-isoquinoline-1,3-dione;

4-[(3,4-Dihydroxy-benzylamino)-methylene]-6-phenyl-4H-isoquinoline-1,3-dione;

4-[(3,4-Dihydroxy-benzylamino)-methylene]-6-furan-2-yl-4H-isoquinoline-1,3-dione;

6-(3-Phenyl-propenyl)-4-[(4-pyrrolidin-1-ylmethyl-phenylamino)-methylene]-4H-isoquinoline-1,3-dione;

{4-[(6-Naphthalen-1-yl-1,3-dioxo-2,3-dihydro-1H-isoquinolin-4-ylidenemethyl)-amino]-phenyl}-acetonitrile;

{4-[(6-Naphthalen-2-yl-1,3-dioxo-2,3-dihydro-1H-isoquinolin-4-ylidenemethyl)-amino]-phenyl}-acetonitrile;

{4-[(1,3-Dioxo-6-quinolin-8-yl-2,3-dihydro-1H-isoquinolin-4-ylidenemethyl)-amino]-phenyl}-acetonitrile;

{4-[(6-Benzofuran-2-yl-1,3-dioxo-2,3-dihydro-1H-isoquinolin-4-ylidenemethyl)-amino]-phenyl}-acetonitrile;

{4-[(6-Benzo[b]thiophen-2-yl-1,3-dioxo-2,3-dihydro-1H-isoquinolin-4-ylidenemethyl)-amino]-phenyl}-acetonitrile;

{4-[(6-Benzo[b]thiophen-3-yl-1,3-dioxo-2,3-dihydro-1H-isoquinolin-4-ylidenemethyl)-amino]-phenyl}-acetonitrile;

(4-{[6-(1H-Indol-5-yl)-1,3-dioxo-2,3-dihydro-1H-isoquinolin-4-ylidenemethyl]-amino}-phenyl)-acetonitrile;

(4-{[1,3-Dioxo-6-(1H-pyrrol-2-yl)-2,3-dihydro-1H-isoquinolin-4-ylidenemethyl]-amino}-phenyl)-acetonitrile;

(4-{[1,3-Dioxo-6-(1H-pyrrol-3-yl)-2,3-dihydro-1H-isoquinolin-4-ylidenemethyl]-amino}-phenyl)-acetonitrile;

4-{[(6-Naphthalen-2-yl-1,3-dioxo-2,3-dihydro-1H-isoquinolin-4-ylidenemethyl)-amino]-methyl}-benzenesulfonamide;

4-{[(1,3-Dioxo-6-quinolin-8-yl-2,3-dihydro-1H-isoquinolin-4-ylidenemethyl)-amino]-methyl}-benzenesulfonamide;

4-{[(6-Benzofuran-2-yl-1,3-dioxo-2,3-dihydro-1H-isoquinolin-4-ylidenemethyl)-amino]-methyl}-benzenesulfonamide;

4-{[(6-Benzo[b]thiophen-2-yl-1,3-dioxo-2,3-dihydro-1H-isoquinolin-4-ylidenemethyl)-amino]-methyl}-benzenesulfonamide;

4-{[(6-Benzo[b]thiophen-3-yl-1,3-dioxo-2,3-dihydro-1H-isoquinolin-4-ylidenemethyl)-amino]-methyl}-benzenesulfonamide;

4-({[6-(1H-Indol-5-yl)-1,3-dioxo-2,3-dihydro-1H-isoquinolin-4-ylidenemethyl]-amino}-methyl)-benzenesulfonamide;

4-({[1,3-Dioxo-6-(1H-pyrrol-2-yl)-2,3-dihydro-1H-isoquinolin-4-ylidenemethyl]-amino}-methyl)-benzenesulfonamide;

4-({[1,3-Dioxo-6-(1H-pyrrol-3-yl)-2,3-dihydro-1H-isoquinolin-4-ylidenemethyl]-amino}-methyl)-benzenesulfonamide;

4-[(3,4-Dihydroxy-benzylamino)-methylene]-6-naphthalen-1-yl-4H-isoquinoline-1,3-dione;

4-[(3,4-Dihydroxy-benzylamino)-methylene]-6-naphthalen-2-yl-4H-isoquinoline-1,3-dione;

4-[(3,4-Dihydroxy-benzylamino)-methylene]-6-quinolin-8-yl-4H-isoquinoline-1,3-dione;

6-Benzofuran-2-yl-4-[(3,4-dihydroxy-benzylamino)-methylene]-4H-isoquinoline-1,3-dione;

6-Benzo[b]thiophen-2-yl-4-[(3,4-dihydroxy-benzylamino)-methylene]-4H-isoquinoline-1,3-dione;

6-Benzo[b]thiophen-3-yl-4-[(3,4-dihydroxy-benzylamino)-methylene]-4H-isoquinoline-1,3-dione;

4-[(3,4-Dihydroxy-benzylamino)-methylene]-6-(1H-indol-5-yl)-4H-isoquinoline-1,3-dione;

4-[(3,4-Dihydroxy-benzylamino)-methylene]-6-(1H-pyrrol-2-yl)-4H-isoquinoline-1,3-dione;

(4-{[1,3-Dioxo-6-(2-pyridin-2-yl-vinyl)-2,3-dihydro-1H-isoquinolin-4-ylidenemethyl]-amino}-phenyl)-acetonitrile;

(4-{[1,3-Dioxo-6-(2-pyridin-4-yl-vinyl)-2,3-dihydro-1H-isoquinolin-4-ylidenemethyl]-amino}-phenyl)-acetonitrile;

{4-[(1,3-Dioxo-6-styryl-2,3-dihydro-1H-isoquinolin-4-ylidenemethyl)-amino]-phenyl}-acetonitrile;

(4-{[6-(2-Imidazol-1-yl-vinyl)-1,3-dioxo-2,3-dihydro-1H-isoquinolin-4-ylidenemethyl]-amino}-phenyl)-acetonitrile;

4-({[1,3-Dioxo-6-(2-pyridin-2-yl-vinyl)-2,3-dihydro-1H-isoquinolin-4-ylidenemethyl]-amino}-methyl)-benzenesulfonamide;

4-({[1,3-Dioxo-6-(2-pyridin-4-yl-vinyl)-2,3-dihydro-1H-isoquinolin-4-ylidenemethyl]-amino}-methyl)-benzenesulfonamide;

4-{[(1,3-Dioxo-6-styryl-2,3-dihydro-1H-isoquinolin-4-ylidenemethyl)-amino]-methyl}-benzenesulfonamide;

4-({[1,3-Dioxo-6-(2-pyrazin-2-yl-vinyl)-2,3-dihydro-1H-isoquinolin-4-ylidenemethyl]-amino}-methyl)-benzenesulfonamide;

4-({[6-(2-Cyclohexyl-vinyl)-1,3-dioxo-2,3-dihydro-1H-isoquinolin-4-ylidenemethyl]-amino}-methyl)-benzenesulfonamide;

4-({[6-(3-Imidazol-1-yl-propenyl)-1,3-dioxo-2,3-dihydro-1H-isoquinolin-4-ylidenemethyl]-amino}-methyl)-benzenesulfonamide;

4-({[6-(2-Imidazol-1-yl-vinyl)-1,3-dioxo-2,3-dihydro-1H-isoquinolin-4-ylidenemethyl]-amino}-methyl)-benzenesulfonamide;

4-[({6-[2-(4-Methyl-thiazol-5-yl)-vinyl]-1,3-dioxo-2,3-dihydro-1H-isoquinolin-4-ylidenemethyl}-amino)-methyl]-benzenesulfonamide;

4-[(3,4-Dihydroxy-benzylamino)-methylene]-6-(3-phenyl-propenyl)-4H-isoquinoline-1,3-dione;

4-[(3,4-Dihydroxy-benzylamino)-methylene]-6-(2-naphthalen-2-yl-vinyl)-4H-isoquinoline-1,3-dione;
4-[(3,4-Dihydroxy-benzylamino)-methylene]-6-(2-pyridin-2-yl-vinyl)-4H-isoquinoline-1,3-dione;
4-[(3,4-Dihydroxy-benzylamino)-methylene]-6-(2-pyridin-4-yl-vinyl)-4H-isoquinoline-1,3-dione;
6-(2-Cyclohexyl-vinyl)-4-[(3,4-dihydroxy-benzylamino)-methylene]-4H-isoquinoline-1,3-dione;
4-[(3,4-Dihydroxy-benzylamino)-methylene]-6-(3-imidazol-1-yl-propenyl)-4H-isoquinoline-1,3-dione;
4-[(3,4-Dihydroxy-benzylamino)-methylene]-6-(3-piperazin-1-yl-propenyl)-4H-isoquinoline-1,3-dione;
4-[(3,4-Dihydroxy-benzylamino)-methylene]-6-(2-imidazol-1-yl-vinyl)-4H-isoquinoline-1,3-dione;
4-{[4-(4-Methyl-piperazin-1-yl)-phenylamino]-methylene}-6-naphthalen-2-yl-4H-isoquinoline-1,3-dione;
6-Benzofuran-2-yl-4-{[4-(4-methyl-piperazin-1-yl)-phenylamino]-methylene}-4H-isoquinoline-1,3-dione;
6-Benzo[b]thiophen-2-yl-4-{[4-(4-methyl-piperazin-1-yl)-phenylamino]-methylene}-4H-isoquinoline-1,3-dione;
6-(1H-Indol-5-yl)-4-{[4-(4-methyl-piperazin-1-yl)-phenylamino]-methylene}-4H-isoquinoline-1,3-dione;
4-{[4-(4-Methyl-piperazin-1-yl)-phenylamino]-methylene}-6-(1H-pyrrol-2-yl)-4H-isoquinoline-1,3-dione;
4-{[4-(4-Methyl-piperazin-1-yl)-phenylamino]-methylene}-6-(1H-pyrrol-3-yl)-4H-isoquinoline-1,3-dione;
4-{[4-(4-Methyl-piperazin-1-yl)-phenylamino]-methylene}-6-(2-naphthalen-2-yl-vinyl)-4H-isoquinoline-1,3-dione;
4-{[4-(4-Methyl-piperazin-1-yl)-phenylamino]-methylene}-6-(2-pyridin-2-yl-vinyl)-4H-isoquinoline-1,3-dione;
4-{[4-(4-Methyl-piperazin-1-yl)-phenylamino]-methylene}-6-(2-pyridin-4-yl-vinyl)-4H-isoquinoline-1,3-dione;
4-{[4-(4-Methyl-piperazin-1-yl)-phenylamino]-methylene}-6-styryl-4H-isoquinoline-1,3-dione;
4-{[4-(4-Methyl-piperazin-1-yl)-phenylamino]-methylene}-6-(2-pyrazin-2-yl-vinyl)-4H-isoquinoline-1,3-dione;
6-(3-Imidazol-1-yl-propenyl)-4-{[4-(4-methyl-piperazin-1-yl)-phenylamino]-methylene}-4H-isoquinoline-1,3-dione;
6-(2-Imidazol-1-yl-vinyl)-4-{[4-(4-methyl-piperazin-1-yl)-phenylamino]-methylene}-4H-isoquinoline-1,3-dione;
4-{[4-(4-Methyl-piperazin-1-yl)-phenylamino]-methylene}-6-[2-(4-methyl-thiazol-5-yl)-vinyl]-4H-isoquinoline-1,3-dione;
6-(4-Methoxy-phenyl)-4-{[4-(4-methyl-piperazin-1-yl)-phenylamino]-methylene}-4H-isoquinoline-1,3-dione;
6-(2-Methoxy-phenyl)-4-{[4-(4-methyl-piperazin-1-yl)-phenylamino]-methylene}-4H-isoquinoline-1,3-dione;
6-(2-Fluoro-phenyl)-4-{[4-(4-methyl-piperazin-1-yl)-phenylamino]-methylene}-4H-isoquinoline-1,3-dione;
4-(4-{[4-(4-Methyl-piperazin-1-yl)-phenylamino]-methylene}-1,3-dioxo-1,2,3,4-tetrahydro-isoquinolin-6-yl)-benzoic acid;
3-(4-{[4-(4-Methyl-piperazin-1-yl)-phenylamino]-methylene}-1,3-dioxo-1,2,3,4-tetrahydro-isoquinolin-6-yl)-benzoic acid;
4-{[4-(4-Methyl-piperazin-1-yl)-phenylamino]-methylene}-6-(4-trifluoromethyl-phenyl)-4H-isoquinoline-1,3-dione;
6-(4-Acetyl-phenyl)-4-{[4-(4-methyl-piperazin-1-yl)-phenylamino]-methylene}-4H-isoquinoline-1,3-dione;
6-(4-Chloro-phenyl)-4-{[4-(4-methyl-piperazin-1-yl)-phenylamino]-methylene}-4H-isoquinoline-1,3-dione;
6-(3-Chloro-phenyl)-4-{[4-(4-methyl-piperazin-1-yl)-phenylamino]-methylene}-4H-isoquinoline-1,3-dione;
6-(2-Chloro-phenyl)-4-{[4-(4-methyl-piperazin-1-yl)-phenylamino]-methylene}-4H-isoquinoline-1,3-dione;
4-{[4-(4-Methyl-piperazin-1-yl)-phenylamino]-methylene}-6-p-tolyl-4H-isoquinoline-1,3-dione;
4-{[4-(4-Methyl-piperazin-1-yl)-phenylamino]-methylene}-6-m-tolyl-4H-isoquinoline-1,3-dione;
4-{[4-(4-Methyl-piperazin-1-yl)-phenylamino]-methylene}-6-o-tolyl-4H-isoquinoline-1,3-dione;
3-(4-{[4-(4-Methyl-piperazin-1-yl)-phenylamino]-methylene}-1,3-dioxo-1,2,3,4-tetrahydro-isoquinolin-6-yl)-benzonitrile;
6-Biphenyl-4-yl-4-{[4-(4-methyl-piperazin-1-yl)-phenylamino]-methylene}-4H-isoquinoline-1,3-dione;
6-Biphenyl-3-yl-4-{[4-(4-methyl-piperazin-1-yl)-phenylamino]-methylene}-4H-isoquinoline-1,3-dione;
3-[4-(4-{[4-(4-Methyl-piperazin-1-yl)-phenylamino]-methylene}-1,3-dioxo-1,2,3,4-tetrahydro-isoquinolin-6-yl)-phenyl]-acrylic acid;
3-[3-(4-{[4-(4-Methyl-piperazin-1-yl)-phenylamino]-methylene}-1,3-dioxo-1,2,3,4-tetrahydro-isoquinolin-6-yl)-phenyl]-acrylic acid;
4-{[4-(4-Methyl-piperazin-1-yl)-phenylamino]-methylene}-6-(4-methylsulfanyl-phenyl)-4H-isoquinoline-1,3-dione;
(4-{[6-(4-Methoxy-phenyl)-1,3-dioxo-2,3-dihydro-1H-isoquinolin-4-ylidenemethyl]-amino}-phenyl)-acetonitrile;
(4-{[6-(3-Methoxy-phenyl)-1,3-dioxo-2,3-dihydro-1H-isoquinolin-4-ylidenemethyl]-amino}-phenyl)-acetonitrile;
(4-{[6-(2-Methoxy-phenyl)-1,3-dioxo-2,3-dihydro-1H-isoquinolin-4-ylidenemethyl]-amino}-phenyl)-acetonitrile;
(4-{[6-(4-Fluoro-phenyl)-1,3-dioxo-2,3-dihydro-1H-isoquinolin-4-ylidenemethyl]-amino}-phenyl)-acetonitrile;
(4-{[6-(3-Fluoro-phenyl)-1,3-dioxo-2,3-dihydro-1H-isoquinolin-4-ylidenemethyl]-amino)-phenyl)-acetonitrile;
(4-{[6-(2-Fluoro-phenyl)-1,3-dioxo-2,3-dihydro-1H-isoquinolin-4-ylidenemethyl]-amino}-phenyl)-acetonitrile;
4-{4-[(4-Cyanomethyl-phenylamino)-methylene]-1,3-dioxo-1,2,3,4-tetrahydro-isoquinolin-6-yl}-benzoic acid;
3-{4-[(4-Cyanomethyl-phenylamino)-methylene]-1,3-dioxo-1,2,3,4-tetrahydro-isoquinolin-6-yl}-benzoic acid;
(4-{[1,3-Dioxo-6-(4-trifluoromethyl-phenyl)-2,3-dihydro-1H-isoquinolin-4-ylidenemethyl]-amino}-phenyl)-acetonitrile;
(4-{[6-(4-Acetyl-phenyl)-1,3-dioxo-2,3-dihydro-1H-isoquinolin-4-ylidenemethyl]-amino}-phenyl)-acetonitrile;
(4-{[6-(2-Acetyl-phenyl)-1,3-dioxo-2,3-dihydro-1H-isoquinolin-4-ylidenemethyl]-amino}-phenyl)-acetonitrile;
(4-{[6-(4-Chloro-phenyl)-1,3-dioxo-2,3-dihydro-1H-isoquinolin-4-ylidenemethyl]-amino}-phenyl)-acetonitrile;
(4-{[6-(3-Chloro-phenyl)-1,3-dioxo-2,3-dihydro-1H-isoquinolin-4-ylidenemethyl]-amino}-phenyl)-acetonitrile;
(4-{[6-(2-Chloro-phenyl)-1,3-dioxo-2,3-dihydro-1H-isoquinolin-4-ylidenemethyl]-amino}-phenyl)-acetonitrile;
{4-[(1,3-Dioxo-6-p-tolyl-2,3-dihydro-1H-isoquinolin-4-ylidenemethyl)-amino]-phenyl}-acetonitrile;
{4-[(1,3-Dioxo-6-m-tolyl-2,3-dihydro-1H-isoquinolin-4-ylidenemethyl)-amino]-phenyl}-acetonitrile;
{4-[(1,3-Dioxo-6-o-tolyl-2,3-dihydro-1H-isoquinolin-4-ylidenemethyl)-amino]-phenyl}-acetonitrile;
4-{4-[(4-Cyanomethyl-phenylamino)-methylene]-1,3-dioxo-1,2,3,4-tetrahydro-isoquinolin-6-yl}-benzonitrile;
3-{4-[(4-Cyanomethyl-phenylamino)-methylene]-1,3-dioxo-1,2,3,4-tetrahydro-isoquinolin-6-yl}-benzonitrile;
{4-[(6-Biphenyl-4-yl-1,3-dioxo-2,3-dihydro-1H-isoquinolin-4-ylidenemethyl)-amino]-phenyl}-acetonitrile;
{4-[(6-Biphenyl-3-yl-1,3-dioxo-2,3-dihydro-1H-isoquinolin-4-ylidenemethyl)-amino]-phenyl}-acetonitrile;

(4-{[6-(4-Isopropyl-phenyl)-1,3-dioxo-2,3-dihydro-1H-isoquinolin-4-ylidenemethyl]-amino}-phenyl)-acetonitrile;

(4-{[6-(4-Methylsulfanyl-phenyl)-1,3-dioxo-2,3-dihydro-1H-isoquinolin-4-ylidenemethyl]-amino}-phenyl)-acetonitrile;

6-(3-Hydroxy-propenyl)-4-{[4-(4-methyl-piperazin-1-yl)-phenylamino]-methylene}-4H-isoquinoline-1,3-dione;

6-[2-(4-Amino-phenyl)-vinyl]-4-{[4-(4-methyl-piperazin-1-yl)-phenylamino]-methylene}-4H-isoquinoline-1,3-dione;

6-[2-(4-Chloro-phenyl)-vinyl]-4-{[4-(4-methyl-piperazin-1-yl)-phenylamino]-methylene}-4H-isoquinoline-1,3-dione;

4-[2-(4-{[4-(4-Methyl-piperazin-1-yl)-phenylamino]-methylene}-1,3-dioxo-1,2,3,4-tetrahydro-isoquinolin-6-yl)-vinyl]-benzoic acid;

4-[2-(4-{[4-(4-Methyl-piperazin-1-yl)-phenylamino]-methylene}-1,3-dioxo-1,2,3,4-tetrahydro-isoquinolin-6-yl)-vinyl]-benzenesulfonamide;

4-{[4-(4-Methyl-piperazin-1-yl)-phenylamino]-methylene}-6-[2-(4-trifluoromethyl-phenyl)-vinyl]-4H-isoquinoline-1,3-dione;

6-(3,4-Dihydroxy-but-1-enyl)-4-{[4-(4-methyl-piperazin-1-yl)-phenylamino]-methylene}-4H-isoquinoline-1,3-dione;

6-[2-(4-Fluoro-phenyl)-vinyl]-4-{[4-(4-methyl-piperazin-1-yl)-phenylamino]-methylene}-4H-isoquinoline-1,3-dione;

6-[2-(4-Methoxy-phenyl)-vinyl]-4-{[4-(4-methyl-piperazin-1-yl)-phenylamino]-methylene}-4H-isoquinoline-1,3-dione;

4-[(3-Hydroxy-4-methoxy-benzylamino)-methylene]-6-(2-imidazol-1-yl-vinyl)-4H-isoquinoline-1,3-dione;

4-[(3-Hydroxy-4-methoxy-benzylamino)-methylene]-6-(2-imidazol-1-yl-vinyl)-4H-isoquinoline-1,3-dione;

4-[(3-Hydroxy-4-methoxy-benzylamino)-methylene]-6-(2-pyridin-2-yl-vinyl)-4H-isoquinoline-1,3-dione;

4-[(3,4-Dihydroxy-benzylamino)-methylene]-6-[2-(4-dimethylaminomethyl-phenyl)-vinyl]-4H-isoquinoline-1,3-dione;

4-({[6-(3-Methoxy-phenyl)-1,3-dioxo-2,3-dihydro-1H-isoquinolin-4-ylidenemethyl]-amino}-methyl)-benzenesulfonamide;

4-({[6-(4-Fluoro-phenyl)-1,3-dioxo-2,3-dihydro-1H-isoquinolin-4-ylidenemethyl]-amino}-methyl)-benzenesulfonamide;

4-({[6-(3-Fluoro-phenyl)-1,3-dioxo-2,3-dihydro-1H-isoquinolin-4-ylidenemethyl]-amino}-methyl)-benzenesulfonamide;

4-({[6-(2-Fluoro-phenyl)-1,3-dioxo-2,3-dihydro-1H-isoquinolin-4-ylidenemethyl]-amino}-methyl)-benzenesulfonamide;

4-{1,3-Dioxo-4-[(4-sulfamoyl-benzylamino)-methylene]-1,2,3,4-tetrahydro-isoquinolin-6-yl}-benzoic acid;

3-{1,3-Dioxo-4-[(4-sulfamoyl-benzylamino)-methylene]-1,2,3,4-tetrahydro-isoquinolin-6-yl}-benzoic acid;

4-({[1,3-Dioxo-6-(4-trifluoromethyl-phenyl)-2,3-dihydro-1H-isoquinolin-4-ylidenemethyl]-amino}-methyl)-benzenesulfonamide;

4-({[1,3-Dioxo-6-(3-trifluoromethyl-phenyl)-2,3-dihydro-1H-isoquinolin-4-ylidenemethyl]-amino}-methyl)-benzenesulfonamide;

4-({[1,3-Dioxo-6-(2-trifluoromethyl-phenyl)-2,3-dihydro-1H-isoquinolin-4-ylidenemethyl]-amino}-methyl)-benzenesulfonamide;

4-({[6-(4-Acetyl-phenyl)-1,3-dioxo-2,3-dihydro-1H-isoquinolin-4-ylidenemethyl]-amino}-methyl)-benzenesulfonamide;

4-({[6-(3-Acetyl-phenyl)-1,3-dioxo-2,3-dihydro-1H-isoquinolin-4-ylidenemethyl]-amino}-methyl)-benzenesulfonamide;

4-({[6-(2-Acetyl-phenyl)-1,3-dioxo-2,3-dihydro-1H-isoquinolin-4-ylidenemethyl]-amino}-methyl)-benzenesulfonamide;

4-({[6-(4-Chloro-phenyl)-1,3-dioxo-2,3-dihydro-1H-isoquinolin-4-ylidenemethyl]-amino}-methyl)-benzenesulfonamide;

4-({[6-(3-Chloro-phenyl)-1,3-dioxo-2,3-dihydro-1H-isoquinolin-4-ylidenemethyl]-amino}-methyl)-benzenesulfonamide;

4-({[6-(2-Chloro-phenyl)-1,3-dioxo-2,3-dihydro-1H-isoquinolin-4-ylidenemethyl]-amino}-methyl)-benzenesulfonamide;

4-{[(1,3-Dioxo-6-p-tolyl-2,3-dihydro-1H-isoquinolin-4-ylidenemethyl)-amino]-methyl}-benzenesulfonamide;

4-{[(1,3-Dioxo-6-m-tolyl-2,3-dihydro-1H-isoquinolin-4-ylidenemethyl)-amino]-methyl}-benzenesulfonamide;

4-{[(1,3-Dioxo-6-o-tolyl-2,3-dihydro-1H-isoquinolin-4-ylidenemethyl)-amino]-methyl}-benzenesulfonamide;

4-({[6-(4-Cyano-phenyl)-1,3-dioxo-2,3-dihydro-1H-isoquinolin-4-ylidenemethyl]-amino}-methyl)-benzenesulfonamide;

4-({[6-(3-Cyano-phenyl)-1,3-dioxo-2,3-dihydro-1H-isoquinolin-4-ylidenemethyl]-amino}-methyl)-benzenesulfonamide;

4-{[(6-Biphenyl-4-yl-1,3-dioxo-2,3-dihydro-1H-isoquinolin-4-ylidenemethyl)-amino]-methyl}-benzenesulfonamide;

4-{[(6-Biphenyl-3-yl-1,3-dioxo-2,3-dihydro-1H-isoquinolin-4-ylidenemethyl)-amino]-methyl}-benzenesulfonamide;

3-(4-{1,3-Dioxo-4-[(4-sulfamoyl-benzylamino)-methylene]-1,2,3,4-tetrahydro-isoquinolin-6-yl}-phenyl)-acrylic acid;

3-(3-{1,3-Dioxo-4-[(4-sulfamoyl-benzylamino)-methylene]-1,2,3,4-tetrahydro-isoquinolin-6-yl}-phenyl)-acrylic acid;

4-({[6-(4-Isopropyl-phenyl)-1,3-dioxo-2,3-dihydro-1H-isoquinolin-4-ylidenemethyl]-amino}-methyl)-benzenesulfonamide;

4-({[6-(3-Isopropyl-phenyl)-1,3-dioxo-2,3-dihydro-1H-isoquinolin-4-ylidenemethyl]-amino}-methyl)-benzenesulfonamide;

4-({[6-(4-Methylsulfanyl-phenyl)-1,3-dioxo-2,3-dihydro-1H-isoquinolin-4-ylidenemethyl]-amino}-methyl)-benzenesulfonamide;

4-[(3,4-Dihydroxy-benzylamino)-methylene]-6-(4-methoxy-phenyl)-4H-isoquinoline-1,3-dione;

4-[(3,4-Dihydroxy-benzylamino)-methylene]-6-(3-methoxy-phenyl)-4H-isoquinoline-1,3-dione;

4-[(3,4-Dihydroxy-benzylamino)-methylene]-6-(2-methoxy-phenyl)-4H-isoquinoline-1,3-dione;

4-[(3,4-Dihydroxy-benzylamino)-methylene]-6-(4-fluoro-phenyl)-4H-isoquinoline-1,3-dione;

4-[(3,4-Dihydroxy-benzylamino)-methylene]-6-(3-fluoro-phenyl)-4H-isoquinoline-1,3-dione;

4-[(3,4-Dihydroxy-benzylamino)-methylene]-6-(2-fluoro-phenyl)-4H-isoquinoline-1,3-dione;

4-{4-[(3,4-Dihydroxy-benzylamino)-methylene]-1,3-dioxo-1,2,3,4-tetrahydro-isoquinolin-6-yl}-benzoic acid;

3-{4-[(3,4-Dihydroxy-benzylamino)-methylene]-1,3-dioxo-1,2,3,4-tetrahydro-isoquinolin-6-yl}-benzoic acid;

4-[(3,4-Dihydroxy-benzylamino)-methylene]-6-(4-trifluoromethyl-phenyl)-4H-isoquinoline-1,3-dione;
4-[(3,4-Dihydroxy-benzylamino)-methylene]-6-(3-trifluoromethyl-phenyl)-4H-isoquinoline-1,3-dione;
4-[(3,4-Dihydroxy-benzylamino)-methylene]-6-(2-trifluoromethyl-phenyl)-4H-isoquinoline-1,3-dione;
6-(4-Acetyl-phenyl)-4-[(3,4-dihydroxy-benzylamino)-methylene]-4H-isoquinoline-1,3-dione;
6-(3-Acetyl-phenyl)-4-[(3,4-dihydroxy-benzylamino)-methylene]-4H-isoquinoline-1,3-dione;
6-(2-Acetyl-phenyl)-4-[(3,4-dihydroxy-benzylamino)-methylene]-4H-isoquinoline-1,3-dione;
6-(4-Chloro-phenyl)-4-[(3,4-dihydroxy-benzylamino)-methylene]-4H-isoquinoline-1,3-dione;
6-(3-Chloro-phenyl)-4-[(3,4-dihydroxy-benzylamino)-methylene]-4H-isoquinoline-1,3-dione;
6-(2-Chloro-phenyl)-4-[(3,4-dihydroxy-benzylamino)-methylene]-4H-isoquinoline-1,3-dione;
4-[(3,4-Dihydroxy-benzylamino)-methylene]-6-p-toly-4H-isoquinoline-1,3-dione;
4-[(3,4-Dihydroxy-benzylamino)-methylene]-6-m-tolyl-4H-isoquinoline-1,3-dione;
4-[(3,4-Dihydroxy-benzylamino)-methylene]-6-o-tolyl-4H-isoquinoline-1,3-dione;
4-{4-[(3,4-Dihydroxy-benzylamino)-methylene]-1,3-dioxo-1,2,3,4-tetrahydro-isoquinolin-6-yl}-benzonitrile;
3-{4-[(3,4-Dihydroxy-benzylamino)-methylene]-1,3-dioxo-1,2,3,4-tetrahydro-isoquinolin-6-yl}-benzonitrile;
6-Biphenyl-4-yl-4-[(3,4-dihydroxy-benzylamino)-methylene]-4H-isoquinoline-1,3-dione;
6-Biphenyl-3-yl-4-[(3,4-dihydroxy-benzylamino)-methylene]-4H-isoquinoline-1,3-dione;
3-(4-{4-[(3,4-Dihydroxy-benzylamino)-methylene]-1,3-dioxo-1,2,3,4-tetrahydro-isoquinolin-6-yl}-phenyl)-acrylic acid;
3-(3-{4-[(3,4-Dihydroxy-benzylamino)-methylene]-1,3-dioxo-1,2,3,4-tetrahydro-isoquinolin-6-yl}-phenyl)-acrylic acid;
4-[(3,4-Dihydroxy-benzylamino)-methylene]-6-(4-isopropyl-phenyl)-4H-isoquinoline-1,3-dione;
4-[(3,4-Dihydroxy-benzylamino)-methylene]-6-(3-isopropyl-phenyl)-4H-isoquinoline-1,3-dione;
4-[(3,4-Dihydroxy-benzylamino)-methylene]-6-(4-methylsulfanyl-phenyl)-4H-isoquinoline-1,3-dione;
4-[(3,4-Dihydroxy-benzylamino)-methylene]-6-(2-methylsulfanyl-phenyl)-4H-isoquinoline-1,3-dione;
6-[2-(2-Diethylamino-ethoxy)-vinyl]-4-{[4-(4-methyl-piperazin-1-yl)-phenylamino]-methylene}-4H-isoquinoline-1,3-dione;
5-(4-{[4-(4-Methyl-piperazin-1-yl)-phenylamino]-methylene}-1,3-dioxo-1,2,3,4-tetrahydro-isoquinolin-6-yl)-pent-4-enoic acid;
6-(4-Hydroxy-but-1-enyl)-4-{[4-(4-methyl-piperazin-1-yl)-phenylamino]-methylene}-4H-isoquinoline-1,3-dione;
6-(5-Hydroxy-pent-1-enyl)-4-{[4-(4-methyl-piperazin-1-yl)-phenylamino]-methylene}-4H-isoquinoline-1,3-dione;
6-(6-Hydroxy-hex-1-enyl)-4-{[4-(4-methyl-piperazin-1-yl)-phenylamino]-methylene}-4H-isoquinoline-1,3-dione;
6-[3-(2-Hydroxy-ethoxy)-propenyl]-4-{[4-(4-methyl-piperazin-1-yl)-phenylamino]-methylene}-4H-isoquinoline-1,3-dione;
6-[3-(2,4-Dioxo-imidazolidin-1-yl)-propenyl]-4-{[4-(4-methyl-piperazin-1-yl)-phenylamino]-methylene}-4H-isoquinoline-1,3-dione;
6-[3-(2-Hydroxy-phenyl)-propenyl]-4-{[4-(4-methyl-piperazin-1-yl)-phenylamino]-methylene}-4H-isoquinoline-1,3-dione;
2-Methyl-3-(4-{[4-(4-methyl-piperazin-1-yl)-phenylamino]-methylene}-1,3-dioxo-1,2,3,4-tetrahydro-isoquinolin-6-yl)-but-2-enenitrile;
{4-[2-(4-{[4-(4-Methyl-piperazin-1-yl)-phenylamino]-methylene}-1,3-dioxo-1,2,3,4-tetrahydro-isoquinolin-6-yl)-vinyl]-phenyl}-acetonitrile;
4-[(3,4-Dihydroxy-benzylamino)-methylene]-6-[3-(2-hydroxy-3-methoxy-phenyl)-propenyl]-4H-isoquinoline-1,3-dione;
[4-(2-{4-[(3,4-Dihydroxy-benzylamino)-methylene]-1,3-dioxo-1,2,3,4-tetrahydro-isoquinolin-6-yl}-vinyl)-phenyl]-acetonitrile;
6-Benzo[1,3]dioxol-5-yl-4-{[4-(4-methyl-piperazin-1-yl)-phenylamino]-methylene}-4H-isoquinoline-1,3-dione;
6-(4-Dimethylamino-phenyl)-4-{[4-(4-methyl-piperazin-1-yl)-phenylamino]-methylene}-4H-isoquinoline-1,3-dione;
6-(4-Hydroxymethyl-phenyl)-4-{[4-(4-methyl-piperazin-1-yl)-phenylamino]-methylene}-4H-isoquinoline-1,3-dione;
3-[4-(4-{[4-(4-Methyl-piperazin-1-yl)-phenylamino]-methylene}-1,3-dioxo-1,2,3,4-tetrahydro-isoquinolin-6-yl)-phenyl]-propionic acid;
6-(3-Amino-phenyl)-4-{[4-(4-methyl-piperazin-1-yl)-phenylamino]-methylene}-4H-isoquinoline-1,3-dione;
6-(2,4-Dichloro-phenyl)-4-{[4-(4-methyl-piperazin-1-yl)-phenylamino]-methylene}-4H-isoquinoline-1,3-dione;
6-Benzo[1,3]dioxol-5-yl-4-[(3,4-dihydroxy-benzylamino)-methylene]-4H-isoquinoline-1,3-dione;
4-[(3,4-Dihydroxy-benzylamino)-methylene]-6-(3,4-dimethoxy-phenyl)-4H-isoquinoline-1,3-dione;
4-[(3,4-Dihydroxy-benzylamino)-methylene]-6-(2,4-dimethoxy-phenyl)-4H-isoquinoline-1,3-dione;
4-[(3,4-Dihydroxy-benzylamino)-methylene]-6-(3,4,5-trimethoxy-phenyl)-4H-isoquinoline-1,3-dione;
4-[(3,4-Dihydroxy-benzylamino)-methylene]-6-(4-dimethylamino-phenyl)-4H-isoquinoline-1,3-dione;
4-[(3,4-Dihydroxy-benzylamino)-methylene]-6-(4-hydroxymethyl-phenyl)-4H-isoquinoline-1,3-dione;
4-[(3,4-Dihydroxy-benzylamino)-methylene]-6-(4-trifluoromethoxy-phenyl)-4H-isoquinoline-1,3-dione;
3-(4-{4-[(3,4-Dihydroxy-benzylamino)-methylene]-1,3-dioxo-1,2,3,4-tetrahydro-isoquinolin-6-yl}-phenyl)-propionic acid;
4-[(3,4-Dihydroxy-benzylamino)-methylene]-6-(3-nitro-phenyl)-4H-isoquinoline-1,3-dione;
6-(3-Amino-phenyl)-4-[(3,4-dihydroxy-benzylamino)-methylene]-4H-isoquinoline-1,3-dione;
N-(3-{4-[(3,4-Dihydroxy-benzylamino)-methylene]-1,3-dioxo-1,2,3,4-tetrahydro-isoquinolin-6-yl}-phenyl)-acetamide;
6-(2,4-Dichloro-phenyl)-4-[(3,4-dihydroxy-benzylamino)-methylene]-4H-isoquinoline-1,3-dione;
4-[(3-Hydroxy-4-methoxy-benzylamino)-methylene]-6-(2-pyridin-4-yl-vinyl)-4H-isoquinoline-1,3-dione;
4-[(3-Hydroxy-4-methoxy-benzylamino)-methylene]-6-styryl-4H-isoquinoline-1,3-dione;
6-[3-(2,4-Dioxo-imidazolidin-1-yl)-propenyl]-4-[(3-hydroxy-4-methoxy-benzylamino)-methylene]-4H-isoquinoline-1,3-dione;
4-[(3-Hydroxy-4-methoxy-benzylamino)-methylene]-6-[3-(2-hydroxy-3-methoxy-phenyl)-propenyl]-4H-isoquinoline-1,3-dione;

6-Cyclopentylidenemethyl-4-{[4-(4-methyl-piperazin-1-yl)-phenylamino]-methylene}-4H-isoquinoline-1,3-dione;

4-{[4-(4-Methyl-piperazin-1-yl)-phenylamino]-methylene}-6-[2-(4-nitro-phenyl)-vinyl]-4H-isoquinoline-1,3-dione;

6-Furan-2-yl-4-{[4-(4-methyl-piperazin-1-yl)-phenylamino]-methylene}-4H-isoquinoline-1,3-dione;

4-{[4-(4-Methyl-piperazin-1-yl)-phenylamino]-methylene}-6-phenyl-4H-isoquinoline-1,3-dione;

4-[(3-Hydroxy-4-methoxy-benzylamino)-methylene]-6-phenyl-4H-isoquinoline-1,3-dione;

4-[(3-Hydroxy-4-methoxy-benzylamino)-methylene]-6-(4-methoxy-phenyl)-4H-isoquinoline-1,3-dione;

4-[(3-Hydroxy-4-methoxy-benzylamino)-methylene]-6-naphthalen-2-yl-4H-isoquinoline-1,3-dione;

4-[(3-Hydroxy-4-methoxy-benzylamino)-methylene]-6-(1H-indol-5-yl)-4H-isoquinoline-1,3-dione;

4-[(3-Hydroxy-4-methoxy-benzylamino)-methylene]-6-(1H-pyrrol-2-yl)-4H-isoquinoline-1,3-dione;

6-Furan-2-yl-4-[(3-hydroxy-4-methoxy-benzylamino)-methylene]-4H-isoquinoline-1,3-dione;

4-[(4-Pyrrolidin-1-ylmethyl-phenylamino)-methylene]-6-(1H-pyrrol-2-yl)-4H-isoquinoline-1,3-dione;

4-{1,3-Dioxo-4-[(4-pyrrolidin-1-ylmethyl-phenylamino)-methylene]-1,2,3,4-tetrahydro-isoquinolin-6-yl}-benzonitrile;

6-(4-Hydroxymethyl-phenyl)-4-[(4-pyrrolidin-1-ylmethyl-phenylamino)-methylene]-4H-isoquinoline-1,3-dione;

7-Bromo-4-[(4-methoxy-phenylamino)-methylene]-1,4-dihydro-2H-isoquinolin-3-one;

7-Bromo-4-{[4-(4-methyl-piperazin-1-yl)-phenylamino]-methylene}-1,4-dihydro-2H-isoquinolin-3-one;

6-[1-(2-Methoxy-ethyl)-1H-pyrrol-3-yl]-4-{[4-(4-methyl-piperazin-1-yl)-phenylamino]-methylene}-4H-isoquinoline-1,3-dione;

6-Bromo-4-[(4-methoxy-phenylamino)-methylene]-1,4-dihydro-2H-isoquinolin-3-one;

8-Bromo-4-[(4-methoxy-phenylamino)-methylene]-1,4-dihydro-2H-isoquinolin-3-one;

6-Bromo-4-{[4-(4-methyl-piperazin-1-yl)-phenylamino]-methylene}-1,4-dihydro-2H-isoquinolin-3-one;

8-Bromo-4-{[4-(4-methyl-piperazin-1-yl)-phenylamino]-methylene}-1,4-dihydro-2H-isoquinolin-3-one;

6-Bromo-4-[(4-pyrrolidin-1-ylmethyl-phenylamino)-methylene]-1,4-dihydro-2H-isoquinolin-3-one;

8-Bromo-4-[(4-pyrrolidin-1-ylmethyl-phenylamino)-methylene]-1,4-dihydro-2H-isoquinolin-3-one;

7-Bromo-4-[(4-pyrrolidin-1-ylmethyl-phenylamino)-methylene]-1,4-dihydro-2H-isoquinolin-3-one;

4-{[4-(4-Methyl-piperazin-1-yl)-phenylamino]-methylene}-7-thiophen-2-yl-1,4-dihydro-2H-isoquinolin-3-one;

4-[(4-Methoxy-phenylamino)-methylene]-7-(1H-pyrrol-2-yl)-1,4-dihydro-2H-isoquinolin-3-one;

4-[(4-Methoxy-phenylamino)-methylene]-7-(1H-pyrrol-3-yl)-1,4-dihydro-2H-isoquinolin-3-one;

2-[5-(4-{[4-(4-Methyl-piperazin-1-yl)-phenylamino]-methylene}-1,3-dioxo-1,2,3,4-tetrahydro-isoquinolin-6-yl)-indol-1-yl]-acetamide;

6-[1-(2-Diethylamino-ethyl)-1H-indol-5-yl]-4-{[4-(4-methyl-piperazin-1-yl)-phenylamino]-methylene}-4H-isoquinoline-1,3-dione;

2-[3-(4-{[4-(4-Methyl-piperazin-1-yl)-phenylamino]-methylene}-1,3-dioxo-1,2,3,4-tetrahydro-isoquinolin-6-yl)-pyrrol-1-yl]-acetamide;

6-[1-(2-Diethylamino-ethyl)-1H-pyrrol-3-yl]-4-{[4-(4-methyl-piperazin-1-yl)-phenylamino]-methylene}-4H-isoquinoline-1,3-dione;

4-[3-(4-{[4-(4-Methyl-piperazin-1-yl)-phenylamino]-methylene}-1,3-dioxo-1,2,3,4-tetrahydro-isoquinolin-6-yl)-pyrrol-1-yl]-butyronitrile;

7-Chloro-4-[(3-hydroxy-phenylamino)-methylene]-1,4-dihydro-2H-isoquinolin-3-one;

4-[(7-Chloro-3-oxo-2,3-dihydro-1H-isoquinolin-4-ylidenemethyl)-amino]-benzamidine;

7-Methyl-4-[(4-morpholin-4-yl-phenylamino)-methylene]-1,4-dihydro-2H-isoquinolin-3-one;

4-[(3-Hydroxy-phenylamino)-methylene]-1,4-dihydro-2H-isoquinolin-3-one;

4-[(4-Piperidin-1-yl-phenylamino)-methylene]-1,4-dihydro-2H-isoquinolin-3-one;

4-[(7-Bromo-3-oxo-2,3-dihydro-1H-isoquinolin-4-ylidenemethyl)-amino]-benzamidine;

7-Bromo-4-[(3-hydroxy-4-methoxy-phenylamino)-methylene]-1,4-dihydro-2H-isoquinolin-3-one;

7-Bromo-4-{[4-(2-hydroxy-ethyl)-phenylamino]-methylene}-1,4-dihydro-2H-isoquinolin-3-one;

(4Z)-6-Bromo-4-[({4-[methyl(2-pyrrolidin-1-ylethyl)amino]phenyl}amino)methylene]isoquinoline-1,3(2H,4H)-dione;

(4Z)-B-bromo-4-[({4-[methyl(2-piperidin-1-ylethyl)amino]phenyl}amino)methylene]isoquinoline-1,3(2H,4H)-dione;

(4Z)-6-Bromo-4-[({4-[{2-[butyl(methyl)amino]ethyl}(methyl)amino]phenyl}amino)methylene]isoquinoline-1,3(2H,4H)-dione;

(4Z)-6-Bromo-4-[({4-[2-(dimethylamino)ethoxy]phenyl}amino)methylene]isoquinoline-1,3(2H,4H)-dione;

(4Z)-6-Bromo-4-{[(2-methyl-2,3-dihydro-1H-isoindol-5-yl)amino]methylene}isoquinoline-1,3(2H,4H)-dione;

(4Z)-6-Bromo-4-({[4-(1H-imidazol-1-yl)phenyl]amino}methylene)isoquinoline-1,3(2H,4H)-dione;

(4Z)-6-Bromo-4-{[(4-{methyl[2-(4-methylpiperazin-1-yl)ethyl]amino}phenyl)amino]methylene}isoquinoline-1,3(2H,4H)-dione;

(4Z)-6-Bromo-4-[({4-[methyl(2-morpholin-4-ylethyl)amino]phenyl}amino)methylene]isoquinoline-1,3(2H,4H)-dione;

6-({[(Z)-(6-Bromo-1,3-dioxo-2,3-dihydroisoquinolin-4(1H)-ylidene)methyl]amino}methyl)-2,2-dimethyl-1,3-benzodioxol-4-yl acetate;

6-({[(Z)-(6-Bromo-1,3-dioxo-2,3-dihydroisoquinolin-4(1H)-ylidene)methyl]amino}methyl)-2,2-dimethyl-1,3-benzodioxol-4-yl cyclopropanecarboxylate;

(4Z)-6-Bromo-4-[({4-[3-(dimethylamino)propyl]phenyl}amino)methylene]isoquinoline-1,3(2H,4H)-dione;

(Methoxyamino)propyl]phenyl}amino)methylene]isoquinoline-1,3(2H,4H)-dione;

(4Z)-6-Bromo-4-[({4-[[3-(dimethylamino)propyl](methyl)amino]phenyl}amino)methylene]isoquinoline-1,3(2H,4H)-dione;

(4Z)-6-Bromo-4-[({4-[(1-methylpyrrolidin-3-yl)oxy]phenyl}amino)methylene]isoquinoline-1,3(2H,4H)-dione;

6-Bromo-1,1-dimethyl-4-{[4-(4-methyl-piperazin-1-yl)-phenylamino]-methylene}-1,4-dihydro-2H-isoquinolin-3-one;

6-Furan-3-yl-1,1-dimethyl-4-{[4-(4-methyl-piperazin-1-yl)-phenylamino]-methylene}-1,4-dihydro-2H-isoquinolin-3-one; and (4Z)-1,2-Diacetyl-4-{[(3-hydroxy-4-methoxybenzyl)
amino]methylene}-1,4-dihydrocinnolin-3(2H)-one.

In another embodiment, e is 1; f is 0; $Y^1$ is $CR_3$; $Y^2$ is $NR_1$; $G^2$ is NHaryl; Z is phenyl substituted with $C_{1-6}$ alkylheterocyclyl.

In an additional embodiment, are illustrative examples or pharmaceutically acceptable salts thereof of Formula (I) which include:

(4Z)-6-[(3-aminophenyl)amino]-4-({[4-(piperidin-1-ylmethyl)phenyl]amino}methylene)isoquinoline-1,3(2H,4H)-dione;

(4Z)-6-[(3-methylphenyl)amino]-4-({[4-(piperidin-1-ylmethyl)phenyl]amino}methylene)isoquinoline-1,3(2H,4H)-dione;

(4Z)-6-[(3-acetylphenyl)amino]-4-({[4-(piperidin-1-ylmethyl)phenyl]amino}methylene)isoquinoline-1,3(2H,4H)-dione;

(4Z)-4-({[4-(piperidin-1-ylmethyl)phenyl]amino}methylene)-6-{[3-(trifluoromethyl)phenyl]amino}isoquinoline-1,3(2H,4H)-dione;

(4Z)-6-anilino-4-({[4-(piperidin-1-ylmethyl)phenyl]amino}methylene)isoquinoline-1,3(2H,4H)-dione;

(4Z)-6-{[4-(dimethylamino)phenyl]amino}-4-({[4-(piperidin-1-ylmethyl)phenyl]amino}methylene)isoquinoline-1,3(2H,4H)-dione;

(4Z)-6-[(4-methylphenyl)amino]-4-({[4-(piperidin-1-ylmethyl)phenyl]amino}methylene)isoquinoline-1,3(2H,4H)-dione;

(4Z)-6-[(4-chlorophenyl)amino]-4-({[4-(piperidin-1-ylmethyl)phenyl]amino}methylene)isoquinoline-1,3(2H,4H)-dione;

(4Z)-6-[(2-methoxyphenyl)amino]-4-({[4-(piperidin-1-ylmethyl)phenyl]amino}methylene)isoquinoline-1,3(2H,4H)-dione;

(4Z)-6-[(3-methoxyphenyl)amino]-4-({[4-(piperidin-1-ylmethyl)phenyl]amino}methylene)isoquinoline-1,3(2H,4H)-dione;

3-{[(4Z)-1,3-dioxo-4-({[4-(piperidin-1-ylmethyl)phenyl]amino}methylene)-1,2,3,4-tetrahydroisoquinolin-6-yl]amino}benzonitrile;

4-{[(4Z)-1,3-dioxo-4-({[4-(piperidin-1-ylmethyl)phenyl]amino}methylene)-1,2,3,4-tetrahydroisoquinolin-6-yl]amino}benzamide;

(4Z)-6-(2,3-dihydro-1H-inden-5-ylamino)-4-({[4-(piperidin-1-ylmethyl)phenyl]amino}methylene)isoquinoline-1,3(2H,4H)-dione;

(4Z)-6-(1,3-benzodioxol-5-ylamino)-4-({[4-(piperidin-1-ylmethyl)phenyl]amino}methylene)isoquinoline-1,3(2H,4H)-dione;

4-{[(4Z)-1,3-dioxo-4-({[4-(piperidin-1-ylmethyl)phenyl]amino}methylene)-1,2,3,4-tetrahydroisoquinolin-6-yl]amino}benzonitrile;

(4Z)-6-[(4-methoxyphenyl)amino]-4-({[4-(piperidin-1-ylmethyl)phenyl]amino}methylene)isoquinoline-1,3(2H,4H)-dione;

(4Z)-6-[(3-fluorophenyl)amino]-4-({[4-(piperidin-1-ylmethyl)phenyl]amino}methylene)isoquinoline-1,3(2H,4H)-dione;

(4Z)-6-{[3-methoxy-5-(trifluoromethyl)phenyl]amino}-4-({[4-piperidin-1-ylmethyl)phenyl]amino}methylene)isoquinoline-1,3(2H,4H)-dione;

(4Z)-6-[(4-acetylphenyl)amino]-4-({[4-(piperidin-1-ylmethyl)phenyl]amino}methylene)isoquinoline-1,3(2H,4H)-dione;

2-{[(4Z)-1,3-dioxo-4-({[4-(piperidin-1-ylmethyl)phenyl]amino}methylene)-1,2,3,4-tetrahydroisoquinolin-6-yl]amino}benzonitrile;

ethyl 4-{[(4Z)-1,3-dioxo-4-({[4-(piperidin-1-ylmethyl)phenyl]amino}methylene)-1,2,3,4-tetrahydroisoquinolin-6-yl]amino}benzoate;

(4Z)-6-[(2-chlorophenyl)amino]-4-({[4-(piperidin-1-ylmethyl)phenyl]amino}methylene)isoquinoline-1,3-(2H,4H)-dione;

(4Z)-6-[(3-chlorophenyl)amino]-4-({[4-piperidin-1-ylmethyl)phenyl]amino}methylene)isoquinoline-1,3(2H,4H)-dione;

(4Z)-6-anilino-4-[({4-[(dimethylamino)methyl]phenyl}amino)methylene]isoquinoline-1,3(2H,4H)-dione;

(4Z)-4-[({4-[(dimethylamino)methyl]phenyl}amino)methylene]-6-[(3-methoxyphenyl)amino]isoquinoline-1,3(2H,4H)-dione;

(4Z)-4-[({4-[(dimethylamino)methyl]phenyl}amino)methylene]-6-[(4-methoxyphenyl)amino]isoquinoline-1,3(2H,4H)-dione;

(4Z)-6-[(3-acetylphenyl)amino]-4-[({4-[(dimethylamino)methyl]phenyl}amino)methylene]isoquinoline-1,3(2H,4H)-dione;

(4Z)-6-[(3-acetylphenyl)amino]-4-({[4-(3,5-dimethylpiperazin-1-yl)phenyl]amino}methylene)isoquinoline-1,3(2H,4H)-dione;

(4Z)-4-[({4-[(diethylamino)methyl]phenyl}amino)methylene]-6-[(4-methylphenyl)amino]isoquinoline-1,3(2H,4H)-dione;

(4Z)-6-(1H-indol-5-ylamino)-4-({[4-piperidin-1-ylmethyl)phenyl]amino}methylene)isoquinoline-1,3(2H,4H)-dione; and (4Z)-4-({[4-(piperidin-1-ylmethyl)phenyl]amino}methylene)-6-(quinolin-5-ylamino)isoquinoline-1,3(2H,4H)-dione.

DETAILED DESCRIPTION OF THE INVENTION

The compounds of this invention are certain substituted isoquinoline-1,3(2H,4H)-diones, 1-thioxo-1,4-dihydro-2H-isoquinoline-3-ones, and 1,4-dihydro-3(2H)-isoquinolones containing compounds which are particularly useful, in an embodiment of the invention, for the treatment of cancer. The isoquinoline-1,3(2H,4H)-dione, 1-thioxo-1,4-dihydro-2H-isoquinoline-3-one, and 1,4-dihydro-3(2H)-isoquinolone ring systems will be numbered as indicated in the formulae:

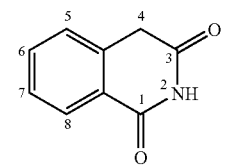 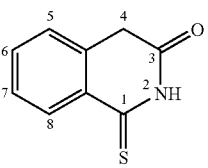

isoquinoline-1,3(2H, 4H)-dione    1-thioxo-1,4-dihydro-2H-isoquinoline-3-one

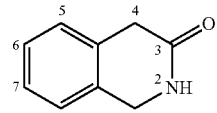

1,4-dihydro-3(2H)isoquinolne

The terms used in this specification may have their ordinary meanings in the art, the meaning within the context of the invention, and the meaning in the specific context where each term is used. Certain terms are discussed below, or elsewhere in the specification, to provide additional guidance to the practitioner in describing the compounds, compositions, and methods of the invention and how to make and use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. The use of examples anywhere in this specification, including examples of any terms discussed herein, is illustrative only, and in no way limits the scope and meaning of the invention or of any exemplified term. Likewise, the invention is not limited to the examples presented.

"About" or "approximately" shall generally mean within 20 percent, but can be lower so as to be within 10 percent, or within 5 percent of a given value or range.

AcCl is sometimes used for the chemical name "acetyl chloride".

$Ac_2O$ is sometimes used for the chemical name "acetic anhydride".

"Acyl" denotes a radical of the formula —(C═O) alkyl or —(C═O) perfluoroalkyl wherein the alkyl radical or perfluoroalkyl radical is 1 to 7 carbon atoms; some examples include but are not limited to, acetyl, propionyl, butyryl, trifluoroacetyl.

Alkenyl refers to unsaturated aliphatic groups analogous in length and possible substitution to alkyls described herein, but which contain at least one carbon-carbon double bond. Alkenyl may be used synonymously with the term olefin and includes alkylidenes and includes both straight and branched carbon chains of 2-6 carbon atoms in all possible configurational isomers, for example cis and trans, and includes ethenyl, 3-hexen-1-yl and the like. Exemplary alkenyl groups include ethenyl, propenyl, 1,4-butadienyl, 3-hexen-1-yl and the like optionally substituted with phenyl or phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

The term "alkynyl" refers to unsaturated aliphatic groups analogous in length and possible substitution to the alkyls described herein, but which contain at least one triple carbon-carbon bond, respectively. Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls. The alkenyl portion of the alkenyl, alkenoyloxymethyl, alkenyloxy, alkenylsulfonamido, substituents include both straight chain as well as branched carbon chains and one or more sites of unsaturation. The term "aralkyl", as used herein, refers to an alkyl group substituted with an aryl group (e.g., an aromatic or heteroaromatic group).

Alkoxy means an alkyl-O— group. Exemplary alkoxy groups include methoxy, ethoxy, n-propoxy, i-propoxy, n-butoxy, t-butoxy and polyethers including —O—$(CH_2)_2OCH_3$.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups.

In an embodiment, a straight chain or branched chain alkyl has 12 or fewer carbon atoms in its backbone. The term "alkyl" can be used alone or as part of a chemical name as in for example, "trialkylorthoformate". The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. Moreover, the term "alkyl" as used throughout the specification and claims is intended to include both "unsubstituted alkyls" and "substituted alkyls", the latter of which refers to alkyl moieties having substituents replacing a hydrogen on one or more carbons of the hydrocarbon backbone.

Alkylamino may be defined as a nitrogen atom substituted with an alkyl of 1 to 12 carbon atoms.

The term "aryl" includes 4-, 5-, 6-, 7- and 10-membered single ring or fused polycyclic aromatic carbocyclic moiety having two or more rings in which two or more carbons are common to two adjoining rings. Aryl groups have 6 to 14 carbon atoms and include for example phenyl and bicyclicaryl for example napthyl. The aromatic rings can be optionally independently mono-, di-, tri- or tetra-substituted. Substituents are selected from the group consisting of, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties and —CN. The fused rings require at least one of the carbocyclic rings to be aromatic, e.g., the other rings can be cycloalkyls, cycloalkenyls, cycloalkynyls, and/or aryls.

The compounds of this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in the formulas the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center.

Azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A piperidino-N-alkyl substituent is a piperidine ring substituted on one of the nitrogen atoms with a straight or branch chain alkyl radical. A N-alkyl-piperidino-N-alkyl substituent is a piperidine ring substituted on one of the nitrogen atoms with a straight or branched chain alkyl group and on the other nitrogen atom with a straight or branch chain alkyl radical.

The term "base" refers to any compound which yields hydroxyl ions in aqueous solution; and which reacts with an acid to form water and a salt. In the schemes presented herein the base may be selected from a catalyst, a ligand, $Cs_2CO_3$, KOt-Bu, and t-BuOK.

The term "carbonyl" represents the radical —C═O.

CDI is sometimes used for the chemical name "1,1'-carbonyldiimidazole".

The term "cyano" represents the radical —CN.

Cycloalkyl means a simple carbocycle having a saturated ring having from 3 to 10 carbon atoms optionally substituted with 1 to 3 independently selected alkyl groups of 1 to 12 carbon atoms. Exemplary cycloalkyl rings include, but are not limited to, cyclopropyl, cyclobutyl, cyclopentyl, cyclohexyl and adamantyl. Cycloalkyl rings may contain heteroatoms and be called a cycloheteroalkyl.

Dialkylamino is defined as a nitrogen atom disubstituted with an alkyl of 1 to 12 carbon atoms.

DME is sometimes used for the chemical name "1,2-dimethoxyethane".

DMAP is sometimes used for the chemical name "4-N,N-dimethylaminopyridine".

DMF-acetal is sometimes used for the chemical name "N,N-dimethylformamide acetal".

The compounds of this invention may include a "divalent group" as a linking group, for example, —$CH_2CH_2$—.

$Et_3N$ is sometimes used for the chemical name "triethylamine".

When referring to timing in the example and intermediate processes the symbol "h" or "H" stands for "hour(s)".

The term "halogen" refers to an atom of fluorine, chlorine, bromine, or iodine.

The term "heteroaryl" refers to a 4 to 10 membered ring structure, which ring structure includes one to four heteroatoms selected from O, N and S. Heteroaryls include, but are not limited to, acridine, benzofuran, benzothiophene, benzimidazole, benzotriazole, benzothiazole, benzoxazole, benzisoxazole, 1,2-benzopyran, cinnoline, carbazole, chromene, furan, furazan, isothiazole, isoxazole, indolizine, isoindole, indole, indazole, imidazole, isobenzofuran, isoquinoline, 2,3-dihydroindole, isoindazole, morpholine, naphthyridine, 1,8-naphthyridine, oxazole, oxolane, phthalazine, pyrido[3,2-b]pyridine, pyrido[3,4-b]pyridine, pyrido[4,3-b]pyridine, pyrido[2,3-d]pyrimidine, purine, and pteridine, perimidine, phenanthroline, phenazine, phenothiazine, phenoxazine, phenoxathiin, phenanthridine, piperidine, piperazine, pteridine, purine, pyrazole, pyran, pyridine, pyrazine, pyridazine and pyrimidine, pyrrole, pyrrolidine, quinazoline, quinolizine, quinoline, quinoxaline, thiolane, thiophene, thiazole, triazole, thianthrene, tetrahydroquinoline, xanthene, and the like. In an embodiment, heteroaryl is a 5-10 membered heteroaryl ring system having one or two rings and having up to four ring members selected from O, N, and S. A heteroaryl can form a heterocyclic ring system of one to three fused rings, in which at least one ring may have an aromatic character and contains 1 to 4 heteroatoms the same or different selected from the group consisting of S, N, and O. The remaining rings of the ring system may be fully unsaturated, partially saturated, or fully saturated. The heteroaryl can be independently substituted at one or more positions. In an embodiment heteroaryl may also be bicyclic heteroaryl having two fused rings. Preferred is a six membered ring structure having 1 to 4 heteroatoms.

Heterocyclyl or heterocyclic refers to a saturated or partially unsaturated monocyclic radical containing preferably 3 to 8 ring atoms selected from carbon, nitrogen, oxygen and sulfur. Preferred is a ring having six ring atoms. Heterocycles can include 2 or 3 fused rings. Specific examples include but are not limited to morpholine, thiomorpholine, thiomorpholine-S-oxide, thiomorpholine-S,S-dioxide, piperidine, piperazine, pyrrolidine, aziridine, oxirane, tetrahydrothiophene, tetrahydrofuran, 1,2-pyran, 1,4-pyran, dioxane, 1,3-dioxolane, diazabicyclo[2.2.1]heptane and tetrahydropyran. The heterocyclyl ring may be oxidized on a tri-substituted nitrogen atom to provide the corresponding N-oxide, such as N-ethylpiperazine-N-oxide, or the heterocyclyl ring may contain a carbonyl group on one of the carbon atoms, such as pyrrolidinone, pyridine and pyrone. Preferred is pyridine and pyrone. The heteroaryl may be oxidized on a nitrogen atom to provide the corresponding N-oxide, such as pyridine-N-oxide or quinoline —N-oxide. The heteroaryl may also be oxidized on a tri-substituted nitrogen atom to provide the corresponding N-oxide, such as N-ethylpiperazine-N-oxide.

In another embodiment the heteroaryl may contain a carbonyl group on one of the carbon atoms, such as pyrrolidinone, 1,3,4-oxadiazol-2-one, or 2-indanone.

The term "heteroatom" as used herein means an atom of any element other than carbon or hydrogen and include for example nitrogen, oxygen, sulfur, phosphorus, and selenium.

Im is sometimes used for the chemical name "imidazole".

iPrHCl is sometimes used for the chemical name "1,3-bis (2,6-di-i-propylphenyl)-4,5-dihydroimidazonium chloride".

The letter "J" is used in the schemes to symbolize Cl, Br, or I.

LAH is sometimes used in place of the chemical name "lithium aluminum hydride".

LDA is sometimes used for the chemical name "lithium diisopropylamide".

LG is sometimes used for the term "leaving group". Examples of leaving groups are Cl, Br, I, OTf, OMs, OTs.

MDS is sometimes used in place of the chemical name "1,1,1,3,3,3-hexamethyldisilazane".

MeI is sometimes used for the chemical name "methyl iodide".

MOM is sometimes used in place of the term "methoxymethyl".

MS is sometimes used to signify "mass spectroscopy" or "mass spectrum".

Ms is sometimes used to signify the compound "methanesulfonyl".

Halogen is defined as I, Br, Cl, F.

OTf is sometimes used for the chemical name "trifluoromethanesulfonate".

$Pd_2(dba)_3$ is sometimes used for the chemical name "tris(dibenzylideneacetone)dipalladium (0)".

$PPh_3$ is sometimes used for the chemical name "triphenylphosphine".

Phenyl as used herein refers to a 6-membered aromatic ring. The term phenoxy represents the radical PhO, a form of phenol. A phenol is an aryl hydroxide. Both terms can be used alone or in conjunction with terms described herein, such as, thiophenoxy or phenylamino.

For purposes of this invention "PEG" is any polyethylene glycol of the formula —$(OCH_2CH_2)_rOCH_3$ where r is 2 to 1800.

Starting material is periodically referred to as "SM" in the procedures for the intermediates and examples.

A "spirocyclic ring" is an organic compound having 2 rings joined by a carbon atom common to both.

The term "substituted" is contemplated to include all permissible substituents of organic compounds. In a broad aspect, the permissible substituents of organic compounds include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Examples of possible substituents include but are not limited to halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, acyl, aldehyde, ester, a cycloheteroalkyl, an aromatic or heteroaromatic moiety, —CN.

TBDMS or TBS are sometimes used for the chemical name "tert-butyldimethylsilyl".

TFA is sometimes used to signify the compound "trifluoroacetic acid".

TLC is sometimes used to signify the term "thin-layer chromatography".

THF is sometimes used for the chemical name "tetrahydrofuran".

Tri-alkylsilyl applies to alkyl (as hereinbefore defined) derivatives of the silyl group, $(alkyl)_3Si$, wherein each alkyl may be the same or different.

Ts is sometimes used for the chemical name "p-toluenesulfonyl".

"Inhibition" refers to a method of contacting a cell with an amount of a compound of the invention effective to decrease or prevent cancer. The cell may be a mammalian cell and more specifically a human cell. The cell may also be a bacterial cell such as for example E. coli. The cell may include any cell that can be isolated and includes for example, a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell, a ganglion cell or a stem cell. The cell may be a normal cell, an activated cell, a neoplastic cell, a diseased cell, or an infected cell.

For purposes of this invention a "neoplasm" is used interchangeably with "cancer" and is defined as cells selected from for example the breast, kidney, bladder, mouth, larynx, esophagus, stomach, colon, ovary, pancreas, brain, bone, prostrate and lung. The cell is one having a morphology not found in the majority of the cells of a mammal. In one embodiment, the present invention provides for a method of inhibiting the neoplasm.

The present invention accordingly provides to a mammal (including a human), a pharmaceutical composition that comprises a compound of this invention in combination or association with a pharmaceutically acceptable carrier. The compound of this invention may also be administered alone or in combination with other therapeutically effective compounds or therapies for the treatment or prevention of the neoplasm.

In one embodiment, the administration of an effective amount of a compound of Formula (I) and in combination an effective amount of another therapeutically effective anticancer agent inhibits the resistance of a cancer to the compound of Formula (I) and/or the other anticancer agent. In an embodiment, the cancer is a solid tumor.

In another embodiment, other anticancer agents useful in the methods and compositions of the present invention include, but are not limited to, therapeutically effective compounds or drugs in the following lists or a pharmaceutically acceptable salt thereof.

Nitrogen mustards: Cyclophosphamide, Ifosfamide, Trofosfamide, Chlorambucil;
Nitrosoureas: Carmustine (BCNU), Lomustine (CCNU)
Alkylsulphonates: Busulfan, Treosulfan;
Triazenes: Dacarbazine, Procarbazine, Temozolomide;
Platinum complexes: Cisplatin, Carboplatin, Aroplatin, Oxaliplatin;
Vinca alkaloids: Vincristine, Vinblastine, Vindesine, Vinorelbine
Taxanes: Paclitaxel, Docetaxel;
Epipodophyllins: Etoposide, Teniposide, Topotecan, Irinotecan, 9-aminocamptothecin, Camptothecin;
DNA Topoisomerase Inhibitors, Crisnatol;
Mitomycins: Mitomycin C;
DHFR inhibitors: Methotrexate, Trimetrexate;
IMP dehydrogenase Inhibitors: Mycophenolic acid, Tiazofurin, Ribavirin, EICAR;
Ribonucleotide reductase Inhibitors: Hydroxyurea, Deferoxamine;
Uracil analogs: 5-Fluorouracil, Fluoxuridine, Doxifluridine, Ralitrexed;
Cytosine analogs: Cytarabine, Cytosine arabinoside, Fludarabine, Gemcitabine, Capecitabine;
Purine analogs: Mercaptopurine, Thioguanine, O-6-benzylguanine;
DNA Antimetabolites: 3-HP, 2'-deoxy-5-fluorouridine, 5-HP, alpha-TGDR;
DNA Antimetabolites: aphidicolin glycinate, ara-C, 5-aza-2'-deoxycytidine, beta-TGDR, cyclocytidine, guanazole, inosine glycodialdehyde, macebecin II, Pyrazoloimidazole;
Anti-estrogen: Tamoxifen, Raloxifene, Megestrol;
LHRH agonists: Goserelin, Leuprolide acetate;
Anti-androgens: Flutamide, Bicalutamide;
Retinoids/Deltoids: Cis-retinoic acid
Vitamin A derivative: All-trans retinoic acid (ATRA-IV)
Vitamin D3 analogs: EB 1089, CB 1093, KH 1060;
Photodynamic therapies: Vertoporfin (BPD-MA), Phthalocyanine, Photosensitizer Pc4, Demethoxy-hypocrellin A, (2BA-2-DMHA);
Cytokines: Interferon-α, Interferon-β, Interferon-γ, Tumor necrosis factor, Interleukin-2;
Angiogenesis Inhibitors Angiostatin (plasminogen fragment), antiangiogenic antithrombin III Angiozyme, ABT-627, Bay 12-9566, Benefin, Bevacizumab, BMS-275291, cartilage-derived inhibitor (CDI), CAI, CD59 complement fragment, CEP-7055, Col 3, Combretastatin A-4, Endostatin (collagen XVIII fragment), Fibronectin fragment, Gro-beta, Halofuginone, Heparinases, Heparin, hexasaccharide fragment, HMV833, Human chorionic gonadotropin (hCG), IM-862, Interleukins. Kringle 5 (plasminogen fragment), Marimastat; Metalloproteinase inhibitors, 2-Methoxyestradiol, MMI 270 (CGS 27023A), MoAb IMC-1C11, Neovastat, NM-3, Panzem, PI-88, Placental ribonuclease inhibitor, Plasminogen activator inhibitor, Platelet factor-4 (PF4), Prinomastat, Prolactin 16 kD fragment, Proliferin-related protein (PRP), PTK 787/ZK 222594, Retinoids, Solimastat, Squalamine, SS 3304, SU 5416, SU6668,
SU 11248, Tetrahydrocortisol-S, Tetrathiomolybdate, Thalidomide, Thrombospondin-1 (TSP-1), TNP-470, Transforming growth factor-beta (TGF-☐), Vasculostatin, Vasostatin (calreticulin fragment);
Angiogenesis Inhibitors: ZD6126, ZD 6474, farnesyl transferase inhibitors (FTI), Bisphosphonates;
Antimitotic agents: Allocolchicine, Halichondrin B, Colchicine, colchicine derivative, dolastatin 10, Maytansine, Rhizoxin, Thiocolchicine, trityl cysteine;
Dopaminergic neurotoxins: 1-methyl-4-phenylpyridinium ion
Cell cycle inhibitors: Staurosporine;
Actinomycins: Actinomycin D, Dactinomycin;
Bleomycins: Bleomycin A2, Bleomycin B2, Peplomycin;

Anthracyclines: Daunorubicin, Doxorubicin, Idarubicin, Epirubicin, Pirarubicin, Zorubicin, Mitoxantrone;
MDR inhibitors: Verapamil
$Ca^{2+}$ ATPase inhibitors: Thapsigargin Additional suitable other anticancer agents useful in the methods and compositions of the present invention include, but are not limited to abiraterone, acivicin, aclarubicin, acodazole, acronine, acylfulvene, adecypenol, adozelesin, aldesleukin, an ALL-TK antagonist, altretamine, ambamustine, ambomycin, ametantrone, amidox, amifostine, aminoglutethimide, aminolevulinic acid, amrubicin, amsacrine, anagrelide, anastrozole, andrographolide, an angiogenesis inhibitor, antarelix, anthramycin, an apoptosis gene modulator, apurinic acid, ara-CDP-DL-PTBA, arginine deaminase, L-asparaginase, asperlin, asulacrine, atamestane, atrimustine, axinastatin 1, axinastatin 2, axinastatin 3, azacitidine, azasetron, azatoxin, azetepa, azatyrosine, azotomycin, batimastat, benzodepa, bisantrene, bisnafide, bizelesin, brequinar, bropirimine, balanol, a BCR/ABL antagonist, beta-alethine, betaclamycin B, betulinic acid, bisaziridinylspermine, bisnafide, bistratene A, bizelesin, calcipotriol, calphostin C, calusterone, canarypox IL-2, carubicin, carboxyamidotriazole, CaRest M3, CARN 700, carzelesin, castanospermine, cecropin B, cetrorelix, chloroquinoxaline, cicaprost, cirolemycin, cladribine, clotrimazole, collismycin A, collismycin B, conagenin, crambescidin 816, crisnatol, cryptophycin 8, cryptophycin A derivatives, curacin A, cyclopentanthraquinones, cycloplatam, cypemycin, cytostatin, dacliximab, decitabine, dehydrodidemnin B, deslorelin, dexifosfamide, dexormaplatin, dexrazoxane, dexdiaziquone, didemnin B, didox, diethylnorspermine, dihydro-5-acytidine, dihydrotaxol, dioxamycin, diphenyl spiromustine, docosanol, dolasetron, droloxifene, dronabinol, duazomycin, duocarmycin SA, ecomustine, edatrexate, eflornithine, elsamitrucin, enloplatin, enpromate, epipropidine, erbulozole, esorubicin, estramustine, estramustine, an estrogen antagonist, etanidazole, etoprine, exemestane, fadrozole, fazarabine, fenretinide, finasteride, flavopiridol, flezelastine, fluasterone, fluorodaunorunicin, floxuridine, fluorocitabine, forfenimex, formestane, fostriecin, fotemustine, gadolinium texaphyrin, galocitabine, ganirelix, a gelatinase inhibitor, a glutathione inhibitor, hepsulfam, herbimycin A, heregulin, hexamethylene bisacetamide, hypericin, ibandronic acid, idoxifene, idramantone, ilmofosine, ilomastat, imatinib mesylate, imidazoacridones, imiquimod, an IGF-1 inhibitor, iobenguane, iodoipomeanol, iproplatin, irsogladine, isobengazole, isohomohalicondrin B, itasetron, jasplakinolide, leucovorin, levamisole, leuprorelin, liarozole, lissoclinamide 7, lobaplatin, lombricine, lometrexol, lonidamine, losoxantrone, lovastatin, loxoribine, lurtotecan, lutetium texaphyrin, lysofylline, mannostatin A, masoprocol, maspin, a matrix metalloproteinase inhibitor, mechlorethamine, megestrol acetate melphalan, metoclopramide, mifepristone, miltefosine, mirimostim, mitoguazone, mitolactol, mitonafide, mofarotene, molgramostim, mopidamol, a multiple drug resistance gene inhibitor, myriaporone, N-acetyldinaline, nafarelin, nagrestip, napavin, naphterpin, nartograstim, nedaplatin, nemorubicin, neridronic acid, nilutamide, nisamycin, a nitrogen mustard, a nitric oxide modulator, a nitrosourea, nitrullyn, nocodazole, octreotide, okicenone, onapristone, oracin, ormaplatin, osaterone, oxaunomycin, palauamine, palmitoylpamidronic acid, panaxytriol, panomifene, parabactin, pazelliptine, pegaspargase, peldesine, peliomycin, pentamustine, pentosan, pentostatin, pentrozole, peplomycin, perfosfamide, perflubron, perfosfamide, phenazinomycin, a phosphatase inhibitor, picibanil, pilocarpine, pipobroman, piposulfan, piritrexim, placetin A, placetin B, plicamycin, porfiromycin, plomestane, porfimer sodium, porfiromycin, prednimustine, prednisone, prostaglandin J2, microalgal, puromycin, pyrazoloacridine, pyrazofurin, a raf antagonist, raltitrexed, ramosetron, a ras farnesyl protein transferase inhibitor, a ras-GAP inhibitor, retelliptine demethylated, RII retinamide, riboprine, rogletimide, rohitukine, romurtide, roquinimex, rubiginone B1, ruboxyl, safingol, saintopin, SarCNU, sarcophytol A, sargramostim, semustine, a signal transduction modulator, simtrazene, sizofuran, sobuzoxane, solverol, sonermin, sparfosic acid, sparfosate, sparsomycin, spicamycin D, spiromustine, spiroplatin, splenopentin, spongistatin 1, a stem-cell division inhibitor, stipiamide, streptonigrin, a stromelysin inhibitor, sulfinosine, suradista, suramin, swainsonine, talisomycin, tallimustine, tauromustine, tazarotene, tecogalan, tegafur, tellurapyrylium, a telomerase inhibitor, teloxantrone, temoporfin, teroxirone, testolactone, tetrachlorodecaoxide, tetrazomine, thaliblastine, thiamiprine, thiocoraline, thrombopoietin, thymalfasin, thymotrinan, tirapazamine, titanocene, topsentin, toremifene, trestolone, tretinoin, triacetyluridine, triciribine, trimetrexate, triptorelin, tropisetron, tubulozole, turosteride, a tyrosine kinase inhibitor, ubenimex, uracil mustard, uredepa, vapreotide, variolin B, velaresol, veramine, verteporfin, vinxaltine, vinepidine, vinglycinate, vinleurosine, vinrosidine, vinzolidine, vitaxin, vorozole, zanoterone, zeniplatin, zilascorb, zinostatin, and zorubicin. The other anticancer agent may optionally be an alkylating agent, a platinum-containing agent, an anthracycline, a vinca alkaloid, a taxane, a topoisomerase inhibitor or an angiogenesis inhibitor.

A "therapeutically effective amount" or "therapeutically effective dose" is an amount sufficient to ameliorate symptoms of cancer, restenosis, atherosclerosis, blood vessel proliferative disorders, angiogenesis, chronic obstructive pulmonary disease, bone disease, osteoporosis, psoriasis, inflammatory disorders, arthritis, central nervous system disorders, Alzheimers, pain sesation, autoimmune disease, transplant rejection, thrombosis, diabetes, metabolic disorders, infectious disease, viral infection, adenomatosis, neurofibromatosis, fungal infections, endotoxic shock, vascular smooth cell proliferation, atherosclerosis, pulmonary fibrosis, glomerulonephritis, post-surgical stenosis and testenosis, apoptosis, prevention of AIDS, inflammatory bowel disease, amyotrophic lateral sclerosis, retinitis pigmentosa, spinal muscular atrophy, cerebellar degeneration, chronic and aplastic anemia, ischemia, liver disease, osteoporosis, rhinosinusitis, cystic fibrosis, multiple sclerosis, kidney disease, pain, alopecia, and parasitic protozoa. For purposes of this invention the dose provided to a patient will vary depending upon what is being administered, the purpose of the administration, the manner of administration, and the like.

The administration of compounds of the invention may be provided orally, by intralesional, intraperitoneal, intramuscular or intravenous injection, infusion, liposome-mediated delivery, topical, nasal, anal, vaginal, sublingual, uretheral, transdermal, intrathecal, ocular or otic delivery. In order to obtain consistency in providing the compounds of this invention the form administered is a unit dose. Suitable unit dose forms include tablets, capsules and powders in sachets or vials. Such unit dose forms may contain from 0.1 to 1000 mg of a compound of the invention. The compounds of the present invention can be administered orally at a dose range determined by dose ranging studies. Such compounds may be administered multiple times a day. The effective amount will be dependent upon the form of the compound. One of skill in the art could routinely perform empirical activity tests to determine the bioactivity of the compound in bioassays and thus determine what dosage to administer. The compound of the present invention may be delivered locally via a capsule that allows a sustained release of the compound over a period of time. Controlled or sustained release compositions include formulation in lipophilic depots (for example, fatty acids, waxes, oils).

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules. When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multi-lamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound.

The terms "prevent" or "prevention", as used herein, refer to the partial or complete inhibition of the development of a condition that impairs the performance of a function of the human body. The terms "treat" or "treatment", as used herein, refer to an attempt to ameliorate a disease problem. Further, the term "suppress" or "suppression" refers to a complete or partial inhibition of a condition, e.g., as evidenced by a lessening of the severity of the symptoms associated with that condition.

Pharmaceutically acceptable salts of the compounds of Formula (I) with an acidic moiety may be formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be formed from organic and inorganic acids. For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. The compounds can also be used in the form of esters, carbamates and other conventional prodrug forms, which when administered in such form, convert to the active moiety in vivo.

In addition to the utilities, described herein some of the compounds of this invention are intermediates useful for the preparation of other compounds of this invention.

An embodiment of this invention is a method of treating IGFR related disorder in a mammal in need thereof comprising administering to said mammal an effective amount of a compound of Formula (I) wherein said IGFR related disorder is cancer.

An embodiment of this invention is a method of treating or inhibiting familial adenomatosis polyposis, psoriasis, neurofibromatosis, fungal infections, endotoxic shock, transplantation rejection, vescular smooth cell proliferation associated with atherosclerosis, pulmonary fibrosis, arthritis, glomerulonephritis, and post-surgical stenosis and testenosis, in a mammal in need thereof comprising administering to said mammal an effective amount of a compound of Formula (I).

An embodiment of this invention is a method for treating or treating viral infections, for example, herpevirus, poxvirus, Epstein-Barr virus, Sindbis virus and adenovirus; prevention of AIDS, autoimmune diseases, systemic lupus, erythenalosus, autoimmune medicated glomerulonephritis, rheumatoid arthritis, psoriasis, inflammatory bowel disease, and autoimmune diabetes mellitus, neurodegenerative disorders, for example, Alzheimer's disease, AID-related dementia, Parkinson's disease, amyotrophic lateral sclerosis, retinitis pigmentosa, spinal muscular atrophy and cerebellar degeneration; myelodysplastic syndromes, splastic anemia, ischemic injury associated with myocardial infarctions, stroke and reperfusion injury, arrhythmia, atherosclerosis, toxin-induced or alcohol related liver diseases, hematological diseases, for example, chronice anemia and aplastic anemia; degenerative diseases of the musculoskeletal system, for example, osteroporosis and arthritis, aspirin-sensentive rhinosinusitis, cystic fibrosis, multiple sclerosis, kidney diseases and cancer pain, in a mammal in need thereof comprising administering to said mammal an effective amount of a compound of Formula (I).

Examples of synthetic pathways that are useful for making isoquinoline-1,3(2H,4H)-diones, 1-thioxo-1,4-dihydro-2H-isoquinoline-3-ones, and 1,4-dihydro-3(2H)-isoquinolones of Formula (I) are set forth in the Examples below and generalized in Schemes 1-52. In general, variables such as $G^1$, $G^2$, $G^3$, $G^4$, $A^1$, $A^2$, $Y^1$, $Y^2$, $L^1$, Z, e and f and the like are as defined above for Formula (I).

Scheme 1, illustrates further a method useful for making compounds of Formula (I). Substituted oxo compound 1 can be reacted with an orthoformate 2 which includes trimethyl orthoformate and triethyl orthoformate in the presence of an anhydride which includes acetic anhydride in a polar solvent such as N,N-dimethylformamide (DMF) to provide ether 3. Further, condensing ether 3 with intermediate 4 in the presence of a polar solvent which includes DMF affords substituted oxo compound 5.

SCHEME 1

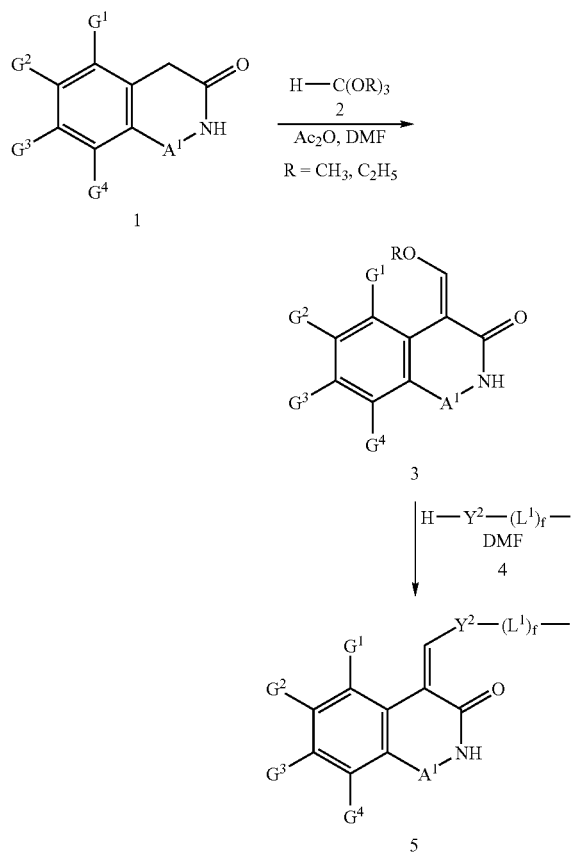

As presented in Scheme 2, oxo compound 6 can be reacted with an acetal which includes DMF-acetal to provide amine 7 which can be further reacted with intermediate 4 in a solvent which includes DMF to give substituted oxo compound 8.

SCHEME 2

According to Scheme 3, oxidation of substituted oxo or di-one compound 1 provides tri-one 9 using methods which include ruthenium oxide, in the presence of aqueous sodium periodate in ethyl acetate. Intermediate 11 can be prepared by reaction of amine 10 with sodium nitrite in the presence of aqueous acid followed by further treatment with tin (II) chloride also in the presence of aqueous acid. Further reaction of tri-one 9 with intermediate 11 provides substituted oxo 12.

SCHEME 3

Alternatively, as shown in Scheme 4, reaction of substituted oxo compound 1 with diazonium 13 prepared by reacting amine 10 with sodium nitrite in the presence of aqueous acid in DMF to provide substituted oxo 12.

Amine 10 may be reacted with sodium nitrite in the presence of aqueous acid to give the diazonium salt 13, which may be reacted with oxo compound 1 in ethanol containing sodium acetate to give hydrazone 12.

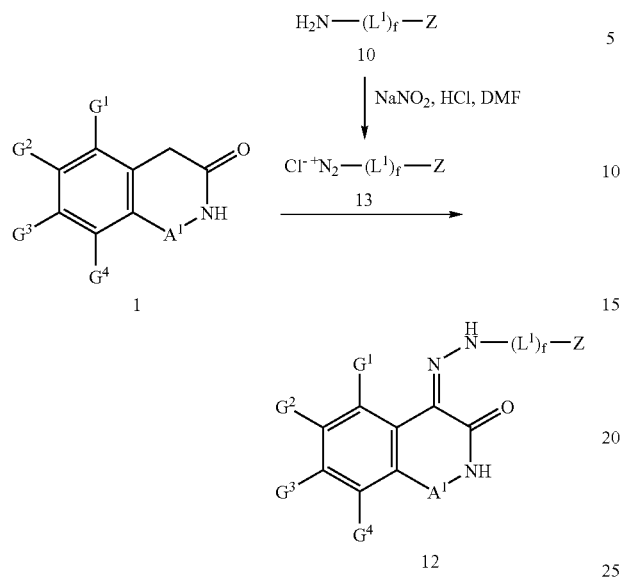

As described in Scheme 5, ester 15 is formed from carboxylic acid 14 where J is halogen by reaction with an acetoacetate in the presence of alkoxide, copper bromide and an alcohol where R is for example methyl or ethyl. Base hydrolysis which includes aqueous alkali metal hydroxide (lithium, potassium and sodium hydroxide) of ester 15 affords di-carboxylic acid 16 which is further reacted with urea or thiourea in a solvent such as 1,2-dichlorobenzene to provide dione 17.

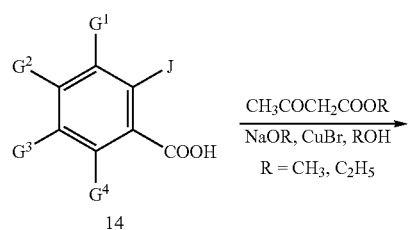

According to Scheme 6, carboxylic acid 18 can be converted to dicarboxylic acid 16 by reaction with lithium diisopropylamide (LDA) followed by reaction with a diakylcarbonate where R is for example methyl or ethyl, followed by treating with water. Reaction of dicarboxylic acid 16 with urea or thiourea in a solvent such as 1,2-dichlorobenzene to provide dione 17. Carboxylic acid 18 can be converted to ester 15 by reaction with LDA followed by reaction with a dialkylcarbonate where R is for example methyl or ethyl, followed by treating with acetic acid. Ester 15 may be hydrolyzed with aqueous base to afford di-carboxylic acid 16.

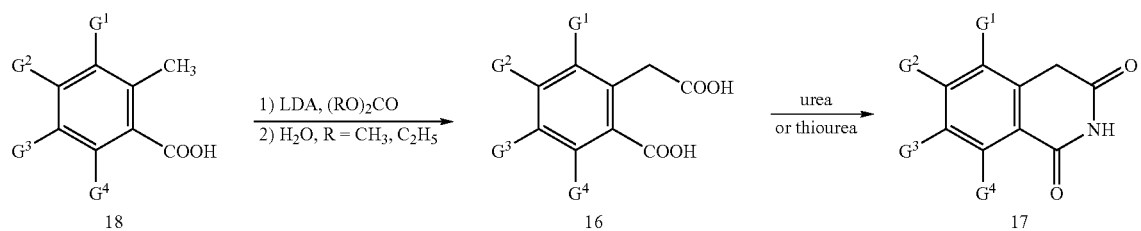

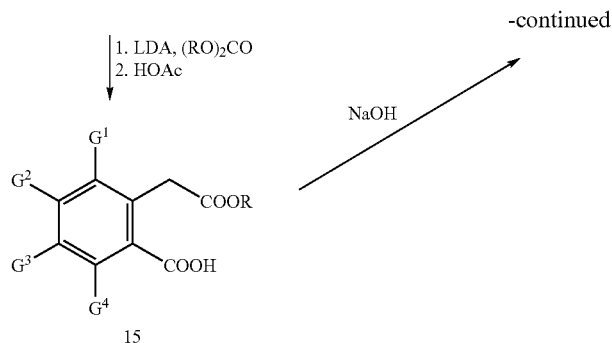

As described in Scheme 7, ester 15 may be hydrolyzed with aqueous base to give di-carboxylic acid 16 which may be further reacted with acetyl chloride to afford dione 17. Amide 18 may be prepared by reaction of ester 15 or dione 17 with ammonia. Reaction of amide 18 with carbonyl diimidazole (CDI) provides dione 17.

SCHEME 7

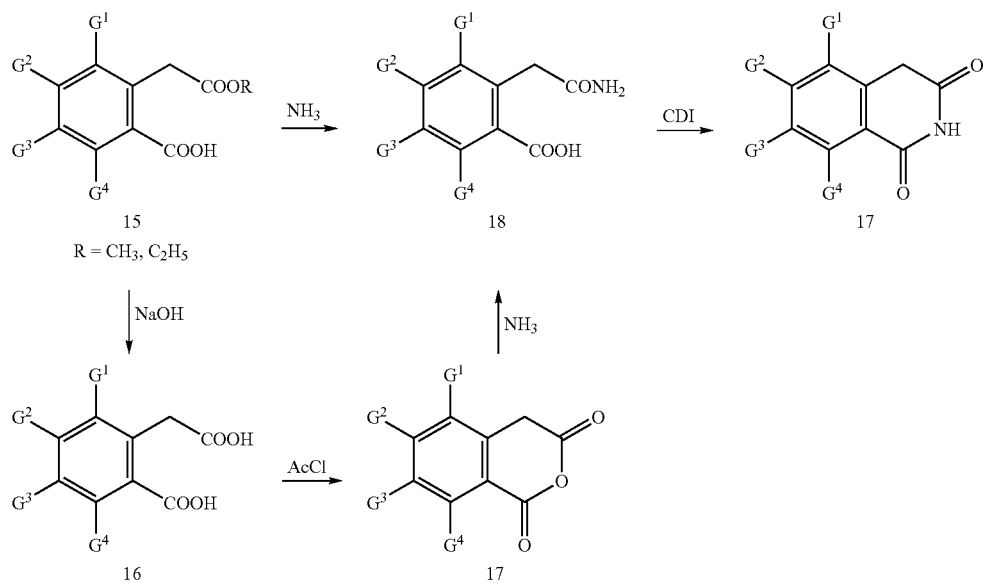

As shown in Scheme 8, carboxylic acid 19 may be converted to isothiocyanate 20 by reaction with thionyl chloride followed by reaction with lead(II) thiocyanate. Reaction of isothiocyanate 20 with aluminum chloride and carbon disulfide provides thioxo 21.

SCHEME 8

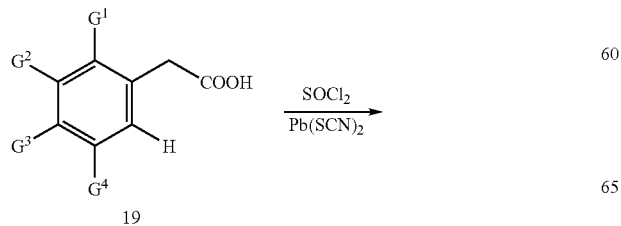

-continued

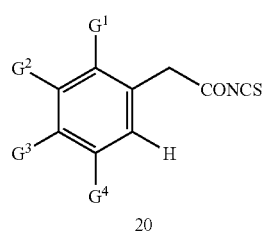
20

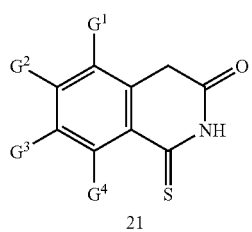
21

As presented in Scheme 9, treatment of thioxo 21 with aqueous base provides di-carboxylic acid 16 which when treated with urea forms dione 17.

SCHEME 9

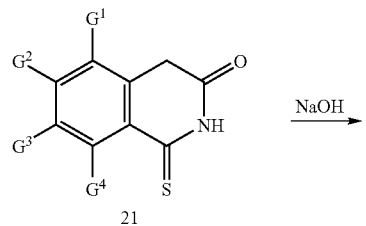
21

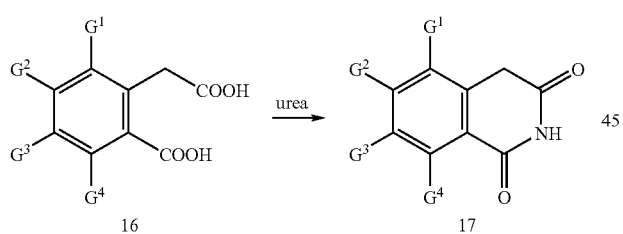
16    17

As illustrated in Scheme 10, amide 22 may be reacted with ketone 23 in the presence of pyrophosphoric acid ($H_4P_2O_7$) to give oxo 6.

SCHEME 10

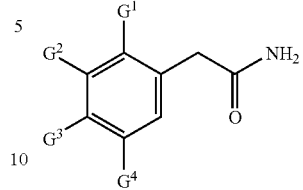
22

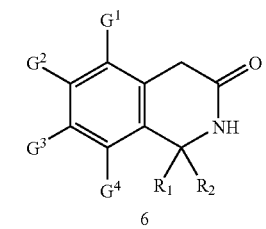
6

As shown in Scheme 11, amine 23 may be treated with dilute hydrochloric acid followed by sodium carbonate to provide oxo compound 24.

SCHEME 11

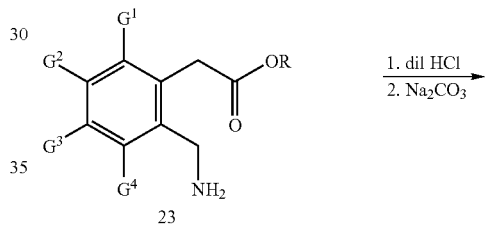
23

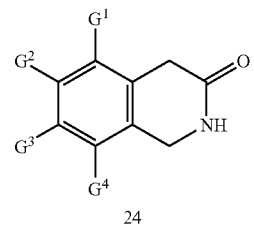
24

As illustrated in Scheme 12, ether 3 or amine 25 may be reacted with aniline 26 in a polar solvent such as DMF to provide substituted oxo compound 27. Substituted oxo compound 27 may be reacted with acid chloride 28 or anhydride 29 to provide amide 30. Thioamide 32 may be formed by reaction of substituted oxo 27 with sulfonyl chloride 31 where J is halogen.

SCHEME 12

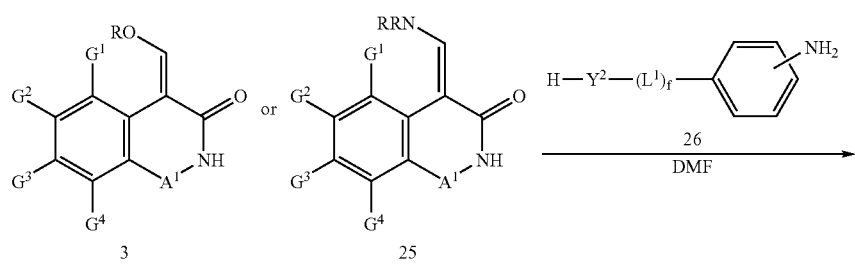
3    25

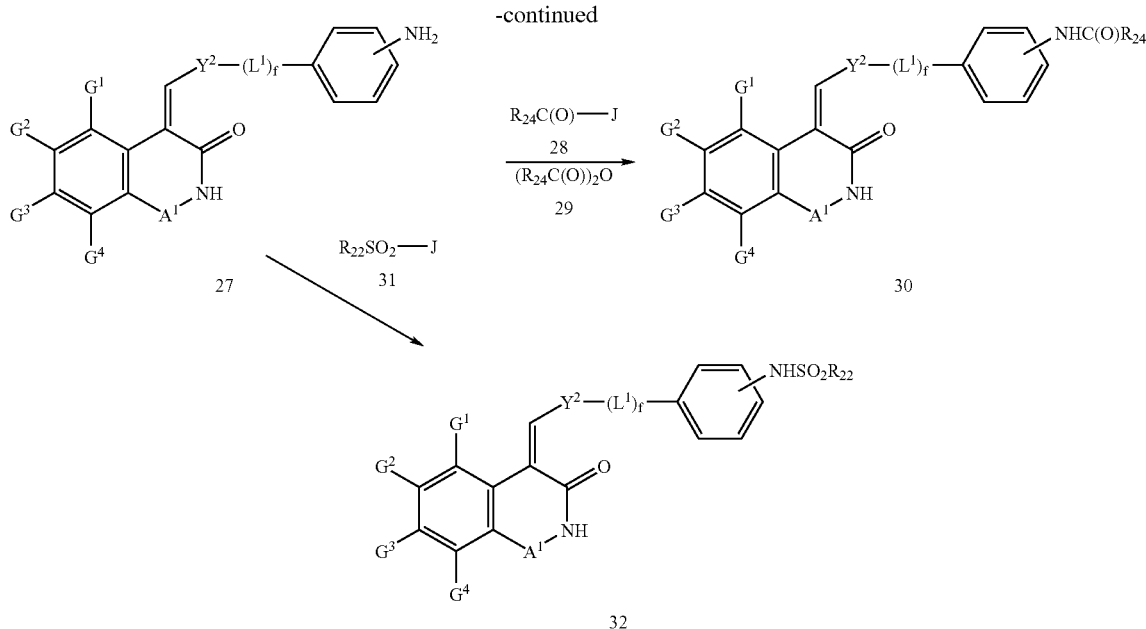
According to Scheme 13, substituted oxo 27 may be reacted with benzyl chloride to provide benzylamine 34 and dibenzylamine 35, that may be separated by chromatography.
As illustrated in Scheme 14, substituted one 27 may be reacted with amine 36 to provide piperazine 37 which is further alkylated with $R_{21}$-J to further provide substituted piperazine 39.

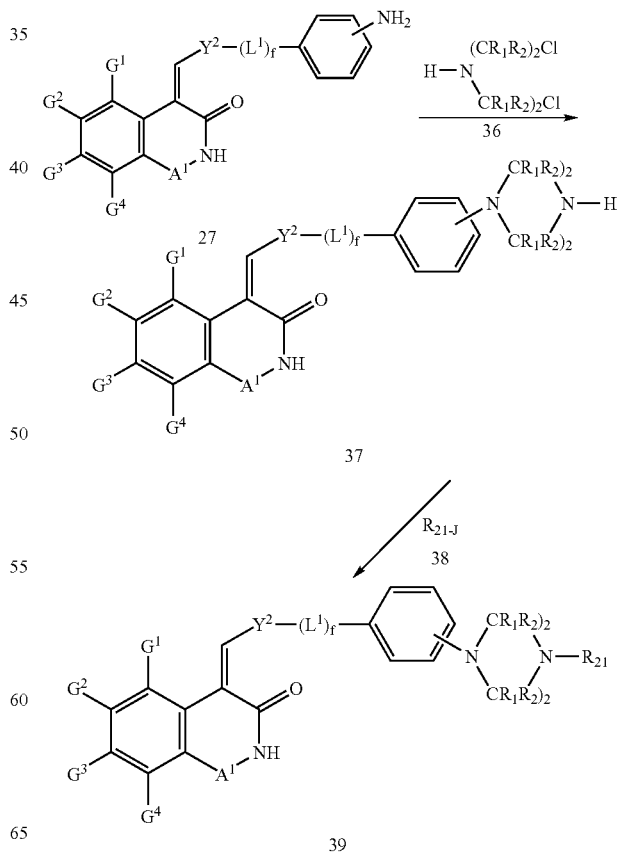

As shown in Scheme 15, nitro compound 40 may be reacted with substituted piperidine 41 to provide piperazine compound 42 which is then reduced to give aniline 43. Reacting aniline 43 with ether 3 or amine 25 provides piperazine 44.

SCHEME 15

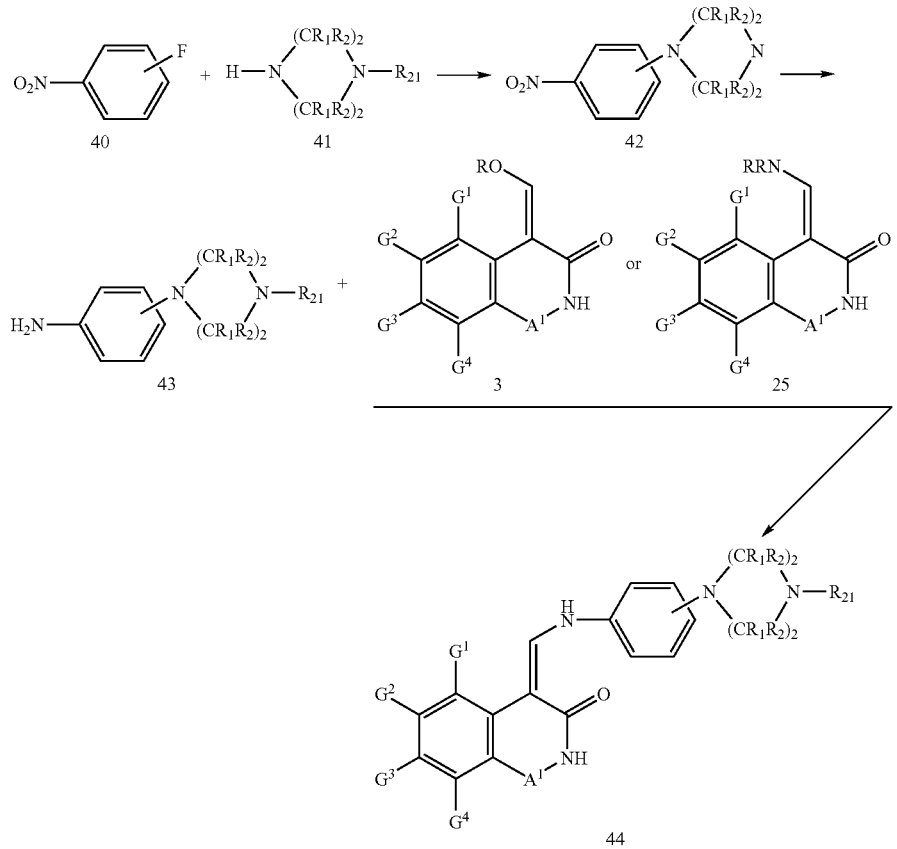

As described in Scheme 16, aniline 43 may be diazotized with sodium nitrite in the presence of hydrochloric acid in DMF to afford substituted piperazine 45 which may be further reacted with substituted oxo 1 to give substituted piperazine 46.

SCHEME 16

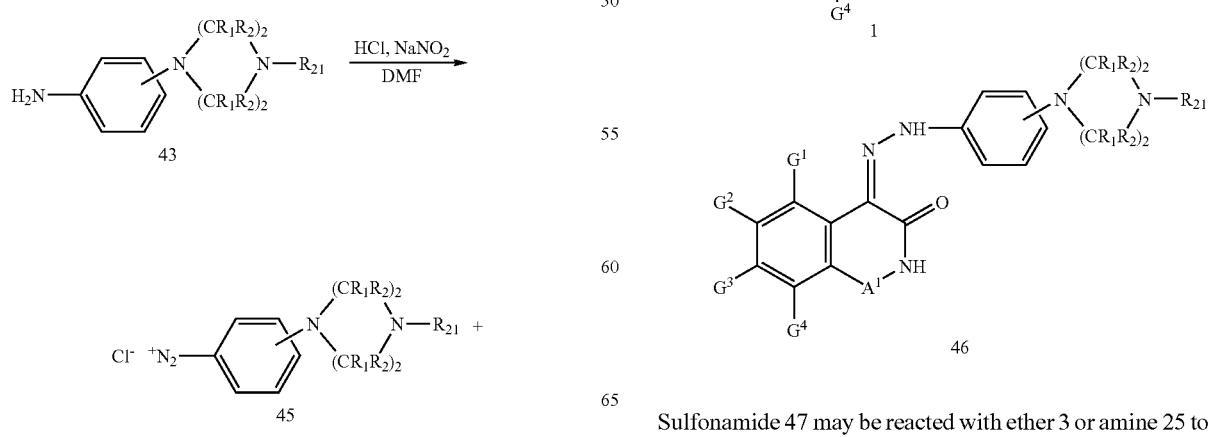

Sulfonamide 47 may be reacted with ether 3 or amine 25 to provide sulfonamide 48 which may be further reacted with aldehyde 49 in the presence of reducing agent including NaBH$_3$CN and NaBH(OAc)$_3$ to provide substituted sulfonamide 50 as illustrated in Scheme 17.

SCHEME 17

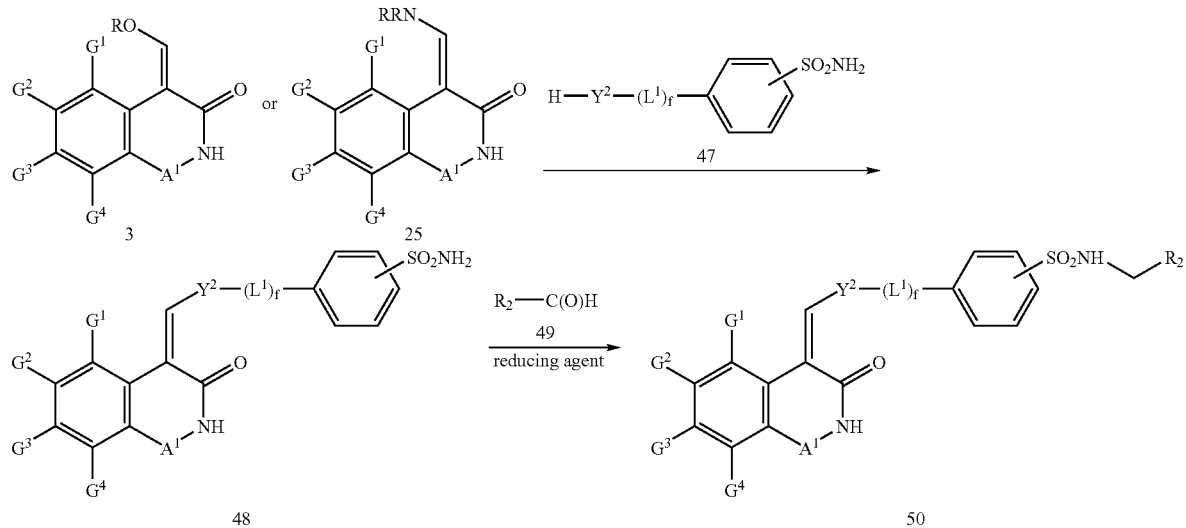

As shown in Scheme 18, amine 51 may be reacted with acid chloride 52 where J is halogen to provide nitro compound 53 which may be reduced to give aniline 54. Aniline 54 may be further reacted with ether 3 or amine 25 to give amide 55.

SCHEME 18

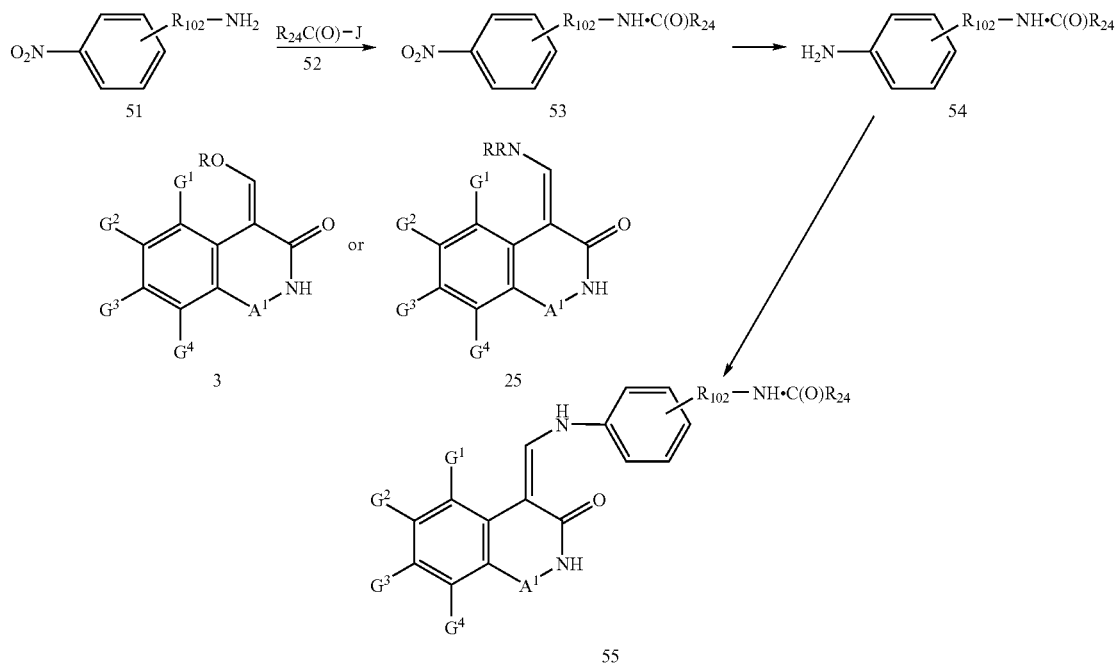

As described in Scheme 19, aniline 54 may be diazotized with sodium nitrite in the presence of hydrochloric acid in DMF to afford diazonium 56 which may be further reacted with substituted oxo compound 1 to give substituted amide 57.

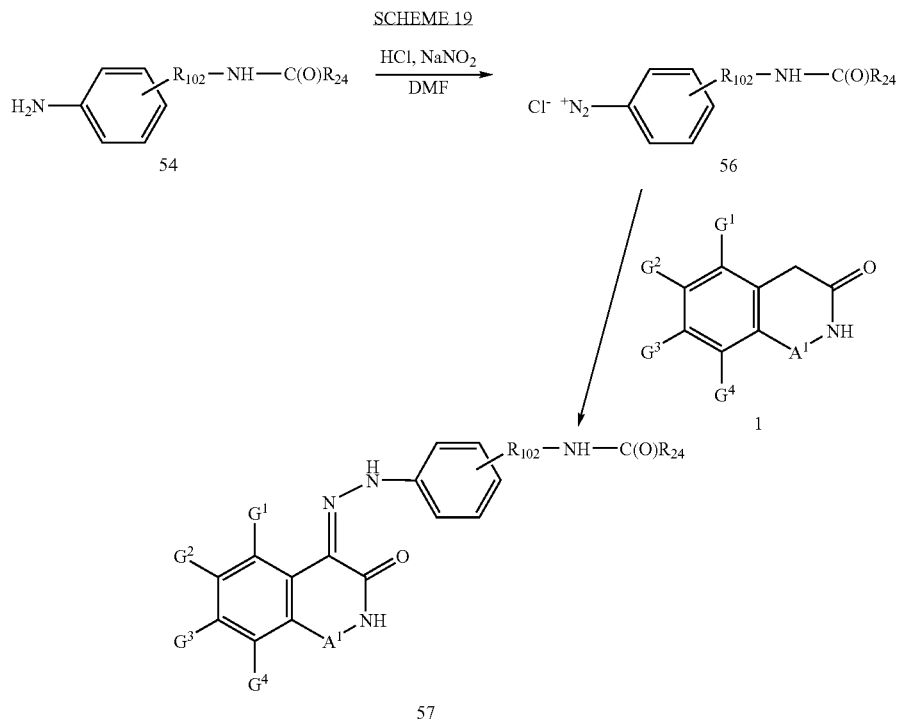
As illustrated in Scheme 20, amine 51 may be reacted with sulfonyl chloride 58 to provide nitro compound 59 which may be reduced to give aniline 60. Aniline 60 may be further reacted with ether 3 or amine 25 to give substituted sulfonamide 61.
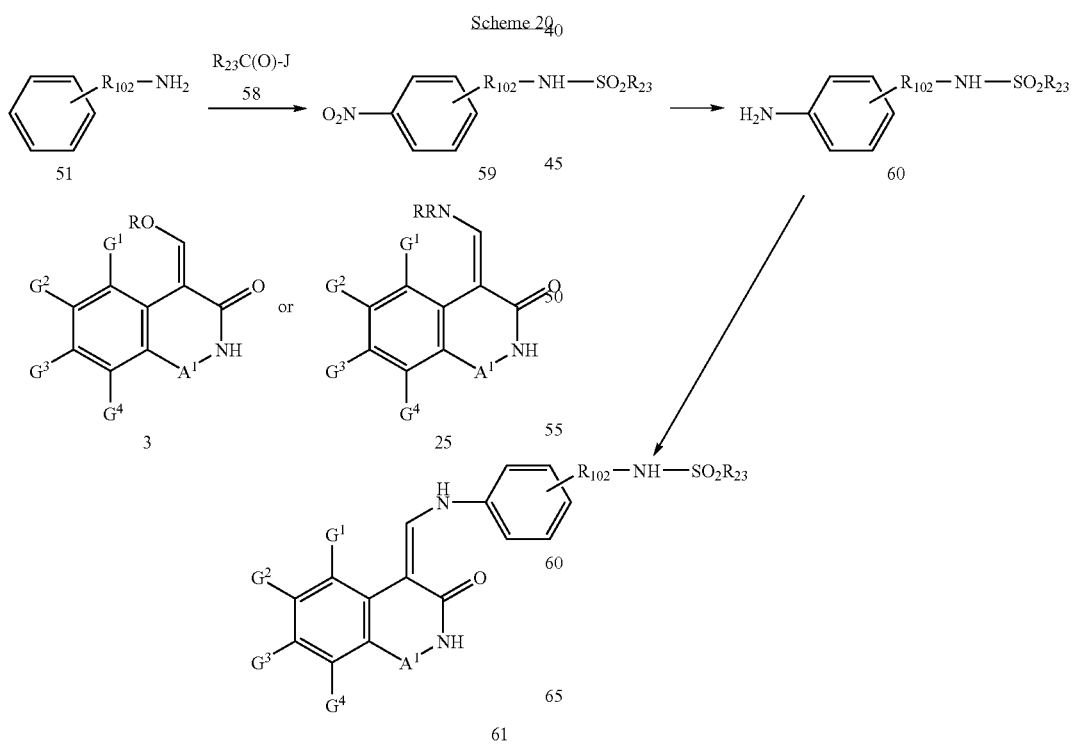

As described in Scheme 21, aniline 60 may be diazotized with sodium nitrite in the presence of hydrochloric acid in DMF to afford diazonium 62 which may further be reacted with substituted oxo compound 1 to give substituted sulfonamide 63.

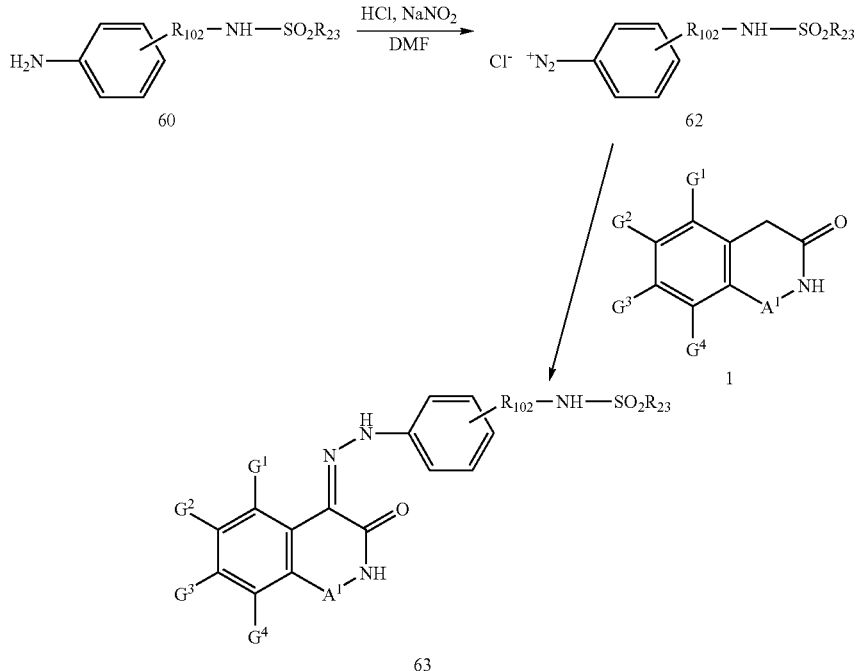

As described in Scheme 22, nitro compound 64 may be reacted with amine 65 then reduced to afford aniline 66. Alternatively, alcohol 67 may be reacted with methanesulfonyl chloride or p-toluenesulfonyl chloride to give nitro compound 68 which may be reacted with amine 65 followed by reduction to give aniline 66. Additional reaction of aniline 66 with ether 3 or amine 25 provides amine 69.

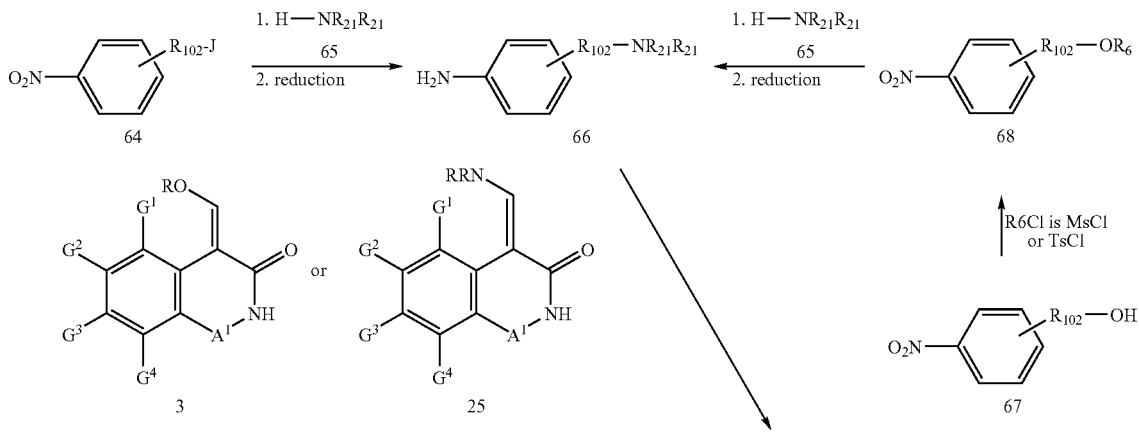

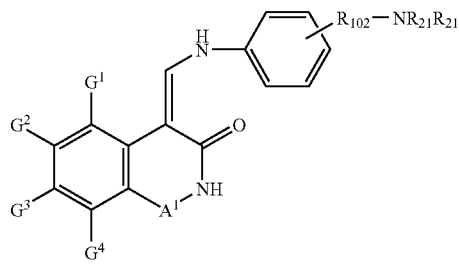

As described in Scheme 23, nitro compound 70 where J is halogen may be reacted with amine 65 to provide after reduction aniline 71. Alternatively, alcohol 73 may be reacted with methanesulfonyl chloride or p-toluenesulfonyl chloride to give nitro compound 72 which may be reacted with amine 65 followed by reduction to give aniline 71. Aniline 71 may be diazotized with sodium nitrite in the presence of hydrochloric acid in DMF to afford diazonium 74 which may be further reacted with substituted oxo 1 to give amine 75.

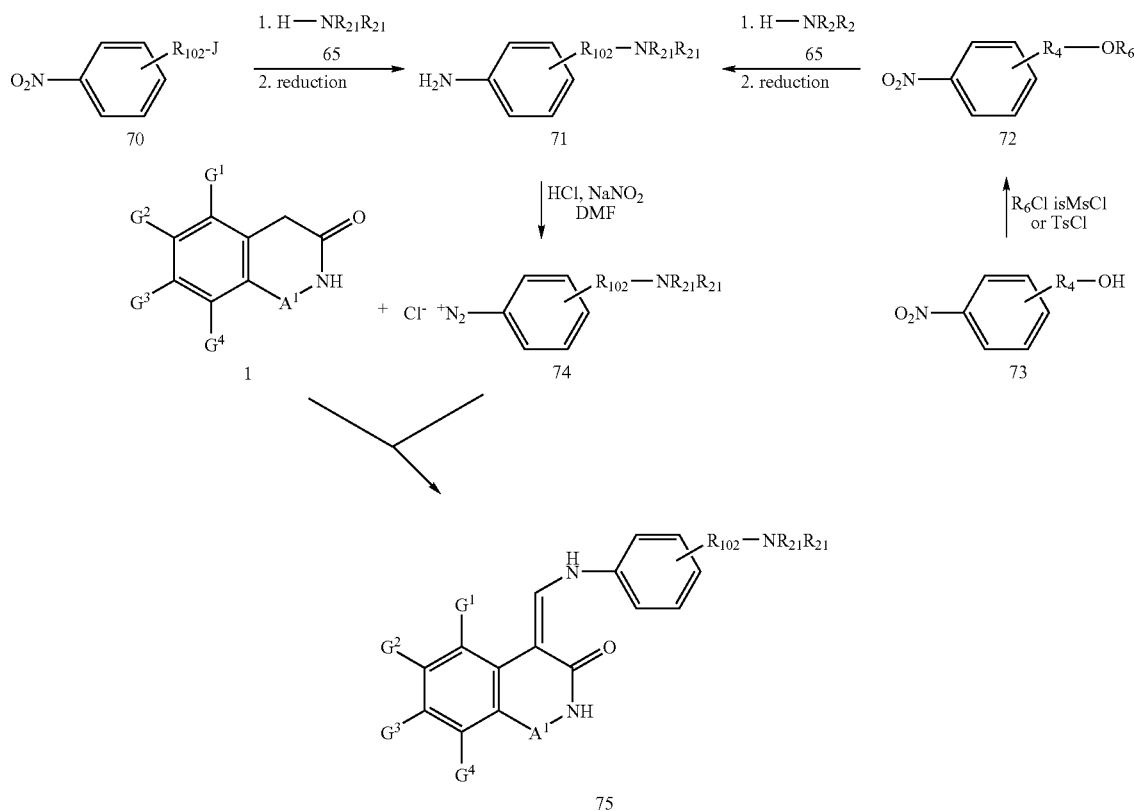

As described in Scheme 24, aniline 76 prepared by reduction of alcohol 73 may be reacted with ether 3 or amine 25 to afford alcohol 77 which may be further reacted with methanesulfonyl chloride or p-toluenesulfonyl chloride to give oxo 78. Reaction of oxo 78 with amine 65 affords amine 79.

SCHEME 24

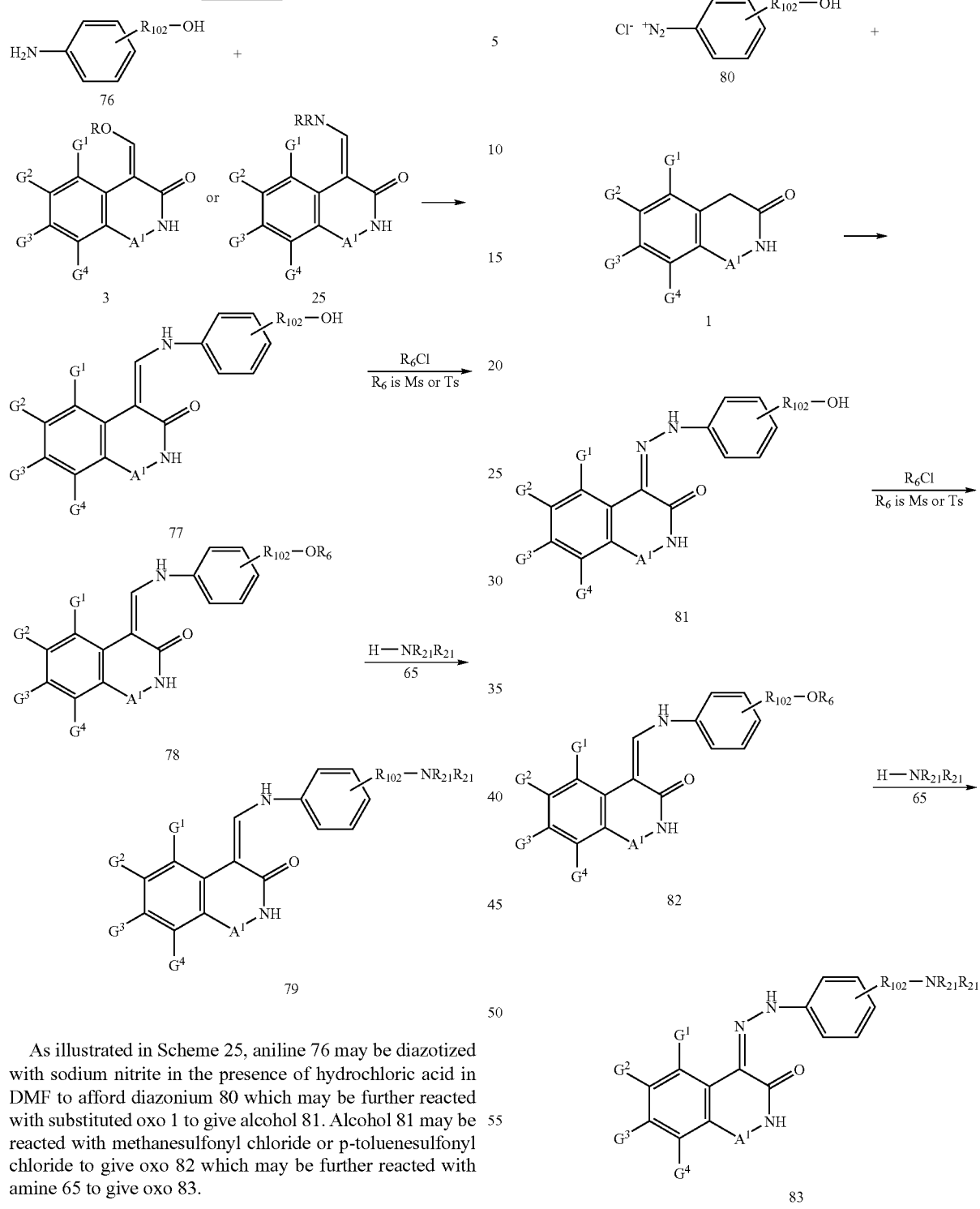

As illustrated in Scheme 25, aniline 76 may be diazotized with sodium nitrite in the presence of hydrochloric acid in DMF to afford diazonium 80 which may be further reacted with substituted oxo 1 to give alcohol 81. Alcohol 81 may be reacted with methanesulfonyl chloride or p-toluenesulfonyl chloride to give oxo 82 which may be further reacted with amine 65 to give oxo 83.

SCHEME 25

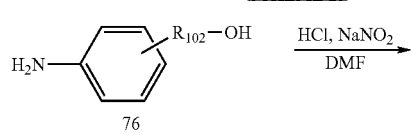

As presented in Scheme 26, aldehyde 84 may be converted to phenol 85 which may be subsequently converted to O-methyl-oxime 86 by reaction with O-methyl-hydroxylamine hydrochloride which may be further reduced to afford benzylamine 87. Additional reaction of benzylamine 87 with ether 3 or amine 25 provides phenol 88.

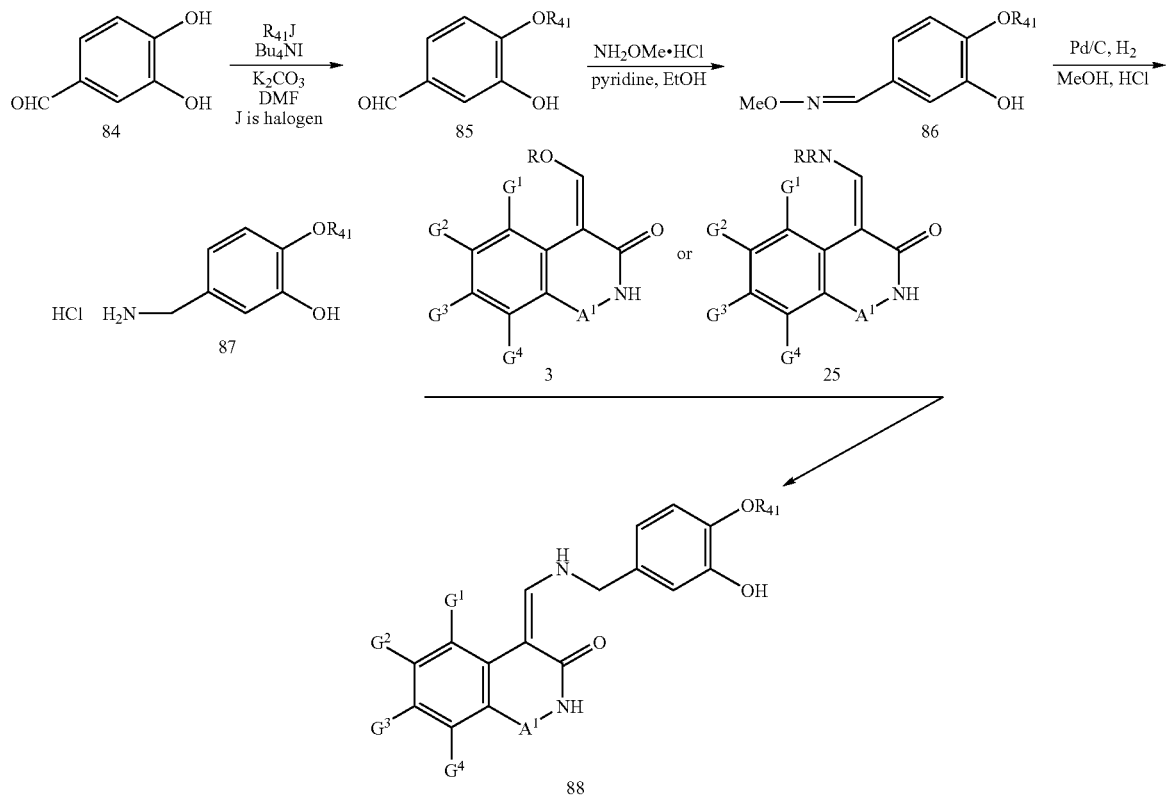
As shown in Scheme 27, aldehyde 89 may be converted to O-methyl-oxime 90 by reaction with O-methyl-hydroxylamine hydrochloride and which may be further reduced to afford benzylamine 91. Reaction of benzylamine 91 with ether 3 or amine 25 provides aniline 92.
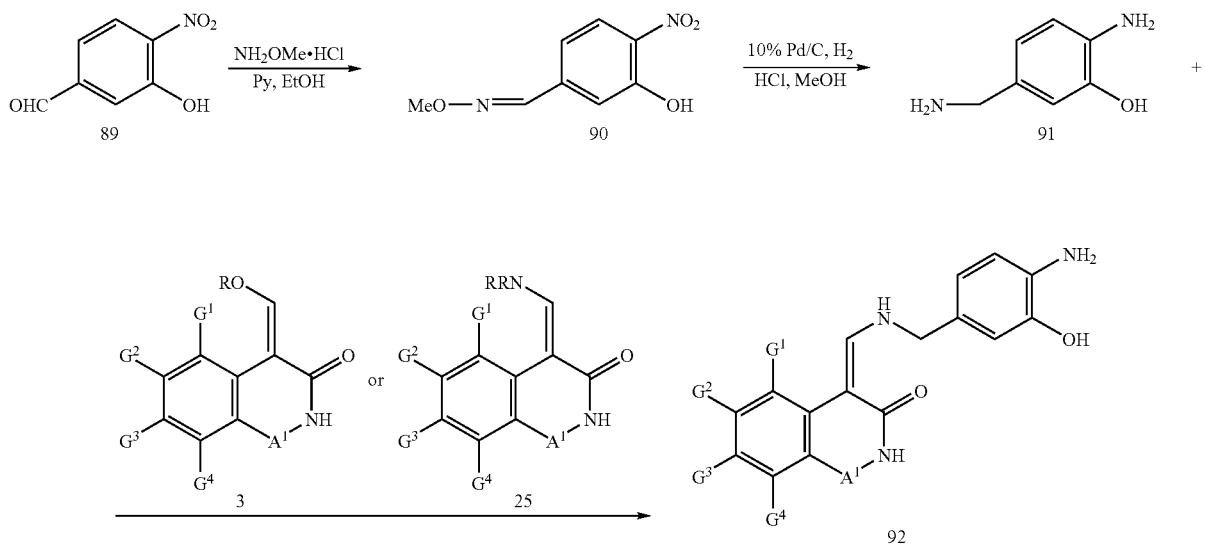

As shown in Scheme 28, one 93 containing a leaving group (LG) which includes Br, I or OTf (tirflate) may be reacted with organoboron ($R_{211}$—$BR_{213}R_{214}$), organotin ($R_{211}$—Sn($R_{21}$)$_3$, organozinc reagents ($R_{212}$—ZnBr), alkenes ($R_{212}$—C≡CH) or alkynes (($R_{212}$)$_2$C═CH($R_{212}$)) in the presence of catalysts which include tetrakis (triphenylphosphine)palladium (0) [Pd(PPh$_3$)$_4$], bis(diphenylphosphine)palladium (II) chloride and [1,1'-bis(diphenylphosphino)ferrocene]palladium (II) dichloride [PdCl$_2$ (dppf)$_2$] to afford one 94. Other catalysts including palladium (II) chloride, palladium (II) diacetate, tris(dibenzylideneacetone)dipalladium (0) [Pd$_2$(dba)$_3$] in the presence of ligands including triphenylphosphine, tri-t-butylphosphine with or without copper (I) iodide may be used to generate one 94. Preferred solvents include N,N-dimethylformamide, N-methylpyrrolidinone, dimethoxyethane and dioxane. Preferred bases include aqueous sodium carbonate, cesium carbonate and triethylamine. The reactions take place by heating from 110 C to 200 C in oil bath or in microwave oven. $R_{213}$ and $R_{214}$ groups are independently hydroxyl, alkyl of 1 to 12 carbon atoms or alkoxy of 1 to 12 carbon atoms. In addition, the ligands $R_{213}R_{214}$ may be taken together with the boron to which they are attached to form a cyclic boron ester, where $R_{213}R_{214}$ may be oxyethyleneoxy.

SCHEME 28

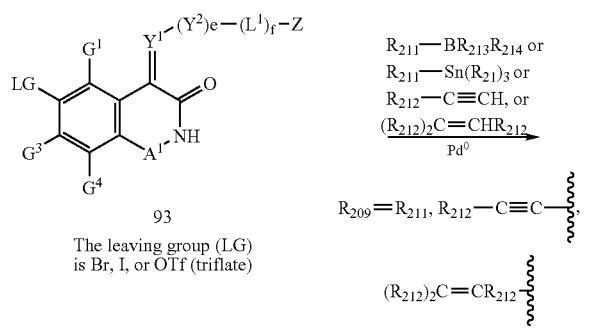

93

The leaving group (LG) is Br, I, or OTf (triflate)

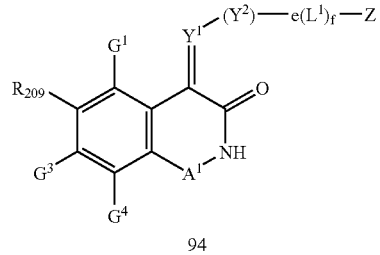

94

As presented in Scheme 29, one 93 may be reacted with $R_{209}$—Br, hexamethylditin and a catalyst such as tetrakis (triphenylphosphine)palladium (o) in dioxane at elevated temperature to generate substituted one 96.

SCHEME 29

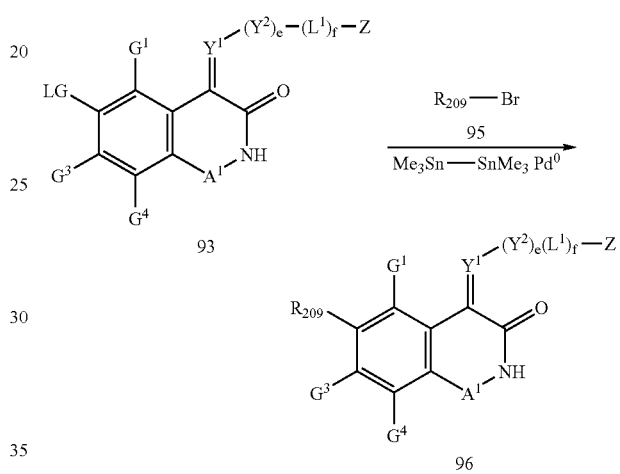

As described in Scheme 30, oxo 93 may be reacted with tin reagent 97 in the presence of Pd° to afford dioxolane 98 which may be treated with acid to afford oxo 101. Alternatively, treating oxo 93 with aldehyde 99 in the presence of Pd° affords oxo 101. Further treatment of oxo 101 with amine 102 in the presence of a reducing agent such as sodium cyanoborohydride or sodium triacetoxyborohydride gives amine 103.

SCHEME 30

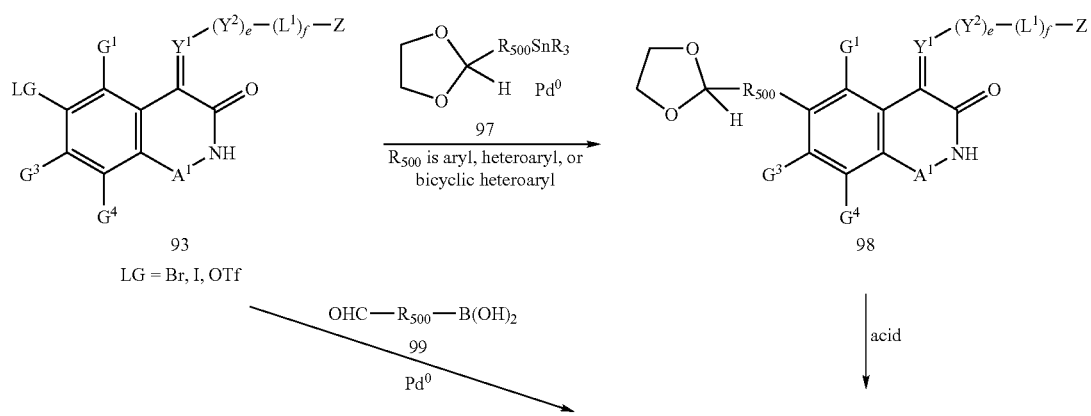

-continued

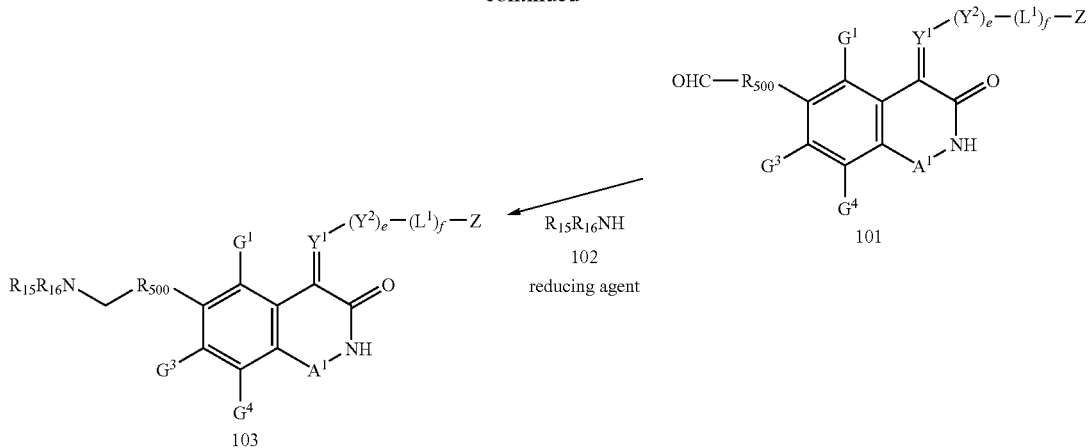

101

102 $R_{15}R_{16}NH$ reducing agent

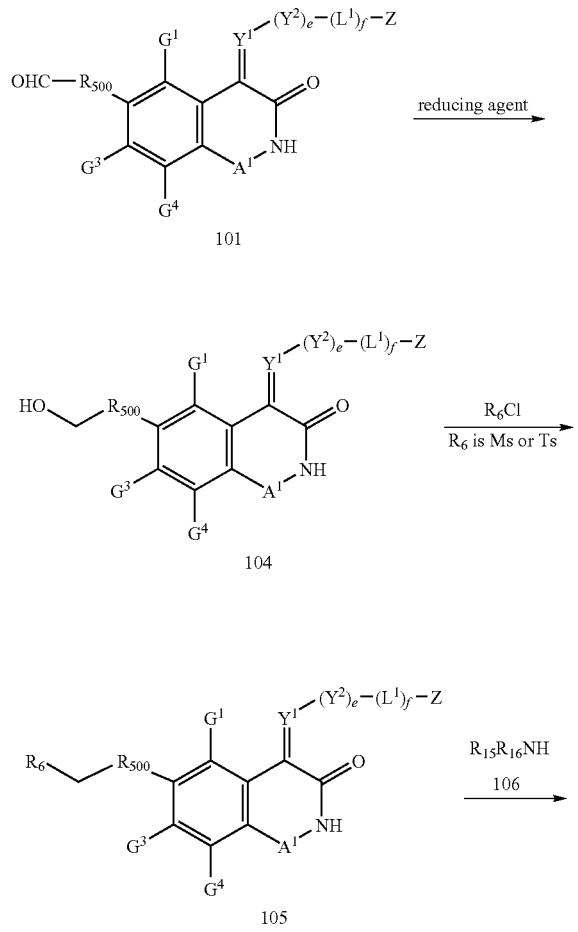

103

As described in Scheme 31, oxo 101 may be reduced using reducing agents which include catalytical hydrogenation, $NaBH_4$ or $BH_3$ to afford alcohol 104 which may be converted to oxo 105 wherein $R_6Cl$ may be MsCl or TsCl followed by reacting with amine 106 to form amine 103.

SCHEME 31

101 reducing agent

104

$R_6Cl$
$R_6$ is Ms or Ts

105

$R_{15}R_{16}NH$
106

-continued

103

As shown in Scheme 32, diester 106 containing a leaving group (LG) which include Br, I or OTf (tirflate) may be reacted with organoboron ($R_{211}$—$BR_{213}R_{214}$), organotin ($R_{211}$—$Sn(R_{21})_3$, organozinc reagents ($R_{211}$—$ZnBr$), alkenes ($R_{13}$—$C\equiv CH$) or alkynes (($R_{13})_2C\equiv CH(R_{13})$) in the presence of catalysts which include tetrakis (triphenylphosphine)palladium (0) [$Pd(PPh_3)_4$], bis(diphenylphosphine) palladium (II) chloride and [1,1'-bis(diphenylphosphino)ferrocene]palladium (II) dichloride [$PdCl_2$ $(dppf)_2$] afford diester 107. Other catalysts including palladium (II) chloride, palladium (II) diacetate, tris(dibenzylideneacetone)dipalladium (0) [$Pd_2(dba)_3$] in the presence of triphenylphosphine, tri-t-butylphosphine with or without copper (I) iodide may be used to generate one 94. Preferred solvents include N,N-dimethylformamide, N-methylpyrrolidinone, dimethoxyethane and dioxane. Preferred bases include aqueous sodium carbonate, cesium carbonate and triethylamine. The reactions take place by heating from about 110° C. to 200° C. in oil bath or in microwave oven. $R_{213}$ and $R_{214}$ groups are independently hydroxyl, alkyl of 1 to 12 carbon atoms or alkoxy of 1 to 12 carbon atoms. In addition, the ligands $R_{213}R_{214}$ may be taken together with the boron to which they are attached to form a cyclic boron ester, where $R_{213}R_{214}$ may be oxyethyleneoxy and the like.

Diester 107 may be hydrolyzed with aqueous base to give diacid 108. Treating diacid 108 with urea gives dione 109 which may be treated with orthoformate 2 which includes trimethyl orthoformate in the presence of an anhydride which includes acetic anhydride in a polar solvent such as N,N-dimethylformamide (DMF) to give ether 110. Further condensing ether 110 with intermediate 4 in the presence of a solvent including DMF affords substituted dione 111.

SCHEME 32

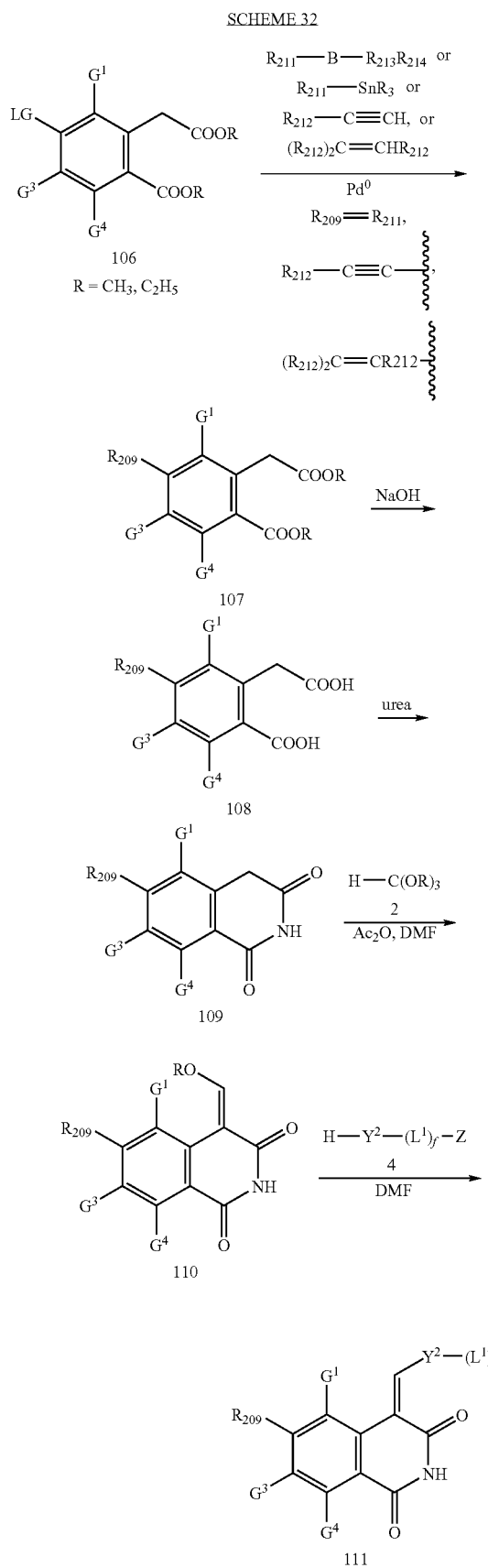

As described in Scheme 33, reaction of oxo 112 with amine 65 in the presence of Pd° such as tris(dibenzylideneacetone)dipalladium(0) ligand such as tri-tert-butylphosphine, base such as sodium t-butoxide abd, 1,3-bis(2,6-di-1-propylphenyl)-4,5-dihydroimidazonium chloride (IPr HCl) In a polar solvent which includes DMF and N-methylpyrrodinone affords amine 113.

SCHEME 33

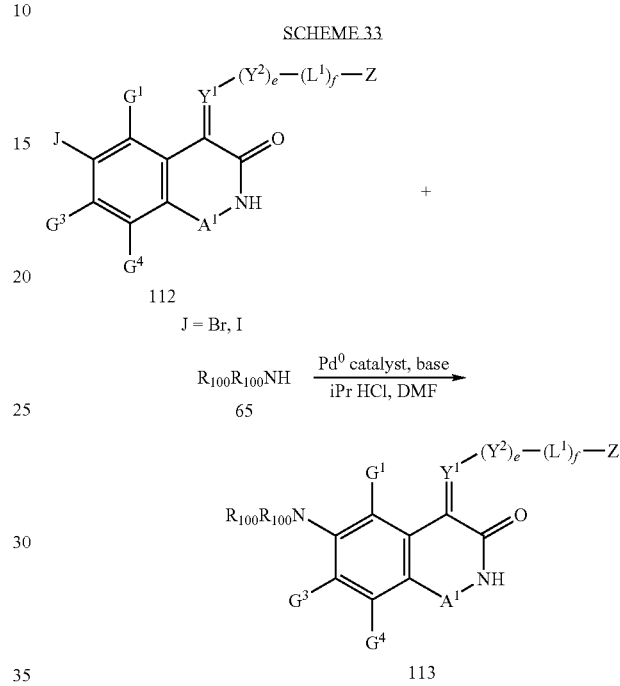

As described in Scheme 34, reaction of oxo 114 with 2,5-dimethoxytetrahydrofuran 115 in acetic acid or DMF containing 4-chloropyridine hydrochloride affords pyrrole 116 which may be reacted with orthoformate 2 which includes trimethyl orthoformate in the presence of an anhydride which includes acetic anhydride in a polar solvent such as N,N-dimethylformamide (DMF) to give ether 117 or with DMF-acetal to produce amine 118 which may be further reacted with intermediate 4 to give oxo 119.

SCHEME 34

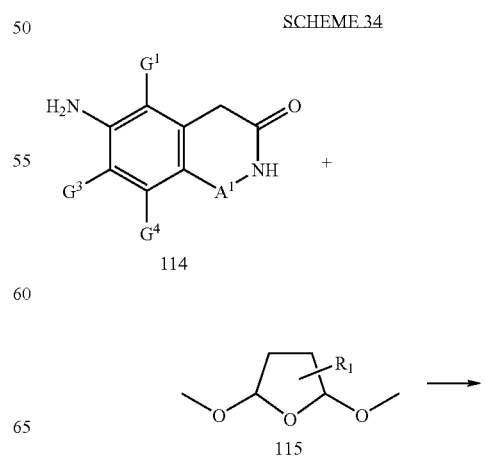

-continued

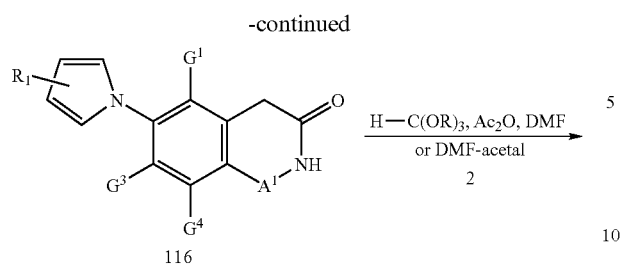

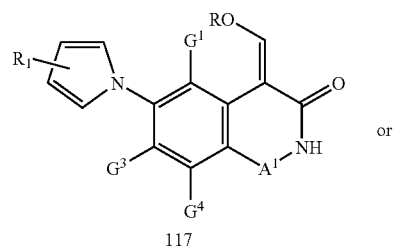

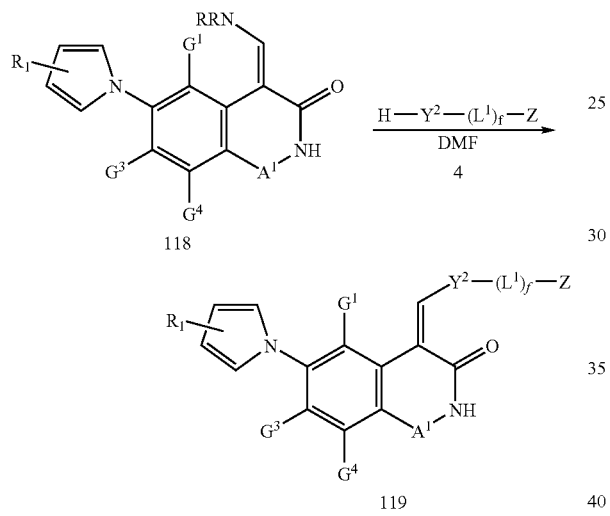

As described in Scheme 35, reaction of pyrrole 116 with diazonium 13 prepared by reaction of amine 10 with sodium nitrite in the presence of aqueous acid provides substituted oxo 119.

SCHEME 35

-continued

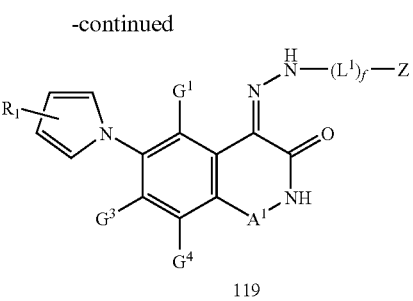

As described in Scheme 36 reaction of substituted oxo 120 with substituted tetrahydrofuran 121 or furan 122 affords pyrrole 123 which may be further reacted with amine 106 in the presence of a reducing agent including sodium cyanoborohydride and sodium triacetoxyborohydride to afford substituted pyrrole 124.

SCHEME 36

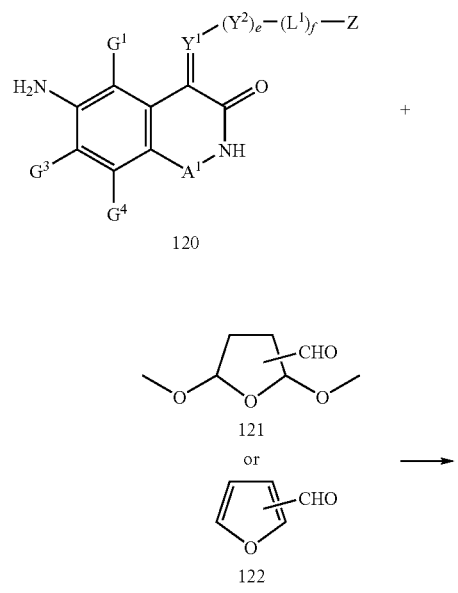

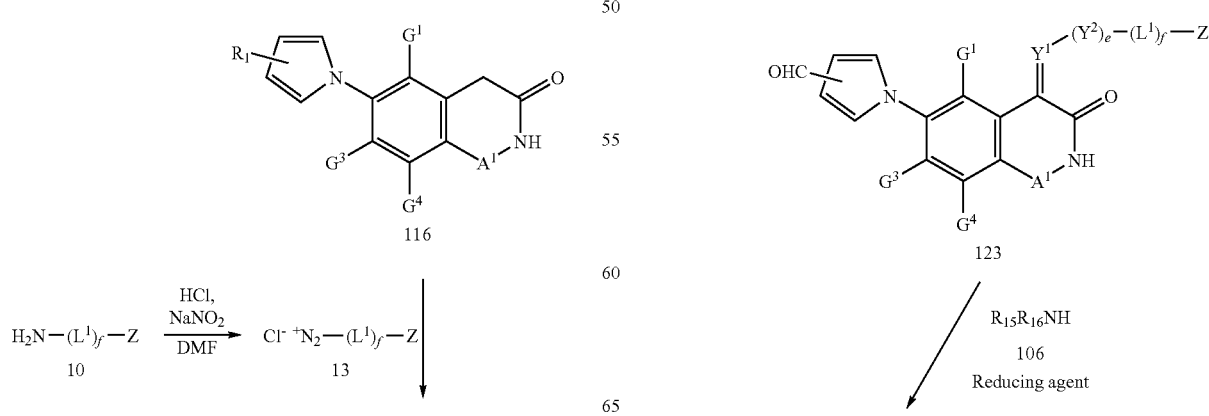

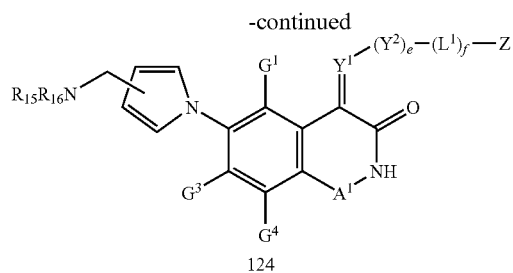

As shown in Scheme 37, pyrrole 123 may be reduced by catalytical hydrogenation, NaBH$_4$ or BH$_3$ to form alcohol 125 which may be further reacted with MsCl or TsCl to form oxo 126. Further reaction of oxo 126 with amine 106 provides oxo 124.

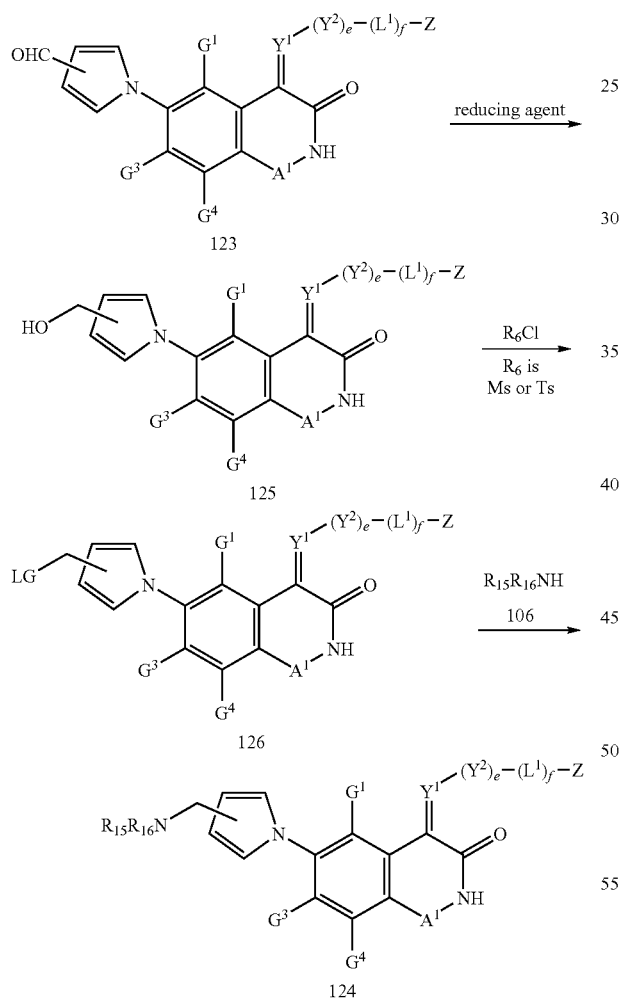

As described in Scheme 38 reaction of substituted oxo 120 with 2,5-dimethoxytetrahydrofuran 127 in acetic acid or DMF containing 4-chloropyridine hydrochloride affords pyrrole 128 which may be further reacted with amine 106 in the presence of paraformaldehyde to afford substituted pyrrole 129.

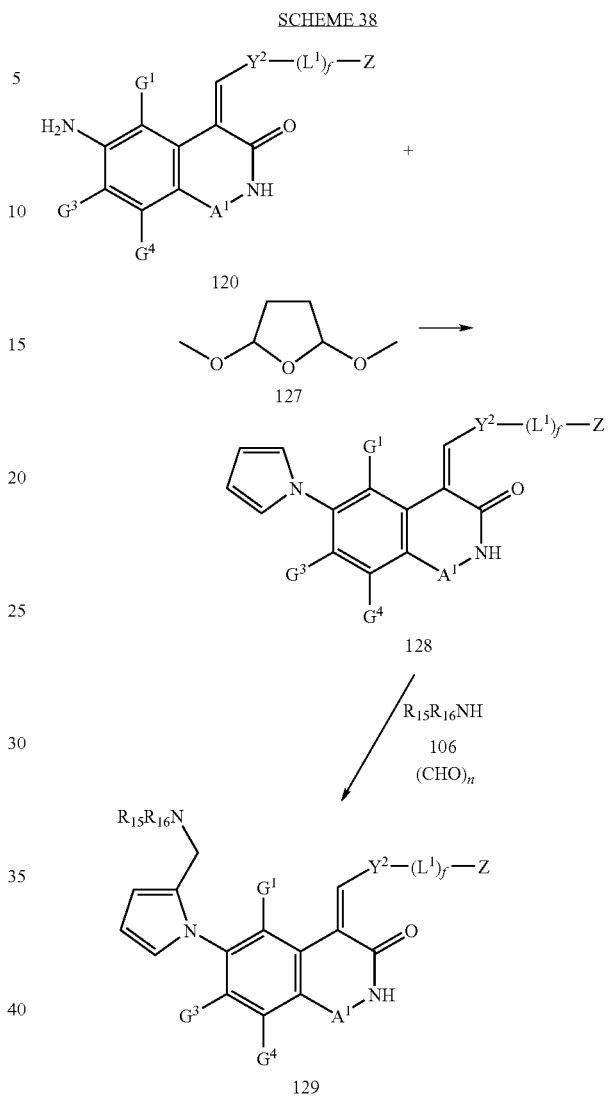

According to Scheme 39, reaction of oxo 114 with 2,5-dimethoxytetrahydrofuran 115 in the presence of sodium borohydride and trifluoroacetic acid (TFA) affords pyrrolidine 130 which may be reacted with orthoformate 2 which includes trimethyl orthoformate in the presence of an anhydride which includes acetic anhydride in a polar solvent such as N,N-dimethylformamide (DMF) to give ether 131 or with DMF-acetal to give amine 132 which may be further reacted with intermediate 4 to give oxo 133.

SCHEME 39

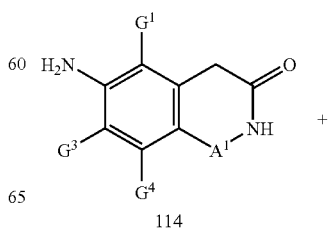

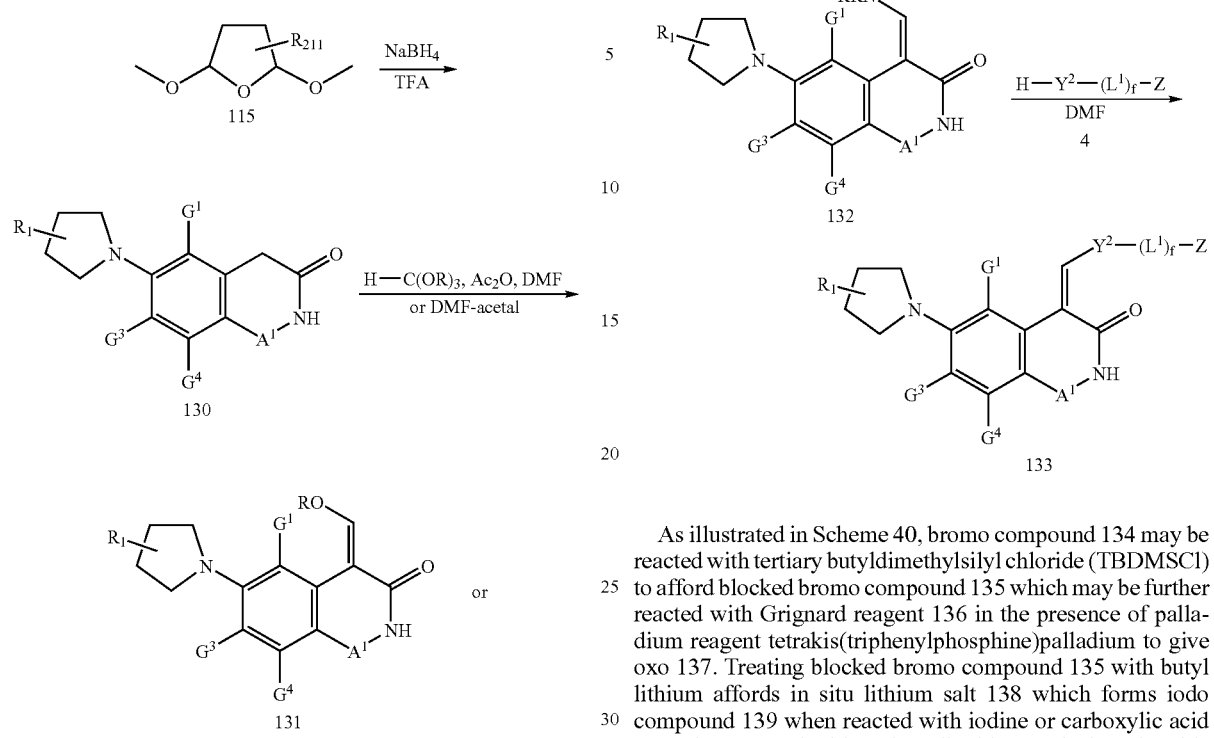

As illustrated in Scheme 40, bromo compound 134 may be reacted with tertiary butyldimethylsilyl chloride (TBDMSCl) to afford blocked bromo compound 135 which may be further reacted with Grignard reagent 136 in the presence of palladium reagent tetrakis(triphenylphosphine)palladium to give oxo 137. Treating blocked bromo compound 135 with butyl lithium affords in situ lithium salt 138 which forms iodo compound 139 when reacted with iodine or carboxylic acid 140 when reacted with carbon dioxide or substituted amide 142 when reacted with reagent 141.

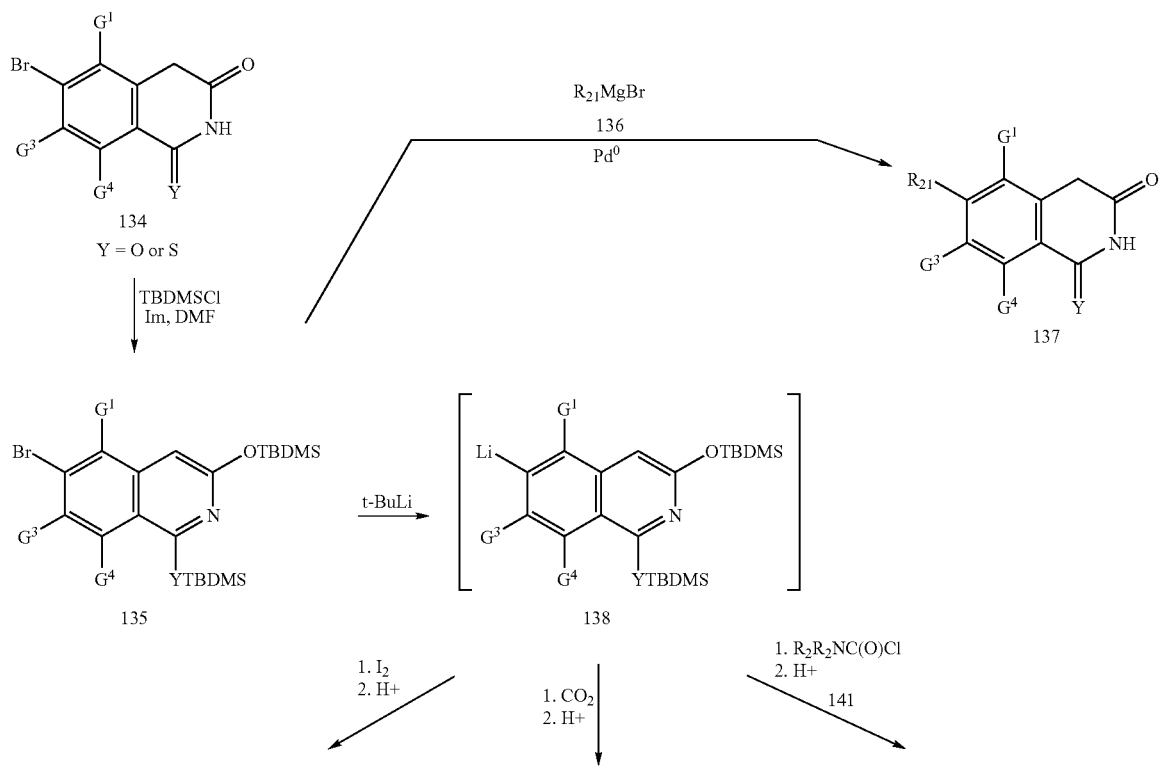

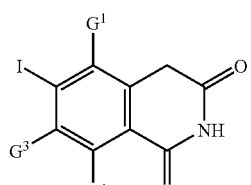 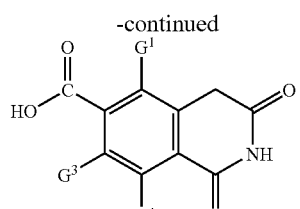 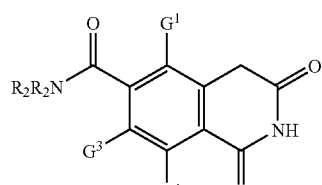

139 140 142

As described in Scheme 41, reaction of oxo 143 with zinc cyanide and tetrakis(triphenylphosphine)palladium in a polar solvent DMF to give cyano compound 144.

SCHEME 41

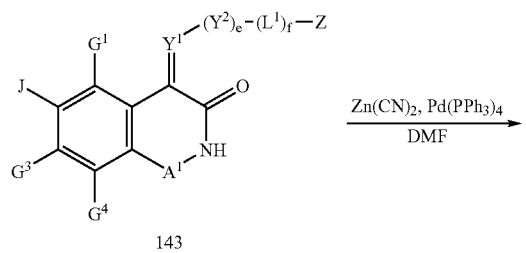

143

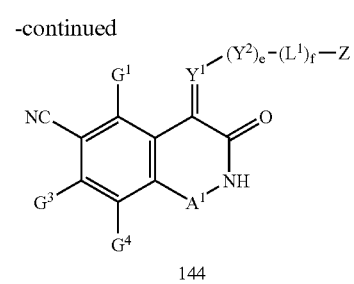

144

As illustrated in Scheme 43, carboxylic acid 145 may be reacted with iodine in acetic acid or iodine, potassium iodide and ammonium hydroxide to give iodo compound 146 which may be further reacted with isobutylchloroformate and triethylamine (TEA) followed by treating with ammonia to give amide 147. Reacting amide 147 with thionyl chloride in an inert solvent such as toluene affords amine 148 which may be further reacted to afford substituted phenol 149 which may be reduced with diborane in an inert solvent such as THF to give amine 150.

SCHEME 43

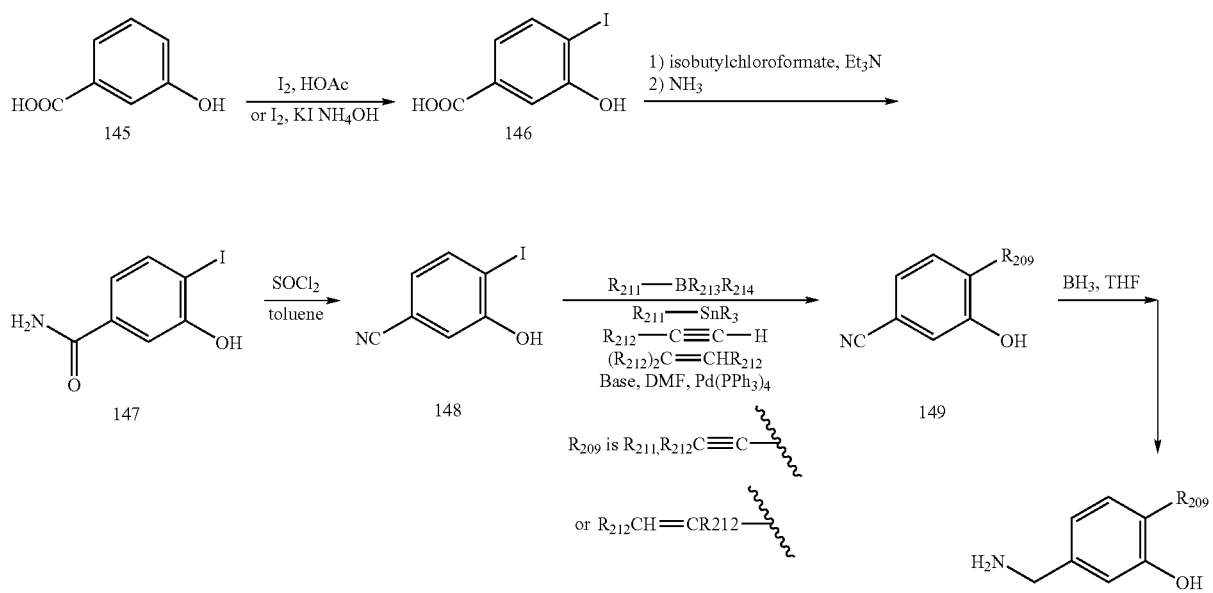

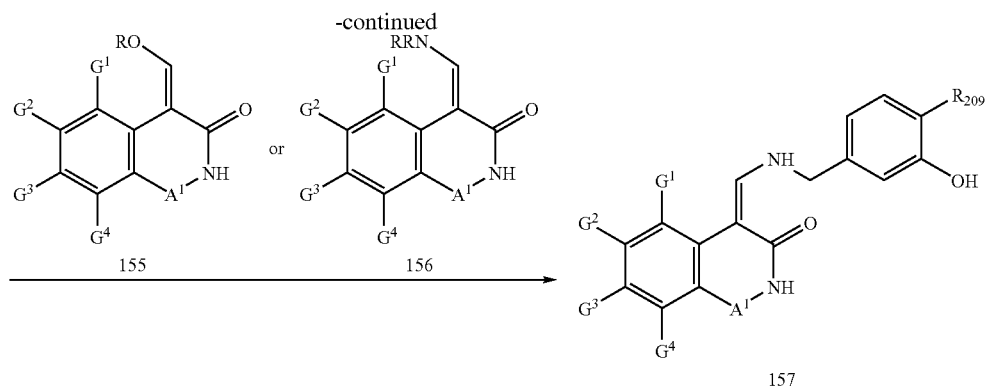

As described in Scheme 44, alkoxy 151 may be converted to carboxylic acid 152 which may be reduced with lithium aluminum hydride to give alcohol 153. Further reaction of alcohol 153 with thionyl chloride in methylene chloride followed by treating with boron tribromide and then sodium azide in DMF provides azide 154 which may be converted to amine 149 by reacting with triphenylphosphine in THF-water. Reacting ether 155 or amine 156 with amine 149 provides oxo 157.

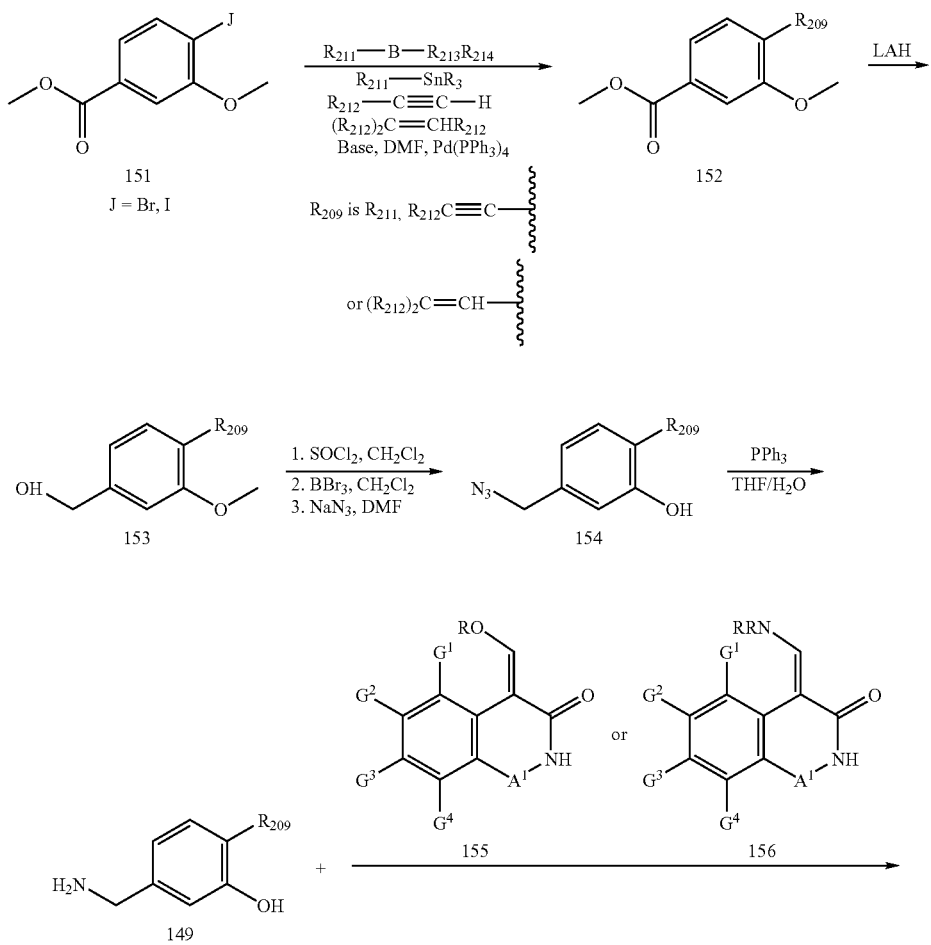

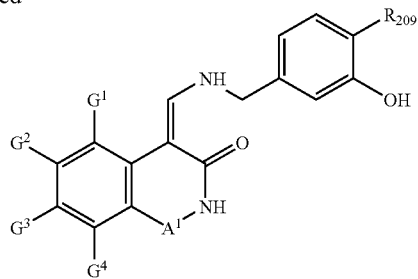

157

As illustrated in Scheme 45, oxo 158 may be reacted with formaldehyde in DMF-water under microwave irradiation to provide alcohol 159.

SCHEME 45

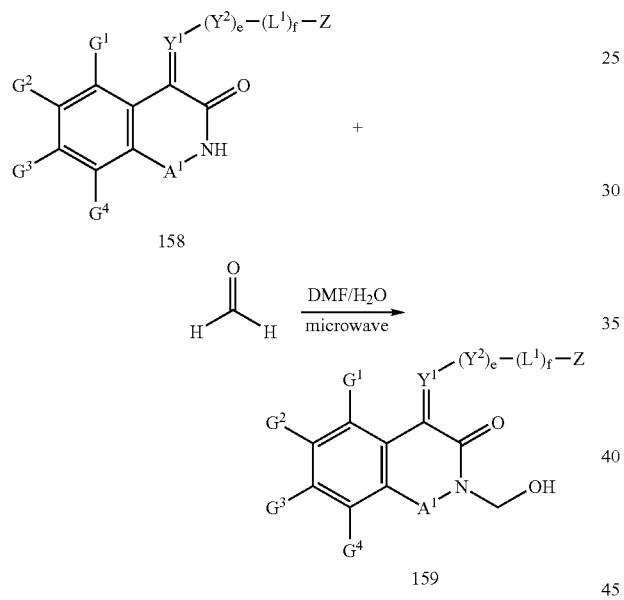

As described in Scheme 46, pyrone acid 160 may be reacted with an halide (X=Cl, Br, I) in acetone, methylethylketone or DMF with potassium carbonate and potassium iodide to give alkoxypyrone 161. Alkoxypyrone 161 may be heated with ammonia to afford pyridinol 162. Pyridinol 162 may be reacted with thionyl chloride, followed by sodium azide in DMF to afford azide 163. Further reaction of azide with triphenylphosphine in THF, followed by addition of water affords amine 164, which may be further reacted with one 3 to give pyridinol 165.

SCHEME 46

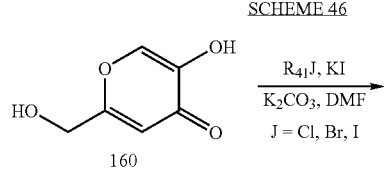

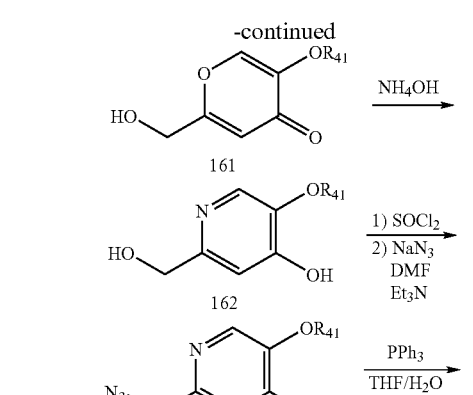

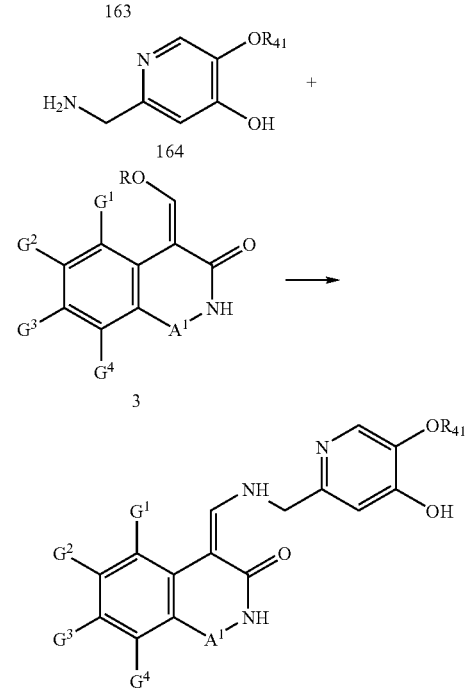

As illustrated in Scheme 47, silylprotected 4-pyrone triflate 166 may be coupled with an aryl- or heteroaryl-boronic acid in dioxane, potassium carbonate and [1,1'-bis(diphenylphosphino)ferrocene]palladium (II) dichloride [PdCl$_2$(dppf)$_2$] as described by, T. Kamino, et. al.; Tet. Lett. 44

(2003) 7349 to afford compound 167 which may be treated with t-butylammonium fluoride to provide alcohol 168. Reaction of alcohol 168 with ammonium hydroxide in the presence of TFA provides pyridinol 169 which may be further treated with thionyl chloride or triphenylphosphine in the presence of $CX_4$ (X=Cl or Br) to provide compound 170. Further reaction of compound 170 with sodium azide in DMF provides azide 171 which may be converted to amine 172 by reaction with triphenylphosphine in aqueous THF which may be further reacted with oxo 3 to give pyridinol 173.

SCHEME 47

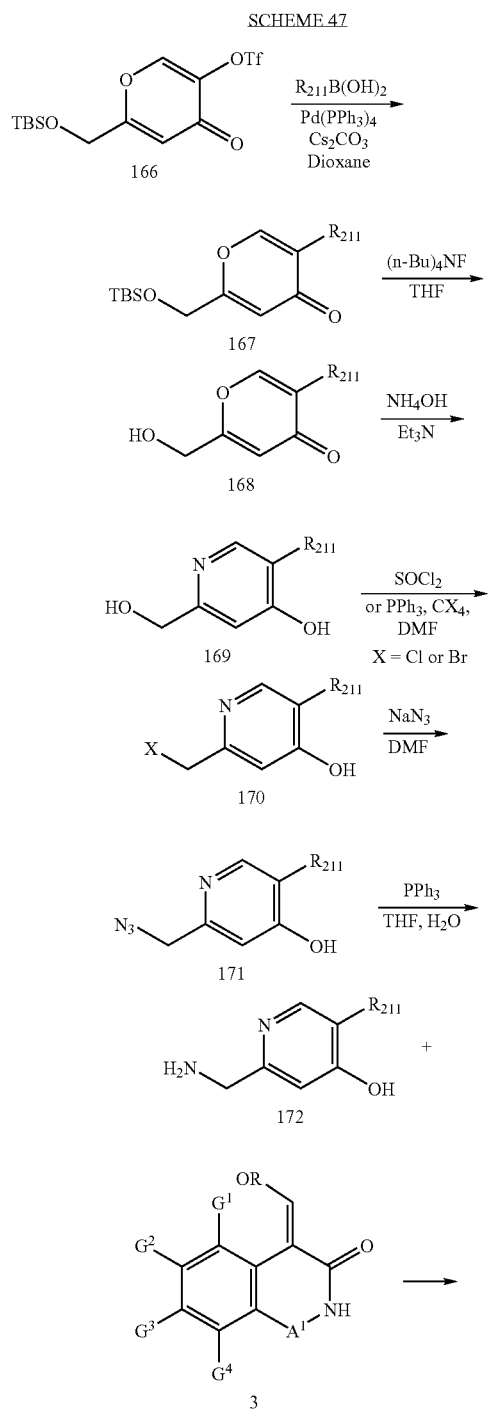

-continued

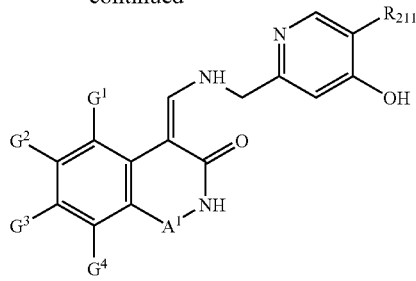

173

As described in Scheme 48, 2-chloro-3-hydroxypyridine 174 may be hydroxymethylated as reported [D. G. Wishka, et.al.; J. Med. Chem. 41(9) 1357 (1998)) to give hydroxylpyridine 175 which may be alkylated using $R_{208}J$, to give pyridine 176. Protection of the hydroxymethyl of pyridine 176 using tirisopropylsilylchloride (TIPSCl), triethylamine and dichloromethane gives triisopropylsilyl ether 177. Further treatment of triisopropylsilyl ether 177 with sodium benzyloxide in benzyl alcohol (1M) gives after chromatography, 2-benzyloxypyridine 178 which may be further reacted with tetrabutylammonium fluoride in THF to give alcohol 179. Alcohol 179 may be converted to chloromethyl compound 179 using thionyl chloride in methylene chloride then further reacted with sodium azide in DMF to provide azidomethyl compound 181. Reaction of azidomethyl compound 181 with triphenylphosphine in aqueous THF provides aminomethyl compound 182 which may be hydrogenated in ethanol with 10% palladium on carbon under oxo atmosphere of hydrogen for about 6 hours to provide amine 183. Reaction of amine 183 with oxo 3 provides pyridinol compound 184.

SCHEME 48

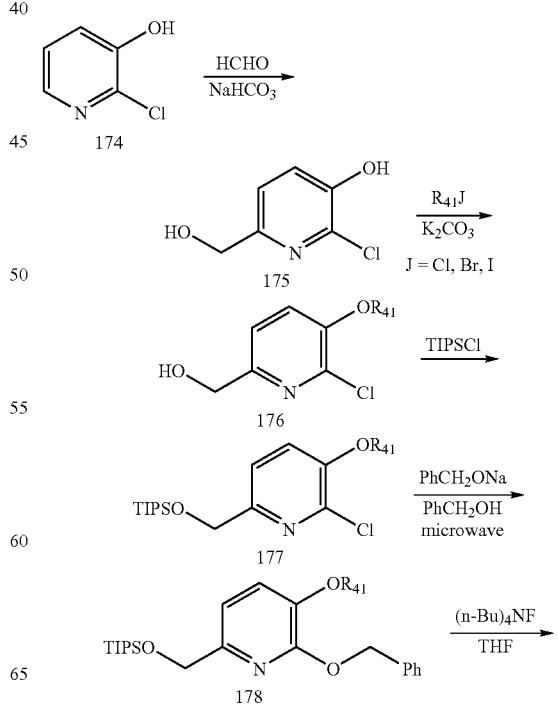

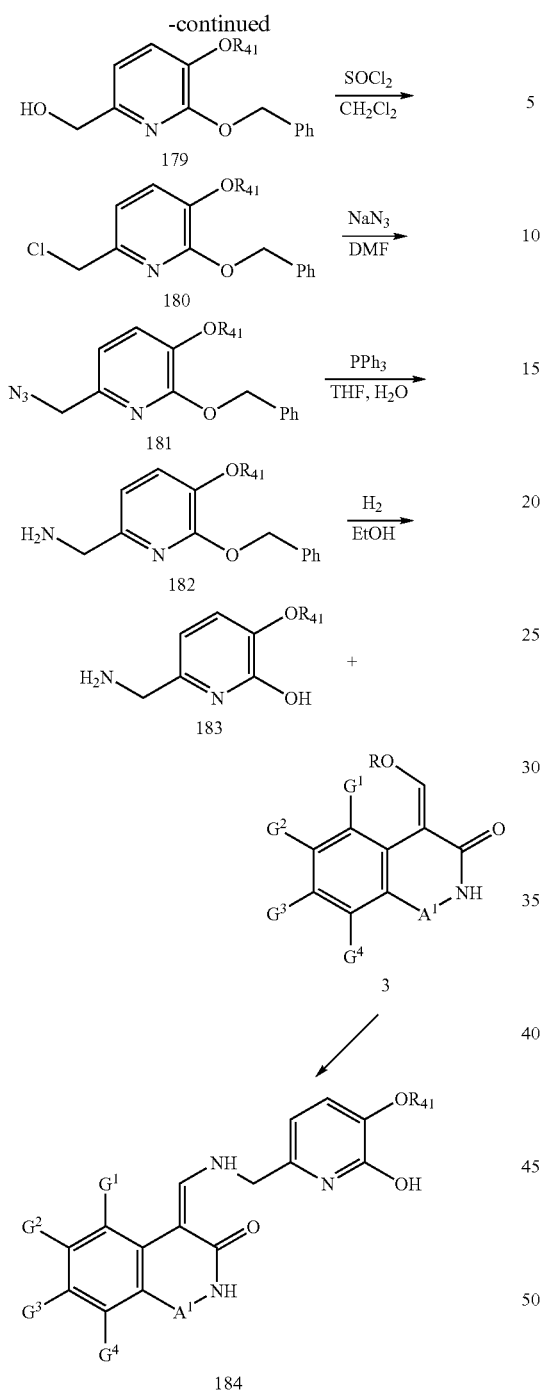

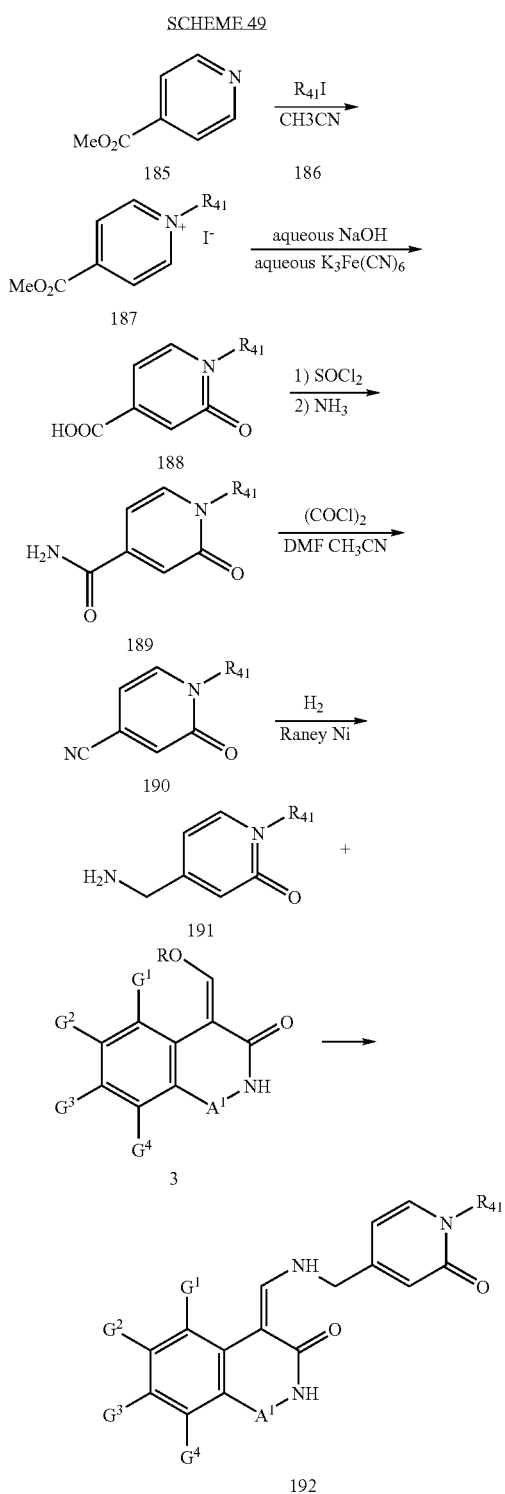

As described in Scheme 49, ester 185 may be alkylated as reported (Fronk and Mosher, J Org Chem. Vol 24, 1959, 196-198) which may be alkylated using $R_{41}J$ to give pyridinium salt 187, which may be further reacted with aqueous base and $K_3Fe(CN)_6$ to give pyridone 188. Reaction of pyridone 188 with thionyl chloride followed by ammonia provides amide 189 which may be further reacted with oxalyl chloride and acetonitrile in a polar solvent such as DMF to provide cyano compound 190 which may be reduced with hydrogen and Raney Ni to give amine 191. Reaction of amine 191 with oxo 3 provides pyridine compound 192.

As provided in Scheme 50, pyridone compound 193 may be reacted with Kt-OBu, n-Bu4NI in DMSO at 0C., followed by reacting with compound 194 ($R_{2141}X$, where $R_{214}X$ is a substituted alkyl halide $R_{41}X$ (X is Br, I) to yield N-substituted pyridone 195. Alternatively, pyridone compound 193 may be reacted with compound 194 ($R_{214}X$, where $R_{214}X$ is a substituted aryl or heteroaryl halide $R_{211}X$, X=Br, I), copper salt including Cu(I)I, Cu(I)Br, Cu₂O, Cu(II)Br₂, or Cu powder, preferably Cu(I)I, base including KOAc, K₃PO₄, and K₂CO₃, preferably K₂CO₃, in a solvent including DMF, DMSO, dimethylacetamide, N-methylpyrrolidinone, dioxane, toluene and xylene, preferably DMF, in an oil bath or under microwave irradiation at 100° C. to 200° C., preferably at 150° C. to afford N-substituted pyridone 195.

Pyridone 195 may be reacted with tert-butoxybis(dimethylamino)methane (Bredereck's reagent) in DMF, dioxane, toluene, or xylene, preferably DMF at 80° C. to 150° C., preferably at 100° C. to yield enamine 196. Enamine 196 when oxidized with NaIO₄ in THF provides aldehyde 197, which may be reduced with metal hydride salt, preferably sodium borohydride in methanol to give alcohol 198. Reaction of alcohol 198 with methanesulfonyl chloride and triethylamine followed by sodium azide provides azide compound 199 which may be reduced by reaction with triphenylphosphine in aqueous THF to provide amine 200. Reaction of amine 200 with one 3 provides pyridone 201.

SCHEME 50

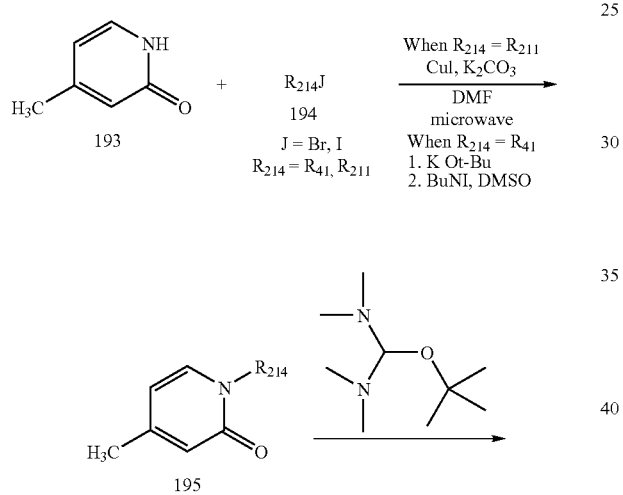

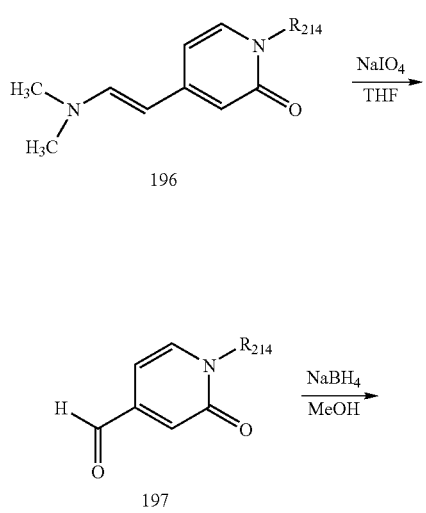

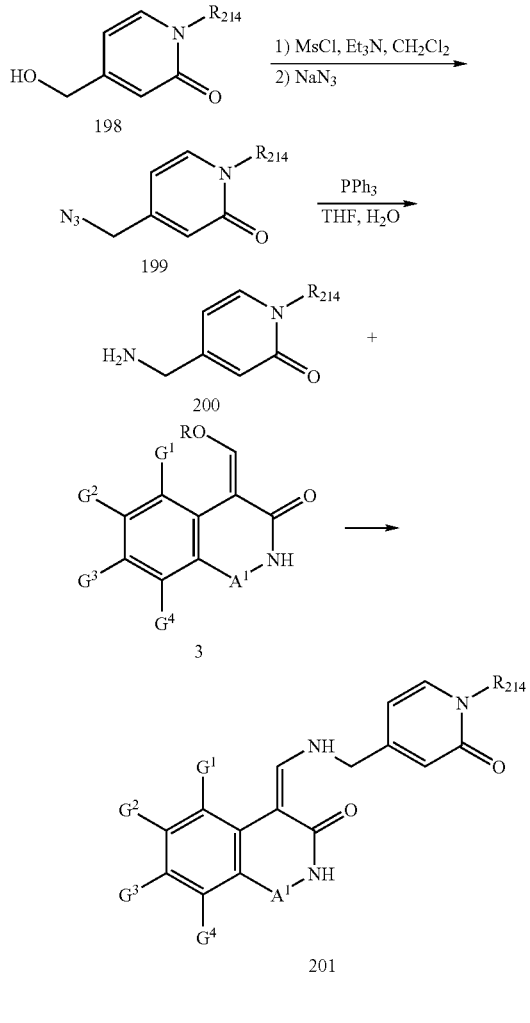

The phenol 202 is treated with sodium hydride, followed by reacting with methoxymethyl chloride 203 to afford methoxymethyl ether 204, which may be reacted with organoboron ($R_{211}$—$BR_{213}R_{214}$), organotin ($R_{211}$—$Sn(R_{21})_3$), organozinc reagents ($R_{211}$—ZnBr), alkenes ($R_{13}$—C≡CH) or alkynes (($R_{13}$)₂C═CH($R_{13}$)) in the presence of catalysts which include tetrakis (triphenylphosphine)palladium (0) [Pd(PPh₃)₄], bis(diphenylphosphine)palladium (II) chloride and [1,1'-bis(diphenylphosphino)ferrocene]palladium (II) dichloride [PdCl₂ (dppf)₂] afford cyano compound 205. Other catalysts including palladium (II) chloride, palladium (II) diacetate, tris(dibenzylideneacetone)dipalladium (0) [Pd₂(dba)₃] in the presence of triphenylphosphine, tri-t-butylphosphine with or without copper (I) iodide may be used to generate one 94. Preferred solvents include N,N-dimethylformamide, N-methylpyrrolidinone, dimethoxyethane and dioxane. Preferred bases include aqueous sodium carbonate, cesium carbonate and triethylamine. The reactions take place by heating from 110° C. to 200° C. in oil bath or in microwave oven. The cyano compound 205 may be reduced by lithium aluminum hydride to afford the benzylamine 206. Reacting ether 155 or amine 156 with the benzylamine 206 provides one 157.

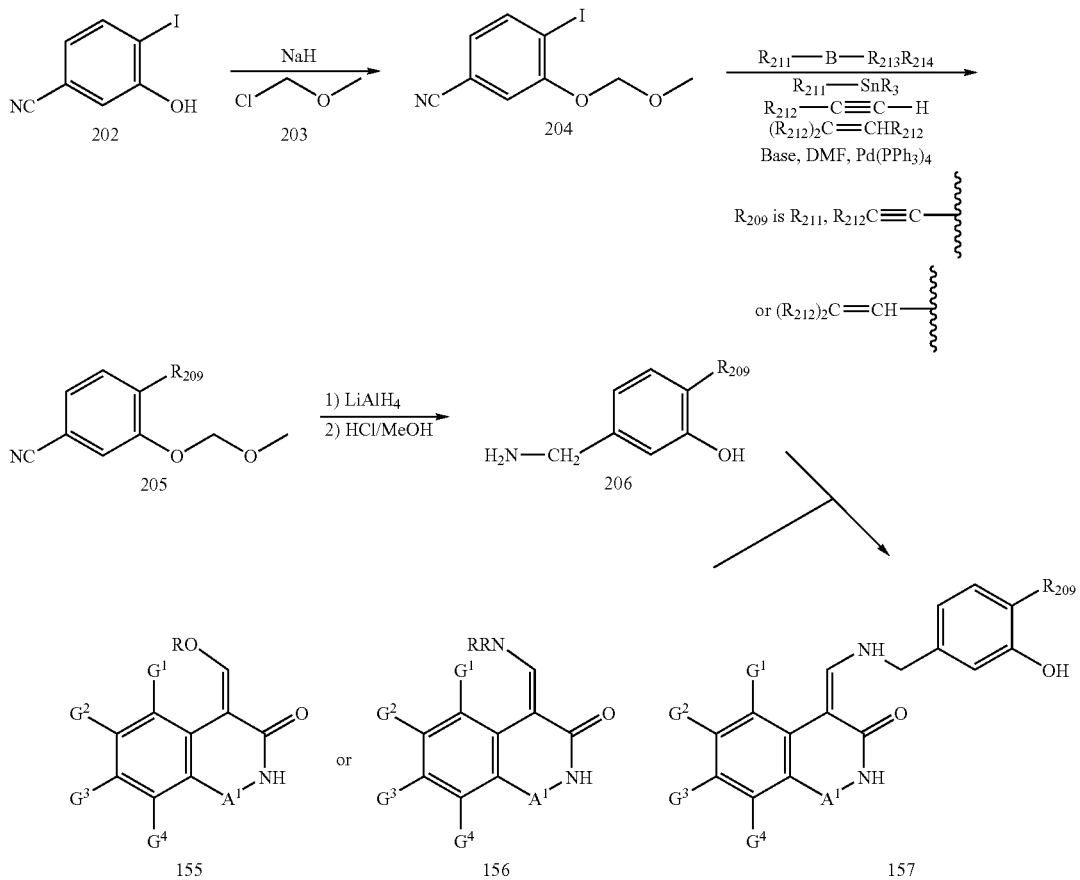

As illustrated in Scheme 52, pyrone acid 160 may be reacted with an halide (X=Cl, Br, I) in acetone, methylethylketone or DMF with potassium carbonate and potassium iodide to give alkoxypyrone 161 which may be further reacted with thionyl chloride, followed by sodium azide in DMF to afford azide 207. Further reaction of azide 207 with triphenylphosphine in THF, followed by addition of water affords amine 208, which may be further reacted with oxo 3 to give substituted pyrone 209.

SCHEME 52

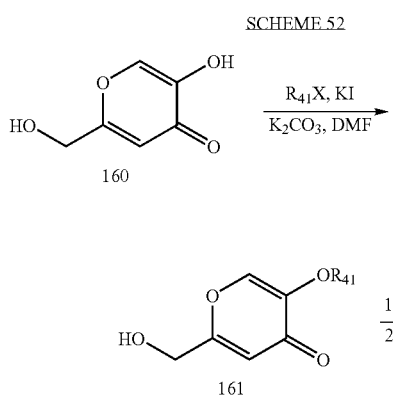

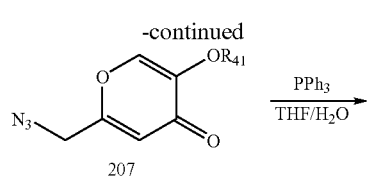

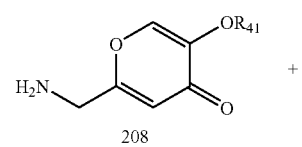

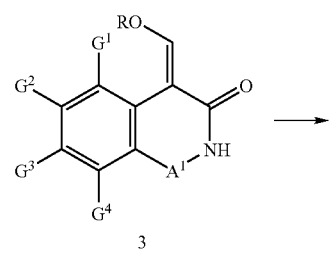

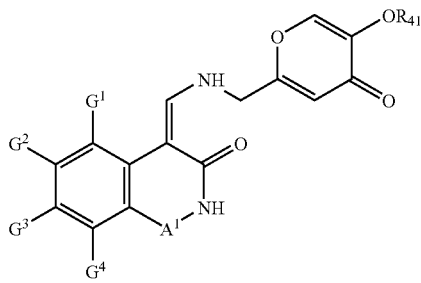

The invention will be more fully described in conjunction with the following specific examples which are not to be construed as limiting the scope of the invention.

EXPERIMENTAL

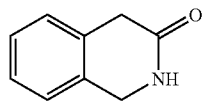

Intermediate 1

1,4-Dihydro-3(2H)-isoquinolinone

A mixture of phenylacetamide (5 g, 37 mmol), pyrophosphonic acid (80 g, 449.5 mmol) and paraformaldehyde (1.22 g, 40.7 mmol) is heated at 155° C. for 1 h to give a viscous black solution. It is poured into ice water and treated with potassium carbonate to pH 7. The solution is extracted with ethyl acetate, and the organic solution is washed with saturated potassium carbonate, dried over magnesium sulfate, and evaporated to dryness to give 1.145 g (21%) of the product as a yellow solid; MS (ESI) m/z 148.0 (M+1). [Ref: Heterocycles 26(9), 2385 (1987)].

Intermediate 2

(4E)-4-[(Dimethylamino)methylene]-1,4-dihydro-3(2H)-isoquinolinone

A N,N-dimethylformamide (1 mL) solution containing 1,4-dihydro-3(2H)-isoquinolinone (300 mg, 2.04 mmol) and N,N-dimethylformamide dimethylacetal (0.65 mL, 4.89 mmol) is heated at 100° C. for 2.5 hours. After removing the solvents, the residue is washed with ether, water and ether to give 88 mg of the product as a pink solid. The filtrate is evaporated to dryness, and the residue is treated with ether, water and ether to give 105 mg of a second crop of the product with a total yield of 47% (193 mg); MS (ESI) m/z 203.2 (M+1). Ref: Chemistry of Heterocyclic compd. 370-374 (1981).

Intermediate 3

4-(4-Nitro-phenyl)-1H-imidazole

Sulfuric acid (95-98%, 250 mL) is placed in a 1 L 4-neck round bottomed flask equipped with mechanical stirrer, thermometer and cooled to 0° C. 4-Phenylimidazole (87.2 g, 0.606 mol) is added in portions to keep the temperature under 10° C. The starting material is dissolved completely after stirring for 20 minutes. The mixture is cooled to 0° C., fuming nitric acid (28.42 mL, 0.606 mol) is added dropwise to keep the temperature at 0-5° C. The addition took about 1.5 h. After stirring at 0° C. for 1 h, the reaction mixture is poured into ice (3 Kg) and stirred for 20 minutes, neutralized with sodium hydroxide (340 g) and then sodium carbonate (10%) to pH~10. The mixture is filtered; the solid is washed with water (3×500 mL), methanol (500 mL) and air-dried. The crude product is recrystallized with ethanol (20 mL/g) to give 50.5 g product as tan crystals. The mother liquor is concentrated and the residue is recrystallized with ethanol to give another crop of the product (11.2 g) with a total yield of 61.7 g (53.9%); mp 226-228° C.

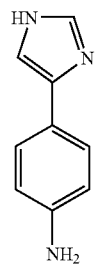

Intermediate 4

4-(1H-Imidazol-4-yl)aniline

A suspension of 4-(4-nitro-phenyl)-1H-imidazole (50 g, 0.2646 mol), 5% Pd/C (6 g) in 600 mL of methanol is hydrogenated at 7 psi of hydrogen at room temperature. After 1 h, the pressure of hydrogen remained unchanged, the mixture is filtered through a Celite cake. The filtrate is evaporated to give a red residue. After drying at high vacuum overnight, 43.2 g of a beige foam is isolated. It is hydroscopic, and sensitive to light and air.

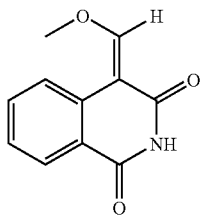

Intermediate 5

4-Methoxymethylene-4H-isoquinoline-1,3-dione

Trimethyl orthoformate (5.648 mL, 51.56 mmol) is added to a solution of 4H-Isoquinoline-1,3-dione (4 g, 24.82 mmol) in acetic anhydride (41.6 mL) and N,N-dimethylformamide (10.4 mL). After it is heated at 125° C. for 50 min, it is cooled and filtered to collected 3.698 g (73%) of the title compound as a yellow solid. mp 260-261° C.; MS (ESI) m/z 204.04 (M+1). Found: C, 58.34; H, 3.63; N, 10.21.

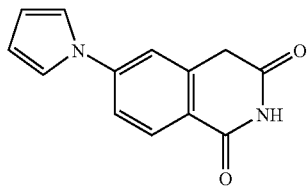

Intermediate 6

6-(1H-Pyrrol-1-yl)isoquinoline-1,3(2H,4H)-dione

A mixture of 6-amino-4H-isoquinoline-1,3-dione (1 g, 5.68 mmol), 2,5-dimethoxytetrahydrofuran (0.736 mL, 5.68 mmol), 4-chloropyridine hydrochloride (0.417 g, 2.78 mmol) in dioxane (20 mL) is heated at 70° C. for 2 h [Ref: J. Heterocyclic Chem. 35, 1313, (1998)] After cooling, the solid is filtered, washed successively with water, ether and hexane to yield 0.86 g (67%) of the title compound as a light brown solid, mp 212-213° C.; HRMS (ESI) m/z calcd for $C_{13}H_{10}N_2O_2$ 227.08151. found 227.08151 (M+H)$^{+1}$. Analysis for $C_{13}H_{10}N_2O_2$ (0.5H2O): Calcd: C, 66.37; H, 4.71; N, 11.91. Found: C, 66.19; H, 4.56; N, 11.09.

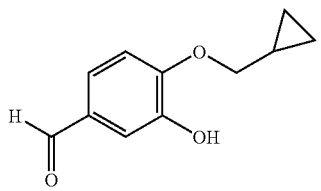

Intermediate 7

4-(Cyclopropylmethoxy)-3-hydroxybenzaldehyde

A mixture of 3,4-dihydroxybenzaldehyde (4.14 g, 30 mmol), cyclopropylmethyl bromide (3.06 mL, 31.5 mmol), potassium carbonate (8.29 g, 60 mmol) in acetone (90 mL) is heated at 50 C overnight. After filtration, the solution is dried to a gum, which is dissolved in ethyl acetate, and washed with water. It is dried to an oil and then chromatographed to yield 0.42 g (7%) of the title compound as a white powder. MS (ESI) m/z 191.2 (M–H)$^{-1}$.

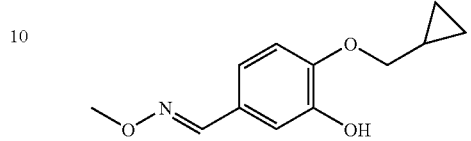

Intermediate 8

4-Cyclopropylmethoxy-3-hydroxy-benzaldehyde O-methyl-oxime

A solution of 4-(cyclopropylmethoxy)-3-hydroxybenzaldehyde O-methyloxime, 4-(cyclopropylmethoxy)-3-hydroxybenzaldehyde (192 mg, 1 mmol), O-methyl-hydroxylamine hydrochloride (167 mg, 2 mmol), pyridine (0.162 mL, 2 mmol) and ethanol (2.5 mL) is stirred at room temperature overnight. After evaporation to dryness, the residue is dissolved in ether, followed by addition of ice water and two drops of HCl. The ether layer is separated, and is washed extensively with aqueous sodium chloride solution to pH neutral. It is dried up to give 0.211 (95%) of white crystals of the title compound. MS (ESI) m/z 222.1(M+H)+1

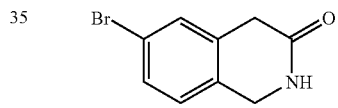

Intermediate 9

6-Bromo-1,4-dihydroisoquinolin-3(2H)-one

A mixture of 6-bromo-1,4-dihydroisoquinolin-3(2H)-one and 8-bromo-1,4-dihydroisoquinolin-3(2H)-one is separated by chromatography to yield 80 mg of 6-bromo-1,4-dihydroisoquinolin-3(2H)-one. MS (ESI) m/z 226.0, 228.0 (M+H)+1.

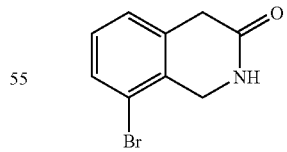

Intermediate 10

8-Bromo-1,4-dihydroisoquinolin-3(2H)-one

A mixture of 6-bromo-1,4-dihydroisoquinolin-3(2H)-one and 8-bromo-1,4-dihydroisoquinolin-3(2H)-one is separated by chromatography to yield 80 mg of 8-bromo-1,4-dihydroisoquinolin-3(2H)-one. MS (ESI) m/z 226.0, 228.0 (M+H)+1.

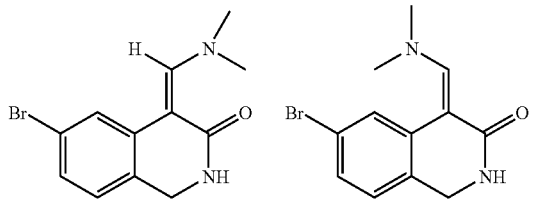

Intermediate 11a and 11b (4E)-6-Bromo-4-[(dimethylamino)methylene]-1,4-dihydroisoquinolin-3(2H)-one-(4Z)-6-Bromo-4-[(dimethylamino)methylene]-1,4-dihydroisoquinolin-3(2H)-one (1:1)

Using the procedure described for the preparation of (4E)-4-[(dimethylamino)methylene]-1,4-dihydro-3(2H)-isoquinolinone the title compound is obtained from 6-bromo-1,4-dihydroisoquinolin-3(2H)-one (113 mg, 0.5 mmol), N,N-dimethylformamide diethylacetal (0.206 mL, 1.2 mmol) and N,N-dimethylformamide (0.55 mL) in 60% yield as a yellowish-brown solid. MS (ESI) m/z 281, 283 (M+H)$^{+1}$

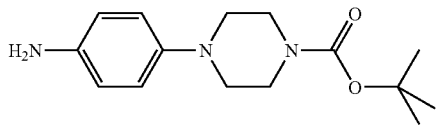

Intermediate 12 tert-Butyl 4-(4-aminophenyl)piperazine-1-carboxylate

A mixture of tert-butyl 4-(4-nitrophenyl)piperazine-1-carboxylate (307 mg, 1 mmol), iron powder (196 mg, 3.5 mmol), acetic acid (0.4 mL, 7 mmol) and methanol (5 mL) is heated at 66 C until no nitro compound left. After it is dried it is treated with ethyl acetate and water, and filtered through a pad of celite. The ethyl acetate layer is washed with saturated sodium bicarbonate solution and saturated sodium chloride solution, and then dried to yield the title compound.

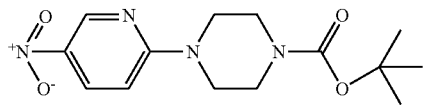

Intermediate 13 tert-Butyl 4-(5-nitropyridin-2-yl)piperazine-1-carboxylate

A mixture of 2-bromo-5-nitro-pyridine (1.719 g, 8.468 mmol), piperazine-1-carboxylic acid tert-butyl ester (1.58 g, 8.468 mmol), triethylamine (3.54 mL, 25.4 mmol) in acetonitrile (6 mL) is heated at 86 C for 2 h. After it is evaporated, the residue is dissolved in methylene chloride, and washed with saturated sodium bicarbonate solution. The organic layer is evaporated to yield 2.6 g (99%) of the title compound as a pale-yellow solid. NMR (CDCl$_3$) showed it is pure.

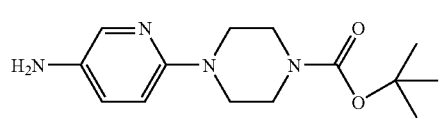

Intermediate 14 tert-Butyl 4-(5-aminopyridin-2-yl)piperazine-1-carboxylate

A mixture of tert-butyl 4-(5-nitropyridin-2-yl)piperazine-1-carboxylate (0.5 g, 1.62 mmol), iron powder (0.35 g, 6.26 mmol), acetic acid (0.72 mL, 11.34 mmol) in methanol (6 mL) is heated at 66 C for 1 h. After it is evaporated to dryness, ethyl acetate is added, and then the mixture is filtered through a pad of Celite. The filtrate is evaporated to yield 0.32 g (72%) of the title compound as an orange gum. NMR (CDCl$_3$) spectrum of the product showed it is pure.

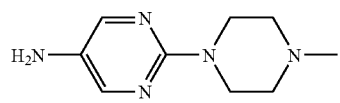

Intermediate 15

2-(4-Methyl-piperazin-1-yl)-pyrimidin-5-ylamine

2-Nitro-malonaldehyde (1.57 g, 10 mmol) is dissolved in water (15 mL), followed by addition of 2-methyl-isothiourea (1.56 g, 5.6 mmol) and N-methylpiperazine (1.92 mL, 17.3 mL). After stirring at room temperature overnight, it is filtered and washed with water and hexane to yield 1.38 g (62%) of 2-(4-methyl-piperazin-1-yl)-5-nitro-pyrimidine as a white solid. MS (ESI) m/z 224.3 (M+H)$^{+1}$. [Heterocycles. 1977, 6(12), 1999-2004].

A mixture of 2-(4-methyl-piperazin-1-yl)-5-nitro-pyrimidine (446 mg, 2 mmol), iron powder (432 mg, 7.6 mmol), acetic acid (0.884 mL, 14 mmol) in methanol (8 mL) is heated at 65 C for 2 h. It is worked up as before to yield 302 mg (78%) of the title compound. MS (ESI) m/z 194 (M+H)$^{+1}$.

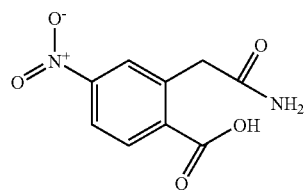

Intermediate 16

2-Carboxy-5-nitrobenzeneacetamide

A stirred mixture of 2.25 g (10 mmol) of 2-carboxy-5-nitrobenzeneacetic acid (J. Org. Chem. 1998, 63, 4116), 2.5 ml (35 mmol) of acetyl chloride, and 8 ml of acetone is refluxed for 60 m. The resulting solution is evaporated to dryness. The resulting tan solid is shown to be the corresponding cyclic anhydride by 1H NMR (DMSO-d$_6$) δ 4.40 (s, 2H). The anhydride is mixed at 0° with 16 ml of conc NH$_4$OH and 16 ml of H$_2$O. The resulting mixture is warmed to 250, stirred 15 m, and evaporated to dryness at <30° The residue is stirred in 25 ml of H$_2$O, acidified at 10° C. with 4 ml of 4N HCl, and stirred 10 m. The resulting tan solid is filtered, washed with H$_2$O, and dried to give 2.01 g (90%), mp 185-190° C. (dec); 1H NMR (DMSO-d$_6$) δ 8.20 (d, J=2.4 Hz, 1H), 8.16 (dd, J=2.4, 8.4 Hz, 1H), 8.02 (d, J=8.4 Hz, 1H), 7.47 (s, 1H), 6.96 (s, 1H), 3.96 (s, 2H); MS (ES−) m/z 223.1 (M−H)$^{-1}$: Analysis for C$_9$H$_8$N$_2$O$_5$: Calcd: C, 48.22; H, 3.60; N, 12.50. Found: C, 48.27; H, 3.40; N, 12.10.

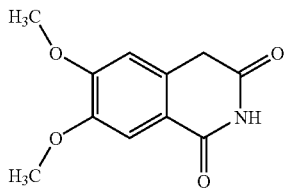

Intermediate 17

6,7-Dimethoxyisoquinoline-1,3(2H,4H)-dione

A solution of 8.2 g (34.1 mmol) of 2-carboxy-4,5-dimethoxybenzeneacetic acid (Tetrahedron 1975, 31, 2607) in 17 ml of conc NH$_4$OH is evaporated to dryness. This operation is repeated. The resulting tan solid ammonium salt is suspended in 34 ml of 1,2-dichlorobenzene. The stirred mixture is boiled in an oil bath at 210° while collecting some distillate during 90 m. The cooled mixture is stirred in hexane and H$_2$O, and the resulting solid is collected by filtration. The white solid is stirred in satd NaHCO$_3$ for 15 m, filtered, washed with H$_2$O, and dried to give 3.45 g (46%), mp 234-238°; MS (ES−) m/z 220.1 (M−H)$^{-1}$.

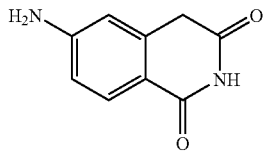

Intermediate 18

6-Aminoisoquinoline-1,3(2H,4H)-dione

A solution of 6.19 g (30 mmol) of 6-nitroisoquinoline-1,3 (2H,4H)-dione in 15 ml of MeOH and 150 ml of N,N-dimethylformamide is hydrogenated at 1 atmosphere of H$_2$ at 25° in the presence of 1.5 g of 10% Pd/C for 7 h. The catalyst is removed by filtration through Celite. The filtrate is evaporated to give 5.4 g (100%) of a tan solid, mp 200-220° (dec); MS (ES+) m/z 177.2 (M+H)$^{+1}$.

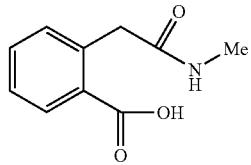

Intermediate 19

N-Methyl-2-carboxybenzeneacetamide

To 20 ml of 2.0 M methylamine in THF is added 1.62 g (10 mmol) of isochroman-1,3-dione at 0° C. The mixture is stirred at 25° C. for 45 m and concentrated to dryness. The residue is stirred in 40 ml of 0.3 N HCl. The white solid is filtered off, washed with water, and dried to give 1.74 g (90%); $^1$H NMR (DMSO-d$_6$) δ 7.80 (s, 1H), 7.81 (s, 1H), 7.40 (m, 3H), 3.83 (s, 2H), 2.57 (s, 3H); MS (ES−) m/z 192.1 (M−H)$^{-1}$: Analysis for C$_{10}$H$_{11}$NO$_3$: Calcd: C, 62.17; H, 5.74; N, 7.25. Found: C, 62.16; H, 5.81; N, 7.24

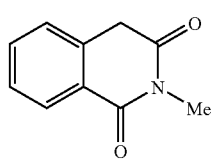

Intermediate 20

N-Methylisoquinoline-1,3(2H,4H)-dione

A mixture of 2.28 g (11.8 mmol) of N-methyl-(2-carboxybenzeneacetamide and 24 ml of 1,2-dichlorobenzene is refluxed for 1 h and evaporated to dryness. The residue is recrystallized from EtOAc-hexane to give an off-white solid, 1.55 g (75%), mp 113-115° C.; MS (ES+) m/z 176.1 (M+H)$^+$ 1.

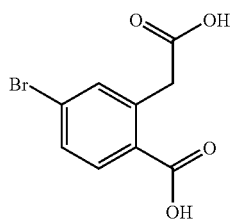

Intermediate 21

2-Carboxylmethyl-benzoic acid

To a stirring solution of diisopropylamine (47.4 g, 465 mmol) in dry THF at −78° C. is added drop wise n-butyl lithium (37.3 g, 581 mmol). Mixture is stirred at −78° C. for 0.5 hour and then allowed to warm to 25° C. for five minutes causing a yellow suspension to form. Suspension is cooled to −78° C. 2-Methyl-benzoic acid (25.0 g, 116 mmol) and diethylcarbonate (10.5 g, 116 mmol) were dissolved together in 100 ml of dry THF. This solution is added drop wise to the reaction mixture over 30 minutes causing a deep reddish-brown color. The resulting mixture is stirred at −78° C. for 1 hour and then allowed to warm to room temperature causing a precipitate to form. Mixture is stirred overnight at room temperature and then cooled in an ice bath. 400 mL of water is slowly added to the mixture keeping the internal temperature below 20° C. causing two layers to form. The layers were separated. The organic layer is extracted with 150 ml of $H_2O$, and all aqueous layers combined. Aqueous layers were acidified with concentrated HCl causing an off-white solid to form. This solid is filtered and washed with 200 ml of $H_2O$ to afford the desired product (18.6 g, 71.8 mmol, 62%); $^1$H NMR (DMSO-$d_6$) δ 3.51 (s, 2H), 7.32 (d, J=2.0 Hz, 1H), 7.39 (dd, J=1.7, 8.5 Hz, 1H), 7.51 (d, J=8.4 Hz, 1H).

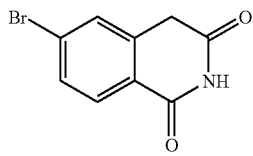

Intermediate 22

6-Bromo-4H-isoquinoline-1,3 dione

2-Carboxylmethyl-benzoic acid (5.00 g, 19.0 mmol) and urea (2.45 g, 40.8 mmol) were suspended in 150 ml of 1,2-dichlorobenzene. This mixture is heated to 150° C. forming a homogeneous mixture. Temperature is maintained for 2 hours during which time a yellow precipitant formed. Mixture is cooled to room temperature and filtered. Residue is washed with 100 ml of ethyl acetate, 100 ml of methanol, and 100 ml of water to afford the product as a yellow solid (3.80 g, 15.8 mmol, 83%); $^1$H NMR (DMSO-$d_6$) δ 4.01 (s, 2H), 7.65-7.69 (m, 2H), 7.89 (d, J=8.7 Hz, 1H), 11.36 (s, 1H).

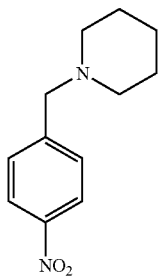

Intermediate 23

1-(4-nitro-benzyl)-piperidine

4-Nitrobenzyl chloride (0.086 g, 0.501 mmol) is dissolved in THF (1 mL), and to this solution, is added piperidine (0.059 mL, 0.601 mmol) followed by $Et_3N$ (0.210, 1.50 mmol). After stirring the mixture at 50° C. for 5 h, the resulting solution is filtered, and then the solvent is removed via high vacuum to afford the product (0.090 g, 82%); $^1$H NMR (DMSO-$d_6$) δ 1.25-1.35 (m, 2H), 1.40-1.48 (m, 4H), 2.23-2.32 (m, 4H), 3.47 (s, 2H), 7.50 (d, J=8.8 Hz, 2H), 8.11 (d, J=8.8 Hz, 2H); mass spectrum [(+) ESI], m/z 221 (M+H)$^+$.

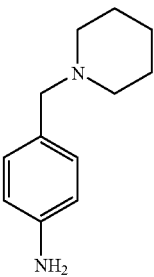

Intermediate 24

4-Piperidin-1-ylmethyl-phenylamine 1-(4-Nitro-benzyl)-piperidine (0.089 g, 0.404 mmol) is dissolved in MeOH (5 mL), and to this solution is added 10% Pd/C (0.009 g, 0.404 mmol). The reaction mixture is stirred under an atmosphere of $H_2$ for 18 h. The resulting mixture is filtered through celite, and the filtered catalyst is washed with excess EtOAc. The filtrate is concentrated under high vacuum to afford the product as a solid (0.076 g, 99%); $^1$H NMR (DMSO-$d_6$) δ 1.29-1.40 (m, 2H), 1.40-1.51 (m, 4H), 2.17-2.30 (m, 4H), 3.18 (s, 2H), 4.88 (s, 2H), 6.46 (d, J=8.4 Hz, 2H), 6.87 (d, J=8.4 Hz, 2H); mass spectrum [(+) ESI], m/z 191 (M+H)$^+$

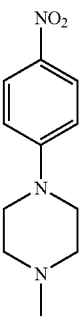

Intermediate 25

4-Piperidin-1-ylmethyl-phenylamine

1-Fluoro-4-nitro-benzene (1.00 g, 7.09 mmol) is dissolved in N,N-dimethylformamide (20 mL), and to this solution, is added 1-methyl-piperazine (0.944 mL, 8.51 mmol) followed by $K_2CO_3$ (1.47 g, 10.6 mmol). After stirring the mixture at room temperature for 18 h, the solvent is removed via high vacuum. The resulting residue is dissolved in EtOAc (100 mL) and washed with $H_2O$ (10 mL) and brine (10 mL) and then dried ($Na_2SO_4$). The solvent is taken off via high vacuum to afford the product as a solid (1.50 g, 96%); $^1$H NMR (DMSO-$d_6$) δ 2.17 (s, 3H), 2.37-2.42 (m, 4H), 3.39-3.43 (m, 4H), 6.98 (d, J=9.6 Hz, 2H), 8.00 (d, J=9.5 Hz, 2H); mass spectrum [(+) ESI], m/z 222 (M+H)⁺.

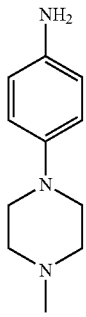

Intermediate 26

4-(4-Methyl-piperazin-1-yl)-phenylamine

4-Methyl-1-(4-nitro-phenyl)-piperazine (1.50 g, 6.78 mmol) is dissolved in MeOH (50 mL), and to this solution is added 10% Pd/C (0.145 g, 6.78 mmol). The reaction mixture is stirred under an atmosphere of $H_2$ for 18 h. The resulting mixture is filtered through celite, and the filtered catalyst is washed with excess EtOAc. The filtrate is concentrated under high vacuum to afford the product as a purple solid (1.28 g, 98%); ¹H NMR (DMSO-$d_6$) δ 2.15 (s, 3H), 2.37-2.40 (m, 4H), 2.83-2.87 (m, 4H), 4.48 (s, 2H), 6.43 (d, J=8.8 Hz, 2H), 6.62 (d, J=8.8 Hz, 2H); mass spectrum [(+) ESI], m/z 192 (M+H)⁺.

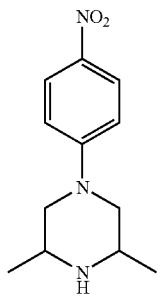

Intermediate 27

3,5-Dimethyl-1-(4-nitro-phenyl)-piperazine

1-Fluoro-4-nitro-benzene (1.00 g, 8.75 mmol) and 2,6-dimethyl-piperazine (1.20 g, 10.5 mmol) were dissolved in 100 ml of acetonitrile forming a yellow homogeneous mixture. Mixture is heated at 90° C. overnight. Mixture is reduced on rotovap to afford the product as an orange solid (1.40 g, 65%); ¹H NMR (DMSO-$d_6$) δ 1.00 (d, J=6.3 Hz, 6H), 2.37-2.80 (m, 5H), 3.87 (dd, J=2.1, 12.4 Hz, 2H), 7.00 (d, J=9.5 Hz, 2H), 8.00 (d, J=9.5 Hz, 2H).

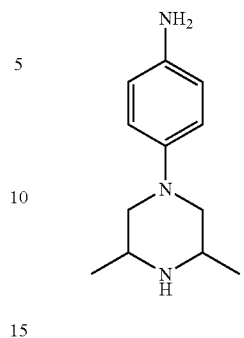

Intermediate 28

4-(3,5-Dimethyl-piperazin-1-yl)-phenylamine 3,5-Dimethyl-1-(4-nitro-phenyl)-piperazine (1.40 g, 5.90 mmol) is dissolved in 20 ml of methanol with ~1 g of Raney nickel suspension. Hydrazine (0.576 g, 14.9 mmol) is dissolved in 20 ml of methanol and added dropwise to the reaction mixture over 20 minutes. Mixture is stirred at room temperature for 3 hours. Mixture is filtered through celite and reduced on rotovap to afford the product as a black solid (1.05 g, 67%); ¹H NMR (DMSO-$d_6$) δ 0.94 (d, J=6.3 Hz, 6H), 1.93-2.00 (m, 2H), 2.65-2.85 (m, 3H), 3.13-3.20 (m, 2H), 4.45 (bs, 2H), 6.43 (d, J=8.5 Hz, 2H), 6.61 (d, J=8.5 Hz, 2H).

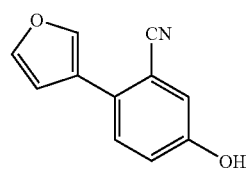

Intermediate 29

2-Furan-3-yl-5-hydroxy-benzonitrile

5-Hydroxy-2-iodo-benzonitrile (70 mg, 0.29 mmol), $Pd_2$(dba)3.CHCl$_3$(25 mg, 0.01 mmol) and P(tBu)$_3$ (0.05 mL, 10% in hexane, 0.016 mmol), 3-furanboronic acid (40 mg, 0.36 mmol) and CsF (200 mg, 1.32 mmol) were suspended in N,N-dimethylformamide (5 mL). The mixture is then degassed and stirred at room temperature for 4 hours. After aqueous workup, the residue is purified with chromatography and directly employed in the next step.

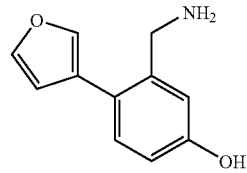

Intermediate 30

3-Aminomethyl-4-furan-3-yl-phenol

The 2-Furan-3-yl-5-hydroxy-benzonitrile obtained above is dissolved in EtOH and to which Raney Ni (1 g of suspension in water) is added. The mixture is then subjected to hydrogenation under H$_2$ (50 psi) for 24 hours. After which Raney Ni is filtered off from celite and EtOH is removed to provide the title compound (40 mg, 72% for two steps). MS (ESI): 190 (M+1)$^{+1}$, 173 (M+1-NH$_3$)$^{+1}$.

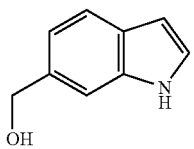

Intermediate 31

(1H-Indol-6-yl)-methanol

To a solution of 6-indole carboxylic acid (5 g, 31.05 mmol) in tetrahydrofuran (310 ml) is added lithium aluminum hydride (5.89 mg, 155.2 mmol) at 0° C. The reaction mixture is refluxed for 6 hours. The resulting mixture is then quenched with 5% potassium hydrogen sulfate (100 ml) and extracted with ether (100 mL). The organic layer is then dried with sodium sulfate and concentrated to give a white solid (156 mg) MS (ESI) m/z 148.8 (M+1).

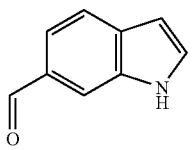

Intermediate 32

1H-Indole-6-carbaldehyde

To a dissolved solution of (1H-Indol-6-yl)-methanol (100 mg, 0.68 mmole) in dichloromethane (31 ml), manganese (IV) oxide (1.9 g, 21.9 mmol) is added. The reaction mixture stirred at room temperature for 8 hours and then passed through celite. The reaction mixture is then concentrated to give a yellow oil (80 mg, 0.55 mmole). MS (ESI) m/z 146.2 (M+1).

Intermediate 33

1H-Indole-6-carbaldehyde O-methyl-oxime

An amount of 1H-Indole-6-carbaldehyde (50 mg, 0.34 mmol) is added to pyridine (2.0 ml) at room temperature, followed by addition of methoxylamine hydrogen chloride (31.6 mg, 0.38 mmol). The mixture is stirred at ambient temperature for 24 h, and 10 mL of water is added. After the solvents were evaporated, the residue is dissolved 10 mL of anhydrous ether, washed successively with 10 mL of aqueous sodium bicarbonate, 10 mL of sodium bisulfite, and 10 mL of brine. Dried over magnesium sulfate, evaporated to give a white solid (49 mg, 0.281 mmol). MS (ESI) m/z 176.3 (M+1)

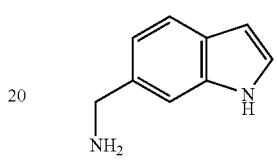

Intermediate 34

C-(1H-Indol-6-yl)-methylamine

An amount of 1H-Indole-6-carbaldehyde O-methyl-oxime (150 mg, 0.86 mmol) is dissolved in ethanol (6.5 mL). Then hydrogen chloride (0.62 mL) is added, followed by 10% Pd/C (15 mg). After hydrogenation at 35 psi for 3 h, the solution is filtered through Celite and evaporated to dryness. The residue is recrystallized from ethyl acetate to give 110 mg of crude product as a yellow solid. MS (ESI) m/z 147.3 (M+1).

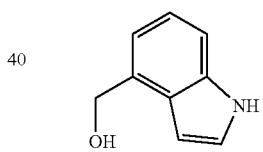

Intermediate 35

(1H-Indol-4-yl)-methanol

To a solution of 6-indole carboxylic acid (500 mg, 3.1 mmol) in tetrahydrofuran (31 ml) is added lithium aluminum hydride (590 mg, 15.5 mmol) at 0° C. The reaction mixture is refluxed for 6 hours. The resulting mixture is then quenched with 5% potassium hydrogen sulfate (20 ml) and extracted with ether (20 mL). The organic layer is then dried with sodium sulfate and concentrated to give a yellow solid (230 mg). MS (ESI) m/z 146.6 (M+1).

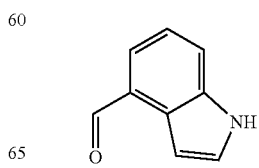

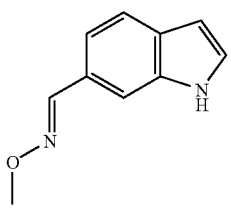

Intermediate 36

1H-Indole-4-carbaldehyde

To a dissolved solution of (1H-Indol-4-yl)-methanol (100 mg, 0.69 mmole) in dichloromethane (0.500 ml), manganese (IV) oxide (597 mg, 6.9 mmol) is added. The reaction mixture stirred at room temperature for 8 hours and then passed through Celite. The reaction mixture is then concentrated to give a yellow oil (90 mg). MS (ESI) m/z 146.1 (M+1).

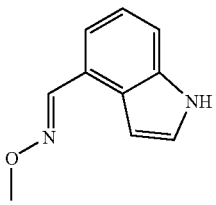

Intermediate 37

1H-Indole-4-carbaldehyde O-methyl-oxime

To an amount of 1H-Indole-4-carbaldehyde (50 mg, 0.34 mmol) is added pyridine (10 ml) at room temperature, followed by addition of methoxylamine hydrogen chloride (31.6 mg, 0.38 mmol). The mixture is stirred at ambient temperature for 24 h, and 2 mL of water is added. After the solvents were evaporated, the residue is dissolved 2 mL of anhydrous ether, washed successively with 2 mL of aqueous sodium bicarbonate, 2 mL of sodium bisulfite, and 2 mL of brine. Dried over magnesium sulfate, evaporated to give a white solid (35 mg). MS (ESI) m/z 175.2 (M+1)

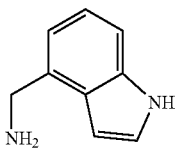

Intermediate 38

C-(1H-Indol-4-yl)-methylamine

An amount of 1H-Indole-4-carbaldehyde O-methyl-oxime (50 mg, 0.30 mmol) is dissolved in ethanol (5 mL). Then hydrogen chloride (0.217 mL) is added, followed by 10% Pd/C (5.0 mg). After hydrogenation at 35 psi for 3 h, the solution is filtered through Celite and evaporated to dryness. The residue is recrystallized from ethyl acetate to give 42 mg of crude product as an orange residue. MS (ESI) m/z 147.2 (M+1).

Intermediate 39

3-Hydroxy-4-(2-pyrrolidin-1-yl-ethoxy)-benzaldehyde

To a solution of 1-(2-chloroethyl)pyrrolidine HCl (3.2 g, 18.7 mmol) and tetrabutylammonium iodide (4.85 g, 18.0 mmol) in anhydrous N,N-dimethylformamide (53 mL) is added potassium carbonate (5.7 g, 41.3 mmol). The mixture stirred at room temperature and 1,2-dihydroxy-4 benzaldehyde (1.0 g, 7.2 mmol) is added. After the mixture is stirred at 65° C. for 30 min, the resulting mixture is concentrated and the residue is then partitioned between water (25 ml) and ethyl acetate (25 ml). The organic layer is then dried and purified by flash chromatography to give 1.12 g of a brown solid. MS (ESI) m/z 237.0 (M+1)

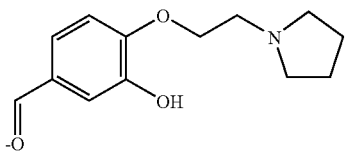

Intermediate 40

3-Hydroxy-4-(2-pyrrolidin-1-yl-ethoxy)-benzaldehyde O-methyl-oxime

An amount of 3-hydroxy-4-(2-pyrrolidin-1-yl-ethoxy)-benzaldehyde (150 mg, 0.64 mmol) is added pyridine (3.5 ml) at room temperature, followed by addition of methoxylamine hydrogen chloride (58.2 mg, 0.70 mmol). The mixture is stirred at ambient temperature for 24 h, and 4 mL of water is added. After the solvents were evaporated, the residue is dissolved 8 mL of anhydrous ether, washed successively with 2 mL of aqueous sodium bicarbonate, 2 mL of sodium bisulfite, and 2 mL of brine. Dried over magnesium sulfate, evaporated to give a yellow solid (100 mg). MS (ESI) m/z 265.8 (M+1)

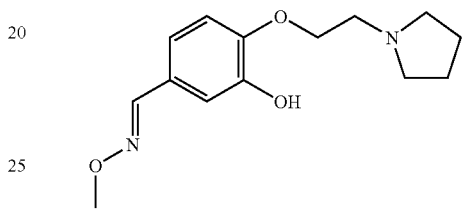

Intermediate 41

5-Aminomethyl-2-(2-pyrrolidin-1-yl-ethoxy)-phenol

An amount of 3-Hydroxy-4-(2-pyrrolidin-1-yl-ethoxy)-benzaldehyde O-methyl-oxime (50 mg, 0.18 mmol) is dissolved in ethanol (10 mL). Then hydrogen chloride (0.130 mL) is added, followed by 10% Pd/C (5.0 mg). After hydrogenation at 35 psi for 3 h, the solution is filtered through Celite and evaporated to dryness. The residue is recrystallized from

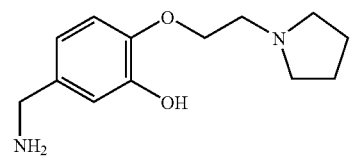

ethyl acetate to give 45 mg of crude product as a white solid. MS (ESI) m/z 283.1 (M+1)

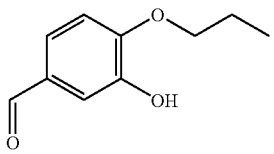

Intermediate 42

3-hydroxy-4-propoxybenzaldehyde

To a solution of 1-bromopropane (1.7 mL, 18.7 mmol) in anhydrous N,N-dimethylformamide (25 mL) is added potassium carbonate (5.7 g, 41.0 mmol). The mixture stirred at room temperature and 1,2-dihydroxy-4 benzaldehyde (1.0 g, 7.2 mmol) is added. After the mixture is stirred at 65° C. for 30 min, the resulting mixture is concentrated and the residue is then partitioned between water (25 ml) and ethyl acetate (25 ml). The organic layer is then dried and purified by flash chromatography to give 0.200 g of a brown solid. MS (ESI) m/z 181.2 (M+1).

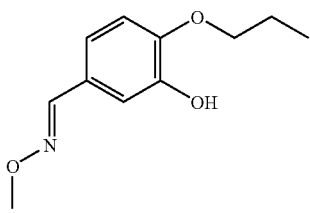

Intermediate 43

3-hydroxy-4-propoxybenzaldehyde O-methyloxime

An amount of 3-hydroxy-4-propoxybenzaldehyde (150 mg, 0.83 mmol) is added pyridine (4.0 ml) at room temperature, followed by addition of methoxylamine hydrogen chloride (101.2 mg, 1.2 mmol). The mixture is stirred at ambient temperature for 24 h, and 4 mL of water is added. After the solvents were evaporated, the residue is dissolved 8 mL of anhydrous ether, washed successively with 2 mL of aqueous sodium bicarbonate, 2 mL of sodium bisulfite, and 2 mL of brine. Dried over magnesium sulfate, evaporated to give a yellow solid (210 mg). MS (ESI) m/z 210.5 (M+1)

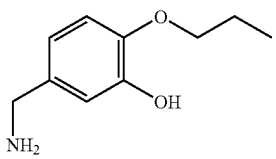

Intermediate 44

5-(aminomethyl)-2-propoxyphenol

An amount of 3-hydroxy-4-propoxybenzaldehyde O-methyloxime (150 mg, 0.83 mmol) is dissolved in ethanol (4 mL). Then hydrogen chloride (0.600 mL) is added, followed by 10% Pd/C (15.0 mg). After hydrogenation at 35 psi for 3 h, the solution is filtered through Celite and evaporated to dryness. The residue is recrystallized from ethyl acetate to give 112 mg of crude product as a white solid. MS (ESI) m/z 182.3 (M+1)

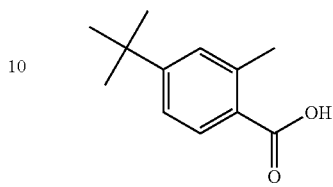

Intermediate 45

4-tert-Butyl-2-methyl-benzoic acid

An amount of 10.0 g (61.62 mmol) of 4-tert-butyl-o-xylene is added to 100 mL solution of 20% water in pyridine and stirred at 80° C. for one hour. 25 g (154.05 mmol) of potassium permanganate is also added and continued to stir at 80° C. for three hours more. After cooling to room temperature, the mixture is filtered through a thick pack of celite and washed many times with water. The water layer is acidify to pH ~2, and the precipitate is filtered and crystallized out of water: methanol to give 2.4 g (8.5% yield) as a white solid. $^1$H NMR (300 MHz, DMSO-d$_6$) □ 1.282 (S, 9H), 2.530 (S, 3H), 7.295 (d, J=6.9 Hz 2H), 7.821 (d, J=2.1 Hz 1H). Ref: JACS, 66, 154-5(1944)

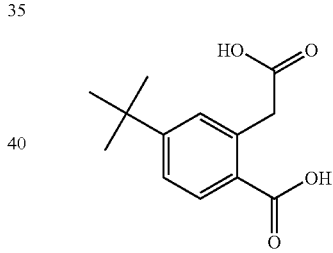

Intermediate 46

4-tert-butyl-2-(carboxymethyl)benzoic acid

An amount of 26 mL (198 mmol) of Lithium diiopropylamide (Aldrich) is added to a three neck flask cooled to −40° C. To this is added drops wise, a mixture of 4-tert-butyl-2-methyl-benzoic acid 1.9 g (9.9 mmol) and dimethyl carbonate 3.3 mL (39.6 mmol) in 5 mL of tetrahydrofuran, while keeping the temperature at −60° C. After the addition, the temperature is kept between −40° C. to −60° C. for four hours, then brought to 0° C. and quenched with 25 mL of water. The mixture is allowed to stir at room temperature for two hours and acidify to pH 2 with hydrogen chloride, extracted 3× with ethyl acetate, dried over magnesium sulfate and evaporated.

The desired product is collected by column chromatography with 5-15% methanol methylene chloride to give 1.4 g (61% yield) as a light-yellow white solid. MS (ESI) m/z 237.1

(M+1). ¹H NMR (300 MHz, DMSO-d₆) 1.299 (S, 9H), 0.930 (S, 2H), 7.345-7.514 (m, 2H), 7.840 (d, J=8.16 Hz 1H).

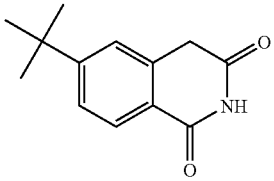

Intermediate 47

6-tert-butylisoquinoline-1,3(2H,4H)-dione

An amount of 1.5 g (6.35 mmol) of 4-tert-butyl-2-(carboxymethyl)benzoic acid and urea (763 mg, 12.7 mmol) were heated neat at 145-148° C. for 1.5 hours. The mixture is cooled to room temperature and 200 mL of chloroform is added and washed 3× with water, dried over sodium sulfate and evaporated. The crude product is purified by column chromatography 4% methanol methylene chloride to give 580 mg (41% yield) of the product as a brown solid. MS (ESI) m/z 218.2 (M+1).

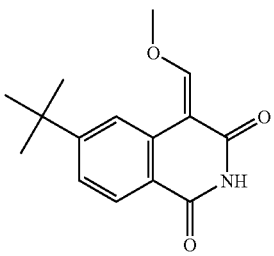

Intermediate 48

(4E)-6-tert-butyl-4-(methoxymethylene)isoquinoline-1,3(2H,4H)-dione

An amount 200 mg (0.92 mmol) of 6-tert-butylisoquinoline-1,3(2H,4H)-dione is dissolved in acetic acid 1.0 mL followed by addition of trimethyl orthoformate (25 uL, 2.3 mmol). After, the mixture is heated at 90° C. for 1 h, and cooled to room temperature. The yellow solution evaporated to dryness. Small amounts of anhydrous ether is added and hexane. The yellow solid is collected with hexane to give 188 mg (79% yield) MS (ESI) m/z 260.2 (M+1). ¹H NMR (300 MHz, DMSO-d₆) 1.346 (S, 9H), 4.178 (S, 3H), 7.472-7.505 (dd, J=1.8 Hz, J=1.8 Hz 1H), 8.007 (d, J=8.52 Hz 2H), 8.31 (d, J=1.71 Hz 1H).

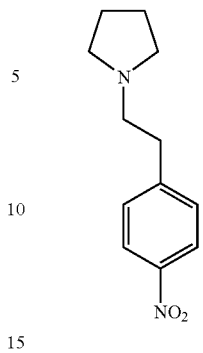

Intermediate 49

1-[2-(4-nitrophenyl)-ethyl]-pyrrolidine

Pyrrolidine (3.89 g, 54.8 mmol) is added to a mixture of 8.40 g (36.5 mmol) of 1-(2-bromoethyl)-4-nitrobenzene and 6.14 g (73.0 mmol) of NaHCO₃ in 60 mL of CH₃CN at 0° C. The mixture is stirred for 0.5 h at 0° C. and then at 25° C. overnight. The reaction is filtered, the insoluble material is washed with CH₃CN and the filtrate and wash were combined. Darco is added, the solution is dried (MgSO₄) and evaporated to a viscous red oil. Stirring this material with Et₂O caused crystallization of the product. It is collected, washed with Et₂O and dried in vacuo to give 7.60 g (95%) of a tan hygroscopic solid. ¹H NMR (DMSO-d₆) δ 8.22 (d, 2H, J=6.57 Hz), 7.62 (d, 2H, J=6.57 Hz), 3.47 (m, 2H), 3.25 (m, 2H), 3.10 (m, 4H), 1.94 (m, 4H); MS (ESI) m/z 221.2 (M+1).

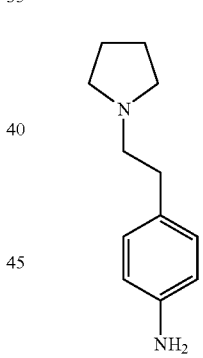

Intermediate 50

4-(2-Pyrrolidin-1-yl-ethyl)-phenylamine

A mixture of 7.49 g (34.0 mmol) of CAT 968910, 7.63 g (136 mmol) of powdered Fe and 9.01 g (170 mmol) of NH₄Cl in 65 mL of H₂O+155 mL of MeOH is stirred and refluxed for 1.5 h. The cooled reaction mixture is filtered through Celite and the combined filtrate and wash is treated with an aq soln of 5.71 g (68 mmol) of NaHCO₃ and evaporated. The residue is extracted with 10% MeOH in CHCl₃, dried (MgSO₄) and evaporated. The residue is dissolved in H₂O, treated with an aq soln of K₂CO₃ (4.69 g (34 mmol) and extracted with CHCl₃. The organic material is dried (MgSO₄), evaporated and dried in vacuo to give 3.63 g (56%) of brown liquid. ¹H NMR (DMSO-d₆) δ 6.83 (d, 2H, J=6.62 Hz), 6.46 (d, 2H, J=6.62 Hz), 4.79 (s, 2H), 2.49 (m, 4H), 2.44 (m, 4H), 1.65 (m, 4H); MS (ESI) m/z 191.1 (M+H).

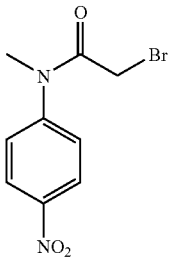

Intermediate 51

2-Bromo-N-methyl-N-(4-nitrophenyl)-acetamide

A mixture of 2.00 g (13.2 mmol) of N-methyl-4-nitroaniline and 1.46 g (14.5 mmol) of $Et_3N$ in 20 mL of $CH_2Cl_2$ at 0° C. under $N_2$ is treated with a solution of 5.33 g (26.4 mmol) of bromoacetyl bromide in 4 mL of $CH_2Cl_2$. After 3.5 h, the reaction is poured into ice water and extracted with $CH_2Cl_2$. The extract is treated with Darco, dried ($MgSO_4$) and evaporated. The residue is filtered through Magnesol ($CHCl_3$), evaporated and dried in vacuo to give 3.57 g (100%) of yellow solid. $^1$H NMR (DMSO-$d_6$) δ 8.27 (d, 2H, J=7.47 Hz), 7.66 (d, 2H, J=7.47 Hz), 4.06 (s, 2H), 3.28 (s, 3H); MS (ESI) m/z 273.0 (M+1).

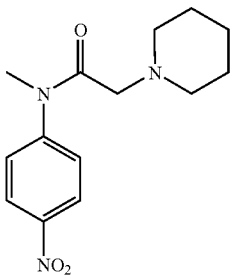

Intermediate 52

N-Methyl-N-(4-nitrophenyl)-2-piperidin-1-yl-acetamide

A solution of 2.82 g (10.3 mmol) of 2-Bromo-N-methyl-N-(4-nitrophenyl)-acetamide and 2.08 g (20.6 mmol) of $Et_3N$ in 30 mL of $CH_2Cl_2$ at 0° C. under $N_2$ is treated with 0.875 g (10.3 mmol) of piperidine for 5 min at 0° C. and refluxed for 1.25 h. The cooled reaction mixture is washed with $H_2O$, treated with Darco, dried ($MgSO_4$) and evaporated to give 3.00 g (100%) of brown oil. $^1$H NMR (DMSO-$d_6$) δ 8.25 (d, 2H, J=6.9 Hz), 7.63 (d, 2H, J=6.9 Hz), 3.30 (s, 3H), 3.09 (s, 2H), 2.25 (s, 4H), 1.31 (m, 6H); MS (ESI) m/z 278.0 (M+H).

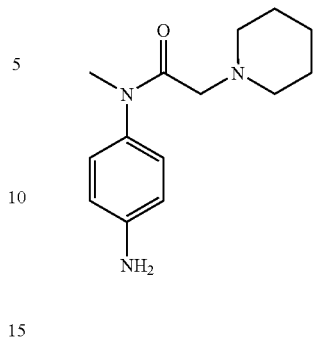

Intermediate 53

N-(4-Aminophenyl)-N-methyl-2-piperidin-1-yl-acetamide

A mixture of 3.12 g (11.3 mmol) of N-Methyl-N-(4-nitrophenyl)-2-piperidin-1-yl-acetamide, 2.52 g (45.1 mmol) of Fe powder and 2.99 g (56.5 mmol) of $NH_4Cl$ in 65 mL of MeOH+25 mL of $H_2O$ is stirred and refluxed for 3.5 h. The cooled reaction is filtered, the precipitate is washed with MeOH and the filtrate and wash were combined and evaporated. The residue is redissolved in $H_2O$, neutralized with $K_2CO_3$ and extracted with EtOAc. The combined extracts were treated with Darco, dried ($MgSO_4$), evaporated and dried in vacuo to give 2.36 g (85%) of brown oil. $^1$H NMR (DMSO-$d_6$ δ 6.85 (d, 2H, J=7.1 Hz), 6.51 (d, 2H, J=7.1 Hz), 3.30 (s, 2H), 2.78 (s, 3H), 2.24 (s, 4H), 1.50 (m, 6H); MS (ESI) m/z 248.0 (M+H).

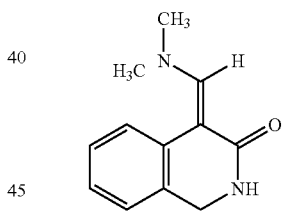

Intermediate 54

4-Dimethylaminomethylene-1,4-dihydro-2H-isoquinolin-3-one

A solution of 2.10 g (14.3 mmol) of 1,4-Dihydro-3(2H)-isoquinolinone and 4.42 g (37.2 mmol) of N,N-dimethylformamide-DMA in 21 mL of N,N-dimethylformamide is heated at 90° C. for 1 h. An additional 1.5 mL of N,N-dimethylformamide-DMA is added and heating is continued for 30 min. Volatile material is removed and the residue is slurried with $Et_2O$, collected, washed with a large volume of $Et_2O$ and dried in vacuo to give 1.50 g (52%) of red-brown crystals: mp 188-190° C. (dec); $^1$H NMR (DMSO-$d_6$) δ 7.48 (s, 1H), 7.23 (m, 2H), 7.11 (d, 1H, J=6.96 Hz), 7.01 (m, 1H), 6.87 (d, 1H, J=7.62 Hz), 4.11 (s, 2H), 2.88 (s, 6H); MS (ESI) m/z 203.1 (M+1). Analysis for $C_{12}H_{14}N_2O \cdot 0.1H_2O$: Calcd:

C, 70.62; H, 7.03; N, 13.73. Found: C, 70.75; H, 7.17; N, 13.40.

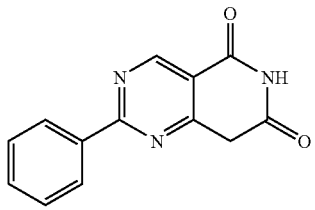

Intermediate 55

2-Phenyl-8H-pyrido[4,3-d]pyrimidine-5,7-dione

A solution of 0.670 g (2.61 mmol) of 4-Carbamoylmethyl-2-phenyl-pyrimidine-5-carboxylic Acid and 0.528 g (3.26 mmol) of CDI in 20 mL of N,N-dimethylformamide is stirred overnight at 25° C. The solvent is evaporated and the residue is washed with Et$_2$O (3×). The insoluble material is boiled with CHCl$_3$, collected, washed with hot CHCl$_3$ and Et$_2$O and dried in vacuo to give 0.372 g (60%) of yellow-orange crystals: mp 216-217.5° C. (dec); $^1$H NMR (DMSO-d$_6$) δ 8.99 (s, 1H), 8.41 (m, 2H), 7.56 (m, 4H), 5.45 (s, 2H); HRMS (ESI) m/e calcd for C$_{13}$H$_9$N$_3$O$_2$ 240.07645. found 240.07652 (M+H)$^{+1}$. Analysis for C$_{13}$H$_9$N$_3$O$_2$·0.25H$_2$O: Calcd: C, 64.05; H, 3.94; N, 17.24. Found: C, 63.67; H, 3.91; N, 17.38.

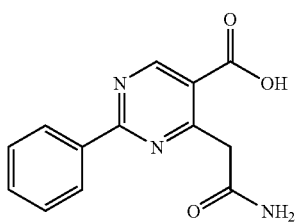

Intermediate 56

4-Carbamoylmethyl-2-phenyl-pyrimidine-5-carboxylic Acid

A solution of 2.65 g (9.56 mmol) of 4-Methoxycarbonyl-methyl-2-phenyl-pyrimidine-5-carboxylic Acid in 11.6 mL of conc NH$_4$OH is stirred at 25° C. for 3 h. The reaction is then diluted with H$_2$O, chilled in ice and acidified with 6M HCl. The product is collected, washed with H$_2$O (2×) and dried in vacuo (low heat) to give 1.55 g (63%) of orange solid: $^1$H NMR (DMSO-d$_6$) δ 9.17 (s, 1H), 8.44 (m, 2H), 7.67 (s, 1H), 7.60 (m, 3H), 7.02 (s, 1H), 4.12 (s, 2H); MS (ESI)) m/z 256. (M−H). Analysis for C$_{13}$H$_{11}$N$_3$O$_3$·0.5H$_2$O: Calcd: C, 58.63; H, 4.55; N, 15.78. Found: C, 58.88; H, 4.53; N, 15.46.

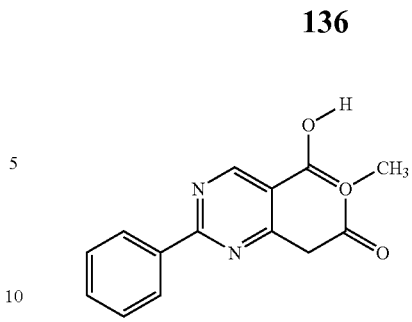

Intermediate 57

4-Methoxycarbonylmethyl-2-phenyl-pyrimidine-5-carboxylic Acid

A solution of 3.00 g (14.0 mmol) of 4-Methyl-2-phenyl-pyrimidine-5-carboxylic Acid and 2.53 g (28.0 mmol) of dimethyl carbonate in 75 mL of THF is added dropwise with rapid overhead stirring to a slurry of 6.00 g (56.1 mmol) of LDA in 24 mL of THF at −78° C. The mixture is stirred at 25° C. for 5 h and then chilled to −78° C. The reaction is added all at once and rapidly (overhead stirring) to 81 mL (1.40 mol) of glacial HOAc in 210 mL of THF, also held at −78° C. The mixture is warmed to 25° C. and the THF and some HOAc is removed. Water (180 mL) is added and the product is extracted into EtOAc. The extract is washed with H$_2$O (5×), dried (MgSO$_4$) and evaporated. The residue is dissolved in excess aqueous NaHCO$_3$ and extracted with Et$_2$O (5×). These washes were discarded. The aqueous solution is acidified with 2M HCl and extracted with Et$_2$O. The ethereal extracts were backwashed with H$_2$O (6×), dried (MgSO$_4$) and evaporated to give 3.4 g (89%) of orange crystals: mp 173-175° C. (dec); $^1$H NMR (DMSO-d$_6$) δ 9.29 (s, 1H), 8.44 (m, 2H), 7.60 (m, 3H), 4.45 (s, 2H), 3.65 (s, 3H); MS (ESI) m/z 271.0 (M−H). Analysis for C$_{14}$H$_{12}$N$_2$O: Calcd: C, 61.76; H, 4.44; N, 10.29. Found: C, 61.90; H, 4.73; N, 10.11.

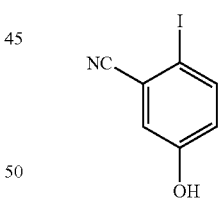

Intermediate 58

5-Hydroxy-2-iodo-benzonitrile

3-Hydroxy-benzonitrile (15 g, 0.126 mol) and iodine monochloride (28 g, 0.172 mol) is heated in acetic acid for 15 hours at 45° C. H$_2$O is added to precipitate the product out. After the precipitate is collected and washed with Na$_2$SO$_3$, the residue is chromatographed with chloroform to get the product (2 g, 7%). MS (ESI): 244.0 (M−1)⁻¹.

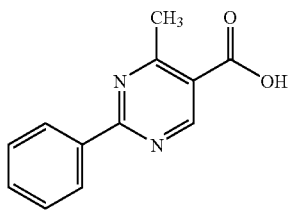

Intermediate 59

4-Methyl-2-phenyl-pyrimidine-5-carboxylic Acid

The preparation of this compound followed the literature procedure exactly: P. Schenone, L. Sansebastiano, L. Mosti J. Heterocyclic Chemistry, 27, 295 (1990). Starting from 17.0 g (70.2 mmol) of 4-Methyl-2-phenyl-pyrimidine-5-carboxylic acid ethyl ester, there is obtained 13.8 g (92%) of white solid.

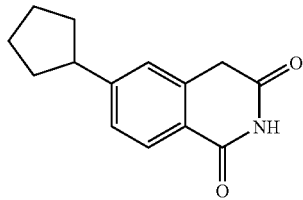

Intermediate 60

6-Cyclopentyl-4H-isoquinoline-1,3-dione

To 6-bromo-1,3-bis-(tert-butyl-dimethyl-silanyloxy)-isoquinoline (1.76 g, 3.75 mmole) is added tetrakis(triphenylphosphine)palladium (110 mg, 0.095 mmole) and 2M cyclopentyl magnesium bromide in ether (3.0 mL, 6.0 mmole). This mixture is heated using a microwave reactor at 75° C. for 600 sec. The mixture is cooled to room temperature, transferred to a flask with THF and water, then 2M hydrochloric acid (20 mL) is added and stirred for 4 hours at room temperature. The organic solvents were removed in vacuo, the mixture extracted with ethyl acetate, the organic layer dried over sodium sulfate filtered, evaporated and chromatographed with hexanes-ethyl acetate on silica gel to give a white solid, 268 mg (31%) MS (ESI): m/z 230.2 (M+H).

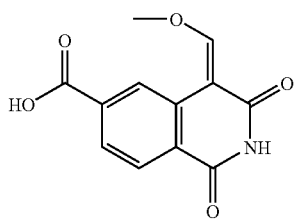

Intermediate 61

(4E)-4-(Methoxymethylene)-1,3-dioxo-1,2,3,4-tetrahydroisoquinoline-6-carboxylic acid Trimethyl orthoformate (0.114 mL, 1.04 mmol) is added to a solution of 1,3-Dioxo-1,2,3,4-tetrahydro-isoquinoline-6-carboxylic acid (102.5 mg, 0.5 mmol) in acetic anhydride (0.8 mL) and N,N-dimethylformamide (0.2 mL). After it is heated at 125° C. for 30 min, it is cooled and filtered to collected 75 mg (60%) of the title compound as a yellow solid. MS (ESI) m/z 246.1 (M−1).

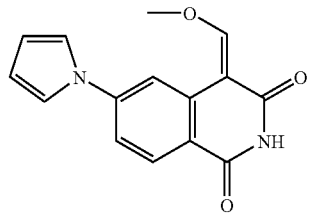

Intermediate 62

(4E)-4-(Methoxymethylene)-6-(1H-pyrrol-1-yl)isoquinoline-1,3(2H,4H)-dione 6-(1H-pyrrol-1-yl)isoquinoline-1,3(2H,4H)-dione (0.1 g, 0.442 mmol) is dissolved in acetic anhydride (0.6 mL), N,N-dimethylformamide (0.15 mL) and trimethyl orthoformate (0.1 mL, 0.919 mmol). After heating at 120° C. for 0.5 h, it is cooled and the solid is filtered and washed successively with acetic anhydride, ether and hexane to yield 47 mg (40%) solid of the title compound; mp 272-273° C.; HRMS (ESI) m/z calcd for $C_{15}H_{12}N_2O_3$ 269.09207. found 269.09210 (M+H)⁺₁.

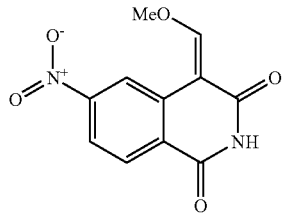

Intermediate 63

(4E)-4-(Methoxymethylene)-6-nitroisoquinoline-1,3(2H,4H)-dione

To a stirred mixture of 0.41 g (2.0 mmol) of 6-nitroisoquinoline-1,3(2H,4H)-dione, 3.2 ml (34 mmol) of $Ac_2O$, and 0.80 ml of N,N-dimethylformamide is added 0.44 ml (4.0 mmol) of trimethyl orthoformate. The mixture is heated to 125° and maintained for 30 m, cooled, diluted with ether, and stirred for 10 m. The resulting brown solid is filtered, washed with ether, and dried to give 372 mg (74%); 1H NMR (DMSO-d$_6$) δ 11.55 (s, 1H), 8.99 (d, J=2.0 Hz, 1H), 8.30 (d, J=8.6 Hz, 1H), 8.19 (dd J=2.0, 8.6 Hz, 1H), 4.33 (s, 3H).

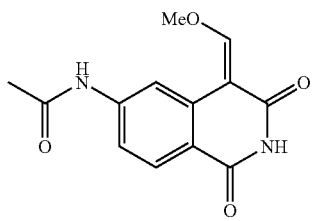

Intermediate 64

N-[(4E)-1,3-Dioxo-4-(methoxy)methylene-1,2,3,4-tetrahydroisoquinolin-6-yl]acetamide To a stirred mixture of 90 mg (0.50 mmol) of 6-aminoisoquinoline-1,3(2H,4H)-dione, 0.80 ml (8.5 mmol) of Ac$_2$O, and 0.20 ml of N,N-dimethylformamide is added 0.11 ml 1.0 mmol) of trimethyl orthoformate. The mixture is heated to 125° and maintained for 30 m, cooled, diluted with ether, and stirred for 10 minutes. The resulting amber solid is filtered, washed with ether, and dried to give 96 mg (74%); MS (ES+) m/z 261.1 (M+H)$^{+1}$.

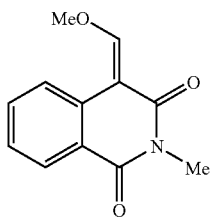

Intermediate 65

(4E)-N-Methyl-4-(methoxymethylene)isoquinoline-1,3(2H,4H)-dione

To a stirred mixture of 0.35 g (2.0 mmol) of (N-methyl) isoquinoline-1,3(2H,4H)-dione, 3.2 ml of Ac$_2$O, and 0.80 ml of N,N-dimethylformamide is added 0.44 ml (4.0 mmol) of (MeO)$_3$CH at 25° C. The mixture is stirred at 125° C. for 30 m, cooled, and concentrated under high vacuum. The residue is recrystallized from Et$_2$O-hexane to give 0.20 g of tan solid, mp 145-150° C. (dec); MS (ES+) m/z 218.2 (M+H)$^{+1}$: Analysis for C$_{12}$H$_{11}$NO$_3$: Calcd: C, 66.35; H, 5.10; N, 6.45. Found: C, 65.98; H, 4.99; N, 6.42.

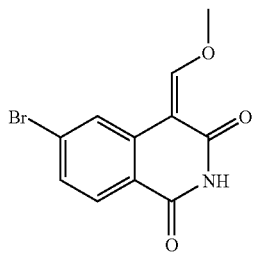

Intermediate 66

6-Bromo-4-methoxymethylene-4H-isoquinoline-1,3-dione

6-Bromo-4H-isoquinoline-1,3-dione (120 mg, 0.500 mmol) and trimethyl orthoformate (106 mg, 1.00 mmol) were suspended in 1.25 ml of a 1:4 ratio mixture of acetic anhydride and N,N-dimethylformamide. Mixture is heated at 125° C. for 2 hours causing a yellow solid to form. Mixture is cooled to room temperature and filtered. Residue is washed with 20 ml of ethyl ether to afford the product as a yellow solid (109 mg, 0.380 mmol, 77%); $^1$H NMR (DMSO-d$_6$) δ 4.25 (s, 3H), 7.60 (dd, J=1.9, 8.4 Hz, 1H), 7.96 (d, J=8.5 Hz, 1H), 8.07 (s, 1H), 8.36 (d, J=1.9 Hz, 1H), 11.38 (s, 1H); mass spectrum [(+) ESI], m/z 282/284 (M+H)$^+$.

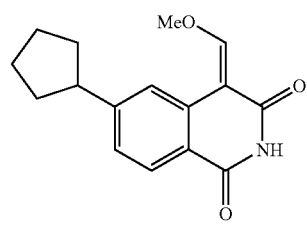

Intermediate 67

6-Cyclopentyl-4-methoxymethylene-4H-isoquinoline-1,3-dione

A mixture of 6-cyclopentyl-4H-isoquinoline-1,3-dione (222 mg, 0.97 mmole), 10 mL of acetic acid and trimethylorthoformate (212 mg, 2.0 mmole) is stirred and heated to 90° C. After 2 hours at that temperature the reaction mixture is cooled and the solvents were removed in-vacuo and the residue taken up in 4% methanol in dichloromethane, passed through a short pad of Florisil and eluted with 4% methanol in dichloromethane. The eluate is evaporated and the product is treated with 4:1 hexanes-ethyl acetate and collected by filtration to give a yellow solid, 165 mg, (62%), MS (ES+): m/z 272.2 (M+H).

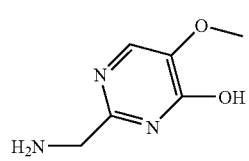

Intermediate 68

2-Aminomethyl-5-methoxy-pyrimidin-4-ol

The 2-(4-Hydroxy-5-methoxy-pyrimidin-2-ylmethyl)-isoindole-1,3-dione (50 mg, 0.18 mmol) is suspended in EtOH (2 mL) and to which NH$_2$NH$_2$ (0.5 mL) is added and the mixture is stirred till no starting material left. The precipitate is filtered and the filtrate is concentrated to provide the-desired product, which is used directly without further treatment. MS (ESI): 156 (M+1)$^{+1}$.

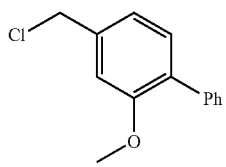

Intermediate 69

4-Chloromethyl-2-methoxy-biphenyl (2-Methoxy-biphenyl-4-yl)-methanol (170 mg, 0.79 mmol) [PCT Int. Appl. 1999, WO 9955726 A1 19991104] is dissolved in CH$_2$Cl$_2$ (2 mL) and cooled to 0° C. SOCl$_2$ (1 mL) is then added dropwise. The mixture is then allowed to stir till no starting material left. The volatiles were then removed and the crude product is employed in the next step directly.

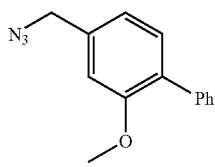

Intermediate 70

4-Azidomethyl-2-methoxy-biphenyl

4-Chloromethyl-2-methoxy-biphenyl (obtained from the above reaction) is dissolved in CH$_2$Cl$_2$ (3 mL) and cooled to −78° C. BBr$_3$ (3 mL, 1 M solution in CH$_2$Cl$_2$, 3 mmol) is added. The cooling bath is then removed and the mixture is allowed to stir at room temperature for 1 hour. Analysis of Thin Layer Chromatography (TLC) suggests the consumption of the starting material. The mixture is quenched with ice water and the methylene chloride layer is dried and concentrated. The residue is passed through a column to obtain a pure product. This product (170 mg) is then dissolved in N,N-dimethylformamide (5 mL) and to which NaN$_3$ (100 mg, 1.53 mmol) is added at room temperature. The reaction is monitored by TLC. After around 1 hour, analysis of the TLC suggests the consumption of starting material. Et$_2$O and H$_2$O were then added and the ether layer is washed with water and dried over Na$_2$SO$_4$. Removal of ether provided the desired azide (100 mg, 53% over three steps).

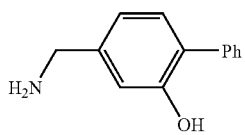

Intermediate 71

4-Aminomethyl-biphenyl-2-ol

4-Azidomethyl-2-methoxy-biphenyl (100 mg, 0.42 mmol) is dissolved in THF (5 mL) and H$_2$O (0.5 mL) and to which PPh$_3$ (100 mg, 0.38 mmol) is added. The mixture is allowed to stir at room temperature overnight. After analysis of TLC suggested the disappearance of the starting azide, the reaction is stopped and THF evaporated. The residue is purified through chromatography to provide the title compound (84 mg, 100%).

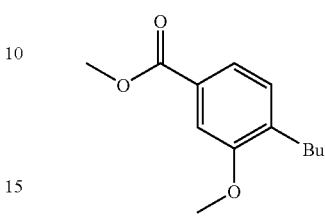

Intermediate 72

4-Butyl-3-methoxy-benzoic acid methyl ester

4-Iodo-3-methoxy-benzoic acid methyl ester (292 mg, 1 mmol) and Pd$_2$(dba)3.CHCl3 (25 mg, 0.025 mmol) and P(tBu)$_3$ (0.25 mL, 10% in hexane, 0.08 mmol) and n-BuZnBr (4 mL, 0.5 M in THF, 2.0 mmol) is mixed in N,N-dimethylformamide (4 mL) together and degassed. After stirring at room temperature for 1 hour, analysis of TLC suggested no starting material left and reaction is stopped. Et$_2$O and H$_2$O were then added and the ether layer is washed with water and dried. After the removal of ether, the residue is directly used in the next step after pass through a short column.

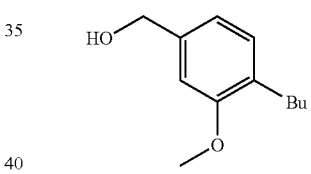

Intermediate 73

(4-Butyl-3-methoxy-phenyl)-methanol

4-Butyl-3-methoxy-benzoic acid methyl ester (obtained from the above step) is allowed to dissolve in ether and cooled. LiAlH$_4$ (70 mg, 1.84 mmol) is then added and the suspension is then stirred overnight. After aqueous work up, the alcohol is isolated and used directly in the next step.

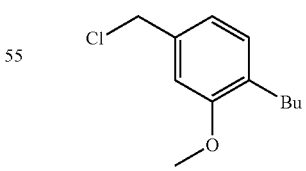

Intermediate 74

1-Butyl-4-chloromethyl-2-methoxy-benzene

Following the same procedure for the preparation of 4-Chloromethyl-2-methoxy-biphenyl, the title compound is prepared from (4-Butyl-3-methoxy-phenyl)-methanol (crude material from the previous step). The crude material is used directly in the next step.

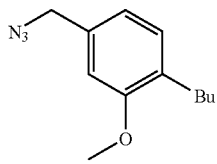

Intermediate 75

4-Azidomethyl-1-butyl-2-methoxy-benzene

Following the same procedure for the preparation of 4-Azidomethyl-2-methoxy-biphenyl, the title compound is prepared from 1-Butyl-4-chloromethyl-2-methoxy-benzene (crude material from the previous step) in 36% yield (overall yield for 4 steps).

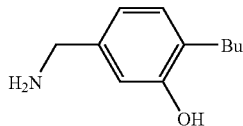

Intermediate 76

5-Aminomethyl-2-butyl-phenol

Following the same procedure for the preparation of 4-Aminomethyl-biphenyl-2-ol the title compound is prepared from 4-Azidomethyl-1-butyl-2-methoxy-benzene (78 mg, 0.36 mmol) in 83% yield.

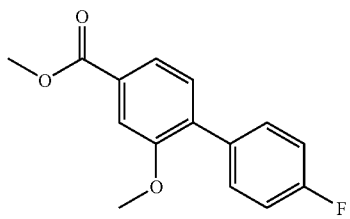

Intermediate 77

4'-Fluoro-2-methoxy-biphenyl-4-carboxylic acid methyl ester

4-Iodo-3-methoxy-benzoic acid methyl ester (292 mg, 1 mmol) and para-fluorophenylboronic acid (160 mg, 1.14 mmol) and Pd(PPh$_3$)$_4$ (80 mg, 0.069 mmol) and Cs$_2$CO$_3$ (600 mg, 1.84 mmol) is mixed in N,N-dimethylformamide (10 mL) and degassed and then heated at 100° C. for 4 hours. After which, the mixture is allowed to cool to room temperature and an aqueous work up is performed and the residue purified to afford the desired product (240 mg, 92%).

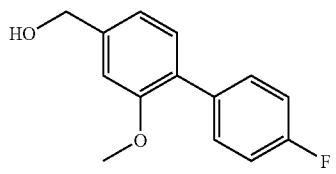

Intermediate 78

(4'-Fluoro-2-methoxy-biphenyl-4-yl)-methanol

4'-Fluoro-2-methoxy-biphenyl-4-carboxylic acid methyl ester (220 mg, 0.85 mmol) is allowed to dissolve in ether and cooled. LiAlH$_4$ (80 mg, 2.12 mmol) is then added and the suspension is then stirred overnight. After aqueous work up, the alcohol is isolated and used directly in the next step.

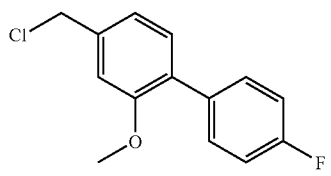

Intermediate 79

4-Chloromethyl-4'-fluoro-2-methoxy-biphenyl

Following the same procedure for the preparation of 4-Chloromethyl-2-methoxy-biphenyl, the title compound is prepared from (4'-Fluoro-2-methoxy-biphenyl-4-yl)-methanol (crude material from the previous step). The crude material is used directly in the next step.

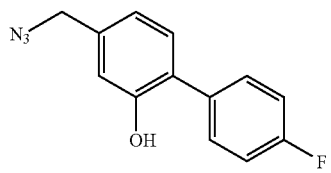

Intermediate 80

4-Azidomethyl-4'-fluoro-biphenyl-2-ol

Following the same procedure for the preparation of 4-Azidomethyl-biphenyl-2-ol, the title compound is prepared from 1-Butyl-4-chloromethyl-2-methoxy-benzene (crude material from the previous step). The crude material is used in the next step.

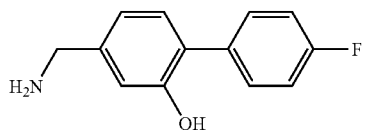

Intermediate 81

4-Aminomethyl-4'-fluoro-biphenyl-2-ol

Following the same procedure for the preparation of 4-Aminomethyl-biphenyl-2-ol, the title compound is prepared from 4-Azidomethyl-4'-fluoro-biphenyl-2-ol (crude material from the previous step) in 54% yield (over 4 steps). MS (ESI): 218 (M+1)$^{+1}$.

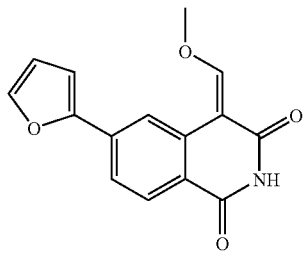

Intermediate 82

6-Furan-2-yl-4-methoxymethylene-4H-isoquinoline-1,3-dione

6-Bromo-4-methoxymethylene-4H-isoquinoline-1,3-dione (1.24 g, 4.4 mmol) and PdCl$_2$(PPh$_3$)$_2$ (200 mg, 0.28 mmol) and 2-furyltributyltin (2 g, 5.6 mmol) in N,N-dimethylformamide (20 mL) is degassed and heated at 100° C. for 1 hour. Upon cooling to room temperature, the product precipitated out. After filtration, the precipitate is washed with Et$_2$O and dried to provide the desired product (800 mg, 68%). MS (ESI): 270.1 (M+1)$^{+1}$.

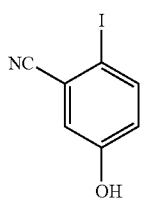

Intermediate 83

5-Hydroxy-2-iodo-benzonitrile

3-Hydroxy-benzonitrile (15 g, 0.126 mol) and iodine monochloride (28 g, 0.172 mol) is heated in acetic acid for 15 hours at 45° C. H$_2$O is added to precipitate the product out. After the precipitate is collected and washed with Na$_2$SO$_3$, the residue is chromatographed with chloroform to get the product (2 g, 7%).

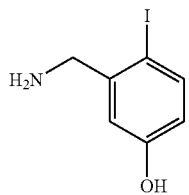

Intermediate 84

3-Aminomethyl-4-iodo-phenol

To a solution of 5-Hydroxy-2-iodo-benzonitrile (245 mg, 1 mmol) in THF (3 mL) is added BH$_3$.THF (6 mL, 1 M solution in THF) under N$_2$. The mixture is then allowed to stir at room temperature for 24 hours. The reaction is then quenched with 6N HCl. THF is then removed and the aqueous layer is then neutralized with ammonium hydroxide to pH 9. The mixture is then extracted with CHCl$_3$/MeOH (9:1). The organic layer dried and evaporated and the residue is chromatographed to provide the desired product (80 mg, 32%).

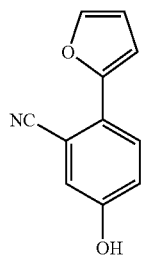

Intermediate 85

2-Furan-2-yl-5-hydroxy-benzonitrile

5-Hydroxy-2-iodo-benzonitrile (200 mg, 0.82 mmol) and PdCl$_2$(PPh$_3$)$_2$ (20 mg, 0.028 mmol) and 2-furyltributyltin (400 g, 1.12 mmol) in N,N-dimethylformamide (5 mL) is degassed and heated at 100° C. for 15 min. After the mixture cooled to room temperature, an aqueous work up is performed and the product is isolated from chromatography (100 mg, 66%). MS (ESI): 184 (M−1)$^{-1}$.

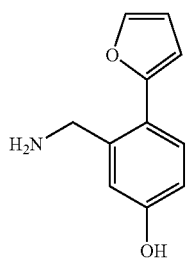

Intermediate 86

3-Aminomethyl-4-furan-2-yl-phenol

2-Furan-2-yl-5-hydroxy-benzonitrile (100 mg, 0.54 mmol) is dissolved in EtOH (10 mL) to which Raney Ni (excess) is added. The mixture is subjected to hydrogenation under $H_2$ (50 psi) for overnight. The mixture is then filtered and solvent removed to afford the crude product, which is carried over to the next step without further purification.

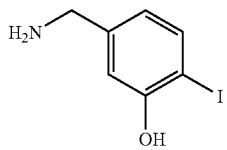

Intermediate 87

5-Aminomethyl-2-iodo-phenol

To a solution of 3-Hydroxy-4-iodo-benzonitrile (300 mg, 1.22 mmol) in THF (5 mL) is added $BH_3$.THF (10 mL, 1 M solution in THF, 10 mmol) under $N_2$. The mixture is then allowed to stir at room temperature for 24 hours. The reaction is quenched with 6N HCl. THF is removed and the aqueous layer is neutralized with ammonium hydroxide to pH 9. The mixture is extracted with $CHCl_3$/MeOH (9:1). The organic layer dried and evaporated and the residue is chromatographed to provide the desired product (60 mg, 20%). MS (ESI): 250 $(M+1)^{-1}$.

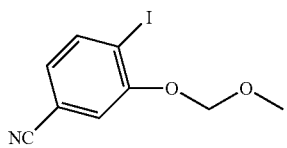

Intermediate 88

4-Iodo-3-methoxymethoxy-benzonitrile 3-hydroxy-4-iodobenzonitrile (500 mg, 2.04 mmol) and MOMCl (350 mg, 4.37 mmol) were dissolved in anhydrous N,N-dimethylformamide (5 mL) and cooled to 0° C. NaH (100 mg, 60% suspension in mineral oil, 2.5 mmol) is then added. The resulting mixture is allowed to stir at room temperature for 1 h before TLC analysis suggested the consumption of the starting iodide. Ether is then added and washed with $H_2O$ (3×20 mL) and brine. After drying over $Na_2SO_4$, the ether is removed and the residue is purified through chromatography to afford the desired MOM ether (570 mg, 96%). $^1H$ NMR (300 MHz, $CDCl_3$) δ 7.90 (1H, d, J=8.01 Hz), 7.32 (1H, d, J=1.7 Hz), 7.03 (1H, dd, J=8.01 and 1.71 Hz), 5.27 (2H, s), 3.51 (3H, s).

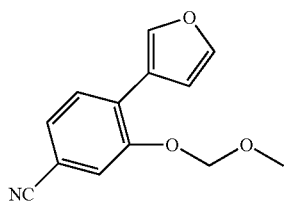

Intermediate 89

4-Furan-3-yl-3-methoxymethoxy-benzonitrile

4-Iodo-3-methoxymethoxy-benzonitrile (150 mg, 0.52 mmol) and 3-furanboronic acid (96 mg, 0.86 mmol) and Pd(PPh3)4 (60 mg, 0.052 mmol) and $Cs_2CO_3$ (500 mg, 1.53 mmol) is mixed in N,N-dimethylformamide (10 mL) and degassed and then heated at 100° C. for 4 hours. After which, the mixture is allowed to cool to room temperature and an aqueous work up is performed and the residue purified to afford the desired product (100 mg, 84%).

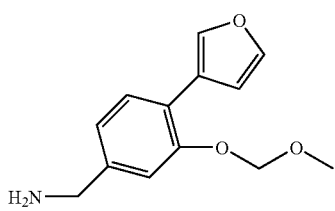

Intermediate 90

4-Furan-3-yl-3-methoxymethoxy-benzylamine

The cyanide obtained above (120 mg, 0.52 mmol) is then dissolved in ether (10 mL). The resulting solution is slowly added to a suspension of $LiAlH_4$ (100 mg, 2.6 mmol) in $Et_2O$. After addition, the mixture is stirred for another 10 min before quenching with $H_2O$ and 5 N NaOH. After which, EtOAc is added and the organic layer is collected and washed with brine and dried over $Na_2SO_4$. Removal of the solvent provided the crude amine (90 mg, 74%).

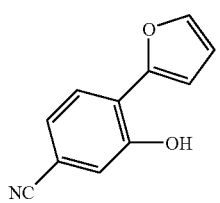

Intermediate 91

4-Furan-2-yl-3-hydroxy-benzonitrile

3-Hydroxy-4-iodo-benzonitrile (120 mg, 0.49 mmol) and $PdCl_2(PPh_3)_2$ (35 mg, 0.049 mmol) and 2-furyltributyltin (200 g, 0.56 mmol) in N,N-dimethylformamide (DMF) (5 mL) is degassed and heated at 100° C. for 30 minutes (min). After the mixture cooled to room temperature, an aqueous work up is performed and the product is isolated from chromatography (80 mg, 88%).

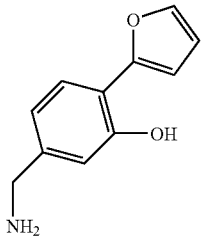

Intermediate 92

5-Aminomethyl-2-furan-2-yl-phenol

To a solution of 4-Furan-2-yl-3-hydroxy-benzonitrile (180 mg, 0.97 mmol) in THF (5 mL) is added $BH_3$.THF (5 mL, 1 M solution in THF, 5 mmol) under $N_2$. The mixture is then allowed to stir at room temperature for 24 hours. The reaction is then quenched with 6N HCl. THF is then removed and the aqueous layer is then neutralized with ammonium hydroxide to pH 9. The mixture is then extracted with $CHCl_3$/MeOH (9:1). The organic layer dried and evaporated and the residue is chromatographed to provide the desired product (60 mg, 33%). MS (ESI): 190 $(M+1)^{+1}$.

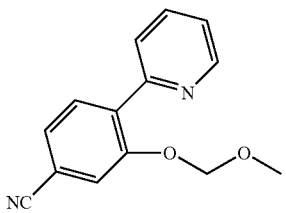

Intermediate 93

3-Methoxymethoxy-4-pyridin-2-yl-benzonitrile

The 4-Iodo-3-methoxymethoxy-benzonitrile (190 mg, 0.66 mmol) and 2-pyridinyl tributyltin (370 mg, 1 mmol) and $PdCl_2(PPh_3)_2$ (60 mg, 0.084 mmol) and CuI (40 mg, 0.21 mmol) were mixed in N,N-dimethylformamide (10 mL). This mixture is then degassed and heated at 100° C. for 1 h. TLC suggested full conversion and after aqueous workup, the residue is purified through chromatography to yield the desired product (162 mg, 93%). $^1$H NMR (300 MHz, $CDCl_3$) δ 8.74 (1H, m), 7.26-7.91 (6H, m), 5.22 (2H, s), 3.48 (3H, s). MS (ESI): 241 $(M+1)^{+1}$.

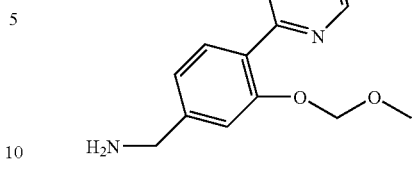

Intermediate 94

3-Methoxymethoxy-4-pyridin-2-yl-benzylamine

3-Methoxymethoxy-4-pyridin-2-yl-benzonitrile (160 mg, 0.67 mmol) is then dissolved in ether (10 mL). The resulting solution is slowly added to a suspension of $LiAlH_4$ (100 mg, 2.6 mmol) in $Et_2O$. After addition, the mixture is stirred for another 10 min before quenched with $H_2O$ and 5 N NaOH. After which, EtOAc is added and the organic layer is collected and washed with brine and dried over $Na_2SO_4$. Removal of the solvent provided the crude amine, which is used directly in the next step. MS (ESI): 245 $(M+1)^{+1}$.

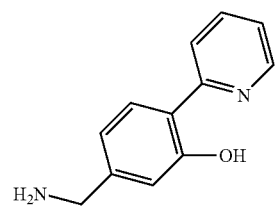

Intermediate 95

5-Aminomethyl-2-pyridin-2-yl-phenol

This MOM protected amine (crude material from above) is then dissolved in 2N aq HCl/MeOH (1:1). The solution resulted is heated at reflux for 15 min and TLC suggested no starting material left. The mixture is then allowed to cool to room temperature and basified with aqueous ammonium hydroxide and the product is extracted with $CH_2Cl_2$/MeOH (9:1). The organic layer is dried. After removal of the solvent, the residue is purified with chromatography to provide the desired primary amine (63 mg, 47% over two steps). $^1$H NMR (300 MHz, CDCl3) δ8.50 (1H, m), 7.76-7.92 (3H, m), 7.24 (1H, m), 6.86-6.97 (2H, m), 3.87 (2H, s). MS (ESI): 201 $(M+1)^{+1}$.

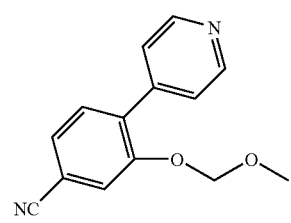

Intermediate 96

3-Methoxymethoxy-4-pyridin-4-yl-benzonitrile

The 4-Iodo-3-methoxymethoxy-benzonitrile (200 mg, 0.69 mmol) and 4-pyridinyl tributyltin (360 mg, 0.97 mmol) and PdCl$_2$(PPh$_3$)$_2$ (60 mg, 0.084 mmol) and CuI (20 mg, 0.11 mmol) were mixed in N,N-dimethylformamide (10 mL). This mixture is then degassed and heated at 100° C. for 4 h. TLC suggested full conversion and after aqueous workup, the residue is purified through chromatography to yield the desired product (122 mg, 64%).

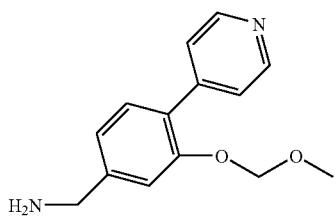

Intermediate 97

3-Methoxymethoxy-4-pyridin-4-yl-benzylamine

3-Methoxymethoxy-4-pyridin-4-yl-benzonitrile (122 mg, 0.51 mmol) is dissolved in ether (10 mL). The resulting solution is slowly added to a suspension of LiAlH$_4$ (100 mg, 2.6 mmol) in Et$_2$O. After addition, the mixture is stirred for another 10 min before quenched with H$_2$O and 5 N NaOH. After which, EtOAc is added and the organic layer is collected and washed with brine and dried over Na$_2$SO$_4$. Removal of the solvent provided the crude amine, which is used directly in the next step. MS (ESI): 245 (M+1)$^{+1}$.

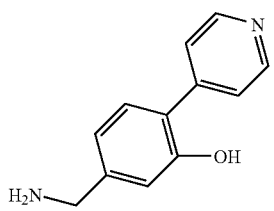

Intermediate 98

5-Aminomethyl-2-pyridin-4-yl-phenol

This MOM protected amine (crude material from above) is dissolved in 2N aq HCl/MeOH (1:1). The resulting solution is heated at reflux for 15 min and TLC indicated that no starting material is left. The mixture is then allowed to cool to room temperature and basified with aqueous ammonium hydroxide and the product is extracted with CH$_2$Cl$_2$/MeOH (9:1). The organic layer is dried. After removal of the solvent, the residue is purified with chromatography to provide the desired primary amine (40 mg, 39% over two steps). MS (ESI): 201 (M+1)$^{+1}$.

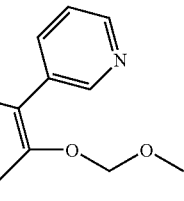

Intermediate 99

3-Methoxymethoxy-4-pyridin-3-yl-benzonitrile

The 4-Iodo-3-methoxymethoxy-benzonitrile (200 mg, 0.69 mmol) and 4-pyridinyl tributyltin (360 mg, 0.97 mmol) and PdCl$_2$(PPh$_3$)$_2$ (60 mg, 0.084 mmol) and CuI (20 mg, 0.11 mmol) were mixed in N,N-dimethylformamide (10 mL). This mixture is then degassed and heated at 100° C. for 3 h. TLC suggested full conversion and after aqueous workup, the residue is purified through chromatography to yield the desired product (150 mg, 79%).

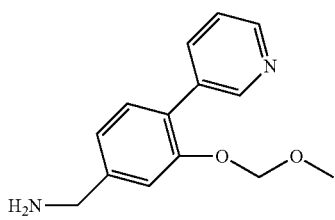

Intermediate 100

3-Methoxymethoxy-4-pyridin-3-yl-benzylamine

3-Methoxymethoxy-4-pyridin-4-yl-benzonitrile (150 mg, 0.63 mmol) is then dissolved in ether (10 mL). The resulting solution is slowly added to a suspension of LiAlH$_4$ (100 mg, 2.6 mmol) in Et$_2$O. After addition, the mixture is stirred for another 10 min before quenched with H$_2$O and 5 N NaOH. After which, EtOAc is added and the organic layer is collected and washed with brine and dried over Na$_2$SO$_4$. Removal of the solvent provided the crude amine, used directly in the next step. MS (ESI): 245 (M+1)$^{+1}$.

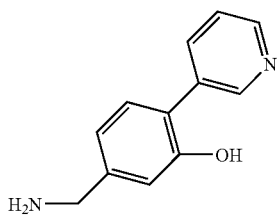

Intermediate 101

5-Aminomethyl-2-pyridin-3-yl-phenol

This MOM protected amine (crude material from above) is dissolved in 2N aq HCl/MeOH (1:1). The resulting solution is heated at reflux for 15 min and TLC indicated that no starting material is left. The mixture is then allowed to cool to room temperature and basified with aqueous ammonium hydroxide. The product is extracted with $CH_2Cl_2$/MeOH (9:1). The organic layer is dried. After removal of the solvent, the residue is purified with chromatography to provide the desired primary amine (53 mg, 42% over two steps). MS (ESI): 201 $(M+1)^{+1}$.

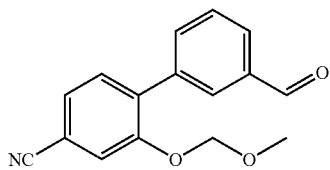

Intermediate 102

3'-Formyl-2-methoxymethoxy-biphenyl-4-carbonitrile

4-Iodo-3-methoxymethoxy-benzonitrile (600 mg, 2.08 mmol), 3-formylphenylboronic acid (450 mg, 3.0 mmol), $Pd(PPh_3)_4$ (200 mg, 0.17 mmol) and $Cs_2CO_3$ (1.2 g, 3.7 mmol) were mixed in N,N-dimethylformamide (15 mL), degassed and heated at 100° C. for 2 hours. After which, the mixture is allowed to cool to room temperature, an aqueous work up is performed, and the residue purified to afford the desired product (500 mg, 90%).

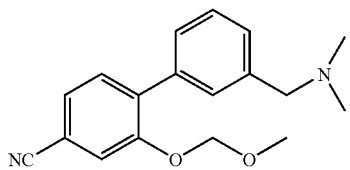

Intermediate 103

3'-Dimethylaminomethyl-2-methoxymethoxy-biphenyl-4-carbonitrile

3'-Formyl-2-methoxymethoxy-biphenyl-4-carbonitrile (128 mg, 0.48 mmol) is dissolved in $CH_2Cl_2$ (5 mL), and to which dimethylamine (2 mL, 2 M solution in THF, 4 mmol) is added. Triacetylborohydride (300 mg, 1.59 mmol) is added and the mixture is stirred at room temperature for 1 hour before it is quenched with ice water. The organic layer is washed with $NH_4OH$ and dried over $Na_2SO_4$. After concentration, the residue is directly used in the next step. MS (ESI): 297 $(M+1)^{+1}$.

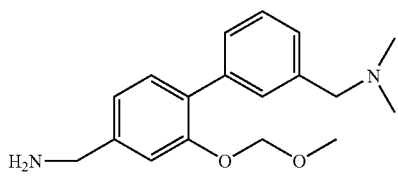

Intermediate 104

C-(3'-Dimethylaminomethyl-2-methoxymethoxy-biphenyl-4-yl)-methylamine

3'-Dimethylaminomethyl-2-methoxymethoxy-biphenyl-4-carbonitrile (crude material from above) is dissolved in ether (10 mL). The resulting solution is slowly added to a suspension of $LiAlH_4$ (100 mg, 2.6 mmol) in $Et_2O$. After addition, the mixture is stirred for another 10 min before quenching with $H_2O$ and 5 N NaOH. After which, EtOAc is added and the organic layer is collected and washed with brine and dried over $Na_2SO_4$. Removal of the solvent provided the crude amine, which is used directly in the next step. MS (ESI): 301 $(M+1)^{+1}$.

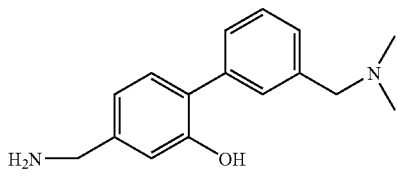

Intermediate 105

4-Aminomethyl-3'-dimethylaminomethyl-biphenyl-2-ol

This MOM protected amine (crude material from above) is dissolved in 2N aq HCl/MeOH (1:1). The resulting solution is heated at reflux for 15 min and TLC indicated that no starting material is left. The mixture is allowed to cool to room temperature and basified with aqueous ammonium hydroxide. The product is extracted with $CH_2Cl_2$/MeOH (9:1). The organic layer is dried. After removal of the solvent, the residue is chromatography purified to provide the desired primary amine (50 mg, 40% over three steps). MS (ESI): 257 $(M+1)^{+1}$.

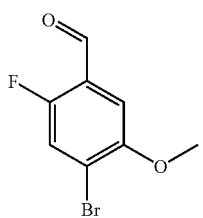

Intermediate 106

4-Bromo-2-fluoro-5-methoxy-benzaldehyde

To a $N_2$ purged flask is added $TiCl_4$ (0.44 mL) followed by 2-Bromo-4-fluoro-1-methoxy-benzene (400 mg, 1.95 mmol). The stirred mixture is cooled in an ice water bath and treated dropwise with 1,1-dichloromethyl methyl ether (0.35 mL, 1.95 mmol). After stirring for 90 minutes, the resulting slurry is treated with $CH_2Cl_2$ (200 mL) and reaction is allowed to warm up to room temperature. After passing through a column, the title compound is isolated (220 mg, 48%). MS (ESI): 232.9 (M+1)$^{+1}$.

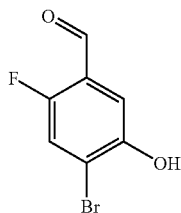

Intermediate 107

4-Bromo-2-fluoro-5-hydroxy-benzaldehyde

4-Bromo-2-fluoro-5-methoxy-benzaldehyde (100 mg, 0.43 mmol) is dissolved in CH$_2$Cl$_2$ and cooled to −78° C. and then BBr$_3$ (2 mL, 1 M solution in CH$_2$Cl$_2$, 2 mmol) is added. The resulting mixture is allowed to stir at room temperature until no starting material is left. The reaction is quenched and the product is isolated after chromatography (60 mg, 57%). MS (ESI): 216.9 (M−1)$^{−1}$.

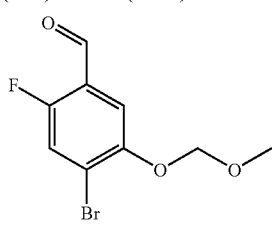

Intermediate 108

4-Bromo-2-fluoro-5-methoxymethoxy-benzaldehyde

4-Bromo-2-fluoro-5-hydroxy-benzaldehyde (750 mg, 3.41 mmol) and MOMCl (545 mg, 6.82 mmol) were dissolved in anhydrous N,N-dimethylformamide (5 mL) and cooled to 0° C. NaH (160 mg, 60% suspension in mineral oil, 4 mmol) is then added. The resulting mixture is allowed to stir at room temperature for 1 h. Ether is then added and washed with H$_2$O (3×20 mL) and brine. After dried over Na$_2$SO$_4$, the ether is removed and the residue is purified through chromatography to afford the desired MOM ether (700 mg, 78%).

Intermediate 109

2-Fluoro-4-furan-3-yl-5-methoxymethoxy-benzaldehyde

4-Bromo-2-fluoro-5-methoxymethoxy-benzaldehyde (160 mg, 0.61 mmol) and 3-furanboronic acid (100 mg, 0.90 mmol) and Pd(PPh$_3$)$_4$ (60 mg, 0.052 mmol) and Cs$_2$CO$_3$ (400 mg, 1.23 mmol) were mixed in N,N-dimethylformamide (10 mL) and degassed and then heated at 100° C. for 1 hour. The mixture is allowed to cool to room temperature and an aqueous work up is performed. The residue is purified to afford the desired product (60 mg, 39%).

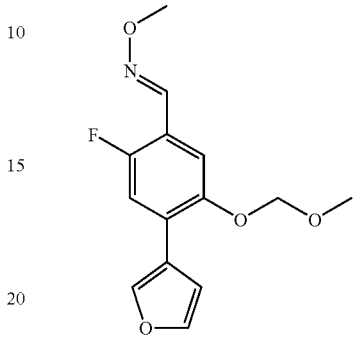

Intermediate 110

2-Fluoro-4-furan-3-yl-5-methoxymethoxy-benzaldehyde O-methyl-oxime

2-Fluoro-4-furan-3-yl-5-methoxymethoxy-benzaldehyde (200 mg, 0.8 mmol) is dissolved in pyridine (5 mL). Methoxyamine hydrochloride (100 mg, 1.2 mmol) is added. The mixture is stirred at room temperature for 1 hour, the pyridine is evaporated and the product purified through chromatography (248 mg, 100%). MS (ESI): 280 (M+1)$^{+1}$.

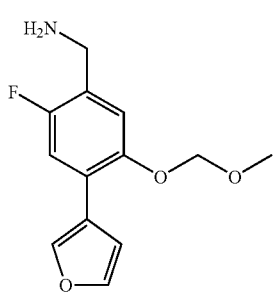

Intermediate 111

2-Fluoro-4-furan-3-yl-5-methoxymethoxy-benzaldehyde O-methyl-oxime

The oxime ether (248 mg, 0.8 mmol) is dissolved in ether and LiAlH$_4$ (250 mg, 6.57 mmol) is added. The resulting mixture is heated at reflux for 20 minutes and then quenched with EtOAc and 5 N NaOH. The product is extracted out with EtOAc. After the ethyl acetate layer is dried and evaporated, the product obtained is directly used in the next step. MS (ESI): 252 (M+1)$^{+1}$.

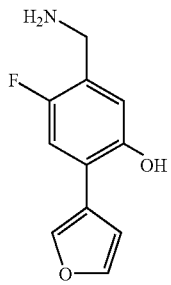

Intermediate 112

5-Aminomethyl-4-fluoro-2-furan-3-yl-phenol

The MOM protected amine (crude material from above) is dissolved in 2N aq HCl/MeOH (1:1). The resulting solution is heated at reflux for 15 minutes and TLC suggested no starting material is left. The mixture is allowed to cool to room temperature and basified with aqueous ammonium hydroxide and the product is extracted with $CH_2Cl_2$/MeOH (9:1). The organic layer is dried. After removal of the solvent, the product is purified with chromatography (96 mg, 58% over two steps). MS (ESI): 208(M+1)$^{+1}$.

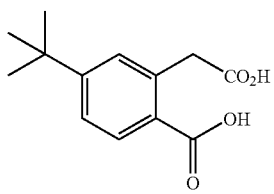

Intermediate 113

4-tert-Butyl-2-carboxymethyl-benzoic acid

To a magnetically stirred solution of diisopropyl amine (0.75 g, 7.4 mmol) in THF (5 mL) at −30° C. is added BuLi (3.4 mL, 2.5 M in hexanes, 8.5 mmol). The mixture is stirred for 10 minutes at this temperature and cooled to −78° C. A solution of 4-tert-Butyl-2-methyl-benzoic acid [J. Am. Chem. Soc. 1944, 66, 154] (250 mg, 1.3 mmol) and dimethylcarbonate (150 mg, 1.67 mmol) in THF (3 mL) is added dropwise at −78° C. The mixture is allowed to stir at this temperature for 2 hours before it is allowed to warm to room temperature. The mixture is quenched with MeOH and water once it reached room temperature. After removal of THF, the water layer is extracted with ether. The water layer is acidified with HCl and the product is extracted from ether. After chromatography, the title compound is isolated pure (125 mg, 41%). MS (ESI): 237.1 (M+1)$^{+1}$.

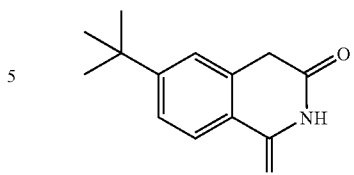

Intermediate 114

6-tert-Butyl-4H-isoquinoline-1,3-dione 4-tert-Butyl-2-carboxymethyl-benzoic acid (90 mg, 0.38 mmol) and urea (45 mg, 0.75 mmol) were grinded and mixed in a round bottle flask, then placed into an oil bath, preheated to 145° C. The flask is kept at this temperature for 1 hour before it is cooled to room temperature. Chromatography of the residue afforded the title compound (45 mg, 55%). MS (ESI): 216.1 (M−1)$^{-1}$.

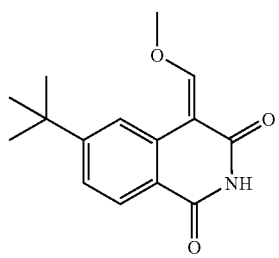

Intermediate 115

6-tert-Butyl-4-methoxymethylene-4H-isoquinoline-1,3-dione 6-tert-Butyl-4H-isoquinoline-1,3-dione (45 mg, 0.21 mmol) is dissolved in N,N-dimethylformamide (1 mL) and acetic anhydride (2 mL). Trimethylorthoformate (0.2 mL) is added and the mixture is heated to 120° C. for 1 hour. The volatiles were removed under vacuum and the residue passed through a column to afford the crude product, is used directly in the next step. MS (ESI): 258.3 (M−1)$^{-1}$.

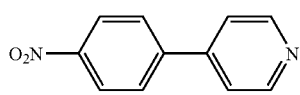

Intermediate 116

4-(4-Nitro-phenyl)-pyridine

To a 25 mL round bottom flask is added 1-bromo-4-nitrobenzene (404 mg, 2.0 mmol), 4-pyridinylboronic acid (248 mg, 2.0 mmol), $Na_2CO_3$ (424 mg, 4.0 mmol) and Pd(PPh$_3$)$_4$ (100 mg, 0.087 mmol), DME (10 mL) and $H_2O$ (3 mL). The mixture is degassed and heated at reflux for 14 h. TLC is used to establish the completion of starting bromide, the mixture is allowed to cool to room temperature. EtOAc is added, and the EtOAc layer is washed with H₂O (15 mL) and brine (10 mL) and dried over MgSO₄. After removal of EtOAc, the resulting residue is subjected to flash chromatography with CH₂Cl₂/EtOAc (3:1) as eluent to provide the coupling product 4-(4-nitro-phenyl)-pyridine (288 mg, 72%). ¹H NMR (400 MHz, CDCl₃) ∂ 8.75 (2H, dd, J=6.0 and 2.8 Hz), 8.36 (2H, dd, J=9.6 and 3.2 Hz), 7.80 (2H, dd, J=8.8 and 2.4 Hz), 7.54 (2H, dd, J=5.6 and 2.0 Hz).

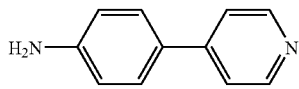

Intermediate 117

4-Pyridin-4-yl-phenylamine 4-(4-nitro-phenyl)-pyridine (250 mg, 1.25 mmol) is dissolved in MeOH (20 mL). To this solution is added FeCl₃.6H₂O (24 mg, 0.09 mmol) and active charcoal (12 mg, 1.0 mmol). The suspension is heated to reflux. Hydrazine hydrate (1.3 mL) is added, and reflux is continued for 3 h. After the mixture is cooled to room temperature, the active charcoal is filtered off through Celite, and the MeOH is removed under reduced pressure. The residue is purified with flash chromatography to provide the 4-pyridin-4-yl-phenylamine (200 mg, 94%). ¹H NMR (400 MHz, CDCl₃) ∂ 8.57 (2H, d, J=8.8 Hz), 7.44-7.52 (4H, m), 6.77 (2H, d, J=7.2 Hz), 3.87 (2H, br); MS (ESI) m/z 171 (M+H)⁺¹.

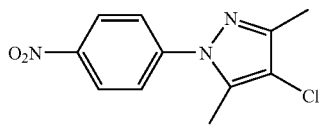

Intermediate 118

4-Chloro-3,5-dimethyl-1-(4-nitro-phenyl)-1H-pyrazole

4-Nitro-phenyl)-hydrazine (0.50 g, 3.3 mmol) and 3-Chloro-pentane-2,4-dione (0.45 g, 3.3 mmol) is heated in EtOH at reflux in the presence of concentrated HCl (1 mL). TLC is used to monitor the consumption of the starting material, the mixture is allowed to cool to room temperature at which time, a precipitate formed. The precipitate is collected and dried to provide the 4-Chloro-3,5-dimethyl-1-(4-nitro-phenyl)-1H-pyrazole in the HCl salt form (0.5 g, 53%). ¹H NMR (300 MHz, DMSO) ∂ 8.33-8.38 (2H, m), 7.84-7.88 (2H, m), 4.37 (2H, br), 2.41 (3H, s), 2.24 (3H, s).

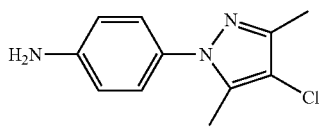

Intermediate 119

4-(4-Chloro-3,5-dimethyl-pyrazol-1-yl)-phenylamine

4-Chloro-3,5-dimethyl-1-(4-nitro-phenyl)-1H-pyrazole hydrochloride (450 mg, 1.56 mmol) is dissolved in MeOH (40 mL). To this solution is then added FeCl₃.6H₂O (24 mg, 0.09 mmol) and active carbon (12 mg, 1 mmol). The suspension is heated to reflux. Hydrazine (2.0 mL) is added, and reflux is continued for 3 h or until TLC detected full conversion. After conversion the mixture is cooled to room temperature, the active carbon is filtered off using celite and the MeOH under reduced pressure. The residue is purified with flash chromatography to provide the 4-(4-Chloro-3,5-dimethyl-pyrazol-1-yl)-phenylamine (360 mg, 91%). MS (ESI): 222, 224 (M+1)⁺¹.

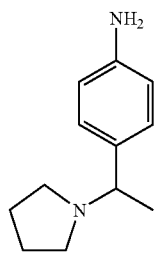

Intermediate 120

4-(1-Pyrrolidin-1-yl-ethyl)-phenylamine

LiHMDS (1 mL, 1 M solution in THF, 1.0 mmol) is added to a 25 mL round bottom flask, THF is removed. Toluene (4 mL) is added followed by addition of Pd₂(dba)₃.CHCl₃ (10 mg, 0.01 mmol) and P(tBu)₃ (10 mg, 0.05 mmol). The mixture is degassed. 1-[1-(4-Bromo-phenyl)-ethyl]-pyrrolidine (330 mg, 1.3 mmol) in toluene (2 mL) is added to the flask. The resulting mixture is stirred at room temperature overnight. TLC is used to determine complete consumption of starting bromide, the reaction mixture is diluted with ether at this point and poured into dilute HCl (aq). The ether layer is discarded, the aqueous layer is basified with NH₄OH and extracted with CH₂Cl₂. The CH₂Cl₂ layer is dried and concentrated. The residue is subjected to chromatography to provide the desired product 4-(1-Pyrrolidin-1-yl-ethyl)-phenylamine (60 mg, 24%). ¹H NMR (300 MHz, CDCl₃) ∂ 7.09-7.13(2H, m), 6.61-6.66 (2H, m), 3.47 (2H, br), 3.11 (1H, q, J=6.6 Hz), 2.52-2.58 (2H, m), 2.33-2.39 (2H, m), 1.73-1.79 (4H, m), 1.38 (3H, d, J=6.9 Hz). MS (ESI): 191 (M+1)⁺¹.

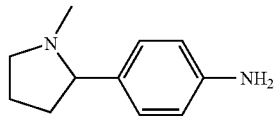

Intermediate 121

4-(1-Methyl-pyrrolidin-2-yl)-phenylamine

LiHMDS (5.0 g, 30.0 mmol) is added to a 250 mL round bottom flask. Toluene (60 mL) is then added followed by addition of Pd₂(dba)₃.CHCl₃ (390 mg, 0.39 mmol) and P(tBu)₃.HBF₄ (300 mg, 1.03 mmol) and 2-(4-Bromo-phenyl)-1-methyl-pyrrolidine (3.5 g, 14.5 mmol). The mixture is degassed. The resulting mixture is then stirred at room temperature overnight. After TLC suggested no starting bromide left, the reaction mixture is diluted with ether and poured into dilute HCl (aq). The ether layer is discarded, the aqueous layer is basified with NH₄OH and extracted with CH₂Cl₂. The CH₂Cl₂ layer is dried and concentrated. The residue is judged by NMR to be 90% purity product (2.52 g, 90%).

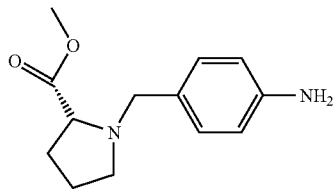

Intermediate 122

D-1-(4-Amino-benzyl)-pyrrolidine-2-carboxylic acid methyl ester

D-1-(4-Nitro-benzyl)-pyrrolidine-2-carboxylic acid methyl ester (1.0 g, 3.7 mmol) is dissolved in MeOH (20 mL) and Fe (1.5 g, 26.7 mmol). NH₄Cl (1.5 g, 28.0 mmol) is added followed by addition of H₂O (10 mL). The mixture is heated at reflux for 2 h. The resulting solid is filtered and MeOH removed. EtOAc and NaHCO₃ (aq) is added. The EtOAc layer is washed and dried over Na₂SO₄. After removal of EtOAc, the residue is used directly in the next step.

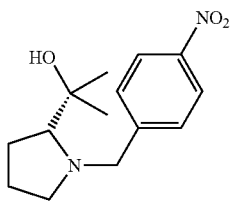

Intermediate 123

2-[1-(4-Nitro-benzyl)-pyrrolidin-2-yl]-propan-2-ol

2-Pyrrolidin-2-yl-propan-2-ol (100 mg, 0.78 mmol) is dissolved in CH₃CN (5 mL) to which K₂CO₃ (300 mg, 2.17 mmol) and p-nitrobenzylbromide (250 mg, 1.16 mmol) were added. The resulting mixture is stirred until MS suggested no starting alcohol is present. The suspension is filtered to remove the potassium salts and the acetonitrile is removed under vacuum. The residue is purified to afford the product (105 mg, 51%). ¹H NMR (300 MHz, CDCl₃) δ8.18 (2H, d, J=8.7 Hz), 7.54 (2H, d, J=8.7 Hz), 4.25 (1H, d, J=15 Hz), 3.72 (1H, d, J=15 Hz), 2.90-2.95 (1H, m), 2.76-2.80 (1H, m), 2.28-2.38 (2H, m), 1.71-1.91 (4H, m), 1.24 (3H, s), 1.20 (3H, s).

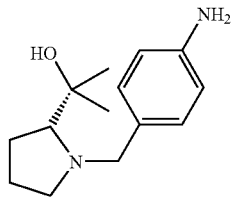

Intermediate 124

2-[1-(4-Amino-benzyl)-pyrrolidin-2-yl]-propan-2-ol

2-[1-(4-Nitro-benzyl)-pyrrolidin-2-yl]-propan-2-ol (105 mg, 0.40 mmol) is dissolved in MeOH (20 mL). To this solution is added FeCl₃.6H2O (30 mg, 0.11 mmol) and active charcoal (15 mg, 1.2 mmol). The suspension is heated to reflux. Hydrazine hydrate (1.2 mL) is added, and reflux is continued for 3 h. After the mixture is cooled to room temperature, the active charcoal is filtered off through Celite, and the MeOH is removed under reduced pressure. The residue is purified with flash chromatography to provide the 4-pyridin-4-yl-phenylamine (72 mg, 77%). ¹H NMR (300 MHz, CDCl₃) δ7.14 (2H, d, J=7.8 Hz), 6.62-6.67 (2H, m), 4.0 (1H, d, J=12.9 Hz), 3.61 (2H, br), 3.46 (1H, d, J=12.9 Hz), 2.82-2.89 (1H, m), 2.69-2.74 (1H, m), 2.39-2.47 (1H, m), 1.62-1.89 94H, m), 1.25 (3H, s), 1.15 (3H, s).

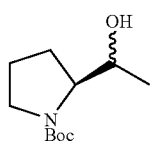

Intermediate 125

2-(1-Hydroxy-ethyl)-pyrrolidine-1-carboxylic acid tert-butyl ester

L-2-Formyl-pyrrolidine-1-carboxylic acid tert-butyl ester (2.0 g, 10.0 mmol) is dissolved in THF (30 mL) and cooled to −78° C. MeMgBr (5.0 mL, 3.0 M in ether, 15.0 mmol) is added dropwise, the mixture is allowed to stir overnight to room temperature. After removal of THF, the residue is partitioned between EtOAc and H₂O. The EtOAc layer is dried over Na₂SO₄. After removal of the EtOAc, the residue (2.0 g, 93%) is used directly in the next step.

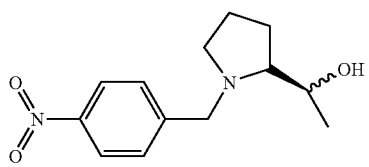

Intermediate 126

1-[1-(4-Nitro-benzyl)-pyrrolidin-2-yl]-ethanol 2-(1-Hydroxy-ethyl)-pyrrolidine-1-carboxylic acid tert-butyl ester (1.0 g, 4.6 mmol) in CH₂Cl₂ is cooled to 0° C. and TFA (2.5 mL) is added dropwise. The mixture is allowed to stir at room temperature overnight. All the volatiles were removed and CH₃CN (20 mL) is added. After addition of 4-nitrobenzyl bromide (1.25 g, 5.78 mmol) and K₂CO₃ (2.0 g, 14.4 mmol), the mixture is stirred at room temperature for 5 hours.

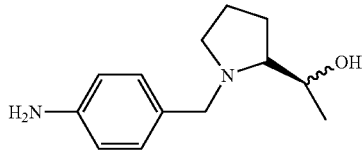

Intermediate 127

1-[1-(4-Amino-benzyl)-pyrrolidin-2-yl]-ethanol

1-[1-(4-Nitro-benzyl)-pyrrolidin-2-yl]-ethanol (370 mg, 1.48 mmol) is dissolved in MeOH (15 mL), to this solution is added FeCl₃.6H₂O (30 mg, 0.11 mmol) and active charcoal (15 mg, 1.2 mmol). The suspension is heated to reflux. Hydrazine hydrate (1.0 mL) is added, and reflux is continued for 3 h. After the mixture is cooled to room temperature, the active charcoal is filtered off through Celite, and the MeOH is removed under reduced pressure. The residue (200 mg, 61%) is directly used in the next step.

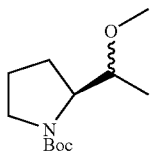

Intermediate 128

2-(1-Methoxy-ethyl)-pyrrolidine-1-carboxylic acid tert-butyl ester 2-(1-Hydroxy-ethyl)-pyrrolidine-1-carboxylic acid tert-butyl ester (1.0 g, 4.3 mmol) in N,N-dimethylformamide (15 mL) is cooled to 0° C., MeI (1 mL) is added followed by NaH (380 mg, 60% suspension in mineral oil, 9.5 mmol). The resulting mixture is allowed to stir at room temperature for 2 hours until TLC reported no remaining starting material. The reaction is quenched with ice and ether is added. N,N-dimethylformamide is washed away with H₂O and the ether layer is dried and concentrated to afford the crude product used directly in the next step.

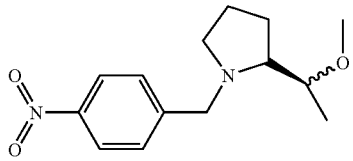

Intermediate 129

2-(1-Methoxy-ethyl)-1-(4-nitro-benzyl)-pyrrolidine 2-(1-methoxy-ethyl)-pyrrolidine-1-carboxylic acid tert-butyl ester (1.0 g, 4.4 mmol) in CH₂Cl₂ (25 mL) is cooled to 0° C. and TFA (2.5 mL) is added dropwise. The mixture is allowed to stir at room temperature overnight. The volatiles were removed and CH₃CN (20 mL) is added. After addition of 4-nitrobenzyl bromide (1.25 g, 5.78 mmol) and K₂CO₃ (2.0 g, 14.4 mmol) the mixture is stirred at room temperature for 5 hours. Aqueous workup followed by chromatography. (260 mg, 25%). ¹H NMR (300 MHz, CDCl3) ∂8.17 (2H, d, J=8.7 Hz), 7.51 (2H, d, J=8.4 Hz), 4.29 (1H, d, J=14.4 Hz), 3.48 (1H, d, J=14.4 Hz), 3.30-3.33 (1H, m), 3.32 (3H, s), 2.88-2.91 (1H, m), 2.73-2.78 (1H, m), 2.14-2.19 (1H, m), 1.61-1.85 (4H, m), 1.15 (3H, d, J=6.6 Hz).

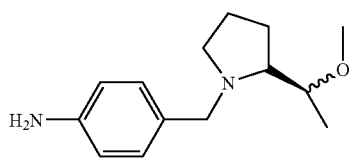

Intermediate 130

4-[2-(1-Methoxy-ethyl)-pyrrolidin-1-ylmethyl]-phenylamine 2-(1-Methoxy-ethyl)-1-(4-nitro-benzyl)-pyrrolidine (250 mg, 0.95 mmol) is dissolved in MeOH (10 mL). To this solution is added FeCl₃.6H₂O (25 mg, 0.09 mmol) and active charcoal (12 mg, 1.0 mmol). The suspension is heated to reflux. Hydrazine hydrate (1.0 mL) is added, and reflux is continued for 4 h. After the mixture is cooled to room temperature, the active charcoal is filtered off through Celite, and the MeOH is removed under reduced pressure. The residue (200 mg, 90%) is used directly in the next step.

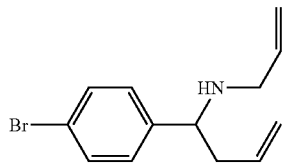

Intermediate 131

Allyl-[1-(4-bromo-phenyl)-but-3-enyl]-amine

Allyl-(4-bromo-benzylidene)-amine (1.13 g, 5.0 mmol) is dissolved in THF (15 mL) and the mixture is cooled to 0° C. with an ice bath. Allyl magnesium bromide (6.0 mL, 1.0 M in ethyl ether, 6.0 mmol) is added. The resulting mixture is stirred at 0° C. for 1 hour and warmed to room temperature followed by reaction quenching. EtOAc and water were added and the EtOAc layer is washed with brine and dried.

After removal of EtOAc, the product (1.0 g, 75%) is obtained. MS (ESI): 266, 268 (M+1)$^{+1}$.

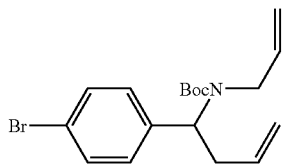

Intermediate 132

Allyl-[1-(4-bromo-phenyl)-but-3-enyl]-carbamic acid tert-butyl ester

Allyl-[1-(4-bromo-phenyl)-but-3-enyl]-amine (1.0 g, 3.7 mmol) is dissolved in CH$_3$CN (17 mL), (Boc)$_2$O (1.2 g, 5.5 mmol) is added, followed by addition of DMAP (50-100 mg, 0.41-0.82 mmol). The mixture is stirred until no starting amine is left. After removal of CH$_3$CN, the residue is subjected to chromatography to provide the desired product (0.9 g, 66%). $^1$H NMR (300 MHz, CDCl3) ∂7.47 (2H, d, J=8.7 Hz), 7.20-7.27 (2H, m), 5.0-5.83 (7H, m), 3.60 (2H, m), 2.75 (2H, m), 1.52 (9H, s).

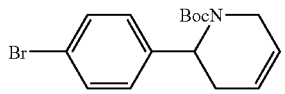

Intermediate 133

2-(4-Bromo-phenyl)-3,6-dihydro-2H-pyridine-1-carboxylic acid tert-butyl ester

Allyl-[1-(4-bromo-phenyl)-but-3-enyl]-carbamic acid tert-butyl ester (300 mg, 0.82 mmol) in CH$_2$Cl$_2$ (10 mL) is degassed and the 2$^{nd}$ generation of Grubb's catalyst (40 mg, 5%) is added under N$_2$. The reaction did not proceed at room temperature and the mixture is brought to reflux. TLC is used to determine complete reaction of the olefin. The mixture is loaded onto a column and purified to provide the desired product (208 mg, 75%). $^1$H NMR (300 MHz, CDCl3) ∂7.43 (2H, d, J=8.1 Hz), 7.17-7.26 (2H, m), 5.89-5.95 (1H, m), 5.34-5.58 (2H, m), 4.14-4.36 (1H, m), 3.35-3.44 (1H, m), 2.73-2.81 (1H, m), 2.41-2.62 (1H, m), 1.48 (9H, s).

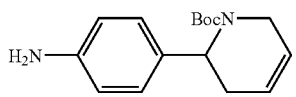

Intermediate 134

2-(4-Amino-phenyl)-3,6-dihydro-2H-pyridine-1-carboxylic acid tert-butyl ester

To a solution of 2-(4-Bromo-phenyl)-3,6-dihydro-2H-pyridine-1-carboxylic acid tert-butyl ester (400 mg, 1.18 mmol) in toluene (4 mL) is added Pd$_2$(dba)$_3$.CHCl$_3$ (50 mg, 0.05 mmol) and P(tBu)$_3$ (40 mg, 0.20 mmol). The mixture is degassed at −30° C. KHMDS (7.0 mL, 0.5 M solution in toluene, 3.5 mmol)) is added to the flask. The resulting mixture is stirred at room temperature overnight. TLC is used to detect when the starting bromide is consumed, the reaction mixture is diluted with ether and poured into dilute HCl (aq). The ether layer is discarded, the aqueous layer is basified with NH$_4$OH and extracted with CH$_2$Cl$_2$. The CH$_2$Cl$_2$ layer is dried and concentrated. The residue (300 mg) is directly employed in the next step.

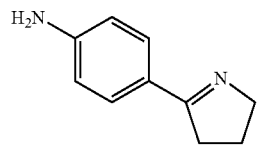

Intermediate 135

4-(4,5-Dihydro-3H-pyrrol-2-yl)-phenylamine

LiHMDS (1.67 g, 10.0 mmol) is added to a 100 mL round bottom flask. Toluene (25 mL) is added followed by addition of Pd$_2$(dba)$_3$.CHCl$_3$ (100 mg, 0.1 mmol) and P(tBu)$_3$.HBF$_4$ (78 mg, 0.27 mmol). 5-(4-Bromo-phenyl)-3,4-dihydro-2H-pyrrole (1.5 g, 6.7 mmol) is added to the flask. After degassing, the mixture is stirred at room temperature overnight. TLC is used to determine complete consumption of the starting bromide. The reaction mixture is diluted with ether and poured into dilute HCl (aq). The ether layer is discarded and the aqueous layer is basified with NH$_4$OH and extracted with CH$_2$Cl$_2$. The CH$_2$Cl$_2$ layer is dried and concentrated to provide the desired product (820 mg, 76%). $^1$H NMR (300 MHz, CDCl$_3$) ∂ 7.66 (2H, d, J=8.4 Hz), 6.67 (2H, d, J=8.1 Hz), 3.98-4.03(2H, m), 3.88 (2H, br), 2.85-2.92 (2H, m), 1.97-2.04 (2H, m). MS (ESI): 162 (M+1)$^{+1}$.

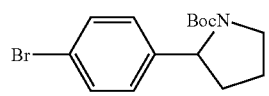

Intermediate 136

2-(4-Bromo-phenyl)-pyrrolidine-1-carboxylic acid tert-butyl ester 5-(4-Bromo-phenyl)-3,4-dihydro-2H-pyrrole (5.0 g, 22.3 mmol) is dissolved in MeOH (100 mL). The resulting solution is cooled to 0° C. in an ice bath. NaBH$_4$ (1.0 g, 26.3 mmol) is added to this solution slowly. After the mixture is stirred for 1 h, the MeOH is removed and the residue is suspended in CH$_2$Cl$_2$. At this point, (Boc)$_2$O (7.0 g, 32.1 mmol) is added. The resulting mixture is stirred for another 2 h and loaded on the column and purified to provide the Boc compound (3.5 g, 48%). $^1$H NMR (300 MHz, CDCl3) ∂7.39-7.44 (2H, m), 7.03-7.06 (2H, m), 4.72-4.88 (1H, m), 3.58 (2H, br), 2.28-2.30 (1H, m), 1.72-1.94 (3H, m), 1.45 (3H, br), 1.20 (6H, s).

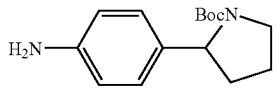

Intermediate 137

2-(4-Amino-phenyl)-pyrrolidine-1-carboxylic acid tert-butyl ester

LiHMDS (1.6 g, 9.6 mmol) is added to a 100 mL round bottom flask. Toluene (20 mL) is added followed by addition of $Pd_2(dba)_3 \cdot CHCl_3$ (50 mg, 0.05 mmol) and $P(tBu)_3 \cdot HBF_4$ (40 mg, 0.14 mmol). 2-(4-Bromo-phenyl)-pyrrolidine-1-carboxylic acid tert-butyl ester (1.5 g, 4.6 mmol) is added to the flask. After degasing, the mixture is stirred at room temperature overnight. After TLC suggested no starting bromide is left, the reaction mixture is diluted with ether and poured into dilute HCl (aq). The ether layer is discarded, the aqueous layer is basified with $NH_4OH$ and extracted with EtOAc. The EtOAc layer is dried and concentrated to provide the desired product (1.0 g, 83%). $^1$H NMR (300 MHz, $CDCl_3$) ∂ 6.94-6.96 (2H, m), 6.60-6.67 (2H, m), 4.67-4.85 (1H, m), 3.58 (4H, br), 2.24 (1H, m), 1.73-1.97 (3H, m), 1.44 (3H, s), 1.21 (6H, s).

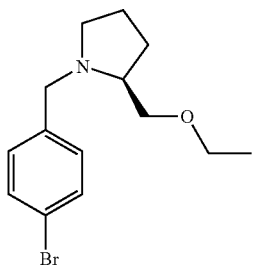

Intermediate 138

1-(4-Bromo-benzyl)-2-ethoxymethyl-pyrrolidine

[1-(4-Bromo-benzyl)-pyrrolidin-2-yl]-methanol (269 mg, 1.0 mmol) and EtI (234 mg, 1.5 mmol) is mixed at 0° C. in DMF (DMF) (10 mL). To this mixture is then added NaH (60 mg, 60% suspension in mineral oil, 1.5 mmol). The resulting mixture is stirred at room temperature for 1 h before aqueous workup. The resulting residue is directly used in the next step.

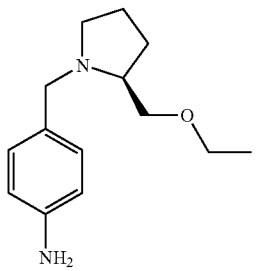

Intermediate 139

4-(2-Ethoxymethyl-pyrrolidin-1-ylmethyl)-phenylamine

Using the same procedure described for the preparation of 2-(4-Amino-phenyl)-pyrrolidine-1-carboxylic acid tert-butyl ester, the title compound is prepared from 1-(4-Bromo-benzyl)-2-ethoxymethyl-pyrrolidine (using the crude product obtained in the previous step) in 47% yield (two steps, based on crude residue, ~85%).

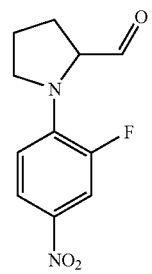

Intermediate 140

1-(2-Fluoro-4-nitro-phenyl)-pyrrolidine-2-carbaldehyde

[1-(2-Fluoro-4-nitro-phenyl)-pyrrolidin-2-yl]-methanol (100 mg, 0.42 mmol) and Dess-Martin periodate (175 mg, 0.42 mmol) is stirred in $CH_2Cl_2$ overnight. After chromatography, the desired product is isolated (100 mg, ~100%): $^1$H NMR (300 MHz, CDCl3) ∂9.67 (1H, s), 7.85-7.98 (2H, m), 6.66 (1H, t, J=9.0 Hz), 4.65-4.72 (1H, m), 3.49-3.75 (2H, m), 1.89-2.30 (4H, m).

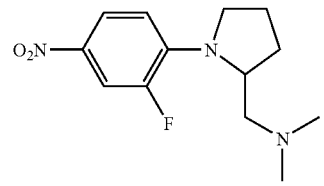

Intermediate 141

[1-(2-Fluoro-4-nitro-phenyl)-pyrrolidin-2-ylmethyl]-dimethyl-amine 1-(2-Fluoro-4-nitro-phenyl)-pyrrolidine-2-carbaldehyde (100 mg, 0.42 mmol) and dimethylamine (large excess) is stirred at room temperature in $CH_2Cl_2$ for 5 min and $NaBH(OAc)_3$ (120 mg, 0.57 mmol) is added. The reaction is stopped after 30 min as TLC suggested complete conversion and the-desired product (77 mg, 69%) is isolated after chromatography.

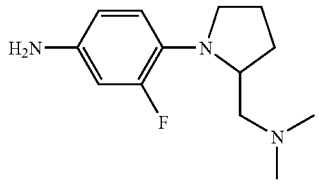

Intermediate 142

4-(2-Dimethylaminomethyl-pyrrolidin-1-yl)-3-fluoro-phenylamine

[1-(2-Fluoro-4-nitro-phenyl)-pyrrolidin-2-ylmethyl]-dimethyl-amine (77 mg, 0.29 mmol) and Pd/C (16 mg, 10% weight) is shaken under $H_2$ (50 psi) in MeOH overnight. After filtrating the Pd/C, the MeOH is removed and the residue obtained (65 mg, 95%) is directly employed in the next step.

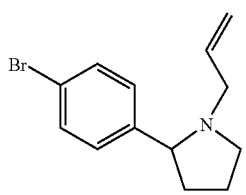

Intermediate 143

1-Allyl-2-(4-bromo-phenyl)-pyrrolidine 2-(4-Bromo-phenyl)-pyrrolidine (640 mg, 2.83 mmol) and allyl bromide (343 mg, 2.83 mmol) is mixed in THF (15 mL) and $K_2CO_3$ (390 mg, 2.83 mmol) is then added. The mixture is heated at reflux for 2 h before THF is removed under reduced pressure and the residue is partitioned between EtOAc and $H_2O$. The EtOAc layer is dried and concentrated and the residue is then subjected to chromatography to provide the desired product (470 mg, 62.4%).

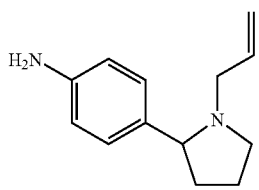

Intermediate 144

4-(1-Allyl-pyrrolidin-2-yl)-phenylamine

Using the same procedure described for the preparation of 2-(4-Amino-phenyl)-pyrrolidine-1-carboxylic acid tert-butyl ester, the title compound is prepared from 1-Allyl-2-(4-bromo-phenyl)-pyrrolidine (470 mg, 1.77 mmol) in 87% yield.

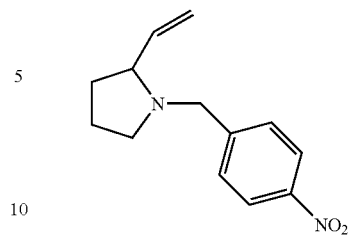

Intermediate 145

1-(4-Nitro-benzyl)-2-vinyl-pyrrolidine

2-Vinyl-pyrrolidine-1-carboxylic acid tert-butyl ester (300 mg, 1.52 mmol) is dissolved in $CH_2Cl_2$ (4 mL) to which TFA (0.55 mL) is added dropwisely. The resulting mixture is stirred until TLC showed no starting material. All the volatiles were removed under vacuum. $CH_3CN$ (5 mL) is added followed by 4-nitrobenzylbromide (400 mg, 1.85 mmol) and $K_2CO_3$ (1 g, 7.2 mmol). The mixture is stirred until TLC suggested no starting material left. EtOAc and H2O were added and the EtOAc layer is washed with brine and dried. After evaporating the EtOAc, the residue is purified with flash chromatography to provide the desired product (300 mg, 85%).

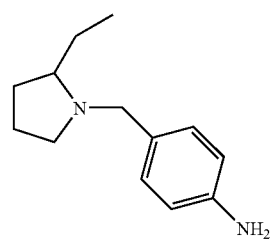

Intermediate 146

4-(2-Ethyl-pyrrolidin-1-ylmethyl)-phenylamine

Using the same procedure described for the preparation of 2-(4-Amino-phenyl)-pyrrolidine-1-carboxylic acid tert-butyl ester, the title compound is prepared from 1-(4-Nitro-benzyl)-2-vinyl-pyrrolidine (220 mg, 0.95 mmol) in 44% yield.

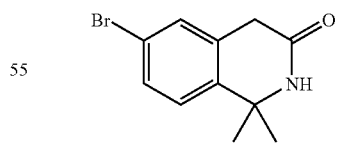

Intermediate 147

6-Bromo-1,1-dimethyl-1,4-dihydro-2H-isoquinolin-3-one

PPA (100 g) is heated to 140° C. (3-Bromo-phenyl)-acetonitrile (10 g, 5.1 mmol) is added. After stirring for 5 minutes, acetone (6 g, 0.1 mol) is added. The mixture is stirred for 1 hour at 140° C. The viscous mixture is poured into ice H₂O and extracted with chloroform. The chloroform layer is washed with H₂O and NaHCO₃, brine and dried. After evaporating the solvent, the crude product obtained is directly used in the next step.

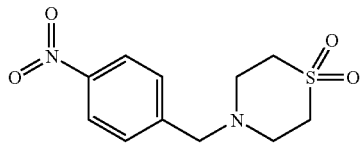

Intermediate 148

4-(4-Nitro-benzyl)-thiomorpholine 1,1-dioxide

To a flask containing thiomorpholine 1,1-dioxide hydrochloride (0.65 g, 3.8 mmol) in CH₃CN is added 4-nitrobenzylbromide (1.1 g, 5.1 mmol) and K₂CO₃ (1.9 g, 13.7 mmol). The mixture is then allowed to stir at room temperature overnight. After aqueous work up, the product is obtained through chromatography. MS (ESI): 271.1 (M+1)$^{+1}$

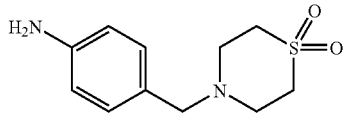

Intermediate 149

4-(4-Amino-benzyl)-thiomorpholine 1,1-dioxide 4-(4-Nitro-benzyl)-thiomorpholine 1,1-dioxide (110 mg, 0.41 mmol) is dissolved in MeOH (7 mL). To this solution is added FeCl₃.6H₂O (~20 mg, 0.07 mmol) and active Charcoal (12 mg, 1.0 mmol). The suspension is heated to reflux. Hydrazine hydrate (0.5 mL) is added, and reflux is continued for 4 h until full conversion, the active Charcoal is filtered off through Celite, and the MeOH is removed under reduced pressure. The residue (85 mg, 86%) is directly used in the next step.

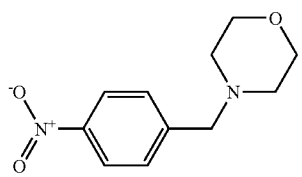

Intermediate 150

4-(N-Nitro-benzyl)-morpholine

An amount of 10 g (46.30 mmol) of 1-bromomethyl-4-nitro-benzene is stirred in dichloromethane (125 mL), followed by addition of triethylamine (12.90 mL, 92.6 mmol), and morpholine (4.03 g, 46.30 mmol). The reaction mixture is refluxed for 1 h, subsequently washed 3 times with aqueous sodium bicarbonate, dried over sodium sulfate, followed by evaporation to dryness, to give white crystals (7.5 g, 73%).

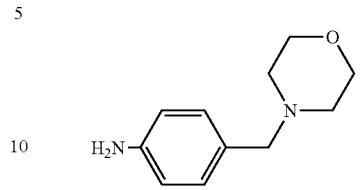

Intermediate 151

4-Morpholin-4-ylmethyl-phenylamine

Seven grams (31.52 mmol) of 4-N-nitrobenzyl-morpholine, ammonium chloride (15.14 g, 283.68 mmol), and iron (10.56 g, 189.12 mmol) were added to 266 mL of methanol/water (4.75:1) and refluxed until there is no appearance of starting materials. After filtering through celite, the solvent is evaporated. The residue is dissolved in water, basified with potassium carbonate, and extracted three times with ethyl acetate. The organic solution is dried with magnesium sulfate, and evaporated to afford 6 g (99% yield) of orange solid.

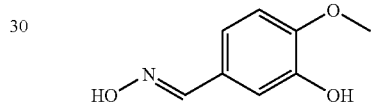

Intermediate 152

3-hydroxy-4-methoxy-benzylaldehyde oxime

An amount of 1.52 g (10.0 mmol) of 3-hydroxy-4-methoxy-benzylaldehyde is added to ethanol (20 ml), and pyridine (10 ml) at room temperature followed by addition of hydroxylamine hydrogen chloride (764.39 mg, 11.0 mmol). The mixture is stirred at ambient temperature for 24 h, and 200 mL of water is added. After the solvents were evaporated, the residue is dissolved 400 mL of anhydrous ether, washed successively with 100 mL of aqueous sodium bicarbonate, 100 mL of sodium bisulfite, and 100 mL of brine, dried over magnesium sulfate, and evaporated to give a white solid 1.39 g (83% yield).

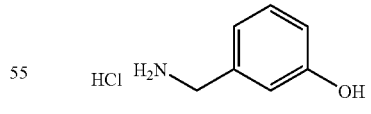

Intermediate 153

3-hydroxy-benzylamine hydrogen chloride

An amount of 2 g (16.79 mmol) of 3-cyanophenol is dissolved in tetrahydrofuran (40 mL). After cooling to 0° C., borane tetrahydrofuran complex (32.0 mL, 2.0 M) is added dropwise to the solution. Allowed to stir at 0° C. for 15 min, then at room temperature for 25 min. After refluxing for 3 h, it is cooled to room temperature and evaporated to dryness. Methanol (14 mL) is added, and evaporated to dryness. Concentrated hydrogen chloride (155 mL) is added, and evaporated to dryness. The residue is recrystallized from ethyl acetate to give 3 g of the product as a white solid. MS (ESI) m/z 123.15 (M+1).

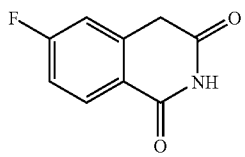

Intermediate 154

6-fluoroisoquinoline-1,3(2H,4H)-dione

An amount of 200 mg (1.01 mmol) of 2-carboxymethyl-4-fluoro-benzoic acid and urea (72.47 mg, 1.22 mmol) were heated neat at 180-190° C. for 45 min. The mixture is cooled to room temperature followed by recrystallization from water and anhydrous ether to give 175 mg (80% yield) of brown solid. MS (ESI) m/z 179.15 (M+1).

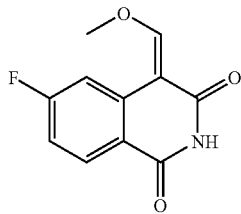

Intermediate 155

(4E)-6-fluoro-4-(methoxymethylene)isoquinoline-1,3(2H,4H)-dione

An amount 2 g (11.16 mmol) of 6-fluoro-isoquinoline-(4H)-1,3-dione is dissolved in N,N-dimethylformate and acetic anhydride (1:4) followed by addition of trimethyl orthoformate (2.37 mL, 22.32 mmol). After the mixture is heated at 120° C. for 1 h, it is cooled. The yellow precipitate is collected and washed several times with anhydrous ether to give 2.3 g (94% yield) of yellow solid. MS (ESI) m/z 221.19 (M+1).

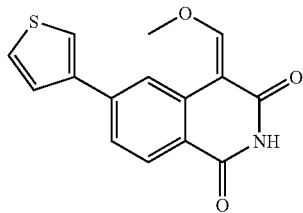

Intermediate 156

(4E)-4-(methoxymethylene)-6-(1H-thiophin-3-yl)isoquinoline-1,3(2H,4H)-dione

To a mixture of 4 g (13.93 mmol) of 4-bromo-2-methoxycarbonylmethyl-benzoic acid-methyl ester, Pd$_2$(dba)$_3$ (446 mg, 0.49 mmol), P$_2$(t-Bu)$_2$ (299 mg, 1.07 mmol), Cs$_2$CO$_3$ (9.07 mg, 27.66 mmol) and 3-thiophine boronic acid (2.67 g, 20.90 mmol) is added dioxane (20 mL) under N$_2$. The mixtures were placed in a pre-heated oil bath 80° C. for 4 hours. After cooling, the mixtures were filtered through celite and washed with ethyl acetate, extraction with aqueous NaHCO$_3$ followed by drying with NaSO$_4$ and evaporation. The resulting yellow oil is crystallized. The crystal is collected and washed with anhydrous ether to give 2.6 g (70%) of 2-methoxycarbonylmethyl-4-thiophine-3-yl-benzoic acid methyl ester as a brown solid.

2-methoxycarbonylmethyl-4-thiophine-3-yl-benzoic acid methyl ester (2.4 g, 8.27 mmol) is added to 2.2 M solution of sodium hydroxide in water (10 mL) at room temperature and stirred overnight. After adjusting the pH to 4, 2.0 g of 2-carboxymethyl-4-thiophin-3-ylbenzoic acid is isolated as a yellow solid.

Using the procedure described for the preparation of 6-fluoroisoquinoline-1,3(2H,4H)-dione, 1.3 g (80% yield) of 6-thiophin-3-yl-isoquinoline-(4H)-1,3-dione as a brown solid is obtained from 1.6 g (6.11 mmol) of 2-carboxymethyl-4-thiophin-3-ylbenzoic acid is used.

Using the procedure described for the preparation of (4E)-6-fluoro-4-(methoxymethylene)isoquinoline-1,3(2H,4H)-dione, 1.2 g (95% yield) of 4-methoxymethylene-6-thiophin-3-yl-isoquinolin-(4H)-1,3-dione as green-yellow solid is obtained from 1.10 g (4.11 mmol) of 6-thiophin-3-yl-isoquinoline-(4H)-1,3-dione.

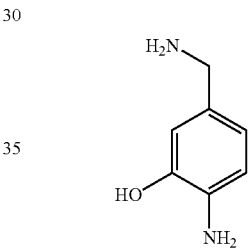

Intermediate 157

2-Amino-5-(aminomethyl)phenol

Using the procedure described for the preparation of (4E)-6,7-dimethoxy-4-(methoxymethylene)isoquinoline-1,3(2H,4H)-dione and 3-hydroxy-4-methoxy-benzylamine hydrogen chloride, 2.5 g (89% yield) of purple solid is obtained from 2.2 g (16.1 mmol) of 3-hydroxy-4-nitrobenzaldehyde O-methyloxime; MS (ESI) m/z 138.9 (M+H)$^+$.

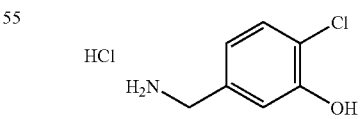

Intermediate 158

5-Aminomethyl-2-chloro-phenol hydrogen chloride

An amount of 1 g (5.57 mmol) of 4-chloro-3-hydroxy benzoic acid is added 10 ml (115.8 mmol) of oxalyl chloride and refluxed at 60° C. till the solid had gone into solution. After cooling, the mixture is evaporated to dryness to give 4-chloro-3-hydroxy-benzoyl chloride.

4-Chloro-3-hydroxy-benzoyl chloride is cooled to 0° C. and 20 ml of ammonium hydroxide were added within 5 minutes. The mixture is allowed to stir at 0° C. for 30 minutes, then at room temperature for additional 30 minutes. 30 ml of water is added to the mixture and the white precipitate is filtered, the pH of the water layer is adjusted to 3, followed by extraction with ethyl acetate, dried over MgSO$_4$ to give 4-chloro-3-hydroxy-benzamide as a white solid 850 mg (86% yield).

Using the procedure described for the preparation of 450 mg (50% yield) of 5-Aminomethyl-2-chloro-phenol hydrogen chloride as white solid is obtained from 850 mg (4.95 mmol) of 4-chloro-3-hydroxy-benzamide and borane tetrahydrofuran complex (25 ml, 2.0 M).

Intermediate 159

N-(1,3-dioxo-1,2,3,4-tetrahydroisoquinolin-6-yl) acetamide

Using the procedure described for the preparation of 4-Chloromethyl-2-methoxy-biphenyl, 450 mg (73% yield) of green solid is obtained from 500 mg (2.8 mmol) of 6-aminoisoquinoline-1,3(2H,4H)-dione, and acetyl chloride 1.1 ml (14.2 mmol), substituting dimethylacetamide as a solvent in place of N,N-dimethylformamide. Base is excluded; MS (ESI) m/z 217.1 (M−1).

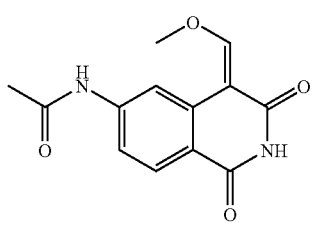

Intermediate 160

(4E)-6-acetamide-4-(methoxymethylene)isoquinoline-1,3(2H,4H)-dione

Using the procedure described for the preparation of (4E)-6-fluoro-4-(methoxymethylene)isoquinoline-1,3(2H,4H)-dione, 410 mg (73% yield) of yellow solid is obtained from 450 mg (1.72 mmol) of N-(1,3-dioxo-1,2,3,4-tetrahydroisoquinolin-6-yl)acetamide.

MS (ESI) m/z 261.1 (M+1)$^+$.

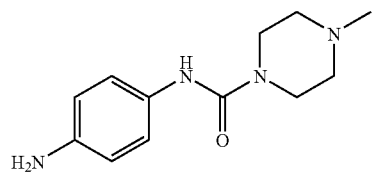

Intermediate 161

Using the procedure described for the preparation of 4-{[4 (4-methyl-piperazin-1-yl)-phenylamino]-methylene}-1,3-dioxo-1,2,3,4-tetrahyro-isoquinolin-6-yl)-carbamic acid 4-nitro-phenyl ester 5 g (26.0 mmol) of para-nitroanilin and 4-nitrophenyl chloroformate 14.6 g (72.4 mmol) were reacted to give (4-nitro-phenyl)-carbamic acid 4-nitro-phenyl ester, 11.0 g (100% yield) of yellow solid.

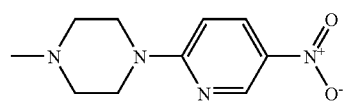

Intermediate 162

1-Methyl-4-(5-nitro-pyridin-2-yl)-piperazine

An amount of 2 g (9.85 mmol) of 2-bromo-5-nitro-pyridin is stirred in dichloromethane (50 mL), followed by addition of 1-methylpiperazine (10.9 mL, 98.5 mmol). The reaction mixture is refluxed for 1 h. After cooling, the mixture is extracted 3× with sodium bicarbonate, followed by additional washing with brine, dried over sodium sulfate, evaporated, to afford 2 g (91% yield) of yellow crystals; mp 75-76° C.

MS (ESI) m/z 223.1 (M+1)$^+$.

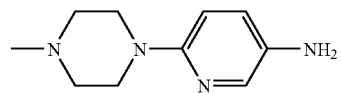

Intermediate 163

'6-(4-methylpiperazin-1-yl)pyridin-3-amine

An amount of 1 g (4.48 mmol) of 1-Methyl-4-(5-nitropyridin-2-yl)-piperazine is dissolved in methanol (50 mL), followed by a catalytic amount of 10% Pd/C. The mixture is hydrogenated at 35-40 psi for 3 hours, filtrated through celite followed by evaporation to give 900 mg (100% yield) of purple solid; mp 97-98° C. MS (ESI) m/z 193.1 (M+1)$^+$.

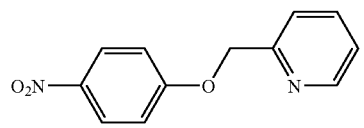

Intermediate 164

'2-[(4-nitrophenoxy)methyl]pyridine

An amount of 1.36 mL (14.14 mmol) of pyridin-2-yl-methanol is dissolved in N,N-dimethylformamide (10 mL) and cooled to 0° C., addition of 678.72 mg (28.28 mmol) of sodium hydride followed. The reaction mixture is kept at 0° C. for 1.5 hours. 1-Fluoro-4-nitrobenzene 1.5 mL (14.14 mmol) is subsequent added and stirred at room temperature overnight. 100 mL of water is added to the mixture and stirred for 10 more mins. The precipitate is filtered and washed many times with water. The white solid is re-dissolved in methylene chloride extracted three times with brine, dried over darko and magnesium sulfate, and evaporated to give the desired product as a white solid 2.7 g (85% yield); mp: 116-117° C.

MS (ESI) m/z 231.1 (M+1)⁺.

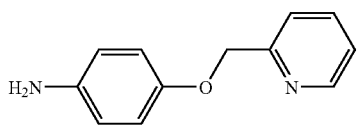

Intermediate 165

'[4-(pyridin-2-ylmethoxy)phenyl]amine

Using the procedure described for the preparation of 4-Morpholin-4-ylmethyl-phenylamine, 1.16 g (100%) of white crystals is obtained from 1.5 g (5.55 mmol) of '2-[(4-nitrophenoxy)methyl]pyridine; mp 50-51° C. MS (ESI) m/z 201.1 (M+1)⁺.

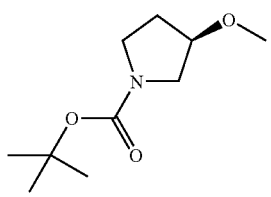

Intermediate 166

Tert-butyl-(3R)-3-methoxypyrrolidin-1-yl carboxylate

An amount of 10.0 g (53.41 mmol) of tert-butyl-(3R)-3-pyrrolidinol-1-carboxylate is dissolved in Tetrahydrofurane (200 mL) and cooled to 0° C., sodium hydride 1.92 g (80.12 mmol) is added and the reaction mixture is kept at 0° C. for 1.5 hours. Methyl iodine 5 mL (80.12 mmol) is subsequently added and stirred at room temperature overnight. The solvent (tetrahydrofuran) is evaporated and the oil is re-dissolved in ethyl acetate and extracted three times with brine, dried over darko and magnesium sulfate, evaporated to give the first intermediate as a light-yellow oil 10.65 g (99% yield).

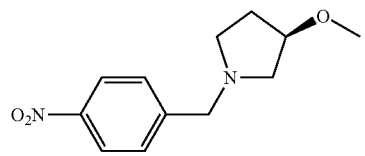

Intermediate 167

3-Methoxy-1-(4-nitrobenzyl)-pyrrolidine

An amount of 1.8 g (9.02 mmol) of tert-butyl-(3R)-3-methoxypyrrolidin-1-yl carboxylate is stirred in concentrated hydrogen chloride (10 mL) for two hours. Anhydrous ether (100 mL) is added and stirred for additional 30 minutes. The ether is decanted and this is repeated three times. The mixture is neutralized with excess triethylamine and after evaporating to dryness, the mixture is re-dissolved in methylene chloride (100 mL) and 1.5 g (6.94 mmol) of 4-nitrobenzylbromide is added and refluxed for two hours. After cooling, the mixture is washed three times with aqueous sodium bicarbonate, dried over magnesium sulfate and evaporated to give 1.1 g (67% yield) of the nitro intermediates as a yellow oil.

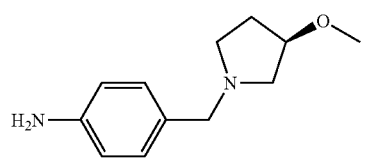

Intermediate 168

4-{[(3R)-3-methoxypyrrolidin-1-yl]methyl}phenyl) amine

Using the procedure described for the preparation of (4-Morpholin-4-ylmethyl-phenylamine) 910 mg (95% yield) is obtained as a dark yellow oil from 1.1 g (4.66 mmol) of 3-Methoxy-1-(4-nitro-benzyl)-pyrrolidine. MS (ESI) m/z 207.1 (M+1)⁺.

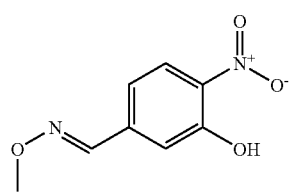

Intermediate 169

3-hydroxy-4-nitrobenzaldehyde O-methyloxime

Using the procedure described for the preparation of intermediate 168 4.38 g (94% yield) is obtained as a yellow solid from 4.0 g (23.93 mmol) of 3-hydroxy-4-nitrobenzylaldehyde; MS (ESI) m/z 196.0 (M−1).

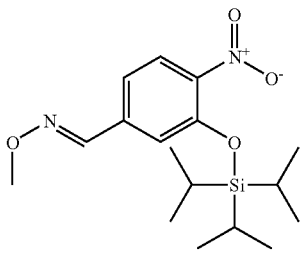

Intermediate 170

4-nitro-3-[(triisopropylsilyl)oxy]benzaldehyde O-methyloxime

An amount of 3.0 g (15.39 mmol) of 3-hydroxy-4-nitrobenzaldehyde O-methyloxime is stirred in N,N-dimethylformamide (8 mL), followed by addition of imidazole (3.14 g, 46.17 mmol) and 4.89 mL (23.1 mmol) of triisopropylsilyl chloride. The reaction mixture is stirred at room temperature over night. 1:1 ethyl acetate: ether (300 mL) is added and extracted 3× with water, followed by additional washing with brine, dried over magnesium sulfate, evaporated, to afford 5.02 g (93% yield) as a yellow crystals.

MS (ESI) m/z 353.1 (M+1)$^+$.

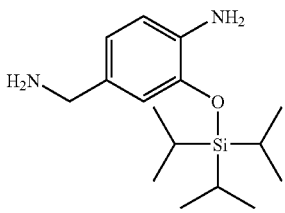

Intermediate 171

{4-(aminomethyl)-2-[(triisopropylsilyl)oxy]phenyl}amine

Using the procedure described for the preparation of 3-hydroxy-4-methoxy-benzylamine hydrogen chloride, 3.0 g (88% yield) is obtained as a brown solid from 4.0 g (11.42 mmol) of 4-nitro-3-[(triisopropylsilyl)oxy]benzaldehyde O-methyloxime; MS (ESI) m/z 294.0 (M+1)$^+$.

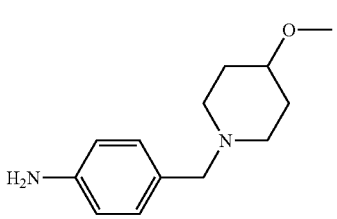

Intermediate 172

{4-[(4-methoxypiperidin-1-yl)methyl]phenyl}amine

Using the procedure described for the preparation of (4-Morpholin-4-ylmethyl-phenylamine), 1.8 g (95% yield) is obtained as a yellow oil from 2.2 g (8.79 mmol) 4-methoxy-1-(4-nitrobenzyl)piperidine. MS (ESI) m/z 221.1 (M+1)$^+$.

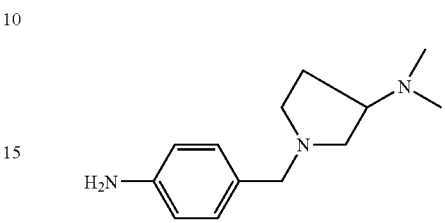

Intermediate 173

3-(dimethylamino)pyrrolidin-1-yl]methyl}phenyl)amine

Using the procedure described for the preparation of (4-Morpholin-4-ylmethyl-phenylamine), 1.8 g (85% yield) is obtained as a yellow oil from 2.0 g (8.03 mmol) 3-(dimethylamino)-1-(4-nitrobenzyl)pyrrolidine (L27615-85). MS (ESI) m/z 220.4(M+1)$^+$.

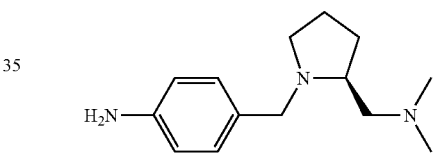

Intermediate 174

(2R)-2-[(dimethylamino)methyl]pyrrolidin-1-yl}methyl)phenyl]amine

An amount of 2.0 g (9.99 mmol) of (S)-2-(aminomethyl)-1-n-boc-pyrrolidine and formylaldehyde (2.4 g, 79.9 mmol) were dissolved in tetrahydrofuran (20 mL) and methanol (5 mL). After stirring for ten minutes, a mixture of sodium cyanoborohydride (5.1 g, 79.9 mmol) and acetic acid (4.6 mL, 79.9 mmol) in methanol (5 mL) is added drop-wise. The mixture is allowed to stir over night. The mixture is concentrated to dryness and using the procedure described for the preparation of 4-{[(3R)-3-methoxypyrrolidin-1-yl]methyl}phenyl)amine the desired product is obtain 200 (45% yield) as a yellow oil. MS (ESI) m/z 235.0 (M+1)$^+$.

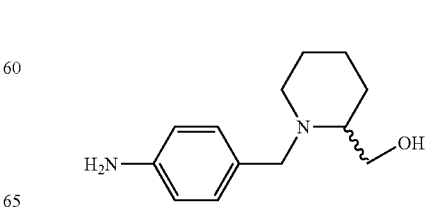

Intermediate 175

2-(hydroxymethyl)piperidin-1-yl]methyl}phenyl)amine

Using the procedure described for the preparation of (4-Morpholin-4-ylmethyl-phenylamine), 2.5 g (57% yield) is obtained as a yellow solid from 5.0 g (19.9 mmol) of 2-(hydroxymethyl)-1-(4-nitrobenzyl)piperadine (L27615-90). MS (ESI) m/z 220.4(M+1)⁺.

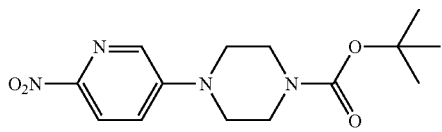

Intermediate 176 tert-butyl 4-(6-nitropyridin-3-yl)piperazine-1-carboxylate

A mixture of 3 g (14.78 mmol) of 5-bromo-2-nitropyridine, 5.5 g (29.56 mmol) of tert-butyl 1-piperazinecarboxylate, 5.46 g (14.78 mmol) of tetra-butylammonium iodine and 4.1 g (29.56 mmol) of potassium carbonate were placed in a flask. Dimethylsulfoxide (45 mL) is added and heat up to 80° C. for 24 hours. After cooling to room temperature, the precipitate is filtered and washed with ethyl acetate. Excess amount of water is added and extracted 4×. Dried with sodium sulfate and evaporated to give 2.7 g (59% yield) as a yellow solid. MS (ESI) m/z 309.1(M+1)

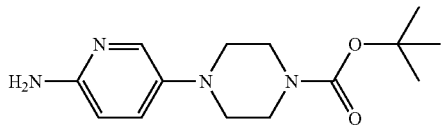

Intermediate 177 tert-butyl 4-(6-aminopyridin-3-yl)piperazine-1-carboxylate

An amount of 2 g (6.48 mmol) of, tert-butyl 4-(6-nitropyridin-3-yl)piperazine-1-carboxylate, 1.4 g (25.9 mmol) of iron, and acetic acid (3.1 mL, 48.6 mmol) were placed in a flask. Methanol (30 mL) is added and heat at 60° C. for 2 hours. After cooling to room temperature, the precipitate is filtered, the methanol is removed in a vacuum and saturated sodium bicarbonate is added. The mixture is extracted 3× with ethyl acetate. Dried over sodium sulfate, and evaporated to give 1.43 g (78% yield) as a purple solid. MS (ESI) m/z 279.1(M+1)⁺.

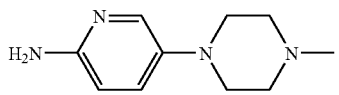

Intermediate 178

5-(4-methylpiperazin-1-yl)pyridin-2-yl]amine

Using the procedure described for the preparation of tert-butyl 4-(6-aminopyridin-3-yl)piperazine-1-carboxylate, 2.6 g (90% yield) is obtained as a purple solid from 3.4 g (15.3 mmol) of 1-Methyl-4-(2-nitro-pyridin-2-yl)-piperazine (L27615-112). MS (ESI) m/z 193.1(M+1)⁺.

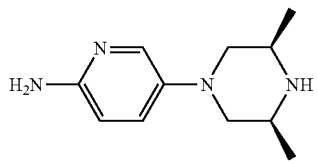

Intermediate 179

5-[(3R,5S)-3,5-dimethylpiperazin-1-yl]pyridin-2-yl}amine

Using the procedure described for the preparation of tert-butyl 4-(6-aminopyridin-3-yl)piperazine-1-carboxylate, 1.4 g (47% yield) is obtained as a orange solid from 3.4 g (12.8 mmol) of 5-(3R,5S)-3,5-dimethyl-1-(6-nitro-pyridin-3-yl)piperazine. MS (ESI) m/z 207.1 (M+1)⁺.

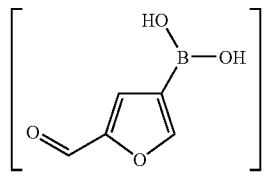

Intermediate 180

5-Formyl-2-furan boronic acid

An amount of 1.0 g (4.1 mmol) of 4-bromo-2-(diethoxymethyl)furan, is dissolved in ether (15 mL) and cooled to −78° C. To this is added 4.3 mL (6.02 mmol) of sec-butyllithium. After stirring at −78° C. for 30 minutes, triisopropyl borate (1.10 mL, 5.01 mmol) is added dropwise. The mixture is stirred at −78° C. for 1.5 hours and brought to room temperature for 2 hours. The mixture is hydrolyzed with 2N HCl and stirred at room temperature for 1 hour. The ether layer is separated and the water layer is washed once more with ether. The combined ether layers is washed once with brine and dried with sodium sulfate. Evaporated to give 563 mg of the boronic acid as dark oil.

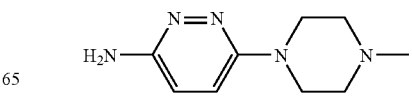

Intermediate 181

[6-(4-methylpiperazin-1-yl)pyridazin-3-yl]amine

An amount of 1.0 g (7.72 mmol) of 3-amino-6-chloropyridazine, 5-chloro pyridine hydrogen chloride (4.46 g, 38.6 mmol), and piperazine (5.1 mL, 72 mmol) were placed in a pre-heated oil bath at 165-170° C. for 4 hours. After cooling, the mixture is basified with saturated potassium carbonate, extracted 3× with ethyl acetate and dried over magnesium sulfate. The oily residue is purified by column chromatography to give a brown solid 800 mg (53% yield). MS (ESI) m/z 194.3 (M+1)+

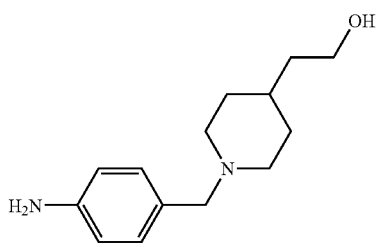

Intermediate 182

4-(2-hydroxyethyl)piperidin-1-yl]methyl}phenyl)amine

Using the procedure described for the preparation of (4-Morpholin-4-ylmethyl-phenylamine), 1.6 g (72% yield) is obtained as a yellow solid from 2.4 g (11.99 mmol) of 4-(2-hydroxyethyl)-1-(4-nitrobenzyl)piperadine (L27615-135). MS (ESI) m/z 234.3(M+1)+.

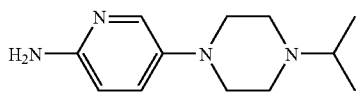

Intermediate 183

[5-(4-isopropylpiperazin-1-yl)pyridin-2-yl]amine

Using the procedure described for the preparation of tert-butyl 4-(6-aminopyridin-3-yl)piperazine-1-carboxylate, 750 mg (68% yield) is obtained as a brown solid from 1.2 g (4.7 mmol) of 4-isopropyl-1-(6-nitro-pyridin-2-yl)piperazine. MS (ESI) m/z 221.1(M+1)+.

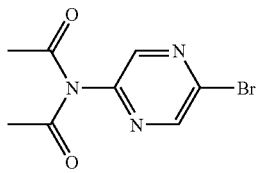

Intermediate 184

N-Acetyl-N-(bromo-phenyl)-acetamide

An amount of 3.0 g (17.24 mmol) of 2-amino-5-bromopyrazine is dissolved in N,N-dimethylformamide (20 mL) and cooled to 0° C. Sodium hydride (1.05 g, 43.09 mmol) is added and stirred at 0° C. for 10 minutes. Acetyl chloride (6.2 mL, 86.2 mmol) is added and stirred at room temperature for over night. The mixture is quenched with water and extracted 3× with ether. Dried over magnesium sulfate followed by column chromatography to give 1.35 g (31% yield) of yellow oil. MS (ESI) m/z 259.0 (M+1)+

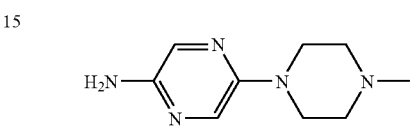

Intermediate 185

[5-(4-methylpiperazin-1-yl)pyrazin-2-yl]amine

Using the procedure described for the preparation of (4Z)-6-(4-fluorophenyl)-4-({[4-(piperidin-1-ylmethyl)phenyl]amino}methylene)isoquinoline-1,3(2H,4H)-dione 200 mg (20% yield) is obtained as a dark oil from 1.33 g (5.14 mmol) N-Acetyl-N-(bromo-phenyl)-acetamide and N-methylpiperazine 2.9 mL, (25.7 mmol).

The N-acetyl is cleaved with concentrated hydrogen chloride.

MS (ESI) m/z 195.1 (M+1)+

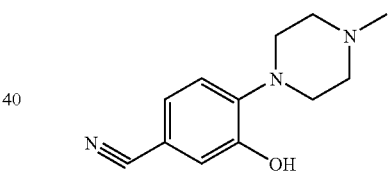

Intermediate 186

3-Methoxymethoxy-4-(4-methylpiperazin-1-yl)-benzonitrile

Using the procedure described for the preparation of tert-butyl 4-(6-aminopyridin-3-yl)piperazine-1-carboxylate except potassium t-butoxide is used as a base, 720 mg (46% yield) is obtained as a yellow oil from 1.5 g (5.2 mmol) of 4-iodo-3-methoxymethoxy benzonitrile and 1-methylpiperazine 1.73 mL, (15.6 mmol).

MS (ESI) m/z 263.1 (M+1)+

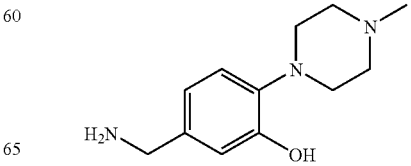

Intermediate 187

[3-hydroxy-4-(4-methylpiperazin-1-yl)benzyl]amine

The desired product is obtained when 3-Methoxymethoxy-4-(4-methylpiperazin-1-yl)-benzonitrile is treated with lithium aluminum hydride and concentrated hydrogen chloride.

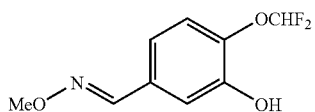

Intermediate 188

3-Hydroxy-4-difluoromethoxy-benzylaldehyde O-methyl-oxime

An amount of 734 mg (3.90 mmol) of 3-hydroxy-4-difluoromethoxy-benzaldehyde[3] is added to ethanol (9 ml), and pyridine (4.5 ml) at room temperature, followed by addition of hydroxylamine hydrogen chloride (669 mg, 8.01 mmol). The mixture is stirred at ambient temperature for 24 h, and 150 mL of water is added. After the solvents were evaporated, the residue is dissolved 400 mL of anhydrous ether, washed successively with 100 mL of aqueous sodium bicarbonate, 100 mL of sodium bisulfite, and 100 mL of brine. Dried over magnesium sulfate, evaporated, chromatographed with 10:1 hexanes/ethyl acetate to give the oxime as a white solid 0.169 mg (20% yield), m.p. 78-9° C., MS (ES−): m/z 216.0 (M−H).

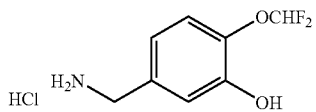

Intermediate 189

3-Hydroxy-4-difluoromethoxy-benzylamine hydrochloride

An amount of 500 mg (3.0 mmol) of 3-hydroxy-4-difluoromethoxy-benzylaldehyde O-methyl-oxime is dissolved in ethanol (50 mL). Then hydrochloric acid (2 mL) is added, followed by 10% Pd/C (200 mg). After hydrogenation at 45 psi for 2 h, the solution is filtered through Celite and evaporated to dryness. The residue is triturated with ether to give 419 mg (62%)$_g$ of hydrochloride salt as a white solid; mp 195-196° C. dec, MS (ES+): m/z 190.2 (M+H).

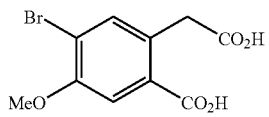

Intermediate 190

2-Carboxymethyl-4-bromo-5-methoxy-benzoic Acid

To a mixture of 5-bromo-6-methoxy-indan-1,2-dione 2-oxime (20.0 g, 74.0 mmole) and 160 mL of tetrahydrofuran is added lithium bis(trimethydisilyl)amide (74.0 mL of 1 M in hexanes, 74.0 mmole) and stirred. After stirring for 30 minutes p-toluenesulfonyl chloride (14.1 g, 74.0 mmole) is added. After 30 mins a solution of potassium hydroxide (25.0 g, 0.44 mole in 200 mL water) is added and stirred for 1 hour. The tetrahydrofuran is removed and the mixture refluxed overnight, cooled, acidified with 2 N hydrochloric acid and the solid collected, washed with water and dried, 8.45 g (34%), MS (ES−): m/z 287.1, 289.1 (M−H).

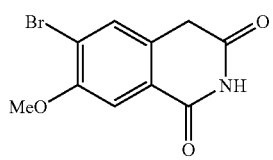

Intermediate 191

6-bromo-7-methoxy-isoquinoline-1,3(2H,4H)-dione

2-Carboxymethyl-4-bromo-5-methoxy-benzoic acid (228 mg, 0.785 mmole) and urea (0.110 g, 1.82 mmole) is stirred and heated using an oil bath at 195° C. After one hour the mixture is cooled to room temperature and treated with water, collected by filtration, washed with water and dried to give a brown-black solid, 106 mg, (50%); MS (ES−): m/z 268.1, 270.1 (M−H).

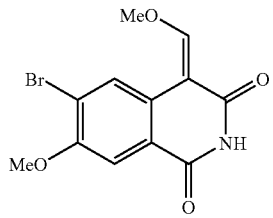

Intermediate 192

(4E)-6-bromo-7-methoxy-4-(methoxymethylene) isoquinoline-1,3(2H,4H)-dione

A mixture of 6-Bromo-7-methoxy-4H-isoquinoline-1,3-dione (275 mg, 1.02 mmole), 7 mL of a 4:1 mixture of acetic anhydride and N,N-dimethylformamide and trimethylorthoformate (0.8 mL, 7.28 mmole) is stirred and heated to reflux. After 30 minutes the solvents are removed and the solid collected with ether. A brown solid, 202 mg, (63%), mp 245-248° C. dec, MS (ESI): m/z 310.1, 312.1 (M−H).

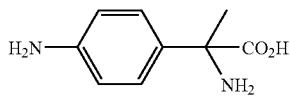

Intermediate 193

2-Amino-2-(4-amino-phenyl)-propionic acid

A mixture of 5-(4-Amino-phenyl)-5-methyl-imidazolidine-2,4-dione[2] (3.0 g, 14.6 mmole), 6N hydrochloric acid is stirred and refluxed for 6 hours, cooled, evaporated. The residue is treated with water and the pH adjusted to 6 and the light yellow solid collected by filtration, washed with water and dried, 1.47 g (55%), mp 120-155° C. dec; MS (ES+): m/z 181.2 (M+H).

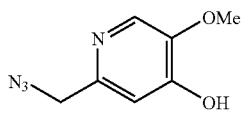

Intermediate 194

2-Azidomethyl-5-methoxy-pyridin-4-ol

To a suspension of sodium azide (1.30 g, 20.0 mmole) in 12 mL of N,N-dimethylformamide is added 2-chloromethyl-5-methoxy-pyridin-4-ol[1] (3.47 g, 20.0 mmole). This is stirred for overnight at ambient temperature then quenched into ice water. The solid formed is filtered, washed with cold water dried to give a light brown solid, 1.53 g, (42%), mp 111-4° C. dec; MS (ES–): m/z 179.3 (M–H).

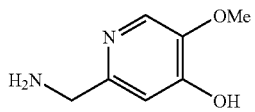

Intermediate 195

2-Aminomethyl-5-methoxy-pyridin-4-ol

A mixture of 2-azidomethyl-5-methoxy-pyridin-4-ol (1.45 g, 8.05 mole), is then suspended in 20 mL of tetrahydrofuran and treated with triphenylphosphine (2.11 g, 8.05 mmole) after stirring for 10 mins at ambient temperature water is added (1.76 mL, 15 equivalents) and the reaction mixture is stirred at ambient temperature overnight. The solids gradually dissolved followed by the formation of a precipitate. The resulting solid is filtered, washed with fresh 10:1 tetrahydrofuran:water and dried to give, 0.897 g, (88%), mp 196-201° C. dec; MS (ES+): m/z 155.3 (M+H).

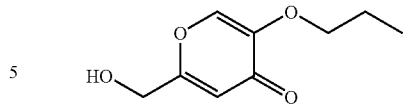

Intermediate 196

2-Hydroxymethyl-5-propoxy-pyran-4-one

A mixture of kojic acid (28.4 g, 0.20 mole), 120 mL of N,N-dimethylformamide, potassium carbonate powder (27.6 g, 0.20 mole), potassium iodide (1.66 g, 0.01 mole), and 1-bromopropane (24.6 g, 0.20 mole) is stirred for 15 minutes at ambient temperature then stirred at 90° C. for 3 hours. The reaction mixture is cooled, evaporated to dryness in vacuo and then portioned between water and chloroform. The aqueous layer is extracted with chloroform (3×100 mL) and ethyl acetate (6×100 mL). The combined organics were dried with sodium sulfate and passed through a pad of magnesol and silica gel eluting with ethyl acetate. The eluate is evaporated in vacuo and crystallized with hexane/ethyl acetate (2/1) to give an off-white solid, 22.60 g, (61%); MS (ES+): m/z 185.3 (M+H).

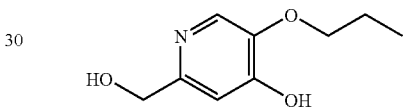

Intermediate 197

2-Hydroxymethyl-5-propoxy-pyridin-4-ol

A mixture of 2-hydroxymethyl-5-propoxy-pyran-4-one (30.0 g, 0.163 mole), 150 mL ammonium hydroxide is stirred and heated in a sealed vessel at 90° C. for 2 hours. The reaction mixture is cooled, evaporated to dryness in-vacuo, taken up in 15% methanol in chloroform and passed thru a pad of magnesol and silica gel eluting with the same solvent. The eluate is evaporated, treated with acetone, filtered, washed with acetone and air dried to give a-grey solid, 8.03 g, (80%), m.p. 159-60° C.; MS (ES+): m/z 184.3 (M+H).

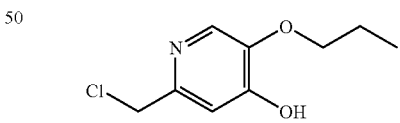

Intermediate 198

2-Chloromethyl-5-propoxy-pyridin-4-ol

To a mixture of 2-hydroxymethyl-5-propoxy-pyridin-4-ol (5.56 g, 30.3 mmole) and 30 mL of chloroform stirred cooled with an ice bath is added 30 mL of thionyl chloride (x g, 0.x mole). This is stirred for 15 minutes at ice bath temperature and then refluxed for 1 hour. The reaction mixture is cooled, evaporated to dryness in vacuo and then treated with isopropanol. The solid is filtered, washed with fresh isopropanol, then ether and air dried to give an off-white solid, 3.4 g, (48%), m.p. 165-7° C.; MS (ES+): m/z 202.3 (M+H).

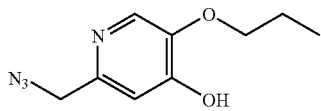

Intermediate 199

2-Azidomethyl-5-propoxy-pyridin-4-ol

To a suspension of sodium azide (2.82 g, 43.3 mmole) in 30 mL of N,N-dimethylformamide is added 2-chloromethyl-5-propoxy-pyridin-4-ol (8.74 g, 43.3 mmole). This is stirred for overnight at ambient temperature then quenched into ice water. The solid formed is filtered, washed with cold water and dried to give an off white solid, 5.74 g, (63%); MS (ES+): m/z 209.3 (M+H).

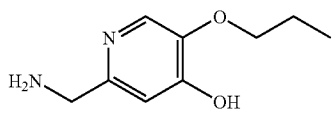

Intermediate 200

2-Aminomethyl-5-propoxy-pyridin-4-ol

A mixture of 2-azidomethyl-5-propoxy-pyridin-4-ol (9.70 g, 46.6 mole), is then suspended in 120 mL of tetrahydrofuran and treated with triphenylphosphine (12.22 g, 46.6 mmole) after stirring for 10 mins at ambient temperature water is added (12.6 mL, 15 equivalents) and the reaction mixture is stirred at ambient temperature overnight. The solids gradually dissolved followed by the formation of a precipitate. The resulting solid is filtered, washed with fresh 10:1 tetrahydrofuran:water and dried to give, 5.92 g, (69%), mp 159-60° C.; MS (ES+): m/z 183.3 (M+H).

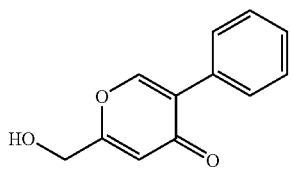

Intermediate 201

2-Hydroxymethyl-5-phenyl-pyran-4-one

A mixture of 2-(tert-butyl-dimethyl-silanyloxymethyl)-5-phenyl-pyran-4-one[1] (791 mg, 2.5 mmole), tetrahydrofuran (7.5 mL) and tetrabutylammonium fluoride 1M solution in tetrahydrofuran (7.5 mL, 7.5 mmole) is stirred at room temperature overnight. The reaction mixture is diluted with water and extracted with ethyl acetate. The combined ethyl acetate layers were combined and washed with water, dried over sodium sulfate, filtered, diluted with an equal volume of hexanes and passed thru a short column of magnesol and silica gel eluting with 1:1 hexanes/ethyl acetate. The product is eluted with 2:1 ethyl acetate/hexanes, the solvents were evaporated, the resulting residue is triturated with 1:1 hexanes/ethyl acetate, filtered, washed with the same solvent and air dried to give an off white solid, 404 mg, (80%); MS (ES+): m/z 203.3 (M+H). (T. Kamino, et. al.; Tet. Lett. 44 (2003) 7349)

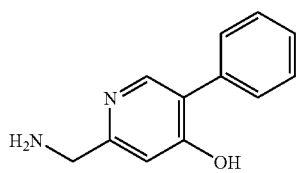

Intermediate 202

2-Aminomethyl-5-phenyl-pyridin-4-ol

To a mixture of 2-hydroxymethyl-5-phenyl-pyridin-4-ol (0.40 g, 2.0 mmole) and 5 mL of thionyl chloride stirred and heated to a gentle reflux. After 4 hours the reaction mixture is cooled and evaporated to dryness in vacuo, the residue is treated with water and neutralized with sodium bicarbonate. The resulting solid is collected by filtration, washed with water and dried to give 256 mg of the chloromethyl compound. This chloromethyl compound (252 mg, 1.15 mmole) is then stirred with 3 mL of dimethyl formamide and sodium azide is then added (75 mg, 1.15 mmole) and the reaction mixture stirred for 24 hrs at ambient temperature. The solvent is removed in vacuo and the residue treated with water, filtered, washed with water and dried to give 231 mg of the azidomethyl compound. This azidomethyl compound (228 mg, 1.01 mmole) is then suspended in 3 mL of tetrahydrofuran and treated with triphenylphosphine (264 mg, 1.01 mmole) after stirring for 10 mins at ambient temperature water is added (272 µL, 15 equivalents) and the reaction mixture warmed with an oil bath at 60° C. and stirred at that temperature overnight. The reaction mixture is evaporated to dryness in vacuo and treated with a 2:1 mixture of ethyl acetate and hexanes. The resulting solid is filtered, washed with fresh 2:1 ethyl acetate and hexanes and dried to give a grey solid, 116 mg, (57%); MS (ES+): m/z 201.1 (M+H).

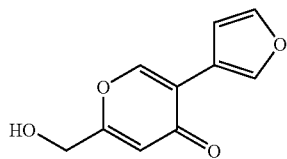

Intermediate 203

2-Hydroxymethyl-5-furan-3-yl-pyran-4-one

A mixture of trifluoro-methanesulfonic acid 6-(tert-butyl-dimethyl-silanyloxymethyl)-4-oxo-4H-pyran-3-yl ester[1] (6.94 g, 17.8 mmole), furan-3-boronic acid (4.0 g, 35.7 mmole), tetrakistriphenylphosphine palladium (1.024 g, 0.87 mmole), cesium carbonate (16.32 g, 50.1 mmole) and potassium bromide (10.63 g, 89.3 mmole) in (250 mL) dioxane (250 mL) is heated to 60° C. and stirred overnight. The reaction mixture is cooled to room temperature and diluted with saturated aqueous ammonium chloride and extracted with ethyl acetate. The combined ethyl acetate layers were washed with water, dried over sodium sulfate, filtered, diluted with an equal volume of hexanes and passed thru a short column of magnesol and silica gel eluting with 1:1 hexanes/ethyl acetate. The product is eluted with 2:1 ethyl acetate/hexanes, the solvents were evaporated, triturated with 1:1 hexanes/ethyl acetate, filtered, washed with the same solvent and air dried to give an off white solid, 2.58 g; MS (ES+): m/z 307.3(M+H). This solid is dissolved in tetrahydrofuran and tetrabutylammonium fluoride solution in tetrahydrofuran (40.0 mL, 40.0 mmole) is added and the mixture stirred at room temperature overnight. The reaction mixture is diluted with water and extracted with ethyl acetate. The combined ethyl acetate layers were combined and washed with water, dried over sodium sulfate, filtered, diluted with an equal volume of hexanes and passed thru a short column of magnesol and silica gel eluting with 1:1 hexanes/ethyl acetate. The product is eluted with 2:1 ethyl acetate/hexanes, the solvents were evaporated, triturated with 1:1 hexanes/ethyl acetate, filtered, washed with the same solvent and air dried to give an off white solid, 2.06 g, (37%); MS (ES+): m/z 193.2(M+H). (T. Kamino, et. al.; Tet. Lett. 44 (2003) 7349)

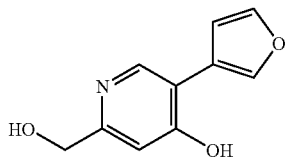

Intermediate 204

2-Hydroxymethyl-5-(3-furyl)-pyridin-4-ol

A mixture of 2-hydroxymethyl-5-furan-3-yl-pyran-4-one (1.92 g, 10.0 mmole) and 7 M ammonia in methanol (50.0 mL) is stirred and heated in a sealed vessel at 90° C. overnight. The reaction mixture is cooled, evaporated to dryness in-vacuo, taken up in 15% methanol in chloroform and passed thru a pad of magnesol and silica gel eluting with the same solvent. The eluate is evaporated, treated with acetone, filtered, washed with acetone and air dried to give a-grey solid, 1.21 g, (63%); MS (ES+): m/z 192.2 (M+H).

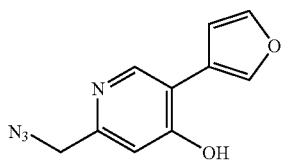

Intermediate 205

2-azidomethyl-5-furan-3-yl)-pyridin-4-ol

To a mixture of 2-hydroxymethyl-5-furan-3-yl-pyridin-4-ol (1.148 g, 6.00 mmole) and 30 mL of N,N-dimethylformamide stirred and cooled with an ice bath to 0° C. is added triphenylphosphine (2.361 g, 9.00 mmole) followed by carbon tetrabromide (2.988 g, 9.00 mmole). This is stirred for 15 minutes maintaining temperature between 0-5°. Sodium azide is then added (1.172 g, 18.03 mmole) and the reaction mixture stirred for 24 hrs at ambient temperature. The reaction mixture is diluted with water and extracted with ethyl acetate. The combined extracts were dried over sodium sulfate, filtered, evaporated and the residue chromatographed on silica gel eluting with ethyl acetate to give a-white solid, 0.417 g, (32%), mp 198-200° C. dec; MS (ES+): m/z 217.3 (M+H).

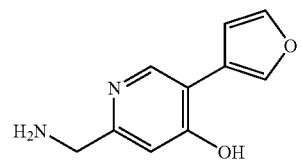

Intermediate 206

2-Aminomethyl-5-furan-3-yl-pyridin-4-ol

To a mixture of 2-azidoxymethyl-5-(3-furyl)-pyridin-4-ol (216 mg, 1.00 mmole), 6 mL of tetrahydrofuran, and triphenylphosphine (262 mg, 1.00 mmole) then water (270 □L, 15.0 mmole) is added and this is stirred for overnight at ambient temperature then stirred at 60° C. for overnight. The reaction mixture is cooled, evaporated to dryness in vacuo and then treated with warm toluene. This mixture is cooled and the solid is filtered, washed with toluene and dried, to give an off-white solid, 0.170 g, (89%), mp 183-7° C. dec; MS (ES+): m/z 191.3 (M+H).

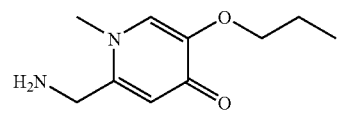

Intermediate 207

2-Aminomethyl-1-methyl-5-propoxy-1H-pyridin-4-one

A mixture of 2-hydroxymethyl-5-propoxy-pyran-4-one (3.69 g, 20.0 mmole) and 40% methylamine in water (25.0 mL) is stirred and heated in a sealed vessel at 90° C. overnight. The reaction mixture is cooled, evaporated to dryness in-vacuo, taken up in 15% methanol in chloroform and passed thru a pad of magnesol and silica gel eluting with the same solvent. The eluate is evaporated, treated with acetone, filtered, washed with acetone and air dried to give a-grey solid, 3.43 g, (87%); MS (ES+): m/z 198.3 (M+H). To this hydroxy compound is added 25 mL of thionyl chloride stirred and heated to a gentle reflux. After 4 hours the reaction mixture is cooled and evaporated to dryness in vacuo, the residue is treated with 2-propanol. The resulting solid is collected by filtration, washed with 2-propanol and dried to give 3.51 g (69%) of the chloromethyl compound as the HCl salt, MS (ES+): m/z 218.3 (M+H). This chloromethyl compound (3.28 g, 13.0 mmole) is then stirred with 30 mL of dimethyl formamide and triethylamine (1.81 mL, 13.0 mmole) for 15 mins. Then sodium azide is then added (0.85 g, 13.0 mmole) and the reaction mixture stirred for 24 hrs at ambient temperature.

The solvent is removed in vacuo and the residue treated with water, extracted 6 times with ethyl acetate. The combined extracts were dried over sodium sulfate passed thru a short pad of magnesol, evaporated and dried to give a light brown solid, 1.23 g of the azidomethyl compound. This azidomethyl compound (1.11 mg, 5.0 mmole) is then suspended in 30 mL of tetrahydrofuran and treated with triphenylphosphine (1.31 g, 5.0 mmole) after stirring for 10 mins at ambient temperature water is added (1.36 mL, 15 equivalents) and the reaction mixture warmed with an oil bath at 60° C. and stirred at that temperature overnight. The reaction mixture is evaporated to dryness in vacuo and treated with a 2:1 mixture of ethyl acetate and hexanes. The resulting solid is filtered, washed with fresh 2:1 ethyl acetate and hexanes and dried to give a brown solid, 398 mg, (40%); MS (ES+): m/z 197.4 (M+H).

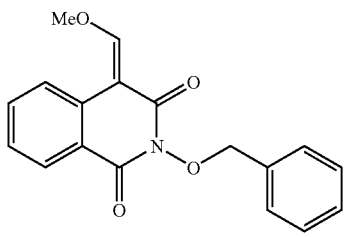

Intermediate 208

2-Benzyloxy-4-methoxymethylene-4H-isoquinoline-1,3-dione

A mixture of 2-benzyloxy-4H-isoquinoline-1,3-dione[1] (4.01 g, 15.0 mmole), 50 mL of a 4:1 mixture of acetic anhydride and N,N-dimethylformamide and trimethylorthoformate (12 mL, 0.11 mole) is stirred and heated to reflux. After 30 minutes the solvents are removed, the residue treated with hexane-ethyl acetate, the solid collected by filtration, washed with fresh hexane-ethyl acetate and dried to give a yellow solid, 3.67 g, (79%), mp 161-2° C., MS (ESI): m/z 310.1 (M+H). (Ames and Gray; J. Chem. Soc.; 3518 (1955)

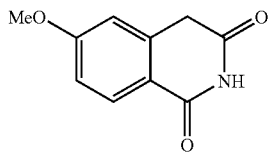

Intermediate 209

6-methoxy-isoquinoline-1,3(2H,4H)-dione

2-Carboxymethyl-4-methoxy-benzoic acid (946 mg, 4.5 mmole) and urea (629 mg, 10.4 mmole) is stirred and heated using an oil bath at 180° C. After one hour the mixture is cooled to room temperature and treated with water, collected by filtration, washed with water and dried to give a brown solid, 498 mg, (57%); mp 212-5° C., MS (ESI): m/z 192.1 (M+H).

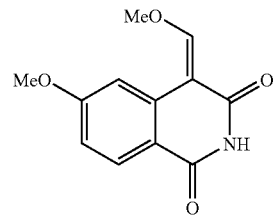

Intermediate 210

6-Methoxy-4-methoxymethylene-4H-isoquinoline-1,3-dione

A mixture of 6-methoxy-4H-isoquinoline-1,3-dione (400 mg, 2.1 mmole), 8 mL of a 4:1 mixture of acetic anhydride and N,N-dimethylformamide and trimethylorthoformate (1.7 mL, 15.5 mmole) is stirred and heated to reflux. After 30 minutes the solvents are removed, the residue treated with hexane-ethyl acetate, the solid collected by filtration, washed with fresh hexane-ethyl acetate and dried to give a yellow solid, 317 mg, (65%), mp 245-7° C., MS (ESI): m/z 234.1 (M+H).

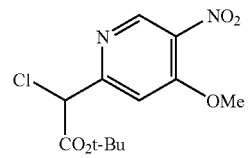

Intermediate 211

Chloro-(4-methoxy-5-nitro-pyridin-2-yl)-acetic acid tert-butyl ester

A solution of 4-methoxy-3-nitro-pyridine (5.15 g, 33.4 mole) and t-butyl dichloroacetate1 (6.80 g, 36.8 mmole) in 30 mL N,N-dimethylformamide is added dropwise to a stirred solution of potassium t-butoxide (11.24 g, 0.10 mole) in 90 mL N,N-dimethylformamide at −5° C. After the addition is complete the reaction is stirred for 15 minutes and quenched into 400 mL of cold 5% hydrochloric acid and extracted with dichloromethane. The organic layer is dried with anhydrous magnesium sulfate, filtered, evaporated and chromatographed on silica gel with hexanes/ether, to yield a yellow orange oil 3.07 g, (30%), MS (ES+): m/z 303.2, 305.2 (M+H).

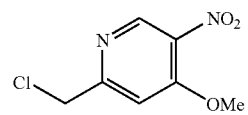

Intermediate 212

2-Chloromethyl-4-methoxy-5-nitro-pyridine

A mixture of chloro-(4-methoxy-5-nitro-pyridin-2-yl)-acetic acid tert-butyl ester (2.98 g, 9.84 mole) and acetic acid (25 mL) is refluxed for 6 hours, cooled and evaporated. The residue is dissolved in dichloromethane, passed thru a pad of magnesol, evaporated to dryness and crystallized from 3:1 hexanes/ethyl acetate to give a light yellow solid, 1.78 g, (89%); MS (ES+): m/z 203.2, 205.2 (M+H).

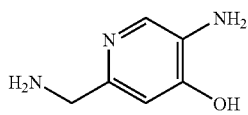

Intermediate 213

5-Amino-2-aminomethyl-pyridin-4-ol

A mixture of 2-(4-methoxy-5-nitro-pyridin-2-ylmethyl)-isoindole-1,3-dione (0.24 g, 7.7 mmole) and 48% hydrobromic acid (3 mL), is refluxed for 3 hours. The reaction mixture is cooled, evaporated to dryness in vacuo, dissolved in absolute ethanol (25 mL) and 10% Palladium on carbon (100 mg) is added under an inert atmosphere. This is then hydrogenated on a Par apparatus at 45 psi for 2 hours. The reaction mixture is filtered and evaporated to give a brown solid, 60 mg, (23%), MS (ES+): m/z 140.2 (M+H). Used as is for the next step.

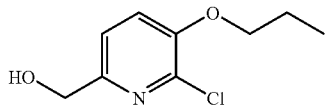

Intermediate 214

(6-Chloro-5-propoxy-pyridin-2-yl)-methanol

A mixture of 2-chloro-6-hydroxymethyl-pyridin-3-ol[8] (27.92 g, 0.175 mole), 120 mL of 2-butanone, potassium carbonate powder (48.37 g, 0.35 mole) and 1-iodopropane (37.19 g, 0.219 mole) is stirred for 15 minutes at ambient temperature then stirred at 90° C. for 3 hours. The reaction mixture is cooled, evaporated to dryness in vacuo and then portioned between water and dichloromethane. The organic layer is dried, filtered and crystallized with 2/1 hexane/ethyl acetate to give a pale yellow solid, 5.875 g, (16%), mp 59-60° C.; MS (ES+): m/z 160.3, 162.3 (M+H) (Wishka et al.; J. Org. Chem.; 63(22) 7851 (1998)

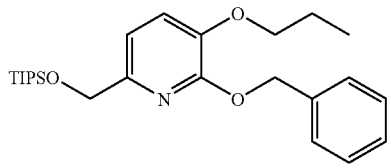

Intermediate 215

2-Benzyloxy-3-propoxy-6-triisopropylsilanyloxymethyl-pyridine

A mixture of (6-chloro-5-propoxy-pyridin-2-yl)-methanol (0.93 g, 4.61 mmole), 20 mL of dichloromethane, tri(isopropyl)silyl chloride (1.0 g, 5.19 mmole) and imidazole (0.47 g, 6.9 mmole) is stirred overnight at ambient temperature. The reaction mixture is washed with water, dried over sodium sulfate, filtered and evaporated in-vacuo to give an oil which is chromatographed on silica gel with 10:1 hexane/ethyl acetate to give 2-chloro-3-propoxy-6-triisopropylsilanyloxymethyl-pyridine as a clear liquid, 1.06 g, (64%); MS (ES+): m/z 358.2, 360.2 (M+H). A portion of this (716 mg, 2.0 mmole) and 5 mL of 1M sodium benzyloxide in benzyl alcohol is heated in a microwave reactor 5 minutes at 120° C. The reaction mixture is cooled, transferred to a separatory funnel with ethyl acetate, washed with water, the organic layer is dried, filtered, evaporated and chromatographed on silica gel with hexane/ethyl acetate to give a clear liquid, 524 mg, (61%); MS (ES+): m/z 430.3 (M+H).

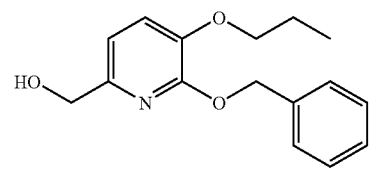

Intermediate 216

(6-Benzyloxy-5-propoxy-pyridin-2-yl)-methanol

To a solution of 2-benzyloxy-3-propoxy-6-triisopropylsilanyloxymethyl-pyridine (860 mg, 2.0 mmole) is added 1M tetrabutylammonium fluoride solution in tetrahydrofuran (4.0 mL, 4.0 mmole) and the mixture stirred at room temperature for four hours. The reaction mixture is diluted with water and extracted with ether. The combined ether layers were combined and washed with water, dried over sodium sulfate, filtered, chromatographed on silica gel eluting with 1:1 hexanes/ether to give a white solid, 355 mg, (65%); m.p. 50-1° C., MS (ES+): m/z 274.1 (M+H).

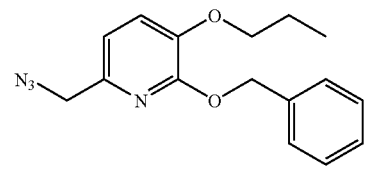

Intermediate 217

6-Azidomethyl-2-benzyloxy-3-propoxy-pyridine

To a mixture of (6-benzyloxy-5-propoxy-pyridin-2-yl)-methanol (1.09 g, 4.0 mmole) and 20 mL of N,N-dimethylformamide stirred and cooled with an ice bath to 0° C. is added triphenylphosphine (1.57 g, 6.0 mmole) followed by carbon tetrabromide (1.99 g, 6.0 mmole). This is stirred for 15 minutes maintaining temperature between 0-5°. Sodium azide is then added (781 mg, 12.0 mmole) and the reaction mixture stirred for 24 hrs at ambient temperature. The reaction mixture is diluted with water and extracted with ether. The combined extracts were dried over sodium sulfate, filtered, evaporated and the residue chromatographed on silica gel eluting with hexane/ethyl acetate to give a-clear liquid, 1.05 g, (88%); MS (ES+): m/z 299.1 (M+H).

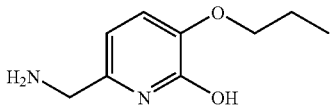

Intermediate 218

6-Aminomethyl-3-propoxy-pyridin-2-ol

To a mixture of 6-azidomethyl-2-benzyloxy-3-propoxy-pyridine (544 mg, 2.00 mmole), 12 mL of tetrahydrofuran, and triphenylphosphine (524 mg, 2.00 mmole) then water (540 □L, 30.0 mmole) is added and this is stirred at ambient temperature overnight. The reaction mixture is evaporated to dryness in vacuo and then washed with 2:1 hexanes/ethyl acetate and filtered. This resulting solid is taken up in ethanol and hydrogenated over 10% palladium on carbon at 1 atmosphere. The reaction mixture is filtered washed with ethanol, evaporated to give a brownish green solid, 93 mg, (25%), MS (ES+): m/z 183.3 (M+H). This is used as is for the next step.

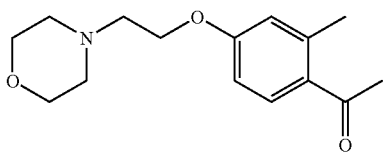

Intermediate 219

1-[2-Methyl-4-(2-morpholin-4-yl-ethoxy)-phenyl]-ethanone

A mixture of 1-(4-hydroxy-2-methyl-phenyl)-ethanone (15.0 g, 0.10 mole), sodium iodide (15.0 g, 0.10 mole), 4-(2-chloro-ethyl)-morpholine; hydrochloride (18.6 g, 0.10 mole), anhydrous powdered potassium carbonate (67.0 g, 0.50 mole) and 2-butanone (500 mL) is stirred and heated at a gentle reflux overnight. The mixture is cooled to room temperature, filtered, the solids washed with acetone. The combined filtrates were evaporated in-vacuo, the residue treated with water and extracted with ether. The ether layer is washed with 1N sodium hydroxide, water, brine, dried over anhydrous sodium sulfate, filtered and evaporated to give an oil, 19.2 g. (73%) used as is for the next step.

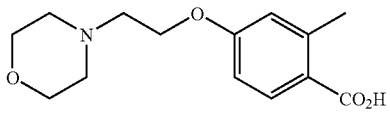

Intermediate 220

2-Methyl-4-(2-morpholin-4-yl-ethoxy)-benzoic acid

A solution of sodium hypobromite, prepared at 0° C. by dissolving sodium hydroxide (45.71 g, 1.14 mole) in water (200 mL) and bromine (16.3 mL, 0.30 mole) over 5 minutes. This solution is then added dropwise over 30 minutes to a solution of 1-[2-methyl-4-(2-morpholin-4-yl-ethoxy)-phenyl]-ethanone (19.2 g, 0.073 mole) in dioxane (140 mL), then warmed to 40° C. and stirred for 30 minutes. Sodium bisulfite is added to destroy the excess sodium hypobromite and then diluted with water (800 mL) and stirred overnight at ambient temperature. The volume is reduced in-vacuo by about 300 mL and then acidified with 3 N hydrochloric acid to pH 6. This is then extracted repeatedly with ethyl acetate. The combined organic layers were dried over sodium sulfate, filtered and evaporated to give a white solid, 4.09 g (21%), MS (ESI): m/z 266.2 (M+H).

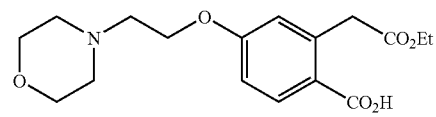

Intermediate 221

2-Ethoxycarbonylmethyl-4-(2-morpholin-4-yl-ethoxy)-benzoic acid

A solution of 2-methyl-4-(2-morpholin-4-yl-ethoxy)-benzoic acid (3.58 g, 13.5 mmole) and diethylcarbonate (2.40 g, 20.4 mmole) in tetrahydrofuran (30 mL) is added dropwise to a solution of lithium diisopropylamide (30.0 mmole) at −78° C. (freshly prepared from diisopropylamine (3.04 g, 30.0 mmole) and n-butyllithium (18.8 mL of 1.6M in hexanes, 30.1 mmole) in tetrahydrofuran (20 mL)) over 15 minutes. This mixture is allowed to warm to room temperature and stirred for 1.5 hours. The reaction mixture is cooled with an ice bath then glacial acetic acid (3.1 mL, 54.0 mmole) is added dropwise. The tetrahydrofuran evaporated in vacuo and the mixture is then extracted with ethyl acetate (3×25 mL). The ethyl acetate layer is dried over sodium sulfate, filtered and evaporated. This is purified by HPLC (acetonitrile-water without trifluoroacetic acid and dried to give, 2.81 g, (61%), MS (ESI): m/z 338.1 (M+H).

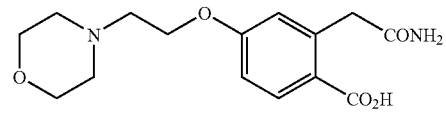

Intermediate 222

2-Carbamoylmethyl-4-(2-morpholin-4-yl-ethoxy)-benzoic acid

A solution of 2-ethoxycarbonylmethyl-4-(2-morpholin-4-yl-ethoxy)-benzoic acid (2.65 g, 10.0 mmole) and saturated ammonia in dioxane (15 mL) in a pressure bottle is stirred and heated using an oil bath at 95° C. overnight. This mixture is cooled and followed by lc/ms, reaction not complete. The dioxane is evaporated and replaced with 15 mL of 7M ammonia in methanol and heated overnight in a pressure bottle using an oil bath at 70° C., still a small amount of starting material left. The solvent is removed in vacuo and used as is in the next step MS (ESI): m/z 309.3 (M+H).

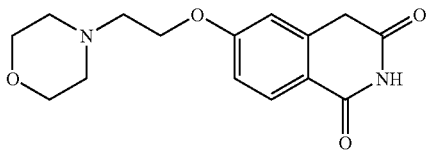

Intermediate 223

To 2-carbamoylmethyl-4-(2-morpholin-4-yl-ethoxy)-benzoic acid (224 mg, 0.726 mmole) in 4 mL of N,N-dimethylformamide is added N,N-carbonyldiimidazole (118 mg, 0.726 mmole) and stirred for 15 minutes at room temperature. The reaction mixture stirred and heated using an oil bath at 1100. After 2 hours the mixture is cooled to room temperature, 20 mL of water is added, stirred, filtered, washed with water and dried to give a brown solid, 134 mg (63%) MS (ESI): m/z 291.2 (M+H).

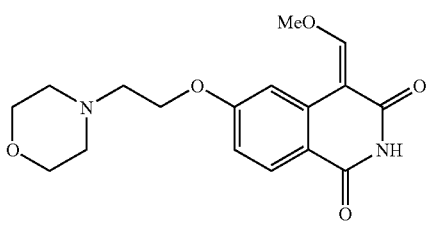

Intermediate 224

4-Methoxymethylene-6-(2-morpholin-4-yl-ethoxy)-4H-isoquinoline-1,3-dione

A mixture of 6-(2-morpholin-4-yl-ethoxy)-4H-isoquinoline-1,3-dione (390 mg, 1.34 mmole), 10 mL of a 4:1 mixture of acetic anhydride and N,N-dimethylformamide and trimethylorthoformate (1.1 mL, 10.1 mmole) is stirred and heated to reflux. After 30 minutes the solvents are removed and the residue treated with 2:1 hexanes/ethyl acetate, the product is collected by filtration, a yellow solid, 230 mg, (52%), MS (ES+): m/z 333.2 (M+H), used as is in the next step.

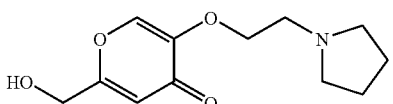

Intermediate 225

2-Hydroxymethyl-5-(2-pyrrolidin-1-yl-ethoxy)-pyran-4-one

A mixture of kojic acid (28.4 g, 0.20 mole), 300 mL of 2-butanone, potassium carbonate powder (27.6 g, 0.20 mole), potassium iodide (1.66 g, 0.01 mole), and 1-(2-chloro-ethyl)-pyrrolidine (26.7 g, 0.20 mole) is stirred at a gentle reflux overnight. The reaction mixture is cooled, filtered, washed with acetone and the filtrate evaporated. Water is added and extracted with chloroform (3×100 mL) and ethyl acetate (6×100 mL). The combined organics were dried with sodium sulfate and passed through a pad of magnesol and silica gel eluting with ethyl acetate. The eluate is evaporated in vacuo and crystallized with hexane/ethyl acetate (2/1) to give an off-white solid, 3.05 g, (6%); MS (ES+): m/z 240.3 (M+H).

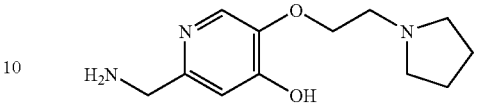

Intermediate 226

2-Aminomethyl-5-(2-pyrrolidin-1-yl-ethoxy)-pyridin-4-ol

A mixture of 2-hydroxymethyl-5-(2-pyrrolidin-1-yl-ethoxy)-pyran-4-one (479 mg, 2.0 mmole) and 7 M ammonia in methanol (5.0 mL) is stirred and heated in a sealed vessel at 90° C. overnight. The reaction mixture is cooled, evaporated to dryness, to give the pyridine as a brown solid (MS (ES+): m/z 239.3 (M+H)). This is treated with 12 mL of N,N-dimethylformamide stirred and cooled with an ice bath to 0° C. is added triphenylphosphine (786 mg, 3.00 mmole) followed by carbon tetrabromide (995 mg, 3.00 mmole). This is stirred for 15 minutes maintaining temperature between 0-50. Sodium azide is then added (390 mg, 6.0 mmole) and the reaction mixture stirred for 24 hrs at ambient temperature. The reaction mixture is filtered and chromatographed on the HPLC (acetonitrile, water without trifluoroacetic acid), to give the azide as a light brown solid 221 mg, (42%), (MS (ES+): m/z 264.4 (M+H)). To this is added 6 mL of tetrahydrofuran, and triphenylphosphine (262 mg, 1.00 mmole) followed by water (270 μL, 15.0 mmole) this is then stirred at ambient temperature overnight. The reaction mixture is evaporated to dryness in vacuo, dissolved in N,N-dimethylformamide, filtered and chromatographed on the HPLC (acetonitrile, water without trifluoroacetic acid), to give the amine as an off white solid 95 mg, (47%) (MS (ES+): m/z 238.3 (M+H)). This is used as is for the next step.

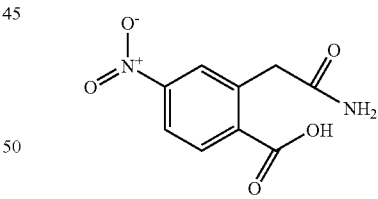

Intermediate 227

2-Carboxy-5-nitrobenzeneacetamide

A stirred mixture of 2.25 g (10 mmol) of 2-carboxy-5-nitrobenzeneacetic acid (J. Org. Chem. 1998, 63, 4116), 2.5 ml (35 mmol) of acetyl chloride, and 8 ml of acetone is refluxed for 60 m. The resulting solution is evaporated to dryness. The resulting tan solid is shown to be the corresponding cyclic anhydride by 1H NMR (DMSO-$d_6$) δ 4.40 (s, 2H). The anhydride is mixed at 0° with 16 ml of conc NH$_4$OH and 16 ml of H$_2$O. The resulting mixture is warmed to 250, stirred 15 m, and evaporated to dryness at <30° The residue is stirred in 25 ml of H₂O, acidified at 100 with 4 ml of 4N HCl, and stirred 10 m. The resulting tan solid is filtered, washed with H₂O, and dried to give 2.01 g (90%), mp 185-1900 (dec); 1H NMR (DMSO-d₆) δ 8.20 (d, J=2.4 Hz, 1H), 8.16 (dd, J=2.4, 8.4 Hz, 1H), 8.02 (d, J=8.4 Hz, 1H), 7.47 (s, 1H), 6.96 (s, 1H), 3.96 (s, 2H); MS (ES−) m/z 223.1 (M−H)⁻¹.

Analysis for C₉H₈N₂O₅: Calcd: C, 48.22; H, 3.60; N, 12.50. Found: C, 48.27; H, 3.40; N, 12.10.

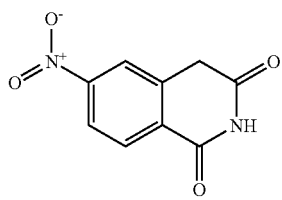

Intermediate 228

6-Nitroisoquinoline-1,3(2H,4H)-dione

A stirred suspension of 11.1 g (49.3 mmol) of 2-carboxy-5-nitrobenzeneacetamide in 99 ml of 1,2-dichlorobenzene is refluxed for 3 h. The residue obtained after evaporation of the solvent under vacuum is washed with ether and dried to give 7.34 g (72%) of a tan solid, mp 255-260° (dec); 1H NMR (DMSO-d₆) δ 11.6 (s, 1H), 8.2-8.3 (m, 3H), 4.17 (s, 2H); MS (ES−) m/z 205.2 (M−H)⁻

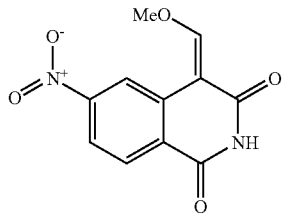

Intermediate 229

(4E)-4-(Methoxymethylene)-6-nitroisoquinoline-1,3(2H,4H)-dione

To a stirred mixture of 0.41 g (2.0 mmol) of 6-nitroisoquinoline-1,3(2H,4H)-dione, 3.2 ml (34 mmol) of Ac₂O, and 0.80 ml of N,N-DIMETHYLFORMAMIDE is added 0.44 ml (4.0 mmol) of trimethyl orthoformate. The mixture is heated to 125° and maintained for 30 m, cooled, diluted with ether, and stirred for 10 m. The resulting brown solid is filtered, washed with ether, and dried to give 372 mg (74%); 1H NMR (DMSO-d₆) δ 11.55 (s, 1H), 8.99 (d, J=2.0 Hz, 1H), 8.30 (d, J=8.6 Hz, 1H), 8.19 (dd J=2.0, 8.6 Hz, 1H), 4.33 (s, 3H).

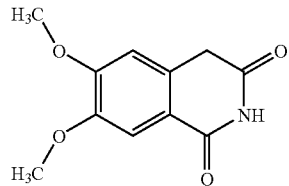

Intermediate 230

6,7-Dimethoxyisoquinoline-1,3(2H,4H)-dione

A solution of 8.2 g (34.1 mmol) of 2-carboxy-4,5-dimethoxybenzeneacetic acid (*Tetrahedron* 1975, 31, 2607) in 17 ml of concentrated NH₄OH is evaporated to dryness. This operation is repeated. The resulting tan solid ammonium salt is suspended in 34 ml of 1,2-dichlorobenzene. The stirred mixture is boiled in an oil bath at 2100 while collecting some distillate during 90 m. The cooled mixture is stirred in hexane and H₂O, and the resulting solid is collected by filtration. The white solid is stirred in satd NaHCO₃ for 15 m, filtered, washed with H₂O, and dried to give 3.45 g (46%), mp 234-238°; MS (ES−) m/z 220.1 (M−H)⁻¹.

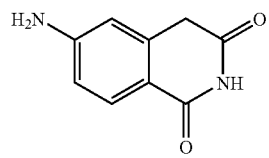

Intermediate 231

6-Aminoisoquinoline-1,3(2H,4H)-dione

A solution of 6.19 g (30 mmol) of 6-nitroisoquinoline-1,3(2H,4H)-dione in 15 ml of MeOH and 150 ml of N,N-DIMETHYLFORMAMIDE is hydrogenated at 1 atmosphere of H₂ at 250 in the presence of 1.5 g of 10% Pd/C for 7 h. The catalyst is removed by filtration through Celite. The filtrate is evaporated to give 5.4 g (100%) of a tan solid, mp 200-2200 (dec); MS (ES+) m/z 177.2 (M+H)⁺¹.

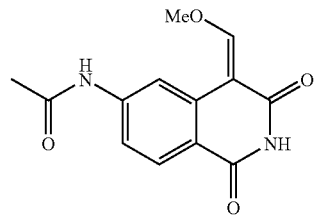

Intermediate 232

N-[(4E)-1,3-Dioxo-4-(methoxy)methylene-1,2,3,4-tetrahydroisoquinolin-6-yl]acetamide To a stirred mixture of 90 mg (0.50 mmol) of 6-aminoisoquinoline-1,3(2H,4H)-dione, 0.80 ml (8.5 mmol) of Ac₂O, and 0.20 ml of N,N-DIMETHYLFORMAMIDE (DMF) is added 0.11 ml 1.0 mmol) of trimethyl orthoformate. The mixture is heated to 125° and maintained for 30 m, cooled, diluted with ether, and stirred for 10 m. The resulting amber solid is filtered, washed with ether, and dried to give 96 mg (74%); MS (ES+) m/z 261.1 (M+H)$^{+1}$.

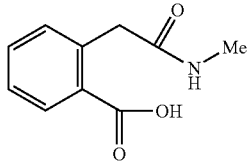

Intermediate 233

N-Methyl-2-carboxybenzeneacetamide

To 20 ml of 2.0 M methylamine in THF is added 1.62 g (10 mmol) of isochroman-1,3-dione at 0° C. The mixture is stirred at 25° C. for 45 m and concentrated to dryness. The residue is stirred in 40 ml of 0.3 N HCl. The white solid is filtered off, washed with water, and dried to give 1.74 g (90%); $^1$H NMR (DMSO-d$_6$) δ 7.80 (s, 1H), 7.81 (s, 1H), 7.40 (m, 3H), 3.83 (s, 2H), 2.57 (s, 3H); MS (ES−) m/z 192.1 (M−H)$^{-1}$.

Analysis for C$_{10}$H$_{11}$NO$_3$: Calcd: C, 62.17; H, 5.74; N, 7.25. Found: C, 62.16; H, 5.81; N, 7.24

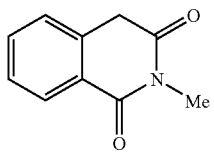

Intermediate 234

N-Methylisoquinoline-1,3(2H,4H)-dione

A mixture of 2.28 g (11.8 mmol) of N-methyl-(2-carboxybenzeneacetamide and 24 ml of 1,2-dichlorobenzene is refluxed for 1 h and evaporated to dryness. The residue is recrystallized from EtOAc-hexane to give an off-white solid, 1.55 g (75%), mp 113-115° C.; MS (ES+) m/z 176.1 (M+H)$^+$$^1$.

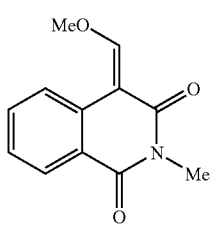

Intermediate 235

(4E)-N-Methyl-4-(methoxymethylene)isoquinoline-1,3(2H,4H)-dione

To a stirred mixture of 0.35 g (2.0 mmol) of (N-methyl) isoquinoline-1,3(2H,4H)-dione, 3.2 ml of Ac$_2$O, and 0.80 ml of N,N-DIMETHYLFORMAMIDE (DMF) is added 0.44 ml (4.0 mmol) of (MeO)$_3$CH at 25° C. The mixture is stirred at 125° C. for 30 m, cooled, and concentrated under high vacuum. The residue is recrystallized from Et$_2$O-hexane to give 0.20 g of tan solid, mp 145-150° C. (dec); MS (ES+) m/z 218.2 (M+H)$^{+1}$.

Analysis for C$_{12}$H$_{11}$NO$_3$: Calcd: C, 66.35; H, 5.10; N, 6.45. Found: C, 65.98; H, 4.99; N, 6.42.

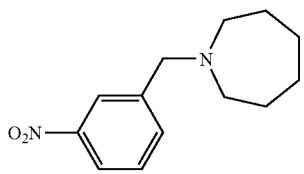

Intermediate 236

1-(3-Nitro-benzyl)-azepane

To a solution of 3-nitrobenzyl bromide (10.5 g, 48.7 mmol) in methylene chloride is added azepane (5.5 mL, 48.7 mmol) and 20.0 mL (146.1 mmol) of triethylamine, and the reaction solution is heated at 60° C under N$_2$ for 20 minutes. After evaporating to dryness, the resulting brown residue is dissolved in methylene chloride and washed twice with saturated Na$_2$CO$_3$ solution, and once with brine solution. After drying over Mg$_2$SO$_4$, the organic solution is filtered and concentrated to give 8.0 g (70.1% yield) of brown oil.

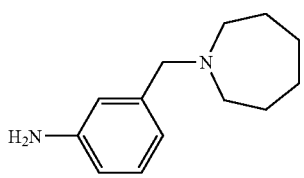

Intermediate 237

3-(azepan-1-ylmethyl)aniline

To a solution of 1-(3-nitro-benzyl)-azepane (4.0 g, 17.05 mmol) in 120 mL of 20% H$_2$O/MeOH is added 5.05 g (102.3 mmol) of fresh iron powder, 8.25 g (153.5 mmol) of NH$_4$Cl and the reaction mixture is refluxed under N$_2$ for 45 min. The reaction mixture is filtered through a pad of celite to give yellow solution. After evaporating to dryness, the yellow residue is dissolved in EtOAc, washed twice with saturated NaHCO$_3$ solution. After drying over Mg$_2$SO$_4$, the organic

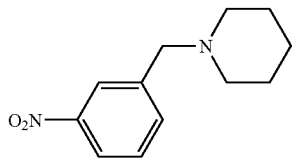

Intermediate 238

1-(3-Nitro-benzyl)-piperidine

Using the procedure described for the preparation of 1-(3-nitro-benzyl)-azepane, 4.7 g (46.5% yield) of yellow oil is obtained from 10.0 g (46.3 mmol) of 3-nitrobenzyl bromide, 4.58 mL (46.3 mmol) of piperidine, and 16.1 mL (115.7 mmol) of triethylamine.

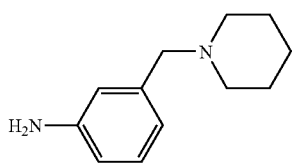

Intermediate 239

3-Piperidin-1-ylmethyl-phenylamine

Using the procedure described for the preparation of 3-(azepan-1-ylmethyl)aniline, 3.37 g (83% yield) of colorless solid is obtained from 4.7 g (21.4 mmol) of 1-(3-Nitro-benzyl)-piperidine, 7.17 g (128.1 mmol) of iron powder, 10.28 g (192.2 mmol) of $NH_4Cl$.

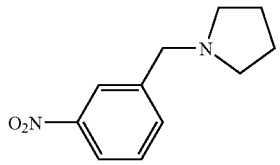

Intermediate 240

1-(3-Nitro-benzyl)-pyrrolidine

Using the procedure described for the preparation of 1-(3-Nitro-benzyl)-azepane, 7.67 g (62.0% yield) of brown oil is obtained from 13.0 g (60.2 mmol) of 3-nitrobenzyl bromide, 5.0 mL (60.2 mmol) of pyrrolidine, and 21 mL (150.4 mmol) of triethylamine.

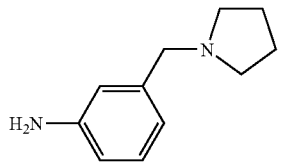

Intermediate 241

3-Pyrrolidin-1-ylmethyl-phenylamine

Using the procedure described for the preparation of 3-(azepan-1-ylmethyl)aniline, 2.63 g (40.1% yield) of colorless solid is obtained from 7.67 g (37.2 mmol) of 1-(3-Nitro-benzyl)-pyrrolidine, 12.5 g (223.0 mmol) of iron powder, 17.9 g (334.8 mmol) of $NH_4Cl$.

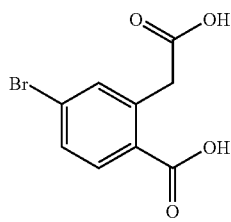

Intermediate 242

4-bromo-2-(carboxymethyl)benzoic acid

In a 500 mL 3-neck round bottom flask, an amount of diisopropylamine (28.0 mL 200 mmol) in 65 mL of tetrahydrofuran is cooled to −78° C. and slowly added 80.0 mL (200 mmol) of n-butyllithium (2.5 M in hexane) with vigorous stirring. Allow to warming up to 0° C. and keeping at this temperature for 5 min, the reaction is cooled back to −78° C. To this mixture is slowly added a solution of 10.8 g (50.0 mmol) of 4-bromo-2-methylbenzoic acid and 8.42 mL (100 mmol) of dimethylcarbonate in 65 mL of tetrahydrofuran keeping the internal temperature of the reaction mixture below −50° C. After addition, the dry-ice bath is removed and the reaction mixture is stirred at room temperature for 4 h. Precipitate is observed as the internal temperature raising to room temperature. The reaction is quenched with 80 mL of water and stirred overnight to give a homogenous solution. Separate the organic layer. The aqueous solution is acidified with concentrated HCl to pH=2 and extracted with 3×100 mL of ethyl acetate. The combined organic solution is washed twice with water. After drying over $Mg_2SO_4$, the organic solution is filtered and concentrated to give white solid. Recrystallization from EtOAc (hot)/hexane yielded 8.86 g (68.2% yield) of white solid: $^1$H NMR (DMSO-$d_6$) δ 12.62 (bs, 1H); 7.82 (d, J=6.3 Hz, 1H), 6.18 (m, 2H), 3.95 (s, 2H); MS (ESI) m/z 257.1 and 259.1 $(M-H)^{-1}$ Analysis for C₉H₇BrO₄.(0.2 EtOAc) Calcd: C, 42.54; H, 3.13; N, 0.00. Found: C, 42.41; H, 2.93; N, −0.25.

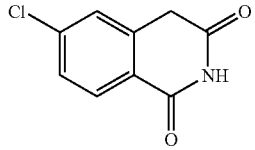

Intermediate 243

6-chloroisoquinoline-1,3(2H,4H)-dione

An amount of 2-(carboxymethyl)-4-chlorobenzoic acid (8.4 g, 39.14 mmol) and 2.82 g (47 mmol) of urea is vigorously stirred at 160° C. Solids were melted, boiled and hardened after 15 min. Continue to heat and blow nitrogen through to remove water generated from reaction until total dryness. After cooling, the solid is ground to fine powder. After successively washing with saturated NaHCO₃ solution, water, methanol, ether and hexane, the powder is dried in oven (60° C.) overnight to give 2.6 g (34.0% yield) of light yellow solid: MS (ESI) m/z 194.0 (M−H)⁻¹ Analysis for C₉H₆ClNO₂, Calcd: C, 55.26; H, 3.09; N, 7.16. Found: C, 54.86; H, 2.96; N, 7.12

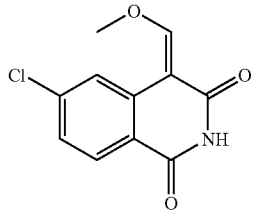

Intermediate 244

(4E)-6-Chloro-4-(methoxymethylene)isoquinoline-1,3(2H,4H)-dione

A solution of 4b (2.40 g, 12.2 mmol), 2.68 mL (24.4 mmol) of trimethylorthoformate, and 20 mL of acetic anhydride in 10 mL of N,N'-dimethylformamide is heated at 120° C. under N₂ for 2 hrs. Mass spectroscopy suggested that the reaction is completed. After cooling, ethyl ether is added, and the precipitate is collected, and washed successively with MeOH, Et₂O and hexane. After drying in oven (60° C.) overnight, 2.1 g (72.5% yield) of brown solid is obtained: MS (ESI) m/z 221.95 (M+H)⁺¹

Analysis for C₁₁H₈ClNO₃ $_{Calcd:\ C}$, 55.60; H, 3.39; N, 5.89. Found: C, 54.20; H, 3.14; N, 5.92.

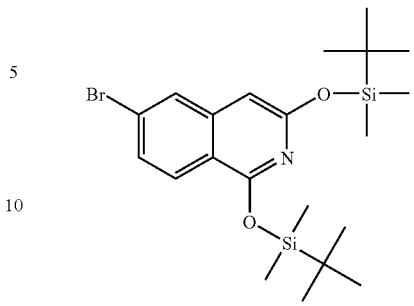

Intermediate 245

6-Bromo-1,3-bis{[tert-butyl(dimethyl)silyl]oxy}isoquinoline

A solution of 6-bromo-isoquinoline-1,3(2H,4H)-dione (1.0 g, 4.17 mmol), 1.875 g (12.51 mmol) of tert-butyldimethylsilyl chloride, 1.13 g (16.68 mmol) of imidazole in N,N'-dimethylformamide is stirred at room temperature overnight. After evaporating to dryness, the brown oil is extracted with 4×100 mL of 25% diethyl ether/hexane. The organic solution is washed with 3×100 mL of water, dried over Mg₂SO₄, filtered and concentrated to give brown oil. This brown oil is dissolved in 50 mL of 20% CH₂Cl₂/hexane and passed through a pad of magnesol, followed by rinsing with 500 mL of the same solvent mixture. The organic solution is concentrated to give 1.184 g (60.6% yield) of colorless solid: MS (ESI) m/z 468.2 and 470.2 (M+H)⁺¹

Analysis for C₂₁H₃₄BrNO₂Si₂ $_{Calcd:\ C}$, 53.83; H, 7.31; N, 2.99. Found: C, 53.86; H, 7.11; N, 2.99.

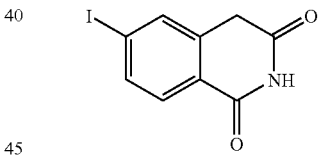

Intermediate 246

6-Iodoisoquinoline-1,3(2H,4H)-dione

An amount of 6-bromo-1,3-bis{[tert-butyl(dimethyl)silyl]oxy}isoquinoline (15.0 g, 32.0 mmol) in 100 mL of anhydrous tetrahydrofuran is cooled to −78° C. and then 47 mL (80.0 mmol) of tert-butyllithium (1.7 M in pentane) is added slowly with stirring. After stirring at this temperature for 2 hr, 12.0 g (48 mmol) of fresh iodine crystal is quickly add into the mixture, and stirred at this temperature for additional 5 h. The dry-ice bath is removed, and the reaction mixture is allowed to warm up to room temperature and stirred over weekend. Evaporating the brown solution yielded brown oil. The reaction mixture is acidified with 48 mL of 2 M HCl solution and stirred at room temperature for 1 h. The mixture is filtered to give light tan solid. The solid is dissolved in hot DMSO, then 20% MeOH/H2O solution is added to give a precipitate. The precipitate is collected and washed successively with water, methanol, ether and hexane to afford 5.1 g (55.6% yield) of off-white solid: MS (ESI) m/z 286.08 (M−H)⁻¹

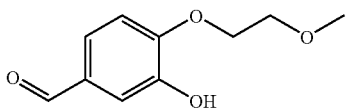

Intermediate 247

3-Hydroxy-4-(2-methoxyethoxy)benzaldehyde

An amount of 3,4-dihydroxybenzaldehyde (5.0 g, 36.2 mmol) in 20 mL of N,N'-dimethylformamide is added 2-bromoethyl methyl ether (3.4 mL, 36.2 mmol), and sodium carbonate (5.0 g, 72.4 mmol). The reaction mixture is stirred at room temperature for 3 days. After removal solids by filtration, the solution is subsequently evaporated under high-pressure vacuum to dark brown liquid. The residue is added water and acidified with 12 N HCl solution to pH~2, then extracted 4×100 mL of EtOAc. The combined organic layer is washed with brine, dried over Mg₂SO₄, stirred in darko, filtered and evaporated to give yellow liquid. Purification is performed by column chromatography over silica gel using 40% EtOAc/Hex as eluent to give 2.13 g of colorless solid: mp 74-75° C.; MS (ESI) m/z 195.1 (M+H)⁻¹

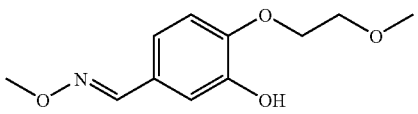

Intermediate 248

3-Hydroxy-4-(2-methoxyethoxy)benzaldehyde O-methyloxime

An amount of 3-hydroxy-4-(2-methoxyethoxy)benzaldehyde (1.24 g, 6.32 mmol) in 20 mL of EtOH and 10 mL of pyridine is added methoxy]amine hydrochloride (1.06 g, 12.64 mmol). The reaction mixture is stirred at room temperature over weekend. Solvent is removed under vacuum to give colorless oil which is added ether, washed twice with saturated NaHCO₃ solution, once with brine, dried over Mg₂SO₄, filtered and evaporated to give colorless oil. Leaving this oil overnight at room temperature gave 1.15 g (81.0% yield) of colorless solid: mp: 63-64° C.; MS (ESI) m/z 226.1 (M+H)⁺¹

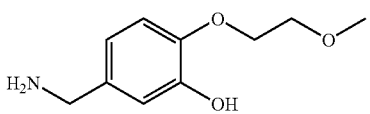

Intermediate 249

5-(Aminomethyl)-2-(2-methoxyethoxy)phenol

An amount of 3-hydroxy-4-(2-methoxyethoxy)benzaldehyde O-methyloxime (0.75 g, 3.33 mmol) in 10 mL of EtOH is added 1 mL of 12 N HCl and palladium on carbon. The reaction mixture is hydrogenated for 4 h. After removal of solid by filtration, solvent is evaporated to give yellow oil. Colorless solid is afforded after the oil is washed 5 times with EtOAc. Recrystallization from MeOH/EtOAc afforded 0.45 g (68.5% yield) of colorless solid: mp: 89-90° C.; MS (ESI) m/z 198.1 (M+H)⁺¹

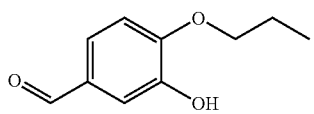

Intermediate 250

3-Hydroxy-4-propoxybenzaldehyde

Using the procedure described for the preparation of 3-hydroxy-4-(2-methoxyethoxy)benzaldehyde, 5.26 g (40.5% yield) of colorless solid, after purified by column chromatography over silica gel using 40% EtOAc/Hex as eluent, is obtained from 3,4-dihydroxybenzaldehyde (10.0 g, 72.4 mmol), 7.77 mL (80 mmol) of 1-iodo propane, and 10 g of sodium carbonate: mp 67-68° C.; MS (ESI) m/z 179.1 (M+H)⁻¹.

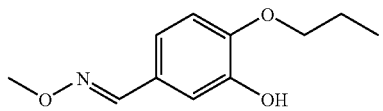

Intermediate 251

3-Hydroxy-4-propoxybenzaldehyde O-methyloxime

Using the procedure described for the preparation of 3-hydroxy-4-(2-methoxyethoxy)benzaldehyde O-methyloxime, 1.12 g (42.0% yield) of colorless solid, after purified by column chromatography over silica gel using 25% EtOAc/Hex as eluent, is obtained from 3-hydroxy-4-propoxybenzaldehyde (2.30 g, 12.76 mmol), 2.13 g (25.52 mmol) of methoxy]amine hydrochloride: mp 39-40° C.; MS (ESI) m/z 210.1 (M+H)⁺¹

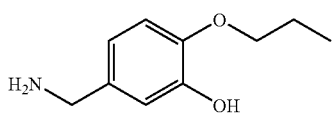

Intermediate 252

5-(Aminomethyl)-2-propoxyphenol

Using the procedure described for the preparation of 5-(aminomethyl)-2-(2-methoxyethoxy)phenol, 2.35 g (75.3% yield) of colorless solid is obtained from 3-hydroxy- 4-propoxybenzaldehyde O-methyloxime (3.0 g, 14.34 mmol): mp 125-126° C.; MS (ESI) m/z 182.1 (M+H)+1

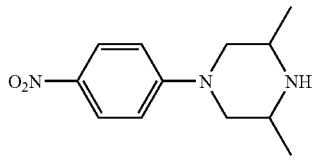

Intermediate 253

3,5-Dimethyl-1-(4-nitrophenyl)piperazine

An amount 4-nitrophenylfluoride (2.0 mL, 18.85 mmol) in 20 mL of acetonitrile is added 2,6-dimethylpiperazine (2.58 g, 22.62 mmol). The reaction mixture is reflux under $N_2$ overnight. Mass spectroscopy suggested the completion of reaction. Solvent is subsequently evaporated under vacuum. The collected yellow solid is dissolved in chloroform and washed twice with 200 mL of saturated $NaHCO_3$ solution, and once with 100 mL of brine. The organic portion is dried over $Mg_2SO_4$, filtered, evaporated to give yellow solid which is re-crystallized from EtOAc/Hexane to give 3.98 g (89.8% yield) of bright yellow crystals: mp 124-125° C.; MS (ESI) m/z 236.1 (M+H)+1

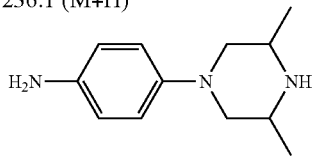

Intermediate 254

[4-(3,5-Dimethylpiperazin-1-yl)phenyl]amine

An amount of 3,5-dimethyl-1-(4-nitrophenyl)piperazine (1.86 g, 7.90 mmol) in EtOH is hydrogenated with Pd/C catalyst for 4 h. The solid is removed by filtration, and solvent is evaporated under vacuum to give pinkish residue. Recrystallization of this residue from MeOH/ether gives 1.30 g (80.2% yield) of pinkish crystal: mp 124-125° C.; MS (ESI) m/z 206.1 (M+H)+1

(Z)-1,1'-(4-(Methoxymethylene)-3-oxo-3,4-dihydrocinnoline-1,2-diyl)diethanone

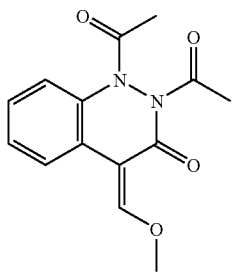

Intermediate 257

To a solution of 1,2-diacetyl-1,4-dihydro-3(2H)cinnolinone (0.34 g, 1.5 mmol) in dimethylformamide (3.6 mL) is added acetic anhydride (5 mL), followed by trimethylorthoformate (0.64 mL). The mixture is heated at reflux for 12 hours. After cooling to room temperature, the mixture is purified by semi-preparative reverse-phase HPLC, employing a gradient elution from 5% acetonitrile in water with 0.1% trifluoroacetic acid to 100% acetonitrile over 60 minutes. The desired fractions were concentrated under reduced pressure to afford 0.18 g of (Z)-1,1'-(4-(methoxymethylene)-3-oxo-3,4-dihydrocinnoline-1,2-diyl)diethanone.

Calculated MW: 274.3.

MS (ES−): 273.0 (M−H)− observed.

Intermediate 258

6-Bromo-4-methoxymethylene-4H-isoquinoline-1,3-dione

Step 1

4-Bromo-2-carboxylmethyl-benzoic acid

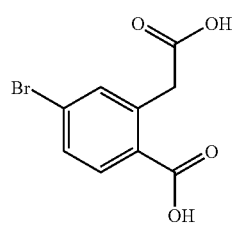

To a stirring solution of diisopropylamine (47.4 g, 465 mmol) in dry THF at −78° C. is added drop wise n-butyl lithium (37.3 g, 581 mmol). Mixture is stirred at −78° C. for 0.5 hour and then allowed to warm to 25° C. for five minutes causing a yellow suspension to form. Suspension is cooled to −78° C. 4-Bromo-2-methyl-benzoic acid (25.0 g, 116 mmol) and diethylcarbonate (10.5 g, 116 mmol) are dissolved together in 100 ml of dry THF. This solution is added drop wise to the reaction mixture over 30 minutes causing a deep reddish-brown color. The resulting mixture is stirred at −78° C. for 1 hour and then allowed to warm to room temperature causing a precipitate to form. Mixture is stirred overnight at room temperature and then cooled in an ice bath. 400 mL of water is slowly added to the mixture keeping the internal temperature below 20° C. causing two layers to form. The layers are separated. The organic layer is extracted with 150 ml of $H_2O$, and all aqueous layers combined. Aqueous layers are acidified with con. HCl causing an off-white solid to form. This solid is filtered and washed with 200 ml of $H_2O$ to afford the desired product (18.6 g, 71.8 mmol, 62%); 1H NMR (DMSO-d$_6$) δ 3.51 (s, 2H), 7.32 (d, J=2.0 Hz, 1H), 7.39 (dd, J=1.7, 8.5 Hz, 1H), 7.51 (d, J=8.4 Hz, 1H).

Step 2

6-Bromo-4H-isoquinoline-1,3 dione

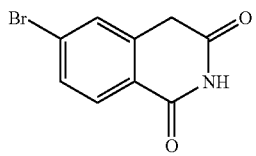

4-Bromo-2-carboxylmethyl-benzoic acid (5.00 g, 19.0 mmol) and urea (2.45 g, 40.8 mmol) are suspended in 150 ml of 1,2-dichlorobenzene. This mixture is heated to 150° C. forming a homogeneous mixture. Temperature is maintained for 2 hours during which time a yellow precipitant formed. Mixture is cooled to room temperature and filtered. Residue is washed with 100 ml of ethyl acetate, 100 ml of methanol, and 100 ml of water to afford the product as a yellow solid (3.80 g, 15.8 mmol, 83%); $^1$H NMR (DMSO-d$_6$) δ 4.01 (s, 2H), 7.65-7.69 (m, 2H), 7.89 (d, J=8.7 Hz, 1H), 11.36 (s, 1H).

Step 3

6-Bromo-4-methoxymethylene-4H-isoquinoline-1,3-dione

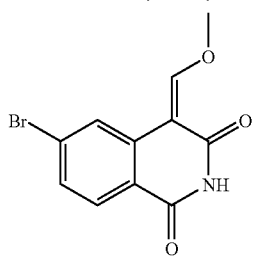

6-Bromo-4H-isoquinoline-1,3-dione (120 mg, 0.500 mmol) and trimethyl orthoformate (106 mg, 1.00 mmol) are suspended in 1.25 ml of a 1:4 ratio mixture of acetic anhydride and dimethylformamide. Mixture is heated at 125° C. for 2 hours causing a yellow solid to form. Mixture is cooled to room temperature and filtered. Residue is washed with 20 ml of ethyl ether to afford the product as a yellow solid (109 mg, 0.380 mmol, 77%); $^1$H NMR (DMSO-d$_6$) δ 4.25 (s, 3H), 7.60 (dd, J=1.9, 8.4 Hz, 1H), 7.96 (d, J=8.5 Hz, 1H), 8.07 (s, 1H), 8.36 (d, J=1.9 Hz, 1H), 11.38 (s, 1H); mass spectrum [(+) ESI], m/z 282/284 (M+H)$^+$.

Intermediate 259

4-Piperidin-1-ylmethyl-phenylamine

Step 1

1-(4-nitro-benzyl)-piperidine

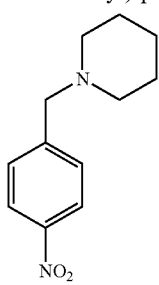

4-Nitrobenzyl chloride (0.086 g, 0.501 mmol) is dissolved in THF (1 mL), and to this solution, is added piperidine (0.059 mL, 0.601 mmol) followed by Et$_3$N (0.210, 1.50 mmol). After stirring the mixture at 50° C. for 5 h, the resulting solution is filtered, and then the solvent is removed via high vacuum to afford the product (0.090 g, 82%); $^1$H NMR (DMSO-d$_6$) δ 1.25-1.35 (m, 2H), 1.40-1.48 (m, 4H), 2.23-2.32 (m, 4H), 3.47 (s, 2H), 7.50 (d, J=8.8 Hz, 2H), 8.11 (d, J=8.8 Hz, 2H); mass spectrum [(+) ESI], m/z 221 (M+H)$^+$.

Step 2

4-Piperidin-1-ylmethyl-phenylamine

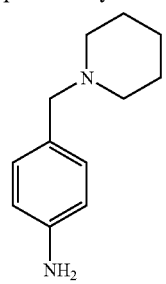

1-(4-Nitro-benzyl)-piperidine (0.089 g, 0.404 mmol) is dissolved in MeOH (5 mL), and to this solution is added 10% Pd/C (0.009 g, 0.404 mmol). The reaction mixture is stirred under an atmosphere of H$_2$ for 18 h. The resulting mixture is filtered through celite, and the filtered catalyst is washed with excess EtOAc. The filtrate is concentrated under high vacuum to afford the product as a solid (0.076 g, 99%); $^1$H NMR (DMSO-d$_6$) δ 1.29-1.40 (m, 2H), 1.40-1.51 (m, 4H), 2.17-2.30 (m, 4H), 3.18 (s, 2H), 4.88 (s, 2H), 6.46 (d, J=8.4 Hz, 2H), 6.87 (d, J=8.4 Hz, 2H); mass spectrum [(+) ESI], m/z 191 (M+H)$^+$.

Intermediate 260

4-(3,5-Dimethyl-piperazin-1-yl)-phenylamine

Step 1

4-Methyl-1-(4-nitro-phenyl)-piperazine

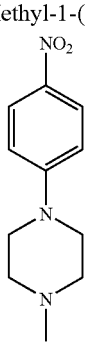

1-Fluoro-4-nitro-benzene (1.00 g, 7.09 mmol) is dissolved in DMF (20 mL), and to this solution, is added 1-methyl-piperazine (0.944 mL, 8.51 mmol) followed by K$_2$CO$_3$ (1.47 g, 10.6 mmol). After stirring the mixture at rt for 18 h, the solvent is removed via high vacuum. The resulting residue is dissolved in EtOAc (100 mL) and washed with H$_2$O (10 mL) and brine (10 mL) and then dried (Na$_2$SO$_4$). The solvent is taken off via high vacuum to afford the product as a solid (1.50 g, 96%); $^1$H NMR (DMSO-d$_6$) δ 2.17 (s, 3H), 2.37-2.42 (m, 4H), 3.39-3.43 (m, 4H), 6.98 (d, J=9.6 Hz, 2H), 8.00 (d, J=9.5 Hz, 2H); mass spectrum [(+) ESI], m/z 222 (M+H)$^+$.

Step 2

4-(4-Methyl-piperazin-1-yl)-phenylamine

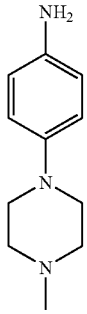

4-Methyl-1-(4-nitro-phenyl)-piperazine (1.50 g, 6.78 mmol) is dissolved in MeOH (50 mL), and to this solution is added 10% Pd/C (0.145 g, 6.78 mmol). The reaction mixture is stirred under an atmosphere of $H_2$ for 18 h. The resulting mixture is filtered through celite, and the filtered catalyst is washed with excess EtOAc. The filtrate is concentrated under high vacuum to afford the product as a purple solid (1.28 g, 98%); $^1$H NMR (DMSO-$d_6$) δ 2.15 (s, 3H), 2.37-2.40 (m, 4H), 2.83-2.87 (m, 4H), 4.48 (s, 2H), 6.43 (d, J=8.8 Hz, 2H), 6.62 (d, J=8.8 Hz, 2H); mass spectrum [(+) ESI], m/z 192 (M+H)$^+$.

Intermediate 261

4-(3,5-Dimethyl-piperazin-1-yl)-phenylamine

Step 1

3,5-Dimethyl-1-(4-nitro-phenyl)-piperazine

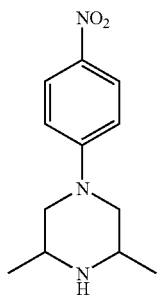

1-Fluoro-4-nitro-benzene (1.00 g, 8.75 mmol) and 2,6-dimethyl-piperazine (1.20 g, 10.5 mmol) are dissolved in 100 ml of acetonitrile forming a yellow homogeneous mixture. Mixture is heated at 90° C. overnight. Mixture is reduced on rotovap to afford the product as an orange solid (1.40 g, 65%); $^1$H NMR (DMSO-$d_6$) δ 1.00 (d, J=6.3 Hz, 6H), 2.37-2.80 (m, 5H), 3.87 (dd, J=2.1, 12.4 Hz, 2H), 7.00 (d, J=9.5 Hz, 2H), 8.00 (d, J=9.5 Hz, 2H).

Step 2

4-(3,5-Dimethyl-piperazin-1-yl)-phenylamine

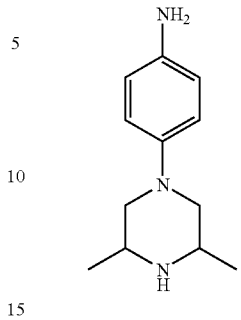

3,5-Dimethyl-1-(4-nitro-phenyl)-piperazine (1.40 g, 5.90 mmol) is dissolved in 20 ml of methanol with ~1 g of Raney nickel suspension. Hydrazine (0.576 g, 14.9 mmol) is dissolved in 20 ml of methanol and added dropwise to the reaction mixture over 20 minutes. Mixture is stirred at room temperature for 3 hours. Mixture is filtered through celite and reduced on rotovap to afford the product as a black solid (1.05 g, 67%); $^1$H NMR (DMSO-$d_6$) δ 0.94 (d, J=6.3 Hz, 6H), 1.93-2.00 (m, 2H), 2.65-2.85 (m, 3H), 3.13-3.20 (m, 2H), 4.45 (bs, 2H), 6.43 (d, J=8.5 Hz, 2H), 6.61 (d, J=8.5 Hz, 2H).

Intermediate 262

Dimethylaminomethyl-phenylamine

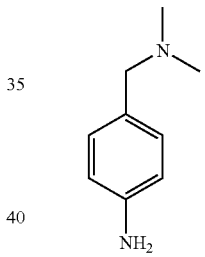

Dimethylaminomethyl-phenylamine is prepared using a procedure of steps 1-2 of Intermediate 259 and dimethylamine as the starting amine.

Intermediate 263

Diethylaminomethyl-phenylamine

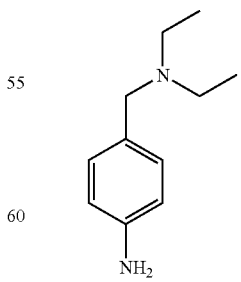

Diethylaminomethyl-phenylamine is prepared using a procedure of steps 1-2 of Intermediate 259 and diethylamine as the starting amine.

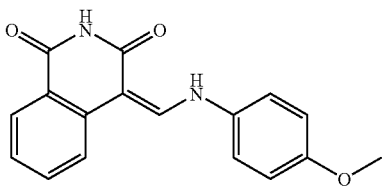

Example 1

(4Z)-4-{[(4-Methoxyphenyl)amino]methylene}isoquinoline-1,3(2H,4H)-dione

A toluene (3 mL) solution containing (4E)-4-[(dimethylamino)methylene]-1,4-dihydro-3(2H)-isoquinolinone (300 mg, 1.48 mmol) and 4-methoxyphenylamine (204 mg, 1.66 mmol) is heated at 110° C. for 4 h. After cooling in the refrigerator, the crystalline product is collected and washed with ether to give 0.11 g (26.5%) yellow solid mp 150-151° C.; HRMS (ESI) m/z calcd for $C_{17}H_{16}N_2O_6$ 281.12846. found 281.12865 $(M+H)^{-1}$. Analysis for $C_{17}H_{16}N_2O_6$: Calcd: C, 72.84; H, 5.75; N, 9.99. Found: C, 72.72; H, 5.88; N, 9.76.

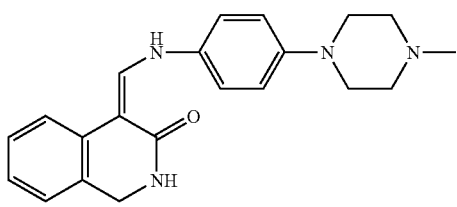

Example 2

(4Z)-4-({[4-(4-Methyl-1-piperazinyl)phenyl]amino}methylene)-1,4-dihydro-3(2H)-isoquinolinone A toluene (3 mL) solution containing (4E)-4-[(dimethylamino)methylene]-1,4-dihydro-3(2H)-isoquinolinone (300 mg, 1.48 mmol) and 4-(4-methyl-piperazin-1-yl)-phenylamine (318 mg, 1.66 mmol) is heated at 110° C. for 4 h. Using the same workup as example 1, 0.13 g (25%) orange solid is obtained: mp 186-187° C. (dec.); HRMS (ESI) m/z calcd for C21H24N4O 349.20229. found 349.20180 $(M+H)^{+1}$.

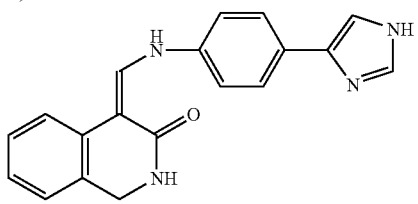

Example 3

(4Z)-4-({[4-(1H-Imidazol-4-yl)phenyl]amino}methylene)-1,4-dihydro-3(2H)-isoquinolinone A toluene (3 mL) solution containing (4E)-4-[(dimethylamino)methylene]-1,4-dihydro-3(2H)-isoquinolinone (300 mg, 1.48 mmol) and 4-(1H-imidazol-4-yl)aniline (265 mg, 1.66 mmol) is heated at 110° C. for 4 h. Using the same workup as example 1, 0.13 g (28%) orange solid is obtained: mp 151-152° C. (dec.); HRMS (ESI) m/z calcd for C19H16N4O 317.13969. found 317.13894 $(M+H)^{+1}$.

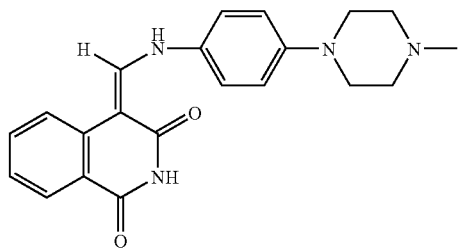

Example 4

(4Z)-4-({[4-(4-Methylpiperazin-1-yl)phenyl]amino}methylene)isoquinoline 1,3(2H,4H)-dione A mixture of 4-methoxymethylene-4H-isoquinoline-1,3-dione (101.5 mg, 0.5 mmol), 4-(4-methyl-piperazin-1-yl)-phenylamine (95.6 mg, 0.5 mmol) in 1 mL of N,N-dimethylformamide is heated at 110° C. for 1 h. After cooling in the refrigerator, the precipitate is collected, and washed with ether to give 163 mg (90%) of yellow solid mp 245-246° C.; MS (ESI) m/z 363.19 (M+1); Analysis for $C_{21}H_{22}N_4O_2$: Calcd: C, 69.59; H, 6.12; N, 15.46. Found: C, 69.49; H, 6.10; N, 15.36.

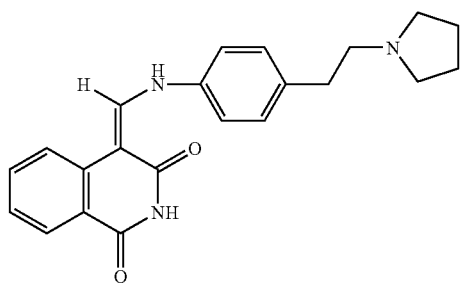

Example 5

(4Z)-4-({[4-(2-Pyrrolidin-1-ylethyl)phenyl]amino}methylene)isoquinoline-1,3(2H,4H)-dione A mixture of 4-methoxymethylene-4H-isoquinoline-1,3-dione (101.5 mg, 0.5 mmol), 4-(2-pyrrolidin-1-yl-ethyl)-phenylamine (95.2 mg, 0.5 mmol) in 1 mL of N,N-dimethylformamide is heated at 110° C. for 1.5 h. After cooling in the refrigerator, the precipitate is collected, and washed with ether to give 129 mg (71%) of yellow solid mp 224-225° C.; MS (ESI) m/z 362.20 (M+1); Analysis for $C_{22}H_{23}N_3O_2$:

Calcd: C, 73.11; H, 6.41; N, 11.63. Found: C, 72.33; H, 6.45; N, 11.59.

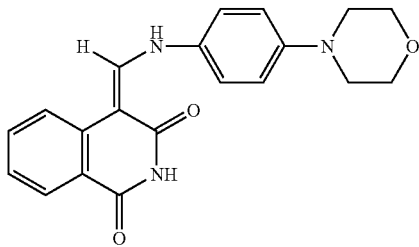

(4Z)-4-{[(4-Morpholin-4-ylphenyl)amino]methylene}isoquinoline-1,3(2H,4H)-dione

A mixture of 4-methoxymethylene-4H-isoquinoline-1,3-dione (101.5 mg, 0.5 mmol), 4-morpholin-4-yl-phenylamine (89.12 mg, 0.5 mmol) in 1 mL of N,N-dimethylformamide is heated at 110° C. for 1 h. After cooling in the refrigerator, the precipitate is collected, and washed with ether to give 139 mg (80%) of greenish yellow solid mp 257-258° C.; MS (ESI) m/z 350.17 (M+1); Analysis for $C_{20}H_{19}N_3O_3$: Calcd: C, 68.75; H, 5.48; N, 12.03. Found: C, 68.49; H, 5.57; N, 11.90.

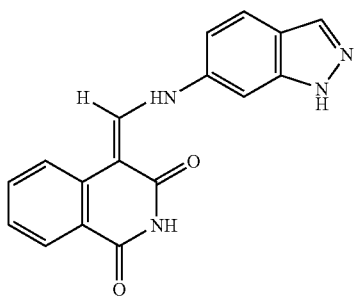

Example 7

(4Z)-4-[(1H-Indazol-6-ylamino)methylene]isoquinoline-1,3(2H,4H)-dione

A mixture of 4-methoxymethylene-4H-isoquinoline-1,3-dione (101.5 mg, 0.5 mmol), 1H-indazol-6-ylamine (66.6 mg, 0.5 mmol) in 1 mL of N,N-dimethylformamide is heated at 110° C. for 1 h. After cooling in the refrigerator, the precipitate is collected, and washed with ether to give 79.4 mg (52%) of yellow solid mp >300° C.; MS (ESI) m/z 305.10 (M+1);

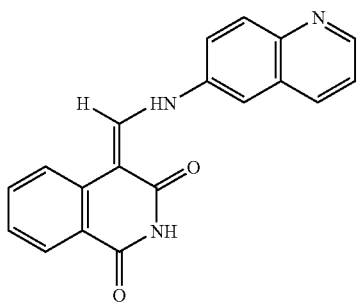

Example 8

(4Z)-4-[(Quinolin-6-ylamino)methylene]isoquinoline-1,3(2H,4H)-dione

A mixture of 4-methoxymethylene-4H-isoquinoline-1,3-dione (101.5 mg, 0.5 mmol), quinolin-6-ylamine (72.2 mg, 0.5 mmol) in 1 mL of N,N-dimethylformamide is heated at 110° C. for 1 h. After cooling in the refrigerator, the precipitate is collected, and washed with ether to give 130 mg (82%) of greenish yellow solid mp 277-278° C.; MS (ESI) m/z 316.10 (M+1); Analysis for $C_{19}H_{13}N_3O_2$: Calcd: C, 72.37; H, 4.16; N, 13.33. Found: C, 71.86; H, 4.02; N, 13.25.

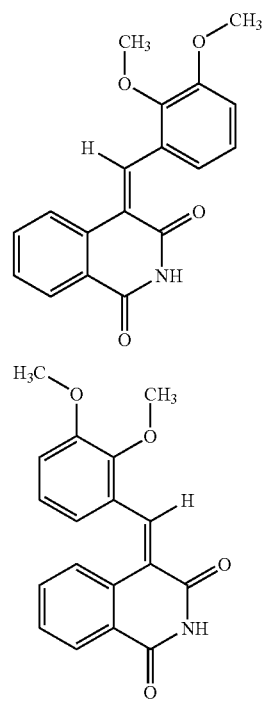

Example 9

(4E)-4-(2,3-dimethoxybenzylidene)isoquinoline-1,3 (2H,4H)-dione-(4Z)-4-(2,3-dimethoxybenzylidene) isoquinoline-1,3(2H,4H)-dione (1:1):

An amount of 100 mg (0.62 mmol) of isoquinoline-1,3 (4H)-dione (CL-243165) and 2,3-dimethoxybenzylaldehyde (168.53 mg, 0.070 mmol) were stirred in 1% piperidine in isopropanol (2-propanol) (3.0 mL) at 90° C. for four hours. After cooling, the mixture is concentrated to dryness. The residue is dissolved in ethyl acetate and the precipitate is filtered. The solution is purified by preparative thin layer chromatography (1:2=ethyl acetate:hexane), to give a yellow solid 41 mg (21% yield): mp 154-155° C.;

MS (ESI) m/z 310.1 (M+1)

$^1$H NMR (400 MHz, DMSO-D6) ppm 3.74-3.78 (m, 3H) 3.82-3.89 (m, 3H) 6.84 (d, J=7.05 Hz, 1H) 6.98-7.23 (m, 2H) 7.34-7.54 (m, 3H) 7.92-8.23 (m, 2H) 11.64 (s, 1H)

Anal. (C$_{18}$H$_{15}$NO$_4$.C$_{18}$H$_{15}$NO$_4$) C, H, N Calcd: C, 69.41; H, 4.93; N, 4.50. Found: C, 69.34; H, 5.15; N, 4.35.

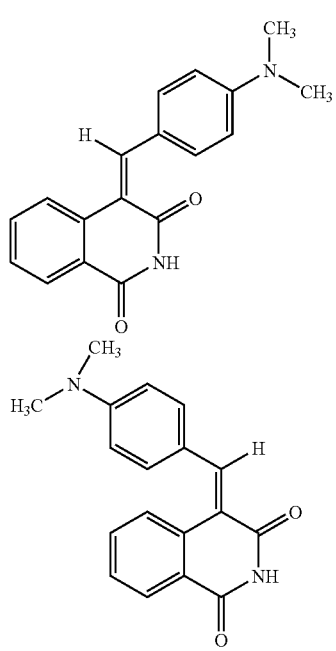

Example 10

(4E)-4-[4-(dimethylamino)benzylidene]isoquinoline-1,3(2H,4H)-dione-(4Z)-4-[4-(dimethylamino)benzylidene]isoquinoline-1,3(2H,4H)-dione (1:1):

Using the procedure described for the preparation of (4E)-4-(2,3-dimethoxybenzylidene)isoquinoline-1,3(2H,4H)-dione-(4Z)-4-(2,3-dimethoxybenzylidene)isoquinoline-1,3 (2H,4H)-dione (1:1) 60 mg (33% yield) of red solid is obtained from 100 mg (0.68 mmol) of isoquinoline-1,34H)-dione (CL-243165) and 4-dimethylaminobenzylaldehyde (204 mg, 1.24 mmol): mp 179-180° C.;

MS (ESI) m/z 293.2 (M+1).

$^1$H NMR (400 MHz, DMSO-D6) δ ppm 3.01 (s, 6H) 3.06 (s, 4H) 6.73 (dd, J=14.86, 9.07 Hz, 3H) 7.29-7.55 (m, 5H) 7.70 (s, 1H) 7.93-8.00 (m, 2H) 8.01-8.08 (m, 2H) 8.12 (d, J=8.06 Hz, 1H) 8.17 (d, J=8.81 Hz, 2H) 11.27 (s, 1H) 11.40 (s, 2H)

Anal. (C$_{16}$H$_{11}$NO$_3$.C$_{16}$H$_{11}$NO$_3$.0.4H$_2$O)C, H, N Calcd: C, 70.52; H, 4.37; N, 5.14. Found: C, 70.68; H, 4.16; N, 5.02.

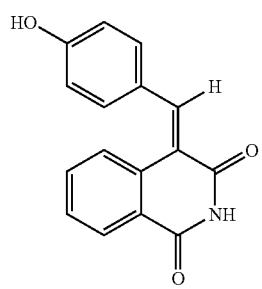

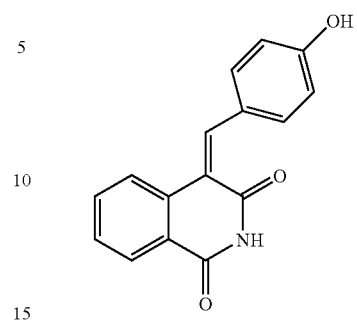

Example 11

(4E)-4-(4-hydroxybenzylidene)isoquinoline-1,3(2H, 4H)-dione

Using the procedure described for the preparation of (4E)-4-(2,3-dimethoxybenzylidene)isoquinoline-1,3(2H,4H)-dione-(4Z)-4-(2,3-dimethoxybenzylidene)isoquinoline-1,3 (2H,4H)-dione (1:1), 160 mg (24% yield) of orange solid is obtained from 400 mg (2.48 mmol) of isoquinoline-1,34H)-dione and 4-hydroxybenzylaldehyde (666 mg, 5.46 mmol): mp 242-243° C.;

MS (ESI) m/z 266.2 (M+1).

$^1$H NMR (400 MHz, DMSO-D6) δ ppm 6.45-7.04 (m, 3H) 7.35-7.58 (m, 5H) 7.66-7.82 (m, 2H) 7.89-8.00 (m, 2H) 7.93-7.99 (m, 2H) 8.01-8.09 (m, 2H) 8.12 (d, J=8.06 Hz, 1H) 10.10 (s, 2H) 11.36 (s, 1H) 11.51 (s, 1H)

Anal. (C$_{18}$H$_{15}$NO$_4$.C$_{18}$H$_{15}$NO$_4$ 0.1H$_2$O)C, H, N Calcd: C, 69.48; H, 4.93; N, 4.50. Found: C, 69.41; H, 4.85; N, 4.39.

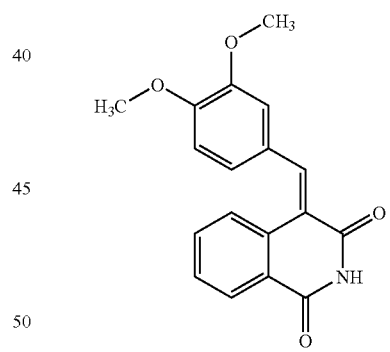

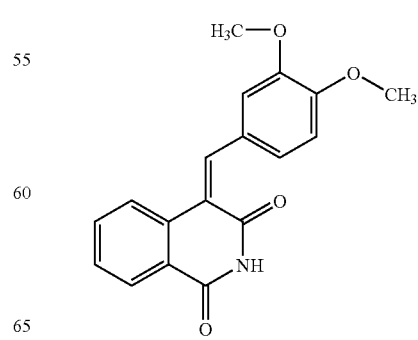

Example 12

(4E)-4-(3,4-dimethoxybenzylidene)isoquinoline-1,3(2H,4H)-dione

Using the procedure described for the preparation of (4E)-4-(2,3-dimethoxybenzylidene)isoquinoline-1,3(2H,4H)-dione-(4Z)-4-(2,3-dimethoxybenzylidene)isoquinoline-1,3(2H,4H)-dione (1:1), 300 mg (39% yield) of yellow solid is obtained from 400 mg (2.48 mmol) of isoquinoline-1,34H)-dione and 3,4-dimethoxybenzylaldehyde (618.19 mg, 3.72 mmol): mp 194-195° C.;

MS (ESI) m/z 310.1 (M+1).

$^1$H NMR (400 MHz, DMSO-D6) ppm 2.35 (s, 6H) 7.16-7.27 (m, 2H) 7.30-7.38 (m, 2H) 7.47 (dd, J=7.55, 1.76 Hz, 2H) 7.62 (dd, J=7.93, 1.13 Hz, 2H)

Anal. ($C_{18}H_{16}N_2O_2 \cdot C_{18}H_{16}N_2O_2 \cdot 0.3H_2O$)C, H, N Calcd: C, 72.60; H, 5.62; N, 9.41. Found: C, 72.64; H, 5.72; N, 9.34.

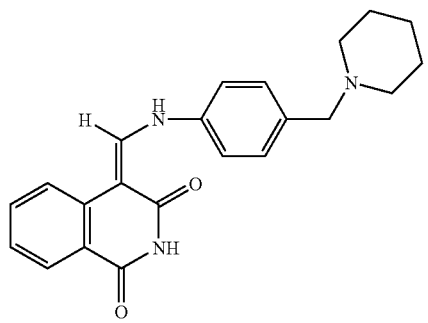

Example 13

(4Z)-4-({[4-(Piperidin-1-ylmethyl)phenyl]amino}methylene)isoquinoline-1,3(2H,4H)-dione A mixture of 4-methoxymethylene-4H-isoquinoline-1,3-dione (101.5 mg, 0.5 mmol), 4-piperidin-1-ylmethyl-phenylamine (95.14 mg, 0.5 mmol) in 1 mL of N,N-dimethylformamide is heated at 110° C. for 2 h. After cooling in the refrigerator, the precipitate is collected, and washed with ether to give 92 mg (51%) of yellow solid mp 185-186° C.; HRMS (ESI) m/z calcd for C22H23N3O2 362.18546. found 362.18631 (M+H)$^{+1}$.

Example 14

(4Z-4-[{3-Chloro-4[(1-methyl-1H-imidazole-2-uy)thio]phenyl}amino)methylene]isoquinoline-1,3(2H,4H)-dione An amount of 150 mg (0.74 mmol) (4E)-4-(methoxymethylene)isoquinoline-1,3(2H,4H)-dione is stirred in N,N-dimethylformamide (8.5 mL) followed by addition of 3-chloro-4-(1H-imidazole-2-ylsulfanyl)-phenylamine (168.53 mg, 0.070 mmol). The reaction mixture is heated at 110° C. for 1 h. After cooling to room temperature, ether is added, and the precipitate is filtered to give a yellow solid (170 mg, 56%): mp 264-265° C.; MS (ESI) m/z 410.2 (M+1)

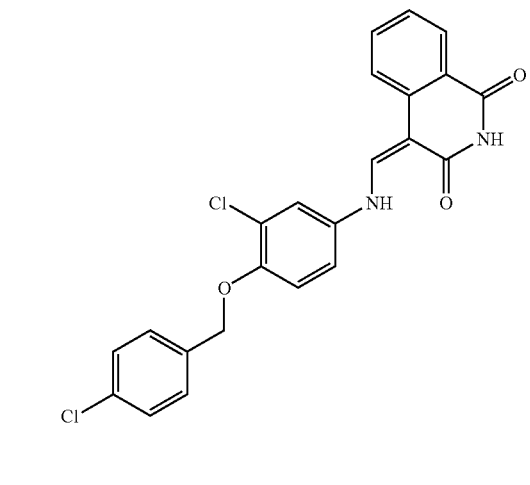

Example 15

(4Z)-4-[({3-Chloro-4-{(4chlorobenzyl)oxy]phenyl}amino)methylene]isoquinoline-1,3(2H,4H-dione Using the procedure described for the preparation of example 14165 mg, (48% yield) of brown-yellow solid is obtained from 150 mg (0.74 mmol) of (4E)-4-(methoxymethylene)isoquinoline-1,3(2H,4H)-dione, and 187.72 mg (0.95 mmol) of 4-chloro-3-(4-chloro-benzyloxy)-phenylamine; mp 278-279° C., MS (ESI) m/z 457.4 (M−1)

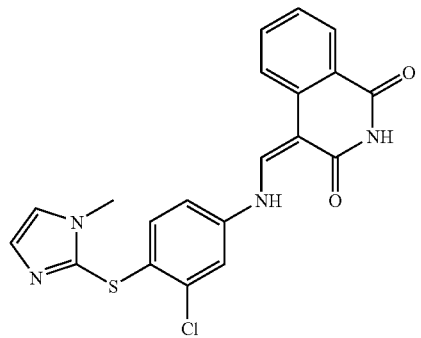

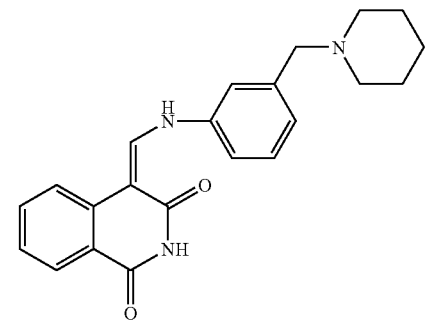

Example 16

(4Z)-4-({[3-(Piperidin-1-ylmethyl)phenyl]amino}methylene)isoquinoline-1,3(2H,4H)-dione) (1b)

Using the procedure described for the preparation of (4Z)-4-({[3-(azepan-1-ylmethyl)phenyl]amino}methylene)isoquinoline-1,3(2H,4H)-dione, 0.52 g (58.5%) of yellow solid is obtained from 0.5 g (2.46 mmol) of (4E)-4-(methoxymethylene)-isoquinoline-1,3(2H,4H)-dione and 0.47 g (2.46 mmol) of 3-Piperidin-1-ylmethyl-phenylamine. mp 173-174° C.; $^1$H NMR (DMSO-d$_6$) δ 12.44 (d, J=9 Hz, 1H), 11.33 (s, 1H), 8.90 (d, J=9 Hz, 1H), 8.18 (d, J=9 Hz, 1H), 8.03 (d, J=9 Hz, 1H), 7.63 (m, 1H), 7.46 (s, 1H), 7.39 (m, 2H), 7.29 (t, J=6 Hz, 1H), 7.12 (d, J=6 Hz, 1H), 3.46 (s, 2H), 2.35 (s, 4H), 1.52 (m, 4H), 1.40 (d, J=3.6 Hz, 2H); MS (ESI) m/z 362.2 (M+H)$^{+1}$; Analysis for C$_{22}$H$_{23}$N$_3$O$_2$; Calcd: C, 73.1; H, 6.41; N, 11.60. Found: C, 72.85; H, 6.33; N, 11.42.

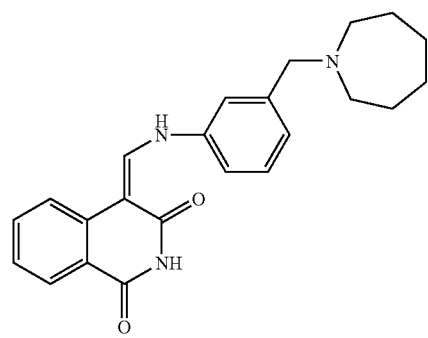

Example 17

(4Z)-4-({[3-(Azepan-1-ylmethyl)phenyl]amino}methylene)isoquinoline-1,3(2H,4H)-dione An amount of (4E)-4-(methoxymethylene)-isoquinoline-1,3(2H,4H)-dione (1.0 g, 4.9 mmol) is added to N,N'-dimethylformamide, followed by 3-(azepan-1-ylmethyl)aniline (1.0 g, 4.9 mmol). The reaction mixture is heated at 120° C. under N$_2$ for 40 minutes. After evaporating to dryness, the red oil is dissolved in warm ethyl acetate and filtered through a pad of celite to give a yellow solution. Addition of hexane into this organic solution yielded an orange precipitate, which is collected and recrystallized from EtOAc/Hex to give orange crystal (0.925 g, 50.05% yield): mp 116-117° C.; $^1$H NMR (DMSO-d$_6$) δ 12.43 (d, J=9 Hz, 1H), 11.33 (s, 1H), 8.80 (d, J=9 Hz, 1H), 8.18 (d, J=9 Hz, 1H), 8.04 (d, J=9 Hz, 1H), 7.63 (t, J=6 Hz, 1H), 7.46 (s, 1H), 7.39 (m, 2H), 7.30 (t, J=3 Hz, 1H), 7.17 (d, J=6 Hz, 1H), 3.64 (s, 2H), 2.60 (s, 4H), 1.58 (m, 8H); MS (ESI) m/z 376.1 (M+H)$^{+1}$; Analysis for C$_{23}$H$_{25}$N$_3$O$_2$; Calcd: C, 73.6; H, 6.71; N, 11.2. Found: C, 72.92; H, 6.45; N, 11.03.

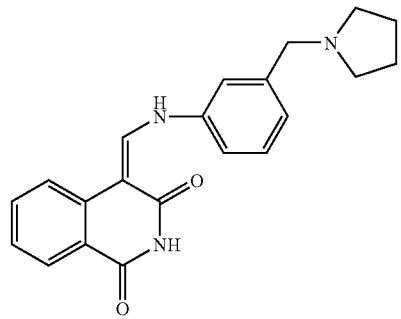

Example 18

(4Z)-4-({[3-(Pyrrolidin-1-ylmethyl)phenyl]amino}methylene)isoquinoline-1,3(2H,4H)-dione) (1c)

Using the procedure described for the preparation of (4Z)-4-({[3-(azepan-1-ylmethyl)phenyl]amino}methylene)isoquinoline-1,3(2H,4H)-dione, 0.61 g (71.3%) of yellow solid is obtained from 0.5 g (2.46 mmol) of (4E)-4-(methoxymethylene)-isoquinoline-1,3(2H,4H)-dione and 0.434 g (2.46 mmol) of 3-Pyrrolidin-1-ylmethyl-phenylamine, mp 172-173° C.; $^1$H NMR (DMSO-d$_6$) δ 12.43 (d, J=9 Hz, 1H), 11.33 (s, 1H), 8.90 (d, J=9 Hz, 1H), 8.18 (d, J=6 Hz, 1H), 8.03 (d, J=6 Hz, 1H), 7.64 (t, J=6 Hz, 1H), 7.46 (m, 2H), 7.38 (t, J=6 Hz, 1H), 7.29 (d, J=6 Hz, 1H), 7.13 (d, J=6 Hz, 1H), 3.61 (s, 2H), 2.46 (s, 4H), 1.70 (t, J=2.7 Hz, 4H); MS (ESI) m/z 346.2 (M−H)$^{-1}$; Analysis for C$_{21}$H$_{21}$N$_3$O$_2$; Calcd: C, 73.6; H, 6.09; N, 12.1. Found: C, 72.2; H, 5.99; N, 11.96.

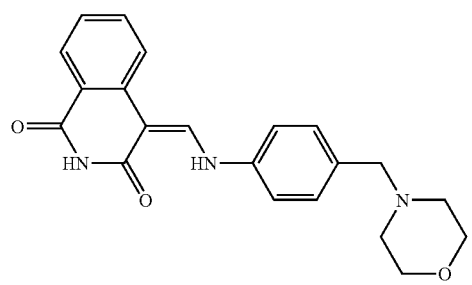

Example 19

(4Z)-4-({[4-(Morpholin-4-ylmethyl)phenyl]amino}methylene)isoquinoline-1,3(2H,4H)-dione (3)

Using the procedure described for the preparation of elxample 14, 100 mg (15% yield) of a yellow solid from 300 amine 283.5 mg (1.47 mmol); mp 221-2MS (ESI) m/z 463.1 mg (1.47 mmol) of (4E)-4-(methoxymethylene)isoquino

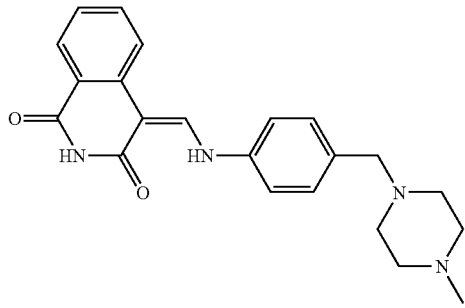

Example 20

(4Z)-4-[({4-[(4-Methylpiperazin-1-yl)methyl]phenylamino)mathylene]isoquilin-1,3(2H,4H)-dione (4)

Using the procedure described for the preparation of example 14, 170 mg (18% yield) is obtained as a yellow solid from 500 mg (2.46 mmol) of (4E)-4-(methoxymethylene)isoquinoline-1,3(2H,4H)-dione and 500 mg (2.46 mmol) 4-(4-methylpiperazin-1-yl)methyl-phenylamine (4-Morpholin-4-ylmethyl-phenylamine); mp 231-232° C.; MS (ESI) m/z 376.5 (M−1).

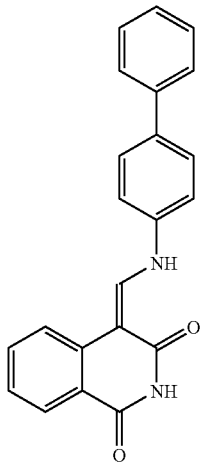

Example 21

(4Z)-4-[(1,1'-Biphenyl-4-ylamino)methylene]isoquinoline-1,3(2H,4H)-dione

A mixture of 0.500 g (2.46 mmol) of 4-methoxymethylene-4H-isoquinoline-1,3-dione and 0.416 g (2.46 mmol) of 4-aminobiphenyl in 8 mL of N,N-dimethylformamide is heated at 105° C. under $N_2$ for 1.5 h. The reaction is then chilled in ice and the solid product is collected. It is washed with cold N,N-dimethylformamide (DMF) and $Et_2O$ and dried in vacuo to give 0.295 g (35%) of yellow crystals: mp 261-262° C.; $^1$H NMR (DMSO-$d_6$) δ 12.5 (d, 1H, J=9 Hz), 11.4 (s, 1H), 9.94 (d, 1H, J=9 Hz), 8.21 (d, 1H, J=6 Hz), 8.05 (d, 1H, J=6 Hz), 7.68 (m, 7H), 7.47 (m, 2H), 7.36 (m, 2H); HRMS (ESI) m/z calcd for $C_{22}H_{16}N_2O_2$ 341.12846. found 341.12811 (M+H)$^{+1}$; Analysis for $C_{22}H_{16}N_2O_2$; Calcd: C, 77.63; H, 4.74; N, 8.23. Found: C, 77.36; H, 4.66; N, 8.25.

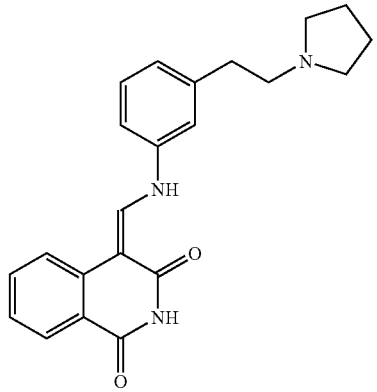

Example 22

(4Z)-4-({[3-(2-Pyrrolidin-1-ylethyl)phenyl]amino}methylene)isoquinoline-1,3(2H,4H)-dione Prepared from a solution of 0.256 g (1.26 mmol) of 4-methoxymethylene-4H-isoquinoline-1,3-dione and 0.240 g (1.26 mmol) of 3-(2-pyrrolidin-1-yl-ethyl)-phenylamine in 4 mL of N,N-dimethylformamide (DMF) at 100° C. under $N_2$ as described for example 21. After heating for 1 h, solvent is removed and the residue is filtered through Magnesol (20% MeOH in CHCl$_3$). Solvent evaporation gave 0.420 g (92%) of a red glass: $^1$H NMR (DMSO-$d_6$) δ 12.40 (d, 1H, J=9.0 Hz), 11.33 (s, 1H), 8.90 (d, 1H, J=9.0 Hz), 8.17 (d, 1H, J=6.0 Hz), 8.03 (d, 1H, J=6.0 Hz), 7.62 (m, 1H), 7.46 (s, 1H), 7.30 (m, 3H), 7.04 (d, 1H, J=6.0 Hz), 2.70 (m, 4H), 2.50 (m, 4H), 1.67 (m, 4H); HRMS (ESI) m/z calcd for $C_{22}H_{23}N_3O_2$ 362.18631. found 362.18574 (M+H)$^{-1}$; Analysis for $C_{22}H_{23}N_3O_2 \cdot 0.75H_2O$; Calcd: C, 70.46; H, 6.60; N, 11.21. Found: C, 70.83; 6.61; N, 11.24.

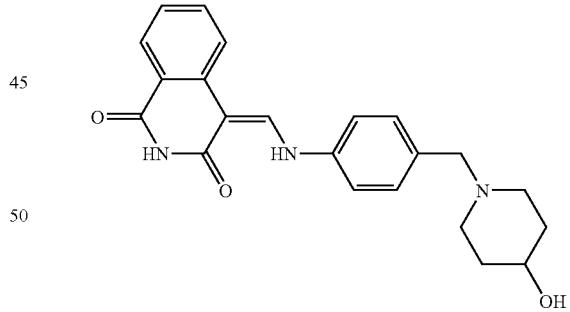

Example 23

(4Z)-4-[({4-[(4-Hydroxypiperidin-1-yl)methyl]phenyl}amino)methylene]isoquinolin-1,3(2H,4H)-dione Using the procedure described for the preparation of -(4Z)-4-[(1H-Indazol-6-ylamino)methylene]isoquinoline-1,3(2H,4H)-dione, 450 mg (48% yield) of a white solid is obtained from 500 mg (2.46 mmol) of (4E)-4-(methoxymethylene)isoquinoline-1,3(2H,4H)-dione and 4-(4-hydroxypiperidin- 1-yl)methylphenyl-amine 500 mg (2.46 mmol) (4-Morpholin-4-ylmethyl-phenylamine); mp 224-225° C.; MS (ESI) m/z 377.4 (M+1).

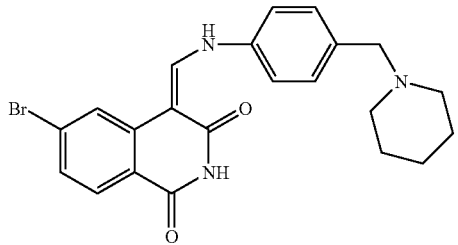

Example 24

(4Z)-6-Bromo-4-{[(4-piperidin-1-ylmethyl)phenyl]amino}methyleneisoquinoline-1,3(2H,4H)-dione Using the procedure described for (4Z)-4-({[4-(piperidin-1-ylmethyl)phenyl]amino}methylene)isoquinoline-1,3(2H,4H)-dione (Example 13), 141 mg (0.50 mmol) of (4E)-6-bromo-4-(methoxymethylene)isoquinoline-1,3(2H,4H)-dione is reacted with 100 mg (0.525 mmol) of 4-(piperidin-1-ylmethyl)phenylamine to give 138 mg (63%) of off-white solid, mp 222-225°; MS (ES+) m/z 440.1, 442.1 (M+H)$^{+1}$.

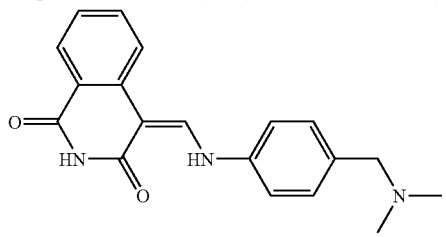

Example 25

(4Z)-4-[({4[(Dimethylamino)methyl]phenyl}amino)methylene]isoquinolin-1,3(2H,4H)-dione Using the procedure described for the preparation of example 14, 320 mg (40% yield) of yellow crystals is obtained from 500 mg (2.46 mmol) of (4E)-4-(methoxymethylene)isoquinoline-1,3(2H,4H)-dione and 4-dimethylaminomethyl-phenylamine 334.90 mg (2.46 mmol) (4-Morpholin-4-ylmethyl-phenylamine); mp 151-152° C., MS (ESI) m/z 321.4 (M−1).

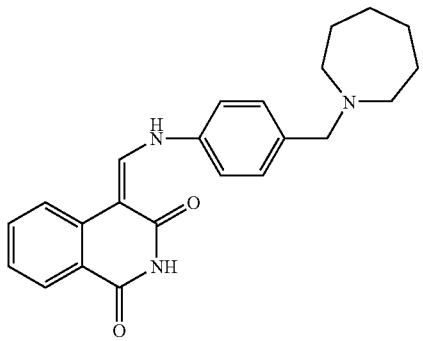

Example 26

(4Z)-4-({[4-(Azepan-1-ylmethyl)phenyl]amino}methylene)isoquinoline-1,3(2H,4H)-dione (1d)

Using the procedure described for the preparation of (4Z)-4-({[3-(azepan-1-ylmethyl)phenyl]amino}methylene)isoquinoline-1,3(2H,4H)-dione, 0.64 g (69.6%) of yellow solid is obtained from 0.5 g (2.46 mmol) of (4E)-4-(methoxymethylene)-isoquinoline-1,3(2H,4H)-dione, and 0.5 g (2.46 mmol) of 4-(azepan-1-ylmethyl)-aniline: mp 198-200° C.; $^1$H NMR (CDCl$_3$) δ 12.20 (d, J=9 Hz, 1H), 8.46 (s, 1H), 8.25 (d, J=6 Hz, 1H); 7.63 (m, 2H), 7.40 (d, J=6 Hz, 2H), 7.29 (m, 1H), 7.18 (d, J=9 Hz, 2H), 3.64 (s, 2H), 2.62 (s, 4H), 1.63 (s, 8H); MS (ESI) m/z 374.2 (M−H)$^1$. Analysis for C$_{23}$H$_{25}$N$_3$O$_2$. (0.67H$_2$O), Calcd: C, 71.29; H, 6.85; N, 10.84. Found: C, 71.02; H, 6.72; N, 10.76.

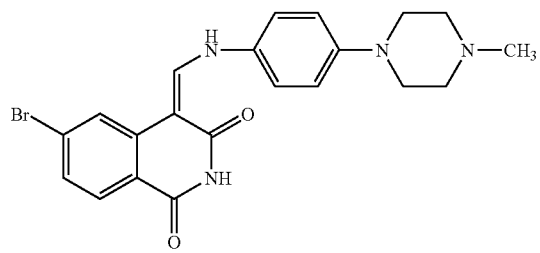

Example 27

(4Z)-6-Bromo-4-({[4-(4-methylpiperazin-1-yl)phenyl}amino}methylene)isoquinoline-1,3(2H,4H)-dione To a stirred mixture of 0.24 g (1.0 mmol) of 6-bromoisoquinoline-1,3(2H,4H)-dione, 0.20 g (1.05 mmol) of 4-(4-methylpiperazin-1-yl)methyl-phenylamine, and 1.0 ml of ethylene glycol is added 0.18 ml of triethyl orthoformate. The mixture is stirred for 5 m at 1500, warmed to 1800 during 10 m, and maintained at that temperature for 20 m. After cooling to 250, the mixture is stirred in 5:1 ether-hexane and H2O. The resulting solid is filtered, washed with water and 5:1 ether-hexane, and dried to give 0.4 g of foam. Recrystallization from DCM-EtOAC-hexane gave 78 mg (18%) of amber solid, mp 220-2230; MS (ES+) m/z 441.0, 443.0 (M+H)$^{+1}$

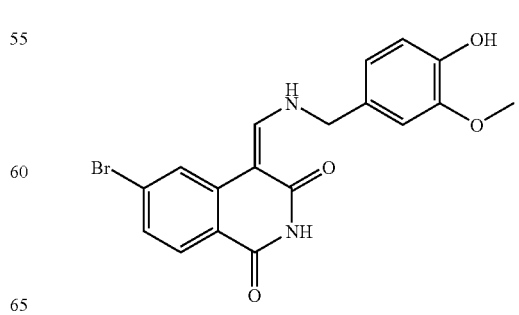

Example 28

(4Z)-6-Bromo-4-{[(4-hydroxy-3-methoxybenzyl)amino]methylene}isoquinoline-1,3(2H,4H)-dione (3a)

An amount of (4E)-6-bromo-4-(methoxymethylene)isoquinoline-1,3(2H,4H)-dione (0.3 g, 1.06 mmol) in N,N'-dimethylformamide is added to 0.2 g (1.06 mmol) of 4-hydroxyl-3-methoxybenzylamine hydrochloride, and 0.22 mL (2.12 mmol) of triethylamine. The reaction mixture is stirred at room temperature under $N_2$ for 2 h. Diethyl ether is added and the resulting tan precipitate is collected and washed successively with methanol, ether, and hexane to yield 0.28 g (65.1% yield) of light yellow solid: mp 260-261° C.; $^1$H NMR (DMSO-d$_6$) δ 11.07 (s, 1H), 10.69 (m, 1H), 9.02 (bs, 1H), 8.71 (d, J=9 Hz, 1H), 8.10 (s, 1H), 7.87 (d, J=9 Hz, 1H), 7.30 (d, J=6 Hz, 1H), 7.02 (s, 1H), 6.78 (m, 2H), 4.60 (d, J=4.8 Hz, 2H), 3.78 (s, 3H); MS (ESI) m/z 403.1 (M–H)$^{-1}$, Analysis for $C_{18}H_{15}BrN_2O_4$.(0.33H$_2$O), Calcd: C, 52.98; H, 3.76; N, 6.96. Found: C, 52.83; H, 3.86; N, 6.85.

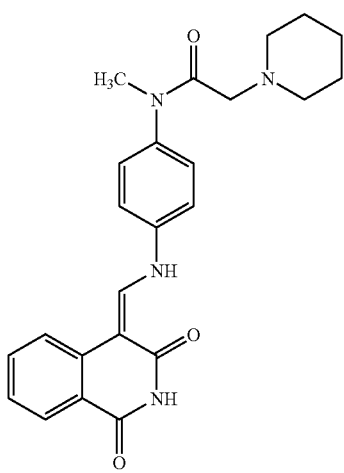

Example 29

N-(4-{[(Z)-(1,3-Dioxo-2,3-dihydroisoquinolin-4(1H)-ylidene)methyl]amino}phenyl)-1,3(2H,4H)-dione N-Methyl-2-piperidin-1-ylacetamide Prepared from a solution of 0.600 g (2.96 mmol) of 4-methoxymethylene-4H-isoquinoline-1,3-dione and 0.730 g (2.96 mmol) of N-methyl-N-phenyl-2-piperidin-1-yl-acetamide in 10 mL of N,N-dimethylformamide (DMF) at 100° C. under $N_2$ as described for example 21. Solvent removal after heating for 1 h gave a red oil which is diluted with 5% MeOH in CHCl$_3$. Insoluble material is filtered off and the filtrate is evaporated. The residue is again treated with 5% MeOH in CHCl$_3$ and filtered to give 0.187 g (15%) of insoluble orange crystals: mp 223-224° C.; $^1$H NMR (DMSO-d$_6$) δ 12.43 (d, 1H, J=12 Hz), 11.37 (s, 1H), 8.90 (d, 1H, J=12 Hz), 8.19 (d, 1H, J=9 Hz), 8.04 (d, 1H, J=6 Hz), 7.63 (d, 3H, J=9 Hz), 7.37 (m, 3H), 3.16 (s, 2H), 2.88 (m, 2H), 2.27 (s, 4H), 1.35 (m, 7H); HRMS (ESI) m/e calcd for $C_{24}H_{26}N_4O_3$ 419.20777. found 419.20746 (M+H)$^+$, Analysis for $C_{24}H_{26}N_4O_3$·CHCl$_3$: Calcd: C, 55.83; H, 5.07; N, 10.42. Found: C, 56.23; H, 4.96; N, 10.24.

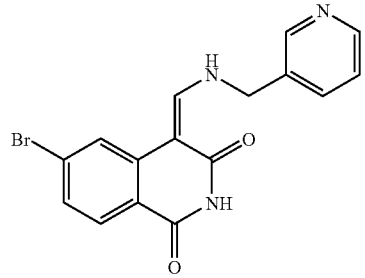

Example 30

(4Z)-6-Bromo-4-{[(pyridin-3-ylmethyl)amino]methylene}isoquinoline-1,3(2H,4H)-dione To a solution of (4E)-6-bromo-4-(methoxymethylene)isoquinoline-1,3(2H,4H)-dione (0.2 g, 0.71 mmol) in N,N'-dimethylformamide is added 3-(aminomethyl)pyridine (0.073 mL, 0.71 mmol). The reaction mixture is heated at 60° C. under $N_2$. After reaction is completed, diethyl ether is added, and the red precipitate is isolated and washed with methanol, ether, and hexane respectively to afford 0.16 g (63.2% yield) of orange solid: mp 299-300° C.; $^1$H NMR (DMSO-d$_6$) δ 11.09 (s, 1H), 10.69 (m, 1H), 8.74 (d, J=9 Hz, 1H), 8.63 (s, 1H), 8.52 (d, J=3 Hz, 1H), 8.10 (s, 1H), 7.84 (m, 2H), 7.42 (m, 1H), 7.31 (d, J=9 Hz, 1H), 3.40 (d, J=4.8 Hz, 2H); MS (ESI) m/z 355.7 and 357.7 (M–H)$^{-1}$, Analysis for $C_{16}H_{12}BrN_3O_2$, Calcd: C, 53.70; H, 3.38; N, 11.70. Found: C, 53.45; H, 3.23; N, 11.74.

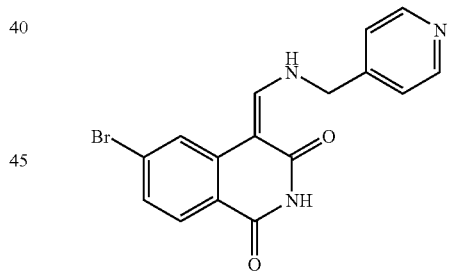

Example 31

(4Z)-6-Bromo-4-{[(pyridin-4-ylmethyl)amino]methylene}isoquinoline-1,3(2H,4H)-dione Using the procedure described for the preparation of 4-bromo-2-(carboxymethyl)benzoic acid, 0.11 g (43.5% yield) of tan solid is obtained from 0.2 g (0.71 mmol) of (4E)-6-bromo-4-(methoxymethylene)isoquinoline-1,3(2H,4H)-dione and 0.072 mL (0.71 mmol) of 2-(aminomethyl)-pyridine: mp 258-259° C.; $^1$H NMR (DMSO-d$_6$) δ 11.12 (s, 1H), 10.69 (m, 1H), 8.71 (d, J=9 Hz, 1H), 8.56 (s, 2H), 8.08 (s, 1H), 7.88 (d, J=9 Hz, 1H), 7.33 (m, 3H), 3.75 (d, J=4.8 Hz, 2H); MS (ESI) m/z 355.7 and 357.7 (M–H)$^{-1}$, Analysis for $C_{23}H_{25}N_3O_2 \cdot H_2O$, Calcd: C, 51.08; H, 3.75; N, 11.17. Found: C, 50.89; H, 3.49; N, 11.16.

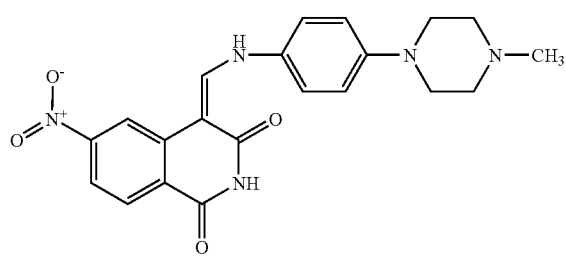

Example 33

(4Z)-6-Nitro-4-({[4-(4-methylpiperazin-1-yl)phenyl}amino}methylene)isoquinoline-1,3(2H,4H)-dione Using the procedure described for (4Z)-6-bromo-4-({[4-(4-methylpiperazin-1-yl)phenyl}amino}methylene)isoquinoline-1,3(2H,4H)-dione (Example 27), 0.21 g (1.0 mmol) of 6-nitroisoquinoline-1,3(2H,4H)-dione, 0.20 g of 4-(4-methylpiperazin-1-yl)methyl-phenylamine, 0.18 ml (1.1 mmol) of triethyl orthoformate, and 2.0 ml of ethylene glycol were reacted to give 0.13 g (32%) of amber solid, mp 250-2600 (dec); MS (ES+) m/z 408.2 (M+H)$^{+1}$

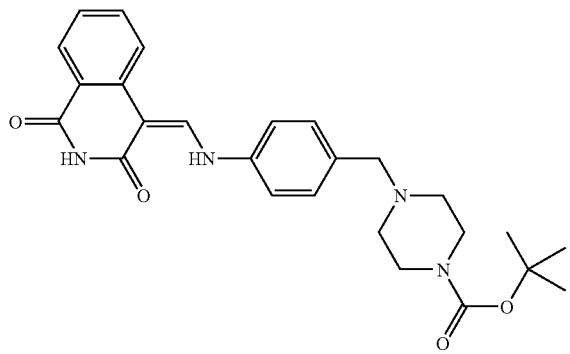

Example 34 tert-Butyl 4-(4-{[(Z)-1,3-dioxo-2,3-dihydroisoquinolin-4(1H)-ylidene)methyl]amino}piperazine-1-carboxylate Using the procedure described for the preparation of example 14, 3.2 g (70% yield) of a yellow solid is obtained from 2.0 g (9.84 mmol) of (4E)-4-(methoxymethylene)isoquinoline-1,3(2H,4H)-dione and 4-(4-amino-benzyl)-piperazine-1-carboxylic acid tert-butyl ester 2.86 g (9.84 mmol) (4-Morpholin-4-ylmethyl-phenylamine); mp 219-220° C., MS (ESI) m/z 462.6 (M−1).

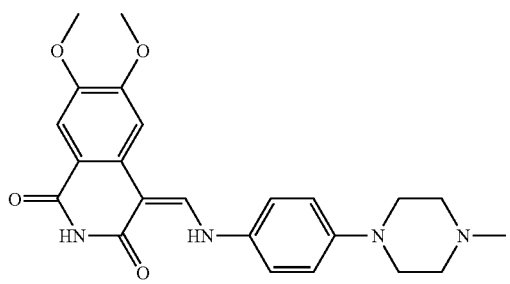

Example 37

(4Z)-6,7-Dimethoxy-4-({[4-(-methylpiperazin-1-yl)phenyl}amino)methylene] isoquinolin-1,3(2H,4H)-dione Using the procedure described for the preparation of example 14, 260 mg (76% yield of a yellow solid is obtained from 200 mg (0.80 mmol) of (4E)-6,7-dimethoxy-4-(methoxymethylene)isoquinoline-1,3(2H,4H)-dione and 4-(4-methylpiperazin-1-yl)phenylamine (153.08 mg, 0.80 mmol) mp 273-274° C., MS (ESI) m/z 422.48 (M−1).

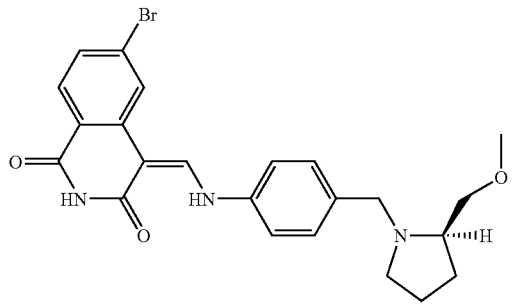

Example 38

(4Z)-6-Bromo-4-{[(4-{[(2s)-2-(methoxymethyl)pyrrolidin-1-yl]methyl}phenyl)amino)methylene}isoquinoline-1,3(2H,4H-dione Using the procedure described for the preparation of example 14, 200 mg (40% yield) of a yellow solid is obtained from 300 mg (1.063 mmol) of (4E)-6-bromo-4-(methoxymethylene)isoquinoline-1,3(2H,4H)-dione and 4-{[(2S)-2-(methoxymethyl)pyrrolidin-1-yl]methyl}phenylamine) (253.35 mg, 1.063 mmol), mp 129-130° C., MS (ESI) m/z 470.4 (M−1).

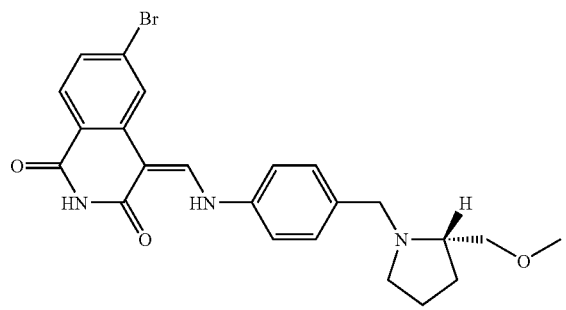

Example 39

(4Z)-6-Bromo-4-{[(4-{[(2R)-2-(methoxymethyl)pyrrolidin-1-yl]methyl}phenyl)amino)methylene}isoquinoline-1,3(2H,4H-dione Using the procedure described for the preparation of example 14, 250 mg (50% yield) of an orange solid is obtained from 300 mg (1.063 mmol) of (4E)-6-bromo-4-(methoxymethylene)isoquinoline-1,3(2H,4H)-dione and 4-{[(2R)-2-(methoxymethyl)pyrrolidin-1-yl]

methyl}phenylamine) (253.35 mg, 1.063 mmol), mp 129-130° C., MS (ESI) m/z 470.4 (M−1).

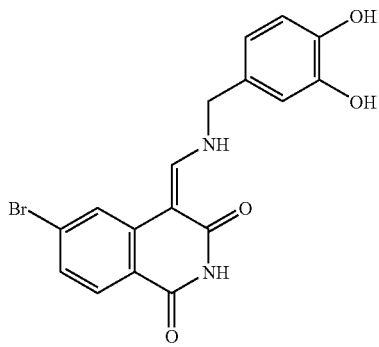

Example 40

(4Z)-6-Bromo-4-{[(3,4-dihydroxybenzyl)amino]methylene}isoquinoline-1,3(2H,4H)-dione According to general procedure 1, an amount of 3, 4 dihydroxybenzylamine (0.596 g, 4.3 mmol), is dissolved in N,N-dimethylformamide (61 mL). 1.8 ml (12.9 mmol) of triethylamine is added followed by 1.21 g (4.3 mmol) of (4E)-6-bromo-4-(methoxymethylene)isoquinoline-1,3(2H,4H)-dione. After the mixture is stirred at room temperature for 30 min, water (5 mL) is added and the reaction mixture is stirred for 60 min. The precipitate is filtered and washed several times with anhydrous ether. The crude solid is then purified by high performance liquid chromatography to give 910 mg of a white solid. MS (ESI) m/z 389.7 (M+1).

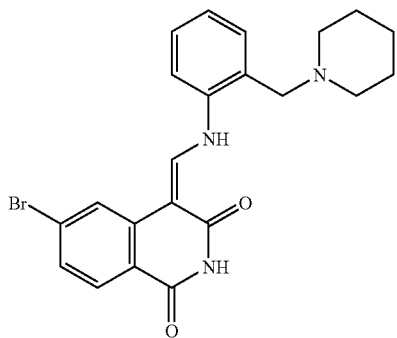

Example 41

(4Z)-6-Bromo-4-({[2-(piperidin-1-ylmethyl)phenyl}amino)methylene]isoquinolin-1,3(2H,4H)-dione Using the procedure described for the preparation of example 14, 200 mg (43% yield) of a yellow solid is obtained from 300 mg (1.06 mmol) of (4E)-6,7-dimethoxy-4-(methoxymethylene)isoquinoline-1,3(2H,4H)-dione and 2-piperidin-1-ylmethyl-phenylamine (213.11 mg, 1.06 mmol); mp 170-171° C., MS (ESI) m/z 440.34 (M+1).

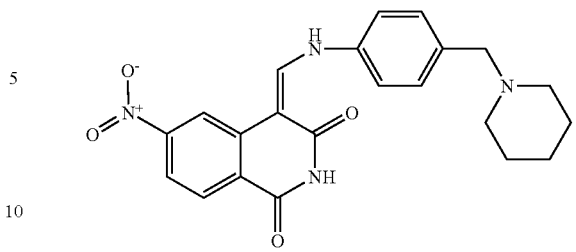

Example 42

(4Z)-6-Nitro-4-{[(4-piperidin-1-ylmethyl)phenyl]amino}methyleneisoquinoline-1,3(2H,4H)-dione Using the procedure described for (4Z)-4-[({3-chloro-4-[(1-methyl-1H-imidazol-2-yl)thio]phenyl}amino)methylene]isoquinoline-1,3(2H,4H)-dione, 115 mg (0.46 mmol) of (4E)-4-(methoxy)methylene-6-nitroisoquinoline-1,3(2H,4H)-dione is reacted with 93 mg (0.49 mmol) of 4-piperidin-1-ylmethyl-phenylamine to give 137 mg (73%) of brown solid, mp 225-235 (dec); MS (ES−) m/z 405.2 (M−H)$^{−1}$.

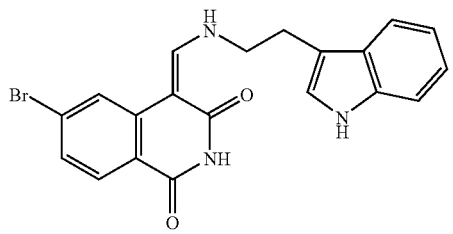

Example 43

(4Z)-6-Bromo-4-({[2-(1H-indol-3-yl)ethyl]amino}methylene)isoquinoline-1,3(2H,4H)-dione A mixture of 6-bromo-4-methoxymethylene-4H-isoquinoline-1,3-dione (124.5 mg, 0.44 mmol), tryptamine (70.7 mg, 0.44 mmol) in 1 mL of N,N-dimethylformamide is heated at 110° C. for 1.5 h. After cooling in the refrigerator, the precipitate is collected, and washed with ether to give 100 mg (55%) of yellow solid mp 278-280° C.; HRMS (ESI) m/z calcd for $C_{20}H_{16}BrN_3O_2$ 408.03531. found 408.03493 (M+H)$^{+1}$, Analysis for $C_{20}H_{16}BrN_3O_2$; Calcd: C, 58.55; H, 3.93; N, 10.24. Found: C, 58.34; H, 3.63; N, 10.21.

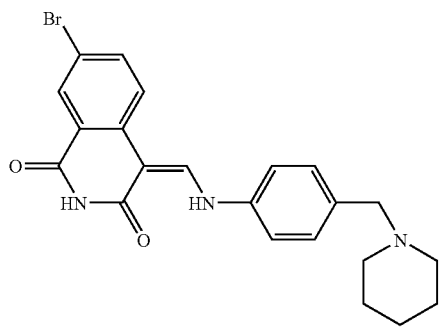

Example 44

(4Z)-7-Bromo-4-({[4-(Piperidin-1-ylmethyl)phenyl]amino}methylene)isoquinoline-1,3(2H,4H)-dione Using the procedure described for the preparation of example 14, 200 mg (43%) yield of a yellow solid is obtained from 300 mg (1.06 mmol) of (4E)-7-bromo-4-(methoxymethylene)isoquinoline-1,3(2H,4H)-dione and 4-piperidin-1-ylmethyl-phenylamine, mp 242-243° C., MS (ESI) m/z 440.34 (M+1).

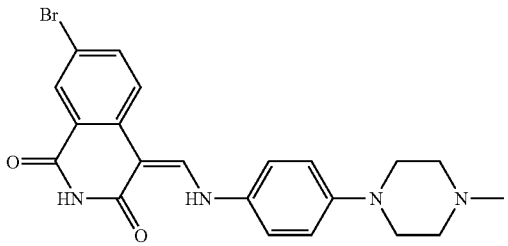

Example 45

(4Z)-7-Bromo-4-({[4-(4-methylPiperzin-1-yl)phenyl]amino}methylene)isoquinoline-1,3(2H,4H)-dione Using the procedure described for the preparation of example 14, 380 mg (81% yield) of a green-yellow solid is obtained from 300 mg (1.06 mmol) of (4E)-7-bromo-4-(methoxymethylene)isoquinoline-1,3(2H,4H)-dione and 4-(4-methylpiperazin-1-yl)-phenylamine (211.10 mg, 1.06 mmol), mp ° C., MS (ESI) m/z 441.33 (M+1).

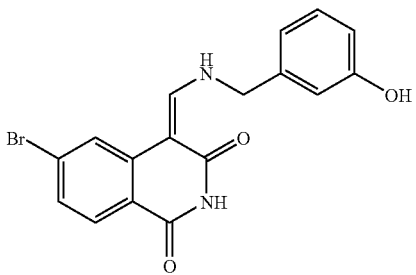

Example 46

(4Z)-6-Bromo-4-{[(3-hydroxybenzyl)amino)methylene}isoquinoline-1,3(2H,4-dione

An amount of 56 mg (0.35 mmol) of 3-hydroxy benzylamine hydrogen chloride (CL-119773), is dissolved in N,N-dimethylformamide (5 mL). 50 ul (0.75 mmol) of triethylamine is added followed by 100 mg (0.35 mmol) of (4E)-6-bromo-4-(methoxymethylene)isoquinoline-1,3(2H,4H)-dione. After the mixture is stirred at room temperature for 30 min, water (5 mL) is added and the reaction mixture is stirred for 5 min. The precipitate is filtered and washed several times with anhydrous ether to give 120 mg of example 46 as a off white solid (92% yield); mp ° C., MS (ESI) m/z 373.21 (M+1).

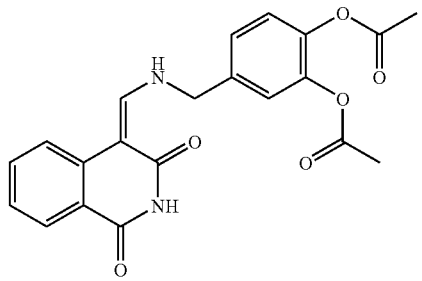

Example 47

2-(Acetyloxy)-4-({[(Z)-(1,3-dioxo-2,3-dihydroisoquinolin-4(1H)-ylidene)methyl]amino}-methyl)phenyl acetate A solution of 4Z)-4-{[(3,4-dihydroxybenzyl)amino]methylene}-isoquinoline-1,3(2H,4H)-dione, (0.2 g, 0.644 mmol) in 0.27 mL (1.93 mmol) of triethylamine and 5 mL of pyridine is stirred at room temperature for 10 min, then 0.1 mL (1.42 mmol) of acetyl chloride is added. The reaction mixture is stirred at room temperature under $N_2$ for 3 h. After evaporating the solvent, the residue is dissolved in dichloromethane, washed twice with water, dried over $Mg_2SO_4$, filtered and concentrated to give yellow solid. Recrystallized in EtOAc/Hex to afford 0.28 g (65.1% yield) of light yellow solid: mp 184-186° C.; MS (ESI) m/z 395.3 $(M+H)^{+1}$, Analysis for $C_{21}H_{18}N_2O_6$. Calcd: C, 63.96; H, 4.60; N, 7.10. Found: C, 63.56; H, 4.69; N, 6.72.

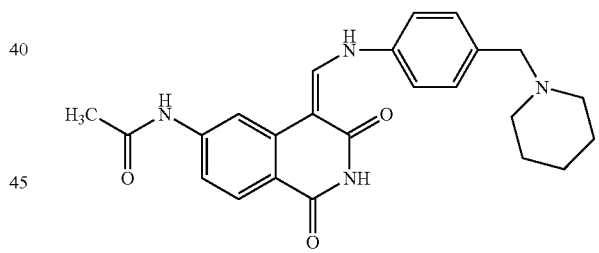

Example 48

N-[(4Z)-1,3-Dioxo-4-({[4-piperidin-1-ylmethyl)phenyl]amino}methylene)-1,2,3,4-tetrahydroisoquinolin-6-yl]acetamide Using the procedure of (4Z)-4-({[4-(4-methylpiperazin-1-yl)phenyl]amino}methylene)isoquinoline 1,3(2H,4H)-dione (Example 4), 94 mg (0.36 mmol) of N-[(4E)-1,3-dioxo-4-(methoxy)methylene-1,2,3,4-tetrahydroisoquinolin-6-yl]acetamide, 76 mg (0.40 mmol) of 4-(piperidin-1-ylmethyl)phenylamine, and 0.72 ml of N,N-dimethylformamide (DMF)

were reacted to give 89 mg (59%) of brown solid, mp >320°. MS (ES+) m/z 419.3 (M+H)$^{+1}$.

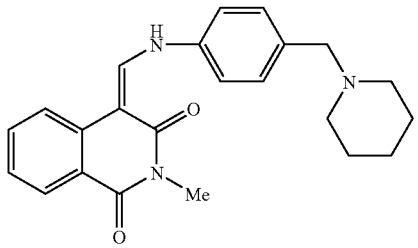

Example 49

(4Z)-2-Methyl-4-{[(4-piperidin-1-ylmethyl)phenyl]amino}methyleneisoquinoline-1,3(2H,4H)-dione A solution of 119 mg (0.55 mmol) of (4E)-N-methyl-4-(methoxymethylene)isoquinoline-1,3(2H,4H)-dione and 110 mg (0.58 mmol) of 4-piperidin-1-ylmethylaniline in 1.1 ml of N,N-dimethylformamide (DMF) is heated at 110° C. for 45 m, cooled, and diluted with Et$_2$O. After filtration the solution is concentrated under high vacuum to give 173 mg amorphous solid (82%), homogeneous on TLC; MS (ES+) m/z 376.3 (M+H)$^{+1}$, Analysis for C$_{23}$H$_{25}$N$_3$O$_2$.0.33H2O, Calcd: C, 72.42; H, 6.78; N, 11.02. Found: C, 72.68; H, 7.01; N, 11.15.

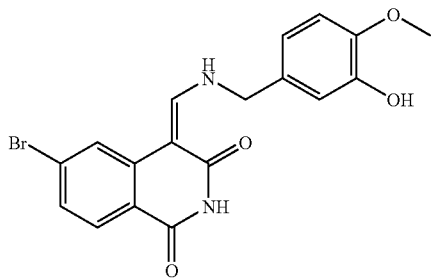

Example 50

(4Z)-6-Bromo-4-{[(3-hydroxy-4-methoxybenzyl)amino)methylene}isoquinoline-1,3(2H,4H-dione Using the procedure described for the preparation of example 46, 340 mg of light-brown solid (77% yield) is obtained from 300 mg (1.06 mmol) of (4E)-6,7-dimethoxy-4-(methoxymethylene)isoquinoline-1,3(2H,4H)-dione and 3-hydroxy-4-methoxy-benzylamine hydrogen chloride (201.2 mg, 1.06 mmol); mp 243-244° C., MS (ESI) m/z 413.23 (M+1).

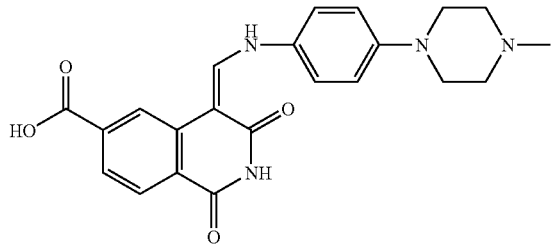

Example 51

(4Z)-4-({[4-(4-Methylpiperazin-1-yl)phenyl]amino}methylene)-1,3-dioxo-1,2,3,4-tetrahydroisoquinoline-6-carboxylic acid A mixture of 4-methoxymethylene-1,3-dioxo-1,2,3,4-tetrahydro-isoquinoline-6-carboxylic acid (90 mg, 0.364 mmol), 4-(4-methyl-piperazin-1-yl)-phenylamine (69.6 mg, 0.364 mmol) in 1 mL of N,N-dimethylformamide is heated at 100° C. for 1 h. After cooling in the refrigerator, the precipitate is collected, and washed with ether to give 96 mg (65%) of yellow solid mp 278-280° C.; HRMS (ESI) m/z calcd for C$_{22}$H$_{22}$N$_4$O$_4$ 407.17139. found 407.17128 (M+H)$^{+1}$, Analysis for C$_{22}$H$_{22}$N$_4$O$_4$, Calcd: C, 63.60; H, 5.58; N, 13.49. Found: C, 63.67; H, 5.98; N, 13.20.

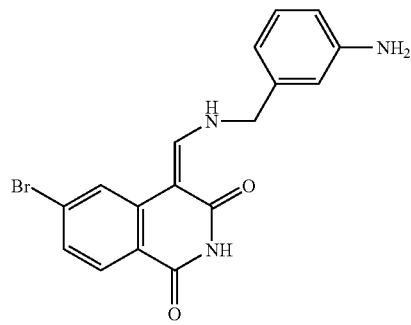

Example 52

(4Z)-4-{[(3-Aminobenzyl)amino]methylene}-6-bromoisoquinoline-1,3(2H,4H)-dione

A mixture of 6-bromo-4-methoxymethylene-4H-isoquinoline-1,3-dione (141 mg, 0.5 mmol), 4-(4-methyl-piperazin-1-yl)-phenylamine (61.1 mg, 0.5 mmol) in 1 mL of N,N-dimethylformamide is stirred at room temperature for 40 min. After cooling in the refrigerator, the precipitate is collected, and washed with ether to give 61 mg (33%) of yellow solid mp 214-215° C.; HRMS (ESI) m/z calcd for C$_{17}$H$_{14}$BrN$_3$O$_2$ 370.01966. found 370.01900 (M+H)$^{-1}$, Analysis for C$_{17}$H$_{14}$BrN$_3$O$_2$ (0.33H2O); Calcd: C, 53.98; H, 3.91; N, 11.11. Found: C, 54.07; H, 3.52; N, 10.91.

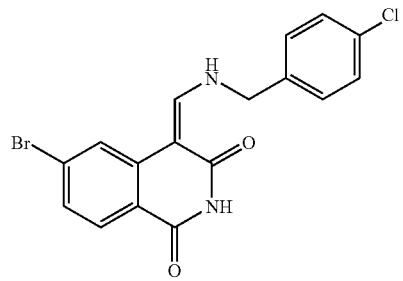

Example 53

(4Z)-6-Bromo-4-{[(4-chlorobenzyl)amino)methylene}isoquinoline-1,3(2H,4H)-dione

Using the procedure described for the preparation of example 46, 300 mg of brown solid (72% yield) is obtained from 300 mg (1.06 mmol) of (4E)-6,7-dimethoxy-4-(methoxymethylene)isoquinoline-1,3(2H,4H)-dione and 4-chlorobenzylamine (150.10 mg, 1.06 mmol); mp 234-235° C., MS (ESI) m/z 391.65 (M+1).

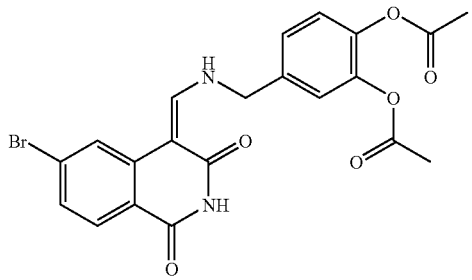

Example 54

2-(Acetyloxy)-4-({[(Z)-(6-bromo-1,3-dioxo-2,3-dihydroisoquinolin-4(1H)-ylidene)methyl]-amino}methyl)phenyl acetate Using the procedure described for the preparation of 2-(acetyloxy)-4-({[(Z)-(1,3-dioxo-2,3-dihydroisoquinolin-4(1H)-ylidene)methyl]amino}-methyl)phenyl acetate, 0.21 g (86.4% yield) of yellow solid is obtained from 0.2 g (0.51 mmol) of (4Z)-6-bromo-4-{[(3,4-dihydroxybenzyl)-amino]-methylene}isoquinoline-1,3(2H,4H)-dione (3b) and 0.91 mL (1.28 mmol) of acetyl chloride: mp 239-240° C., MS (ESI) m/z 473.1 and 475.2 (M+H)$^{+1}$, Analysis for $C_{21}H_{17}BrN_2O_6$. (0.67H$_2$O+0.3 EtOAc), Calcd: C, 52.30; H, 3.91; N, 5.44. Found: C, 52.12; H, 4.11; N, 5.44.

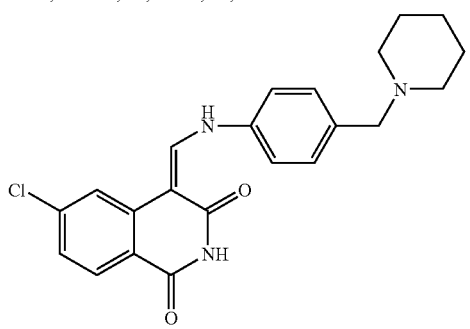

Example 55

(4Z)-6-Chloro-4-({[4-(piperidin-1-ylmethyl)phenyl]amino}methylene)isoquinoline-1,3(2H,4H)-dione Using the procedure described for the preparation of (4Z)-6-bromo-4-({[4-(pyrrolidin-1-ylmethyl)phenyl]amino}methylene)isoquinoline-1,3(2H,4H)-dione, 0.165 g (66.0% yield) of yellow solid is obtained from 0.15 g (0.63 mmol) of (4E)-6-chloro-4-(methoxymethylene)isoquinoline-1,3(2H,4H)-dione and 0.145 g (0.756 mmol) of 4-piperidin-1-ylmethyl-phenylamine: mp 225-226° C., MS (ESI) m/z 396.1 (M+H)$^{+1}$, Analysis for $C_{22}H_{22}ClN_3O_2$.(0.167 N,N-dimethylformamide (DMF)+0.167H$_2$O), Calcd: C, 65.74; H, 5.76; N, 10.79. Found: C, 65.76; H, 5.78; N, 10.34.

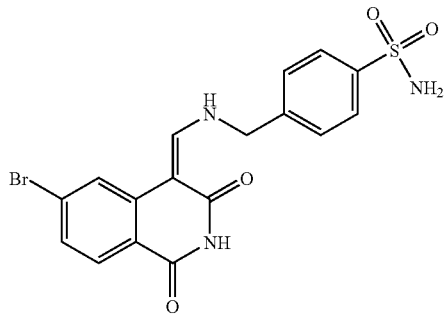

Example 56

4-({[(Z)-(6-Bromo-1,3-dioxo-2,3-dihydroisoquinolin-4(1H)-ylidene)methyl]amino}methyl)benzenesulfonamide Using the procedure described for the preparation of example 46, 180 mg of green solid (39% yield) is obtained from 300 mg (1.06 mmol) of (4E)-6,7-dimethoxy-4-(methoxymethylene)isoquinoline-1,3(2H,4H)-dione and 4-aminomethyl-benzenesulfonamide (197.5 mg, 1.06 mmol); mp 273-274° C., MS (ESI) m/z 434.29.65 (M+1).

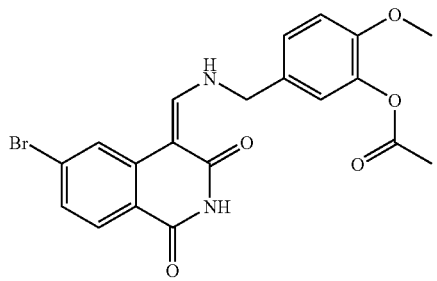

Example 57

5-({[(Z)-(6-Bromo-1,3-dioxo-2,3-dihydroisoquinolin-4(1H)-ylidene)methyl]amino}methyl)-2-methoxyphenyl acetate Using the procedure described for the preparation of 2-(acetyloxy)-4-({[(Z)-(1,3-dioxo-2,3-dihydroisoquinolin-4(1H)-ylidene)methyl]amino}-methyl)phenyl acetate, 0.132 g (70.2% yield) of tan solid is obtained from 0.17 g (0.42 mmol) of (4Z)-6-bromo-4-{[(3-hydroxy-4-methoxybenzyl)amino]methylene}isoquinoline-1,3(2H,4H)-dione and 0.75 mL (1.05 mmol) of acetyl chloride: mp 226-227 and 246-247° C., MS (ESI) m/z 445.0 and 446.9 (M+H)$^{+1}$, Analysis for $C_{20}H_{17}BrN_2O_5$.(0.8H$_2$O), Calcd: C, 51.86; H, 3.64; N, 5.99. Found: C, 52.26; H, 4.08; N, 6.09.

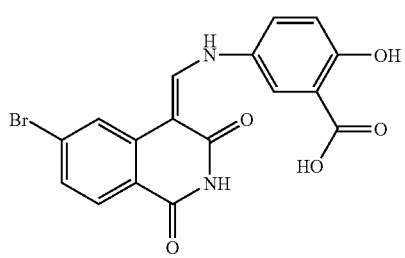

Example 58

5-{[(Z)-(6-Bromo-1,3-dioxo-2,3-dihydroisoquinolin-4(1H)-ylidene)methyl]amino}-2-hydroxybenzoic acid Using the procedure described for the preparation of (4Z)-6-bromo-4-{[(pyridin-3-ylmethyl)amino]methylene}isoquinoline-1,3(2H,4H)-dione, 1.46 g (68.2% yield) of tan solid is obtained from 0.15 g (0.53 mmol) of (4E)-6-bromo-4-(methoxy-methylene)isoquinoline-1,3(2H,4H)-dione and 0.0814 g (0.53 mmol) of 5-aminosalicylic acid heating at 120° C.: mp 336-337° C.; $^1$H NMR (DMSO-d$_6$) δ 12.57 (d, J=12 Hz, 1H), 11.37 (s, 1H), 8.88 (d, J=12 Hz, 1H), 8.43 (s, 1H), 7.89 (m, 3H), 7.39 (d, J=9 Hz, 1H), 7.05 (d, J=6 Hz, 1H); MS (ESI) m/z 401.0 (M−H)$^{-1}$, Analysis for C$_{17}$H$_{11}$BrN$_2$O$_5$.(0.75H$_2$O), Calcd: C, 49.00; H, 3.02; N, 6.72. Found: C, 48.72; H, 2.77; N, 6.60.

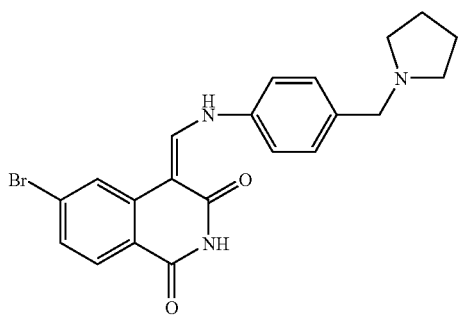

Example 59

(4Z)-6-Bromo-4-({[4-(pyrrolidin-1-ylmethyl)phenyl]amino}methylene)isoquinoline-1,3(2H,4H)-dione To a solution of (4E)-6-bromo-4-(methoxymethylene)isoquinoline-1,3(2H,4H)-dione, (0.15 g, 0.53 mmol) in N,N'-dimethylformamide is added 4-(pyrrolidinyl-methyl)aniline (0.10 mL, 0.58 mmol). The reaction mixture is heated at 120° C. under N$_2$. Reaction is monitored by mass spectroscopy. After reaction is completed after 1.5 h. After evaporating the solvent, warm ethyl acetate is added to the residue to generate reddish orange residue. It is filtered through a pad of celite to give a yellow solution, which upon addition of hexane generated 0.24 g (62.8% yield) of orange solid: mp 165-166° C., Analysis for C$_{21}$H$_{20}$BrN$_3$O$_2$, Calcd: C, 59.17; H, 4.73; N, 9.86. Found: C, 58.77; H, 4.42; N, 9.81.

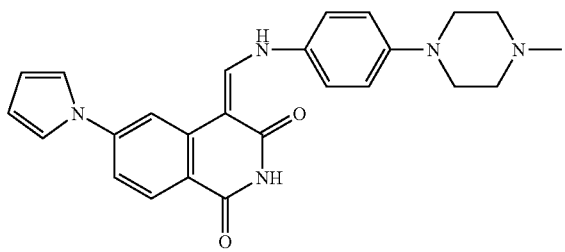

Example 60

(4Z)-4-({[4-(4-Methylpiperazin-1-yl)phenyl]amino}methylene)-6-(1H-pyrrol-1-yl)isoquinoline-1,3(2H,4H)-dione A mixture of 4-methoxymethylene-6-pyrrol-1-yl-4H-isoquinoline-1,3-dione, (100 mg, 0.3727 mmol), 4-(4-methylpiperazin-1-yl)-phenylamine (71.3 mg, 0.3727 mmol) in 1 mL of N,N-dimethylformamide is heated at 100° C. for 0.5 h. After the solvent is evaporated, ether is added to the residue. The precipitate is collected, and washed with ether to give 122 mg (77%) of light brown solid mp 239-240° C.; HRMS (ESI) m/z calcd for C$_{25}$H$_{25}$N$_5$O$_2$ 428.20811. found 428.20865 (M+H)$^{+1}$, Analysis for C25H25N5O2 (0.6H2O), Calcd: C, 68.51; H, 6.02; N, 15.98. Found: C, 68.67; H, 5.85; N, 15.62.

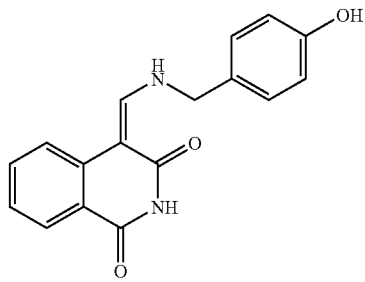

Example 61

(4Z)-4-{[(4-Hydroxybenzyl)amino)methylene}isoquinoline-1,3(2H,4H-dione

Using the procedure described for the preparation of example 46, 200 mg of red-brown solid (46% yield) is obtained from 300 mg (1.48 mmol) of (4E)-4-(methoxymethylene)isoquinoline-1,3(2H,4H)-dione and 4-hydroxy-benzylamine (235.0 mg, 1.48 mmol), mp 272-273° C., MS (ESI) m/z 294.31 (M−1).

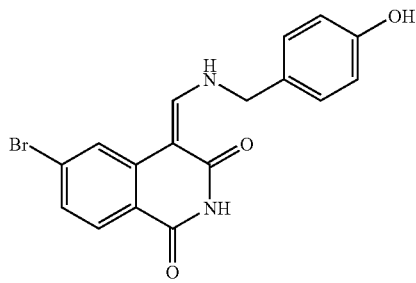

Example 62

(4Z)-6-Bromo-4-{[(4-hydroxybenzyl)amino)methylene}isoquinoline-1,3(2H,4H-dione

Using the procedure described for the preparation of example 46, 250 mg of red-brown solid (63% yield) is obtained from 300 mg (1.06 mmol) of (4E)-6,7-dimethoxy-4-(methoxymethylene)isoquinoline-1,3(2H,4H)-dione and 4-hydroxy-benzylamine (169.73 mg, 1.06 mmol); mp 296-297° C.; MS (ESI) m/z 373.21 (M+1).

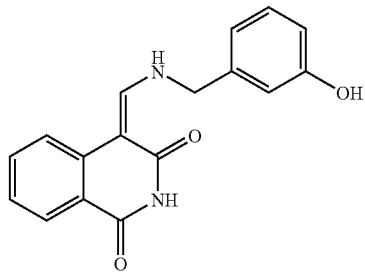

Example 63

(4Z)-4-{[(3-Hydroxybenzyl)amino]methylene}isoquinoline-1,3(2H,4H)-dione

Using the procedure described for the preparation of example 46, 200 mg reddish-brown solid (46% yield) is obtained from 300 mg (1.48 mmol) of (4E)-4-(methoxymethylene)isoquinoline-1,3(2H,4H)-dione and 3-hydroxy-benzylamine (235.0 mg, 1.48 mmol), mp 261-262° C., MS (ESI) m/z 294.31 (M−1).

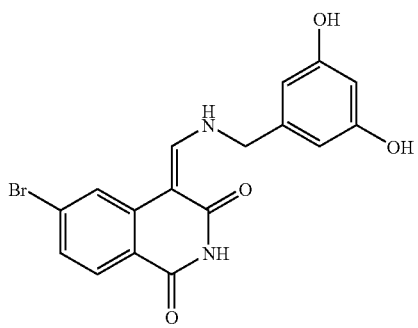

Example 64

(4Z)-6-Bromo-4-{[(3,5-dihydroxybenzyl)amino]methylene}isoquinoline-1,3(2H,4H)-dione Using the procedure described for the preparation of example 46, 250 mg of brown solid (56% yield) is obtained from 322.9 mg (1.15 mmol) of (4E)-6,7-dimethoxy-4-(methoxymethylene)isoquinoline-1,3(2H,4H)-dione and 3,5-dihydroxy-benzylamine (201 mg, 1.15 mmol), mp 318-319° C., MS (ESI) m/z 389.21 (M+1).

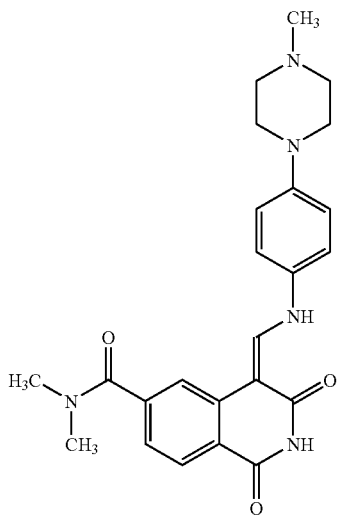

Example 65

(4Z)-N,N-Dimethyl-4-({[4-(4-methylpiperazin-1-yl)phenyl]amino}methylene)-1,3-dioxo-1,2,3,4-tetrahydroisoquinoline-6-carboxamide Prepared from a slurry of 81.7 mg (0.298 mmol) of 4-methoxymethylene-1,3-dioxo-1,2,3,4-tetrahydro-isoquinoline-6-carboxylic acid dimethylamide and 56.9 mg (0.298 mmol) of 4-(4-methylpiperazin-1-yl)methyl-phenylamine in 1.5 mL of N,N-dimethylformamide (DMF) at 100° C. under $N_2$ as described for example 21. After heating for 0.5 h, the reaction is chilled in ice. The solid product is collected, washed with N,N-dimethylformamide (DMF) and $Et_2O$ and dried to give 111 mg (86%) of yellow crystals: mp >300° C.; $^1$H NMR (DMSO-$d_6$) δ 12.55 (d, 1H, J=12.8 Hz), 11.25 (s, 1H), 8.88 (d, 1H, J=12.8 Hz), 8.14 (s, 1H), 8.03 (d, 1H, J=8.07 Hz), 7.46 (d, 2H, J=8.94), 7.16 (d, 1H, J=8.07 Hz), 6.98 (d, 2H, J=8.94 Hz), 3.14 (m, 4H), 3.04 (s, 3H), 2.90 (s, 3H), 2.46 (m, 4H), 2.22 (s, 3H); HRMS (ESI) m/e calcd for $C_{24}H_{27}N_5O_3$ 432.20411. found 432.20337 (M+H)$^{+1}$, Analysis for $C_{24}H_{27}N_5O_3$, Calcd: C, 66.50; H, 6.28; N, 16.16. Found: C, 66.33; H, 6.43; N, 16.28.

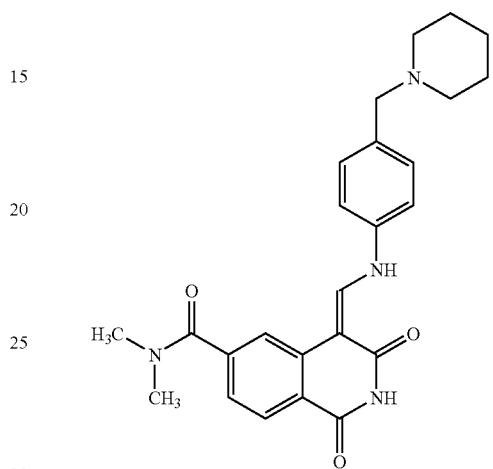

Example 66

(4Z)-N,N-Dimethyl-1,3-dioxo-4-({[4-(piperidinylmethyl)phenyl]amino}methylene)-1,2,3,4-tetrahydroisoquinoline-6-carboxamide Prepared from a solution of 70 mg (0.255 mmol) of 4-methoxymethylene-1,3-dioxo-1,2,3,4-tetrahydro-isoquinoline-6-carboxylic acid dimethylamide and 48.5 mg (0.255 mmol) of 4-piperidin-1-ylmethyl-phenylamine in 1.6 mL of N,N-dimethylformamide (DMF) at 110° C. under $N_2$ as described for example 21. After heating for 0.25 h, the reaction is chilled in ice. The solid product is collected, washed with N,N-dimethylformamide (DMF) and $Et_2O$ and dried to give 82.4 mg (74%) of bright yellow crystals: mp 266-267° C. (dec); $^1$H NMR (DMSO-$d_6$) δ 12.45 (d, 1H, J=9 Hz), 11.40 (s, 1H), 8.95 (d, 1H, J=9 Hz), 8.17 (s, 1H), 8.06 (d, 1H, J=6 Hz), 7.53 (d, 2H, J=9 Hz), 7.32 (d, 2H, J=9 Hz), 7.20 (d, 1H, J=6 Hz), 3.42 (s, 2H), 3.04 (s, 3H), 2.90 (s, 3H), 2.32 (s, 4H), 1.48 (m, 4H), 1.38 (s, 2H); HRMS (ESI) m/e calcd for $C_{25}H_{28}N_4O_3$ 431.20886, fond 431.20820 (M−H)$^{-1}$.

Analysis for $C_{25}H_{28}N_4O_3 \cdot 0.25H_2O$: Calcd: C, 68.70; H, 6.59; N, 12.82. Found: C, 68.73; H, 6.38; N, 13.08.

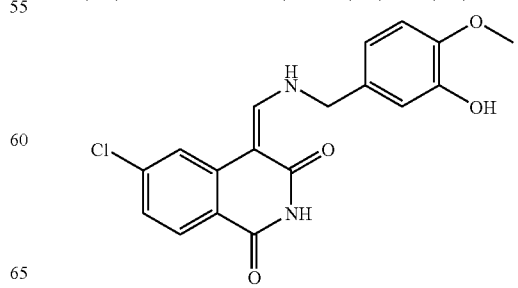

Example 67

(4Z)-6-Chloro-4-{[(3-hydroxy-4-methoxybenzyl)amino]methylene}isoquinoline-1,3(2H,4H)-dione Using the procedure described for the preparation of (4Z)-6-bromo-4-{[(4-hydroxy-3-methoxybenzyl)amino]methylene}isoquinoline-1,3(2H,4H)-dione, 0.182 g (80.2% yield) of tan solid is obtained from 0.15 g (0.63 mmol) of (4E)-6-chloro-4-(methoxymethylene)-isoquinoline-1,3(2H,4H)-dione and 0.114 g (0.756 mmol) of 3-hydroxyl-4-methoxy]-benzylamine hydrochloride, and 0.264 mL (1.89 mmol) of triethylamine: mp 265-266° C.; MS (ESI) m/z 357.5 (M–H)$^{-1}$ Analysis for $C_{18}H_{15}ClN_2O_4 \cdot (0.8H_2O)$ Calcd: C, 57.93; H, 4.48; N, 7.51. Found: C, 57.56; H, 4.06; N, 7.45.

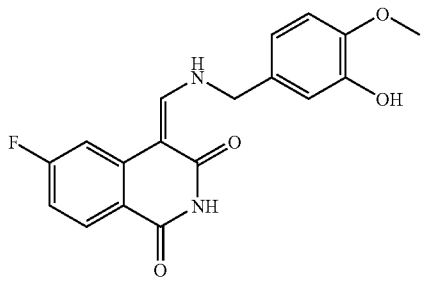

Example 68

(4Z)-6-Fluoro-4-{[(3-hydroxy-4-methoxybenzyl)amino)methylene}isoquinoline-1,3(2H,4H-dione Using the procedure described for the preparation of example 46, 340 mg of light-brown solid (94% yield) is obtained from 300 mg (1.06 mmol) of (4E)-6-fluoro-4-(methoxymethylene)isoquinoline-1,3(2H,4H)-dione and 3-hydroxy-4-methoxy-benzylamine hydrogen chloride, (201.2 mg, 1.06 mmol); mp 200-201° C.

MS (ESI) m/z 342.33 (M+1).

Example 69

Acetic acid 3-acetoxy-5-{[(6-bromo-1,3-dioxo-2,3-dihydro-1H-isoquinolin-4-ylidenemethyl)-amino]-methyl}-phenyl ester An amount of 100 mg (0.26 mmol) of (4Z)-6-bromo-4-{[(3,5-dihydroxybenzyl)amino)methylene}isoquinoline-1,3(2H,4H)-dione is dissolved in N,N-dimethylformamide (5 mL), and pyridin (5 mL), and acetic anhydride (5 mL) is subsequently added. The mixture is allowed to stir at room temperature for 1 h, then 10 mL of water is added and stirring continued with white precipitate formed. The precipitate is filtered to give 120 mg of the title compound as a white-brown solid (98%) yield; mp 257-258° C.

MS (ESI) m/z 471.1 (M–1)

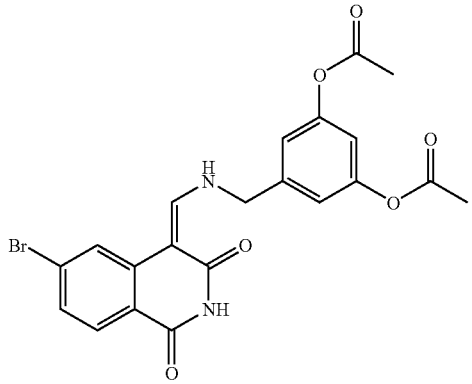

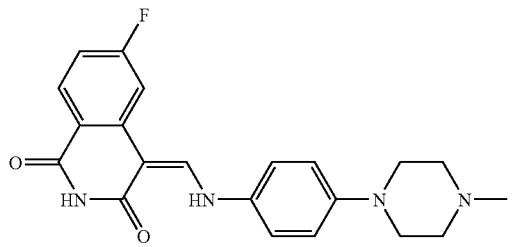

Example 70

(4Z)-6-Fluoro-4-({[4-(4-methylPiperzin-1-yl)phenyl]amino}methylene)isoquinoline-1,3(2H,4H)-dione Using the procedure described for the preparation of example 14, 280 mg (81% yield) of green-yellow solid is obtained from 200 mg (0.91 mmol) of (4E)-6-fluoro-4-(methoxymethylene)isoquinoline-1,3(2H,4H)-dione and 4-(4-methylpiperazin-1-yl)-phenylamine (172.95 mg, 0.91 mmol); mp 242-243° C.

MS (ESI) m/z 380 (M+1).

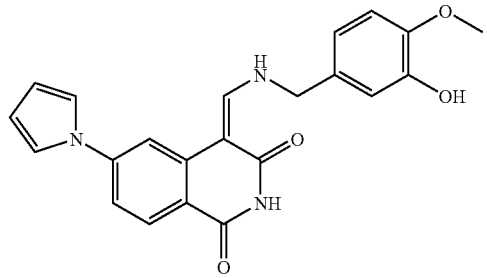

Example 71

(4Z)-6-Fluoro-4-{[(3-hydroxy-4-methoxybenzyl)amino)methylene}-6-(1H-pyrrol-1-yl)isoquinoline-1,3(2H,4H-dione Using the procedure described for the preparation of example 46, 90 mg of light-brown solid (66% yield) is obtained from 100 mg (0.038 mmol) of (4E)-4-(methoxymethylene)-6-(1H-pyrrol-1-yl)isoquinoline-1,3(2H,4H)-dione and 3-hydroxy-4-methoxy-benzylamine (60 mg, 0.35 mmol; mp 252-253° C.

MS (ESI) m/z 389.41 (M+1).

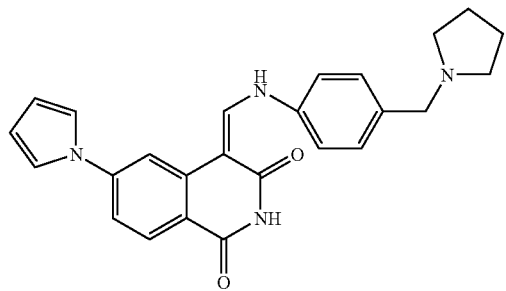

Example 72

(4Z)-4-({[4-Pyrrolidin-1-ylmethyl)phenyl]amino}methylene)}-6-(1H-pyrrol-1-yl)isoquinoline-1,3(2H,4H)-dione Using the procedure described for the preparation of example 14, 80 mg (51% yield) of yellow solid is obtained from 100 mg (0.38 mmol) of (4E)-4-(methoxymethylene)-6-(1H-pyrrol-1-yl)isoquinoline-1,3(2H,4H)-dione of and 4-pyrrolidin-1-ylmethyl)-phenylamine (65.70 mg, 0.38 mmol); mp 2002-203° C.

MS (ESI) m/z 412.49 (M+1).

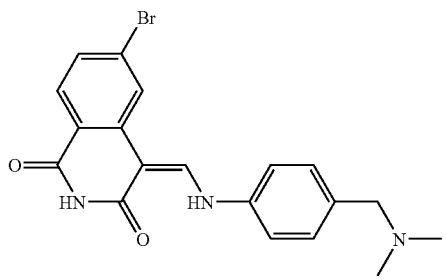

Example 73

(4Z)-6-Bromo-4-{[(4-{[(4-[(dimethylamino)methyl)methyl}phenyl)amino)methylene}isoquinoline-1,3(2H,4H-dione Using the procedure described for the preparation of example 14, 200 mg (47% yield) of a yellow solid is obtained from 300 mg (1.063 mmol) (4E)-6,7-dimethoxy-4-(methoxymethylene)isoquinoline-1,3(2H,4H)-dione and 4-dimethylamino-methyl-phenylamine (144.7 mg, 1.063 mmol); mp 159-160° C.

MS (ESI) m/z 400.27 (M+1).

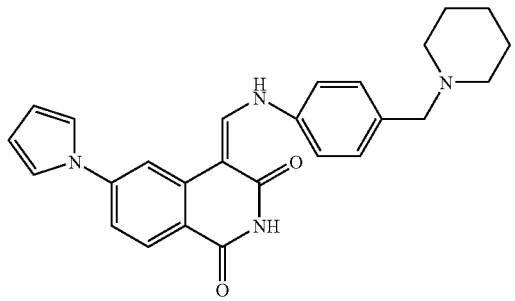

Example 74

(4Z)-4-({[4-Piperidin-1-ylmethyl)phenyl]amino}methylene)}-6-(1H-pyrrol-1-yl)isoquinoline-1,3(2H,4H)-dione Using the procedure described for the preparation of example 14, 50 mg (31% yield) of yellow solid is obtained from 100 mg (0.38 mmol) of (4E)-4-(methoxymethylene)-6-(1H-pyrrol-1-yl)isoquinoline-1,3(2H,4H)-dione of and 4-piperidin-1-ylmethyl)-phenylamine, preparation similar to 4-Morpholin-4-ylmethyl-phenylamine (70.70 mg, 0.38 mmol).; mp 207-208° C.

MS (ESI) m/z 426.21 (M+1).

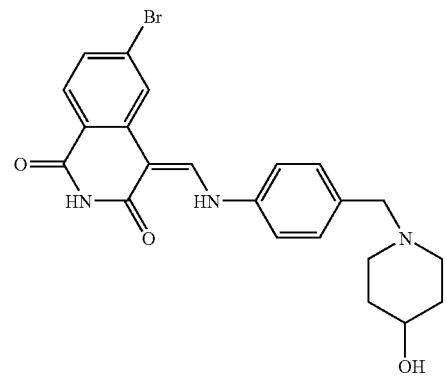

Example 75

(4Z)-6-Bromo-4-{[(4-[(4-hydroxypiperidin-1-yl)methyl}phenyl)amino)methylene}isoquinoline-1,3(2H,4H-dione Using the procedure described for the preparation of example 14, 250 mg (51% yield) of a yellow solid is obtained from 300 mg (1.063 mmol) of (4E)-6,7-dimethoxy-4-(methoxymethylene)isoquinoline-1,3(2H,4H)-dione and 4-4-hydroxypiperidin-methyl-phenylamine (144.7 mg, 1.063 mmol) (prepared similarly as 4-Morpholin-4-ylmethyl-phenylamine, mp 249-250° C.

MS (ESI) m/z 456.34 (M+1).

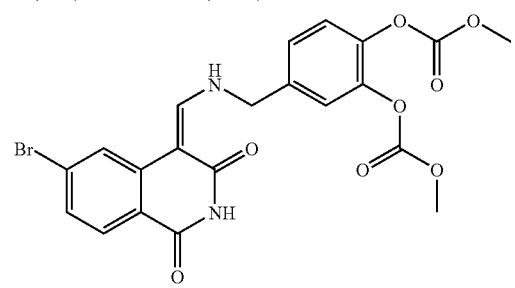

Example 76

Carbonic acid 5-{[(6-bromo-1,3-dioxo-2,3-dihydro-1H-isoquinolin-4-ylidenemethyl)-amino]-methyl}-2-methoxycarbonyloxy-phenyl ester methyl ester An amount (4Z)-6-bromo-4-{[(3,4-dihydroxybenzyl)amino]methylene)isoquinoline-1,3(2H,4H)-dione (0.15 g, 0.385 mmol) is stirred in 2 mL of pyridine and cooled to 0° C., followed by a slow addition of 0.124 mL (1.156 mmol) of dimethylpyrocarbonate. The reaction mixture is stirred under $N_2$ at 0° C. for 15 min and then allowed to warm up to room temperature and continued to stir for 2.5 h. Mass spectroscopy suggested the reaction is completed. The reaction mixture is evaporated to dryness, and the residue is recrystallized from ethyl acetate/Hexane to afford 0.162 g (83.1% yield) of light yellow solid: mp 239-240° C.; MS (ESI) m/z 473.1 and 475.2 $(M+H)^{+1}$ Analysis for C₂₁H₁₇BrN₂O₈.(0.33H₂O) Calcd: C, 49.33; H, 3.48; N, 5.48. Found: C, 49.09; H, 3.11; N, 5.51.

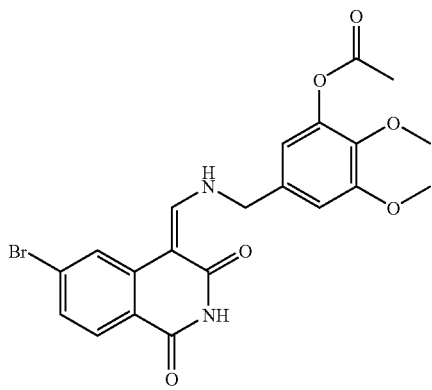

Example 77

5-({[(Z)-(6-Bromo-1,3-dioxo-2,3-dihydroisoquinolin-4(1H)-ylidene)methyl]amino}methyl)-2,3-dimethoxyphenyl acetate Using the procedure described for the preparation of example 69, 160 mg (99% yield) of white-brown solid is obtained from 150 mg (0.34 mmol) of example 78 is used and; mp 244-245° C.

MS (ESI) m/z 475.30 (M+1).

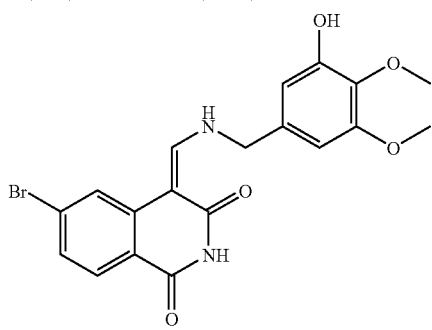

Example 78

(4Z)-6-Bromo-4-{[(3-hydroxy-4,5-dimethoxybenzyl)amino)methylene}isoquinoline-1,3(2H,4H)-dione Using the procedure described for the preparation of example 46, 400 mg of brown solid (65% yield) is obtained from 400 mg (1.42 mmol) of (4E)-6,7-dimethoxy-4-(methoxymethylene)isoquinoline-1,3(2H,4H)-dione and 3-hydroxy-4,5-dimethoxybenzylamine (272 mg, 1.15 mmol), (preparation similar to (4E)-6,7-dimethoxy-4-(methoxymethylene)isoquinoline-1,3(2H,4H)-dione and 3-hydroxy-4-methoxy-benzylamine hydrogen chloride, except methoxy amine hydrogen chloride is used instead of hydroxylamine hydrogen chloride); mp 262-263° C.

MS (ESI) m/z 433.26 (M−1).

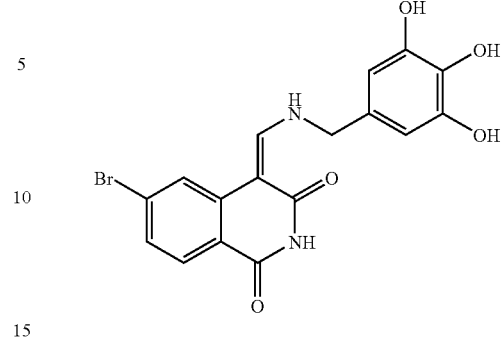

Example 79

(4Z)-6-Bromo-4-{[(3,4,5-trihydroxybenzyl)amino)methylene}isoquinoline-1,3(2H,4H)-dione Using the procedure described for the preparation of example 46, 300 mg of green solid (70% yield) is obtained from 300 mg (1.06 mmol) of (4E)-6,7-dimethoxy-4-(methoxymethylene)isoquinoline-1,3(2H,4H)-dione and 3,4,5-trihydroxybenzylamine 203.68 mg (1.06 mmol), (prepared similarly to (4E)-6,7-dimethoxy-4-(methoxymethylene)isoquinoline-1,3(2H,4H)-dione and 3-hydroxy-4-methoxy-benzylamine hydrogen chloride, except methoxy amine hydrogen chloride is used instead of hydroxylamine hydrogen chloride); mp 244-245° C.

MS (ESI) m/z undetectable.

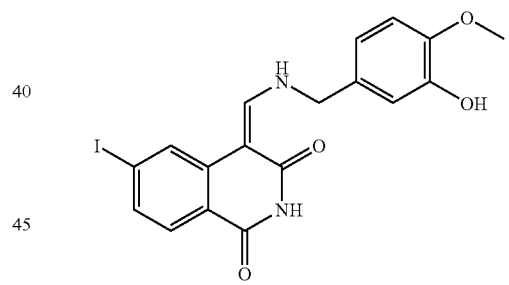

Example 80

(4Z)-6-Iodo-4-{[(3-hydroxy-4-methoxybenzyl)amino]methylene}isoquinoline-1,3(2H,4H)-dione
(5c)

Using the procedure described for the preparation of (4Z)-6-bromo-4-{[(4-hydroxy-3-methoxybenzyl)amino]methylene}isoquinoline-1,3(2H,4H)-dione, 0.28 g (68.3% yield) of tan solid is obtained from 0.3 g (0.91 mmol) of (4E)-6-iodo-4-(methoxymethylene)-isoquinoline-1,3(2H,4H)-dione and 0.19 g (1.00 mmol) of 3-hydroxyl-4-methoxy]-benzylamine hydrochloride, and 0.14 mL (1.37 mmol) of triethylamine: mp 209-210° C.; MS (ESI) m/z 449.0 (M−H)⁻¹

Analysis for $C_{18}H_{15}IN_2O_4$ Calcd: C, 48.02; H, 3.36; N, 6.22. Found: C, 47.65; H, 3.12; N, 6.03.

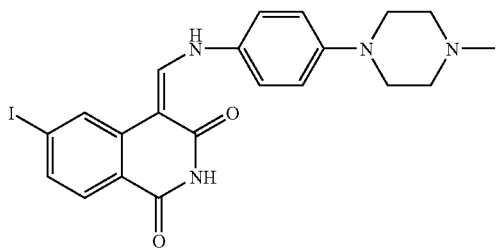

Example 81

(4Z)-6-Iodo-4-({[4-(4-methylpiperazin-1-yl)phenyl]amino}methylene)isoquinoline-1,3(2H,4H)-dione (11c)

To a solution of (4E)-6-iodo-4-(methoxymethylene)isoquinoline-1,3(2H,4H)-dione (0.15 g, 0.61 mmol) in 2 mL of N,N'-dimethylformamide is added benzenamine, 4-(4-methyl-1-piperazinyl) (0.096 g, 0.67 mmol). The reaction mixture is heated at 120° C. under $N_2$ for 2 h. The reaction mixture is concentrated under high-pressure vacuum, then treated with MeOH to give tan precipitate. It is filtered and washed successively with MeOH, $Et_2O$ and hexane to afford 0.202 g (91.0% yield) as brown solid: mp 220-221° C.; MS (ESI) m/z 489.1 $(M+H)^{+1}$ Analysis for $C_{21}H_{21}IN_4O_2 \cdot (0.33H_2O)$. Calcd: C, 51.02; H, 4.42; N, 11.33. Found: C, 50.65; H, 4.07; N, 11.02.

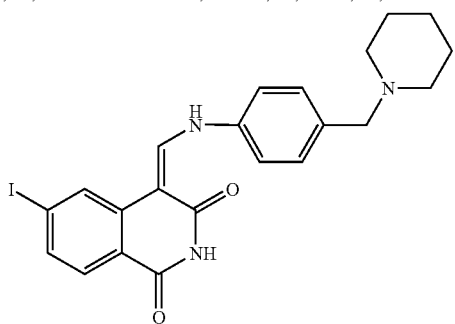

Example 82

(4Z)-6-Iodo-4-({[4-(piperidin-1-ylmethyl)phenyl]amino}methylene)isoquinoline-1,3(2H,4H)-dione (1a)

To a solution of 0.2 g (0.60 mmol) of (4E)-6-iodo-4-(methoxymethylene)isoquinoline-1,3(2H,4H)-dione in 2 mL of N,N'-dimethylformamide is added 4-piperidin-1-ylmethylphenylamine (0.127 mL, 0.67 mmol). The reaction mixture is heated at 120° C. under $N_2$ for 1.5 h. After cooling, ethyl ether is added and left in refrigerator overnight to give dark brown crystal. The crystal is collected and dissolved in 4 mL of dimethyl sulfoxide, followed by addition of 6 mL of 65% MeOH/$H_2O$ solution to give a precipitate. The solid is collected and washed thoroughly with water, MeOH, $Et_2O$ and hexane, and air-dried to give 0.143 g (48.3% yield) of tan solid: mp 202-203° C., MS (ESI) m/z 488.1 $(M+H)^{+1}$ Analysis for $C_{22}H_{22}IN_3O_2$ Calcd: C, 54.22; H, 4.55; N, 8.62. Found: C, 53.82; H, 4.57; N, 8.50.

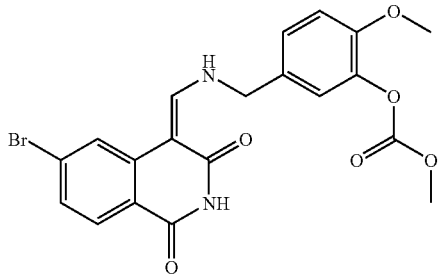

Example 83

5-({[(Z)-(6-Bromo-1,3-dioxo-2,3-dihydroisoquinolin-4(1H)-ylidene)methyl]amino}methyl)-2-methoxyphenyl methyl carbonate (8b)

Using the procedure described for the preparation of carbonic acid 5-{[(6-bromo-1,3-dioxo-2,3-dihydro-1H-isoquinolin-4-ylidenemethyl)-amino]- methyl)-2-methoxycarbonyloxy-phenyl ester methyl ester, 0.083 g (70.2% yield) of brown solid is obtained from 0.10 g (0.25 mmol) of (4Z)-6-bromo-4-{[(3-hydroxy-4-methoxybenzyl)amino]methylene}isoquinoline-1,3(2H,4H)-dione and 0.04 mL (0.30 mmol) of dimethylpyrocarbonate: mp 186-187° C.; MS (ESI) m/z 445.0 and 446.9 $(M+H)^{+1}$ Analysis for $C_{20}H_{17}BrN_2O_6$ Calcd: C, 52.08; H, 3.71; N, 6.07. Found: C, 51.74; H, 3.65; N, 6.00.

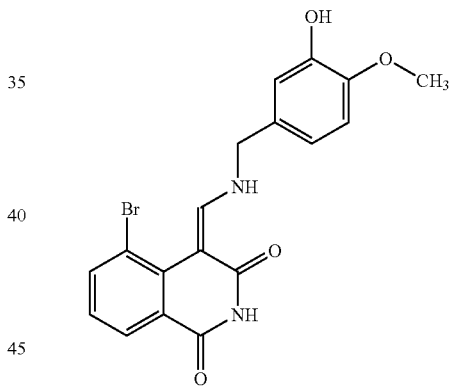

Example 84

(4Z)-5-Bromo-4-{[(3-hydroxy-4-methoxybenzyl)amino]methylene}isoquinoline-1,3(2H,4H)-dione A solution of 88.5 mg (0.468 mmol) of 3-hydroxy-4-methoxy-benzylamine hydrogen chloride in 1.8 mL of N,N-dimethylformamide (DMF) at RT under $N_2$ is treated with 94.5 mg (0.936 mmol) of $Et_3N$. (4E)-5-bromo-4-(methoxymethylene)isoquinoline-1,3(2H,4H)-dione (132 mg, 0.468 mmol) is added and the mixture is stirred for 3.5 h. Water is added and the product is collected, washed with $H_2O$ and $Et_2O$ and dried to give 163 mg (86%) of pale yellow amorphous solid: mp 204-206° C.; $^1$H NMR (DMSO-$d_6$) δ 11.11 (s, 1H), 10.56 (m, 1H), 9.08 (s, 1H), 8.93 (d, 1H, J=13.6 Hz), 8.05 (d, 1H, J=6.9 Hz), 7.87 (d, 1H, J=6.9 Hz), 7.09 (m, 1H), 6.91 (d, 1H, J=8.07 Hz), 6.78 (m, 2H), 4.49 (d, 2H, J=5.37 Hz), 3.75 (s, 3H); HRMS (ESI) m/z calcd for $C_{18}H_{15}BrN_2O_4$ 403.02880. found 403.02840 $(M+H)^{+1}$.

Analysis for C$_{18}$H$_{15}$BrN$_2$O$_4$.1.25H$_2$O: Calcd: C, 50.77; H, 4.15; N, 6.59. Found: C, 51.14; H, 4.08; N, 6.64.

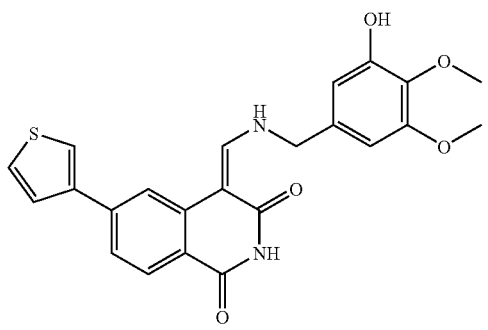

Example 85

(4Z)-4-{[(3-Hydroxy-4,5-dimethoxybenzyl)amino)methylene}-6-thien-3-ylisoquinoline-1,3(2H,4H-dione Using the procedure described for the preparation of example 46, 140 mg of brown solid (60% yield) is obtained from 150 mg (0.53 mmol) of 4-methoxymethylene-6-thiophin-3-yl-isoquinolin-(4H)-1,3-dione and 3-hydroxy-4,5-dimethoxybenzylamine 115 mg (0.53 mmol), (prepared similarly to (4E)-6,7-dimethoxy-4-(methoxymethylene)isoquinoline-1,3(2H,4H)-dione and 3-hydroxy-4-methoxy-benzylamine hydrogen chloride, except methoxy amine hydrogen chloride is used instead of hydroxylamine hydrogen chloride); mp 255-256° C.

MS (ESI) m/z 436.49 (M−1).

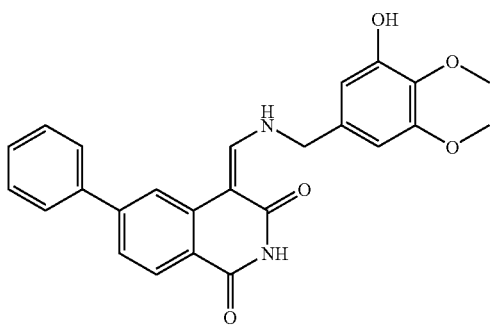

Example 86

(4Z)-4-{[(3-Hydroxy-4,5-dimethoxybenzyl)amino)methylene}-6-phenylisoquinoline-1,3(2H,4H)-dione Using the procedure described for the preparation of example 46, 50 mg of orange solid (40% yield) is obtained from 80 mg (0.29 mmol) of 4-methoxymethylene-6-phenyl-3-yl-isoquinolin-(4H)-1,3-dione and 3-hydroxy-4,5-dimethoxybenzylamine 115 mg (0.29 mmol), (prepared similarly to (4E)-6,7-dimethoxy-4-(methoxymethylene) isoquinoline-1,3(2H,4H)-dione and 3-hydroxy-4-methoxy-benzylamine hydrogen chloride, except methoxy amine hydrogen chloride is used instead of hydroxylamine hydrogen chloride); mp 250-251° C.

MS (ESI) m/z 430.46 (M−1).

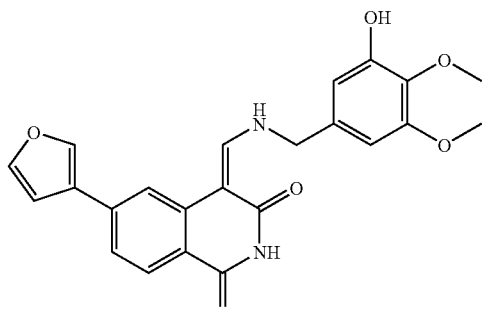

Example 87

(4Z)-6-(3-Furyl)-4-{[(3-hydroxy-4,5-dimethoxybenzyl)amino)methylene}isoquinoline-1,3(2H,4H-dione Using the procedure described for the preparation of example 46, 120 mg of brown solid (50%) yield is obtained from 150 mg (0.57 mmol) of (4E)-6-(3-furyl)methoxymethylene-isoquinoline-1,3(2H,4H)-dione, (prepared similarly to 4-methoxymethylene-6-thiophin-3-yl-isoquinolin-(4H)-1,3-dione) and 3-hydroxy-4,5-dimethoxybenzylamine (115 mg, 0.57 mmol), (prepared similarly to (4E)-6,7-dimethoxy-4-(methoxymethylene)isoquinoline-1,3(2H,4H)-dione and 3-hydroxy-4-methoxy-benzylamine hydrogen chloride, except methoxy amine hydrogen chloride is used instead of hydroxylamine hydrogen chloride); mp 263-264° C.

MS (ESI) m/z 420.43 (M−1).

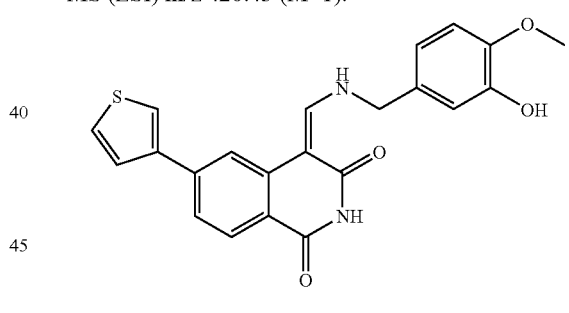

Example 88

(4Z)-4-{[(3-Hydroxy-4-methoxybenzyl)amino]methylene}-6-thien-3-ylisoquinoline-1,3(2H,4H)-dione
(5b)

Using the procedure described for the preparation of (4Z)-6-bromo-4-{[(4-hydroxy-3-methoxybenzyl)amino] methylene}isoquinoline-1,3(2H,4H)-dione, 0.18 g (85.7% yield) of tan solid is obtained from 0.15 g (0.53 mmol) (4E)-4-(methoxymethylene)-6-(1H-thiophin-3-yl)isoquinoline-1,3(2H,4H)-dione and 0.11 g (0.62 mmol) of 3-hydroxyl-4-methoxy]-benzylamine hydrochloride, and 0.08 mL (0.8 mmol) of triethylamine: mp 219-220° C., MS (ESI) m/z 407.1 (M+H)$^{+1}$ Analysis for $C_{22}H_{18}N_2O_4S \cdot (0.8H_2O)$ Calcd: C, 64.06; H, 4.56; N, 6.79. Found: C, 63.75; H, 4.34; N, 6.90.

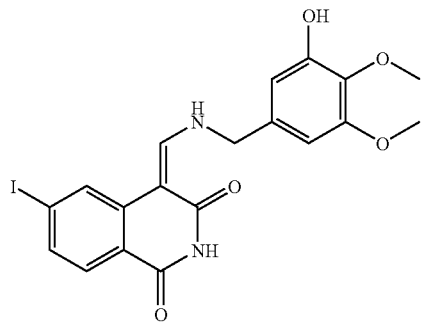

Example 89

(4Z)-6-Iodo-4-{[(3-hydroxy-4,5-dimethoxybenzyl) amino)methylene}isoquinoline-1,3(2H,4H)-dione Using the procedure described for the preparation of example 46, 110 mg of brown solid (50%) yield is obtained from 150 mg (0.46 mmol) of (4E)-6-iodo-4-(methoxymethylene)isoquinoline-1,3(2H,4H)-dione and 3-hydroxy-4,5-dimethoxybenzylamine 101 mg (0.46 mmol), (prepared similarly to (4E)-6,7-dimethoxy-4-(methoxymethylene) isoquinoline-1,3(2H,4H)-dione and 3-hydroxy-4-methoxybenzylamine hydrogen chloride, except methoxy amine hydrogen chloride is used instead of hydroxylamine hydrogen chloride); mp 265-266° C.

MS (ESI) m/z 480.30 (M+1).

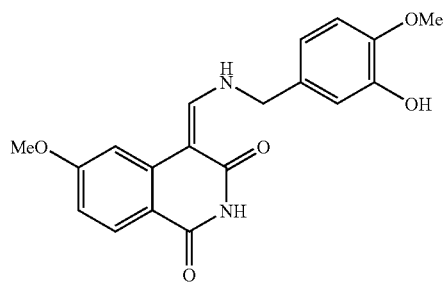

Example 90

4-[(3-Hydroxy-4-methoxy-benzylamino)-methylene]-6-methoxy-4H-isoquinoline-1,3-dione A mixture of 5-aminomethyl-2-methoxy-phenol hydrochloride (145 mg, 0.50 mmole), 4 mL of N,N-dimethylformamide and triethylamine (75 □L, 0.54 mmole) is stirred for 15 minutes. Then (4E)-6-methoxy-4-methoxymethylene-4H-isoquinoline-1,3-dione (117 mg, 0.50 mmole) is added and the reaction mixture stirred for one hour. The reaction mixture is diluted with ether, filtered washed with water, washed with ether and dried to give an light beige solid, 161 mg, (91%), mp 240-2° C. dec; MS (ESI): m/z 355.2 (M–H).

Example 91

6-Methoxy-4-[(4-piperidin-1-ylmethyl-phenylamino)-methylene]-4H-isoquinoline-1,3-dione A mixture of (4E)-6-methoxy-4-methoxymethylene-4H-isoquinoline-1,3-dione (117 mg, 0.50 mmole), N,N-dimethylformamide (1 mL) and 4-piperidin-1-ylmethyl-phenylamine (95 mg, 0.50 mmole) is stirred and heated at 110° C. for one hour, cooled in the refrigerator overnight. The reaction mixture is evaporated to dryness, taken up in 7.5% methanol in chloroform and passed through a short pad of Florisil eluting with 7.5% methanol in chloroform. The eluate is evaporated in vacuo, treated with acetonitrile, filtered and dried to give a yellow solid 152 mg (78%), mp 272-5° C. dec; MS (ESI): m/z 392.4 (M+H).

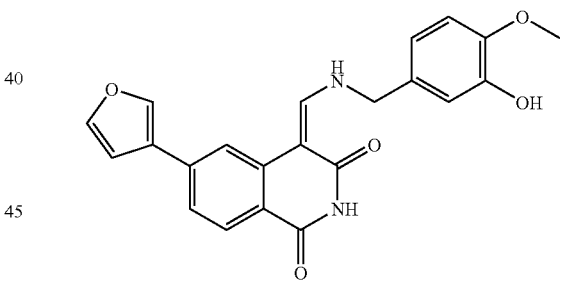

Example 92

(4Z)-6-(3-Furyl)-4-{[(3-hydroxy-4-methoxybenzyl) amino)methylene}isoquinoline-1,3(2H,4H-dione Using the procedure described for the preparation of example 46, 150 mg of brown solid (65% yield) is obtained from 160 mg (0.59 mmol) of (4E)-6-(3-furyl)methoxymethylene-isoquinoline-1,3(2H,4H-dione and 3-hydroxy-4-methoxybenzylamine (94.63 mg, 0.59 mmol), (prepared similarly to (4E)-6,7-dimethoxy-4-(methoxymethylene)isoquinoline-1,3(2H,4H)-dione and 3-hydroxy-4-methoxy-benzylamine hydrogen chloride); mp 254-255° C.

MS (ESI) m/z 390.40 (M–1).

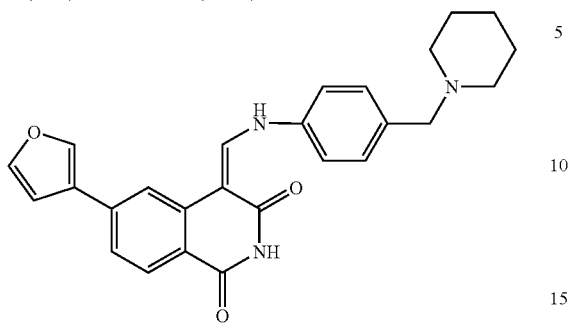

Example 93

(4Z)-6-(3-Furyl)-4-({[4-piperidin-1-ylmethyl)phenyl]amino}methylene)}isoquinoline-1,3(2H,4H)-dione Using the procedure described for the preparation of example 14, 50 mg (32%) yield of a yellow solid is obtained from 100 mg (0.37 mmol) of (4E)-6-(3-furyl) methoxymethylene}isoquinoline-1,3(2H,4H-dione and 4-piperidin-1-ylmethyl)-phenylamine (70.53 mg, 0.37 mmol), (prepared similarly to 4-morpholin-4-ylmethyl-phenylamine), mp 204-205° C.

MS (ESI) m/z 427.50 (M+1).

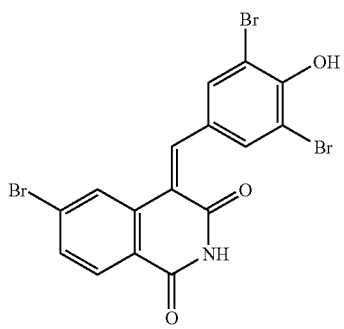

Example 94

(4Z)-6-Bromo-4-(3,5-dibromo-4-hydroxybenzylidene)isoquinoline-1,3(2H,4H)-dione

6-Bromo-4H-isoquinoline-1,3-dione (0.12 g, 0.5 mmol), 3,5-dibromo-4-hydroxybenzaldehyde (0.14 g, 0.5 mmol), and piperidine (0.075 mL, 0.75 mmol) were dissolved in i-propanol (2 mL). After heating at 95° C. for 3 h, it is cooled, and the solid is filtered and washed with I-propanol, ether and hexane to yield 0.25 g (99.6%) solid; mp 167-168° C.; HRMS (ESI) m/z 499.8 (M–H)$^{-1}$.

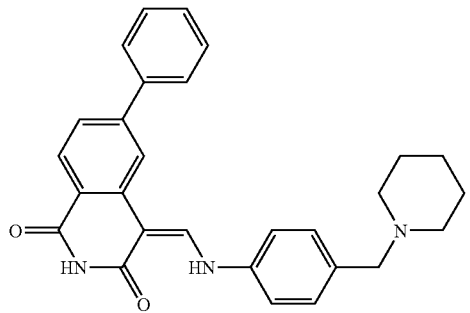

Example 95

(4Z)-6-Phenyl-4-({[4-piperidin-1-ylmethyl)phenyl]amino}methylene)}isoquinoline-1,3(2H,4H)-dione A mixture of 300 mg (0.68 mmol) of (4Z)-6-bromo-4-({[4-(Piperidin-1-ylmethyl)phenyl]amino}methylene)isoquinoline-1,3(2H,4H)-dione, Pd(PPh$_3$)$_4$ (118.0 mg, 0.102 mmol), saturated aqueous sodium carbonate (2 mL), and phenyl boronic acid (123.42 mg, 1.02 mmol) is placed in a three neck flask. Under N$_2$, N,N-dimethylformamide (8 mL) is added, and the mixture is then placed in a pre-heated oil bath at 120° C. for 45 min. After cooling, the mixture is treated with CH$_2$Cl$_2$ and filtered through celite. After evaporating all the solvents, the residue is dissolved in methylene chloride, washed three times with sodium bicarbonate solution, dried over magnesium sulfate and evaporated. The yellow oily residue is purified by preparative thin layer chromatography (5:95=methanol:methylene chloride), to give a yellow solid 90 mg (30% yield); mp 214-215° C.

MS (ESI) m/z 437.54 (M+1).

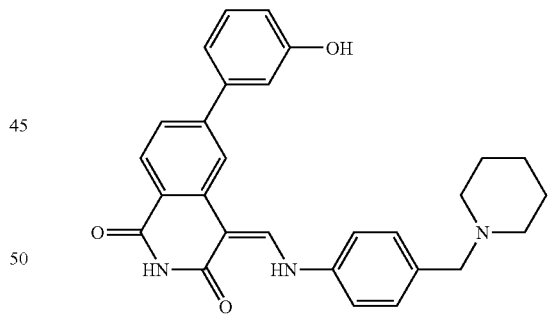

Example 96

(4Z)-6-(3-Hydroxyphenyl)-4-({[4-piperidin-1-ylmethyl)phenyl]amino}methylene)}isoquinoline-1,3(2H,4H)-dione Using the procedure described for the preparation of example 95, 120 mg (39%) of yellow solid is obtained from 300 mg (0.68 mmol) of (4Z)-6-bromo-4-({[4-(piperidin-1-ylmethyl)phenyl]amino}methylene)isoquinoline-1,3(2H, 4H)-dione and 3-(4,4,5,5-tetramethyl-[1,3,2]dioxaborolan-2-yl)-phenol (300 mg, 1.36 mmol); mp 235-236° C.

MS (ESI) m/z 453.54 (M+1).

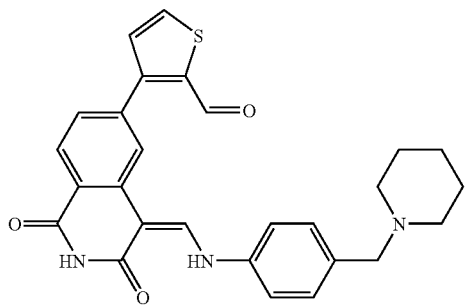

Example 97

3-[(4Z)-1,3-Dioxo-4-({[4-piperidin-1-ylmethyl)phenyl]amino}methylene)-1,2,3,4-tetrahydroisoquinoline-6-yl]thiophene-2-carbaldehyde Using the procedure described for the preparation of example 95, 100 mg (31%) of yellow solid is obtained from 300 mg (0.68 mmol) of (4Z)-6-bromo-4-({[4-(piperidin-1-ylmethyl)phenyl]amino}methylene)isoquinoline-1,3(2H,4H)-dione and 2-formyl-3-thienylboronic acid (213.48 mg, 1.36 mmol); mp 224-225° C.

MS (ESI) m/z 471.58 (M+1).

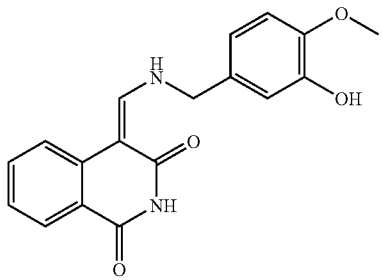

Example 98

(4Z)-4-{[(3-Hydroxy-4-methoxybenzyl)amino]methylene}isoquinoline-1,3(2H,4H)-dione (3d)

Using the procedure described for the preparation of (4Z)-6-bromo-4-{[(4-hydroxy-3-methoxybenzyl)amino]methylene}isoquinoline-1,3(2H,4H)-dione, 0.25 g (78% yield) of off-white solid is obtained from 0.2 g (0.98 mmol) of (4E)-4-(methoxymethylene)-isoquinoline-1,3(2H,4H)-dione and 0.2 g (1.08 mmol) of 4-methoxy]-3-hydroxyl-benzylamine hydrochloride, and 0.3 mL (2.94 mmol) of triethylamine: mp 192-193° C.; $^1$H NMR (DMSO-$d_6$) δ 10.97 (s, 1H), 10.60 (m, 1H), 9.04 (s, 1H), 8.62 (d, J=9 Hz, 1H), 7.98 (d, J=6 Hz, 1H), 7.83 (d, J=6 Hz, 1H), 7.55 (t, J=6 Hz, 1H), 7.17 (t, J=6 Hz, 1H), 6.91 (d, J=6 Hz, 1H), 6.78 (m, 2H), 4.56 (d, J=4.5 Hz, 2H), 3.75 (s, 3H); MS (ESI) m/z 325.1 (M+H)$^{+1}$.

Analysis for $C_{18}H_{16}N_2O_4$·(0.25$H_2O$) Calcd: C, 65.75; H, 5.06; N, 8.52. Found: C, 65.70; H, 5.02; N, 8.54.

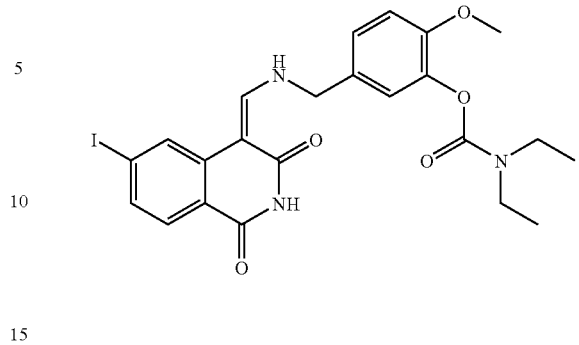

Example 99

5-({[(Z)-(6-Iodo-1,3-dioxo-2,3-dihydroisoquinolin-4(1H)-ylidene)methyl]amino}methyl)-2-methoxyphenyl diethylcarbamate To a solution of (4Z)-6-iodo-4-{[(3-hydroxy-4-methoxybenzyl)amino]methylene}isoquinoline-1,3(2H,4H)-dione (0.30 g, 0.67 mmol) in 3 mL of N,N'-dimethylformamide and 2 mL of pyridine is added diethylcarbamylchloride (0.10 mL, 0.80 mmol) and 0.21 mL (2.00 mmol) of triethylamine. The reaction mixture is stirred at 80° C. for 4 h and then at room temperature over weekend under $N_2$. Mass spectroscopy suggested the completion of reaction. The reaction mixture is concentrated, and 2 mL of MeOH is added to break up the solid, followed by addition of excess amount of $Et_2O$. The precipitate is filtered, washed successively with water, methanol, ether and hexane, and dried in oven (60° C.) overnight to afford 0.207 g (56.6% yield) of tan solid: mp 128-130° C.; MS (ESI) m/z 548.2 (M−H)$^{-1}$ Analysis for $C_{23}H_{24}IN_3O_5$ Calcd: C, 50.29; H, 4.40; N, 7.65. Found: C, 49.89; H, 4.17; N, 7.49.

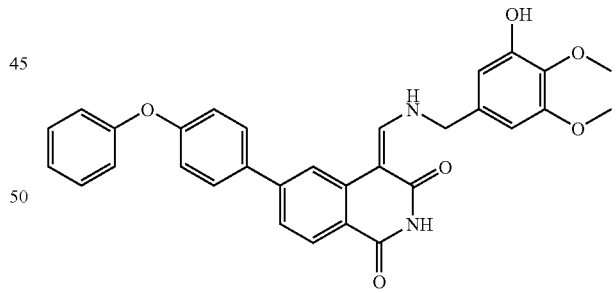

Example 100

(4Z)-6-(4-Phenoxyphenyl)-4-{[(3-hydroxy-4,5-dimethoxybenzyl)amino]methylene}isoquinoline-1,3(2H,4H)-dione Using the procedure described for the preparation of example 95, 250 mg (70%) of green solid is obtained from 300 mg (0.68 mmol) of example 78 and 4-phenoxyphenyl boronic acid (216.56 mg, 1.38 mmol); mp 240-241° C.

MS (ESI) m/z 522.18 (M−1).

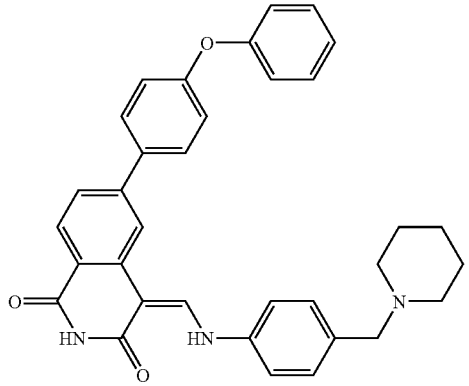

Example 101

(4Z)-6-(4-Phenoxyphenyl)-4-({([4-piperidin-1-ylmethyl)phenyl]amino}methylene)}isoquinoline-1,3 (2H,4H)-dione Using the procedure described for the preparation of example 95, 70 mg (19%) of yellow solid is obtained from 300 mg (0.68 mmol) of (4Z)-6-bromo-4-({[4-(piperidin-1-ylmethyl)phenyl]amino}methylene)isoquinoline-1,3(2H,4H)-dione and 4-phenoxyphenyl boronic acid (291.1 mg, 1.36 mmol).; mp 132-133° C.

MS (ESI) m/z 529.64 (M+1).

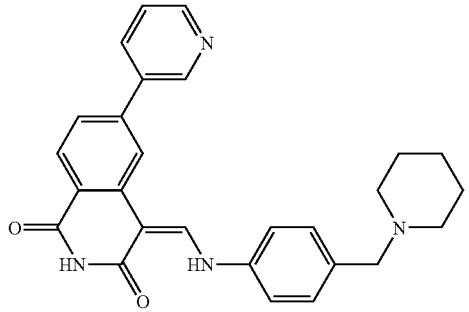

Example 102

(4Z)-4-({[4-Piperidin-1-ylmethyl)phenyl] amino}methylene)-6-pyridin-3-ylisoquinoline-1,3 (2H,4H)-dione Using the procedure described for the preparation of example 95, 100 mg (34%) of yellow solid is obtained from 300 mg (0.68 mmol) of (4Z)-6-bromo-4-({[4-(piperidin-1-ylmethyl)phenyl]amino}methylene)isoquinoline-1,3(2H,4H)-dione and 3-pyridylboronic acid (166.21 mg, 1.36 mmol); mp 247-248° C.

MS (ESI) m/z 438.53 (M+1).

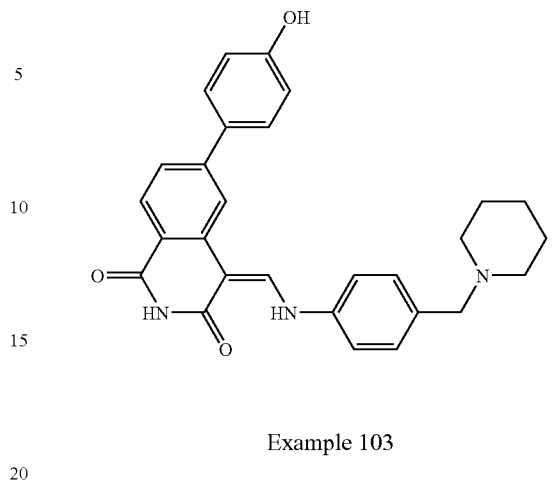

Example 103

(4Z)-6-(4-Hydroxyphenyl)-4-({[4-piperidin-1-ylmethyl)phenyl]amino}methylene)}isoquinoline-1,3 (2H,4H)-dione Using the procedure described for the preparation of example 95, 120 mg (39% yield) of yellow solid is recovered is obtained from 300 mg (0.68 mmol) of (4Z)-6-bromo-4-({[4-(piperidin-1-ylmethyl)phenyl]amino}methylene)isoquinoline-1,3(2H,4H)-dione and 4-(4,4,5,5-tetramethyl-[1,3,2]dioxaborolan-2-yl)-phenol (300 mg, 1.36 mmol); mp 244-245° C.

MS (ESI) m/z 453.54 (M+1).

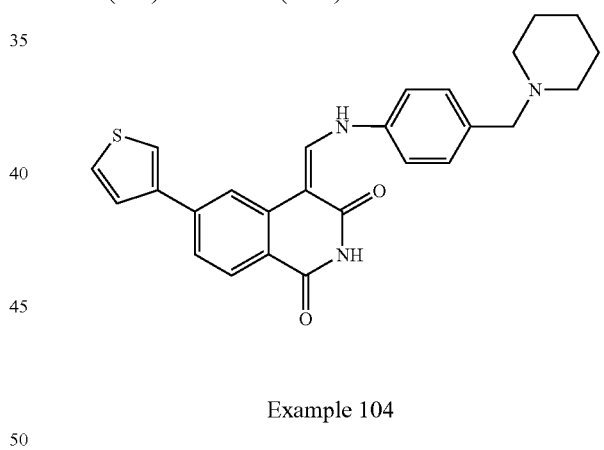

Example 104

(4Z)-4-({[4-(Piperidin-1-ylmethyl)phenyl] amino}methylene)-6-thien-3-ylisoquinoline-1,3(2H, 4H)-dione Using the procedure described for the preparation of (4Z)-4-({[4-(4-methylpiperazin-1-yl)phenyl]amino}methylene)-6-thien-3-ylisoquinoline-1,3(2H,4H)-dione, 0.041 g (13.7% yield) of yellow solid is obtained from 0.3 g (0.68 mmol) of (4Z)-6-bromo-4-({[4-(piperidin-1-ylmethyl)phenyl] amino}methylene)isoquinoline-1,3(2H,4H)-dione, 0.13 g (1.0 mmol) of 3-thiopheneboronic acid, 0.06 g (0.068 mmol) of tris(dibenzyldenea-acetone)-dipalladium(0), 0.04 g (0.136 mmol) of 2-(di-t-butyl-phosphino)-biphenyl, 0.144 g (1.36 mmol) of sodium carbonate and 4 mL of 80% N,N-dimethylformamide (DMF)/H$_2$O solution: mp 166-167° C., MS (ESI) m/z—-(M+H)$^{+1}$ Analysis for C$_{26}$H$_{25}$N$_3$O$_2$S.(0.33H$_2$O) Calcd: C, 69.46; H, 5.75; N, 9.35. Found: C, 79.49; H, 5.75; N, 9.11.

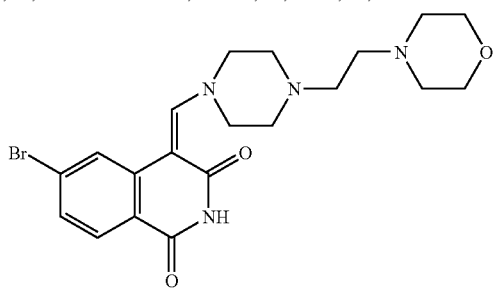

Example 105

(4Z)-6-Bromo-4-{[4-(2-morpholin-4-ylethyl)piperazin-1-yl]methylene}isoquinoline-1,3(2H,4H)-dione A mixture of 6-bromo-4-methoxymethylene-4H-isoquinoline-1,3-dione (200 mg, 0.709 mmol), 2-morpholinylethylpiperazine (141.3 mg, 0.709 mmol) in 1 mL of N,N-dimethylformamide is stirred at room temperature for 15 min. After cooling in the refrigerator, the precipitate is collected, and washed with N,N-dimethylformamide (DMF) and ether to give 64 mg (20%) of yellow solid mp 156-156.5° C.; HRMS (ESI) m/z 449 (M+H)$^{+1}$.

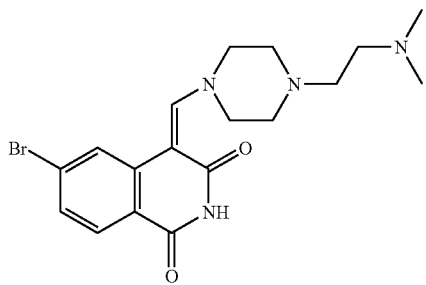

Example 106

(4Z)-6-Bromo-4-({4-[2-(dimethylamino)ethyl]piperazin-1-yl}methylene)isoquinoline-1,3(2H,4H)-dione Using the procedure described for the preparation of example 105, the title compound is obtained from (4E)-6-bromo-4-(methoxy-methylene)isoquinoline-1,3(2H,4H)-dione (282 mg, 1 mmol), 2-dimethylaminoethylpiperazine (162 mg, 1 mmol), and N,N-dimethylformamide (DMF) (1.5 mL) in 54% yield as a yellow solid: mp 166-167° C.; MS (ESI) m/z 431.1, 407.1 (M+H)$^{+1}$

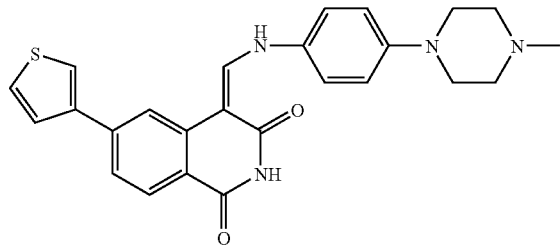

Example 107

(4Z)-4-({[4-(4-Methylpiperazin-1-yl)phenyl]amino}methylene)-6-thien-3-ylisoquinoline-1,3(2H,4H)-dione A mixture of example 27 (1.0 g, 2.26 mmol), 0.43 g (3.4 mmol) of 3-thiopheneboronic acid, 0.2 g (0.226 mmol) of tris(dibenzyldenea-acetone)-dipalladium(0), 0.126 g (0.45 mmol) of 2-(di-t-butyl-phosphino)-biphenyl, and 0.5 g (4.52 mmol) of sodium carbonate in 10 mL of N,N'-dimethylformamide and 2 mL of water is added to a 50 mL round bottom flask, sealed with a rubber septum. It is degassed and flushed with nitrogen gas three times. The reaction mixture is stirred vigorously at 120° C. in an oil bath under nitrogen. Mass spectroscopy suggested the completion of reaction after 1.5 h. The reaction mixture is evaporated under high-pressure vacuum to give a brown residue. It is dissolved in chloroform, filtered through a pad of celite to give a reddish brown solution. It is concentrated and re-dissolved in 10 mL of chloroform and filtered through a pad of florisil, followed by washing 5% MeOH/CHCl$_3$ solution to give a dark orange solution. The organic solution is concentrated to give orange residue. Addition of methanol to the solid gave a yellow precipitate, which is collected and washed successively with an excess amount of methanol, ether and hexane to yield 0.38 g (38% yield) of yellow solid: mp 224-226° C.; MS (ESI) m/z 445.2 (M+H)$^{+1}$ Analysis for C$_{25}$H$_{24}$N$_4$O$_2$S.(0.25H$_2$O+0.25 N,N-dimethylformamide (DMF)) Calcd: C, 66.18; H, 5.66; N, 12.74. Found: C, 65.56; H, 5.37; N, 12.23.

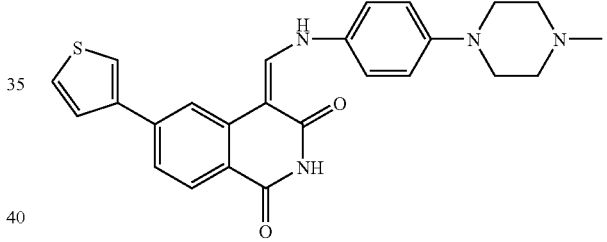

Example 108

(4Z)-4-({[4-(4-Methylpiperazin-1-yl)phenyl]amino}methylene)-6-thien-3-ylisoquinoline-1,3(2H,4H)-dione A mixture of example 27, (1.0 g, 2.26 mmol), 0.43 g (3.4 mmol) of 3-thiopheneboronic acid, 0.2 g (0.226 mmol) of tris(dibenzyldenea-acetone)-dipalladium(0), 0.126 g (0.45 mmol) of 2-(di-t-butyl-phosphino)-biphenyl, and 0.5 g (4.52 mmol) of sodium carbonate in 10 mL of N,N'-dimethylformamide and 2 mL of water is added to a 50 mL round bottom flask, sealed with a rubber septum. It is degassed and flushed with nitrogen gas three times. The reaction mixture is stirred vigorously at 120° C. in an oil bath under nitrogen. Mass spectroscopy suggested the completion of reaction after 1.5 h. The reaction mixture is evaporated under high-pressure vacuum to give a brown residue. It is dissolved in chloroform, filtered through a pad of celite to give a reddish brown solution. It is concentrated and re-dissolved in 10 mL of chloroform and filtered through a pad of florisil, followed by washing 5% MeOH/CHCl$_3$ solution to give a dark orange solution. The organic solution is concentrated to give orange residue. Addition of methanol to the solid gave a yellow precipitate, which is collected and washed successively with an excess amount of methanol, ether and hexane to yield 0.38 g (38% yield) of yellow solid: mp 224-226° C.; MS (ESI) m/z 445.2 (M+H)$^{+1}$ Analysis for $C_{25}H_{24}N_4O_2S \cdot (0.25H_2O + 0.25$ N,N-dimethylformamide (DMF)) Calcd: C, 66.18; H, 5.66; N, 12.74. Found: C, 65.56; H, 5.37; N, 12.23.

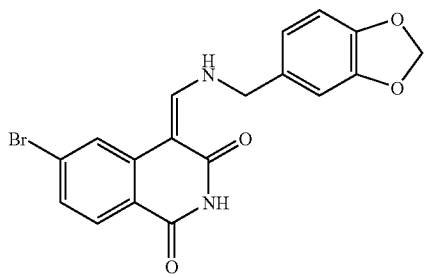

Example 109

(4Z)-4-{[(1,3-Benzodioxol-5-ylmethyl)amino]methylene}-6-bromoisoquinoline-1,3(2H,4H)-dione Using the procedure described for the preparation of (4Z)-6-bromo-4-{[(4-hydroxy-3-methoxybenzyl)amino]methylene}isoquinoline-1,3(2H,4H)-dione, 0.0196 g (92.0% yield) of white solid is obtained from 0.15 g (0.53 mmol) of 4-bromo-2-(carboxymethyl)benzoic acid and 0.08 mL (0.636 mmol) of 1,3-Benzodioxole-5-methanamine: mp 227-228° C.; MS (ESI) m/z 400.9 (M+H)$^{+1}$ Analysis for $C_{18}H_{13}BrN_2O_4$ Calcd: C, 53.89; H, 3.27; N, 6.98. Found: C, 53.71; H, 3.28; N, 6.97.

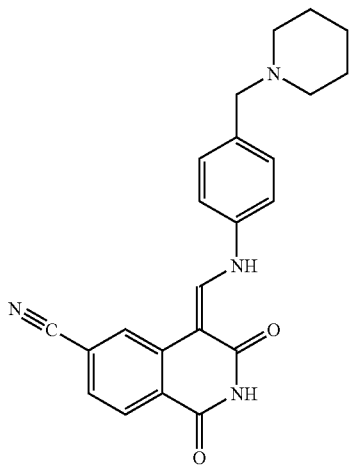

Example 110

(4Z)-1,3-Dioxo-4-({[4-(piperidin-1-ylmethyl)phenyl]amino}methylene)1,2,3,4-tetrahydroisoquinoline-6-carbonitrile A mixture of 1.00 g (2.27 mmol) of 4Z)-6-bromo-4-({[4-(piperidin-1-ylmethyl)phenyl]amino}methylene)isoquinoline-1,3(2H,4H)-dione, 239 mg (2.05 mmol) of Zn(CN)$_2$ and 394 mg (0.341 mmol) of (PPh$_3$)$_4$Pd in 17 mL of N,N-dimethylformamide (DMF) under N$_2$ is heated at 100° C. in the dark for 1.75 h. The reaction is then poured into 40 mL of ice water and the product is collected, washed with H$_2$O and Et$_2$O and dried. The crude product is boiled with 10% MeOH in CHCl$_3$ and filtered. The filtrate is washed with 2 M NH$_4$OH and brine, dried and evaporated. The residue is washed with boiling CH$_3$CN and the insoluble material is dried to yield 200 mg (23%) of yellow-orange crystals: mp 254-256° C. (dec); $^1$H NMR (DMSO-d$_6$) δ 12.46 (d, 1H, J=9 Hz), 11.58 (s, 1H), 9.01 (d, 1H, J=9 Hz), 8.76 (s, 1H), 8.13 (d, 1H, J=6 Hz), 7.60 (m, 3H), 7.35 (d, 2H, J=6 Hz), 3.43 (s, 2H), 2.33 (s, 4H), 1.49 (m, 4H), 1.39 (m, 2H); HRMS (ESI) m/e calcd for $C_{23}H_{22}N_4O_2$ 387.18156. found 387.18121 (M+H)$^{+1}$.

Analysis for $C_{23}H_{22}N_4O_2 \cdot 0.25$ CHCl$_3$: Calcd: C, 67.07; H, 5.40; N, 13.46. Found: C, 65.63; H, 5.05; N, 13.87.

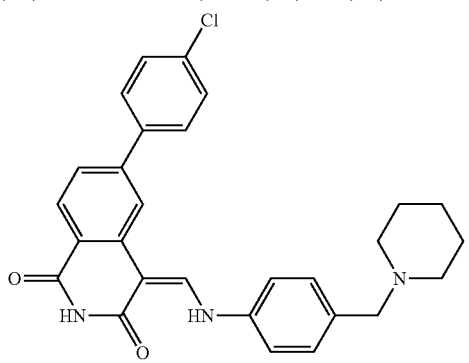

Example 111

(4Z)-6-(4-Chlorophenyl)-4-({[4-(piperidin-1-ylmethyl)phenyl]amino}methylene)isoquinoline-1,3(2H,4H)-dione Using the procedure described for the preparation of example 95, 250 mg (79%) of yellow solid is obtained from 300 mg (0.68 mmol) of (4Z)-6-bromo-4-({[4-(piperidin-1-ylmethyl)phenyl]amino}methylene)isoquinoline-1,3(2H,4H)-dione and 4-chloro phenyl boronic acid (214.0 mg, 1.36 mmol); mp 204-205° C.

MS (ESI) m/z 464.90 (M+1).

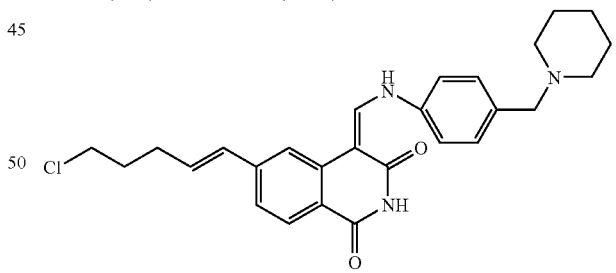

Example 112

(4Z)-6-[(1E)-5-Chloropent-1-enyl]-4-({[4-(piperidin-1-ylmethyl)phenyl]amino}methylene)isoquinoline-1,3(2H,4H)-dione Using the procedure described for the preparation of example 95, 100 mg (32%) of yellow solid is obtained from 300 mg (0.68 mmol) of (4Z)-6-bromo-4-({[4-(piperidin-1-ylmethyl)phenyl]amino}methylene)isoquinoline-1,3(2H, 4H)-dione and (1E)-5-chloropent-1-enylboronic acid (202.04 mg, 1.36 mmol); mp 268-269° C.

MS (ESI) m/z 464.0 (M+1).

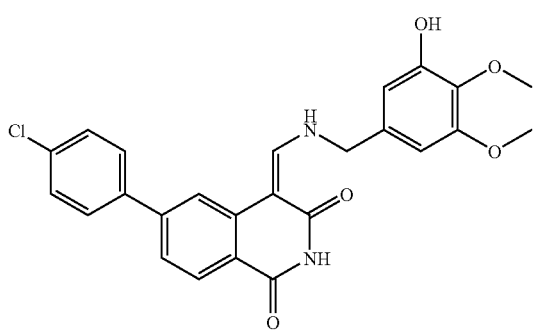

Example 113

(4Z)-6-(4-Chlorophenyl)-4-{[(3-hydroxy-4,5-dimethoxybenzyl)amino]methylene}isoquinoline-1,3(2H,4H)-dione Using the procedure described for the preparation of example 95, 250 mg (79%) of green solid is obtained from 300 mg (0.68 mmol) of example 78 ((4Z)-6-bromo-4-{[(3-hydroxy-4,5-dimethoxybenzyl)amino)methylene}isoquinoline-1,3(2H,4H-dione) and 4-chlorophenyl boronic acid (216.56 mg, 1.38 mmol); mp 240-241° C.

MS (ESI) m/z 464.11 (M−1).

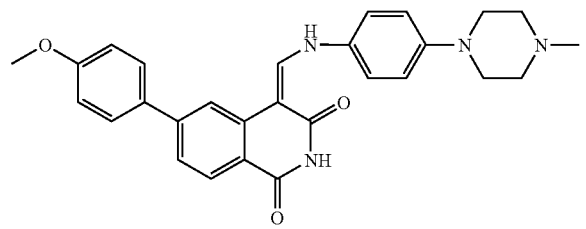

Example 114

(4Z)-6-(4-methoxyphenyl)-4-({[4-(4-methylpiperazin-1-yl)phenyl]amino}methylene)-isoquinoline-1,3(2H,4H)-dione Using the procedure described for the preparation of (4Z)-4-({[4-(4-methylpiperazin-1-yl)phenyl]amino}methylene)-6-thien-3-ylisoquinoline-1,3(2H,4H)-dione, 0.11 g (37.1% yield) of brown solid is obtained from 0.3 g (0.68 mmol) of (4Z)-6-bromo-4-({[4-(4-methylpiperazin-1-yl)phenyl]amino}-methylene)-isoquinoline-1,3(2H,4H)-dione, 0.155 g (1.02 mmol) of 4-methoxyphenylboronic acid, 0.0623 g (0.068 mmol) of tris(dibenzyldeneaacetone)-dipalladium(0), 0.041 g (0.136 mmol) of 2-(di-t-butyl-phosphino)-biphenyl, 0.144 g (1.36 mmol) of sodium carbonate and 5 mL of 80% N,N-dimethylformamide (DMF)/H2O solution: mp 224-225° C., MS (ESI) m/z 469.3 (M+H)$^{+1}$ Analysis for $C_{28}H_{28}N_4O_3.(0.67H_2O)$ Calcd: C, 69.98; H, 6.15; N, 11.66. Found: C, 69.75; H, 5.97; N, 11.31.

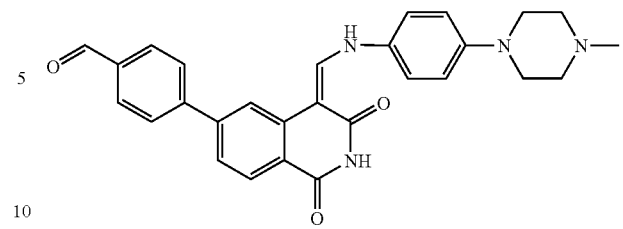

Example 115

4-[(4Z)-4-({[4-(4-Methylpiperazin-1-yl)phenyl]amino}methylene)-1,3-dioxo-1,2,3,4-tetra-hydroisoquinolin-6-yl]benzaldehyde Using the procedure described for the preparation of (4Z)-4-({[4-(4-methylpiperazin-1-yl)phenyl]amino}methylene)-6-thien-3-ylisoquinoline-1,3(2H,4H)-dione, 0.054 g (10.2% yield) of yellow solid is obtained from 0.5 g (1.13 mmol) of (4Z)-6-bromo-4-({[4-(4-methylpiperazin-1-yl)phenyl]amino}-methylene)-isoquinoline-1,3(2H,4H)-dione, 0.25 g (1.7 mmol) of 4-formylphenylboronic acid, 0.10 g (0.113 mmol) of tris(dibenzyldenea-acetone)-dipalladium(0), 0.067 g (0.226 mmol) of 2-(di-t-butyl-phosphino)-biphenyl, 0.24 g (2.26 mmol) of sodium carbonate and 6 mL of 80% N,N-dimethylformamide (DMF)/H2O solution: mp 152-153° C., MS (ESI) m/z 467.2 (M+H)$^{+1}$ Analysis for $C_{28}H_{26}N_4O_3.(0.67H_2O)$ Calcd: C, 70.28; H, 5.76; N, 11.71. Found: C, 70.09; H, 5.62; N, 12.10.

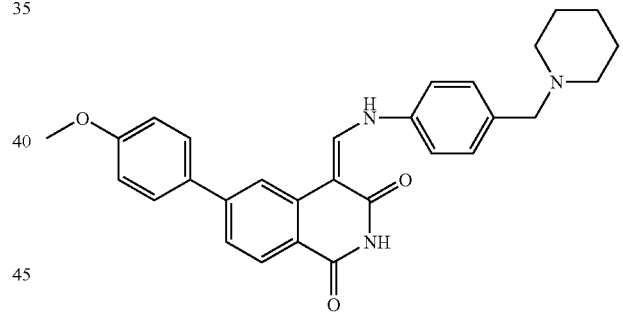

Example 116

(4Z)-6-(4-Methoxyphenyl)-4-({[4-(piperidin-1-ylmethyl)phenyl]amino}methylene)-isoquinoline-1,3(2H,4H)-dione Using the procedure described for the preparation of (4Z)-4-({[4-(4-methylpiperazin-1-yl)phenyl]amino}methylene)-6-thien-3-ylisoquinoline-1,3(2H,4H)-dione, 0.12 g (22.6% yield) of yellow solid is obtained from 0.5 g (1.136 mmol) of (4Z)-6-bromo-4-({[4-(piperidin-1-ylmethyl)phenyl]amino}methylene)isoquinoline-1,3(2H,4H)-dione, 0.26 g (1.7 mmol) of 4-methoxyphenylboronic acid, 0.10 g (0.14 mmol) of tris(dibenzyldenea-acetone)-dipalladium(0), 0.068 g (0.28 mmol) of 2-(di-t-butyl-phosphino)-biphenyl, 0.25 g (2.27 mmol) of sodium carbonate and 6 mL of 80% N,N-dimethylformamide (DMF)/H2O solution: mp 168-169° C., MS (ESI) m/z 468.2 (M+H)$^{+1}$ Analysis for $C_{29}H_{29}N_3O_3 \cdot (1.2H_2O)$ Calcd: C, 71.20; H, 6.47; N, 8.59. Found: C, 70.81; H, 6.06; N, 8.52.

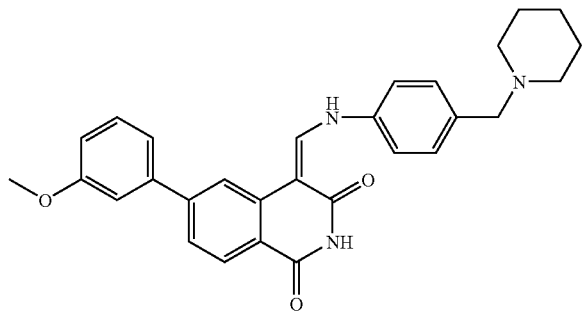

Example 117

(4Z)-6-(3-Methoxyphenyl)-4-({[4-(piperidin-1-ylmethyl)phenyl]amino}methylene)-isoquinoline-1,3(2H,4H)-dione Using the procedure described for the preparation of (4Z)-4-({[4-(4-methylpiperazin-1-yl)phenyl]amino}methylene)-6-thien-3-ylisoquinoline-1,3(2H,4H)-dione, 0.096 g (18.1% yield) of yellow solid is obtained from 0.5 g (1.136 mmol) of (4Z)-6-bromo-4-({[4-(piperidin-1-ylmethyl)phenyl]amino}methylene)isoquinoline-1,3(2H,4H)-dione (14), 0.26 g (1.7 mmol) of 3-methoxyphenylboronic acid, 0.10 g (0.14 mmol) of tris(dibenzyldenea-acetone)-dipalladium(0), 0.068 g (0.28 mmol) of 2-(di-t-butyl-phosphino)-biphenyl, 0.25 g (2.27 mmol) of sodium carbonate and 6 mL of 80% N,N-dimethylformamide (DMF)/$H_2O$ solution: mp 169-170° C., MS (ESI) m/z 468.3 (M+H)$^{+1}$ Analysis for $C_{29}H_{29}N_3O_3 \cdot (0.2H_2O)$ Calcd: C, 73.78; H, 6.30; N, 8.90. Found: C, 73.62; H, 6.33; N, 8.55.

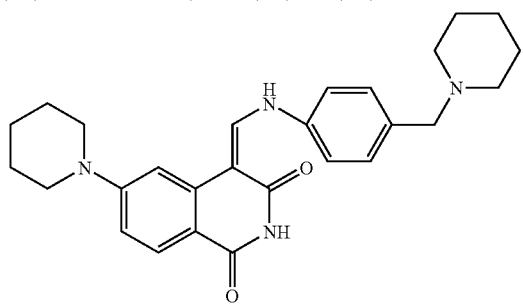

Example 118

(4Z)-6-Piperidin-1-yl-4-({[4-(piperidin-1-ylmethyl)phenyl]amino}methylene)isoquinoline-1,3(2H,4H)-dione A mixture of 300 mg (0.68 mmol) of (4Z)-6-bromo-4-({[4-(Piperidin-1-ylmethyl)phenyl]amino}methylene)isoquinoline-1,3(2H,4H)-dione, tris(dibenzylideneacetone)-dipalladium (0) (Pd$_2$(dba)$_3$) (118.30 mg, 0.129 mmol), 1,3-bis(2,6-di-isopropylphenyl)imidazolium chloride (Ipr.HCl) 78.04 mg (0.184 mmol), potassium t-butoxide, (194.41 mg, 1.36 mmol), and piperidine (200 mg, 2.04 mmol) is placed in a three neck flask. Under $N_2$, N,N-dimethylformamide (8 ML) is added, and the mixture is then stirred in a pre-heated oil bath 100° C. for 45 min. After cooling, the mixture is treated with $CH_2Cl_2$ and filtered through celite. After evaporating all the solvents, the residue is dissolved in methylene chloride, washed three times with sodium bicarbonate solution, dried over magnesium sulfate and evaporated. The yellow oily residue is purified by preparative thin layer chromatography (5:95=methanol:methylene chloride), to give a yellow solid 80 mg (25% yield); mp 211-212° C.

MS (ESI) m/z 464.0 (M+1).

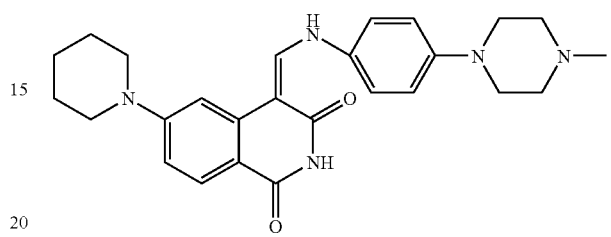

Example 119

(4Z)-6-Piperidin-1-yl-4-({[4-(methylPiperzin-1-yl)phenyl]amino}methylene)isoquinoline-1,3(2H,4H)-dione Using the procedure described for the preparation of example 118, 70 mg (23% yield) of yellow solid is obtained from 300 mg (0.68 mmol) of 4Z)-6-bromo-4-({[4-(piperidin-1-ylmethyl)phenyl]amino}methylene)isoquinoline-1,3(2H, 4H)-dione and piperidine (200 mg, 2.04 mmol);

mp 223-224° C.

MS (ESI) m/z 445.56 (M+1).

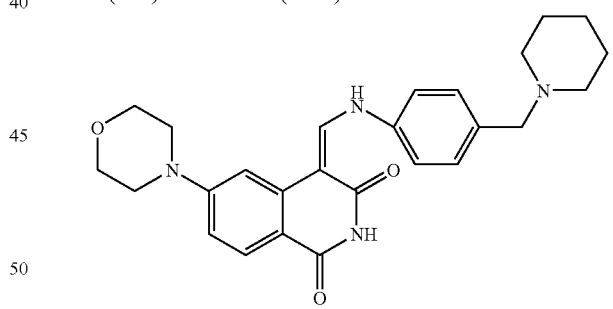

Example 120

(4Z)-6-Morpholin-4-yl-4-({[4-(piperidin-1-ylmethyl)phenyl]amino}methylene)isoquinoline-1,3(2H,4H)-dione Using the procedure described for the preparation of example 118, 95 mg (31% yield) of yellow solid is obtained from 300 mg (0.68 mmol) of 4Z)-6-bromo-4-({[4-(piperidin-1-ylmethyl)phenyl]amino}methylene)isoquinoline-1,3(2H, 4H)-dione and morpholine (178 mg, 2.04 mmol); mp 216-217° C.

MS (ESI) m/z 446.55 (M+1).

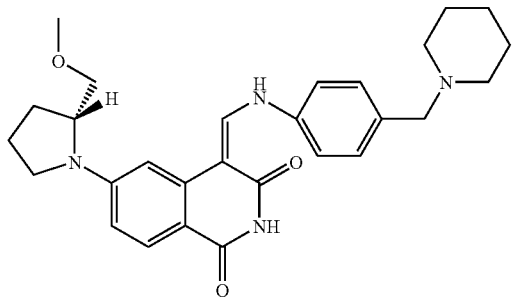

Example 121

(4Z)-6-[(2R)-2-(Methoxymethyl)pyrrolidin-1-yl]-4-({[4-(piperidin-1-ylmethyl)phenyl]amino}methylene)isoquinoline-1,3(2H,4H)-dione Using the procedure described for the preparation of example 118, 120 mg (37% yield) of yellow solid is obtained from 300 mg (0.68 mmol) of 4Z)-6-bromo-4-({[4-(piperidin-1-ylmethyl)phenyl]amino}methylene)isoquinoline-1,3(2H,4H)-dione and (2R)-2-methoxymethyl-pyrrolidine 234.95 mg (2.04 mmol); mp 135-136° C.

MS (ESI) m/z 474.60 (M+1).

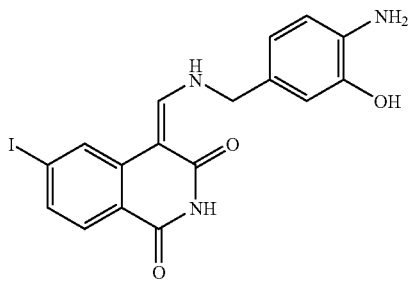

Example 122

(4Z)-4-{[(4-Amino-3-hydroxybenzyl)amino]methylene}-6-iodoisoquinoline-1,3(2H,4H)-dione Using the procedure described for the preparation of example 46, 200 mg of yellow-brown solid (60% yield) is obtained from 250 mg (0.76 mmol) of 6-iodo-4-methoxymethylene-isoquinoline-4H-1,3-dione and 2-amino-5-(aminomethyl)phenol (160.43 mg, 0.76 mmol);

mp 250-251° C.

MS (ESI) m/z 435.22 (M+1).

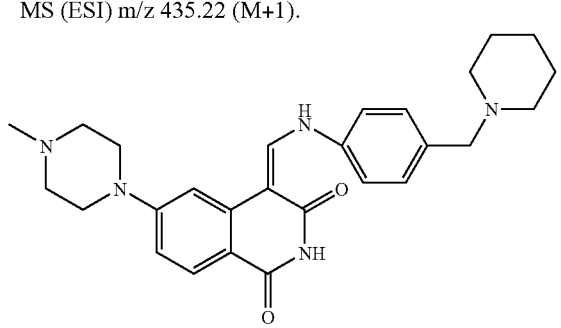

Example 123

(4Z)-6-[(4-Methyl-piperazin-1-yl]-4-({[4-(piperidin-1-ylmethyl)phenyl]amino}methylene)isoquinoline-1,3(2H,4H)-dione Using the procedure described for the preparation of example 118, 90 mg (29% yield) of yellow solid is obtained from 300 mg (0.68 mmol) of 4Z)-6-bromo-4-({[4-(piperidin-1-ylmethyl)phenyl]amino}methylene)isoquinoline-1,3(2H,4H)-dione and 4-methyl-piperazine 204.41 mg (2.04 mmol); mp 192-193° C.

MS (ESI) m/z 459.59 (M+1).

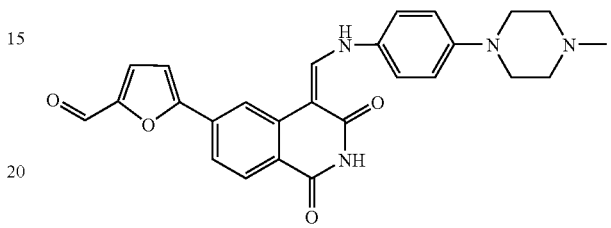

Example 124

5-[(4Z)-4-({[4-(4-Methylpiperazin-1-yl)phenyl]amino}methylene)-1,3-dioxo-1,2,3,4-tetrahydroisoquinolin-6-yl]-2-furaldehyde Using the procedure described for the preparation of (4Z)-4-({[4-(4-methylpiperazin-1-yl)phenyl]amino}methylene)-6-thien-3-ylisoquinoline-1,3(2H,4H)-dione, 0.36 g (36% yield) of yellow solid is obtained from 1.00 g (2.27 mmol) of (4Z)-6-bromo-4-({[4-(4-methylpiperazin-1-yl)phenyl]amino}-methylene)-isoquinoline-1,3(2H,4H)-dione, 0.38 g (2.72 mmol) of 2-formylfuran-5-boronic acid, 0.20 g (0.227 mmol) of tris(dibenzyldenea-acetone)-dipalladium(0), 0.135 g (0.534 mmol) of 2-(di-t-butyl-phosphino)-biphenyl, 0.5 g (5.34 mmol) of sodium carbonate and 6 mL of 80% N,N-dimethylformamide (DMF)/H$_2$O solution: mp 218-220° C., MS (ESI) m/z 457.2 (M+H)$^{+1}$ Analysis for $C_{26}H_{24}N_4O_4 \cdot (0.57H_2O)$ Calcd: C, 66.90; H, 5.43; N, 12.00. Found: C, 66.86; H, 5.38; N, 12.13.

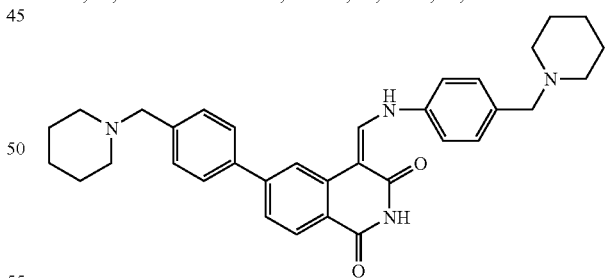

Example 125

6-(4-Piperidin-1-ylmethyl-phenyl)-4-[(4-piperidin-1-ylmethyl-phenylamino)-methylene]-4H-isoquinoline-1,3-dione A solution of (4Z)-6-bromo-4-({[4-(piperidin-1-ylmethyl)phenyl]amino}methylene)isoquinoline-1,3(2H,4H)-dione (14) (0.40 g, 0.90 mmol) in 5 mL of N,N'-dimethylformamide is added to 1-(4-tributylstannanyl-benzyl)-piperidine (0.60 g, 1.35 mmol) and 0.03 g (0.045 mmol) of dichlorobis(triphenylphosphine)-palladium(II). The flask is sealed with a rubber septum, degassed and flushed with nitrogen gas three times. The reaction mixture is heated at 110° C. under $N_2$. Mass spectroscopy suggested the completion of reaction after 2 h. The reaction mixture is concentrated to give dark brown residue. Purification is performed by florisil chromatography using 10% MeOH/CHCl3 solution as eluting solvent to generate 0.045 g (9.87% yield) of yellow solid: mp 159-160° C.; MS (ESI) m/z 455.2 $(M+H)^{+1}$ Analysis for $C_{34}H_{38}N_4O_2$ $_{Calcd:\ C}$, 50.29; H, 4.40; N, 7.65. Found: C, 49.89; H, 4.17; N, 7.49.

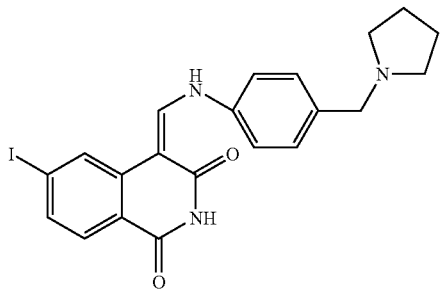

Example 126

4Z)-6-Iodo-4-({[4-(pyrrolidin-1-ylmethyl)phenyl}amino)methylene]isoquinolin-1,3(2H,4H)-dione Using the procedure described for the preparation of example 14, 200 mg (56% yield) of yellow solid is obtained from 250 mg (0.76 mmol) of 6-iodo-4-methoxymethylene-isoquinoline-4H-1,3-dione and 4-pyrrolidin-1-ylmethyl-phenylamine 133.96 mg (0.76 mmol), (prepared similarly to 4-morpholin-4-ylmethyl-phenylamine); mp 186-187° C.

MS (ESI) m/z 473.31 (M+1).

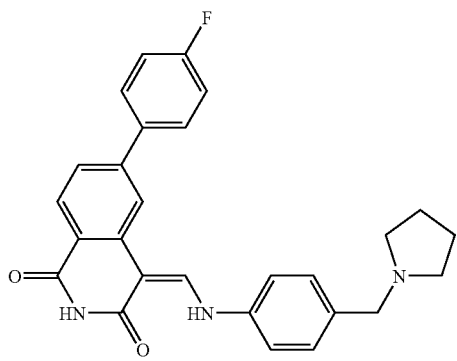

Example 127

(4Z)-6-(4-Fluorophenyl)-4-({[4-(pyrrolidin-1-ylmethyl)phenyl]amino}methylene)isoquinoline-1,3(2H, 4H)-dione Using the procedure described for the preparation of example 95, 80 mg (27%) of yellow solid is obtained from 300 mg (0.68 mmol) of example 126 and 4-fluorophenyl boronic acid (214.0 mg, 1.36 mmol); mp 152-153° C.

MS (ESI) m/z 443.51 (M+1).

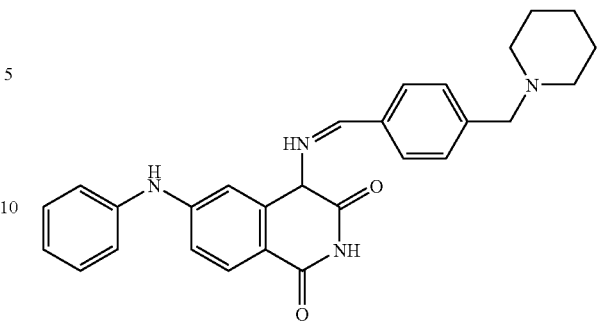

Example 128

(4Z)-6-Anilino-4-({[4-(piperidin-1-ylmethyl)phenyl]amino}methylene)isoquinoline-1,3(2H,4H)-dione Using the procedure described for the preparation of example 118, the title compound is obtained as yellow solid (70% yield) from 6-bromo-4-[(4-piperidin-1-ylmethyl-phenylamino)-methylene]-4H-isoquinoline-1,3-dione and aniline.

MS (ESI) m/z 453.22 (M+1).

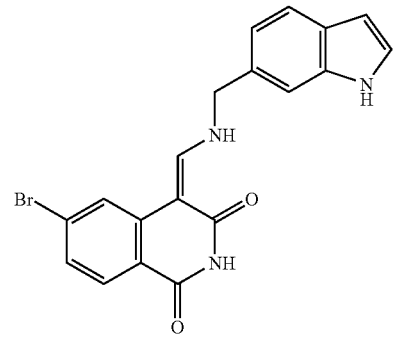

Example 129

(4Z)-6-Bromo-4-{[(1H-indol-6-ylmethyl)amino]methylene}isoquinoline-1,3(2H,4H)-dione General procedure 1: An amount of 200 mg (1.30 mmol) of C-(1H-Indol-6-yl)-methylamine, is dissolved in N,N-dimethylformamide (10 mL). 0.542 mL (3.9 mmol) of triethylamine is added followed by 366 mg (1.30 mmol) of (4E)-6-bromo-4-(methoxymethylene)isoquinoline-1,3(2H,4H)-dione. After the mixture is stirred at room temperature for 30 min, water (2 mL) is added and the reaction mixture is stirred for 60 min. The precipitate is filtered and washed several times with anhydrous ether. The crude material is purified by high performance liquid chromatography to give 45 mg of a pink solid. MS (ESI) m/z 396.1 (M+1).

According to general procedure 1, an amount of 100 mg (0.35 mmol) of C-(1H-Indol-4-yl)-methylamine, is dissolved in N,N-dimethylformamide (5 mL). 106 μl (1.05 mmol) of triethylamine is added followed by 52 mg (0.35 mmol) of (4E)-6-bromo-4-(methoxymethylene)isoquinoline-1,3(2H, 4H)-dione. After the mixture is stirred at room temperature for 30 min, water (2 mL) is added and the reaction mixture is stirred for 60 min. The precipitate is filtered and washed several times with anhydrous ether to give a red solid. The crude solid is then purified by high performance liquid chromatography to give 7 mg of a pink solid. MS (ESI) m/z 396.2 (M+1).

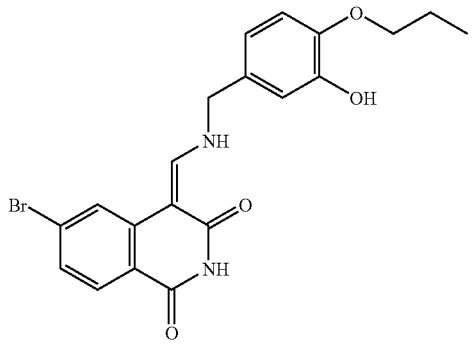

Example 130

(4Z)-6-Bromo-4-{[(3-hydroxy-4-propoxybenzyl)amino]methylene}isoquinoline-1,3(2H,4H)-dione According to the general procedure of example 129, an amount of 100 mg (0.55 mmol) of 5-(aminomethyl)-2-propoxyphenol is dissolved in N,N-dimethylformamide (5 mL). 228 µl (1.65 mmol) of triethylamine is added followed by 171 mg (0.607 mmol) of (4E)-6-bromo-4-(methoxymethylene)isoquinoline-1,3(2H,4H)-dione. After the mixture is stirred at room temperature for 30 min, water (3 mL) is added and the reaction mixture is stirred for 3 hours. The precipitate is filtered and washed several times with anhydrous ether. The crude solid is then purified by high performance liquid chromatography to give 67 mg of a white solid. MS (ESI) m/z 430.8 (M+1).

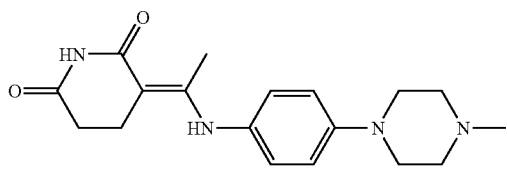

Example 131

(3Z)-3-(1-{[4-(4-Methylpiperazin-1-yl)phenyl]amino}ethylidene)piperidine-2,6-dione Following the procedure of Kato and Noda (Chem. Pharm. Bull. Jpn 22, 12, 2947-2952, 1974), to a 0.6 M solution of sodium ethoxide (50 mL, 30 mmol) is added acetoacetamide (3.5 g, 35 mmol), followed by ethyl acrylate (3.2 mL, 30 mmol). After 10 minutes of stirring at room temperature an additional volume of ethanol (40 mL) is added. The reaction mixture is stirred at room temperature for one week, then neutralized to pH 7 by the addition of 10% aqueous hydrochloric acid solution. The quenched mixture is then concentrated under reduced pressure to give a white suspension. The suspension is partitioned between ethyl acetate and water. The aqueous phase is extracted 3× with ethyl acetate. The combined extracts were washed with saturated aqueous sodium chloride solution, dried over anhydrous sodium sulfate, decanted, and concentrated under reduced pressure to give a dark oil (1.0 g), which is purified by flash chromatography (50% ethyl acetate/hexanes) to give (3Z)-3-(1-hydroxyethylidene)-piperidine-2,6-dione as white powder.

To a suspension of 4-(4-methyl-1-piperazinyl)-benzenamine (43 mg, 0.23 mmol) and (3Z)-3-(1-hydroxyethylidene)-piperidine-2,6-dione (35 mg, 0.23 mmol) in absolute ethanol (1.5 mL) is added concentrated ethanolic hydrogen chloride (2 drops), which caused the precipitation of a white solid. The mixture is heated in a 65° C. oil bath for 20 minutes. Then N,N-dimethylformamide (0.4 mL) is added to the mixture and the temperature of the oil bath is increased to 70° C. An additional volume of N,N-dimethylformamide (0.6 mL) is added and the temperature of the oil bath is increased to 135° C., at which setting it stirred for 30 minutes. The mixture is stirred overnight at 130° C. After cooling to room temperature, the semi-solid reaction mixture is triturated with methanol. The solid that formed is collected by filtration and washed with diethyl ether, water, and methanol to give (3Z)-3-(1-{[4-(4-methylpiperazin-1-yl)phenyl]amino}ethylidene)piperidine-2,6-dione as a light beige solid.

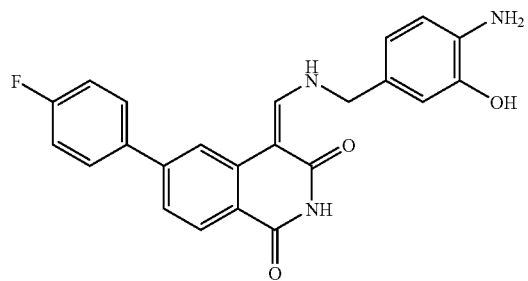

Example 134

(4Z)-4-{[(4-Amino-3-hydroxybenzyl)amino]methylene}-6-(4 fluorophenyl)isoquinoline-1,3(2H,4H)-dione Using the procedure described for the preparation of example 95, 80 mg of brown solid (39% yield) is obtained from 200 mg (0.52 mmol) (4Z)-4-{[(4-amino-3-hydroxybenzyl)amino]methylene}-6-bromoisoquinoline-1,3(2H,4H)-dione and 4-Fluorophenyl boronic acid 215.57 mg, (1.55 mmol).; mp 227-228° C.

MS (ESI) m/z 404.3 (M+1)⁺.

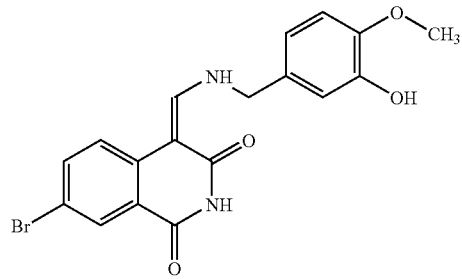

Example 135

(4Z)-7-Bromo-4-{[(3-hydroxy-4-methoxybenzyl)amino]methylene}isoquinoline-1,3(2H,4H)-dione Using the procedure described for the preparation of example 46, 150 mg (52%) yield of a brown solid is obtained from 200 mg (0.71 mmol) of (4E)-7-bromo-4-(methoxymethylene)isoquinoline-1,3(2H,4H)-dione and 3-hydroxy-4-methoxy-benzylamine); mp 297-298° C.

MS (ESI) m/z 403.13 (M+1).

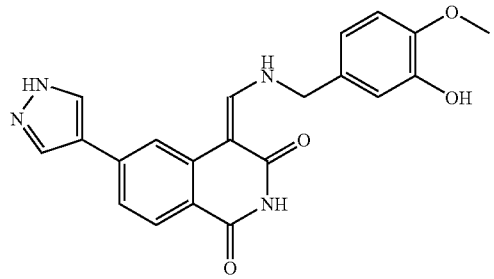

Example 136

(4Z)-4-{[(3-Hydroxy-4-methoxybenzyl)amino]methylene}-6-(1H-pyrazol-4-yl)isoquinoline-1,3(2H,4H)-dione Using the procedure described for the preparation of example 95, 200 mg of green solid (82% yield) is obtained from 250 mg (0.62 mmol) (4Z)-6-bromo-4-{[(3-hydroxy-4-methoxybenzyl)amino]methylene}isoquinoline-1,3(2H,4H)-dione and 4-(4,4,5,5-tetramethyl-1,2-dioxaborolan-2-yl)-1H-pyrazol, 361.26 mg (1.86 mmol).; mp 252-253° C.

MS (ESI) m/z 390.3 (M+1)

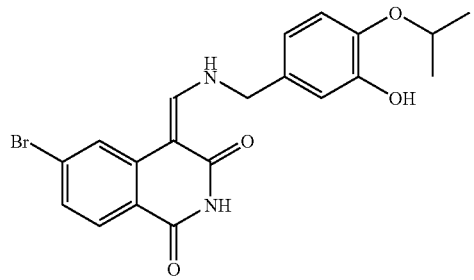

Example 137

(4Z)-6-Bromo-4-{[(3-hydroxy-4-isopropoxybenzyl)amino]methylene}isoquinoline-1,3(2H,4H)-dione To a solution of (4Z)-6-bromo-4-{[(3,4-dihydroxybenzyl)-amino]methylene}isoquinoline-1,3(2H,4H)-dione (0.74 g, 1.9 mmol) in 5 mL of N,N'-dimethylformamide is added 2-iodopropane (0.19 mL, 1.9 mmol) and 0.52 g (3.8 mmol) of potassium carbonate. The reaction mixture is heated at 70° C. under $N_2$. Mass spectroscopy indicated the completion of reaction after 3.5 h. The reaction mixture is filtered through a pad of celite, and water is added to give a precipitate. It is filtered and washed successively with MeOH, $Et_2O$ and hexane, dried in oven (60° C.) overnight to afford 0.58 g (70.7% yield) of tan solid: mp 212-213° C.; MS (ESI) m/z 431.2 and 433.2 (M+H)$^{+1}$ Analysis for $C_{20}H_{19}BrN_2O_4 \cdot (1.6H_2O)$ Calcd: C, 52.21; H, 4.86; N, 6.09. Found: C, 51.86; H, 4.42; N, 6.21.

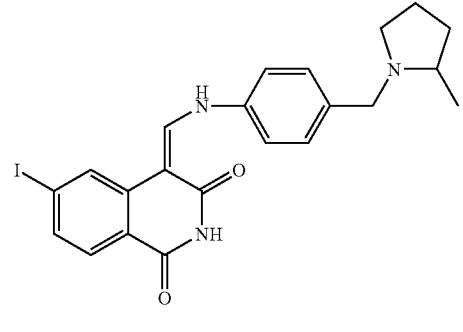

Example 138

(4Z)-6-Iodo-4-[({4-[(2-methylpyrrolidin-1-yl)methyl]phenyl}amino)methylene]isoquinoline-1,3(2H,4H)-dione To a solution of 0.2 g (0.61 mmol) of (4E)-6-iodo-4-(methoxymethylene)-isoquinoline-1,3(2H,4H)-dione in 2 mL of N,N'-dimethylformamide is added {4-[(2-methylpyrrolidin-1-yl)methyl]phenyl}amine (0.14 mL, 0.73 mmol). The reaction mixture is heated at 100° C. under $N_2$. Mass spectroscopy suggested the completion of reaction after 45 min. The reaction mixture is concentrated under high-pressure vacuum. Purification is performed by silica gel chromatography using 5% MeOH/CHCl$_3$ as solvent. Concentrating the organic layer containing product afforded 0.043 g (14.5% yield) of yellow solid: mp 157-158° C.; MS (ESI) m/z 488.4 (M+H)$^{+1}$ Analysis for $C_{22}H_{22}IN_3O_2$ Calcd: C, 54.22; H, 4.55; N, 8.62. Found: C, 53.55; H, 4.63; N, 8.33.

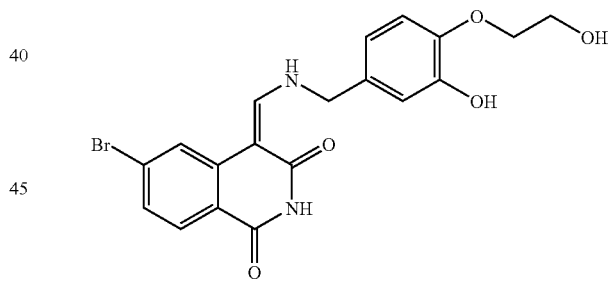

Example 139

(4Z)-6-Bromo-4-({[3-hydroxy-4-(2-hydroxyethoxy)benzyl]amino}methylene)isoquinoline-1,3(2H,4H)-dione Using the procedure described for the preparation of (4Z)-6-Bromo-4-{[(3-hydroxy-4-isopropoxybenzyl)amino]methylene}isoquinoline-1,3(2H,4H)-dione, 0.41 g (73.7% yield) of tan solid is obtained from 0.5 g (1.29 mmol) of (4Z)-6-bromo-4-{[(3,4-dihydroxybenzyl)amino]methylene}isoquinoline-1,3(2H,4H)-dione, 0.10 mL (1.29 mmol) of 2-iodoethanol, and 0.36 g (2.58 mmol) of potassium carbonate: mp 166-167° C.; MS (ESI) m/z 431.1 and 433.0 (M+H)$^{+1}$ Analysis for C$_{18}$H$_{15}$BrN$_2$O$_4$.(0.5H$_2$O) Calcd: C, 51.60; H, 4.10; N, 6.33. Found: C, 51.58; H, 4.11; N, 6.30.

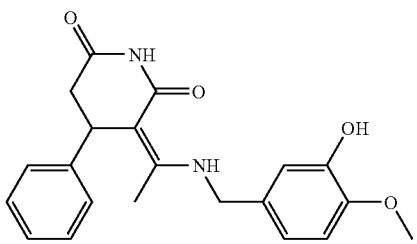

Example 140

(3Z)-3-{1-[(3-hydroxy-4-methoxybenzyl)amino]ethylidene}-4-phenylpiperidine-2,6-dione Following the procedure of Kato and Noda (Chem. Pharm. Bull. Jpn 22, 12, 2947-2952, 1974), to a 0.6 M solution of sodium ethoxide (50 mL, 30 mmol) is added acetoacetamide (3.5 g, 35 mmol), followed by methyl cinnamate (4.9 mL, 30 mmol). After 10 minutes of stirring at room temperature an additional volume of ethanol (40 mL) is added. The reaction mixture is stirred at room temperature for three weeks, then neutralized to pH 7 by the addition of 10% aqueous hydrochloric acid solution. The quenched mixture is then concentrated under reduced pressure to give a white suspension. The suspension is partitioned between ethyl acetate and water. The aqueous phase is extracted thrice with ethyl acetate. The combined extracts were washed with saturated aqueous sodium chloride solution, dried over anhydrous sodium sulfate, decanted, and concentrated under reduced pressure to give a white suspension, which is triturated with hot ethanol and then cooled in freezer. The white solid is collected by Buchner filtration, washed with ethanol, and dried under vacuum to give (3Z)-3-(1-hydroxyethylidene)-4-phenylpiperidine-2,6-dione as white powder (1.2 g, 17%).

To a suspension of (3Z)-3-(1-hydroxyethylidene)-4-phenylpiperidine-2,6-dione (0.12 g, 0.52 mmol) and 5-(aminomethyl)-2-methoxyphenol (98 mg, 0.52 mmol) in absolute ethanol (5 mL) is added sodium acetate (0.75 mmol). The mixture is heated at reflux overnight and then allowed to cool to room temperature. The solvent is evaporated under reduced pressure and the residue is triturated with diethyl ether. The solid is collected, washed with diethyl ether, water, and methanol, and dried under vacuum to give (3Z)-3-{1-[(3-hydroxy-4-methoxybenzyl)amino]ethylidene}-4-phenylpiperidine-2,6-dione as a white powder (0.17 g, 88%).

MS (ES$^+$): 367.4 (M+H)$^+$

Example 141

2-(Acetylamino)-5-({[(Z)-(6-bromo-1,3-dioxo-2,3-dihydroisoquinolin-4(1H)-'ylidene)methyl]amino}methyl)phenyl acetate Using the procedure described for the preparation of example 69, 450 mg (99% yield) of brown solid is obtained from 500 mg (1.29 mmol) of (4Z)-4-{[(4-amino-3-hydroxybenzyl)amino]methylene}-6-bromoisoquinoline-1,3(2H,4H)-dione, and acetic anhydride 529.42 mg (5.16 mmol); mp 264-265° C.

MS (ESI) m/z 472.1 (M−1)$^-$.

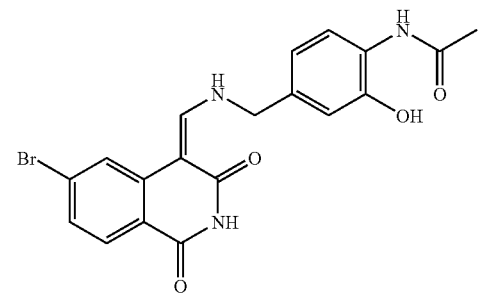

Example 142

N-[4-({[(Z)-(6-Bromo-1,3-dioxo-2,3-dihydroisoquinolin-4(1H)-'ylidene)methyl]amino}methyl)-2-hydroxyphenyl]acetamide An amount of 200 mg (0.74 mmol) of 2-(acetylamino)-5-({[(Z)-(6-bromo-1,3-dioxo-2,3-dihydroisoquinolin-4(1H)-ylidene)methyl]amino}methyl)phenyl acetate is stirred in N,N-dimethylformamide followed by addition of potassium carbonate 176.7 mg (1.27 mmol). The reaction mixture is stirred at room temperature for 3 hours, and then neutralized with 1N solution of hydrogen chloride to PH 7. The precipitate is filtered and washed with water and ether to give a brown solid (150 mg, 83%); mp: 252-253

MS (ESI) m/z 428(M−1)

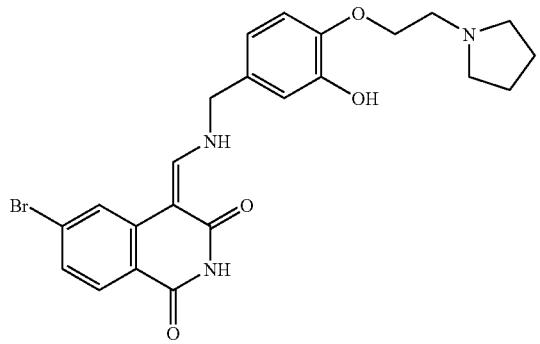

Example 143

(4Z)-6-Bromo-4-({[3-hydroxy-4-(2-pyrrolidin-1-ylethoxy)benzyl]amino}methylene) isoquinoline-1,3(2H,4H)-dione An amount of 33.5 mg (0.142 mmol) of 5-Aminomethyl-2-(2-pyrrolidin-1-yl-ethoxy)-phenol, is dissolved in N,N-dimethylformamide (2 ML). 30 µl (0.213 mmol) of triethy-

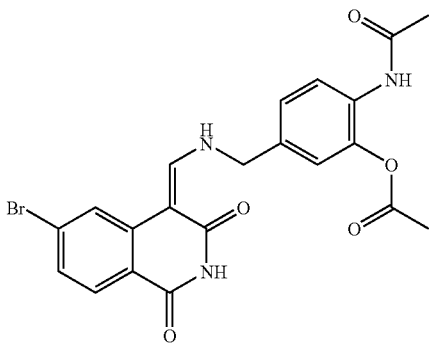

lamine is added followed by 20 mg (0.071 mmol) of (4E)-6-bromo-4-(methoxymethylene)isoquinoline-1,3(2H,4H)-dione. After the mixture is stirred at room temperature for 30 min, water (2 mL) is added and the reaction mixture is stirred for 60 min. The precipitate is filtered and washed several times with anhydrous ether. The crude solid is then purified by high performance liquid chromatography to give 23 mg of a yellow solid. MS (ESI) m/z 486.3 (M+1).

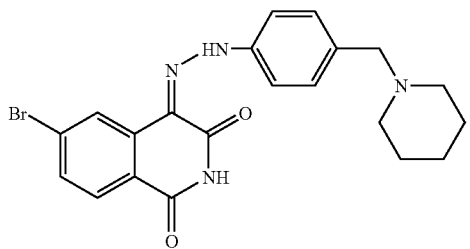

Example 144

6-Bromo-4-[(4-piperidin-1-ylmethyl-phenyl)-hydrazono]-4H-isoquinoline-1,3-dione Hydrochloride A solution of 4-piperidin-1-ylmethyl-phenylamine (0.110 g, 0.580 mmol) in 1.12 mL of conc HCL is chilled in an ice-salt bath and treated with 100 μL (0.040 g, 0.580 mmol) of 40% aq NaNO$_2$ for a few minutes. In a separate flask, a solution of 0.127 g (0.530 mmol) of the homophthalimide in 3 mL of N,N-dimethylformamide (DMF) is chilled to 20° C. The diazonium salt solution is then added and the mixture is stirred at 25° C. for 6 hr. The reaction is filtered and the insoluble material is washed with a small amount of N,N-dimethylformamide (DMF). The remaining precipitate is dissolved in 90% EtOH and filtered. This solution is evaporated and the residue is slurried in a few mL of 90% EtOH. Filtration, washing the solid twice with small volumes of 90% EtOH and drying in vacuo gave 0.212 g (76%) of yellow solid: mp 298-299° C. (dec); $^1$H NMR (DMSO-d$_6$) δ 11.95 (s, 1H), 10.39 (s, 1H), 8.34 (s, 1H), 7.96 (d, 1H, J=2.4 Hz), 7.69 (m, 5H), 4.25 (d, 2H, J=4.77 Hz), 3.34 (s, 1H), 2.83 (s(br), 2H), 1.77 (m, 5H), 1.21 (s(br), 1H); HRMS (ESI) m/z calcd for C$_{21}$H$_{21}$BrN$_4$O$_2$ 441.09207. found 441.09244 (M+H)$^{+1}$.

Analysis for C$_{21}$H$_{21}$BrN$_4$O$_2$.HCl.H$_2$O: Calcd: C, 51.24; H, 4.84; N, 11.38. Found: C, 51.37; H, 4.87; N, 11.31.

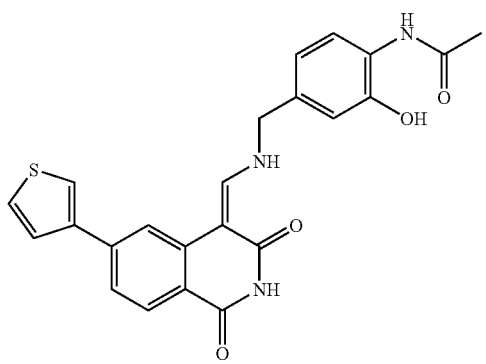

Example 145

N-[4-({[(Z)-(1,3-Dioxo-6-thien-3-yl-2,3-dihydroisoquinolin-4(1H)-'ylidene)methyl]amino}methyl)-2-hydroxyphenyl]acetamide Using the procedure described for the preparation of example 95, 250 mg of brown solid (91% yield) is obtained from 300 mg (0.64 mmol) '2-(acetylamino)-5-({[(Z)-(6-bromo-1,3-dioxo-2,3-dihydroisoquinolin-4(1H)-'ylidene)methyl]amino}methyl)phenyl acetate and 3-thiophine boronic acid 162.66 mg, (1.27 mmol).; mp 286-287° C.
MS (ESI) m/z 443.1 (M+1)$^+$.

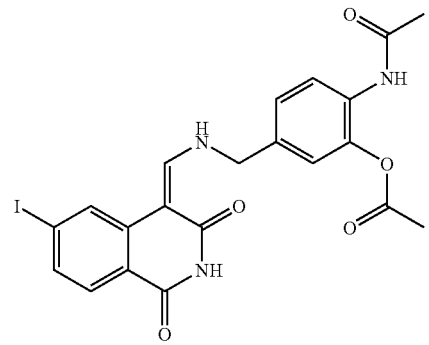

Example 146

2-(Acetylamino)-5-({[(Z)-(6-iodo-1,3-dioxo-2,3-dihydroisoquinolin-4(1H)-'ylidene)methyl]amino}methyl)phenyl acetate Using the procedure described for the preparation of example 69, 300 mg (84% yield) of brown solid is obtained from 300 mg (0.69 mmol) of (4Z)-4-{[(4-amino-3-hydroxybenzyl)amino]methylene}-6-iodoisoquinoline-1,3(2H,4H)-dione and acetic anhydride 422.28 mg (4.14 mmol);
mp: 264-265° C.
MS (ESI) m/z 520.0 (M+1)$^+$.

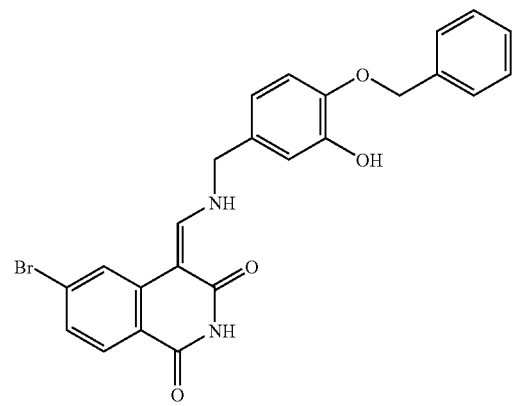

Example 147

(4Z)-4-({[4-(Benzyloxy)-3-hydroxybenzyl]amino}methylene)-6-bromoisoquinoline-1,3(2H,4H)-dione To a solution of benzyl bromide (33.0 μl, 0.28 mmol) and tetrabutylammonium iodide (104 mg, 0.283 mmol) in anhydrous N,N-dimethylformamide (2 ML) is added of potassium carbonate (207 mg, 1.5 mmol). The mixture stirred at room temperature and (4Z)-6-bromo-4-{[(3,4-dihydroxybenzyl)amino]methylene}isoquinoline-1,3(2H,4H)-dione (100 mg, 0.26 mmol) is added. After the mixture is stirred at 65° C. for 30 min, the resulting mixture is concentrated and the residue is then partitioned between water (20 ml) and ethyl acetate (20 ml). The organic layer is then dried and purified by high performance liquid chromatography to give 22 mg of a white solid. MS (ESI) m/z 478.9 (M+1).

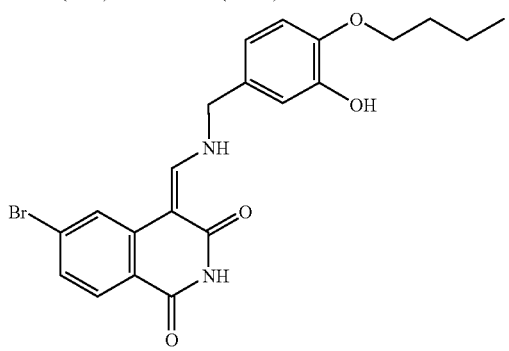

Example 148

(4Z)-6-Bromo-4-{[(4-butoxy-3-hydroxybenzyl)amino]methylene}isoquinoline-1,3(2H,4H)-dione To a solution of 1-bromobutane (30.4 μl, 0.28 mmol) and tetrabutylammonium iodide (104 mg, 0.283 mmol) in anhydrous N,N-dimethylformamide (2 ML) is added potassium carbonate (207 mg, 1.5 mmol). The mixture stirred at room temperature and (4Z)-6-bromo-4-{[(3,4-dihydroxybenzyl)amino]methylene} isoquinoline-1,3(2H,4H)-dione (100 mg, 0.26 mmol) is added. After the mixture is stirred at 65° C. for 30 min, the resulting mixture is concentrated and the residue is then partitioned between water (20 ml) and ethyl acetate (20 ml). The organic layer is then dried and purified by high performance liquid chromatography to give 43 mg of a white solid. MS (ESI) m/z 444.1 (M+1).

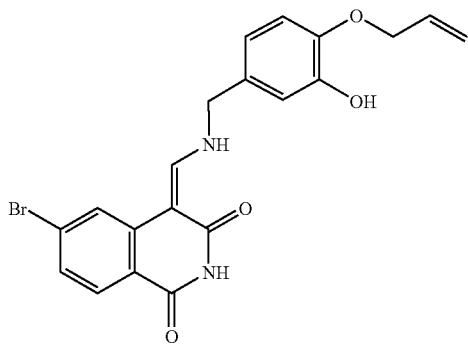

Example 149

(4Z)-4-({[4-(Allyloxy)-3-hydroxybenzyl]amino}methylene)-6-bromoisoquinoline-1,3(2H,4H)-dione To a solution of allyl iodide (25.6 μl, 0.28 mmol) and tetrabutylammonium iodide (104 mg, 0.283 mmol) in anhydrous N,N-dimethylformamide (2 ML) is added of potassium carbonate (207 mg, 1.5 mmol). The mixture stirred at room temperature and (4Z)-6-bromo-4-{[(3,4-dihydroxybenzyl)amino]methylene}isoquinoline-1,3(2H,4H)-dione (100 mg, 0.26 mmol) is added. After the mixture is stirred at 65° C. for 30 min, the resulting mixture is concentrated and the residue is then partitioned between water (20 ml) and ethyl acetate (20 ml). The organic layer is then dried and purified by high performance liquid chromatography to give 36 mg of a white solid. MS (ESI) m/z 428.6 (M+1).

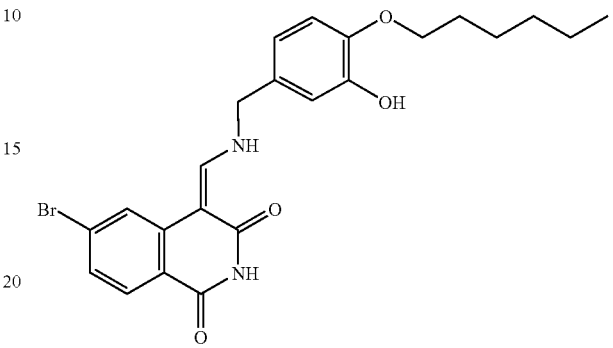

Example 150

(4Z)-6-Bromo-4-({[4-(hexyloxy)-3-hydroxybenzyl]amino}methylene)isoquinoline-1,3(2H,4H)-dione To a solution of 1-bromohexane (40.0 μl, 0.28 mmol) and tetrabutylammonium iodide (104 mg, 0.283 mmol) in anhydrous N,N-dimethylformamide (2 ML) is added of potassium carbonate (207 mg, 1.5 mmol). The mixture stirred at room temperature and (4Z)-6-bromo-4-{[(3,4-dihydroxybenzyl)amino]methylene}isoquinoline-1,3(2H,4H)-dione (100 mg, 0.26 mmol) is added. After the mixture is stirred at 65° C. for 30 min, the resulting mixture is concentrated and the residue is then partitioned between water (20 ml) and ethyl acetate (20 ml). The organic layer is then dried and purified by high performance liquid chromatography to give 35 mg of a white solid. MS (ESI) m/z 472.5 (M+1).

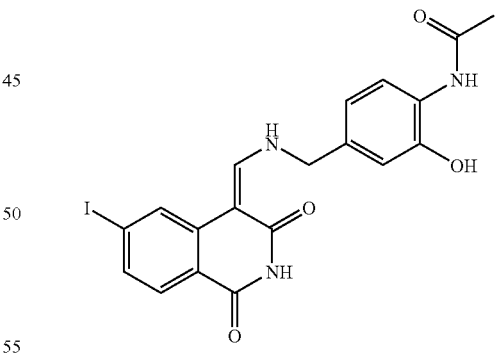

Example 151

N-[2-Hydroxy-4-({[(Z)-(6-iodo-1,3-dioxo-2,3-dihydroisoquinolin-4(1H)-'ylidene)methyl]amino}methyl)phenyl]acetamide Using the procedure described for the preparation of N-[4-({[(Z)-(6-bromo-1,3-dioxo-2,3-dihydroisoquinolin-4(1H)-ylidene)methyl]amino}methyl)-2-hydroxyphenyl]acetamide, 150 mg (84% yield) of light brown solid is obtained from 200 mg (0.39 mmol) of 2-(acetylamino)-5-({[(Z)-(6-iodo-1,3-dioxo-2,3-dihydroisoquinolin-4(1H)-ylidene)methyl]amino}methyl)phenyl acetate, and potassium carbonate 10.69 mg (1.16 mmol);
mp: 345-346° C.
MS (ESI) m/z 478.2 (M+1)$^+$.

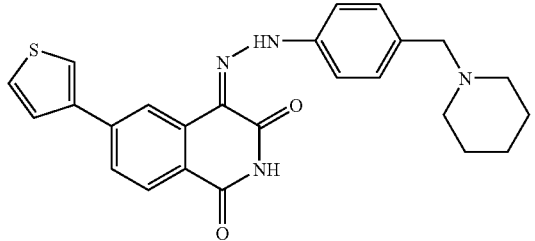

Example 152

4-[(4-Piperidin-1-ylmethyl-phenyl)-hydrazono]-6-thiophen-3-yl-4H-isoquinoline-1,3-dione The following reactants were placed in a 25 mL 3-neck RBF with an N$_2$ inlet and a vacuum outlet: 0.200 g (0.418 mmol) of example 144, 0.080 g (0.627 mmol) of 3-thiopheneboronic acid, 0.0249 g (0.0836 mmol) of Ph$_2$P(t-Bu)$_2$, 0.136 g (1.28 mmol) of Na$_2$CO$_3$, 2.1 mL of N,N-dimethylformamide (DMF) and 0.51 mL of H$_2$O. The vessel is evacuated and refilled with N$_2$ (6×) and 0.040 g (0.0397 mmol) of Pd$_2$(dba)$_3$ is added. The mixture is heated at 125° C. for 1.5 h. It is then diluted with N,N-dimethylformamide (DMF), filtered, the insoluble material is washed with N,N-dimethylformamide (DMF) and the filtrate is evaporated. The crude product is redissolved in 8% MeOH in CHCl$_3$ and filtered through Magnesol. The yellow eluent is collected and evaporated. The residue is boiled with MeOH and the crystalline product is collected. After further washing with MeOH and Et$_2$O and drying in vacuo, there is obtained 0.070 g (38%) of yellow-orange crystals: mp 164-168° C. (dec); $^1$H NMR (DMSO-d$_6$) δ 11.8 (s, 1H), 8.41 (s, 1H), 8.21 (s, 1H), 8.06 (d, 1H, J=8.16 Hz), 7.86 (d, 2H, J=8.16 Hz), 7.75 (s, 2H), 7.59 (d, 2H, J=8.22 Hz), 7.35 (d, 2H, J=8.22 Hz), 3.43 (s, 2H), 2.33 (s(br), 2H), 1.40 (m, 6H); HRMS (ESI) m/e calcd for C$_{25}$H$_{24}$N$_4$O$_2$S 445.16928. found 445.16907 (M+H)$^{+1}$.

Analysis for C$_{25}$H$_{24}$N$_4$O$_2$S: Calcd: C, 67.54; H, 5.44; N, 12.60. Found: C, 68.99; H, 5.76; N, 11.27.

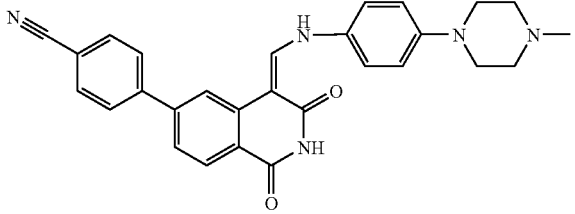

Example 153

4-(4-{[4-(4-Methyl-piperazin-1-yl)-phenylamino]-methylene}-1,3-dioxo-1,2,3,4-tetrahydro-isoquinolin-6-yl)-benzonitrile Step 1:
To a suspension of 6-Bromo-4H-isoquinoline-1,3-dione (1.0 g, 4.15 mmol) in 8.7 mL of a 4:1 mixture of acetic anhydride and N,N-dimethylformamide, respectively, is added trimethylorthoformate (940 μL, 8.6 mmol). The reaction mixture is shaken in a heating block at 125° C. for 1 hour. Upon cooling to room temperature, the product precipitated out. The precipitate is then filtered off, rinsed with copious amounts of ether, and dried under vacuum to yield 1.0 g of 6-Bromo-4-methoxymethylene-4H-isoquinoline-1,3-dione.
HPLC: Rt=2.02 min; MS 282.0 [M+H].

Step 2:
To a suspension of crude 6-Bromo-4-methoxymethylene-4H-isoquinoline-1,3-dione (423 mg, 1.5 mmol) in N,N-dimethylformamide (3 mL) is added 4-(4-Methyl-piperazin-1-yl)-phenylamine (290 mg, 1.5 mmol). The reaction mixture is shaken at 115° C. for 1.5 hours. Upon cooling to room temperature and addition of 2 mL of water, the product precipitated out. The precipitate is then filtered off, washed with water, and dried to yield 0.5 g of crude 6-bromo-4-{[4-(4-methyl-piperazin-1-yl)-phenylamino]-methylene}-4H-isoquinoline-1,3-dione, which is used as such for the next reaction.
HPLC: Rt=1.69 min; MS 440.0 [M−H].

Step 3:
To a suspension of 6-bromo-4-{[4-(4-methyl-piperazin-1-yl)-phenylamino]-methylene}-4H-isoquinoline-1,3-dione (221 mg, 0.5 mmol) in N,N-dimethylformamide (5 mL) is added 4-cyanophenylboronic acid (88 mg, 0.6 mmol), followed by 300 μL of 2M aqueous cesium carbonate and tetrakis triphenylphosphine palladium (30 mg, 0.06 mmol). The reaction mixture is subjected to microwave heating at 180° C. for 300 seconds. The reaction mixture is then diluted with N,N-dimethylformamide and purified by C18 reverse phase HPLC. The pure fractions were combined and concentrated to yield 4-(4-{[4-(4-Methyl-piperazin-1-yl)-phenylamino]-methylene}-1,3-dioxo-1,2,3,4-tetrahydro-isoquinolin-6-yl)-benzonitrile (68.4 mg).
$^1$H NMR (DMSO-d$_6$): 12.6 (1H, d); 11.4 (1H, s); 9.0 (1H, d); 8.4 (1H, s); 8.12 (1H, d); 8.09 (2H, d); 8.0 (2H, d); 7.6 (1H, d); 7.5 (2H, d); 7.1 (2H, d); 3.7 (4H, dd); 3.1 (4H, dt); 2.9 (3H, s).
MS (ESI) m/z 464.1
HPLC: Rt=1.79 min; MS 464.0 [M+H].

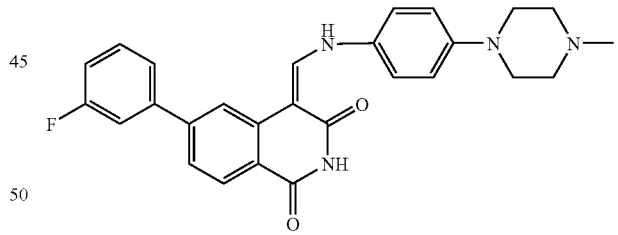

Example 154

6-(3-Fluoro-phenyl)-4-{[4-(4-methyl-piperazin-1-yl)-phenylamino]-methylene}-4H-isoquinoline-1,3-dione Step 1:
To a suspension of 6-Bromo-4H-isoquinoline-1,3-dione (1.0 g, 4.15 mmol) in 8.7 mL of a 4:1 mixture of acetic anhydride and N,N-dimethylformamide, respectively, is added trimethylorthoformate (940 μL, 8.6 mmol). The reaction mixture is shaken in a heating block at 125° C. for 1 hour. Upon cooling to room temperature, the product precipitated out. The precipitate is then filtered off, rinsed with copious amounts of ether, and dried under vacuum to yield 1.0 g of 6-Bromo-4-methoxymethylene-4H-isoquinoline-1,3-dione.

HPLC: Rt=2.02 min; MS 282.0 [M+H].

Step 2:

To a suspension of crude 6-Bromo-4-methoxymethylene-4H-isoquinoline-1,3-dione (423 mg, 1.5 mmol) in N,N-dimethylformamide (3 mL) is added 4-(4-Methyl-piperazin-1-yl)-phenylamine (290 mg, 1.5 mmol). The reaction mixture is shaken at 115° C. for 1.5 hours. Upon cooling to room temperature and addition of 2 mL of water, the product precipitated out. The precipitate is then filtered off, washed with water, and dried to yield 0.5 g of crude 6-bromo-4-{[4-(4-methyl-piperazin-1-yl)-phenylamino]-methylene}-4H-isoquinoline-1,3-dione, which is used as such for the next reaction.

HPLC: Rt=1.69 min; MS 440.0 [M–H].

Step 3:

To a suspension of 6-bromo-4-{[4-(4-methyl-piperazin-1-yl)-phenylamino]-methylene}-4H-isoquinoline-1,3-dione (221 mg, 0.5 mmol) in N,N-dimethylformamide (5 mL) is added 3-fluorobenzeneboronic acid (84 mg, 0.6 mmol), followed by 300 □L of 2M aqueous cesium carbonate and tetrakis triphenylphosphine palladium (30 mg, 0.06 mmol). The reaction mixture is subjected to microwave heating at 180° C. for 300 seconds. The reaction mixture is then diluted with N,N-dimethylformamide and purified by C18 reverse phase HPLC. The pure fractions were combined and concentrated to yield 6-(3-Fluoro-phenyl)-4-{[4-(4-methyl-piperazin-1-yl)-phenylamino]-methylene}-4H-isoquinoline-1,3-dione (65.2 mg).

$^1$H NMR (DMSO-$d_6$): □12.6 (1H, d); 11.3 (1H, s); 9.0 (1H, d); 8.3 (1H, s); 8.1 (1H, d); 7.8 (1H, d); 7.7 (1H, d); 7.6 (2H, m); 7.5 (2H, d); 7.3 (1H, t); 7.1 (2H, d); 3.7 (4H, dd); 3.1 (4H, dt); 2.9 (3H, s).

MS (ESI) m/z 457.

HPLC: Rt=1.88 min; MS 457.0 [M+H].

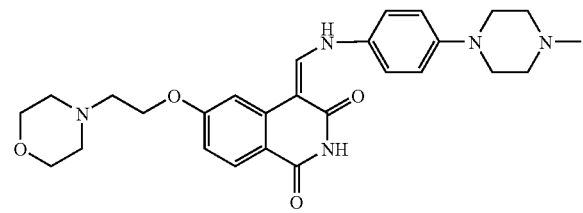

Example 155

4-{[4-(4-Methyl-piperazin-1-yl)-phenylamino]-methylene}-6-(2-morpholin-4-yl-ethoxy)-4H-isoquinoline-1,3-dione A mixture of 4-methoxymethylene-6-(2-morpholin-4-yl-ethoxy)-4H-isoquinoline-1,3-dione (115 mg, 0.35 mmole), N,N-dimethylformamide (1 mL) and 4-(4-methyl-piperazin-1-yl)-phenylamine (66 mg, 0.35 mmole) is stirred and heated at 110° C. for one hour, cooled in the refrigerator. The reaction mixture is evaporated to dryness, taken up in 5% methanol in chloroform and passed through a short pad of Florisil eluting with 5% methanol in chloroform. The eluate is evaporated in vacuo and treated with ether, filtered and dried to give a yellow solid 72 mg (42%), mp 142-143° C.; MS (ES+): m/z 492.2 (M+H).

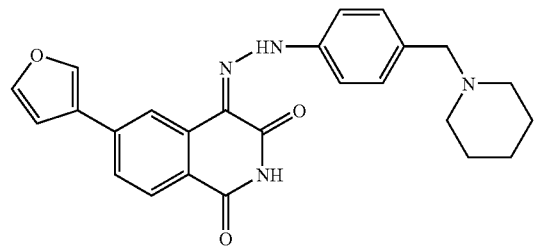

Example 156

6-Furan-3-yl-4-[(4-piperidin-1-ylmethyl-phenyl)-hydrazono]-4H-isoquinoline-1,3-dione The following reactants were placed in a 3-neck 25 mL round-bottom flask with an $N_2$ inlet and a vacuum outlet: 0.200 g (0.418 mmol) of example 144, 0.070 g (0.627 mmol) of furan-3-boronic acid, 0.136 g (1.28 mmol) of $Na_2CO_3$, 2.1 mL of N,N-dimethylformamide (DMF) and 0.5 mL of $H_2O$. The reaction vessel is evacuated and filled with $N_2$ (6×) and then protected from light. Tetrakistriphenylphosphine Pd (0) (0.048 g, 0.0418 mmol) is added and the mixture is heated at 120° C. for 4.5 h. An additional 0.5 mL of N,N-dimethylformamide (DMF), 0.020 g of boronic acid and 0.015 g of the Pd catalyst were added and the mixture is heated for 3.5 h. The reaction is diluted with N,N-dimethylformamide (DMF), filtered and the insoluble material is washed well with N,N-dimethylformamide (DMF). The combined filtrate and wash were evaporated and the residue is filtered through Magnesol (5% MeOH in $CHCl_3$). The yellow eluent is collected and evaporated. This residue is slurried with MeOH, collected, washed with small quantities of MeOH and $Et_2O$ and dried to give 0.115 g (64%) of yellow crystals: mp 223-225° C. (dec); $^1$H NMR (DMSO-$d_6$) δ 11.8 (s, 1H), 8.52 (s, 1H), 8.30 (s, 1H), 8.05 (d, 1H, J=8.22 Hz), 7.86 (s, 1H), 7.76 (d, 1H, J=8.13 Hz), 7.61 (d, 2H, J=8.22 Hz), 7.35 (d, 2H, J=8.22 Hz), 7.19 (s, 1H), 3.43 (s, 2H), 2.33 (s, 4H), 1.50 (s(br), 6H); HRMS (ESI) m/z calcd for $C_{25}H_{24}N_4O_3$ 429.19212. found 429.19164 $(M+H)^{+1}$.

Analysis for $C_{25}H_{24}N_4O_3$. $0.3H_2O$: Calcd: C, 69.19; H, 5.72; N, 13.08. Found: C, 68.83; H, 5.29; N, 12.67.

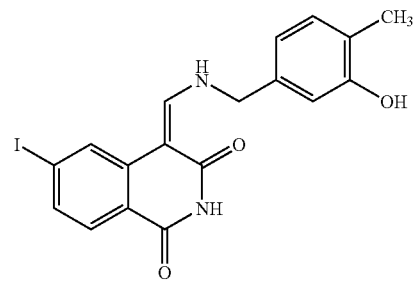

Example 157

(4Z)-4-{[(4-Methyl-3-hydroxybenzyl)amino]methylene}-6-iodoisoquinoline-'1,3(2H,4H)-dione Using the procedure described for the preparation of example 46, 120 mg (45%) yield of a orange solid is obtained from 200 mg (0.61 mmol) of (4E)-6-iodo-4-(methoxymethylene)isoquinoline-1,3(2H,4H)-dione and 5-Aminomethyl-2-methyl-phenol hydrogen chloride, 105.64 mg (0.61 mmol); mp 312-313° C.

MS (ESI) m/z 435.2 (M+1).

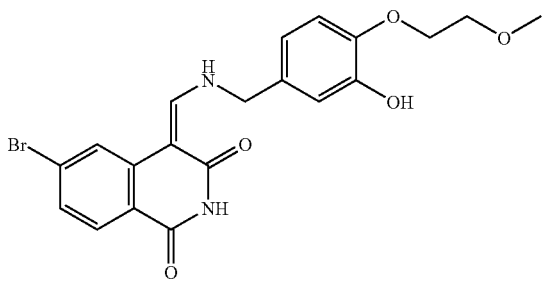

Example 158

(4Z)-6-Bromo-4-({[3-hydroxy-4-(2-ethoxyethoxy)benzyl]amino}methylene)isoquinoline-1,3(2H,4H)-dione An amount of (4E)-6-bromo-4-(methoxymethylene)isoquinoline-1,3(2H,4H)-dione (0.40 g, 1.42 mmol) in 5 mL of N,N'-dimethylformamide is added 5-(aminomethyl)-2-(2-methoxyethoxy)phenol (0.33 g, 1.70 mmol) and 0.44 mL (4.26 mmol) of triethylamine. The reaction mixture is heated at room temperature overnight under $N_2$. Mass spectroscopy suggested the completion of reaction. Reaction mixture is subsequently evaporated under high-pressure vacuum to brown solid. The solid is stirred in 5 mL of methanol for 10 min, then filtered, and washed in turn with 100 mL of water, 100 mL of methanol, and ether and hexane to afford 0.48 g (76.2% yield) of tan solid: mp 179-180° C.; MS (ESI) m/z 447.0-449.0 $(M+H)^{+1}$

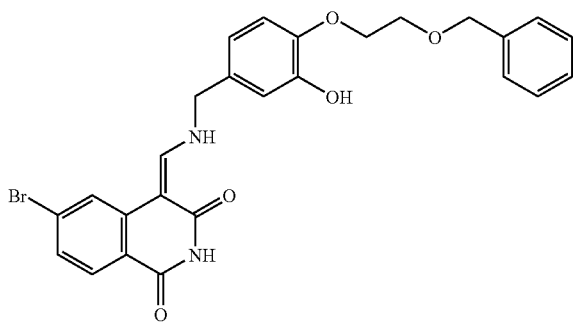

Example 159

(4Z)-4-[({4-[2-(Benzyloxy)ethoxy]-4-hydroxybenzyl}amino)methylene]-6-bromoisoquinoline-1,3(2H,4H)-dione A mixture of (4Z)-6-bromo-4-{[(3,4-dihydroxybenzyl)amino]methylene}isoquinoline-1,3(2H,4H)-dione (150.0 mg, 0.385 mmol), benzyl-2-bromoethylether (82.89 mg, 0.385 mmol), tetrabutyl ammonium iodide (142.2 mg, 0.385 mmol) and $K_2CO_3$ (106.42 mg, 0.77 mmol) in 2.5 mL N,N-dimethylformamide (DMF) is reacted in microwave at 100° C. for 10 minutes. The reaction mixture is filtered through celite. The residues is concentrated in vacuo. Water is added and the solution is stirred at room temperature for 1 hour. The brown solid is filtered and dried in vacuo. The solid is dissolved in DMSO and purified in Gilson reverse phase HPLC Elution system: 50% (0.1% TFA in 5% acetonitrile/water/50% acetonenitrile to 70% acetonenitrile) over 60 minutes. Peak II is collected, concentrated to give 10 mg (5%) product as a yellow solid: MS (EI) m/z 522 $(M-H)^{-1}$; MS (EI) m/z 431; HRMS: calcd for $C_{26}H_{23}BrN_2O_5+H+$, 523.08631. found (ESI+, $[M+H]^{1+}$), 523.08586; $^1H$ NMR (400 MHz, DMSO-D6) □ ppm 2.46 (bs, 1H) 3.72-3.79 (m, 2H) 4.05-4.14 (m, 2H) 4.49-4.59 (m, 4H) 6.74 (dd, J=8.31, 2.01 Hz, 1H) 6.83 (d, J=2.27 Hz, 1H) 6.93 (d, J=8.31 Hz, 1H) 7.22-7.39 (m, 5H) 7.87 (d, J=8.56 Hz, 1H) 8.11 (d, J=1.76 Hz, 1H) 8.72 (d, J=13.35 Hz, 1H) 9.08 (s, 1H) 10.54-10.72 (m, 1H) 11.09 (s, 1H).

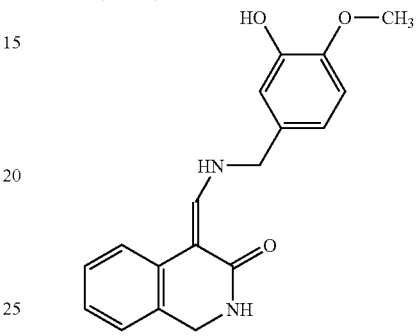

Example 160

4-[(3-Hydroxy-4-methoxy-benzylamino)-methylene]-1,4-dihydro-2H-isoquinoline-3-one A mixture of 0.400 g (1.98 mmol) of (4E)-4-[(dimethylamino)methylene]-1,4-dihydro-3(2H)-isoquinolinone and 0.412 g (2.18 mmol) of 2-piperidin-1-ylmethyl-phenylamine in 4 mL of $PhCH_3$ is heated at 110° C. for 50 min. The solvent is decanted and the solid residue is warmed and pulverized with MeOH and then chilled. The product is collected, washed with cold MeOH and $Et_2O$ and dried to give 0.479 g (78%) of tan crystals: mp 177-179° C. (dec); $^1H$ NMR (DMSO-$d_6$) δ 9.31 (m, 1H), 9.01 (s, 1H), 7.60 (d, 1H, J=12.4 Hz), 7.31 (d, 1H, J=7.86 Hz), 7.01 (m, 3H), 6.95 (m, 2H), 6.72 (m, 2H), 4.31 (s, 4H), 3.74 (s, 3H); HRMS (ESI) m/e calcd for $C_{18}H_{18}N_2O_3$ 311.13902. found 311.13859 $(M+H)^{+1}$.

Analysis for $C_{18}H_{18}N_2O_3$: Calcd: C, 69.66; H, 5.85; N, 9.03. Found: C, 69.94; H, 6.23; N, 8.91.

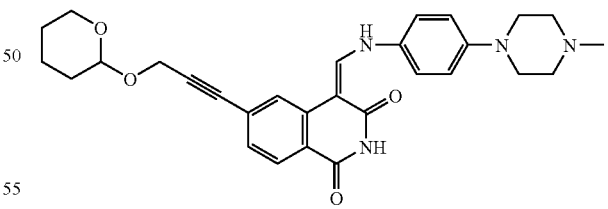

Example 161

(4Z)-4-({[4-(4-Methylpiperazin-1-yl)phenyl]amino}methylene)-6-[3-(tetrahydro-2H-pyran-2-yloxy)prop-1-ynyl]isoquinoline-1,3(2H,4H)-dione (7

Using the procedure described for the preparation of (4Z)-4-({[4-(4-methylpiperazin-1-yl)phenyl]amino}methylene)-6-(phenylethynyl)isoquinoline-1,3(2H,4H)-dione, 0.017 g (15.0% yield) of brown solid is obtained by prep TLC purification from 0.1 g (0.23 mmol) of (4Z)-6-bromo-4-({[4-(4-methylpiperazin-1-yl)phenyl]amino}methylene)isoquinoline-1,3(2H,4H)-dione and 0.023 mL (0.028 mmol) of tetrahydro-2-(2-propyloxy)2H-pyran: mp 175-176° C.; MS (ESI) m/z 501.2 (M+H)$^{+1}$

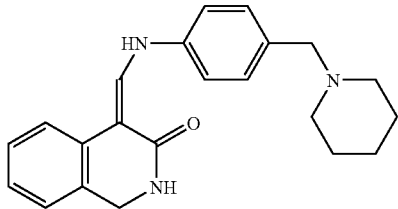

Example 162

4-[(4-Piperidin-1-ylmethyl-phenylamino)-methylene]-1,4-dihydro-2H-isoquinolin-3-one A solution of 0.400 g (1.98 mmol) of (4E)-4-[(Dimethylamino)methylene]-1,4-dihydro-3(2H)-isoquinolinone and 0.300 g (1.58 mmol) of 4-piperidin-1-ylmethyl-phenylamine in 4 mL of N,N-dimethylformamide (DMF) is heated at 125° C. for 3 h. The solvent is removed and the residue is slurried with Et$_2$O and filtered. The Et$_2$O soluble material is evaporated, redissolved in a small volume of PhCH$_3$ and chilled. A precipitate is collected, boiled with MeOH (ca 20 mL) and filtered. The filtrate is evaporated and the residue is recrystallized from a minimum volume of MeOH. The resulting solid is collected, washed with cold MeOH and Et$_2$O and dried in vacuo to yield 0.087 g (13%) of yellow crystals: mp 188-189° C. (dec); $^1$H NMR (DMSO-d$_6$) δ 11.5 (d, 1H, J=11.8 Hz), 8.04 (d, 1H, J=11.8 Hz), 7.66 (m, 2H), 7.20 (s, 5H), 7.08 (m, 2H), 4.41 (s, 2H), 3.34 (s, 2H), 2.29 (s(br), 4H), 1.46 (m, 6H); HRMS (ESI) m/e calcd for C$_{22}$H$_{25}$N$_3$O 348.20704. found 348.20704 (M+H)$^{+1}$.

Analysis for C$_{22}$H$_{25}$N$_3$O.0.1H$_2$O: Calcd: C, 75.64; H, 7.29; N, 12.03. Found: C, 75.66; H, 7.28; N, 11.69.

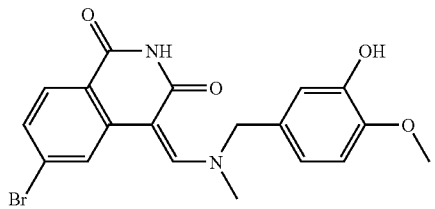

Example 163

(4Z)-6-Bromo-4-{[(3-hydroxy-4-methoxybenzyl)(methyl)amino]methylene}isoquinoline-1,3(2H,4H)-dione Methylamine (40% aqueous solution, 2.2 mL, 25 mmol) is added to a solution of 3-hydroxy-4-methoxybenzaldehyde (3.0 g, 20 mmol) in ethanol (35 mL). The resulting slurry is stirred for 30 minutes at room temperature. Then the solvents were evaporated under reduced pressure. The resulting solid is dissolved in methanol (300 mL) and sodium borohydride (0.90 g, 24 mmol) is added. The reaction mixture is stirred for 2 hours at room temperature and then concentrated under reduced pressure. The residue is partitioned between saturated aqueous potassium carbonate solution and ethyl acetate. The aqueous phase is extracted 3× with ethyl acetate, and the combined extracted were concentrated under reduced pressure to give 2-methoxy-5-methylaminomethyl-phenol as a granular white solid (2.5 g, 75%).

MS (ES$^+$): 168.2 (M+H)$^+$ (4E)-6-Bromo-4-(methoxymethylene)isoquinoline-1,3 (2H,4H)-dione (0.15 g, 0.53 mmol) and 2-methoxy-5-methylaminomethyl-phenol (80 mg, 0.48 mmol) were stirred in tetrahydrofuran (10 mL) at room temperature. The reaction mixture is concentrated under reduced pressure. The solid material is then collected, washed with diethyl ether, water, and methanol, and then dried under vacuum to give (4Z)-6-bromo-4-{[(3-hydroxy-4-methoxybenzyl)(methyl)amino] methylene}isoquinoline-1,3(2H,4H)-dione as a yellow solid (0.19 g, 95%).

MS (ES$^+$): 417.9, 419.9 (M+H)$^+$

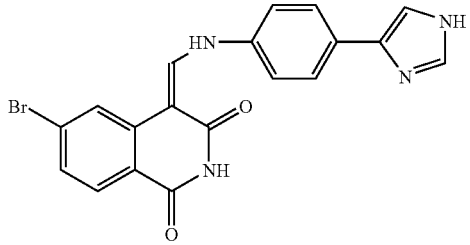

Example 164

6-Bromo-4-{[4-(1H-imidazol-4-yl)-phenylamino]-methylene}-4H-isoquinolin-1,3-dione A mixture of 2.00 g (7.09 mmol) of (4E)-6-bromo-4-(methoxymethylene)isoquinoline-1,3(2H,4H)-dione and 1.24 g (7.80 mmol) of 4-(1H-Imidazol-4-yl)aniline in 22 mL of N,N-dimethylformamide (DMF) is heated at 120° C. for 1.25 h. The chilled reaction mixture is filtered and the insoluble material is washed with N,N-dimethylformamide (DMF) and Et$_2$O. In order to remove residual N,N-dimethylformamide (DMF), the solid is boiled with MeOH (2×), washed with Et$_2$O and dried in vacuo. The yield is 2.10 g (72%) of yellow-brown crystals: mp >300° C. (dec); $^1$H NMR (DMSO-d$_6$) δ 12.6 (d, 1H, J=12.7 Hz), 12.2 (s, 1H), 11.4 (s, 1H), 8.98 (d, 1H, J=12.7 Hz), 8.49 (s, 1H), 7.86 (m, 3H), 7.67 (m, 4H), 7.41 (d, 1H, J=8.34 Hz); HRMS (ESI) m/e calcd for C$_{19}$H$_{13}$BrN$_4$O$_2$ 409.02947. found 409.02902 (M+H)$^{+1}$.

Analysis for C$_{19}$H$_{13}$BrN$_4$O$_2$.H$_2$O: Calcd: C, 53.41; H, 3.55; N, 13.12. Found: C, 53.18; H, 3.52; N, 12.78.

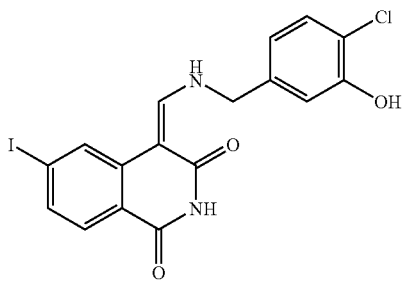

Example 165

(4Z)-4-{[(4-Chloro-3-hydroxybenzyl)amino]methylene}-6-iodoisoquinoline-'1,3(2H,4H)-dione Using the procedure described for the preparation of example 46, 200 mg (72% %) yield of a off white solid is obtained from 200 mg (0.61 mmol) of (4E)-6-iodo-4-(methoxymethylene)isoquinoline-1,3(2H,4H)-dione and 5-Aminomethyl-2-chloro-phenol hydrogen chloride, 117.99 (0.61 mmol); mp 324-325° C.

MS (ESI) m/z 452.8 (M−1).

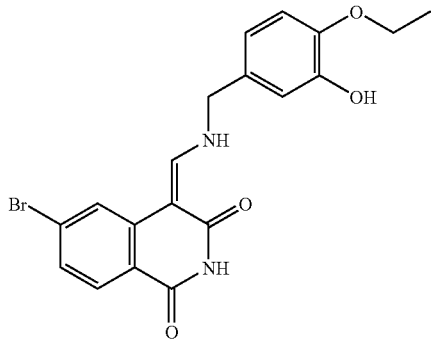

Example 166

(4Z)-6-Bromo-4-{[(4-ethoxy-3-hydroxybenzyl)amino]methylene}isoquinoline-1,3(2H,4H)-dione To a solution of 1-iodoethane (43.3 µl, 0.28 mmol) in anhydrous N,N-dimethylformamide (2 ML) is added potassium carbonate (207 mg, 1.5 mmol). The mixture stirred at room temperature and (4Z)-6-bromo-4-{[(3,4-dihydroxybenzyl)amino]methylene} isoquinoline-1,3(2H,4H)-dione (100 mg, 0.26 mmol) is added. After the mixture is stirred at 65° C. for 30 min, the resulting mixture is concentrated and the residue is then partitioned between water (50 ml) and ethyl acetate (50 ml). The organic layer is then dried and purified by high performance liquid chromatography to give 26 mg of a white solid. MS (ESI) m/z 416.7 (M+1).

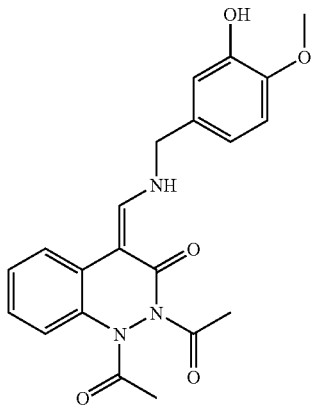

Example 167

(4Z)-1,2-Diacetyl-4-{[(3-hydroxy-4-methoxybenzyl)amino]methylene}-1,4-dihydrocinnolin-3(2H)-one 3-Hydroxycinnoline is prepared according to the literature (Alford, E. J. and Schofield, K. J Chem. Soc. 1952, 2102-2108). Reduction of 3-hydroxycinnoline to tetrahydrocinnolin-3-one and subsequent acetylation to give 1,2-diacetyltetrahydrocinnolin-3-one were achieved following the work of Winters, G.; Aresi, V.; Nathansohn, G. J. Heterocyclic Chem., 11, 1974, 997-1000.

To a solution of 1,2-diacetyltetrahydrocinnolin-3-one (0.34 g, 1.5 mmol) in N,N-dimethylformamide (3.6 mL) is added acetyl chloride (5 mL) and trimethylorthoformate (0.64 mL, 6.0 mmol). The mixture is heated at reflux in a 130° C. oil bath for 12 hours under a nitrogen atmosphere and then is allowed to cool to room temperature. The reaction mixture is purified in three batches via semi-preparative HPLC (Prodigy ODS3 column, 5% MeCN/95% water/0.01% trifluoroacetic acid to 100% acetonitrile over 1 hour at 10 mL/min) to give 1,2-diacetyl-4-methoxymethylene-1,4-dihydro-2H-cinnolin-3-one (0.18 g).

To a suspension of 1,2-diacetyl-4-methoxymethylene-1,4-dihydro-2H-cinnolin-3-one (0.18 g, 0.66 mmol) and 5-(aminomethyl)-2-methoxyphenol hydrochloride (0.13 g, 0.66 mmol) in tetrahydrofuran (5 mL) is added triethylamine (0.21 mL). After the addition of a few drops of N,N-dimethylformamide, the reaction mixture is stirred for five days at room temperature. The solvent is then evaporated under reduced pressure to give a maroon oil, which is then purified by via semi-preparative HPLC (Prodigy ODS3 column, 40% MeCN/60% water/0.01% trifluoroacetic acid to 70% acetonitrile over 1 hour at 10 mL/min) to give (4Z)-1,2-diacetyl-4-{[(3-hydroxy-4-methoxybenzyl)amino]methylene}-1,4-dihydrocinnolin-3(2H)-one (0.14 g, 54%) as a straw-colored foam, which is crushed to a powder.

MS (ES$^+$): 396.1 (M+H)$^+$

Example 168

This compound is prepared using appropriate starting materials according to the procedure of Example 169.

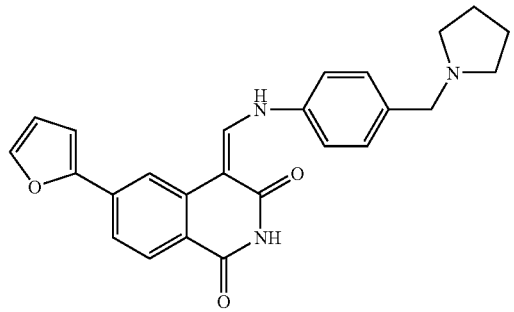

Example 169

6-Furan-2-yl-4-[(4-pyrrolidin-1-ylmethyl-phenylamino)-methylene]-4H-isoquinoline-1,3-dione Step 1:

To a suspension of 6-Bromo-4H-isoquinoline-1,3-dione (120 mg, 0.5 mmol) in 1.25 mL of a 4:1 mixture of acetic anhydride and N,N-dimethylformamide, respectively, is added trimethylorthoformate (110 µL, 1.0 mmol). The reaction mixture is shaken in a heating block at 125° C. for 1 hour. Upon cooling to room temperature, the product precipitated out. The precipitate is then filtered off, rinsed with copious amounts of ether, and dried to yield 126.3 mg of 6-bromo-4-methoxymethylene-4H-isoquinoline-1,3-dione.

Step 2:

To a suspension of crude 6-Bromo-4-methoxymethylene-4H-isoquinoline-1,3-dione (56.4 mg, 0.2 mmol) in N,N-dimethylformamide (500 µL) is added 4-pyrrolidin-1-ylmethylphenylamine (35.2 mg, 0.2 mmol). The reaction mixture is shaken at 115° C. for 1.5 hours. Upon cooling to room temperature, the product precipitated out. The precipitate is then filtered off, rinsed with copious amounts of ether, and dried to yield 78.8 mg of 6-Bromo-4-[(4-pyrrolidin-1-ylmethyl-phenylamino)-methylene]-4H-isoquinoline-1,3-dione.

Step 3:

To a suspension of 6-bromo-4-[(4-pyrrolidin-1-ylmethyl-phenylamino)-methylene]-4H-isoquinoline-1,3-dione (40 mg, 0.1 mmol) in N,N-dimethylformamide (1 mL) is added 2-furanboronic acid (11.2 mg, 0.1 mmol), followed by 60 μL of 2M aqueous cesium carbonate and tetrakis triphenylphosphine palladium (6 mg, 0.005 mmol). The reaction mixture is subjected to microwave heating at 150° C. for 100 seconds. The reaction mixture is then diluted to 2 mL with N,N-dimethylformamide and purified by C18 reverse phase HPLC. The pure fractions were combined and concentrated to yield Example 169.

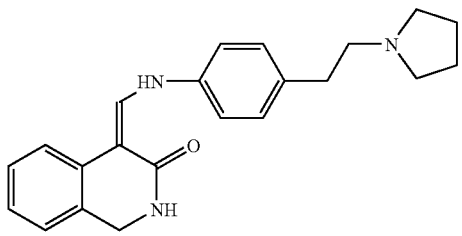

Example 170

4-{[4-(2-Pyrrolidin-1-yl-ethyl)-phenylamino]-methylene}-1,4-dihydro-2H-isoquinolin-3-one A mixture of 0.400 g (1.98 mmol) of (4E)-4-[(dimethylamino)methylene]-1,4-dihydro-3(2H)-isoquinolinone and 0.414 g (2.18 mmol) of 4-(2-Pyrrolidin-1-yl-ethyl)-phenylamine in 4 mL of PhCH$_3$ is heated at 110° C. for 2.5 h. The reaction is placed in a freezer and the precipitated material is collected, washed with cold PhCH$_3$ (2×) and Et$_2$O and dried in vacuo to give 0.280 g (41%) of gold crystals: mp 169-173° C. (dec); $^1$H NMR (DMSO-d$_6$) δ 11.4 (d, 1H, J=11.8 Hz), 8.01 (d, 1H, J=11.8 Hz), 7.63 (m, 2H), 7.16 (s, 4H), 7.07 (m, 2H), 4.40 (s, 2H), 2.60 (m, 4H), 2.50 (m, 2H), 1.67 (s (br), 4H); HRMS (ESI) m/e calcd for C$_{22}$H$_{25}$N$_3$O 348.20704. found 348.20588 (M+H)$^{+1}$.

Analysis for C$_{22}$H$_{25}$N$_3$O·0.5H$_2$O: Calcd: C, 74.11; H, 7.36; N, 11.79. Found: C, 74.50; H, 7.13; N, 11.51.

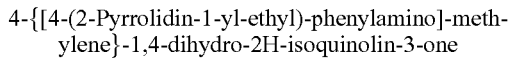

Example 171

(4Z)-4-({[4-(4-Methylpiperazin-1-yl)phenyl]amino}methylene)-6-(phenylethynyl)-isoquinoline-1,3(2H,4H)-dione A mixture of (4Z)-6-bromo-4-({[4-(4-methylpiperazin-1-yl)phenyl]amino}methylene)isoquinoline-1,3(2H,4H)-dione (0.10 g, 0.23 mmol), 0.03 mL (0.27 mmol) of phenylacetylene, 0.04 g (0.046 mmol) of dichlorobis(triphenylphosphine)-palladium(II), 0.0043 g (0.023 mmol) of CuI, and 0.12 mL (1.14 mmol) of triethylamine in 2 mL of N,N'-dimethylformamide is added to a 10 mL round bottom flask, sealed with a rubber septum, de-aired and backfilled with nitrogen gas 3 times, and wrapped around with aluminum foil. The reaction mixture is stirred vigorously at 70° C. in an oil bath under nitrogen. Mass spectroscopy suggested the completion of reaction after 45 min. The reaction mixture is filtered through celite, and subsequently evaporated under high-pressure vacuum to brown solid. The solid is dissolved in warm chloroform and ran through a pad of florisil, which is rinsed with 200 mL of warm chloroform. The collected organic portion is evaporated under vacuum to give 0.057 g (54.3% yield) of brown solid: mp 169-170° C.; MS (ESI) m/z 463.1 (M+H)$^{+1}$

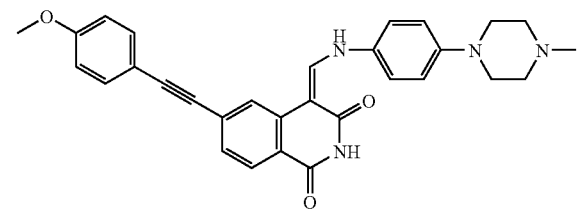

Example 172

(4Z)-6-[(4-Methoxyphenyl)ethynyl]-4-({[4-(4-methylpiperazin-1-yl)phenyl]amino}-methylene)isoquinoline-1,3(2H,4H)-dione Using the procedure described for the preparation of (4Z)-4-({[4-(4-methylpiperazin-1-yl)phenyl]amino}methylene)-6-(phenylethynyl)isoquinoline-1,3(2H,4H)-dione, 0.013 g (11.7.0% yield) of yellow solid is obtained by HPLC purification from 0.1 g (0.23 mmol) of (4Z)-6-bromo-4-({[4-(4-methylpiperazin-1-yl)phenyl]amino}-methylene)isoquinoline-1,3(2H,4H)-dione and 0.023 mL (0.028 mmol) of 4-ethylnylanisole: mp 155-156° C.; MS (ESI) m/z 493.1 (M+H)$^{+1}$

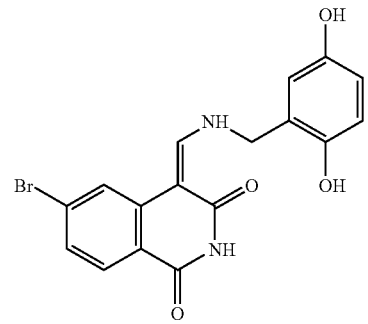

Example 173

(4Z)-6-Bromo-4-{[(2,5-dihydroxybenzyl)amino]methylene}isoquinoline-1,3(2H,4H)-dione To a mixture of 6-bromo-4-methoxymethylene-4H-isoquinoline-1,3-dione (400 mg, 1.42 mmol) and 2-aminomethyl-benzene-1,4-diol hydrochloride salt (250 mg, 1.42 mmol) in N,N-dimethylformamide (DMF) (10 mL) is added triethylamine (Et$_3$N) (0.3 mL, 2.13 mmol). The resulting

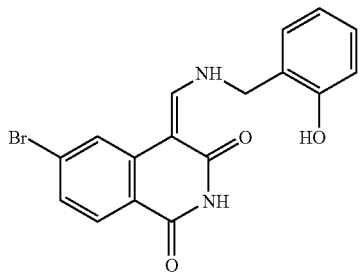

Example 174

(4Z)-6-Bromo-4-{[(2-hydroxybenzyl)amino]methylene}isoquinoline-1,3(2H,4H)-dione

Mixture of 6-bromo-4-methoxymethylene-4H-isoquinoline-1,3-dione (194 mg, 0.69 mmol) and 2-aminomethyl-phenol hydrochloride salt (110 mg, 0.69 mmol) in N,N-dimethylformamide (DMF) (5 mL) is added Et$_3$N (0.145 mL, 1.04 mmol). The precipitate is filtered to give 76 mg (30%) of the title compound as a beige solid. MS (ESI) m/z 371.0 (M–H)$^{-1}$.

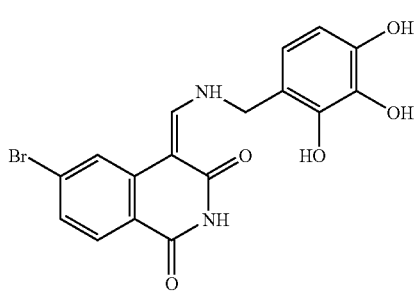

Example 175

(4Z)}-6-Bromo-4-{[(2,3,4-trihydroxybenzyl)amino]methylene}isoquinoline-1,3(2H,4H)-dione To a mixture of 6-Bromo-4-methoxymethylene-4H-isoquinoline-1,3-dione (200 mg, 0.71 mmol) and 4-aminomethyl-benzene-1,2,3-triol hydrochloride salt (139.6 mg, 1 mmol) in N,N-dimethylformamide (DMF) (10 mL) is added Et$_3$N (0.25 mL, 1.83 mmol). The resulting precipitate is filtered to give 83 mg (28.9%) of the title compound as a dark brown solid. (ESI) m/z 403.0 (M–H)$^{-1}$. $^1$H NMR (DMSO-d$_6$) δ 4.53 (d, 2H, J=6 Hz), 6.29 (d, 1H, J=8 Hz), 6.55 (d, 1H, J=8 Hz), 7.28 (d, 1H, J=8 Hz), 7.85 (d, 1H, J=8 Hz), 8.05 (s, 1H), 8.39 (s, 1H), 8.67 (d, 1H, J=12 Hz), 8.80 (s, 1H), 9.18 (s, 1H), 10.63-10.68 (m, 1H), 11.05 (s, 1H).

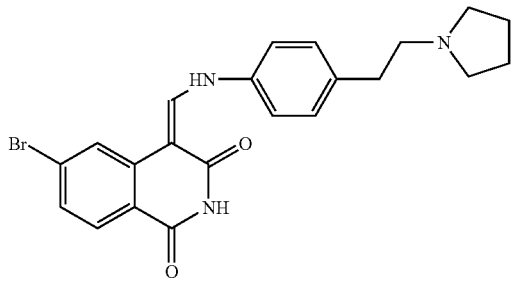

Example 176

6-Bromo-4-{[4-(2-pyrrolidin-1-yl-ethyl)-phenylamino]-methylene}-4H-isoquinolin-1,3-dione A solution of 0.300 g (1.06 mmol) of 6-bromo-4-methoxymethylene-4H-isoquinoline-1,3-dione and 0.222 g (1.17 mmol) of 4-(2-pyrrolidin-1-yl-ethyl)-phenylamine in 1.8 mL of N,N-dimethylformamide (DMF) is heated at 120° C. for 1 h. The reaction is placed in a freezer and the precipitated material is collected, washed with cold N,N-dimethylformamide (DMF) (2×), cold MeOH (2×) and Et$_2$O and dried in vacuo to give 0.307 g (66%) of brick red crystals: mp 212-214° C. (dec);

$^1$H NMR (DMSO-d$_6$) δ 12.5 (d, 1H, J=15 Hz), 11.4 (s, 1H), 8.93 (d, 1H, J=15 Hz), 8.46 (s, 1H), 7.91 (d, 1H, J=9 Hz), 7.52 (d, 2H, J=9 Hz), 7.41 (d, 1H, J=9 Hz), 7.29 (d, 2H, J=6 Hz), 2.64 (m, 6H), 2.47 (m, 4H), 1.67 (s(br), 4H); HRMS (ESI) m/e calcd for C$_{22}$H$_{22}$BrN$_3$O$_2$ 440.09682. found 440.09635 (M+H)$^{+1}$.

Analysis for C$_{22}$H$_{22}$BrN$_3$O$_2$: Calcd: C, 60.01; H, 5.04; N, 9.54. Found: C, 59.63; H, 4.94; N, 9.50.

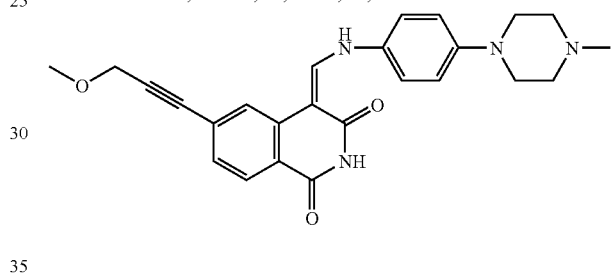

Example 177

(4Z)-6-(3-Methoxyprop-1-ynyl)-4-({[4-(4-methylpiperazin-1-yl)phenyl]amino}-methylene)isoquinoline-1,3(2H,4H)-dione Using the procedure described for the preparation of (4Z)-4-({[4-(4-methylpiperazin-1-yl)phenyl]amino}methylene)-6-(phenylethynyl)isoquinoline-1,3(2H,4H)-dione, 0.030 g (31.0% yield) of yellow solid is obtained by HPLC purification from 0.1 g (0.23 mmol) of (4Z)-6-bromo-4-({[4-(4-methylpiperazin-1-yl)phenyl]amino}-methylene)isoquinoline-1,3(2H,4H)-dione and 0.023 mL (0.028 mmol) of methylpropargyl ether: mp 209-210° C.; MS (ESI) m/z 431.1 (M+H)$^{+1}$

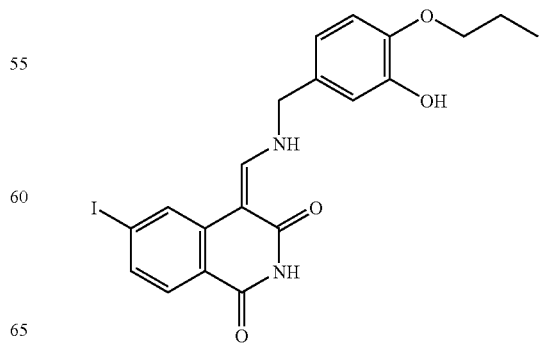

Example 178

(4Z)-4-{[(3-Hydroxy-4-propoxybenzyl)amino]methylene}-6-iodoisoquinoline-1,3(2H,4H)-dione An amount of 5-(aminomethyl)-2-propoxyphenol (60 mg, 0.33 mmol) is dissolved in N,N-dimethylformamide (2 mL). 0.137 m/(1.0 mmol) of triethylamine is added followed by 100 mg (0.30 mmol) of (4E)-6-iodo-4-(methoxymethylene)isoquinoline-1,3(2H,4H)-dione. After the mixture is stirred at room temperature for 30 min, water (5 mL) is added and the reaction mixture is stirred for 60 min. The precipitate is filtered and washed several times with anhydrous ether. The crude solid is then purified by high performance liquid chromatography to give 54 mg of a white solid. MS (ESI) m/z 480.3 (M+1).

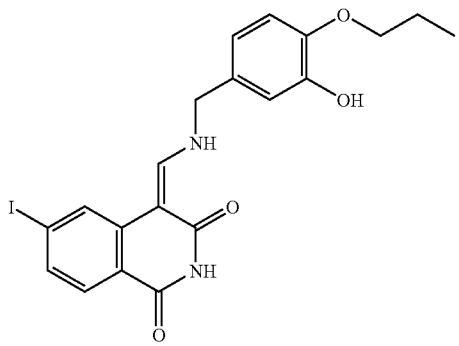

Example 178

(4Z)-4-{[(3-Hydroxy-4-propoxybenzyl)amino]methylene)-6-iodoisoquinoline-1,3(2H,4H)-dione An amount of 5-(aminomethyl)-2-propoxyphenol (60 mg, 0.33 mmol) is dissolved in N,N-dimethylformamide (2 mL). 0.137 m/(1.0 mmol) of triethylamine is added followed by 100 mg (0.30 mmol) of (4E)-6-iodo-4-(methoxymethylene)isoquinoline-1,3(2H,4H)-dione. After the mixture is stirred at room temperature for 30 min, water (5 mL) is added and the reaction mixture is stirred for 60 min. The precipitate is filtered and washed several times with anhydrous ether. The crude solid is then purified by high performance liquid chromatography to give 54 mg of a white solid. MS (ESI) m/z 480.3 (M+1).

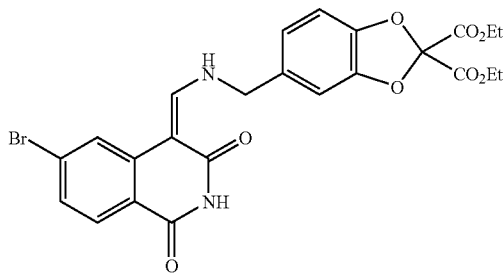

Example 179

(Z)-Diethyl 5-(((6-bromo-1,3-dioxo-2,3-dihydroisoquinolin-4(1H)-ylidene)methylamino)methyl)benzo[d][1,3]dioxole-2,2-dicarboxylate A mixture of (Z)-6-bromo-4-((3,4-dihydroxybenzylamino)methylene)isoquinoline-1,3(2H,4H)-dione (195 mg, 0.50 mmole), dimethylformamide (5 mL), potassium carbonate (415 mg, 3.0 mmole) and diethyl 2,2-dibromomalonate (159 mg, 0.50 mmole) is stirred at room temperature overnight. The reaction mixture is filtered and washed with dimethylformamide, the filtrate is evaporated dissolved in 2% methanol in chloroform and passed through a pad of Florisil. The eluate is evaporated to give a beige solid, 114 mg, (41%), mp 222-3° C.; MS (ES+): m/z 545.1 (M+H).

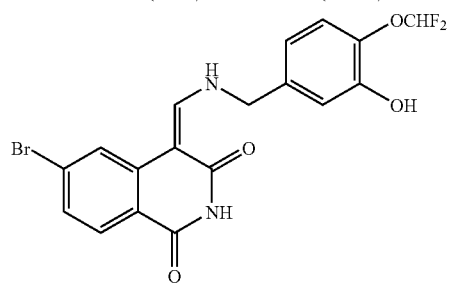

Example 180

(4Z)-6-Bromo-4-{[(4-difluoromethoxy-3-hydroxybenzyl)amino)methylene}isoquinoline-1,3(2H,4-dione An amount of 90 mg (0.40 mmol) of 4-difluoromethoxy-3-hydroxy benzylamine hydrochloride, is dissolved in N,N-dimethylformamide (4 mL). 50 ul (0.75 mmol) of triethylamine is added followed by 112 mg (0.40 mmol) of (4E)-6-bromo-4-(methoxymethylene)isoquinoline-1,3(2H,4H)-dione. After the mixture is stirred at room temperature for 30 min, the solvent is removed in-vacuo and the residue dissolved in 7.5% methanol in chloroform and passed thru a short pad of Florisil eluting with 7.5% methanol in chloroform, the eluate is evaporated and the solid triturated with ether, filtered and washed several times with anhydrous ether to give 116 mg of a pink solid (67% yield); mp 256-8° C., MS data ES(−) 437.0, 439.0 (M−1).

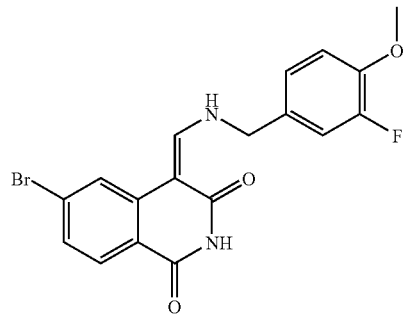

Example 181

(4Z)-6-Bromo-4-{[(3-fluoro-4-methoxybenzyl)amino]methylene}isoquinoline-1,3(2H,4H)-dione To a solution of 3-fluoro-4-methoxybenzaldehyde (1.5 g, 10 mmol) in pyridine (55 mL) is added methoxy]amine hydrochloride (97 mg, 11 mmol). The reaction mixture is stirred overnight at room temperature. The mixture is then concentrated under reduced pressure; the residue is taken up in ethyl acetate and washed 3× with water and 1× with saturated aqueous sodium chloride solution, dried over anhydrous sodium sulfate, and concentrated under reduced pressure to give 3-fluoro-4-methoxy-benzaldehyde O-methyl-oxime as a white solid.

To a solution of 3-fluoro-4-methoxy-benzaldehyde O-methyl-oxime (0.60 g, 3.3 mmol) in ethanol (25 mL) is added concentrated ethanolic hydrogen chloride (2 mL) and palladium on carbon (10%, 250 mg). The suspension is hydrogenated at atmospheric pressure for 18 hours, then filtered through diatomaceous earth and finally concentrated to give 3-fluoro-4-methoxy-benzylamine hydrochloride as a white solid.

To a suspension of (4E)-6-bromo-4-(methoxymethylene) isoquinoline-1,3(2H,4H)-dione (0.11 g, 0.39 mmol) and 3-fluoro-4-methoxy-benzylamine hydrochloride (75 mg, 0.39 mmol) in tetrahydrofuran (5 mL) is added triethylamine (0.13 mL, 0.98 mmol). After 15 minutes of stirring, the solvent is evaporated under reduced pressure. The solid material is collected by Buchner filtration, washed successively with diethyl ether, water, and methanol, and then dried under house vacuum to give (4Z)-6-bromo-4-{[(3-fluoro-4-methoxybenzyl)amino]methylene}isoquinoline-1,3(2H,4H)-dione as an off-white solid (0.11 g, 69%).

MS (ES⁻): 403.1, 405.1 (M−H)⁻

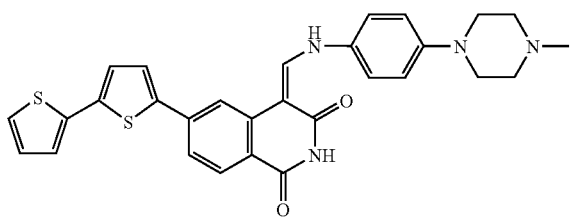

Example 182

(4Z)-6-(2,2'-Bithien-5-yl)-4-({[4-(4-methylpiperazin-1-yl)phenyl]amino}methylene)-isoquinoline-1,3 (2H,4H)-dione To an amount of (4E)-6-bromo-4-(methoxymethylene)-isoquinoline-1,3(2H,4H)-dione (0.20 g, 0.45 mmol) in 2 mL of N,N'-dimethylformamide is added 5-(4,4,5,5-Tetramethyl-1,3,2-dioxaborolan-2-yl)-2,2'-bisthiophene (0.26 g, 0.91 mmol), 0.03 g (0.04 mmol) of dichlorobis(triphenylphosphine)-palladium(II) and 0.4 mL of saturated sodium carbonate solution. The reaction mixture is heated at 120° C. under N₂ for 2 h. Mass spectroscopy suggested the completion of reaction. Reaction mixture is subsequently evaporated under high-pressure vacuum to brown solid. The solid is dissolved in 10 mL of 5% MeOH/CHCl₃, passed through a pad of florisil, and rinsed with 200 mL of the same solvent. The organic fraction is evaporated under vacuum to collect light brown solid. The compound is further purified by HPLC to give 0.051 g (21.4% yield) of yellow solid: mp 204-205° C.; MS (ESI) m/z 527.0 (M+H)⁺¹

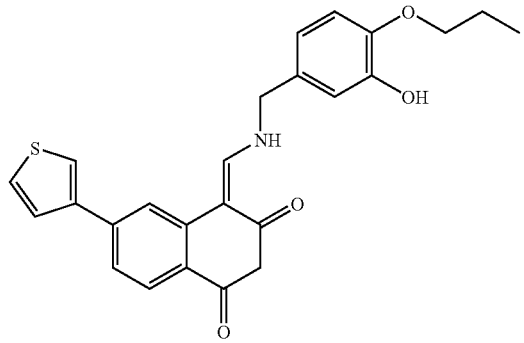

Example 183

(4Z)-4-{[(3-Hydroxy-4-propoxybenzyl)amino]methylene}-6-thiene-3-ylisoquinoline-,3(2H,4H)-dione An amount of (4Z)-6-bromo-4-{[(3-hydroxy-4-propoxybenzyl)amino]methylene}isoquinoline}-1,3(2H,4H)-dione (135.0 mg, 0.32 mmol) is dissolved in 80% mixture of N,N dimethylformamide/water (4 mL). Tetrakistriphenylphosphine (44.0 mg, 0.04 mmol) is added followed by 3-thiopheneboronic acid (48.4 mg, 0.38 mmol) along with sodium carbonate (67.8 mg, 0.64 mmol). The reaction mixture is heated to 150° C.-180° C. for 3 minutes under microwave irradiation. The solvent is concentrated and the reaction mixture is partitioned between ethyl acetate (50 ml) and water (50 ml). The crude solid is then purified by high performance liquid chromatography to give 25.0 mg of a white solid. MS (ESI) m/z 549.8 (M+1).

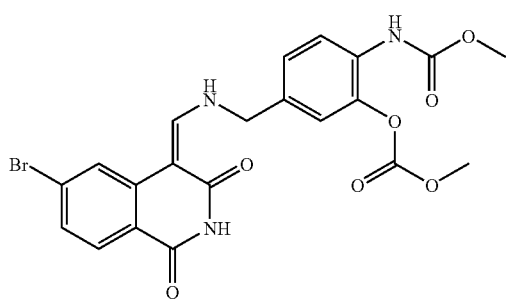

Example 184

5-({[(Z)-(6-Bromo-1,3-dioxo-2,3-dihydroisoquinolin-4(1H)-'ylidene)methyl]amino}methyl)-2-[(methoxycarbonyl)amino]phenyl methyl carbonate Using the procedure described for the preparation of example 69, 100 mg (26% yield) of reddish-brown solid is obtained from 300 mg (0.77 mmol) of (4Z)-4-{[(4-amino-3-hydroxybenzyl)amino]methylene}-6-bromoisoquinoline-1, 3(2H,4H)-dione, and methyl chloroformate 0.6 mL (7.7 mmol); mp 179-180° C.

MS (ESI) m/z 504.2 (M+1)+.

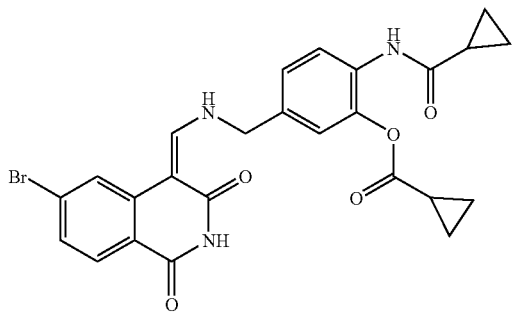

Example 185

5-({[(Z)-(6-Bromo-1,3-dioxo-2,3-dihydroisoquino-lin-4(1H)-'cyclopropanecarboxylate 'ylidene)methyl]amino}methyl)-2-[(cyclopropylcarbonyl)amino]phenyl Using the procedure described for the preparation of example 69, 100 mg (25% yield) of reddish-brown solid is obtained from 300 mg (0.77 mmol) of (4Z)-4-{[(4-amino-3-hydroxybenzyl)amino]methylene}-6-bromoisoquinoline-1,3(2H,4H)-dione, and cyclopropanecarbonyl chloride 0.7 mL (7.7 mmol); mp 245-246° C.

MS (ESI) m/z 525.4 (M+1).

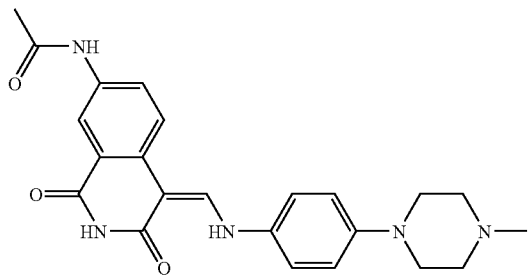

Example 186

N-[(4Z)-4-({[4-(4-Methylpiperazin-1-yl)phenyl]amino}methylene)-1,3-dioxo-1,2,3,4-tetrahydroisoquinolin-6-yl]acetamide Using the procedure described for the preparation of example 14, 450 mg (68% yield) is obtained as a yellow solid from 410 mg (1.57 mmol) of (4E)-6-acetamide-4-(methoxymethylene)isoquinoline-1,3(2H,4H)-dione and 300 mg (1.57 mmol) 4-(4-methylpiperazin-1-yl)methyl-phenylamine; mp 292-293° C.

MS (ESI) m/z 420.2 (M+1)+

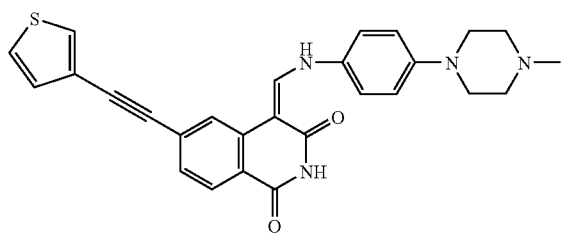

Example 187

(4Z)-4-({[4-(4-Methylpiperazin-1-yl)phenyl]amino}methylene)-6-(thien-3-ylethynyl)-isoquinoline-1,3(2H,4H)-dione Using the procedure described for the preparation of (4Z)-4-({[4-(4-methylpiperazin-1-yl)phenyl]amino}methylene)-6-(phenylethynyl)isoquinoline-1,3(2H,4H)-dione, 0.018 g (8.6% yield) of yellow solid is obtained by prep. TLC purification from 0.2 g (0.45 mmol) of (4Z)-6-bromo-4-({[4-(4-methylpiperazin-1-yl)phenyl]amino}methylene)-isoquinoline-1,3(2H,4H)-dione and 0.067 mL (0.68 mmol) of 3-ethylnylthiophene: mp 193-194° C.; MS (ESI) m/z 469.2 (M+H)+1

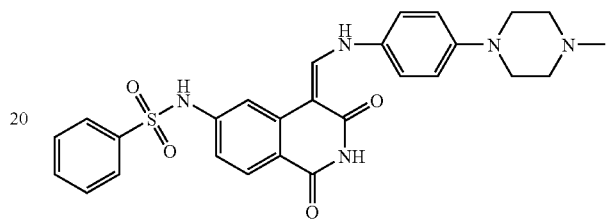

Example 188

1,2,3,4-Tetrahydroisoquinolin-6-yl]benzenesulfonamide'N-[(4Z)-4-({[4-(4-methylpiperazin-1-yl)phenyl]amino}methylene)-1,3-dioxo Using the procedure described for the preparation of example 14, 120 mg of yellow solid (69% yield) is obtained from 130 mg (0.36 mmol) of N-(4-methoxymethylene-1,3-dioxo-1,2,3,4-tetrahydro-isoquinolin-6-yl)benzensulfonamide prepared using the same procedure as (4E)-6-acetamide-4-(methoxymethylene)isoquinoline-1,3(2H,4H)-dione and 70 mg (0.70 mmol) of 4-(4-methylpiperazin-1-yl)methyl-phenylamine; mp 289-290° C.

MS (ESI) m/z 518.2 (M+H)+.

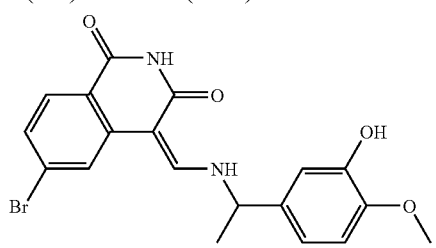

Example 189

(4Z)-6-Bromo-4-({[1-(3-hydroxy-4-methoxyphenyl)ethyl]amino}methylene)isoquinoline-1,3(2H,4H)-dione To a solution of 3-hydroxy-4-methoxybenzaldehyde (5.0 g, 33 mmol) in N,N-dimethylformamide (165 mL) is added benzyl bromide (4.3 mL, 36 mmol), followed by potassium carbonate (~325 mesh, 14 g, 100 mmol). The reaction mixture is stirred for 4 hours at room temperature and partitioned between diethyl ether and water. The aqueous phase is extracted with ether (3×50 mL). The combined ethereal extracts were washed twice with water and once with saturated aqueous sodium chloride solution, dried over anhydrous magnesium sulfate, filtered, and concentrated under reduced pressure to give 3-benzyloxy-4-methoxybenzaldehyde as golden oil, which crystallized upon standing to afford a white solid. The material is used in the following step without further purification.

A solution of 3-benzyloxy-4-methoxybenzaldehyde (33 mmol maximum) in tetrahydrofuran (150 mL) is cooled to −78° C. Methyllithium (Aldrich, 1.6 M solution in diethyl ether, 31 mL, 49 mmol) is added dropwise via syringe. Following completion of the addition, the cooling bath is removed and the reaction mixture is allowed to warm to room temperature. After 90 minutes at that temperature, the mixture is cooled to 0° C. and quenched by the addition of saturated aqueous sodium hydrogen carbonate. The quenched reaction mixture, after warming to room temperature, is acidified with 1 M hydrochloric acid solution to pH 1 and extracted thrice with diethyl ether. The combined extracts were washed with saturated aqueous sodium chloride solution, dried over anhydrous magnesium sulfate, filtered, and concentrated under reduced pressure to give 1-(3-benzyloxy-4-methoxy-phenyl)-ethanol.

To a 0° C. mixture of crude 1-(3-benzyloxy-4-methoxyphenyl)-ethanol (10 mmol maximum) and diphenylphosphoryl azide (2.6 mL, 12 mmol) in toluene (18 mL) is added 1,8-diazabicyclo[5.4.0]undec-7-ene (DBU, 1.6 mL, 11 mmol). The mixture is stirred at 0° C. for two hours and then at room temperature overnight. The reaction mixture is washed with water and concentrated to give 4-(1-azido-ethyl)-2-benzyloxy-1-methoxybenzene, which is used in the next step without purification.

Crude 4-(1-azido-ethyl)-2-benzyloxy-1-methoxybenzene is hydrogenated at 50 psi, using 10% Pd/C in ethanolic hydrogen chloride solution to give 5-(1-amino-ethyl)-2-methoxyphenol.

(4E)-6-bromo-4-(methoxymethylene)isoquinoline-1,3 (2H,4H)-dione (0.10 g, 0.35 mmol) and 5-(1-amino-ethyl)-2-methoxyphenol hydrochloride (excess) were coupled in N,N-dimethylformamide (2 mL) with triethylamine (0.15 mL). The solid material is collected by Buchner filtration, washed with diethyl ether and acetonitrile, and then dried under house vacuum to give (4Z)-6-bromo-4-({[1-(3-hydroxy-4-methoxyphenyl)ethyl]amino}methylene)isoquinoline-1,3(2H,4H)-dione as a light tan powder (0.11 g, 73%).

MS (ES$^+$): 417.1 (M+H)$^+$

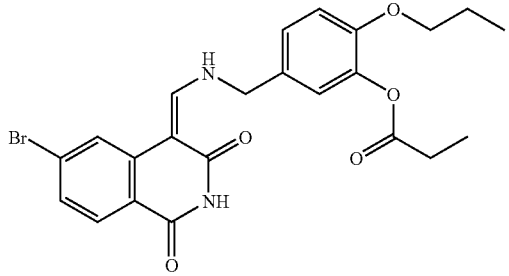

Example 190

5-({[(Z)-(6-Bromo-1,3-dioxo-2,3-dihydroisoquinolin-4(1H)-ylidene)methyl]amino}-methyl)-2-propoxyphenyl propionate Using the procedure described for the preparation of 5-({[(Z)-(6-bromo-1,3-dioxo-2,3-dihydroisoquinolin-4(1H)-ylidene)methyl]amino}methyl)-2-propoxyphenyl cyclopropanecarboxylate, 0.067 g (49.3% yield) of tan solid is obtained from 0.12 g (0.28 mmol of (4Z)-6-bromo-4-{[(3-hydroxy-4-propoxybenzyl)amino]methylene}isoquinoline-1,3(2H,4H)-dione), 0.048 mL (0.56 mmol) of propionyl chloride, and 0.90 mL (0.84 mmol) of triethylamine: mp 206-207° C.; MS (ESI) m/z 487.2 (M+H)$^{+1}$.

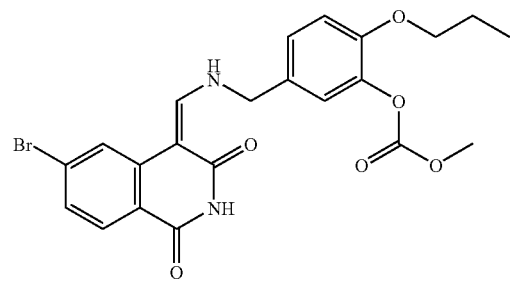

Example 191

5-({[(Z)-(6-Bromo-1,3-dioxo-2,3-dihydroisoquinolin-4(1H)-ylidene)methyl]amino}-methyl)-2-propoxyphenyl methyl carbonate Using the procedure described for the preparation of 5-({[(Z)-(6-bromo-1,3-dioxo-2,3-dihydroisoquinolin-4(1H)-ylidene)methyl]amino}methyl)-2-propoxyphenyl cyclopropanecarboxylate, 0.118 g (86.8% yield) of tan solid is obtained from 0.12 g (0.28 mmol of (4Z)-6-bromo-4-{[(3-hydroxy-4-propoxybenzyl)amino]methylene}isoquinoline-1,3(2H,4H)-dione), and 0.09 mL (0.84 mmol) of dimethyl pyrocarbonate: mp 211-212° C.; MS (ESI) m/z 487.1-489.1 (M+H)$^{+1}$

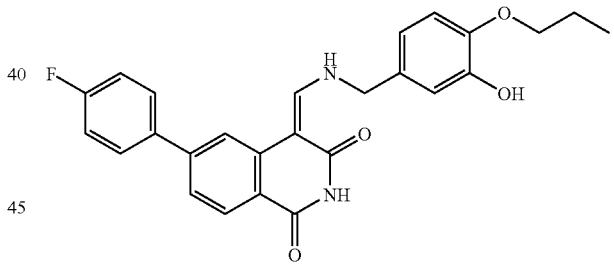

Example 192

(4Z)-6-(4-Fluorophenyl)-4-{[(3-hydroxy-4-propoxybenzyl)amino]methylene}-isoquinoline-1,3(2H,4H)-dione An amount of (4Z)-6-bromo-4-{[(3-hydroxy-4-propoxybenzyl)amino]methylene}isoquinoline-1,3(2H,4H)-dione (0.15 g, 0.35 mmol) in 2 mL of N,N'-dimethylformamide is added to 4-fluorophenylboronic acid (0.073 g, 0.52 mmol), 0.02 g (0.03 mmol) of tetrakis(triphenylphosphine)-palladium(0) and 0.4 mL of saturated sodium carbonate solution. The reaction mixture is stirred at 100° C. under N$_2$ for 2 h. Mass spectroscopy suggested the completion of the reaction. Solids were removed by filtration, and solvent is subsequently evaporated under high-pressure vacuum to brown solid. The residue is purified by HPLC to give 0.055 g (35.5% yield) of light brown solid: mp 194-195° C.; MS (ESI) m/z 445.2 (M+H)$^{-1}$.

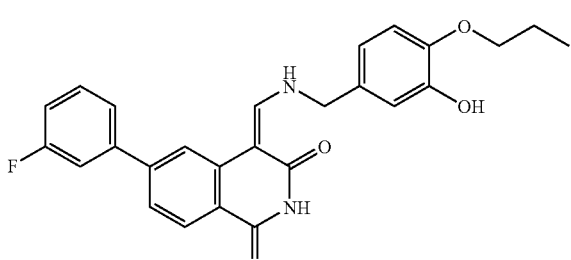

Example 193

(4Z)-6-(3-Fluorophenyl)-4-{[(3-hydroxy-4-propoxy-benzyl)amino]methylene}-isoquinoline-1,3(2H,4H)-dione Using the procedure described for the preparation of (4Z)-6-(4-fluorophenyl)-4-{[(3-hydroxy-4-propoxybenzyl)amino]methylene}-isoquinoline-1,3(2H,4H)-dione, 0.067 g (43.2% yield) of yellow solid is obtained from 0.15 g (0.35 mmol) of (4Z)-6-bromo-4-{[(3-hydroxy-4-propoxybenzyl)amino]methylene}isoquinoline-1,3(2H,4H)-dione, 0.073 g (0.52 mmol) of 3-fluorophenylboronic acid, 0.02 g (0.03 mmol) of tetrakis-(triphenylphosphine)-palladium(0) and 0.4 mL of saturated sodium carbonate solution: mp 209-210° C.; MS (ESI) m/z 445.2 (M+H)$^{+1}$

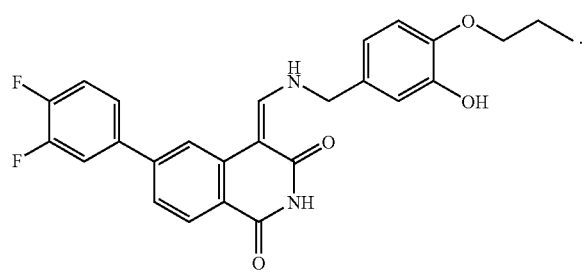

Example 194

(4Z)-6-(3,4-Difluorophenyl)-4-{[(3-hydroxy-4-propoxybenzyl)amino]methylene}-isoquinoline-1,3(2H,4H)-dione Using the procedure described for the preparation of (4Z)-6-(4-fluorophenyl)-4-{[(3-hydroxy-4-propoxybenzyl)amino]methylene}-isoquinoline-1,3(2H,4H)-dione, 0.092 g (59.4% yield) of tan solid is obtained from 0.15 g (0.35 mmol) of (4Z)-6-bromo-4-{[(3-hydroxy-4-propoxybenzyl)amino]methylene}isoquinoline-1,3(2H,4H)-dione, 0.082 g (0.52 mmol) of 3,4-difluorophenylboronic acid, 0.02 g (0.03 mmol) of tetrakis(tri-phenylphosphine)-palladium(0) and 0.4 mL of saturated sodium carbonate solution: mp 227-228° C.; MS (ESI) m/z 463.2 (M+H)$^{-1}$

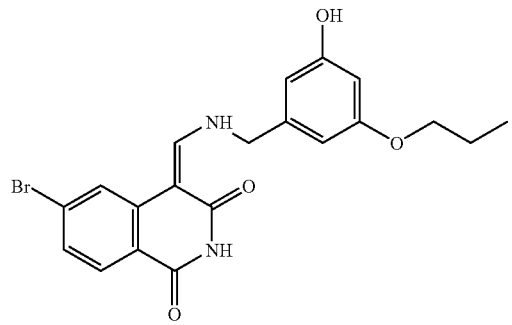

Example 195

(4Z)}-6-Bromo-4-{[(3-hydroxy-5-propoxybenzyl)amino]methylene}isoquinoline-1,3(2H,4H)-dione (4Z)-6-bromo-4-{[(3,5-dihydroxybenzyl)amino]methylene}isoquinoline-1,3(2H,4H)-dione (50 mg, 0.128 mmol) is dissolved in 1 mL N,N-dimethylformamide (DMF) (1 mL). To the resulting solution is added 1-iodo-propane (25 µL, 0.256 mmol) and K$_2$CO$_3$ (53 mg, 0.384 mmol). The reaction mixture is heated at 100° C. for 2 hours. The solid is filtered and purified by HPLC eluting with 20% CH$_3$CN/H$_2$O to 100% CH$_3$CN over 30 minutes to give 19 mg (34%) of the title compound as a tan powder. MS (ESI) m/z 431.1(M+H)$^+$

Example 196

N-((4Z)-4-{[(3-Hydroxy-4-methoxybenzyl)amino]methylene}-1,3-dioxo-1,2,3,4-'tetrahydroisoquinolin-6-yl)benzenesulfonamide N-(4-Methoxymethylene-1,3-dioxo-1,2,3,4-tetrahydro-isoquinolin-6-yl)benzenesulfonamide is prepared using the same procedure as (4E)-6-acetamide-4-(methoxymethylene) isoquinoline-1,3(2H,4H)-dione. Using the procedure described for the preparation of example 46, 50 mg of brown solid (37% yield) is obtained from 100 mg (0.28 mmol) of N-(4-methoxymethylene-1,3-dioxo-1,2,3,4-tetrahydro-iso-quinolin-6-yl)benzenesulfonamide and 3-hydroxy-4-methoxy-benzylamine hydrogen chloride (42.16 mg, 0.28 mmol);

mp 245-246° C.

MS (ESI) m/z 480.2 (M+H)+.

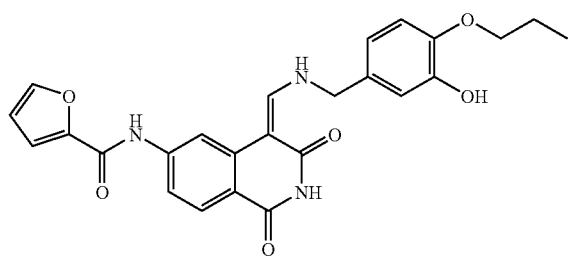

Example 197

N-((4Z)-4-{[(3-Hydroxy-4-propoxybenzyl)amino]
methylene}-1,3-dioxo-1,2,3,4-1,2,3,4-tetrahydroiso-
quinolin-6-yl]-2-thien-2-ylacetamide14

Furan-2-carboxylic acid (4-methoxymethylene-1,3-di-oxo-1,2,3,4-tetrahydro-isoquinolin-6-yl)-amide, prepared using the same procedure as for (4E)-6-acetamide-4-(methoxymethylene)isoquinoline-1,3(2H,4H)-dione. Using the procedure described for the preparation of example 46, 200 mg of light green solid (51% yield) is obtained from 200 mg (0.64 mmol) of furan-2-carboxylic acid (4-methoxymethylene-1,3-dioxo-1,2,3,4-tetrahydro-isoquinolin-6-yl)-amide and 5-(aminomethyl)-2-propoxyphenol hydrogen chloride, (140 mg, 0.64 mmol);

mp 233-234° C.

MS (ESI) m/z 462.2 (M+H)+.

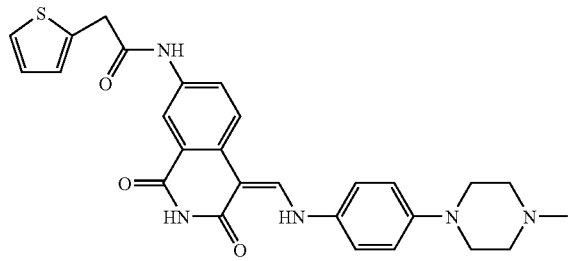

Example 198

1,2,3,4-Tetrahydroisoquinolin-6-yl]-2-thien-2-ylac-
etamide 'N-[(4Z)-4-({[4-(4-methylpiperazin-1-yl)
phenyl]amino}methylene)-1,3-dioxo A solution of 200 mg (0.53 mmol) of (4Z)-6-amino-4-({[4-(4-methylpiperazin-1-yl)phenyl]amino}methylene)isoquinoline-1,3(2H,4H)-dione and thiophen-2-yl-acetyl chloride (0.33 mL, 2.64 mmol) in dimethylacetamide is stirred overnight at room temperature and then diluted with water. The precipitate is collected by filtration, washed successively with diethyl ether, water and methanol, and then dried to give 170 mg (64% yield) of the title compound as yellow solid; mp 230-231° C.

MS (ESI) m/z 502.3 (M+1).

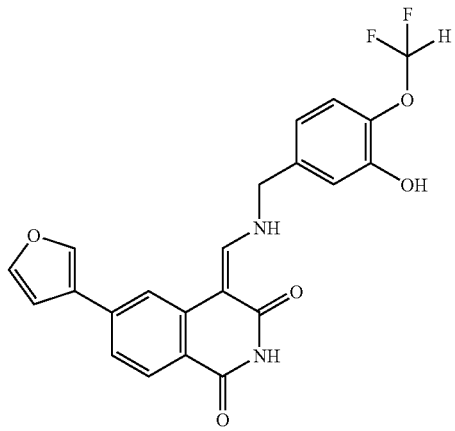

Example 199

(4Z)-4-({[4-(Difluoromethoxy)-3-hydroxybenzyl]
amino}methylene)-6-(3-furyl)isoquinoline-1,3(2H,
4H)-dione A mixture of example 180 (155.4 mg, 0.354 mmol), 3-furanboronic acid (47.51 mg, 0.425 mmol), tetrakis(triphenylphosphine)palladium(0) (40.46 mg, 0.035 mmol) and Na$_2$CO$_3$ (75.05 mg, 0.708 mmol) in 3 mL 80% N,N-dimethylformamide (DMF)/H$_2$O is reacted in microwave at 150° C. for 6 minutes. The reaction mixture is partitioned in ethyl acetate/water. The aqueous layer is separated and extracted 2 times with ethyl acetate. The combined organic extracts were evaporated in vacuo. The resulting residue is treated with 1 mL MeOH/CH$_2$Cl$_2$ and the fine solid precipitated out of solution. It is allowed to sit at room temperature overnight. The precipitate is filtered to get 73.4 mg (48.6%) product as a yellow solid: MS (ESI) m/z 425.2 (M−H)$^{-1}$; HRMS: calcd for C$_{22}$H$_{16}$F$_2$N$_2$O$_5$+H+, 427.11001. found (EFI FT, [M+H]$^{1+}$), 427.11023; $^1$H NMR (400 MHz, DMSO-D6) ppm 4.66 (d, J=6.30 Hz, 2 H) 6.70-6.90 (m, 1 H) 6.91-7.03 (m, 1 H) 7.06-7.23 (m, 2 H) 7.45 (dd, J=8.18, 1.38 Hz, 1 H) 7.82 (t, J=1.76 Hz, 1 H) 7.88-8.09 (m, 2 H) 8.36 (s, 1 H) 8.75 (d, J=13.09 Hz, 1 H) 10.02 (s, 1 H) 10.47-10.75 (m, 1H) 10.98 (s, 1 H); Analysis for C$_{22}$H$_{16}$F$_2$N$_2$O$_5$: Calcd: C, 61.97; H, 3.78; N, 6.57. Found: C, 62.22; H, 3.74; N, 6.94.

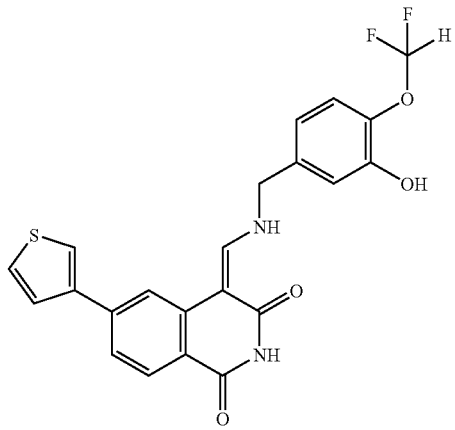

Example 200

(4Z)-4-({[4-(Difluoromethoxy)-3-hydroxybenzyl]amino}methylene)-6-thien-3-ylisoquinoline-1,3(2H,4H)-dione A mixture of example 180 (151.11 mg, 0.344 mmol), 3-thiophene boronic acid (52.83 mg, 0.413 mmol), tetrakis(triphenylphosphine)palladium(0) (39.77 mg, 0.034 mmol) and Na$_2$CO$_3$ (72.93 mg, 0.688 mmol) in 3 mL 80% N,N-dimethylformamide (DMF)/H$_2$O is reacted in microwave at 150° C. for 6 minutes. The reaction mixture is partition in ethyl acetate/water. The aqueous layer is separated and extracted 2 times with ethyl acetate. The combined organic extracts were evaporated in vacuo. The resulting residue is treated with 1 mL MeOH/CH$_2$Cl$_2$, and the fine solid precipitated out of solution. It is allowed to sit at room temperature overnight. The precipitate is filtered to get 86.4 mg (56.7%) product as a yellow solid. MS (ESI) m/z 441.1 (M−H)$^{-1}$; HRMS: calcd for C$_{22}$H$_{16}$F$_2$N$_2$O$_4$S+H+, 443.08716. found (ESI FT, [M+H]$^{1+}$), 443.08671; $^1$H NMR (400 MHz, DMSO-D6) ppm 4.67 (d, J=6.29 Hz, 2 H) 6.78-6.86 (m, 1 H) 6.94-7.03 (m, 1 H) 7.08-7.20 (m, 1 H) 7.55 (dd, J=8.31, 1.51 Hz, 1 H) 7.68-7.73 (m, 1H) 7.77 (dd, J=5.04, 1.26 Hz, 1 H) 7.99 (d, J=8.31 Hz, 1 H) 8.08-8.16 (m, 2 H) 8.80 (d, J=13.09 Hz, 1 H) 10.01 (s, 1 H) 10.59-10.75 (m, 1 H) 10.99 (s, 1 H);

Analysis for C$_{22}$H$_{16}$F$_2$N$_2$O$_4$S: Calcd C, 59.72; H, 3.65; N, 6.33. Found: C, 59.94; H, 3.59; N, 6.32.

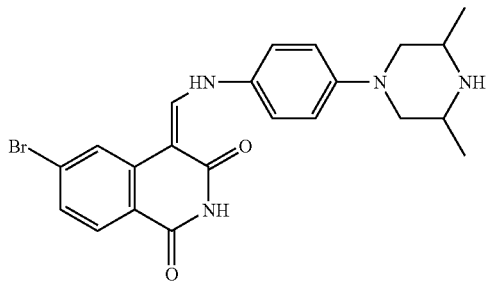

Example 201

4Z)-6-Bromo-4-({[4-(3,5-dimethylpiperazin-1-yl)phenyl]amino}methylene)isoquinoline-1,3(2H,4H)-dione An amount of (4E)-6-bromo-4-(methoxymethylene)isoquinoline-1,3(2H,4H)-dione (0.5 g, 1.77 mmol) in 5 mL of N,N'-dimethylformamide is added [4-(3,5-dimethylpiperazin-1-yl)phenyl]amine (0.44 g, 2.13 mmol). The mixture reaction is stirred at 100° C. for 3 h. Mass spectroscopy suggested the completion of reaction. Solvent is subsequently evaporated under high-pressure vacuum to brown solid. The solid is stirred in ether, filtered and washed with a small amount of methanol, excess amount of ether and hexane, and dried in oven overnight to give 0.65 g (80.0% yield) of yellow solid:

mp 229-230° C.; MS (ESI) m/z 455.1-457.1 (M+H)$^{+1}$

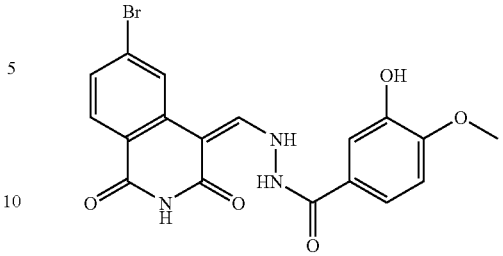

Example 202

N'-[(Z)-(6-Bromo-1,3-dioxo-2,3-dihydroisoquinolin-4(1H)-ylidene)methyl]-3-hydroxy-4-methoxybenzohydrazide 3-Hydroxy-4-methoxybenzoic acid (1.0 g, 5.9 mmol) is coupled to tert-butyl carbazate (0.94 g, 7.1 mmol) using EDC (2.3 g, 12 mmol), HOBT (1.6 g, 15 mmol), and NMM (1.6 mL, 15 mmol) in tetrahydrofuran (30 mL). Following an aqueous work-up, the crude product is purified by reverse-phase high performance liquid chromatography to give N'-(3-hydroxy-4-methoxy-benzoyl)-hydrazinecarboxylic acid tert-butyl ester.

N'-(3-Hydroxy-4-methoxy-benzoyl)-hydrazinecarboxylic acid tert-butyl ester (0.14 g, 0.50 mmol) is converted to 3-hydroxy-4-methoxy-benzoic acid hydrazide hydrochloride by stirring in 4 N hydrogen chloride in dioxane (2 mL). The white precipitate is washed with diethyl ether.

(4E)-6-bromo-4-(methoxymethylene)isoquinoline-1,3 (2H,4H)-dione (0.18 g, 0.64 mmol) and 3-hydroxy-4-methoxy-benzoic acid hydrazide hydrochloride (0.18 g, 0.64 mmol) were coupled in N,N-dimethylformamide (5 mL) with triethylamine (0.30 mL) at 100° C. After cooling to room temperature and addition of 5% aqueous potassium hydrogen sulfate solution, the solid material is collected by Buchner filtration, washed with diethyl ether, water, and methanol, and then dried under house vacuum to give N'-[(Z)-(6-bromo-1,3-dioxo-2,3-dihydroisoquinolin-4(1H)-ylidene)methyl]-3-hydroxy-4-methoxybenzohydrazide as a tan powder.

MS (ES$^-$): 430.1, 432.1 (M−H)$^-$

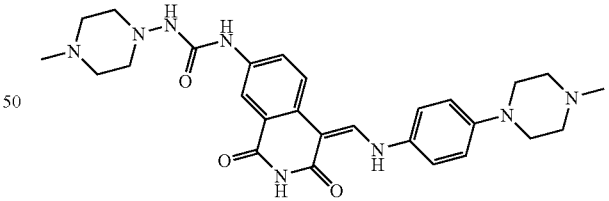

Example 203

N-(4-Methylpiperazin-1-yl)-N'-[(4Z)-4-({[4-(4-methylpiperazin-1-'yl)phenyl]amino}methylene)-1,3-dioxo-1,2,3,4-tetrahydroisoquinolin-6-yl]urea An amount of 200 mg (0.53 mmol) of (4Z)-6-amino-4-({[4-(4-methylpiperazin-1-yl)phenyl]amino}methylene)isoquinoline-1,3(2H,4H)-dione and 4-nitrophenyl chloroformate 320.0 mg (1.59 mmol) is stirred in N,N-dimethylacetamide at 100° C. for 1 hour. After cooling, the solvent is evaporated and stirred in 3 mL of water for 10 minutes. The solid precipitate is collected with ether to give 180 mg (70% yield) of (4-{[4(4-methyl-piperazin-1-yl)-phenylamino]-methylene}-1,3-dioxo-1,2,3,4-tetrahyro-isoquinolin-6-yl)-carbamic acid 4-nitro-phenyl ester.

An amount of 100 mg (0.18 mmol) (4-{[4(4-methyl-piperazin-1-yl)-phenylamino]-methylene}-1,3-dioxo-1,2,3,4-tetrahyro-isoquinolin-6-yl)-carbamic acid 4-nitro-phenyl ester and 4-amino methyl piperazine, 1 mL is stirred in N,N-dimethylacetamide for 1 hour. The solvent is evaporated and taken up in dichloromethane. The residue is purified by preparative thin layer chromatography (1:10:89=ammonium hydroxide:methanol:methylene chloride), to give a yellow solid 30 mg (32% yield); mp 195-196° C.

MS (ESI) m/z 519.3 (M+1)$^+$.

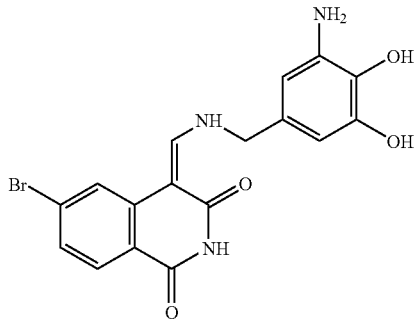

Example 204

(4Z)-4-{[(3-Amino-4,5-dihydroxybenzyl)amino]methylene}-6-bromoisoquinoline-1,3(2H,4H)-dione 6-Bromo-4-methoxymethylene-4H-isoquinoline-1,3-dione (124 mg, 0.44 mmol), 3-amino-5-aminomethyl-benzene-1,2-diol dihydrochloride salt (100 mg, 0.44 mmol) and Et$_3$N (0.15 mL, 1.1 mmol) in N,N-dimethylformamide (DMF) (5 mL) is stirred at 25° C. for 24 hours. Water (10 mL) is added to the reaction mixture. The resulting solid is filtered and washed with water. The crude solid is purified by HPLC, eluting with 20% CH$_3$CN/H$_2$O to 100% CH$_3$CN over 30 minutes to give 51 mg (22%) of the title compound as a brown solid. HRMS (ESI) m/z calcd for C$_{17}$H$_{14}$BrN$_3$O$_4$ (M+H)$^+$ 404.02405. found: 404.02336.

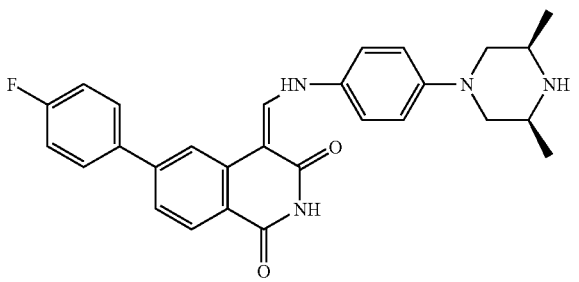

Example 205

(4Z)-4-({[4-(3,5-Dimethylpiperazin-1-yl)phenyl]amino}methylene)-6-(4-fluorophenyl)-isoquinoline-1,3(2H,4H)-dione Using the procedure described for the preparation of (4Z)-6-(4-fluorophenyl)-4-{[(3-hydroxy-4-propoxybenzyl)amino]methylene}-isoquinoline-1,3(2H,4H)-dione, 0.095 mg (61.6% yield) of brown solid is obtained from 0.15 g (0.33 mmol) of 4Z)-6-bromo-4-({[4-(3,5-dimethylpiperazin-1-yl)phenyl]amino}methylene)isoquinoline-1,3(2H,4H)-dione, 0.070 g of 4-fluorophenylboronic acid, 0.02 g (0.017 mmol) of tetrakis-(triphenylphosphine)-palladium(0) and 0.5 mL of saturated sodium carbonate solution: mp 193-194° C.; MS (ESI) m/z 471.2 (M+H)$^{+1}$

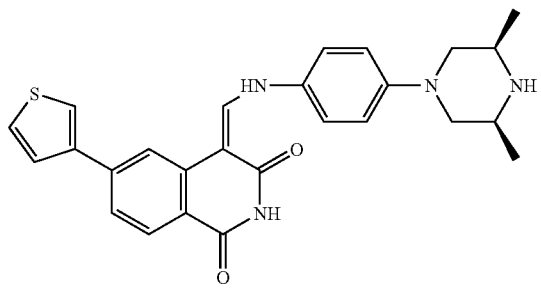

Example 206

(4Z)-4-({[4-(3,5-Dimethylpiperazin-1-yl)phenyl]amino}methylene)-6-thien-3-ylisoquinoline-1,3(2H,4H)-dione Using the procedure described for the preparation of (4Z)-6-(4-fluorophenyl)-4-{[(3-hydroxy-4-propoxybenzyl)amino]methylene}-isoquinoline-1,3(2H,4H)-dione, 0.021 mg (15.0% yield) of brown solid is obtained from 0.15 g (0.33 mmol) of 4Z)-6-bromo-4-({[4-(3,5-dimethylpiperazin-1-yl)phenyl]amino}-methylene)isoquinoline-1,3(2H,4H)-dione, 0.063 g of 3-thiopheneboronic acid, 0.02 g (0.017 mmol) of tetrakis-(triphenylphosphine)-palladium(0) and 0.5 mL of saturated sodium carbonate solution: mp 164-165° C.; MS (ESI) m/z 459.1 (M+H)$^{+1}$.

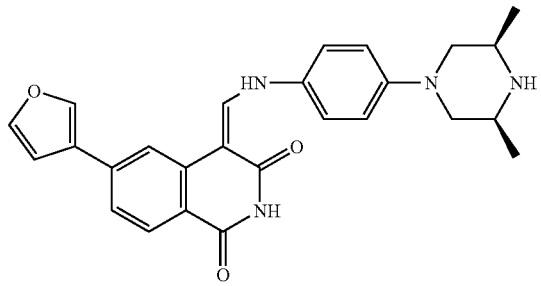

Example 207

(4Z)-4-({[4-(3,5-Dimethylpiperazin-1-yl)phenyl]amino}methylene)-6-(3-furyl)iso-quinoline-1,3(2H,4H)-dione Using the procedure described for the preparation of (4Z)-6-(4-fluorophenyl)-4-{[(3-hydroxy-4-propoxybenzyl)amino]methylene}-isoquinoline-1,3(2H,4H)-dione, 0.045 mg (31.0% yield) of brown solid is obtained from 0.15 g (0.33 mmol) of 4Z)-6-bromo-4-({[4-(3,5-dimethylpiperazin-1-yl)phenyl]amino}-methylene)isoquinoline-1,3(2H,4H)-dione, 0.055 g of 3-furanboronic acid, 0.02 g (0.017 mmol) of tetrakis-(triphenylphosphine)-palladium(0) and 0.5 mL of saturated sodium carbonate solution: mp 199-200° C.; MS (ESI) m/z 443.2 (M+H)$^{+1}$.

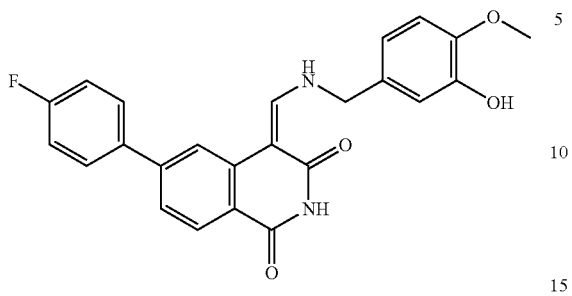

Example 208

(4Z)-6-(4-Fluorophenyl)-4-{[(3-hydroxy-4-methoxy-benzyl)amino]methylene}iso-quinoline-1,3(2H,4H)-dione Using the procedure described for the preparation of (4Z)-6-(4-fluorophenyl)-4-{[(3-hydroxy-4-propoxybenzyl)amino]methylene)-isoquinoline-1,3(2H,4H)-dione, 0.12 g (61.1% yield) of tan solid is obtained from 0.20 g (0.55 mmol) of (4Z)-6-bromo-4-{[(3-hydroxy-4-methoxybenzyl)amino] methylene}isoquinoline-1,3(2H,4H)-dione, 0.1 g (0.74 mmol) of 4-fluorophenylboronic acid, 0.028 g (0.025 mmol) of tetrakis-(triphenylphosphine)-palladium(0) and 0.5 mL of saturated sodium carbonate solution: mp 239-240° C.; MS (ESI) m/z 419.1 (M+H)$^{+1}$

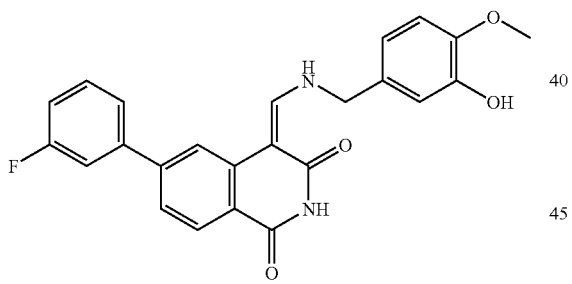

Example 209

(4Z)-6-(3-Fluorophenyl)-4-{[(3-hydroxy-4-methoxy-benzyl)amino]methylene}iso-quinoline-1,3(2H,4H)-dione Using the procedure described for the preparation of (4Z)-6-(4-fluorophenyl)-4-{[(3-hydroxy-4-propoxybenzyl) amino]methylene}-isoquinoline-1,3(2H,4H)-dione, 0.092 g (46.0% yield) of tan solid is obtained from 0.20 g (0.55 mmol) of (4Z)-6-bromo-4-{[(3-hydroxy-4-methoxybenzyl)amino] methylene}isoquinoline-1,3(2H,4H)-dione, 0.1 g (0.74 mmol) of 4-fluorophenylboronic acid, 0.028 g (0.025 mmol) of tetrakis-(triphenyl-phosphine)palladium(0) and 0.5 mL of saturated sodium carbonate solution: mp 204-205° C.; MS (ESI) m/z 419.1 (M+H)$^{+1}$

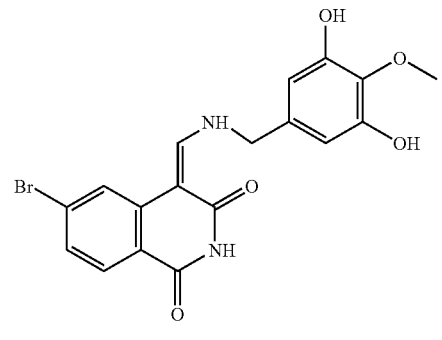

Example 210

(4Z)-6-Bromo-4-{[(3,5-dihydroxy-4-methoxyben-zyl)amino]methylene}isoquinoline-1,3(2H,4H)-dione 6-Bromo-4-methoxymethylene-4H-isoquinoline-1,3-dione (89 mg, 0.32 mmol), 5-aminomethyl-2-methoxy-benzene-1,3-diol hydrochloride salt (66 mg, 0.32 mmol) and Et$_3$N (111 µL, 0.8 mmol) in N,N-dimethylformamide (DMF) (2 mL) is stirred at 25° C. for 24 hours. H$_2$O (10 mL) is added to the reaction mixture. The resulting precipitate is filtered, washed with H$_2$O and dried in vacuo to give 144 mg of the title compound as a beige powder. HRMS (ESI) m/z calcd for C$_{18}$H$_{15}$BrN$_2$O$_5$ (M+H)$^{+1}$ 419.02371. found: 419.02294.

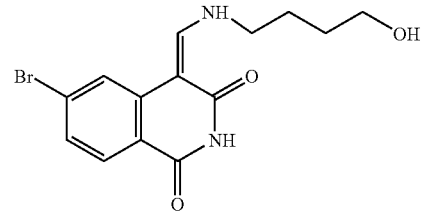

Example 211

(4Z)-6-Bromo-4-{[(4-hydroxybutyl)amino]methylene}isoquinoline-1,3(2H,4H)-dione

6-Bromo-4-methoxymethylene-4H-isoquinoline-1,3-dione (250 mg, 0.89 mmol), and 4-amino-butan-1-ol (79 mg, 0.89 mmol) in N,N-dimethylformamide (DMF) (5 mL) is stirred at 25° C. for 3 days. A precipitate formed. The reaction mixture is cooled to 0° C. The precipitate is filtered and dried in vacuo to give 195 mg (64.5%) of the title compound as a tan powder. HRMS (ESI) m/z calcd for C$_{14}$H$_{15}$BrN$_2$O$_3$ (M+H)$^{+1}$ 339.03389. found: 339.03308.

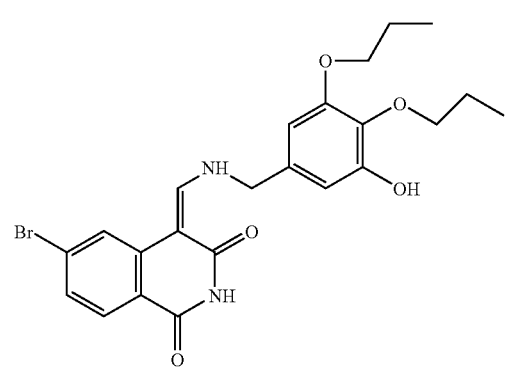

Example 212

(4Z)-6-Bromo-4-{[(3-hydroxy-4,5-dipropoxybenzyl)amino]methylene}isoquinoline-1,3(2H,4H)-dione 6-Bromo-4-methoxymethylene-4H-isoquinoline-1,3-dione (110 mg, 0.39 mmol), 5-aminomethyl-2,3-dipropoxyphenol hydrochloride salt (93 mg, 0.39 mmol) and Et$_3$N (112 µL, 0.8 mmol) in N,N-dimethylformamide (DMF) (2 mL) is stirred at 25° C. for 24 hours. H$_2$O (10 mL) is added to the reaction mixture. The resulting precipitate is filtered, washed with H$_2$O and dried in vacuo to give 170 mg (91%) of the title compound as a tan powder. HRMS (ESI) m/z calcd for C$_{23}$H$_{25}$BrN$_2$O$_5$ (M+H)$^{+1}$ 489.10196. found: 489.10078.

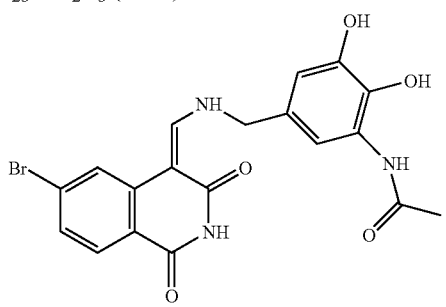

Example 213

N-[5-({[(Z)-(6-Bromo-1,3-dioxo-2,3-dihydroisoquinolin-4(1H)-ylidene)methyl]-2,3-dihydroxyphenyl]acetamide (4Z)-4-{[(3-Amino-4,5-dihydroxybenzyl)amino]methylene}-6 bromoisoquinoline-1,3(2H,4H)-dione (50 mg, 0.12 mmol) and acetic anhydride (1 mL, 10.59 mmol) in N,N-dimethylformamide (DMF) (4 mL) is stirred overnight. The reaction mixture is concentrated in vacuo and the residue is stirred in H$_2$O for 24 hours. The precipitate is filtered, and dried in vacuo to give the title compound (30 mg, 44.6%) as a tan solid. HRMS (ESI) m/z calcd for C$_{19}$H$_{16}$BrN$_3$O$_5$ (M+H)$^{+1}$ 446.03461. found: 446.03378.

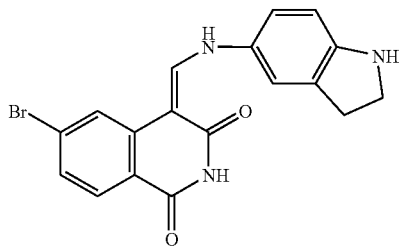

Example 214 (AZ)

(4Z)-6-Bromo-4-[(2,3-dihydro-1H-indol-5-ylamino)methylene]isoquinoline-1,3(2H,4H)-dione 6-Bromo-4-methoxymethylene-4H-isoquinoline-1,3-dione (250 mg, 0.89 mmol), 2,3-dihydro-1H-indol-5-ylamine× 2HCl (184 mg, 0.89 mmol) and Et$_3$N (0.37 mL, 2.67 mmol) in N,N-dimethylformamide (DMF) (10 mL) is stirred for 4 days. The reaction mixture is concentrated in vacuo and the residue is triturated in H$_2$O for 24 hours. The precipitate is filtered, washed with H$_2$O and dried in vacuo to give 370 mg of the title compound as a brown solid. HRMS (ESI) m/z calcd for C$_{18}$H$_{14}$BrN$_3$O$_2$ (M+H)$^{+1}$ 384.03422. found: 384.03553. The compound is contains 29% of 4-(5-amino-2,3-dihydro-indol-1-ylmethylene)-6-bromo-4H-isoquinoline-1,3-dione.

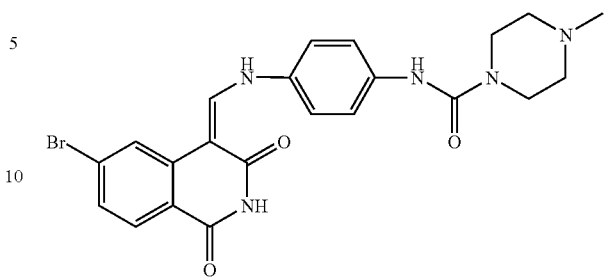

Example 215

N-(4-{[(Z)-(6-Bromo-1,3-dioxo-2,3-dihydroisoquinolin-4(1H)-'ylidene)methyl]amino}phenyl)-4-methylpiperazine-1-carboxamide Using the procedure described for the preparation of example 14, 120 mg (34% yield) is obtained as a yellow solid from 200 mg (0.71 mmol) of (4E)-6-bromo-4-(methoxymethylene)isoquinoline-1,3(2H,4H)-dione and 166 mg (0.71 mmol) of N-(4-aminophenyl)-4-methylpiperazine-1-carboxamide; mp >300° C.
MS (ESI) m/z 484.1 (M+1)$^+$

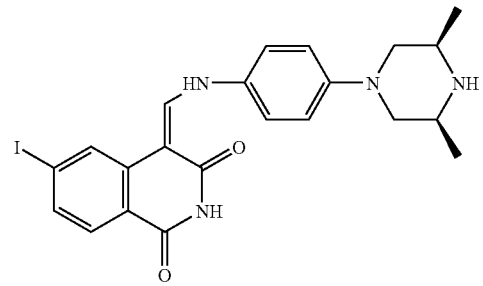

Example 216

(4Z)-4-({[4-(3,5-Dimethylpiperazin-1-yl)phenyl]amino}methylene)-6-iodoisoquinoline-1,3(2H,4H)-dione (30)

Using the procedure described for the preparation of 4Z)-6-bromo-4-({[4-(3,5-dimethylpiperazin-1-yl)phenyl]amino}methylene)isoquinoline-1,3(2H,4H)-dione, 0.15 g (63.5% yield) of light brown solid is obtained from 0.15 g (0.46 mmol) of (4E)-6-iodo-4-(methoxymethylene)isoquinoline-1,3(2H,4H)-dione and [4-(3,5-dimethylpiperazin-1-yl)phenyl]amine (0.44 g, 2.13 mmol): mp 222-223° C.; MS (ESI) m/z 503.1 (M+H)$^{+1}$

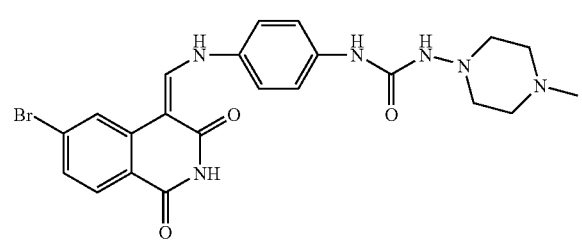

Example 217

N-(4-{[(Z)-(6-Bromo-1,3-dioxo-2,3-dihydroiso-quinolin-4(1H)-'ylidene)methyl]amino}phenyl)-N'-(4-methylpiperazin-1-yl)urea Using the procedure described for the preparation of example 14, 179.4 mg (68% yield) of the title compound is obtained as a yellow solid from 200 mg (0.71 mmol) of (4E)-6-bromo-4-(methoxymethylene)isoquinoline-1,3(2H, 4H)-dione and 177 mg (0.71 mmol) of 1-(4-amino-phenyl)-3-(4-methyl-piperazin-1-yl)-urea; mp 270-271° C.

MS (ESI) m/z 499.0 (M+1)$^+$

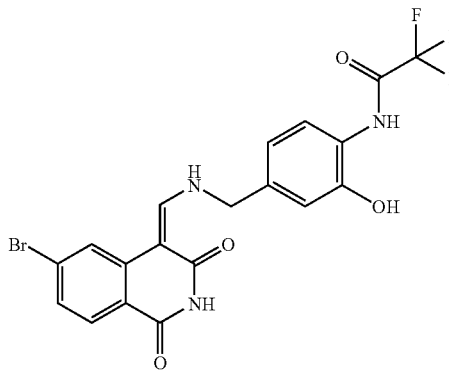

Example 218

N-[4-({[(Z)-(6-Bromo-1,3-dioxo-2,3-dihydroiso-quinolin-4(1H)-'ylidene)methyl]amino}methyl)-2-hydroxyphenyl]-2,2,2-trifluoroacetamide Using the procedure described for the preparation of example 69, 80 mg (32% yield) of the title compound as an orange solid is obtained from 200 mg (0.52 mmol) of (4Z)-4-{[(4-amino-3-hydroxybenzyl)amino]methylene}-6-bromoisoquinoline-1,3(2H,4H)-dione and 0.22 mL (1.56 mmol) of trifluoroacetic anhydride;

mp: 278-279° C.

MS (ESI) m/z 482.1 (M−1)$^-$

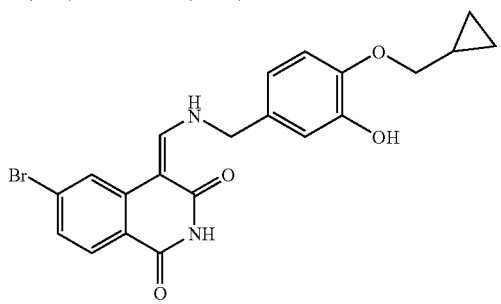

Example 219

(4Z)-6-Bromo-4-({[4-(cyclopropylmethoxy)-3-'hydroxybenzyl]amino}methylene)isoquinoline-1,3(2H, 4H)-dione Using the same procedure as intermediate 45, intermediate 9 is reduced to 5-aminomethyl-2-cyclopropylmethoxy-phenol hydrochloride. Using the procedure described for the preparation of example 46, 300 mg (64%) yield of the title compound as a brown solid is obtained from 300 mg (1.06 mmol) of (4E)-6-bromo-4-(methoxymethylene)isoquinoline-1,3(2H,4H)-dione and 5-aminomethyl-2-cyclopropyl-methoxy-phenol hydrogen chloride.; mp 210-211° C.

MS (ESI) m/z 445.0 (M+1)$^+$.

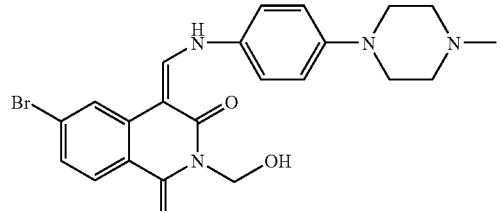

Example 220

(4Z)-6-Bromo-2-(hydroxymethyl)-4-({[4-(4-methylpiperazin-1-yl)phenyl]amino}methylene)isoquinoline-1,3(2H,4H)-dione An amount of 300 mg of (0.68 mmol) example 27 and paraformyl aldehyde 612 mg (20.4 mmol) were dissolved in 1:1 water:N,N-dimethylformamide. The mixture is agitated in a microwave at 180° C. for 400 s. Followed by filtration through celite, evaporated after washing with methylene chloride. The yellow residue is then stirred in water for 20 minutes, the solid is collected with methanol to give 200 mg (63% yield) of the desired product; mp: 141-142

MS (ESI) m/z 473.1 (M+1)$^+$.

Example 221

6-Iodo-4-{[4-(5-methyl-2,5-diaza-bicyclo[2.2.1]hept-2-yl)-phenylamino]-methylene}-4H-isoquinoline-1,3-dione A solution of 2-methyl-2,5-diaza-bicyclo[2.2.1]heptane (0.4402 g, 1.6 mmol), p-fluoro-nitrobenzene (0.56 mL, 5.4 mmol), N,N-diisopropylethylamine (0.84 mL, 4.82 mmol) in 5 mL of acetonitrile is heated at 100° C. overnight. After the solvent is removed, the residue is treated with saturated sodium bicarbonate solution and extracted with chloroform. The organic layer is washed with brine, dried over magnesium sulfate, filtered, and evaporated to dryness. The oil is washed with hexane to give a yellow solid, which is recrystallized from ethyl acetate/hexane to yield 0.246 g (65% yield) of 2-methyl-5-(4-nitro-phenyl)-2,5-diaza-bicyclo[2.2.1]heptane.

A mixture of 2-methyl-5-(4-nitro-phenyl)-2,5-diaza-bicyclo[2.2.1]heptane (0.19 g, 0.815 mmol) and a catalytic amount of Pd/C in ethanol (0.2 mL) is hydrogenated at 1 atmosphere at room temperature overnight. It is filtered through Celite, and the organic solution is evaporated, and then treated with 10 mL of methanol. It is then treated with hydrochloric acid in methanol, followed by ethyl ether, and filtered to give 4-(5-methyl-2,5-diaza-bicyclo[2.2.1]hept-2-yl)-phenylamine as bluish solid (0.107 g, 65%). MS (ESI) m/z 204.2 (M−H)$^{+1}$.

A solution of 4-(5-methyl-2,5-diaza-bicyclo[2.2.1]hept-2-yl)-phenylamine (0.1 g, 0.49 mmol), 6-Iodo-4-methoxymethylene-4H-isoquinoline-1,3-dione (0.2 g, 0.6 mmol), and N,N-dimethylformamide (0.2 mL) is heated at 90° C. overnight. After the solvent is removed, the residue is treated with ethyl ether and filtered to give crude product as light brown solid. It is purified by HPLC to yield 97 mg (39% yield) of 6-iodo-4-{[4-(5-methyl-2,5-diaza-bicyclo[2.2.1]hept-2-yl)-phenylamino]-methylene}-4H-isoquinoline-1,3-dione as bright orange solid. mp 210-211° C.

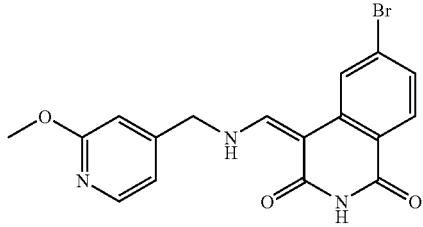

Example 222

(4Z)-6-Bromo-4-({[(2-methoxypyridin-4-yl)methyl]amino}methylene)isoquinoline-1,3(2H,4H)-dione 2-Methoxy-4-cyanopyridine is prepared according to Brown, T. H. et al. Eur J Med Chem. 28, 1993, 601-608. Reduction of 2-methoxy-4-cyanopyridine to 4-(2-methoxypyridyl)methylamine is achieved through the method of Walpole, C. S. J. J Med Chem. 36, 16, 1993, 2362-2372.

(4E)-6-bromo-4-(methoxymethylene)isoquinoline-1,3 (2H,4H)-dione (0.15 g, 0.53 mmol) and 4-(2-methoxypyridyl)methylamine hydrochloride (93 mg, 0.53 mmol) were coupled in tetrahydrofuran (3 mL) with triethylamine (0.21 mL) at room temperature. After addition of methanol, the solid material is collected by Buchner filtration, washed with diethyl ether and water. The crude material is dissolved in a minimum of 5% methanol in chloroform and then passed through a Florisil plug, eluting with the same solvent mixture. The filtrate is concentrated under reduced pressure to give (4Z)-6-bromo-4-({[(2-methoxypyridin-4-yl)methyl]amino}methylene)isoquinoline-1,3(2H,4H)-dione (0.13 g, 62%) as a golden solid.

MS (ES+): 388.0, 390.0 (M+H)+

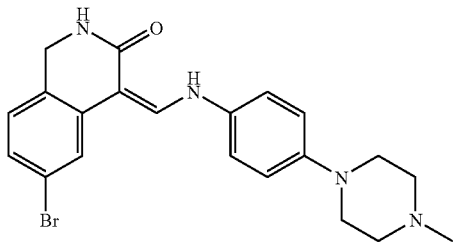

Example 223

(4Z)-6-Bromo-4-({[4-(4-methylpiperazin-1-yl)phenyl]amino}methylene)-1,4-dihydroisoquinolin-3(2H)-one A toluene solution (0.75 mL) of 6-bromo-4-[(dimethylamino)methylene]-1,4-dihydroisoquinolin-3(2H)-one (60 mg, 0.213 mmol) and 4-(N-methylpiperazinyl)aniline (42.9 mg, 0.224 mmol) is heated at 110° C. for 3 h. It is dried up and triturated with ether and hexane to yield 23 mg (25%) of the title compound as a light-brown solid.

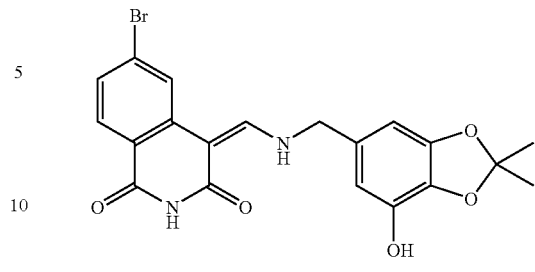

Example 224

(4Z)-6-Bromo-4-({[(7-hydroxy-2,2-dimethyl-1,3-benzodioxol-5-yl)methyl]amino}methylene)isoquinoline-1,3(2H,4H)-dione 7-Hydroxy-2,2-dimethyl-benzo[1,3]dioxole-5-carboxylic acid methyl ester is prepared from methyl gallate and acetone according to Percec, Virgil; Bera, Tushar K.; Tetrahedron; 58; 20; 2002; 4031-4040.

TOF MS (ES−): 223.0 (M−H)−

7-Hydroxy-2,2-dimethyl-benzo[1,3]dioxole-5-carboxylic acid methyl ester (1.5 g, 6.7 mmol) is converted to 7-benzyloxy-2,2-dimethyl-benzo[1,3]dioxole-5-carboxylic acid methyl ester by reaction with benzyl bromide (1.2 mL, 10 mmol) in acetone (35 mL) and in the presence of potassium carbonate (13 g). After an aqueous work-up, the crude solid is triturated with hexanes and then filtered to give the desired product in quantitative yield.

TOF MS (ES+): 315.1 (M+H)+

A −78° C. solution of 7-benzyloxy-2,2-dimethyl-benzo[1,3]dioxole-5-carboxylic acid methyl ester (0.62 g, 2.0 mmol) in toluene (17 mL) is treated with di-isobutylaluminum hydride (1.0 M solution I hexanes, 4.4 mL, 4.4 mmol), which is added dropwise over 15 minutes. After 5 minutes of stirring, the reaction is quenched by the addition of 10% aqueous hydrochloric acid solution. After warming to room temperature, the mixture is extracted 3× with ethyl acetate. The combined extracts were washed with saturated aqueous sodium chloride solution, dried over anhydrous sodium sulfate, and concentrated under reduced pressure to provide (7-benzyloxy-2,2-dimethyl-benzo[1,3]dioxol-5-yl)-methanol in quantitative yield.

To a 0° C. mixture of (7-benzyloxy-2,2-dimethyl-benzo[1,3]dioxol-5-yl)-methanol (0.57 g, 2.0 mmol) and diphenylphosphoryl azide (0.52 mL, 2.4 mmol) in tetrahydrofuran (10 mL) is added 1,8-diazabicyclo[5.4.0]undec-7-ene (DBU, 0.33 mL, 2.2 mmol). The mixture is allowed to warm to room temperature over the weekend and then quenched with the addition of water. The reaction mixture is extracted 3× with ethyl acetate, and the combined extracts were washed with 5% aqueous potassium hydrogen sulfate solution and saturated aqueous sodium chloride solution, dried over anhydrous sodium sulfate, and then concentrated to give 6-azidomethyl-4-benzyloxy-2,2-dimethyl-benzo[1,3]dioxole, which is used in the next step without purification.

A solution of 6-azidomethyl-4-benzyloxy-2,2-dimethyl-benzo[1,3]dioxole (2.0 mmol maximum) in ethanol (20 mL) and 6 M aqueous hydrochloric acid (2 mL) is hydrogenated at 50 psi over 5% Pd/C. After 18 hours, the reaction mixture is filtered through a Celite pad and concentrated under reduced pressure to give C-(7-benzyloxy-2,2-dimethyl-benzo[1,3]dioxol-5-yl)-methylamine hydrochloride.

MS (ES+): 196.2 (M+H)+

(4E)-6-bromo-4-(methoxymethylene)isoquinoline-1,3(2H,4H)-dione (0.42 g, 1.5 mmol) and C-(7-benzyloxy-2,2-dimethyl-benzo[1,3]dioxol-5-yl)-methylamine hydrochloride (1.5 mmol) were coupled in N,N-dimethylformamide (10 mL) with triethylamine (0.6 mL). The crude material is dissolved in a minimum of 7.5% methanol in chloroform and then passed through a Florisil plug, eluting with 5% methanol in chloroform. The filtrate is concentrated under reduced pressure to give (4Z)-6-bromo-4-({[(7-hydroxy-2,2-dimethyl-1,3-benzodioxol-5-yl)methyl]amino}methylene)isoquinoline-1,3(2H,4H)-dione as a light pink powder.

MS (ES+): 445.0, 446.9 (M+H)+

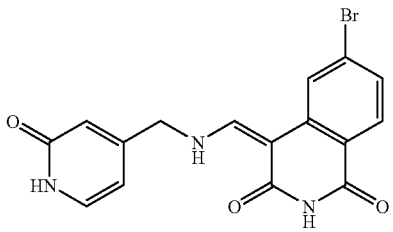

Example 225

(4Z)-6-Bromo-4-({[(2-oxo-1,2-dihydropyridin-4-yl)methyl]amino}methylene)isoquinoline-1,3(2H,4H)-dione A solution of 4-(2-methoxypyridyl)methylamine (0.19 g, 1.1 mmol) in water (50 mL) and 3 M aqueous hydrochloric acid (25 mL) is heated at reflux for 5 hours and then solvent is reduced to approximately 10 mL. The remainder of the water is then removed under reduced pressure to give 4-aminomethyl-1H-pyridin-2-one hydrochloride (0.15 g, 83%) as an off-white solid.

(4E)-6-bromo-4-(methoxymethylene)isoquinoline-1,3(2H,4H)-dione (0.26 g, 0.94 mmol) and 4-aminomethyl-1H-pyridin-2-one hydrochloride (0.15 g, 0.94 mmol) were coupled in tetrahydrofuran (5 mL) and N,N-dimethylformamide (3 mL) with triethylamine (0.28 g) at room temperature overnight. After the addition of water, the solid material is collected by Buchner filtration, washed with diethyl ether, water, and methanol, and dried under vacuum to give (4Z)-6-bromo-4-({[(2-oxo-1,2-dihydropyridin-4-yl)methyl]amino}methylene)isoquinoline-1,3(2H,4H)-dione (0.19 g, 54%) as a gray powder.

MS (ES−): 372.0, 347.0 (M−H)−

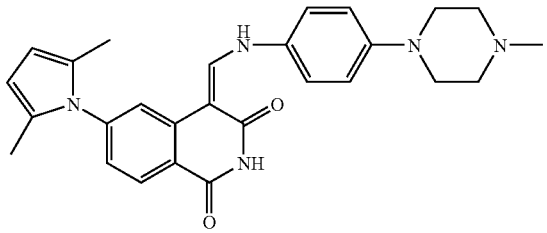

Example 226

(4Z)-6-(2,5-Dimethyl-1H-pyrrol-1-yl)-4-({[4-(4-methylpiperazin-1-'yl)phenyl]amino}methylene)isoquinoline-1,3(2H,4H)-dione An amount of 300 mg (0.74 mmol) of (4Z)-6-amino-4-({[4-(4-methylPiperzin-1-yl)phenyl]amino}methylene)isoquinoline-1,3(2H,4H)-dione and toluene sulfonic acid (226.45, 1.19 mmol), and acetonylacetone is stirred in N,N-dimethylformamide (5 mL). The reaction mixture is heated at 110° C. for 1 h. After cooling to room temperature, the mixture is filtered through celite and washed with methylene chloride, evaporated. The residue is purified by preparative thin layer chromatography (10:90=methanol:methylene chloride), to give a yellow solid 100 mg (28% yield); mp 222-223° C.

mp 264-265° C.;

MS (ESI) m/z 456.1 (M+1)

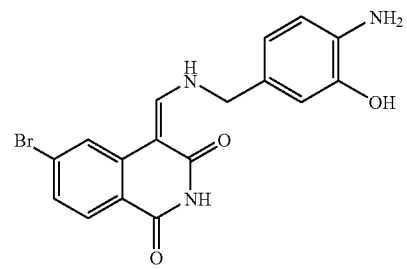

Example 227

(4Z)-4-{[(4-Amino-3-hydroxybenzyl)amino]methylene}-6-bromoisoquinoline-1,3(2H,4H)-dione Using the procedure described for the preparation of example 46, 700 mg of yellow-brown solid (100% yield) is obtained from 500 mg (1.77 mmol) of 6-bromo-4-methoxymethylene-isoquinoline-4H-1,3-dione and 2-amino-5-(aminomethyl)phenol (448 mg, 0.76 mmol);

mp 245-246° C.

MS (ESI) m/z 390 (M+H)+.

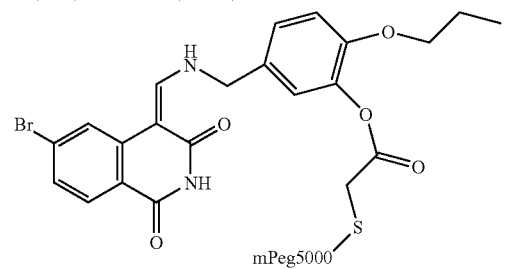

Example 228

PEG5000thio-acetic acid 5-{[(6-bromo-1,3-dioxo-2,3-dihydro-1H-isoquinolin-4-ylidenemethyl)-amino]-methyl}-2-propoxy-phenyl ester To iodoacetic acid (43 mg, 0.232 mmol) in dimethylformamide (DMF) (1 mL) at −20° C. is added N-methylmorpholine (25 uL, 0.232 mmol) and isobutylchloroformate (30 uL, 0.232 mmol). After 5 min (4Z)-6-bromo-4-{[(3-hydroxy-4-propoxybenzyl)amino]methylene}isoquinoline-1,3(2H,4H)-dione (100 mg, 0.232 mmol) is added. The reaction mixture is allowed to warm to 25° C. After 2 h N-methylmorpholine is added (25 uL). After 1 h 15% aq. citric acid is added. The resulting precipitate is filtered and washed with water to give as a tan solid (116 mg). A solution of this material in CH3CN is treated with mPEGSH 5000 (500 mg, 0.1 mmol) and Hunig's base. After 1 h tetrabutylammoniumiodide (10 mg) and dimethylaminopyridine (DMAP) (5 mg) is added. After 4 days the reaction mixture is concentrated in vacuo dissolved in water and extracted with CH2Cl2 to give a solid after concentration. Chromatography on silica gel (CH2Cl2/methanol) gave the desired compound (235 mg) as a tan powder.

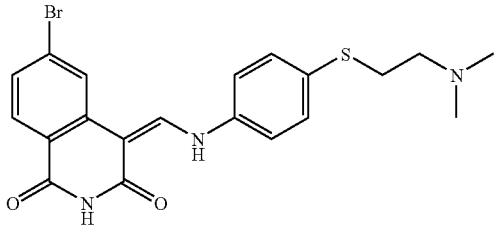

Example 229

(4Z)-6-Bromo-4-{[(4-{[2-(dimethylamino)ethyl]thio}phenyl)amino]methylene}isoquinoline-1,3(2H,4H)-dione To a solution of N,N-dimethylaminoethanethiol hydrochloride (2.9 g, 14 mmol) in N,N-dimethylformamide (DMF) (70 mL) is added potassium carbonate (19 g, 140 mmol), followed by 4-fluoronitrobenzene (1.5 mL, 14 mmol). After stirring overnight at room temperature, the reaction mixture is diluted with water and extracted 3× with ethyl acetate. The combined extracts were washed five times with water and with saturated aqueous sodium chloride solution, dried over anhydrous sodium sulfate, and concentrated under reduced pressure. The crude oil is purified by flash chromatography (Isco 40 g Redi-Sep column, MeOH/CHCl₃) to give N,N-dimethyl-N-{2-[(4-nitrophenyl)thio]ethyl}amine (2.3 g, 72%) as a golden oil.

TOF MS (ES⁺): 227.2 (M+H)⁺

To a solution of N,N-dimethyl-N-{2-[(4-nitrophenyl)thio]ethyl}amine (0.58 g, 3.0 mmol) in ethanol (45 mL), tetrahydrofuran (23 mL), and saturated aqueous ammonium chloride solution is added iron powder (1.1 g, 6.4 mmol). The mixture is heated in a 100° C. oil bath for one hour. While still hot, the reaction mixture is filtered through a pad of diatomaceous earth. The concentrated filtrate is partitioned between ethyl acetate and saturated aqueous sodium chloride solution. The organic phase is dried over anhydrous sodium sulfate and concentrated under reduced pressure. The crude material is purified by reverse-phase high performance liquid chromatography to give 4-(2-dimethylamino-ethylsulfanyl)-phenylamine.

MS (ES⁻): 195.0 (M–H)⁻

(4E)-6-Bromo-4-(methoxymethylene)isoquinoline-1,3(2H,4H)-dione (0.21 g, 0.76 mmol) and 4-(2-dimethylaminoethylsulfanyl)-phenylamine (0.15 g, 0.76 mmol) were stirred in N,N-dimethylformamide (5 mL) and triethylamine (0.3 mL) at 60-70° C. for 5 minutes and then at room temperature for 10 minutes. The reaction mixture is quenched by the addition of water. The solid material is then collected, washed with diethyl ether, water, and methanol, and then dried under vacuum to give (4Z)-6-bromo-4-{[(4-{[2-(dimethylamino)ethyl]thio}phenyl)amino]methylene}isoquinoline-1,3(2H,4H)-dione (0.22 mg, 65%) as a golden powder.

MS (ES⁺): 446.1, 448.1 (M+H)⁺

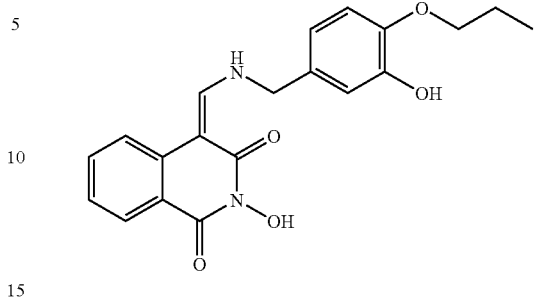

Example 230

2-Hydroxy-4-[(3-hydroxy-4-propoxy-benzylamino)-methylene]-4H-isoquinoline-1,3-dione A mixture of 5-Aminomethyl-2-propoxy-phenol hydrochloride (109 mg, 0.50 mmole), 4 mL of N,N-dimethylformamide and triethylamine (75 □L, 0.54 mmole) is stirred for 15 minutes. Then (4E)-6-bromo-7-methoxy-4-(methoxymethylene)isoquinoline-1,3(2H,4H)-dione (225 mg, 0.50 mmole) is added and the reaction mixture stirred for one hour. The product is isolated as before, to give an off-white solid, 81 mg, (44%), mp 176-8° C.; MS (ESI): m/z 369.1 (M+H).

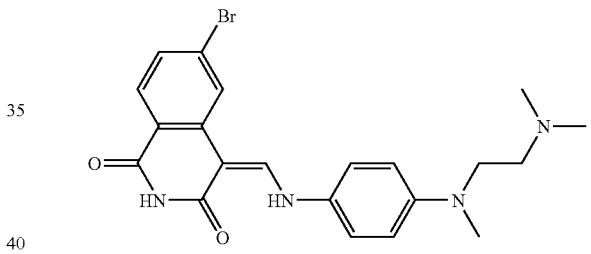

Example 231

(4Z)-6-Bromo-4-[({4-[[2-(dimethylamino)ethyl](methyl)amino]phenyl}amino)methylene]isoquinoline-1,3(2H,4H)-dione A mixture of 4-fluoronitrobenzene (0.35 g, 2.5 mmol) and N,N,N'-trimethylethylenediamine (1.5 g, 1.9 mmol) in N-methylpyrrolidinone (10 mL) is heated for 19 hours in a 100° C. shaking block. After cooling to room temperature, the reaction mixture is partitioned between ethyl acetate and water. The organic phase is washed four times with water and with saturated aqueous sodium chloride solution and then concentrated under reduced pressure to give N,N,N'-trimethyl-N'-(4-nitrophenyl)ethane-1,2-diamine as a brown semisolid.

TOF MS (ES⁺): 224.1 (M+H)⁺

A solution of N,N,N'-trimethyl-N'-(4-nitrophenyl)ethane-1,2-diamine in ethanol, containing 5 drops of concentrated hydrochloric acid, is hydrogenated overnight at atmospheric pressure over 10% Pd/C. The mixture is filtered through a pad of diatomaceous earth and concentrated under reduced pressure to give N-[2-(dimethylamino)ethyl]-N-methylbenzene-1,4-diamine as a dark maroon oil.

TOF MS (ES$^+$): 194.1 (M+H)$^+$ (4E)-6-bromo-4-(methoxymethylene)isoquinoline-1,3 (2H,4H)-dione (0.28 g, 1.0 mmol) and N-[2-(dimethylamino) ethyl]-N-methylbenzene-1,4-diamine hydrochloride (0.30 g, 1.0 mmol) were stirred in N,N-dimethylformamide (5 mL) with triethylamine (0.6 mL). The reaction mixture is quenched by the addition of water. The solid material is then collected, washed with diethyl ether, water, and methanol and then dried under vacuum to give (4Z)-6-bromo-4-[({4-[[2-(dimethylamino)ethyl](methyl)amino]phenyl}amino)methylene]isoquinoline-1,3(2H,4H)-dione (0.24 g, 55%) as a golden powder.

MS (ES$^+$): 443.1, 445.1 (M+H)$^+$

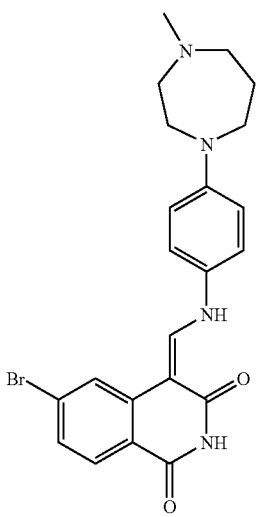

Example 232

(4Z)-6-Bromo-4-({[4-(4-methyl-1,4-diazepan-1-yl) phenyl]amino}methylene)isoquinoline-1,3(2H,4H)-dione A mixture of 4-fluoronitrobenzene (0.35 g, 2.5 mmol) and 1-methylhomopiperazine (1.7 g, 15 mmol) in N-methylpyrrolidinone (10 mL) is heated for 19 hours in a 100° C. shaking block. After cooling to room temperature, the reaction mixture is poured onto ice, precipitating 1-methyl-4-(4-nitrophenyl)-1,4-diazepane as a fine tan solid, which is collected by Buchner filtration and used in the next step without further purification.

TOF MS (ES$^+$): 236.1 (M+H)$^+$

A solution 1-methyl-4-(4-nitrophenyl)-1,4-diazepane in ethanol is hydrogenated overnight at atmospheric pressure over 10% Pd/C. The mixture is filtered through a pad of diatomaceous earth and concentrated under reduced pressure to give 4-(4-methyl-[1,4]-diazepan-1-yl)phenylamine as a dark maroon oil.

TOF MS (ES$^+$): 206.1 (M+H)$^+$ (4E)-6-bromo-4-(methoxymethylene)isoquinoline-1,3 (2H,4H)-dione (0.15 g, 0.54 mmol) and [4-(4-methyl-1,4-diazepan-1-yl)phenyl]amine (0.11 g, 0.54 mmol) were stirred in N,N-dimethylformamide (3 mL) with triethylamine (0.3 mL). The reaction mixture is quenched by the addition of water. The solid material is then collected, washed with diethyl ether, water, and methanol. The crude material is dissolved in a minimum of 5% methanol in chloroform and then passed through a Florisil plug, eluting with 5% methanol in chloroform. The filtrate is concentrated under reduced pressure to give and then dried under vacuum to give (4Z)-6-bromo-4-({[4-(4-methyl-1,4-diazepan-1-yl)phenyl] amino}methylene)isoquinoline-1,3(2H,4H)-dione (64 mg, 26%) as a rust colored powder.

MS (ES$^+$): 455.1, 457.1 (M+H)$^+$

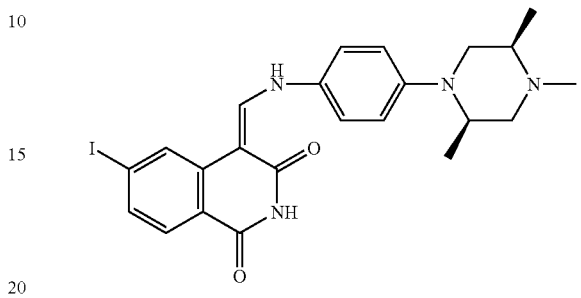

Example 233

(4Z)-6-Iodo-4-[({4-[(2S,5R)-2,4,5-trimethylpiperazin-1-yl]phenyl}amino)methylene]-isoquinoline-1,3 (2H,4H)-dione Using the procedure described for the preparation of 4Z)-6-bromo-4-({[4-(3,5-dimethylpiperazin-1-yl)phenyl] amino}methylene)isoquinoline-1,3(2H,4H)-dione, 0.078 g (49.7% yield) of light brown solid is obtained from 0.10 g (0.30 mmol) of (4E)-6-iodo-4-(methoxymethylene)isoquinoline-1,3(2H,4H)-dione and 4-(2,4,5-trimethyl-piperazin-1-yl)-phenylamine (0.073 g, 0.33 mmol) after purified by column chromatography over silica gel using 5% MeOH/CHCl$_3$ as eluent: mp 199-200° C.; MS (ESI) m/z 517.1 (M+H)$^{+1}$

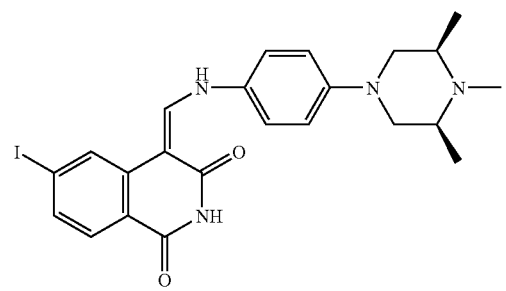

Example 234

(4Z)-6-Iodo-4-[({4-[(3R,5S)-3,4,5-trimethylpiperazin-1-yl]phenyl}amino)methylene]-isoquinoline-1,3 (2H,4H)-dione Using the procedure described for the preparation of 4Z)-6-bromo-4-({[4-(3,5-dimethylpiperazin-1-yl)phenyl] amino}methylene)isoquinoline-1,3(2H,4H)-dione, 0.089 g (56.7% yield) of light brown solid is obtained from 0.10 g (0.30 mmol) of (4E)-6-iodo-4-(methoxymethylene)isoquinoline-1,3(2H,4H)-dione, and 0.073 g (0.33 mmol) of 4-(3,4,5-trimethyl-piperazin-1-yl)-phenylamine after purified by column chromatography over silica gel using 5%

MeOH/CHCl₃ as eluent: mp 224-225° C.; MS (ESI) m/z 517.1 (M+H)$^{+1}$

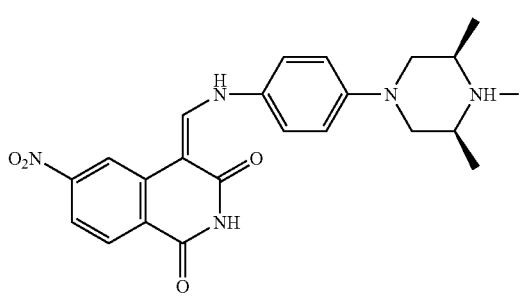

Example 235

(4Z)-4-({[4-(3,5-Dimethylpiperazin-1-yl)phenyl]amino}methylene)-6-nitroisoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 0.032 g (12.8% yield) of dark brown solid is obtained from 0.15 g (0.60 mmol) of 4-methoxymethylene-6-nitro-4H-isoquinoline-1,3-dione and [4-(3,5-dimethylpiperazin-1-yl)phenyl]amine (0.15 g, 0.72 mmol): mp >300° C.; MS (ESI) m/z 422.2 (M+H)$^{+1}$

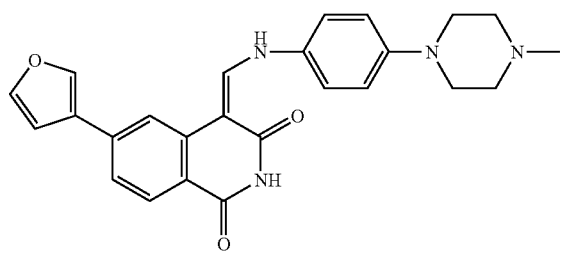

Example 236

(4Z)-6-(3-Furyl)-4-({[4-(4-methylpiperazin-1-yl)phenyl]amino}methylene)isoquinoline-1,3(2H,4H)-dione (42)

Using the procedure described for the preparation of (4Z)-6-(3-furyl)-4-[({4-[(3R,5S)-3,4,5-trimethylpiperazin-1-yl]phenyl}amino)methylene]isoquinoline-1,3(2H,4H)-dione, after purified by column chromatography over silica gel using 5% MeOH/CHCl₃ as eluent, 0.096 mg (66.2% yield) of yellow solid is obtained from 0.15 g (0.34 mmol) of (4Z)-6-bromo-4-({[4-(4-methylpiperazin-1-yl)phenyl]amino}methylene)isoquinoline-1,3(2H,4H)-dione, 0.076 g (0.64 mmol) of 3-furanboronic acid, 0.02 g (0.017 mmol) of tris(dibenzyldeneaacetone)-dipalladium(0), 0.02 g (0.064 mmol) of 2-(di-t-butyl-phosphino)-biphenyl, and 0.072 g (0.64 mmol) of sodium carbonate: mp 190-191° C.; MS (ESI) m/z 429.2 (M+H)$^{+1}$

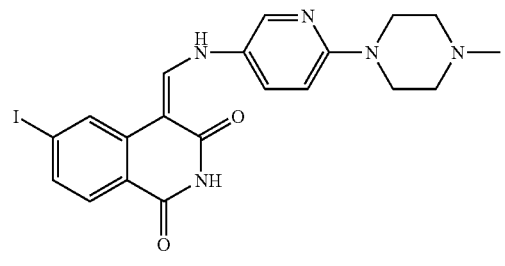

Example 237

(4Z)-6-Iodo-4-({[6-(4-methylpiperazin-1-yl)pyridin-3-'yl]amino}methylene)isoquinoline-1,3(2H,4H)-dione Using the procedure described for the preparation of example 14, 300 mg (68% yield) is obtained as a orange solid from 300 mg (0.91 mmol) of (4E)-6-iodo-4-(methoxymethylene)isoquinoline-1,3(2H,4H)-dione and 175 mg (0.91 mmol) of 6-(4-methylpiperazin-1-yl)pyridin-3-amine; mp 189-190° C.

MS (ESI) m/z 490.0 (M+1)$^+$

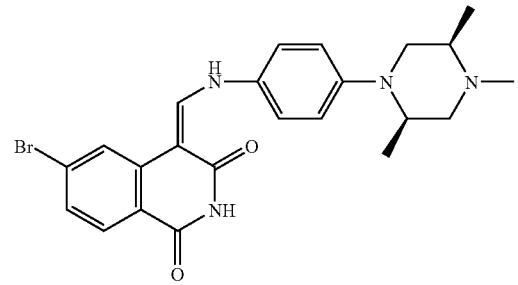

Example 238

(4Z)-6-Bromo-4-[({4-[(2S,5R)-2,4,5-trimethylpiperazin-1-yl]phenyl}amino)methylene]-isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 0.68 g (91.0% yield) of yellow solid is obtained from 0.45 g (0.46 mmol) of (4E)-6-bromo-4-(methoxymethylene)isoquinoline-1,3(2H,4H)-dione and 4-(2,4,5-trimethyl-piperazin-1-yl)-phenylamine (0.38 g, 1.76 mmol): mp 184-185° C.; MS (ESI) m/z 469.1-471.1 (M+H)$^{+1}$

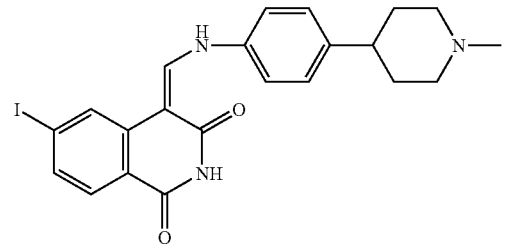

Example 239

(4Z)-6-Iodo-4-({[4-(1-methylpiperidin-4-yl)phenyl]amino}methylene)isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, after purified from HPLC, 0.064 g (53.4% yield) of light brown solid is obtained from 0.082 g (0.25 mmol) of (4E)-6-iodo-4-(methoxymethylene)isoquinoline-1,3(2H,4H)-dione and [4-(3,5-dimethylpiperazin-1-yl)phenyl]amine (0.048 g, 0.25 mmol): mp 215-216° C.; MS (ESI) m/z 488.1 (M+H)$^{+1}$

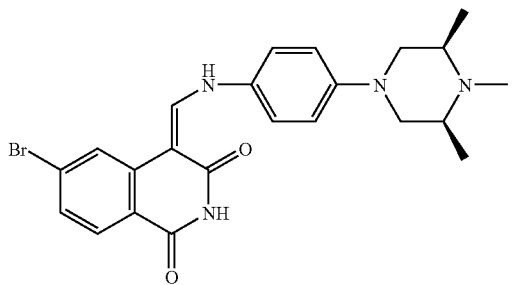

Example 240

(4Z)-6-Bromo-4-[({4-[(3R,5S)-3,4,5-trimethylpiperazin-1-yl]phenyl}amino)methylene]-isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, after purified using silica gel chromatography (using 5% MeOH/CHCl3 as solvent), 0.68 g (91.0% yield) of light brown solid is obtained from 0.45 g (1.60 mmol) of (4E)-6-bromo-4-(methoxymethylene)isoquinoline-1,3(2H,4H)-dione, and 0.38 g (1.76 mmol) of 4-(3,4,5-trimethyl-piperazin-1-yl)-phenylamine: mp 213-214° C.; MS (ESI) m/z 469.1-471.1 (M+H)$^{+1}$

Example 241

(4Z)-6-(3-Furyl)-4-[({4-[(3R,5S)-3,4,5-trimethylpiperazin-1-yl]phenyl}amino)-methylene]isoquinoline-1,3(2H,4H)-dione An amount of 0.15 g (0.32 mmol) of (4Z)-6-bromo-4-[({4-[(3R,5S)-3,4,5-trimethylpiperazin-1-yl]phenyl}amino)-methylene]-isoquinoline-1,3(2H,4H)-dione in 2 mL of DMF is added 0.076 g (0.64 mmol) of 3-furanboronic acid, 0.02 g (0.017 mmol) of tris(dibenzyldeneaacetone)-dipalladium(0), 0.02 g (0.064 mmol) of 2-(di-t-butyl-phosphino)-biphenyl, and 0.072 g (0.64 mmol) of sodium carbonate. The reaction mixture is stirred at 100 oC under N2 for 2 h. Mass spectroscopy suggested the completion of reaction. Solids were removed by filtration, and solvent is subsequently evaporated under high-pressure vacuum to brown solid. The residue is purified using silica gel chromatography (using 5% MeOH/CHCl3 as eluent), 0.064 mg (43.8% yield) of yellow solid is obtained: mp 204-205 oC; MS (ESI) m/z 457.2 (M+H)+1

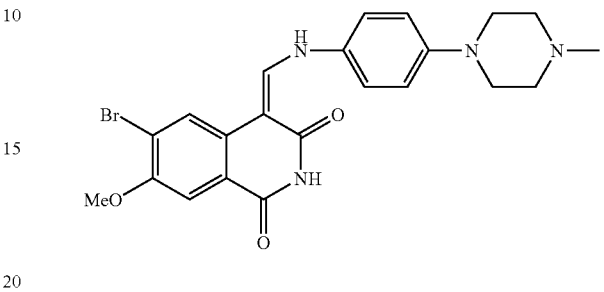

Example 242

6-Bromo-7-methoxy-4-{[4-(4-methyl-piperazin-1-yl)-phenylamino]-methylene}-4H-isoquinoline-1,3-dione A mixture of (4E)-6-bromo-7-methoxy-4-(methoxymethylene)isoquinoline-1,3(2H,4H)-dione (156 mg, 0.50 mmole), N,N-dimethylformamide (1 mL) and 4-(4-Methyl-piperazin-1-yl)-phenylamine (96 mg, 0.50 mmole) is stirred and heated at 110° C. for one hour, cooled in the refrigerator. The reaction mixture is evaporated to dryness, taken up in 5% methanol in chlororform and passed through a short pad of Florisil eluting with 5% methanol in chloroform. The eluate is evaporated in vacuo and treated with acetonitrile, filtered and dried to give a brown solid 110 mg (47%), mp 274-276° C.; MS (ESI): m/z 471.1, 473.1 (M+H).

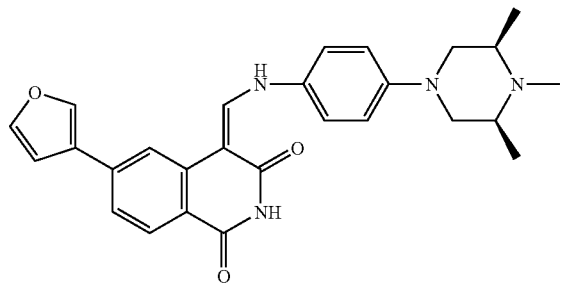

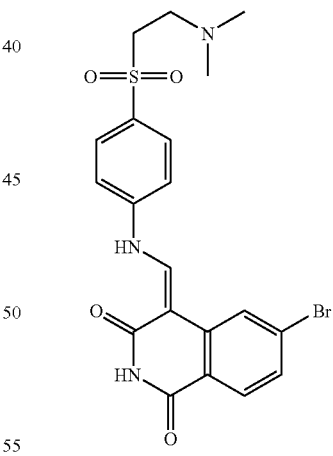

Example 243

(4Z)-6-Bromo-4-{[(4-{[2-(dimethylamino)ethyl]sulfonyl}phenyl)amino]methylene}isoquinoline-1,3(2H,4H-dione To a 0° C. solution of give N,N-dimethyl-N-{2-[(4-nitrophenyl)thio]ethyl}amine (0.50 g, 2.2 mmol) in methanol/tetrahydrofuran/water (33 mL, 1:1:1) is added dropwise an aqueous solution of OXONE®, monopersulfate compound (2.7 g, 9.5 mL). The reaction mixture is stirred for one week at room temperature and then quenched by the addition of an aqueous sodium hydrogen sulfite solution (3 g, 20 mL). The mixture is then basified to pH 8 with concentrated ammonium hydroxide and extracted 3× with dichloromethane. The combined extracts were washed with aqueous 5% sodium thiosulfite solution (100 mL) and water, dried over anhydrous magnesium sulfate, and concentrated under reduced pressure to give a golden oil, which solidified upon standing. The crude solid (0.31 g) is purified by flash chromatography (Isco 12 g Redi-Sep column, MeOH/CHCl$_3$) to give dimethyl-[2-(4-nitro-benzenesulfonyl)-ethyl]-amine.

MS (ES$^+$): 259.2 (M+H)$^+$

A solution of dimethyl-[2-(4-nitro-benzenesulfonyl)-ethyl]-amine (0.39 mmol) in ethanol (15 mL) is hydrogenated for 90 minutes at atmospheric pressure over 10% Pd/C. The mixture is filtered through a pad of diatomaceous earth and concentrated under reduced pressure to give 4-(2-dimethylamino-ethanesulfonyl)-phenylamine as a white solid.

MS (ES$^+$): 229.3 (M+H)$^+$ (4E)-6-bromo-4-(methoxymethylene)isoquinoline-1,3 (2H,4H)-dione (0.17 g, 0.61 mmol) and 4-(2-dimethylamino-ethanesulfonyl)-phenylamine (0.14 g, 0.61 mmol) were stirred in N,N-dimethylformamide (3 mL) and triethylamine (0.16 mL) at 60-70° C. The reaction mixture is quenched by the addition of water. The solid material is then collected, washed with diethyl ether, water, and methanol, and then dried under vacuum to give (4Z)-6-bromo-4-{[(4-{[2-(dimethylamino)ethyl]sulfonyl}-phenyl)amino]methylene}isoquinoline-1,3(2H,4H)-dione (0.11 g, 36%) as a golden powder.

MS (ES$^+$): 478.1, 480.0 (M+H)$^+$

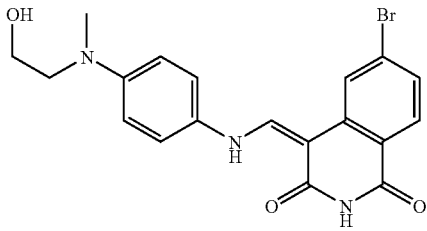

Example 244

(4Z)-6-Bromo-4-[({4-[(2-hydroxyethyl)(methyl)amino]phenyl}amino)methylene]isoquinoline-1,3 (2H,4H)-dione A mixture of 4-fluoronitrobenzene (2.8 g, 20 mmol) and 2-(methylamino)ethanol (8.9 g, 120 mmol) in N-methylpyrrolidinone (80 mL) is heated for 19 hours in a 85° C. oil bath. After cooling to room temperature, the reaction mixture is partitioned between ethyl acetate and water. The organic phase is washed five times with water and with saturated aqueous sodium chloride solution, dried over anhydrous sodium sulfate, and then concentrated under reduced pressure to give 2-(methyl-4-nitroanilino)ethanol (3.1 g, 79%) as a yellow solid.

MS (ES$^+$): 197.2 (M+H)$^+$

A solution of 2-(methyl-4-nitroanilino)ethanol (0.20 g, 1.0 mmol) in ethanol (25 mL) is hydrogenated for two hours at atmospheric pressure over 10% Pd/C. The mixture is filtered through a pad of diatomaceous earth and concentrated under reduced pressure to give 2-[(4-amino-phenyl)-methylamino]-ethanol as a dark oil, which solidified upon standing.

MS (ES$^+$): 167.3 (M+H)$^+$ (4E)-6-bromo-4-(methoxymethylene)isoquinoline-1,3 (2H,4H)-dione (0.17 g, 0.61 mmol) and 2-[(4-amino-phenyl)-methyl-amino]-ethanol (0.10 g, 0.61 mmol) were stirred in N,N-dimethylformamide (3 mL) and triethylamine (0.16 mL) at 60-70° C. The reaction mixture is quenched by the addition of water. The solid material is then collected, washed with diethyl ether, water, and methanol, and then dried under vacuum to give (4Z)-6-bromo-4-[({4-[(2-hydroxyethyl)(methyl)amino]phenyl}amino)methylene]isoquinoline-1,3(2H, 4H)-dione (0.16 g, 64%) as a rust colored powder.

MS (ES$^+$): 416.0, 418.1 (M+H)$^+$

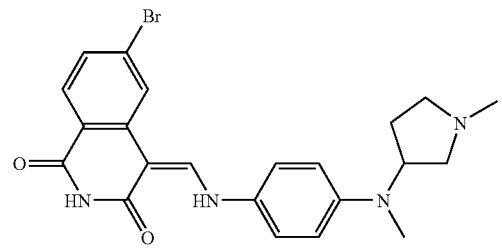

Example 245

(4Z)-6-Bromo-4-[({4-[methyl(1-methylpyrrolidin-3-yl)amino]phenyl}amino)methylene]isoquinoline-1,3 (2H,4H)-dione To a suspension of potassium hydroxide (1.4 g, 25 mmol) and N,N'-dimethyl-3-aminopyrrolidine (1.4 g, 12 mmol) in dimethylsulfoxide (13 mL) is added dropwise 4-fluoronitrobenzene (1.1 mL, 10 mmol). The mixture is heated in a 60-65° C. oil bath for 4 hours. After cooling to room temperature, ice is added to the reaction mixture. The resulting precipitate is collected, washed with water, and dried under vacuum to give methyl-(1-methyl-pyrrolidin-3-yl)-(4-nitrophenyl)-amine.

MS (ES$^+$): 236.3 (M+H)$^+$

A solution of methyl-(1-methyl-pyrrolidin-3-yl)-(4-nitrophenyl)-amine (0.25 g, 1.1 mmol) in ethanol (20 mL) is hydrogenated overnight at atmospheric pressure over 10% Pd/C. The mixture is filtered through a pad of diatomaceous earth and concentrated under reduced pressure to give N-methyl-N-(1-methyl-pyrrolidin-3-yl)-benzene-1,4-diamine as a dark oil (0.21 g, 95%).

MS (ES$^+$): 206.3 (M+H)$^+$ (4E)-6-Bromo-4-(methoxymethylene)isoquinoline-1,3 (2H,4H)-dione (0.17 g, 0.61 mmol) and N-methyl-N-(1-methyl-pyrrolidin-3-yl)-benzene-1,4-diamine (0.12 g, 0.61 mmol) were stirred in N,N-dimethylformamide (3 mL) and triethylamine (0.16 mL) at 60-70° C. The reaction mixture is quenched by the addition of water. The solid material is then collected, washed with diethyl ether, water, and methanol, and then dried under vacuum to give (4Z)-6-bromo-4-[({4-[methyl(1-methylpyrrolidin-3-yl)amino]phenyl}amino)methylene]isoquinoline-1,3(2H,4H)-dione (0.12 g, 44%) as a rust colored powder.

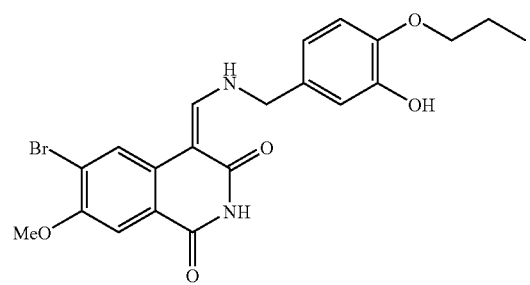

Example 246

6-Bromo-4-[(3-hydroxy-4-propoxy-benzylamino)-methylene]-7-methoxy-4H-isoquinoline-1,3-dione A mixture of 5-Aminomethyl-2-propoxy-phenol hydrochloride (109 mg, 0.50 mmole), 4 mL of N,N-dimethylformamide and triethylamine (75 μL, x mmole) were stirred for 15 minutes. Then (4E)-6-bromo-7-methoxy-4-(methoxymethylene)isoquinoline-1,3(2H,4H)-dione (156 mg, 0.50 mmole) is added and the reaction mixture stirred for one hour. The product is isolated as before, to give an off-white solid, 119 mg, (51%), mp 212-214° C. dec; MS (ESI): m/z 459.1, 461.2 (M−H).

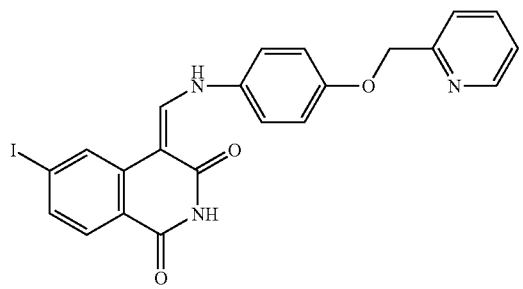

Example 247

(4Z)-6-Iodo-4-({[4-(pyridin-2-ylmethoxy)phenyl]amin 'methylene)isoquinoline1,3(2H,4H)-dione Using the procedure described for the preparation of example 14, 400 mg (77% yield) is obtained as a orange-yellow solid from 300 mg (0.91 mmol) (4E)-6-iodo-4-(methoxymethylene)isoquinoline-1,3(2H,4H)-dione and 183.72 mg (0.91 mmol) of '[4-(pyridin-2-ylmethoxy)phenyl]amine; mp 265-266° C.

MS (ESI) m/z 498.0 (M+1)$^+$

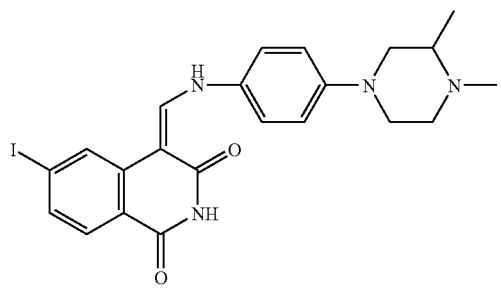

Example 248

(4Z)-4-({[4-(3,4-Dimethylpiperazin-1-yl)phenyl]amino}methylene)-6-iodoisoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, after purified from HPLC, 0.052 g (22.6% yield) of light brown solid is obtained from 0.15 g (0.46 mmol) of (4E)-6-iodo-4-(methoxymethylene)isoquinoline-1,3(2H,4H)-dione and 4-(3,4-Dimethyl-piperazin-1-yl)-phenylamine (0.11 g, 0.50 mmol): mp 157-158° C.; MS (ESI) m/z 503.1 (M+H)$^{+1}$

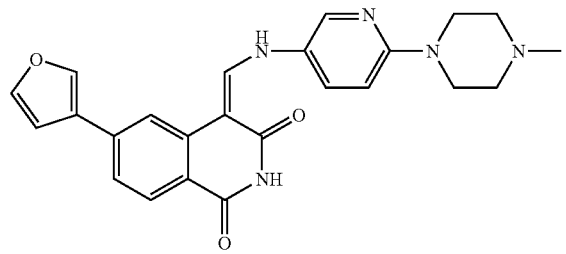

Example 249

(4Z)-6-(3-Furyl)-4-({[6-(4-methylpiperazin-1-yl)pyridin-3-'yl]amino}methylene)isoquinoline-1,3(2H,4H)-dione A mixture of 300 mg (0.68 mmol) of (4Z)-6-bromo-4-({[6-(4-methylpiperazin-1-yl)pyridin-3-'yl]amino}methylene)isoquinoline-1,3(2H,4H)-dione '(4Z)-6-(3-furyl)-4-({[6-(4-methylpiperazin-1-yl)pyridin-3-'yl]amino}methylene)isoquinoline-1,3(2H,4H)-dione, Pd$_2$(dba)$_3$ (125 mg, 0.136 mmol), tri-tert-butylphosphine (0.13 mL, 0.64 mmol), cesium carbonate, (663 mg, 1.36 mmol), and 3-furan boronic acid (189.72 mg, 1.7 mmol) is placed in a three neck flask under N$_2$, N,N-dimethylformamide (8 ML) is added, and the mixture is then stirred in a pre-heated oil bath 130° C. for 30 minutes. After cooling, the mixture is treated with CH$_2$Cl$_2$ and filtered through celite. After evaporating all the solvents, the residue is dissolved in methylene chloride, washed three times with Brine, dried over sodium sulfate and evaporated. The orange oily residue is purified by silica plug chromatography (10:90=methanol:methylene chloride), to give a yellow solid 130 mg (45% yield); mp 200-201° C.

MS (ESI) m/z 430.2 (M+1)$^+$

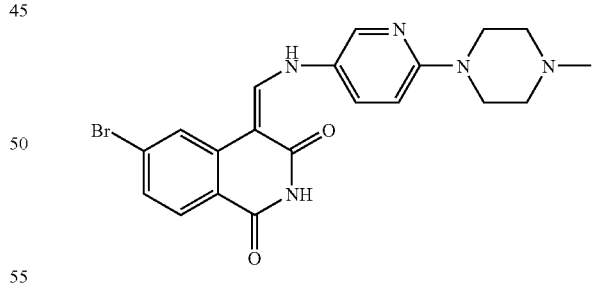

Example 250

(4Z)-6-Bromo-4-({[6-(4-methylpiperazin-1-yl)pyridin-3-'yl]amino}methylene)isoquinoline-1,3(2H,4H)-dione Using the procedure described for the preparation of example 14, 400 mg (66% yield) is obtained as a orange-yellow solid from 384.6 mg (1.36 mmol) (4E)-6-bromo-4-(methoxymethylene)isoquinoline-1,3(2H,4H)-dione and 262 mg (1.36 mmol) of '6-(4-methylpiperazin-1-yl)pyridin-3-amine; mp 265-266° C.
MS (ESI) m/z 444.0 (M+1)+

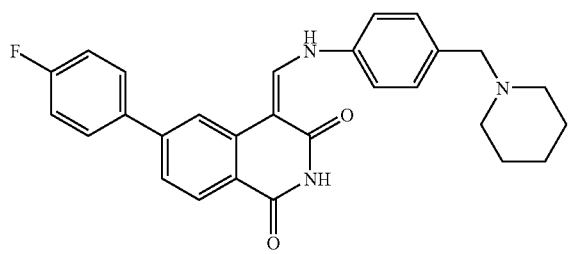

Example 251

(4Z)-6-(4-Fluorophenyl)-4-({[4-(piperidin-1-'ylmethyl)phenyl]amino}methylene)isoquinoline-1,3(2H,4H)-dione Using the procedure described for the preparation of (4Z)-6-(4-fluorophenyl)-4-({[4-(piperidin-1-'ylmethyl)phenyl] amino}methylene)isoquinoline-1,3(2H,4H)-dione, 100 mg of yellow solid (20% yield) is obtained from 500 mg (1.13 mmol) (4Z)-6-bromo-4-({[4-(piperidin-1-ylmethyl)phenyl] amino}methylene)isoquinoline-1,3(2H,4H)-dione and 4-Fluorophenyl boronic acid 395.27 mg, (2.83 mmol).; mp 195-196° C.
MS (ESI) m/z 456.2 (M+1)+.

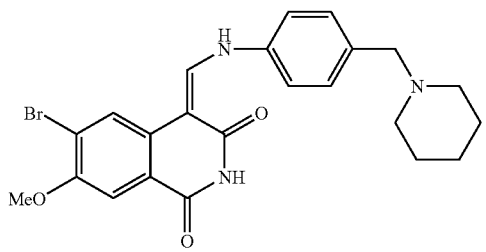

Example 252

6-Bromo-7-methoxy-4-[(4-piperidin-1-ylmethyl-phenylamino)-methylene]-4H-isoquinoline-1,3-dione A mixture of (4E)-6-bromo-7-methoxy-4-(methoxymethylene)isoquinoline-1,3(2H,4H)-dione (156 mg, 0.50 mmole), N,N-dimethylformamide (1 mL) and 4-piperidin-1-ylmethyl-phenylamine (95 mg, 0.50 mmole) is stirred and heated at 110° C. for one hour, cooled in the refrigerator. The reaction mixture is evaporated to dryness, taken up in 5% methanol in chloroform and passed through a short pad of Florisil eluting with 5% methanol in chloroform. The eluate is evaporated in vacuo, treated with acetonitrile, filtered and dried to give a dull yellow solid 134 mg (57%), mp 264-7° C.; MS (ESI): m/z 470.1 (M+H).

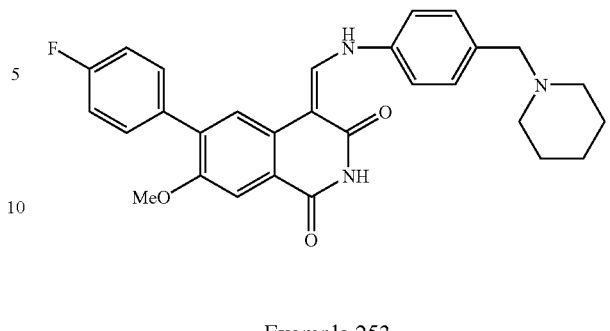

Example 253

6-(4-Fluoro-phenyl)-7-methoxy-4-[(4-piperidin-1-ylmethyl-phenylamino)-methylene]-4H-isoquinoline-1,3-dione A mixture of 6-Bromo-7-methoxy-4-[(4-piperidin-1-ylmethyl-phenylamino)-methylene]-4H-isoquinoline-1,3-dione (272 mg, 0.578 mmole), N,N-dimethylformamide (2 mL), 4-fluorophenylboronic acid (202 mg, 1.44 mmole), tris (dibenzylideneacetone)dipalladium(0)-chloroform adduct (78 mg, 0.075 mmole), tri(t-butyl)phosphine (28 mg, 0.138 mmole) and cesium carbonate (377 mg, 1.16 mmole) is stirred and heated at 110° C. for one hour, cooled in the refrigerator. The reaction mixture is evaporated to dryness, taken up in 5% methanol in chlororform and passed through a short pad of Florisil eluting with 5% methanol in chloroform. The eluate is evaporated in vacuo and treated with acetonitrile, filtered and dried to give a yellow-brown solid 138 mg (48%), mp 227-230° C.; MS (ESI): m/z 486.2 (M+H).

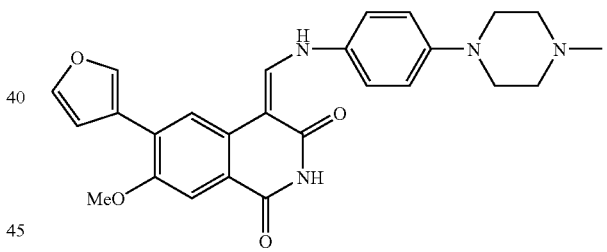

Example 254

6-Furan-3-yl-7-methoxy-4-{[4-(4-methyl-piperazin-1-yl)-phenylamino]-methylene}-4H-isoquinoline-1,3-dione A mixture of 6-Bromo-7-methoxy-4-{[4-(4-methyl-piperazin-1-yl)-phenylamino]-methylene}-4H-isoquinoline-1,3-dione (241 mg, 0.51 mmole), N,N-dimethylformamide (2 mL), furan-3-boronic acid (143 mg, 1.28 mmole), tris(dibenzylideneacetone)dipalladium(0)-chloroform adduct (64 mg, 0.062 mmole), tri(t-butyl)phosphine (25 mg, 0.124 mmole) and cesium carbonate (334 mg, 1.02 mmole) is stirred and heated at 110° C. for one hour, cooled in the refrigerator. The reaction mixture is evaporated to dryness, taken up in 5% methanol in chlororform and passed through a short pad of Florisil eluting with 5% methanol in chloroform. The eluate is evaporated in vacuo and treated with acetonitrile, filtered and dried to give a brown solid 161 mg (68%), mp 198-220° C.; MS (ESI): m/z 459.2, 461.2 (M+H).

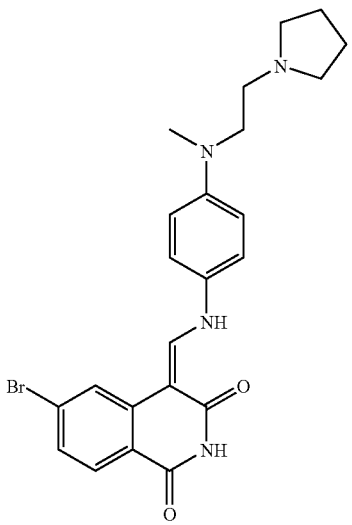

Example 255

(4Z)-6-Bromo-4-[({4-[methyl(2-pyrrolidin-1-yl-ethyl)amino]phenyl}amino)methylene]isoquinoline-1,3(2H,4H)-dione To a solution of 2-(methyl-4-nitroanilino)ethanol (2.9 g, 15 mmol) in pyridine (75 mL) is added p-toluenesulfonyl chloride (3.1 g, 1.6 mmol) and 4-(dimethylamino)pyridine (1.8 g, 15 mmol). After stirring for three days at room temperature, the reaction is quenched by the addition of saturated aqueous sodium chloride solution and then extracted 3× with ethyl acetate. The combined extracts were dried over anhydrous magnesium sulfate and concentrated under reduced pressure to give a viscous brown oil, which is purified by reverse phase high performance liquid chromatography to give toluene-4-sulfonic acid 2-[methyl-(4-nitro-phenyl)-amino]-ethyl ester as a trifluoroacetic acid salt (0.52 g, 9.8%).

LC/MS (ES+): 351.0 (M+H)+

To a solution of toluene-4-sulfonic acid 2-[methyl-(4-nitro-phenyl)-amino]-ethyl ester TFA salt (74 mg, 0.21 mmol) in toluene (1 mL) is added triethylamine (50 μL) and pyrrolidine (53 μL, 0.63 mmol). The mixture is shaken in 70° C. block shaker overnight. The reaction mixture is concentrated and purified by reverse phase high performance liquid chromatography to give methyl-(4-nitro-phenyl)-(2-pyrrolidin-1-yl-ethyl)-amine as a di-TFA salt (85 mg).

A solution of methyl-(4-nitro-phenyl)-(2-pyrrolidin-1-yl-ethyl)-amine•2 TFA (85 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-(2-pyrrolidin-1-yl-ethyl)-benzene-1,4-diamine as a di-TFA salt.

(4E)-6-bromo-4-(methoxymethylene)isoquinoline-1,3 (2H,4H)-dione (59 mg, 0.21 mmol) and N-methyl-N-(2-pyrrolidin-1-yl-ethyl)-benzene-1,4-diamine•2 TFA (0.21 mmol maximum) were stirred in N,N-dimethylformamide (1 mL) and triethylamine (50 μL) at 60-70° C. for 12 hours. The reaction mixture is purified by reverse phase high performance liquid chromatography to give (4Z)-6-bromo-4-[({4-- [methyl(2-pyrrolidin-1-ylethyl)amino]phenyl}amino)methylene]isoquinoline-1,3(2H,4H)-dione.

MS (ES+): 469.2, 471.2 (M+H)+

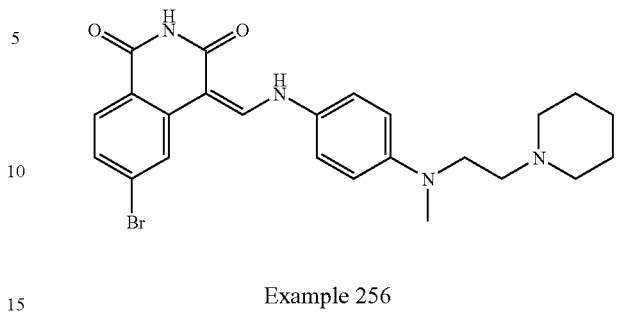

Example 256

(4Z)-6-Bromo-4-[({4-[methyl(2-piperidin-1-ylethyl)amino]phenyl}amino)methylene]isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 μL) and piperidine (62 μL, 0.63 mmol). The mixture is shaken in 70° C. block shaker overnight. The reaction mixture is concentrated and purified by reverse phase high performance liquid chromatography to give methyl-(4-nitro-phenyl)-(2-piperidin-1-yl-ethyl)-amine as a di-TFA salt (74 mg).

MS (ES+): 264.3 (M+H)+

A solution of methyl-(4-nitro-phenyl)-(2-piperidin-1-yl-ethyl)-amine•2 TFA (74 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-(2-piperidin-1-yl-ethyl)-benzene-1,4-diamine as a di-TFA salt.

(4E)-6-bromo-4-(methoxymethylene)isoquinoline-1,3 (2H,4H)-dione (59 mg, 0.21 mmol) and N-methyl-N-(2-piperidin-1-yl-ethyl)-benzene-1,4-diamine•2 TFA (0.21 mmol maximum) were stirred in N,N-dimethylformamide (1 mL) and triethylamine (50 μL) at 60-70° C. for 12 hours. The reaction mixture is purified by reverse phase high performance liquid chromatography to give (4Z)-6-bromo-4-[({4-[methyl(2-piperidin-1-ylethyl)amino]phenyl}amino)methylene]isoquinoline-1,3(2H,4H)-dione.

MS (ES+): 483.2 (M+H)+

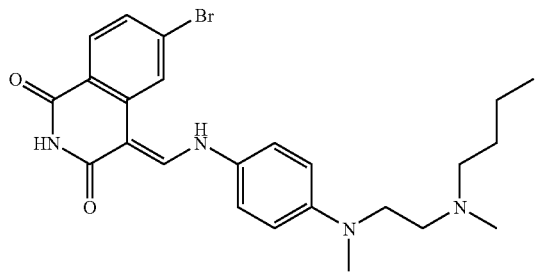

Example 257

(4Z)-6-Bromo-4-[({4-[{2-[butyl(methyl)amino]ethyl}(methyl)amino]phenyl}amino)methylene]isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 μL) and N-methylbutylamine (75 μL, 0.63 mmol). The mixture is shaken in 70° C. block shaker overnight. The reaction mixture is concentrated and purified by reverse phase high performance liquid chromatography to give N-butyl-N,N'-dimethyl-N'-(4-nitro-phenyl)-ethane-1,2-diamine as a di-TFA salt (71 mg, 68%).

A solution of N-butyl-N,N'-dimethyl-N'-(4-nitro-phenyl)-ethane-1,2-diamine•2 TFA (71 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-[2-(butyl-methyl-amino)-ethyl]-N-methyl-benzene-1,4-diamine as a di-TFA salt.

(4E)-6-bromo-4-(methoxymethylene)isoquinoline-1,3 (2H,4H)-dione (59 mg, 0.21 mmol) and N-[2-(butyl-methyl-amino)-ethyl]-N-methyl-benzene-1,4-diamine•2 TFA (0.21 mmol maximum) were stirred in N,N-dimethylformamide (1 mL) and triethylamine (50 μL) at 60-70° C. for 12 hours. The reaction mixture is purified by reverse phase high performance liquid chromatography to give (4Z)-6-bromo-4-[({4-[{2-[butyl(methyl)amino]ethyl}(methyl)amino]phenyl}amino)methylene]isoquinoline-1,3(2H,4H)-dione.

MS (ES$^+$): 487.3 (M+H)$^+$

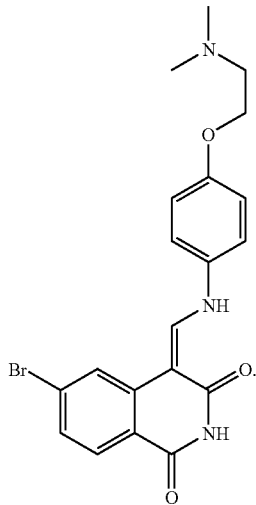

Example 258

(4Z)-6-Bromo-4-[({4-[2-(dimethylamino)ethoxy]phenyl}amino)methylene]isoquinoline-1,3(2H,4H)-dione Dimethyl-[2-(4-nitro-phenoxy)-ethyl]-amine is prepared according to Hunter, D. H.; Ponce, Y. Z.; Brown, G. W.; Chamberlain, M. J.; Driedger, A. A.; Morrissey, G. Can J. Chem. 62, 2015-2019, 1984.

MS (ES$^+$): 211.3 (M+H)$^+$

A solution of dimethyl-[2-(4-nitro-phenoxy)-ethyl]-amine hydrochloride (0.29 g, 1.2 mmol) in ethanol (20 mL) is hydrogenated at atmospheric pressure over 10% palladium on carbon. The reaction mixture is filtered through a pad of diatomaceous earth and concentrated to give 4-(2-dimethylamino-ethoxy)-phenylamine hydrochloride (0.24 g, 96%).

MS (ES$^+$): 181.3 (M+H)$^+$ (4E)-6-bromo-4-(methoxymethylene)isoquinoline-1,3 (2H,4H)-dione (70 mg, 0.25 mmol) and 4-(2-dimethylamino-ethoxy)-phenylamine hydrochloride (50 mg, 0.23 mmol) were stirred in N,N-dimethylformamide (1 mL) and triethylamine (50 μL) at 70° C. The reaction mixture is quenched by the addition of water. The solid material is then collected, washed with diethyl ether, water, and methanol, and then dried under vacuum to give (4Z)-6-bromo-4-[({4-[2-(dimethylamino)ethoxy]phenyl}amino)methylene]isoquinoline-1,3(2H,4H)-dione (81 mg, 82%).

MS (ES$^+$): 430.0, 432.0 (M+H)$^+$

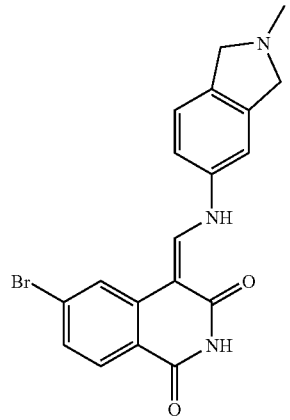

Example 259

(4Z)-6-Bromo-4-{[(2-methyl-2,3-dihydro-1H-isoindol-5-yl)amino]methylene}isoquinoline-1,3(2H,4H)-dione The methylation of 4-nitrophthalimide to give 2-methyl-5-nitro-isoindole-1,3-dione (0.93 g, 43%) is accomplished via the procedure of Billman, J. H. and Cash, V. J Am Chem Soc. 75(10), 1953, 2499-2501.

A solution of give 2-methyl-5-nitro-isoindole-1,3-dione (1.1 g, 5.3 mmol) in ethanol/tetrahydrofuran (1:1, 50 mL) is hydrogenated at 45 psi over Raney nickel catalyst. The reaction mixture is filtered through a pad of diatomaceous earth and concentrated to give 5-amino-2-methyl-isoindole-1,3-dione as a yellow cottony solid (0.85 g, 91%).

$^1$H NMR (300 MHz, DMSO-d$_6$) ppm 2.94 (s, 3H), 6.44 (s, 2H), 6.77 (dd, J=8.2 Hz, 1H), 6.91 (d, J=2.0 Hz, 1H), 7.47 (d, J=8.2 Hz, 1H).

To a suspension of lithium aluminum hydride (0.55 g, 14 mmol) in tetrahydrofuran (7 mL) is added solid 5-amino-2-methyl-isoindole-1,3-dione (0.85 g, 4.8 mmol). The resulting suspension is heated at reflux for 15 minutes and is then cooled to 0° C. At this temperature, the reaction is quenched by the addition of ethanol and then water. The resulting slurry is filtered through a pad of diatomaceous earth, and the filtrate is concentrated under reduced pressure to give a brown solid. The crude solid is dissolved in absolute ethanol and acidified with concentrated ethanolic hydrochloric acid. With the addition of diethyl ether, a brown solid precipitated and is collected by filtration to give 2-methyl-2,3-dihydro-1H-isoindol-5-ylamine as a dihydrochloride salt (0.61 g, 55%).

MS (ES$^+$): 149.3 (M+H)$^+$ (4E)-6-bromo-4-(methoxymethylene)isoquinoline-1,3 (2H,4H)-dione (0.20 g, 0.71 mmol) and 2-methyl-2,3-dihydro-1H-isoindol-5-ylamine•2HCl (0.52 mg, 2.3 mmol) were stirred in N,N-dimethylformamide (5 mL) and triethylamine (0.83 mL) at 70° C. The reaction mixture is quenched by the addition of water. The solid material is then collected, washed with diethyl ether, water, and methanol, and then dried under vacuum to give a crude solid, which is then purified by reverse phase high performance liquid chromatography to provide (4Z)-6-bromo-4-{[(2-methyl-2,3-dihydro-1H-isoindol-5-yl)amino]methylene}isoquinoline-1,3(2H,4H)-dione•trifluoroacetic acid (80 mg, 22%).

MS (ES⁻): 396.1, 398.2 (M–H)⁻

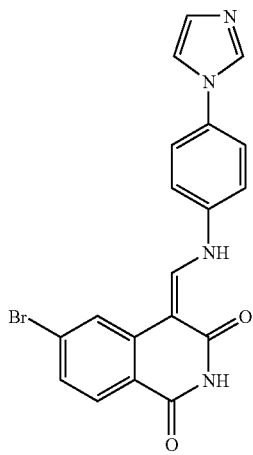

Example 260

(4Z)-6-Bromo-4-({[4-(1H-imidazol-1-yl)phenyl]amino}methylene)isoquinoline-1,3(2H,4H)-dione In a 20 mL vial were combined 4-fluoronitrobenzene (1.1 mL, 10 mmol), imidazole (0.68 g, 10 mmol), and sodium carbonate (1.1 g, 11 mmol) in N,N-dimethylformamide (5 mL). The mixture is shaken at 100° C. for 24 hours and then allowed to cool to room temperature and then diluted with water. Concentrated hydrochloric acid is added to bring the pH to 1, and then the mixture is extracted thrice with chloroform (10 mL). The acidic aqueous phase is then treated with 2.5 M sodium hydroxide solution to give a pH of 10. A light yellow solid is collected and washed with water to give 1-(4-nitrophenyl)-1H-imidazole.

MS (ES⁺): 190.2 (M+H)⁺

A solution of 1-(4-nitrophenyl)-1H-imidazole (0.38 g, 2.0 mmol) in ethanol (20 mL), water (3 mL), and concentrated hydrochloric acid (5 drops) is hydrogenated for overnight at atmospheric pressure over 10% Pd/C. The mixture is filtered through a pad of diatomaceous earth and concentrated under reduced pressure to give 4-(1H-imidazol-1-yl)-benzenamine trihydrochloride as a gray powder.

MS (ES⁺): 160.2 (M+H)⁺

(4E)-6-bromo-4-(methoxymethylene)isoquinoline-1,3(2H,4H)-dione (70 mg, 0.25 mmol) and 4-(1H-imidazol-1-yl)-benzenamine•3HCl (70 mg, 0.25 mmol) were stirred in N,N-dimethylformamide (1.5 mL) and triethylamine (0.15 mL) at 75° C.

The reaction mixture is quenched by the addition of water. The solid material is then collected, washed with diethyl ether, water, and methanol, and then dried under vacuum to give (4Z)-6-bromo-4-({[4-(1H-imidazol-1-yl)phenyl]amino}methylene)isoquinoline-1,3(2H,4H)-dione (95 mg, 93%)

MS (ES⁺): 409.0, 411.0 (M+H)⁺

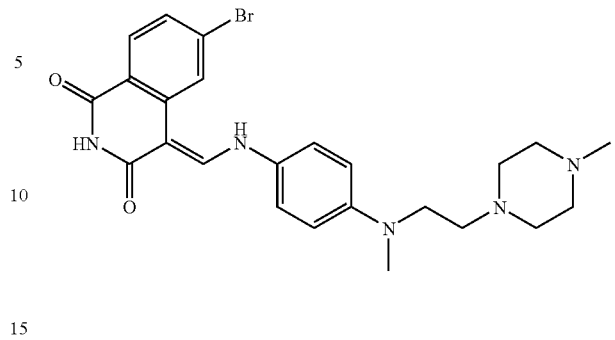

Example 261

(4Z)-6-Bromo-4-{[(4-{methyl[2-(4-methylpiperazin-1-yl)ethyl]amino}phenyl)amino]methylene}isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 µL) and N-methylpiperazine (70 µL, 0.63 mmol). The mixture is shaken in 70° C. block shaker overnight. The reaction mixture is concentrated and purified by reverse phase high performance liquid chromatography to give methyl-[2-(4-methyl-piperazin-1-yl)-ethyl]-(4-nitro-phenyl)-amine as a tri-TFA salt (98 mg, 98%).

A solution of methyl-[2-(4-methyl-piperazin-1-yl)-ethyl]-(4-nitro-phenyl)-amine•3 TFA (98 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-[2-(4-methyl-piperazin-1-yl)-ethyl]-benzene-1,4-diamine as a tri-TFA salt.

(4E)-6-bromo-4-(methoxymethylene)isoquinoline-1,3(2H,4H)-dione (59 mg, 0.21 mmol) and N-Methyl-N-[2-(4-methyl-piperazin-1-yl)-ethyl]-benzene-1,4-diamine•3 TFA (0.21 mmol maximum) were stirred in N,N-dimethylformamide (1 mL) and triethylamine (50 µL) at 60-70° C. for 12 hours. The reaction mixture is purified by reverse phase high performance liquid chromatography to give (4Z)-6-bromo-4-{[(4-{methyl[2-(4-methylpiperazin-1-yl)ethyl]amino}phenyl)amino]methylene}isoquinoline-1,3(2H,4H)-dione as a tri-TFA salt.

MS (ES⁺): 500.2 (M+H)⁺

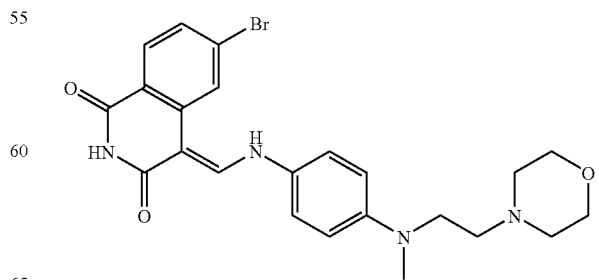

Example 262

(4Z)-6-Bromo-4-[({4-[methyl(2-morpholin-4-yl-ethyl)amino]phenyl}amino)methylene]isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 µL) and morpholine (55 µL, 0.63 mmol). The mixture is shaken in 70° C. block shaker overnight. The reaction mixture is concentrated and purified by reverse phase high performance liquid chromatography to give methyl-(2-morpholin-4-yl-ethyl)-(4-nitro-phenyl)-amine as a di-TFA salt (80 mg, 77%).

MS (ES+): 266.3 (M+H)+

A solution of methyl-(2-morpholin-4-yl-ethyl)-(4-nitrophenyl)-amine•2 TFA (80 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-(2-morpholin-4-yl-ethyl)-benzene-1,4-diamine as a di-TFA salt.

(4E)-6-bromo-4-(methoxymethylene)isoquinoline-1,3 (2H,4H)-dione (59 mg, 0.21 mmol) and N-Methyl-N-(2-morpholin-4-yl-ethyl)-benzene-1,4-diamine•2 TFA (0.21 mmol maximum) were stirred in N,N-dimethylformamide (1 mL) and triethylamine (50 µL) at 60-70° C. for 12 hours. The reaction mixture is purified by reverse phase high performance liquid chromatography to give (4Z)-6-bromo-4-[({4-[methyl(2-morpholin-4-ylethyl)amino]phenyl}amino)methylene]isoquinoline-1,3(2H,4H)-dione.

MS (ES+): 587.2 (M+H)+

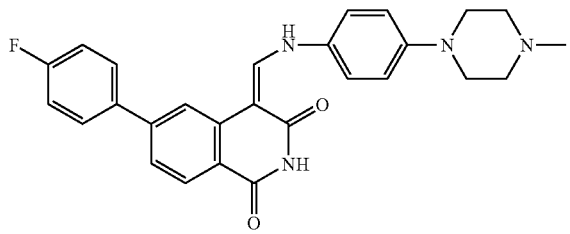

Example 263

(4Z)-6-(4-Fluorophenyl)-4-({[4-(4-methylpiperazin-1-yl)phenyl]amino}methylene)-isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, after purified by column chromatography over silica gel using 5% MeOH/CHCl₃ as eluent, 0.098 mg (47.3% yield) of yellow solid is obtained from 0.20 g (0.45 mmol) of (4Z)-6-bromo-4-({[4-(4-methylpiperazin-1-yl)phenyl] amino}methylene)isoquinoline-1,3(2H,4H)-dione, 0.095 g (0.68 mmol) of 4-fluorophenylboronic acid, 0.041 g (0.05 mmol) of tris(dibenzyldeneaacetone)-dipalladium(0), 0.46 g (0.10 mmol) of 2-(di-t-butyl-phosphino)-biphenyl, and 0.48 g (0.90 mmol) of sodium carbonate: mp 228-229° C.; MS (ESI) m/z 455.2 (M+H)⁻¹

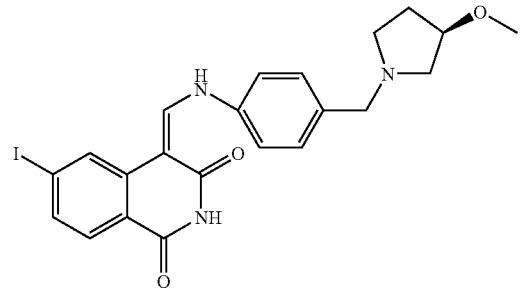

Example 264

(4Z)-6-Iodo-4-{[(4-{[(3R)-3-methoxypyrrolidin-1-yl]methyl}phenyl)amino]methylene}isoquinoline-1,3(2H,4H)-dione Using the procedure described for the preparation of example 14, 300 mg (84% yield) is obtained as a yellow solid from 300 mg (1.1 mmol) (4E)-6-iodo-4-(methoxymethylene) isoquinoline-1,3(2H,4H)-dione and 190.57 mg (1.1 mmol) of 4-{[(3R)-3-methoxypyrrolidin-1-yl]methyl}phenyl)amine, mp 160-161° C.

MS (ESI) m/z 504.0 (M+1)+

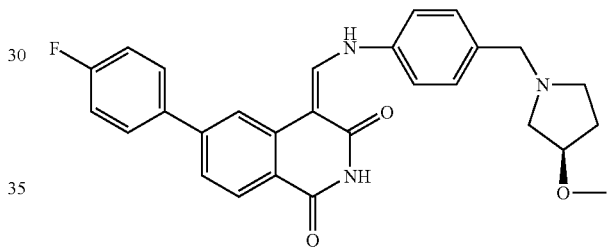

Example 265

(4Z)-6-(4-Fluorophenyl)-4-{[(4-{[(3S)-3-methoxy-pyrrolidin-1-yl]methyl}phenyl)amino] methylene}isoquinoline-1,3(2H,4H)-dione Using the procedure described for the preparation of'(4Z)-6-(4-fluorophenyl)-4-({[4-(piperidin-1-'ylmethyl)phenyl]amino}methylene)isoquinoline-1,3(2H,4H)-dione, 100 mg of yellow solid (21% yield) is obtained from 461 mg (1.01 mmol) (4Z)-6-bromo-4-({[4-(piperidin-1-ylmethyl)phenyl] amino}methylene)isoquinoline-1,3(2H,4H)-dione and 4-Fluorophenyl boronic acid 353.38 mg, (2.53 mmol).; mp 145-146° C.

MS (ESI) m/z 472.2 (M+1)+.

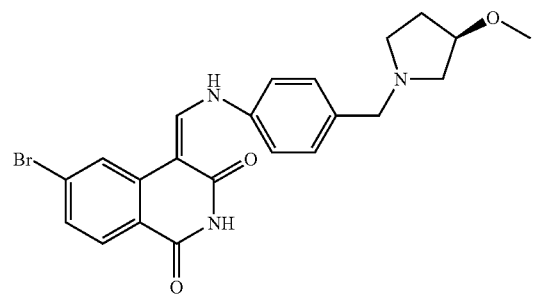

Example 266

(4Z)-6-Bromo-4-{[(4-{[(3R)-3-methoxypyrrolidin-1-yl]methyl}phenyl)amino]methylene}isoquinoline-1,3(2H,4H)-dione Using the procedure described for the preparation of example 14, 800 mg (71% yield) is obtained as a yellow solid from 700 mg (2.48 mmol) (4E)-6-bromo-4-(methoxymethylene)isoquinoline-1,3(2H,4H)-dione and 514 mg (2.48 mmol) of 4-{[(3R)-3-methoxypyrrolidin-1-yl]methyl}phenyl)amine, mp 132-133° C.
MS (ESI) m/z 458.1 (M+1)+

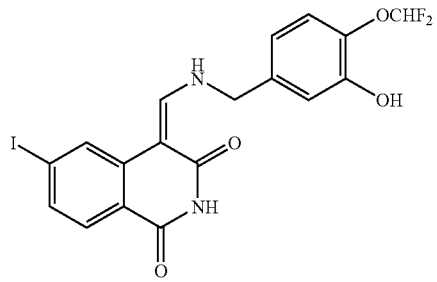

Example 267

(4Z)-6-Iodo-4-{[(4-difluoromethoxy-3-hydroxybenzyl)amino)methylene}isoquinoline-1,3(2H,4-dione An amount of 4-difluoromethoxy-3-hydroxy benzylamine hydrochloride (113 mg, 0.50 mmol), is dissolved in N,N-dimethylformamide (5 mL), triethylamine (50 µL 0.75 mmol) is added followed by (4E)-6-iodo-4-(methoxymethylene)isoquinoline-1,3(2H,4H)-dione (165 mg, 0.50 mmol). After the mixture is stirred at room temperature for 30 min, the solvent is removed in-vacuo and the residue dissolved in 7.5% methanol in chloroform and passed thru a short pad of Florisil eluting with 7.5% methanol in chloroform, the eluate is evaporated and the solid triturated with ether, filtered and washed several times with anhydrous ether to give 193 mg of (4Z)-6-Iodo-4-{[(4-difluoromethoxy-3-hydroxybenzyl)amino)methylene}isoquinoline-1,3(2H,4-dione as a beige solid (79% yield); mp 254-5° C., MS data ES(−) 485.0 m/e.

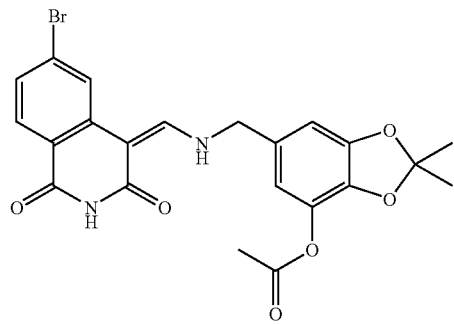

Example 268

6-({[(Z)-(6-Bromo-1,3-dioxo-2,3-dihydroisoquinolin-4(1H)-ylidene)methyl]amino}methyl)-2,2-dimethyl-1,3-benzodioxol-4-yl acetate To a solution of (4Z)-6-bromo-4-({[(7-hydroxy-2,2-dimethyl-1,3-benzodioxol-5-yl)methyl]amino}methylene)isoquinoline-1,3(2H,4H)-dione (30 mg, 67 µmol) in N,N-dimethylformamide (0.5 mL) is added pyridine (12 µL, 0.17 mmol) and acetyl chloride (10 µL). The reaction mixture is shaken overnight at room temperature and then purified by reverse-phase high performance liquid chromatography to give 6-({[(Z)-(6-bromo-1,3-dioxo-2,3-dihydroisoquinolin-4(1H)-ylidene)methyl]amino}methyl)-2,2-dimethyl-1,3-benzodioxol-4-yl acetate.

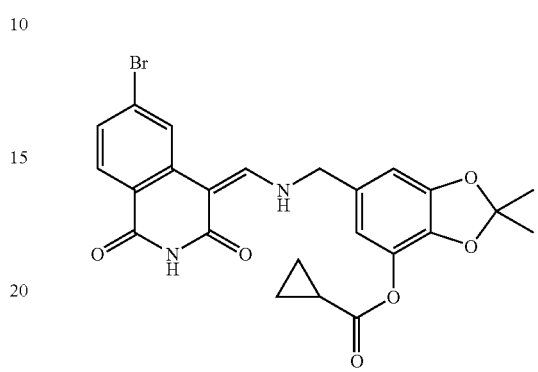

Example 269

6-({[(Z)-(6-Bromo-1,3-dioxo-2,3-dihydroisoquinolin-4(1H)-ylidene)methyl]amino}methyl)-2,2-dimethyl-1,3-benzodioxol-4-yl cyclopropanecarboxylate To a solution of (4Z)-6-bromo-4-({[(7-hydroxy-2,2-dimethyl-1,3-benzodioxol-5-yl)methyl]amino}methylene)isoquinoline-1,3(2H,4H)-dione (30 mg, 67 µmol) in N,N-dimethylformamide (0.5 mL) is added pyridine (12 µL, 0.17 mmol) and cyclopropanecarbonyl chloride (10 µL). The reaction mixture is shaken overnight at room temperature and then purified by reverse-phase high performance liquid chromatography to give 6-({[(Z)-(6-bromo-1,3-dioxo-2,3-dihydroisoquinolin-4(1H)-ylidene)methyl]amino}methyl)-2,2-dimethyl-1,3-benzodioxol-4-yl cyclopropanecarboxylate.

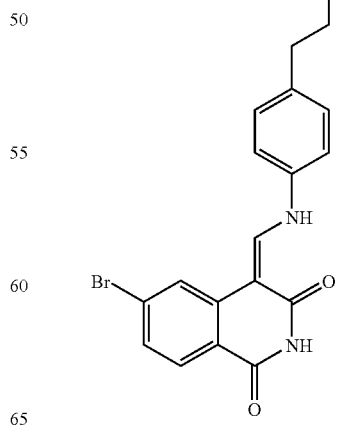

Example 270

(4Z)-6-Bromo-4-[({4-[3-(dimethylamino)propyl]phenyl}amino)methylene]isoquinoline-1,3(2H,4H)-dione N-[4-(3-Oxo-propyl)-phenyl]-acetamide is prepared according to Björnestedt, R.; Zhong, G.; Lerner, R. A.; Barbas, C. F. J Am Chem Soc. 118, 1996, 11720-11724.

To a suspension of N-[4-(3-Oxo-propyl)-phenyl]-acetamide (96 mg, 0.50 mmol), dimethylamine hydrochloride (82 mg, 1.0 mmol), and sodium acetate (66 mg, 0.80 mmol) in methanol (0.5 mL) is added sodium cyanoborohydride (47 mg, 0.75 mmol). Upon completion of the reaction, the solvent is evaporated under reduced pressure and the residue is partitioned between ethyl acetate and water. The aqueous phase is extracted with ethyl acetate. The combined extracts were concentrated to give N-[4-(3-dimethylamino-propyl)-phenyl]-acetamide (0.14 g, >100%).

MS (ES$^+$): 221.3 (M+H)$^+$

To a solution of N-[4-(3-dimethylamino-propyl)-phenyl]-acetamide (0.50 mmol maximum) in methanol (8 mL) is added 20% aqueous hydrochloric acid solution. After 3½ hours of shaking at 56° C., an additional 2 drops of concentrated hydrochloric acid is added and shaking is continued for 3 days. The mixture is concentrated to give 4-(3-dimethylamino-propyl)-phenylamine hydrochloride, which is used without further purification in the following step.

MS (ES$^+$): 179.3 (M+H)$^+$ (4E)-6-Bromo-4-(methoxymethylene)isoquinoline-1,3 (2H,4H)-dione (50 mg, 0.18 mmol) 4-(3-dimethylamino-propyl)-phenylamine hydrochloride (0.40 mmol) were stirred in N,N-dimethylformamide (1 mL) and triethylamine (140 µL) at 78° C. The reaction mixture is quenched by the addition of water. The solid material is then collected, washed with water, and then dried under vacuum to give (4Z)-6-bromo-4-[({4-[3-(dimethylamino)propyl]phenyl}amino)methylene]isoquinoline-1,3(2H,4H)-dione (58 mg, 75%) as a golden solid.

MS (ES$^+$): 428, 430 (M+H)$^+$

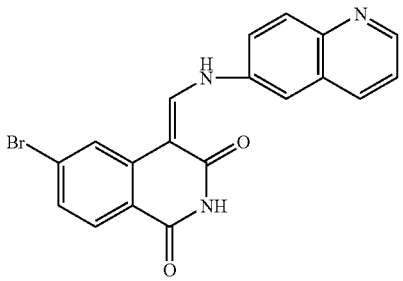

Example 271

(4Z)-6-Bromo-4-[(quinolin-6-ylamino)methylene]isoquinoline-1,3(2H,4H)-dione

A mixture of 6-bromo-4-methoxymethylene-4H-isoquinoline-1,3-dione (141 mg, 0.5 mmol), 6-aminoquinoline (72.2 mg, 0.5 mmol) in 1 mL of N,N-dimethylformamide is heated at 110° C. for 0.5 h. After cooling in the refrigerator, the precipitate is collected, and washed with N,N-dimethylformamide (DMF) and ether to give 169 mg (85%) of yellow solid. MS (ESI) m/z 394.0, 396.0 (M+H)$^{+1}$

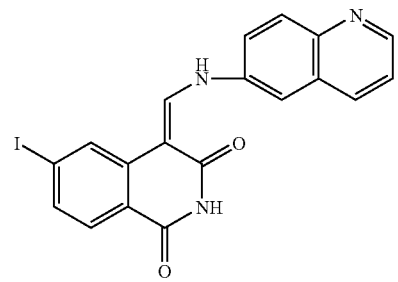

Example 272

(4Z)-6-Iodo-4-[(quinolin-6-ylamino)methylene]isoquinoline-1,3(2H,4H)-dione

A mixture of 6-iodo-4-methoxymethylene-4H-isoquinoline-1,3-dione (164.5 mg, 0.5 mmol), 6-aminoquinoline (72.2 mg, 0.5 mmol) in 1 mL of N,N-dimethylformamide is heated at 110° C. for 0.5 h. After cooling in the refrigerator, the precipitate is collected, and washed with N,N-dimethylformamide (DMF) and ether to give 189 mg (85%) of yellow solid. MS (ESI) m/z 442.0 (M+H)$^{+1}$

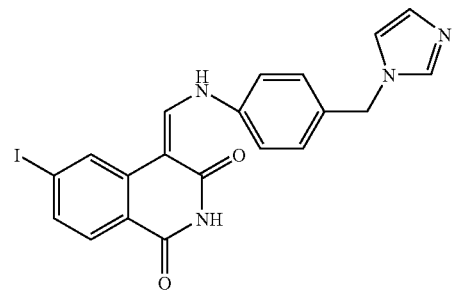

Example 273

(4Z)-4-({[4-(1H-Imidazol-1-ylmethyl)phenyl]amino}methylene)-6-iodoisoquinoline-1,3(2H,4H)-dione Using the procedure described for the preparation of example 14, 350 mg (70% yield) is obtained as a brown solid from 300 mg (0.92 mmol) (4E)-6-iodo-4-(methoxymethylene)isoquinoline-1,3(2H,4H)-dione and 160 mg (0.92 mmol) of 4-(1H-imidazol-1-ylmethyl)aniline, mp 275-276° C.

MS (ESI) m/z 471.0 (M+1)$^+$

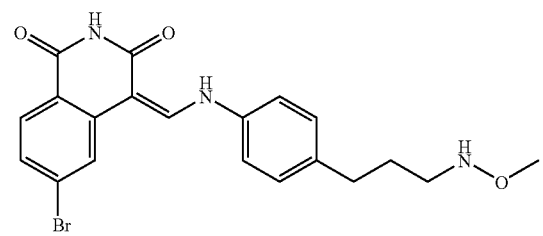

Example 274

(4Z)-6-Bromo-4-[({4-[3-(methoxyamino)propyl]phenyl}amino)methylene]isoquinoline-1,3(2H,4H)-dione 3-(4'-Acetamidophenyl)propanal is prepared according to Bjornestedt, R.; Zhong, G.; Lerner, R. A.; Barbas, C. F. JACS (1996), 118(47), 11720-11724.

LC/MS (ES+): 192.7 (M+H)+

A mixture of 3-(4-acetamidophenyl)propanal (96 mg, 0.50 mmol), methoxy]amine hydrochloride (92 mg, 1.1 mmol), and pyridine (110 µL) in methanol (0.7 mL) is heated in a 70° C. oil bath for 18 hours and then allowed to cool to room temperature. Methanol (1 mL) is added and the mixture is cooled to 0° C. in an ice-water bath. Borane.pyridine complex (0.11 mL, 1.1 mmol) is added, followed by the dropwise addition of 10% aqueous hydrochloric acid. The mixture is allowed to warm to room temperature and then concentrated under reduced pressure. The residue is purified by reverse-phase HPLC to give N-[4-(3-methoxyamino-propyl)-phenyl]-acetamide.

MS (ES+): 223.3 (M+H)+

A mixture of N-[4-(3-methoxyamino-propyl)-phenyl]-acetamide (0.50 mmol) and 20% aqueous hydrochloric acid (2 mL) in methanol (8 mL) is heated for 18 hours at 60° C. and then concentrated under reduced pressure to give N-[3-(4-amino-phenyl)-propyl]-O-methyl-hydroxylamine dihydrochloride (62 mg, 0.24 mmol) and is used in the following step without further purification.

MS (ES+): 181.3 (M+H)+

(4E)-6-Bromo-4-(methoxymethylene)isoquinoline-1,3(2H,4H)-dione (69 mg, 0.24 mmol) and N-[3-(4-amino-phenyl)-propyl]-O-methyl-hydroxylamine dihydrochloride (62 mg, 0.24 mmol) were coupled in N,N-dimethylformamide (1.4 mL) with triethylamine (0.15 mL). The mixture is heated at 75° C. for one hour and then cooled to 0° C. in an ice-water bath. Water is added and resulting solid is collected and then purified by reverse-phase HPLC to give (4Z)-6-bromo-4-[({4-[3-(methoxyamino)propyl]phenyl}amino)methylene]isoquinoline-1,3(2H,4H)-dione as its trifluoroacetate salt (30 mg, 23%).

LC/MS (ES−): 428.4, 430.4 (M−H)−

Example 275

(4Z)-6-Bromo-4-[({4-[[3-(dimethylamino)propyl](methyl)amino]phenyl}amino)methylene]isoquinoline-1,3(2H,4H)-dione To a suspension of potassium hydroxide (1.4 g, 25 mmol) in dimethylsulfoxide (13 mL) is added N,N,N'-trimethyl-1,3-propanediamine (1.8 mL, 12 mmol). While stirring vigorously and while heating to 65° C., 4-fluoronitrobenzene (1.1 mL, 10 mmol) is added dropwise. After stirring at this temperature for 6 hours, the mixture is allowed to cool to room temperature. Water is added and the mixture is acidified to pH 1 with concentrated hydrochloric acid and then extracted 3× with chloroform (3×30 mL). The acidic phase is then basified to pH 11 with 2.5 M sodium hydroxide solution. The basic phase is extracted thrice with chloroform (3×30 mL), dried over anhydrous sodium sulfate, and concentrated under reduced pressure to give an orange-red oil, which is purified by reverse phase high performance liquid chromatography to give N,N,N'-trimethyl-N'-(4-nitrophenyl)propane-1,3-diamine as its ditrifluoroacetate salt.

MS (ES+): 238.1 (M+H)+

A solution of give N,N,N'-trimethyl-N'-(4-nitrophenyl)propane-1,3-diamine•2 TFA (0.57 g, 1.2 mmol) in ethanol/tetrahydrofuran (1:1, 20 mL) is hydrogenated at atmospheric pressure over 10% palladium on carbon. The reaction mixture is filtered through a pad of diatomaceous earth and concentrated to give N-(3-dimethylamino-propyl)-N-methyl-benzene-1,4-diamine•2 TFA as a dark oil.

MS (ES+): 208.4 (M+H)+

(4E)-6-Bromo-4-(methoxymethylene)isoquinoline-1,3(2H,4H)-dione (52 mg, 0.18 mmol) and N-(3-dimethylamino-propyl)-N-methyl-benzene-1,4-diamine•2 TFA (80 mg, 0.18 mmol) were stirred in N,N-dimethylformamide (1 mL) and triethylamine (100 µL) at 75° C. The reaction mixture is quenched by the addition of water. The solid material is then collected, washed with diethyl ether, water, and methanol, and then dried under vacuum to give (4Z)-6-bromo-4-[({4-[[3-(dimethylamino)propyl](methyl)amino]phenyl}amino)methylene]isoquinoline-1,3(2H,4H)-dione.2 TFA (43 mg, 35%).

MS (ES+): 457.1, 459.1 (M+H)+

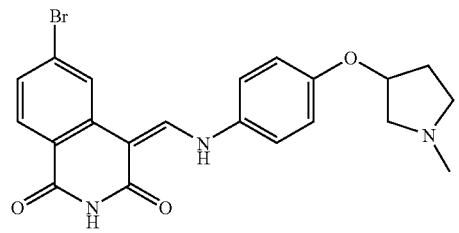

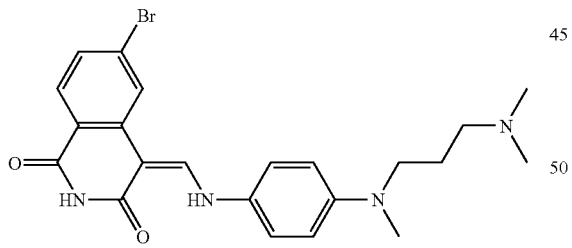

Example 276

(4Z)-6-Bromo-4-[({4-[(1-methylpyrrolidin-3-yl)oxy]phenyl}amino)methylene]isoquinoline-1,3(2H,4H)-dione To a suspension of sodium hydride (60% dispersion in mineral oil, 0.65 g, 16 mmol) in tetrahydrofuran (50 mL) is added 1-methyl-3-pyrrolidinol (0.50 g, 4.9 mmol) as a solution in tetrahydrofuran (100 mL). After 2½ hours of stirring at room temperature, a solution of 4-fluoronitrobenzene (0.73 mL, 6.9 mmol) in tetrahydrofuran (30 mL) is added to the mixture. After stirring overnight, the mixture is quenched with water and extracted thrice with diethyl ether. The combined extracts were washed with water and saturated aqueous sodium chloride solution, dried over anhydrous magnesium sulfate, and concentrated under reduced pressure. The crude product is purified by reverse phase high performance liquid chromatography to give 1-methyl-3-(4-nitro-phenoxy)-pyrrolidine•TFA as a colorless oil which solidified upon standing.

MS (ES+): 223.3 (M+H)+

A solution of 1-methyl-3-(4-nitro-phenoxy)-pyrrolidine•TFA (0.34 g, 1.0 mmol) in ethanol (10 mL) is hydrogenated for one hour at atmospheric pressure over 10% Pd/C. The mixture is filtered through a pad of diatomaceous earth and concentrated under reduced pressure to give 4-(1-methyl-pyrrolidin-3-yloxy)-phenylamine•TFA as a black solid.

(4E)-6-Bromo-4-(methoxymethylene)isoquinoline-1,3 (2H,4H)-dione (52 mg, 0.18 mmol) and 4-(1-methyl-pyrrolidin-3-yloxy)-phenylamine•TFA (55 mg, 0.18 mmol) were stirred in N,N-dimethylformamide (1 mL) and triethylamine (100 μL) at 75° C. The reaction mixture is purified by reverse phase high performance liquid chromatography to give (4Z)-6-bromo-4-[({4-[(1-methylpyrrolidin-3-yl)oxy]phenyl}amino)methylene]isoquinoline-1,3(2H,4H)-dione as its TFA salt.

MS (ES+): 442.2, 444.2 (M+H)+

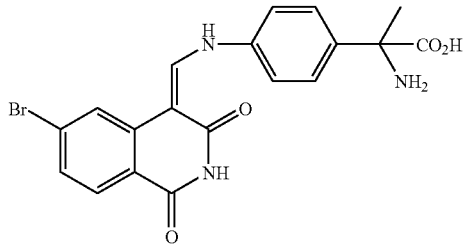

Example 277

2-Amino-2-{4-[(6-bromo-1,3-dioxo-2,3-dihydro-1H-isoquinolin-4-ylidenemethyl)-amino]-phenyl}-propionic acid A mixture of (4E)-6-bromo-4-(methoxymethylene)isoquinoline-1,3(2H,4H)-dione (191 mg, 0.50 mmole), N,N-dimethylformamide (2 mL) and 2-Amino-2-(4-amino-phenyl)-propionic acid (90 mg, 0.50 mmole) is stirred and heated at 110° C. for one hour, cooled in the refrigerator. The reaction mixture is diluted with ether, filtered, washed with acetonitrile and dried to give a dull yellow solid 71 mg (33%), mp 250-253° C.; MS (ESI): m/z 428.2, 430.2 (M−H).

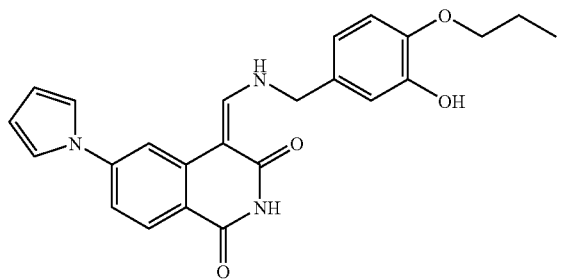

Example 278

4-[(3-Hydroxy-4-propoxy-benzylamino)-methylene]-6-pyrrol-1-yl-4H-isoquinoline-1,3-dione A mixture of 5-aminomethyl-2-propoxy-phenol hydrochloride (109 mg, 0.50 mmole), 4 mL of N,N-dimethylformamide and triethylamine (75 μL, 0.54 mmole) is stirred for 15 minutes. Then (4-methoxymethylene-6-pyrrol-1-yl-4H-isoquinoline-1,3-dione (134 mg, 0.50 mmole) is added and the reaction mixture stirred for one hour. The reaction mixture is evaporated to dryness, taken up in 5% methanol in chloroform and passed through a short pad of Florisil eluting with 5% methanol in chloroform. The eluate is evaporated in vacuo and treated with acetonitrile, filtered and dried to give a beige solid, 94 mg, (45%), mp 215-216° C. dec; MS (ES+): m/z 418.2 (M+H).

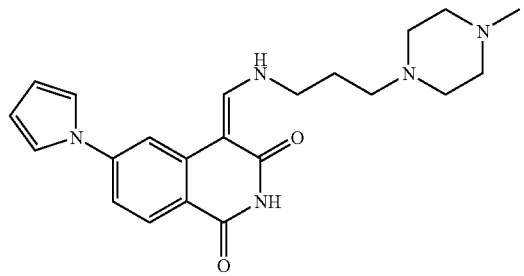

Example 279

4-{[3-(4-Methyl-piperazin-1-yl)-propylamino]-methylene}-6-pyrrol-1-yl-4H-isoquinoline-1,3-dione A mixture of 4-methoxymethylene-6-pyrrol-1-yl-4H-isoquinoline-1,3-dione (134 mg, 0.50 mmole), N,N-dimethylformamide (2 mL) and 3-(4-methyl-piperazin-1-yl)-propylamine (79 mg, 0.50 mmole) is stirred at room temperature for one hour. The reaction mixture is evaporated to dryness, taken up in 2 mL of DMSO and purified by reversed phase HPLC. The fractions containing the product were combined and evaporated, the solid is triturated with ether, filtered and dried to give the product as a di-TFA salt, a grey solid 152 mg (49%), mp 207-210° C.; MS (ES+): m/z 394.2 (M+H).

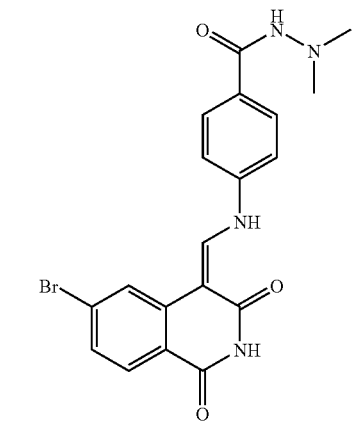

Example 280

4-{[(Z)-(6-Bromo-1,3-dioxo-2,3-dihydroisoquinolin-4(1H)-ylidene)methyl]amino}-N',N'-dimethylbenzohydrazide To a solution of 4-tert-butoxycarbonylamino-benzoic acid (0.10 g, 0.42 mmol) in N,N-dimethylformamide (2 mL) is added sequentially 1-hydroxybenzotriazole hydrate (0.11 g, 0.80 mmol), 1-(3-dimethylaminopropyl)-3-ethylcarbodiimide hydrochloride (0.15 g, 0.80 mmol), N-methylmorpholine (0.14 mL, 1.2 mmol), and N,N-dimethylhydrazine (64 μL, 0.80 mmol). The mixture is stirred overnight at room temperature and then purified by reverse phase high performance liquid chromatography to give (4-tert-butoxycarbonylamino-phenyl)-N,N-dimethylbenzohydrazide as its trifluoroacetate salt.

MS (ES⁺): 280.3 (M+H)⁺

A 0° C. ethanolic hydrochloric acid solution (2.9 M, 3.5 mL, 10 mmol) is added (4-tert-butoxycarbonylamino-phenyl)-N,N-dimethylbenzohydrazide•TFA. After 15 minutes, the reaction mixture is concentrated to give (4-amino-phenyl)-N,N-dimethylbenzohydrazide as its hydrochloride salt.

MS (ES⁺): 180.3 (M+H)⁺

(4E)-6-Bromo-4-(methoxymethylene)isoquinoline-1,3 (2H,4H)-dione (71 mg, 0.25 mmol) and (4-amino-phenyl)-N, N-dimethylbenzohydrazide.HCl (54 mg, 0.25 mmol) were stirred in N,N-dimethylformamide (1.25 mL) and triethylamine (100 µL) at 75° C. The reaction mixture is quenched by the addition of water. The solid material is then collected, washed with diethyl ether, water, and methanol, and then dried under vacuum to give 4-{[(Z)-(6-bromo-1,3-dioxo-2,3-dihydroisoquinolin-4(1H)-ylidene)methyl]amino}-N',N'-dimethylbenzohydrazide as its TFA salt.

MS (ES⁺): 429.0, 431.1 (M+H)⁺

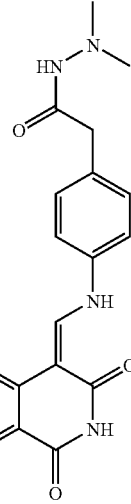

Example 281

(4Z)-6-Bromo-4-({[4-(1,3-thiazolidin-3-ylmethyl) phenyl]amino}methylene)isoquinoline-1,3(2H,4H)-dione Using the procedure described for the preparation of example 14, 680 mg (86% yield) is obtained as a yellow solid from 500 mg (1.77 mmol) (4E)-6-bromo-4-(methoxymethylene)isoquinoline-1,3(2H,4H)-dione and 688 mg (3.54 mmol) 4-thiazolidin-3-ylmethyl)phenyl]amine; mp 224-225° C.

MS (ESI) m/z 446.0 (M+1)⁺

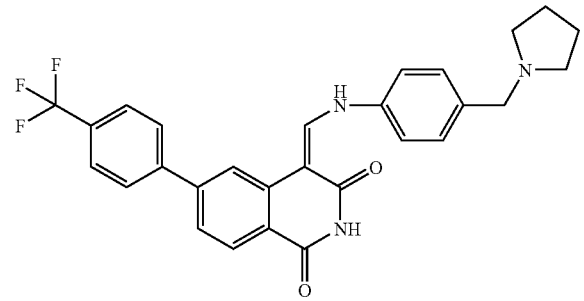

Example 282

(4Z)-4-({[4-(Pyrrolidin-1-ylmethyl)phenyl] amino}methylene)-6-[4-(trifluoromethyl)phenyl] isoquinoline-1,3(2H,4H)-dione Using the procedure described for the preparation of '(4Z)-6-(4-fluorophenyl)-4-({[4-(piperidin-1-ylmethyl)phenyl] amino}methylene)isoquinoline-1,3(2H,4H)-dione, 210 mg (36%) of yellow solid is obtained from 500 mg (1.17 mmol) of 4Z)-6-bromo-4-({[4-(pyrrolidin-1-ylmethyl) phenyl}amino)methylene] isoquinolin-1,3(2H,4H)-dione and 4-fluorophenyl boronic acid 556.5 mg, (2.93 mmol); mp 176-177° C.

MS (ESI) m/z 492.2 (M+1).

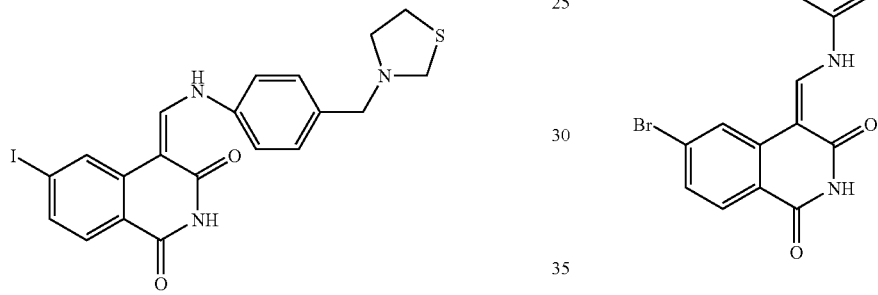

Example 283

2-(4-{[(Z)-(6-Bromo-1,3-dioxo-2,3-dihydroiso-quinolin-4(1H)-ylidene)methyl]amino}phenyl)-N', N'-dimethylacetohydrazide A mixture of 4-nitrophenylacetic acid (0.27 g, 1.5 mmol) and di-tert-butyldicarbonate (0.65 g, 3.0 mmol) in ethyl acetate (10 mL) is hydrogenated at atmospheric pressure over 10% palladium on carbon. The reaction mixture is filtered through a pad of diatomaceous earth, and after concentration of the filtrate, the residue is taken up in dioxane/water (1:1, 10 mL). Aqueous sodium hydroxide solution (1 M, 3 mL) is added, followed by di-tert-butyldicarbonate (0.47 g, 2.1 mmol). After stirring for 3 hours at room temperature, the reaction is quenched by the addition of 5% aqueous potassium hydrogen sulfate solution. The mixture is extracted thrice with dichloromethane, dried over anhydrous magnesium sulfate, and concentrated under reduced pressure to afford (4-tert-butoxycarbonylamino-phenyl)-acetic acid, which is purified by reverse phase high performance liquid chromatography.

MS (ES⁻): 250.2 (M–H)⁻

To a solution of (4-tert-butoxycarbonylamino-phenyl)-acetic acid (0.10 g, 0.40 mmol) in N,N-dimethylformamide (2 mL) is added sequentially 1-hydroxybenzotriazole hydrate (0.11 g, 0.84 mmol), 1-(3-dimethylaminopropyl)-3-ethylcarbodiimide hydrochloride (0.16 g, 0.84 mmol), N-methylmorpholine (0.14 mL, 1.3 mmol), and N,N-dimethylhydrazine (64 µL, 0.84 mmol). The mixture is stirred overnight at room temperature and then purified by reverse phase high performance liquid chromatography to give (4-tert-butoxycarbonylamino-phenyl)-N,N-dimethylacetohyrazide as its trifluoroacetate salt.

MS (ES+): 294.3 (M+H)+

A 0° C. ethanolic hydrochloric acid solution (2.9 M, 3.5 mL, 10 mmol) is added to (4-tert-butoxycarbonylamino-phenyl)-N,N-dimethylacetohyrazide•TFA. After 15 minutes, the reaction mixture is concentrated to give (4-amino-phenyl)-N,N-dimethylacetohydrazide as its hydrochloride salt.

MS (ES+): 194.3 (M+H)+

(4E)-6-Bromo-4-(methoxymethylene)isoquinoline-1,3 (2H,4H)-dione (71 mg, 0.25 mmol) and (4-amino-phenyl)-acetic acid N,N-dimethylhydrazide.HCl (57 mg, 0.25 mmol) were stirred in N,N-dimethylformamide (1.25 mL) and triethylamine (100 μL) at 75° C. The reaction mixture is purified by reverse phase high performance liquid chromatography to give 2-(4-{[(Z)-(6-bromo-1,3-dioxo-2,3-dihydroisoquinolin-4(1H)-ylidene)methyl]amino}phenyl)-N',N'-dimethylacetohydrazide as its TFA salt.

TOF MS (ES+): 443.1, 445.1 (M+H)+

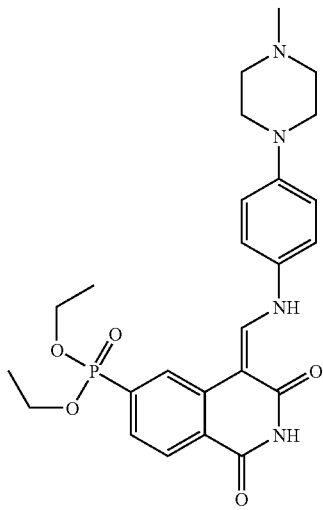

Example 284

Diethyl [(4Z)-4-({[4-(4-methylpiperazin-1-yl)phenyl]amino}methylene)-1,3-dioxo-1,2,3,4-tetrahydroisoquinolin-6-yl]phosphonate To a solution of (4Z)-6-bromo-4-({[4-(4-methylpiperazin-1-yl)phenyl]amino}methylene)isoquinoline-1,3(2H,4H)-dione (67 mg, 0.15 mmol) in N,N-dimethylformamide (1 mL) is added diethyl phosphite (22 μL) and tetrakis(triphenylphosphine)palladium(0) (9 mg, 8 μmol, 0.05 mol %). The mixture is heated in a 120° C. oil bath for 6 hour and then purified by reverse phase high performance liquid chromatography to give diethyl [(4Z)-4-({[4-(4-methylpiperazin-1-yl)phenyl]amino}methylene)-1,3-dioxo-1,2,3,4-tetrahydroisoquinolin-6-yl]phosphonate as its ditrifluoroacetate salt (8.8 mg, 3.1%).

MS (ES+): 499.2 (M+H)+

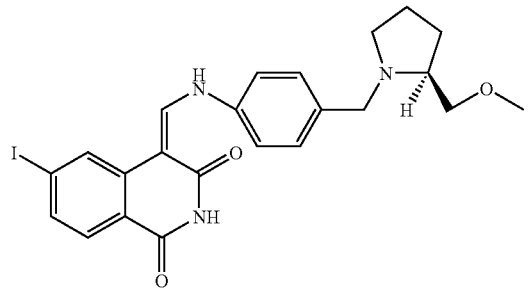

Example 285

(4Z)-6-Iodo-4-{[(4-{[(2S)-2-(methoxymethyl)pyrrolidin-1-yl]methyl}phenyl)amino]methylene}isoquinoline-1,3(2H,4H)-dione Using the procedure described for the preparation of example 14, 150 mg (47% yield) is obtained as a yellow solid from 200 mg (0.61 mmol) (4E)-6-iodo-4-(methoxymethylene)isoquinoline-1,3(2H,4H)-dione and 135.5 mg (0.61 mmol) of {[(4-{[(2S)-2-(methoxymethyl)pyrrolidin-1-yl]methyl}phenyl)amine; mp 1150-151° C.

MS (ESI) m/z 518.1 (M+1)+

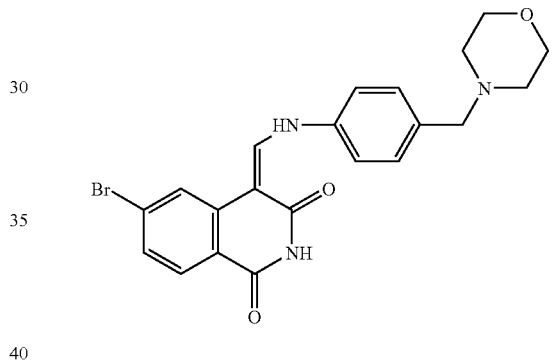

Example 286

(4Z)-6-Bromo-4-(([4-(morpholin-4-ylmethyl)phenyl]amino}methylene)isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione (24), 2.38 g (75.9% yield) of light brown solid is obtained from 2.0 g (7.09 mmol) of (4E)-6-bromo-4-(methoxymethylene)isoquinoline-1,3(2H,4H)-dione, and 1.63 g (8.5 mmol) of 4-Morpholin-4-ylmethyl-phenylamine mp 209-210° C.; MS (ESI) m/z 442.1 (M+H)+1

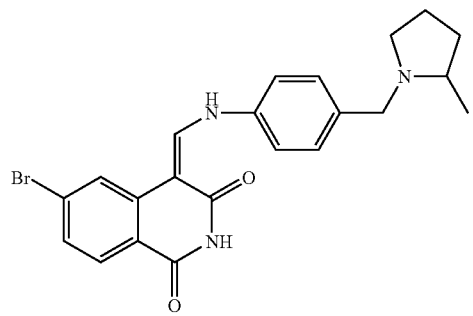

Example 287

(4Z)-6-Bromo-4-[({4-[(2-methylpyrrolidin-1-yl)methyl]phenyl}amino)methylene]-isoquinoline-1,3(2H,4H)-dione (60)

Using the procedure described for the preparation of 4Z)-6-bromo-4-({[4-(3,5-dimethylpiperazin-1-yl)phenyl]amino}methylene)isoquinoline-1,3(2H,4H)-dione, 5.11 g (81.9% yield) of yellow solid is obtained from 4.0 g (14.18 mmol) of (4E)-6-bromo-4-(methoxymethylene)isoquinoline-1,3(2H,4H)-dione and 3.24 g (17.0 mmol) of 4-[(2-methylpyrrolidin-1-yl)methyl]phenyl}amine: mp 183-184° C.; MS (ESI) m/z 440.0 (M+H)$^{+1}$

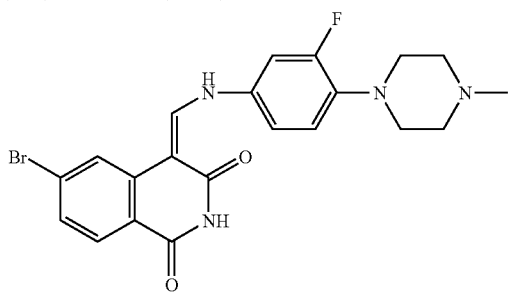

Example 288

(4Z)-6-Bromo-4-({[3-fluoro-4-(4-methylpiperazin-1-yl)phenyl]amino}methylene)-isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 3.0 g (92.0% yield) of light brown solid is obtained from 2.0 g (7.09 mmol) of (4E)-6-bromo-4-(methoxymethylene)isoquinoline-1,3(2H,4H)-dione and 1.63 g (7.8 mmol) of [3-fluoro-4-(4-methylpiperazin-1-yl)phenyl]amine and 25 mL of N,N-dimethylformamide: mp 206-207° C.; MS (ESI) m/z 459.0-461.0 (M+H)$^{+1}$

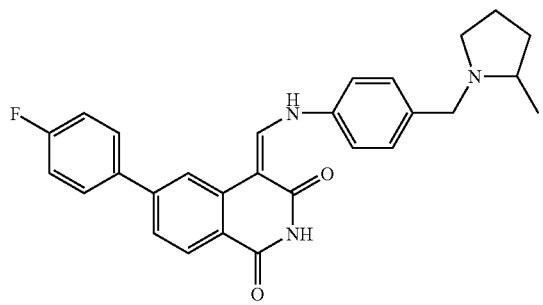

Example 289

(4Z)-6-(4-Fluorophenyl)-4-[({4-[(2-methylpyrrolidin-1-yl)methyl]phenyl}amino)-methylene]isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.13 g (65. % yield) of light brown solid is obtained from 0.20 (0.454 mmol) of (4Z)-6-bromo-4-[({4-[(2-methylpyrrolidin-1-yl)methyl]phenyl}amino)methylene]-isoquinoline-1,3(2H,4H)-dione, 0.095 g (0.681 mmol) of 4-fluorobenzylboronic acid, 0.043 g (0.045 mmol) of Pd(dba)$_3$, 0.02 g (0.09 mmol) of t-Bu$_3$P, and 0.15 g (0.90 mmol) of Na$_2$CO$_3$: mp 165-166° C.; MS (ESI) m/z 456.2 (M+H)$^{+1}$

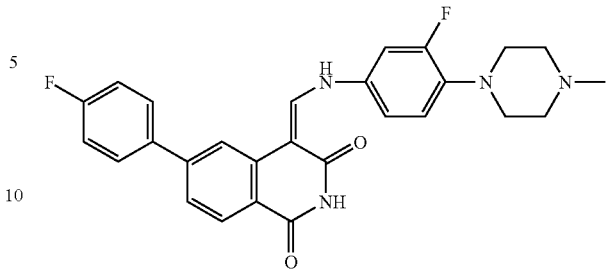

Example 290

(4Z)-4-({[3-Fluoro-4-(4-methylpiperazin-1-yl)phenyl]amino}methylene)-6-(4-fluorophenyl)isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione., 0.12 g (55. % yield) of yellow solid is obtained from 0.21 (0.454 mmol) of (4Z)-4-({[3-fluoro-4-(4-methylpiperazin-1-yl)phenyl]amino}methylene)-6-iodoisoquinoline-1,3(2H,4H)-dione, 0.095 g (0.681 mmol) of 4-fluorobenzylboronic acid, 0.043 g (0.045 mmol) of Pd(dba)$_3$, 0.02 g (0.09 mmol) of t-Bu$_3$P, and 0.15 g (0.90 mmol) of Na$_2$CO$_3$: mp 166-167° C.; MS (ESI) m/z 475.2 (M+H)$^{+1}$

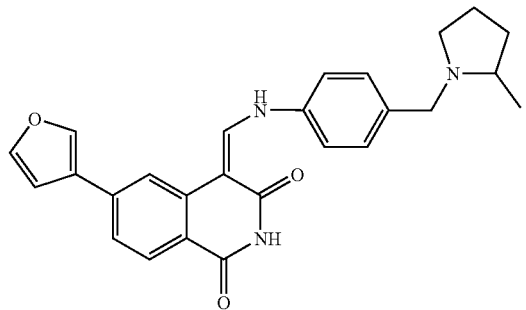

Example 291

(4Z)-6-(3-Furyl)-4-[({4-[(2-methylpyrrolidin-1-yl)methyl]phenyl}amino)methylene]-isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.041 g (21.6. % yield) of light brown solid is obtained from 0.20 (0.454 mmol) of (4Z)-6-bromo-4-[({4-[(2-methylpyrrolidin-1-yl)methyl]phenyl}amino)methylene]-isoquinoline-1,3(2H,4H)-dione, 0.076 g (0.681 mmol) of 3-furanboronic acid, 0.043 g (0.045 mmol) of Pd(dba)$_3$, 0.02 g (0.09 mmol) of t-Bu$_3$P, and 0.15 g (0.90 mmol) of Na$_2$CO$_3$: mp 165-166° C.; MS (ESI) m/z 428.2 (M+H)$^{+1}$

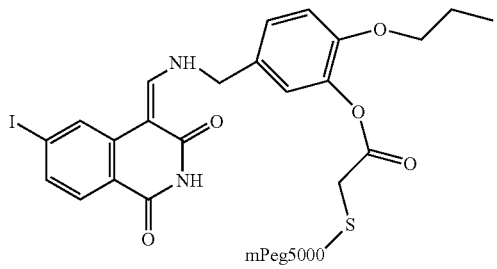

Example 292

PEG5000thio-acetic acid 5-{[(6-iodo-1,3-dioxo-2,3-dihydro-1H-isoquinolin-4-ylidenemethyl)-amino]-methyl}-2-propoxy-phenyl ester To (4Z)-4-{[(3-hydroxy-4-propoxybenzyl)amino]methylene}-6-iodoisoquinoline-1,3(2H,4H)-dione (40 mg, 0.084 mmol), mPEG5000SCH2CO2H (460 mg, 0.092 mmol), 1-(3-dimethylaminopropyl)-3-ethylcarbodiimide hydrochloride (EDC) (26 mg, 0.138 mmol), 1-hydroxybenzotirazole hydrate (HOBT hydrate) (18.6 mg, 0.138 mmol) were added dimethylformamide (5 mL) and triethylamine (38 uL, 0.28 mmol). After 3 h concentrate in vacuo and chromatograph on silica gel (CH2Cl2/methanol). The desired compound is obtained as a solid (289 mg).

Example 293

5-({[(Z)-(6-Iodo-1,3-dioxo-2,3-dihydroisoquinolin-4 (1H)-ylidene)methyl]amino}methyl)-2-propoxyphenyl chloroacetate To iodoacetic acid (242 mg, 1.3 mmol) in N,N-dimethylformamide (2 mL) at −20 C is added N-methylmorpholine (142 uL, 1.3 mmol) and isobutylchloroformate (178 uL, 1.3 mmol). After 5 min (4Z)-4-{[(3-hydroxy-4-propoxybenzyl)amino]methylene}-6-iodoisoquinoline-1,3(2H,4H)-dione (250 mg, 0.52 mmol) is added. The reaction mixture is allowed to warm to 25 C. After 24 h 15% aq. Citric acid is added. The resulting precipitate is filtered and washed with water to give a brown solid (352 mg). A portion of this material (50 mg) is chromatographed on silica gel (CH$_2$Cl$_2$/MeOH) to give the title compound as a tan powder (23 mg). MS (ESI) m/z 555 (M+H)$^{+1}$.

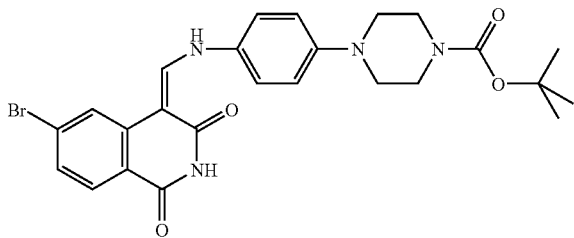

Example 294 tert-Butyl 4-(4-{[(Z)-(6-bromo-1,3-dioxo-2,3-dihydroisoquinolin-4(1H)-ylidene)methyl]amino}phenyl) piperazine-1-carboxylate A N,N-dimethylformamide solution (2.2 mL) of 6-bromo-4-methoxymethylene-4H-isoquinoline-1,3-dione (280 mg, 0.99 mmol), and tert-butyl 4-(4-aminophenyl)piperazine-1-carboxylate (300 mg, 1.08 mmol) is heated at 90° C. for 0.5 h. After cooling in the refrigerator, the precipitate is collected, and washed with N,N-dimethylformamide and ether to give 222 mg (42%) of the title compound as a yellow solid. MS (ESI) m/z 527.529 (M+H)$^{+1}$

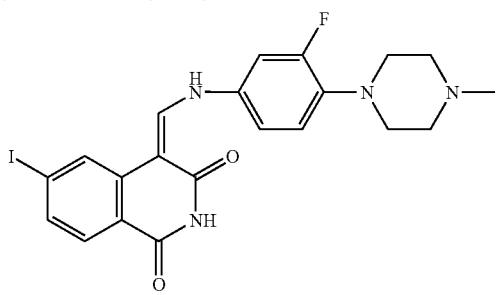

Example 295

(4Z)-4-({[3-Fluoro-4-(4-methylpiperazin-1-yl)phenyl]amino}methylene)-6-iodoisoquinoline-1,3(2H, 4H)-dione Using the procedure described for the preparation of 4Z)-6-bromo-4-({[4-(3,5-dimethylpiperazin-1-yl)phenyl] amino}methylene)isoquinoline-1,3(2H,4H)-dione, 0.27 g (90.0% yield) of light brown solid is obtained from 0.2 g (0.61 mmol) of (4E)-6-iodo-4-(methoxymethylene)isoquinoline-1,3(2H,4H)-dione and 0.15 g (0.73 mmol) of [3-fluoro-4-(4-methylpiperazin-1-yl)phenyl]amine: mp 211-212° C.; MS (ESI) m/z 507.1 (M+H)$^{+1}$

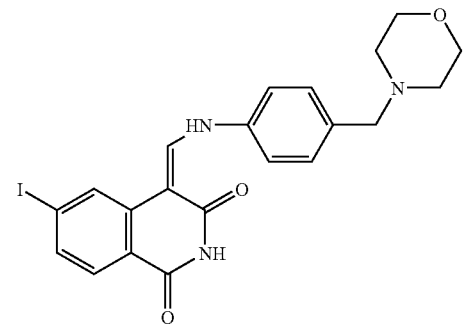

Example 296

(4Z)-6-Iodo-4-({[4-(morpholin-4-ylmethyl)phenyl] amino}methylene)isoquinoline-1,3(2H,4H)-dione Using the procedure described for the preparation of 4Z)-6-bromo-4-({[4-(3,5-dimethylpiperazin-1-yl)phenyl] amino}methylene)isoquinoline-1,3(2H,4H)-dione, 0.27 g (91.0% yield) of tan solid is obtained from 0.20 g (0.608 mmol) of (4E)-6-iodo-4-(methoxymethylene)isoquinoline-1,3(2H,4H)-dione, and 0.14 g (0.608 mmol) of 4-Morpholin-4-ylmethyl-phenylamine: mp 186-187 oC; MS (ESI) m/z 490.1 (M+H)+1

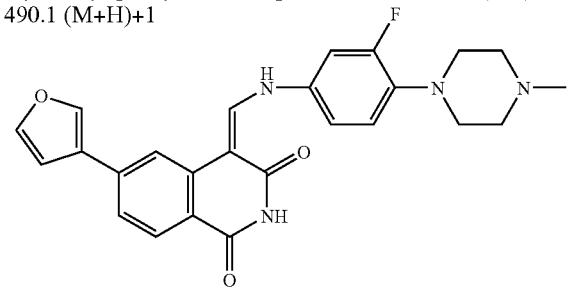

Example 297

(4Z)-4-({[3-Fluoro-4-(4-methylpiperazin-1-yl)phenyl]amino}methylene)-6-(3-furyl)isoquinoline-1,3 (2H,4H)-dione Using the procedure described for the preparation of (4Z)-6-(3-furyl)-4-[({4-[(3R,5S)-3,4,5-trimethylpiperazin-1-yl] phenyl}amino)-methylene]isoquinoline-1,3(2H,4H)-dione, 0.32 g (65.8% yield) of light brown solid is obtained from 0.5 (1.09 mmol) of (4Z)-6-bromo-4-({[3-fluoro-4-(4-methylpiperazin-1-yl)phenyl]amino}methylene)-isoquinoline-1,3(2H, 4H)-dione, 0.2 g (1.78 mmol) of 3-furanboronic acid, 0.10 g (0.11 mmol) of Pd(dba)₃, 0.05 g (0.24 mmol) of t-Bu₃P, and 0.38 g (3.58 mmol) of Na₂CO₃: mp 203-204° C.; MS (ESI) m/z 447.2 (M+H)⁺¹

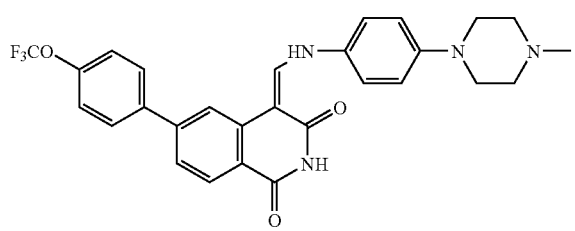

Example 298

(4Z)-4-({[4-(4-Methylpiperazin-1-yl)phenyl]amino}methylene)-6-[4-(trifluoromethoxy)phenyl]isoquinoline-1,3(2H,4H)-dione An amount of 6-bromo-4-{[4-(4-methyl-piperazin-1-yl)-phenylamino]-methylene}-4H-isoquinoline-1,3-dione (0.1 g, 0.2267 mmol) in 1 mL of N,N'-dimethylformamide is added to 4-(trifluoromethoxy)phenylboronic acid (0.07 g, 0.34 mmol), 0.032 g (0.034 mmol) of tris(dibenzylideneacetone)dipalladium(0), tri(t-butyl)phosphine (0.014 g, 0.068 mmol) and cesium carbonate (0.148 g, 0.4534 mmol). The reaction mixture is stirred at 130 oC under N2 for 15 min. Mass spectroscopy suggested the completion of the reaction. The mixture is diluted with chloroform and filtered through Celite. The filtrate is evaporated to dryness and purified by column chromatography using 5% methanol/methylene chloride as eluent to yield 85 mg (72% yield) of the title compound as orange solid. MS (ESI) m/z 523.2 (M+H)+1.

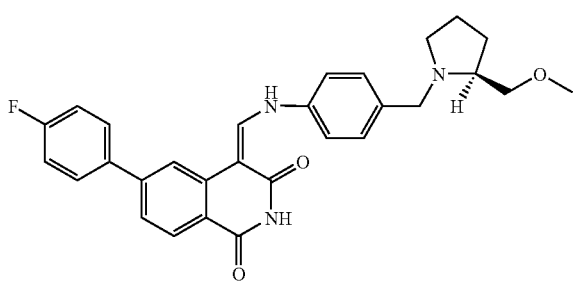

Example 299

(4Z)-6-(4-Fluorophenyl)-4-{[(4-{[(2S)-2-(methoxymethyl)pyrrolidin-1-yl]methyl}phenyl)amino]methylene}isoquinoline-1,3(2H,4H)-dione Using the procedure described for the preparation of '(4Z)-6-(4-fluorophenyl)-4-({[4-(piperidin-1-'ylmethyl)phenyl]amino}methylene)isoquinoline-1,3(2H,4H)-dione, 228 mg (44% yield) is obtained as a yellow solid from 500 mg (1.06 mmol) of (4Z)-6-bromo-4-{[(4-{[(2R)-2-(methoxymethyl)pyrrolidin-1-yl]methyl}phenyl)amino)methylene)isoquinoline-1,3(2H,4H-dione and 4-Fluorophenyl boronic acid 372 mg, (2.65 mmol).; mp 162-163° C.

MS (ESI) m/z 486.2 (M+1)⁺

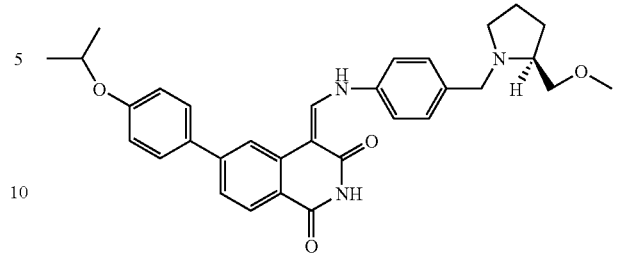

Example 300

(4Z)-6-(4-Isopropoxyphenyl)-4-{[(4-{[(2R)-2-(methoxymethyl)pyrrolidin-1-yl]methyl}phenyl)amino]methylene}isoquinoline-1,3(2H,4H)-dione Using the procedure described for the preparation of (4Z)-6-(4-fluorophenyl)-4-({[4-(piperidin-1-ylmethyl)phenyl]amino}methylene)isoquinoline-1,3(2H,4H)-dione, 196 mg (44% yield) is obtained as a yellow solid from 400 mg (0.85 mmol) of (4Z)-6-bromo-4-{[(4-{[(2R)-2-(methoxymethyl)pyrrolidin-1-yl]methyl}phenyl)amino)methylene}isoquinoline-1,3(2H,4H-dione and 4-isopropoxyphenyl boronic acid 383 mg, (2.13 mmol).; mp 200-201° C.

MS (ESI) m/z 526.2 (M+1)⁺

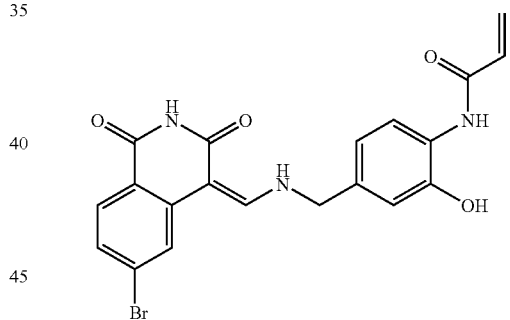

Example 301

N-[4-({[(Z)-(6-Bromo-1,3-dioxo-2,3-dihydroisoquinolin-4(1H)-ylidene)methyl]amino}methyl)-2-hydroxyphenyl]acrylamide Following the acetylation and desilylation procedure employed for the preparation of N-[2-hydroxy-4-({[(Z)-(6-iodo-1,3-dioxo-2,3-dihydroisoquinolin-4(1H)-ylidene)methyl]amino}methyl)phenyl]benzamide, (4Z)-4-[({4-amino-3-[(triisopropylsilyl)oxy]benzyl}-amino)methylene]-6-bromoisoquinoline-1,3(2H,4H)-dione (54 mg, 0.10 mmol) is reacted with acryloyl chloride (41 μL, 0.50 mmol). Following desilylation, precipitation, and washing with methanol and diethyl ether, N-[4-({[(Z)-(6-bromo-1,3-dioxo-2,3-dihydroisoquinolin-4(1H)-ylidene)methyl]amino}methyl)-2-hydroxyphenyl]acrylamide is obtained (8 mg, 18

MS (ES⁻): 440.3 (M−H)⁻

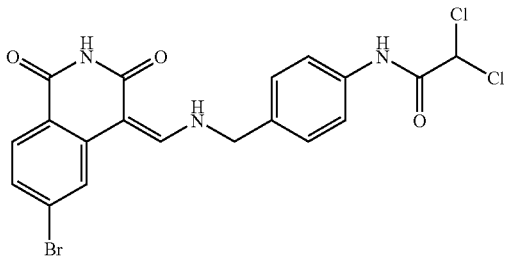

Example 302

N-[4-({[(Z)-(6-Bromo-1,3-dioxo-2,3-dihydroisoquinolin-4(1H)-ylidene)methyl]amino}methyl)phenyl]-2,2-dichloroacetamide A suspension of (4E)-6-bromo-4-(methoxymethylene)isoquinoline-1,3(2H,4H)-dione (0.10 g, 0.35 mmol) and 4-aminobenzylamine (43 mg, 0.35 mmol) in N,N-dimethylformamide (1 mL) is stirred overnight at room temperature and then diluted with water. The precipitate is collected by filtration, washed successively with diethyl ether, water, and methanol, and then dried under house vacuum to give (4Z)-4-{[4-amino benzylamino]methylene}-6-iodoisoquinoline-1,3(2H,4H)-dione (0.11 g, 85%).

MS (ES⁻): 370.1 (M−H)⁻

To a 0° C. solution of (4Z)-4-{[4-amino benzylamino]methylene}-6-iodoisoquinoline-1,3(2H,4H)-dione (37 mg, 0.10 mmol) in N,N-dimethylformamide/dimethylsulfoxide (1:1, 2 mL) is added triethylamine (26 µL, 0.20 mmol) followed by dichloroacetyl chloride (19 µL, 0.20 mmol). After 30 minutes of stirring at 0° C., additional volumes of triethylamine (26 µL, 0.20 mmol) and dichloroacetyl chloride (50 µL, 0.53 mmol) were added. After stirring at room temperature for 60 hours, the reaction mixture is quenched by the addition of water. The precipitated solid is collected, dissolved in dimethylsulfoxide, and purified by reverse phase HPLC to give N-[4-({[(Z)-(6-bromo-1,3-dioxo-2,3-dihydroisoquinolin-4(1H)-ylidene)methyl]amino}methyl)phenyl]-2,2-dichloroacetamide (7 mg, 15%).

MS (ES⁺): 484.1 (M+H)⁺

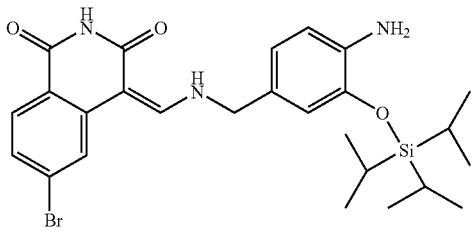

Example 303

(4Z)-4-[({4-Amino-3-[(triisopropylsilyl)oxy]benzyl}amino)methylene]-6-bromoisoquinoline-1,3(2H,4H)-dione A solution of 4-nitro-3-[(triisopropylsilyl)oxy]benzaldehyde O-methyloxime (0.70 g, 2.0 mmol) in ethanol (13 mL) and tetrahydrofuran (3 mL) is degassed with solid carbon dioxide, then charged with 5% palladium on carbon (100 mg) and 88% formic acid (0.8 mL). The mixture is stirred under 1 atm hydrogen gas overnight. The mixture is then filtered through a pad of diatomaceous earth, and the filtrate is concentrated under reduced pressure to give {4-(aminomethyl)-2-[(triisopropylsilyl)oxy]phenyl}amine as its diformic acid salt. This material is used in the subsequent step without further purification.

GC-MS (ES⁺): 294 (M+)

To a mixture of {4-(aminomethyl)-2-[(triisopropylsilyl)oxy]phenyl}amine diformate (0.51 g, 1.3 mmol) and triethylamine (0.68 mL, 5.2 mmol) in N,N-dimethylformamide (6.5 mL) is added (4E)-6-bromo-4-(methoxymethylene)isoquinoline-1,3(2H,4H)-dione (0.34 g, 1.2 mmol). The mixture is stirred overnight at room temperature and then 1 mL of the reaction mixture is purified by reverse phase HPLC to give a sample of (4Z)-4-[({4-amino-3-[(triisopropylsilyl)oxy]benzyl}amino)methylene]-6-bromoisoquinoline-1,3(2H,4H)-dione as its trifluoroacetate salt (10 mg).

MS (ES⁺): 546.2 (M+H)⁺

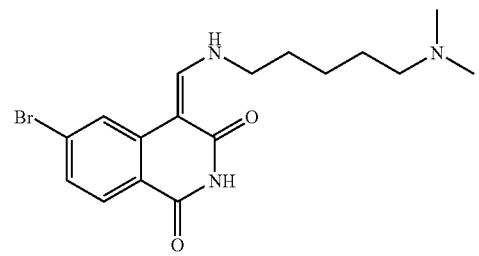

Example 304

(Z)-6-Bromo-4-((5-(dimethylamino)pentylamino)methylene)isoquinoline-1,3(2H,4H)-dione A mixture of 6-bromo-4-(methoxymethylene)-isoquinoline-1,3(2H,4H)-dione (70.5 mg, 0.25 mmole), dimethylformamide (2 mL) and N1,N1-dimethylpentane-1,5-diamine (32.6 mg, 0.25 mmole) is stirred at room temperature for one hour. The reaction mixture is diluted with ether, filtered and washed with fresh ether and dried to give a light salmon solid, 61.1 mg, (64% yield) MS (ES⁺): 382.2, (M+H).

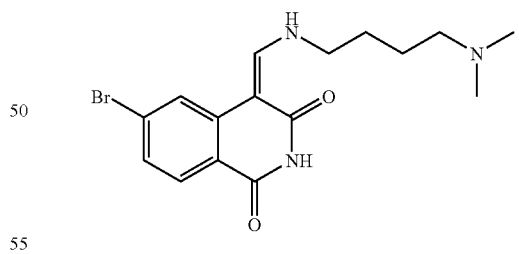

Example 305

(Z)-6-Bromo-4-((4-(dimethylamino)butylamino)methylene)isoquinoline-1,3(2H,4H)-dione A mixture of 6-bromo-4-(methoxymethylene)-isoquinoline-1,3(2H,4H)-dione (70.5 mg, 0.25 mmole), dimethylformamide (2 mL) and N1,N1-dimethylbutane-1,4-diamine (29.1 mg, 0.25 mmole) is stirred at room temperature for one hour. The reaction mixture is diluted with ether, filtered and washed with fresh ether and dried to give a light salmon solid, 65.5 mg, (73% yield) MS (ES+): 366.2, (M+H).

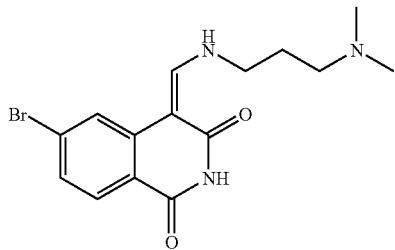

Example 306

(Z)-6-Bromo-4-((3-(dimethylamino)propylamino)methylene)isoquinoline-1,3(2H,4H)-dione A mixture of 6-bromo-4-(methoxymethylene)-isoquinoline-1,3(2H,4H)-dione (70.5 mg, 0.25 mmole), dimethylformamide (2 mL) and N1,N1-dimethylpropane-1,3-diamine (25.6 mg, 0.25 mmole) is stirred at room temperature for one hour. The reaction mixture is diluted with ether, filtered and washed with fresh ether and dried to give a light brown solid, 65.8 mg, (66% yield) MS (ES+): 352.2, (M+H).

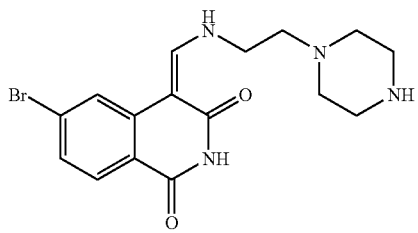

Example 307

(Z)-6-Bromo-4-((2-(piperazin-1-yl)ethylamino)methylene)isoquinoline-1,3(2H,4H)-dione A mixture of 6-bromo-4-(methoxymethylene)-isoquinoline-1,3(2H,4H)-dione (70.5 mg, 0.25 mmole), dimethylformamide (2 mL) and 2-(piperazin-1-yl)ethanamine (32.3 mg, 0.25 mmole) is stirred at room temperature for one hour. The reaction mixture is diluted with ether, filtered and washed with fresh ether and dried to give a light brown solid, 66.6 mg, (70% yield) MS (ES+): 379.2, (M+H).

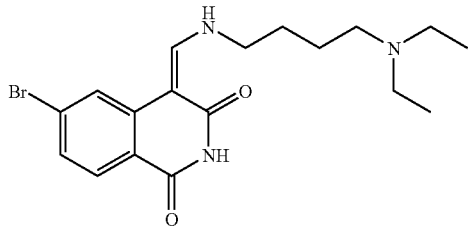

Example 308

(Z)-6-Bromo-4-((4-(diethylamino)butylamino)methylene)isoquinoline-1,3(2H,4H)-dione A mixture of 6-bromo-4-(methoxymethylene)-isoquinoline-1,3(2H,4H)-dione (70.5 mg, 0.25 mmole), dimethylformamide (2 mL) and N1,N1-diethylbutane-1,4-diamine (36.1 mg, 0.25 mmole) is stirred at room temperature for one hour. The reaction mixture is diluted with ether, filtered and washed with fresh ether and dried to give a light brown solid, 26.0 mg, (26% yield) MS (ES+): 394.2, (M+H).

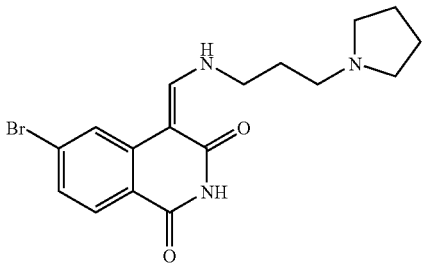

Example 309

(Z)-6-Bromo-4-((3-(pyrrolidin-1-yl)propylamino)methylene)isoquinoline-1,3(2H,4H)-dione A mixture of 6-bromo-4-(methoxymethylene)-isoquinoline-1,3(2H,4H)-dione (70.5 mg, 0.25 mmole), dimethylformamide (2 mL) and 3-(pyrrolidin-1-yl)propan-1-amine (32.1 mg, 0.25 mmole) is stirred at room temperature for one hour. The reaction mixture is diluted with ether, filtered and washed with fresh ether and dried to give a light brown solid, 73.3 mg, (77% yield) MS (ES+): 378.2, (M+H).

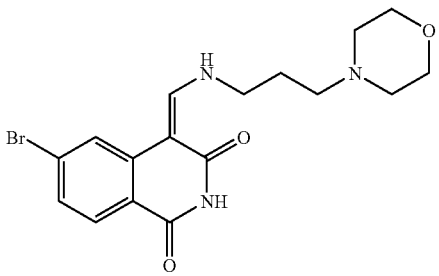

Example 310

(Z)-6-Bromo-4-((3-morpholinopropylamino)methylene)isoquinoline-1,3(2H,4H)-dione

A mixture of 6-bromo-4-(methoxymethylene)-isoquinoline-1,3(2H,4H)-dione (70.5 mg, 0.25 mmole), dimethylformamide (2 mL) and 3-morpholinopropan-1-amine (36.1 mg, 0.25 mmole) is stirred at room temperature for one hour. The reaction mixture is diluted with ether, filtered and washed with fresh ether and dried to give a cream solid, 53.6 mg, (54% yield) MS (ES+): 394.2, (M+H).

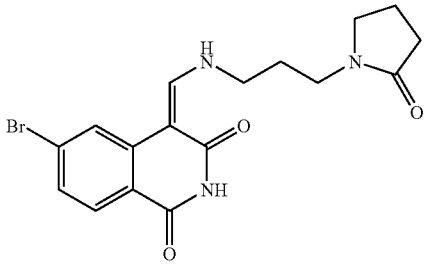

Example 311

(Z)-6-Bromo-4-((3-(2-oxopyrrolidin-1-yl)propylamino)methylene)isoquinoline-1,3(2H,4H)-dione A mixture of 6-bromo-4-(methoxymethylene)-isoquinoline-1,3(2H,4H)-dione (70.5 mg, 0.25 mmole), dimethylformamide (2 mL) and 1-(3-aminopropyl)pyrrolidin-2-one (35.6 mg, 0.25 mmole) is stirred at room temperature for one hour. The reaction mixture is diluted with ether, filtered and washed with fresh ether and dried to give a beige solid, 63.5 mg, (65% yield) MS (ES+): 392.2, (M+H).

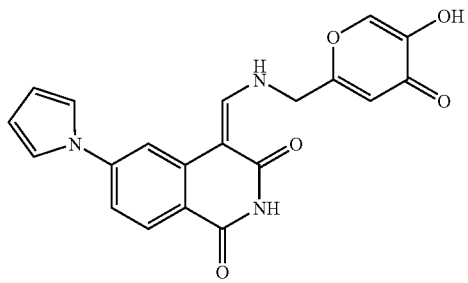

Example 312

4-{[(5-Hydroxy-4-oxo-4H-pyran-2-ylmethyl)-amino]-methylene}-6-pyrrol-1-yl-4H-isoquinoline-1,3-dione A mixture of 2-aminomethyl-5-hydroxy-pyran-4-one (106 mg, 0.75 mmole), 4 mL of N,N-dimethylformamide and 4-methoxymethylene-6-pyrrol-1-yl-4H-isoquinoline-1,3-dione (201 mg, 0.80 mmole) is stirred for one hour at ambient temperature. The reaction mixture is evaporated to dryness, dissolved in 7.5% methanol in chloroform passed through Florisil eluting with 7.5% methanol in chloroform. The eluate is evaporated, treated with acetonitrile, the resulting solid filtered and dried to give a beige solid, 157 mg, (55%), mp 310-2° C. dec; MS (ES+): m/z 378.1 (M+H).

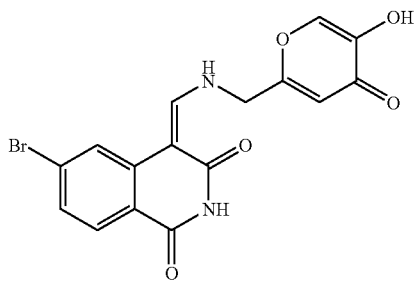

Example 313

6-Bromo-4-{[(5-hydroxy-4-oxo-4H-pyran-2-ylmethyl)-amino]-methylene}-4H-isoquinoline-1,3-dione A mixture of 2-aminomethyl-5-hydroxy-pyran-4-one (106 mg, 0.75 mmole), 4 mL of N,N-dimethylformamide and 4-methoxymethylene-6-bromo-4H-isoquinoline-1,3-dione (212 mg, 0.75 mmole) is stirred for one hour at ambient temperature. The reaction mixture is evaporated to dryness, dissolved in 7.5% methanol in chloroform passed through Florisil eluting with 7.5% methanol in chloroform. The eluate is evaporated, treated with acetonitrile, the resulting solid filtered and dried to give an off white solid, 220 mg, (75%), mp 293-7° C. dec; MS (ES+): m/z 391 (M+H).

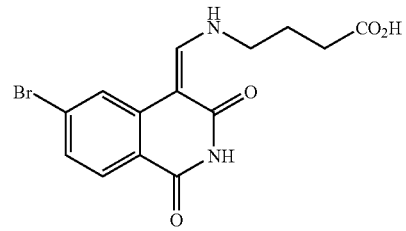

Example 314

(Z)-4-((6-Bromo-1,3-dioxo-2,3-dihydroisoquinolin-4(1H)-ylidene)methylamino)butanoic acid A mixture of (E)-6-bromo-4-(methoxymethylene)isoquinoline-1,3(2H,4H)-dione (212 mg, 0.75 mmole), dimethylformamide (5 mL), and 4-aminobutanoic acid (78 mg, 0.75 mmole) is stirred at room temperature for 1 hour. The reaction mixture is diluted with ether, filtered, washed with fresh ether and dried to give a salmon solid, 164 mg, (61%), mp 260-2° C. dec; MS (ES+): m/z 353.0 (M+H).

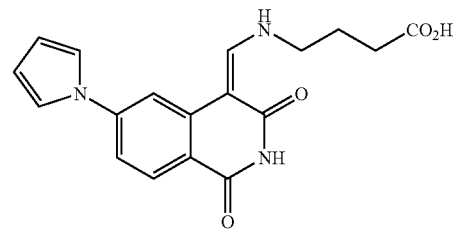

Example 315

(Z)-4-((1,3-Dioxo-6-(1H-pyrrol-1-yl)-2,3-dihydroisoquinolin-4(1H)-ylidene)methylamino)butanoic acid A mixture of (E)-4-(methoxymethylene)-6-(1H-pyrrol-1-yl)isoquinoline-1,3(2H,4H)-dione (201 mg, 0.75 mmole), dimethylformamide (5 mL), and 4-aminobutanoic acid (78 mg, 0.75 mmole) is stirred at room temperature for 1 hour. The reaction mixture is diluted with ether, filtered, washed with fresh ether and dried to give a beige solid, 215 mg, (84%), mp 230-40° C. dec; MS (ES+): m/z 338.1 (M+H).

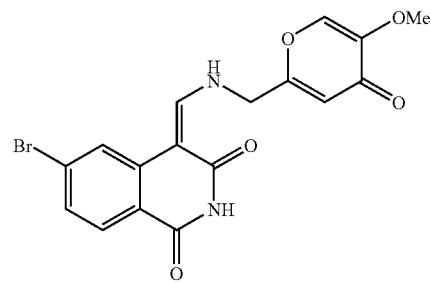

Example 316

6-Bromo-4-{[(5-methoxy-4-oxo-4H-pyran-2-ylmethyl)-amino]-methylene}-4H-isoquinoline-1,3-dione A mixture of 2-aminomethyl-5-methoxy-pyran-4-one (116 mg, 0.75 mmole), 4 mL of N,N-dimethylformamide and 4-methoxymethylene-6-bromo-4H-isoquinoline-1,3-dione (212 mg, 0.75 mmole) is stirred for one hour at ambient temperature. The reaction mixture is evaporated to dryness, dissolved in 7.5% methanol in chloroform passed through Florisil eluting with 7.5% methanol in chloroform. The eluate is evaporated, treated with acetonitrile, the resulting solid filtered and dried to give a light pink solid, 152 mg, (50%), mp 259-61° C. dec; MS (ES⁻): m/z 403 (M−H).

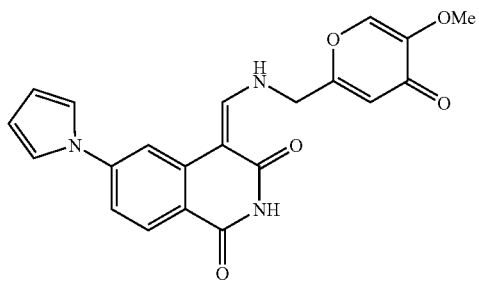

Example 317

4-{[(5-Methoxy-4-oxo-4H-pyran-2-ylmethyl)-amino]-methylene}-6-pyrrol-1-yl-4H-isoquinoline-1,3-dione A mixture of 2-aminomethyl-5-methoxy-pyran-4-one (116 mg, 0.75 mmole), 4 mL of N,N-dimethylformamide and 4-methoxymethylene-6-pyrrol-1-yl-4H-isoquinoline-1,3-dione (201 mg, 0.80 mmole) is stirred for one hour at ambient temperature. The reaction mixture is evaporated to dryness, dissolved in 7.5% methanol in chloroform passed through Florisil eluting with 7.5% methanol in chloroform. The eluate is evaporated, treated with acetonitrile, the resulting solid filtered and dried to give a beige solid, 106 mg, (36%), mp 251-4° C. dec; MS (ES⁻): m/z 390.1 (M−H).

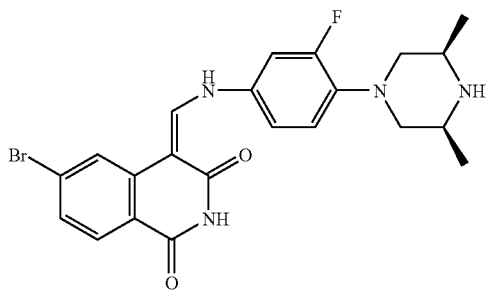

Example 318

(4Z)-6-Bromo-4-[({4-[(3R,5S)-3,5-dimethylpiperazin-1-yl]-3-fluorophenyl}amino)methylene]isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione 1.28 g (76.6% yield) of yellow solid is obtained from 1.00 g (3.50 mmol) of (4E)-6-bromo-4-(methoxymethylene)isoquinoline-1,3(2H,4H)-dione, and 1.00 g (4.20 mmol) of {4-[(3R,5S)-3,5-dimethylpiperazin-1-yl]-3-fluorophenyl}amine: mp 168-169° C.; MS (ESI) m/z 473.0 (M+H)⁺¹

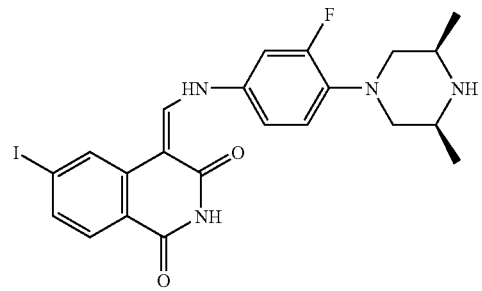

Example 319

(4Z)-4-[({4-[(3R,5S)-3,5-Dimethylpiperazin-1-yl]-3-fluorophenyl}amino)methylene]-6-iodoisoquinoline-1,3(2H,4H)-dione (75)

Using the procedure described for the preparation of 4Z)-6-bromo-4-({[4-(3,5-dimethylpiperazin-1-yl)phenyl]amino}methylene)isoquinoline-1,3(2H,4H)-dione, 0.21 g (65.6% yield) of yellow solid is obtained from 0.2 g (0.60 mmol) of (4E)-6-iodo-4-(methoxymethylene)isoquinoline-1,3(2H,4H)-dione, and 0.17 g (0.72 mmol) of {4-[(3R,5S)-3,5-dimethylpiperazin-1-yl]-3-fluorophenyl}amine: mp 173-174° C.; MS (ESI) m/z 521.0 (M+H)⁺¹

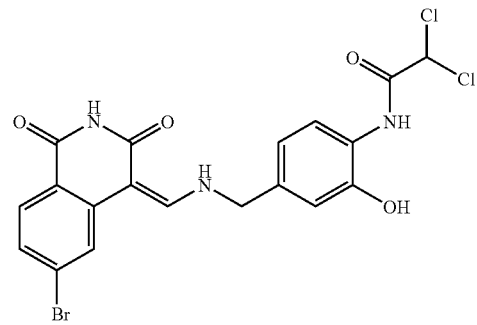

Example 320

N-[4-({[(Z)-(6-Bromo-1,3-dioxo-2,3-dihydroisoquinolin-4(1H)-ylidene)methyl]amino}methyl)-2-hydroxyphenyl]-2,2-dichloroacetamide Following the acetylation and desilylation procedure employed for the preparation of N-[2-hydroxy-4-({[(Z)-(6-iodo-1,3-dioxo-2,3-dihydroisoquinolin-4(1H)-ylidene)methyl]amino}methyl)phenyl]benzamide, (4Z)-4-[({4-amino-3-[(triisopropylsilyl)oxy]benzyl}amino)methylene]-6-bromoisoquinoline-1,3(2H,4H)-dione (60 mg, 0.11 mmol) is reacted with dichloroacetyl chloride (110 µL, 1.1 mmol). Following desilylation and precipitation, N-[4-({[(Z)-(6-bromo-1,3-dioxo-2,3-dihydroisoquinolin-4(1H)-ylidene)

methyl]amino}methyl)-2-hydroxyphenyl]-2,2-dichloroacetamide is obtained 8.8 mg, 16%).

MS (ES−): 498.0, 500.0 (M−H)−

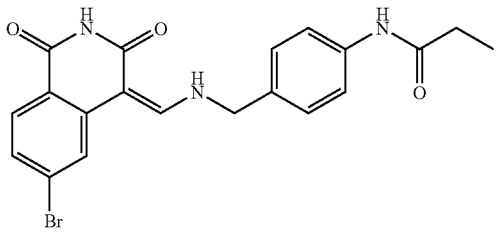

Example 321

N-[4-({[(Z)-(6-Bromo-1,3-dioxo-2,3-dihydroisoquinolin-4(1-ylidene)methyl]amino}methyl)phenyl]propanamide To a 0° C. solution of (4Z)-4-{[4-amino benzylamino]methylene}-6-iodoisoquinoline-1,3(2H,4H)-dione (35 mg, 0.10 mmol) in N,N-dimethylformamide/dimethylsulfoxide (1:1, 2 mL) is added triethylamine (26 μL, 0.20 mmol) followed by propionyl chloride (87 μL, 1.0 mmol). After stirring at room temperature for 30 minutes, the reaction mixture is quenched by the addition of water. The precipitated solid is collected, washed successively with water, diethyl ether, and methanol, and dried under house vacuum to give N-[4-({[(Z)-(6-bromo-1,3-dioxo-2,3-dihydroisoquinolin-4(1H)-ylidene)methyl]amino}methyl)phenyl]propanamide (38 mg, 88%).

MS (ES−): 426.1, 428.2 (M−H)−

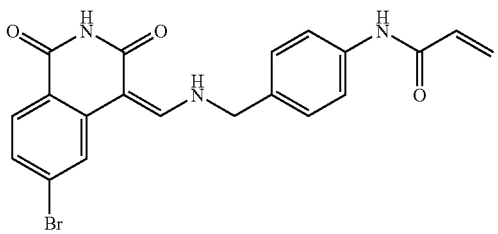

Example 322

N-[4-({[(Z)-(6-Bromo-1,3-dioxo-2,3-dihydroisoquinolin-4(1H)-ylidene)methyl]amino}methyl)phenyl]acrylamide To a 0° C. solution of (4Z)-4-{[4-amino benzylamino]methylene}-6-iodoisoquinoline-1,3(2H,4H)-dione (35 mg, 0.10 mmol) in N,N-dimethylformamide/dimethylsulfoxide (1:1, 2 mL) is added triethylamine (26 μL, 0.20 mmol) followed by acryloyl chloride (81 μL, 1.0 mmol). After stirring at room temperature for 30 minutes, the reaction mixture is quenched by the addition of water. The precipitated solid is collected, washed successively with water, diethyl ether, and methanol, and dried under house vacuum to give N-[4-({[(Z)-(6-bromo-1,3-dioxo-2,3-dihydroisoquinolin-4(1H)-ylidene)methyl]amino}methyl)phenyl]propanamide (25 mg, 58%).

MS (ES−): 424.1 (M−H)−

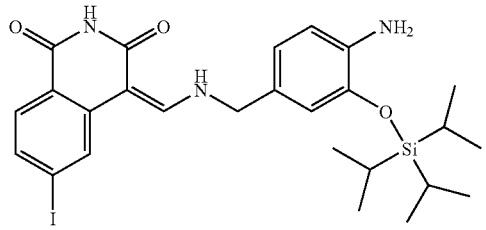

Example 323

(4Z)-4-[({4-Amino-3-[(triisopropylsilyl)oxy]benzyl}amino)methylene]-6-iodoisoquinoline-1,3(2H,4H)-dione A mixture of 3-hydroxy-4-nitrobenzaldehyde (1.3 g, 7.5 mmol), and methoxy]amine hydrochloride (0.7 g, 8.4 mmol) in pyridine (40 mL) is stirred overnight at room temperature. The solvent is then evaporated under reduced pressure, and the residue is partitioned between ethyl acetate and water. The organic layer is washed once with water and once with saturated aqueous sodium chloride solution, dried over anhydrous sodium sulfate, decanted, and concentrated under reduced pressure to give 3-hydroxy-4-nitrobenzaldehyde O-methyloxime as a yellow solid (1.5 g, 100%).

MS (ES−): 195.2 (M−H)−

To a solution of 3-hydroxy-4-nitrobenzaldehyde O-methyloxime (5.0 g, 25 mmol) in N,N-dimethylformamide (40 mL) is added imidazole (1.8 g, 27 mmol), followed by triisopropylsilyl chloride (6.0 mL, 28 mmol), and 4-(dimethylamino)pyridine (catalytic amount). After stirring overnight at room temperature, the reaction mixture is diluted with diethyl ether (200 mL) and then washed twice with water and once with saturated aqueous sodium chloride solution. The organic phase is then dried over anhydrous magnesium sulfate, filtered, and concentrated under reduced pressure. The crude solid is purified by flash chromatography (hexanes/ethyl acetate) to give 4-nitro-3-[(triisopropylsilyl)oxy]benzaldehyde O-methyloxime as a white solid (6.2 g, 70%).

TOF MS (ES+): 353.2 (M+H)+

A solution of 4-nitro-3-[(triisopropylsilyl)oxy]benzaldehyde O-methyloxime (3.1 g, 9.8 mmol) in ethanol (100 mL) and tetrahydrofuran (80 mL) is degassed with solid carbon dioxide, then charged with 10% palladium on carbon (200 mg) and glacial acetic acid (1.3 mL). The mixture is shaked under 45 psi hydrogen gas for 36 hours. The mixture is then filtered through a pad of diatomaceous earth, and the filtrate is concentrated under reduced pressure to give {4-(aminomethyl)-2-[(triisopropylsilyl)oxy]phenyl}amine, a golden semi-solid, as its diacetic acid salt. This material is used in the subsequent step without further purification.

GC-MS (ES+): 294 (M+)

To a suspension of (4E)-6-iodo-4-(methoxymethylene)isoquinoline-1,3(2H,4H)-dione (0.66 g, 2.0 mmol) and {4-(aminomethyl)-2-[(triisopropylsilyl)oxy]phenyl}amine diacetic acid (0.84 g, 2.0 mmol) in tetrahydrofuran (20 mL) is added triethylamine (0.78 mL, 6.0 mmol). The mixture is stirred at room temperature for three hours and then concentrated under reduced pressure. The residue is triturated with water, and the resulting solid is collected by filtration and washed successively with water and diethyl ether. Following drying under house vacuum, (4Z)-4-[({4-amino-3-[(triisopropylsilyl)oxy]benzyl}-amino)methylene]-6-iodoiso-quinoline-1,3(2H,4]-dione is obtained (0.97 g, 81%).

MS (ES+): 592.2 (M+H)+

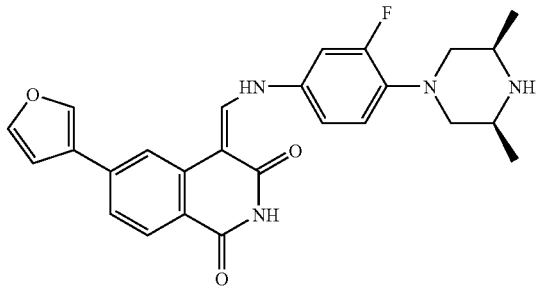

Example 324

(4Z)-4-[({4-[(3R,5S)-3,5-Dimethylpiperazin-1-yl]-3-fluorophenyl}amino)methylene]-6-(3-furyl)iso-quinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.21 g (56.7% yield) of yellow solid is obtained from 0.40 (0.85 mmol) of 4Z)-6-bromo-4-[({4-[(3R,5S)-3,5-dimethylpiperazin-1-yl]-3-fluorophenyl}amino)methylene]iso-quinoline-1,3(2H,4H)-dione, 0.14 g (1.3 mmol) of 3-furanboronic acid, 0.08 g (0.085 mmol) of Pd(dba)$_3$, 0.03 g (0.17 mmol) of t-Bu$_3$P, and 0.18 g (1.70 mmol) of Na$_2$CO$_3$: mp 222-223° C.; MS (ESI) m/z 461.1 (M+H)$^{+1}$

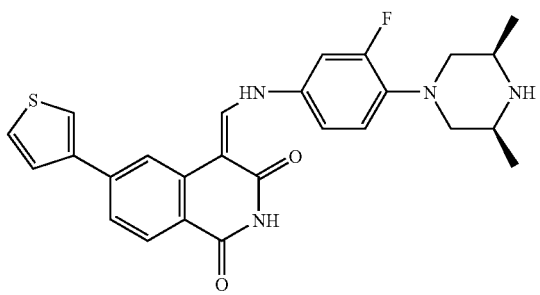

Example 325

(4Z)-4-[({4-[(3R,5S)-3,5-Dimethylpiperazin-1-yl]-3-fluorophenyl}amino)methylene]-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.18 g (45.0% yield) of yellow solid is obtained from 0.40 (0.85 mmol) of 4Z)-6-bromo-4-[({4-[(3R,5S)-3,5-dimethylpiperazin-1-yl]-3-fluorophenyl}amino)methylene]iso-quinoline-1,3(2H,4H)-dione, 0.16 g (1.3 mmol) of 3-thiopheneboronic acid, 0.08 g (0.085 mmol) of Pd(dba)$_3$, 0.03 g (0.17 mmol) of t-Bu$_3$P, and 0.18 g (1.70 mmol) of Na$_2$CO$_3$: mp 214-215° C.; MS (ESI) m/z 477.1 (M+H)$^{+1}$

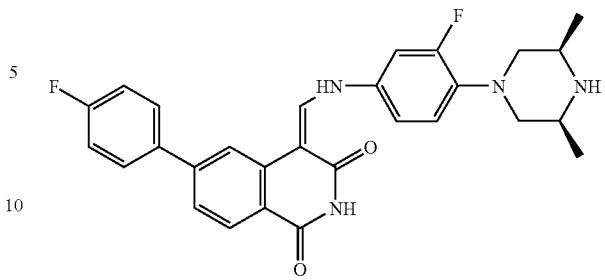

Example 326

(4Z)-4-[({4-[(3R,5S)-3,5-Dimethylpiperazin-1-yl]-3-fluorophenyl}amino)methylene]-6-(4-fluorophenyl)isoquinoline-1,3(2H,4H)-dione (78)

Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.16 g (39.0% yield) of yellow solid is obtained from 0.40 (0.85 mmol) of 4Z)-6-bromo-4-[({4-[(3R,5S)-3,5-dimethylpiperazin-1-yl]-3-fluorophenyl}amino)methylene]iso-quinoline-1,3(2H,4H)-dione, 0.18 g (1.3 mmol) of 4-fluorophenylboronic acid, 0.08 g (0.085 mmol) of Pd(dba)$_3$, 0.03 g (0.17 mmol) of t-Bu$_3$P, and 0.18 g (1.70 mmol) of Na$_2$CO$_3$: mp 182-183° C.; MS (ESI) m/z 489.1 (M+H)$^{+1}$

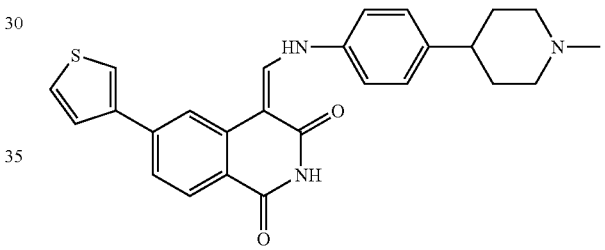

Example 327

(4Z)-4-({[4-(1-Methylpiperidin-4-yl)phenyl]amino}methylene)-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.041 g (21.6. % yield) of yellow solid is obtained from 0.40 (0.68 mmol) of (4Z)-6-bromo-4-({[4-(1-methylpiperidin-4-yl)phenyl]amino}methylene)isoquinoline-1,3(2H,4H)-dione, 0.17 g (1.02 mmol) of 3-thiopheneboronic acid, 0.08 g (0.09 mmol) of Pd(dba)$_3$, 0.03 g (0.15 mmol) of t-Bu$_3$P, and 0.16 g (1.51 mmol) of Na$_2$CO$_3$: mp 217-218° C.; MS (ESI) m/z 444.2 (M+H)$^{+1}$

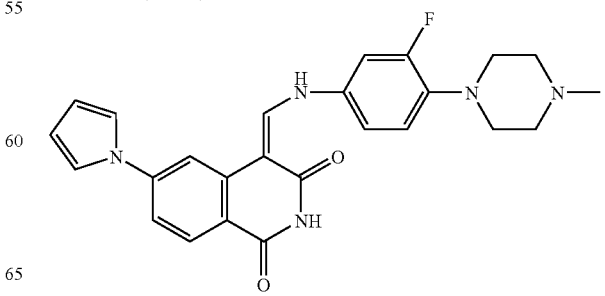

Example 328

(4Z)-4-({[3-Fluoro-4-(4-methylpiperazin-1-yl)phenyl]amino}methylene)-6-(1H-pyrrol-1-yl)isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 0.28 g of tan solid is obtained from 0.2 g (0.746 mmol) of (4E)-4-(methoxy-8.42 g (methylene)-6-(1H-pyrrol-1-yl)isoquinoline-1,3(2H,4H)-dione and 0.187 g (0.895 mmol) of [3-fluoro-4-(4-methylpiperazin-1-yl)phenyl]amine: mp 206-207° C.; MS (ESI) m/z 446.2 (M+H)$^{+1}$

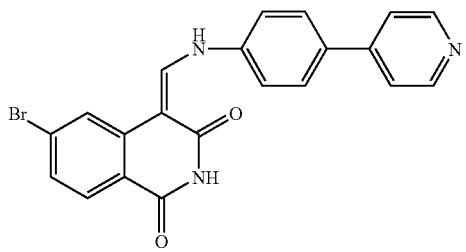

Example 329

6-Bromo-4-[(4-pyridin-4-yl-phenylamino)-methylene]-4H-isoquinoline-1,3-dione

4-Pyridin-4-yl-phenylamine (130 mg, 0.76 mmol) and 6-bromo-4-methoxymethylene-4H-isoquinoline-1,3-dione (200 mg, 0.71 mmol) is heated in N,N-dimethylformamide (10 mL) at 100° C. for 2 h. EtOAc (100 mL) and H$_2$O (20 mL) is then added. The EtOAc layer is washed with H$_2$O (3×20 mL) and brine (15 mL) and dried over MgSO$_4$. After removal of EtOAc, the precipitate is collected and washed with MeOH and Et$_2$O and dried to provide the title compound (230 mg, 77%). $^1$H NMR (300 MHz, DMSO) δ 12.59 (1H, d, J=12.9 Hz), 11.50 (1H, s), 9.0 (1H, d, J=12.6 Hz), 8.53-8.64 (3H, m), 7.43-7.95 (8H, m). MS (ESI) m/z 420.0, 422.0 (M+H)$^{+1}$; Anal. Cacl. for C21H14BrN3O2: C, 60.02; H, 3.36; N, 10.00. Found: C, 59.4; H, 3.26; N, 9.34.

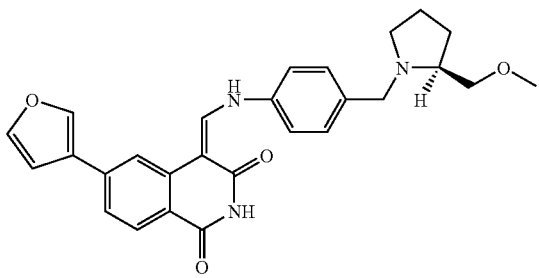

Example 330

(4Z)-6-(3-Furyl)-4-{[(4-{[(2R)-2-(methoxymethyl)pyrrolidin-1-yl]methyl}phenyl)amino]methylene}isoquinoline-1,3(2H,4H)-dione Using the procedure described for the preparation of (4Z)-6-(4-fluorophenyl)-4-({[4-(piperidin-1-'ylmethyl)phenyl]amino}methylene)isoquinoline-1,3(2H,4H)-dione, 130 mg (33% yield) is obtained as a yellow solid from 400 mg (0.85 mmol) of (4Z)-6-bromo-4-{[(4-{[(2R)-2-(methoxymethyl)pyrrolidin-1-yl]methyl}phenyl)amino)methylene}isoquinoline-1,3(2H,4H)-dione and 3-furan boronic acid 238 mg, (2.13 mmol).; mp 130-131° C.
MS (ESI) m/z 458.1 (M+1)$^+$

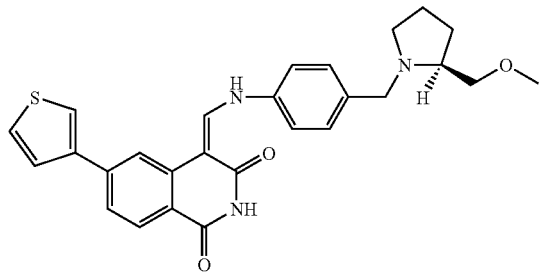

Example 331

(4Z)-4-{[(4-{[(2R)-2-(Methoxymethyl)pyrrolidin-1-yl]methyl}phenyl)amino]methylene}-6-thien-3-yl-isoquinoline-1,3(2H,4H)-dione Using the procedure described for the preparation of (4Z)-6-(4-fluorophenyl)-4-({[4-(piperidin-1-ylmethyl)phenyl]amino}methylene)isoquinoline-1,3(2H,4H)-dione, 90 mg (18% yield) is obtained as a yellow solid from 500 mg (1.06 mmol) of (4Z)-6-bromo-4-{[(4-{[(2R)-2-(methoxymethyl)pyrrolidin-1-yl]methyl}phenyl)amino)methylene}isoquinoline-1,3(2H,4H)-dione and 3-thiophine boronic acid 340 mg, (2.65 mmol).; mp 95-96° C.
MS (ESI) m/z 474.1 (M+1)$^+$

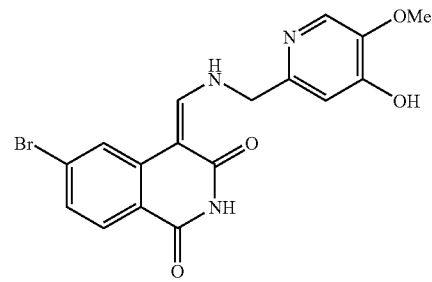

Example 332

6-Bromo-4-{[(4-hydroxy-5-methoxy-pyridin-2-ylmethyl)-amino]-methylene}-4H-isoquinoline-1,3-dione A mixture of 2-aminomethyl-5-methoxy-pyridin-4-ol (123 mg, 0.80 mmole), 4 mL of N,N-dimethylformamide and 4-methoxymethylene-6-bromo-1-yl-4H-isoquinoline-1,3-dione (226 mg, 0.80 mmole) is added and the reaction mixture and stirred for one hour. The reaction mixture is filtered and washed with acetonitrile, the solid filtered and dried to give a white solid, 90 mg, (28%), mp 209-11° C. dec;
MS (ES$^+$): m/z 402 (M+H).

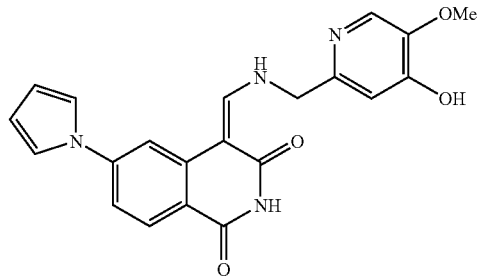

Example 333

4-[(3-Hydroxy-4-methoxy-benzylamino)-methylene]-6-pyrrol-1-yl-4H-isoquinoline-1,3-dione A mixture of 2-aminomethyl-5-methoxy-pyridin-4-ol (123 mg, 0.80 mmole), 4 mL of N,N-dimethylformamide and 4-methoxymethylene-6-pyrrol-1-yl-4H-isoquinoline-1,3-dione (215 mg, 0.80 mmole) is added and the reaction mixture stirred for one hour. The reaction mixture is evaporated to dryness and treated with acetonitrile, the solid filtered and dried to give a white solid, 199 mg, (65%), mp 199-209° C. dec; MS (ES$^+$): m/z 391.1 (M+H).

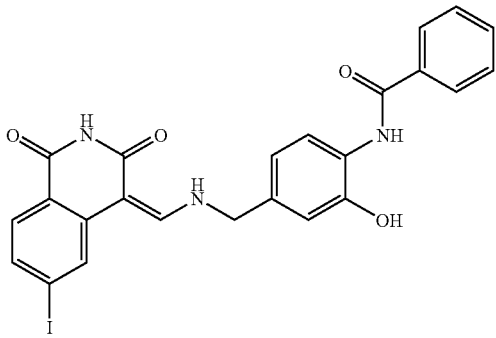

Example 334

N-[2-Hydroxy-4-({[(Z)-(6-iodo-1,3-dioxo-2,3-dihydroisoquinolin-4(1H)-ylidene)methyl]amino}methyl)phenyl]benzamide To a solution of (4Z)-4-[({4-amino-3-[(triisopropylsilyl)oxy]benzyl}amino)methylene]-6-iodoisoquinoline-1,3(2H,4H)-dione (65 mg, 0.11 mmol) in tetrahydrofuran (6 mL) is added 4-methylmorpholine (36 μL, 0.33 mmol), and the mixture is cooled to 0° C. in an ice-water bath. Benzoyl chloride (38 μL, 0.33 mmol) is added and the mixture is allowed to stir at room temperature for one hour. To the mixture is then added 1.0 M tetrabutylammonium fluoride solution in tetrahydrofuran (1 mL, 1 mmol). After heating for 10 minutes at 55° C., water is added. The precipitated solid is collected by filtration, washed with water and acetonitrile, and dried under house vacuum to give N-[2-hydroxy-4-({[(Z)-(6-iodo-1,3-dioxo-2,3-dihydroisoquinolin-4(1H)-ylidene)methyl]amino}methyl)phenyl]benzamide (34 mg, 58%).

MS (ES$^-$): 538.2 (M−H)$^-$

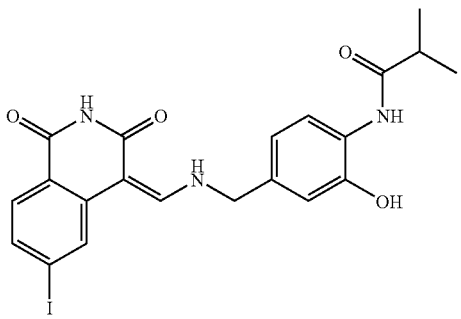

Example 335

N-[2-Hydroxy-4-({[(Z)-(6-iodo-1,3-dioxo-2,3-dihydroisoquinolin-4(1H)-ylidene)methyl]amino}methyl)phenyl]-2-methylpropanamide Following the acetylation and desilylation procedure employed for the preparation of N-[2-hydroxy-4-({[(Z)-(6-iodo-1,3-dioxo-2,3-dihydroisoquinolin-4(1H)-ylidene)methyl]amino}methyl)phenyl]benzamide, (4Z)-4-[({4-amino-3-[(triisopropylsilyl)oxy]benzyl}amino)methylene]-6-iodoisoquinoline-1,3(2H,4H)-dione (65 mg, 0.11 mmol) is reacted with isobutyryl chloride (38 μL, 0.33 mmol). Following desilylation and precipitation, N-[2-hydroxy-4-({[(Z)-(6-iodo-1,3-dioxo-2,3-dihydroisoquinolin-4(1H)-ylidene)methyl]amino}methyl)phenyl]-2-methylpropanamide is obtained (31 mg, 56%).

MS (ES$^-$): 504.2 (M−H)$^-$

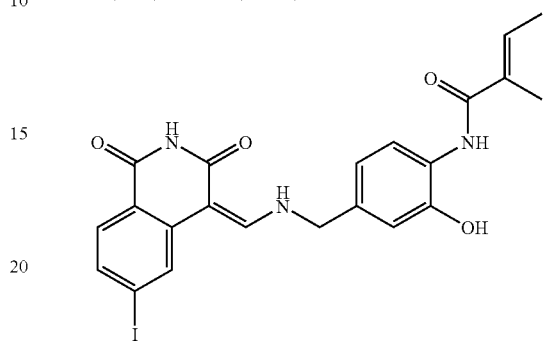

Example 336

(2E)-N-[2-Hydroxy-4-({[(Z)-(6-iodo-1,3-dioxo-2,3-dihydroisoquinolin-4(1H)-ylidene)methyl]amino}methyl)phenyl]-2-methylbut-2-enamide General Acylation, Desilylation Procedure B:

To a suspension or solution of carboxylic acid, in this case tiglic acid (0.11 g, 1.1 mmol) in anhydrous acetonitrile (3 mL) is added oxalyl chloride (neat, 100 μL, 1.1 mmol). The mixture is shaken at 65° C. for 30 minutes and then reduced to half volume under reduced pressure. The resulting acetonitrile solution is then added to a solution of (4Z)-4-[({4-amino-3-[(triisopropylsilyl)oxy]benzyl}amino)methylene]-6-iodo-isoquinoline-1,3(2H,4H)-dione (65 mg, 0.11 mmol) and diisopropylethylamine (380 μL, 2.2 mmol) in tetrahydrofuran (3 mL) After stirring overnight at room temperature, the reaction mixture is concentrated to dryness under reduced pressure. Tetrabutylammonium fluoride solution (1.0 M, 2.0 mL, 2.0 mmol) is added and the mixture is shaken at 55° C. for 2 hours and then allowed to cool to room temperature. Following concentration, the residue is triturated with water and the resulting solid collected by filtration, washed with acetonitrile, and dried under house vacuum to give (2E)-N-[2-hydroxy-4-({[(Z)-(6-iodo-1,3-dioxo-2,3-dihydroisoquinolin-4(1H)-ylidene)methyl]amino}methyl)phenyl]-2-methylbut-2-enamide (12 mg, 21%).

MS (ES$^-$): 516.1 (M−H)$^-$

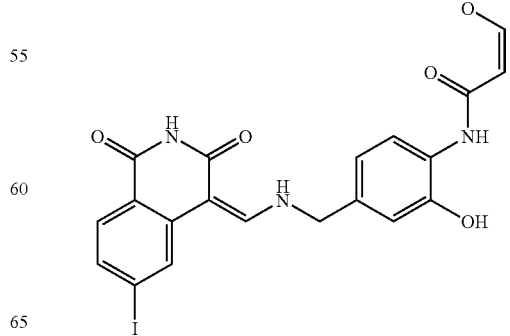

Example 337

(2Z)-3-Chloro-N-[2-hydroxy-4-({[(Z)-(6-iodo-1,3-dioxo-2,3-dihydroisoquinolin-4(1H)-ylidene)methyl]amino}methyl)phenyl]acrylamide Following the acetylation and desilylation procedure employed for the preparation of (2E)-N-[2-hydroxy-4-({[(Z)-(6-iodo-1,3-dioxo-2,3-dihydroisoquinolin-4(1H)-ylidene)methyl]amino}methyl)phenyl]-2-methylbut-2-enamide, (4Z)-4-[({4-amino-3-[(triisopropylsilyl)oxy]benzyl}amino)methylene]-6-iodoisoquinoline-1,3(2H,4H)-dione (65 mg, 0.11 mmol) is reacted with acid chloride derived from cis-3-chloroacrylic acid (0.12 g, 1.1 mmol). Following desilylation and precipitation, (2Z)-3-chloro-N-[2-hydroxy-4-({[(Z)-(6-iodo-1,3-dioxo-2,3-dihydroisoquinolin-4(1H)-ylidene)methyl]amino}methyl)phenyl]acrylamide is obtained as a solid (10 mg, 17

MS (ES−): 522.0 (M−H)−

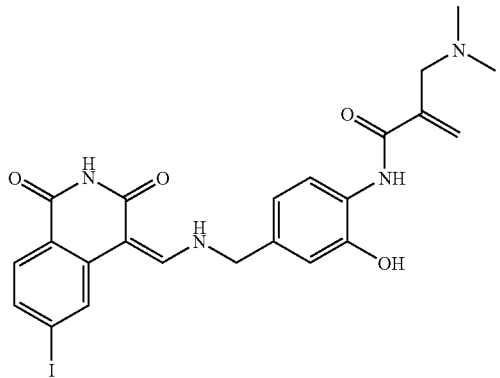

Example 338

2-[(Dimethylamino)methyl]-N-[2-hydroxy-4-({[(Z)-(6-iodo-1,3-dioxo-2,3-dihydroisoquinolin-4(1H)-ylidene)methyl]amino}methyl)phenyl]acrylamide Following the acetylation and desilylation procedure employed for the preparation of (2E)-N-[2-hydroxy-4-({[(Z)-(6-iodo-1,3-dioxo-2,3-dihydroisoquinolin-4(1H)-ylidene)methyl]amino}methyl)phenyl]-2-methylbut-2-enamide, (4Z)-4-[({4-amino-3-[(triisopropylsilyl)oxy]benzyl}amino)methylene]-6-iodoisoquinoline-1,3(2H,4H)-dione (65 mg, 0.11 mmol) is reacted with acid chloride derived from 2-dimethylaminomethyl acrylic acid (Wissner, A.; Overbeek, E.; Reich, M. F.; Floyd, M. B.; Johnson, B. D.; Mamuya, N.; Rosfjord, E. C.; Discafani, C.; Davis, R.; Shi, X.; Rabindran, S. K.; et al. J. Med. Chem. 46; 1; 2003; 49-63, 0.18 g, 1.1 mmol). Following desilylation and precipitation, 2-[(dimethylamino)methyl]-N-[2-hydroxy-4-({[(Z)-(6-iodo-1,3-dioxo-2,3-dihydroisoquinolin-4(1H)-ylidene)methyl]amino}methyl)phenyl]acrylamide is obtained as a solid (19 mg, 32%).

MS (ES−): 545.2 (M−H)−

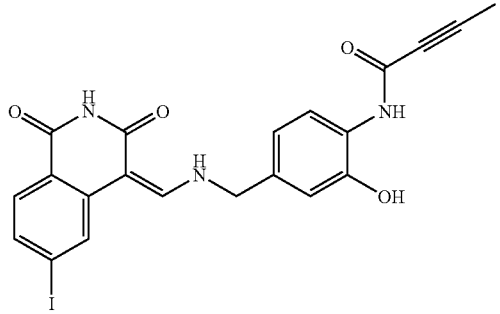

Example 339

N-[2-Hydroxy-4-({[(Z)-(6-iodo-1,3-dioxo-2,3-dihydroisoquinolin-4(1H)-ylidene)methyl]amino}methyl)phenyl]but-2-ynamide Following the acetylation and desilylation procedure employed for the preparation of (2E)-N-[2-hydroxy-4-({[(Z)-(6-iodo-1,3-dioxo-2,3-dihydroisoquinolin-4(1H)-ylidene)methyl]aminomethyl)phenyl]-2-methylbut-2-enamide, (4Z)-4-[({4-amino-3-[(triisopropylsilyl)oxy]benzyl}amino)methylene]-6-iodoisoquinoline-1,3(2H,4H)-dione (65 mg, 0.11 mmol) is reacted with acid chloride derived from 2-butynoic acid (92 mg, 1.1 mmol). Following desilylation and precipitation, N-[2-hydroxy-4-({[(Z)-(6-iodo-1,3-dioxo-2,3-dihydroisoquinolin-4(1H)-ylidene)methyl]amino}methyl)phenyl]but-2-ynamide is obtained as a solid (20 mg, 36%).

MS (ES−): 500.0 (M−H)−

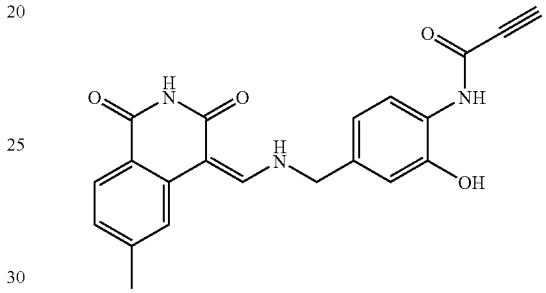

Example 340

N-[2-Hydroxy-4-({[(Z)-(6-iodo-1,3-dioxo-2,3-dihydroisoquinolin-4(1H)-ylidene)methyl]amino}methyl)phenyl]prop-2-ynamide Following the acetylation and desilylation procedure employed for the preparation of (2E)-N-[2-hydroxy-4-({[(Z)-(6-iodo-1,3-dioxo-2,3-dihydroisoquinolin-4(1H)-ylidene)methyl]amino}methyl)phenyl]-2-methylbut-2-enamide(4Z)-4-[({4-amino-3-[(triisopropylsilyl)oxy]benzyl}amino)methylene]-6-iodoisoquinoline-1,3(2H,4H)-dione (65 mg, 0.11 mmol) is reacted with acid chloride derived from propiolic acid (77 mg, 1.1 mmol). Following desilylation and precipitation, N-[2-hydroxy-4-({[(Z)-(6-iodo-1,3-dioxo-2,3-dihydroisoquinolin-4(1H)-ylidene)methyl]amino}methyl)phenyl]prop-2-ynamide is obtained as a solid (22 mg, 41%).

MS (ES−): 486.0 (M−H)−

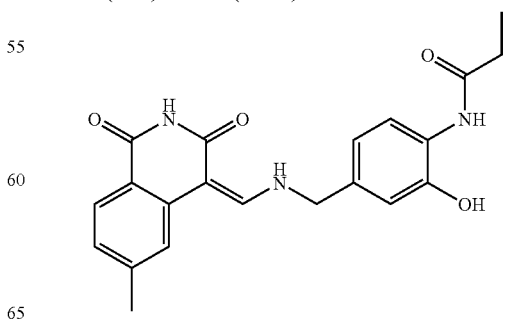

Example 341

N-[2-Hydroxy-4-({[(Z)-(6-iodo-1,3-dioxo-2,3-dihydroisoquinolin-4(1H)-ylidene)methyl]amino}methyl)phenyl]propanamide Following the acetylation and desilylation procedure employed for the preparation of N-[2-hydroxy-4-({[(Z)-(6-iodo-1,3-dioxo-2,3-dihydroisoquinolin-4(1H)-ylidene)methyl]amino}methyl)phenyl]benzamide, (4Z)-4-[({4-amino-3-[(triisopropylsilyl)oxy]benzyl}amino)methylene]-6-iodoisoquinoline-1,3(2H,4H)-dione (75 mg, 0.13 mmol) is reacted with propionyl chloride (110 μL, 1.3 mmol). Following desilylation and precipitation, N-[2-hydroxy-4-({[(Z)-(6-iodo-1,3-dioxo-2,3-dihydroisoquinolin-4(1H)-ylidene)methyl]amino}methyl)phenyl]-2-methylpropanamide is obtained (9.3 mg, 15%).

MS (ES⁻): 490.1 (M−H)⁻

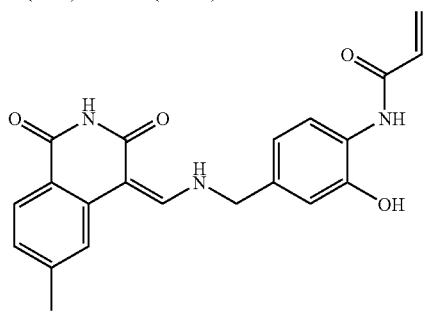

Example 342

N-[2-Hydroxy-4-({[(Z)-(6-iodo-1,3-dioxo-2,3-dihydroisoquinolin-4(1H)-ylidene)methyl]amino}methyl)phenyl]acrylamide A solution of 3-hydroxy-4-nitrobenzaldehyde O-methyloxime (5.9 g, 30 mmol) in ethanol (100 mL) and tetrahydrofuran (100 mL) is degassed with solid carbon dioxide, then charged with 10% palladium on carbon (500 mg) and concentrated hydrochloric acid (5.5 mL). The mixture is shaken under 50 psi hydrogen gas until consumption of hydrogen had ceased. The mixture is then filtered through a pad of diatomaceous earth, and the filtrate is concentrated under reduced pressure to give 2-amino-5-(aminomethyl)phenol dihydrochloride (6.1 g, 97%).

¹H NMR (300 MHz, DMSO-d₆) ppm 3.92 (d, J=5.58 Hz, 2 H), 6.99 (dd, J=8.10 Hz, 1H), 7.14 (d, J=1.4 Hz, 1H), 7.39 (d, J=8.0 Hz, 1H), 8.52 (s, 3H), 10.0 (brs, 3H), 11.0 (s, 1H).

To a suspension of (4E)-6-iodo-4-(methoxymethylene)isoquinoline-1,3(2H,4H)-dione (1.0 g, 3.0 mmol) and 2-amino-5-(aminomethyl)phenol dihydrochloride (0.64 g, 3.0 mmol) in N,N-dimethylformamide (15 mL) is added triethylamine (1.2 mL, 9.0 mmol). The mixture is stirred at room temperature for 60 hours and then concentrated to dryness under reduced pressure. The residue is then triturated with water, and the solid is collected by filtration, washed successively with diethyl ether and acetonitrile, and dried under house vacuum to provide (4Z)-4-{[(4-amino-3-hydroxybenzyl)amino]methylene}-6-iodoisoquinoline-1,3(2H,4H)-dione as a golden powder (1.3 g, 100%).

A solution of (4Z)-4-{[(4-amino-3-hydroxybenzyl)amino]methylene}-6-iodoisoquinoline-1,3(2H,4H)-dione (1.1 g, 2.3 mmol) in dimethylacetamide (12 mL) is cooled to 0° C. in an ice water bath. Acryloyl chloride (1.9 mL, 23 mmol) is added and the mixture is stirred at 0° C. for 15 minutes. The reaction mixture is then concentrated under reduced pressure and combined with impure material from a previous batch. The material is adsorbed onto flash silica gel, which is then subjected to flash chromatography (methanol/chloroform) to give N-[2-hydroxy-4-({[(Z)-(6-iodo-1,3-dioxo-2,3-dihydroisoquinolin-4(1H)-ylidene)methyl]amino}methyl)phenyl]acrylamide (1.6 g).

MS (ES⁻): 488.0 (M−H)⁻

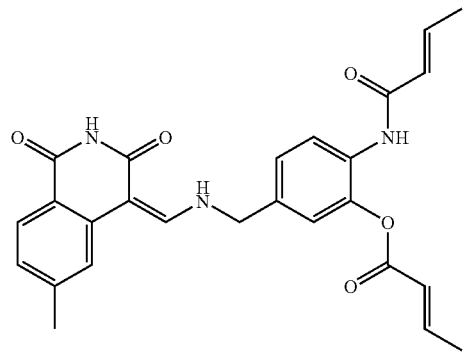

Example 343

2-[(2E)-But-2-enoylamino]-5-({[(Z)-(6-iodo-1,3-dioxo-2,3-dihydroisoquinolin-4(1H)-ylidene)methyl]amino}methyl)phenyl (2E)-but-2-enoate Following the acetylation and desilylation procedure employed for the preparation of N-[2-hydroxy-4-({[(Z)-(6-iodo-1,3-dioxo-2,3-dihydroisoquinolin-4(1H)-ylidene)methyl]amino}methyl)phenyl]benzamide, (4Z)-4-[({4-amino-3-[(triisopropylsilyl)oxy]benzyl}amino)methylene]-6-iodoisoquinoline-1,3(2H,4H)-dione (65 mg, 0.11 mmol) is reacted with crotonic anhydride (49 μL, 0.33 mmol). Following desilylation and precipitation, 2-[(2E)-but-2-enoylamino]-5-({[(Z)-(6-iodo-1,3-dioxo-2,3-dihydroisoquinolin-4(1H)-ylidene)methyl]amino}methyl)phenyl (2E)-but-2-enoate is obtained (17 mg, 27%)

MS (ES⁻): 570.1 (M−H)⁻

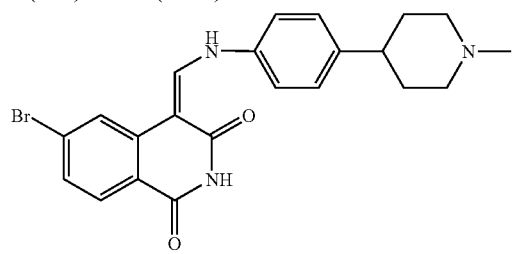

Example 344

(4Z)-6-Bromo-4-({[4-(1-methylpiperidin-4-yl)phenyl]amino}methylene)isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione (24), 1.17 g (62.6% yield) of yellow solid is obtained from 1.2 g (4.25 mmol) of (4E)-6-bromo-4-(methoxymethylene)isoquinoline-1,3(2H,4H)-dione and 0.97 g (5.10 mmol) of [4-(methylpiperidin-1-yl)phenyl]amine: mp 217-218° C.; MS (ESI) m/z 440.1-442.1 (M+H)$^{+1}$

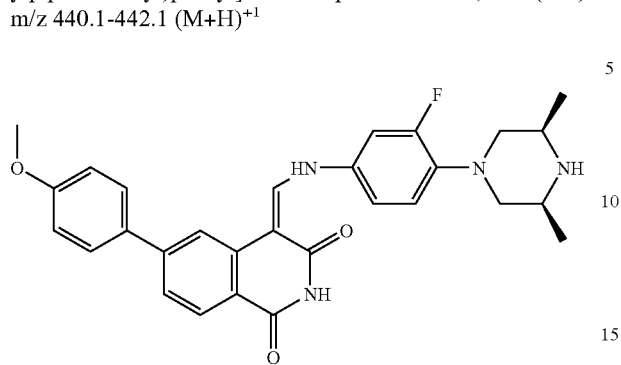

Example 345

(4Z)-4-[({4-[(3R,5S)-3,5-Dimethylpiperazin-1-yl]-3-fluorophenyl}amino)methylene]-6-(4-methoxyphenyl)isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.29 g (69.0% yield) of yellow solid is obtained from 0.40 (0.85 mmol) of (4Z)-6-bromo-4-[({4-[(3R,5S)-3,5-dimethylpiperazin-1-yl]-3-fluorophenyl}amino)methylene]isoquinoline-1,3(2H,4H)-dione, 0.18 g (1.3 mmol) of 4-methoxyphenylboronic acid, 0.08 g (0.085 mmol) of Pd(dba)$_3$, 0.03 g (0.17 mmol) of t-Bu$_3$P, and 0.18 g (1.70 mmol) of Na$_2$CO$_3$: mp 227-228° C.; MS (ESI) m/z 501.2 (M+H)$^{+1}$

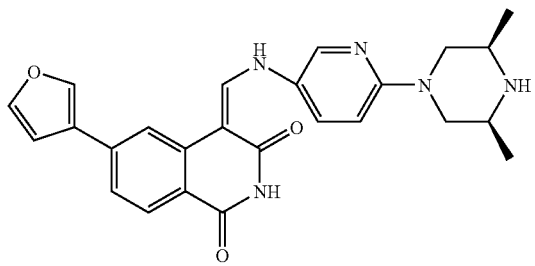

Example 346

(4Z)-4-[({5-[(3R,5S)-3,5-Dimethylpiperazin-1-yl]pyridin-3-yl}amino)methylene]-6-(3-furyl)isoquinoline-1,3(2H,4H)-dione Using the procedure described for the preparation of (4Z)-6-(3-furyl)-4-({[6-(4-methylpiperazin-1-yl)pyridin-3-yl]amino}methylene)isoquinoline-1,3(2H,4H)-dione 500 mg (47% yield) is obtained as a yellow solid from 500 mg (1.09 mmol) of 4Z)-6-bromo-4-[({5-[(3R,5S)-3,5-dimethylpiperazin-1-yl]pyridin-3-yl}amino)methylene]isoquinoline-1,3 (2H,4H)-dione and 3-furan boronic acid 245 mg, (2.19 mmol): mp 175-176° C.;

MS (ESI) m/z 444.1 (M+1)$^+$

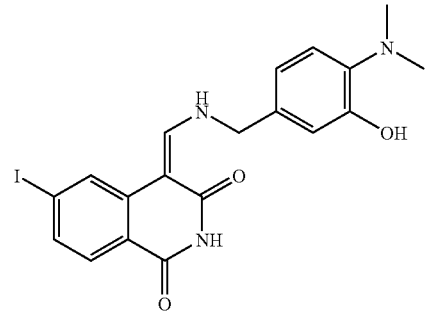

Example 347

(4Z)-4-({[4-(Dimethylamino)-3-hydroxybenzyl]amino}methylene)-6-iodoisoquinoline-1,3(2H,4H)-dione An amount of 300 mg (0.51 mmol) of (4Z)-4-[({4-amino-3-[(triisopropylsilyl)oxy]benzyl}amino)methylene]-6-iodo-isoquinoline-1,3(2H,4H)-dione and formylaldehyde (45.9 mg, 1.53 mmol) were dissolved in tetrahydrofuran (3 mL) and methanol (2 mL). After stirring for ten minutes, a mixture of sodium cyanoborohydride (64.1 mg, 1.02 mmol) and acetic acid (0.4 mL, 5.1 mmol) were added drop-wise. The mixture is allowed to stir for 2.5 hours. Tetrabutylammonium fluoride (2 mL) is added and stirred for additional 1 hour. The mixture is neutralized with 1 NHCl solution and extracted with dichloromethane (200 ml), dried over sodium sulfate and evaporated. The desired final product is purified by column chromatography to afford 60 mg (26% yield) of a light brown solid.; mp 198-199° C.

MS (ESI) m/z 464.0 (M+1)$^+$.

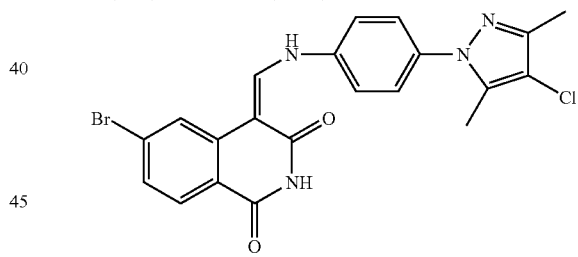

Example 348

6-Bromo-4-{[4-(4-chloro-3,5-dimethyl-pyrazol-1-yl)-phenylamino]-methylene}-4H-isoquinoline-1,3-dione The 4-(4-Chloro-3,5-dimethyl-pyrazol-1-yl)-phenylamine (130 mg, 0.58 mmol) and 6-Bromo-4-methoxymethylene-4H-isoquinoline-1,3-dione (120 mg, 0.43 mmol) is heated in N,N-dimethylformamide (10 mL) at 100° C. for 4 h. EtOAc (100 mL) and H$_2$O (20 mL) is then added. The EtOAc layer is washed with H$_2$O (3×20 mL) and brine (15 mL) and dried over MgSO$_4$. Upon removal of EtOAc, precipitate formed and the precipitate is collected and washed with MeOH and Et$_2$O and dried to provide the title compound (64 mg, 32%). $^1$H NMR (400 MHz, DMSO) δ 12.56(1H, d, J=12.4 Hz), 11.46 (1H, s), 8.98 (1H, d, J=12.4 Hz), 8.50 (1H, s), 7.43-7.94 (6H, m), 2.30 (3H, s), 2.21 (3H, s); MP: 290-

291° C.; Anal. Cacl. for $C_{21}H_{16}BrClN_4O_2$: C, 53.47; H, 3.42; N, 11.88. Found: C, 51.49; H, 2.94; N, 11.31.

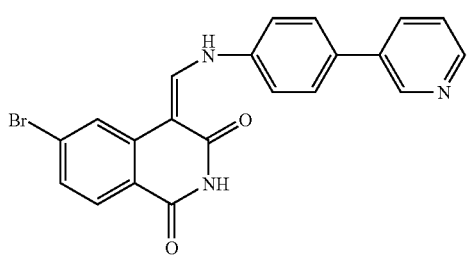

Example 349

6-Bromo-4-[(4-pyridin-3-yl-phenylamino)-methylene]-4H-isoquinoline-1,3-dione: (4Z)-6-bromo-4-{[(3-hydroxy-4propoxybenzyl)amino]methylene}isoquinoline-1,3(2H,4H)-dione Using the procedure described for the preparation of 6-bromo-4-[(4-pyridin-4-yl-phenylamino)-methylene]-4H-isoquinoline-1,3-dione, the title compound is obtained from 4-Pyridin-3-yl-phenylamine (100 mg, 0.59 mmol), 6-Bromo-4-methoxymethylene-4H-isoquinoline-1,3-dione (200 mg, 0.71 mmol) in 43% yield as a solid: $^1$H NMR (300 MHz, DMSO) δ 12.59 (1H, d, J=12.6 Hz), 11.48 (1H, s), 8.95-9.03 (2H, m), 8.53-8.57 (2H, m), 8.13 (1H, d, J=7.8 Hz), 7.73-7.94 (5H, m), 7.43-7.51 (2H, m). MS (ESI) m/z 420.0, 422.0 (M+H)$^{+1}$; Anal. Cacl. for C21H14BrN3O2: C, 60.02; H, 3.36; N, 10.00. Found: C, 57.94; H, 2.81; N, 9.66.

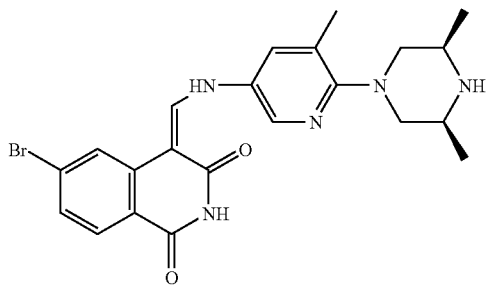

Example 350

(4Z)-6-Bromo-4-[({6-[(2R,6S)-2,6-dimethylpiperidin-4-yl]-5-methylpyridin-3-yl}amino)methylene]isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 900 mg (86% yield) of solid is obtained from 630 mg (2.23 mmol) of (4E)-6-bromo-4-(methoxymethylene)isoquinoline-1,3(2H,4H)-dione, and 0.14 g (0.608 mmol) of 6-[(2R,6S)-2,6-dimethylpiperidin-4-yl]-5-methylpyridin-3-yl}amine; mp: 194-195° C.;

MS (ESI) m/z 470.1 (M–H)$^{-1}$

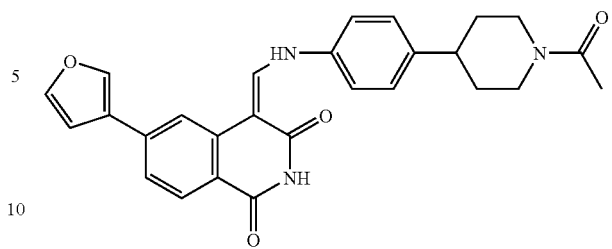

Example 351

(4Z)-4-({[4-(1-Acetylpiperidin-4-yl)phenyl]amino}methylene)-6-(3-furyl)isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.21 g (72.4 % yield) of yellow solid is obtained from 0.30 (0.68 mmol) of (4Z)-4-({[4-(1-acetylpiperidin-4-yl)phenyl]amino}methylene)-6-bromoisoquinoline-1,3(2H,4H)-dione, 0.11 g (0.98 mmol) of 3-furanboronic acid, 0.06 g (0.06 mmol) of Pd(dba)$_3$, 0.026 g (0.13 mmol) of t-Bu$_3$P, and 0.14 g (1.32 mmol) of Na$_2$CO$_3$: mp 178-179° C.; MS (ESI) m/z 456.2 (M+H)$^{+1}$

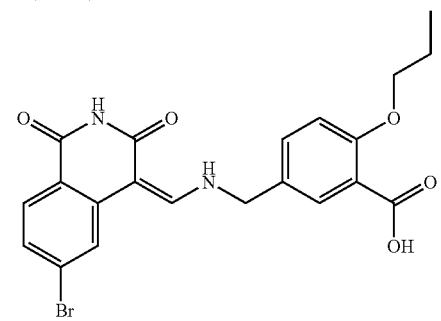

Example 352

5-({[(Z)-(6-Bromo-1,3-dioxo-2,3-dihydroisoquinolin-4(1H)-ylidene)methyl]amino}methyl)-2-propoxybenzoic acid To a solution of 5-formylsalicylic acid (5.0 g, 30 mmol) in N,N-dimethylformamide (150 mL) is added potassium carbonate (25 g, 180 mmol). The mixture is heated in an 80° C. oil bath and 1-iodopropane (6.4 mL, 66 mmol) is added. The reaction mixture is stirred overnight in a 90° C. bath and then concentrated under reduced pressure. The residue is diluted with water and acidified with concentrated hydrochloric acid to pH 8. After extracting 3× with ethyl acetate, the combined extracts were washed with saturated aqueous sodium chloride solution, dried over anhydrous sodium sulfate, decanted, and concentrated under reduced pressure. The crude oil is purified is flash chromatography (hexanes/ethyl acetate) to give propyl 5-formyl-2-propoxybenzoate as a solid (5.1 g, 68%).

TOF MS (ES$^+$): 251.1 (M+H)$^+$

To a solution of propyl 5-formyl-2-propoxybenzoate (1.0 g, 4.0 mmol) in tetrahydrofuran/methanol/water (20 mL: 20 mL: 8 mL) is added 5 N sodium hydroxide solution (2 mL, 10 mmol). The mixture is heated in a 70° C. oil bath for three hours and then allowed to cool to room temperature. While acidifying to pH 1 with concentrated hydrochloric acid, a white solid precipitated, which is collected and discarded. The filtrate is concentrated under reduced pressure, and the solid residue is collected by filtration and washed with water to give 5-formyl-2-propoxybenzoic acid as flocculent white needles (0.79 g, 95%).

TOF MS (ES⁻): 207.0 (M–H)⁻

A mixture of 5-formyl-2-propoxybenzoic acid (1.4 g, 6.7 mmol) and methoxy]amine hydrochloride (0.62 g, 7.4 mmol) in pyridine (36 mL) is stirred overnight at room temperature. After 30 minutes, the reaction mixture is concentrated under reduced pressure. The residue is taken up in ethyl acetate, washed thrice with water, dried over anhydrous sodium sulfate, decanted, and concentrated. The white crystalline product is washed with water and acetonitrile and then dried under house vacuum to give 5-[(methoxyimino)methyl]-2-propoxybenzoic acid.

TOF MS (ES⁻): 236.1 (M–H)⁻

To a solution of 5-[(methoxyimino)methyl]-2-propoxybenzoic acid (0.70 g, 2.9 mmol) in ethanol/tetrahydrofuran (1:1, 50 mL) is added concentrated hydrochloric acid (250 µL). The mixture is degassed by the addition of a small piece of dry ice; then palladium on carbon (10%, 100 mg) is added. The incomplete reaction mixture is shaken for two hours under 45 psi hydrogen, filtered through a pad of diatomaceous earth, and concentrated under reduced pressure. The material is then redissolved in ethanol/tetrahydrofuran (1:1, 50 mL), degassed, and treated with a RaNi slurry (1 mL). The mixture is shaken overnight under 45 psi hydrogen. After passing the mixture through a pad of Celite and concentrated under reduced pressure, the residue is triturated with methanol to give a solid material, which is collected by filtration. The filtrate is purified by reverse phase HPLC to give 5-(aminomethyl)-2-propoxybenzoic acid trifluoroacetate (0.15 g, 16

MS (ES⁺): 210.3 (M+H)⁺

(4E)-6-bromo-4-(methoxymethylene)isoquinoline-1,3 (2H,4H)-dione (67 mg, 0.24 mmol) and 5-(aminomethyl)-2-propoxybenzoic acid trifluoroacetate (50 mg, 0.16 mmol) were coupled in N,N-dimethylformamide (2 mL) and tetrahydrofuran (2 mL) with triethylamine (0.13 mL). The mixture is heated at 50° C. for 30 minutes and then at 65° C. overnight. Water is added and resulting mixture purified by reverse-phase HPLC to give a white solid material which is collected by filtration, washed with water, methanol, and diethyl ether and then dried under house vacuum to give 5-({[(Z)-(6-bromo-1,3-dioxo-2,3-dihydroisoquinolin-4(1H)-ylidene)methyl]amino}methyl)-2-propoxybenzoic acid (42 mg, 59%).

MS (ES⁻): 457.2, 459.2 (M–H)⁻

Example 353

5-({[(Z)-(6-Bromo-1,3-dioxo-2,3-dihydroisoquinolin-4(1H)-ylidene)methyl]amino}methyl)-2-propoxybenzamide To a solution of 5-({[(Z)-(6-bromo-1,3-dihydroisoquinolin-4(1H)-ylidene)methyl]amino}methyl)-2-propoxybenzoic acid (30 mg, 65 µmol) in N,N-dimethylformamide (1 mL) is added 1-hydroxybenzotriazole hydrate (22 mg, 0.16 mmol), 1-(3-dimethylaminopropyl)-3-ethylcarbodiimide hydrochloride (31 mg, 0.16 mmol), and 1-methylmorpholine (25 µL, 0.23 mmol). After shaking at room temperature for 1 hour, to the reaction mixture is added 30% aqueous ammonium hydroxide (5 drops). After 10 minutes of agitation, water is added to the mixture, precipitating a solid, which is collected by filtration, washed with water and methanol, and then dried under house vacuum to give 5-({[(Z)-(6-bromo-1,3-dioxo-2,3-dihydroisoquinolin-4(1H)-ylidene)methyl]amino}methyl)-2-propoxybenzamide (17 mg, 57%).

MS (ES⁻): 457.3 (M–H)⁻

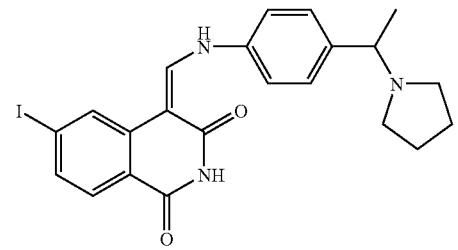

Example 354

6-Iodo-4-{[4-(1-pyrrolidin-1-yl-ethyl)-phenylamino]-methylene}-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(1-Pyrrolidin-1-yl-ethyl)-phenylamine (49 mg, 0.26 mmol), 6-iodo-4-methoxymethylene-4H-isoquinoline-1,3-dione (80 mg, 0.24 mmol) in 23% yield as a brown solid: ¹H NMR (300 MHz, CDCl3) δ 12.27(1H, d, J=12.6 Hz), 8.33-8.43(2H, m), 7.90-7.97 (2H, m), 7.46-7.62 (3H, m), 7.23(2H, d, J=8.4 Hz), 3.30 (1H, q, J=5.7 Hz), 2.65 (2H, m), 2.48 (2H, m), 1.82 (4H, m), 1.47 (3H, d, J=6.6 Hz). MS (ES pos): 488, 417. Anal. Cacl. for $C_{22}H_{22}IN_3O_2$: C, 54.22; H, 4.55; N, 8.62. Found: C, 53.72; H, 4.04; N, 7.83.

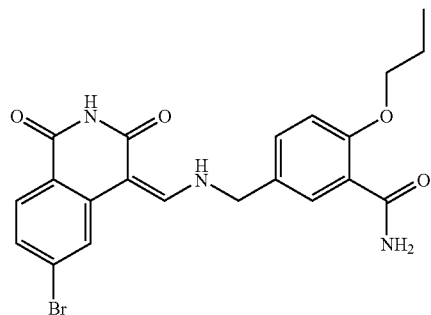

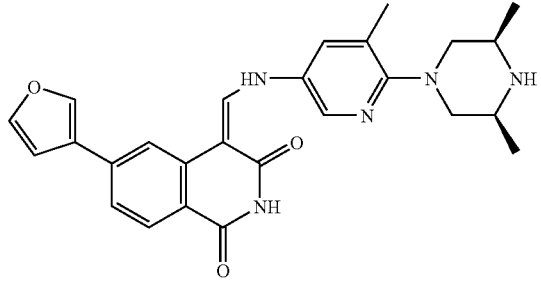

Example 355

(4Z)-4-[({6-[(3R,5S)-3,5-Dimethylpiperazin-1-yl]-5-methylpyridin-3-yl}amino)methylene]-6-(3-furyl)isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione (41), 100 mg (47.0% yield) of yellow solid is obtained from 220 mg (0.46 mmol) of, and 104 mg (0.94 mmol) of 3-furan boronic acid,: mp 195-196° C.; MS (ESI) m/z 458.1 (M+H)$^{+1}$

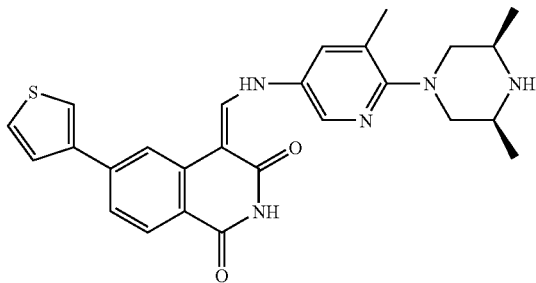

Example 356

(4Z)-4-[({6-[(3R,5S)-3,5-Dimethylpiperazin-1-yl]-5-methylpyridin-3-yl}amino)methylene]-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione (41), 120 mg (55.0% yield) of yellow solid is obtained from 220 mg (0.46 mmol) of, and 120 mg (0.94 mmol) of 3-thiophine boronic acid; mp 219-220° C.; MS (ESI) m/z 474.2 (M+H)$^{+1}$

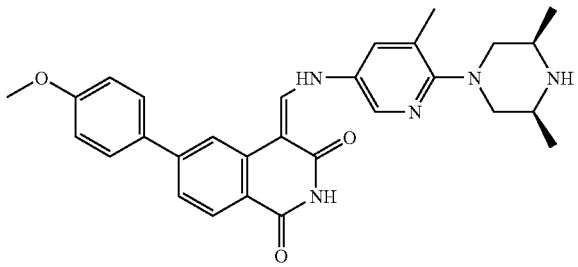

Example 357

(4Z)-4-[({6-[(3R,5S)-3,5-Dimethylpiperazin-1-yl]-5-methylpyridin-3-yl}amino)methylene]-6-(4-methoxyphenyl)isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione (41), 94 mg (41% yield) of yellow solid is obtained from 220 mg (0.46 mmol) of, and 140 mg (0.94 mmol) of 4-methoxyphenyl boronic acid: mp 213-214° C.; MS (ESI) m/z 498.2 (M+H)

Example 358

(4Z)-6-(4-Methoxyphenyl)-4-[({4-[(2-methylpyrrolidin-1-yl)methyl]phenyl}amino)-methylene]-isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.23 g (6.4.% yield) of light brown solid is obtained from 0.40 (0.91 mmol) of (4Z)-6-bromo-4-[({4-[(2-methylpyrrolidin-1-yl)methyl]phenyl}amino)methylene]-isoquinoline-1,3 (2H,4H)-dione, 0.2 g (1.31 mmol) of 4-methoxybenzylboronic acid, 0.086 g (0.90 mmol) of Pd(dba)$_3$, 0.04 g (0.18 mmol) of t-Bu$_3$P, and 0.30 g (1.8 mmol) of Na$_2$CO$_3$: mp 232-233° C.; MS (ESI) m/z 466.2 (M+H)$^{+1}$

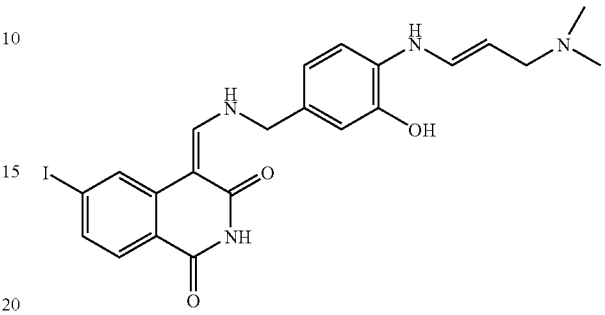

Example 359

(2E)-4-(Dimethylamino)-N-[2-hydroxy-4-({[(Z)-(6-iodo-1,3-dioxo-2,3-dihydroisoquinolin-4(1H)-ylidene)methyl]amino}methyl)phenyl]but-2-enamide An amount of 8.3 g (50.6 mmol) of (E)-4-(dimethylamino)-2-butenioc acid is added excess of 2.0M oxalyl chloride (10 mL) and refluxed at 60° C. until all the solid is in solution. To a separate flask is added 2.2 g (5.06 mmol) of '2-(acetylamino)-5-({[(Z)-(6-iodo-1,3-dioxo-2,3-dihydroisoquinolin-4(1H)-ylidene)methyl]amino}methyl)phenyl acetate, and N,N-dimethylacetamide (5 mL) and placed in an ice bath for ten minutes. The mixture containing the acid chloride is cooled to room temperature and evaporated to dryness. Dichloromethane (5 mL) is added and transferred to the flask in the ice bath slowly. The mixture is allowed to stir in the ice bath for 3 hours. It is evaporated and purified by column chromatography with 10% methanol: 80% dichloromethane: 1.5% ammonium hydroxide to give the desired product (1.2 g 43% yield) as a light-brown solid.; mp 185-186° C.

MS (ESI) m/z 547.0 (M+1)$^+$.

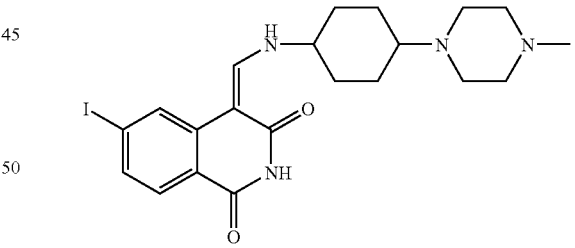

Example 360

6-Iodo-4-{[4-(4-methyl-piperazin-1-yl)-cyclohexylamino]-methylene}-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(4-Methyl-piperazin-1-yl)-cyclohexylamine (40 mg, 0.20 mmol), 6-iodo-4-methoxymethylene-4H-isoquinoline-1,3-dione (60 mg, 0.18 mmol) in 28% yield as a pale yellow solid: $^1$H NMR (400 MHz, CD3OD) δ 8.44(1H, s), 8.17 (1H, d, J=1.2 Hz), 7.76 (1H, d, J=8.4 Hz), 7.52 (1H, dd, J=8.4 and 1.6 Hz), 2.76-3.51 (10H, m), 2.75 (3H, s), 2.05-2.20 (4H, m), 1.51-1.59 (4H, m). MS (ESI): 495 (M+1)$^{+1}$. Anal. Cacl. for C$_{21}$H$_{27}$IN$_4$O$_2$: C, 51.02; H, 5.50; N, 11.33. Found: C, 39.87; H, 3.93; N, 7.41.

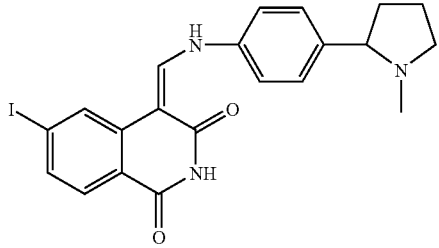

Example 361

6-Iodo-4-{[4-(1-methyl-pyrrolidin-2-yl)-phenylamino]-methylene}-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(1-Methyl-pyrrolidin-2-yl)-phenylamine (2.52 g, 90% pure, 12.8 mmol), 6-iodo-4-methoxymethylene-4H-isoquinoline-1,3-dione (4.0 g, 12.1 mmol) in 61% yield as a brown solid: $^1$H NMR (300 MHz, CDCl3) δ 12.29(1H, d, J=12.6 Hz), 8.37-8.43(2H, m), 7.91-7.97 (2H, m), 7.42-7.61 (3H, m), 7.22 (2H, d, J=8.4 Hz), 3.24-3.29 (1H, m), 3.05-3.11 (1H, m), 2.19 (3H, s), 1.70-2.36 (5H, m). MS (ESI): 474 (M+1)$^{+1}$. Anal. Cacl. for C$_{21}$H$_{20}$IN$_3$O$_2$: C, 53.29; H, 4.26; N, 8.88. Found: C, 53.23; H, 3.91; N, 8.54.

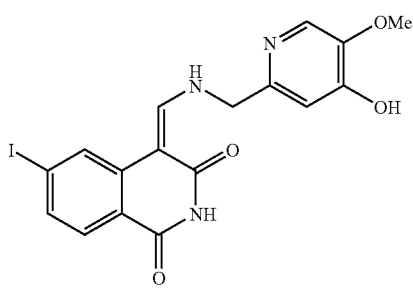

Example 362

6-Iodo-4-{[(4-hydroxy-5-methoxy-pyridin-2-ylmethyl)-amino]-methylene}-4H-isoquinoline-1,3-dione A mixture of 2-aminomethyl-5-methoxy-pyridin-4-ol (116 mg, 0.75 mmole), 4 mL of N,N-dimethylformamide and 4-methoxymethylene-6-iodo-4H-isoquinoline-1,3-dione (247 mg, 0.75 mmole) is added and the reaction mixture stirred for one hour. The reaction mixture is evaporated to dryness and treated with acetonitrile, the solid filtered and dried to give a pink solid, 293 mg, (87%); MS (ES$^+$): m/z 451.9 (M+H).

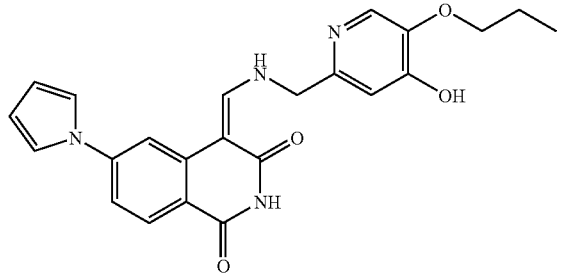

Example 363

4-{[(4-Hydroxy-5-propoxy-pyridin-2-ylmethyl)-amino]-methylene}-6-pyrrol-1-yl-4H-isoquinoline-1,3-dione A mixture of 2-aminomethyl-5-propoxy-pyridin-4-ol (137 mg, 0.75 mmole) IN 10 mL of N,N-dimethylformamide is stirred, then 4-methoxymethylene-6-pyrrol-1-yl-4H-isoquinoline-1,3-dione (201 mg, 0.75 mmole) is added and the reaction mixture stirred for one hour. The reaction mixture is evaporated to dryness, triturated with 5% methanol in chlororform, filtered, washed with fresh 5% methanol in chloroform, washed with acetonitrile and dried to give a grey solid, 290 mg, (92%); MS (ES$^+$): m/z 419.1 (M+H).

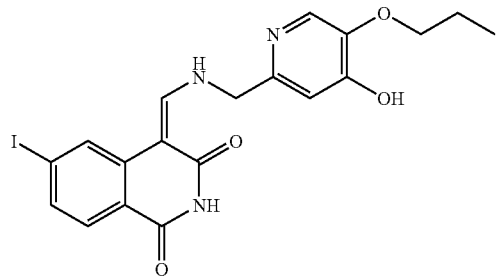

Example 364

4-{[(4-Hydroxy-5-propoxy-pyridin-2-ylmethyl)-amino]-methylene}-6-iodo-4H-isoquinoline-1,3-dione A mixture of 2-aminomethyl-5-propoxy-pyridin-4-ol (137 mg, 0.75 mmole) in 10 mL of N,N-dimethylformamide is stirred, then 4-methoxymethylene-6-iodo-4H-isoquinoline-1,3-dione (247 mg, 0.75 mmole) is added and the reaction mixture stirred for one hour. The reaction mixture is evaporated to dryness, triturated with 5% methanol in chloroform, filtered washed with fresh 5% methanol in chloroform, washed with acetonitrile and dried to give a pink solid, 313 mg, (87%); MS (ES$^+$): m/z 479.9 (M+H).

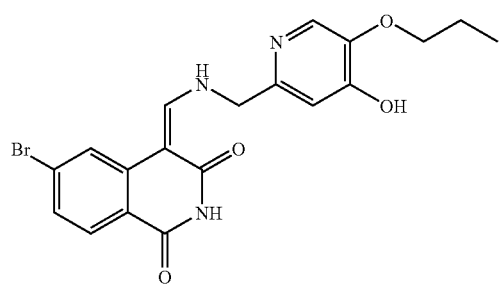

Example 365

4-{[(4-Hydroxy-5-propoxy-pyridin-2-ylmethyl)-amino]-methylene}-6-bromo-4H-isoquinoline-1,3-dione A mixture of 2-aminomethyl-5-propoxy-pyridin-4-ol (137 mg, 0.75 mmole) in 10 mL of N,N-dimethylformamide is stirred, then 4-methoxymethylene-6-bromo-4H-isoquinoline-1,3-dione (212 mg, 0.75 mmole) is added and the reaction mixture stirred for one hour. The reaction mixture is evaporated to dryness, triturated with 5% methanol in chlororform, filtered washed with fresh 5% methanol in chloroform, washed with acetonitrile and dried to give a beige solid, 303 mg, (93%); MS (ES+): m/z 432.0 (M+H).

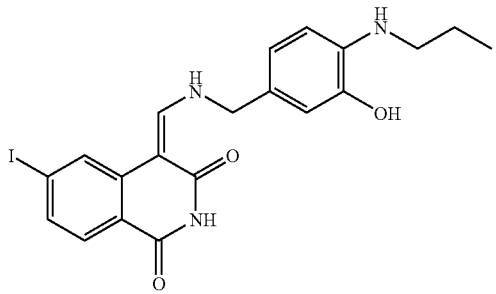

Example 366

(4Z)-4-({[3-Hydroxy-4-(propylamino)benzyl]amino}methylene)-6-iodoisoquinoline-1,3(2H,4H)-dione Using the procedure described for the preparation of (4Z)-4-({[4-(dimethylamino)-3-hydroxybenzyl]amino}methylene)-6-iodoisoquinoline-1,3(2H,4H)-dione, 122 mg of yellow-brown solid (51% yield) is obtained from 300 mg (1.01 mmol) of (4Z)-4-[({4-amino-3-[(triisopropylsilyl)oxy]benzyl}amino)methylene]-6-iodoisoquinoline-1,3(2H,4H)-dione and propylaldehyde 41 uL, (0.56 mmol).; mp 236-237° C.

MS (ESI) m/z 478.0 (M+1)+.

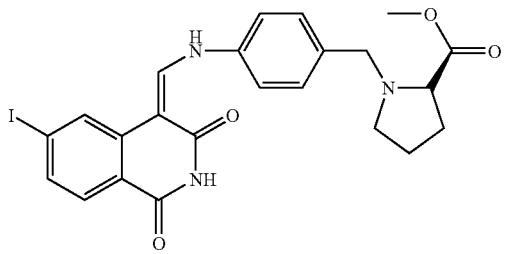

Example 367

D-1-{4-[(6-Iodo-1,3-dioxo-2,3-dihydro-1H-isoquinolin-4-ylidenemethyl)-amino]-benzyl}-pyrrolidine-2-carboxylic acid methyl ester Using the procedure described for the preparation of 6-Bromo-4-[(4-pyridin-4-yl-phenylamino)-methylene]-4H-isoquinoline-1,3-dione, the title compound is obtained from D-1-(4-Amino-benzyl)-pyrrolidine-2-carboxylic acid methyl ester (100 mg, 0.43 mmol), 6-iodo-4-methoxymethylene-4H-isoquinoline-1,3-dione (160 mg, 0.49 mmol) in 44% yield as a brown solid: $^1$H NMR (400 MHz, DMSO) δ 12.55 (1H, d, J=12.8 Hz), 11.39 (1H, s), 8.93 (1H, d, J=12.8 Hz), 8.59 (1H, s), 7.32-7.74 (6H, m), 3.85 (1H, d, J=12.8 Hz), 3.60 (3H, s), 3.53 (1H, d, J=13.2 Hz), 3.26-3.30 (1H, m), 2.85-2.89 (1H, m), 2.37-2.39 (1H, m), 1.72-2.10 (4H, m). MS (ESI): 532 (M+1)$^{+1}$. Anal. Cacl. for $C_{23}H_{22}IN_3O_4$: C, 51.99; H, 4.17; N, 7.91. Found: C, 51.37; H, 3.59; N, 7.64.

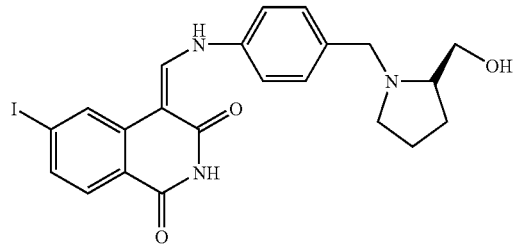

Example 368

D-4-{[4-(2-Hydroxymethyl-pyrrolidin-1-ylmethyl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from D-[1-(4-Amino-benzyl)-pyrrolidin-2-yl]-methanol (2.36 g, 11.4 mmol), 6-iodo-4-methoxymethylene-4H-isoquinoline-1,3-dione (3.0 g, 9.1 mmol) in 76% yield as a brown solid: $^1$H NMR (400 MHz, DMSO) δ 12.55 (1H, d, J=12.4 Hz), 11.38 (1H, s), 8.93 (1H, d, J=12.8 Hz), 8.59 (1H, s), 7.36-7.74 (6H, m), 4.44 (1H, br), 4.06 (1H, d, J=13.2 Hz), 3.31-3.48 (3H, m), 2.79 (1H, m), 2.5-2.6 (1H, m), 2.33 (1H, m), 1.88-1.90 (1H, m), 1.54-1.63 (3H, m). MS (ESI): 504.0 (M+1)$^{+1}$. Anal. Cacl. for $C_{22}H_{22}IN_3O_3$: C, 52.50; H, 4.41; N, 8.35. Found: C, 52.46; H, 4.04; N, 8.15.

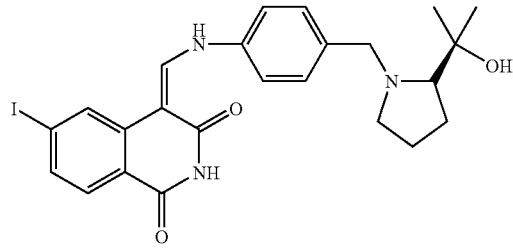

Example 369

D-4-({4-[2-(1-Hydroxy-1-methyl-ethyl)-pyrrolidin-1-ylmethyl]-phenylamino}-methylene)-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 2-[1-(4-Amino-benzyl)-pyrrolidin-2-yl]-propan-2-ol (70 mg, 0.30 mmol), 6-iodo-4-methoxymethylene-4H-isoquinoline-1,3-dione (110 mg, 0.33 mmol) in 35% yield as a brown solid: $^1$H NMR (400 MHz, DMSO) δ 12.53 (1H, d, J=12.8 Hz), 11.38 (1H, s), 8.92 (1H, d, J=13.2 Hz), 8.58 (1H, s), 7.40-7.74 (6H, m), 4.34 (1H, d, J=13.6 Hz), 4.08 (1H, br), 3.36 (1H, m), 2.78 (1H, m), 2.61 (1H, m), 2.19 (1H, m), 1.59-1.90 (4H, m), 1.14 (3H, s), 1.10 (3H, s). MS (ESI): 532 (M+1)$^{+1}$. HRMS Cacl. for $C_{24}H_{27}IN_3O_3$: 532.10917. Found: 532.10965.

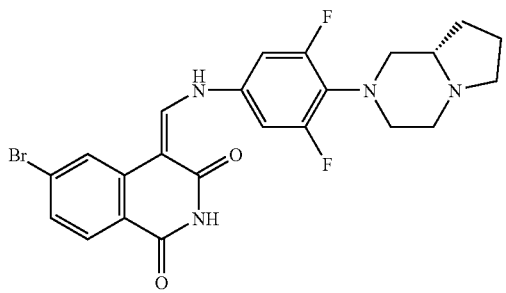

Example 370

(4Z)-6-Bromo-4-[({3,5-difluoro-4-[(8aS)-hexahydropyrrolo[1,2-a]pyrazin-2(1H)-yl]phenyl}amino)methylene]isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 1.87 g (72.2% yield) of light brown solid is obtained from 1.45 g (5.14 mmol) of (4E)-6-bromo-4-(methoxymethylene)isoquinoline-1,3(2H,4H)-dione, and 1.3 g (5.14 mmol) of {3,5-difluoro-4-[(8aS)-hexahydropyrrolo[1,2-a]pyrazin-2(1H)-yl]phenyl}amine: mp 190-191° C.; MS (ESI) m/z 503.1 (M+H)$^{+1}$

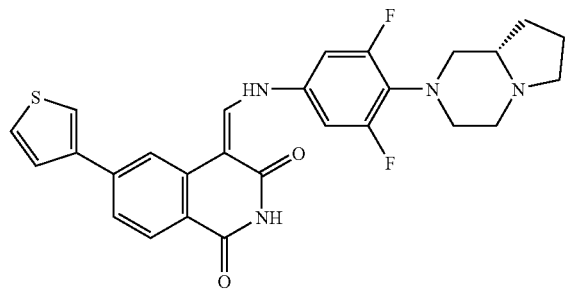

Example 371

(4Z)-4-[({3,5-Difluoro-4-[(8aS)-hexahydropyrrolo[1,2-a]pyrazin-2(1H)-yl]phenyl}amino)-methylene]-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.13 g (43.3% yield) of yellow solid is obtained from 0.3 (0.6 mmol) of (4Z)-6-bromo-4-[({3,5-difluoro-4-[(8aS)-hexahydropyrrolo[1,2-a]pyrazin-2(1H)-yl]phenyl}amino)methylene]isoquinoline-1,3(2H,4H)-dione, 0.11 g (0.9 mmol) of 3-thiopheneboronic acid, 0.06 g (0.06 mmol) of Pd(dba)$_3$, 0.024 g (0.12 mmol) of t-Bu$_3$P, and 0.13 g (1.2 mmol) of Na$_2$CO$_3$: mp 190-191° C.; MS (ESI) m/z 507.1 (M+H)$^{+1}$

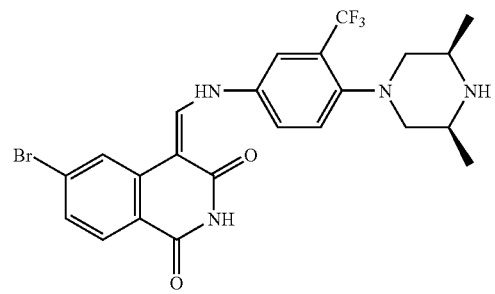

Example 372

(4Z)-6-Bromo-4-({[4-[(3R,5S)-3,5-dimethylpiperazin-1-yl]-3-(trifluoromethyl)phenyl]amino}methylene)isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, \2.28 g (62% yield) of yellow solid is obtained from 2.0 g (7.0 mmol) of (4E)-6-bromo-4-(methoxymethylene)isoquinoline 1,3 (2H,4H)-dione, and 2.13 g (7.7 mmol) of 4-[(3R,5S)-3,5-dimethylpiperazin-1-yl]-3-(trifluoromethyl)phenyl]amine; mp: 224-225° C.; MS (ESI) m/z 523.1 (M+H)$^{+1}$

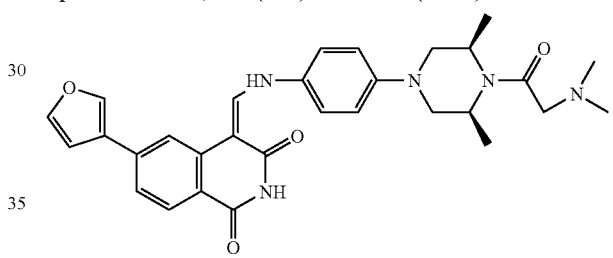

Example 373

(4Z)-4-[({4-[(3R,5S)-4-(N,N-Dimethylglycyl)-3,5-dimethylpiperazin-1-yl]phenyl}amino)methylene]-6-(3-furyl)isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione (41), 150 mg (51% yield) of yellow solid is obtained from 300 mg (0.56 mmol) of (4Z)-6-bromo-4-[({4-[(3R,5S)-4-(N,N-dimethylglycyl)-3,5-dimethylpiperazin-1-yl]phenyl}amino)methylene]isoquinoline-1,3(2H,4H)-dione (CATS-1265844), and 125 mg (1.12 mmol) of 3-furan boronic acid: mp 191-192° C.; MS (ESI) m/z 528.1 (M+H)

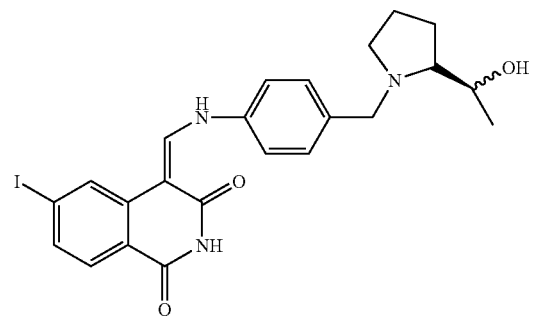

Example 374

4-({4-[2-(1-Hydroxy-ethyl)-pyrrolidin-1-ylmethyl]-phenylamino}-methylene)-6-iodo-4H-isoquinoline-1,3-dione Using the procedure described for the preparation of 6-bromo-4-[(4-pyridin-4-yl-phenylamino)-methylene]-4H-isoquinoline-1,3-dione, the title compound is obtained from 1-[1-(4-Amino-benzyl)-pyrrolidin-2-yl]-ethanol (200 mg, 0.91 mmol), 6-iodo-4-methoxymethylene-4H-isoquinoline-1,3-dione (290 mg, 0.88 mmol) in 22% yield as a single diastereomer: $^1$H NMR (400 MHz, DMSO) δ12.53 (1H, d, J=12.8 Hz), 11.38 (1H, s), 8.93 (1H, d, J=12.8 Hz), 8.59 (1H, s), 7.36-7.74 (6H, m), 4.47 (1H, br), 4.12 (1H, d, J=12.8 Hz), 3.69 (1H, m), 3.36-3.39 (1H, m), 2.81 (1H, m), 2.67 (1H, m), 2.22 (1H, m), 1.54-1.76 (4H, m), 1.05 (3H, d, J=6.4 Hz). MS (ESI): 518.1 (M+1)$^{+1}$. Anal. Cacl. for C$_{23}$H$_{24}$IN$_3$O$_3$: C, 53.4; H, 4.68; N, 8.12. Found: C, 48.24; H, 4.18; N, 6.97.

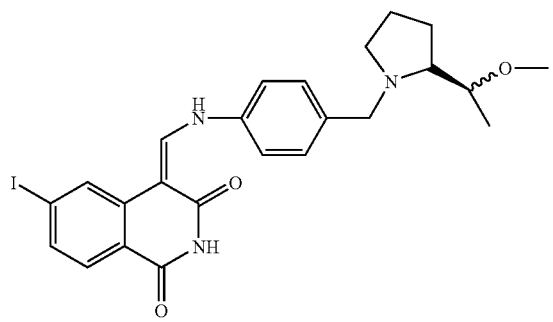

Example 375

6-Iodo-4-({4-[2-(1-methoxy-ethyl)-pyrrolidin-1-ylmethyl]-phenylamino}-methylene)-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-[2-(1-Methoxy-ethyl)-pyrrolidin-1-ylmethyl]-phenylamine (200 mg, 0.85 mmol), 6-iodo-4-methoxymethylene-4H-isoquinoline-1,3-dione (325 mg, 0.99 mmol) in 33% yield as a brown solid: $^1$H NMR (300 MHz, CDCl3) δ12.28 (1H, d, J=12.9 Hz), 8.53 (1H, br), 8.35 (1H, d, J=12.9 Hz), 7.91-7.96 (2H, m), 7.57-7.60 (1H, m), 7.41 (2H, d, J=8.1 Hz), 7.20 (2H, d, J=8.4 Hz), 4.18 (1H, d, J=13.5 Hz), 3.34-3.40 (2H, m), 3.38 (3H, s), 2.92 (1H, m), 2.72-2.76 (1H, m), 2.19 (1H, m), 1.61-1.83 (5H, m), 1.16 (3H, d, J=6.0 Hz). MS (ESI): 532.1 (M+1)$^{+1}$. Anal. Cacl. for C$_{24}$H$_{26}$IN$_3$O$_3$: C, 54.25; H, 4.93; N, 7.91. Found: C, 53.51; H, 4.41; N, 7.63.

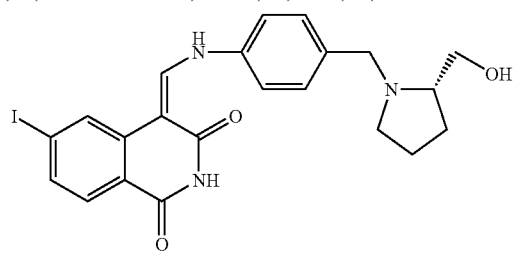

Example 376

L-4-{[4-(2-Hydroxymethyl-pyrrolidin-1-ylmethyl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from L-[1-(4-Amino-benzyl)-pyrrolidin-2-yl]-methanol (230 g, 1.14 mmol), 6-iodo-4-methoxymethylene-4H-isoquinoline-1,3-dione (200 mg, 0.61 mmol) in 72% yield as a brown solid: MS (ESI): 504.1 (M+1)$^{+1}$. Anal. Cacl. for C$_{22}$H$_{22}$IN$_3$O$_3$: C, 52.50; H, 4.41; N, 8.35. Found: C, 52.07; H, 4.21; N, 8.11.

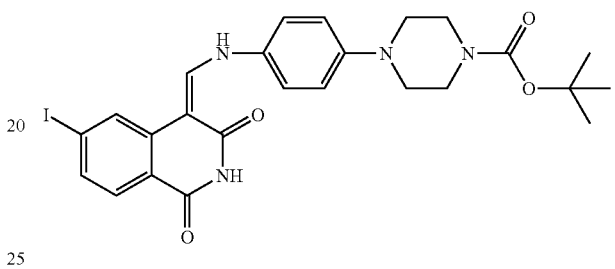

Example 377 tert-Butyl 4-(4-{[(Z)-(6-iodo-1,3-dioxo-2,3-dihydroisoquinolin-4(1H)-ylidene)methyl]amino}phenyl)piperazine-1-carboxylate A N,N-dimethylformamide solution (2.2 mL) of 6-iodo-4-methoxymethylene-4H-isoquinoline-1,3-dione (329 mg, 1 mmol), and tert-butyl 4-(4-aminophenyl)piperazine-1-carboxylate (277 mg, 1 mmol) is heated at 90° C. for 0.5 h. After cooling in the refrigerator, the precipitate is collected, and washed with N,N-dimethylformamide and ether to give 423 mg (74%) of the title compound as a yellow solid. MS (ESI) m/z 575.2 (M+H)$^{+1}$

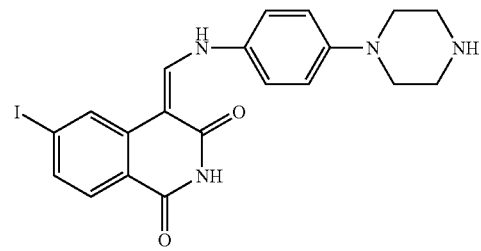

Example 378

(4Z)-6-Iodo-4-{[(4-piperazin-1-ylphenyl)amino]methylene}isoquinoline-1,3(2H,4H)-dione A N,N-dimethylformamide mixture (0.6 mL) of tert-butyl 4-(4-{[(Z)-(6-iodo-1,3-dioxo-2,3-dihydroisoquinolin-4(1H)-ylidene)methyl]amino}phenyl)piperazine-1-carboxylate (50 mg, 0.087 mmol) and concentrated phosphoric acid (0.6 mL) is heated at 60 C for 2 h. After evaporating to dryness, the residue is partitioned between methylene chloride and saturated sodium bicarbonate. The organic layer is washed with water, dried, and evaporated to yield 10 mg (24%) of the title compound as an orange solid. MS (ESI) m/z 475.2 (M+H)$^{+1}$

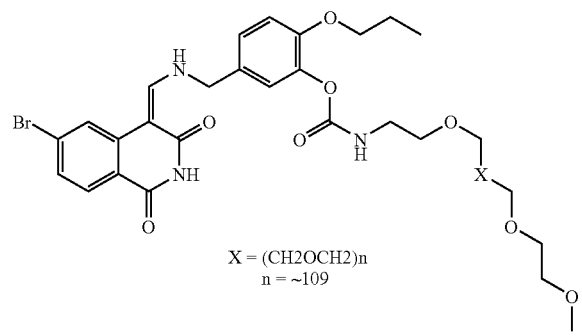

X = (CH2OCH2)n
n = ~109

Example 379

(Z)-4-(((6-Bromo-5-propoxypyridin-2-yl)methy-lamino)methylene)-6-iodoisoquinoline-1,3(2H,4H)-dione A mixture of (E)-6-bromo-4-(methoxymethylene)isoquinoline-1,3(2H,4H)-dione (173 mg, 0.40 mmole), dimethylformamide (4 mL), and mPEG-NCO$^1$ (2.0 g, ~0.4 mmole) is stirred at room temperature for one hour. The reaction mixture is diluted with acetonitrile, filtered, washed with fresh acetonitrile and dried to give an off-white solid, 877 mg, (41%); MS (ESI): MW 5380, 5424, 5469, 5512, 5556, 5599, 5644, 5687.

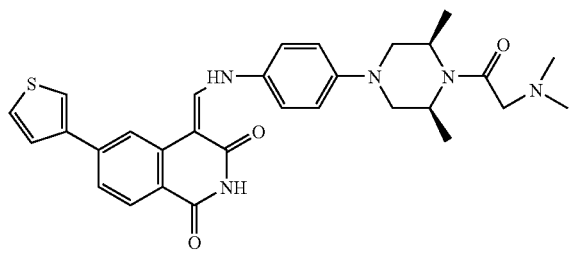

Example 380

(4Z)-4-[({4-[(3R,5S)-4-(N,N-Dimethylglycyl)-3,5-dimethylpiperazin-1-yl]phenyl}amino)methylene]-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione (41), 130 mg (43% yield) of yellow solid is obtained from 300 mg (0.56 mmol) of (4Z)-6-bromo-4-[({4-[(3R,5S)-4-(N,N-dimethylglycyl)-3,5-dimethylpiperazin-1-yl]phenyl}amino)methylene]isoquinoline-1,3(2H,4H)-dione (CATS-1265844), and 143.4 mg (1.12 mmol) of 3-thiophine boronic acid: mp 198-199° C.; MS (ESI) m/z 545.2 (M+H)

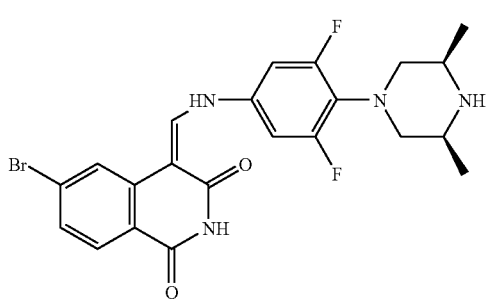

Example 381

(4Z)-6-Bromo-4-[({4-[(3R,5S)-3,5-dimethylpiper-azin-1-yl]-3,5-difluorophenyl}amino)-methylene]isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione 7.58 g (87.0% yield) of tan solid is obtained from 5.0 g (17.7 mmol) of (4E)-6-bromo-4-(methoxymethylene)isoquinoline-1,3 (2H,4H)-dione, and 4.7 g (19.5 mmol) of {4-[(3R,5S)-3,5-dimethylpiperazin-1-yl]-3,5-difluorophenyl}amine: mp 187-188° C.; MS (ESI) m/z 491.1 (M+H)$^{+1}$

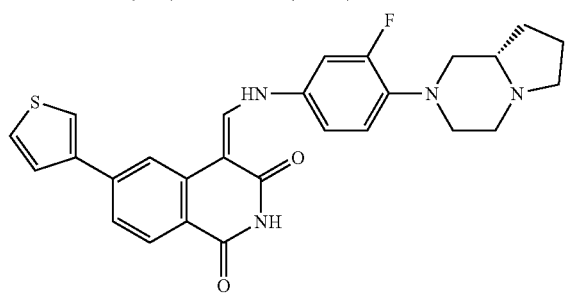

Example 382

(4Z)-4-[({3-Fluoro-4-[(8aS)-hexahydropyrrolo[1,2-a]pyrazin-2(1H)-yl]phenyl}amino)-methylene]-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl] phenyl}amino)-methylene]isoquinoline-1,3(2H,4H)-dione 0.38 g (76.0% yield) of yellow solid is obtained from 0.5 (1.03 mmol) of (4Z)-6-bromo-4-[({3-fluoro-4-[(8aS)-hexahydropyrrolo[1,2-a]pyrazin-2(1H)-yl]phenyl}amino) methylene]isoquinoline-1,3(2H,4H)-dione, 0.2 g (1.55 mmol) of 3-thiopheneboronic acid, 0.10 g (0.10 mmol) of Pd(dba)$_3$, 0.02 g (0.21 mmol) of t-Bu$_3$P, and 0.22 g (2.06 mmol) of Na$_2$CO$_3$: mp 208-209° C.; MS (ESI) m/z 489.2 (M+H)$^{+1}$

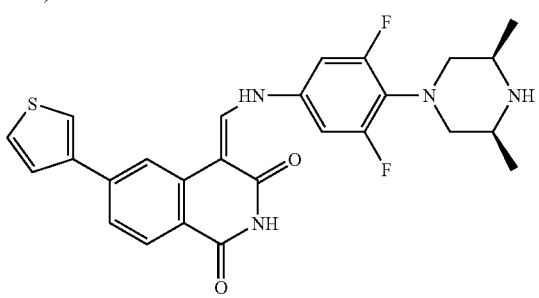

Example 383

(4Z)-4-[({4-[(3R,5S)-3,5-Dimethylpiperazin-1-yl]-3,5-difluorophenyl}amino)methylene]-6-thien-3-ylisoquinoline-1,3(2H,4H)-dione (83)

Using the procedure described for the preparation of (4Z)-6-(3-furyl)-4-[({4-[(3R,5S)-3,4,5-trimethylpiperazin-1-yl] phenyl}amino)-methylene]isoquinoline-1,3(2H,4H)-dione, 4.12 g (82.0% yield) of yellow solid is obtained from 5.0 (10.18 mmol) of (4Z)-6-bromo-4-[({4-[(3R,5S)-3,5-dimeth ylpiperazin-1-yl]-3,5-difluorophenyl}amino)-methylene]
isoquinoline-1,3(2H,4H)-dione 1.95 g (15.27 mmol) of 3-thiopheneboronic acid, 0.93 g (1.02 mmol) of Pd(dba)₃, 0.02 g (2.04 mmol) of t-Bu₃P, and 2.16 g (20.4 mmol) of Na₂CO₃: mp 195-196° C.; MS (ESI) m/z 495.2 (M+H)$^{+1}$

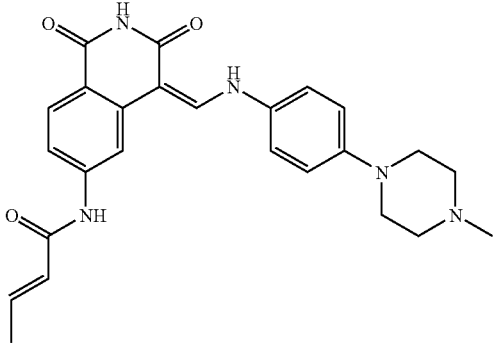

Example 384

(2E)-N-[(4Z)-4-({[4-(4-Methylpiperazin-1-yl)phenyl]amino}methylene)-1,3-dioxo-1,2,3,4-tetrahydroisoquinolin-6-yl]but-2-enamide Following the acetylation procedure employed for the preparation of N-[2-hydroxy-4-({[(Z)-(6-iodo-1,3-dioxo-2,3-dihydroisoquinolin-4(1H)-ylidene)methyl]amino}methyl)phenyl]acrylamide, a solution of (4Z)-6-amino-4-({[4-(4-methylpiperazin-1-yl)phenyl]amino}methylene)isoquinoline-1,3(2H,4H)-dione in dimethylacetamide (1 mL) is cooled to 0° C. in an ice water bath. Trans-crotonyl chloride (110 μL, 1.0 mmol) is added and the mixture is stirred at 0° C. for 5 minutes. The reaction mixture is then concentrated under reduced pressure and then purified by reverse phase HPLC to provide (2E)-N-[(4Z)-4-({[4-(4-methylpiperazin-1-yl)phenyl]amino}methylene)-1,3-dioxo-1,2,3,4-tetrahydroisoquinolin-6-yl]but-2-enamide trifluoroacetate (18 mg, 32%).

MS (ES⁻): 443.4, 445.4 (M–H)⁻

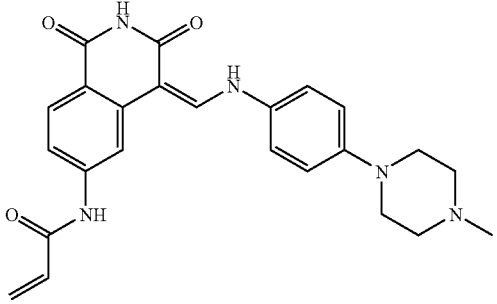

Example 385

N-[(4Z)-4-({[4-(4-Methylpiperazin-1-yl)phenyl]amino}methylene)-1,3-dioxo-1,2,3,4-tetrahydroisoquinolin-6-yl]acrylamide Following the acetylation procedure employed for the preparation of N-[2-hydroxy-4-({[(Z)-(6-iodo-1,3-dioxo-2,3-dihydroisoquinolin-4(1H)-ylidene)methyl]amino}methyl)phenyl]acrylamide, a solution (4Z)-6-amino-4-({[4-(4-methylpiperazin-1-yl)phenyl]amino}methylene)isoquinoline-1,3(2H,4H)-dione in dimethylacetamide (1 mL) is cooled to 0° C. in an ice water bath. Acryloyl chloride (82 μL, 1.0 mmol) is added and the mixture is stirred at 0° C. for 5 minutes. The reaction mixture is then concentrated under reduced pressure and then purified by reverse phase HPLC to provide N-[(4Z)-4-({[4-(4-methylpiperazin-1-yl)phenyl]amino}methylene)-1,3-dioxo-1,2,3,4-tetrahydroisoquinolin-6-yl]acrylamide trifluoroacetate (18 mg, 33%).

MS (ES⁺): 432.3, 433.4 (M+H)⁺

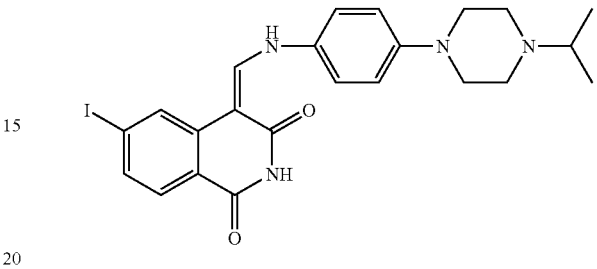

Example 386

(4Z)-6-Iodo-4-({[4-(4-isopropylpiperazin-1-yl)phenyl]amino}methylene)isoquinoline-1,3(2H,4H)-dione (4Z)-6-iodo-4-{[(4-piperazin-1-ylphenyl)amino]methylene}isoquinoline-1,3(2H,4H)-dione (23.7 mg, 0.05 mmol) is dissolved in N-methylpyrrolidinone (0.5 mL) and methylene chloride (0.15 mL), followed by addition of sodium triacetoxyborohydride (122 mg, 0.575 mmol), acetone (0.095 mL, 1.29 mmol) and acetic acid (0.075 mL, 1.31 mmol). After stirring at room temperature for 1 h, methylene chloride and saturated sodium bicarbonate solution were added. The organic layer is separated and dried to give 18.8 mg (73%) of the title compound as a yellow solid. MS (ESI) m/z 517.0 (M+H)$^{+1}$

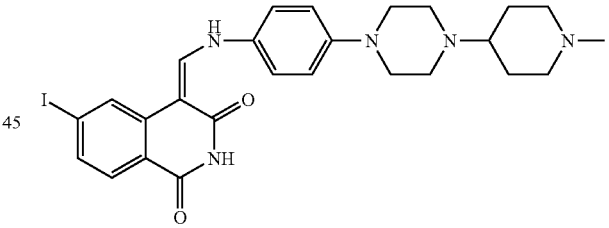

Example 387

(4Z)-6-Iodo-4-[({4-[4-(1-methylpiperidin-4-yl)piperazin-1-yl]phenyl}amino)methylene]isoquinoline-1,3(2H,4H)-dione (4Z)-6-iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), 1-methyl-piperidin-4-one (0.318 mL, 2.58 mmol) and acetic acid (0.15 mL, 2.6 mmol). After stirring at room temperature for 40 min, methylene chloride and saturated sodium bicarbonate solution were added. The organic layer is separated and dried to give 45 mg (78%) of the title compound as a yellow solid. MS (ESI) m/z 572.2 (M+H)$^{+1}$.

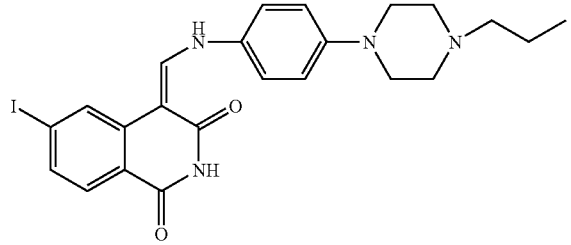

Example 388

(4Z)-6-Iodo-4-({[4-(4-propylpiperazin-1-yl)phenyl]amino}methylene)isoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), propionaldehyde (0.186 mL, 2.6 mmol) and acetic acid (0.15 mL, 2.6 mmol). After stirring at room temperature for 40 min, methylene chloride and saturated sodium bicarbonate solution were added. The organic layer is separated and dried to give 36 mg (70%) of the title compound as a yellow solid. MS (ESI) m/z 517 (M+H)$^{+1}$.

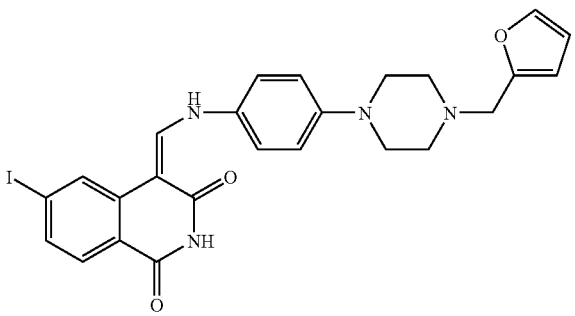

Example 389

(4Z)-4-[({4-[4-(2-Furylmethyl)piperazin-1-yl]phenyl}amino)methylene]-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), furan-2-carbaldehyde (0.214 mL, 2.58 mmol) and acetic acid (0.15 mL, 2.6 mmol). After stirring at room temperature for 40 min, methylene chloride and saturated sodium bicarbonate solution were added. The organic layer is separated and dried to give 49 mg (88%) of the title compound as a yellow solid. MS (ESI) m/z 555.4 (M+H)$^{+1}$.

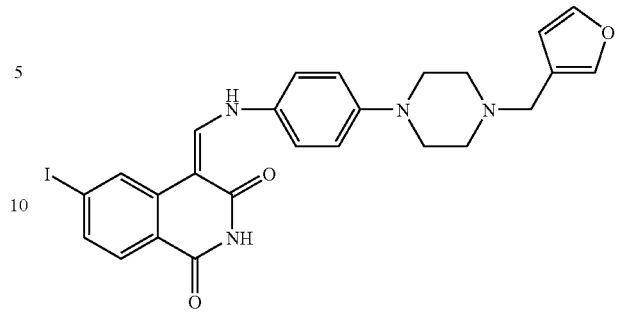

Example 390

(4Z)-4-[({4-[4-(3-Furylmethyl)piperazin-1-yl]phenyl}amino)methylene]-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), furan-3-carbaldehyde (0.214 mL, 2.58 mmol) and acetic acid (0.15 mL, 2.6 mmol). After stirring at room temperature for 40 min, methylene chloride and saturated sodium bicarbonate solution were added. The organic layer is separated and dried to give 45 mg (81%) of the title compound as an orange solid. MS (ESI) m/z 555.4 (M+H)$^{+1}$.

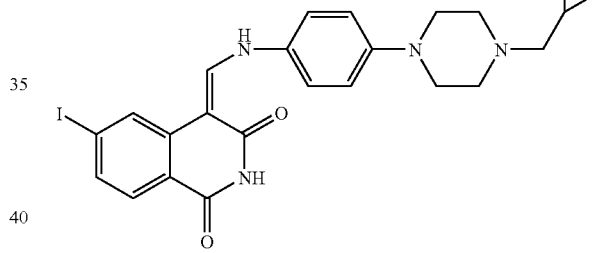

Example 391

(4Z)-4-[({4-[4-(Cyclopropylmethyl)piperazin-1-yl]phenyl}amino)methylene]-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), cyclopropanecarbaldehyde (0.195 mL, 2.58 mmol) and acetic acid (0.15 mL, 2.6 mmol). After stirring at room temperature for 40 min, methylene chloride and saturated sodium bicarbonate solution were added. The organic layer is separated and dried to give 44 mg (83%) of the title compound as a yellow solid. MS (ESI) m/z 529.4 (M+H)$^{+1}$.

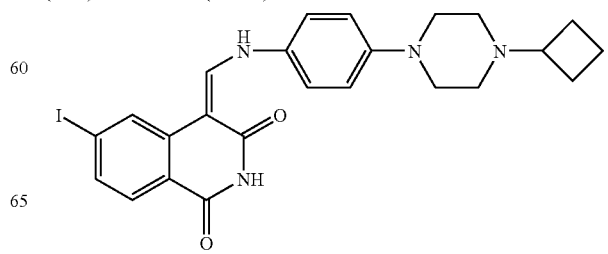

Example 392

(4Z)-4-({[4-(4-Cyclobutylpiperazin-1-yl)phenyl]amino}methylene)-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), cyclobutanone (0.195 mL, 2.58 mmol) and acetic acid (0.15 mL, 2.6 mmol). After stirring at room temperature for 40 min, methylene chloride and saturated sodium bicarbonate solution were added. The organic layer is separated and dried to give 32 mg (60%) of the title compound as a yellow solid. MS (ESI) m/z 529.4 (M+H)$^{+1}$.

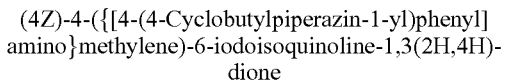

Example 393

(4Z)-4-({[4-(4-Ethylpiperazin-1-yl)phenyl]amino}methylene)-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), acetaldehyde (0.15 mL, 2.58 mmol) and acetic acid (0.15 mL, 2.6 mmol). After stirring at room temperature for 40 min, methylene chloride and saturated sodium bicarbonate solution were added. The organic layer is separated and dried to give 33 mg (60%) of the title compound as a yellow solid. MS (ESI) m/z 503.3 (M+H)$^{+1}$.

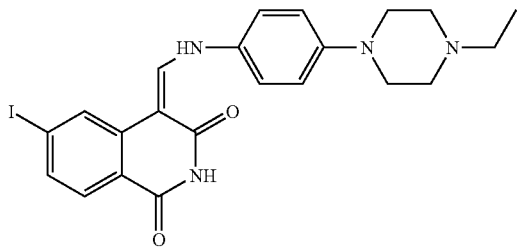

Example 394

(4Z)-6-Iodo-4-[({4-[(4-methoxypiperidin-1-yl)methyl]phenyl}amino)methylene]isoquinoline-1,3(2H,4H)-dione Using the procedure described for the preparation of example 14, 230 mg (73% yield) is obtained as a yellow solid from 200 mg (0.61 mmol) (4E)-6-iodo-4-(methoxymethylene)isoquinoline-1,3(2H,4H)-dione and 134.3 mg (0.61 mmol) of {4-[(4-methoxypiperidin-1-yl)methyl]phenyl}amine, mp 199-200° C.

MS (ESI) m/z 518.0 (M+1)$^+$

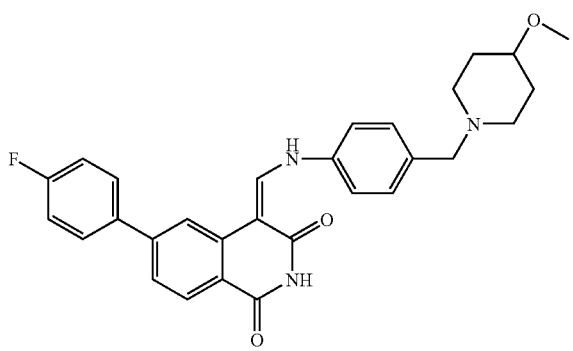

Example 395

(4Z)-6-(4-Fluorophenyl)-4-[({4-[(4-methoxypiperidin-1-yl)methyl]phenyl}amino)methylene]isoquinoline-1,3(2H,4H)-dione Using the procedure described for the preparation of (4Z)-6-(4-fluorophenyl)-4-({[4-(piperidin-1-'ylmethyl)phenyl]amino}methylene)isoquinoline-1,3(2H,4H)-dione, 380 mg (74% yield) is obtained as a yellow solid from 500 mg (1.06 mmol) of (4Z)-6-bromo-4-[({4-[(4-methoxypiperidin-1-yl)methyl]phenyl}amino)methylene]isoquinoline-1,3(2H,4H)-dione and 4-Fluorophenyl boronic acid 296 mg, (2.13 mmol).; mp 188-189° C.

MS (ESI) m/z 486.1 (M+1)$^+$

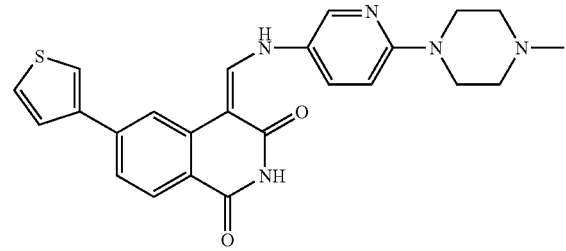

Example 396

(4Z)-4-({[6-(4-Methylpiperazin-1-yl)pyridin-3-yl]amino}methylene)-6-thien-3-ylisoquinoline-1,3(2H,4H)-dione Using the procedure described for the preparation of (4Z)-6-(3-furyl)-4-({[6-(4-methylpiperazin-1-yl)pyridin-3-'yl]amino}methylene)isoquinoline-1,3(2H,4H)-dione, 600 mg (60% yield) is obtained as a yellow solid from 1.0 g (2.26 mmol) of (4Z)-6-bromo-4-({[6-(4-methylpiperazin-1-yl)pyridin-3-'yl]amino}methylene)isoquinoline-1,3(2H,4H)-dione and 3-thiophine boronic acid 296 mg, (2.26 mmol).; mp 165-166° C.

MS (ESI) m/z 466.1 (M+1)$^+$

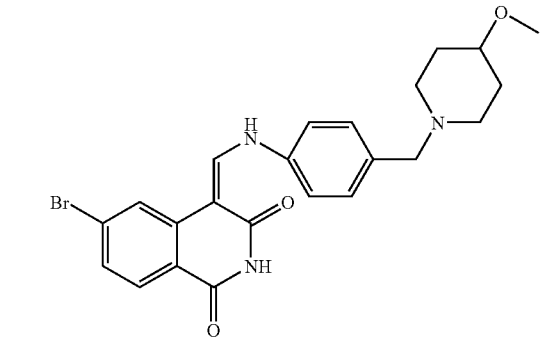

Example 397

(4Z)-6-Bromo-4-[({4-[(4-methoxypiperidin-1-yl)methyl]phenyl}amino)methylene]isoquinoline-1,3(2H,4H)-dione Using the procedure described for the preparation of example 14, 1.14 g (68% yield) is obtained as a yellow solid from 1.0 g (3.54 mmol) (4E)-6-bromo-4-(methoxymethylene)isoquinoline-1,3(2H,4H)-dione and 781 mg (3.54 mmol) of {4-[(4-methoxypiperidin-1-yl)methyl]phenyl}amine, mp 176-177° C.

MS (ESI) m/z 518.0 (M+1)$^+$

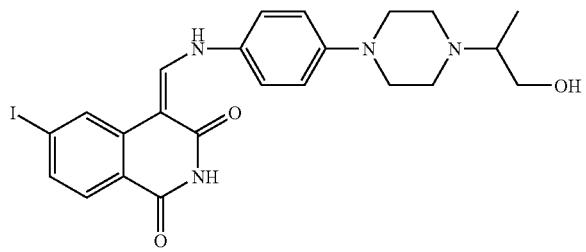

Example 398

(4Z)-4-[({4-[4-(2-Hydroxy-1-methylethyl)piperazin-1-yl]phenyl}amino)methylene]-6-iodoisoquinoline-1,3(2H,4H)-dione (4Z)-4-({[4-(4-ethylpiperazin-1-yl)phenyl]amino}methylene)-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), 1-hydroxy-propan-2-one (0.177 mL, 2.58 mmol) and acetic acid (0.15 mL, 2.6 mmol). After stirring at room temperature for 40 min, methylene chloride and saturated sodium bicarbonate solution were added. The organic layer is separated and dried to give 38 mg (71%) of the title compound as a yellow solid. MS (ESI) m/z 533.4 (M+H)$^{+1}$.

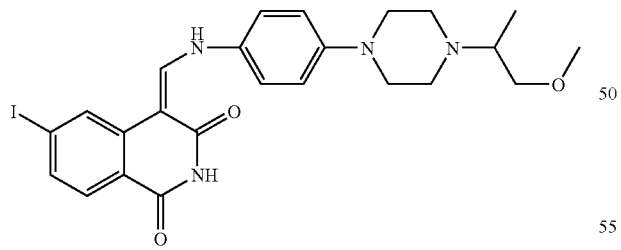

Example 399

(4Z)-6-Iodo-4-[({4-[4-(2-methoxy-1-methylethyl)piperazin-1-yl]phenyl}amino)methylene]isoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), 1-methoxy-propan-2-one (0.232 mL, 2.58 mmol) and acetic acid (0.15 mL, 2.6 mmol). After stirring at room temperature for 40 min, methylene chloride and saturated sodium bicarbonate solution were added. The organic layer is separated and dried to give 39 mg (71%) of the title compound as a yellow solid. MS (ESI) m/z 547.4 (M+H)$^{+1}$.

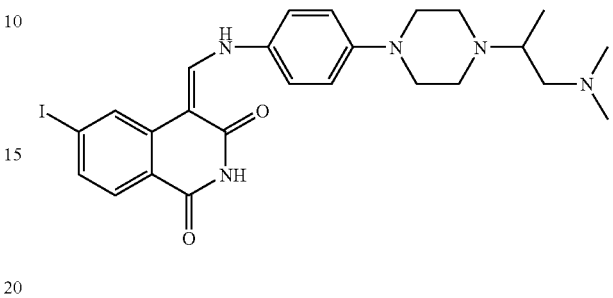

Example 400

(4Z)-4-{[(4-{4-[2-(Dimethylamino)-1-methylethyl]piperazin-1-yl}phenyl)amino]methylene}-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), 1-dimethylamino-propan-2-one (0.296 mL, 2.58 mmol) and acetic acid (0.15 mL, 2.6 mmol). After stirring at room temperature for 40 min, methylene chloride and saturated sodium bicarbonate solution were added. The organic layer is separated and dried to give 32 mg (57%) of the title compound as a yellow solid. MS (ESI) m/z 560.4 (M+H)$^{+1}$.

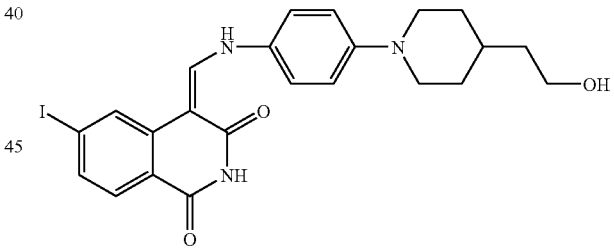

Example 401

(4Z)-4-[({4-[4-(2-Hydroxyethyl)piperazin-1-yl]phenyl}amino)methylene]-6-iodoisoquinoline-1,3(2H,4H)-dione (4Z)-6-Iodo-4-{[(4-piperazin-1-ylphenyl)amino]methylene}isoquinoline-1,3(2H,4H)-dione (47.4 mg, 0.1 mmol) is dissolved in N-methylpyrrolidinone (1 mL) and methylene chloride (0.3 mL), followed by addition of sodium triacetoxyborohydride (244 mg, 1.15 mmol), glycoaldehyde (155 mg, 2.58 mmol) and acetic acid (0.15 mL, 2.6 mmol). After stirring at room temperature for 40 min, methylene chloride and saturated sodium bicarbonate solution were added. The organic layer is separated and dried to give 43 mg

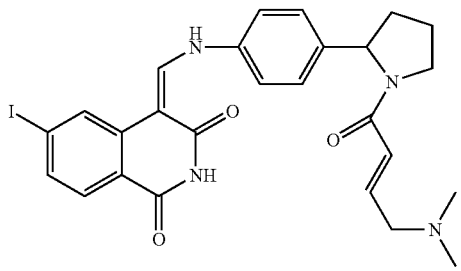

Example 402

4-({4-[1-(4-Dimethylamino-but-2-enoyl)-pyrrolidin-2-yl]-phenylamino}-methylene)-6-iodo-4H-isoquinoline-1,3-dione 4-Dimethylamino-but-2-enoic acid hydrochloride salt (66 mg, 0.40 mmol) in N,N-dimethylformamide (1 mL) is treated with Et₃N (0.06 mL) at 0° C. To the mixture is then added isobutylchloroformate (0.05 mL). The mixture is then stirred at this temperature for 30 min before addition of 6-Iodo-4-[(4-pyrrolidin-2-yl-phenylamino)-methylene]-4H-isoquinoline-1,3-dione (80 mg, 0.17 mmol) in N,N-dimethylformamide (3 mL) dropwisely and the reaction is allowed to stir at room temperature overnight. After an aqueous workup, the final residue is purified with prep-TLC to afford the title compound (20 mg, 21%). ¹H NMR (400 MHz, DMSO) δ12.52 (1H, d, J=12.4 Hz), 11.39-11.41 (1H, m), 8.90-8.94 (1H, m), 8.59 (1H, m), 7.21-7.75 (6H, m), 6.48-6.59 (1.4H, m), 6.01-6.05 (0.6H, m), 5.1-5.24 (1H, m), 3.57-3.91 (2H, m), 3.06-3.07 (1H, m), 2.82-2.84 (1H, m), 2.1-2.39 (2H, m), 2.18 (3H, s), 1.96 (3H, s), 1.77-1.95 (2H, m). MS (ESI): 571.0 (M+1)⁺¹.

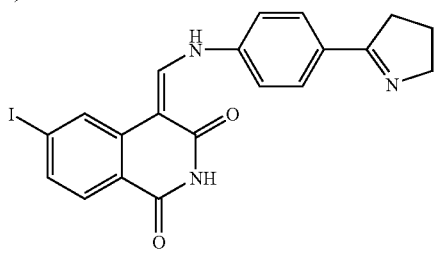

Example 403

4-{[4-(4,5-Dihydro-3H-pyrrol-2-yl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(4,5-Dihydro-3H-pyrrol-2-yl)-phenylamine (220 mg, 1.36 mmol), 6-iodo-4-methoxymethylene-4H-isoquinoline-1,3-dione (400 mg, 1.22 mmol) in 81% yield as a yellow solid: ¹H NMR (400 MHz, CDCl3) δ 12.34 (1H, d, J=12.4 Hz), 8.39 (1H, d, J=12.4 Hz), 8.22 (1H, s), 7.92-8.01 (2H, m), 7.62-7.64 (1H, m), 7.24-7.30 (2H, m), 4.07-4.12 (2H, m), 2.88-2.98 (2H, m), 2.04-2.11 (2H, m). MS (ESI): 458.0 (M+1)⁺¹. Anal. Cacl. for C20H16IN3O3: C, 52.53; H, 3.53; N, 9.19. Found: C, 51.87; H, 3.26; N, 9.

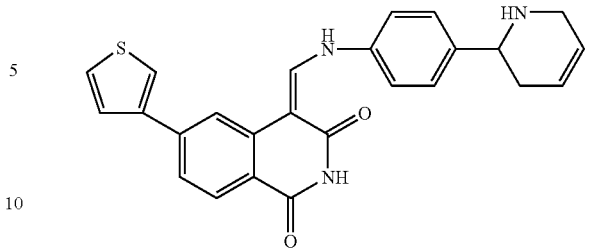

Example 404

4-{[4-(1,2,3,6-Tetrahydro-pyridin-2-yl)-phenylamino]-methylene}-6-thiophen-3-yl-4H-isoquinoline-1,3-dione 2-{4-[(1,3-Dioxo-6-thiophen-3-yl-2,3-dihydro-1H-isoquinolin-4-ylidenemethyl)-amino]-phenyl}-3,6-dihydro-2H-pyridine-1-carboxylic acid tert-butyl ester (230 mg, ~60-70% pure, ~0.26-0.31 mmol) is mixed with H₃PO₄ (1 mL) in CH₂Cl₂ (1 mL) at room temperature. The resulting mixture is stirred until no starting material is detected by TLC. CH₃CN and H₂O and ice were then added to dilute the sample. The mixture is neutralized by NaOH and extracted with EtOAc. The EtOAc layer is washed with brine and dried. After removal of EtOAc, the residue is purified by flash chromatography to provide the title compound (80 mg, 78% for two steps). ¹H NMR (400 MHz, DMSO) δ 12.53 (1H, d, J=12.8 Hz), 11.30 (1H, s), 9.02 (1H, d, J=12.4 Hz), 8.34 (1H, s), 8.21 (1H, s), 8.05 (1H, d, J=7.6 Hz), 7.44-7.85 (7H, m), 5.76-5.84 (2H, m), 3.77-3.81 (1H, m), 3.31-3.50 (2H, m), 2.09-2.21 (2H, m). MS (ESI): 428.1 (M+1)⁻¹.

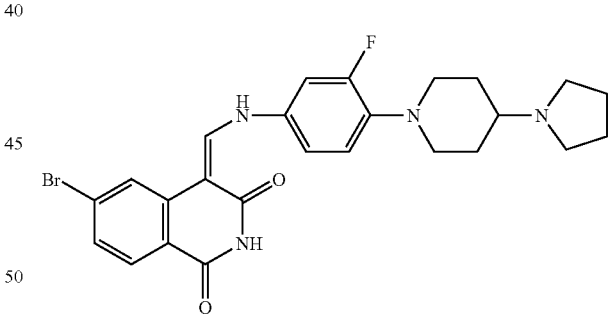

Example 405

(4Z)-6-Bromo-4-({[3-fluoro-4-(4-pyrrolidin-1-ylpiperidin-1-yl)phenyl]amino}-methylene)-isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 0.18 g (40.0% yield) of brown solid is obtained from 0.25 g (0.89 mmol) of (4E)-6-bromo-4-(methoxymethylene)isoquinoline-1,3(2H,4H)-dione, and 0.25 g (1.07 mmol) of [3-fluoro- 4-(4-pyrrolidin-1-ylpiperidin-1-yl)phenyl]amine: mp 204-205° C.; MS (ESI) m/z 513.0 (M+H)$^{+1}$

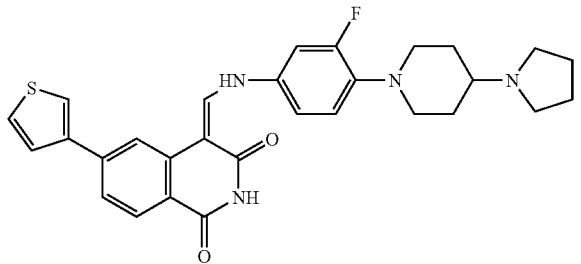

Example 406

(4Z)-4-({[3-Fluoro-4-(4-pyrrolidin-1-ylpiperidin-1-yl)phenyl]amino}methylene)-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 0.092 g (61.3% yield) of light brown solid is obtained from 0.15 (0.29 mmol) of (4Z)-6-bromo-4-({[3-fluoro-4-(4-pyrrolidin-1-ylpiperidin-1-yl)phenyl]amino}-methylene)-isoquinoline-1,3(2H,4H)-dione, 0.06 g (0.44 mmol) of 3-thiopheneboronic acid, 0.027 g (0.03 mmol) of Pd(dba)$_3$, 0.006 g (0.06 mmol) of t-Bu$_3$P, and 0.06 g (0.60 mmol) of Na$_2$CO$_3$: mp 200-201° C.; MS (ESI) m/z 517.1 (M+H)$^{+1}$

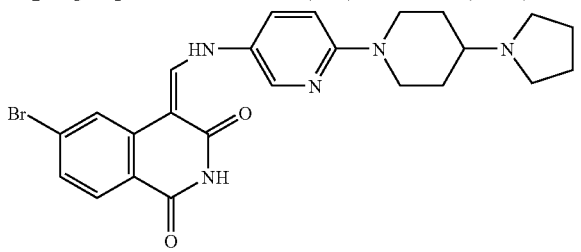

Example 407

(4Z)-6-Bromo-4-({[6-(4-pyrrolidin-1-ylpiperidin-1-yl)pyridin-3-yl]amino}methylene)isoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione (24), 0.53 g (86% yield) of brown solid is obtained from 0.335 g (1.24 mmol) of (4E)-6-bromo-4-(methoxymethylene)isoquinoline 1,3(2H,4H)-dione, and 0.30 g (1.24 mmol) of 6-(4-pyrrolidin-1-ylpiperidin-1-yl)pyridin-3-yl]amine; mp: 214-215° C.; MS (ESI) m/z 498.1 (M+H)$^{+1}$

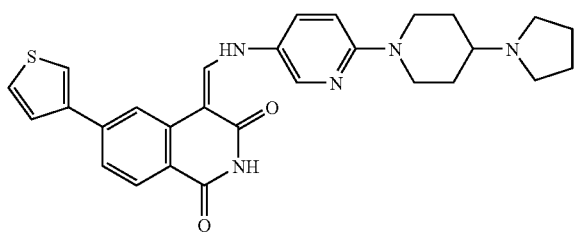

Example 408

(4Z)-4-[({4-[(3R,5S)-4-(N,N-Dimethylglycyl)-3,5-dimethylpiperazin-1-yl]phenyl}amino)methylene]-6-thien-3-ylisoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione (41), 50 mg (20% yield) of light brown solid is obtained from 250 mg (0.50 mmol) of (4Z)-6-bromo-4-({[6-(4-pyrrolidin-1-ylpiperidin-1-yl)pyridin-3-yl]amino}methylene)isoquinoline-1,3(2H,4H)-dione and 128 mg (1.0 mmol) of 3-thiophine boronic acid: mp 203-204° C.; MS (ESI) m/z 500.7 (M+H)

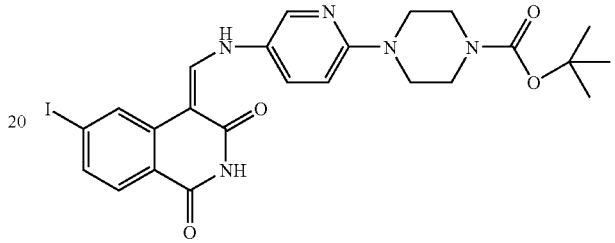

Example 409 tert-Butyl 4-(5-{[(Z)-(6-iodo-1,3-dioxo-2,3-dihydroisoquinolin-4(1H)-ylidene)methyl]amino}pyridin-2-yl)piperazine-1-carboxylate A N,N-dimethylformamide solution (1 mL) of 6-iodo-4-methoxymethylene-4H-isoquinoline-1,3-dione (106.4 mg, 0.323 mmol), and tert-butyl 4-(5-aminopyridin-2-yl)piperazine-1-carboxylate (90 mg, 0.323 mmol) is heated at 90° C. for 40 min. After cooling in the refrigerator, the precipitate is collected, and washed with N,N-dimethylformamide and ether to give 147 mg (79%) of the title compound as a yellow solid. MS (ESI) m/z 576.1 (M+H)$^{+1}$

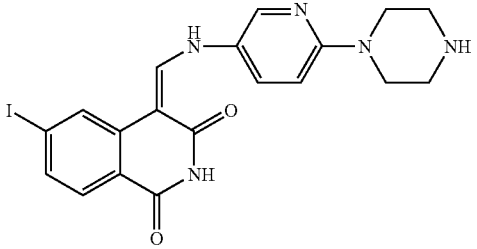

Example 410

(4Z)-6-Iodo-4-{[(6-piperazin-1-ylpyridin-3-yl)amino]methylene}isoquinoline-1,3(2H,4H)-dione A N,N-dimethylformamide mixture (0.35 mL) of tert-butyl 4-(5-{[(Z)-(6-iodo-1,3-dioxo-2,3-dihydroisoquinolin-4(1H)-ylidene)methyl]amino}pyridin-2-yl)piperazine-1-carboxylate (100 mg, 0.1738 mmol) and concentrated phosphoric acid (1.1 mL) is heated at 60 C. for 2 h. The reaction solution is then treated with an ice-cold aqueous solution of potassium carbonate (1.8 g), and filtered, the solid which is washed exhaustively with water yielded 70 mg (85%) of the title compound as a solid. MS (ESI) m/z 476.1 (M+H)⁺¹

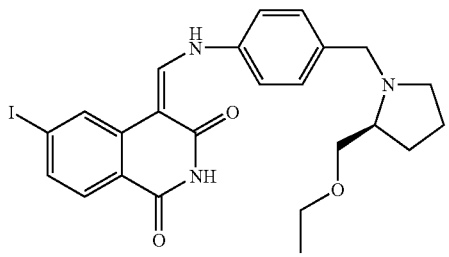

Example 411

4-{[4-(2-Ethoxymethyl-pyrrolidin-1-ylmethyl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(2-Ethoxymethyl-pyrrolidin-1-ylmethyl)-phenylamine (130 g, ~85% pure, 0.47 mmol), 6-iodo-4-methoxymethylene-4H-isoquinoline-1,3-dione (100 mg, 0.30 mmol) in 63% yield as a yellow solid: ¹H NMR (400 MHz, DMSO) δ12.54 (1H, d, J=12.8 Hz), 11.38 (1H, S), 8.93 (1H, d, J=12.8 Hz), 8.59 (1H, s), 7.34-7.74 (6H, m), 4.06 (1H, d, J=9.6 Hz), 3.35-3.46 (4H, m), 3.24-3.29 (1H, m), 2.67-2.78 (2H, m), 2.16-2.18 (1H, m), 1.84-1.89 (1H, m), 1.50-1.63 (3H, m), 1.10 (3H, t, J=7.2 Hz). MS (ESI): 531.9 (M+1)⁺¹. Anal. Cacl. for C24H26IN3O3: C, 54.25; H, 4.93; N, 7.91. Found: C, 55.03; H, 5.12; N, 7.61. HRMS Cacl. for C24H26IN3O3: 532.10917. Found: 532.11104, (M+1)⁺¹.

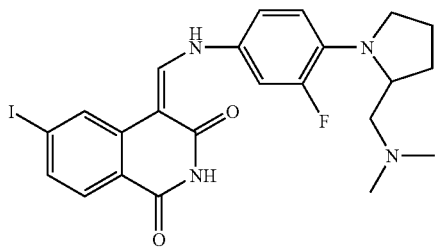

Example 412

4-{[4-(2-Dimethylaminomethyl-pyrrolidin-1-yl)-3-fluoro-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(2-Dimethylaminomethyl-pyrrolidin-1-yl)-3-fluoro-phenylamine (65 mg, 0.27 mmol), 6-iodo-4-methoxymethylene-4H-isoquinoline-1,3-dione (60 mg, 0.18 mmol) in 64% yield as a brownish solid: ¹H NMR (400 MHz, DMSO) δ 12.54 (1H, d, J=12.8 Hz), 11.33 (1H, s), 8.80 (1H, d, J=12.4 Hz), 8.56 (1H, s), 7.56-7.73 (3H, m), 7.19-7.22 (1H, m), 6.81 (1H, t, J=9.2 Hz), 4.03 (1H, m), 3.49-3.51 (1H, m), 3.37 (2H, m, buried with water signal), 3.16 (1H, m), 2.19 (6H, s), 1.83-2.03 (4H, m). MS (ESI): 535.0 (M+1)⁺¹. Anal. Cacl. for C23H24FIN4O2: C, 51.7; H, 4.53; N, 10.78. Found: C, 50.88; H, 3.93; N, 9.76.

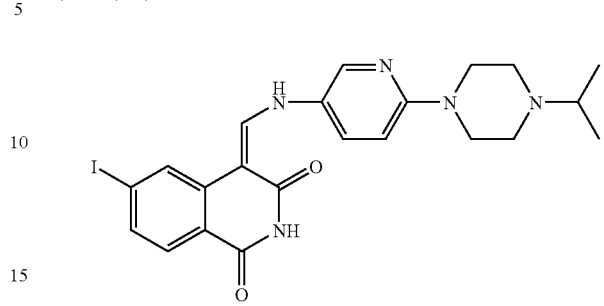

Example 413

(4Z)-6-Iodo-4-({([6-(4-isopropylpiperazin-1-yl)pyridin-3-yl]amino}methylene)isoquinoline-1,3(2H,4H)-dione (4Z)-6-Iodo-4-{[(6-piperazin-1-ylpyridin-3-yl)amino]methylene}isoquinoline-1,3(2H,4H)-dione (150 mg, 0.315 mmol) is dissolved in N-methylpyrrolidinone (3 mL) and methylene chloride (0.9 mL), followed by addition of sodium triacetoxyborohydride (0.77 mg, 3.63 mmol), acetone (0.6 mL, 8.14 mmol) and acetic acid (0.47 mL, 8.2 mmol). After stirring at room temperature for 4 h, methylene chloride and saturated sodium bicarbonate solution were added. The organic layer is separated and dried to give 105 mg (64%) of the title compound as a yellow solid. MS (ESI) m/z 517.4 (M+H)⁺¹

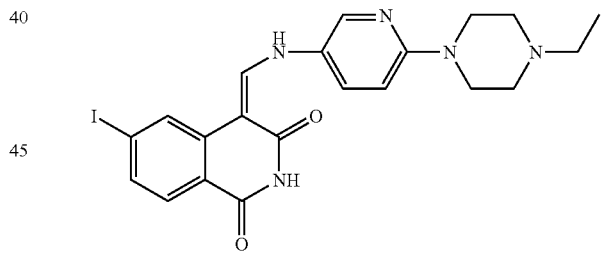

Example 414

(4Z)-4-({[6-(4-Ethylpiperazin-1-yl)pyridin-3-yl]amino}methylene)-6-iodoisoquinoline-1,3(2H,4H)-dione (4Z)-6-Iodo-4-{[(6-piperazin-1-ylpyridin-3-yl)amino]methylene}isoquinoline-1,3(2H,4H)-dione (150 mg, 0.315 mmol) is dissolved in N-methylpyrrolidinone (3 mL) and methylene chloride (0.9 mL), followed by addition of sodium triacetoxyborohydride (0.77 mg, 3.63 mmol), acetaldehyde (0.46 mL, 8.14 mmol) and acetic acid (0.47 mL, 8.2 mmol). After stirring at room temperature for 1 h, methylene chloride and saturated sodium bicarbonate solution were added. The organic layer is separated and dried to give 110 mg (69%) of the title compound as a brown solid. MS (ESI) m/z 504.2 (M+H)$^{+1}$

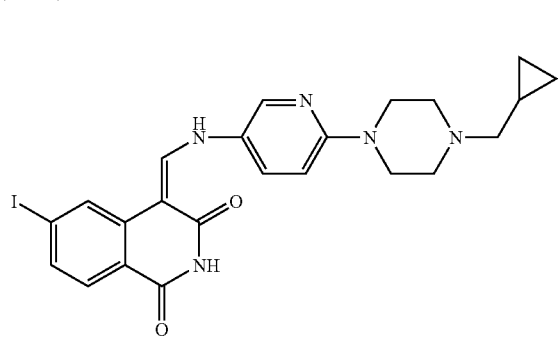

Example 415

(4Z)-4-[({6-[4-(Cyclopropylmethyl)piperazin-1-yl]pyridin-3-yl}amino)methylene]-6-iodoisoquinoline-1,3(2H,4H)-dione (4Z)-6-Iodo-4-{[(6-piperazin-1-ylpyridin-3-yl)amino]methylene}isoquinoline-1,3(2H,4H)-dione (150 mg, 0.315 mmol) is dissolved in N-methylpyrrolidinone (3 mL) and methylene chloride (0.9 mL), followed by addition of sodium triacetoxyborohydride (0.77 mg, 3.63 mmol), cyclopropanecarbaldehyde (0.61 mL, 8.14 mmol) and acetic acid (0.47 mL, 8.2 mmol). After stirring at room temperature for 1 h, methylene chloride and saturated sodium bicarbonate solution were added. The organic layer is separated and dried to give 110 mg (69%) of the title compound as a brown solid. MS (ESI) m/z 530.4 (M+H)$^{+1}$

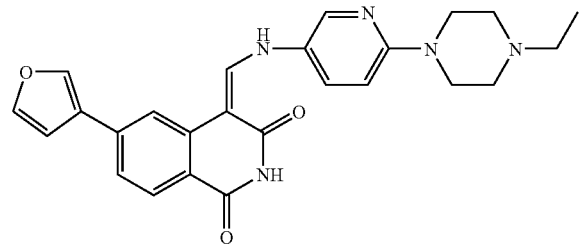

Example 416

(4Z)-4-({[6-(4-Ethylpiperazin-1-yl)pyridin-3-yl]amino}methylene)-6-(3-furyl)isoquinoline-1,3(2H,4H)-dione (4Z)-4-({[6-(4-Ethylpiperazin-1-yl)pyridin-3-yl]amino}methylene)-6-iodoisoquinoline-1,3(2H,4H)-dione (50.3 mg, 0.1 mmol) is mixed with 3-furanboronic acid (22 mg, 0.2 mmol), Pd$_2$(dba)$_3$ (13.7 mg, 0.015 mmol), and cesium carbonate (65 mg, 0.2 mmol). After the solids were degassed, N,N-dimethylformamide (0.7 mL) and P(t-Bu)$_3$ (6 mg, 0.03 mmol) were added. The mixture is heated at 100 C for 10 min, diluted with methylene chloride, and filtered. The filtrate is evaporated to dryness and purified by column chromatography to yield 30 mg (67%) of the title compound as an orange solid. MS (ESI) m/z 444 (M+H)$^{+1}$

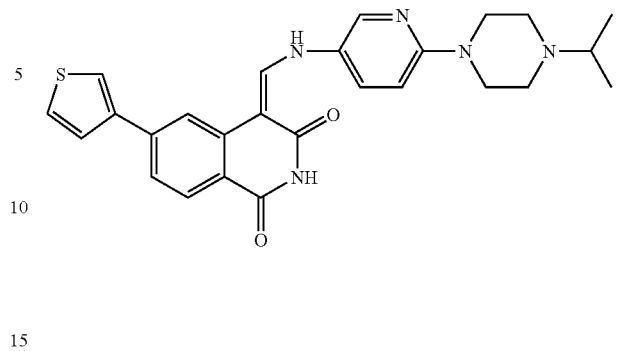

Example 417

(4Z)-4-({[6-(4-Isopropylpiperazin-1-yl)pyridin-3-yl]amino}methylene)-6-(3-thienyl)isoquinoline-1,3(2H,4H)-dione (4Z)-6-Iodo-4-({[6-(4-isopropylpiperazin-1-yl)pyridin-3-yl]amino}methylene)isoquinoline-1,3(2H,4H)-dione (63 mg, 0.1218 mmol) is mixed with 3-furanboronic acid (32 mg, 0.224 mmol), Pd$_2$(dba)$_3$ (16.7 mg, 0.018 mmol), and cesium carbonate (80 mg, 0.24 mmol). After the solids were degassed, N,N-dimethylformamide (0.8 mL) and P(t-Bu)$_3$ (7.4 mg, 0.037 mmol) were added. The mixture is heated at 100 C for 10 min, diluted with methylene chloride, and filtered. The filtrate is evaporated to dryness and purified by column chromatography to yield 33 mg (57%) of the title compound as a yellow solid. MS (ESI) m/z 474 (M+H)$^{+1}$

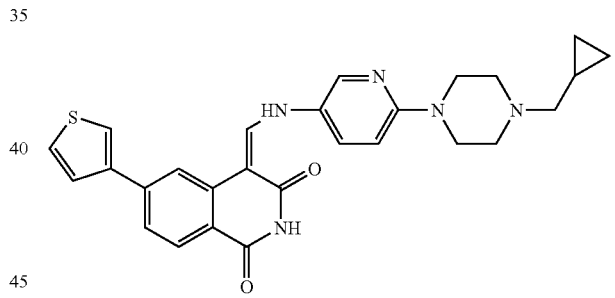

Example 418

(4Z)-4-[({6-[4-(Cyclopropylmethyl)piperazin-1-yl]pyridin-3-yl}amino)methylene]-6-(3-thienyl)isoquinoline-1,3(2H,4H)-dione (4Z)-4-[({6-[4-(Cyclopropylmethyl)piperazin-1-yl]pyridin-3-yl}amino)methylene]-6-iodoisoquinoline-1,3(2H,4H)-dione (72 mg, 0.136 mmol) is mixed with 3-furanboronic acid (35 mg, 0.272 mmol), Pd$_2$(dba)$_3$ (18.7 mg, 0.02 mmol), and cesium carbonate (89 mg, 0.272 mmol). After the solids were degassed, N,N-dimethylformamide (0.8 mL) and P(t-Bu)$_3$ (8.25 mg, 0.04 mmol) were added. The mixture is heated at 100 C for 10 min, diluted with methylene chloride, and filtered. The filtrate is evaporated to dryness and purified by column chromatography to yield 27 mg (41%) of the title compound as a yellow solid. MS (ESI) m/z 486 (M+H)$^{+1}$

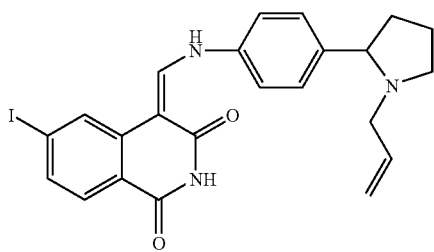

Example 419

4-{[4-(1-Allyl-pyrrolidin-2-yl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(1-Allyl-pyrrolidin-2-yl)-phenylamine (190 mg, 0.58 mmol), 6-iodo-4-methoxymethylene-4H-isoquinoline-1,3-dione (190 mg, 0.18 mmol) in 74% yield as a redish solid: MS (ESI): 500.0 (M+1)$^{+1}$.

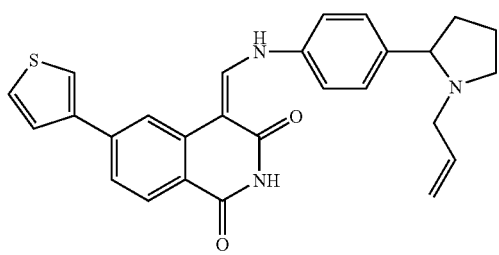

Example 420

4-{[4-(1-Allyl-pyrrolidin-2-yl)-phenylamino]-methylene}-6-thiophen-3-yl-4H-isoquinoline-1,3-dione Using the procedure described for the preparation of 4-{[4-(2-Hydroxymethyl-pyrrolidin-1-ylmethyl)-phenylamino]-methylene}-6-thiophen-3-yl-4H-isoquinoline-1,3-dione, the title compound is obtained from 4-{[4-(1-Allyl-pyrrolidin-2-yl)-phenylamino]-methylene}-6-iodo-4H-isoquinoline-1,3-dione (100 mg, 0.20 mmol) in 42% yield as a yellow powder: MS (ESI): 456.2 (M+1)$^{+1}$.

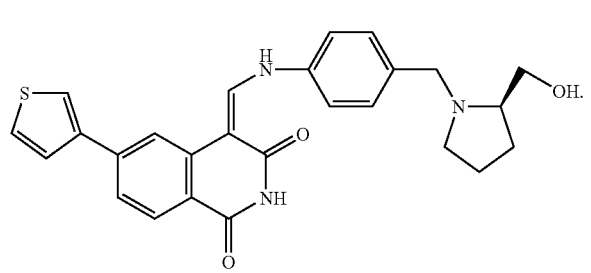

Example 421

4-{[4-(2-Hydroxymethyl-pyrrolidin-1-ylmethyl)-phenylamino]-methylene}-6-thiophen-3-yl-4H-isoquinoline-1,3-dione To a solution of 4-{[4-(2-Hydroxymethyl-pyrrolidin-1-ylmethyl)-phenylamino]-methylene}-6-iodo-4H-isoquinoline-1,3-dione (200 mg, 0.40 mmol) in N,N-dimethylformamide (10 mL) were added 3-thienylboronic acid (120 mg, 0.94 mmol) and Na$_2$CO$_3$ (216 mg, 2.0 mmol). Pd$_2$(dba)$_3$.CHCl$_3$ (20 mg, 0.02 mmol) and P(tBu)$_3$.HBF$_4$ (19 mg, 0.06 mmol) were then added. The mixture is then degassed and heated at 100° C. for 1 h. The N,N-dimethylformamide is then evaporated under reduced pressure and the residue is taken up in EtOAc and H$_2$O. The EtOAc layer is dried and evaporated. The residue, which resulted, is subjected to chromatography to provide the desired product (90 mg, 49%). MS (ESI): 460.2 (M+1)$^{+1}$

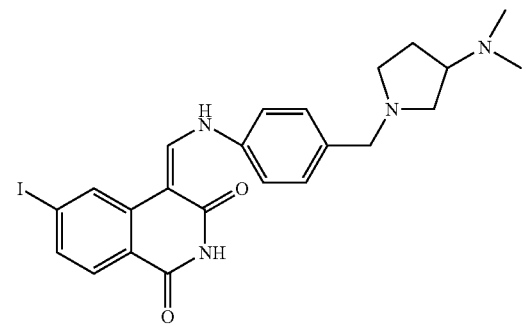

Example 422

(4Z)-4-{[(4-{[3-(Dimethylamino)pyrrolidin-1-yl]methyl}phenyl)amino]methylene}-6-iodoisoquinoline-1,3(2H,4H)-dione Using the procedure described for the preparation of example 14, 230 mg (49% yield) is obtained as a yellow solid from 300 mg (0.92 mmol) (4E)-6-iodo-4-(methoxymethylene)isoquinoline-1,3(2H,4H)-dione and 202 mg (0.92 mmol) of 3-(dimethylamino)pyrrolidin-1-yl]methyl}phenyl)amine; mp 134-135° C.

MS (ESI) m/z 517.0 (M+1)$^+$

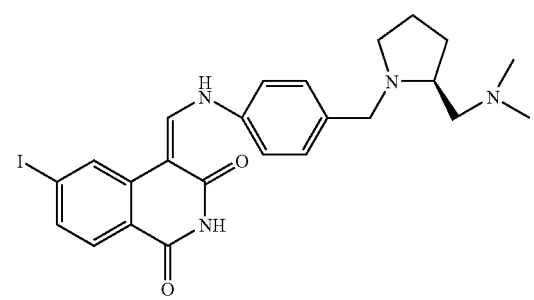

Example 423

(4Z)-4-{[(4-{[3-(Dimethylamino)pyrrolidin-1-yl]methyl}phenyl)amino]methylene}-6-iodoisoquinoline-1,3(2H,4H)-dione Using the procedure described for the preparation of example 14, 20 mg (5% yield) is obtained as a yellow solid from 281.4 mg (0.92 mmol) (4E)-6-iodo-4-(methoxymethylene)isoquinoline-1,3(2H,4H)-dione and 234 mg (0.85 mmol) of (2R)-2-[(dimethylamino)methyl]pyrrolidin-1-yl}methyl)phenyl]amine; mp 130-131° C.

MS (ESI) m/z 531.1 (M+1)+

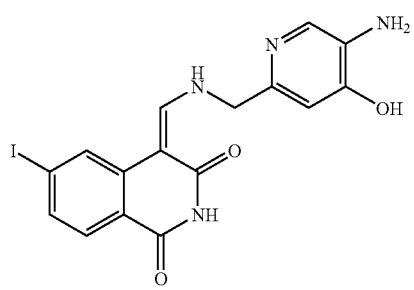

Example 424

4-{[(5-Amino-4-hydroxy-pyridin-2-ylmethyl)-amino]-methylene}-6-iodo-4H-isoquinoline-1,3-dione A mixture of 5-amino-2-aminomethyl-pyridin-4-ol (60 mg, 0.19 mmole as the dihydrobromide), 3 mL of N,N-dimethylformamide and triethylamine (101 uL, 0.72 mmole) were stirred for 15 mins, 4-methoxymethylene-6-iodo-4H-isoquinoline-1,3-dione (63 mg, 0.19 mmole) is added and the reaction mixture stirred for one hour. The reaction mixture is evaporated to dryness, taken up in dimethylsulfoxide and purified by HPLC (acetonitrile-water with 0.2% trifluoroacetic acid). The product is isolated by evaporation in-vacuo to give a brown solid, 5.5 mg, (5%); MS (ES+): m/z 437.0 (M+H).

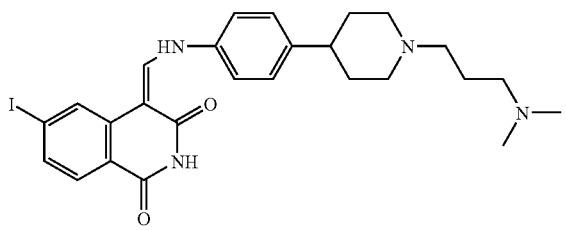

Example 425

(4Z)-4-{[(4-{1-[3-(Dimethylamino)propyl]piperidin-4-yl}phenyl)amino]methylene}-6-iodoisoquinoline-1,3(2H,4H)-dione Using the procedure described for the preparation of 4Z)-6-bromo-4-({[4-(3,5-dimethylpiperazin-1-yl)phenyl]amino}methylene)isoquinoline-1,3(2H,4H)-dione, 0.079 g (73.1% yield) of greenish tan solid is obtained from 0.064 g (0.19 mmol) of (4E)-6-iodo-4-(methoxymethylene)isoquinoline-1,3(2H,4H)-dione and 0.061 g (0.23 mmol) of (4-{1-[3-(dimethylamino)propyl]piperidin-4-yl}phenyl)amine: mp 139-140° C.; MS (ESI) m/z 559.0 (M+H)+1

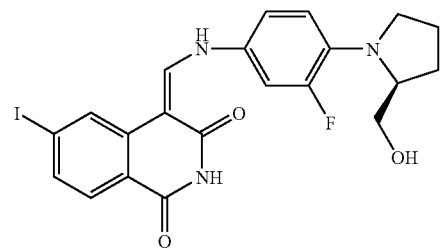

Example 426

4-{[3-Fluoro-4-(2-hydroxymethyl-pyrrolidin-1-yl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from [1-(4-Amino-2-fluoro-phenyl)-pyrrolidin-2-yl]-methanol (150 g, 0.71 mmol), 6-iodo-4-methoxymethylene-4H-isoquinoline-1,3-dione (100 mg, 0.30 mmol) in 98% yield as a redish solid: 1H NMR (400 MHz, DMSO) δ12.56 (1H, d, J=12.8 Hz), 11.33 (1H, s), 8.80 (1H, d, J=12.4 Hz), 8.56 (1H, s), 7.56-7.73 (3H, m), 7.17-7.20 (1H, m), 6.83 (1H, t, J=9.2 Hz), 4.67 (1H, t, J=5.6 Hz), 3.89 (1H, m), 3.43-3.55 (2H, m), 3.15-3.25 (2H, m), 1.84-1.98 (4H, m). MS (ESI): 507.9 (M+1)+1. Anal. Cacl. for C21H19FIN3O3: C, 49.72; H, 3.78; N, 8.28. Found: C, 49.62; H, 3.37; N, 8.13.

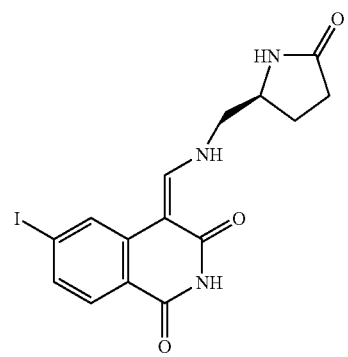

Example 427

6-Iodo-4-{[(5-oxo-pyrrolidin-2-ylmethyl)-amino]-methylene}-4H-isoquinoline-1,3-dione 5-Aminomethyl-pyrrolidin-2-one (140 mg, ~80-90% pure, 1.04 mmol) is stirred with 6-iodo-4-methoxymethylene-4H-isoquinoline-1,3-dione (150 mg, 0.46 mmol) in N,N-dimethylformamide (5 mL) at room temperature. The suspension become clear in 10 minutes and further stirring gave a pale yellow precipitate. The precipitate is filtered and washed with MeOH, Et₂O and dried to provide the title compound (110 mg, 58%). MS (ESI): 411.8 (M+1)⁺¹.

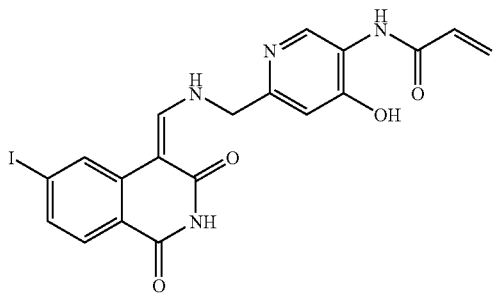

Example 428

N-(4-Hydroxy-6-{[(6-iodo-1,3-dioxo-2,3-dihydro-1H-isoquinolin-4-ylidenemethyl)-amino]-methyl}-pyridin-3-yl)-acrylamide A mixture of 4-{[(5-Amino-4-hydroxy-pyridin-2-ylmethyl)-amino]-methylene}-6-iodo-4H-isoquinoline-1,3-dione (334 mg, 0.766 mmole), 20 mL of dimethylacetamide is stirred, acryoyl chloride (651 uL, 7.66 mmole) is added and the reaction mixture stirred for one hour. The reaction mixture is evaporated to dryness, stirred overnight with a saturated aqueous sodium bicarbonate solution, filtered, washed well with water, and dried to give a green solid, 98 mg, (27%); MS (ES⁻): m/z 489 (M−H).

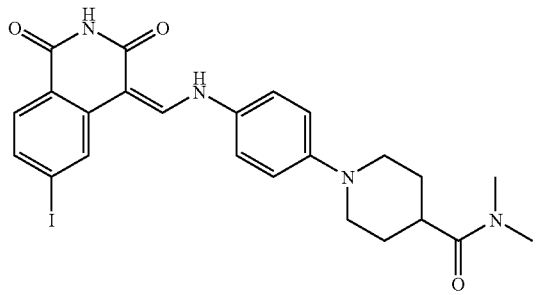

Example 429

1-(4-{[(Z)-(6-Iodo-1,3-dioxo-2,3-dihydroisoquinolin-4(1H)-ylidene)methyl]amino}phenyl)-N,N-dimethylpiperidine-4-carboxamide Dimethylamine (2.0 M solution in tetrahydrofuran, 2 mL) is added to 1-(4-nitrophenyl)piperidine-4-carboxylic acid chloride hydrochloride (0.15 g, 0.5 mmol). When the combined compounds fully reacted, the reaction mixture is concentrated under reduced pressure, then taken up in methanol. Water is added and the resulting solid is collected to give 1-(4-nitro-phenyl)-piperidine-4-carboxylic acid dimethylamide, which is used without further purification in the subsequent step.

MS (ES⁺): 278.3 (M+H)⁺

A solution 1-(4-nitro-phenyl)-piperidine-4-carboxylic acid dimethylamide in ethanol/tetrahydrofuran and concentrated hydrochloric acid is degassed with dry ice. Palladium on carbon (10%, 50 mg) is added and the mixture is shaken for two hours under 50 psi of hydrogen. The mixture is filtered through a pad of diatomaceous earth and concentrated under reduced pressure to give 1-(4-amino-phenyl)-piperidine-4-carboxylic acid dimethylamide dihydrochloride, which is used in the next step without further purification.

(4E)-6-iodo-4-(methoxymethylene)isoquinoline-1,3(2H,4H)-dione (0.14 g, 0.44 mmol) and 1-(4-amino-phenyl)-piperidine-4-carboxylic acid dimethylamide dihydrochloride (0.14 g, 0.44 mmol) were coupled in N,N-dimethylformamide (2.5 mL) with triethylamine (0.57 mL). The mixture is heated in a 100° C. block shaker until complete. Water is added to precipitate the solid product. The solid is collected by filtration, purified by reverse phase HPLC to give 1-(4-{[(Z)-(6-iodo-1,3-dioxo-2,3-dihydroisoquinolin-4(1H)-ylidene)methyl]amino}phenyl)-N,N-dimethylpiperidine-4-carboxamide, trifluoroacetic acid salt (37 mg, 13%).

MS (ES⁺): 545.1 (M+H)⁺

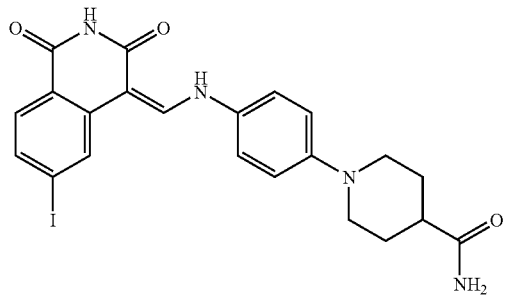

Example 430

1-(4-{[(Z)-(6-Iodo-1,3-dioxo-2,3-dihydroisoquinolin-4(1H)-ylidene)methyl]amino}phenyl)piperidine-4-carboxamide Three drops of triethylamine were added to a suspension of 1-(4-nitrophenyl)piperidine-4-carboxylic acid chloride hydrochloride (0.15 g, 0.5 mmol) in tetrahydrofuran (5 mL). Ammonia gas is bubbled into the mixture for 10 minutes. When completed, the reaction mixture is concentrated under reduced pressure. Water is added and the resulting solid is collected to give 1-(4-nitro-phenyl)-piperidine-4-carboxamide, which is used without further purification in the subsequent step.

MS (ES⁺): 250.3 (M+H)⁺

A solution of 1-(4-nitro-phenyl)-piperidine-4-carboxamide in ethanol/tetrahydrofuran and concentrated hydrochloric acid is degassed with dry ice. Palladium on carbon (10%, 50 mg) is added and the mixture is shaken for two hours under 50 psi of hydrogen. The mixture is filtered through a pad of diatomaceous earth and concentrated under reduced pressure to give 1-(4-amino-phenyl)-piperidine-4-carboxamide dihydrochloride, which is used the next step without further purification.

(4E)-6-iodo-4-(methoxymethylene)isoquinoline-1,3(2H,4H)-dione (0.14 g, 0.44 mmol) and 1-(4-amino-phenyl)-piperidine-4-carboxamide dihydrochloride (0.13 g, 0.44 mmol) were coupled in N,N-dimethylformamide (2.5 mL) with triethylamine (0.57 mL). The mixture is heated in a 100° C. block shaker until complete. Water is added to precipitate the solid product. This solid is collected by filtration, then purified by reverse phase HPLC to give 1-(4-{[(Z)-(6-iodo-1,3-dioxo-2,3-dihydroisoquinolin-4(1H)-ylidene)methyl] amino}phenyl)piperidine-4-carboxamide, trifluoroacetic acid salt (11 mg, 4.0%).

MS (ES⁺): 517.3 (M+H)⁺

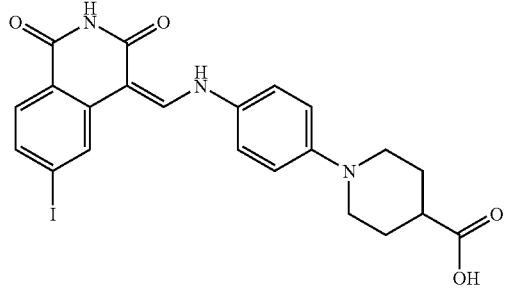

Example 431

1-(4-{[(Z)-(6-Iodo-1,3-dioxo-2,3-dihydroisoquinolin-4(1H)-ylidene)methyl]amino}phenyl)piperidine-4-carboxylic acid To a suspension of isonipocotic acid (8.3 g, 64 mmol) in methanol (250 mL) is added tetrabutylammonium hydroxide (40% aqueous solution, 42 mL). Solvents were then removed under reduced pressure. Residual water is removed by azeotropic distillation with toluene. The semisolid tetrabutylammonium isonipecotate is dried under high vacuum. To a solution of tetrabutylammonium isonipecotate (64 mmol) in dimethylsulfoxide (150 mL) is added 4-fluoronitrobenzene (7.5 mL, 71 mmol) and potassium carbonate (9.6 g, 70 mmol). The reaction mixture is heated in a 75° C. oil bath for three hours and then allowed to cool to room temperature. Water is added, followed by concentrated hydrochloric acid to bring the mixture to pH 6. The precipitated material is collected by filtration, washed with acetonitrile, and dried under house vacuum to provide 1-(4-nitrophenyl)piperidine-4-carboxylic acid as a yellow powder (14 g, 88%).

MS (ES$^+$): 251.1 (M+H)$^+$

In a 75-mL Parr bottle, 1-(4-nitrophenyl)piperidine-4-carboxylic acid (0.13 g, 0.52 mmol) is dissolved in ethanol/ethyl acetate (1:1, 30 mL). Concentrated hydrochloric acid (0.5 mL) is added. After degassing the mixture with dry ice, palladium on carbon (10%, 30 mg) is added. The reaction mixture is shaken overnight under 50 psi hydrogen, then filtered through a pad of diatomaceous earth and concentrated under reduced pressure to give 1-(4-aminophenyl)piperidine-4-carboxylic acid dihydrochloride.

(4E)-6-iodo-4-(methoxymethylene)isoquinoline-1,3(2H,4H)-dione (0.19 g, 0.58 mmol) and 1-(4-aminophenyl)piperidine-4-carboxylic acid dihydrochloride (0.17 g, 0.58 mmol) were coupled in N,N-dimethylformamide (2.5 mL) with triethylamine (760 μL). The mixture is heated in a 100° C. block shaker until complete. Water is added to precipitate the solid product. This solid is collected by filtration, then purified by reverse phase HPLC to give 1-(4-{[(Z)-(6-iodo-1,3-dioxo-2,3-dihydroisoquinolin-4(1H)-ylidene)methyl]amino}phenyl)piperidine-4-carboxylic acid trifluoroacetate (3.4 mg, 0.9%).

MS (ES$^-$): 516.3 (M−H)$^-$

Example 432

1-(4-{[(Z)-(6-Iodo-1,3-dioxo-2,3-dihydroisoquinolin-4(1H)-ylidene)methyl]amino}phenyl)-N-methoxy-N-methylpiperidine-4-carboxamide A suspension of 1-(4-nitrophenyl)piperidine-4-carboxylic acid (0.76 g, 3.0 mmol) in dichloromethane (15 mL) is cooled to 0° C. in an ice-water bath. Carbonyldiimidazole (0.59 g, 3.6 mmol) is added and the mixture is allowed to warm to room temperature. An additional volume of dichloromethane (10 mL) is added and the mixture continued to stir for 30 minutes before the addition of N,O-dimethylhydroxylamine hydrochloride (0.73 g, 7.5 mmol). After stirring overnight, the reaction mixture is filtered. The insoluble material is washed with diethyl ether, and the combined filtrate is washed with 5% aqueous potassium hydrogen carbonate solution, water, and saturated aqueous sodium chloride solution. The organic phase is dried over anhydrous magnesium sulfate, filtered, and concentrated under reduced pressure to give 1-(4-nitro-phenyl)-piperidine-4-carboxylic acid methoxy-methyl-amide as a bright yellow powder (0.84 g, 95%).

MS (ES$^+$): 294.3 (M+H)$^+$

A solution of 1-(4-nitro-phenyl)-piperidine-4-carboxylic acid methoxy-methyl-amide (approximately 0.20 g, 0.8 mmol) in ethanol/ethyl acetate (1:1, 30 mL) and concentrated hydrochloric acid (1 mL) is degassed with dry ice. Palladium on carbon (10%, 35 mg) is added and the mixture is shaken for two hours under 40 psi of hydrogen. The mixture is filtered through a pad of diatomaceous earth and concentrated under reduced pressure to give 1-(4-amino-phenyl)-piperidine-4-carboxylic acid methoxy-methyl-amide dihydrochloride (0.30 g, >100%).

MS (ES$^+$): 264.3 (M+H)$^+$ (4E)-6-iodo-4-(methoxymethylene)isoquinoline-1,3(2H,4H)-dione (0.30 g, 0.89 mmol) and 1-(4-amino-phenyl)-piperidine-4-carboxylic acid methoxy-methyl-amide dihydrochloride (0.30 g, 0.89 mmol) were coupled in N,N-dimethylformamide (2.5 mL) with triethylamine (1.2 mL). The mixture is heated in a 100° C. block shaker until complete. Then water is added in order to precipitate the solid product. This solid is collected by filtration, then purified by reverse phase HPLC to give 1-(4-{[(Z)-(6-iodo-1,3-dioxo-2,3-dihydroisoquinolin-4(1H)-ylidene)methyl]amino}phenyl)-N-methoxy-N-methylpiperidine-4-carboxamide trifluoroacetate (6.5 mg, 1.1%).

MS (ES$^+$): 561.1 (M+H)$^+$

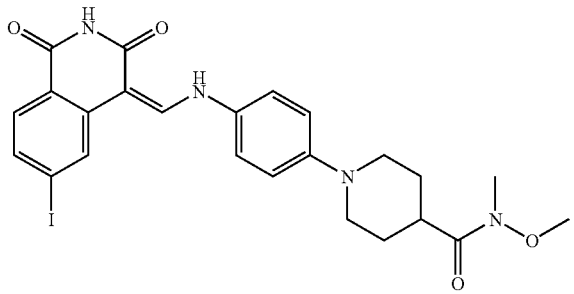

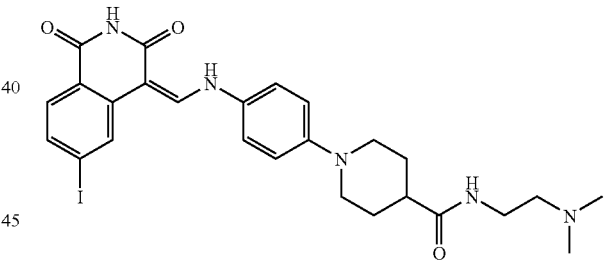

Example 433

N-[2-(Dimethylamino)ethyl]-1-(4-{[(Z)-(6-iodo-1,3-dioxo-2,3-dihydroisoquinolin-4(1H)-ylidene)methyl]amino}phenyl)piperidine-4-carboxamide To a suspension of 1-(4-nitrophenyl)piperidine-4-carboxylic acid (0.75 g, 3.0 mmol) in dichloromethane (15 mL) is added oxalyl chloride (0.32 mL, 3.6 mmol) and then one drop of N,N-dimethylformamide. The reaction mixture is heated in a 60° C. oil bath under a nitrogen atmosphere for 30 minutes, concentrated under reduced pressure to provide 1-(4-nitrophenyl)piperidine-4-carboxylic acid chloride hydrochloride. N,N-dimethylethylenediamine (1.0 mmol) is added neat to 1-(4-nitrophenyl)piperidine-4-carboxylic acid chloride hydrochloride (0.15 g, 0.5 mmol). The resulting solid is purified by reverse-phase HPLC to provide 1-(4-nitrophenyl)-piperidine-4-carboxylic acid (2-dimethylaminoethyl)-amide trifluoroacetate.

MS (ES$^+$): 321.4 (M+H)$^+$

A solution of 1-(4-nitro-phenyl)-piperidine-4-carboxylic acid (2-dimethylamino-ethyl)-amide trifluoroacetate in ethanol/tetrahydrofuran and concentrated hydrochloric acid is degassed with dry ice. Palladium on carbon (10%, 50 mg) is added and the mixture is shaken for two hours under 50 psi of hydrogen. The mixture is filtered through a pad of diatomaceous earth and concentrated under reduced pressure to give 1-(4-amino-phenyl)-piperidine-4-carboxylic acid (2-dimethylamino-ethyl)-amide trihydrochloride.

(4E)-6-iodo-4-(methoxymethylene)isoquinoline-1,3(2H,4H)-dione (0.16 g, 0.50 mmol) and 1-(4-amino-phenyl)-piperidine-4-carboxylic acid (2-dimethylamino-ethyl)-amide trihydrochloride (0.20 g, 0.50 mmol) were coupled in N,N-dimethylformamide (2.5 mL) with triethylamine (0.65 mL). The mixture is heated in a 100° C. block shaker until complete. Then water is added in order to precipitate the solid product. This solid is collected by filtration, then purified by reverse phase HPLC to give N-[2-(dimethylamino)ethyl]-1-(4-{[(Z)-(6-iodo-1,3-dioxo-2,3-dihydroisoquinolin-4(1H)-ylidene)methyl]amino}phenyl)piperidine-4-carboxamide ditrifluoroacetate (118 mg, 29%).

MS (ES$^+$): 588.0 (M+H)$^+$

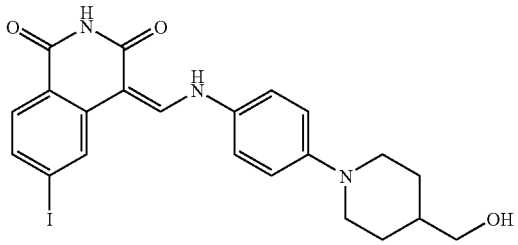

Example 434

(4Z)-4-[({4-[4-(Hydroxymethyl)piperidin-1-yl]phenyl}amino)methylene]-6-iodoisoquinoline-1,3(2H,4H)-dione To a 0° C. solution of 1-(4-nitrophenyl)piperidine-4-carboxylic acid (1.0 g, 4.0 mmol) in tetrahydrofuran (14 mL) is added borane.tetrahydrofuran complex (1.8 M, 7 mL, 13 mmol). After completion of the dropwise addition, the coolant is removed. The mixture is stirred overnight at room temperature and re-cooled to 0° C. in an ice-water bath. Sodium hydroxide solution (1M, 6 mL) is added dropwise. The basic mixture is neutralized by the addition of saturated aqueous ammonium chloride solution. The mixture is extracted 3× with ethyl acetate, and the combined extracts were washed with saturated aqueous sodium chloride solution, dried over anhydrous magnesium sulfate, and concentrated under reduced pressure to give [1-(4-nitro-phenyl)-piperidin-4-yl]-methanol.

MS (ES$^+$): 237.3 (M+H)$^+$

A solution of [1-(4-nitro-phenyl)-piperidin-4-yl]-methanol. (0.15 g, 0.64 mmol) in ethanol/tetrahydrofuran/water (2:2:1 mL) and concentrated hydrochloric acid (10 drops) is degassed with dry ice. Palladium on carbon (10%, 50 mg) is added and the mixture is stirred overnight under 1 atm of hydrogen. The mixture is filtered through a pad of diatomaceous earth and concentrated under reduced pressure to give [1-(4-amino-phenyl)-piperidin-4-yl]-methanol dihydrochloride (0.19 g, >100%).

MS (ES$^+$): 207.4 (M+H)$^+$ (4E)-6-iodo-4-(methoxymethylene)isoquinoline-1,3(2H,4H)-dione (0.22 g, 0.68 mmol) and [1-(4-amino-phenyl)-piperidin-4-yl]-methanol dihydrochloride (0.19 g, 0.68 mmol) were coupled in N,N-dimethylformamide (2.5 mL) with triethylamine (0.89 mL). The mixture is heated in a 100° C. block shaker until complete. Water is added to precipitate the solid product. This solid is collected by filtration and purified by reverse phase HPLC to give (4Z)-4-[({4-[4-(hydroxymethyl)piperidin-1-yl]phenyl}amino)methylene]-6-iodoisoquinoline-1,3(2H,4H)-dione trifluoroacetate (28 mg, 6.7%).

MS (ES$^+$): 504.3 (M+H)$^+$

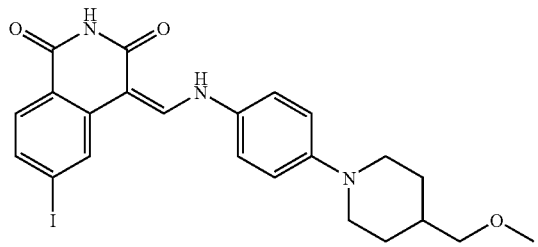

Example 435

(4Z)-6-Iodo-4-[({4-[4-(methoxymethyl)piperidin-1-yl]phenyl}amino)methylene]isoquinoline-1,3(2H,4H)-dione To a 0° C. mixture of [1-(4-nitro-phenyl)-piperidin-4-yl]-methanol and iodomethane (0.25 mL, 4.0 mmol) in N,N-dimethylformamide (3 mL) is added sodium hydride (60% dispersion in mineral oil, 80 mg, 2.0 mmol). The cooling bath is removed and the mixture is stirred at room temperature for five hours before it is re-cooled to 0° C. and quenched by the addition of saturated aqueous sodium hydrogen carbonate solution. The precipitated solid is collected by Büchner filtration, washed with water, and dried under house vacuum to give 4-methoxymethyl-1-(4-nitro-phenyl)-piperidine as pale yellow crystals (0.15 g, 60%).

MS (ES$^+$): 251.4 (M+H)$^+$

A solution of 4-methoxymethyl-1-(4-nitro-phenyl)-piperidine (0.15 g, 0.60 mmol) in ethanol/tetrahydrofuran/water (2:2:1 mL) and concentrated hydrochloric acid (10 drops) is degassed with dry ice. Palladium on carbon (10%, 50 mg) is added and the mixture is stirred for seven hours under 1 atm of hydrogen. The mixture is filtered through a pad of diatomaceous earth and concentrated under reduced pressure to give 4-methoxymethyl-1-(4-amino-phenyl)-piperidine dihydrochloride (0.18 g, 100%).

MS (ES$^+$): 221.4 (M+H)$^+$ (4E)-6-iodo-4-(methoxymethylene)isoquinoline-1,3(2H,4H)-dione (0.20 g, 0.61 mmol) and 4-methoxymethyl-1-(4-amino-phenyl)-piperidine dihydrochloride (0.18 g, 0.61 mmol) were coupled in N,N-dimethylformamide (2.5 mL) with triethylamine (0.80 mL). The mixture is heated in a 100° C. block shaker until complete. Water is added in to precipitate the solid product. The solid is collected by filtration and purified by reverse phase HPLC to give (4Z)-6-iodo-4-[({4-[4-(methoxymethyl)piperidin-1-yl]phenyl}amino)methylene]isoquinoline-1,3(2H,4H)-dione trifluoroacetate (37 mg, 9.6%).

MS (ES⁻): 516.6 (M−H)⁻

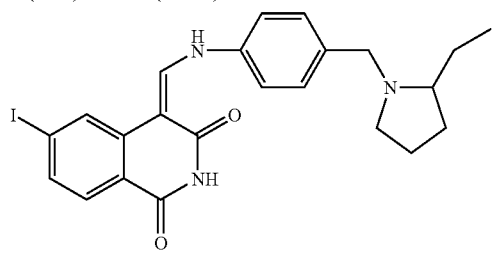

Example 436

4-{[4-(2-Ethyl-pyrrolidin-1-ylmethyl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(2-Ethyl-pyrrolidin-1-ylmethyl)-phenylamine (85 mg, 0.41 mmol), 6-iodo-4-methoxymethylene-4H-isoquinoline-1,3-dione (95 mg, 0.29 mmol) in 48% yield as a yellow solid: MS (ESI): 502.1 (M+1)$^{+1}$.

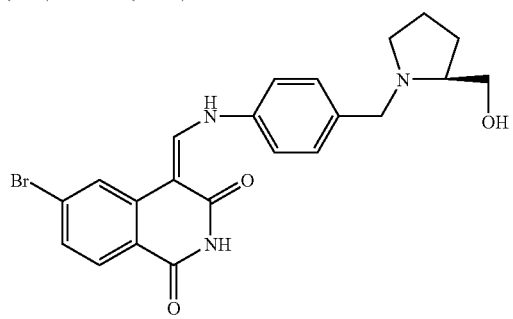

Example 437

6-Bromo-4-{[4-(2-hydroxymethyl-pyrrolidin-1-ylmethyl)-phenylamino]-methylene}-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from [1-(4-Amino-benzyl)-pyrrolidin-2-yl]-methanol (1.3 g, 6.3 mmol), 6-bromo-4-methoxymethylene-4H-isoquinoline-1, 3-dione (1.4 g, 5.0 mmol) in 73% yield as a brown solid: MS (ESI): 456.1, 458.1 (M+1)$^{+1}$.

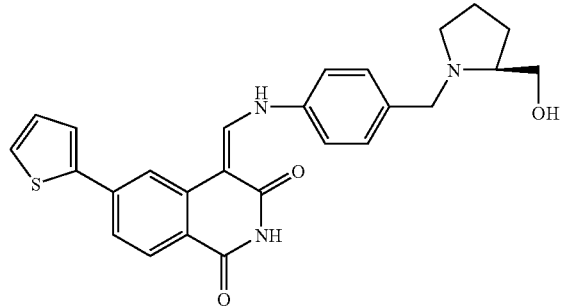

Example 438

4-{[4-(2-Hydroxymethyl-pyrrolidin-1-ylmethyl)-phenylamino]-methylene}-6-thiophen-2-yl-4H-isoquinoline-1,3-dione To a mixture of 6-Bromo-4-{[4-(2-hydroxymethyl-pyrrolidin-1-ylmethyl)-phenylamino]-methylene}-4H-isoquinoline-1,3-dione (100 mg, 0.2 mmol) in N,N-dimethylformamide (1 mL) is added Pd$_2$(dba)$_3$.CHCl$_3$ (10 mg, 0.01 mmol) and P(tBu)$_3$ (20 µL, 1 M solution in N,N-dimethylformamide, 0.02 mmol). After degassing the mixture, 2-thienyl zinc chloride (2.2 mL, 0.5 M solution in THF, 1.1 mmol) is then added and the resulting mixture is stirred for 2 h. N,N-dimethylformamide is then removed and the residue is purified through chromatography to provide the title compound (35 mg, 38%). MS (ESI): 460.1 (M+1)$^{+1}$.

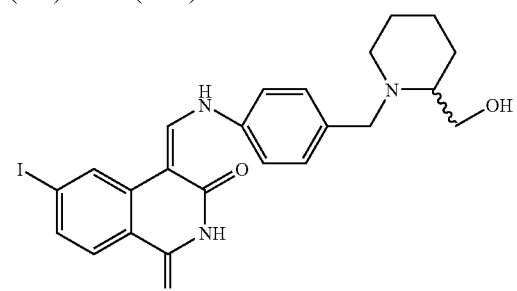

Example 439

(4Z)-4-{[(4-{[2-(Hydroxymethyl)piperidin-1-yl]methyl}phenyl)amino]methylene}-6-iodoisoquinoline-1,3(2H,4H)-dione Using the procedure described for the preparation of example 14, 68 mg (14% yield) is obtained as a orange solid from 300 mg (0.91 mmol) (4E)-6-iodo-4-(methoxymethylene)isoquinoline-1,3(2H,4H)-dione and 200 mg (0.91 mmol) of 2-(hydroxymethyl)piperidin-1-yl]methyl}phenyl)amino; mp 205-206° C.

MS (ESI) m/z 518.1 (M+1)$^+$

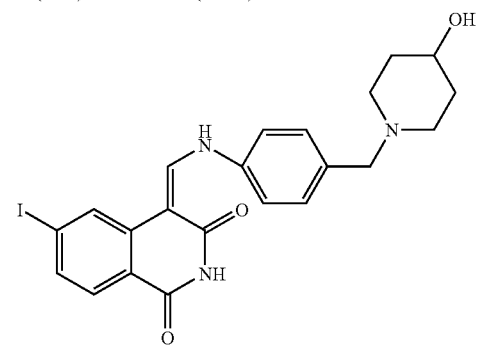

Example 440

(4Z)-4-[({4-[(4-Hydroxypiperidin-1-yl)methyl]phenyl}amino)methylene]-6-iodoisoquinoline-1,3(2H,4H)-dione Using the procedure described for the preparation of example 1 (4Z)-4-[({3-chloro-4-[(1-methyl-1H-imidazol-2-yl)thio]phenyl}amino)methylene]isoquinoline-1,3(2H,4H)-dione 450 mg (89% yield) of an orange solid is obtained from 330 mg (1.0 mmol) of 4E)-6-iodo-4(methoxymethylene)isoquinoline-1,3(2H,4H)-dione and 206.3 mg, (1.0 mmol) of 1-(4-aminobenzyl)piperidin-4-ol mp 255-256° C.
MS (ESI) m/z 504.1 (M+1).

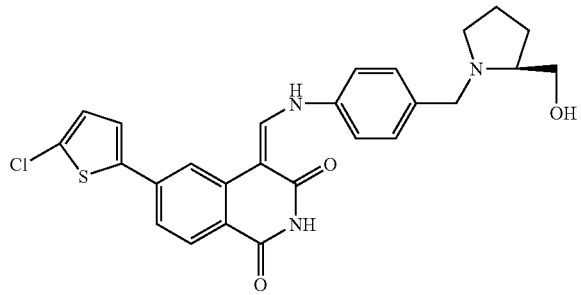

Example 441

6-(5-Chloro-thiophen-2-yl)-4-{[4-(2-hydroxymethyl-pyrrolidin-1-ylmethyl)-phenylamino]-methylene}-4H-isoquinoline-1,3-dione Using the procedure described for the preparation of 4-{[4-(2-Hydroxymethyl-pyrrolidin-1-ylmethyl)-phenylamino]-methylene}-6-thiophen-2-yl-4H-isoquinoline-1,3-dione, the title compound is obtained from 6-Bromo-4-{[4-(2-hydroxymethyl-pyrrolidin-1-ylmethyl)-phenylamino]-methylene}-4H-isoquinoline-1,3-dione (200 mg, 0.4 mmol), 5-chloro-2-thienyl zinc chloride (4.4 mL, 0.5 M solution in THF, 2.2 mmol) in 48% yield as a yellow solid: MS (ESI): 494.1 (M+1)$^{+1}$.

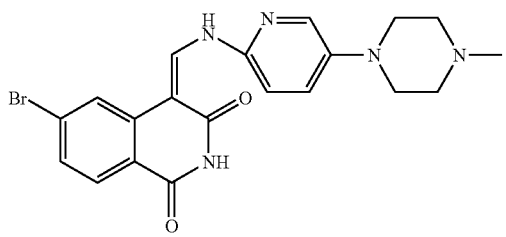

Example 442

(4Z)-6-Bromo-4-({[5-(4-methylpiperazin-1-yl)pyridin-2-yl]amino}methylene)isoquinoline-1,3(2H,4H)-dione Using the procedure described for the preparation of example 14, 1.2 g (75% yield) is obtained as a orange solid from 1.0 g (3.54 mmol) (4E)-6-bromo-4-(methoxymethylene)isoquinoline-1,3(2H,4H)-dione and 670 mg (3.54 mmol) of 5-(4-methylpiperazin-1-yl)pyridin-2-yl]amine; mp 191-192° C.
MS (ESI) m/z 444.0 (M+1)$^+$

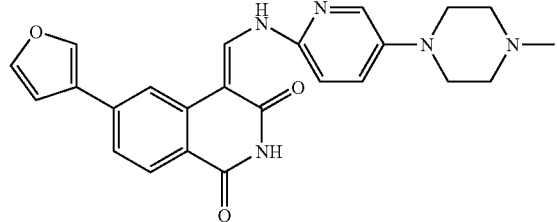

Example 443

(4Z)-6-(3-Furyl)-4-({[5-(4-methylpiperazin-1-yl)pyridin-2-yl]amino}methylene)isoquinoline-1,3(2H,4H)-dione Using the procedure described for the preparation of (4Z)-6-(3-furyl)-4-({[6-(4-methylpiperazin-1-yl)pyridin-3-yl]amino}methylene)isoquinoline-1,3(2H,4H)-dione 1.2 g (63% yield) is obtained as a yellow solid from 2.0 g (4.52 mmol) (4Z)-6-bromo-4-({[5-(4-methylpiperazin-1-yl)pyridin-2-yl]amino}methylene)isoquinoline-1,3(2H,4H)-dione and 3-furan boronic acid 1.3 g, (11.3 mmol).; mp 262-263° C.
MS (ESI) m/z 430.1 (M+1)$^+$

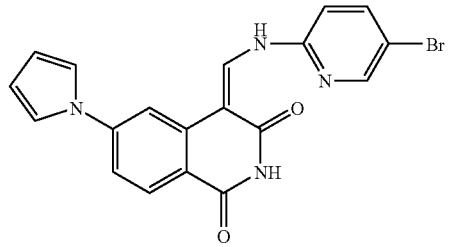

Example 444

(Z)-4-((5-Bromopyridin-2-ylamino)methylene)-6-(1H-pyrrol-1-yl)isoquinoline-1,3(2H,4H)-dione A mixture of (E)-4-(methoxymethylene)-6-(1H-pyrrol-1-yl)isoquinoline-1,3(2H,4H)-dione (268 mg, 1.0 mmole), dimethylformamide (8 mL), and 5-bromopyridin-2-amine (173 mg, 1.0 mmole) is heated at 125° C. for four hours. The reaction mixture is cooled, diluted with ether, filtered, washed with fresh ether and dried to give a salmon solid, 176 mg, (43%), mp 317-8° C. dec; MS (ES$^-$): m/z 407.0 (M–H).

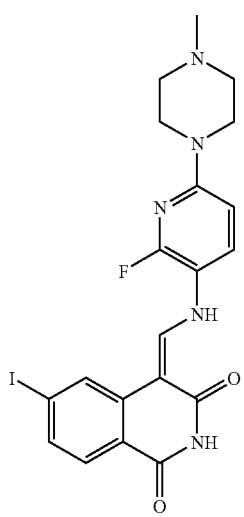

Example 445

(4Z)-4-({[2-Fluoro-6-(4-methylpiperazin-1-yl)pyridin-3-yl]amino}methylene)-6-iodoisoquinoline-1,3(2H,4H)-dione Into a suspension of 2,6-dichloro-3-nitropyridine (13 g, 68 mmol) in ethanol (65 mL) is bubbled anhydrous ammonia gas for 20 minutes. The mixture is allowed to stir at room temperature for 64 hours and then the volume is reduced by 50% under reduced pressure. Water is added to the suspension, and the solid is collected by Büchner filtration, washed with water and methanol, and dried under house vacuum to give 6-chloro-3-nitropyridin-2-amine as a yellow powder (10 g, 85

MS (ES⁻): 172.2 (M–H)⁻

To a suspension of 6-chloro-3-nitropyridin-2-amine (1.7 g, 9.8 mmol) in methanol (17 mL) is added N-methylpiperazone (1.6 mL, 15 mmol). The mixture is stirred at room temperature overnight and then concentrated to dryness under reduced pressure. The solid material is collected by Büchner filtration, washed with methanol, and dried under house vacuum to give 6-(4-methylpiperazin-1-yl)-3-nitropyridin-2-amine as a yellow powder (10 g, 85%).

MS (ES⁺): 238.3 (M+H)⁺

A solution of 6-(4-methylpiperazin-1-yl)-3-nitropyridin-2-amine (1.2 g, 5.0 mmol) in hydrogen fluoride.pyridine (15 mL) is cooled to 0° C. in an ice-water bath. Sodium nitrite (0.36 g, 5.2 mmol) is added in a single portion, and the mixture is stirred for 30 minutes at 0° C. The bath is removed and the mixture is heated for 15 minutes in an oil bath on a 70° C. hot plate. After cooling to room temperature, the reaction mixture is poured onto ice (50 g), neutralized with saturated aqueous sodium hydrogen carbonate solution, and basified with 10 N sodium hydroxide solution. The mixture is extracted 3× with dichloromethane, dried over anhydrous magnesium sulfate, and concentrated under reduced pressure. Eighty-percent of the crude residue is purified by reverse-phase HPLC to give 1-(6-fluoro-5-nitropyridin-2-yl)-4-methylpiperazine.trifluoroacetic acid salt (0.40 g, 29%).

MS (ES⁺): 241.3 (M+H)⁺

To a suspension of 1-(6-fluoro-5-nitropyridin-2-yl)-4-methylpiperazine.trifluoroacetic acid salt (0.38 g, 1.1 mmol) in ethanol (30 mL) is added triethylamine dropwise with agitation until all of the solid had dissolved. The mixture is then degassed with dry ice and treated with an aqueous slurry of Raney nickel (approx 1.5 mL). After shaking under 50 psi of hydrogen, the reaction mixture is filtered through a pad of diatomaceous earth and concentrated under reduced pressure to give 2-fluoro-6-(4-methyl-piperazin-1-yl)-pyridin-3-ylamine (contaminated with triethylammonium trifluoroacetate) as a red wine colored solid.

MS (ES⁺): 211.3 (M+H)⁺

(4E)-6-Iodo-4-(methoxymethylene)isoquinoline-1,3(2H,4H)-dione (0.26 g, 0.80 mmol), 2-fluoro-6-(4-methyl-piperazin-1-yl)-pyridin-3-ylamine (contaminated with triethylammonium trifluoroacetate, approximately 0.80 mmol) were coupled in N,N-dimethylformamide (10 mL) with triethylamine (0.66 mL). The mixture is heated in a 100° C. oil bath for one hour. The reaction mixture is purified by reverse phase HPLC and then flash silica gel chromatography (methanol/chloroform) to give (4Z)-4-({[2-fluoro-6-(4-methylpiperazin-1-yl)pyridin-3-yl]amino}methylene)-6-iodoisoquinoline-1,3(2H,4H)-dione (0.20 g, 49%).

MS (ES⁺): 508.1 (M+H)⁺

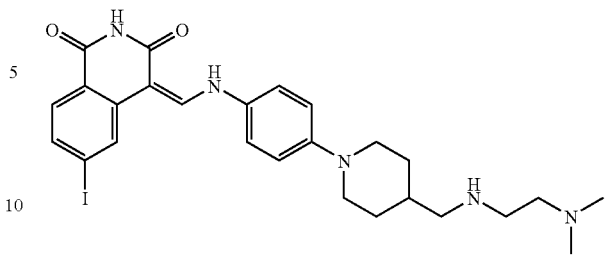

Example 446

(4Z)-4-[({4-[4-({[2-(Dimethylamino)ethyl]amino}methyl)piperidin-1-yl]phenyl}amino)methylene]-6-iodoisoquinoline-1,3(2H,4H)-dione To a mixture of 1-(4-aminophenyl)piperidine-4-carboxylic acid dihydrochloride (2.1 g, 7.2 mmol) in 50% aqueous dioxane (34 mL) is added sodium hydroxide (1.0 g, 25 mmol), followed by di-tert-butyldicarbonate (1.9 g, 8.6 mmol). After stirring overnight at room temperature, the mixture is acidified to pH 3 with 5% aqueous potassium hydrogen sulfate solution. The mixture is extracted 3× with dichloromethane. The combined extracts were dried over anhydrous magnesium sulfate, filtered, and concentrated under reduced pressure to give 1-{4-[(tert-butoxycarbonyl)amino]phenyl}piperidine-4-carboxylic acid as a light tan solid (1.3 g, 57%).

MS (ES⁺): 321.3 (M+H)⁺

To a suspension of 1-{4-[(tert-butoxycarbonyl)amino]phenyl}piperidine-4-carboxylic acid (1.3 g, 4.1 mmol) in dichloromethane (40 mL) is added carbonyldiimidazole (0.79 g, 4.9 mmol) and the mixture is stirred at room temperature for 30 minutes before N,O-dimethylhydroxylamine hydrochloride (1.0 g, 10 mmol) is added. After stirring for 30 minutes, the reaction mixture is concentrated under reduced pressure. The residue is partitioned between diethyl ether and water. The ethereal phase is washed 2× with water and once with saturated aqueous sodium chloride solution, dried over anhydrous magnesium sulfate, and concentrated under reduced pressure to provide tert-butyl [4-(4-{[methoxy(methyl)amino]carbonyl}piperidin-1-yl)phenyl]carbamate as a pale yellow solid (1.5 g, 100%).

MS (ES⁺): 364.4 (M+H)⁺

A solution of tert-butyl [4-(4-{[methoxy(methyl)amino]carbonyl}piperidin-1-yl)phenyl]carbamate (1.4 g, 3.9 mmol) in tetrahydrofuran (15 mL) is cooled to 0° C. in an ice-water bath. Lithium aluminum hydride (0.21 g, 5.4 mmol) is added in several portions to the solution. The reaction mixture is allowed to warm to room temperature where it stirred for 30 minutes. It is cooled to 0° C. and quenched with 5% aqueous potassium hydrogen sulfate solution. The insoluble material is removed via filtration. The filtrate is concentrated under reduced pressure and taken up in ethyl acetate. The organic liquor is washed once with water and once with saturated aqueous sodium chloride solution, dried over anhydrous magnesium sulfate, and concentrated under reduced pressure to tert-butyl [4-(4-formyl-piperidin-1-yl)-phenyl]carbamate as an off-white solid (0.90 g, 75%).

MS (ES⁺): 305.3 (M+H)⁺

To a suspension of tert-butyl [4-(4-formyl-piperidin-1-yl)-phenyl]carbamate (0.30 g, 1.0 mmol) in methanol (5 mL) is added N,N-dimethylethylenediamine (0.18 g, 2.0 mmol).

The reaction mixture is stirred for 10 minutes and then a mixture of zinc chloride (82 mg, 0.6 mmol) and sodium cyanoborohydride (75 mg, 1.2 mmol) in methanol (2 mL) is added in a dropwise fashion. After stirring for two hours at room temperature, the reaction mixture is diluted with water and extracted 3× with ethyl acetate. The combined extracts were washed once with saturated aqueous sodium chloride solution, dried over anhydrous magnesium sulfate, and concentrated under reduced pressure to give tert-butyl {4-[4-({[2-(dimethylamino)ethyl]amino}methyl)piperidin-1-yl]phenyl}carbamate as a white foam (0.4 g, 100%).

MS (ES+): 377.4 (M+H)+

To a sample of tert-butyl {4-[4-({[2-(dimethylamino)ethyl]amino}methyl)piperidin-1-yl]phenyl}carbamate (approximately 1.0 mmol) is added hydrogen chloride solution (4 N in dioxane (10 mL). After stirring overnight at room temperature, the solvent is evaporated under reduced pressure. The solid material is collected, washed with diethyl ether, and dried under house vacuum to give the intermediate N-[1-(4-amino-phenyl)-piperidin-4-ylmethyl]-N',N'-dimethyl-ethane-1,2-diamine tetrahydrochloride (0.29 g, 69%), which is used in the following step without further purification.

(4E)-6-Iodo-4-(methoxymethylene)isoquinoline-1,3(2H,4H)-dione (0.23 g, 0.69 mmol), N-[1-(4-amino-phenyl)-piperidin-4-ylmethyl]-N',N'-dimethyl-ethane-1,2-diamine tetrahydrochloride (0.29 g, 0.69 mmol) were coupled in N,N-dimethylformamide (5 mL) with triethylamine (1.0 mL). The mixture is heated in a 100° C. block shaker for three hours. Then water is added in order to precipitate the solid product. This solid is collected by filtration, then a portion thereof is purified by reverse phase HPLC to give (4Z)-4-[({4-[4-({[2-(dimethylamino)ethyl]amino}methyl)piperidin-1-yl]phenyl}amino)methylene]-6-iodoisoquinoline-1,3(2H,4H)-dione trifluoroacetate (44 mg).

MS (ES+): 574.2 (M+H)+ magnesium sulfate, and concentrated under reduced pressure. Eighty-percent of the crude residue is purified by reverse-phase HPLC to give 6-(4-methylpiperazin-1-yl)-3-nitropyridin-2-ol.trifluoroacetic acid salt (0.18 g, 7.8%).

MS (ES+): 239.3 (M+H)+

To a suspension 6-(4-methylpiperazin-1-yl)-3-nitropyridin-2-ol.trifluoroacetic acid salt (0.17 g, 0.48 mmol) in ethanol (25 mL) is added triethylamine dropwise with agitation until all of the solid had dissolved. The mixture is then degassed with dry ice and treated with an aqueous slurry of Raney nickel (approx 1 mL). After shaking under 50 psi of hydrogen, the reaction mixture is filtered through a pad of diatomaceous earth and concentrated under reduced pressure to give 3-amino-6-(4-methyl-piperazin-1-yl)-pyridin-2-ol (0.15 g, contaminated with triethylammonium trifluoroacetate) as a blue solid.

MS (ES+): 209.3 (M+H)+

(4E)-6-iodo-4-(methoxymethylene)isoquinoline-1,3(2H,4H)-dione (0.12 g, 0.35 mmol), 3-amino-6-(4-methyl-piperazin-1-yl)-pyridin-2-ol (0.15 g, contaminated with triethylammonium trifluoroacetate) were coupled in N,N-dimethylformamide (3 mL) with triethylamine (0.27 mL). The mixture is heated in a 100° C. oil bath for three hours. The reaction mixture is purified by reverse phase HPLC to give (4Z)-4-({[2-hydroxy-6-(4-methylpiperazin-1-yl)pyridin-3-yl]amino}methylene)-6-iodoisoquinoline-1,3(2H,4H)-dione.2 trifluoroacetic acid salt (18 mg, 7.0%).

MS (ES+): 506.2 (M+H)+

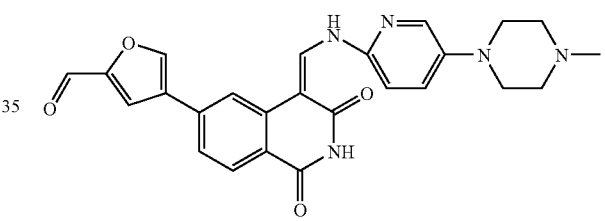

Example 448

4-[(4Z)-4-({[5-(4-Methylpiperazin-1-yl)pyridin-2-yl]amino}methylene)-1,3-dioxo-1,2,3,4-tetrahydroisoquinolin-6-yl]-2-furaldehyde Using the procedure described for the preparation of '(4Z)-6-(3-furyl)-4-({[6-(4-methylpiperazin-1-yl)pyridin-3-'yl]amino}methylene)isoquinoline-1,3(2H,4H)-dione, 170 mg (27% yield) is obtained as a orange solid from 600 mg (1.36 mmol) of (4Z)-6-bromo-4-({[5-(4-methylpiperazin-1-yl)pyridin-2-yl]amino}methylene)isoquinoline-1,3(2H,4H)-dione and 5-formyl-3-furyl boronic acid (L27615-102) 563 mg, (4.08 mmol).; mp 183-184° C.

MS (ESI) m/z 458.1 (M+1)+

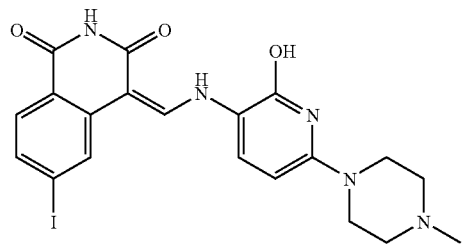

Example 447

(4Z)-4-({[2-Hydroxy-6-(4-methylpiperazin-1-yl)pyridin-3-yl]amino}methylene)-6-iodoisoquinoline-1,3(2H,4H)-dione A solution of 6-(4-methylpiperazin-1-yl)-3-nitropyridin-2-amine (1.2 g, 5.0 mmol) in hydrogen fluoride.pyridine (15 mL) is cooled to 0° C. in an ice-water bath. Sodium nitrite (0.36 g, 5.2 mmol) is added in a single portion, and the mixture is stirred for 30 minutes at 0° C. The bath is removed and the mixture is heated for 15 minutes in an oil bath on a 70° C. hot plate. After cooling to room temperature, the reaction mixture is poured onto ice (50 g), neutralized with saturated aqueous sodium hydrogen carbonate solution, and basified with 10 N sodium hydroxide solution. The mixture is extracted 3× with dichloromethane, dried over anhydrous

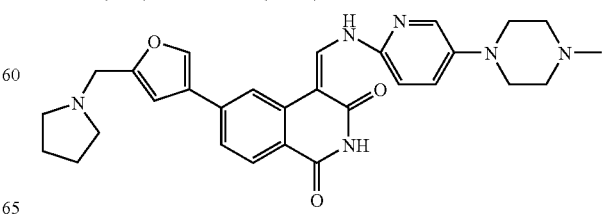

Example 449

(4Z)-4-({[5-(4-Methylpiperazin-1-yl)pyridin-2-yl]amino}methylene)-6-[5-(pyrrolidin-1-ylmethyl)-3-furyl]isoquinoline-1,3(2H,4H)-dione Using the procedure described for the preparation of (4Z)-4-({[4-(dimethylamino)-3-hydroxybenzyl]amino}methylene)-6-iodoisoquinoline-1,3(2H,4H)-dione, 30 mg (45% yield) is obtained as a yellow solid, from 60 mg (1.36 mmol) of 4-[(4Z)-4-({[5-(4-methylpiperazin-1-yl)pyridin-2-yl]amino}methylene)-1,3-dioxo-1,2,3,4-tetrahydroisoquinolin-6-yl]-2-furaldehyde and pyrrolidine 0.11 mL, (1.3 mmol).; mp 194-195° C.

MS (ESI) m/z 271.1 (M+2H)$^+$

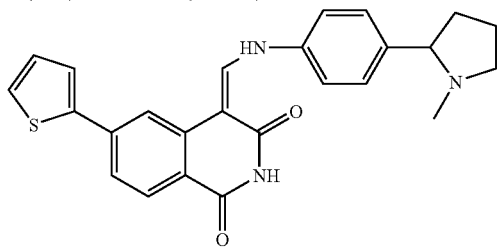

Example 450

4-{[4-(1-Methyl-pyrrolidin-2-yl)-phenylamino]-methylene}-6-thiophen-2-yl-4H-isoquinoline-1,3-dione Using the procedure described for the preparation of 4-{[4-(2-Hydroxymethyl-pyrrolidin-1-ylmethyl)-phenylamino]-methylene}-6-thiophen-2-yl-4H-isoquinoline-1,3-dione, the title compound is obtained from Iodo-4-{[4-(1-methyl-pyrrolidin-2-yl)-phenylamino]-methylene}-4H-isoquinoline-1,3-dione (150 mg, 0.3 mmol), 2-thienyl zinc chloride (2.0 mL, 0.5 M solution in THF, 1.0 mmol) in 69% yield as a yellow solid: MS (ESI): 430.1 (M+1)$^{+1}$.

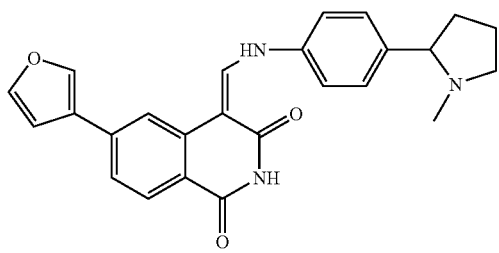

Example 451

6-Furan-3-yl-4-{[4-(1-methyl-pyrrolidin-2-yl)-phenylamino]-methylene}-4H-isoquinoline-1,3-dione Using the procedure described for the preparation of 4-{[4-(2-Hydroxymethyl-pyrrolidin-1-ylmethyl)-phenylamino]-methylene}-6-thiophen-3-yl-4H-isoquinoline-1,3-dione the title compound is obtained from 6-Iodo-4-{[4-(1-methyl-pyrrolidin-2-yl)-phenylamino]-methylene}-4H-isoquinoline-1,3-dione (200 mg, 0.42 mmol), 3-furyl boronic acid (100 mg, 0.78 mmol) in 24% yield as a yellow solid: MS (ESI): 414.1 (M+1)$^{+1}$.

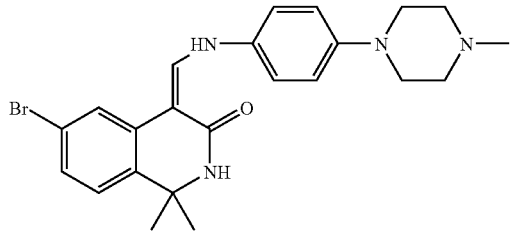

Example 452

6-Bromo-1,1-dimethyl-4-{[4-(4-methyl-piperazin-1-yl)-phenylamino]-methylene}-1,4-dihydro-2H-isoquinolin-3-one 6-Bromo-1,1-dimethyl-1,4-dihydro-2H-isoquinolin-3-one (210 mg, 0.83 mmol) and dimethoxymethyl-dimethyl-amine (250 mg, 2.1 mmol) in (N,N-dimethylformamide) DMF (4 mL) is heated at 100° C. for 1 hour. After which the DMF is evaporated and toluene (6 mL) is added. This solution is then mixed with a solution of 4-(4-Methyl-piperazin-1-yl)-phenylamine (450 mg, 2.4 mmol) in toluene (4 mL) and the mixture is heated at reflux for 6 hours. The mixture is then allowed to cool to room temperature, upon cooling, precipitates formed. The precipitate is collected and further purified through chromatography to provide the title compound (120 mg, 31%). MS (ESI): 455.1, 457.1 (M+1)$^{+1}$.

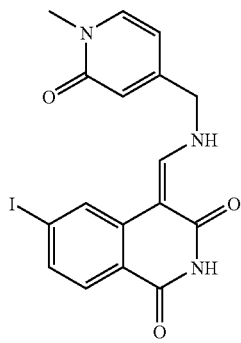

Example 453

(4Z)-6-Iodo-4-({[(1-methyl-2-oxo-1,2-dihydropyridin-4-yl)methyl]amino}methylene)isoquinoline-1,3(2H,4H)-dione To a solution of methyl isonicotinate (5.0 g, 36 mmol) in benzene (165 mL) is added iodomethane (4.5 mL, 72 mmol). The mixture is heated in a 110° C. oil bath for two hours and then allowed to cool to room temperature. The solid is collected by Büchner filtration, washed with hexanes and diethyl ether, and dried under house vacuum to give 4-methoxycarbonyl-1-methylpyridinium iodide (4.6 g, 46%).

MS (ES$^+$): 152.3 (M$^+$–I)$^+$

1-Methyl-2-oxo-1,2-dihydropyridine-4-carboxylic acid is prepared according to the procedure of Fronk, M. H. and Mosher, H. S. JOC. 24, 1959, 196-198.

MS (ES$^-$): 152.1 (M–H)$^-$

1-Methyl-2-oxo-1,2-dihydropyridine-4-carboxamide is prepared according to a procedure modified from Fronk, M. H. and Mosher, H. S. JOC. 24, 1959, 96-198.

MS (ES$^+$): 153.3 (M+H)$^+$

4-Aminomethyl-1-methyl-1H-pyridin-2-one is prepared in two steps from 1-methyl-2-oxo-1,2-dihydropyridine-4-carboxamide from WO 03/051868A1

MS (ES+): 139.3 (M+H)+
(4E)-6-iodo-4-(methoxymethylene)isoquinoline-1,3(2H,4H)-dione (130 mg, 0.40 mmol), 4-aminomethyl-1-methyl-1H-pyridin-2-one (55 mg, 0.40 mol) were coupled in N,N-dimethylformamide (2 mL) at room temperature. The reaction mixture is diluted with water and the precipitate is collected by Büchner filtration and then dried under house vacuum to give (4Z)-6-iodo-4-({[(1-methyl-2-oxo-1,2-dihydropyridin-4-yl)methyl]amino}methylene)isoquinoline-1,3 (2H,4H)-dione as an orange solid (0.15 g, 88%).
MS (ES+): 436.2 (M+H)+

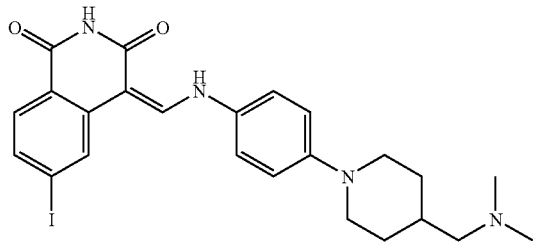

Example 454

(4Z)-4-{[(4-{4-[(Dimethylamino)methyl]piperidin-1-yl}phenyl)amino]methylene}-6-iodoisoquinoline-1,3(2H,4H)-dione To a suspension of tert-butyl [4-(4-formyl-piperidin-1-yl)-phenyl]carbamate (0.20 g, 0.66 mmol) in methanol (5 mL) is added dimethylamine (2.0 M solution in tetrahydrofuran, 0.66 mL, 1.3 mmol). The reaction mixture is stirred for 20 minutes and then a mixture of zinc chloride (53 mg) and sodium cyanoborohydride (50 mg) in methanol (2 mL) is added in a dropwise fashion. After stirring overnight at room temperature, the reaction mixture is diluted with water and extracted 3x with ethyl acetate. The combined extracts were washed once with saturated aqueous sodium chloride solution, dried over anhydrous magnesium sulfate, and concentrated under reduced pressure to give tert-butyl [4-(4-dimethylaminomethyl-piperidin-1-yl)-phenyl]-carbamate as a white foam (0.33 g, >100%).
MS (ES+): 333.4 (M+H)+
Tert-butyl [4-(4-dimethylaminomethyl-piperidin-1-yl)-phenyl]-carbamate (approximately 0.66 mmol) in dichloromethane (5 mL) is treated with trifluoroacetic acid (1 mL). After being stirred overnight at room temperature, the reaction mixture is concentrated under reduced pressure to afford 4-(4-dimethylaminomethyl-piperidin-1-yl)-phenylamine•3 trifluoroacetic acid, which is subsequently used without further purification.
(4E)-6-Iodo-4-(methoxymethylene)isoquinoline-1,3(2H,4H)-dione (0.17 g, 0.50 mmol), 4-(4-dimethylaminomethyl-piperidin-1-yl)-phenylamine•3 trifluoroacetic acid (0.50 mmol) were coupled in N,N-dimethylformamide (2 mL) with triethylamine (0.5 mL). The mixture is heated in a 100° C. oil bath overnight. The reaction mixture is purified by reverse phase HPLC to give (4Z)-4-{[(4-{4-[(dimethylamino)methyl]piperidin-1-yl}phenyl)amino]methylene}-6-iodoisoquinoline-1,3(2H,4H)-dione.2 trifluoroacetic acid (45 mg, 12%).
MS (ES+): 531.2 (M+H)+

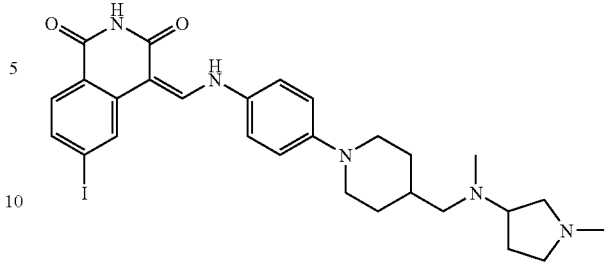

Example 455

(4Z)-6-Iodo-4-({[4-(4-{[methyl(1-methylpyrrolidin-3-yl)amino]methyl}piperidin-1-yl)phenyl]amino}methylene)isoquinoline-1,3(2H,4H)-dione To a suspension of tert-butyl [4-(4-formyl-piperidin-1-yl)-phenyl]carbamate (0.20 g, 0.66 mmol) in methanol (5 mL) is added N,N'-dimethyl-3-aminopyrrolidine (0.15 g, 1.3 mmol). The reaction mixture is stirred for 20 minutes and then a mixture of zinc chloride (53 mg) and sodium cyanoborohydride (50 mg) in methanol (2 mL) is added in a dropwise fashion. After stirring overnight at room temperature, the reaction mixture is diluted with water and extracted 3x with ethyl acetate. The combined extracts were washed once with saturated aqueous sodium chloride solution, dried over anhydrous magnesium sulfate, and concentrated under reduced pressure to give tert-butyl [4-(4-{[methyl-(1-methyl-pyrrolidin-3-yl)-amino]-methyl}-piperidin-1-yl)-phenyl]-carbamate as a foam (0.27 g, 100%).
MS (ES+): 403.5 (M+H)+
Tert-butyl [4-(4-{[methyl-(1-methyl-pyrrolidin-3-yl)-amino]-methyl}-piperidin-1-yl)-phenyl]-carbamate (0.66 mmol) in dichloromethane (5 mL) is treated with trifluoroacetic acid (1 mL). After being stirred overnight at room temperature, the reaction mixture is concentrated under reduced pressure to afford [1-(4-amino-phenyl)-piperidin-4-ylmethyl]-methyl-(1-methyl-pyrrolidin-3-yl)-amine•4 trifluoroacetic acid, which is subsequently used without further purification.
(4E)-6-Iodo-4-(methoxymethylene)isoquinoline-1,3(2H,4H)-dione (0.17 g, 0.50 mmol), [1-(4-amino-phenyl)-piperidin-4-ylmethyl]-methyl-(1-methyl-pyrrolidin-3-yl)-amine•4 trifluoroacetic acid (0.50 mmol) were coupled in N,N-dimethylformamide (2 mL) with triethylamine (0.5 mL). The mixture is heated in a 100° C. oil bath overnight. The reaction mixture is purified by reverse phase HPLC to give (4Z)-6-iodo-4-({[4-(4-{[methyl(1-methylpyrrolidin-3-yl)amino]methyl}piperidin-1-yl)phenyl]amino}methylene)isoquinoline-1,3(2H,4H)-dione.3 trifluoroacetic acid (41 mg, 4.4%).
MS (ES+): 600.3 (M+H)+

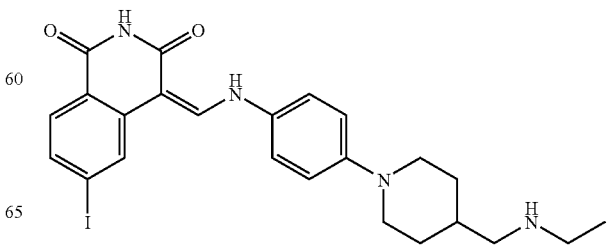

Example 456

(4Z)-4-{[(4-{4-[(Ethylamino)methyl]piperidin-1-yl}phenyl)amino]methylene}-6-iodoisoquinoline-1,3(2H,4H)-dione To a suspension of tert-butyl [4-(4-formyl-piperidin-1-yl)-phenyl]carbamate (0.20 g, 0.66 mmol) in methanol (5 mL) is added ethylamine (2.0 M solution in tetrahydrofuran, 0.66 mL, 1.3 mmol). The reaction mixture is stirred for 20 minutes and then a mixture of zinc chloride (53 mg) and sodium cyanoborohydride (50 mg) in methanol (2 mL) is added in a dropwise fashion. After stirring overnight at room temperature, the reaction mixture is diluted with water and extracted 3× with ethyl acetate. The combined extracts were washed once with saturated aqueous sodium chloride solution, dried over anhydrous magnesium sulfate, and concentrated under reduced pressure to give tert-butyl [4-(4-ethylaminomethyl-piperidin-1-yl)-phenyl]-carbamate as a foam (0.27 g, >100%).

MS (ES+): 334.4 (M+H)+

Tert-butyl [4-(4-ethylaminomethyl-piperidin-1-yl)-phenyl]-carbamate (approximately 0.66 mmol) in dichloromethane (5 mL) is treated with trifluoroacetic acid (1 mL). After being stirred overnight at room temperature, the reaction mixture is concentrated under reduced pressure to afford 4-(4-ethylaminomethyl-piperidin-1-yl)-phenylamine•3 trifluoroacetic acid, which is subsequently used without further purification.

(4E)-6-Iodo-4-(methoxymethylene)isoquinoline-1,3(2H,4H)-dione (0.17 g, 0.50 mmol), 4-(4-ethylaminomethyl-piperidin-1-yl)-phenylamine•3 trifluoroacetic acid (0.50 mmol) were coupled in N,N-dimethylformamide (2 mL) with triethylamine (0.5 mL). The mixture is heated in a 100° C. oil bath overnight. The reaction mixture is purified by reverse phase HPLC to give (4Z)-4-{[(4-{4-[(ethylamino)methyl]piperidin-1-yl}phenyl)amino]methylene}-6-iodoisoquinoline-1,3(2H,4H)-dione.2 trifluoroacetic acid (45 mg, 12%).

MS (ES+): 531.3 (M+H)+

Example 457

(4Z)-4-({[2-Fluoro-6-(4-methylpiperazin-1-yl)pyridin-3-yl]amino}methylene)-6-(3-furyl)isoquinoline-1,3(2H,4H)-dione

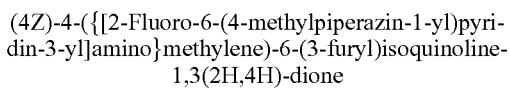

Example 458

6-Furan-3-yl-1,1-dimethyl-4-{[4-(4-methyl-piperazin-1-yl)-phenylamino]-methylene}-1,4-dihydro-2H-isoquinolin-3-one Using the procedure described for the preparation of 4-{[4-(2-Hydroxymethyl-pyrrolidin-1-ylmethyl)-phenylamino]-methylene}-6-thiophen-3-yl-4H-isoquinoline-1,3-dione, the title compound is obtained from 6-Bromo-4-{([4-(2-hydroxymethyl-pyrrolidin-1-ylmethyl)-phenylamino]-methylene}-4H-isoquinoline-1,3-dione (100 mg, 0.22 mmol), 3-furyl boronic acid (50 mg, 0.39 mmol) in 21% yield as a yellow solid: MS (ESI): 443.2 (M+1)+1

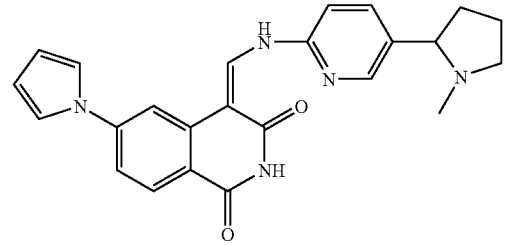

Example 459

(Z)-4-((5-Bromopyridin-2-ylamino)methylene)-6-(1H-pyrrol-1-yl)isoquinoline-1,3(2H,4H)-dione A mixture of (E)-4-(methoxymethylene)-6-(1H-pyrrol-1-yl)isoquinoline-1,3(2H,4H)-dione (189 mg, 0.705 mmole), dimethylformamide (5 mL), and 5-(1-methylpyrrolidin-2-yl)pyridin-2-amine (125 mg, 0.705 mmole) is heated at 125° C. for four hours. The reaction mixture is cooled, diluted with ether, filtered, washed with fresh ether and dried to give a red solid, 15 mg, (5%), mp 186-96° C. dec; MS (ES+): m/z 414.1 (M+H).

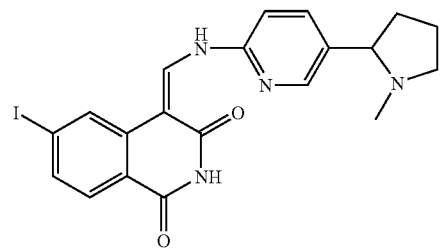

Example 460

(Z)-6-Iodo-4-((5-(1-methylpyrrolidin-2-yl)pyridin-2-ylamino)methylene)isoquinoline-1,3(2H,4H)-dione A mixture of (E)-6-iodo-4-(methoxymethylene)isoquinoline-1,3(2H,4H)-dione (696 mg, 2.12 mmole), dimethylformamide (15 mL), and 5-(1-methylpyrrolidin-2-yl)pyridin-2-amine (375 mg, 2.12 mmole) is heated at 125° C. for four hours. The reaction mixture is cooled, diluted with ether, filtered, washed with fresh ether and dried to give a yellow solid, 580 mg, (58%), mp 174-206° C. dec; MS (ES+): m/z 475.0 (M+H).

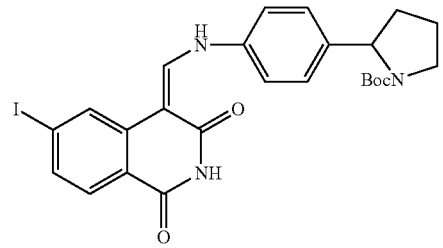

Example 461

2-{4-[(6-Iodo-1,3-dioxo-2,3-dihydro-1H-isoquinolin-4-ylidenemethyl)-amino]-phenyl}-pyrrolidine-1-carboxylic acid tert-butyl ester Using the procedure described for the preparation of 6-Bromo-4-[(4-pyridin-4-yl-phenylamino)-methylene]-4H-isoquinoline-1,3-dione, the title compound is obtained from 2-(4-Amino-phenyl)-pyrrolidine-1-carboxylic acid tert-butyl ester (1.0 g, 3.82 mmol), 6-iodo-4-methoxymethylene-4H-isoquinoline-1,3-dione (1.0 g, 3.03 mmol) in 59% yield as a yellow solid: $^1$H NMR (400 MHz, DMSO) δ12.55-12.57 (1H, M), 11.38 (1 h, S), 8.93 (1H, d, J=12.4 Hz), 8.59 (1H, s), 7.73 (1H, d, J=8.4 Hz), 7.54-7.61 (3H, m), 7.22 (2H, d, J=7.2 Hz), 4.73-4.87 (1H, m), 3.42-3.57 (2H, m), 2.29 (1H, m), 1.70-1.83 (3H, m), 1.40 (4H, s), 1.14 (5H, s). [Two rotamers exist in the NMR.] MS (ESI): 560.1 (M+1)$^{+1}$. Anal. Cacl. for $C_{25}H_{26}IN_3O_4$: C, 53.68; H, 4.68; N, 7.51. Found: C, 53.42; H, 4.94; N, 7.42.

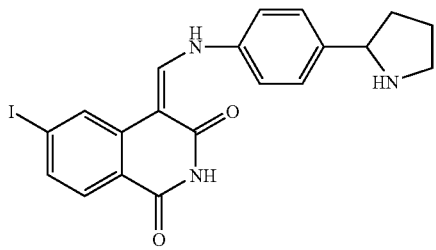

Example 462

6-Iodo-4-[(4-pyrrolidin-2-yl-phenylamino)-methylene]-4H-isoquinoline-1,3-dione

Using the procedure described for the preparation of 4-{[4-(1,2,3,6-Tetrahydro-pyridin-2-yl)-phenylamino]-methylene}-6-thiophen-3-yl-4H-isoquinoline-1,3-dione, the title compound is obtained from 2-{4-[(6-Iodo-1,3-dioxo-2,3-dihydro-1H-isoquinolin-4-ylidenemethyl)-amino]-phenyl}-pyrrolidine-1-carboxylic acid tert-butyl ester (0.9 g, 1.61 mmol) in 74% yield as a yellow solid: $^1$H NMR (400 MHz, DMSO) δ12.55 (1H, d, J=13.2 Hz), 11.40 (1H, br), 8.93 (1H, d, J=11.6 Hz), 8.59 (1H, s), 7.73 (1H, d, J=8.4 Hz), 7.42-7.61 (5H, m), 4.1 (1H, t, J=8.4 Hz), 3.03-3.12 (1H, m), 2.90-2.97 (1H, m), 2.12-2.17 (1H, m), 1.75-2.00 (2H, m), 1.51-1.57 (1H, m). MS (ESI): 460.0 (M+1)$^{+1}$. Anal. Cacl. for C20H18IN3O2: C, 52.3; H, 3.95; N, 5.15. Found: C, 46.16; H, 4.31; N, 7.88. HRMS Cacl. for $C_{20}H_{19}IN_3O_2$: 460.05154. Found: 460.05165, (M+1)$^{+1}$.

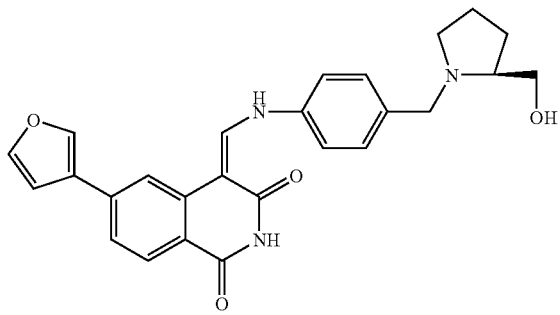

Example 463

6-Furan-3-yl-4-{[4-(2-hydroxymethyl-pyrrolidin-1-ylmethyl)-phenylamino]-methylene}-4H-isoquinoline-1,3-dione Using the procedure described for the preparation of 4-{[4-(2-Hydroxymethyl-pyrrolidin-1-ylmethyl)-phenylamino]-methylene}-6-thiophen-3-yl-4H-isoquinoline-1,3-dione, the title compound is obtained from 6-Bromo-4-{[4-(2-hydroxymethyl-pyrrolidin-1-ylmethyl)-phenylamino]-methylene}-4H-isoquinoline-1,3-dione (200 mg, 0.4 mmol), 3-furyl boronic acid (120 mg, 0.94 mmol) in 99% yield as a yellow solid: MS (ESI): 444.1 (M+1)$^{+1}$.

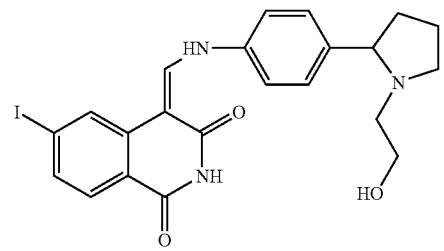

Example 464

4-({4-[1-(2-Hydroxy-ethyl)-pyrrolidin-2-yl]-phenylamino}-methylene)-6-iodo-4H-isoquinoline-1,3-dione 6-Iodo-4-[(4-pyrrolidin-2-yl-phenylamino)-methylene]-4H-isoquinoline-1,3-dione (250 mg, 0.54 mmol) and Na2CO3 (2.0 g, 18.9 mmol) in THF (10 mL) is heated to reflux and bromoethanol (0.15 mL) is added every 45 min for 4 hours. The resulting mixture is then allowed to reflux overnight. After TLC suggested no starting material left, the THF is removed and after an aqueous work up, the desired product is isolated through chromatography (75 mg, 28%). MS (ESI): 504.0 (M+1)$^{+1}$.

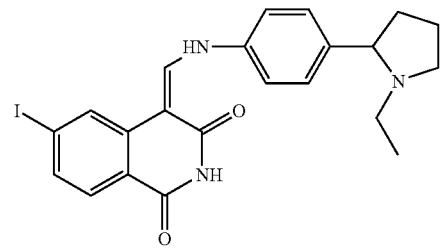

Example 465

4-{[4-(1-Ethyl-pyrrolidin-2-yl)-phenylamino]-methylene}-6-iodo-4H-isoquinoline-1,3-dione 6-Iodo-4-[(4-pyrrolidin-2-yl-phenylamino)-methylene]-4H-isoquinoline-1,3-dione (250 mg, 0.54 mmol) and K$_2$CO$_3$ (170 mg, 1.23 mmol) and EtI (155 mg, 0.99 mmol) in N,N-dimethylformamide (5 mL) were stirred at room temperature for 2 hours. After TLC suggested no starting material left, the N,N-dimethylformamide is removed through an aqueous work up, and the desired product is isolated through chromatography (125 mg, 48%). MS (ESI): 488.0 (M+1)$^{+1}$.

trans-Dichlorobis(triphenylphosphine)palladium(II): mp 159-160° C.; MS (ESI) m/z 458.1 (M+H).

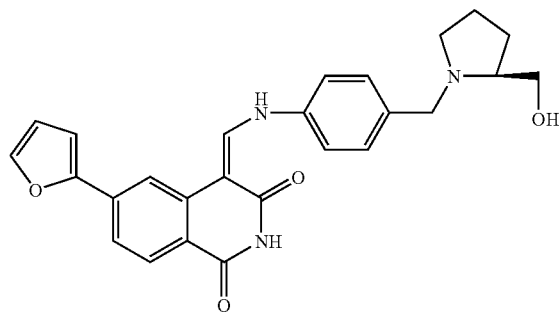

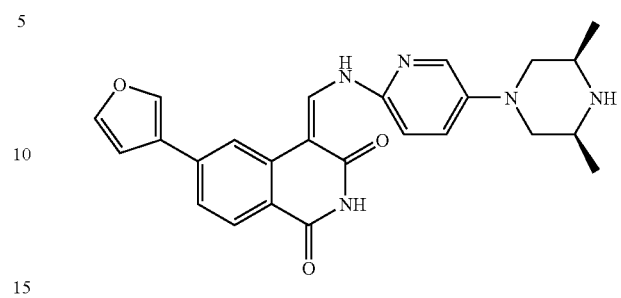

Example 466

6-Furan-2-yl-4-{[4-(2-hydroxymethyl-pyrrolidin-1-ylmethyl)-phenylamino]-methylene}-4H-isoquinoline-1,3-dione 6-Bromo-4-{[4-(2-hydroxymethyl-pyrrolidin-1-ylmethyl)-phenylamino]-methylene}-4H-isoquinoline-1,3-dione (130 mg, 0.26 mmol) and 2-furyltributyltin (270 mg, 0.76 mmol) and PdCl$_2$(PPh$_3$)$_2$ (30 mg) is mixed in N,N-dimethylformamide (4 mL) and degassed. The solution resulted is heated at 100° C. for 1 hour. After the mixture cooled to room temperature, the N,N-dimethylformamide is removed and the residue is purified through chromatography to afford the title compound (68 mg, 59%). MS (ESI): 444.1 (M+1)$^{+1}$.

Example 468

(4Z)-4-[({5-[(3R,5S)-3,5-Dimethylpiperazin-1-yl]pyridin-2-yl}amino)methylene]-6-(3-furyl)isoquinoline-1,3(2H,4H)-dione Using the procedure described for the preparation of (4Z)-6-(3-furyl)-4-({[6-(4-methylpiperazin-1-yl)pyridin-3-'yl]amino}methylene)isoquinoline-1,3(2H,4H)-dione, 500 mg (47% yield) is obtained as a yellow solid from 500 mg (1.09 mmol) of (4Z)-6-bromo-4-[({5-[(3R,5S)-3,5-dimethylpiperazin-1-yl]pyridin-2-yl}amino)methylene]isoquinoline-1,3(2H,4H)-dione and 3-furan boronic acid 245 mg, (2.19 mmol).; mp 230-231° C.

MS (ESI) m/z 444.0 (M+1)$^+$

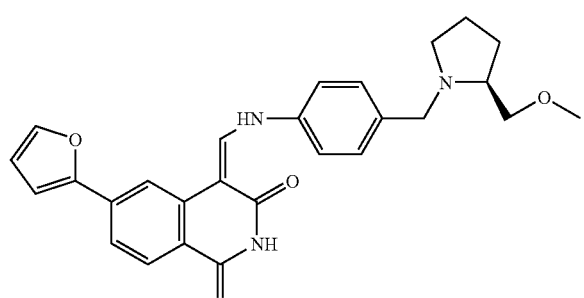

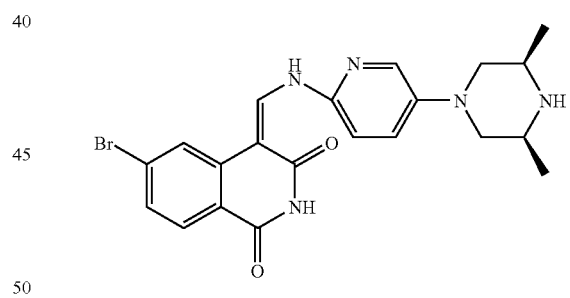

Example 467

(4Z)-6-(2-Furyl)-4-{[(4-{[(2S)-2-(methoxymethyl)pyrrolidin-1-yl]methyl}phenyl)amino]methylene}isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione, 136 mg (77% yield) of yellow solid is obtained from 200 mg (0.39 mmol) of (4Z)-6-bromo-4-{[(4-{[(2s)-2-(methoxymethyl)pyrrolidin-1-yl]methyl}phenyl)amino]methylene}isoquinoline-1,3(2H,4H-dione, 0.4 mL (1.17 mmol) of 2-(tributyltsannyl)furan and 40 mg (0.059 mmol) of

Example 469

(4Z)-6-Bromo-4-[({5-[(3R,5S)-3,5-dimethylpiperazin-1-yl]pyridin-2-yl}amino)methylene]isoquinoline-1,3(2H,4H)-dione Using the procedure described for the preparation of example 14, 1.1 mg (58% yield) is obtained as a brown solid from 1.2 g (4.25 mmol) (4E)-6-bromo-4-(methoxymethylene)isoquinoline-1,3(2H,4H)-dione and 880.0 mg (4.25 mmol) of 5-[(3R,5S)-3,5-dimethylpiperazin-1-yl]pyridin-2-yl)amine; mp 245-246° C.
MS (ESI) m/z 456.0 (M+1)+

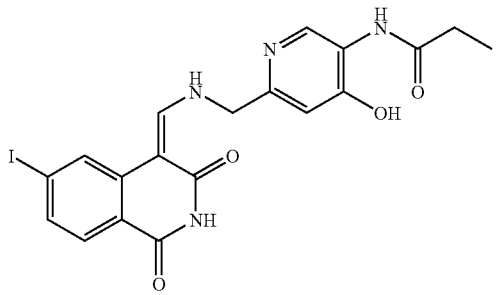

Example 470

N-(4-Hydroxy-6-{[(6-iodo-1,3-dioxo-2,3-dihydro-1H-isoquinolin-4-ylidenemethyl)-amino]-methyl}-pyridin-3-yl)-propionamide A mixture of 4-{[(5-Amino-4-hydroxy-pyridin-2-ylmethyl)-amino]-methylene}-6-iodo-4H-isoquinoline-1,3-dione (332 mg, 0.761 mmole), 6 mL of dimethylacetamide is stirred, then propionyl chloride (705 mg, 7.61 mmole) is added and the reaction mixture stirred for one hour. The reaction mixture is evaporated to dryness, and then stirred overnight with a saturated aqueous sodium bicarbonate solution, the solid is filtered, washed well with water and dried to give a yellow solid, 46 mg, (11%); m.p. 210-18° C. dec; MS (ES+): m/z 492.9 (M+H).

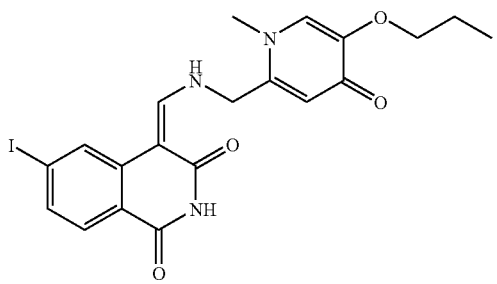

Example 471

6-Iodo-4-{[(1-methyl-4-oxo-5-propoxy-1,4-dihydro-pyridin-2-ylmethyl)-amino]-methylene}-4H-iso-quinoline-1,3-dione A mixture of 2-aminomethyl-1-methyl-5-propoxy-1H-pyridin-4-one (196 mg, 1.0 mmole), 10 mL of N,N-dimethylformamide is stirred, 4-methoxymethylene-6-iodo-4H-isoquinoline-1,3-dione (329 mg, 1.0 mmole) is added and the reaction mixture stirred for one hour. The reaction mixture is evaporated to dryness, triturated with 5% methanol in chloroform, filtered washed with fresh 5% methanol in chloroform, washed with acetonitrile and dried to give an off-white solid, 124 mg, (24%); m.p. 176-96° C. dec; MS (ES+): m/z 494.0 (M+H).

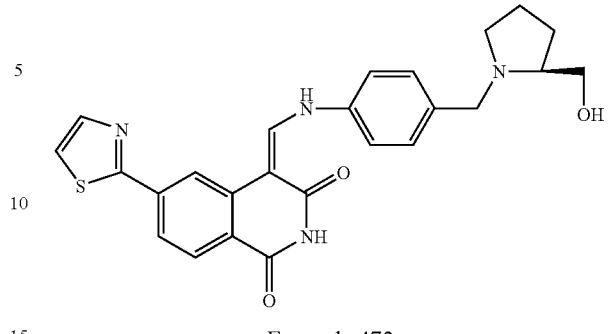

Example 472

4-{[4-(2-Hydroxymethyl-pyrrolidin-1-ylmethyl)-phenylamino]-methylene}-6-thiazol-2-yl-4H-iso-quinoline-1,3-dione Using the procedure described for the preparation of 4-{[4-(2-Hydroxymethyl-pyrrolidin-1-ylmethyl)-phenylamino]-methylene}-6-thiophen-2-yl-4H-isoquinoline-1,3-dione, the title compound is obtained from 6-Bromo-4-{[4-(2-hydroxymethyl-pyrrolidin-1-ylmethyl)-phenylamino]-methylene}-4H-isoquinoline-1,3-dione (166 mg, 0.33 mmol), 2-thiazolyl zinc chloride (3.6 mL, 0.5 M solution in THF, 1.8 mmol) in 21% yield as a yellow solid: MS (ESI): 461.1 (M+1)+1.

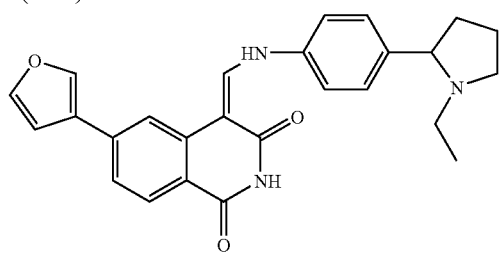

Example 473

4-{[4-(1-Ethyl-pyrrolidin-2-yl)-phenylamino]-methylene}-6-furan-3-yl-4H-isoquinoline-1,3-dione Using the procedure described for the preparation of 4-{[4-(2-Hydroxymethyl-pyrrolidin-1-ylmethyl)-phenylamino]-methylene}-6-thiophen-3-yl-4H-isoquinoline-1,3-dione, the title compound is obtained from 4-{[4-(1-Ethyl-pyrrolidin-2-yl)-phenylamino]-methylene}-6-iodo-4H-isoquinoline-1,3-dione (90 mg, 0.18 mmol), 3-furyl boronic acid (90 mg, 0.70 mmol) in 65% yield as a yellow solid: MS (ESI): 428.1 (M+1)+1.

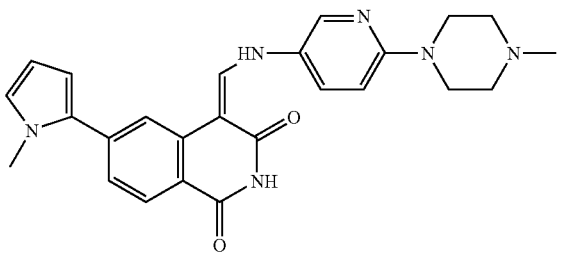

Example 474

(4Z)-4-({[6-(4-Methylpiperazin-1-yl)pyridin-3-yl]amino}methylene)-6-(1-methyl-1H-pyrrol-2-yl)isoquinoline-1,3(2H,4H)-dione Using the procedure described for the preparation of (4Z)-6-(3-furyl)-4-[({4-[(3R,5S)-3,4,5-trimethylpiperazin-1-yl]phenyl}amino)-methylene]isoquinoline-1,3(2H,4H)-dione (41), 79 mg (40% yield) of yellow solid is obtained from 200 mg (0.45 mmol) of (4Z)-6-bromo-4-({[6-(4-methylpiperazin-1-yl)pyridin-3-'yl]amino}methylene)isoquinoline-1,3(2H,4H)-dione 330 mg (0.45 mmol), 2-(tributyltsannyl)thiazole and 50 mg (0.90 mmol) of trans-Dichlorobis(triphenylphosphine)palladium(II): mp 216-217° C.; MS (ESI) m/z 443.1 (M+H).

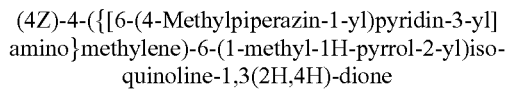

Example 475

(4Z)-6-Iodo-4-({[2-(4-methylpiperazin-1-yl)pyrimidin-5-yl]amino}methylene)isoquinoline-1,3(2H,4H)-dione A N,N-dimethylformamide solution (1.6 mL) of 6-iodo-4-methoxymethylene-4H-isoquinoline-1,3-dione (254 mg, 0.77 mmol), and 2-(4-methyl-piperazin-1-yl)-pyrimidin-5-ylamine (157 mg, 0.813 mmol) is heated at 90° C. for 40 min. After cooling in the refrigerator, the precipitate is collected, and washed with N,N-dimethylformamide and ether to give 259 mg (65%) of the title compound as a yellow solid. MS (ESI) m/z 491 (M+H)$^{+1}$

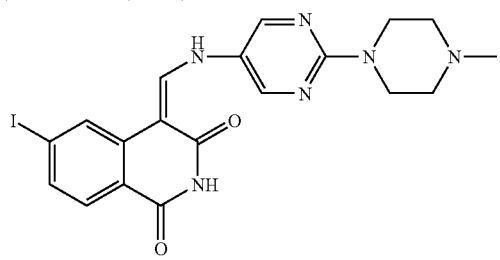

Example 476

(4Z)-6-(3-Furyl)-4-({[6-(4-methylpiperazin-1-yl)pyridazin-3-yl]amino}methylene)isoquinoline-1,3(2H,4H)-dione Using the procedure described for the preparation of '(4Z)-6-(3-furyl)-4-({[6-(4-methylpiperazin-1-yl)pyridin-3-'yl]amino}methylene)isoquinoline-1,3(2H,4H)-dione, 90 mg (23% yield) is obtained as yellow solid from 400 mg (0.9 mmol) of (4Z)-6-bromo-4-({[6-(4-methylpiperazin-1-yl)pyridazin-3-yl]amino}methylene)isoquinoline-1,3(2H,4H)-dione and furan boronic acid 252 mg, (2.25 mmol).; mp 275-276° C.

MS (ESI) m/z 431.1 (M+1)$^+$

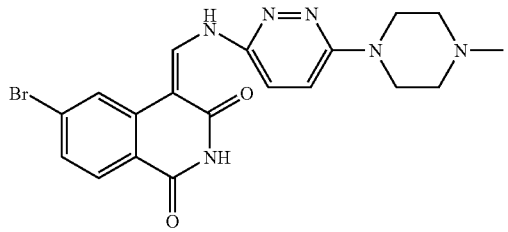

Example 477

(4Z)-6-Bromo-4-({[6-(4-methylpiperazin-1-yl)pyridazin-3-yl]amino}methylene)isoquinoline-1,3(2H,4H)-dione Using the procedure described for the preparation of example 14, 700 mg (89% yield) is obtained as a yellow solid from 500 g (1.77 mmol) (4E)-6-bromo-4-(methoxymethylene)isoquinoline-1,3(2H,4H)-dione and 342.0 mg (1.77 mmol) of [6-(4-methylpiperazin-1-yl)pyridazin-3-yl]amine; mp 245-246° C.

MS (ESI) m/z 445.0 (M+1)$^+$

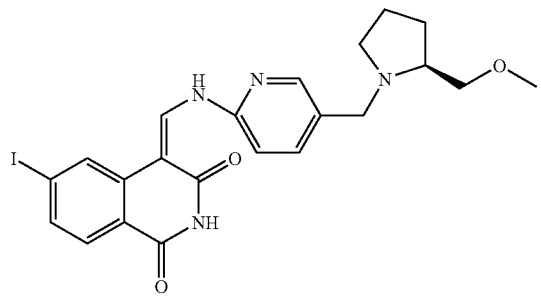

Example 478

(4Z)-6-Iodo-4-{[(5-{[(2S)-2-(methoxymethyl)pyrrolidin-1-yl]methyl}pyridin-2-yl)amino]methylene}isoquinoline-1,3(2H,4H)-dione Using the procedure described for the preparation of example 14, 30 mg (11% yield) is obtained as a yellow solid from 170 g (0.52 mmol) (4E)-6-iodo-4-(methoxymethylene)isoquinoline-1,3(2H,4H)-dione and 137.2 mg (0.62 mmol) of (5-{[(2S)-2-(methoxymethyl)pyrrolidin-1-yl]methyl}pyridin-2-yl)amine; mp 185-186° C.

MS (ESI) m/z 519.0 (M+1)$^+$

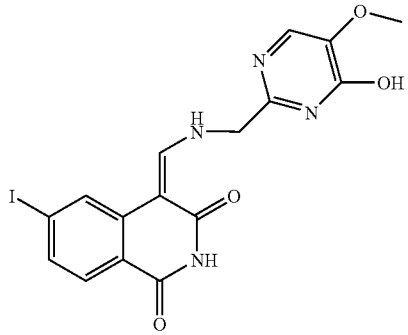

Example 479

4-{[(4-Hydroxy-5-methoxy-pyrimidin-2-ylmethyl)-amino]-methylene}-6-iodo-4H-isoquinoline-1,3-dione 2-Aminomethyl-5-methoxy-pyrimidin-4-ol (10 mg, 0.064 mmol) and 6-iodo-4-methoxymethylene-4H-isoquinoline-1,3-dione (50 mg, 0.15 mmol) in N,N-dimethylformamide (3 mL) is stirred at room temperature for 1 hour. The N,N-dimethylformamide is then removed and residue purified to provide the title compound (10 mg, 34%). MS (ESI): 453 (M+1)$^{+1}$.

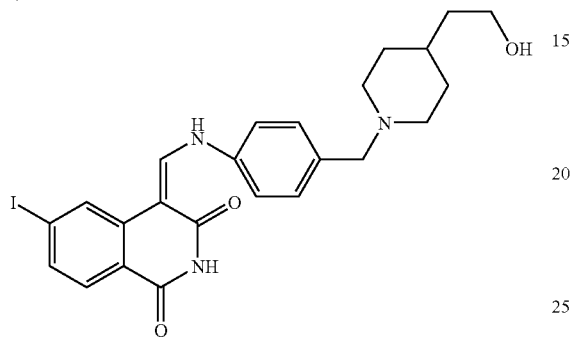

Example 480

(4Z)-4-{[(4-{[4-(2-Hydroxyethyl)piperidin-1-yl]methyl}phenyl)amino]methylene}-6-iodoisoquinoline-1,3(2H,4H)-dione Using the procedure described for the preparation of example 14, 135 mg (42% yield) is obtained as a yellow solid from 200 g (0.61 mmol) (4E)-6-iodo-4-(methoxymethylene)isoquinoline-1,3(2H,4H)-dione and 145 mg (0.61 mmol) of 4-(2-hydroxyethyl)piperidin-1-yl]methyl}phenyl)amine; mp 223-224° C.

MS (ESI) m/z 532.0 (M+1)$^+$

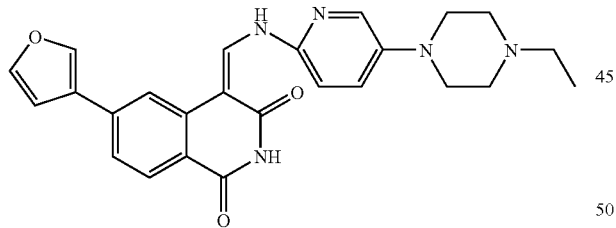

Example 481

(4Z)-4-({[5-(4-Ethylpiperazin-1-yl)pyridin-2-yl]amino}methylene)-6-(3-furyl)isoquinoline-1,3(2H,4H)-dione Using the procedure described for the preparation of '(4Z)-6-(3-furyl)-4-({[6-(4-methylpiperazin-1-yl)pyridin-3-'yl]amino}methylene)isoquinoline-1,3(2H,4H)-dione, 220 mg (45% yield) is obtained as a yellow solid from 500 mg (1.1 mmol) of (4Z)-6-bromo-4-({[5-(4-ethylpiperazin-1-yl)pyridin-2-yl]amino}methylene)isoquinoline-1,3(2H,4H)-dione and furan boronic acid 246 mg, (2.2 mmol).; mp 256-257° C.

MS (ESI) m/z 444.1 (M+1)$^+$

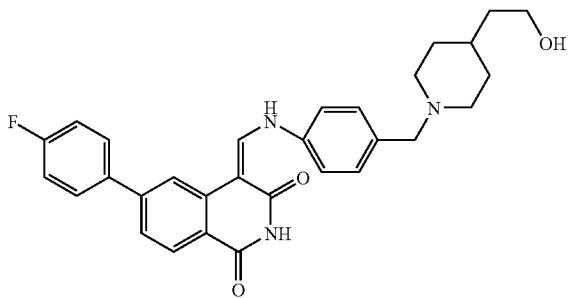

Example 482

(4Z)-6-(4-Fluorophenyl)-4-{[(4-{[4-(2-hydroxyethyl)piperidin-1-yl]methyl}phenyl)amino]methylene}isoquinoline-1,3(2H,4H)-dione Using the procedure described for the preparation of'(4Z)-6-(4-fluorophenyl)-4-({[4-(piperidin-1-'ylmethyl)phenyl]amino}methylene)isoquinoline-1,3(2H,4H)-dione, 141 mg (27% yield) is obtained as a yellow solid from 500 mg (1.03 mmol) of (4Z)-6-bromo-4-{[(4-{[4-(2-hydroxyethyl)piperidin-1-yl]methyl}phenyl)amino]methylene}isoquinoline-1,3 (2H,4H)-dione and 4-Fluorophenyl boronic acid 289 mg, (2.06 mmol).; mp 202-203° C.

MS (ESI) m/z 500. (M+1)$^+$

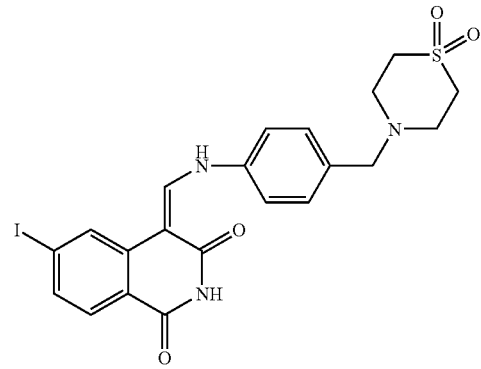

Example 483

4-{[4-(1,1-Dioxo-1-thiomorpholin-4-ylmethyl)-phenylamino]-methylene}-6-iodo-4H-isoquinoline-1,3-dione Using the procedure described for the preparation of 6-Bromo-4-[(4-pyridin-4-yl-phenylamino)-methylene]-4H-isoquinoline-1,3-dione, the title compound is obtained from 4-(4-Amino-benzyl)-thiomorpholine 1,1-dioxide (85 mg, 0.35 mmol), 6-iodo-4-methoxymethylene-4H-isoquinoline-1,3-dione (102 mg, 0.31 mmol) in 82% yield as a yellow solid: MS (ESI): 535.9 (M−1)$^{-1}$.

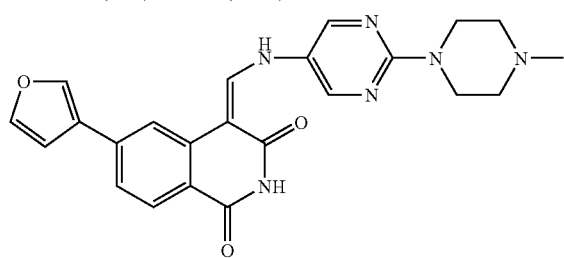

Example 484

(4Z)-6-(3-Furyl)-4-({[2-(4-methylpiperazin-1-yl)pyrimidin-5-yl]amino}methylene)isoquinoline-1,3(2H,4H)-dione (4Z)-6-Iodo-4-({[2-(4-methylpiperazin-1-yl)pyrimidin-5-yl]amino}methylene)isoquinoline-1,3(2H,4H)-dione (73.5 mg, 0.15 mmol) is mixed with 3-furanboronic acid (33 mg, 0.3 mmol), Pd$_2$(dba)$_3$ (20.6 mg, 0.022 mmol), and cesium carbonate (98 mg, 0.3 mmol). After the solids were degassed, N,N-dimethylformamide (1.05 mL) and P(t-Bu)$_3$ (9.1 mg, 0.045 mmol) were added. The mixture is heated at 100 C for 55 min, diluted with methylene chloride, and filtered. The filtrate is evaporated to dryness and purified by column chromatography to yield 36 mg (55%) of the title compound as a yellow solid. MS (ESI) m/z 431 (M+H)$^{+1}$

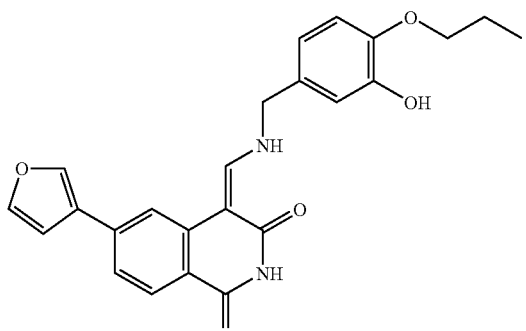

Example 485

(4Z)-6-(3-Furyl)-4-{[(3-hydroxy-4-propoxybenzyl)amino]methylene}isoquinoline-1,3(2H,4H)-dione (4Z)-6-Bromo-4-{[(3-hydroxy-4-propoxybenzyl)amino]methylene}isoquinoline-1,3(2H,4H)-dione (110 mg, 0.255 mmol) is mixed with 3-furanboronic acid (58 mg, 0.51 mmol), Pd$_2$(dba)$_3$ (35 mg, 0.038 mmol), and cesium carbonate (166 mg, 0.51 mmol). After the solids were degassed, N,N-dimethylformamide (1.7 mL) and P(t-Bu)$_3$ (15.5 mg, 0.077 mmol) were added. The mixture is heated at 100 C for 1 h, diluted with methylene chloride, and filtered. The filtrate is evaporated to dryness and purified by column chromatography to yield 8.5 mg (8%) of the title compound as a white solid. MS (ESI) m/z 417, 419 (M+H)$^{+1}$

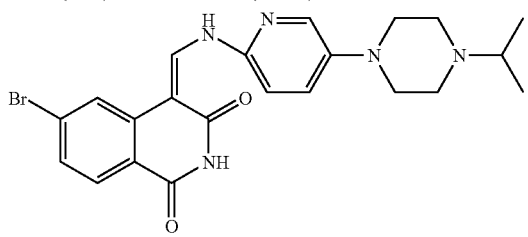

Example 486

(4Z)-6-Bromo-4-({[5-(4-isopropylpiperazin-1-yl)pyridin-2-yl]amino}methylene)isoquinoline-1,3(2H,4H)-dione Using the procedure described for the preparation of example 14, 650 mg (65% yield) is obtained as a brown solid from 600 mg (2.13 mmol) (4E)-6-bromo-4-(methoxymethylene)isoquinoline-1,3(2H,4H)-dione and 468 mg (2.13 mmol) of [5-(4-isopropylpiperazin-1-yl)pyridin-2-yl]amine; mp 223-224° C.
MS (ESI) m/z 472.0 (M+1)$^+$

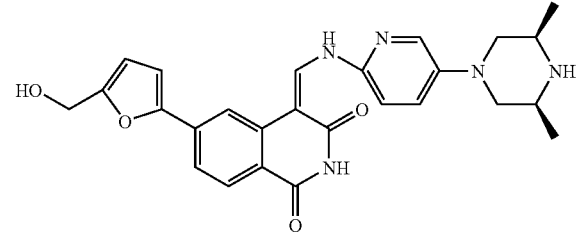

Example 487

(4Z)-4-[({6-[(3R,5S)-3,5-Dimethylpiperazin-1-yl]pyridin-3-yl}amino)methylene]-6-[5-(hydroxymethyl)-2-furyl]isoquinoline-1,3(2H,4H)-dione An amount of 100 mg (0.22 mmol) of (4Z)-4-[({6-[(3R,5S)-3,5-dimethylpiperazin-1-yl]pyridin-3-yl}amino)methylene]-6-)-[2-furanaldehyde]isoquinoline-1,3(2H,4H)-dione and 10% Pd/C were dissolved in 1:1 mathanol:N,N-dimethylformamide (20 mL) and hydrogenated at 40 psi for 2 hours. After filtering the palladium, the mixture is evaporated and crystallized the desired product from acetonitrile to give 60 mg (60% yield) of yellow solid.; mp 253-254° C.
MS (ESI) m/z 474.1 (M+1)$^+$

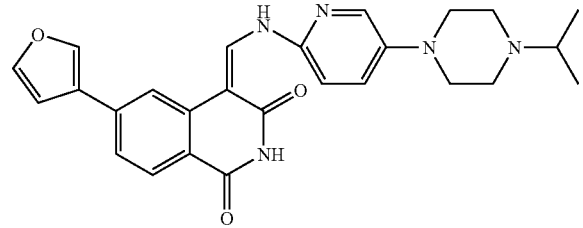

Example 488

(4Z)-6-(3-Furyl)-4-({[5-(4-isopropylpiperazin-1-yl)pyridin-2-yl]amino}methylene)isoquinoline-1,3(2H,4H)-dione Using the procedure described for the preparation of'(4Z)-6-(3-furyl)-4-({[6-(4-methylpiperazin-1-yl)pyridin-3-'yl]amino}methylene)isoquinoline-1,3(2H,4H)-dione, 260 mg (67% yield) is obtained as a yellow solid from 400 mg (0.85 mmol) of (4Z)-4-({[5-(4-ethylpiperazin-1-yl)pyridin-2-yl]amino}methylene)-6-(3-furyl)isoquinoline-1,3(2H,4H)-dion and furan boronic acid 190.2 mg, (1.7 mmol).; mp 278-279° C.
MS (ESI) m/z 458.1 (M+1)$^+$

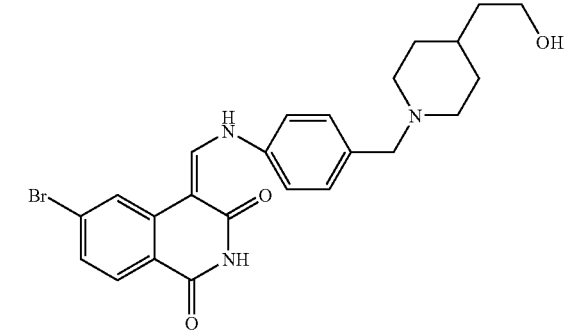

Example 489

(4Z)-6-Bromo-4-{[(4-{[4-(2-hydroxyethyl)piperidin-1-yl]methyl}phenyl)amino]methylene}isoquinoline-1,3(2H,4H)-dione Using the procedure described for the preparation of example 14, 950 mg (92% yield) is obtained as a yellow solid from 600 g (2.13 mmol) (4E)-6-bromo-4-(methoxymethylene)isoquinoline-1,3(2H,4H)-dione and 500 mg (2.13 mmol) of 4-(2-hydroxyethyl)piperidin-1-yl]methyl}phenyl)amine; mp 200-201° C.

MS (ESI) m/z 486.2 (M+1)+

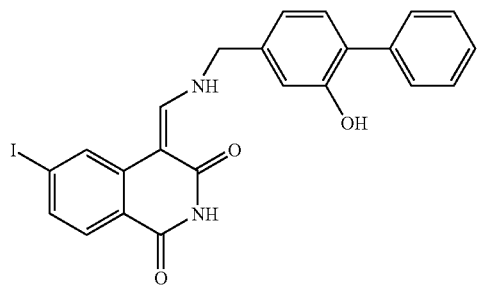

Example 490

4-{[(2-Hydroxy-biphenyl-4-ylmethyl)-amino]-methylene}-6-iodo-4H-isoquinoline-1,3-dione 4-Aminomethyl-biphenyl-2-ol (80 mg, 0.4 mmol) and 6-iodo-4-methoxymethylene-4H-isoquinoline-1,3-dione (110 mg, 0.34 mmol) is stirred in N,N-dimethylformamide (5 mL). After which N,N-dimethylformamide is removed under vacuum and the residue is triturated with MeOH. The precipitate thus formed is collected and washed with MeOH and dried to provide the title compound (151 mg, 89%). MS (ESI): 495.1 (M−1)−1.

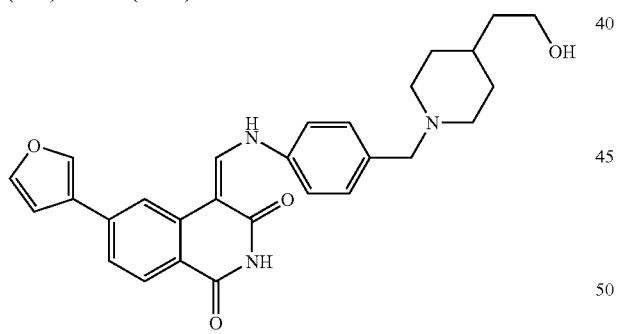

Example 491

(4Z)-6-(3-Furyl)-4-{[(4-{[4-(2-hydroxyethyl)piperidin-1-yl]methyl}phenyl)amino]methylene}isoquinoline-1,3(2H,4H)-dione Using the procedure described for the preparation of '(4Z)-6-(4-fluorophenyl)-4-({[4-(piperidin-1-'ylmethyl)phenyl]amino}methylene)isoquinoline-1,3(2H,4H)-dione, 210 mg (43% yield) is obtained as a yellow solid from 500 mg (1.03 mmol) of (4Z)-6-bromo-4-{[(4-{[4-(2-hydroxyethyl)piperidin-1-yl]methyl}phenyl)amino]methylene}isoquinoline-1,3(2H,4H)-dione and 3-furan boronic acid 288 mg, (2.6 mmol).; mp 152-153° C.

MS (ESI) m/z 456.1 (M+1)+

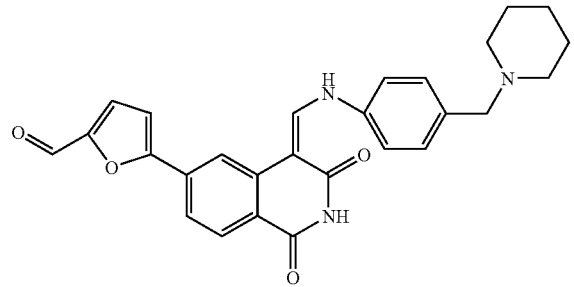

Example 492

5-[(4Z)-1,3-Dioxo-4-({[4-(piperidin-1-ylmethyl)phenyl]amino}methylene)-1,2,3,4-tetrahydroisoquinolin-6-yl]-2-furaldehyde Using the procedure described for the preparation of '(4Z)-6-(4-fluorophenyl)-4-({[4-(piperidin-1-'ylmethyl)phenyl]amino}methylene)isoquinoline-1,3(2H,4H)-dione, 310 mg (43% yield) is obtained as a yellow solid from 720 mg (1.64 mmol) of 4Z)-6-bromo-4-({[4-(piperidin-1-ylmethyl)phenyl]amino}methylene)isoquinoline-1,3(2H,4H)-dione and 5-formyl-2-furylboronic acid 459 mg, (3.28 mmol).; mp 173-174° C.

MS (ESI) m/z 472.0 (M+1)+

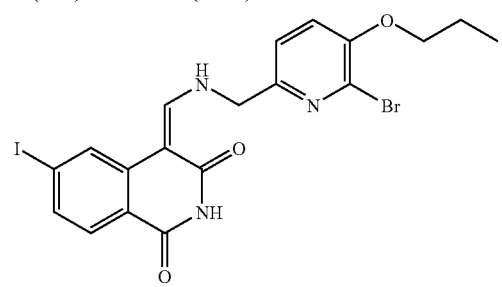

Example 493

(Z)-4-(((6-Bromo-5-propoxypyridin-2-yl)methylamino)methylene)-6-iodoisoquinoline-1,3(2H,4H)-dione A mixture of (E)-6-iodo-4-(methoxymethylene)isoquinoline-1,3(2H,4H)-dione (329 mg, 1.0 mmole), dimethylformamide (8 mL), and (6-bromo-5-propoxypyridin-2-yl)methanamine (245 mg, 1.0 mmole) is stirred at room temperature for one hour. The reaction mixture is diluted with acetonitrile, filtered, washed with fresh acetonitrile and dried to give a yellow solid, 434 mg, (80%), mp 251-3° C. dec; MS (ES−): m/z 540.2 (M−H).

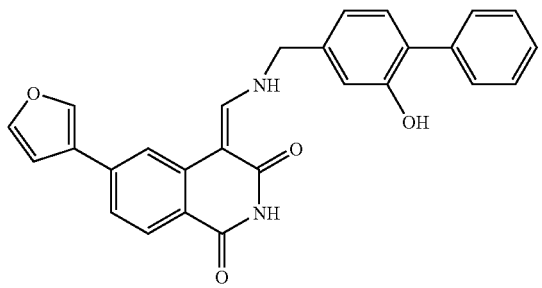

Example 494

6-Furan-3-yl-4-{[(2-hydroxy-biphenyl-4-ylmethyl)-amino]-methylene}-4H-isoquinoline-1,3-dione Using the procedure described for the preparation of 4-{[4-(2-Hydroxymethyl-pyrrolidin-1-ylmethyl)-phenylamino]-methylene}-6-thiophen-3-yl-4H-isoquinoline-1,3-dione, the title compound is obtained from 4-{[(2-Hydroxy-biphenyl-4-ylmethyl)-amino]-methylene}-6-iodo-4H-isoquinoline-1,3-dione (75 mg, 0.15 mmol) and 3-furylboronic acid (50 mg, 0.39 mmol) as a yellow solid in 76% yield.

MS (ESI): 435.3 (M−1)$^{−1}$.

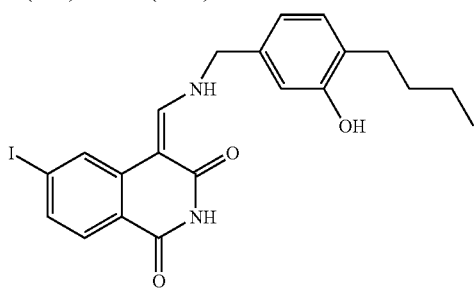

Example 495

4-[(4-Butyl-3-hydroxy-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (85 mg, 0.26 mmol) and 5-Aminomethyl-2-butyl-phenol (54 mg, 0.3 mmol) in 65% yield: MS (ESI): 475.2 (M−1)$^{−1}$.

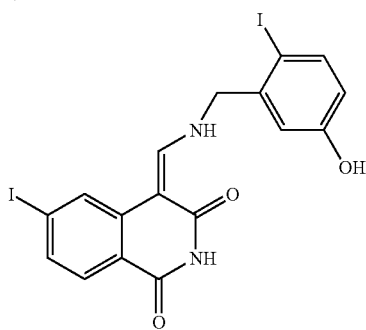

Example 496

4-[(5-Hydroxy-2-iodo-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (100 mg, 0.30 mmol) and 3-Aminomethyl-4-iodo-phenol (80 mg, 0.32 mmol) in 73% yield: MS (ESI): 545.0 (M−1)$^{−1}$.

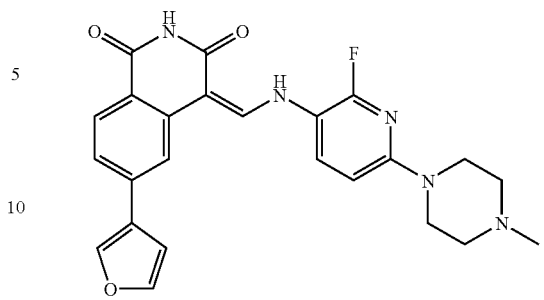

Example 497

(4Z)-4-({[2-Fluoro-6-(4-methylpiperazin-1-yl)pyridin-3-yl]amino}methylene)-6-(3-furyl)isoquinoline-1,3(2H,4H)-dione A suspension of (4Z)-4-({[2-fluoro-6-(4-methylpiperazin-1-yl)pyridin-3-yl]amino}methylene)-6-iodoisoquinoline-1,3(2H,4H)-dione (0.10 g, 0.20 mmol), 3-furanboronic acid (55 mg, 0.50 mmol), tris(dibenzylideneacetone)dipalladium(0) (27 mg, 0.03 mmol) and cesium carbonate (0.13 g) in N,N-dimethylformamide (2 mL) is heated in a 120° C. oil bath for 10 minutes. Tri-tert-butylphosphine (20 mg/mL solution in N,N-dimethylformamide, 0.50 mL, 10 mg, 0.05 mmol) is added, and the mixture continued to stir in the oil bath for one hour. After cooling to room temperature, the reaction mixture is diluted with chloroform and washed with saturated aqueous sodium hydrogen carbonate solution. The organic layer is concentrated under reduced pressure and purified via reverse phase HPLC to provide (4Z)-4-({[2-fluoro-6-(4-methylpiperazin-1-yl)pyridin-3-yl]amino}methylene)-6-(3-furyl)isoquinoline-1,3(2H,4H)-dione.3 trifluoroacetic acid salt (53 mg, 34%).

MS (ES$^+$): 448.3 (M+H)$^+$

Example 498

As you said Examples 497 and 498 have the same way. The only difference is their batch #. Since the second batch is purer than the first batch, please use the biological data from the second batch.

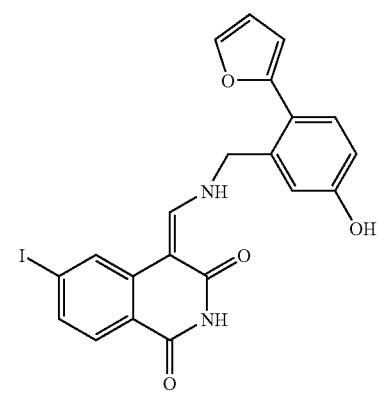

Example 499

4-[(2-Furan-2-yl-5-hydroxy-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (100 mg, 0.30 mmol) and 3-Aminomethyl-4-furan-2-yl-phenol (crude material from the previous reaction in 56% yield: MS (ESI): 485.1 (M−1)$^{-1}$.

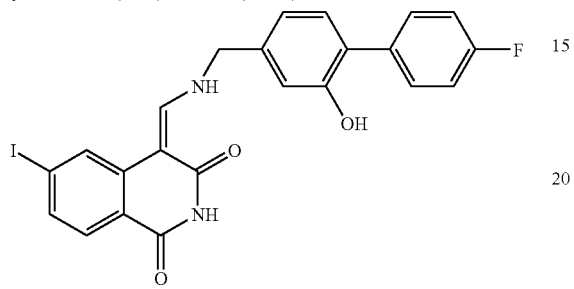

Example 500

4-{[(4'-Fluoro-2-hydroxy-biphenyl-4-ylmethyl)-amino]-methylene}-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione-2, the title compound is prepared from 6-iodo-4-methoxymethylene-4H-isoquinoline-1,3-dione (90 mg, 0.27 mmol) and 4-Aminomethyl-4'-fluoro-biphenyl-2-ol (66 mg, 0.3 mmol) in 60% yield: MS (ESI): 513.1 (M−1)$^{-1}$.

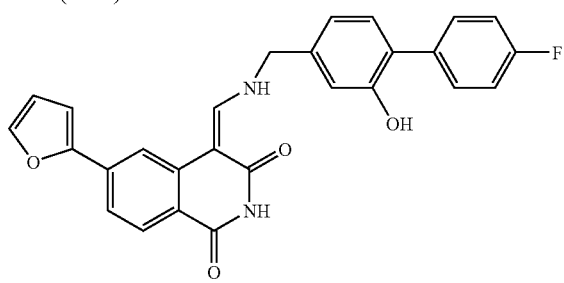

Example 501

4-{[(4'-Fluoro-2-hydroxy-biphenyl-4-ylmethyl)-amino]-methylene}-6-furan-2-yl-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-Furan-2-yl-4-methoxymethylene-4H-isoquinoline-1,3-dione (40 mg, 0.15 mmol) and 4-Aminomethyl-4'-fluoro-biphenyl-2-ol (33 mg, 0.15 mmol) in 62% yield: MS (ESI): 453.2 (M−1)$^{-1}$.

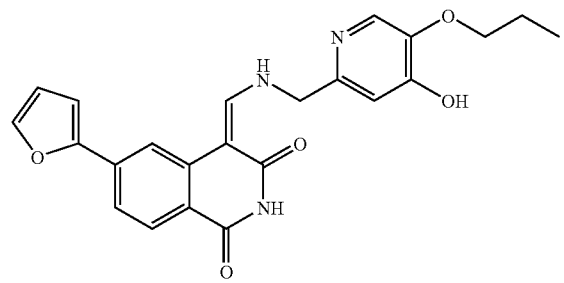

Example 502

6-Furan-2-yl-4-{[(4-hydroxy-5-propoxy-pyridin-2-ylmethyl)-amino]-methylene}-4H-isoquinoline-1,3-dione A mixture of 2-aminomethyl-5-propoxy-pyridin-4-ol (73 mg, 0.40 mmole), 5 mL of N,N-dimethylformamide is stirred, then 4-methoxymethylene-6-(furan-2-yl)-4H-isoquinoline-1,3-dione (108 mg, 0.40 mmole) is added and the reaction mixture stirred for one hour. The reaction mixture is evaporated to dryness, triturated with 5% methanol in chlororform, filtered washed with fresh 5% methanol in chloroform, washed with acetonitrile and dried to give a pale yellow solid, 139 mg, (83%); m.p. 288-90° C. dec; MS (ES+): m/z 420.2 (M+H).

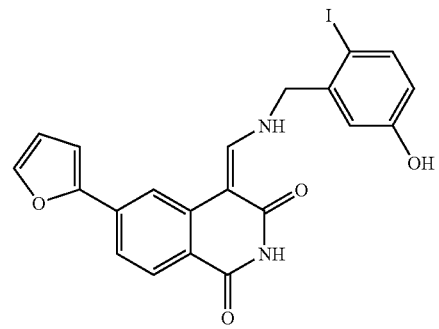

Example 503

6-Furan-2-yl-4-[(5-hydroxy-2-iodo-benzylamino)-methylene]-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-Furan-2-yl-4-methoxymethylene-4H-isoquinoline-1,3-dione (400 mg, 1.5 mmol) and 3-Aminomethyl-4-iodo-phenol (400 mg, 1.61 mmol) in 77% yield: MS (ESI): 485.1 (M−1)$^{-1}$.

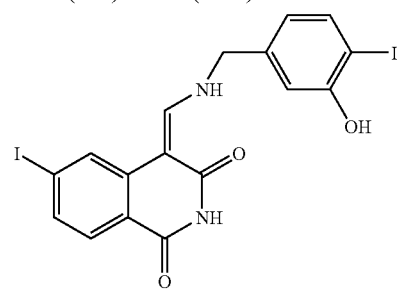

Example 504

4-[(3-Hydroxy-4-iodo-benzylamino)-methylene]-6-iodo-4H-isoquinoline-1,3-dione

Following the same procedure for the preparation of 4-{[(2-Hydroxy-biphenyl-4-ylmethyl)-amino]-methylene}-6-iodo-4H-isoquinoline-1,3-dione, the title compound is prepared from 6-Furan-2-yl-4-methoxymethylene-4H-isoquinoline-1,3-dione (60 mg, 0.22 mmol) and 5-Aminomethyl-2-iodo-phenol (58 mg, 0.23 mmol) in 80% yield: MS (ESI): 485.1 (M−1)$^{-1}$.

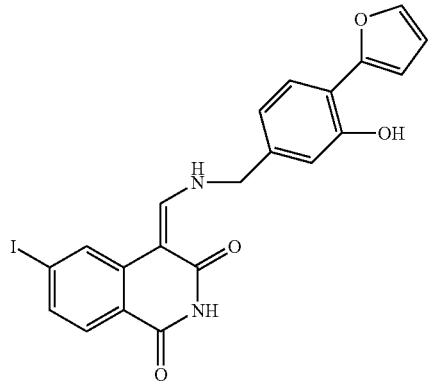

Example 505

4-[(4-Furan-2-yl-3-hydroxy-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (80 mg, 0.24 mmol) and 5-Aminomethyl-2-furan-3-yl-phenol (50 mg, 0.26 mmol) in 53% yield: MS (ESI): 485.1 (M−1)$^{-1}$.

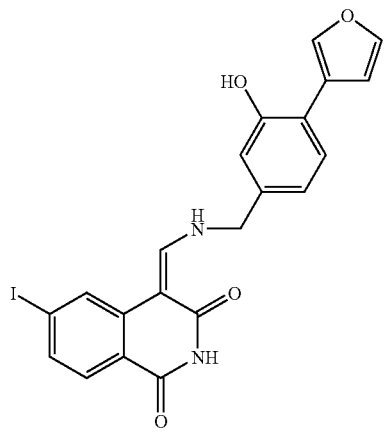

Example 506

4-[(4-Furan-3-yl-3-hydroxy-benzylamino)-methylene]-6-iodo-4H-isoquinoline-1,3-dione Following the same procedure for the preparation of 4-{[(2-Hydroxy-biphenyl-4. -ylmethyl)-amino]-methylene}-6-iodo-4H-isoquinoline-1,3-dione, the title compound is prepared from 6-iodo-4-methoxymethylene-4H-isoquinoline-1,3-dione (85 mg, 0.26 mmol) and 5-Aminomethyl-2-furan-3-yl-phenol in 56% yield: MS (ESI): 487.1 (M+1)$^{+1}$.

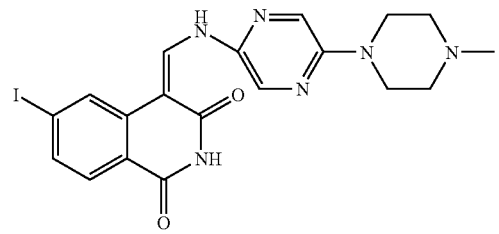

Example 507

(4Z)-6-Iodo-4-({[5-(4-methylpiperazin-1-yl)pyrazin-2-yl]amino}methylene)isoquinoline-1,3(2H,4H)-dione Using the procedure described for the preparation of example 14, 280 mg (57% yield) is obtained as a brown solid from 330 g (1.03 mmol) (4E)-6-iodo-4-(methoxymethylene)isoquinoline-1,3(2H,4H)-dione and 200 mg (1.03 mmol) of [5-(4-methylpiperazin-1-yl)pyrazin-2-yl]amine; mp 238-239° C.

MS (ESI) m/z 491.1 (M+1)$^{+}$

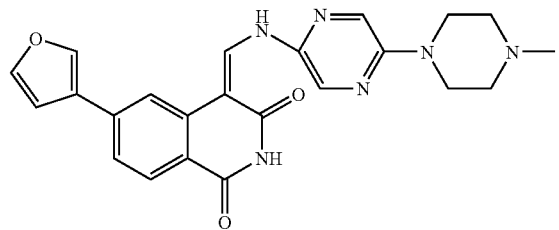

Example 508

(4Z)-6-(3-Furyl)-4-({[5-(4-methylpiperazin-1-yl)pyrazin-2-yl]amino}methylene)isoquinoline-1,3(2H,4H)-dione Using the procedure described for the preparation of '(4Z)-6-(3-furyl)-4-({[6-(4-methylpiperazin-1-yl)pyridin-3-'yl]amino}methylene)isoquinoline-1,3(2H,4H)-dione, 40 mg (23% yield) is obtained as a yellow solid from 500 mg (0.41 mmol) of (4Z)-6-iodo-4-({[5-(4-methylpiperazin-1-yl)pyrazin-2-yl]amino}methylene)isoquinoline-1,3(2H,4H)-dione and furan boronic acid 114 mg, (1.02 mmol).; mp 226-227° C.

MS (ESI) m/z 431.1 (M+1)$^{+}$

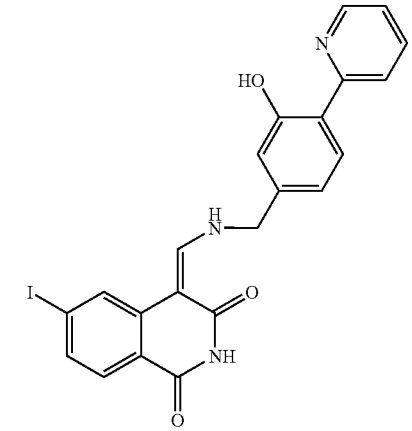

Example 509

4-[(3-Hydroxy-4-pyridin-2-yl-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (98 mg, 0.30 mmol) and 5-Aminomethyl-2-pyridin-2-yl-phenol (60 mg, 0.30 mmol) in 57% yield: MS (ESI): 498.1 (M+1)$^{+1}$.

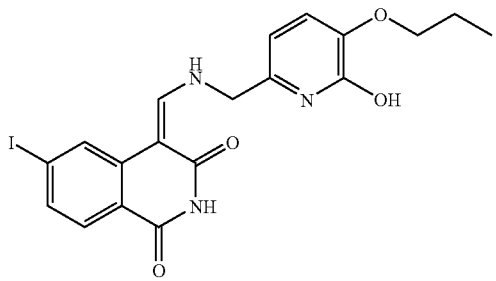

Example 510

4-{[(6-Hydroxy-5-propoxy-pyridin-2-ylmethyl)-amino]-methylene}-6-iodo-4H-isoquinoline-1,3-dione A mixture of 6-aminomethyl-3-propoxy-pyridin-2-ol (91 mg, 0.50 mmole), 7 mL of N,N-dimethylformamide is stirred, then 4-methoxymethylene-6-iodo-4H-isoquinoline-1,3-dione (165 mg, 0.50 mmole) is added and the reaction mixture stirred for 4 hours. The reaction mixture is evaporated to dryness, triturated with 5% methanol in chlororform, filtered washed with fresh 5% methanol in chloroform, washed with acetonitrile and dried to give a beige solid, 152 mg, (63%); m.p. 275-81° C. dec; MS (ES +): m/z 478.1 (M+H).

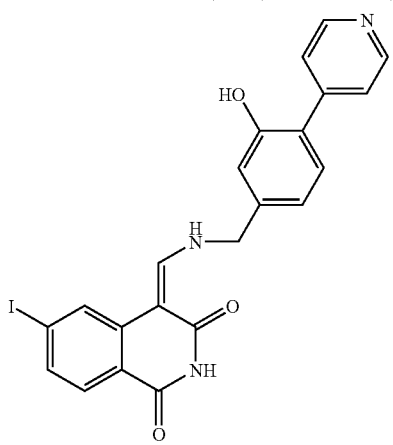

Example 511

4-[(3-Hydroxy-4-pyridin-4-yl-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (50 mg, 0.15 mmol) and 5-Aminomethyl-2-pyridin-2-yl-phenol (40 mg, 0.20 mmol) in 40% yield: MS (ESI): 498.1 (M+1)$^{+1}$.

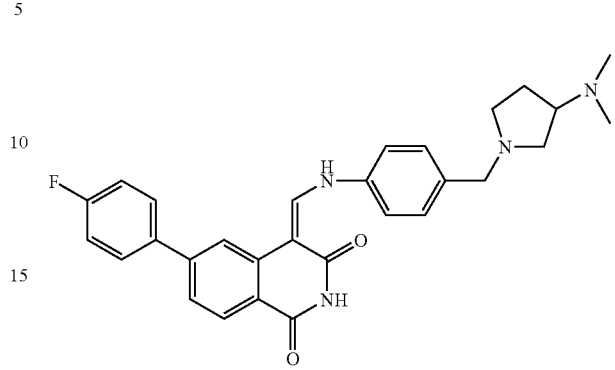

Example 512

(4Z)-4-{[(4-{[3-(Dimethylamino)pyrrolidin-1-yl]methyl}phenyl)amino]methylene}-6-(4-fluorophenyl)isoquinoline-1,3(2H,4H)-dione Using the procedure described for the preparation of '(4Z)-6-(3-furyl)-4-({[6-(4-methylpiperazin-1-yl)pyridin-3-'yl]amino}methylene)isoquinoline-1,3(2H,4H)-dione, 65 mg (16% yield) is obtained as a yellow solid from 400 mg (0.85 mmol) of (4Z)-4-{[(4-{([3-(dimethylamino)pyrrolidin-1-yl]methyl}phenyl)amino]methylene}-6-bromoisoquinoline-1,3(2H,4H)-dione and 4-fluorophenyl boronic acid 298 mg, (2.13 mmol).; mp 95-96° C.

MS (ESI) m/z 485.3 (M+1)$^+$

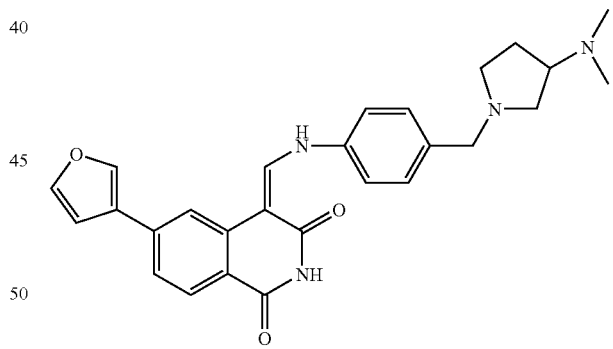

Example 513

(4Z)-4-{[(4-{[3-(Dimethylamino)pyrrolidin-1-yl]methyl}phenyl)amino]methylene}-6-(3-furyl)isoquinoline-1,3(2H,4H)-dione Using the procedure described for the preparation of '(4Z)-6-(3-furyl)-4-({[6-(4-methylpiperazin-1-yl)pyridin-3-'yl]amino}methylene)isoquinoline-1,3(2H,4H)-dione, 90 mg (19% yield) is obtained as a yellow solid from 500 mg (1.07 mmol) of (4Z)-4-{[(4-{[3-(dimethylamino)pyrrolidin-1-yl]methyl}phenyl)amino]methylene}-6-bromoisoquinoline-1, 3(2H,4H)-dione and 3-furan boronic acid 305 mg, (2.9 mmol).

MS (ESI) m/z 457.0 (M+1)+

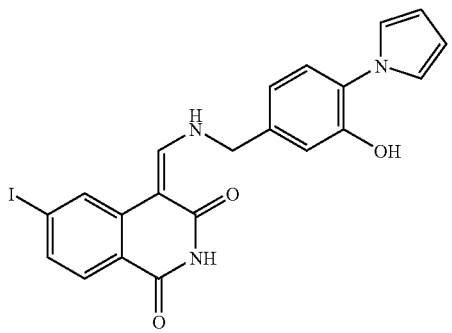

Example 514

(4Z)-4-({[3-Hydroxy-4-(1H-pyrrol-1-yl)benzyl]amino}methylene)-6-iodoisoquinoline-1,3(2H,4H)-dione A mixture of (4Z)-4-{[(4-amino-3-hydroxybenzyl)amino]methylene}-6-iodoisoquinoline-1,3(2H,4H)-dion (300 mg, 0.67 mmol), 2,5-dimethoxytetrahydrofuran (182.2 mg 1.4 mmol), and 4-chloropyridine hydrochloride (101 mg, 0.67 mmol) were placed in a flask and N,N-dimethylformamide (5 mL) is added. The mixture is then placed in a pre-heated oil bath at 80° C. for 2 hours. After cooling, all the solvent is evaporated. The brown solid is stirred in water and washed with ether to give the product as a brown solid 85 mg (25% yield).; mp 230-231° C.

MS (ESI) m/z 484.1 (M−1).

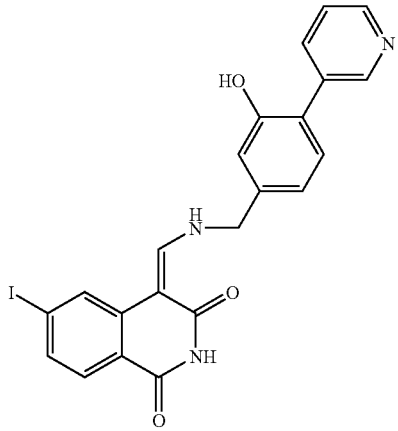

Example 515

4-[(3-Hydroxy-4-pyridin-3-yl-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (50 mg, 0.15 mmol) and 5-Aminomethyl-2-pyridin-2-yl-phenol (53 mg, 0.27 mmol) in 76% yield: MS (ESI): 498.0 (M+1)+1.

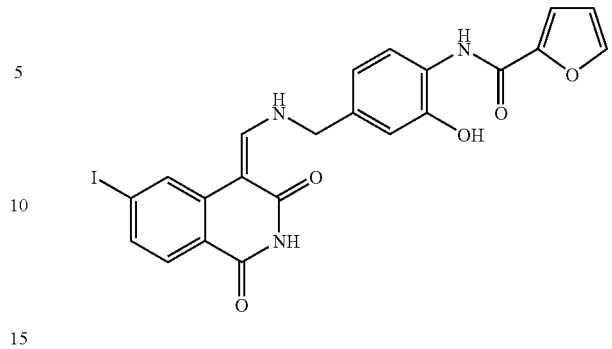

Example 516

N-[2-Hydroxy-4-({[(Z)-(6-iodo-1,3-dioxo-2,3-dihydroisoquinolin-4(1H)-ylidene)methyl]amino}methyl)phenyl]-2-furamide Using the procedure described for the preparation of (example 69), 120 mg (50% yield) of brown solid is obtained from 150 mg (0.46 mmol) of (4Z)-4-{[(4-amino-3-hydroxybenzyl)amino]methylene}-6-iodoisoquinoline-1,3(2H,4H)-dion and 2-furoyl chloride 600 mg (4.6 mmol); mp 229-230° C.

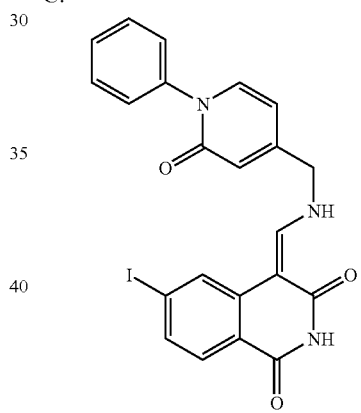

Example 517

(4Z)-6-Iodo-4-({[(2-oxo-1-phenyl-1,2-dihydropyridin-4-yl)methyl]amino}methylene)isoquinoline-1,3(2H,4H)-dione To a solution of 4-aminomethyl-1H-pyridin-2-one hydrochloride in 50% aqueous dioxane (100 mL) is added sodium hydroxide (2.8 g, 69 mmol), followed by di-tert-butyldicarbonate (5.0 g, 23 mmol). After stirring overnight at room temperature, the mixture is neutralized with 5% aqueous potassium hydrogen sulfate solution. The mixture is extracted four times with ethyl acetate. The combined extracts were dried over anhydrous magnesium sulfate, filtered, and concentrated under reduced pressure. A sample of crude material is purified by reverse-phase HPLC to give tert-butyl (2-oxo-1,2-dihydro-pyridin-4-ylmethyl)-carbamate as a straw colored foam.

MS (ES+): 225.3 (M+H)+

To a solution of tert-butyl (2-oxo-1,2-dihydro-pyridin-4-ylmethyl)-carbamate (0.13 g, 0.58 mmol) in dichloromethane (5 mL) is added trimethylphenylstannane (210 µL, 1.2 mmol), followed successively by copper (II) acetate (0.12 g, 0.64 mmol) and tetra-n-butylammonium fluoride (1.0 M solution in tetrahydrofuran, 1.2 mL). The reaction mixture is stirred for 2 days at room temperature and then is quenched by the addition of methanolic ammonia (2 M, 4 mL). The reaction mixture is concentrated and then purified by flash silica gel chromatography (methanol/chloroform) to give tert-butyl (2-oxo-1-phenyl-1,2-dihydropyridin-4-ylmethyl)-carbamate (88 mg, 52%).

MS (ES+): 301.3 (M+H)+

Tert-butyl (2-oxo-1-phenyl-1,2-dihydropyridin-4-ylmethyl)-carbamate (83 mg, 0.28 mmol) is treated with 4N hydrogen chloride in dioxane in order to remove the Boc protecting group. The hydrochloride salt of 4-aminomethyl-1-phenyl-1H-pyridin-2-one, obtained after concentration of the reaction mixture, is dissolved in N,N-dimethylformamide (5 mL) and is coupled to (4E)-6-iodo-4-(methoxymethylene)isoquinoline-1,3(2H,4H)-dione (92 mg, 0.28 mmol) in the presence of triethylamine (200 µL). After one hour, the reaction mixture is concentrated under reduced pressure and purified by flash silica gel chromatography (methanol/chloroform) to provide (4Z)-6-iodo-4-({[(2-oxo-1-phenyl-1,2dihydropyridin-4-yl)methyl]amino}methylene)isoquinoline-1,3(2H,4H)-dione as a pale yellow solid (8.8 mg, 6.3%).

MS (ES+): 498.2 (M+H)+

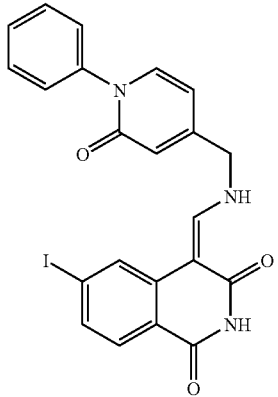

Example 518

(4Z)-6-Iodo-4-({[(2-oxo-1-phenyl-1,2-dihydropyridin-4-yl)methyl]amino}methylene)isoquinoline-1,3(2H,4H)-dione To a solution of 4-aminomethyl-1H-pyridin-2-one hydrochloride in 50% aqueous dioxane (100 mL) is added sodium hydroxide (2.8 g, 69 mmol), followed by di-tert-butyldicarbonate (5.0 g, 23 mmol). After stirring overnight at room temperature, the mixture is neutralized with 5% aqueous potassium hydrogen sulfate solution. The mixture is extracted four times with ethyl acetate. The combined extracts were dried over anhydrous magnesium sulfate, filtered, and concentrated under reduced pressure. A sample of crude material is purified by reverse-phase HPLC to give tert-butyl (2-oxo-1,2-dihydro-pyridin-4-ylmethyl)-carbamate as a straw colored foam.

MS (ES+): 225.3 (M+H)+

To a solution of tert-butyl (2-oxo-1,2-dihydro-pyridin-4-ylmethyl)-carbamate (0.13 g, 0.58 mmol) in dichloromethane (5 mL) is added trimethylphenylstannane (210 µL, 1.2 mmol), followed successively by copper (II) acetate (0.12 g, 0.64 mmol) and tetra-n-butylammonium fluoride (1.0 M solution in tetrahydrofuran, 1.2 mL). The reaction mixture is stirred for 2 days at room temperature and then is quenched by the addition of methanolic ammonia (2 M, 4 mL). The reaction mixture is concentrated and then purified by flash silica gel chromatography (methanol/chloroform) to give tert-butyl (2-oxo-1-phenyl-1,2-dihydropyridin-4-ylmethyl)-carbamate (88 mg, 52%).

MS (ES+): 301.3 (M+H)+

Tert-butyl (2-oxo-1-phenyl-1,2-dihydropyridin-4-ylmethyl)-carbamate (83 mg, 0.28 mmol) is treated with 4N hydrogen chloride in dioxane in order to remove the Boc protecting group. The hydrochloride salt of 4-aminomethyl-1-phenyl-1H-pyridin-2-one, obtained after concentration of the reaction mixture, is dissolved in N,N-dimethylformamide (5 mL) and is coupled to (4E)-6-iodo-4-(methoxymethylene)isoquinoline-1,3(2H,4H)-dione (92 mg, 0.28 mmol) in the presence of triethylamine (200 µL). After one hour, the reaction mixture is concentrated under reduced pressure and purified by flash silica gel chromatography (methanol/chloroform) to provide (4Z)-6-iodo-4-({[(2-oxo-1-phenyl-1,2dihydropyridin-4-yl)methyl]amino}methylene)isoquinoline-1,3(2H,4H)-dione as a pale yellow solid (8.8 mg, 6.3%).

MS (ES+): 498.2 (M+H)+

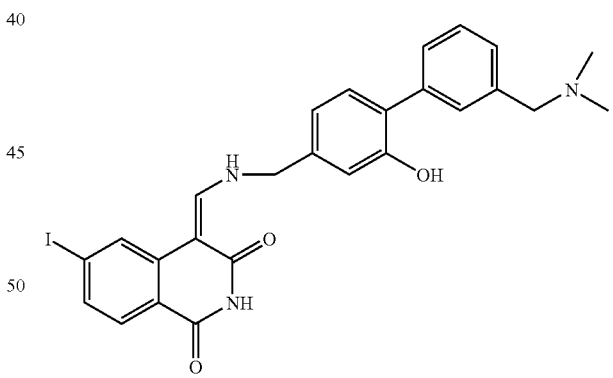

Example 519

4-{[(3'-Dimethylaminomethyl-2-hydroxy-biphenyl-4-ylmethyl)-amino]-methylene}-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound (purified through chromatography) is prepared from 6-iodo-4-methoxymethylene-4H-isoquinoline-1,3-dione (50 mg, 0.15 mmol) and 4-aminomethyl-3'-dimethylaminomethyl-biphenyl-2-ol (50 mg, 0.18 mmol) in 24% yield: MS (ESI): 554.0 (M+1)$^{+1}$.

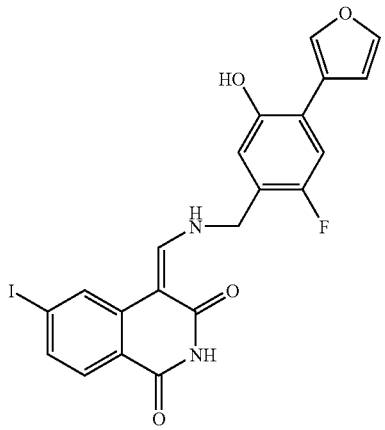

Example 520

4-[(2-Fluoro-4-furan-3-yl-5-hydroxy-benzylamino)-methylene]-6-iodo-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-iodo-4-methoxymethylene-4H-isoquinoline-1,3-dione (40 mg, 0.12 mmol) and 4-Aminomethyl-3'-dimethylaminomethyl-biphenyl-2-ol (26 mg, 0.13 mmol) in 55% yield: MS (ESI): 503.0 (M−1)$^{−1}$.

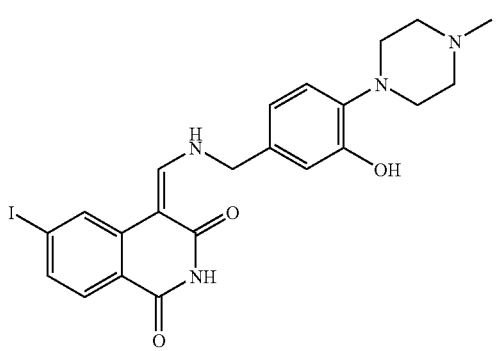

Example 521

(4Z)-4-({[3-Hydroxy-4-(4-methylpiperazin-1-yl)benzyl]amino}methylene)-6-iodoisoquinoline-1,3(2H,4H)-dione Using the procedure described for the preparation of (example 69), 100 mg (64% yield) is obtained as an orange solid from 100 mg (0.46 mmol) of (4E)-6-iodo-4-(methoxymethylene)isoquinoline-1,3(2H,4H)-dione and 13-hydroxy-4-(4-methylpiperazin-1-yl)benzyl]amine 221.3 mg (1.0 mmol).; mp 180-181° C.

MS (ESI) m/z 519.1 (M+1).

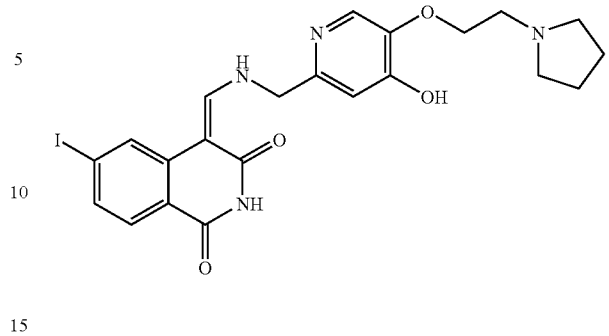

Example 522

4-({[4-Hydroxy-5-(2-pyrrolidin-1-yl-ethoxy)-pyridin-2-ylmethyl]-amino}-methylene)-6-iodo-4H-isoquinoline-1,3-dione A mixture of 2-aminomethyl-5-(2-pyrrolidin-1-yl-ethoxy)-pyridin-4-ol (237 mg, 1.0 mmole), 3 mL of N,N-dimethylformamide is stirred, then 4-methoxymethylene-6-iodo-4H-isoquinoline-1,3-dione (329 mg, 1.0 mmole) is added and the reaction mixture stirred for one hour. The reaction mixture is evaporated to dryness, taken up in methanol and purified by HPLC (acetonitrile/water without trifluoroacetic acid); the fractions belonging to the product peak (as determined by MS) were evaporated and still had impurities. This is re-purified by HPLC (acetonitrile water with 0.2% trifluoroacetic acid). The product is isolated by evaporation in-vacuo to give a yellow-orange solid assumed to be the bis trifluoroacetic acid salt, 30 mg, (4%); MS (ES +): m/z 535.1 (M+H).

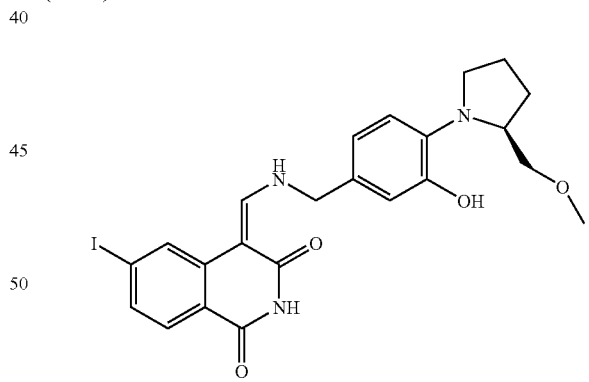

Example 523

(4Z)-4-[({3-Hydroxy-4-[(2S)-2-(methoxymethyl)pyrrolidin-1-yl]benzyl}amino)methylene]-6-iodoisoquinoline-1,3(2H,4H)-dione Using the procedure described for the preparation of (example 69), 45 mg (28% yield) is obtained as a purple solid from 100 mg (0.46 mmol) of (4E)-6-iodo-4-(methoxymethylene)isoquinoline-1,3(2H,4H)-dione and 3-hydroxy-4--

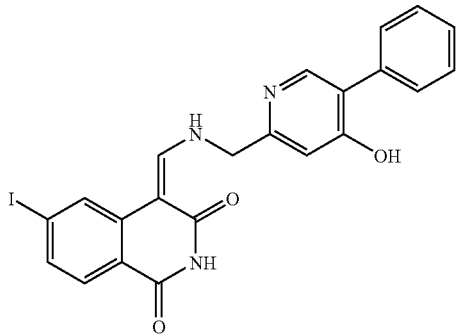

Example 524

(4Z)-{[(4-Hydroxy-5-phenyl-pyridin-2-ylmethyl)-amino]-methylene}-6-iodo-4H-isoquinoline-1,3-dione An amount of 64 mg (0.33 mmol) of 2-aminomethyl-5-phenyl-pyridin-4-ol, is slurried in N,N-dimethylformamide (3 mL), followed by the addition of 110 mg (0.33 mmol) of (4E)-6-iodo-4-(methoxymethylene)isoquinoline-1,3(2H,4H)-dione. After the mixture is stirred at room temperature for 6 hours, the solid is filtered and washed several times with N,N-dimethylformamide, then ether and dried to give 89 mg of example 524 as a light beige solid (53% yield); mp 292-3° C. dec, MS data ES(+) 498.1 m/e.

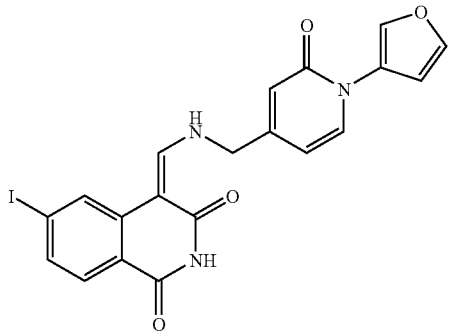

Example 525

(4Z)-4-[({[1-(3-Furyl)-2-oxo-1,2-dihydropyridin-4-yl]methyl}amino)methylene]-6-iodoisoquinoline-1,3(2H,4H)-dione A mixture of 2-hydroxy-4-methylpyridine (0.66 g, 6.0 mmol), 3-bromofuran (1.7 g, 12 mmol), copper (I) iodide (0.11 g, 0.60 mmol), and potassium carbonate (0.84 g, 6.0 mmol) in N,N-dimethylformamide (12 mL) were heated at 180° C. for 2 hours in a 300 W microwave reactor. The completed reaction mixture is diluted with 10% aqueous ammonium hydroxide solution and extracted 3× with ethyl acetate. The combined extracts were washed with saturated aqueous sodium chloride solution, dried over anhydrous magnesium sulfate, and concentrated under reduced pressure to give 1-furan-3-yl-4-methyl-1H-pyridin-2-one (0.65 g, 62%).

LC/MS (ES$^+$): 176.1 (M+H)$^+$

A mixture of 1-furan-3-yl-4-methyl-1H-pyridin-2-one (3.7 g, 21 mmol), tert-butoxybis(dimethylamino)methane (11 g, 63 mmol), and N,N-dimethylformamide (4 mL) is heated in a 150° C. oil bath for 2½ hours and then concentrated to dryness under reduced pressure. A quantitative yield of 4-(2-dimethylamino-vinyl)-1-furan-3-yl-1H-pyridin-2-one is assumed, and the material is carried on without further purification.

MS (ES$^+$): 231.3 (M+H)$^+$

To a solution of 4-(2-dimethylamino-vinyl)-1-furan-3-yl-1H-pyridin-2-one (21 mmol) in 50% aqueous tetrahydrofuran (700 mL) is added sodium periodate (13 g, 63 mmol). After six hours of stirring at room temperature, the reaction mixture is filtered. The filtrate is washed 3× with saturated aqueous sodium hydrogen carbonate solution, dried over anhydrous magnesium sulfate, and concentrated under reduced pressure to provide 1-furan-3-yl-2-oxo-1,2-dihydropyridine-4-carbaldehyde as a yellow powder (2.1 g, 53% over 2 steps).

MS (ES$^+$): 190.3 (M+H)$^+$

A solution of 1-furan-3-yl-2-oxo-1,2-dihydro-pyridine-4-carbaldehyde (1.4 g, 7.4 mmol) in pyridine (40 mL) is treated with methoxy]amine hydrochloride (0.68 g, 8.1 mmol). After bring stirred overnight at room temperature, the reaction mixture is concentrated under reduced pressure. The residue is partitioned between ethyl acetate and water. The organic phase is washed twice with water and once with saturated aqueous sodium chloride solution, dried, and concentrated under reduced pressure to provide 1-furan-3-yl-2-oxo-1,2-dihydro-pyridine-4-carbaldehyde O-methyl-oxime, which is used in the following step without further purification.

MS (ES$^+$): 219.3 (M+H)$^+$

To a mixture of the crude 1-furan-3-yl-2-oxo-1,2-dihydro-pyridine-4-carbaldehyde O-methyl-oxime (approximately 7.4 mmol) and glacial acetic acid (77 mL) is added zinc powder (3.1 g). The reaction mixture is heated for 45 minutes in a 100° C. oil bath and then allowed to cool to room temperature. After filtration of the mixture through a pad of diatomaceous earth and concentration, the residue is purified by reverse-phase HPLC to give 4-aminomethyl-1-furan-3-yl-1H-pyridin-2-one•trifluoroacetic acid (contaminated with zinc salts, 2.3 g).

MS (ES$^+$): 191.3 (M+H)$^+$

To a solution of 4-aminomethyl-1-furan-3-yl-1H-pyridin-2-one•trifluoroacetic acid (contaminated with zinc salts, 2.3 g) in 50% aqueous dioxane (20 mL) is added sodium hydroxide (approximately 800 mg), followed by an additional volume of aqueous dioxane (20 mL) and then the addition of di-tert-butyldicarbonate (600 µL). When complete, the reaction mixture is filtered. The filtrate is neutralized with 5% aqueous potassium hydrogen sulfate solution and extracted 3× with ethyl acetate. The combined extracts were washed with saturated aqueous sodium chloride solution, dried, and concentrated under reduced pressure to provide tert-butyl (1-furan-3-yl-2-oxo-1,2-dihydro-pyridin-4-ylmethyl)-carbamate (0.18 g, 0.62 mmol).

MS (ES$^+$): 291.3 (M+H)$^+$ tert-Butyl (1-furan-3-yl-2-oxo-1,2-dihydro-pyridin-4-ylmethyl)-carbamate (0.18 g, 0.62 mmol) is treated with 4N hydrogen chloride in dioxane in order to remove the Boc protecting group. The hydrochloride salt of 4-aminomethyl-1-furan-3-yl-1H-pyridin-2-one, obtained after concentration of the reaction mixture, is dissolved in N,N-dimethylformamide (4 mL) and is coupled to (4E)-6-iodo-4-(methoxymethylene)isoquinoline-1,3(2H,4H)-dione (0.20 g, 0.62 mmol) in the presence of triethylamine (400 µL). After three hours, the reaction mixture is concentrated under reduced pressure, and the residue is triturated with acetonitrile to provide (4Z)-4-[({[1-(3-furyl)-2-oxo-1,2-dihydropyridin-4-yl]

methyl}amino)methylene]-6-iodoisoquinoline-1,3(2H,4H)-dione as a brown powder (0.12 g, 40%).

MS (ES$^+$): 488.1 (M+H)$^+$

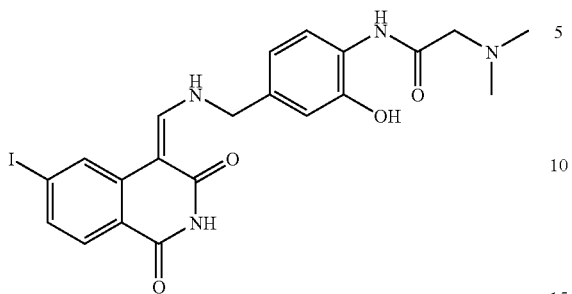

Example 526

N$^1$-[2-Hydroxy-4-({[(Z)-(6-iodo-1,3-dioxo-2,3-dihydroisoquinolin-4(1H)-ylidene)methyl]amino}methyl)phenyl]-N$^2$,N$^2$-dimethylglycinamide 4-[(4-Amino-3-hydroxy-benzylamino)-methylene]-6-iodo-4H-isoquinoline-1,3-dione (89 mg, 0.20 mmol) is dissolved in N,N-dimethylformamide (3.56 mL), followed by addition of triethylamine (0.236 mL, 1.69 mmol), dimethylamino-acetic acid (30.58 mg, 0.30 mmol), 1-[3-(dimethylamino)propyl]-3-ethylcarbodimide hydrochloride (42.6 mg, 0.22 mmol) and 1-hydroxybenzotriazole (13.8 mg, 0.10 mmol). It is stirred at room temperature overnight. It is then evaporated to dryness, and the residue is washed with ether, and then acetonitrile to yield 21 mg (20%) of the title compound as a solid. MS (ESI) m/z 521 (M+H)$^{+1}$

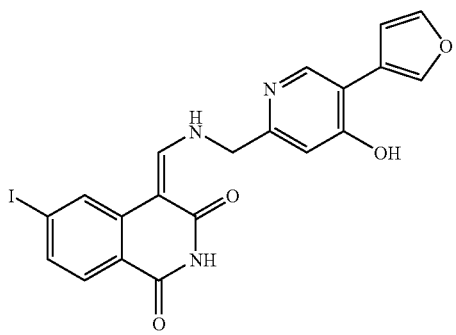

Example 527

(4Z)-{[(5-Furan-3-yl-4-hydroxy-pyridin-2-ylmethyl)-amino]-methylene}-6-iodo-4H-isoquinoline-1,3-dione An amount of 64 mg (0.33 mmol) of 2-aminomethyl-5-furan-3-yl-pyridin-4-ol, is slurried in N,N-dimethylformamide (3 mL), followed by the addition of 110 mg (0.33 mmol) of (4E)-6-iodo-4-(methoxymethylene)isoquinoline-1,3(2H,4H)-dione. After the mixture is stirred at room temperature for 6 hours, the solid is filtered and washed several times with N,N-dimethylformamide, then ether and dried to give 109 mg of the title compound as a light beige solid (67% yield); mp 213-228° C. dec, MS data ES(+) 488.0 m/e.

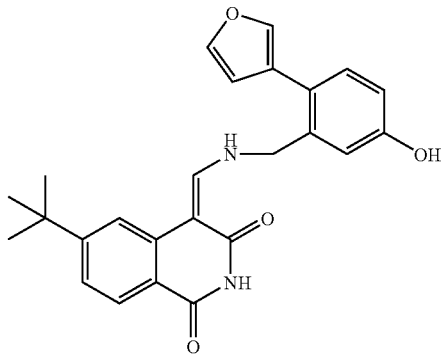

Example 528

6-tert-Butyl-4-[(2-furan-3-yl-5-hydroxy-benzylamino)-methylene]-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound (purified through chromatography) is prepared from 6-tert-Butyl-4-methoxymethylene-4H-isoquinoline-1,3-dione (~15 mg, 0.058 mmol) and 3-Aminomethyl-4-furan-3-yl-phenol (40 mg, 0.21 mmol) in 50% yield: MS (ESI): 415.1 (M−1)$^{-1}$.

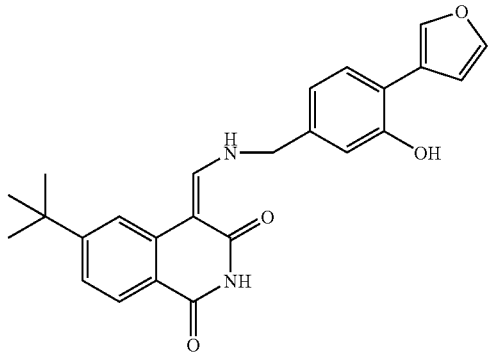

Example 528

6-tert-Butyl-4-[(4-furan-3-yl-3-hydroxy-benzylamino)-methylene]-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound (purified through chromatography) is prepared from 6-tert-Butyl-4-methoxymethylene-4H-isoquinoline-1,3-dione (~15 mg, 0.058 mmol) and 5-Aminomethyl-2-furan-3-yl-phenol (40 mg, 0.21 mmol) in 50% yield: MS (ESI): 415.1 (M−1)$^{-1}$.

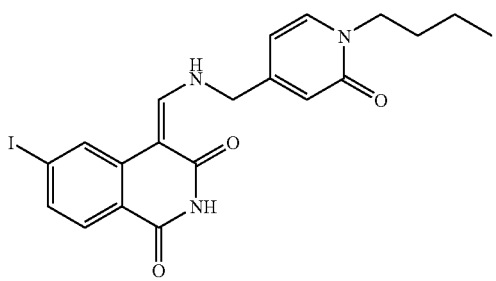

Example 529

(4Z)-6-Iodo-4-({[(1-butyl-2-oxo-1,2-dihydropyridin-4-yl)methyl]amino}methylene)isoquinoline-1,3(2H,4H)-dione 4-Aminomethyl-1-butyl-1H-pyridin-2-one trifluoroacetate is prepared in two steps from 1-butyl-2-oxo-1,2-dihydropyridine-4-carboxamide in a manner analogous to the preparation of 4-aminomethyl-1-methyl-1H-pyridin-2-one. Purification of 4-aminomethyl-1-butyl-1H-pyridin-2-one is accomplished via semi-preparative HPLC (Prodigy ODS3 column, 5% acetonitrile/95% water/0.01% trifluoroacetic acid to 100% acetonitrile at 10 mL/min).

MS (ES+): 181.4 (M+H)+

A mixture of (4E)-6-iodo-4-(methoxymethylene)isoquinoline-1,3(2H,4H)-dione (170 mg, 0.51 mmol) and 4-aminomethyl-1-butyl-1H-pyridin-2-one trifluoroacetate (150 mg, 0.51 mol) is stirred in dimethylformamide (2.7 mL) at room temperature in the presence of triethylamine (0.33 mL) for 18 hours. The reaction mixture is concentrated under reduced pressure. The residue is purified via semi-preparative HPLC (Prodigy ODS3 column, 5% acetonitrile/95% water/0.01% trifluoroacetic acid to 100% acetonitrile at 10 mL/min) to give (4Z)-6-iodo-4-({[(1-butyl-2-oxo-1,2-dihydropyridin-4-yl)methyl]amino}methylene)isoquinoline-1,3(2H,4H)-dione as an peach colored solid (25 mg, 10% due to substantial loss of material during HPLC malfunction).

MS (ES+): 478.0 (M+H)+

Example 530

6-tert-Butyl-4-{[(4-hydroxy-5-propoxy-pyridin-2-ylmethyl)-amino]-methylene}-4H-isoquinoline-1,3-dione An amount of 50.0 mg (0.193 mmol) of (4E)-6-tert-butyl-4-(methoxymethylene)isoquinoline-1,3(2H,4H)-dione, is dissolved in N,N-dimethylformamide (3 mL), followed by the addition of 35 mg (0.193 mmol) of 2-aminomethyl-5-propoxy-pyridin-4-ol. All solids dissolved and after the mixture is stirred at room temperature for 2 hours, the solution is evaporated to dryness in vacuo, treated with acetonitrile, filtered and washed several times with fresh acetonitrile and dried to give 52 mg of the title compound as a light pink solid (66% yield); mp 162-178° C. dec, MS data ES(+) 410.4 m/e.

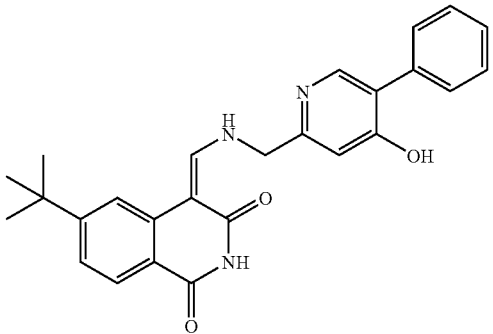

Example 531

6-tert-Butyl-4-{[(4-hydroxy-5-phenyl-pyridin-2-ylmethyl)-amino]-methylene}-4H-isoquinoline-1,3-dione An amount of 40.0 mg (0.154 mmol) of (4E)-6-t-butyl-4-(methoxymethylene)isoquinoline-1,3(2H,4H)-dione (based on a sample that is 39% pure by weight), is dissolved in N,N-dimethylformamide (3 mL), followed by the addition of 31 mg (0.154 mmol) of 2-aminomethyl-5-phenyl-pyridin-4-ol. All solids dissolved and after the mixture is stirred at room temperature for 2 hours, the solution is evaporated to dryness in vacuo, treated with acetonitrile, filtered and washed several times with fresh acetonitrile and dried to give 44 mg of the title compound as a pink solid (66% yield); mp 195-218° C. dec, MS data ES(+) 428.4 m/e.

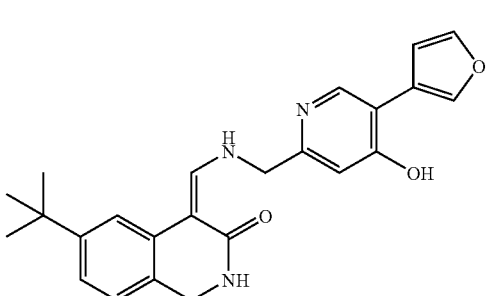

Example 532

6-tert-Butyl-4-{[(5-furan-3-yl-4-hydroxy-pyridin-2-ylmethyl)-amino]-methylene}-4H-isoquinoline-1,3-dione An amount of 40.0 mg (0.154 mmole) of (4E)-6-tert-butyl-4-(methoxymethylene)isoquinoline-1,3(2H,4H)-dione (based on a sample that is 39% pure by weight), is dissolved in N,N-dimethylformamide (3 mL), followed by the addition of 29 mg (0.154 mmole) of 2-aminomethyl-5-furan-3-yl-pyridin-4-ol. All solids dissolved and after the mixture is stirred at room temperature for 2 hours, the solution is evaporated to dryness in vacuo, treated with acetonitrile, filtered and washed several times with fresh acetonitrile and dried to give 41 mg of the title compound as a pink solid (64% yield); mp 215-230° C. dec, MS data ES(+) 418.3

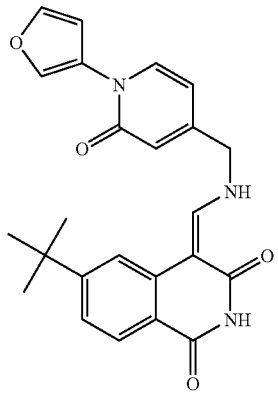

Example 533

(4Z)-6-tert-Butyl-4-[({[1-(3-furyl)-2-oxo-1,2-dihydropyridin-4-yl]methyl}amino)methylene]isoquinoline-1,3(2H,4H)-dione A mixture of (4E)-6-tert-butyl-4-(methoxymethylene)isoquinoline-1,3(2H,4H)-dione (50 mg, 0.19 mmol), 4-aminomethyl-1-furan-3-yl-1H-pyridin-2-one hydrochloride (43 mg, 0.19 mmol), and triethylamine (150 µL, 1.1 mmol) in N,N-dimethylformamide (2 mL) is stirred overnight at room temperature. The reaction mixture is concentrated under reduced pressure, and the residue is triturated with chloroform to provide (4Z)-6-tert-butyl-4-[({[1-(3-furyl)-2-oxo-1,2-dihydropyridin-4-yl]methyl}amino)methylene]isoquinoline-1,3 (2H,4H)-dione as a white solid (34 mg, 43%).

MS (ES⁻): 416.2 (M–H)

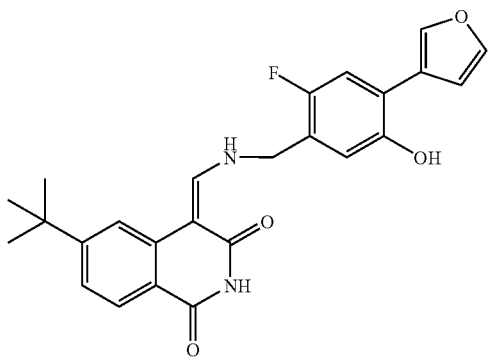

Example 534

6-tert-Butyl-4-[(2-fluoro-4-furan-3-yl-5-hydroxy-benzylamino)-methylene]-4H-isoquinoline-1,3-dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-tert-Butyl-4-methoxymethylene-4H-isoquinoline-1,3-dione (11 mg, 0.042 mmol) and 5-Aminomethyl-4-fluoro-2-furan-3-yl-phenol (12 mg, 0.058 mmol) in 60% yield: MS (ESI): 433.2 (M–1)⁻¹.

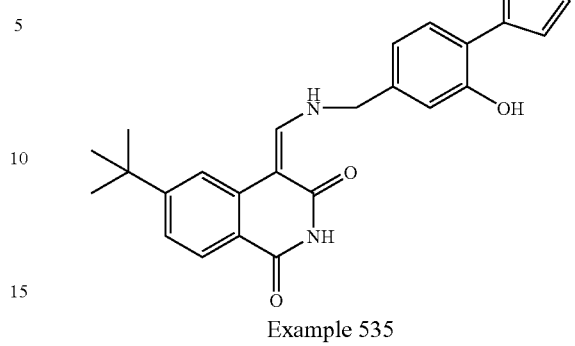

Example 535

6-tert-Butyl-4-[(4-furan-3-yl-3-hydroxy-benzylamino)-methylene]-4H-isoquinoline-1,3. -dione Following the same procedure for the preparation of 4-{[(2-Hydroxy-biphenyl-4-ylmethyl)-amino]-methylene}-6-iodo-4H-isoquinoline-1,3-dione, the title compound is prepared from 6-tert-Butyl-4-methoxymethylene-4H-isoquinoline-1,3-dione (84 mg, 0.32 mmol) and 5-Aminomethyl-2-furan-3-yl-phenol (95 mg, 0.5 mmol) in 56% yield: MS (ESI): 415.4 (M–1)⁻¹.

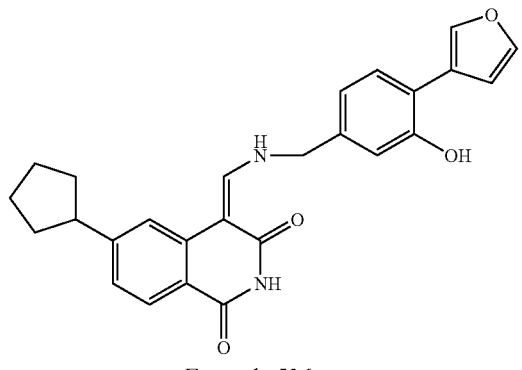

Example 536

6-Cyclopentyl-4-[(4-furan-3-yl-3-hydroxy-benzylamino)-methylene]-4H-isoquinoline-1,3-dione Following the same procedure for the preparation of 4-{[(2-hydroxy-biphenyl-4-ylmethyl)-amino]-methylene}-6-iodo-4H-isoquinoline-1,3-dione, the title compound (purified through chromatography) is prepared from 6-cyclopentyl-4-methoxymethylene-4H-isoquinoline-1,3-dione (108 mg, 0.398 mmol) and 5-Aminomethyl-2-furan-3-yl-phenol (109 mg, 0.57 mmol) in 78% yield: MS (ESI): 427.1 (M–1)⁻¹.

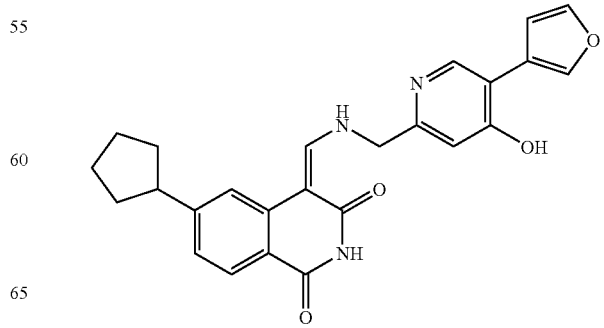

Example 537

6-Cyclopentyl-4-[([(5-furan-3-yl-4-hydroxy-pyridin-2-ylmethyl)-amino]-methylene}-4H-isoquinoline-1,3-dione An amount of 77 mg (0.405 mmol) of 2-aminomethyl-5-furan-3-yl-pyridin-4-ol, is slurried in N,N-dimethylformamide (4 mL), followed by the addition of 110 mg (0.405 mmol) of 6-cyclopentyl-4-methoxymethylene-4H-isoquinoline-1,3-dione. After the mixture is stirred at room temperature overnight. The reaction mixture is evaporated in-vacuo and the residue treated with acetonitrile, the solid is filtered and washed several times with acetonitrile and dried to give 152 mg of the title compound as a pink solid (87% yield); mp 279-283° C. dec, MS data ES(+) 430.1 m/e.

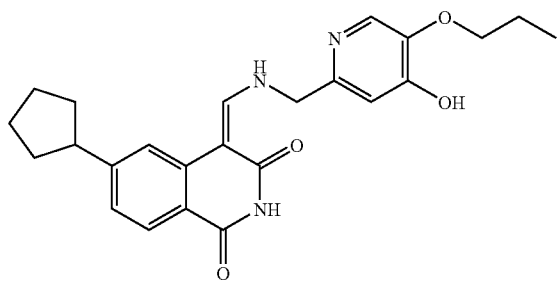

Example 538

6-Cyclopentyl-4-{[(4-hydroxy-5-propoxy-pyridin-2-ylmethyl)-amino]-methylene}-4H-isoquinoline-1,3-dione An amount of 74 mg (0.405 mmole) of 2-aminomethyl-5-phenyl-3-yl-pyridin-4-ol, is slurried in N,N-dimethylformamide (4 mL), followed by the addition of 110 mg (0.405 mmole) of 6-cyclopentyl-4-methoxymethylene-4H-isoquinoline-1,3-dione. After the mixture is stirred at room temperature overnight. The reaction mixture is filtered, washed with N,N-dimethylformamide, then several times with ether and dried to give 162 mg of the title compound as a pink solid (94% yield); mp 263-6° C. dec; MS (ESI): m/z 422.2 (M+H).

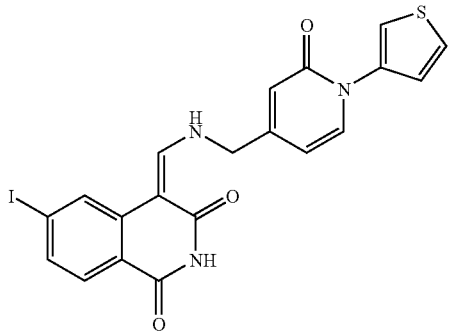

Example 539

(4Z)-6-Iodo-4-[({[2-oxo-1-(3-thienyl)-1,2-dihydropyridin-4-yl]methyl}amino)methylene]isoquinoline-1,3(2H,4H)-dione A mixture of 2-hydroxy-4-methylpyridine (1.5 g, 14 mmol), 3-bromothiophene (4.5 g, 28 mmol), copper (I) iodide (0.27 g, 1.4 mmol), and potassium carbonate (1.9 g, 14 mmol) in N,N-dimethylformamide (30 mL) is heated in a 150° C. oil bath for 6 hours. After cooling to room temperature, the reaction mixture is diluted with 20% aqueous ammonium hydroxide solution and extracted 3× with diethyl ether. The combined extracts were washed with saturated aqueous sodium chloride solution, dried over anhydrous sodium sulfate, and concentrated under reduced pressure to give a crude oil, which is purified by flash chromatography (ethyl acetate/hexanes) to give 4-methyl-1-(3-thienyl)pyridin-2(1H)-one (0.79 g, 29%).

MS (ES+): 192.1 (M+H)+

A mixture of 4-methyl-1-(3-thienyl)pyridin-2(1H)-one (0.73 g, 3.8 mmol), tert-butoxybis(dimethylamino)methane (3 mL, 15 mmol), and N,N-dimethylformamide (4 mL) is heated in a 100° C. oil bath for 3 hours and then concentrated to dryness under reduced pressure. A quantitative yield of 4-(2-dimethylamino-vinyl)-1-thiophen-3-yl-1H-pyridin-2-one is carried on without further purification.

MS (ES+): 247.3 (M+H)+

To a solution of 4-(2-dimethylamino-vinyl)-1-thiophen-3-yl-1H-pyridin-2-one (3.8 mmol) in 50% aqueous tetrahydrofuran (130 mL) is added sodium periodate (2.4 g, 11 mmol). After 17 hours of stirring at room temperature, the reaction mixture is filtered. The filtrate is washed 3× with saturated aqueous sodium hydrogen carbonate solution, dried over anhydrous magnesium sulfate, and concentrated under reduced pressure to provide 1-thiophen-3-yl-2-oxo-1,2-dihydro-pyridine-4-carbaldehyde as a yellow powder (0.27 g, 34% over 2 steps).

MS (ES+): 206.2 (M+H)+

A solution of 1-thiophen-3-yl-2-oxo-1,2-dihydro-pyridine-4-carbaldehyde (0.27 g, 1.3 mmol) in methanol (20 mL) is cooled to 0° C. in an ice-water bath and then treated with sodium borohydride (50 mg, 1.3 mmol). After stirring at 0° C. for two hours, the reaction mixture is quenched by the addition of 10% aqueous hydrochloric acid. The mixture is extracted with ethyl acetate. The combined organic extracts were washed once with saturated aqueous sodium chloride solution, dried, and concentrated under reduced pressure to provide 4-hydroxymethyl-1-thiophen-3-yl-1H-pyridin-2-one (0.18 g, 67%), which is used in the following step without further purification.

MS (ES+): 208.3 (M+H)+

To a 0° C. mixture of the crude 4-hydroxymethyl-1-thiophen-3-yl-1H-pyridin-2-one (0.18 g, 0.87 mmol) and triethylamine (250 µL) in dichloromethane (5 mL) is added methanesulfonyl chloride (125 µL). The reaction mixture is stirred at 0° C. for 30 minutes and then allowed to warm to room temperature, where it stirred for one hour. The mixture is concentrated to dryness under reduced pressure and is then taken up in N,N-dimethylformamide. To the resulting suspension is added sodium azide (150 mg). After stirring for two hours at room temperature, the mixture is poured onto ice and then extracted from the aqueous mixture with diethyl ether. The organic extracts were washed with saturated aqueous sodium chloride solution, dried over anhydrous magnesium sulfate, filtered, and concentrated under reduced pressure to provide 4-azidomethyl-1-thiophen-3-yl-1H-pyridin-2-one (assumed 0.87 mmol).

MS (ES+): 233.2 (M+H)+

To a solution of crude 4-azidomethyl-1-thiophen-3-yl-1H-pyridin-2-one in tetrahydrofuran (2 mL) is added triphenylphosphine (0.19 g). The mixture is stirred for 10 minutes before the addition of water (200 µL). After stirring for 16 hours at room temperature, the mixture is purified by reverse-phase high performance liquid chromatography (5% acetonitrile/95% water to 75% acetonitrile/25% water over 45 minutes) to provide 4-aminomethyl-1-thiophen-3-yl-1H-pyridin-2-one (60 mg, 34% over 2 steps).

MS (ES⁺): 207.3 (M+H)⁺

A mixture of (4E)-6-iodo-4-(methoxymethylene)isoquinoline-1,3(2H,4H)-dione (97 mg, 0.30 mmol), 4-aminomethyl-1-thiophen-3-yl-1H-pyridin-2-one (61 mg, 0.30 mmol), and triethylamine (77 µL, 0.59 mmol) in N,N-dimethylformamide (2 mL) is stirred overnight at room temperature. The reaction mixture is concentrated under reduced pressure, and the residue is triturated with acetonitrile to provide (4Z)-6-iodo-4-[({[2-oxo-1-(3-thienyl)-1,2-dihydropyridin-4-yl]methyl}amino)methylene]isoquinoline-1,3(2H,4H)-dione as a mauve powder (65 mg, 43%).

MS (ES⁻): 502.1 (M–H)⁻

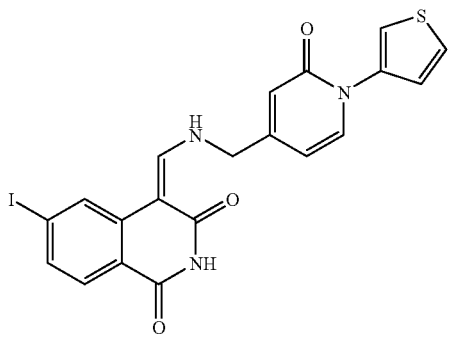

Example 539

(4Z)-6-Iodo-4-[({[2-oxo-1-(3-thienyl)-1,2-dihydropyridin-4-yl]methyl}amino)methylene]isoquinoline-1,3(2H,4H)-dione A mixture of 2-hydroxy-4-methylpyridine (1.5 g, 14 mmol), 3-bromothiophene (4.5 g, 28 mmol), copper (I) iodide (0.27 g, 1.4 mmol), and potassium carbonate (1.9 g, 14 mmol) in N,N-dimethylformamide (30 mL) is heated in a 150° C. oil bath for 6 hours. After cooling to room temperature, the reaction mixture is diluted with 20% aqueous ammonium hydroxide solution and extracted 3× with diethyl ether. The combined extracts were washed with saturated aqueous sodium chloride solution, dried over anhydrous sodium sulfate, and concentrated under reduced pressure to give a crude oil, which is purified by flash chromatography (ethyl acetate/hexanes) to give 4-methyl-1-(3-thienyl)pyridin-2(1H)-one (0.79 g, 29%).

MS (ES⁺): 192.1 (M+H)⁺

A mixture of 4-methyl-1-(3-thienyl)pyridin-2(1H)-one (0.73 g, 3.8 mmol), tert-butoxybis(dimethylamino)methane (3 mL, 15 mmol), and N,N-dimethylformamide (4 mL) is heated in a 100° C. oil bath for 3 hours and then concentrated to dryness under reduced pressure. A quantitative yield of 4-(2-dimethylamino-vinyl)-1-thiophen-3-yl-1H-pyridin-2-one is assumed, and the material is carried on without further purification.

MS (ES⁺): 247.3 (M+H)⁺

To a solution of 4-(2-dimethylamino-vinyl)-1-thiophen-3-yl-1H-pyridin-2-one (3.8 mmol) in 50% aqueous tetrahydrofuran (130 mL) is added sodium periodate (2.4 g, 11 mmol). After 17 hours of stirring at room temperature, the reaction mixture is filtered. The filtrate is washed 3× with saturated aqueous sodium hydrogen carbonate solution, dried over anhydrous magnesium sulfate, and concentrated under reduced pressure to provide 1-thiophen-3-yl-2-oxo-1,2-dihydro-pyridine-4-carbaldehyde as a yellow powder (0.27 g, 34% over 2 steps).

MS (ES⁺): 206.2 (M+H)⁺

A solution of 1-thiophen-3-yl-2-oxo-1,2-dihydro-pyridine-4-carbaldehyde (0.27 g, 1.3 mmol) in methanol (20 mL) is cooled to 0° C. in an ice-water bath and then treated with sodium borohydride (50 mg, 1.3 mmol). After bring stirred at that temperature for two hours, the reaction mixture is quenched by the addition of 10% aqueous hydrochloric acid. The mixture is extracted with ethyl acetate. The combined organic extracts were washed once with saturated aqueous sodium chloride solution, dried, and concentrated under reduced pressure to provide 4-hydroxymethyl-1-thiophen-3-yl-1H-pyridin-2-one (0.18 g, 67%), which is used in the following step without further purification.

MS (ES⁺): 208.3 (M+H)⁺

To a 0° C. mixture of the crude 4-hydroxymethyl-1-thiophen-3-yl-1H-pyridin-2-one (0.18 g, 0.87 mmol) and triethylamine (250 µL) in dichloromethane (5 mL) is added methanesulfonyl chloride (125 µL). The reaction mixture is stirred at 0° C. for 30 minutes and then allowed to warm to room temperature, where it stirred for one hour. The mixture is concentrated to dryness under reduced pressure and is then taken up in N,N-dimethylformamide. To the resulting suspension is added sodium azide (150 mg). After stirring for two hours at room temperature, the mixture is poured onto ice and then extracted from the aqueous mixture with diethyl ether. The organic extracts were washed with saturated aqueous sodium chloride solution, dried over anhydrous magnesium sulfate, filtered, and concentrated under reduced pressure to provide 4-azidomethyl-1-thiophen-3-yl-1H-pyridin-2-one (assumed 0.87 mmol).

MS (ES⁺): 233.2 (M+H)⁺

To a solution of crude 4-azidomethyl-1-thiophen-3-yl-1H-pyridin-2-one in tetrahydrofuran (2 mL) is added triphenylphosphine (0.19 g). The mixture is stirred for 10 minutes before the addition of water (200 µL). After stirring for 16 hours at room temperature, the mixture is purified by reverse-phase high performance liquid chromatography (5% acetonitrile/95% water to 75% acetonitrile/25% water over 45 minutes) to provide 4-aminomethyl-1-thiophen-3-yl-1H-pyridin-2-one (60 mg, 34% over 2 steps).

MS (ES⁺): 207.3 (M+H)⁺

A mixture of (4E)-6-iodo-4-(methoxymethylene)isoquinoline-1,3(2H,4H)-dione (97 mg, 0.30 mmol), 4-aminomethyl-1-thiophen-3-yl-1H-pyridin-2-one (61 mg, 0.30 mmol), and triethylamine (77 µL, 0.59 mmol) in N,N-dimethylformamide (2 mL) is stirred overnight at room temperature. The reaction mixture is concentrated under reduced pressure, and the residue is triturated with acetonitrile to provide (4Z)-6-iodo-4-[({[2-oxo-1-(3-thienyl)-1,2-dihydropyridin-4-yl]methyl}amino)methylene]isoquinoline-1,3(2H,4H)-dione as a mauve powder (65 mg, 43%).

MS (ES⁻): 502.1 (M–H)⁻

Example 540

4-{[(1,3-Dioxo-2,3-dihydro-1H-isoquinolin-4-ylidenemethyl)-amino]-methyl}-benzenesulfonamide This compound is prepared using appropriate starting materials according to the procedure of Example 550.

Example 541

4-[(2-Trifluoromethoxy-phenylamino)-methylene]-4H-isoquinoline-1,3-dione

This compound is prepared using appropriate starting materials according to the procedure of Example 550.

Example 542

3-[(1,3-Dioxo-2,3-dihydro-1H-isoquinolin-4-ylidenemethyl)-amino]-benzoic acid

This compound is prepared using appropriate starting materials according to the procedure of Example 550.

Example 543

N-(2-Diethylamino-ethyl)-4-[(1,3-dioxo-2,3-dihydro-1H-isoquinolin-4-ylidenemethyl)-amino]-benzamide This compound is prepared using appropriate starting materials according to the procedure of Example 550.

Example 544

4-{[2-(3,4-Dihydroxy-phenyl)-ethylamino]-methylene}-4H-isoquinoline-1,3-dione

This compound is prepared using appropriate starting materials according to the procedure of Example 550.

Example 545

4-[(4-Amino-phenylamino)-methylene]-4H-isoquinoline-1,3-dione

This compound is prepared using appropriate starting materials according to the procedure of Example 550.

Example 546

N-{4-[(1,3-Dioxo-2,3-dihydro-1H-isoquinolin-4-ylidenemethyl)-amino]-phenyl}-oxalamic acid This compound is prepared using appropriate starting materials according to the procedure of Example 550.

Example 547

4-[(1,3-Dioxo-2,3-dihydro-1H-isoquinolin-4-ylidenemethyl)-amino]-benzamidine

This compound is prepared using appropriate starting materials according to the procedure of Example 550.

Example 548

{4-[(1,3-Dioxo-2,3-dihydro-1H-isoquinolin-4-ylidenemethyl)-amino]-phenylsulfanyl}-acetic acid This compound is prepared using appropriate starting materials according to the procedure of Example 550.

Example 549

4-[(1,3-Dioxo-2,3-dihydro-1H-isoquinolin-4-ylidenemethyl)-amino]-N-(5-methyl-[1,3,4]thiadiazol-2-yl)-benzenesulfonamide This compound is prepared using appropriate starting materials according to the procedure of Example 550.

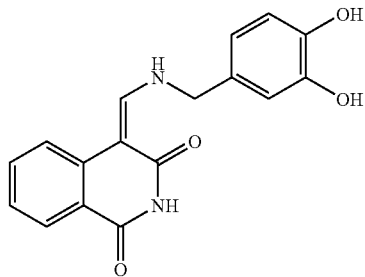

Example 550

4-[(3,4-Dihydroxy-benzylamino)-methylene]-4H-isoquinoline-1,3-dione

Step 1:
To a suspension of 4H-Isoquinoline-1,3-dione (1.5 g, 9.3 mmol) in 22.5 mL of a 4:1 mixture of acetic anhydride and N,N-dimethylformamide, respectively, is added trimethylorthoformate (2.0 mL, 18.6 mmol). The reaction mixture is shaken in a heating block at 125° C. for 1 hour, at which point a beige precipitate formed, product. Upon cooling to room temperature, more product precipitated out. The precipitate is then filtered off, rinsed with copious amounts of ether, and dried to yield 1.47 g of 4-Methoxymethylene-4H-isoquinoline-1,3-dione.

Step 2:
To a suspension of 4-Methoxymethylene-4H-isoquinoline-1,3-dione (20.3 mg, 0.1 mmol) in N,N-dimethylformamide (250 μL) is added 3,4-dihydroxybenzylamine hydrobromide (22 mg, 0.1 mmol), followed by 21 μL of triethylamine. The reaction mixture is shaken at 115° C. for 1.5 hours. The reaction mixture is diluted to 2 mL with N,N-dimethylformamide and purified by C18 reverse phase HPLC. The product peak is collected based on UV absorption, the pure fractions were combined and concentrated to yield Example 550 (28.4 mg).

Example 551

4-{[2-(1H-Benzoimidazol-2-yl)-phenylamino]-methylene}-4H-isoquinoline-1,3-dione

This compound is prepared using appropriate starting materials according to the procedure of Example 550.

Example 552

3-[N'-(1,3-Dioxo-2,3-dihydro-1H-isoquinolin-4-ylidenemethyl)-hydrazino]-benzoic acid This compound is prepared using appropriate starting materials according to the procedure of Example 550.

Example 553

N-(4,5-Dimethyl-oxazol-2-yl)-4-[(1,3-dioxo-2,3-dihydro-1H-isoquinolin-4-ylidenemethyl)-amino]-benzenesulfonamide This compound is prepared using appropriate starting materials according to the procedure of Example 550.

Example 554

N-{4-[(1,3-Dioxo-2,3-dihydro-1H-isoquinolin-4-ylidenemethyl)-amino]-phenyl}-N-methyl-acetamide This compound is prepared using appropriate starting materials according to the procedure of Example 550.

Example 555

{4-[(1,3-Dioxo-2,3-dihydro-1H-isoquinolin-4-ylidenemethyl)-amino]-phenyl}-acetonitrile This compound is prepared using appropriate starting materials according to the procedure of Example 550.

Example 556

4-[(1,3-Dioxo-2,3-dihydro-1H-isoquinolin-4-ylidenemethyl)-amino]-N-(5-methyl-isoxazol-3-yl)-benzenesulfonamide This compound is prepared using appropriate starting materials according to the procedure of Example 550.

Example 557

3-{4-[(1,3-Dioxo-2,3-dihydro-1H-isoquinolin-4-ylidenemethyl)-amino]-phenyl}-acrylic acid This compound is prepared using appropriate starting materials according to the procedure of Example 550.

Example 558

4-{4-[(1,3-Dioxo-2,3-dihydro-1H-isoquinolin-4-ylidenemethyl)-amino]-phenyl}-butyric acid This compound is prepared using appropriate starting materials according to the procedure of Example 550.

Example 559

4-[(4-Hydroxy-phenylamino)-methylene]-4H-isoquinoline-1,3-dione

This compound is prepared using appropriate starting materials according to the procedure of Example 550.

Example 560

4-[(1,3-Dioxo-2,3-dihydro-1H-isoquinolin-4-ylidenemethyl)-amino]-2-hydroxy-benzoic acid This compound is prepared using appropriate starting materials according to the procedure of Example 550.

Example 561

4-[(3-Hydroxy-4-methoxy-phenylamino)-methylene]-4H-isoquinoline-1,3-dione

This compound is prepared using appropriate starting materials according to the procedure of Example 550.

Example 562

2-[(1,3-Dioxo-2,3-dihydro-1H-isoquinolin-4-ylidenemethyl)-amino]-5-hydroxy-benzoic acid This compound is prepared using appropriate starting materials according to the procedure of Example 550.

Example 563

5-[(1,3-Dioxo-2,3-dihydro-1H-isoquinolin-4-ylidenemethyl)-amino]-2-hydroxy-benzoic acid This compound is prepared using appropriate starting materials according to the procedure of Example 550.

Example 564

4-{[2-(3,4-Dihydroxy-phenyl)-2-hydroxy-ethylamino]-methylene}-4H-isoquinoline-1,3-dione This compound is prepared using appropriate starting materials according to the procedure of Example 550.

Example 565

4-[(2,6-Dihydroxy-phenylamino)-methylene]-4H-isoquinoline-1,3-dione

This compound is prepared using appropriate starting materials according to the procedure of Example 550.

Example 566

3-(3,4-Dihydroxy-phenyl)-2-[(1,3-dioxo-2,3-dihydro-1H-isoquinolin-4-ylidenemethyl)-amino]-propionic acid This compound is prepared using appropriate starting materials according to the procedure of Example 550.

Example 567

3-(3,4-Dihydroxy-phenyl)-2-[(1,3-dioxo-2,3-dihydro-1H-isoquinolin-4-ylidenemethyl)-amino]-propionic acid This compound is prepared using appropriate starting materials according to the procedure of Example 550.

Example 568

4-[(2,4-Dihydroxy-phenylamino)-methylene]-4H-isoquinoline-1,3-dione

This compound is prepared using appropriate starting materials according to the procedure of Example 550.

Example 569

4-[(8-Hydroxy-quinolin-5-ylamino)-methylene]-4H-isoquinoline-1,3-dione

This compound is prepared using appropriate starting materials according to the procedure of Example 550.

Example 570

4-[(5-Chloro-2-hydroxy-4-nitro-phenylamino)-methylene]-4H-isoquinoline-1,3-dione

This compound is prepared using appropriate starting materials according to the procedure of Example 550.

Example 571

4-({4-[4-(2-Morpholin-4-yl-ethyl)-piperazin-1-yl]-phenylamino}-methylene)-4H-isoquinoline-1,3-dione

This compound is prepared using appropriate starting materials according to the procedure of Example 596.

Example 572

4-({4-[4-(2-Pyrrolidin-1-yl-ethyl)-piperazin-1-yl]-phenylamino}-methylene)-4H-isoquinoline-1,3-dione

This compound is prepared using appropriate starting materials according to the procedure of Example 596.

Example 573

4-[(3-Amino-benzylamino)-methylene]-4H-isoquinoline-1,3-dione

This compound is prepared using appropriate starting materials according to the procedure of Example 550.

Example 574

4-[(4-Diethylaminomethyl-phenylamino)-methylene]-4H-isoquinoline-1,3-dione

This compound is prepared using appropriate starting materials according to the procedure of Example 576.

Example 575

4-({4-[(Cyclopropylmethyl-propyl-amino)-methyl]-phenylamino}-methylene)-4H-isoquinoline-1,3-dione

This compound is prepared using appropriate starting materials according to the procedure of Example 576.

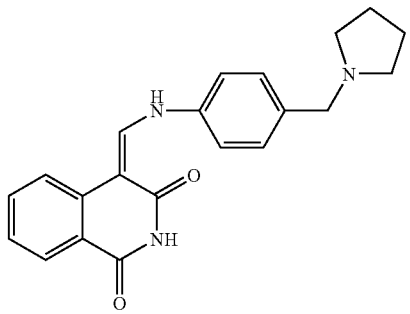

Example 576

4-[(4-Pyrrolidin-1-ylmethyl-phenylamino)-methylene]-4H-isoquinoline-1,3-dione

Step 1:

To a suspension of 4-Methoxymethylene-4H-isoquinoline-1,3-dione (203 mg, 1.0 mmol) in N,N-dimethylformamide (2.5 mL) is added 4-aminobenzyl alcohol (123.2 mg, 1.0 mmol). The reaction mixture is shaken at 115° C. for 1.5 hours. Upon cooling to ambient temperature, product precipitated out of solution. The product is recovered by filtration, rinsing with diethyl ether, and drying to yield 263.3 mg 4-[(4-Hydroxymethyl-phenylamino)-methylene]-4H-isoquinoline-1,3-dione.

Step 2:

To a suspension of 4-[(4-Hydroxymethyl-phenylamino)-methylene]-4H-isoquinoline-1,3-dione (294 mg, 1 mmol) in N,N-dimethylformamide (10 mL) is added methanesulfonyl chloride (0.77 mL, 10 mmol) and triethylamine (2.79 mL, 20 mmol). The reaction mixture is shaken at 115° C. for 1.5 hours. The crude product, methanesulfonic acid 4-[(1,3-dioxo-2,3-dihydro-1H-isoquinolin-4-ylidenemethyl)-amino]-benzyl ester (304 mg), thus obtained is used as such for the next reaction.

Step 3:

To a suspension of crude methanesulfonic acid 4-[(1,3-dioxo-2,3-dihydro-1H-isoquinolin-4-ylidenemethyl)-amino]-benzyl ester (72 mg, 0.23 mmol) in N,N-dimethylformamide (2 mL) is added pyrrolidine (21 μL, 0.25 mmol). The reaction mixture is shaken at ambient temperature for 16 hours. The reaction mixture is diluted to 2 mL with N,N-dimethylformamide and purified by C18 reverse phase HPLC. The pure fractions were combined and concentrated to yield the title compound (3.0 mg).

Example 577

4-({4-[(Cyclohexyl-methyl-amino)-methyl]-phenylamino}-methylene)-4H-isoquinoline-1,3-dione

This compound is prepared using appropriate starting materials according to the procedure of Example 576.

Example 578

4-[(3-Aminomethyl-benzylamino)-methylene]-4H-isoquinoline-1,3-dione

This compound is prepared using appropriate starting materials according to the procedure of Example 550.

Example 579

Thiophene-2-sulfonic acid (3-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 580

Propane-2-sulfonic acid (3-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 581

N-(3-{[(1,3-Dioxo-2,3-dihydro-1H-isoquinolin-4-ylidenemethyl)-amino]-methyl}-phenyl)-methanesulfonamide This compound is prepared using appropriate starting materials according to the procedure of Example 593.

Example 582

2,2,2-Trifluoro-ethanesulfonic acid (3-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 583

Ethanesulfonic acid (3-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 584

Propane-1-sulfonic acid (3-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 585

N-(3-{[(1,3-Dioxo-2,3-dihydro-1H-isoquinolin-4-ylidenemethyl)-amino]-methyl)-phenyl)-acetamide This compound is prepared using appropriate starting materials according to the procedure of Example 593.

Example 586

Cyclopropanecarboxylic acid (3-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 587

Cyclobutanecarboxylic acid (3-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 588

Thiophene-2-sulfonic acid (4-{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 589

N-(4{[(1,3-Dioxo-2,3-dihydro-1H-isoquinolin-4-ylidenemethyl)-amino]-methyl}-phenyl)-methanesulfonamide This compound is prepared using appropriate starting materials according to the procedure of Example 593.

Example 590

N-(4{[(1,3-Dioxo-2,3-dihydro-1H-isoquinolin-4-ylidenemethyl)-amino]-methyl}-phenyl)-C-phenyl-methanesulfonamide This compound is prepared using appropriate starting materials according to the procedure of Example 593.

Example 591

2,2,2-Trifluoro-ethanesulfonic acid (4{[(1,3-dioxo-2,3-dihydro-1H-isoquinolin-4-ylidenemethyl)-amino]-methyl}-phenyl)-amide This compound is prepared using appropriate starting materials according to the procedure of Example 593.

Example 592

Propane-1-sulfonic acid (4{[(1,3-dioxo-2,3-dihydro-1H-isoquinolin-4-ylidenemethyl)-amino]-methyl}-phenyl)-amide This compound is prepared using appropriate starting materials according to the procedure of Example 593.

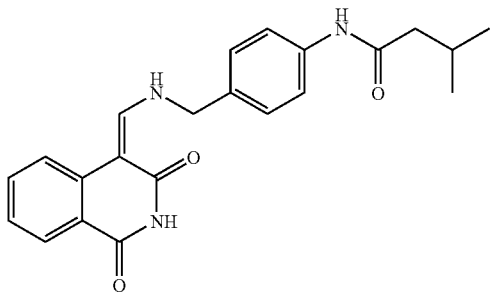

Example 593

N-(4{[(1,3-Dioxo-2,3-dihydro-1H-isoquinolin-4-ylidenemethyl)-amino]-methyl}-phenyl)-3-methyl-butyramide Step 1:
To a suspension of 4-Methoxymethylene-4H-isoquinoline-1,3-dione (406 mg, 2.0 mmol) in N,N-dimethylformamide (250 µL) is added 4-aminobenzylamine (244 mg, 2.0 mmol). The reaction mixture is shaken at ambient temperature for 1.5 hours, then concentrated. Ethyl acetate is added to the solid residue that remained and the solid is recovered by filtration, rinsing with diethyl ether, and drying to yield 555.5 mg of 4-[(4-Amino-benzylamino)-methylene]-4H-isoquinoline-1,3-dione.

Step 2:
To a suspension of 4-[(4-Amino-benzylamino)-methylene]-4H-isoquinoline-1,3-dione (29.3 mg, 0.1 mmol) in pyridine (250 µL) is added isovaleryl chloride (26 µL, 0.2 mmol). The reaction mixture is shaken at room temperature for 1 hour. The reaction mixture is diluted to 2 mL with N,N-dimethylformamide and purified by C18 reverse phase HPLC. The pure fractions were combined and concentrated to yield the title compound (37.2 mg).

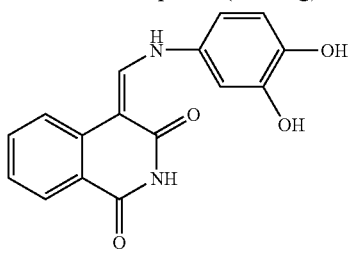

Example 594

4-[(3,4-Dihydroxy-phenylamino)-methylene]-4H-isoquinoline-1,3-dione

Step 1:
To a solution of 4-nitrocatechol (310 mg, 2.0 mmol) in methanol (20 mL) is added hydrazine (200 µL) and a catalytic amount of Raney-Nickel (50 mg). The reaction mixture is left to stir at ambient temperature for 16 hours. The solution is then filtered over celite to remove Raney-Nickel and the filtrate evaporated to dryness. The 3,4-dihydroxyaniline thus produced is used as such for the next reaction.

Step 2:
To a suspension of 4-Methoxymethylene-4H-isoquinoline-1,3-dione (40.6 mg, 0.2 mmol) in N,N-dimethylformamide (0.5 mL) is added 3,4-dihydroxyaniline (25 mg, 0.2 mmol). The reaction mixture is shaken at 115° C. for 1.5 hours. The reaction mixture is diluted to 2 mL with N,N-dimethylformamide and purified by C18 reverse phase HPLC. The pure fractions were combined and concentrated to yield the title compound (15.6 mg).

Example 595

4-{[4-(4-Ethyl-piperazin-1-yl)-phenylamino]-methylene}-4H-isoquinoline-1,3-dione This compound is prepared using appropriate starting materials according to the procedure of Example 596.

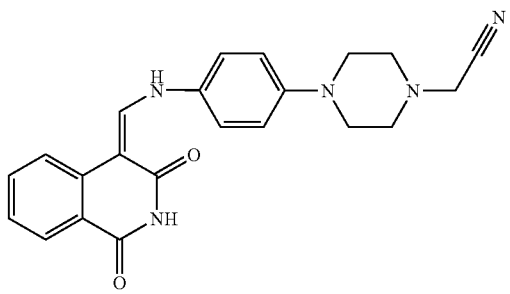

Example 596

(4-{4-[(1,3-Dioxo-2,3-dihydro-1H-isoquinolin-4-ylidenemethyl)-amino]-phenyl}-piperazin-1-yl)-acetonitrile Step 1:
To a suspension of 4-Methoxymethylene-4H-isoquinoline-1,3-dione (203 mg, 1.0 mmol) in N,N-dimethylformamide (2.5 mL) is added 1,4-phenylenediamine (108 mg, 1.0 mmol). The reaction mixture is shaken at 115° C. for 1.5 hours. Upon cooling to ambient temperature, product precipitated out of solution. The product is recovered by filtration, rinsing with diethyl ether, and drying to yield 205.9 mg 4-[(4-Amino-phenylamino)-methylene]-4H-isoquinoline-1,3-dione.

Step 2:
A dry mixture of 4-[(4-Amino-phenylamino)-methylene]-4H-isoquinoline-1,3-dione (140 mg, 0.5 mmol) and bis(chloroethyl)amine hydrochloride (90 mg, 0.5 mmol) is placed in a microwave at 900 W for 10 minutes. The crude product, 4-[(4-piperazin-1-yl-phenylamino)-methylene]-4H-isoquinoline-1,3-dione hydrochloride (192 mg), thus obtained is used as such for the next reaction.

Step 3:
To a suspension of crude 4-[(4-piperazin-1-yl-phenylamino)-methylene]-4H-isoquinoline-1,3-dione hydrochloride (34.8 mg, 0.1 mmol) in N,N-dimethylformamide (250 µL) is added bromoacetonitrile (7 µL, 0.1 mmol) and triethylamine (42 µL). The reaction mixture is shaken at ambient temperature for 16 hours. The reaction mixture is diluted to 2 mL with N,N-dimethylformamide and purified by C18 reverse phase HPLC. The pure fractions were combined and concentrated to yield Example 596 (12.0 mg).

Example 597

4-{[4-(4-Allyl-piperazin-1-yl)-phenylamino]-methylene}-4H-isoquinoline-1,3-dione This compound is prepared using appropriate starting materials according to the procedure of Example 596.

Example 598

4-({4-[4-(2-Hydroxy-ethyl)-piperazin-1-yl]-phenylamino}-methylene)-4H-isoquinoline-1,3-dione This compound is prepared using appropriate starting materials according to the procedure of Example 596.

Example 599

4-({4-[4-(2-Diethylamino-ethyl)-piperazin-1-yl]-phenylamino}-methylene)-4H-isoquinoline-1,3-dione This compound is prepared using appropriate starting materials according to the procedure of Example 596.

Example 600

4-{[4-(4-Isopropyl-piperazin-1-yl)-phenylamino]-methylene}-4H-isoquinoline-1,3-dione This compound is prepared using appropriate starting materials according to the procedure of Example 596.

Example 601

4-{[4-(4-Cyclopentyl-piperazin-1-yl)-phenylamino]-methylene}-4H-isoquinoline-1,3-dione This compound is prepared using appropriate starting materials according to the procedure of Example 596.

Example 602

4-{[4-(4-Cyclobutylmethyl-piperazin-1-yl)-phenylamino]-methylene}-4H-isoquinoline-1,3-dione This compound is prepared using appropriate starting materials according to the procedure of Example 596.

Example 603

4-{[3-(2,2,2-Trifluoro-ethylamino)-benzylamino]-methylene}-4H-isoquinoline-1,3-dione This compound is prepared using appropriate starting materials according to the procedure of Example 604.

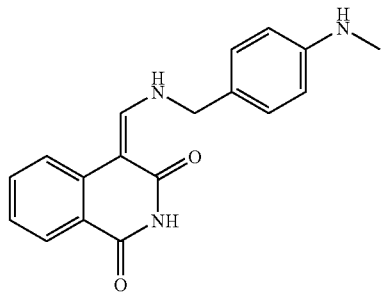

Example 604

4-[(4-Methylamino-benzylamino)-methylene]-4H-isoquinoline-1,3-dione

Step 1:

To a suspension of 4-Methoxymethylene-4H-isoquinoline-1,3-dione (406 mg, 2.0 mmol) in N,N-dimethylformamide (250 µL) is added 4-aminobenzylamine (244 mg, 2.0 mmol). The reaction mixture is shaken at 115° C. for 1.5 hours, then concentrated. Ethyl acetate is added to the solid residue that remained and the solid is recovered by filtration, rinsing with diethyl ether, and drying to yield 555.5 mg of 4-[(4-Amino-benzylamino)-methylene]-4H-isoquinoline-1,3-dione.

Step 2:

To a suspension of 4-[(4-Amino-benzylamino)-methylene]-4H-isoquinoline-1,3-dione (29.3 mg, 0.1 mmol) in N,N-dimethylformamide (400 µL) is added triethylamine (100 µL) and iodomethane (6.2 µL, 0.2 mmol). The reaction mixture is shaken at 80° C. for 18 hours. The reaction mixture is diluted to 2 mL with N,N-dimethylformamide and purified by C18 reverse phase HPLC. The pure fractions were combined and concentrated to yield Example 604 (5 mg).

Example 605

2,2,2-Trifluoro-ethanesulfonic acid 4-[(1,3-dioxo-2,3-dihydro-1H-isoquinolin-4-ylidenemethyl)-amino]-benzylamide This compound is prepared using appropriate starting materials according to the procedure of Example 613.

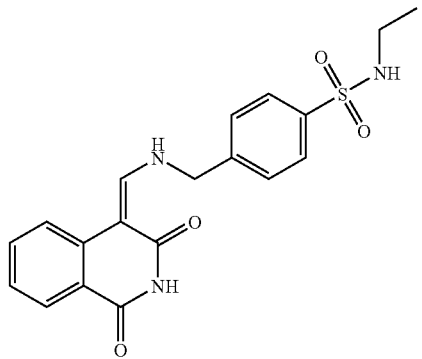

Example 606

4-{[(1,3-Dioxo-2,3-dihydro-1H-isoquinolin-4-ylidenemethyl)-amino]-methyl}-N-ethyl-benzenesulfonamide Step 1:
To a suspension of 4-Methoxymethylene-4H-isoquinoline-1,3-dione (507 mg, 2.5 mmol) in N,N-dimethylformate (250 μL) is added 4-aminoethylbenzene sulfonylamide hydrochloride (556 mg, 2.5 mmol) and triethylamine (525 μL). The reaction mixture is shaken at 115° C. for 1.5 hours, then concentrated. Ethyl acetate is added to the solid residue that remained and the solid is recovered by filtration, rinsing with diethyl ether, and drying to yield 660.8 mg of 4-{[(1,3-Dioxo-2,3-dihydro-1H-isoquinolin-4-ylidenemethyl)-amino]-methyl}benzenesulfonamide.

Step 2:
To a suspension of 4-{[(1,3-Dioxo-2,3-dihydro-1H-isoquinolin-4-ylidenemethyl)-amino]-methyl}-benzenesulfonamide (35.7 mg, 0.1 mmol) in Trifluoroacetic acid (250 μL) is added acetaldehyde (16.3 μL, 0.3 mmol) and sodium borohydride (11.4 mg, 0.3 mmol). The reaction mixture is shaken at ambient temperature for 18 hours. The reaction mixture is diluted to 2 mL with N,N-dimethylformamide and purified by C18 reverse phase HPLC.

Example 607

4-{[(1,3-Dioxo-2,3-dihydro-1H-isoquinolin-4-ylidenemethyl)-amino]-methyl}-N-pyridin-3-ylmethyl-benzenesulfonamide This compound is prepared using appropriate starting materials according to the procedure of Example 606.

Example 608

6-Diethylamino-4-[(3,4-dihydroxy-benzylamino)-methylene]-4H-isoquinoline-1,3-dione This compound is prepared using appropriate starting materials according to the procedure of Example 609.

Example 609

4-[(3,4-Dihydroxy-benzylamino)-methylene]-6-pyrrolidin-1-yl-4H-isoquinoline-1,3-dione Step 1:
To a solution of 6-Amino-4H-isoquinoline-1,3-dione (17.6 mg, 0.1 mmol) in trifluoroacetic acid (250 μL) is added 2,5-dimethoxytetrahydrofuran (15 μL, 0.11 mmol). The reaction mixture is shaken for 5 minutes at ambient temperature, followed by addition of sodium borohydride (9 mg, 0.22 mmol).

After shaking at ambient temperature for 15 minutes, gas evolution had ceased and the reaction mixture is quenched with saturated bicarbonate solution. Upon quenching, a precipitate formed. The precipitate is filtered off, rinsed with water, and dried to yield 19.5 mg of 6-Pyrrolidin-1-yl-4H-isoquinoline-1,3-dione.

Step 2:
To a suspension of 6-Pyrrolidin-1-yl-4H-isoquinoline-1,3-dione (19.5 mg, 0.09 mmol) in 250 μL of a 4:1 mixture of acetic anhydride and N,N-dimethylformamide, respectively, is added trimethylorthoformate (22 μL, 0.2 mmol). The reaction mixture is shaken in a heating block at 125° C. for 1 hour. The reaction mixture is then dried under a stream of nitrogen and the crude product, 4-Methoxymethylene-6-pyrrolidin-1-yl-4H-isoquinoline-1,3-dione, is used as such for the next reaction.

Step 3:
To a solution of crude 4-Methoxymethylene-6-pyrrolidin-1-yl-4H-isoquinoline-1,3-dione in N,N-dimethylformamide (250 μL) is added 3,4-dihydroxybenzylamine hydrobromide (22 mg, 0.1 mmol), followed by 21 μL of triethylamine. The reaction mixture is shaken at 115° C. for 1.5 hours. The reaction mixture is diluted to 2 mL with N,N-dimethylformamide and purified by C18 reverse phase HPLC. The pure fractions were combined and concentrated to yield Example 609 (8.8 mg).

Example 610

6-(1,3-Dihydro-isoindol-2-yl)-4-[(3,4-dihydroxy-benzylamino)-methylene]-4H-isoquinoline-1,3-dione This compound is prepared using appropriate starting materials according to the procedure of Example 609.

Example 611

6-[Bis-(3,3,3-trifluoro-propyl)-amino]-4-[(3,4-dihydroxy-benzylamino)-methylene]-4H-isoquinoline-1,3-dione This compound is prepared using appropriate starting materials according to the procedure of Example 609.

Example 612

N-{4-[(1,3-Dioxo-2,3-dihydro-1H-isoquinolin-4-ylidenemethyl)-amino]-benzyl}-methanesulfonamide This compound is prepared using appropriate starting materials according to the procedure of Example 613.

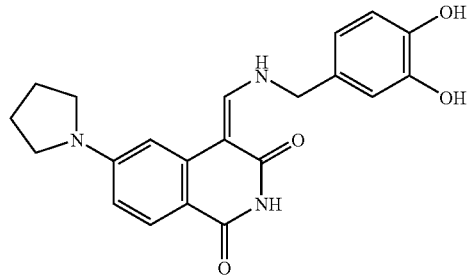

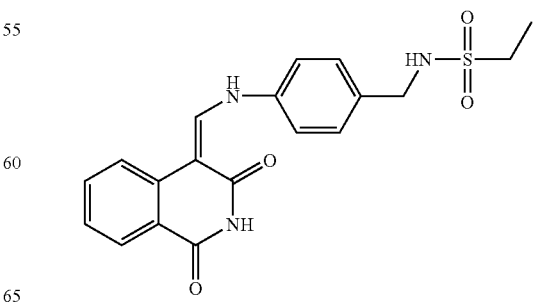

Example 613

Ethanesulfonic acid 4-[(1,3-dioxo-2,3-dihydro-1H-isoquinolin-4-ylidenemethyl)-amino]-benzylamide Step 1:

To a solution of 4-nitro-benzylamine (47.2 mg, 0.25 mmol) in THF (250 µL) is added triethylamine (89 µL) and ethyl sulfonyl chloride (24 µL, 0.25 mmol). The reaction mixture is shaken at ambient temperature for 16 hours. The reaction mixture is then concentrated, methanol is added followed by Novabiochem AM resin to remove unreacted amine. This is then shaken for two hours, filtered, concentrated to yield ethanesulfonic acid 4-nitro-benzylamide, which is used as such for the subsequent reaction.

Step 2:

To the residue of the product from step 1 (0.25 mmol) is added methanol (350 µL), hydrazine (33 µL), and Raney-Nickel (10 mg). The reaction mixture is shaken at room temperature for 16 hours, then filtered and the solution concentrated to yield ethanesulfonic acid 4-amino-benzylamide, which is used as such for the subsequent reaction.

Step 3:

To a suspension of 4-Methoxymethylene-4H-isoquinoline-1,3-dione (20.3 mg, 0.1 mmol) in N,N-dimethylformamide (250 µL) is added ethanesulfonic acid 4-amino-benzylamide (21.4 mg, 0.1 mmol). The reaction mixture is shaken at 115° C. for 1.5 hours. Upon cooling to ambient temperature, product precipitated out of solution. The product is recovered by filtration, rinsing with diethyl ether, and drying to yield Example 613 (15.0 mg).

Example 614

4-[(4-Dipropylaminomethyl-phenylamino)-methylene]-4H-isoquinoline-1,3-dione

This compound is prepared using appropriate starting materials according to the procedure of Example 616.

Example 615

4-{[4-(3-Hydroxy-piperidin-1-ylmethyl)-phenylamino]-methylene}-4H-isoquinoline-1,3-dione This compound is prepared using appropriate starting materials according to the procedure of Example 616.

Example 616

4-[(4-{[(2-Methoxy-ethyl)-methyl-amino]-methyl}-phenylamino)-methylene]-4H-isoquinoline-1,3-dione Step 1:

To a solution of 1-bromomethyl-4-nitro-benzene (86.4 mg, 0.4 mmol) in tetrahydrofuran (800 µL) is added triethylamine (200 µL) and 2-(methoxyethyl)methylamine (43 µL, 0.4 mmol). The reaction mixture is shaken at 50° C. for 5 hours. To the reaction mixture is then added 500 µL each of tetrahydrofuran and methanol followed by 350 mg of PS-Ph₃P resin to remove unreacted alkyl bromide and shaken for 1 h. The resin is filtered off, rinsed with dichloromethane and the filtrate concentrated. To the residue is added 500 µL each of tetrahydrofuran and methanol followed by 350 mg of PS-TsOH resin to remove unreacted amine. This is then shaken for two hours, filtered, washed with dichloromethane, and concentrated to yield (2-methoxy-ethyl)-methyl-(4-nitro-benzyl)-amine, which is used as such for the subsequent reaction.

Step 2:

To a solution of (2-methoxy-ethyl)-methyl-(4-nitro-benzyl)-amine, from step 1, (56 mg, 0.25 mmol) is added methanol (1 mL), hydrazine (33 µL), and Raney-Nickel (10 mg). The reaction mixture is shaken at room temperature for 16 hours, then filtered and the solution concentrated to yield 4-{[(2-Methoxy-ethyl)-methyl-amino]-methyl}-phenylamine, which is used as such for the subsequent reaction.

Step 3:

To a suspension of 4-Methoxymethylene-4H-isoquinoline-1,3-dione (20.3 mg, 0.1 mmol) in N,N-dimethylformamide (250 µL) is added 4-{[(2-methoxy-ethyl)-methyl-amino]-methyl}-phenylamine (19.4 mg, 0.1 mmol). The reaction mixture is shaken at 115° C. for 1.5 hours. Upon cooling to ambient temperature, product precipitated out of solution. The product is recovered by filtration, rinsing with diethyl ether, and drying to yield Example 616 (11.0 mg).

Example 617

4-{[4-(2-Methyl-pyrrolidin-1-ylmethyl)-phenylamino]-methylene}-4H-isoquinoline-1,3-dione This compound is prepared using appropriate starting materials according to the procedure of Example 616.

Example 618

4-(Pyridin-4-ylaminomethylene)-4H-isoquinoline-1,3-dione

This compound is prepared using appropriate starting materials according to the procedure of Example 619.

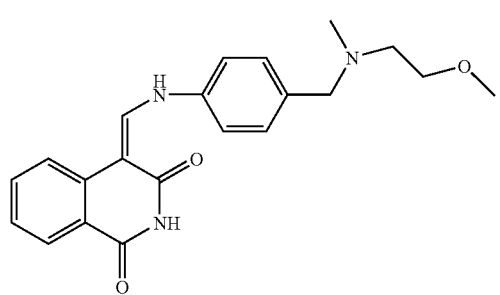

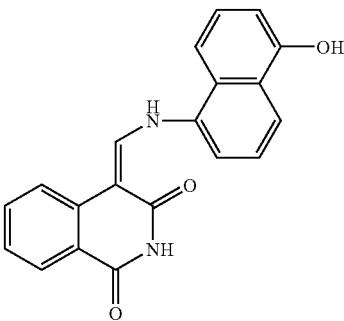

Example 619

4-[(5-Hydroxy-naphthalen-1-ylamino)-methylene]-4H-isoquinoline-1,3-dione

To a suspension of 4-Methoxymethylene-4H-isoquinoline-1,3-dione (20.3 mg, 0.1 mmol) in N,N-dimethylformamide (250 µL) is added 5-amino-1-naphthol (13.5 mg, 0.1 mmol). The reaction mixture is shaken at 115° C. for 1.5 hours. Upon cooling to ambient temperature, product precipitated out of solution. The product is recovered by filtration, rinsing with diethyl ether, and drying to yield Example 619 (7.0 mg).

Example 620

4-[(3,4-Dihydroxy-benzylamino)-methylene]-6-phenyl-4H-isoquinoline-1,3-dione

This compound is prepared using appropriate starting materials according to the procedure of Example 169.

Example 621

4-[(3,4-Dihydroxy-benzylamino)-methylene]-6-furan-2-yl-4H-isoquinoline-1,3-dione This compound is prepared using appropriate starting materials according to the procedure of Example 169.

Example 622

6-(3-Phenyl-propenyl)-4-[(4-pyrrolidin-1-ylmethyl-phenylamino)-methylene]-4H-isoquinoline-1,3-dione This compound is prepared using appropriate starting materials according to the procedure of Example 663.

Example 623

{4-[(6-Naphthalen-1-yl-1,3-dioxo-2,3-dihydro-1H-isoquinolin-4-ylidenemethyl)-amino]-phenyl)-acetonitrile This compound is prepared using appropriate starting materials according to the procedure of Example 169.

Example 624

{4-[(6-Naphthalen-2-yl-1,3-dioxo-2,3-dihydro-1H-isoquinolin-4-ylidenemethyl)-amino]-phenyl}-acetonitrile This compound is prepared using appropriate starting materials according to the procedure of Example 169.

Example 625

{4-[(1,3-Dioxo-6-quinolin-8-yl-2,3-dihydro-1H-isoquinolin-4-ylidenemethyl)-amino]-phenyl}-acetonitrile This compound is prepared using appropriate starting materials according to the procedure of Example 169.

Example 626

{4-[(6-Benzofuran-2-yl-1,3-dioxo-2,3-dihydro-1H-isoquinolin-4-ylidenemethyl)-amino]-phenyl}-acetonitrile This compound is prepared using appropriate starting materials according to the procedure of Example 169.

Example 627

{4-[(6-Benzo[b]thiophen-2-yl-1,3-dioxo-2,3-dihydro-1H-isoquinolin-4-ylidenemethyl)-amino]-phenyl}-acetonitrile This compound is prepared using appropriate starting materials according to the procedure of Example 169.

Example 628

{4-[(6-Benzo[b]thiophen-3-yl-1,3-dioxo-2,3-dihydro-1H-isoquinolin-4-ylidenemethyl)-amino]-phenyl}-acetonitrile This compound is prepared using appropriate starting materials according to the procedure of Example 169.

Example 629

(4-{[6-(1H-Indol-5-yl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 630

(4-{[1,3-Dioxo-6-(1H-pyrrol-2-yl)-2,3-dihydro-1H-isoquinolin-4-ylidenemethyl]-amino}-phenyl)-acetonitrile This compound is prepared using appropriate starting materials according to the procedure of Example 169.

Example 631

(4-{[1,3-Dioxo-6-(1H-pyrrol-3-yl)-2,3-dihydro-1H-isoquinolin-4-ylidenemethyl]-amino}-phenyl)-acetonitrile This compound is prepared using appropriate starting materials according to the procedure of Example 169.

Example 632

4-{[(6-Naphthalen-2-yl-1,3-dioxo-2,3-dihydro-1H-isoquinolin-4-ylidenemethyl)-amino]-methyl}-benzenesulfonamide This compound is prepared using appropriate starting materials according to the procedure of Example 169.

Example 633

4-{[(1,3-Dioxo-6-quinolin-8-yl-2,3-dihydro-1H-isoquinolin-4-ylidenemethyl)-amino]-methyl}-benzenesulfonamide This compound is prepared using appropriate starting materials according to the procedure of Example 169.

Example 634

4-{[(6-Benzofuran-2-yl-1,3-dioxo-2,3-dihydro-1H-isoquinolin-4-ylidenemethyl)-amino]-methyl}-benzenesulfonamide This compound is prepared using appropriate starting materials according to the procedure of Example 169.

Example 635

4-{[(6-Benzo[b]thiophen-2-yl-1,3-dioxo-2,3-dihydro-1H-isoquinolin-4-ylidenemethyl)-amino]-methyl}-benzenesulfonamide This compound is prepared using appropriate starting materials according to the procedure of Example 169.

Example 636

4-{[(6-Benzo[b]thiophen-3-yl-1,3-dioxo-2,3-dihydro-1H-isoquinolin-4-ylidenemethyl)-amino]-methyl}-benzenesulfonamide This compound is prepared using appropriate starting materials according to the procedure of Example 169.

Example 637

4-({[6-(1H-Indol-5-yl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 638

4-({[1,3-Dioxo-6-(1H-pyrrol-2-yl)-2,3-dihydro-1H-isoquinolin-4-ylidenemethyl]-amino}-methyl)-benzenesulfonamide This compound is prepared using appropriate starting materials according to the procedure of Example 169.

Example 639

4-({[1,3-Dioxo-6-(1H-pyrrol-3-yl)-2,3-dihydro-1H-isoquinolin-4-ylidenemethyl]-amino}-methyl)-benzenesulfonamide This compound is prepared using appropriate starting materials according to the procedure of Example 169.

Example 640

4-[(3,4-Dihydroxy-benzylamino)-methylene]-6-naphthalen-1-yl-4H-isoquinoline-1,3-dione This compound is prepared using appropriate starting materials according to the procedure of Example 169.

Example 641

4-[(3,4-Dihydroxy-benzylamino)-methylene]-6-naphthalen-2-yl-4H-isoquinoline-1,3-dione This compound is prepared using appropriate starting materials according to the procedure of Example 169.

Example 642

4-[(3,4-Dihydroxy-benzylamino)-methylene]-6-quinolin-8-yl-4H-isoquinoline-1,3-dione This compound is prepared using appropriate starting materials according to the procedure of Example 169.

Example 643

6-Benzofuran-2-yl-4-[(3,4-dihydroxy-benzylamino)-methylene]-4H-isoquinoline-1,3-dione This compound is prepared using appropriate starting materials according to the procedure of Example 169.

Example 644

6-Benzo[b]thiophen-2-yl-4-[(3,4-dihydroxy-benzylamino)-methylene]-4H-isoquinoline-1,3-dione This compound is prepared using appropriate starting materials according to the procedure of Example 169.

Example 645

6-Benzo[b]thiophen-3-yl-4-[(3,4-dihydroxy-benzylamino)-methylene]-4H-isoquinoline-1,3-dione This compound is prepared using appropriate starting materials according to the procedure of Example 169.

Example 646

4-[(3,4-Dihydroxy-benzylamino)-methylene]-6-(1H-indol-5-yl)-4H-isoquinoline-1,3-dione This compound is prepared using appropriate starting materials according to the procedure of Example 169.

Example 647

4-[(3,4-Dihydroxy-benzylamino)-methylene]-6-(1H-pyrrol-2-yl)-4H-isoquinoline-1,3-dione This compound is prepared using appropriate starting materials according to the procedure of Example 169.

Example 648

(4-{[1,3-Dioxo-6-(2-pyridin-2-yl-vinyl)-2,3-dihydro-1H-isoquinolin-4-ylidenemethyl]-amino}-phenyl)-acetonitrile This compound is prepared using appropriate starting materials according to the procedure of Example 663.

Example 649

(4-{[1,3-Dioxo-6-(2-pyridin-4-yl-vinyl)-2,3-dihydro-1H-isoquinolin-4-ylidenemethyl]-amino}-phenyl)-acetonitrile This compound is prepared using appropriate starting materials according to the procedure of Example 663.

Example 650

{4-[(1,3-Dioxo-6-styryl-2,3-dihydro-1H-isoquinolin-4-ylidenemethyl)-amino]-phenyl}-acetonitrile This compound is prepared using appropriate starting materials according to the procedure of Example 663.

Example 651

(4-{[6-(2-Imidazol-1-yl-vinyl)-1,3-dioxo-2,3-dihydro-1H-isoquinolin-4-ylidenemethyl]-amino}-phenyl)-acetonitrile This compound is prepared using appropriate starting materials according to the procedure of Example 663.

Example 652

4-({[1,3-Dioxo-6-(2-pyridin-2-yl-vinyl)-2,3-dihydro-1H-isoquinolin-4-ylidenemethyl]-amino}-methyl)-benzenesulfonamide

Example 653

4-({[1,3-Dioxo-6-(2-pyridin-4-yl-vinyl)-2,3-dihydro-1H-isoquinolin-4-ylidenemethyl]-amino}-methyl)-benzenesulfonamide This compound is prepared using appropriate starting materials according to the procedure of Example 663.

Example 654

4-{[(1,3-Dioxo-6-styryl-2,3-dihydro-1H-isoquinolin-4-ylidenemethyl)-amino]-methyl}-benzenesulfonamide This compound is prepared using appropriate starting materials according to the procedure of Example 663.

Example 655

4-({[1,3-Dioxo-6-(2-pyrazin-2-yl-vinyl)-2,3-dihydro-1H-isoquinolin-4-ylidenemethyl]-amino}-methyl)-benzenesulfonamide This compound is prepared using appropriate starting materials according to the procedure of Example 663.

Example 656

4-({[6-(2-Cyclohexyl-vinyl)-1,3-dioxo-2,3-dihydro-1H-isoquinolin-4-ylidenemethyl]-amino}-methyl)-benzenesulfonamide This compound is prepared using appropriate starting materials according to the procedure of Example 663.

Example 657

4-({[6-(3-Imidazol-1-yl-propenyl)-1,3-dioxo-2,3-dihydro-1H-isoquinolin-4-ylidenemethyl]-amino}-methyl)-benzenesulfonamide This compound is prepared using appropriate starting materials according to the procedure of Example 663.

Example 658

4-({[6-(2-Imidazol-1-yl-vinyl)-1,3-dioxo-2,3-dihydro-1H-isoquinolin-4-ylidenemethyl]-amino}-methyl)-benzenesulfonamide This compound is prepared using appropriate starting materials according to the procedure of Example 663.

Example 659

4-[({6-[2-(4-Methyl-thiazol-5-yl)-vinyl]-1,3-dioxo-2,3-dihydro-1H-isoquinolin-4-ylidenemethyl}-amino)-methyl]-benzenesulfonamide This compound is prepared using appropriate starting materials according to the procedure of Example 663.

Example 660

4-[(3,4-Dihydroxy-benzylamino)-methylene]-6-(3-phenyl-propenyl)-4H-isoquinoline-1,3-dione This compound is prepared using appropriate starting materials according to the procedure of Example 663.

Example 661

4-[(3,4-Dihydroxy-benzylamino)-methylene]-6-(2-naphthalen-2-yl-vinyl)-4H-isoquinoline-1,3-dione This compound is prepared using appropriate starting materials according to the procedure of Example 663.

Example 662

4-[(3,4-Dihydroxy-benzylamino)-methylene]-6-(2-pyridin-2-yl-vinyl)-4H-isoquinoline-1,3-dione This compound is prepared using appropriate starting materials according to the procedure of Example 663.

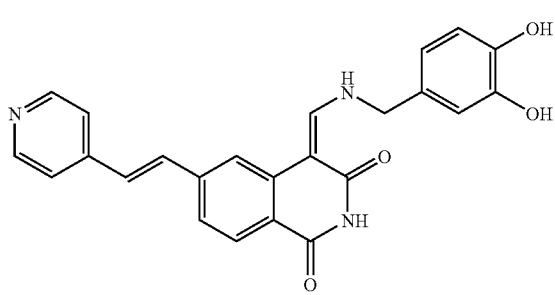

Example 663

4-[(3,4-Dihydroxy-benzylamino)-methylene]-6-(2-pyridin-4-yl-vinyl)-4H-isoquinoline-1,3-dione Step 1:

To a suspension of 6-Bromo-4H-isoquinoline-1,3-dione (4.8 g, 20 mmol) in 50 mL of a 4:1 mixture of acetic anhydride and N,N-dimethylformamide, respectively, is added trimethylorthoformate (4.4 mL, 40 mmol). The reaction mixture is shaken in a heating block at 125° C. for 1 hour. Upon cooling to room temperature, the product precipitated out. The precipitate is then filtered off, rinsed with copious amounts of ether, and dried to yield 4.8 g of 6-Bromo-4-methoxymethylene-4H-isoquinoline-1,3-dione.

Step 2:

To a suspension of crude 6-Bromo-4-methoxymethylene-4H-isoquinoline-1,3-dione (846 mg, 3 mmol) in N,N-dimethylformamide (7.5 mL) is added 3,4-dihydroxy benzylamine hydrobromide (660 mg, 3 mmol) and triethylamine (630 μL, 4.5 mmol). The reaction mixture is shaken at 115° C. for 1.5 hours. Upon cooling to room temperature, the product precipitated out. The precipitate is then filtered off, rinsed with copious amounts of ether, and dried to yield 1.38 g of 6-Bromo-4-[(3,4-dihydroxy-benzylamino)-methylene]-4H-isoquinoline-1,3-dione hydrobromide.

Step 3:

To a mixture of cesium carbonate (39 mg, 0.12 mmol), tetrabutyl ammonium bromide (32.2 mg, 0.1 mmol), tri-o-tolylphosphine (30.4 mg, 0.1 mmol) and palladium acetate (9 mg, 0.04 mmol) in N,N-dimethylformamide (1.2 mL) is added 6-Bromo-4-[(3,4-dihydroxy-benzylamino)-methylene]-4H-isoquinoline-1,3-dione hydrobromide (47 mg, 0.1 mmol) and 4-vinylpyridine (16.2 μL, 0.15 mmol). The reaction mixture is subjected to microwave heating at 200° C. for 120 seconds. The reaction mixture is then diluted to 2 mL with N,N-dimethylformamide and purified by C18 reverse phase HPLC. The pure fractions were combined and concentrated to yield Example 663 (9.4 mg).

Example 664

6-(2-Cyclohexyl-vinyl)-4-[(3,4-dihydroxy-benzylamino)-methylene]-4H-isoquinoline-1,3-dione This compound is prepared using appropriate starting materials according to the procedure of Example 663.

Example 665

4-[(3,4-Dihydroxy-benzylamino)-methylene]-6-(3-imidazol-1-yl-propenyl)-4H-isoquinoline-1,3-dione This compound is prepared using appropriate starting materials according to the procedure of Example 663.

Example 666

4-[(3,4-Dihydroxy-benzylamino)-methylene]-6-(3-piperazin-1-yl-propenyl)-4H-isoquinoline-1,3-dione This compound is prepared using appropriate starting materials according to the procedure of Example 663.

Example 667

4-[(3,4-Dihydroxy-benzylamino)-methylene]-6-(2-imidazol-1-yl-vinyl)-4H-isoquinoline-1,3-dione This compound is prepared using appropriate starting materials according to the procedure of Example 663.

Example 668

4-{[4-(4-Methyl-piperazin-1-yl)-phenylamino]-methylene}-6-naphthalen-2-yl-4H-isoquinoline-1,3-dione This compound is prepared using appropriate starting materials according to the procedure of Example 169.

Example 669

6-Benzofuran-2-yl-4-{[4-(4-methyl-piperazin-1-yl)-phenylamino]-methylene}-4H-isoquinoline-1,3-dione This compound is prepared using appropriate starting materials according to the procedure of Example 169.

Example 670

6-Benzo[b]thiophen-2-yl-4-{[4-(4-methyl-piperazin-1-yl)-phenylamino]-methylene}-4H-isoquinoline-1,3-dione This compound is prepared using appropriate starting materials according to the procedure of Example 169.

Example 671

6-(1H-Indol-5-yl)-4-{[4-(4-methyl-piperazin-1-yl)-phenylamino]-methylene}-4H-isoquinoline-1,3-dione This compound is prepared using appropriate starting materials according to the procedure of Example 169.

Example 672

4-{[4-(4-Methyl-piperazin-1-yl)-phenylamino]-methylene}-6-(1H-pyrrol-2-yl)-4H-isoquinoline-1,3-dione This compound is prepared using appropriate starting materials according to the procedure of Example 169.

Example 673

4-{[4-(4-Methyl-piperazin-1-yl)-phenylamino]-methylene}-6-(1H-pyrrol-3-yl)-4H-isoquinoline-1,3-dione This compound is prepared using appropriate starting materials according to the procedure of Example 169.

Example 674

4-{[4-(4-Methyl-piperazin-1-yl)-phenylamino]-methylene}-6-(2-naphthalen-2-yl-vinyl)-4H-isoquinoline-1,3-dione This compound is prepared using appropriate starting materials according to the procedure of Example 663.

Example 675

4-{[4-(4-Methyl-piperazin-1-yl)-phenylamino]-methylene}-6-(2-pyridin-2-yl-vinyl)-4H-isoquinoline-1,3-dione This compound is prepared using appropriate starting materials according to the procedure of Example 663.

Example 676

4-{[4-(4-Methyl-piperazin-1-yl)-phenylamino]-methylene}-6-(2-pyridin-4-yl-vinyl)-4H-isoquinoline-1,3-dione This compound is prepared using appropriate starting materials according to the procedure of Example 663.

Example 677

4-{[4-(4-Methyl-piperazin-1-yl)-phenylamino]-methylene}-6-styryl-4H-isoquinoline-1,3-dione This compound is prepared using appropriate starting materials according to the procedure of Example 663.

Example 678

4-{[4-(4-Methyl-piperazin-1-yl)-phenylamino]-methylene}-6-(2-pyrazin-2-yl-vinyl)-4H-isoquinoline-1,3-dione This compound is prepared using appropriate starting materials according to the procedure of Example 663.

Example 679

6-(3-Imidazol-1-yl-propenyl)-4-{[4-(4-methyl-piperazin-1-yl)-phenylamino]-methylene}-4H-isoquinoline-1,3-dione This compound is prepared using appropriate starting materials according to the procedure of Example 663.

Example 680

6-(2-Imidazol-1-yl-vinyl)-4-{[4-(4-methyl-piperazin-1-yl)-phenylamino]-methylene}-4H-isoquinoline-1,3-dione This compound is prepared using appropriate starting materials according to the procedure of Example 663.

Example 681

4-{[4-(4-Methyl-piperazin-1-yl)-phenylamino]-methylene}-6-[2-(4-methyl-thiazol-5-yl)-vinyl]-4H-isoquinoline-1,3-dione This compound is prepared using appropriate starting materials according to the procedure of Example 663.

Example 682

6-(4-Methoxy-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 683

6-(2-Methoxy-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 684

6-(2-Fluoro-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 685

4-(4-{[4-(4-Methyl-piperazin-1-yl)-phenylamino]-methylene}-1,3-dioxo-1,2,3,4-tetrahydro-isoquinolin-6-yl)-benzoic acid This compound is prepared using appropriate starting materials according to the procedure of Example 169.

Example 686

3-(4-{[4-(4-Methyl-piperazin-1-yl)-phenylamino]-methylene}-1,3-dioxo-1,2,3,4-tetrahydro-isoquinolin-6-yl)-benzoic acid This compound is prepared using appropriate starting materials according to the procedure of Example 169.

Example 687

4-{[4-(4-Methyl-piperazin-1-yl)-phenylamino]-methylene}-6-(4-trifluoromethyl-phenyl)-4H-isoquinoline-1,3-dione This compound is prepared using appropriate starting materials according to the procedure of Example 169.

Example 688

6-(4-Acetyl-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 689

6-(4-Chloro-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 690

6-(3-Chloro-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 691

6-(2-Chloro-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 692

4-{[4-(4-Methyl-piperazin-1-yl)-phenylamino]-methylene}-6-p-tolyl-4H-isoquinoline-1,3-dione This compound is prepared using appropriate starting materials according to the procedure of Example 169.

Example 693

4-{[4-(4-Methyl-piperazin-1-yl)-phenylamino]-methylene}-6-m-tolyl-4H-isoquinoline-1,3-dione This compound is prepared using appropriate starting materials according to the procedure of Example 169.

Example 694

4-{[4-(4-Methyl-piperazin-1-yl)-phenylamino]-methylene}-6-o-tolyl-4H-isoquinoline-1,3-dione This compound is prepared using appropriate starting materials according to the procedure of Example 169.

Example 695

3-(4-{[4-(4-Methyl-piperazin-1-yl)-phenylamino]-methylene}-1,3-dioxo-1,2,3,4-tetrahydro-isoquinolin-6-yl)-benzonitrile This compound is prepared using appropriate starting materials according to the procedure of Example 169.

Example 696

6-Biphenyl-4-yl-4-{[4-(4-methyl-piperazin-1-yl)-phenylamino]-methylene}-4H-isoquinoline-1,3-dione This compound is prepared using appropriate starting materials according to the procedure of Example 169.

Example 697

6-Biphenyl-3-yl-4-{[4-(4-methyl-piperazin-1-yl)-phenylamino]-methylene}-4H-isoquinoline-1,3-dione This compound is prepared using appropriate starting materials according to the procedure of Example 169.

Example 698

3-[4-(4-{[4-(4-Methyl-piperazin-1-yl)-phenylamino]-methylene}-1,3-dioxo-1,2,3,4-tetrahydro-isoquinolin-6-yl)-phenyl]-acrylic acid This compound is prepared using appropriate starting materials according to the procedure of Example 169.

Example 699

3-[3-(4-{[4-(4-Methyl-piperazin-1-yl)-phenylamino]-methylene}-1,3-dioxo-1,2,3,4-tetrahydro-isoquinolin-6-yl)-phenyl]-acrylic acid This compound is prepared using appropriate starting materials according to the procedure of Example 169.

Example 700

4-{[4-(4-Methyl-piperazin-1-yl)-phenylamino]-methylene}-6-(4-methylsulfanyl-phenyl)-4H-isoquinoline-1,3-dione This compound is prepared using appropriate starting materials according to the procedure of Example 169.

Example 701

(4-{[6-(4-Methoxy-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 702

(4-{[6-(3-Methoxy-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 703

(4-{[6-(2-Methoxy-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 704

(4-{[6-(4-Fluoro-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 705

(4-{[6-(3-Fluoro-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 706

(4-{[6-(2-Fluoro-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 707

4-{4-[(4-Cyanomethyl-phenylamino)-methylene]-1,3-dioxo-1,2,3,4-tetrahydro-isoquinolin-6-yl}-benzoic acid This compound is prepared using appropriate starting materials according to the procedure of Example 169.

Example 708

3-{4-[(4-Cyanomethyl-phenylamino)-methylene]-1,3-dioxo-1,2,3,4-tetrahydro-isoquinolin-6-yl}-benzoic acid This compound is prepared using appropriate starting materials according to the procedure of Example 169.

Example 709

(4-{[1,3-Dioxo-6-(4-trifluoromethyl-phenyl)-2,3-dihydro-1H-isoquinolin-4-ylidenemethyl]-amino}-phenyl)-acetonitrile This compound is prepared using appropriate starting materials according to the procedure of Example 169.

Example 710

(4-{[6-(4-Acetyl-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 711

(4-{[6-(2-Acetyl-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 712

(4-{[6-(4-Chloro-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 713

(4-{[6-(3-Chloro-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 714

(4-{[6-(2-Chloro-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 715

{4-[(1,3-Dioxo-6-p-tolyl-2,3-dihydro-1H-isoquinolin-4-ylidenemethyl)-amino]-phenyl}-acetonitrile This compound is prepared using appropriate starting materials according to the procedure of Example 169.

Example 716

{4-[(1,3-Dioxo-6-m-tolyl-2,3-dihydro-1H-isoquinolin-4-ylidenemethyl)-amino]-phenyl}-acetonitrile This compound is prepared using appropriate starting materials according to the procedure of Example 169.

Example 717

{4-[(1,3-Dioxo-6-o-tolyl-2,3-dihydro-1H-isoquinolin-4-ylidenemethyl)-amino]-phenyl}-acetonitrile This compound is prepared using appropriate starting materials according to the procedure of Example 169.

Example 718

4-{4-[(4-Cyanomethyl-phenylamino)-methylene]-1,3-dioxo-1,2,3,4-tetrahydro-isoquinolin-6-yl}-benzonitrile This compound is prepared using appropriate starting materials according to the procedure of Example 169.

Example 719

3-{4-[(4-Cyanomethyl-phenylamino)-methylene]-1,3-dioxo-1,2,3,4-tetrahydro-isoquinolin-6-yl}-benzonitrile This compound is prepared using appropriate starting materials according to the procedure of Example 169.

Example 720

{4-[(6-Biphenyl-4-yl-1,3-dioxo-2,3-dihydro-1H-isoquinolin-4-ylidenemethyl)-amino]-phenyl}-acetonitrile This compound is prepared using appropriate starting materials according to the procedure of Example 169.

Example 721

{4-[(6-Biphenyl-3-yl-1,3-dioxo-2,3-dihydro-1H-isoquinolin-4-ylidenemethyl)-amino]-phenyl}-acetonitrile This compound is prepared using appropriate starting materials according to the procedure of Example 169.

Example 722

(4-{[6-(4-Isopropyl-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 723

(4-{[6-(4-Methylsulfanyl-phenyl)-1,3-dioxo-2,3-dihydro-1H-isoquinolin-4-ylidenemethyl]-amino}-phenyl)-acetonitrile This compound is prepared using appropriate starting materials according to the procedure of Example 169.

Example 724

6-(3-Hydroxy-propenyl)-4-{[4-(4-methyl-piperazin-1-yl)-phenylamino]-methylene}-4H-isoquinoline-1,3-dione This compound is prepared using appropriate starting materials according to the procedure of Example 663.

Example 725

6-[2-(4-Amino-phenyl)-vinyl]-4-{[4-(4-methyl-piperazin-1-yl)-phenylamino]-methylene}-4H-isoquinoline-1,3-dione This compound is prepared using appropriate starting materials according to the procedure of Example 663.

Example 726

6-[2-(4-Chloro-phenyl)-vinyl]-4-{[4-(4-methyl-piperazin-1-yl)-phenylamino]-methylene}-4H-isoquinoline-1,3-dione This compound is prepared using appropriate starting materials according to the procedure of Example 663.

Example 727

4-[2-(4-{[4-(4-Methyl-piperazin-1-yl)-phenylamino]-methylene}-1,3-dioxo-1,2,3,4-tetrahydro-isoquinolin-6-yl)-vinyl]-benzoic acid This compound is prepared using appropriate starting materials according to the procedure of Example 663.

Example 728

4-[2-(4-{[4-(4-Methyl-piperazin-1-yl)-phenylamino]-methylene}-1,3-dioxo-1,2,3,4-tetrahydro-isoquinolin-6-yl)-vinyl]-benzenesulfonamide This compound is prepared using appropriate starting materials according to the procedure of Example 663.

Example 729

4-{[4-(4-Methyl-piperazin-1-yl)-phenylamino]-methylene}-6-[2-(4-trifluoromethyl-phenyl)-vinyl]-4H-isoquinoline-1,3-dione This compound is prepared using appropriate starting materials according to the procedure of Example 663.

Example 730

6-(3,4-Dihydroxy-but-1-enyl)-4-{[4-(4-methyl-piperazin-1-yl)-phenylamino]-methylene}-4H-isoquinoline-1,3-dione This compound is prepared using appropriate starting materials according to the procedure of Example 663.

Example 731

6-[2-(4-Fluoro-phenyl)-vinyl]-4-{[4-(4-methyl-piperazin-1-yl)-phenylamino]-methylene}-4H-isoquinoline-1,3-dione This compound is prepared using appropriate starting materials according to the procedure of Example 663.

Example 732

6-[2-(4-Methoxy-phenyl)-vinyl]-4-{[4-(4-methyl-piperazin-1-yl)-phenylamino]-methylene}-4H-isoquinoline-1,3-dione This compound is prepared using appropriate starting materials according to the procedure of Example 663.

Example 733

4-[(3-Hydroxy-4-methoxy-benzylamino)-methylene]-6-(2-imidazol-1-yl-vinyl)-4H-isoquinoline-1,3-dione This compound is prepared using appropriate starting materials according to the procedure of Example 663.

Example 734

4-[(3-Hydroxy-4-methoxy-benzylamino)-methylene]-6-(2-imidazol-1-yl-vinyl)-4H-isoquinoline-1,3-dione

Example 735

4-[(3-Hydroxy-4-methoxy-benzylamino)-methylene]-6-(2-pyridin-2-yl-vinyl)-4H-isoquinoline-1,3-dione This compound is prepared using appropriate starting materials according to the procedure of Example 663.

Example 736

4-[(3,4-Dihydroxy-benzylamino)-methylene]-6-[2-(4-dimethylaminomethyl-phenyl)-vinyl]-4H-isoquinoline-1,3-dione This compound is prepared using appropriate starting materials according to the procedure of Example 663.

Example 737

4-({[6-(3-Methoxy-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 738

4-({[6-(4-Fluoro-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 739

4-({[6-(3-Fluoro-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 740

4-({[6-(2-Fluoro-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 741

4-{1,3-Dioxo-4-[(4-sulfamoyl-benzylamino)-methylene]-1,2,3,4-tetrahydro-isoquinolin-6-yl}-benzoic acid This compound is prepared using appropriate starting materials according to the procedure of Example 169.

Example 742

3-{1,3-Dioxo-4-[(4-sulfamoyl-benzylamino)-methylene]-1,2,3,4-tetrahydro-isoquinolin-6-yl}-benzoic acid This compound is prepared using appropriate starting materials according to the procedure of Example 169.

Example 743

4-({[1,3-Dioxo-6-(4-trifluoromethyl-phenyl)-2,3-dihydro-1H-isoquinolin-4-ylidenemethyl]-amino}-methyl)-benzenesulfonamide This compound is prepared using appropriate starting materials according to the procedure of Example 169.

Example 744

4-({[1,3-Dioxo-6-(3-trifluoromethyl-phenyl)-2,3-dihydro-1H-isoquinolin-4-ylidenemethyl]-amino}-methyl)-benzenesulfonamide This compound is prepared using appropriate starting materials according to the procedure of Example 169.

Example 745

4-({[1,3-Dioxo-6-(2-trifluoromethyl-phenyl)-2,3-dihydro-1H-isoquinolin-4-ylidenemethyl]-amino}-methyl)-benzenesulfonamide This compound is prepared using appropriate starting materials according to the procedure of Example 169.

Example 746

4-({[6-(4-Acetyl-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 747

4-({[6-(3-Acetyl-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 748

4-({[6-(2-Acetyl-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 749

4-({[6-(4-Chloro-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 750

4-({[6-(3-Chloro-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 751

4-({[6-(2-Chloro-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 752

4-{[(1,3-Dioxo-6-p-tolyl-2,3-dihydro-1H-isoquinolin-4-ylidenemethyl)-amino]-methyl}-benzenesulfonamide This compound is prepared using appropriate starting materials according to the procedure of Example 169.

Example 753

4-{[(1,3-Dioxo-6-m-tolyl-2,3-dihydro-1H-isoquinolin-4-ylidenemethyl)-amino]-methyl}-benzenesulfonamide This compound is prepared using appropriate starting materials according to the procedure of Example 169.

Example 754

4-{[(1,3-Dioxo-6-o-tolyl-2,3-dihydro-1H-isoquinolin-4-ylidenemethyl)-amino]-methyl}-benzenesulfonamide This compound is prepared using appropriate starting materials according to the procedure of Example 169.

Example 755

4-({[6-(4-Cyano-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 756

4-({[6-(3-Cyano-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 757

4-{[(6-Biphenyl-4-yl-1,3-dioxo-2,3-dihydro-1H-isoquinolin-4-ylidenemethyl)-amino]-methyl}-benzenesulfonamide This compound is prepared using appropriate starting materials according to the procedure of Example 169.

Example 758

4-{[(6-Biphenyl-3-yl-1,3-dioxo-2,3-dihydro-1H-isoquinolin-4-ylidenemethyl)-amino]-methyl}-benzenesulfonamide This compound is prepared using appropriate starting materials according to the procedure of Example 169.

Example 759

3-(4-{1,3-Dioxo-4-[(4-sulfamoyl-benzylamino)-methylene]-1,2,3,4-tetrahydro-isoquinolin-6-yl}-phenyl)-acrylic acid This compound is prepared using appropriate starting materials according to the procedure of Example 169.

Example 760

3-(3-{1,3-Dioxo-4-[(4-sulfamoyl-benzylamino)-methylene]-1,2,3,4-tetrahydro-isoquinolin-6-yl}-phenyl)-acrylic acid This compound is prepared using appropriate starting materials according to the procedure of Example 169.

Example 761

4-({[6-(4-Isopropyl-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 762

4-({[6-(3-Isopropyl-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 763

4-({[6-(4-Methylsulfanyl-phenyl)-1,3-dioxo-2,3-dihydro-1H-isoquinolin-4-ylidenemethyl]-amino}-methyl)-benzenesulfonamide This compound is prepared using appropriate starting materials according to the procedure of Example 169.

Example 764

4-[(3,4-Dihydroxy-benzylamino)-methylene]-6-(4-methoxy-phenyl)-4H-isoquinoline-1,3-dione This compound is prepared using appropriate starting materials according to the procedure of Example 169.

Example 765

4-[(3,4-Dihydroxy-benzylamino)-methylene]-6-(3-methoxy-phenyl)-4H-isoquinoline-1,3-dione This compound is prepared using appropriate starting materials according to the procedure of Example 169.

Example 766

4-[(3,4-Dihydroxy-benzylamino)-methylene]-6-(2-methoxy-phenyl)-4H-isoquinoline-1,3-dione This compound is prepared using appropriate starting materials according to the procedure of Example 169.

Example 767

4-[(3,4-Dihydroxy-benzylamino)-methylene]-6-(4-fluoro-phenyl)-4H-isoquinoline-1,3-dione This compound is prepared using appropriate starting materials according to the procedure of Example 169.

Example 768

4-[(3,4-Dihydroxy-benzylamino)-methylene]-6-(3-fluoro-phenyl)-4H-isoquinoline-1,3-dione This compound is prepared using appropriate starting materials according to the procedure of Example 169.

Example 769

4-[(3,4-Dihydroxy-benzylamino)-methylene]-6-(2-fluoro-phenyl)-4H-isoquinoline-3,3-dione This compound is prepared using appropriate starting materials according to the procedure of Example 169.

Example 770

4-{4-[(3,4-Dihydroxy-benzylamino)-methylene]-1,3-dioxo-1,2,3,4-tetrahydro-isoquinolin-6-yl}-benzoic acid This compound is prepared using appropriate starting materials according to the procedure of Example 169.

Example 771

3-{4-[(3,4-Dihydroxy-benzylamino)-methylene]-1,3-dioxo-1,2,3,4-tetrahydro-isoquinolin-6-yl}-benzoic acid This compound is prepared using appropriate starting materials according to the procedure of Example 169.

Example 772

4-[(3,4-Dihydroxy-benzylamino)-methylene]-6-(4-trifluoromethyl-phenyl)-4H-isoquinoline-1,3-dione This compound is prepared using appropriate starting materials according to the procedure of Example 169.

Example 773

4-[(3,4-Dihydroxy-benzylamino)-methylene]-6-(3-trifluoromethyl-phenyl)-4H-isoquinoline-1,3-dione This compound is prepared using appropriate starting materials according to the procedure of Example 169.

Example 774

4-[(3,4-Dihydroxy-benzylamino)-methylene]-6-(2-trifluoromethyl-phenyl)-4H-isoquinoline-1,3-dione This compound is prepared using appropriate starting materials according to the procedure of Example 169.

Example 775

6-(4-Acetyl-phenyl)-4-[(3,4-dihydroxy-benzylamino)-methylene]-4H-isoquinoline-1,3-dione This compound is prepared using appropriate starting materials according to the procedure of Example 169.

Example 776

6-(3-Acetyl-phenyl)-4-[(3,4-dihydroxy-benzylamino)-methylene]-4H-isoquinoline-1,3-dione This compound is prepared using appropriate starting materials according to the procedure of Example 169.

Example 777

6-(2-Acetyl-phenyl)-4-[(3,4-dihydroxy-benzylamino)-methylene]-4H-isoquinoline-1,3-dione This compound is prepared using appropriate starting materials according to the procedure of Example 169.

Example 778

6-(4-Chloro-phenyl)-4-[(3,4-dihydroxy-benzylamino)-methylene]-4H-isoquinoline-1,3-dione This compound is prepared using appropriate starting materials according to the procedure of Example 169.

Example 779

6-(3-Chloro-phenyl)-4-[(3,4-dihydroxy-benzylamino)-methylene]-4H-isoquinoline-1,3-dione This compound is prepared using appropriate starting materials according to the procedure of Example 169.

Example 780

6-(2-Chloro-phenyl)-4-[(3,4-dihydroxy-benzylamino)-methylene]-4H-isoquinoline-1,3-dione This compound is prepared using appropriate starting materials according to the procedure of Example 169.

Example 781

4-[(3,4-Dihydroxy-benzylamino)-methylene]-6-p-tolyl-4H-isoquinoline-1,3-dione

This compound is prepared using appropriate starting materials according to the procedure of Example 169.

Example 782

4-[(3,4-Dihydroxy-benzylamino)-methylene]-6-m-tolyl-4H-isoquinoline-1,3-dione

This compound is prepared using appropriate starting materials according to the procedure of Example 169.

Example 783

4-[(3,4-Dihydroxy-benzylamino)-methylene]-6-o-tolyl-4H-isoquinoline-1,3-dione

This compound is prepared using appropriate starting materials according to the procedure of Example 169.

Example 784

4-{4-[(3,4-Dihydroxy-benzylamino)-methylene]-1,3-dioxo-1,2,3,4-tetrahydro-isoquinolin-6-yl}-benzonitrile This compound is prepared using appropriate starting materials according to the procedure of Example 169.

Example 785

3-{4-[(3,4-Dihydroxy-benzylamino)-methylene]-1,3-dioxo-1,2,3,4-tetrahydro-isoquinolin-6-yl}-benzonitrile This compound is prepared using appropriate starting materials according to the procedure of Example 169.

Example 786

6-Biphenyl-4-yl-4-[(3,4-dihydroxy-benzylamino)-methylene]-4H-isoquinoline-1,3-dione This compound is prepared using appropriate starting materials according to the procedure of Example 169.

Example 787

6-Biphenyl-3-yl-4-[(3,4-dihydroxy-benzylamino)-methylene]-4H-isoquinoline-1,3-dione This compound is prepared using appropriate starting materials according to the procedure of Example 169.

Example 788

3-(4-{4-[(3,4-Dihydroxy-benzylamino)-methylene]-1,3-dioxo-1,2,3,4-tetrahydro-isoquinolin-6-yl}-phenyl)-acrylic acid This compound is prepared using appropriate starting materials according to the procedure of Example 169.

Example 789

3-(3-{4-[(3,4-Dihydroxy-benzylamino)-methylene]-1,3-dioxo-1,2,3,4-tetrahydro-isoquinolin-6-yl}-phenyl)-acrylic acid This compound is prepared using appropriate starting materials according to the procedure of Example 169.

Example 790

4-[(3,4-Dihydroxy-benzylamino)-methylene]-6-(4-isopropyl-phenyl)-4H-isoquinoline-1,3-dione This compound is prepared using appropriate starting materials according to the procedure of Example 169.

Example 791

4-[(3,4-Dihydroxy-benzylamino)-methylene]-6-(3-isopropyl-phenyl)-4H-isoquinoline-1,3-dione This compound is prepared using appropriate starting materials according to the procedure of Example 169.

Example 792

4-[(3,4-Dihydroxy-benzylamino)-methylene]-6-(4-methylsulfanyl-phenyl)-4H-isoquinoline-1,3-dione This compound is prepared using appropriate starting materials according to the procedure of Example 169.

Example 793

4-[(3,4-Dihydroxy-benzylamino)-methylene]-6-(2-methylsulfanyl-phenyl)-4H-isoquinoline-1,3-dione This compound is prepared using appropriate starting materials according to the procedure of Example 169.

Example 794

6-[2-(2-Diethylamino-ethoxy)-vinyl]-4-{[4-(4-methyl-piperazin-1-yl)-phenylamino]-methylene}-4H-isoquinoline-1,3-dione This compound is prepared using appropriate starting materials according to the procedure of Example 663.

Example 795

5-(4-{[4-(4-Methyl-piperazin-1-yl)-phenylamino]-methylene}-1,3-dioxo-1,2,3,4-tetrahydro-isoquinolin-6-yl)-pent-4-enoic acid This compound is prepared using appropriate starting materials according to the procedure of Example 663.

Example 796

6-(4-Hydroxy-but-1-enyl)-4-{[4-(4-methyl-piperazin-1-yl)-phenylamino]-methylene}-4H-isoquinoline-1,3-dione This compound is prepared using appropriate starting materials according to the procedure of Example 663.

Example 797

6-(5-Hydroxy-pent-1-enyl)-4-{[4-(4-methyl-piperazin-1-yl)-phenylamino]-methylene}-4H-isoquinoline-1,3-dione This compound is prepared using appropriate starting materials according to the procedure of Example 663.

Example 798

6-(6-Hydroxy-hex-1-enyl)-4-{[4-(4-methyl-piperazin-1-yl)-phenylamino]-methylene}-4H-isoquinoline-1,3-dione This compound is prepared using appropriate starting materials according to the procedure of Example 663.

Example 799

6-[3-(2-Hydroxy-ethoxy)-propenyl]-4-{[4-(4-methyl-piperazin-1-yl)-phenylamino]-methylene}-4H-isoquinoline-1,3-dione This compound is prepared using appropriate starting materials according to the procedure of Example 663.

Example 800

6-[3-(2,4-Dioxo-imidazolidin-1-yl)-propenyl]-4-{[4-(4-methyl-piperazin-1-yl)-phenylamino]-methylene}-4H-isoquinoline-1,3-dione This compound is prepared using appropriate starting materials according to the procedure of Example 663.

Example 801

6-[3-(2-Hydroxy-phenyl)-propenyl]-4-{[4-(4-methyl-piperazin-1-yl)-phenylamino]-methylene}-4H-isoquinoline-1,3-dione This compound is prepared using appropriate starting materials according to the procedure of Example 663.

Example 802

2-Methyl-3-(4-{[4-(4-methyl-piperazin-1-yl)-phenylamino]-methylene}-1,3-dioxo-1,2,3,4-tetrahydro-isoquinolin-6-yl)-but-2-enenitrile This compound is prepared using appropriate starting materials according to the procedure of Example 663.

Example 803

{4-[2-(4-{[4-(4-Methyl-piperazin-1-yl)-phenylamino]-methylene}-1,3-dioxo-1,2,3,4-tetrahydro-isoquinolin-6-yl)-vinyl]-phenyl}-acetonitrile This compound is prepared using appropriate starting materials according to the procedure of Example 663.

Example 804

4-[(3,4-Dihydroxy-benzylamino)-methylene]-6-[3-(2-hydroxy-3-methoxy-phenyl)-propenyl]-4H-isoquinoline-1,3-dione This compound is prepared using appropriate starting materials according to the procedure of Example 663.

Example 805

[4-(2-{4-[(3,4-Dihydroxy-benzylamino)-methylene]-1,3-dioxo-1,2,3,4-tetrahydro-isoquinolin-6-yl}-vinyl)-phenyl]-acetonitrile This compound is prepared using appropriate starting materials according to the procedure of Example 663.

Example 806

6-Benzo[1,3]dioxol-5-yl-4-{[4-(4-methyl-piperazin-1-yl)-phenylamino]-methylene}-4H-isoquinoline-1,3-dione This compound is prepared using appropriate starting materials according to the procedure of Example 169.

Example 807

6-(4-Dimethylamino-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 808

6-(4-Hydroxymethyl-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 809

3-[4-(4-{[4-(4-Methyl-piperazin-1-yl)-phenylamino]-methylene}-1,3-dioxo-1,2,3,4-tetrahydroisoquinolin-6-yl)-phenyl]-propionic acid This compound is prepared using appropriate starting materials according to the procedure of Example 169.

Example 810

6-(3-Amino-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 811

6-(2,4-Dichloro-phenyl)-4-{[4-(4-methyl-piperazin-1-yl)-phenylamino]-methylene}-4H-isoquinoline-1,3-dione This compound is prepared using appropriate starting materials according to the procedure of Example 169.

Example 812

6-Benzo[1,3]dioxol-5-yl-4-[(3,4-dihydroxy-benzylamino)-methylene]-4H-isoquinoline-1,3-dione This compound is prepared using appropriate starting materials according to the procedure of Example 169.

Example 813

4-[(3,4-Dihydroxy-benzylamino)-methylene]-6-(3,4-dimethoxy-phenyl)-4H-isoquinoline-1,3-dione This compound is prepared using appropriate starting materials according to the procedure of Example 169.

Example 814

4-[(3,4-Dihydroxy-benzylamino)-methylene]-6-(2,4-dimethoxy-phenyl)-4H-isoquinoline-1,3-dione This compound is prepared using appropriate starting materials according to the procedure of Example 169.

Example 815

4-[(3,4-Dihydroxy-benzylamino)-methylene]-6-(3,4,5-trimethoxy-phenyl)-4H-isoquinoline-1,3-dione This compound is prepared using appropriate starting materials according to the procedure of Example 169.

Example 816

4-[(3,4-Dihydroxy-benzylamino)-methylene]-6-(4-dimethylamino-phenyl)-4H-isoquinoline-1,3-dione This compound is prepared using appropriate starting materials according to the procedure of Example 169.

Example 817

4-[(3,4-Dihydroxy-benzylamino)-methylene]-6-(4-hydroxymethyl-phenyl)-4H-isoquinoline-1,3-dione This compound is prepared using appropriate starting materials according to the procedure of Example 169.

Example 818

4-[(3,4-Dihydroxy-benzylamino)-methylene]-6-(4-trifluoromethoxy-phenyl)-4H-isoquinoline-1,3-dione This compound is prepared using appropriate starting materials according to the procedure of Example 169.

Example 819

3-(4-{4-[(3,4-Dihydroxy-benzylamino)-methylene]-1,3-dioxo-1,2,3,4-tetrahydro-isoquinolin-6-yl}-phenyl)-propionic acid This compound is prepared using appropriate starting materials according to the procedure of Example 169.

Example 820

4-[(3,4-Dihydroxy-benzylamino)-methylene]-6-(3-nitro-phenyl)-4H-isoquinoline-1,3-dione This compound is prepared using appropriate starting materials according to the procedure of Example 169.

Example 821

6-(3-Amino-phenyl)-4-[(3,4-dihydroxy-benzylamino)-methylene]-4H-isoquinoline-1,3-dione This compound is prepared using appropriate starting materials according to the procedure of Example 169.

Example 822

N-(3-{4-[(3,4-Dihydroxy-benzylamino)-methylene]-1,3-dioxo-1,2,3,4-tetrahydro-isoquinolin-6-yl}-phenyl)-acetamide This compound is prepared using appropriate starting materials according to the procedure of Example 169.

Example 823

6-(2,4-Dichloro-phenyl)-4-[(3,4-dihydroxy-benzylamino)-methylene]-4H-isoquinoline-1,3-dione This compound is prepared using appropriate starting materials according to the procedure of Example 169.

Example 824

4-[(3-Hydroxy-4-methoxy-benzylamino)-methylene]-6-(2-pyridin-4-yl-vinyl)-4H-isoquinoline-1,3-dione This compound is prepared using appropriate starting materials according to the procedure of Example 663.

Example 825

4-[(3-Hydroxy-4-methoxy-benzylamino)-methylene]-6-styryl-4H-isoquinoline-1,3-dione This compound is prepared using appropriate starting materials according to the procedure of Example 663.

Example 826

6-[3-(2,4-Dioxo-imidazolidin-1-yl)-propenyl]-4-[(3-hydroxy-4-methoxy-benzylamino)-methylene]-4H-isoquinoline-1,3-dione This compound is prepared using appropriate starting materials according to the procedure of Example 663.

Example 827

4-[(3-Hydroxy-4-methoxy-benzylamino)-methylene]-6-[3-(2-hydroxy-3-methoxy-phenyl)-propenyl]-4H-isoquinoline-1,3-dione This compound is prepared using appropriate starting materials according to the procedure of Example 663.

Example 828

6-Cyclopentylidenemethyl-4-{[4-(4-methyl-piperazin-1-yl)-phenylamino]-methylene}-4H-isoquinoline-1,3-dione This compound is prepared using appropriate starting materials according to the procedure of Example 663.

Example 829

4-{[4-(4-Methyl-piperazin-1-yl)-phenylamino]-methylene}-6-[2-(4-nitro-phenyl)-vinyl]-4H-isoquinoline-1,3-dione This compound is prepared using appropriate starting materials according to the procedure of Example 663.

Example 830

6-Furan-2-yl-4-{[4-(4-methyl-piperazin-1-yl)-phenylamino]-methylene}-4H-isoquinoline-1,3-dione This compound is prepared using appropriate starting materials according to the procedure of Example 169.

Example 831

4-{[4-(4-Methyl-piperazin-1-yl)-phenylamino]-methylene}-6-phenyl-4H-isoquinoline-1,3-dione This compound is prepared using appropriate starting materials according to the procedure of Example 169.

Example 832

4-[(3-Hydroxy-4-methoxy-benzylamino)-methylene]-6-phenyl-4H-isoquinoline-1,3-dione This compound is prepared using appropriate starting materials according to the procedure of Example 169.

Example 833

4-[(3-Hydroxy-4-methoxy-benzylamino)-methylene]-6-(4-methoxy-phenyl)-4H-isoquinoline-1,3-dione This compound is prepared using appropriate starting materials according to the procedure of Example 169.

Example 834

4-[(3-Hydroxy-4-methoxy-benzylamino)-methylene]-6-naphthalen-2-yl-4H-isoquinoline-1,3-dione This compound is prepared using appropriate starting materials according to the procedure of Example 169.

Example 835

4-[(3-Hydroxy-4-methoxy-benzylamino)-methylene]-6-(1H-indol-5-yl)-4H-isoquinoline-1,3-dione This compound is prepared using appropriate starting materials according to the procedure of Example 169.

Example 836

4-[(3-Hydroxy-4-methoxy-benzylamino)-methylene]-6-(1H-pyrrol-2-yl)-4H-isoquinoline-1,3-dione This compound is prepared using appropriate starting materials according to the procedure of Example 169.

Example 837

6-Furan-2-yl-4-[(3-hydroxy-4-methoxy-benzylamino)-methylene]-4H-isoquinoline-1,3-dione This compound is prepared using appropriate starting materials according to the procedure of Example 169.

Example 838

4-[(4-Pyrrolidin-1-ylmethyl-phenylamino)-methylene]-6-(1H-pyrrol-2-yl)-4H-isoquinoline-1,3-dione This compound is prepared using appropriate starting materials according to the procedure of Example 169.

Example 839

4-{1,3-Dioxo-4-[(4-pyrrolidin-1-ylmethyl-phenylamino)-methylene]-1,2,3,4-tetrahydro-isoquinolin-6-yl}-benzonitrile This compound is prepared using appropriate starting materials according to the procedure of Example 169.

Example 840

6-(4-Hydroxymethyl-phenyl)-4-[(4-pyrrolidin-1-ylmethyl-phenylamino)-methylene]-4H-isoquinoline-1,3-dione This compound is prepared using appropriate starting materials according to the procedure of Example 169.

Example 841

7-Bromo-4-[(4-methoxy-phenylamino)-methylene]-1,4-dihydro-2H-isoquinolin-3-one

Step 1:
A mixture of 4-bromo-phenylacetonitrile (0.196 mg, 1 mmol), paraformaldehyde (33 mg, 1.1 mmol) and pyrophosphoric acid (2 g) is treated in a microwave at 160° C. for 10 min. The reaction mixture is poured into ice-water, neutralized with $K_2CO_3$, and then extracted with ethyl acetate. The extract is washed with 10% $K_2CO_3$ and water, dried over $MgSO_4$, filtered and evaporated to give of 7-Bromo-1,4-dihydro-2H-isoquinolin-3-one (167.8 mg).

Step 2:
To a suspension of 7-bromo-1,4-dihydro-2H-isoquinolin-3-one (450 mg, 2 mmol) in 1 mL of N,N-dimethylformamide is added N,N-dimethylformamide dimethylacetal (954 mg, 8 mmol). The reaction mixture is heated in a microwave at 100° C. for 10 min. The reaction mixture is then filtered and washed with N,N-dimethylformamide to give 356 mg of 7-bromo-4-dimethylaminomethylene-1,4-dihydro-2H-isoquinolin-3-one.

Step 3:
To a suspension of crude 7-bromo-4-dimethylaminomethylene-1,4-dihydro-2H-isoquinolin-3-one (56 mg, 0.2 mmol) in N,N-dimethylformamide (250 mL) is added N,N-dimethyl-1,4-phenylenediamine (41.8 mg, 0.2 mmol). The reaction mixture is shaken at 115° C. for 3 hours, then purified by Prep. HPLC. The pure fractions were combined and concentrated to yield Example 841 (10.2 mg).

Example 842

7-Bromo-4-{[4-(4-methyl-piperazin-1-yl)-phenylamino]-methylene}-1,4-dihydro-2H-isoquinolin-3-one This compound is prepared using appropriate starting materials according to the procedure of Example 841.

Example 843

6-[1-(2-Methoxy-ethyl)-1H-pyrrol-3-yl]-4-{[4-(4-methyl-piperazin-1-yl)-phenylamino]-methylene}-4H-isoquinoline-1,3-dione This compound is prepared using appropriate starting materials according to the procedure of Example 853.

Example 844

6-Bromo-4-[(4-methoxy-phenylamino)-methylene]-1,4-dihydro-2H-isoquinolin-3-one & 8-Bromo-4-[(4-methoxy-phenylamino)-methylene]-1,4-dihydro-2H-isoquinolin-3-one This compound is prepared using appropriate starting materials according to the procedure of Example 845.

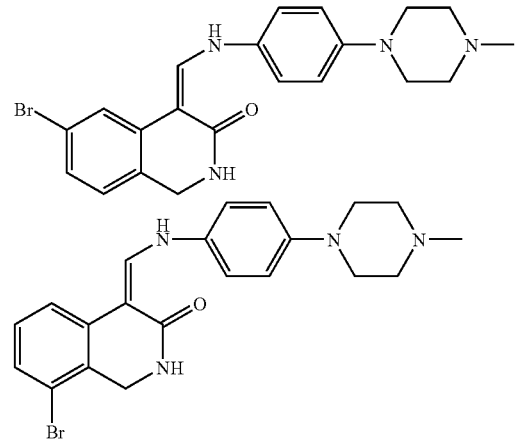

Example 845

6-Bromo-4-{[4-(4-methyl-piperazin-1-yl)-phenylamino]-methylene}-1,4-dihydro-2H-isoquinolin-3-one & 8-Bromo-4-{[4-(4-methyl-piperazin-1-yl)-phenylamino]-methylene}-1,4-dihydro-2H-isoquinolin-3-one Step 1:
A mixture of 3-bromo-phenylacetonitrile (2 mmol, 0.392 g), paraformaldehyde (2.2 mmol, 0.066 g) and pyrophosphoric acid (4 g) is heated in a microwave at 160° C. for 10 min. The reaction mixture is poured into ice-water, neutralized with $K_2CO_3$, and then extracted with ethyl acetate. The extract is washed with 10% $K_2CO_3$ and water, dried over $MgSO_4$, filtered and evaporated to give a mixture of 6(and 8)-bromo-1,4-dihydro-2H-isoquinolin-3-one (0.47 g).

Step 2:
To a suspension of 6(and 8)-bromo-1,4-dihydro-2H-isoquinolin-3-one (0.204 g, 0.8 mmol) in 0.5 mL of N,N-dimethylformamide is added N,N-dimethylformamide dimethylacetal (0.4 g, 3.4 mmol). The reaction mixture is heated in a microwave at 100° C. for 10 min, then evaporated to dryness. The residue is applied on a C18 column and eluted with 25% ACN (30 ml) and 40% ACN (100 mL). The fractions which contained product were combined and evaporated to give 0.321 g of 6(and 8)-bromo-4-dimethylaminomethylene-1,4-dihydro-2H-isoquinolin-3-one.

Step 3:

To a suspension of crude 6(and 8)-bromo-4-dimethylaminomethylene-1,4-dihydro-2H-isoquinolin-3-one (28 mg, 0.1 mmol) in N,N-dimethylformamide (250 ml) is added 4-(4-methyl-piperazin-1-yl)-phenylamine (19 mg, 0.1 mmol). The reaction mixture is shaken at 115° C. for 1.5 hours, then purified by Prep. HPLC. The pure fractions were combined and concentrated to yield Example 845 (17.4 mg).

Example 846

6-Bromo-4-[(4-pyrrolidin-1-ylmethyl-phenylamino)-methylene]-1,4-dihydro-2H-isoquinolin-3-one &
8-Bromo-4-[(4-pyrrolidin-1-ylmethyl-phenylamino)-methylene]-1,4-dihydro-2H-isoquinolin-3-one This compound is prepared using appropriate starting materials according to the procedure of Example 845.

Example 847

7-Bromo-4-[(4-pyrrolidin-1-ylmethyl-phenylamino)-methylene]-1,4-dihydro-2H-isoquinolin-3-one This compound is prepared using appropriate starting materials according to the procedure of Example 841.

Example 848

4-{[4-(4-Methyl-piperazin-1-yl)-phenylamino]-methylene}-7-thiophen-2-yl-1,4-dihydro-2H-isoquinolin-3-one This compound is prepared using appropriate starting materials according to the procedure of Example 849.

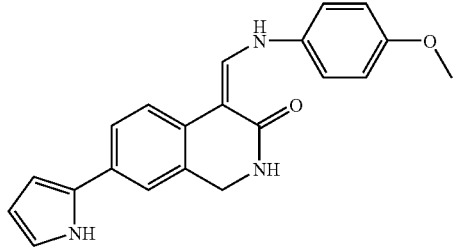

Example 849

4-[(4-Methoxy-phenylamino)-methylene]-7-(1H-pyrrol-2-yl)-1,4-dihydro-2H-isoquinolin-3-one Step 1:

A mixture of 4-bromo-phenylacetonitrile (0.196 mg, 1 mmol), paraformaldehyde (33 mg, 1.1 mmol) and pyrophosphoric acid (2 g) is heated in a microwave at 160° C. for 10 min. The reaction mixture is poured into ice-water, neutralized with $K_2CO_3$, and then extracted with ethyl acetate. The extract is washed with 10% $K_2CO_3$ and water, dried over $MgSO_4$, filtered and evaporated to give 7-bromo-1,4-dihydro-2H-isoquinolin-3-one (167.8 mg).

Step 2:

To a suspension of 7-bromo-1,4-dihydro-2H-isoquinolin-3-one (450 mg, 2 mmol) in 1 mL of N,N-dimethylformamide is added N,N-dimethylformamide dimethylacetal (954 mg, 8 mmol). The reaction mixture is heated in a microwave at 100° C. for 10 min. The reaction mixture is then filtered and washed with N,N-dimethylformamide to give 356 mg of 7-bromo-4-dimethylaminomethylene-1,4-dihydro-2H-isoquinolin-3-one.

Step 3:

To a suspension of crude 7-bromo-4-dimethylaminomethylene-1,4-dihydro-2H-isoquinolin-3-one (400 mg, 1.43 mmol) in N,N-dimethylformamide (250 mL) is added 4-anisidine (193 mg, 1.57 mmol). The reaction mixture is shaken at 115° C. for 1.5 hours. The reaction mixture is filtered and the filtrate is purified by Prep. HPLC. The pure fractions were combined and concentrated to yield 114 mg of 7-Bromo-4-[(4-methoxy-phenylamino)-methylene]-1,4-dihydro-2H-isoquinolin-3-one.

Step 4:

To a suspension of 7-bromo-4-[(4-methoxy-phenylamino)-methylene]-1,4-dihydro-2H-isoquinolin-3-one (36 mg, 0.1 mmol) in N,N-dimethylformamide (1 mL) is add 1-(t-butoxycarbonyl)pyrrole-2-boronic acid (25.3 mg, 0.12 mmol), 2 M aqueous solution of cesium carbonate (300 μL) and tetrakis(triphenylphosphine)-palladium (0) (30 mg). The reaction mixture is heated in a microwave at 180° C. for 5 min. The reaction mixture is then filtered and the filtrate is purified by Prep. HPLC. The pure fractions were combined and concentrated to yield the title compound (12.8 mg).

Example 850

4-[(4-Methoxy-phenylamino)-methylene]-7-(1H-pyrrol-3-yl)-1,4-dihydro-2H-isoquinolin-3-one This compound is prepared using appropriate starting materials according to the procedure of Example 845.

Example 851

2-[5-(4-{[4-(4-Methyl-piperazin-1-yl)-phenylamino]-methylene}-1,3-dioxo-1,2,3,4-tetrahydro-isoquinolin-6-yl)-indol-1-yl]-acetamide This compound is prepared using appropriate starting materials according to the procedure of Example 169.

Example 852

6-[1-(2-Diethylamino-ethyl)-1H-indol-5-yl]-4-{[4-(4-methyl-piperazin-1-yl)-phenylamino]-methylene}-4H-isoquinoline-1,3-dione This compound is prepared using appropriate starting materials according to the procedure of Example 853.

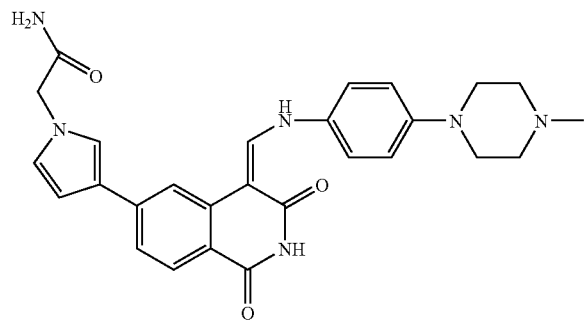

Example 853

2-[3-(4-{[4-(4-Methyl-piperazin-1-yl)-phenylamino]-methylene}-1,3-dioxo-1,2,3,4-tetrahydro-isoquinolin-6-yl)-pyrrol-1-yl]-acetamide Step 1:

To a suspension of 6-bromo-4H-isoquinoline-1,3-dione (2.4 g, 10 mmol) in 25 mL of a 4:1 mixture of acetic anhydride and N,N-dimethylformamide, respectively, is added trimethylorthoformate (2.2 mL, 20 mmol). The reaction mixture is shaken in a heating block at 125° C. for 1 hour. Upon cooling to room temperature, the product precipitated out. The precipitate is then filtered off, rinsed with copious amounts of ether, and dried to yield 2.4 g of 6-bromo-4-methoxymethylene-4H-isoquinoline-1,3-dione.

Step 2:

To a suspension of crude 6-bromo-4-methoxymethylene-4H-isoquinoline-1,3-dione (846 mg, 3 mmol) in N,N-dimethylformamide (7.5 L) is added 4-(4-methyl-piperazin-1-yl)-phenylamine (573 mg, 3 mmol). The reaction mixture is shaken at 115° C. for 1.5 hours, then evaporated to dryness and triturated with ether. The precipitate is then filtered off, rinsed with copious amounts of ether, and dried to yield 1.23 g of 6-bromo-4-{[4-(4-methyl-piperazin-1-yl)-phenylamino]-methylene}-4H-isoquinoline-1,3-dione.

Step 3:

To a suspension of 6-bromo-4-{[4-(4-methyl-piperazin-1-yl)-phenylamino]-methylene}-4H-isoquinoline-1,3-dione (0.2 g, 0.45 mmol) in N,N-dimethylformamide (5 mL) is added N-triisopropylsilyl-3-pyrrole boronic acid (0.16 g, 0.54 mmol), followed by 300 μL of 2M aqueous cesium carbonate and tetrakis triphenylphosphine palladium (30 mg, 0.025 mmol). The reaction mixture is subjected to microwave heating at 180° C. for 300 seconds. The reaction mixture is then divided into 3 fractions and purified by C18 reverse phase HPLC. The pure fractions were combined and concentrated to yield 60 mg of 4-{[4-(4-methyl-piperazin-1-yl)-phenylamino]-methylene}-6-(1H-pyrrol-3-yl)-4H-isoquinoline-1,3-dione.

Step 4:

To a solution of 4-{[4-(4-methyl-piperazin-1-yl)-phenylamino]-methylene}-6-(1H-pyrrol-3-yl)-4H-isoquinoline-1,3-dione (42 mg, 0.1 mmol) in acetone (3 mL) and N,N-dimethylformamide (1 mL) is added potassium carbonate (27 mg, 0.2 mmol) and shaken at room temperature for 2 hours. This is followed by addition of sodium iodide (30 mg, 0.2 mmol) and 2-bromoacetamide (17 mg, 0.12 mmol) and further shaking at room temperature overnight. The reaction mixture is then divided into 2 fractions and purified by C18 reverse phase HPLC. The pure fractions were combined and concentrated to yield the title compound (8.4 mg).

Example 854

6-[1-(2-Diethylamino-ethyl)-1H-pyrrol-3-yl]-4-{[4-(4-methyl-piperazin-1-yl)-phenylamino]-methylene}-4H-isoquinoline-1,3-dione This compound is prepared using appropriate starting materials according to the procedure of Example 853.

Example 855

4-[3-(4-{[4-(4-Methyl-piperazin-1-yl)-phenylamino]-methylene}-1,3-dioxo-1,2,3,4-tetrahydro-isoquinolin-6-yl)-pyrrol-1-yl]-butyronitrile This compound is prepared using appropriate starting materials according to the procedure of Example 853.

Example 856

7-Chloro-4-[(3-hydroxy-phenylamino)-methylene]-1,4-dihydro-2H-isoquinolin-3-one

This compound is prepared using appropriate starting materials according to the procedure of Example 841.

Example 857

4-[(7-Chloro-3-oxo-2,3-dihydro-1H-isoquinolin-4-ylidenemethyl)-amino]-benzamidine This compound is prepared using appropriate starting materials according to the procedure of Example 841.

Example 858

7-Methyl-4-[(4-morpholin-4-yl-phenylamino)-methylene]-1,4-dihydro-2H-isoquinolin-3-one This compound is prepared using appropriate starting materials according to the procedure of Example 841.

Example 859

4-[(3-Hydroxy-phenylamino)-methylene]-1,4-dihydro-2H-isoquinolin-3-one

This compound is prepared using appropriate starting materials according to the procedure of Example 841.

Example 860

4-[(4-Piperidin-1-yl-phenylamino)-methylene]-1,4-dihydro-2H-isoquinolin-3-one

This compound is prepared using appropriate starting materials according to the procedure of Example 841.

Example 861

4-[(7-Bromo-3-oxo-2,3-dihydro-1H-isoquinolin-4-ylidenemethyl)-amino]-benzamidine This compound is prepared using appropriate starting materials according to the procedure of Example 841.

Example 862

7-Bromo-4-[(3-hydroxy-4-methoxy-phenylamino)-methylene]-1,4-dihydro-2H-isoquinolin-3-one This compound is prepared using appropriate starting materials according to the procedure of Example 841.

Example 863

7-Bromo-4-{[4-(2-hydroxy-ethyl)-phenylamino]-methylene}-1,4-dihydro-2H-isoquinolin-3-one This compound is prepared using appropriate starting materials according to the procedure of Example 841.

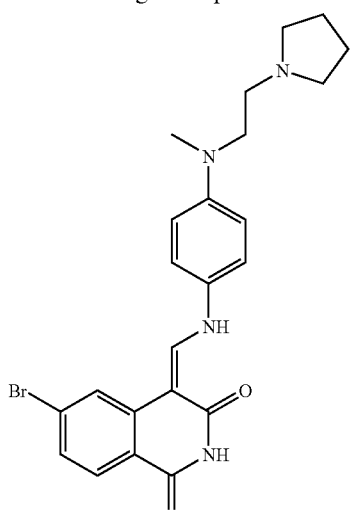

Example 864

(4Z)-6-Bromo-4-[({4-[methyl(2-pyrrolidin-1-yl-ethyl)amino]phenyl}amino)methylene]isoquinoline-1,3(2H,4H)-dione To a solution of 2-(methyl-4-nitroanilino)ethanol (2.9 g, 15 mmol) in pyridine (75 mL) is added p-toluenesulfonyl chloride (3.1 g, 1.6 mmol) and 4-(dimethylamino)pyridine (1.8 g, 15 mmol). After stirring for three days at room temperature, the reaction is quenched by the addition of saturated aqueous sodium chloride solution and then extracted 3× with ethyl acetate. The combined extracts were dried over anhydrous magnesium sulfate and concentrated under reduced pressure to give a viscous brown oil, which is purified by reverse phase high performance liquid chromatography to give toluene-4-sulfonic acid 2-[methyl-(4-nitro-phenyl)-amino]-ethyl ester as a trifluoroacetic acid salt (0.52 g, 9.8%).

LC/MS (ES$^+$): 351.0 (M+H)$^+$

To a solution of toluene-4-sulfonic acid 2-[methyl-(4-nitro-phenyl)-amino]-ethyl ester TFA salt (74 mg, 0.21 mmol) in toluene (1 mL) is added triethylamine (50 µL) and pyrrolidine (53 µL, 0.63 mmol). The mixture is shaken in 70° C. block shaker overnight. The reaction mixture is concentrated and purified by reverse phase high performance liquid chromatography to give methyl-(4-nitro-phenyl)-(2-pyrrolidin-1-yl-ethyl)-amine as a di-TFA salt (85 mg).

A solution of methyl-(4-nitro-phenyl)-(2-pyrrolidin-1-yl-ethyl)-amine•2 TFA (85 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-(2-pyrrolidin-1-yl-ethyl)-benzene-1,4-diamine as a di-TFA salt.

(4E)-6-Bromo-4-(methoxymethylene)isoquinoline-1,3(2H,4H)-dione (59 mg, 0.21 mmol) and N-methyl-N-(2-pyrrolidin-1-yl-ethyl)-benzene-1,4-diamine•2 TFA (0.21 mmol maximum) were stirred in dimethylformamide (1 mL) and triethylamine (50 µL) at 60-70° C. for 12 hours. The reaction mixture is purified by reverse phase high performance liquid chromatography to give (4Z)-6-bromo-4-[({4-[methyl(2-pyrrolidin-1-ylethyl)amino]phenyl}amino)methylene]isoquinoline-1,3(2H,4H)-dione.

MS (ES$^+$): 469.2, 471.2 (M+H)$^+$

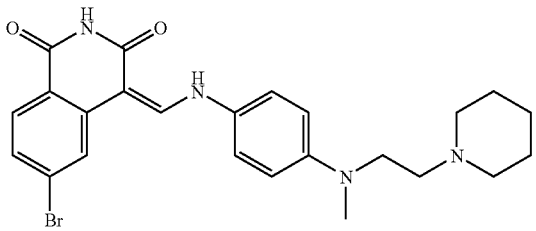

Example 865

(4Z)-B-bromo-4-[({4-[methyl(2-piperidin-1-ylethyl)amino]phenyl}amino)methylene]isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 µL) and piperidine (62 µL, 0.63 mmol). The mixture is shaken in 70° C. block shaker overnight. The reaction mixture is concentrated and purified by reverse phase high performance liquid chromatography to give methyl-(4-nitro-phenyl)-(2-piperidin-1-yl-ethyl)-amine as a di-TFA salt (74 mg).

MS (ES$^+$): 264.3 (M+H)$^+$

A solution of methyl-(4-nitro-phenyl)-(2-piperidin-1-yl-ethyl)-amine•2 TFA (74 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-(2-piperidin-1-yl-ethyl)-benzene-1,4-diamine as a di-TFA salt.

(4E)-6-Bromo-4-(methoxymethylene)isoquinoline-1,3(2H,4H)-dione (59 mg, 0.21 mmol) and N-methyl-N-(2-piperidin-1-yl-ethyl)-benzene-1,4-diamine•2 TFA (0.21 mmol maximum) were stirred in dimethylformamide (1 mL) and triethylamine (50 µL) at 60-70° C. for 12 hours. The reaction mixture is purified by reverse phase high performance liquid chromatography to give (4Z)-6-bromo-4-[({4-[methyl(2-pi-peridin-1-ylethyl)amino]phenyl}amino)methylene]iso-quinoline-1,3(2H,4H)-dione.
MS (ES+): 483.2 (M+H)+

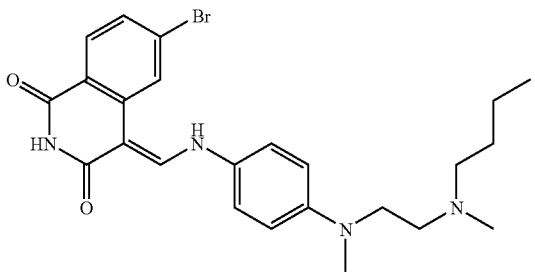

Example 866

(4Z)-6-Bromo-4-[({4-[{2-[butyl(methyl)amino]ethyl}(methyl)amino]phenyl}amino)methylene]isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 μL) and N-methylbutylamine (75 μL, 0.63 mmol). The mixture is shaken in 70° C. block shaker overnight. The reaction mixture is concentrated and purified by reverse phase high performance liquid chromatography to give N-butyl-N,N'-dimethyl-N'-(4-nitro-phenyl)-ethane-1,2-diamine as a di-TFA salt (71 mg, 68%).

A solution of N-butyl-N,N'-dimethyl-N'-(4-nitro-phenyl)-ethane-1,2-diamine•2 TFA (71 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-[2-(butyl-methyl-amino)-ethyl]-N-methyl-benzene-1,4-diamine as a di-TFA salt.

(4E)-6-Bromo-4-(methoxymethylene)isoquinoline-1,3 (2H,4H)-dione (59 mg, 0.21 mmol) and N-[2-(butyl-methyl-amino)-ethyl]-N-methyl-benzene-1,4-diamine•2 TFA (0.21 mmol maximum) were stirred in dimethylformamide (1 mL) and triethylamine (50 μL) at 60-70° C. for 12 hours. The reaction mixture is purified by reverse phase high performance liquid chromatography to give (4Z)-6-bromo-4-[({4-[{2-[butyl(methyl)amino]ethyl}(methyl)amino]phenyl}amino)methylene]isoquinoline-1,3(2H,4H)-dione.
MS (ES+): 487.3 (M+H)+

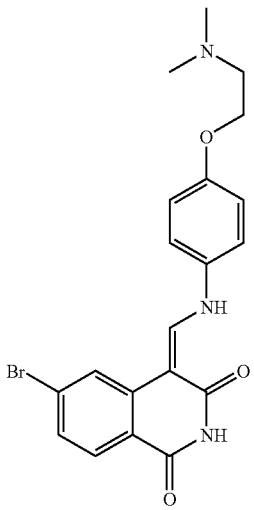

Example 867

(4Z)-6-Bromo-4-[({4-[2-(dimethylamino)ethoxy]phenyl}amino)methylene]isoquinoline-1,3(2H,4H)-dione Dimethyl-[2-(4-nitro-phenoxy)-ethyl]-amine is prepared according to Hunter, D. H.; Ponce, Y. Z.; Brown, G. W.; Chamberlain, M. J.; Driedger, A. A.; Morrissey, G. Can J. Chem. 62, 2015-2019, 1984.
MS (ES+): 211.3 (M+H)+

A solution of dimethyl-[2-(4-nitro-phenoxy)-ethyl]-amine hydrochloride (0.29 g, 1.2 mmol) in ethanol (20 mL) is hydrogenated at atmospheric pressure over 10% palladium on carbon. The reaction mixture is filtered through a pad of diatomaceous earth and concentrated to give 4-(2-dimethylamino-ethoxy)-phenylamine hydrochloride (0.24 g, 96%).
MS (ES+): 181.3 (M+H)+

(4E)-6-Bromo-4-(methoxymethylene)isoquinoline-1,3 (2H,4H)-dione (70 mg, 0.25 mmol) and 4-(2-dimethylamino-ethoxy)-phenylamine hydrochloride (50 mg, 0.23 mmol) were stirred in dimethylformamide (1 mL) and triethylamine (50 μL) at 70° C. The reaction mixture is quenched by the addition of water. The solid material is then collected, washed with diethyl ether, water, and methanol, and then dried under vacuum to give (4Z)-6-bromo-4-[({4-[2-(dimethylamino)ethoxy]phenyl}amino)methylene]isoquinoline-1,3(2H,4H)-dione (81 mg, 82%).
MS (ES+): 430.0, 432.0 (M+H)+

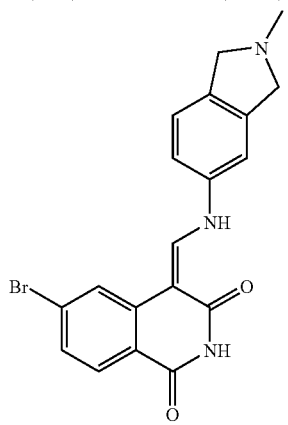

Example 868

(4Z)-6-Bromo-4-{[(2-methyl-2,3-dihydro-1H-isoindol-5-yl)amino]methylene}isoquinoline-1,3(2H,4H)-dione The methylation of 4-nitrophthalimide to give 2-methyl-5-nitro-isoindole-1,3-dione (0.93 g, 43%) is accomplished via the procedure of Billman, J. H. and Cash, V. J Am Chem Soc. 75(10), 1953, 2499-2501.

A solution of give 2-methyl-5-nitro-isoindole-1,3-dione (1.1 g, 5.3 mmol) in ethanol/tetrahydrofuran (1:1, 50 mL) is hydrogenated at 45 psi over Raney nickel catalyst. The reaction mixture is filtered through a pad of diatomaceous earth and concentrated to give 5-amino-2-methyl-isoindole-1,3-dione as a yellow cottony solid (0.85 g, 91%).

1H NMR (300 MHz, DMSO-d6) d ppm 2.94 (s, 3H), 6.44 (s, 2H), 6.77 (dd, J=8.2 Hz, 1H), 6.91 (d, J=2.0 Hz, 1H), 7.47 (d, J=8.2 Hz, 1H).

To a suspension of lithium aluminum hydride (0.55 g, 14 mmol) in tetrahydrofuran (7 mL) is added solid 5-amino-2-methyl-isoindole-1,3-dione (0.85 g, 4.8 mmol). The resulting suspension is heated at reflux for 15 minutes and is then cooled to 0° C. At this temperature, the reaction is quenched by the addition of ethanol and then water. The resulting slurry is filtered through a pad of diatomaceous earth, and the filtrate is concentrated under reduced pressure to give a brown solid. The crude solid is dissolved in absolute ethanol and acidified with concentrated ethanolic hydrochloric acid. With the addition of diethyl ether, a brown solid precipitated and is collected by filtration to give 2-methyl-2,3-dihydro-1H-isoindol-5-ylamine as a dihydrochloride salt (0.61 g, 55%).

MS (ES$^+$): 149.3 (M+H)$^+$ (4E)-6-Bromo-4-(methoxymethylene)isoquinoline-1,3(2H,4H)-dione (0.20 g, 0.71 mmol) and 2-methyl-2,3-dihydro-1H-isoindol-5-ylamine•2HCl (0.52 mg, 2.3 mmol) were stirred in dimethylformamide (5 mL) and triethylamine (0.83 mL) at 70° C. The reaction mixture is quenched by the addition of water. The solid material is then collected, washed with diethyl ether, water, and methanol, and then dried under vacuum to give a crude solid, which is then purified by reverse phase high performance liquid chromatography to provide (4Z)-6-bromo-4-{[(2-methyl-2,3-dihydro-1H-isoindol-5-yl)amino]methylene}isoquinoline-1,3(2H,4H)-dione•trifluoroacetic acid (80 mg, 22%).

MS (ES$^-$): 396.1, 398.2 (M−H)$^-$

Example 869

(4Z)-6-Bromo-4-({[4-(1H-imidazol-1-yl)phenyl]amino}methylene)isoquinoline-1,3(2H,4H)-dione In a 20 mL vial were combined 4-fluoronitrobenzene (1.1 mL, 10 mmol), imidazole (0.68 g, 10 mmol), and sodium carbonate (1.1 g, 11 mmol) in dimethylformamide (5 mL). The mixture is shaken at 100° C. for 24 hours and then allowed to cool to room temperature and then diluted with water. Concentrated hydrochloric acid is added to bring the pH to 1, and then the mixture is extracted thrice with chloroform (10 mL). The acidic aqueous phase is then treated with 2.5 M sodium hydroxide solution to give a pH of 10. A light yellow solid is collected and washed with water to give 1-(4-nitrophenyl)-1H-imidazole.

MS (ES$^+$): 190.2 (M+H)$^+$

A solution of 1-(4-nitrophenyl)-1H-imidazole (0.38 g, 2.0 mmol) in ethanol (20 mL), water (3 mL), and concentrated hydrochloric acid (5 drops) is hydrogenated for overnight at atmospheric pressure over 10% Pd/C. The mixture is filtered through a pad of diatomaceous earth and concentrated under reduced pressure to give 4-(1H-imidazol-1-yl)-benzenamine trihydrochloride as a gray powder.

MS (ES$^+$): 160.2 (M+H)$^+$ (4E)-6-Bromo-4-(methoxymethylene)isoquinoline-1,3(2H,4H)-dione (70 mg, 0.25 mmol) and 4-(1H-imidazol-1-yl)-benzenamine•3HCl (70 mg, 0.25 mmol) were stirred in dimethylformamide (1.5 mL) and triethylamine (0.15 mL) at 75° C. The reaction mixture is quenched by the addition of water. The solid material is then collected, washed with diethyl ether, water, and methanol, and then dried under vacuum to give (4Z)-6-bromo-4-({[4-(1H-imidazol-1-yl)phenyl]amino}methylene)isoquinoline-1,3(2H,4H)-dione (95 mg, 93%)

MS (ES$^+$): 409.0, 411.0 (M+H)$^+$

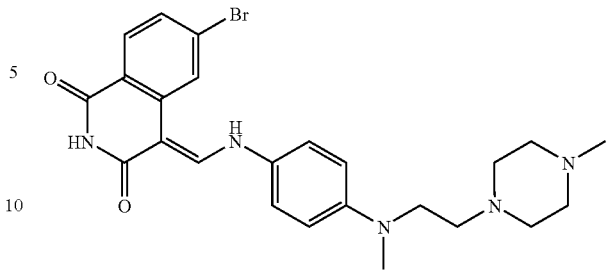

Example 870

(4Z)-6-Bromo-4-{[(4-{methyl[2-(4-methylpiperazin-1-yl)ethyl]amino}phenyl)amino]methylene}isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 μL) and N-methylpiperazine (70 μL, 0.63 mmol). The mixture is shaken in 70° C. block shaker overnight. The reaction mixture is concentrated and purified by reverse phase high performance liquid chromatography to give methyl-[2-(4-methyl-piperazin-1-yl)-ethyl]-(4-nitro-phenyl)-amine as a tri-TFA salt (98 mg, 98%).

A solution of methyl-[2-(4-methyl-piperazin-1-yl)-ethyl]-(4-nitro-phenyl)-amine•3 TFA (98 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-[2-(4-methyl-piperazin-1-yl)-ethyl]-benzene-1,4-diamine as a tri-TFA salt.

(4E)-6-Bromo-4-(methoxymethylene)isoquinoline-1,3(2H,4H)-dione (59 mg, 0.21 mmol) and N-Methyl-N-[2-(4-methyl-piperazin-1-yl)-ethyl]-benzene-1,4-diamine•3 TFA (0.21 mmol maximum) were stirred in dimethylformamide (1 mL) and triethylamine (50 μL) at 60-70° C. for 12 hours. The reaction mixture is purified by reverse phase high performance liquid chromatography to give (4Z)-6-bromo-4-{[(4-{methyl[2-(4-methylpiperazin-1-yl)ethyl]amino}phenyl)amino]methylene}isoquinoline-1,3(2H,4H)-dione as a tri-TFA salt.

MS (ES$^+$): 500.2 (M+H)$^+$

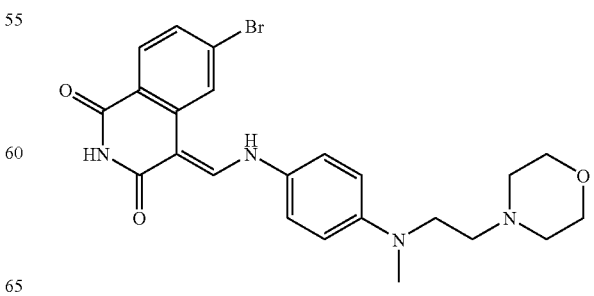

Example 871

(4Z)-6-Bromo-4-[({4-[methyl(2-morpholin-4-yl-ethyl)amino]phenyl}amino)methylene]isoquinoline-1,3(2H,4H)-dione To a solution of toluene-4-sulfonic acid 2-[methyl-(4-nitro-phenyl)-amino]-ethyl ester TFA salt (74 mg, 0.21 mmol) in toluene (1 mL) is added triethylamine (50 μL) and morpholine (55 μL, 0.63 mmol). The mixture is shaken in 70° C. block shaker overnight. The reaction mixture is concentrated and purified by reverse phase high performance liquid chromatography to give methyl-(2-morpholin-4-yl-ethyl)-(4-nitro-phenyl)-amine as a di-TFA salt (80 mg, 77%).

MS (ES$^+$): 266.3 (M+H)$^+$

A solution of methyl-(2-morpholin-4-yl-ethyl)-(4-nitrophenyl)-amine•2 TFA (80 mg) in ethanol/tetrahydrofuran (1:1, 5 mL) is hydrogenated at atmospheric pressure over 10% palladium on carbon. The reaction mixture is filtered through a pad of diatomaceous earth and concentrated to give N-methyl-N-(2-morpholin-4-yl-ethyl)-benzene-1,4-diamine as a di-TFA salt.

(4E)-6-Bromo-4-(methoxymethylene)isoquinoline-1,3(2H,4H)-dione (59 mg, 0.21 mmol) and N-Methyl-N-(2-morpholin-4-yl-ethyl)-benzene-1,4-diamine•2 TFA (0.21 mmol maximum) were stirred in dimethylformamide (1 mL) and triethylamine (50 μL) at 60-70° C. for 12 hours. The reaction mixture is purified by reverse phase high performance liquid chromatography to give (4Z)-6-bromo-4-[({4-[methyl(2-morpholin-4-ylethyl)amino]phenyl}amino)methylene]isoquinoline-1,3(2H,4H)-dione.

MS (ES$^+$): 587.2 (M+H)$^+$

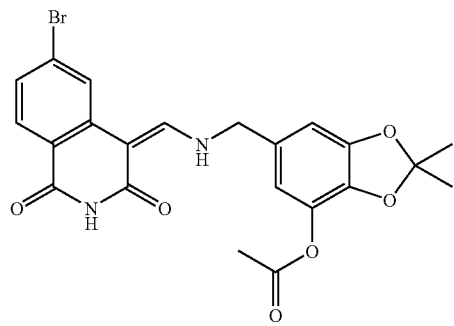

Example 872

6-({[(Z)-(6-Bromo-1,3-dioxo-2,3-dihydroisoquinolin-4(1H)-ylidene)methyl]amino}methyl)-2,2-dimethyl-1,3-benzodioxol-4-yl acetate To a solution of (4Z)-6-bromo-4-({[(7-hydroxy-2,2-dimethyl-1,3-benzodioxol-5-yl)methyl]amino}methylene)isoquinoline-1,3(2H,4H)-dione (30 mg, 67 μmol) in dimethylformamide (0.5 mL) is added pyridine (12 μL, 0.17 mmol) and acetyl chloride (10 μL). The reaction mixture is shaken overnight at room temperature and then purified by reverse-phase high performance liquid chromatography to give 6-({[(Z)-(6-bromo-1,3-dioxo-2,3-dihydroisoquinolin-4(1H)-ylidene)methyl]amino}methyl)-2,2-dimethyl-1,3-benzodioxol-4-yl acetate.

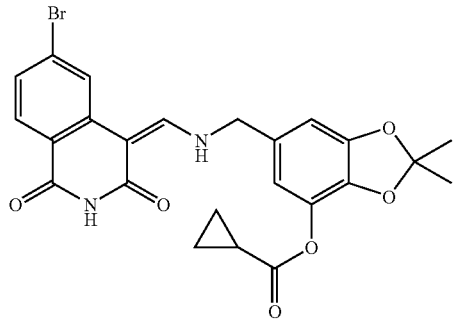

Example 873

6-({[(Z)-(6-Bromo-1,3-dioxo-2,3-dihydroisoquinolin-4(1H)-ylidene)methyl]amino}methyl)-2,2-dimethyl-1,3-benzodioxol-4-yl cyclopropanecarboxylate To a solution of (4Z)-6-bromo-4-({[(7-hydroxy-2,2-dimethyl-1,3-benzodioxol-5-yl)methyl]amino}methylene)isoquinoline-1,3(2H,4H)-dione (30 mg, 67 μmol) in dimethylformamide (0.5 mL) is added pyridine (12 μL, 0.17 mmol) and cyclopropanecarbonyl chloride (10 μL). The reaction mixture is shaken overnight at room temperature and then purified by reverse-phase high performance liquid chromatography to give 6-({[(Z)-(6-bromo-1,3-dioxo-2,3-dihydroisoquinolin-4(1H)-ylidene)methyl]amino}methyl)-2,2-dimethyl-1,3-benzodioxol-4-yl cyclopropanecarboxylate.

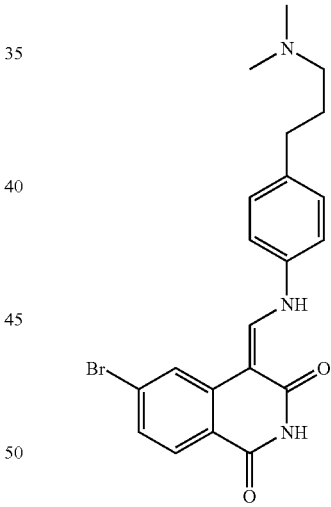

Example 874

(4Z)-6-Bromo-4-[({4-[3-(dimethylamino)propyl]phenyl}amino)methylene]isoquinoline-1,3(2H,4H)-dione N-[4-(3-Oxo-propyl)-phenyl]-acetamide is prepared according to Björnestedt, R.; Zhong, G.; Lerner, R. A.; Barbas, C. F. J Am Chem Soc. 118, 1996, 11720-11724.

To a suspension of N-[4-(3-Oxo-propyl)-phenyl]-acetamide (96 mg, 0.50 mmol), dimethylamine hydrochloride (82 mg, 1.0 mmol), and sodium acetate (66 mg, 0.80 mmol) in methanol (0.5 mL) is added sodium cyanoborohydride (47 mg, 0.75 mmol). Upon completion of the reaction, the solvent is evaporated under reduced pressure and the residue is partitioned between ethyl acetate and water. The aqueous phase is extracted with ethyl acetate. The combined extracts were concentrated to give N-[4-(3-dimethylamino-propyl)-phenyl]-acetamide (0.14 g, >100%).

MS (ES⁺): 221.3 (M+H)⁺

To a solution of N-[4-(3-dimethylamino-propyl)-phenyl]-acetamide (0.50 mmol maximum) in methanol (8 mL) is added 20% aqueous hydrochloric acid solution. After 3½ hours of shaking at 56° C., an additional 2 drops of concentrated hydrochloric acid is added and shaking is continued for 3 days. The mixture is concentrated to give 4-(3-dimethylamino-propyl)-phenylamine hydrochloride, which is used without further purification in the following step.

MS (ES⁺): 179.3 (M+H)⁺

(4E)-6-Bromo-4-(methoxymethylene)isoquinoline-1,3 (2H,4H)-dione (50 mg, 0.18 mmol) 4-(3-dimethylamino-propyl)-phenylamine hydrochloride (0.40 mmol) were stirred in dimethylformamide (1 mL) and triethylamine (140 µL) at 78° C. The reaction mixture is quenched by the addition of water. The solid material is then collected, washed with water, and then dried under vacuum to give (4Z)-6-bromo-4-[({4-[3-(dimethylamino)propyl]phenyl}amino)methylene]isoquinoline-1,3(2H,4H)-dione (58 mg, 75%) as a golden solid.

MS (ES⁺): 428, 430 (M+H)⁺

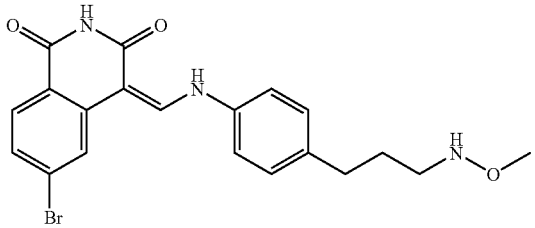

Example 875

(Methoxyamino)propyl]phenyl}amino)methylene]isoquinoline-1,3(2H,4H)-dione 3-(4'-Acetamidophenyl)propanal is prepared according to Bjornestedt, R.; Zhong, G.; Lerner, R. A.; Barbas, C. F. JACS (1996), 118(47), 11720-11724.

LC/MS (ES⁺): 192.7 (M+H)⁺

A mixture of 3-(4-acetamidophenyl)propanal (96 mg, 0.50 mmol), methoxylamine hydrochloride (92 mg, 1.1 mmol), and pyridine (110 µL) in methanol (0.7 mL) is heated in a 70° C. oil bath for 18 hours and then allowed to cool to room temperature. Methanol (1 mL) is added and the mixture is cooled to 0° C. in an ice-water bath. Borane.pyridine complex (0.11 mL, 1.1 mmol) is added, followed by the dropwise addition of 10% aqueous hydrochloric acid. The mixture is allowed to warm to room temperature and then concentrated under reduced pressure. The residue is purified by reverse-phase HPLC to give N-[4-(3-methoxyamino-propyl)-phenyl]-acetamide.

MS (ES⁺): 223.3 (M+H)⁺

A mixture of N-[4-(3-methoxyamino-propyl)-phenyl]-acetamide (0.50 mmol) and 20% aqueous hydrochloric acid (2 mL) in methanol (8 mL) is heated for 18 hours at 60° C. and then concentrated under reduced pressure to give N-[3-(4-amino-phenyl)-propyl]-O-methyl-hydroxylamine dihydrochloride (62 mg, 0.24 mmol) and is used in the following step without further purification.

MS (ES⁺): 181.3 (M+H)⁺

(4E)-6-Bromo-4-(methoxymethylene)isoquinoline-1,3 (2H,4H)-dione (69 mg, 0.24 mmol) and N-[3-(4-amino-phenyl)-propyl]-O-methyl-hydroxylamine dihydrochloride (62 mg, 0.24 mmol) were coupled in dimethylformamide (1.4 mL) with triethylamine (0.15 mL). The mixture is heated at 75° C. for one hour and then cooled to 0° C. in an ice-water bath. Water is added and resulting solid is collected and then purified by reverse-phase HPLC to give (4Z)-6-bromo-4-[({4-[3-(methoxyamino)propyl]phenyl}amino)methylene]isoquinoline-1,3(2H,4H)-dione as its trifluoroacetate salt (30 mg, 23%).

LC/MS (ES⁻): 428.4, 430.4 (M−H)⁻

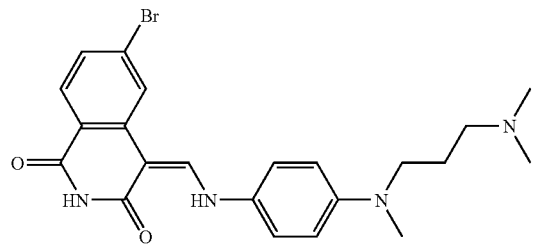

Example 876

(4Z)-6-Bromo-4-[({4-[[3-(dimethylamino)propyl](methyl)amino]phenyl}amino)methylene]isoquinoline-1,3(2H,4H)-dione To a suspension of potassium hydroxide (1.4 g, 25 mmol) in dimethylsulfoxide (13 mL) is added N,N,N'-trimethyl-1,3-propanediamine (1.8 mL, 12 mmol). While stirring vigorously and while heating to 65° C., 4-fluoronitrobenzene (1.1 mL, 10 mmol) is added dropwise. After stirring at this temperature for 6 hours, the mixture is allowed to cool to room temperature. Water is added and the mixture is acidified to pH 1 with concentrated hydrochloric acid and then extracted thrice with chloroform (3×30 mL). The acidic phase is then basified to pH 11 with 2.5 M sodium hydroxide solution. The basic phase is extracted thrice with chloroform (3×30 mL), dried over anhydrous sodium sulfate, and concentrated under reduced pressure to give an orange-red oil, which is purified by reverse phase high performance liquid chromatography to give N,N,N'-trimethyl-N'-(4-nitrophenyl)propane-1,3-diamine as its ditrifluoroacetate salt.

MS (ES⁺): 238.1 (M+H)⁺

A solution of give N,N,N'-trimethyl-N'-(4-nitrophenyl)propane-1,3-diamine•2 TFA (0.57 g, 1.2 mmol) in ethanol/tetrahydrofuran (1:1, 20 mL) is hydrogenated at atmospheric pressure over 10% palladium on carbon. The reaction mixture is filtered through a pad of diatomaceous earth and concentrated to give N-(3-dimethylamino-propyl)-N-methyl-benzene-1,4-diamine•2 TFA as a dark oil.

MS (ES⁺): 208.4 (M+H)⁺

(4E)-6-Bromo-4-(methoxymethylene)isoquinoline-1,3 (2H,4H)-dione (52 mg, 0.18 mmol) and N-(3-dimethylamino-propyl)-N-methyl-benzene-1,4-diamine•2 TFA (80 mg, 0.18 mmol) were stirred in dimethylformamide (1 mL) and triethylamine (100 µL) at 75° C. The reaction mixture is quenched by the addition of water. The solid material is then collected, washed with diethyl ether, water, and methanol, and then dried under vacuum to give (4Z)-6-bromo-4-[({4-[[3-(dimethylamino)propyl](methyl)amino]phenyl}amino)

methylene]isoquinoline-1,3(2H,4H)-dione.2 TFA (43 mg, 35%).

MS (ES+): 457.1, 459.1 (M+H)+

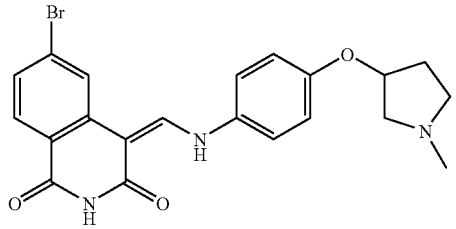

Example 877

(4Z)-6-Bromo-4-[({4-[(1-methylpyrrolidin-3-yl)oxy]phenyl}amino)methylene]isoquinoline-1,3(2H,4H)-dione To a suspension of sodium hydride (60% dispersion in mineral oil, 0.65 g, 16 mmol) in tetrahydrofuran (50 mL) is added 1-methyl-3-pyrrolidinol (0.50 g, 4.9 mmol) as a solution in tetrahydrofuran (100 mL). After 2 Y² hours of stirring at room temperature, a solution of 4-fluoronitrobenzene (0.73 mL, 6.9 mmol) in tetrahydrofuran (30 mL) is added to the mixture. After stirring overnight, the mixture is quenched with water and extracted 3× with diethyl ether. The combined extracts were washed with water and saturated aqueous sodium chloride solution, dried over anhydrous magnesium sulfate, and concentrated under reduced pressure. The crude product is purified by reverse phase high performance liquid chromatography to give 1-methyl-3-(4-nitro-phenoxy)-pyrrolidine•TFA as a colorless oil which solidified upon standing.

MS (ES+): 223.3 (M+H)+

A solution of 1-methyl-3-(4-nitro-phenoxy)-pyrrolidine•TFA (0.34 g, 1.0 mmol) in ethanol (10 mL) is hydrogenated for one hour at atmospheric pressure over 10% Pd/C. The mixture is filtered through a pad of diatomaceous earth and concentrated under reduced pressure to give 4-(1-methyl-pyrrolidin-3-yloxy)-phenylamine•TFA as a black solid.

(4E)-6-Bromo-4-(methoxymethylene)isoquinoline-1,3 (2H,4H)-dione (52 mg, 0.18 mmol) and 4-(1-methyl-pyrrolidin-3-yloxy)-phenylamine•TFA (55 mg, 0.18 mmol) were stirred in N,N-dimethylformamide (1 mL) and triethylamine (100 μL) at 75° C. The reaction mixture is purified by reverse phase high performance liquid chromatography to give (4Z)-6-bromo-4-[({4-[(1-methylpyrrolidin-3-yl)oxy]phenyl}amino)methylene]isoquinoline-1,3(2H,4H)-dione as its TFA salt.

MS (ES+): 442.2, 444.2 (M+H)+

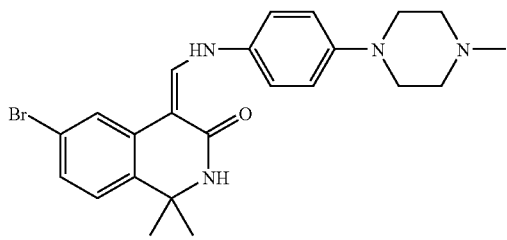

Example 878

6-Bromo-1,1-dimethyl-4-{[4-(4-methyl-piperazin-1-yl)-phenylamino]-methylene}-1,4-dihydro-2H-isoquinolin-3-one 6-Bromo-1,1-dimethyl-1,4-dihydro-2H-isoquinolin-3-one (210 mg, 0.83 mmol) and dimethoxymethyl-dimethylamine (250 mg, 2.1 mmol) in DMF (4 mL) is heated at 100° C. for 1 hour. After which the DMF is evaporated and toluene (6 mL) is added. This solution is then mixed with a solution of 4-(4-Methyl-piperazin-1-yl)-phenylamine (450 mg, 2.4 mmol) in toluene (4 mL) and the mixture is heated at reflux for 6 hours. The mixture is then allowed to cool to room temperature, upon cooling, precipitates formed. The precipitate is collected and further purified through chromatography to provide the title compound (120 mg, 31%). MS (ESI): 455.1, 457.1 (M+1)⁻¹.

¹H NMR (400 MHz, CHLOROFORM-D) □ ppm 1.53 (s, 6 H) 2.35-2.44 (m, 3 H) 2.63 (d, J=4.53 Hz, 4 H) 3.07-3.32 (m, 4 H) 6.90-6.97 (m, 2 H) 6.99-7.03 (m, 1H) 7.03-7.09 (m, 2 H) 7.19 (dd, J=8.31, 1.76 Hz, 1 H) 7.44 (d, J=2.01 Hz, 1 H) 7.72 (d, J=12.34 Hz, 1 H) 11.26 (d, J=12.34 Hz, 1 H)

Anal. ($C_{23}H_{27}BrN_4O \cdot 0.7H_2O$)C, H, N. Calcd: C, 59.13; H, 6.13; N, 12.00. Found: C, 59.40; H, 5.90; N, 11.91.

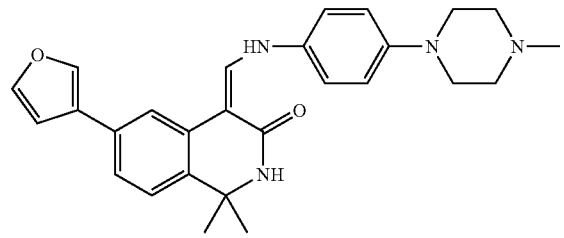

Example 879

6-Furan-3-yl-1,1-dimethyl-4-{[4-(4-methyl-piperazin-1-yl)-phenylamino]-methylene}-1,4-dihydro-2H-isoquinolin-3-one Using the procedure described for the preparation of 4-{[4-(2-Hydroxymethyl-pyrrolidin-1-ylmethyl)-phenylamino]-methylene}-6-thiophen-3-yl-4H-isoquinoline-1,3-dione, the title compound is obtained from 6-Bromo-4-{[4-(2-hydroxymethyl-pyrrolidin-1-ylmethyl)-phenylamino]-methylene}-4H-isoquinoline-1,3-dione (100 mg, 0.22 mmol), 3-furyl boronic acid (50 mg, 0.39 mmol) in 21% yield as a yellow solid: MS (ESI): 443.2 (M+1)+¹.

¹H NMR (400 MHz, DMSO-D6) □ ppm 0.97-1.25 (m, 6 H) 1.40 (s, 4 H) 1.62-1.90 (m, 3 H) 2.29 (s, 1 H) 3.37-3.63 (m, 2 H) 4.59-4.96 (m, 1 H) 7.22 (d, J=7.55 Hz, 2 H) 7.55 (d, J=6.30 Hz, 2 H) 7.60 (d, J=8.31 Hz, 1 H) 7.73 (d, J=8.31 Hz, 1 H) 8.59 (s, 1 H) 8.93 (

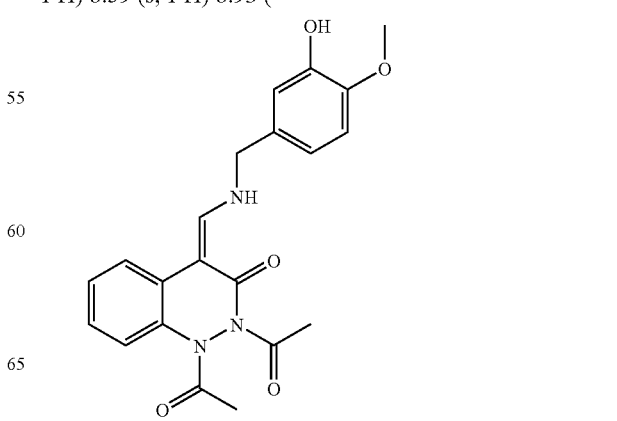

Example 880

(4Z)-1,2-Diacetyl-4-{[(3-hydroxy-4-methoxybenzyl)amino]methylene}-1,4-dihydrocinnolin-3(2H)-one To a solution of (Z)-1,1'-(4-(methoxymethylene)-3-oxo-3,4-dihydrocinnoline-1,2-diyl)diethanone (0.18 g, 0.66 mmol) in tetrahydrofuran (5 mL) is added 3-hydroxy-4-methoxybenzylamine hydrochloride (0.13 g, 0.66 mmol). The suspension is treated with triethylamine (0.21 mL) and dimethylformamide (1 mL). The mixture is stirred at room temperature until LC/MS analysis revealed the consumption of the starting materials. Following concentration under reduced pressure, the crude mixture is purified by semi-preparative reverse-phase HPLC, employing a gradient elution from 40% acetonitrile in water with 0.1% trifluoroacetic acid to 70% acetonitrile in water over 60 minutes. The desired fractions were concentrated under reduced pressure to afford 0.14 g of (4Z)-1,2-diacetyl-4-{[(3-hydroxy-4-methoxybenzyl)amino]methylene}-1,4-dihydrocinnolin-3(2H)-one.

Calculated [M+H]$^+$=396.15540
HRMS (ES$^+$): 396.15482 observed

Example 881

4-{4-(4-methyl-piperazin-1-yl)-phenylamino]methylene}-6-m-acetylphenylamino-4H-isoquinoline-1,3-dione Step 1

6-Bromo-4-{4-(4-methyl-piperazin-1-yl)-phenylamino]methylene}-4H-isoquinoline-1,3-dione

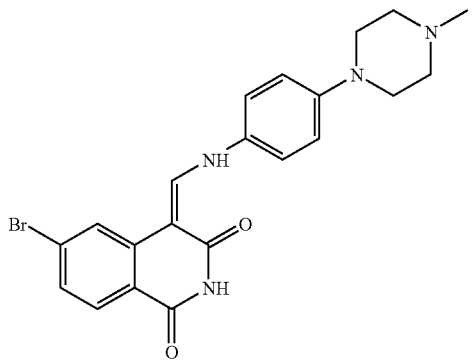

6-Bromo-4-methoxymethylene-4H-isoquinoline-1,3-dione (1.46 g, 5.18 mmol) and 4-(4-methyl-piperazin-1-yl)-phenylamine (990 mg, 5.18 mmol) are suspended in 20 ml of dimethylformamide. Mixture is heated at 110° C. for 2 hours forming a homogeneous mixture. Mixture is cooled to room temperature and reduced on a rotovap to yield an oil. The residue is diluted with H$_2$O and stirred for 10 minutes. The resulting solid is filtered off and washed with H$_2$O and excess Et$_2$O to provide the product as a yellowish-brown solid (1.98 g, 86%); $^1$H NMR (DMSO-d$_6$) δ 2.19 (s, 3H), 2.42-2.47 (m, 4H), 3.10-3.16 (m, 4H), 6.95 (d, J=9.0 Hz, 2H), 7.33 (dd, J=1.7, 8.5 Hz, 1H), 7.43 (d, J=9.0 Hz, 2H), 7.86 (d, J=8.5 Hz, 1H), 8.38 (d, J=1.74 Hz, 1H), 8.84 (d, J=12.9 Hz, 1H), 11.28 (s, 1H), 12.54 (d, J=12.9 Hz, 1H); mass spectrum [(+) ESI], m/z 441/443 (M+H)$^+$.

Step 2

4-{4-(4-methyl-piperazin-1-yl)-phenylamino]methylene}-6-m-acetylphenylamino-4H-isoquinoline-1,3-dione

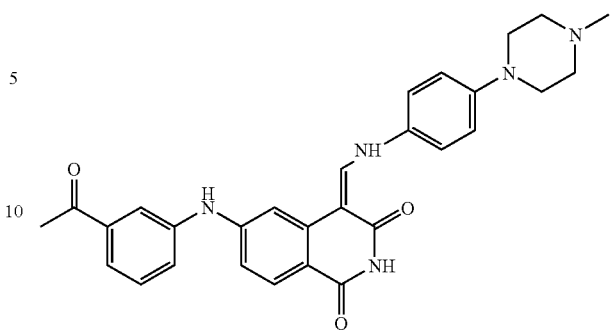

6-Bromo-4-{4-(4-methyl-piperazin-1-yl)-phenylamino]methylene}-4H-isoquinoline-1,3-dione (300 mg, 0.680 mmol), 3-amino-acetophenone (184 mg, 1.36 mmol), allylchloro{1,3-bis(2,6-di-propylphenyl)imidazol-2-yilidine]palladium(II) (IPr.HCl.Pd, 78 mg, 0.136 mmol), [1,1'-bis(diphenylphosphino)-ferrocene]dichloropalladium (II) complex with CH$_2$Cl$_2$ (1:1) (56 mg, 0.0680 mmol), and potassium-t-butoxide (229 mg, 2.04 mmol) are all dissolved in 3.0 ml of N-Methyl-2-pyrrolidinone. Mixture is heated at 150° C. in a microwave for 15 minutes using normal absorption and fixed hold on. The resulting solution is purified by silica gel chromatography (eluent: 1% to 20% MeOH:CHCl$_3$) followed by preparatory plate chromatography (eluent: 10% MeOH:CHCl$_3$) to afford the product as a brownish solid (29 mg, ~10%), mp 268-270° C.; $^1$H NMR (DMSO-d$_6$) δ 2.19 (s, 3H), 2.36-2.48 (m, 4H), 2.54 (s, 3H), 3.04-3.16 (m, 4H), 6.88-6.99 (m, 3H), 7.29 (d, J=9.0 Hz, 2H), 7.39-7.48 (m, 2H), 7.49-7.54 (m, 2H), 7.73 (s, 1H), 7.85 (d, J=8.7 Hz, 1H), 8.46 (d, J=12.8 Hz, 1H), 8.83 (s, 1H), 10.89 (s, 1H), 12.28 (d, J=12.9 Hz, 1H); IR (solid) 3300-2800, 1645, 1595, 1575, 1570, 1535, 1510, 1480, 1455, 1415, 1395, 1335, 1300, 1240, 1150, 1100, 1005, 960, 925, 850, 815, 790, 760, 720, and 690 cm$^{-1}$; mass spectrum [(+) ESI], m/z 496 (M+H)$^+$;

Anal. Calcd. for C$_{29}$H$_{29}$N$_5$O$_3$.0.5CH$_2$Cl$_2$: C, 65.85; H, 5.62; N, 13.02. Found: C, 66.00; H, 4.99; N, 12.72.

Example 882

4-[(4-piperidin-1-ylmethyl-phenylamino)-methylene]-6-o-tolylamino-4H-isoquinoline-1,3-dione Step 1

6-Bromo-4-[(4-piperidin-1-ylmethyl-phenylamino)methylene]-4H-isoquinoline-1,3-dione

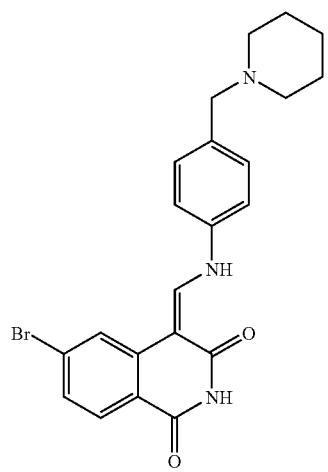

6-Bromo-4-methoxymethylene-4H-isoquinoline-1,3-dione (100 mg, 0.350 mmol) and 4-piperidin-1-ylmethyl-phenylamine (67 mg, 0.35 mmol) are suspended in 5 ml of dimethylformamide. Mixture is heated at 115° C. for 2 hours forming a homogeneous mixture. Mixture is cooled to room temperature and concentrated on high vacuum to yield an orange oil. Residue is taken up in ethyl ether causing an orange solid to form. Mixture is filtered, and residue washed with 50 ml of ethyl ether to afford the product as an orange solid (130 mg, 0.296 mmol, 85%); $^1$H NMR (DMSO-$d_6$) δ 1.37-1.52 (m, 6H), 2.25-2.36 (m, 4H), 3.40 (s, 2H), 7.31 (d, J=8.4 Hz, 2H), 7.39 (dd, J=1.6, 8.4 Hz, 1H), 7.52 (d, J=8.5 Hz, 2H), 7.89 (d, J=8.4 Hz, 1H), 8.44 (d, J=1.6 Hz, 1H), 8.92 (d, J=12.8 Hz, 1H), 11.39 (s, 1H), 12.50 (d, J=12.7 Hz, 1H).

Step 2

4-[(4-piperidin-1-ylmethyl-phenylamino)-methylene]-6-o-tolylamino-4H-isoquinoline-1,3-dione

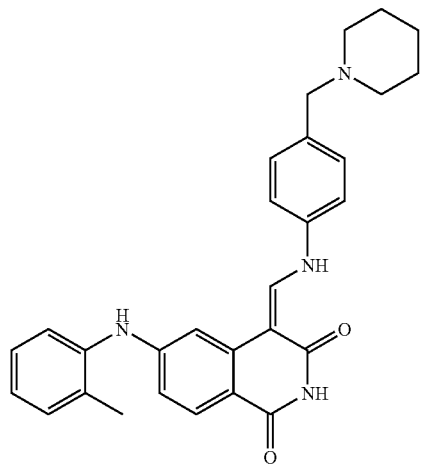

6-Bromo-4-[(4-piperidin-1-ylmethyl-phenylamino)methylene]-4H-isoquinoline-1,3-dione (200 mg, 0.584 mmol), o-tolylamine (125 mg, 1.17 mmol), allylchloro{1,3-bis(2,6-di-i-propylphenyl)imidazol-2-yilidine]palladium(II) ([Pr.HCl.Pd, 72 mg, 0.116 mmol), bis(dibenzylideneacetone) palladium [Pd(dba)$_2$, 33.5 mg, 0.0500 mmol], and potassium-t-butoxide (168 mg, 1.75 mmol) are all dissolved in 3 ml of N-methyl-2-pyrrolidinone. Mixture is heated at 150° C. in a microwave for 20 minutes to afford a dark brown homogeneous mixture. The resulting mixture is flashed on silica column with 5% MeOH/CHCl$_3$. Fractions containing product are condensed on rotovap. Residue is taken up in 3 mL of a 1:1 mixture of DMSO and methanol. Product is purified by HPLC using a C18 column and ramp of 30%-80% acetonitrile (0.05% TFA) and H$_2$O (0.05% TFA). Product containing fractions are combined and basified with 2N sodium hydroxide causing a yellow precipitate to form. Mixture is extracted with ethylacetate. Ethylacetate is removed on rotovap to afford the product as yellow solid (92 mg, 0.115 mmol, 33%); $^1$H NMR (DMSO-$d_6$) δ 1.30-1.40 (m, 2H), 1.40-1.48 (m, 4H), 2.19 (s, 3H), 2.22-2.29 (m, 4H), 3.26 (s, 2H), 6.62 (dd, J=1.85, 8.7 Hz, 1H), 6.98-7.03 (m, 1H), 7.16-7.20 (m, 1H), 7.22-7.30 (m, 5H), 7.30-7.35 (m, 2H), 7.77 (d, J=8.7 Hz, 1H), 7.94 (s, 1H), 8.43 (d, J=12.5 Hz, 1H), 10.87 (s, 1H), 12.18 (d, J=12.6 Hz, 1H); mass spectrum [(+) ESI], m/z 467 (M+H)$^+$.

Examples 883-913 are prepared using the appropriate aniline as shown in the following table and the procedure outlined in steps 1-2 of Example 882.

TABLE 1

| Example | Name | aniline | mass spectrum [(+)ESI], m/z (M + H)$^+$ |
|---|---|---|---|
| 883 | (4Z)-6-[(3-aminophenyl)amino]-4-({[4-(piperidin-1-ylmethyl)phenyl]amino}methylene)isoquinoline-1,3(2H,4H)-dione | m-phenylenediamine | 468 |
| 884 | (4Z)-6-[(3-methylphenyl)amino]-4-({[4-(piperidin-1-ylmethyl)phenyl]amino}methylene)isoquinoline-1,3(2H,4H)-dione | m-toluidine | 467 |
| 885 | (4Z)-6-[(3-acetylphenyl)amino]-4-({[4-(piperidin-1-ylmethyl)phenyl]amino}methylene)isoquinoline-1,3(2H,4H)-dione | 3-amino-acetophenone | 495 |
| 886 | (4Z)-4-({[4-(piperidin-1-ylmethyl)phenyl]amino}methylene)-6-{[3-(trifluoromethyl)phenyl]amino}isoquinoline-1,3(2H,4H)-dione | 3-amino-benzotrifluoride | 521 |
| 887 | (4Z)-6-anilino-4-({[4-(piperidin-1-ylmethyl)phenyl]amino}methylene)isoquinoline-1,3(2H,4H)-dione | aniline | 453 |
| 888 | (4Z)-6-{[4-(dimethylamino)phenyl]amino}-4-({[4-(piperidin-1-ylmethyl)phenyl]amino}methylene)isoquinoline-1,3(2H,4H)-dione | N,N-di-Me-p-phenylenediamine | 496 |
| 889 | (4Z)-6-[(4-methylphenyl)amino]-4-({[4-(piperidin-1-ylmethyl)phenyl]amino}methylene)isoquinoline-1,3(2H,4H)-dione | p-toluidine | 467 |
| 890 | (4Z)-6-[(4-chlorophenyl)amino]-4-({[4-(piperidin-1-ylmethyl)phenyl]amino}methylene)isoquinoline-1,3(2H,4H)-dione | 4-Cl-aniline | 488 |
| 891 | (4Z)-6-[(2-methoxyphenyl)amino]-4-({[4-(piperidin-1-ylmethyl)phenyl]amino}methylene)isoquinoline-1,3(2H,4H)-dione | o-anisidine | 483 |
| 892 | (4Z)-6-[(3-methoxyphenyl)amino]-4-({[4-(piperidin-1-ylmethyl)phenyl]amino}methylene)isoquinoline-1,3(2H,4H)-dione | m-anisidine | 483 |
| 893 | 3-{[(4Z)-1,3-dioxo-4-({[4-(piperidin-1-ylmethyl)phenyl]amino}methylene)-1,2,3,4-tetrahydroisoquinolin-6-yl]amino}benzonitrile | 3-amino-benzonitrile | 478 |
| 894 | 4-{[(4Z)-1,3-dioxo-4-({[4-(piperidin-1-ylmethyl)phenyl]amino}methylene)-1,2,3,4-tetrahydroisoquinolin-6-yl]amino}benzamide | p-amino-benzamide | 496 |

TABLE 1-continued

| Example | Name | aniline | mass spectrum [(+)ESI], m/z (M + H)+ |
|---|---|---|---|
| 895 | (4Z)-6-(2,3-dihydro-1H-inden-5-ylamino)-4-({[4-(piperidin-1-ylmethyl)phenyl]amino}methylene)isoquinoline-1,3(2H,4H)-dione | 5-aminoindan | 493 |
| 896 | (4Z)-6-(1,3-benzodioxol-5-ylamino)-4-({[4-(piperidin-1-ylmethyl)phenyl]amino}methylene)isoquinoline-1,3(2H,4H)-dione | 3,4-(methylene-dioxy)-aniline | 497 |
| 897 | 4-{[(4Z)-1,3-dioxo-4-({[4-(piperidin-1-ylmethyl)phenyl]amino}methylene)-1,2,3,4-tetrahydroisoquinolin-6-yl]amino}benzonitrile | 4-amino-benzonitrile | 478 |
| 898 | (4Z)-6-[(4-methoxyphenyl)amino]-4-({[4-(piperidin-1-ylmethyl)phenyl]amino}methylene)isoquinoline-1,3(2H,4H)-dione | p-anisidine | 483 |
| 899 | (4Z)-6-[(3-fluorophenyl)amino]-4-({[4-(piperidin-1-ylmethyl)phenyl]amino}methylene)isoquinoline-1,3(2H,4H)-dione | 3-F-aniline | 471 |
| 900 | (4Z)-6-{[3-methoxy-5-(trifluoromethyl)phenyl]amino}-4-({[4-piperidin-1-ylmethyl)phenyl]amino}methylene)isoquinoline-1,3(2H,4H)-dione | 3-amino-5-MeO-benzotrifluoride | 551 |
| 901 | (4Z)-6-[(4-acetylphenyl)amino]-4-({[4-(piperidin-1-ylmethyl)phenyl]amino}methylene)isoquinoline-1,3(2H,4H)-dione | 4-amino-acetophenone | 495 |
| 902 | 2-{[(4Z)-1,3-dioxo-4-({[4-(piperidin-1-ylmethyl)phenyl]amino}methylene)-1,2,3,4-tetrahydroisoquinolin-6-yl]amino}benzonitrile | 2-amino-benzonitrile | 478 |
| 903 | ethyl 4-{[(4Z)-1,3-dioxo-4-({[4-(piperidin-1-ylmethyl)phenyl]amino}methylene)-1,2,3,4-tetrahydroisoquinolin-6-yl]amino}benzoate | ethyl 4-aminobenzoate | 525 |
| 904 | (4Z)-6-[(2-chlorophenyl)amino]-4-({[4-(piperidin-1-ylmethyl)phenyl]amino}methylene)isoquinoline-1,3-(2H,4H)-dione | 2-Cl-aniline | 488 |
| 905 | (4Z)-6-[(3-chlorophenyl)amino]-4-({[4-piperidin-1-ylmethyl)phenyl]amino}methylene)isoquinoline-1,3(2H,4H)-dione | 3-Cl-aniline | 488 |
| 906 | (4Z)-6-anilino-4-[({4-[(dimethylamino)methyl]phenyl}amino)methylene]isoquinoline-1,3(2H,4H)-dione | aniline | 413 |
| 907 | (4Z)-4-[({4-[(dimethylamino)methyl]phenyl}amino)methylene]-6-[(3-methoxyphenyl)amino]isoquinoline-1,3(2H,4H)-dione | m-anisidine | 443 |
| 908 | (4Z)-4-[({4-[(dimethylamino)methyl]phenyl}amino)methylene]-6-[(4-methoxyphenyl)amino]isoquinoline-1,3(2H,4H)-dione | p-anisidine | 443 |
| 909 | (4Z)-6-[(3-acetylphenyl)amino]-4-[({4-[(dimethylamino)methyl]phenyl}amino)methylene]isoquinoline-1,3(2H,4H)-dione | 3-amino-acetophenone | 455 |
| 910 | (4Z)-6-[(3-acetylphenyl)amino]-4-({[4-(3,5-dimethylpiperazin-1-yl)phenyl]amino}methylene)isoquinoline-1,3(2H,4H)-dione | 3-amino-acetophenone | 510 |
| 911 | (4Z)-4-[({4-[(diethylamino)methyl]phenyl}amino)methylene]-6-[(4-methylphenyl)amino]isoquinoline-1,3(2H,4H)-dione | p-toluidine | 455 |
| 912 | (4Z)-6-(1H-indol-5-ylamino)-4-({[4-(piperidin-1-ylmethyl)phenyl]amino}methylene)isoquinoline-1,3(2H,4H)-dione | 5-amino-indole | 492 |
| 913 | (4Z)-4-({[4-(piperidin-1-ylmethyl)phenyl]amino}methylene)-6-(quinolin-5-ylamino)isoquinoline-1,3(2H,4H)-dione | 5-amino-quinoline | 504 |

TABLE I

LCMS Data: Molecular ion and retention time

| Example | LC @ 254 nm | M + H |
|---|---|---|
| 168 | 1.783 min | 424.1 |
| 169 | 1.757 min | 414.0 |
| 540 | 1.638 min | 358.0 |
| 541 | 2.700 min | 349.0 |
| 542 | 1.973 min | 309.0 |
| 543 | 1.427 min | 407.1 |
| 544 | 1.748 min | 325.0 |
| 545 | 1.617 min* | 280.1 |
| 546 | 1.735 min* | 350.0 (M − H) |
| 547 | 0.214 min | 307.1 |
| 548 | 2.175 min | 355.0 |
| 549 | 2.256 min* | 440.1 (M − H) |
| 550 | 1.940 min | 311.0 |
| 551 | 2.503 min | 381.1 |
| 553 | 2.247 min | 439.0 |
| 554 | 2.126 min* | 336.1 |
| 555 | 2.447 min | 304.0 |
| 556 | 2.600 min | 425.0 |
| 557 | 2.414 min* | 333.1 (M − H) |
| 558 | 2.402 min | 351.1 |
| 559 | 2.048 min | 281.0 |
| 560 | 1.970 min* | 323.1 (M − H) |
| 561 | 2.159 min* | 311.1 |
| 562 | 1.980 min* | 323.1 (M − H) |
| 563 | 1.959 min* | 325.1 |
| 564 | 1.551 min* | 341.1 |
| 565 | 1.933 min* | 297.0 |
| 566 | 1.692 min* | 369.1 |
| 567 | 1.864 min* | 369.1 |
| 568 | 2.021 min* | 295.1 (M − H) |
| 569 | 2.040 min* | 332.1 |
| 570 | 2.630 min* | 358.1 (M − H) |
| 571 | 1.469 min | 462.1 |
| 572 | 1.348 min | 446.2 |
| 574 | 1.402 min | 350.1 |
| 575 | 1.780 min | 390.2 |
| 576 | 1.297 min | 348.1 |
| 577 | 1.790 min | 390.2 |

TABLE I-continued

LCMS Data: Molecular ion and retention time

| Example | LC @ 254 nm | M + H |
|---|---|---|
| 579 | 2.253 min* | 440.0 |
| 580 | 2.128 min* | 400.1 |
| 581 | 1.911 min* | 372.0 |
| 582 | 2.249 min* | 440.0 |
| 583 | 2.010 min* | 386.0 |
| 584 | 2.165 min* | 400.1 |
| 585 | 1.831 min* | 336.1 |
| 586 | 2.089 min* | 362.1 |
| 587 | 2.240 min* | 376.1 |
| 588 | 2.263 min* | 440.0 |
| 589 | 1.864 min* | 372.0 |
| 590 | 2.357 min* | 448.1 |
| 591 | 2.241 min* | 440.0 |
| 592 | 2.145 min* | 400.1 |
| 593 | 2.283 min* | 378.1 |
| 594 | 1.716 min | 297.1 |
| 595 | 1.467 min* | 377.2 |
| 596 | 2.222 min* | 388.1 |
| 597 | 1.517 min* | 389.1 |
| 598 | 1.170 min* | 393.1 |
| 599 | 1.514 min* | 448.2 |
| 600 | 1.568 min* | 391.2 |
| 601 | 1.670 min* | 417.2 |
| 602 | 1.912 min* | 417.1 |
| 603 | 1.470 min | 377.1 |
| 604 | 1.647 min | 308.2 |
| 605 | 2.311 min | 440.0 |
| 606 | 2.007 min | 368.1 |
| 607 | 1.583 min | 449.0 |
| 608 | 2.082 min | 382.1 |
| 609 | 2.102 min | 380.1 |
| 610 | 2.406 min | 428.1 |
| 611 | 2.521 min | 518.0 |
| 612 | 2.034 min* | 370.1 (M − H) |
| 613 | 2.029 min | 386.0 |
| 614 | 1.614 min | 378.1 |
| 615 | 0.893 min | 378.1 |
| 616 | 2.558 min* | 364.1 (M − H) |
| 617 | 2.819 min | 362.1 |
| 618 | 0.206 min* | 266.1 |
| 619 | 2.30 min* | 329 (M − H) |
| 620 | 2.423 min | 387.0 |
| 621 | 2.160 min | 377.0 |
| 622 | 2.118 min | 464 |
| 623 | 3.048 min | 428.0 (M − H) |
| 624 | 3.057 min | 427.7 (M − H) |
| 625 | 2.525 min | 430.6 |
| 626 | 2.975 min | 417.7 (M − H) |
| 627 | 3.072 min | 433.6 (M − H) |
| 628 | 3.057 min | 434.0 (M − H) |
| 629 | 2.586 min | 417.0 (M − H) |
| 630 | 2.460 min | 367.1 (M − H) |
| 631 | 2.286 min | 367.1 (M − H) |
| 632 | 2.722 min | 482.0 (M − H) |
| 633 | 2.160 min | 484.9 |
| 634 | 2.629 min | 472.0 (M − H) |
| 635 | 2.716 min | 487.9 (M − H) |
| 636 | 2.667 min | 487.9 (M − H) |
| 637 | 2.240 min | 471.0 (M − H) |
| 638 | 2.089 min | 421.0 (M − H) |
| 639 | 1.932 min | 421.0 (M − H) |
| 640 | 2.694 min | 437.0 |
| 641 | 2.729 min | 437.0 |
| 642 | 2.166 min | 438.0 |
| 643 | 2.633 min | 423.0 (M − H) |
| 644 | 2.723 min | 442.9 |
| 645 | 2.669 min | 442.9 |
| 646 | 2.240 min | 426.0 |
| 647 | 2.159 min | 376.1 |
| 648 | 2.224 min | 407 |
| 649 | 1.816 min | 405 (M − H) |
| 650 | 2.941 min | 404 (M − H) |
| 651 | 1.642 min | 396 |
| 652 | 1.789 min | 459 (M − H) |
| 653 | 1.365 min | 461 |
| 654 | 2.598 min | 460 |
| 655 | 1.960 min | 462 |
| 656 | 2.848 min | 464 (M − H) |
| 657 | 0.286 min | 464 |
| 658 | 0.447 min | 450 |
| 659 | 2.125 min | 481 |
| 660 | 2.673 min | 425 (M − H) |
| 661 | 3.003 min | 463 |
| 662 | 1.796 min | 414 |
| 663 | 1.475 min | 414 |
| 664 | 2.951 min | 417 (M − H) |
| 665 | 0.357 min | 417 |
| 666 | 1.821 min | 433 (M − H) |
| 667 | 0.500 min | 403 |
| 668 | 2.111 min | 489.0 |
| 669 | 2.107 min | 479.0 |
| 670 | 2.115 min | 495.0 |
| 671 | 1.798 min | 478.0 |
| 672 | 1.663 min | 428.0 |
| 673 | 1.485 min | 428.1 |
| 674 | 2.279 min | 515 |
| 675 | 1.569 min | 466 |
| 676 | 0.423 min | 466 |
| 677 | 2.134 min | 465 |
| 678 | 1.669 min | 467 |
| 679 | 0.217 min | 469 |
| 680 | 0.312 min | 455 |
| 681 | 2.088 min | 486 |
| 682 | 1.832 min | 469.0 |
| 683 | 1.869 min | 469.0 |
| 684 | 1.943 min | 457.0 |
| 685 | 1.757 min | 483.0 |
| 686 | 1.778 min | 483.0 |
| 687 | 2.108 min | 507.0 |
| 688 | 1.792 min | 481.0 |
| 689 | 2.018 min | 473.0 |
| 690 | 1.999 min | 473.0 |
| 691 | 1.931 min | 473.0 |
| 692 | 2.047 min | 453.0 |
| 693 | 1.960 min | 453.1 |
| 694 | 1.934 min | 453.0 |
| 695 | 1.856 min | 464.0 |
| 696 | 2.231 min | 515.0 |
| 697 | 2.232 min | 515.0 |
| 698 | 1.795 min | 509.0 |
| 699 | 1.837 min | 509.0 |
| 700 | 1.985 min | 485.0 |
| 701 | 2.761 min | 408.0 (M − H) |
| 702 | 2.793 min | 408.0 (M − H) |
| 703 | 2.770 min | 408.0 (M − H) |
| 704 | 2.825 min | 396.0 (M − H) |
| 705 | 2.834 min | 396.0 (M − H) |
| 706 | 2.781 min | 396.0 (M − H) |
| 707 | 2.429 min | 422.1 (M − H) |
| 708 | 2.415 min | 421.0 (M − H) |
| 709 | 3.079 min | 446.0 (M − H) |
| 710 | 2.698 min | 420.0 (M − H) |
| 711 | 2.561 min | 422.0 |
| 712 | 3.003 min | 412.0 (M − H) |
| 713 | 2.982 min | 412.0 (M − H) |
| 714 | 2.878 min | 412.0 (M − H) |
| 715 | 2.946 min | 394.0 |
| 716 | 2.942 min | 392.1 (M − H) |
| 717 | 2.912 min | 394.0 |
| 718 | 2.530 min | 403.0 (M − H) |
| 719 | 2.665 min | 403.0 (M − H) |
| 720 | 3.237 min | 454.0 (M − H) |
| 721 | 3.217 min | 454.0 (M − H) |
| 722 | 3.232 min | 420.1 (M − H) |
| 723 | 2.951 min | 424.0 (M − H) |
| 724 | 1.211 min | 419 |
| 725 | 1.673 min | 480 |
| 726 | 2.257 min | 499 |
| 727 | 1.907 min | 509 |
| 728 | 1.779 min | 544 |

TABLE I-continued

LCMS Data: Molecular ion and retention time

| Example | LC @ 254 nm | M + H |
|---|---|---|
| 729 | 2.362 min | 533 |
| 730 | 0.438 min | 449 |
| 731 | 2.107 min | 495 |
| 732 | 2.107 min | 495 |
| 733 &734 | 1.388 min | 417 |
| 735 | 2.005 min | 428 |
| 736 | 1.625 min | 470 |
| 737 | 2.401 min | 463.7 |
| 738 | 2.433 min | 449.7 (M − H) |
| 739 | 2.447 min | 451.7 |
| 740 | 2.407 min | 451.9 |
| 741 | 1.970 min | 475.8 (M − H) |
| 742 | 2.047 min | 475.7 (M − H) |
| 743 | 2.711 min | 499.9 (M − H) |
| 744 | 2.723 min | 501.9 |
| 745 | 2.568 min | 501.9 |
| 746 | 2.237 min | 474.0 (M − H) |
| 747 | 2.257 min | 474.0 (M − H) |
| 748 | 2.216 min | 474.0 (M − H) |
| 749 | 2.626 min | 466.0 (M − H) |
| 750 | 2.631 min | 465.9 (M − H) |
| 751 | 2.508 min | 467.9 |
| 752 | 2.576 min | 448.0 |
| 753 | 2.574 min | 448.0 |
| 754 | 2.536 min | 448.0 |
| 755 | 2.286 min | 457.0 (M − H) |
| 756 | 2.315 min | 475.0 (M − H) |
| 757 | 2.879 min | 508.0 (M − H) |
| 758 | 2.848 min | 507.7 (M − H) |
| 759 | 2.107 min | 501.8 (M − H) |
| 760 | 2.208 min | 502.0 (M − H) |
| 761 | 2.828 min | 475.8 |
| 762 | 2.816 min | 475.7 |
| 763 | 2.557 min | 477.8 (M − H) |
| 764 | 2.372 min | 416.8 |
| 765 | 2.400 min | 416.8 |
| 766 | 2.367 min | 416.8 |
| 767 | 2.433 min | 402.8 (M − H) |
| 768 | 2.447 min | 402.9 (M − H) |
| 769 | 2.384 min | 404.8 |
| 770 | 2.003 min | 429.0 (M − H) |
| 771 | 2.036 min | 428.8 (M − H) |
| 772 | 2.711 min | 452.8 (M − H) |
| 773 | 2.676 min | 452.7 (M − H) |
| 774 | 2.538 min | 454.7 |
| 775 | 2.162 min | 429.0 |
| 776 | 2.266 min | 429.0 |
| 777 | 2.216 min | 429.0 |
| 778 | 2.641 min | 420.9 |
| 779 | 2.628 min | 420.9 |
| 780 | 2.510 min | 421.0 |
| 781 | 2.578 min | 401.0 |
| 782 | 2.576 min | 401.0 |
| 783 | 2.533 min | 401.0 |
| 784 | 2.291 min | 412.0 |
| 785 | 2.319 min | 412.0 |
| 786 | 2.894 min | 463.0 |
| 787 | 2.883 min | 463.0 |
| 788 | 2.576 min | 412.8 (MH$^+$ − CO$_2$) |
| 789 | 2.208 min | 455.0 (M − H) |
| 790 | 2.875 min | 429.0 |
| 791 | 2.848 min | 429.0 |
| 792 | 2.557 min | 432.7 |
| 793 | 2.489 min | 433.0 |
| 794 | 0.418 min | 504 |
| 795 | 1.629 min | 461 |
| 796 | 1.579 min | 433 |
| 797 | 1.691 min | 447 |
| 798 | 1.828 min | 461 |
| 799 | 1.532 min | 463 |
| 800 | 1.451 min | 501 |
| 801 | 1.884 min | 495 |
| 802 | 1.649 min | 442 |
| 803 | 2.041 min | 504 |
| 804 | 2.457 min | 471 (M − H) |
| 805 | 2.401 min | 452 |
| 806 | 1.851 min | 483.0 |
| 807 | 1.859 min | 482.0 |
| 808 | 1.686 min | 469.0 |
| 809 | 1.783 min | 511.0 |
| 810 | 1.529 min | 454.0 |
| 811 | 2.163 min | 508.9 |
| 812 | 2.364 min | 429.0 (M − H) |
| 813 | 2.243 min | 447.0 |
| 814 | 2.406 min | 447.0 |
| 815 | 2.288 min | 476.9 |
| 816 | 2.354 min | 430.0 |
| 817 | 1.954 min | 415.0 (M − H) |
| 818 | 2.801 min | 467.9 (M − H) |
| 819 | 2.146 min | 459.9 |
| 820 | 2.421 min | 429.9 (M − H) |
| 821 | 1.830 min | 402.0 |
| 822 | 2.008 min | 442.0 (M − H) |
| 823 | 2.760 min | 454.9 (M − H) |
| 824 | 1.613 min | 428 |
| 825 | 2.781 min | 427 |
| 826 | 1.978 min | 463 |
| 827 | 2.62 min | 487 |
| 828 | 1.696 min | 441 (M − H) |
| 829 | 2.132 min | 510 |
| 830 | 1.874 min | 429.1 |
| 831 | 1.918 min | 439.1 |
| 832 | 2.620 min | 401.0 |
| 833 | 2.594 min | 431.0 |
| 834 | 2.920 min | 451.0 |
| 835 | 2.425 min | 440.0 |
| 836 | 2.294 min | 390.0 |
| 837 | 2.432 min | 391.0 |
| 838 | 1.802 min | 413.8 |
| 839 | 1.984 min | 447.8 (M − H) |
| 840 | 1.755 min | 454.8 |
| 843 | 1.823 min | 486.1 |
| 844 | 2.824 min | 360 |
| 845 | 1.968 min | 428 |
| 846 | 1.954 min | 413 |
| 848 | 2.036 min | 431 |
| 849 | 2.659 min | 346 |
| 850 | 2.530 min | 346 |
| 851 | 1.904 min | 535.2 |
| 852 | 1.766 min | 577.3 |
| 853 | 1.625 min | 485.2 |
| 854 | 1.317 min | 527.3 |
| 855 | 1.758 min | 495.2 |
| 841 | 2.822 min | 359 |
| 842 | 1.780 min | 428 |
| 847 | 1.993 min | 413 |
| 856 | 2.509 min | 301 |
| 857 | 1.640 min | 327 |
| 858 | 2.567 min | 350 |
| 859 | 2.245 min | 267 |
| 860 | 1.792 min | 334 |
| 861 | 1.365 min | 372 |
| 862 | 2.529 min | 377 |
| 863 | 2.487 min | 374 |

Standard Pharmacological Test Procedures

Evaluation of representative compounds of this invention in several standard pharmacological test procedures indicated that the compounds of this invention possess significant antiproliferative activity. Based on the activity, which includes protein kinase activity, shown in the standard pharmacological test procedures, the compounds of this invention are therefore useful as antineoplastic agents. The compounds of this invention are useful in the treatment of cancer in mammals. In particular, these compounds are useful in treating, inhibiting the growth of, or eradicating neoplasms such as those of the breast, kidney, bladder, mouth, larynx, esophagus, stomach, colon, ovary, lung, pancreas, liver, prostate and skin.

The standard pharmacological test procedures and the results obtained for representative examples of the invention are shown in the following tables.

Biological Data

CDK1, CDK2, CDK4 and CDK6

Materials and Methods:
1. High-binding ELISA microtiter plates (Costar) were coated with 40 µl of the kinase substrate (GST fusion of C-terminal fragment of the retinoblastoma susceptibility gene product) diluted to 10 µg/ml in tris-buffered saline (TBS), overnight at 4° C.
2. Non-specific binding sites were blocked for 1 hour at 4° C. with Superblock in TBS (Pierce), and the plates rinsed with water.
3. For the screen, 1.5 µl of test compound (200 µg/ml stock in 20% DMSO/20 mM HEPES, pH 7.5) was added to each well. Final dose of the test compound in the assay was 10 ug/ml. For $IC_{50}$ analysis, compounds were tested at 5 doses (10-fold increments).
4. The kinase reaction (30 µl) was dispensed into each well. Reactions contained 200 µM ATP, 0.5 mg/ml bovine serum albumin (BSA; Sigma), and 0.5 µl partially purified cyclin D1/cdk 4 enzyme*. The enzyme complex is expressed in insect cells (Sf9) infected with recombinant baculovirus and partially purified using ammonium sulfate fractionation. Reaction volumes were adjusted to 30 µl with kinase assay buffer (50 mM HEPES, pH 7.5, 10 mM $MgCl_2$, 5% glycerol, 10 mM 2-mercaptoethanol).
   *: For CDK2 assay, 1.0 µl cyclin E/CDK2 enzyme (diluted 1:1000 in kinase assay buffer) was used. The enzyme is isolated from insect cells (Sf9) infected with recombinant baculovirus and partially purified using ammonium sulfate fractionation. For CDK1 assay, 0.08 µl cyclin B/CDK1 enzyme [New England BioLabs; the enzyme is isolated from insect cells (Sf9) infected with recombinant baculovirus carrying human cdc 2 and human cyclin B] was used.

REFERENCES

Hunter, T. and Pines, J. Cyclins and Cancer II: Cyclin D and CDK come of age. Cell 79, 573-582 (1994).
Rao, R. N. Targets for cancer therapy in the cell cycle pathway. Curr. Opinion in Oncol. 8, 516-524 (1996).
5. Plates were incubated at 30° C. for 1 hour.
6. The reaction mixture was removed by aspiration and replaced with 250 µl TBS containing 0.1% Tween-20 and 5% nonfat dry milk (blocking buffer). The plates were incubated at 4° C. for 1 hour.
7. The blocking buffer was removed and replaced with 50 µl of the primary antibody [anti-phospho-Rb ser 795 (New England BioLabs) diluted 1:1000 in blocking buffer]. Incubation was at 4° C. for 16-20 hours.
8. The wells were rinsed 3 times with 250 µl of TBS containing 0.1% Tween-20 followed by the addition of 50 µl of secondary antibody [anti-rabbit IgG conjugated to horseradish peroxidase (Amersham Life Science) diluted 1:1000 in blocking buffer].
9. After a 1 hour incubation at room temperature, the wells were rinsed 3 times with 250 µl of TBS/0.1% Tween 20.
10. TMB (3,3',5,5'-tetramethylbenzidine dihydrochloride) substrate solution (100 µl; Pierce) was added to each well and the color development reaction allowed to proceed 5-10 minutes at room temperature with shaking. The reaction was stopped by the addition of 2N sulfuric acid (100 µl) and the absorbance values read at 450 nm in a microplate reader (Molecular Devices).

Analysis of Results:
1. The percentage of the absorbance value in wells containing the test compound relative to control wells (no test agent) was determined.
2. $IC_{50}$ values of selected compounds were determined from inhibition curves, after subtracting background values (no substrate).

TABLE II

In Vitro Enzyme Assays CDK1, CDK2, CDK4 Activity

| | $IC_{50}$ (µM) | | |
|---|---|---|---|
| EXAMPLE | CDK4 | CDK1 | CDK2 |
| 1 | 38 | >36 | 18.9 |
| 2 | 12.1 | >29 | >29 |
| 3 | 42 | >32 | 13 |
| 4 | 4.1 | >28 | >28 |
| 5 | 10.2 | >28 | >28 |
| 6 | >50 | >29 | >29 |
| 7 | 9.5 | >33 | 5.6 |
| 8 | >50 | >32 | >32 |
| 9 | >50 | >32 | >32 |
| 10 | >50 | >34 | >34 |
| 11 | >50 | >37 | >37 |
| 12 | >50 | >32 | >32 |
| 13 | 7.9 | >28 | 23 |
| 19 | 10.7 | >27 | 21.6 |
| 20 | 6.7 | >26 | 26 |
| 23 | 5.15 | >26 | 26 |
| 24 | 1.1 | >50 | >50 |
| 25 | 6.6 | >29 | 22.7 |
| 26 | 4.3 | >27 | >27 |
| 27 | 1.4 | >50 | >50 |
| 29 | 15 | >23 | >23 |
| 30 | >50 | >50 | 1.4 |
| 31 | >50 | >50 | 2.4 |
| 33 | 11 | 7.2 | >50 |
| 37 | 14.8 | >50 | >50 |
| 38 | 1.1 | >50 | >50 |
| 39 | 1.1 | >50 | >50 |
| 40 | 0.04 | >50 | >50 |
| 42 | 15.1 | >50 | >50 |
| 45 | 12.1 | >50 | 47 |
| 46 | 0.033 | >50 | >50 |
| 47 | 1.1 | >50 | 18.1 |
| 48 | 3.5 | >50 | 8.1 |
| 50 | 0.03 | >50 | >50 |
| 52 | 24.3 | >50 | 4.5 |
| 54 | 0.16 | >50 | >50 |
| 55 | 2.5 | >50 | >50 |
| 56 | 0.48 | 16.2 | 1.3 |
| 58 | 12.4 | 31.8 | 19.4 |
| 59 | 0.23 | >50 | 25.2 |
| 60 | 0.14 | >50 | >50 |
| 61 | >50 | 37.2 | 17.3 |
| 62 | 31.1 | >50 | 4.5 |
| 63 | 0.78 | >50 | 16.9 |
| 64 | 0.015 | 16.5 | 0.62 |
| 65 | 41 | >50 | 47 |
| 66 | 21.2 | >50 | 39.8 |
| 67 | 0.23 | >50 | >50 |
| 68 | 0.17 | >50 | 6.6 |
| 69 | 0.12 | >50 | 44.5 |
| 70 | 9.4 | 16.9 | >50 |
| 71 | 0.004 | 9.7 | 3.1 |
| 72 | 0.19 | >50 | >50 |
| 73 | 0.83 | 43.5 | 7.7 |
| 74 | 0.14 | >50 | >50 |
| 75 | 0.29 | >50 | 7.2 |
| 76 | 0.39 | 40.7 | >50 |

TABLE II-continued

In Vitro Enzyme Assays CDK1, CDK2, CDK4 Activity

| EXAMPLE | IC$_{50}$ (μM) | | |
|---|---|---|---|
| | CDK4 | CDK1 | CDK2 |
| 77 | 0.38 | >50 | >50 |
| 78 | 0.007 | >50 | >50 |
| 79 | 0.026 | 42.6 | 2.2 |
| 80 | 0.01 | 6 | 0.87 |
| 81 | 0.48 | >50 | >50 |
| 82 | 0.3 | >50 | 20.4 |
| 84 | 0.94 | 8.1 | 3.1 |
| 85 | 0.001 | >50 | >50 |
| 86 | 0.002 | >50 | >50 |
| 87 | 0.0008 | 1.2 | 8.1 |
| 88 | 0.002 | 23.3 | 18.3 |
| 89 | 0.002 | >50 | 3.3 |
| 90 | 0.031 | 22.3 | 2.9 |
| 91 | 2 | >50 | >50 |
| 92 | <0.005 | 2.5 | 1.1 |
| 93 | 0.037 | >50 | >50 |
| 94 | 9.4 | >50 | >50 |
| 95 | 0.32 | >50 | >50 |
| 96 | 0.027 | >50 | >50 |
| 97 | 1 | >50 | 6.7 |
| 98 | 0.21 | >50 | 7.1 |
| 99 | 1.4 | >50 | >50 |
| 100 | 0.34 | >50 | >50 |
| 102 | 0.13 | >50 | >50 |
| 103 | 0.041 | >50 | >50 |
| 104 | 0.05 | >50 | >50 |
| 105 | 24.3 | >50 | >50 |
| 106 | 31.5 | >50 | >50 |
| 107 | 0.08 | >50 | >50 |
| 108 | 0.12 | >50 | >50 |
| 110 | 15.8 | 15.8 | 26.5 |
| 111 | 19.4 | >50 | >50 |
| 112 | 2.9 | 3.8 | >50 |
| 113 | 0.02 | 47.6 | 37.2 |
| 114 | 7.4 | >50 | >50 |
| 115 | 0.13 | 8.2 | 7.7 |
| 116 | 0.13 | >50 | >50 |
| 117 | 27.8 | >50 | >50 |
| 118 | 1.0 | >50 | >50 |
| 119 | 1.62 | >50 | >50 |
| 120 | 0.92 | >50 | >50 |
| 122 | 0.04 | 16.1 | 1.6 |
| 123 | 34.7 | >50 | >50 |
| 124 | 0.36 | 50.0 | >50 |
| 125 | 44.4 | >50 | >50 |
| 126 | 0.66 | >50 | 10.0 |
| 127 | 0.37 | >50 | >50 |
| 128 | 1.8 | >50 | >50 |
| 130 | 0.35 | 42.5 | 34.5 |
| 134 | 0.04 | >50 | 13.2 |
| 136 | 0.005 | 4.0 | 0.43 |
| 137 | 0.69 | >50 | 33.9 |
| 138 | 0.14 | >50 | >50 |
| 139 | 0.04 | >50 | 50.0 |
| 141 | 0.19 | >50 | >50 |
| 142 | 0.02 | >50 | 50.0 |
| 143 | 0.06 | 13.6 | 1.1 |
| 144 | 1.90 | >50 | >50 |
| 145 | 0.004 | 26.3 | 6.1 |
| 146 | 0.10 | >50 | 8.6 |
| 147 | 4.6 | >50 | 27.7 |
| 148 | 0.44 | >50 | 31.7 |
| 149 | 0.33 | >50 | 29 |
| 150 | 7.2 | >50 | >50 |
| 151 | 0.03 | 36.4 | 1.8 |
| 152 | 0.06 | 36.3 | >50 |
| 153 | 0.8 | 4.3 | 4.3 |
| 154 | 3.3 | >50 | >50 |
| 156 | 0.04 | >50 | >50 |
| 157 | 0.03 | >50 | 13.6 |
| 158 | 0.04 | >50 | >50 |
| 160 | 20.4 | >50 | 31 |
| 162 | 18.6 | >50 | >50 |
| 163 | >50 | >50 | 44.4 |
| 164 | 43.4 | >50 | 11 |
| 165 | 0.2 | >50 | 18.9 |
| 166 | 0.03 | >50 | 45.5 |
| 168 | 1.9 | >50 | >50 |
| 169 | 0.2 | >50 | >50 |
| 170 | 46.5 | >50 | >50 |
| 171 | 2.3 | 33.2 | >50 |
| 172 | 23.6 | 23.6 | >50 |
| 173 | 0.11 | >50 | 4.7 |
| 175 | 4.5 | 3.1 | 18.5 |
| 176 | 1.3 | >50 | >50 |
| 177 | 1.1 | >50 | >50 |
| 178 | 0.02 | >50 (13.9) | 2.6 |
| 180 | 0.07 | >50 | >50 |
| 182 | 2.3 | 2.3 | >50 |
| 183 | 0.11 | >50 | >50 |
| 184 | 6.0 | >50 | 41.5 |
| 186 | 11.0 | 13.8 | >50 |
| 187 | 2.3 | 1.7 | 3.3 |
| 188 | 33.2 | 24.2 | 39.7 |
| 189 | 0.37 | >50 | >50 |
| 192 | 0.04 | >50 | >50 |
| 193 | 1.4 | >50 | >50 |
| 194 | 15.8 | >50 | >50 |
| 195 | 2.0 | >50 | >50 |
| 196 | 1.1 | >50 | 40.6 |
| 197 | 12.3 | >50 | >50 |
| 198 | 3.1 | 12.0 | 22.1 |
| 199 | <0.005 | >50 | 50.0 |
| 200 | 0.009 | >50 | 26.5 |
| 201 | 4.1 | >50 | >50 |
| 202 | 33.2 | >50 | >50 |
| 203 | 14.7 | >50 | >50 |
| 204 | 0.22 | >50 | 7.0 |
| 205 | 0.44 | 31.0 | 48.6 |
| 206 | 0.16 | 41.9 | >50 |
| 207 | 0.20 | >50 | >50 |
| 208 | 0.009 | >50 | 30.3 |
| 209 | 0.01 | >50 | 9.2 |
| 210 | 0.008 | 18.9 | 2.1 |
| 211 | 2.5 | 38.0 | 20.2 |
| 212 | 0.77 | >50 | >50 |
| 213 | 0.19 | >50 | >50 |
| 214 | 17.6 | >50 | 6.3 |
| 216 | 1.0 | >50 | >50 |
| 217 | 13.9 | 31.7 | >50 |
| 218 | 0.15 | >50 | >50 |
| 219 | 0.27 | >50 | >50 |
| 220 | 3.3 | >50 | >50 |
| 221 | 0.32 | >50 | >50 |
| 222 | 31.7 | >50 | 6.1 |
| 224 | 0.17 | 45.5 | 4.0 |
| 225 | 0.56 | >50 | 2.7 |
| 226 | 0.4 | >50 | 2.4 |
| 227 | 0.08 | >50 | 6.7 |
| 228 | ~1.5 | >50 | >50 |
| 229 | 0.24 | >50 | >50 |
| 230 | 27.7 | >50 | 38 |
| 231 | 3.6 | 29.6 | >50 |
| 232 | 2.7 | >50 | >50 |
| 233 | 3.0 | >50 | >50 |
| 234 | 2.8 | >50 | >50 |
| 235 | 17.3 | 25.3 | 23.1 |
| 236 | 0.22 | >50 | >50 |
| 237 | 0.44 | 32.4 | 22.6 |
| 238 | 4.8 | >50 | >50 |
| 239 | 0.31 | >50 | 4.2 |
| 240 | 17.3 | >50 | >50 |
| 241 | 0.45 | >50 | >50 |
| 243 | 1.2 | 12.3 | 1.9 |
| 244 | 45.5 | >50 | >50 |
| 245 | 2.0 | >50 | >50 |

TABLE II-continued

In Vitro Enzyme Assays CDK1, CDK2, CDK4 Activity

| | IC$_{50}$ (μM) | | |
|---|---|---|---|
| EXAMPLE | CDK4 | CDK1 | CDK2 |
| 246 | 28.3 | >50 | >50 |
| 248 | 2.7 | >50 | >50 |
| 249 | 0.11 | >50 | >50 |
| 250 | 2.8 | >50 | >50 |
| 251 | 0.31 | >50 | >50 |
| 253 | 2.9 | >50 | >50 |
| 254 | 7.4 | >50 | >50 |
| 255 | 2.5 | >50 | >50 |
| 256 | 4.3 | >50 | >50 |
| 258 | 0.48 | >50 | >50 |
| 259 | 1.2 | 20.7 | 2.5 |
| 260 | 22.6 | >50 | 14.7 |
| 261 | 2.6 | >50 | >50 |
| 263 | 0.50 | >50 | >50 |
| 264 | 1.0 | >50 | >50 |
| 265 | 0.3 | >50 | >50 |
| 266 | 1.9 | >50 | >50 |
| 267 | 0.008 | 16.5 | 1.7 |
| 268 | 34.7 | 1.2 | 23.6 |
| 269 | >50 | 1.9 | 24.7 |
| 270 | 3.0 | >50 | 38.8 |
| 272 | 50.0 | >50 | 39.7 |
| 273 | 24.7 | >50 | 12.3 |
| 274 | 1.9 | 15.1 | 2.8 |
| 275 | 14.4 | >50 | >50 |
| 276 | 42.5 | >50 | >50 |
| 277 | 35.5 | >50 | 39.7 |
| 278 | 0.03 | >50 | >50 |
| 279 | 0.19 | >50 | >50 |
| 280 | 29.0 | >50 | 4.5 |
| 282 | 27.7 | >50 | >50 |
| 283 | 10.0 | >50 | >50 |
| 285 | 0.76 | >50 | >50 |
| 286 | 3.0 | >50 | >50 |
| 287 | 1.6 | >50 | >50 |
| 288 | 2.9 | >50 | >50 |
| 289 | 0.31 | >50 | >50 |
| 290 | 0.32 | >50 | >50 |
| 291 | 0.19 | >50 | >50 |
| 292 | ~1.5 | ~19.7 | ~33.9 |
| 293 | 13.8 | >50 | >50 |
| 295 | 1.5 | >50 | >50 |
| 296 | 2.1 | >50 | >50 |
| 297 | 0.08 | >50 | >50 |
| 298 | 29.0 | 40.6 | >50 |
| 299 | 0.19 | >50 | >50 |
| 301 | 0.09 | >50 | 8.4 |
| 303 | 0.39 | 33.9 | 3.7 |
| 304 | 1.5 | >50 | 36.3 |
| 305 | 1.7 | >50 | 39.7 |
| 306 | 6.7 | >50 | >50 |
| 307 | 9.8 | >50 | 38.0 |
| 308 | 2.6 | >50 | >50 |
| 309 | 14.7 | >50 | >50 |
| 310 | 9.4 | >50 | >50 |
| 311 | 8.6 | >50 | >50 |
| 312 | 0.27 | >50 | 21.6 |
| 314 | 1.5 | >50 | 37.1 |
| 315 | 0.19 | 43.4 | 31.0 |
| 316 | 1.3 | >50 | 16.9 |
| 317 | 0.04 | >50 | >50 |
| 319 | 1.4 | >50 | >50 |
| 320 | 0.12 | 6.8 | 4.0 |
| 321 | >50 | >50 | 3.6 |
| 322 | >50 | >50 | 7.8 |
| 323 | 1.9 | >50 | 42.5 |
| 324 | 0.17 | >50 | >50 |
| 325 | 0.14 | 39.7 | >50 |
| 326 | 9.2 | 31.4 | >50 |
| 327 | 0.06 | >50 | >50 |
| 328 | 0.77 | >50 | >50 |
| 330 | 0.2 | >50 | >50 |
| 331 | 0.17 | >50 | >50 |
| 332 | 0.12 | 21.3 | 2.2 |
| 333 | <0.005 | 12.6 | 2.4 |
| 334 | 0.07 | >50 | 7.8 |
| 335 | 0.02 | >50 | 1.4 |
| 336 | 0.04 | >50 | 5.8 |
| 337 | 0.02 | 3.1 | 1.0 |
| 338 | 0.1 | 13.8 | 2.8 |
| 339 | 0.07 | 0.82 | 0.37 |
| 340 | 0.07 | 6.1 | 1.6 |
| 341 | 0.02 | 3.1 | 0.59 |
| 342 | 0.01 | 2.9 | 0.86 |
| 343 | 7.8 | >50 | 22.6 |
| 344 | 0.46 | >50 | >50 |
| 345 | 15.4 | 28.3 | 43.4 |
| 346 | 0.18 | >50 | >50 |
| 347 | 0.005 | 6.7 | 1.5 |
| 349 | 37.1 | >50 | 36.3 |
| 350 | 3.1 | >50 | >50 |
| 351 | 0.13 | >50 | >50 |
| 352 | 1.9 | 22.6 | 12 |
| 353 | >50 | >50 | 31.7 |
| 354 | 0.23 | >50 | 5.0 |
| 355 | 0.36 | >50 | >50 |
| 356 | 0.39 | >50 | >50 |
| 357 | 31.0 | >50 | >50 |
| 358 | 0.31 | 35.5 | 43.4 |
| 359 | 0.02 | 1.5 | 0.26 |
| 360 | 0.46 | >50 | >50 |
| 361 | 0.22 | 45.5 | 17.9 |
| 362 | 0.01 | 14.7 | 0.5 |
| 363 | 0.006 | >50 | 14.7 |
| 364 | 0.03 | 25.3 | 1.6 |
| 365 | 0.07 | >50 | 1.9 |
| 366 | 0.12 | 31.7 | 1.9 |
| 367 | 12.6 | >50 | 43.4 |
| 368 | 0.51 | >50 | 30.3 |
| 369 | 0.46 | >50 | >50 |
| 370 | 21.1 | 42.5 | >50 |
| 371 | 0.10 | >50 | >50 |
| 372 | >50 | >50 | 20.2 |
| 373 | 0.01 | >50 | >50 |
| 374 | 1.30 | >50 | 37.1 |
| 375 | 0.39 | >50 | >50 |
| 376 | 0.43 | >50 | >50 |
| 378 | 0.65 | 20.4 | 15.4 |
| 379 | 0.69 | >50 | >50 |
| 380 | 0.10 | 42.5 | >50 |
| 381 | 13.2 | >50 | 3.1 |
| 382 | 0.29 | >50 | >50 |
| 383 | 0.45 | 14.4 | 25.9 |
| 384 | >50 | 38.8 | >50 |
| 385 | 14.7 | 11.5 | 20.7 |
| 386 | 0.60 | >50 | >50 |
| 387 | 0.90 | >50 | >50 |
| 388 | 2.0 | >50 | >50 |
| 389 | 1.66 | >50 | >50 |
| 390 | 0.88 | 1.45 | 19.3 |
| 391 | 0.50 | >50 | >50 |
| 392 | 0.69 | >50 | 33.2 |
| 393 | 0.47 | >50 | >50 |
| 394 | 0.21 | >50 | >50 |
| 395 | 0.14 | >50 | >50 |
| 396 | 0.02 | >50 | >50 |
| 397 | 0.19 | >50 | >50 |
| 398 | 0.18 | 21.6 | >50 |
| 399 | 0.34 | >50 | >50 |
| 400 | 0.34 | >50 | >50 |
| 401 | 0.47 | 23.1 | >50 |
| 402 | 2.9 | >50 | >50 |
| 404 | 0.10 | 25.3 | 14.4 |
| 405 | 1.8 | >50 | >50 |
| 406 | 0.09 | 31.7 | 49.7 |
| 407 | 1.6 | >50 | >50 |

TABLE II-continued

In Vitro Enzyme Assays CDK1, CDK2, CDK4 Activity

IC$_{50}$ (µM)

| EXAMPLE | CDK4 | CDK1 | CDK2 |
|---|---|---|---|
| 408 | 0.12 | >50 | >50 |
| 410 | 2.1 | 25.3 | 17.6 |
| 411 | 0.7 | >50 | >50 |
| 412 | 3.3 | >50 | >50 |
| 413 | 0.19 | >50 | >50 |
| 414 | 0.50 | >50 | >50 |
| 415 | 1.5 | >50 | >50 |
| 416 | 0.13 | >50 | >50 |
| 417 | 0.03 | >50 | >50 |
| 418 | 0.02 | >50 | >50 |
| 419 | 0.77 | >50 | 31.0 |
| 420 | 0.11 | >50 | >50 |
| 421 | 0.05 | >50 | >50 |
| 422 | 0.29 | >50 | >50 |
| 423 | 1.4 | >50 | >50 |
| 424 | 0.06 | 6.3 | 1.5 |
| 425 | 0.36 | 44.4 | 37.1 |
| 426 | 10.0 | >50 | 31.0 |
| 427 | 2.1 | >50 | >50 |
| 428 | 0.13 | 6.4 | 0.7 |
| 429 | 3.0 | >50 | >50 |
| 430 | 2.3 | 19.3 | 15.4 |
| 431 | 1.3 | 8.6 | 4.1 |
| 432 | 6.5 | >50 | >50 |
| 433 | 1.2 | 50.0 | >50 |
| 434 | >50 | 40.6 | >50 |
| 435 | 4.6 | >50 | 38.8 |
| 436 | 0.26 | >50 | >50 |
| 437 | 0.75 | >50 | 36.3 |
| 438 | 0.04 | >50 | >50 |
| 439 | 0.86 | >50 | >50 |
| 440 | 0.35 | 27.7 | 19.3 |
| 441 | 0.14 | >50 | >50 |
| 442 | 3.3 | 15.8 | 25.3 |
| 443 | 0.13 | >50 | >50 |
| 445 | 0.32 | >50 | >50 |
| 446 | 0.28 | >50 | >50 |
| 447 | 7.5 | 12.9 | 17.6 |
| 448 | 0.04 | 10.0 | >50 |
| 449 | 3.6 | >50 | >50 |
| 450 | 0.18 | >50 | >50 |
| 451 | 0.06 | >50 | >50 |
| 453 | 0.06 | 12.6 | 1.0 |
| 454 | 0.36 | >50 | >50 |
| 455 | 5.0 | >50 | >50 |
| 456 | 0.47 | >50 | >50 |
| 457 | 0.19 | 24.2 | 19.4 |
| 459 | 3.7 | >50 | >50 |
| 460 | 18.3 | >50 | >50 |
| 462 | 0.42 | >50 | >50 |
| 463 | 0.06 | >50 | >50 |
| 464 | 0.14 | >50 | >50 |
| 465 | 0.18 | >50 | 22.0 |
| 466 | 0.13 | >50 | >50 |
| 467 | 0.21 | >50 | >50 |
| 468 | 0.17 | >50 | >50 |
| 469 | 2.2 | 2.7 | 17.6 |
| 470 | 0.05 | 2.5 | 0.19 |
| 471 | 0.007 | >50 | 28.7 |
| 472 | 0.60 | >50 | >50 |
| 473 | 0.05 | >50 | >50 |
| 474 | 4.2 | >50 | >50 |
| 475 | 0.70 | >50 | >50 |
| 476 | 0.82 | 24.7 | >50 |
| 477 | 13.8 | 24.2 | 40.6 |
| 478 | 17.6 | >50 | >50 |
| 479 | 0.44 | >50 | >50 |
| 480 | 0.21 | >50 | 26.5 |
| 481 | 0.19 | >50 | >50 |
| 482 | 0.12 | >50 | >50 |
| 483 | 16.1 | >50 | >50 |
| 484 | 0.25 | 31.0 | >50 |
| 485 | 0.06 | >50 | >50 |
| 487 | 0.44 | >50 | >50 |
| 488 | 0.43 | >50 | >50 |
| 489 | 1.3 | >50 | >50 |
| 490 | 0.13 | 47.8 | 15.1 |
| 491 | 0.05 | >50 | >50 |
| 492 | 0.24 | >50 | >50 |
| 494 | 0.03 | 42.5 | 18.4 |
| 495 | 0.30 | >50 | >50 |
| 496 | 2.7 | >50 | >50 |
| 497 | 0.37 | >50 | >50 |
| 498 | 0.21 | 19.3 | 32.4 |
| 499 | 5.4 | >50 | 41.5 |
| 500 | 0.14 | 43.4 | 15.1 |
| 501 | 0.03 | >50 | 29.3 |
| 502 | <0.005 | 20.2 | 2.8 |
| 503 | 0.02 | >50 | 34.7 |
| 504 | 0.008 | >50 | >50 |
| 505 | 0.10 | >50 | 8.4 |
| 506 | 0.06 | 24.4 | 4.7 |
| 507 | 13.7 | 3 | 16 |
| 508 | 1.3 | 2.2 | >50 |
| 510 | 0.02 | 10.1 | 0.7 |
| 511 | 0.008 | >50 | >50 |
| 512 | 0.20 | >50 | >50 |
| 513 | 0.17 | >50 | 13.2 |
| 514 | 0.06 | >50 | 15.8 |
| 515 | 0.01 | >50 | 3.6 |
| 516 | 0.22 | >50 | >50 |
| 517 | 0.27 | 29.6 | >50 (41.5) |
| 518 | 0.11 | >50 | >50 (4.4) |
| 519 | 0.01 | 17.3 | 6.5 |
| 520 | 0.01 | 32 | 12.1 |
| 521 | 0.02 | 2.6 | 0.56 |
| 522 | 0.11 | 32.4 | 4.5 |
| 523 | 0.2 | >50 | 31.1 |
| 524 | 0.04 | 27.9 | 2.2 |
| 525 | 0.06 | 11.6 | 2.6 |
| 526 | 0.02 | 2.1 | 0.5 |
| 527 | 0.03 | 13.5 | 2.3 |
| 528 | 0.64 | 30.6 | 13.1 |
| 529 | 0.1 | 22.4 | 5 |
| 530 | 0.02 | 6.2 | 0.96 |
| 531 | 0.03 | 16.3 | 2.6 |
| 532 | 0.02 | 9.5 | 1.9 |
| 533 | 0.03 | 6.4 | 3.5 |
| 534 | 0.09 | >50 | >50 |
| 535 | 0.02 | 13.1 | 4 |
| 536 | 0.02 | >50 | 3.1 |
| 537 | <0.005 | 3.1 | 1.3 |
| 538 | <0.005 | 3.1 | 1.2 |
| 539 | 0.29 | >50 | 41.5 |
| 540 | 19.68 | | |
| 541 | 37.10 | | |
| 542 | 34.77 | | |
| 543 | 42.71 | | |
| 544 | 16.20 | | |
| 545 | 17.90 | >50 | 2.5 |
| 546 | 20 | | |
| 547 | 13.20 | >50 | 6.6 |
| 548 | 35.3 | | |
| 549 | 40.2 | | |
| 550 | 1.20 | 36.6 | 12.5 |
| 551 | 14.9 | | |
| 552 | 32.2 | | |
| 553 | 23.7 | | |
| 554 | 36 | | |
| 555 | 14.70 | 45.0 | 21.3 |
| 556 | 48.4 | | |
| 557 | 19.4 | | |
| 558 | 27.4 | | |
| 559 | 19.3 | | |
| 560 | 17.3 | | |
| 561 | 45.2 | | |

TABLE II-continued

In Vitro Enzyme Assays CDK1, CDK2, CDK4 Activity

| EXAMPLE | CDK4 IC$_{50}$ (μM) | CDK1 IC$_{50}$ (μM) | CDK2 IC$_{50}$ (μM) |
|---|---|---|---|
| 562 | 15.9 | | |
| 563 | 8.20 | 18.5 | 15.1 |
| 564 | 12.80 | 16.9 | 13.8 |
| 565 | 38 | | |
| 566 | 29.7 | | |
| 567 | 11.90 | 17.7 | 16.2 |
| 568 | 16.9 | | |
| 569 | 11.20 | 34.8 | 6.2 |
| 570 | 22 | | |
| 571 | 33.8 | | |
| 572 | 37 | | |
| 573 | 30.6 | | |
| 574 | 5.50 | 18.5 | 30.4 |
| 575 | 9.20 | 11.8 | >50 |
| 576 | 7.50 | 13.8 | 39.8 |
| 577 | 34.00 | 17.7 | >50 |
| 578 | 23.7 | | |
| 579 | 20.4 | | |
| 580 | 48.7 | | |
| 581 | 23.6 | | |
| 582 | 9.60 | | |
| 583 | 17.9 | | |
| 584 | 19.4 | | |
| 585 | 42.5 | | |
| 586 | 31.3 | | |
| 587 | 43.5 | | |
| 588 | 37.3 | | |
| 589 | 36.4 | | |
| 590 | 38.5 | | |
| 591 | 23.20 | 20.3 | 25.4 |
| 592 | 29.9 | | |
| 593 | >50 | 44.5 | >50 |
| 594 | 7.80 | | |
| 595 | 27.4 | | |
| 596 | 27.7 | | |
| 597 | 39.2 | | |
| 598 | 33.1 | | |
| 599 | 39.7 | | |
| 600 | 23.1 | | |
| 601 | 12.0 | | |
| 602 | 21.5 | | |
| 603 | 48.3 | | |
| 604 | 23.5 | | |
| 605 | 22.1 | | |
| 606 | 21.2 | | |
| 607 | 45.5 | | |
| 608 | 0.20 | 18.9 | 6.7 |
| 609 | 0.02 | 11.8 | 12.1 |
| 610 | 0.38 | 3.5 | 2.5 |
| 611 | 12.90 | 18.1 | 18.1 |
| 612 | 48.9 | | |
| 613 | 33.1 | | |
| 614 | 25.3 | | |
| 615 | 25.7 | | |
| 616 | 14.8 | | |
| 617 | 16.50 | >50 | 21.3 |
| 618 | 40.1 | | |
| 619 | 14.3 | | |
| 620 | 0.05 | 32.5 | 5.8 |
| 621 | 0.01 | 8.1 | 4.1 |
| 622 | 37.2 | | |
| 623 | 25.08 | | |
| 624 | 13.02 | | |
| 625 | 14.78 | | |
| 626 | 3.70 | | |
| 627 | 10.40 | | |
| 628 | 33.62 | | |
| 629 | 5.50 | | |
| 630 | 0.20 | 31.0 | 17.3 |
| 631 | 4.20 | | |
| 632 | 3.10 | | |
| 633 | 32.26 | | |
| 634 | 9.90 | | |
| 635 | 1.20 | 16.9 | 19.7 |
| 636 | 3.40 | | |
| 637 | 0.81 | 18.0 | 13.5 |
| 638 | 0.05 | 17.3 | 6.0 |
| 639 | 9.20 | >50 | 19.7 |
| 640 | 21.86 | | |
| 641 | 1.90 | >50 | >50 |
| 642 | 1.00 | >50 | 28.3 |
| 643 | 3.50 | >50 | >50 |
| 644 | 2.00 | >50 | >50 |
| 645 | 2.20 | | |
| 646 | 0.04 | 13.5 | 2.9 |
| 647 | <0.005 | 8.6 | 2.6 |
| 648 | 18.63 | | |
| 649 | 19.98 | | |
| 650 | 16.56 | | |
| 651 | 3.00 | | |
| 652 | 2.40 | | |
| 653 | 0.21 | >50 | 45.5 |
| 654 | 2.00 | | |
| 655 | 0.57 | 23.6 | 11.0 |
| 656 | 4.80 | | |
| 657 | 2.20 | | |
| 658 | 0.19 | >50 | 23.1 |
| 659 | 0.44 | >50 | 18.0 |
| 660 | 2.48 | >50 | 33.9 |
| 661 | 5.50 | | |
| 662 | 0.17 | >50 | >50 |
| 663 | 0.01 | >50 | 6.3 |
| 664 | 0.22 | >50 | 31.7 |
| 665 | 0.16 | 42.5 | 8.2 |
| 666 | 2.50 | | |
| 667 | 0.01 | >50 | 4.0 |
| 668 | 21.91 | | |
| 669 | 9.60 | | |
| 670 | 39.82 | | |
| 671 | 2.00 | 11.8 | 38.0 |
| 672 | 0.64 | >50 | >50 |
| 673 | 1.00 | >50 | >50 |
| 674 | 11.67 | | |
| 675 | 1.77 | >50 | >50 |
| 676 | 0.92 | 15.1 | 15.8 |
| 677 | 14.27 | | |
| 678 | 1.16 | 14.4 | >50 |
| 679 | 4.90 | | |
| 680 | 0.23 | >50 | >50 |
| 681 | 17.69 | | |
| 682 | 3.40 | | |
| 683 | 32.85 | | |
| 684 | 12.39 | | |
| 685 | 1.51 | >50 | >50 |
| 686 | 6.40 | | |
| 687 | 20.91 | | |
| 688 | 0.26 | 21.1 | >50 |
| 689 | 4.70 | | |
| 690 | 20.66 | | |
| 691 | 8.30 | | |
| 692 | 30.69 | | |
| 693 | 25.69 | | |
| 694 | 32.28 | | |
| 695 | 14.32 | | |
| 696 | 27.29 | | |
| 697 | 48.58 | | |
| 698 | 0.28 | >50 | >50 |
| 699 | 2.90 | | |
| 700 | 45.00 | | |
| 701 | 6.60 | | |
| 702 | 20.92 | | |
| 703 | 18.51 | | |
| 704 | 7.00 | | |
| 705 | 12.61 | | |
| 706 | 7.30 | | |
| 707 | 3.80 | | |

TABLE II-continued

In Vitro Enzyme Assays CDK1, CDK2, CDK4 Activity

IC$_{50}$ (μM)

| EXAMPLE | CDK4 | CDK1 | CDK2 |
|---|---|---|---|
| 708 | 10.00 | | |
| 709 | 38.58 | | |
| 710 | 27.99 | | |
| 711 | 9.80 | | |
| 712 | 7.90 | | |
| 713 | 12.77 | | |
| 714 | 5.50 | | |
| 715 | 9.30 | | |
| 716 | 9.30 | | |
| 717 | 13.32 | | |
| 718 | 8.20 | | |
| 719 | 27.46 | | |
| 720 | 21.65 | | |
| 721 | 25.88 | | |
| 722 | 25.27 | | |
| 723 | 12.20 | | |
| 724 | 3.60 | | |
| 725 | 2.90 | | |
| 726 | 16.93 | | |
| 727 | 20.44 | | |
| 728 | 0.07 | 1.0 | 1.3 |
| 729 | 10.90 | | |
| 730 | 2.50 | | |
| 731 | 45.24 | | |
| 732 | 25.84 | | |
| 733 | 0.010 | | |
| 734 | <0.005 | 20.2 | 5.0 |
| 735 | 0.14 | >50 | >50 |
| 736 | 0.84 | >50 | 21.1 |
| 737 | 6.00 | | |
| 738 | 0.45 | 32.4 | 32.4 |
| 739 | 1.77 | 30.3 | >50 |
| 740 | 1.81 | 13.5 | 3.7 |
| 741 | 2.30 | | |
| 742 | 13.79 | | |
| 743 | 11.26 | | |
| 744 | 48.55 | | |
| 745 | 19.87 | | |
| 746 | 0.50 | | |
| 747 | 14.46 | | |
| 748 | 46.18 | | |
| 749 | 1.48 | 38.8 | 8.0 |
| 750 | 2.50 | | |
| 751 | 2.50 | | |
| 752 | 1.30 | | |
| 753 | 3.40 | | |
| 754 | 11.03 | | |
| 755 | 0.57 | 12.3 | 7.7 |
| 756 | 20.17 | | |
| 757 | 31.14 | | |
| 758 | 25.67 | | |
| 759 | 1.70 | | |
| 760 | 2.20 | | |
| 761 | 18.38 | | |
| 762 | 33.63 | | |
| 763 | 49.61 | | |
| 764 | 0.06 | 16.5 | 7.3 |
| 765 | 0.27 | 21.1 | 11.5 |
| 766 | 1.29 | 43.4 | 14.4 |
| 767 | 0.17 | 15.4 | 9.0 |
| 768 | 0.55 | 20.6 | 9.6 |
| 769 | 0.03 | 14.7 | 3.9 |
| 770 | 0.09 | 18.5 | 13.8 |
| 771 | 0.82 | 26.5 | 10.0 |
| 772 | 0.51 | 40.6 | 10.7 |
| 773 | 1.18 | >50 | 16.5 |
| 774 | 1.40 | | |
| 775 | 0.20 | >50 | 14.1 |
| 776 | 0.24 | >50 | 13.8 |
| 777 | 3.78 | | |
| 778 | 0.12 | 27.7 | 5.6 |
| 779 | 0.74 | >50 | 31.1 |
| 780 | 0.67 | 23.1 | 3.8 |
| 781 | 0.74 | >50 | 27.7 |
| 782 | 2.12 | >50 | 50.0 |
| 783 | 1.23 | | |
| 784 | 0.06 | 27.7 | 7.3 |
| 785 | 1.20 | >50 | 38.0 |
| 786 | 9.74 | | |
| 787 | 2.27 | | |
| 788 | 0.20 | 17.6 | 17.6 |
| 789 | 0.40 | >50 | 27.7 |
| 790 | 1.45 | | |
| 791 | 4.99 | | |
| 792 | 0.47 | >50 | 22.6 |
| 793 | 1.96 | | |
| 794 | 41.69 | | |
| 795 | 24.18 | | |
| 796 | 2.27 | | |
| 797 | 0.90 | >50 | >50 |
| 798 | 2.50 | | |
| 799 | 6.37 | | |
| 800 | 5.04 | | |
| 801 | 15.51 | | |
| 802 | 15.00 | | |
| 803 | 4.97 | | |
| 804 | 1.00 | 37.1 | 18.0 |
| 805 | 0.29 | 50.0 | 23.1 |
| 806 | 2.10 | | |
| 807 | 14.49 | | |
| 808 | 0.38 | >50 | >50 |
| 809 | 13.84 | | |
| 810 | 2.76 | | |
| 811 | 22.27 | | |
| 812 | 0.13 | >50 | 28.3 |
| 813 | 0.31 | >50 | 33.1 |
| 814 | 2.75 | | |
| 815 | 2.50 | | |
| 816 | 0.31 | >50 | 24.2 |
| 817 | 0.04 | 7.0 | 7.0 |
| 818 | 0.79 | 36.3 | 30.3 |
| 819 | 0.81 | 27.1 | 27.1 |
| 820 | 2.10 | >50 | 27.1 |
| 821 | 0.14 | 24.2 | 20.7 |
| 822 | 0.15 | 46.5 | 18.9 |
| 823 | 0.22 | 9.4 | 2.4 |
| 824 | 0.01 | >50 | 34.7 |
| 825 | 0.02 | >50 | 36.3 |
| 826 | 0.11 | 50.0 | 12.9 |
| 827 | 0.12 | >50 | 45.5 |
| 828 | 4.4 | | |
| 829 | 26.5 | | |
| 830 | 0.17 | >50 | >50 |
| 831 | 0.19 | >50 | >50 |
| 832 | 0.01 | 34.7 | 25.9 |
| 833 | 0.01 | >50 | 15.1 |
| 834 | 0.29 | >50 | 50.0 |
| 835 | 0.04 | 35.5 | 40.6 |
| 836 | 0.01 | 28.3 | 15.4 |
| 837 | 0.02 | >50 | 24.2 |
| 838 | 0.15 | 45.5 | 23.6 |
| 839 | 3.30 | >50 | 38.8 |
| 840 | 3.00 | >50 | 31.0 |
| 841 | 50.00 | >50 | 25.3 |
| 842 | 2.30 | >50 | >50 |
| 843 | 0.18 | >50 | >50 |
| 844 | 34.70 | >50 | >50 |
| 845 | 2.30 | >50 | >50 |
| 846 | 2.50 | >50 | >50 |
| 847 | 5.00 | >50 | >50 |
| 848 | >50 | 44.4 | >50 |
| 849 | >50 | >50 | 40.6 |
| 850 | >50 | >50 | 19.7 |
| 851 | 0.79 | 2.7 | 10.3 |
| 852 | 0.31 | >50 | >50 |
| 853 | 0.12 | >50 | >50 |

TABLE II-continued

In Vitro Enzyme Assays CDK1, CDK2, CDK4 Activity

| | IC$_{50}$ (μM) | | |
|---|---|---|---|
| EXAMPLE | CDK4 | CDK1 | CDK2 |
| 854 | 0.61 | >50 | >50 |
| 855 | 0.31 | >50 | >50 |
| 857 | 18.50 | | |
| 861 | 14.30 | >50 | 3.6 |
| 862 | 31 | | |
| 863 | 20.10 | 37.1 | 18.0 |
| 864 | 2.50 | >50 | >50 |
| 865 | 4.30 | >50 | >50 |
| 867 | 0.48 | >50 | >50 |
| 868 | 1.20 | 20.7 | 2.5 |
| 869 | 22.60 | >50 | 14.7 |
| 870 | 2.60 | >50 | >50 |
| 872 | 34.70 | 1.2 | 23.6 |
| 873 | >50 | 1.9 | 24.7 |
| 874 | 3.00 | >50 | 38.8 |
| 875 | 1.90 | 15.1 | 2.8 |
| 876 | 14.40 | >50 | >50 |
| 877 | 42.50 | >50 | >50 |

Cellular Assay

Methods—IC$_{50}$ Studies on CDK 4 Inhibitors

Cell Lines:

BT474, HCT-116, LoVo and MCF-7 were maintained under 7% CO$_2$ in RPMI 1640 medium supplemented with 10% fetal bovine serum and 50 □g/ml gentamicin.

Cytotoxicity Assay:

Cells were plated in 96-well microtiter dishes (12000 cells/well for BT474, 4000 cells/well for HCT-116, 6000 cells/well for LoVo and 6000 cells/well for MCF-7) in RPMI 1640 medium containing 5% fetal bovine serum and 50 □g/ml gentamicin. The cells were allowed to incubate overnight at 37° C., 7% CO$_2$. Compound dilutions were prepared using the same medium. HCT-116, LoVo and MCF-7 cells were cultured for three days and BT474 cells were cultured for 6 days, in the presence of each compound dilution. Untreated cells were included as controls. The percentage of surviving cells was determined using a protein binding dye (sulforhodamineB, SRB) assay. Cellular protein was precipitated in each well by the addition of 0.05 ml of 50% cold trichloroacetic acid (TCA). After 1 hour, the plates were washed extensively in dH2O and dried. The sulforhodamineB dye solution (0.08 mL of 0.4% SRB in 1% acetic acid) was added to each well, kept at room temperature for ten minutes, then washed in 1% acetic acid and dried. The dye was dissolved in 10 mM Tris-HCl (150 uL) and the absorbency read at 540 nm. The concentration of compound that caused a 50% inhibition of growth (IC$_{50}$) was determined.

TABLE III

In Vitro Cellular Activity

| | IC$_{50}$ (μM) | | | | | |
|---|---|---|---|---|---|---|
| EXAMPLE | HCT116 | LOVO | BT474 | MCF-7 | SK-Br-3 | SK-UT-1B |
| 1 | 29 | 30 | 43 | 19 | | >36 |
| 2 | 7.4 | 7.8 | 21.5 | 6.7 | | 4.3 |
| 3 | 7.8 | 12 | 20 | 11 | | 4.4 |
| 4 | 9.1 | 13 | 18 | 5.5 | | 12.7 |
| 5 | 10.8 | | | 8 | | 10.2 |

TABLE III-continued

In Vitro Cellular Activity

| | IC$_{50}$ (μM) | | | | | |
|---|---|---|---|---|---|---|
| EXAMPLE | HCT116 | LOVO | BT474 | MCF-7 | SK-Br-3 | SK-UT-1B |
| 6 | >50 | >50 | >50 | >50 | | 18.3 |
| 7 | 6.57 | | | 11.2 | | 4.3 |
| 8 | >50 | >50 | >50 | >50 | | 8.9 |
| 9 | 2.5 | 6.8 | 48 | 9.7 | | 15.1 |
| 10 | 2.3 | 5.9 | >50 | 12.5 | | 23.6 |
| 11 | 2.3 | 6.8 | >50 | 18 | | >36 |
| 12 | 2.1 | 5.4 | >50 | 14.5 | | >32 |
| 13 | 8.6 | 15 | 27 | 7.3 | | 11.3 |
| 14 | 8.7 | >50 | 38 | >50 | | 18.4 |
| 15 | 10.3 | 50 | >50 | 28 | | 11.6 |
| 16 | 14 | 14 | 45 | 19 | | 18.5 |
| 17 | 14 | 19 | 30 | 20 | | 16 |
| 18 | 15 | 23 | 31 | 15 | | 15.8 |
| 19 | 20 | | | 15.9 | | 21.4 |
| 20 | 10 | | | 14 | | 18.5 |
| 21 | >50 | >50 | >50 | >50 | | 19.7 |
| 22 | 11 | 19 | 21 | 10 | | 5.4 |
| 23 | 10.5 | | | 8.7 | | 16.3 |
| 24 | 5 | 6 | 4.8 | 3.1 | | 7.8 |
| 25 | 11.5 | | | 5.6 | | 16.2 |
| 26 | 7.3 | | | 8 | | 6.1 |
| 27 | 3.1 | 3.8 | 3.1 | 3 | | 3.6 |
| 28 | 28 | >50 | 39 | >50 | | 33 |
| 29 | 21 | 19 | 21 | 12 | | 17 |
| 30 | 9.2 | 14 | 31 | 15 | | 4.9 |
| 31 | 31 | >50 | 41 | >50 | | >50 |
| 33 | 3.3 | 3.2 | 5.2 | 11 | | 3.3 |
| 34 | 14 | >50 | 25 | 38 | | 15 |
| 38 | 7.3 | 7.9 | 2.8 | 3.7 | | 11 |
| 39 | 7.5 | 9.4 | 7.9 | 6.3 | | 10 |
| 41 | 39 | 49 | 25 | 13 | | 11 |
| 42 | 3 | 5.9 | 4 | 7.6 | | |
| 43 | 26 | >50 | 41 | >50 | | |
| 44 | 3.6 | 4 | 4.6 | 6.6 | | 3.5 |
| 45 | 5 | 33 | 19 | 18.8 | | 31 |
| 46 | 23 | 23 | >50 | >50 | | |
| 47 | 21 | 22 | 20 | 20 | | |
| 49 | 5.5 | 11.5 | 6.85 | 13 | | |
| 52 | 40 | >50 | 41 | >50 | | |
| 53 | 32 | >50 | 37 | >50 | | |
| 54 | 6.4 | 5.9 | 6.5 | 9.2 | | |
| 55 | 5.7 | 7.7 | 11 | 7 | | |
| 56 | 28 | 30 | 23 | 27 | | |
| 57 | 9.6 | 5.2 | 3.7 | >50 | | |
| 59 | 4.7 | 6.1 | 6.3 | 4.13 | | |
| 60 | 1.5 | 2 | 2 | 2.3 | | |
| 61 | 27.6 | >50 | >50 | >50 | | |
| 63 | >50 | >50 | 49 | >50 | | |
| 64 | >50 | >50 | 28 | >50 | | |
| 66 | 3.4 | 4.2 | 3.1 | 4.3 | | |
| 68 | 15 | 19 | 14 | >50 | | |
| 69 | 6.5 | 5.2 | 5.6 | 8.2 | | |
| 70 | 2.55 | 5.18 | 3.23 | 4.06 | | |
| 71 | 4.7 | 3 | 3.8 | 7.8 | | |
| 72 | 3.4 | 3.4 | 4.1 | 2.6 | | |
| 73 | 10 | 13 | 18 | 9.3 | | |
| 74 | 2.7 | 2.4 | 3.3 | 2.1 | | |
| 75 | 5.8 | 6 | 9.7 | 4.3 | | |
| 76 | 5 | 5.9 | 5.5 | 9.1 | | |
| 77 | 4.8 | 8.4 | 7.7 | 14.4 | | |
| 78 | >50 | >50 | 42 | 32.5 | | |
| 79 | >50 | 49.5 | 37.7 | >50 | | |
| 80 | 2 | 1.5 | 1.7 | 3.7 | | |
| 81 | 2.8 | 5.1 | 2.8 | 2.5 | | |
| 82 | 2.7 | 3.1 | 0.6 | 1 | | |
| 83 | 4.5 | 2.6 | 3.2 | 29.9 | | |
| 84 | 3.1 | 4.6 | 2.1 | 6.7 | | |
| 85 | 3.7 | 2.7 | 3.5 | 8.4 | | |
| 86 | 4.5 | 3.7 | 3.2 | 5.1 | | |
| 87 | 4.2 | 4.2 | 1.3 | 4.1 | | |
| 88 | 3.4 | 2.4 | 6 | 9.1 | | |
| 89 | 3.7 | 7.8 | 5.9 | 20 | | |

TABLE III-continued

In Vitro Cellular Activity

IC$_{50}$ (μM)

| EXAMPLE | HCT116 | LOVO | BT474 | MCF-7 | SK-Br-3 | SK-UT-1B |
|---|---|---|---|---|---|---|
| 90 | 9.8 | 24 | 6.9 | 12 | | |
| 91 | 27 | 37 | 40 | 16 | | |
| 92 | 2.5 | 3.2 | 2 | 3.8 | | |
| 93 | 1.9 | 1.8 | 1 | 1.1 | | |
| 94 | 3.4 | 6.4 | 2.0 | 2.3 | | |
| 95 | 2.4 | 3.7 | 3.0 | 2.9 | | |
| 96 | 1.3 | 1.8 | 3.4 | 2.0 | | |
| 97 | 1.5 | 1.9 | 3.1 | 2.8 | | |
| 98 | 17.9 | 19.3 | 16.8 | 24.1 | | |
| 100 | 13.6 | 27.8 | 8.8 | 11.0 | | |
| 101 | 1.2 | 4.3 | 2.9 | 3.2 | | |
| 102 | 11.5 | 43.3 | >50 | >50 | | |
| 103 | 1.6 | 2.3 | 3.7 | 3.0 | | |
| 104 | 1.0 | 1.3 | 3.0 | 3.4 | | |
| 105 | 42.6 | 42.9 | 36.9 | >50 | | |
| 106 | >50 | >50 | 44.6 | >50 | | |
| 107 | 1.4 | 2.3 | 2.5 | 2.3 | | |
| 108 | 1.5 | 2.2 | 2.6 | 2.5 | | |
| 109 | 16.8 | >50 | 34.8 | >50 | | |
| 110 | 1.6 | 2.5 | 3.5 | 5.8 | | |
| 111 | 1.2 | 1.2 | 2.8 | 2.1 | | |
| 112 | 0.98 | 1.9 | 2.3 | 3.3 | | |
| 113 | 5.8 | 2.9 | 11 | 6.2 | | |
| 114 | 1.9 | 6.5 | 5 | 6.3 | | |
| 115 | 1.6 | 6.5 | 6.7 | 4.7 | | |
| 116 | 1.3 | 2.8 | 2.8 | 3.2 | | |
| 117 | 1.4 | 2.4 | 3 | 2.7 | | |
| 118 | 2.7 | 3.2 | 4 | 4.4 | | |
| 119 | 3.3 | 7.3 | 7.5 | 6.2 | | |
| 120 | 4.3 | 7.7 | 8 | 21 | | |
| 121 | 5.5 | 3.8 | 7.7 | 4.6 | | |
| 122 | 7.5 | 9.9 | 5.2 | 17 | | |
| 123 | 3.4 | 4.4 | 9.4 | 7.2 | | |
| 124 | 2.6 | 5 | 9.1 | 7.9 | | |
| 125 | 1.2 | 1.1 | 3.9 | 1.8 | | |
| 126 | 3.4 | 5.1 | 0.9 | 2.3 | | |
| 127 | 1.3 | 2.9 | 1.4 | 1.4 | | |
| 128 | 1.50 | 2.1 | 3.1 | 2.3 | | |
| 129 | 26 | >50 | 30 | 39 | | |
| 130 | 0.73 | 0.94 | 0.65 | 4.0 | | |
| 131 | >50 | >50 | 39 | >50 | | |
| 133 | 43 | >50 | >50 | >50 | | |
| 134 | 13 | 11 | 11 | 12 | | |
| 135 | 31 | >50 | >50 | >50 | | |
| 136 | 25 | 36 | 16 | 48 | | |
| 137 | 4.4 | 5.8 | 3.3 | 17 | | |
| 138 | 3.7 | 4.9 | 0.41 | 1.2 | | |
| 139 | >50 | 26 | 15 | >50 | | |
| 140 | >50 | >50 | 30 | >50 | | |
| 141 | 0.84 | 1.3 | 0.56 | 16 | | |
| 142 | 1.2 | 2 | 0.66 | 31.1 | | |
| 143 | 3 | 8.8 | 5.7 | 4.3 | | |
| 144 | 1.5 | 3.2 | 3.2 | 3.2 | | |
| 145 | 32.5 | 16 | >50 | >50 | | |
| 146 | 0.66 | 0.86 | 0.49 | 2.7 | | |
| 147 | 38 | 40 | >50 | 36 | | |
| 148 | 18 | 22 | 16 | 25 | | |
| 149 | 18 | 27 | 12 | >50 | | |
| 150 | 49 | >50 | >50 | 46 | | |
| 151 | 1.3 | 1.9 | 0.9 | 6.6 | | |
| 152 | 2.8 | 6.6 | 3.4 | 6.2 | | |
| 153 | 1.1 | 3.7 | 3.4 | 3.4 | | |
| 154 | 2.2 | 3.2 | 3 | 2.7 | | |
| 155 | 17 | 19 | 22 | 26 | | |
| 156 | 2.5 | 6.4 | 2.6 | 1.5 | | |
| 157 | 6.7 | 22 | 19 | 8.2 | | |
| 158 | 32 | 30 | 28 | >50 | | |
| 159 | 16 | 18 | 25 | >50 | | |
| 160 | >50 | 43 | >50 | 30 | | |
| 161 | 2.2 | 6.4 | 3.4 | 4 | | |
| 162 | 4.4 | 9.2 | 23 | 3.9 | | |
| 163 | 38 | 34 | 38 | 38 | | |
| 165 | 23 | >50 | >50 | >50 | | |
| 166 | 1.3 | 2.2 | 1.4 | 19 | | |
| 167 | 11 | 12 | 9.6 | 13 | | |
| 168 | 3.2 | 8.3 | 7.8 | 3.6 | | |
| 169 | 2.6 | 5.2 | 1.8 | 2.5 | | |
| 170 | 6.2 | 21 | 27 | 11 | | |
| 171 | 1.2 | 9.7 | 5.1 | 3.0 | | |
| 172 | 8.7 | >50 | 17 | >50 | | |
| 173 | 11 | 17 | 8.3 | 12 | | |
| 174 | 19 | 35 | 30 | 50 | | |
| 175 | 28 | >50 | >50 | >50 | | |
| 176 | 3.4 | 4.5 | 7.2 | 3.8 | | |
| 177 | 3.1 | 3.9 | 3.9 | 4.1 | | |
| 178 | 0.65 | 0.74 | 0.62 | 1.8 | | |
| 179 | 34 | 20 | 17 | 30 | | |
| 180 | 5.9 | 6.2 | 5.1 | 15 | | |
| 181 | 16 | >50 | >50 | >50 | | |
| 182 | >50 | >50 | 17 | >50 | | |
| 183 | 8.4 | 12 | 13 | 8.8 | | |
| 184 | 13 | 20 | 8.5 | 50 | | |
| 185 | 2.8 | 2.7 | 0.87 | >50 | | |
| 186 | 6.6 | 13 | 17 | 11 | | |
| 187 | 1.1 | 8.5 | 2.9 | 3.0 | | |
| 188 | 2.2 | 11 | 3.3 | 12 | | |
| 189 | 7.2 | 6.4 | 5.8 | 9.9 | | |
| 190 | 9.4 | 13 | 1.4 | >50 | | |
| 191 | 35 | >50 | 5.7 | >50 | | |
| 192 | 6.8 | 40 | 16 | 2.4 | | |
| 193 | 16 | >50 | >50 | 4.4 | | |
| 194 | >50 | >50 | >50 | 9.1 | | |
| 195 | 6.9 | 37 | 17 | 14 | | |
| 196 | 35 | 37 | 37 | 38 | | |
| 198 | 1.8 | 3.7 | 4.3 | 4.3 | | |
| 199 | 6.4 | 4.1 | 1.3 | 1.9 | | |
| 200 | 5.4 | 4.7 | 9.3 | 7.2 | | |
| 201 | 1.1 | 1.4 | 1.4 | 1.7 | | |
| 202 | >50 | >50 | 18 | >50 | | |
| 203 | 3.9 | 9.8 | 8.0 | 9.0 | | |
| 205 | 1.1 | 3.1 | 2.4 | 1.5 | | |
| 206 | 1.6 | 7.4 | 2.9 | 3.7 | | |
| 207 | 1.1 | 2.2 | 0.79 | 0.69 | | |
| 208 | 5.7 | 15 | 8.2 | 3.4 | | |
| 209 | 7.0 | 15 | 9.4 | 5.4 | | |
| 210 | 10 | 10 | 13 | 6.6 | | |
| 211 | 27 | 48 | 29 | 24 | | |
| 212 | 25 | 30 | 47 | 37 | | |
| 213 | >50 | 48 | >50 | >50 | | |
| 214 | 39 | >50 | 6.8 | 14 | | |
| 215 | 4.5 | 6.4 | 7.4 | 7.1 | | |
| 216 | 0.76 | 1.3 | 1.1 | 1.6 | | |
| 217 | 2.6 | 4.8 | 3.3 | 7.4 | | |
| 218 | 3.3 | 4.5 | 2.6 | 19 | | |
| 219 | 2.8 | 6.9 | 1.9 | 32 | | |
| 220 | 3.2 | 3.8 | 3.3 | 2.4 | | |
| 221 | 1.9 | 3.2 | 3.2 | 2.6 | | |
| 222 | 14 | 19 | 13 | 13 | | |
| 223 | 4.1 | 2.8 | 8.7 | 3.2 | | |
| 224 | 6.4 | 7.9 | 9.6 | 7.4 | | |
| 225 | >50 | >50 | 19.5 | >50 | | |
| 226 | 2.4 | 4.4 | 3.3 | 5.2 | | |
| 227 | 44.0 | 37.0 | | >50 | | |
| 228 | ~2.1 | ~2.5 | ~1.2 | ~8.6 | | |
| 229 | 3.6 | 8.5 | 4 | 4.6 | | |
| 230 | 2.1 | 3.8 | 6.4 | 3.1 | | |
| 231 | 4.1 | 10 | 8.3 | 2.4 | | |
| 232 | 1.4 | 3.7 | 3.3 | 2.1 | | |
| 233 | 5.0 | 4.4 | 6.9 | 1.0 | | |
| 234 | 2.1 | 3.4 | 2.5 | 1.3 | | |
| 235 | 1.4 | 3.5 | 3 | 3.3 | | |
| 236 | 1.2 | 2.2 | 1 | 1.1 | | |
| 237 | 2.6 | 7.4 | 3.2 | 4 | | |
| 238 | 6.7 | 4.3 | 7.4 | 1.0 | | |

TABLE III-continued

In Vitro Cellular Activity

IC$_{50}$ (μM)

| EXAMPLE | HCT116 | LOVO | BT474 | MCF-7 | SK-Br-3 | SK-UT-1B |
|---|---|---|---|---|---|---|
| 239 | 2.5 | 7.7 | 7.9 | 4 | | |
| 240 | 2.7 | 3.7 | 3.1 | 2.0 | | |
| 241 | 1.9 | 3.8 | 1.2 | 1.3 | | |
| 242 | 2.1 | 4.5 | 3.2 | 5.2 | | |
| 243 | 5 | 12 | 13 | 5 | | |
| 244 | 4.9 | 15 | 9.4 | 19 | | |
| 245 | 3.4 | 6.6 | 8.4 | 3 | | |
| 246 | 22 | 37 | 2 | >50 | | |
| 247 | 18 | >50 | 35 | >50 | | |
| 248 | 2 | 2.8 | 3 | 1.9 | | |
| 249 | 2.1 | 2.4 | 2 | 1.7 | | |
| 250 | 6.2 | 7.1 | 7.6 | 1.6 | | |
| 251 | 1.0 | 1.7 | 1.1 | 0.55 | | |
| 252 | 14 | 21 | 15 | 33 | | |
| 253 | 1.1 | 2.6 | 2.8 | 2 | | |
| 254 | 2 | 4.8 | 2.1 | 2.4 | | |
| 255 | 3.1 | 3.8 | 7.9 | 3.6 | | |
| 256 | 3.1 | 3.6 | 7.5 | 5.3 | | |
| 257 | 2.5 | 4.7 | 6.5 | 3.6 | | |
| 258 | 3.5 | 5.3 | 8.3 | 6.7 | | |
| 259 | 2.5 | 3.9 | 6.8 | 5.5 | | |
| 260 | 5.4 | >50 | >50 | >50 | | |
| 261 | 3 | 10 | 10 | 9.2 | | |
| 262 | 14 | 47 | >50 | 29 | | |
| 263 | 1.3 | 2.9 | 2.9 | 3.1 | | |
| 264 | 4.4 | 8.8 | 2.2 | 2 | | |
| 265 | 2 | 2.8 | 1.7 | 1.4 | | |
| 266 | 6.2 | 8.4 | 9.1 | 4 | | |
| 267 | 3.7 | 3.7 | 3.5 | 4.8 | | |
| 268 | 29 | 47 | >50 | 35 | | |
| 269 | 25 | 41 | 43 | 29 | | |
| 270 | 13 | 24 | 27 | 7.2 | | |
| 271 | 46 | >50 | 32 | 39 | | |
| 272 | 4.2 | 8.9 | 7.2 | 3.1 | | |
| 273 | 3.0 | 7.9 | 7.5 | 13 | | |
| 274 | 9.5 | 12.5 | 12 | 10.3 | | |
| 275 | 4.2 | 8.6 | 10 | 5.3 | | |
| 276 | 3.9 | 6.2 | 8.3 | 4.4 | | |
| 278 | 2.9 | 4.7 | 5 | 6.3 | | |
| 279 | 10 | 11 | 6 | 5.3 | | |
| 280 | 21 | 32 | 28.0 | 17 | | |
| 281 | 20 | 12 | 44.3 | 19 | | |
| 282 | 1.1 | 2.7 | 3 | 1.1 | | |
| 283 | 17 | 17 | 16 | 9.8 | | |
| 284 | 20 | 25 | >50 | 12 | | |
| 285 | 3.6 | 3.6 | 0.37 | 0.79 | | |
| 286 | 5.8 | 11 | 16.0 | 5.5 | | |
| 287 | 4.2 | 5.4 | 1.3 | 1.7 | | |
| 288 | 1.7 | 2.0 | 1.8 | 1.5 | | |
| 289 | 2.2 | 7.4 | 1.3 | 0.90 | | |
| 290 | 1.8 | 5.4 | 2.5 | 2.3 | | |
| 291 | 2.3 | 1.9 | 1.0 | 0.59 | | |
| 292 | ~1.2 | ~1.2 | ~0.9 | ~6.5 | | |
| 293 | 0.78 | 0.9 | 0.69 | 2.2 | | |
| 294 | 9.0 | >50 | 49 | 24 | | |
| 295 | 3.1 | 3.7 | 3.1 | 1.8 | | |
| 296 | 4.0 | 5.0 | 6.2 | 2.6 | | |
| 297 | 2.2 | 2 | 1.2 | 0.95 | | |
| 298 | 2.1 | 9.8 | 6.30 | 2.8 | | |
| 299 | 3.0 | 7.7 | 2 | 0.80 | | |
| 300 | 3.1 | 26 | 17.0 | 8.7 | | |
| 301 | 0.17 | 0.17 | 0.14 | 0.20 | | |
| 302 | 0.55 | 0.59 | 0.56 | 1.2 | | |
| 303 | 5.3 | 4.6 | 3.1 | 10 | | |
| 304 | 13 | 6.7 | 16 | 7.1 | | |
| 305 | 21 | 14 | 23 | 18 | | |
| 306 | 26 | 13 | 37 | 25 | | |
| 307 | 23 | 28 | 46 | 25 | | |
| 308 | 21 | 16 | 23 | 23 | | |
| 309 | 26 | 15 | 26 | 20 | | |
| 310 | 21 | 17 | 27 | 11 | | |
| 311 | 29 | 19 | 38 | 13 | | |
| 312 | >50 | >50 | 39 | >50 | | |
| 313 | 27 | 41 | 43 | 22 | | |
| 316 | 8.9 | 5.7 | 4.9 | 9 | | |
| 317 | 12 | 4.7 | 5.2 | 8.4 | | |
| 318 | 1.3 | 1.5 | 1.9 | 2.5 | | |
| 319 | 1.5 | 2.1 | 3.1 | 2.6 | | |
| 320 | 2.1 | 4.5 | 2 | 4.9 | | |
| 321 | 1.2 | 4.4 | 0.84 | 10 | | |
| 322 | 0.25 | 0.24 | 0.11 | 0.24 | | |
| 323 | 22 | >50 | 18.3 | 10 | | |
| 324 | 0.96 | 3.3 | 0.74 | 0.83 | | |
| 325 | 0.72 | 2.4 | 1.2 | 1 | | |
| 326 | 1 | 3.7 | 0.98 | 1.8 | | |
| 327 | 1.5 | 2.9 | 2.5 | 2.2 | | |
| 328 | 2.4 | 8.7 | 1.6 | 1.9 | | |
| 329 | 4.7 | 30 | 18.5 | 14 | | |
| 330 | 2.1 | 2.3 | 1 | 0.69 | | |
| 331 | 1.5 | 3.3 | 3.3 | 1.7 | | |
| 332 | 3.5 | 1.3 | 0.54 | 3.2 | | |
| 333 | 10 | 5.7 | 1.5 | 7.0 | | |
| 334 | 7.1 | 5.9 | 7.2 | 7.9 | | |
| 335 | 5.0 | 4.5 | 5.1 | 5.9 | | |
| 336 | 12 | 14 | 19 | 6.1 | | |
| 337 | 0.67 | 0.91 | 0.73 | 1.1 | | |
| 338 | 0.95 | 0.87 | 2.0 | 0.94 | | |
| 339 | 10 | 12 | 5.1 | 16 | | |
| 340 | 1.2 | 1.4 | 1.4 | 1.4 | | |
| 341 | 1.0 | 0.95 | 0.93 | 2.5 | | |
| 342 | 0.12 | 0.09 | 0.07 | 0.15 | | |
| 343 | 12 | 9.8 | 7.7 | 14 | | |
| 344 | 2.6 | 2.8 | 4.2 | 1.6 | | |
| 345 | 0.94 | 1.2 | 0.91 | 1.4 | | |
| 346 | 1.9 | 2.1 | 0.96 | 1.4 | | |
| 347 | 3.1 | 2.7 | 2.4 | 2.2 | | |
| 348 | 2.6 | 1.8 | 6.1 | 5.1 | | |
| 350 | 3.5 | 6.5 | 5.6 | 5.6 | | |
| 351 | 3.0 | 2.7 | 1.1 | 2.1 | | |
| 353 | 6.1 | 1.0 | 0.67 | >50 | | |
| 354 | 4.8 | 3.5 | 8.6 | 0.94 | | |
| 355 | 1.2 | 2.0 | 1.7 | 1.4 | | |
| 356 | 1.6 | 2.8 | 3.0 | 2.7 | | |
| 357 | 1.1 | 2.8 | 2.5 | 1.6 | | |
| 358 | 1.4 | 3.0 | 2.6 | 2.5 | | |
| 359 | 0.23 | 0.34 | 0.12 | 0.40 | | |
| 360 | 9.6 | 9.6 | 16 | 8.9 | | |
| 361 | 3.8 | 5.9 | 0.86 | 2.6 | | |
| 362 | 1.3 | 0.7 | 0.2 | 1.0 | | |
| 363 | 3.2 | 2.3 | 1.5 | 2.4 | | |
| 364 | 0.73 | 0.52 | 0.34 | 0.88 | | |
| 365 | 1.3 | 1.0 | 0.76 | 1.2 | | |
| 366 | 3.3 | 2.8 | 3.8 | 6.9 | | |
| 367 | 13 | 26 | 15 | 13 | | |
| 368 | 3.2 | 3.7 | 0.5 | 1.8 | | |
| 369 | 4.3 | 5 | 1.2 | 1.7 | | |
| 370 | 4.2 | 6.4 | 6.3 | 6.7 | | |
| 371 | 1.1 | 2.8 | 3.1 | 4.1 | | |
| 372 | 1.2 | 1.4 | 2.9 | 3.2 | | |
| 373 | 0.75 | 1.9 | 3.5 | 2.1 | | |
| 374 | 3.2 | 3.8 | 0.46 | 1.00 | | |
| 375 | 3.9 | 3.2 | 0.52 | 0.71 | | |
| 376 | 3.6 | 2.6 | 0.37 | 0.55 | | |
| 377 | 11 | >50 | >50 | >50 | | |
| 378 | 1.5 | 2.6 | 2.9 | 1.1 | | |
| 379 | 2.1 | 2.6 | 1.4 | 14 | | |
| 380 | 0.5 | 8.2 | 9.1 | 3.4 | | |
| 381 | 2 | 3.4 | 3 | 4.3 | | |
| 382 | 1.2 | 3.7 | 2.7 | 2.7 | | |
| 383 | 0.84 | 2.6 | 1.3 | 2.1 | | |
| 384 | 12 | 19 | 26 | 24 | | |
| 385 | 1.4 | 3.5 | 0.39 | 1.6 | | |
| 386 | 2.6 | 6.5 | 7 | 2.2 | | |
| 387 | 7.7 | 33 | 25 | 24 | | |

TABLE III-continued

In Vitro Cellular Activity

IC$_{50}$ (μM)

| EXAMPLE | HCT116 | LOVO | BT474 | MCF-7 | SK-Br-3 | SK-UT-1B |
|---|---|---|---|---|---|---|
| 388 | 2.7 | 5.5 | 3.9 | 3.1 | | |
| 389 | 23 | >50 | >50 | 29 | | |
| 390 | 17 | >50 | >50 | 22 | | |
| 391 | 2.4 | 7.3 | 3 | 2.6 | | |
| 392 | 2.5 | 4.8 | 3.8 | 4.2 | | |
| 393 | 2.8 | 6.8 | 5.9 | 2.7 | | |
| 394 | 3.7 | 3.7 | 4.03 | 2.6 | | |
| 395 | 2.3 | 2.8 | 1.49 | 1.4 | | |
| 396 | 1.4 | 3.1 | 2.8 | 3.8 | | |
| 397 | 2.8 | 4.3 | 6.18 | 3.6 | | |
| 398 | 2.3 | 6.3 | 6.19 | 4.4 | | |
| 399 | 3.0 | 7.0 | 7.57 | 5.4 | | |
| 400 | 2.9 | 8.6 | 9.33 | 8.7 | | |
| 401 | 2.6 | 6.7 | 4.45 | 5.1 | | |
| 402 | 4.0 | 6.0 | 7.1 | 7.6 | | |
| 403 | 41.5 | >50 | 40.0 | >50 | | |
| 404 | 1.6 | 3.1 | 3.1 | 7.3 | | |
| 405 | 1.7 | 2.0 | 3.1 | 5.6 | | |
| 406 | 2.6 | 2.7 | 3.9 | 3.4 | | |
| 407 | 3.8 | 8.5 | 10.2 | 9.7 | | |
| 408 | 2.5 | 2.6 | 2.4 | 5.1 | | |
| 409 | 25.6 | 6.4 | 41.6 | 36.6 | | |
| 410 | 2.8 | 6.8 | 2.3 | 5.1 | | |
| 411 | 3.8 | 3.5 | 0.45 | 1.6 | | |
| 412 | 1.8 | 3.2 | 5.6 | 4.3 | | |
| 413 | 1.9 | 3.3 | 5.0 | 5.8 | | |
| 414 | 2.4 | 6.2 | 6.2 | 6.0 | | |
| 415 | 1.2 | 2.0 | 2.9 | 3.6 | | |
| 416 | 2.7 | 3.1 | 2.5 | 6.2 | | |
| 417 | 1.3 | 3.1 | 2.8 | 3.2 | | |
| 418 | 1.4 | 2.4 | 2.7 | 3.2 | | |
| 419 | 7.0 | 12.0 | 12.9 | 7.6 | | |
| 420 | 4.0 | 16.2 | 7.7 | 36.8 | | |
| 421 | 2.6 | 2.7 | 2.9 | 3.8 | | |
| 422 | 2.0 | 3.8 | 3.7 | 5.6 | | |
| 423 | 3.8 | 4.5 | 5.4 | 4.3 | | |
| 424 | >50 | >50 | 12.7 | >50 | | |
| 425 | 0.6 | 1.2 | 1.5 | 2.6 | | |
| 426 | 1.6 | 2.2 | 4.5 | 2.8 | | |
| 427 | 17.8 | 22.7 | 23.2 | 22.4 | | |
| 428 | 0.77 | 0.65 | 0.07 | 1.67 | | |
| 429 | 21.0 | 21.1 | 11.7 | >50 | | |
| 430 | 5.6 | 14.9 | 13.8 | 11.7 | | |
| 431 | 6.1 | 5.8 | 6.4 | 8.8 | | |
| 432 | 11.1 | 8.5 | 9.3 | 24.2 | | |
| 433 | 2.0 | 2.8 | 4.5 | 3.1 | | |
| 434 | 4.5 | 8.2 | 8.1 | 31.5 | | |
| 435 | 3.2 | 5.2 | 8.5 | 26.0 | | |
| 436 | 2.5 | 2.3 | 0.4 | 1.5 | | |
| 437 | 3.7 | 3.6 | 2.9 | 3.1 | | |
| 438 | 1.6 | 1.6 | 2.2 | 1.8 | | |
| 439 | 3.5 | 2.5 | 0.38 | 0.75 | | |
| 440 | 3.2 | 4 | 1.6 | 1.6 | | |
| 441 | 1.1 | 2.9 | 3.2 | 2.3 | | |
| 442 | 1.1 | 4.1 | 3.7 | 2.4 | | |
| 443 | 0.76 | 0.85 | 0.65 | 1.6 | | |
| 444 | 3.2 | 5.0 | 5.2 | 8.9 | | |
| 445 | 1.8 | 2.7 | 2.8 | 3.2 | | |
| 446 | 1.7 | 2.9 | 3.4 | 3.0 | | |
| 447 | 2.0 | 3.5 | 3.0 | 3.6 | | |
| 448 | 2.4 | 4.1 | 6.6 | 5.0 | | |
| 449 | 2.6 | 2.2 | 8.1 | 3.5 | | |
| 450 | 2.5 | 2.8 | 1.9 | 2.5 | | |
| 451 | 2.8 | 2.5 | 1.0 | 1.0 | | |
| 452 | 3.1 | 1.5 | 9.3 | 3.3 | | |
| 453 | 3.7 | 3.3 | 4.0 | 4.3 | | |
| 454 | 7.4 | 10.5 | 10.5 | 11.5 | | |
| 455 | 2.4 | 3.3 | 3.1 | 3.1 | | |
| 456 | 2.7 | 8.3 | 9.2 | 11.0 | | |
| 457 | 0.96 | 1.00 | 1.60 | 2.1 | | |
| 458 | 2.7 | 1.2 | 3.5 | 4.2 | | |
| 459 | 13.0 | 9.5 | 17.3 | 10.7 | | |
| 460 | 8.3 | 9.4 | 10.0 | 10.3 | | |
| 461 | 22.8 | 24.1 | 7.7 | 23.3 | | |
| 462 | 2.6 | 3.6 | 4.8 | 3.5 | | |
| 463 | 2.3 | 2.0 | 1.7 | 0.9 | | |
| 464 | 3.2 | 4.6 | 6.6 | 2.4 | | |
| 465 | 2.9 | 5.0 | 3.8 | 1.3 | | |
| 466 | 2.1 | 2.1 | 1.4 | 1.2 | | |
| 467 | 2.3 | 2.4 | 3.6 | 1.9 | | |
| 468 | 1.1 | 1.6 | 2.1 | 1.5 | | |
| 469 | 0.8 | 1.2 | 2.2 | 2.9 | | |
| 470 | 20.9 | 19.1 | 2 | 37.8 | | |
| 471 | >50 | >50 | 21.9 | >50 | | |
| 472 | 5 | 8.9 | 9.1 | 14.2 | | |
| 473 | 2.4 | 2.3 | 1.5 | 2 | | |
| 474 | 3.5 | 3.8 | 7.4 | 4.0 | | |
| 475 | 3.2 | 7.7 | 8.1 | 2.2 | | |
| 476 | 1.9 | 3.1 | 2.6 | 4.5 | | |
| 477 | 1.6 | 3.9 | 4.1 | 2.3 | | |
| 478 | 24.2 | 46.8 | >50 | 44.8 | | |
| 479 | >50 | >50 | 43 | >50 | | |
| 480 | 3.3 | 4.5 | 1.0 | 1.6 | | |
| 481 | 0.88 | 0.96 | 0.6 | 1.1 | | |
| 482 | 2.5 | 2.7 | 1.3 | 0.84 | | |
| 483 | 13.06 | >50 | >50 | >50 | | |
| 484 | 1.13 | 1.24 | 2.49 | 3.23 | | |
| 485 | 1.36 | 0.94 | 1.07 | 1.42 | | |
| 486 | 7.49 | 7.56 | 3.61 | 10.04 | | |
| 487 | 5.72 | 9.19 | 11.07 | 8.91 | | |
| 488 | 3.16 | 2.41 | 0.96 | 2.27 | | |
| 489 | 4.04 | 4.59 | 6.25 | 3.43 | | |
| 490 | 0.42 | 0.34 | 0.26 | 0.88 | | |
| 491 | 3.5 | 2.7 | 1.2 | 1 | | |
| 492 | 1 | 3 | 3.3 | 4.1 | | |
| 493 | 4.7 | 9.4 | 10.9 | 10.2 | | |
| 494 | 0.58 | 0.52 | 0.53 | 1.0 | | |
| 495 | 4.9 | 6.3 | 4.5 | 3.3 | | |
| 496 | 2.6 | 3.1 | 7.4 | 5.4 | | |
| 497 | 2.6 | 3.2 | 2.7 | 1.4 | | |
| 498 | 1.1 | 1.6 | 1 | 3.5 | | |
| 499 | 4.8 | 8.4 | 9.8 | 9.1 | | |
| 500 | 1.9 | 1.8 | 2.3 | 3.8 | | |
| 501 | 2.6 | 2.9 | 3.5 | 1.4 | | |
| 502 | 1.4 | 0.96 | 0.69 | 1.2 | | |
| 503 | 5.2 | 5.1 | 1.6 | 1.0 | | |
| 504 | 3.9 | 4.3 | 1.0 | 1.5 | | |
| 505 | 0.38 | 0.27 | 0.26 | 0.70 | | |
| 506 | 0.48 | 0.41 | 0.29 | 1.13 | | |
| 507 | 3.1 | 18 | 9.5 | 11 | | |
| 508 | 0.95 | 1.1 | 3.0 | 1.3 | | |
| 509 | 0.25 | 0.19 | 0.13 | 0.54 | | |
| 510 | 0.67 | 0.42 | 0.16 | 1.40 | | |
| 511 | 2.30 | 2.50 | 2.50 | 1.50 | | |
| 512 | 1.19 | 3.05 | 2.36 | 2.70 | | |
| 513 | 1.54 | 3.45 | 1.84 | 2.53 | | |
| 514 | 1.04 | 0.74 | 0.59 | 2.25 | | |
| 515 | 0.44 | 0.38 | 0.34 | 1.10 | | |
| 516 | 3.83 | 21.4 | 18.2 | 24.1 | | |
| 517 | 0.25 | 0.17 | 0.09 | 0.79 | | |
| 518 | 0.23 | 0.15 | 0.08 | 0.64 | | |
| 519 | 0.82 | 1.4 | 2.2 | 1.0 | | |
| 520 | 1.2 | 0.9 | 0.66 | 2.2 | | |
| 521 | 2.57 | 5.44 | 7.55 | 2.6 | | |
| 522 | 1.42 | 1.19 | 2.13 | 0.99 | | |
| 523 | 6.4 | 6.2 | 5.7 | 7.3 | | |
| 524 | 0.11 | 0.12 | 0.03 | 0.89 | | |
| 525 | 0.71 | 0.45 | 0.14 | 0.71 | | |
| 526 | 2.4 | 5.6 | 7.2 | 3.3 | | |
| 527 | 0.55 | 0.49 | 0.09 | 2.7 | | |
| 528 | 16 | 26 | 18.3 | 14.3 | | |
| 529 | 1.7 | 1.5 | 1.2 | 2.4 | | |
| 530 | 0.43 | 0.28 | 0.24 | 0.7 | | |
| 531 | 0.15 | 0.1 | 0.04 | 0.7 | | |

TABLE III-continued

In Vitro Cellular Activity

IC$_{50}$ (μM)

| EXAMPLE | HCT116 | LOVO | BT474 | MCF-7 | SK-Br-3 | SK-UT-1B |
|---|---|---|---|---|---|---|
| 532 | 0.48 | 0.27 | 0.1 | 1.4 | | |
| 533 | 1.5 | 0.73 | 0.49 | 1.5 | | |
| 534 | 1.6 | 1.2 | 0.73 | 2.6 | | |
| 535 | 0.86 | 0.63 | 0.51 | 2 | | |
| 536 | 1.1 | 0.51 | 0.43 | 2.1 | | |
| 537 | 0.81 | 0.3 | 0.13 | 0.83 | | |
| 538 | 0.15 | 0.07 | 0.06 | 0.3 | | |
| 539 | 0.34 | 0.16 | 0.33 | 0.24 | | |
| 545 | 40.1 | >50 | >50 | >50 | >50 | 38.9 |
| 550 | 26.6 | 46.5 | 36.5 | 39.1 | 32.4 | 17.3 |
| 569 | 7.1 | >50 | 14.1 | 7.2 | 8.9 | 2.2 |
| 574 | 10.3 | 29.8 | 10.6 | 14.0 | | |
| 575 | 16.6 | 21.8 | 28.1 | 20.3 | | |
| 576 | 6.3 | 19.1 | 7.4 | 7.6 | | |
| 577 | 9.6 | 14.4 | 24.5 | 20.1 | | |
| 591 | 41.5 | >50 | 36.4 | 40.0 | | |
| 593 | 13.8 | 35.8 | 26.6 | 25.9 | | |
| 608 | 11.4 | 10.4 | 11.6 | 10.7 | | |
| 609 | 30.6 | 19.1 | 18.3 | 13.6 | | |
| 610 | 9.9 | 11.1 | 27.0 | 12.2 | | |
| 611 | 14.1 | 16.1 | 23.6 | 13.2 | | |
| 617 | 7.6 | 14.0 | 18.5 | 11.2 | | |
| 620 | 11.7 | 11.5 | 15.5 | 11.0 | | |
| 621 | 9.7 | 8.7 | 3.5 | 6.8 | | |
| 626 | >50 | >50 | >50 | 34.1 | | |
| 627 | >50 | >50 | 4.3 | 7.3 | | |
| 629 | >50 | >50 | >50 | 50.0 | | |
| 630 | 26.0 | 45.8 | 45.3 | 20.0 | | |
| 632 | >50 | 44.6 | >50 | 17.3 | | |
| 634 | 19.1 | 8.5 | 47.8 | >50 | | |
| 635 | 23.6 | >50 | 37.2 | 11.4 | | |
| 636 | 31.2 | 15.8 | 39.7 | 18.4 | | |
| 637 | >50 | >50 | 29.2 | 22.7 | | |
| 638 | >50 | >50 | 35.9 | >50 | | |
| 639 | >50 | >50 | 18.7 | 25.8 | | |
| 641 | 10.5 | 9.4 | 19.7 | 9.6 | | |
| 642 | 20.5 | 12.1 | 14.2 | 12.7 | | |
| 643 | 14.9 | 11.7 | 13.4 | 9.2 | | |
| 644 | 14.1 | 19.1 | 17.9 | 6.3 | | |
| 645 | 9.0 | 7.2 | 15.5 | 8.8 | | |
| 646 | 8.4 | 10.7 | 11.9 | 7.7 | | |
| 647 | 15.3 | 9.5 | 18.3 | 19.5 | | |
| 651 | >50 | >50 | >50 | 37.1 | | |
| 652 | >50 | >50 | 28.5 | 27.0 | | |
| 654 | 2.4 | 13.1 | 3.1 | 10.7 | | |
| 655 | 1.2 | 7.6 | 2.0 | 7.7 | | |
| 656 | 12.6 | 11.7 | 13.4 | 12.2 | | |
| 659 | 26.0 | >50 | 23.1 | 40.9 | | |
| 660 | 7.0 | 7.6 | 10.4 | 6.1 | | |
| 661 | >50 | >50 | 36.9 | 37.5 | | |
| 662 | >50 | >50 | 35.8 | 30.6 | | |
| 664 | 6.7 | 6.0 | 9.3 | 4.8 | | |
| 665 | 46.8 | >50 | 28.9 | 13.0 | | |
| 667 | >50 | 29.4 | >50 | 12.4 | | |
| 669 | 2.9 | 20.6 | 2.0 | 2.9 | | |
| 671 | 2.3 | 4.1 | 2.8 | 4.4 | | |
| 672 | 3.4 | 2.9 | 7.9 | 3.2 | | |
| 673 | 3.0 | 5.0 | 8.5 | 5.8 | | |
| 675 | 2.3 | 6.8 | 7.7 | 7.2 | | |
| 676 | 2.5 | 4.6 | 7.7 | 7.3 | | |
| 678 | 3.5 | 6.1 | 9.1 | 10.5 | | |
| 679 | 6.4 | 6.9 | 15.5 | 9.2 | | |
| 680 | 5.9 | 4.7 | 15.2 | 6.9 | | |
| 682 | 1.5 | 5.2 | 2.5 | 4.4 | | |
| 685 | 18.4 | 25.0 | 36.9 | 22.1 | | |
| 688 | 2.0 | 4.6 | 3.3 | 5.0 | | |
| 689 | 3.0 | 6.7 | 3.4 | 3.8 | | |
| 691 | 1.3 | 2.2 | 3.0 | 2.8 | | |
| 698 | 46.3 | >50 | 48.1 | >50 | | |
| 699 | 22.9 | >50 | >50 | >50 | | |
| 701 | >50 | >50 | 39.6 | 34.4 | | |
| 704 | >50 | >50 | 26.4 | 28.6 | | |
| 706 | >50 | >50 | >50 | 40.4 | | |
| 711 | >50 | >50 | 46.7 | >50 | | |
| 714 | >50 | >50 | >50 | 31.2 | | |
| 715 | 19.6 | 26.0 | 33.4 | 24.8 | | |
| 716 | >50 | >50 | >50 | 27.2 | | |
| 724 | 5.8 | 10.4 | 16.9 | 14.8 | | |
| 725 | 8.0 | 29.9 | 19.5 | 29.3 | | |
| 728 | 29.1 | >50 | >50 | >50 | | |
| 729 | 1.4 | 17.9 | 4.7 | 2.1 | | |
| 730 | 17.1 | 28.8 | 20.2 | 40.9 | | |
| 734 | 11.9 | 2.5 | 9.9 | 6.7 | | |
| 735 | 18.2 | 11.4 | 20.1 | 21.9 | | |
| 736 | 20.5 | 11.5 | 39.9 | >50 | | |
| 737 | 17.7 | 15.3 | >50 | 12.7 | | |
| 738 | 18.8 | 39.1 | 47.1 | 15.8 | | |
| 739 | 26.4 | >50 | 32.8 | 17.1 | | |
| 740 | 7.7 | 10.0 | 9.7 | 8.3 | | |
| 749 | 20.9 | 47.2 | >50 | 14.1 | | |
| 750 | 29.1 | 27.8 | >50 | 39.0 | | |
| 751 | 6.3 | 10.1 | 7.1 | 8.2 | | |
| 752 | 14.8 | 33.4 | 33.3 | 18.5 | | |
| 753 | 14.4 | 23.4 | 28.9 | 13.3 | | |
| 764 | 9.3 | 8.6 | 23.1 | 10.3 | | |
| 765 | 15.8 | 18.3 | 33.4 | 14.4 | | |
| 766 | 21.6 | 32.3 | 33.9 | 22.1 | | |
| 767 | 25.9 | 21.4 | 44.0 | 25.2 | | |
| 768 | 27.4 | 25.7 | 29.1 | 28.4 | | |
| 769 | 13.4 | 15.5 | 17.9 | 17.9 | | |
| 771 | 39.5 | 48.0 | 33.3 | >50 | | |
| 772 | 15.6 | 15.4 | 28.1 | 12.2 | | |
| 773 | 13.7 | 14.4 | 20.9 | 12.6 | | |
| 776 | 15.2 | 10.3 | 17.2 | 11.2 | | |
| 778 | 11.9 | 9.6 | 27.3 | 10.3 | | |
| 779 | 15.0 | 14.1 | 20.3 | 12.7 | | |
| 780 | 14.4 | 18.2 | 17.7 | 18.9 | | |
| 781 | 14.4 | 14.0 | 23.3 | 12.7 | | |
| 782 | 15.8 | 15.8 | 20.3 | 14.3 | | |
| 784 | 8.7 | 35.1 | >50 | 13.8 | | |
| 785 | >50 | >50 | >50 | 46.2 | | |
| 792 | 14.7 | 15.6 | 41.0 | 13.1 | | |
| 797 | 6.5 | 6.3 | 19.3 | 6.7 | | |
| 804 | 6.1 | 12.4 | 9.7 | 9.8 | | |
| 805 | 13.8 | 36.3 | 21.9 | 33.9 | | |
| 808 | 1.6 | 5.4 | 8.0 | 8.6 | | |
| 812 | 44.7 | >50 | >50 | 49.8 | | |
| 813 | 19.8 | 12.7 | 35.8 | 29.7 | | |
| 816 | 11.6 | 10.2 | 4.0 | 10.1 | | |
| 817 | 46.9 | 34.9 | 16.2 | 24.9 | | |
| 818 | 11.7 | 7.4 | 22.9 | 10.5 | | |
| 820 | 41.5 | 47.9 | >50 | >50 | | |
| 821 | 35.9 | 50.1 | 25.1 | 27.2 | | |
| 822 | 27.2 | 47.9 | 11.0 | 16.8 | | |
| 823 | 11.9 | 12.3 | 21.4 | 14.8 | | |
| 824 | 27.5 | >50 | >50 | 33.2 | | |
| 825 | 11.9 | 22.1 | 24.7 | 12.3 | | |
| 826 | 36.9 | >50 | >50 | >50 | | |
| 827 | 10.8 | 18.1 | 26.5 | 17.5 | | |
| 830 | 2.7 | 3.6 | 1.2 | 3.3 | | |
| 831 | 2.8 | 2.8 | 3.2 | 7.3 | | |
| 832 | 9.9 | 8.5 | 14.9 | 11.8 | | |
| 833 | 16.9 | 19.2 | 25.1 | 26.5 | | |
| 834 | 29.6 | 23.1 | 13.2 | 18.6 | | |
| 835 | 10.0 | 11.3 | 11.7 | 12.6 | | |
| 836 | 12.7 | 6.8 | 12.8 | 17.7 | | |
| 837 | 10.6 | 8.5 | 1.5 | 3.6 | | |
| 838 | 7.2 | 17.2 | 23.5 | 8.2 | | |
| 839 | 14.1 | >50 | 27.2 | 21.6 | | |
| 840 | 19.0 | >50 | 32.8 | 40.0 | | |
| 841 | 36.0 | 34.0 | 47.8 | | | |
| 842 | 4.5 | 5.7 | 7.2 | | | |
| 843 | 54.3 | >50 | >50 | 47.1 | | |
| 844 | 28.0 | 26.7 | 27.1 | 26.1 | | |

TABLE III-continued

In Vitro Cellular Activity

IC$_{50}$ (µM)

| EXAMPLE | HCT116 | LOVO | BT474 | MCF-7 | SK-Br-3 | SK-UT-1B |
|---|---|---|---|---|---|---|
| 845 | 4.2 | 2.5 | 7.5 | 4.5 | | |
| 846 | 2.6 | 4.8 | 10.7 | 4.9 | | |
| 847 | 4.3 | 4.9 | 8.1 | 6.0 | | |
| 848 | 7.1 | 13.3 | 13.8 | 10.9 | | |
| 849 | 12.8 | 15.9 | 6.8 | 4.3 | | |
| 850 | 16.0 | 24.2 | 46.5 | >50 | | |
| 852 | >50 | >50 | >50 | 46.3 | | |
| 855 | >50 | >50 | 43.3 | 42.6 | | |
| 856 | 12.2 | 13.5 | 5.6 | 3.8 | | |
| 857 | 43.1 | >50 | 24.0 | >50 | | |
| 858 | 37.7 | 39.0 | 34.3 | 34.7 | | |
| 859 | 40.7 | 40.0 | 31.2 | 20.6 | | |
| 860 | 33.0 | 36.1 | 35.2 | 40.0 | | |
| 861 | >50 | >50 | 45.4 | >50 | | |
| 863 | 11.2 | 10.2 | 31.1 | 16.3 | | |
| 864 | 3.1 | 3.8 | 7.9 | 3.6 | | |
| 865 | 3.1 | 3.6 | 7.5 | 5.3 | | |
| 866 | 2.5 | 4.7 | 6.5 | 3.6 | | |
| 867 | 3.5 | 5.3 | 8.3 | 6.7 | | |
| 868 | 2.5 | 3.9 | 6.8 | 5.5 | | |
| 869 | 5.4 | >50 | >50 | >50 | | |
| 870 | 3.0 | 10.5 | 10.2 | 9.2 | | |
| 871 | 13.9 | 46.6 | >50 | 29.1 | | |
| 872 | 28.6 | 47.1 | >50 | 34.8 | | |
| 873 | 24.5 | 41.1 | 42.7 | 29.2 | | |
| 874 | 12.6 | 23.7 | 27.4 | 7.2 | | |
| 875 | 9.5 | 12.5 | | 10.3 | | |
| 876 | 4.2 | 8.6 | | 5.3 | | |
| 877 | 3.9 | 6.2 | | 4.4 | | |

Cyclin D1/CDK6 Elisa

Cyclin D1/CDK6 was expressed in insect cells (Sf9) infected with recombinant baculovirus and partially purified using ammonium sulfate fractionation. Test compounds were diluted in 20% DMSO/20 mM HEPES, pH 7.5 and serial dilutions were prepared (5 concentrations; 0.005-50 □M). High-binding ELISA microtiter plates (Costar) were coated with the kinase substrate (glutathione-S-transferase (GST) fusion of C-terminal fragment of the retinoblastoma susceptibility gene product (Rb). Non-specific binding sites were blocked with Superblock in Tris-buffered saline (TBS; Pierce). Kinase reactions contained the test inhibitor, 200 µM ATP, 0.5 mg/ml bovine serum albumin (BSA; Sigma), and 0.1 µl cyclin D1/cdk 6. Reaction volumes were adjusted to 30 µl with kinase assay buffer (50 mM HEPES, pH 7.5, 10 mM MgCl$_2$, 5% glycerol, 10 mM 2-mercaptoethanol), and plates were incubated at 30° C. for 1 hour. Reactions were terminated by aspiration, and non-specific sites were blocked with blocking buffer (TBS containing 0.1% Tween-20 and 5% nonfat dry milk). Phoshporylation of the substrate was detected using phospho-Rb specific antibodies (ser-795) (Cell Signalling Technologies) and anti-rabbit IgG/horseradish peroxidase conjugates (Amersham Life Science) using TMB as substrate. Colourimetric reactions were stopped with 2N sulphuric acid and the absorbance was measured at 450 nm (Molecular Devices). IC$_{50}$ values were determined from inhibition plots.

TABLE IV

In Vitro Cellular Assays CDK 6 Activity

| EXAMPLE | IC$_{50}$ (µM) CDK6 |
|---|---|
| 55 | 0.12 |
| 71 | 0.001 |
| 74 | 0.02 |
| 78 | 0.002 |
| 80 | 0.002 |
| 81 | 0.1 |
| 82 | 0.03 |
| 84 | 0.07 |
| 86 | 0.001 |

Gel Kinase Assay

Compounds were diluted in 20% DMSO/20 mM HEPES, pH 7.5 and serial dilutions were prepared. Kinase reactions contained the test inhibitor, 200 µM ATP, 0.5 mg/ml bovine serum albumin (BSA; Sigma), 0.1-0.5 µl partially purified cyclin D1/cdk enzyme and 5 ug of the substrate (GST-RB fusion protein). Reaction volumes were adjusted to 30 µl with kinase assay buffer (50 mM HEPES, pH 7.5, 10 mM MgCl$_2$, 5% glycerol, 10 mM 2-mercaptoethanol). Reactions were incubated at 30° C. for 30 minutes, stopped with sodium-dodecyl sulphate (SDS)-sample buffer, and analysed by SDS-polyacrylamide gel electrophoresis (SDS-PAGE) and protein immunoblotting. Phosphorylation of the substrate was detected using phospho-Rb specific antibodies (ser-795), and anti rabbit IgG/HRP conjugates using enhanced luminescence (ECL, Amersham). Blots were scanned and quantified using the FluorS multimage analyser (BioRad). IC$_{50}$s were determined from inhibition plots (Kaleidagraph).

RB Phosphorylation in Cells

MCF-7 cells were treated overnight with various concentrations of the compounds. Cell lysates were prepared in lysis buffer (250 mM Tris, pH 7.5, 150 mM sodium chloride, 1% Nonidet P-40, 0.5% sodium deoxycholate, 2 mM phenylmethylsulfonyl fluoride, 100 mM sodium fluoride, 1 mM sodium vanadate, 5 mM DTT). Lysates were fractionated by SDS-PAGE and transferred to nitrocellulose. Phosphorylation of Rb was detected using phospho-RB specific antibodies (Ser-807/811) and anti rabbit IgG/HRP conjugates using enhanced luminescence (ECL, Amersham). Blots were scanned and quantified using the FluorS multiimage analyser (BioRad). IC$_{50}$s were determined from inhibition plots (Kaleidagraph).

TABLE V

Solution Assay

| EXAMPLE | IC$_{50}$ (µM) Soln Assay |
|---|---|
| 2 | 3.7 |
| 44 | 3.9 |
| 49 | 41.4 |
| 51 | 1.3 |
| 101 | 11.2 |
| 121 | 4.2 |
| 135 | 2.8 |
| 160 | 5.9 |
| 161 | 10.6 |
| 162 | <1.0 |
| 215 | 5.9 |
| 223 | 3.3 |
| 230 | 15.4 |

TABLE V-continued

Solution Assay

| EXAMPLE | IC$_{50}$ (µM) Soln Assay |
|---|---|
| 240 | 3.0 |
| 242 | 18.4 |
| 253 | 0.5 |
| 272 | 5.2 |
| 282 | 0.9 |
| 509 | 5.7 |

TABLE VI

I.V. and P.O. Dosing in Mice

| Example | dose I.v. mg/kg | aucinf obs hr * ng/mL | Cl_obs mL/min/kg | Vss_obs L/kg | dose po mg/kg | HL_Lambda_z hr | aucinf obs hr * ng/mL | % bioavailability |
|---|---|---|---|---|---|---|---|---|
| 107 | 2 | 901 | 37 | 11 | 50 | 7.4 | 4098 | 18.2 |
| 178 | 2 | 999 | 33 | 1.5 | 50 | 6.1 | 360 | 14 |
| 364 | 2 | 10979, 15812 (methocel/tween) | 3, 2.1 | 0.2, 0.1 | 50 | 1.8, 2.4 | 17167, 5352 | 6.3, 1.4 |
| 506 | 2 | 423 | 79 | 6.7 | 50 | 2.6 | 5593 | 53 |
| 517 | 2 | 2358 | 14 | 0.5 | 50 | 0.5 | 39 | 0.07 |
| 524 | 2 | 952 | 35 | 2.4 | 50 | 0 | 0 | 0 |
| 525 | 2 | 2750 | 12 | 0.4 | 50 | 3.4 | 11997 | 17 |
| 527 | 2 | 6065 | 5 | 0.5 | 50 | 3.4 | 1403 | 0.9 |
| 530 | 2 | 2241 | 15 | 0.2 | 50 | 5.3 | 7203 | 13 |
| 531 | 2 | 1446 | 23 | 0.9 | 50 | 5.2 | 879 | 2.5 |
| 535 | 2 | 238 | 140 | 4.1 | 50 | 1.9 | 1243 | 21 |
| 538 | 2 | 6630 | 5 | 0.2 | 50 | 7.1 | 1038 | 0.63 |
| 539 | 2 | 1560 | 21 | 0.3 | 50 | 0.8 | 44 | 0.12 |

Standard Pharmacological Test Procedure

TITLE: 96-well assay for inhibitors of IGF1-receptor kinase activity
SHORT TITLE: IGF1-R kinase assay
PURPOSE: Identify inhibitors of IGF-1 receptor kinase activity
MATERIALS AND METHODS: Overview: This is a 96-well FRET (Lance) tyrosine kinase assay.
Materials:
  Purified GST-IGFR; purified Bis-IGFR and Tris-IGFR; expressed in ExpresSF insect cells. Bis and Tris IGFR are made by phosphorylating the IGFR in the presence of ATP and Mg2+, followed by thrombin cleavage to remove the GST-thrombin cleavage site, and purification by HPLC. The Bis and tris IGFR are phosphorylated on two (bis) or all three tyrosines (tris) in the activation loop.
  Biotinylated peptide with a sequence corresponding to the sequence surrounding the autophosphorylation sites in IGF1-R    Biotin-NH2-TRDIYETDYYRK-OH (Anaspec)
  Europium-conjugated phosphotyrosine antibody (PT66) (Perkin-Elmer).
  Surelight APC (Perkin-elmer)
  Plates: 96-well Assay plates (polypropylene plates, natural color)
  96-well-Lance plates (Microfluor 2 black plates; Cat # 7205; Thermolabsystems).
  ATP: (Amersham Pharmacia Cat # 27-2056-01), 100 mM stock.
  IGFR Lance Protocol (96-well format)

Procedure:
Reagents:
Kinase Buffer (10×):
  0.5 M Hepes, pH 7.5 rt
  0.1 M MgCl$_2$
Quench Buffer (to be added straight, 1:1, to rxn mix):
  50 mM Hepes, pH 7.5 rt
  50 mM EDTA
Lance Detection Buffer:
  20 mM Tris-HCl, pH 7.5 rt
  0.15 M NaCl-150
  150 ug/ml BSA (Sigma Cat# A-7284)
  Eu-labeled phosphotyrosine antibody PT66 (Perkin-Elmer): 1:4000 dilution of 200 µg/ml stock
  Streptavidin-APC (Perkin Elmer): 1/250 (4 microgram/ml final)
  ATP (Amersham Pharmacia cat #27-2056-01) 100 mM stock: Dilute to 1 mM (10×) in water. 100 micromolar final conc in reaction.
  Enzyme: GST-IGFR—12.5 ng/rxn (50 microliter 96 well assay); 5 ng/rxn (20 microliter 384 well assay); Bis-IGFR: 9 ng per 50 uL rxn; Tris-IGFR: 0.3 ng per 50 ul rxn.
  Peptide: Anaspec; Biotin-NH2-TRDIYETDYYRK-OH or Anaspec 610SAXAB
  2 micromolar final concentration.
Reaction: Make a mix containing the following relative amounts of reaction components (Include a no ATP control for Bkg subtraction):
  5λ 10× kinase buffer
  0.5λ 100× peptide
  5λ 1.5 mg/ml BSA (Sigma #A-8918 BSA)—note different BSA for rxn than for Lance!
  0.5λ 100% DMSO—DMSO is adjusted to a final conc of 1%
  32 λ water
Mix, then add
  IGFR
Mix gently, then add:
  5 λ 1 mM ATP
Allow reaction to proceed for 1 h then add 50□ of quench buffer.
To a separate plate add 50 λ well of Lance detection buffer with PT66 and APC-streptavidin. Transfer 12.5□ of the kinase reaction to the antibody detection plate. Allow antibody to react for 1 h at rt in the dark. Then read in Victor with an excitation filter of 340 nm and an emission filter of 665 nm.

Compound additions:

When Example compounds are tested, they are added from a 10% DMSO/50 mM Hepes (pH 7.5) 10× stock. 5 microliters of compound in this buffer are added to the enzyme-peptide-buffer mix. After 10' incubation at room temperature, ATP is added to start the reaction. A no ATP background control is included in the assay.

ANALYSIS OF RESULTS: Data are analyzed as follows: % Inhibition={[Sample cpm−Bkg cpm]/[No cmpd cpm−Bkg cpm]}×100%.

The biological activity of representative Examples of the invention is reported in Table VII as: 0.2 ☐M≦x≦10 ☐M or % inhibition@10 ☐M.

TABLE VII

| Example Number | Igfr ic50 (uM) or % Inhibition at 10 uM |
|---|---|
| 881 | 0.361 |
| 882 | 4.47 |
| 883 | 33% |
| 884 | 20% |
| 885 | 0.36 |
| 886 | 32% |
| 887 | 0.208 |
| 888 | 14% |
| 889 | 0.394 |
| 890 | 47% |
| 891 | 0.575 |
| 892 | 0.954 |
| 893 | 0.708 |
| 894 | 1.11 |
| 895 | 7.22 |
| 896 | 0.83 |
| 897 | 1.52 |
| 898 | 0.868 |
| 899 | 3.09 |
| 900 | 20% |
| 901 | 6.03 |
| 902 | 3.7 |
| 903 | 45% |
| 904 | 1.7 |
| 905 | 2.62 |
| 906 | 0.92 |
| 907 | 1.39 |
| 908 | 0.566 |
| 909 | 0.887 |
| 910 | 0.54 |
| 911 | 1.16 |
| 912 | 9% |
| 913 | 6.16 |

What is claimed is:

1. A compound having the Formula (I)

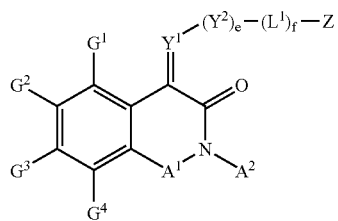

(I)

or a pharmaceutically acceptable salt thereof, $A^1$ is CO;

$A^2$ is H, OH, $CH_2OH$, $C_{1-6}$ alkyl, alkoxy, benzyloxy, arylalkyl, benzyl, aryl, acyl, —C(O)R, —OC(O)O-PEG, —$CH_2$OC(O)O-PEG, —OC(O)NH-PEG, —$CH_2$OC(O)NH-PEG, OC(O)OH, $CH_2$O(C(O)OH, OC(O)halogen, $CH_2$OC(O)halogen, OC(O)$CH_2$halogen, OC(O)$CH_2$S($CH_2$)$_m$O-PEG wherein the aryl or benzyl is optionally substituted with $R_4$;

PEG is —(O$CH_2CH_2$)$_r$O$CH_3$;

$Y^1$ is $CR_3$;

$Y^2$ is $NR_1$;

$L^1$ is $C(R_7)(R_8)$;

$R_1$ is H, $C_{1-6}$ alkyl, aryl, aryl, or benzyl;

$R_3$ is H, aryl, $C_{1-6}$ alkyl, $NR_{10}R_{11}$, or —O—;

$R_4$, is selected from the group consisting of H, aryl, or $C_{1-6}$ alkyl, halogen, —CN, —OCF$_3$, —NO$_2$, —COOH, —CF$_3$, OH, SH, N$_3$, —C(O)H, heteroaryl, $C_{1-6}$alkoxy, heterocycloalkyl, $C_{2-6}$ alkenyl, $C_{2-6}$alkynyl, —COR$_{100}$, —Oaryl, —OR$_{100}$, —NHaryl, —S(O)$_m$R$_{100}$, —C(O)Q, C(O)OR$_{100}$, —NR$_{100}$aryl, —OR$_{100}$aryl, —SR$_{100}$aryl, —NHR$_{102}$OH, —NHR$_{102}$OR$_{100}$, —NHR$_{102}$NHR$_{100}$, —NR$_{100}$R$_{102}$OH, —NHR$_{102}$Q, —NR$_{100}$R$_{102}$NH$_2$, —NR$_{100}$R$_{102}$NHR$_{100}$, —NR$_{100}$R$_{1020}$R$_{100}$, —NR$_{100}$R$_{102}$Q, —OR$_{102}$OH, —OR$_{102}$OR$_{100}$, —OR$_{102}$NH$_2$, —OR$_{102}$NHR$_{100}$, —OR$_{102}$Q, —OCOR$_{100}$, —OR$_{100}$COR$_{100}$, —NHCOR$_{100}$, —NHCONH$_2$, —NHCONHR$_{100}$, —NHR$_{100}$COR$_{100}$, —NHR$_{102}$NH$_2$, —NHOH, —NHOR$_{100}$, —CONR$_{10}$R$_{11}$, —NHSO$_2$R$_{100}$, NR$_{10}$, R$_{11}$, —NHC(O)-heteroaryl, —NHC(O)R$_{102}$-heteroaryl, OC(O)CH$_2$halogen, —OC(O)CH$_2$S(CH)$_m$O-PEG, OC(O)NH-PEG, —N(R$_{10}$)(R$_{11}$), —NHC(O)R$_{102}$-aryl, and —NHC(O)NH-heterocycloalkyl that is optionally substituted with up to three $C_{1-3}$ alkyl groups;

wherein said aryl, said heteroaryl, and said heterocycloalkyl are each optionally substituted with up to four independently selected $R_{12}$ groups;

wherein said $C_{2-6}$ alkenyl, said $C_{1-6}$ alkyl, $C_{1-6}$alkoxy, and said $C_{2-6}$ alkynyl are each optionally substituted with up to three independently selected $R_{13}$ groups;

$R_5$ is selected from the group consisting of $C_{1-6}$ alkyl or alkenyl, wherein the alkyl or alkenyl are optionally substituted with OH, OR, $NR_{10}R_{11}$, $C_{1-6}$ alkyl;

$R_7$ and $R_8$ are selected from the group consisting of H, $C_{1-6}$ alkyl, OR$_{100}$, OH, C(O)H or COOH;

$R_{10}$ and $R_{11}$ are selected from the group consisting of H, $C_{1-6}$ alkyl, $C_{2-6}$alkenyl, $C_{1-6}$ acyl, —S(O)$_2$aryl, —C(O)$_2$alkenyl, $C_{2-6}$ alkynyl, aryl or heteroaryl, wherein said $C_{1-6}$ acyl is optionally substituted with a heteroaryl, wherein said $C_{1-6}$ alkyl is optionally substituted with up to three halogen atoms, wherein said aryl and said heteroaryl are optionally substituted with up to three $R_{12}$ groups, wherein $R_{10}$ and $R_{11}$ may be taken together with the N to which they are attached to form a 3-8 membered heterocyclic ring, wherein said heterocyclic ring may contain additional atoms selected from the group N, O, and —S(O)$_m$ and said heterocyclic ring may be additionally substituted with 1 to 4 substituents selected from the group consisting of $C_{1-6}$alkyl, OH, —OC$_1$alkyl, —OC$_{3-6}$cycloalkyl, —(CH$_2$)$_n$OH, —(CH$_2$)$_n$OC$_{1-6}$alkyl, —(CH$_2$)$_n$OC$_{3-6}$cycloalkyl, —NR$_{10}$R$_{11}$, —(CH$_2$)$_n$NR$_{10}$R$_{11}$, and =O;

$R_{12}$ is independently selected from the group consisting of aryloxy, halogen, OH, —COOH, —C(O)H, —C(O)R, —$C_{1-3}$ perhaloalkyl, —OCF$_3$, $C_{1-6}$ acyl, —CN, —NO$_2$, aryl, heteroaryl, —S—$C_{1-6}$ alkyl, —NHCOC$_{1-6}$alkyl, —N(R$_{15}$)(R$_{16}$), $C_{1-3}$ perhaloalkoxy, $C_{1-6}$ alkyl, $C_{2-6}$ alkenyl, —CONH$_2$, —CF$_3$, SH, N$_3$, heterocycloalkyl, —C(O)R$_{100}$, —OR$_{100}$, —NHaryl, —S(O)$_m$R$_{100}$, —C(O)Q, C(O)OR$_{100}$, —C(O)NHR$_{100}$, —NR$_{100}$aryl, —N(R$_{100}$)R$_{102}$aryl, —OR$_{102}$aryl, —SR$_{102}$aryl, —NHS(O)$_2$—R$_{100}$, —NHR$_{102}$OH, —NHR$_{102}$OR$_{100}$, —NHR$_{102}$NHR$_{100}$—N(R$_{100}$)R$_{102}$OH, —NHR$_{102}$Q, —N(R$_{100}$)R$_{102}$NH$_2$, —N(R$_{100}$)R$_{102}$NHR$_{100}$, —N(R$_{100}$)R$_{102}$OR$_{100}$, —N(R$_{100}$)R$_{102}$Q, —OR$_{102}$OH, —OR$_{102}$OR$_{100}$, —OR$_{102}$NH$_2$, —OR$_{102}$NHR$_{100}$, —OR$_{102}$Q, —OC(O)R$_{100}$, —OR$_{102}$C(O)R$_{100}$, —NHC(O)R$_{100}$, —NHCONH$_2$, —NHCONHR$_{100}$, —NHR$_{102}$C(O)R$_{100}$, —NHR$_{102}$NH$_2$, —NHS(O)$_2$-aryl, —NHOH, —NHC(O)aryl, —NHOR$_{100}$, —NHC(O)-heteroaryl, —NHC(O)R$_{102}$-heteroaryl, —O(O)N(R$_{10}$)(R$_{11}$), —N(R$_{10}$)(R$_{11}$), NHC(O)R$_{102}$aryl, and NHC(O)NH-heterocycloalkyl that is optionally substituted with up to three C$_{1-3}$ alkyl groups, wherein said C$_{2-6}$ alkenyl, said C$_{1-6}$ alkyl, and said C$_{2-6}$ alkynyl are each optionally substituted with up to three independently selected R$_{13}$ groups and —N(R$_{15}$)(R$_{16}$);

R$_{13}$ is independently selected from the group consisting of arylalkyl, aryl, heteroaryl, C$_{1-6}$ alkyl, C$_{3-6}$ cycloalkyl, heterocycle, heterocycloalkyl, heterocycloalkyloxy, CN, OH, C$_{1-6}$ alkoxy, halogen and —COOH, —SH, —COH, —COR$_{100}$, —CONH$_2$, —CONHR$_{100}$, —COQ, —OCOR$_{100}$, —OCONH$_2$, —OCONR$_{100}$, —OCOQ, —OR$_{102}$OH, —OR$_{102}$NR$_{15}$R$_{16}$, and

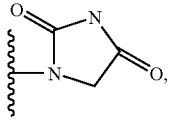

wherein said aryl, heteroaryl, and heterocycloalkyl are optionally substituted with up to three independently selected R$_{18}$ groups;

R$_{15}$ and R$_{16}$ are selected from the group consisting of H, C$_{1-6}$ alkyl, and C$_{1-6}$; and wherein said R$_{15}$ and R$_{16}$ groups taken together with the nitrogen to which they are attached may form a heterocyclic ring of 3 to 8 atoms with 1 or 2 additional heteroatoms selected from the group N, O, and —S(O)$_m$, the heterocyclic ring may be substituted with groups consisting of OH, -OC$_{3-6}$cycloalkyl, —OC$_{1-6}$ alkyl, —(CH$_2$)$_n$OH, —(CH$_2$)$_n$OC$_{1-6}$alkyl, —NR$_{10}$R$_{11}$, —(CH$_2$)$_n$NR$_{10}$R$_{11}$, and —(CH$_2$)$_n$OC$_{3-6}$cycloalkyl;

R$_{18}$ is independently selected from the group consisting of OH, halogen, —NO$_2$, dialkylamino, —N(R$_{15}$)(R$_{16}$), —COOH, —S(O)$_2$NH$_2$, C$_{1-3}$ perhaloalkyl, —OCF$_3$, C$_{1-3}$ alkoxy, C$_{1-6}$ alkyl, CN, C$_{1-8}$ cyanoalkyl and C$_{4-8}$ cycloalkenyl, wherein said cycloalkenyl is optionally substituted with up to three groups independently selected from OH and C$_{1-3}$ alkoxy, and wherein said C$_{1-6}$ alkyl is optionally substituted with —N(R$_{15}$)(R$_{16}$);

R$_{20}$ is selected from the group consisting of C$_{1-6}$ alkyl, C$_{3-6}$ cycloalkyl and C$_{2-6}$ alkenyl, wherein said C$_{1-6}$ alkyl is optionally substituted with up to three halogen atoms or a group of formula —[(CH$_2$)(Q'')]$_k$CH$_3$;

R$_{21}$ is selected from the group consisting of C$_{1-6}$ alkyl and cycloalkyl;

R$_{22}$ is selected from the group consisting of heteroaryl, aryl, arylalkyl and C$_{1-6}$ alkyl, wherein said C$_{1-6}$ alkyl is optionally substituted up to three halogen atoms;

R$_{23}$ is selected from the group consisting of aryl, heteroaryl and C$_{1-6}$ alkyl, wherein said aryl and said heteroaryl is optionally substituted with up to three C$_{1-3}$ alkyl groups, and said C$_{1-6}$ alkyl is optionally substituted with up to three halogen atoms;

R$_{24}$ is selected from the group consisting of H, —COOH, C$_{3-6}$ cycloalkyl, —OCHF$_2$, —OCHCl$_2$, C$_{1-3}$ perhaloalkyl, C$_{1-6}$ alkoxy, heteroaryl, heterocycloalkyl, C$_{2-6}$ alkynyl, C$_{1-6}$ alkyl, C$_{2-6}$ alkenyl, and aryl, wherein said C$_{1-6}$ alkyl is optionally substituted with up to three groups independently selected from halogen and C$_{3-6}$ cycloalkyl, said C$_{2-6}$ alkenyl optionally substituted with up to three groups independently selected from halogen and N(R$_{27}$)(R$_{28}$), said aryl is optionally substituted with up to three OH groups, and said heterocycloalkyl is optionally substituted with up to three independently selected C$_{1-6}$ alkyl groups, —(CH$_2$)$_m$cycloalkyl, —(CH$_2$)$_n$OH, —(CH$_2$)$_n$OR, —(CH)$_2$NR$_{10}$R$_{11}$, —COR$_5$, and Q;

R$_{25}$ is OH, or NR$_{10}$R$_{11}$;

R$_{27}$ and R$_{28}$ are independently selected from the group consisting of C$_{1-6}$ alkyl, C$_{3-6}$ cycloalkyl, heterocycloalkyl, C$_{2-6}$ alkenyl, H, aryl, Q, —C(O) C$_{3-6}$ alkyl (cycloalkyl), —COalkyl, —COalkenyl, —COalkynyl, —COaryl, —COheteroaryl, —COcycloalkyl, C$_{1-6}$ acyl, —C(O)C(O)OH, halogen, —COC$_{1-6}$halogen, C$_{1-3}$alkoxy, and arylalkyl, wherein said C$_{1-6}$ alkyl, aryl, acyl, and heterocycloalkyl are optionally substituted with up to three R$_{52}$ groups; or R$_{27}$ and R$_{28}$ together with the nitrogen atom to which they are attached can form a 5 or 6 membered saturated heterocyclic ring that can include one additional O, N, or S ring atom, said saturated heterocyclic ring optionally substituted with a carboxylate or C$_{1-3}$ alkyl groups;

R$_{31}$ is selected from the group consisting of trialkylsilyl, C$_{1-6}$ alkoxycarbonyl, C$_{1-6}$ alkyl, C$_{2-6}$ alkenyl, heteroarylalkyl, heterocycloalkyl and arylalkyl, wherein said C$_{1-6}$ alkyl, said arylalkyl and said heteroarylalkyl are each optionally substituted with up to three independently selected R$_{53}$ groups, and said heterocycloalkyl is optionally substituted with up to three C$_{1-6}$ alkyl groups;

R$_{32}$ is selected from the group consisting of H, C$_{1-6}$ acyl, heteroaryl and C$_{1-6}$ alkyl, wherein said heteroaryl is optionally substituted with up to three C$_{1-3}$ alkyl groups, and said C$_{1-6}$ alkyl is optionally substituted with up to three heteroaryl or R$_{52}$ groups;

R$_{33}$ is selected from the group consisting of heterocycloalkyl, aryl, C$_{1-6}$ perhaloalkyl, —N(R$_{27}$)(R$_{28}$) and C$_{1-6}$ alkyl, wherein said aryl, C$_{1-6}$ alkyl, heterocycloalkyl, are optionally substituted with up to three groups selected from halogen, C$_{1-6}$ alkyl, aryl, OH and —N(R$_{27}$)(R$_{28}$);

R$_{34}$ is selected from the group consisting of aryloxy, C$_{1-6}$ alkyl, aryl and alkoxy, wherein said aryl is optionally substituted with COOH, and said alkoxy is optionally substituted with —N(R$_{27}$)(R$_{28}$);

R$_{35}$ is selected from the group consisting of dialkylamino, or C$_{1-6}$ alkyl that is optionally substituted with —COOH or with —N(R$_{27}$)(R$_{28}$);

R$_{41}$ is selected from the group consisting of —R$_{100}$, —R$_{102}$R$_{100}$, —R$_{102}$OR$_{100}$, —R$_{102}$OH, and —R$_{102}$Q;

R$_{50}$ is selected from the group consisting of heterocycloalkyl, (N=H), NH$_2$, —NHCOC$_{1-3}$ alkyl, C$_{1-3}$ alkyl, —NHCOC$_{1-3}$ cycloalkyl, —NHCOC$_{1-3}$ heterocycloalkyl, —OH, —CN, —COOH, —N(R$_{27}$)(R$_{28}$), —SO$_2$N(R$_{27}$)(R$_{28}$), halogen, heteroaryl and aryl, wherein said aryl, heteroaryl, or heterocycloalkyl are optionally substituted with a group selected from C$_{1-3}$ alkyl, C(O)H, C$_{1-4}$ alkoxy, and —CONHN(R$_{21}$)$_2$, and up to three groups selected from halogen, and NH$_2$;

R$_{52}$ is independently selected from the group consisting of COH, OH, CN, NH$_2$, —NHR$_{21}$, —N(R$_{21}$)$_2$, C$_{1-6}$ alkyl, aryl, —COaryl, heterocycloalkyl, halogen, $C_{1-3}$ perhaloalkyl, and —$C_{3-6}$cycloalkyl, wherein the aryl can be substituted with COOH;

$R_{53}$ is selected from the group consisting of OH, $C_{1-6}$ alkyl, arylalkyloxy, heterocycloalkyl, $C_{1-3}$ alkoxy, halogen and $C_{3-6}$ cycloalkyl;

$R_{100}$ is selected from the group consisting of $C_{1-12}$alkyl, $C_{3-6}$ cycloalkyl aryl, heteroaryl, $C_{2-6}$alkenyl, and $C_{2-6}$alkynyl;

$R_{102}$ is a divalent $C_{1-6}$alkyl;

$R_{200}$ is selected from the group consisting of —$(CR_{201}R_{201})_qR_{203}$, —$N(R_{201})C(O)(CH_2)_qR_{203}$, $N(R_{201})(CH_2)R_{203}$ and —NHC(O)NH—$R_{203}$;

$R_{201}$ is selected from the group consisting of H and $C_{1-6}$ alkyl;

$R_{203}$ is selected from the group consisting of dialkylamino and a 5-7 membered heterocycloalkyl ring having up to three ring hetero atoms selected from O, N and S, said heterocycloalkyl ring being optionally substituted with up to three independently selected $R_{204}$ groups;

$R_{204}$ is selected from the group consisting of OH, COOH, $C_{1-6}$ alkyl, alkoxycarbonyl, arylalkyl, heteroarylalkyl, $C_{2-6}$ alkenyl, $C_{3-6}$ cycloalkyl, aryl, $C_{1-6}$ alkoxy, $C_{2-6}$ acyl, heterocycloalkyl, —C(O)N($R_{300}$)($R_{300}$), —NHC(O)$R_{300}$, —N($R_{201}$)($R_{201}$), and —NHC(=O)N($R_{201}$)($R_{201}$), wherein said $C_{1-6}$ alkyl is optionally substituted with up to three independently selected $R_{207}$ groups, wherein said arylalkyl and said heteroarylalkyl are each optionally substituted with up to three independently selected $R_{206}$ groups, wherein said $C_{2-6}$ acyl may optionally contain one double bond, and may optionally be substituted with —$NR_{10}R_{11}$, wherein said heterocycloalkyl is optionally substituted with up to three independently selected $C_{1-6}$ alkyl groups;

$R_{206}$ is independently $C_{1-6}$ alkyl or $C(O)NH_2$;

$R_{207}$ is independently selected from the group consisting of CN, heterocycloalkyl, $C_{1-3}$ alkoxy, OH, $N(R_{27})(R_{28})$ and $C_{3-6}$ cycloalkyl;

$R_{209}$ is $R_{211}$, $R_{212}$—C≡C—, or $(R_{212})_2C=C(R_{212})$—;

$R_{210}$ is $C_{1-6}$ alkyl, or $C_{1-6}$ alkoxy;

$R_{211}$ is aryl and heteroaryl wherein said aryl and said heteroaryl, are each optionally substituted with up to four independently selected $R_{12}$ groups;

$R_{212}$ is $C_{1-6}$ alkyl, aryl, and heteroaryl, wherein said $C_{1-6}$ alkyl is optionally substituted with up to three independently selected $R_{13}$ groups wherein said aryl and said heteroaryl, are each optionally substituted with up to four independently selected $R_{12}$ groups;

$R_{214}$ is $R_{41}$, or $R_{211}$;

$R_{300}$ is selected from the group consisting of H, $C_{1-3}$ alkoxy and $C_{1-6}$ alkyl wherein said $C_{1-6}$ alkyl is optionally substituted with a dialkylamino group;

e is 1 provided that $R_3$ is not $N(C_{1-6}$ alkyl$)_2$, $N(aryl)_2$, or $N(pyridyl)_2$;

f is 0-5;

k' is 1-6;

m is 0, 1, or 2;

n is 1-4;

q is 1-3;

r is 2-1800;

$G^1$, $G^2$, $G^3$ and $G^4$ are each independently selected from the group consisting of H, halogen, —CN, —$OCF_3$, —$NO_2$, —COOH, —$CONH_2$, —$CF_3$, OH, SH, $N_3$, —C(O)H, heteroaryl, $C_{1-6}$alkoxy, heterocycloalkyl, aryl, $C_{3-10}$cycloalkyl, $C_{1-12}$ alkyl, $C_{2-6}$ alkenyl, $C_{2-6}$ alkynyl, —$COR_{100}$, —$OC_{3-10}$cycloalkyl, —Oaryl, —$OR_{100}$, $R_{209}$ $R_{211}$, Q, —$OS(O)_2NH_2$, $OS(O)_2R_{22}$, —$S(O)_m$ $R_{100}$, —C(O)Q, $C(O)OR_{100}$, —$NHR_{100}$, —$NR_{100}$aryl, —$OR_{102}$aryl, —$SR_{102}$aryl, —$NHR_{102}$OH, —$NHR_{102}OR_{100}$, —$NHR_{102}NHR_{100}$, —$NR_{100}R_{102}$OH, —$NHR_{102}$Q, —$NR_{100}R_{102}NH_2$, —$NR_{100}R_{102}NHR_{100}$, —$NR_{100}R_{102}OR_{100}$, —$NR_{100}R_{102}$Q, —$OR_{102}$OH, —$OR_{102}OR_{100}$, —$OR_{102}NH_2$, —$OR_{102}NHR_{100}$, —$OR_{102}$Q, —$OCOR_{100}$, —$OR_{102}COR_{100}$, —$NHCOR_{100}$, —NHCONH$_2$, —$NHCONHR_{100}$, —$NHR_{102}COR_{100}$, —$NHR_{102}NH_2$, —NHOH, —$NHOR_{100}$, —$CONR_{10}R_{11}$, —$NHSO_2R_{100}$, —NHC(O)-heteroaryl, —NHC(O)$R_{102}$-heteroaryl, $OC(O)CH_2$halogen, $OC(O)CH_2S(CH)_m$O-PEG, OC(O)NH-PEG,

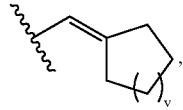

NHC(O)$R_{102}$-aryl, and NHC(O)NH-heterocycloalkyl optionally substituted with up to three $C_{1-3}$ alkyl groups;

wherein said aryl, said heteroaryl, and said heterocycloalkyl are each optionally substituted with up to four independently selected $R_{12}$ groups;

wherein said $C_{2-6}$ alkenyl, said $C_{1-6}$ alkyl, $C_{1-6}$alkoxy, and said $C_{2-6}$ alkynyl are each optionally substituted with up to three independently selected $R_{13}$ groups;

Q is —$NR_{100}R_{100}$ optionally the $R_{100}$ groups taken together with the nitrogen to which they are attached form a heterocyclic ring of 3 to 8 atoms with 1 or 2 additional heteroatoms selected from the group N, O, and S, said heterocyclic ring may optionally be substituted with groups consisting of OH, $OC_{1-6}$ alkyl, $(CH_2)_n$ OH, $(CH_2)_nOC_{1-6}$alkyl, $NR_{10}R_{11}$, $(CH_2)_nNR_{10}R_{11}$, and $C_{1-6}$ alkyl;

Q" is selected from the group consisting of O, S, and NH;

Z is selected from the group consisting of aryl, heteroaryl, cycloalkyl, heterocycle, pyridone, and pyrone, wherein said aryl, said pyridone, said pyrone, said cycloalkyl, said heteroaryl, and said heterocycle are each optionally substituted with up to five substituents independently selected from the group consisting of $R_{210}$, $R_{41}$, $R_{209}$, $R_{211}$, $R_{214}$, $OR_{41}$, (=O), OH, $COOR_{100}$, $C_{1-6}$ alkyl, $C_{106}$ alkoxy, $C_{1-3}$ perhaloalkyl, halogen, $C_{1-3}$ perhaloalkoxy, (=NH), $NH_2$, —$NO_2$, C(O)H, —C(O)OH, —C(O)NH$_2$, CN, Q, heterocycle, heteroaryl, S—$C_{1-3}$ alkyl, S—$C_{1-3}$ perhaloalkyl, S-heteroaryl, aryl, $C_{2-6}$ alkynyl, $C(NH)NH_2$, heterocycloalkyl, $C_{2-6}$ alkenyl, —O—C(O)—$R_{20}$, —O—C(O)$OR_{21}$, —$NHS(O)_2R_{22}$, —$R_{102}NHS(O)_2R_{23}$, —NHC(O)$R_{24}$, —$R_{102}NHC(O)R_{24}$, —NHC(O)$(CH_2)_mR_{25}$, —$CH_2N(R_{27})(R_{28})$, —$OC(O)N(R_{27})(R_{28})$, —$N(R_{27})(R_{28})$, —$OR_{31}$, —$S(O)_2NHR_{32}$, —$S(O)_2R_{33}$, —C(O)$R_{34}$, —$CH_2C(O)OH$, —C(O)$NHR_{35}$, $R_{200}$, —$CH_2NHS(O)_2R_{21}$, $OC(O)CH_2$halogen, $OC(O)R_{100}$, —OC(O)$CH_2S(CH_2)_m$O-PEG, —OC(O)NH-PEG, H, —CN, —$OCF_3$, —$CF_3$, SH, $N_3$, —C(O)H, —$COR_{100}$, —$OR_{100}$, —Saryl, —C(O)Q, $C(O)OR_{100}$, —$C(O)NHR_{100}$, —$NR_{100}$aryl, —$OR_{102}$aryl, —$SR_{102}$aryl, —$NHS(O)_2$—$R_{100}$, —$NHR_{102}$OH, —$NHR_{102}OR_{100}$, —$NHR_{102}NHR_{100}$, —$NR_{100}R_{102}$OH, —$NHR_{102}$Q, —$NR_{100}R_{102}NH_2$, —$NR_{100}R_{102}NHR_{100}$, —$NR_{100}R_{102}OR_{100}$, —$NR_{100}R_{102}$Q, —$OR_{102}$OH, —$OR_{102}OR_{100}$, —$OR_{102}NH_2$, —$OR_{102}NHR_{100}$, —$OR_{102}Q$, —$OCOR_{100}$, —$OR_{102}COR_{102}OR_{102}COR_{100}$, —$OR_{102}COR_{102}OR_{102}OR_{100}$, —$NHCOR_{100}$, —$NHCONH_2$, —$NHCONH_{100}$, —$NHR_{102}COR_{100}$, —$NHR_{102}NH_2$, —$NHS(O)_2$-aryl, —$NHOH$, —$NHC(O)$aryl, —$NHOR_{100}$, —$NHC(O)$-heteroaryl, —$NHC(O)R_{102}$-heteroaryl, $OC(O)CH_2$halogen, $OC(O)CH_2S(CH)_mO$-PEG, $OC(O)NH$-PEG, $OS(O)_2NH_2$, $OS(O)_2R_{22}$, —$N(R_{10})(R_{11})$, $NHC(O)R_{102}$-aryl, and $NHC(O)NH$-heterocycle that is optionally substituted with up to three $C_{1-3}$ alkyl groups, wherein said $C_{2-6}$ alkenyl, said $C_{1-6}$ alkyl, and said $C_{2-6}$ alkynyl are each optionally substituted with up to three independently selected $R_{13}$ groups, wherein said $C_{1-6}$ alkyl, said —$S$—$C_{1-6}$ alkyl, and $C_{1-6}$ alkoxy are each optionally substituted with up to three independently selected $R_{50}$ groups, wherein said aryl is optionally substituted with up to three groups independently selected from OH and $NH_2$, wherein said heteroaryl and said 5-heteroaryl, heterocycle, and said heterocycloalkyl, are each optionally substituted with up to three independently selected $R_{12}$ groups, wherein said $C_{2-6}$ alkenyl is optionally substituted with COOH, wherein any two adjacent carbon atoms of said aryl, heteroaryl or heterocycloalkyl can optionally be joined together by a group of the formula —$O$—$C(Ra)(Rb)$—$O$— wherein $R_a$ and $R_b$ are independently H, $C_{1-3}$ alkyl, phenyl or alkoxycarbonyl; and $C_{1-3}$ alkoxy and $C_{1-3}$ perhaloalkyl, wherein said aryl can be substituted with COOH;

except 4-((2-phenylaminophenylamino)methylene)-2-p-tolylisoquinoline-1,3(2H,4H)-dione, 4-[[(4-methoxyhenyl)amino]methylene]-2-(4-methylphenyl)-1,3(2H,4H)-isoquinolinedione, 2-(4-methoxyphenyl)-4-[[(4-methylphenyl)amino]]methylenel]-1,3(2H,4H)-isoquinolinedione, 2-(4-methoxyphenyl-4-[[(4-methoxyphenyl)amino]methylene]-1,3(2H,4H)-isoquinolinedione, 2-(4-chlorophenyl)-4-[[(4-nitrophenyl)amino]methylene]-1,3(2H,4H)-isoquinolinedione, 2-(4-chlorophenyl)-4-[[(4-methylphenyl)amino]methylene]-1,3(2H,4H)-isoquinolinedione, 2-phenyl-4-((p-tolylamino)methylene)isoquinoline-1,3(2H,4H)-dione, 6,7-dimethoxy-2-methyl-4-[(phenylamino)methylene]-1,3(2H,4H)-isoquinolinedione, 4-[(phenylamino)methylene]-2-(phenylmethyl)-1,3(2H,4H)-isoquinolinedione, 2-methyl-4-[(phenylamino)methylene]-1,3(2H,4H)-isoquinolinedione, 2-methyl-4-[(methylphenylamino)methylene]-1,3(2H,4H)-isoquinolinedione, 4-[(phenylamino)methylene]-1,3(2H,4H)-isoquinolinedione, 4-[[(4-chlorophenyl)amino]methylene]-1,3(2H,4H)-isoquinolinedione, 4-[[(4-chlorophenyl)amino]methylene]-2-methyl-1,3(2H,4H)-isoquinolinedione, 2-(4-methoxyphenyl)-4-[(phenylamino)methylene]-1,3(2H,4H)-isoquinolinedione, and 4-[bis(phenylamino)methylene]-2-methyl-1,3(2H,4H)-isoquinolinedione are excluded.

2. The compound of claim 1, wherein
f is 0;
Z is selected from the group consisting of aryl, heteroaryl, and heterocycle, wherein said aryl, said heteroaryl, and said heterocycle are each optionally substituted with up to five substituents independently selected from the group consisting of —$CH_2N(R_{27})(R_{28})$, —$NHR_{102}NHR_{100}$, —$NHR_{102}Q$, —$NR_{100}R_{102}NH_2$, —$NR_{100}R_{102}NHR_{100}$, —$NR_{100}R_{102}Q$, —$OR_{102}NH_2$, —$OR_{102}NHR_{100}$, —$OR_{102}Q$, and —$NHR_{102}NH_2$;
or a pharmaceutically acceptable salt thereof.

3. The compound of claim 1, wherein
f is 0;
$A^2$ is H;
Z is selected from the group consisting of aryl, heteroaryl, and heterocycle, wherein said aryl, said heteroaryl, and said heterocycle are each optionally substituted with up to five substituents independently selected from the group consisting of —$CH_2N(R_{27})(R_{28})$, —$NHR_{102}NHR_{100}$, —$NHR_{102}Q$, —$NR_{100}R_{102}NH_2$, —$NR_{100}R_{102}NHR_{100}$, —$NR_{100}R_{102}Q$, —$OR_{102}NH_2$, —$OR_{102}NHR_{100}$, —$OR_{102}Q$, and —$NHR_{102}NH2$;
or a pharmaceutically acceptable salt thereof.

4. The compound according to claim 1 wherein:
Z is selected from the group consisting of aryl, heteroaryl, and heterocycle,
wherein said aryl, said heteroaryl, and said heterocycle are each optionally substituted with up to five substituents independently selected from the group consisting of $C_{1-6}$ alkyl, $C_{1-6}$ alkoxy, $S$—$C_{1-3}$ alkyl, $C_{2-6}$ alkynyl, and $C_{2-6}$ alkenyl wherein said alkyl is substituted with $OR_{102}NR_{15}R_{16}$, $NH_2$ or $N(R_{27})(R_{28})$, alkenyl and alkynyl are substituted with $OR_{102}NR_{15}R_{16}$ and wherein said S-alkyl and alkoxy are substituted with $NH_2$ or $N(R_{27})(R_{28})$
or a pharmaceutically acceptable salt thereof.

5. The compound according to claim 1, wherein
$A^2$ is H;
Z is selected from the group consisting of aryl, heteroaryl, and heterocycle,
wherein said aryl, said heteroaryl, and said heterocycle are each optionally substituted with up to five substituents independently selected from the group consisting of $C_{1-6}$ alkyl, $C_{1-6}$ alkoxy, $S$—$C_{1-3}$ alkyl, $C_{2-6}$ alkynyl, and $C_{2-6}$ alkenyl wherein said alkyl is substituted with —$OR_{102}NR_{15}R_{16}$, $NH_2$ or —$N(R_{27})(R_{28})$, alkenyl and alkynyl are substituted with —$OR_{102}NR_{15}R_{16}$ and wherein said S-alkyl and alkoxy are substituted with $NH_2$ or —$N(R_{27})(R_{28})$
or a pharmaceutically acceptable salt thereof.

6. The compound of claim 1, wherein
f is 0;
Z is selected from the group consisting of aryl, or heteroaryl
wherein said aryl, and said heteroaryl, are each optionally substituted with up to three substituents independently selected from the group consisting of
$R_{210}$, $R_{41}$, $R_{209}$, $R_{211}$, $R_{214}$, $OR_{41}$, OH, $C_{1-6}$ alkyl, $C_{1-6}$ alkoxy, $C_{1-3}$ perhaloalkyl, halogen, $C_{1-3}$ perhaloalkoxy, $NH_2$, Q, heterocycle, heteroaryl, $S$—$C_{13}$ alkyl, $S$—$C_{1-3}$ perhaloalkyl, S-heteroaryl, aryl, —$O$—$C(O)$—$R_{20}$, —$NHC(O)R_{24}$, —$NHC(O)(CH_2)_mR_{25}$, —$OC(O)N(R_{27})(R_{28})$, —$N(R_{27})(R_{28})$, —$OR_{31}$, $R_{200}$, $OC(O)R_{100}$, —$OC(O)CH_2S(CH_2)_mO$-PEG, —$OC(O)NH$-PEG, —$OCF_3$, —$CF_3$, SH, —$OR_{100}$, —Saryl, $NR_{100}$aryl, —$OR_{102}$aryl, —$SR_{102}$aryl, —$NHR_{120}OH$, —$NHR_{102}OR_{100}$, —$NR_{100}R_{102}OH$, —$NHR_{102}Q$, —$NR_{100}R_{102}OR_{100}$, —$NR_{100}R_{102}Q$, —$OR_{102}OH$, —$OR_{102}OR_{100}$, —$OR_{102}Q$, —$OCOR_{100}$, $OR_{102}COR_{102}OR_{102}OR_{100}$, —$NHC(O)$aryl, —$NHC(O)$—heteroaryl, —$NHC(O)R_{102}$-heteroaryl, $OC(O)CH_2S(CH)_mO$-PEG, $OC(O)NH$-PEG, —$N(R_{10})(R_{11})$, and $NHC(O)R_{102}$-aryl,
or a pharmaceutically acceptable salt thereof.

7. The compound of claim 1, wherein
f is 0;
$A^1$ is C=O;
$A^2$ is H;
Z is selected from the group consisting of aryl, or heteroaryl
wherein said aryl, and said heteroaryl, are each optionally substituted with up to three substituents independently selected from the group consisting of
$R_{210}$, $R_{41}$, $R_{209}$, $R_{211}$, $R_{214}$, $OR_{41}$, OH, $C_{1-6}$ alkyl, $C_{1-6}$ alkoxy, $C_{1-3}$ perhaloalkyl, halogen, $C_{1-3}$ perhaloalkoxy, $NH_2$, Q, heterocycle, heteroaryl, S—$C_{1-3}$ alkyl, S—$C_{1-3}$ perhaloalkyl, S-heteroaryl, aryl, —O—C(O)—$R_{20}$, —NHC(O)$R_{24}$, —NHC(O)(CH$_2$)$_m$$R_{25}$, —OC(O)N($R_{27}$)($R_{28}$), —N($R_{27}$)($R_{28}$), —O$R_{31}$, $R_{200}$, OC(O)$R_{100}$, —OC(O)CH$_2$S(CH$_2$)$_m$O-PEG, —OC(O)NH-PEG, —OCF$_3$, —CF$_3$, SH, —O$R_{100}$, —Saryl, N$R_{100}$aryl, —O$R_{102}$aryl, —S$R_{102}$aryl, —NH$R_{102}$OH, —NH$R_{102}$O$R_{100}$, —N$R_{100}$$R_{102}$OH, —NH$R_{102}$Q, —N$R_{100}$$R_{102}$O$R_{100}$, —N$R_{100}$$R_{102}$Q, —O$R_{102}$OH, —O$R_{102}$O$R_{100}$, —O$R_{102}$Q, —OCO$R_{100}$, O$R_{102}$CO$R_{102}$O$R_{102}$O$R_{100}$, —NHC(O)aryl, —NHC(O)-heteroaryl, —NHC(O)$R_{102}$-heteroaryl, OC(O)CH$_2$S(CH)$_m$O-PEG, OC(O)NH-PEG, —N($R_{10}$)($R_{11}$), and NHC(O)$R_{102}$-aryl,
or a pharmaceutically acceptable salt thereof.

8. The compound of claim 1, wherein
f is 1;
$Y^1$ is $CR_3$;
$Y^2$ is $NR_1$;
Z is selected from a moiety of the formula

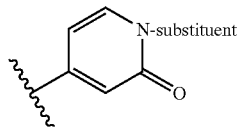

wherein said Z is optionally substituted with a substituent selected from the group consisting of $R_{41}$, $R_{211}$, $R_{214}$, $C_{1-6}$ alkyl, $C_{1-3}$ perhaloalkyl, heterocycle, heteroaryl, aryl, and heterocycloalkyl;
or a pharmaceutically acceptable salt thereof.

9. The compound of claim 1, wherein
f is 1;
$A^2$ is H;
Z is selected from a moiety of the formula

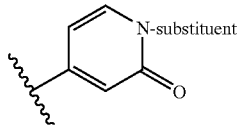

wherein said Z is optionally substituted with a substituent selected from the group consisting of $R_{41}$, $R_{211}$, $R_{214}$, $C_{1-6}$ alkyl, $C_{1-3}$ perhaloalkyl, heterocycle, heteroaryl, aryl, and heterocycloalkyl
or a pharmaceutically acceptable salt thereof.

10. f is 1;
Z is selected from the group consisting of

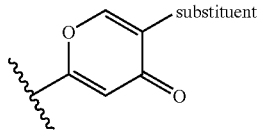

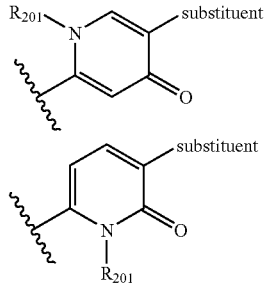

wherein said Z is optionally substituted with a substituent selected from the group consisting of
$R_{211}$, $OR_{41}$, OH, $C_{1-6}$ alkoxy, $C_{1-3}$ perhaloalkoxy, heteroaryl, S—$C_{1-3}$ alkyl, S—$C_{1-3}$ perhaloalkyl, S-heteroaryl, aryl, —O—C(O)—$R_{20}$, —O—C(O)O$R_{21}$, OC(O)N($R_{27}$)($R_{28}$), —O$R_{31}$, OC(O)$R_{100}$, —OC(O)CH$_2$S(CH$_2$)$_m$O-PEG, —OC(O)NH-PEG, —OCF$_3$, —O$R_{100}$, —Saryl, —O$R_{102}$aryl, —S$R_{102}$aryl, —O$R_{102}$OH, —O$R_{102}$O$R_{100}$, —O$R_{102}$Q, —OCO$R_{100}$, O$R_{102}$CO$R_{102}$O$R_{102}$O$R_{100}$, OC(O)CH$_2$S(CH)$_m$O-PEG, and OC(O)NH-PEG,
or a pharmaceutically acceptable salt thereof.

11. The compound of claim 1, wherein
f is 1;
$A^2$ is H;
Z is selected from the group consisting of

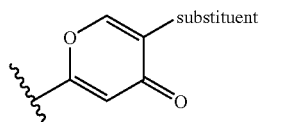

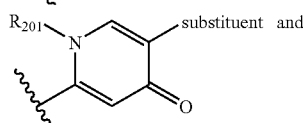

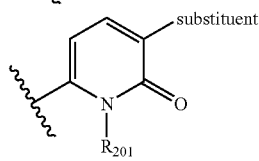

wherein said Z is optionally substituted with a substituent selected from the group consisting of $R_{211}$, $OR_{41}$, OH, $C_{1-6}$ alkoxy, $C_{1-3}$ perhaloalkoxy, heteroaryl, S—$C_{1-3}$ alkyl, S—$C_{1-3}$ perhaloalkyl, S-heteroaryl, aryl, —O—C(O)—$R_{20}$, —O—C(O)O$R_{21}$, OC(O)N($R_{27}$)($R_{28}$), —O$R_{31}$, OC(O)$R_{100}$, —OC(O)CH$_2$S(CH$_2$)$_m$O-PEG, —OC(O)NH-PEG, —OCF$_3$, —O$R_{100}$, —Saryl, —O$R_{102}$aryl, —S$R_{102}$aryl, —O$R_{102}$OH, —O$R_{102}$O$R_{100}$, —O$R_{102}$Q, —OCO$R_{100}$, O$R_{102}$CO$R_{102}$O$R_{102}$O$R_{100}$, OC(O)CH$_2$S(CH)$_m$O-PEG, and OC(O)NH-PEG,
or a pharmaceutically acceptable salt thereof.

12. The compound of claim 1, wherein
$G^1$, $G^3$, and $G^4$=H;
$G^2$ is selected from the group consisting of halogen, heteroaryl, heterocycloalkyl, aryl, $C_{3-10}$cycloalkyl, $C_{1-12}$ alkyl, $C_{2-6}$ alkenyl, $C_{2-6}$ alkynyl, —Oaryl, NHaryl, and

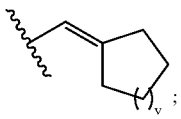

or a pharmaceutically acceptable salt thereof.

13. The compound according to claim 1, wherein the compound is selected from the groups:

(4Z)-4-{[(4-Methoxyphenyl)amino]methylene}isoquinoline-1,3(2H,4H)-dione;
(4Z)-({[4-(4-Methylpiperazin-1-yl)phenyl]lamino}methylene)isoquinoline-1,3(2H,4H)-dione;
(4Z)-4-({[4-(2-Pyrrolidin-1-ylethyl)phenyl]amino}methylene)isoquinoline-1,3(2H,4H)-dione;
(4Z)-4-{[(4-Morpholin-4-ylphenyl)amino]methylene}isoquinoline-1,3(2H,4H)-dione;
(4Z)-4-[(1H-Indazol-6-ylamino)methylene]isoquinoline-1,3(2H,4H)-dione;
(4Z)-4-[(Quinolin-6-ylamino)methylene]isoquinoline-1,3(2H,4H)-dione;
(4Z)-4-({[4-(Piperidin-1-ylmethyl)phenyl]amino}methylene)isoquinoline-1,3(2H,4H)-dione;
(4Z-4-[{3-Chloro-4[(1-methyl-1H-imidazole-2-uy)thio]phenyl}amino]methylene]isoquinoline-1,3(2H,4H)-dione;
(4Z)-4-[({3-Chloro-4-{(4chlorobenzyl)oxy]phenyl}amino)methylene]isoquinohine-1,3(2H,4H-dione;
(4Z)-4-({[3-(Piperidin-1-ylmethyl)phenyl]amino}methylene)isoquinoline-1,3(2H,4H)-dione);
(4Z)-4-({[3-(Azepan-1-ylmethyl)phenyl]amino}methylene)isoquinoline-1,3(2H,4H)-dione;
(4Z)-4-({[3-(Pyrrolidin-1-ylmethyl)phenyl]amino}methylene)isoquinoline-1,3(2H,4H)-dione);
(4Z)-4-({[4-(Morpholin-4-ylmethyl)phenyl]amino}methylene)isoquinoline-1,3(2H,4H)-dione;
(4Z)-4-[({4-[(4-Methylpiperazin-1-yl)methyl]phenylamino)methylene]isoquilin-1,3(2H,4H)-dione-;
(4Z)-4-[(1,1-Biphenyl-4-ylamino)methylene]isoquinoline-1,3(2H,4H)-dione;
(4Z)-4-({[3-2-Pyrrolidin-1-ylethyl)phenyl]amino}methylene)isoquinoline-1,3(2H,4H)-dione;
(4Z)-4-[({4-[(4-Hydroxypiperidin-1-yl)methyl]phenyi}amino)methylene]isoquinolin-1,3(2H,4H)-dione;
(4Z)-6-Bromo-4-{[(4-piperidin-1-ylmethyl)phenyl]amino}methyleneisoquinoline-1,3(2H,4H)-dione;
(4Z)-4-[({4[(Dimethylamino)methyl]phenyl}amino)methylene]isoquinolin-1,3(2H,4H)-diane;
(4Z)-4-({[4-(Azepan-1-ylmethyl)phenyl]amino}methylene)isoquinoline-1,3(2H,4H)-dione);
(4Z)-6-Bromo-4-({[4-(4-methylpiperazin-1-yl)phenyl]amino}methylene)isoquinoline-1,3(2H,4H)-dione;
(4Z)-6-Bromo-4-{[(4-hydroxy-3-methoxybenzyl)amino]methylene}isoquinoline-1,3(2H,4H)-dione;
N-(4-{[(Z)-(1,3-Dioxo-2,3-dihydroisoquinolin-4(1H)-ylidene)methyl]amino}phenyl)-1,3(2H,4H)-dione-N-Methyl-2-piperidin-1-ylacetamide;
(4Z)-6-Bromo-4-{[(pyridin-3-ylmethyl)amino]methylene}isoquinoline-1,3(2H,4H)-dione;
(4Z)-6-Bromo-4-{[(pyridin-4-ylmethyl)amino]methylene}isoq uinoline-1,3(2H,4H)-dione;
(4Z)-6-Nitro-4-({[4-(4-methylpiperazin-1-yl)phenyl}amino}methylene)isoquinoline-1,3(2H,4H)-dione;
tert-Butyl 4-(4-{[(Z)-1,3-dioxo-2,3-dihydroisoquinolin-4(1H)-ylidene)methyl]amino}piperazine-1-carboxytate;
(4Z)-6,7-Dimethoxy-4-({[4-(-methylpiperazin-1-yl)phenyl}amino)methylene]isoquinolin-1,3(2H,4H)-dione;
(4Z)-6-Bromo-4-{[(4-{[(2S)-2-(methoxymethyl)pyrrolidin-1-yl]methyl}phenyl)amino)methylene}isoquinoline-1,3(2H,4H-dione;
(4Z)-6-Bromo-4-{[(4-{[(2R)-2-(methoxymethyl)pyrrolidin-1-yl]methyl}phenyl)amino)methylene}isoquinoline-1,3(2H,4H-dione;
(4Z)-6-Bromo-4-{[(3,4-dihydroxybenzyl)amino]methylene}isoquinoline-1,3(2H,4H)-dione;
(4Z)-6-Bromo-4-({[2-(piperidin-1-ylmethyl)phenyl}amino}methylene]isoquinolin-1,3(2H,4H)-dione;
(4Z)-6—Nitro-4-{[(4-piperidin-1-ylmethyl)phenyl]amino}methyleneisoquinoline-1,3(2H,4H)-dione;
(4Z)-6-Bromo-4-({[2-(1H-indol-3-yl)ethyt]amino}methylene)isoquinoline-1,3(2H,4H)-dione;
(4Z)-7-Bromo-4-({[4-(Piperidin-1-ylmethyl)phenyl]amino}methylene)isoquinoline-1,3(2H,4H)-dione;
(4Z)-7-Bromo-4-({[4-(4-methylPiperzin-1-yl)phenyl]amino}methylene)isoquinoline-1,3(2H,4H)-dione;
(4Z)-6-Bromo-4-{[(3-hydroxybenzyl)amino]methylene}isoquinoline-1,3(2H,4-dione;
2-(Acetyloxy)-4-({[(Z)-(1,3-dioxo-2,3-dihydroisoquinolin-4(1H)-ylidene)methyl]amino}-methyl)phenyl acetate;
N-[(4Z)-1,3-Dioxo-4-({[4-piperidin-1-ylmethyl)phenyl]amino}methylene)-1,2,3,4-tetrahydroisoquinolin-6-yl]acetamide;
(4Z)-2-Methyl-4-{[(4-piperidin-1-ylmethyl)phenyl]amino}methyleneisoquinoline-1,3(2H,4H)-dione;
(4Z)-6-Bromo-4-{[(3-hydroxy-4-methoxybenzyl)amino)methylene}isoquinoline-1,3(2H,4H-dione;
(4Z)-4-({[4-(4-Methylpiperazin-1-yl)phenyl]amino}methylene)-1,3-dioxo-1,2,3,4-tetrahydroisoquinoline-6-carboxylic acid;
(4Z)-4-{[(3-Aminobenzyl)amino]methylene}-6-bromoisoquinoline-1,3(2H,4H)-dione;
(4Z)-6-Bromo-4-{[(4-chlorobenzyl)amino)methylene}isoquinoline-1,3(2H,4H)-dione;
2-(Acetyloxy)-4-({[(Z)-(6-bromo-1,3-dioxo-2,3-dihydroisoquinolin-4(1H)-ylidene)methyl]-amino}methyl)phenyl acetate;
(4Z)-6-Chloro-4-({[4-(piperidin-1-ylmethyl)phenyl]amino}methylene)isoquinoline-1,3(2H,4H)-dione;
4-({[(Z)-(6-Bromo-1,3-dioxo-2,3-didroisoquinolin-4(1H)-ylidene)methyl]amino}methyl)benzenesulfonamide;
5-({[(Z)-(6-Bromo-1,3-dioxo-2,3-dihydroisoquinolin-4(1H)-ylidene)methyl]amino}methyl)-2-methoxyphenyl acetate;
5-{[(Z)-(6-Bromo-1,3-dioxo-2,3-dihydroisoquinolin-4(1H)-ylidene)methyl]amino}-2-hydroxybenzoic acid;
(4Z)-6-Bromo-4-({[4-(pyrroiidin-1-ylmethyl)phenyl]amino}methylene)isoquinoline-1,3(2H,4H)-dione;
(4Z)-4-({[4-(4-Methylpiperazin-1-yl)phenyl]amino}methylene)-6-(1 H-pyrrol-1-yl)isoquinoline-1,3(2H,4H)-dione;
(4Z)-4-{[(4-Hydroxybenzyl)amino]methylene}isoquinoline-1,3(2H,4H-dione;

(4Z)-6-Bromo-4-{[(4-hydroxybenzyl)amino)methylene}isoquinoline-1,3(2H,4H-dione;
(4Z)-4-{[(3-Hydroxybenzyl)amino)methylene}isoquinoline-1,3(2H,4H-dione;
(4Z)-6-Bromo-4-{[(3,5-dihydroxybenzyl)amino)methylene}isoquinoline-1,3(2H,4H-dione;
(4Z)—N,N-Dimethyl-4-({[4-(4-methylpiperazin-1-yl)phenyl]amino}methylene)-1,3-dioxo-1,2,3,4-tetrahydroisoquinoline-6-carboxamide;
(4Z)—N, N-Dimethyl-1,3-dioxo-4-({[4-(piperidinylmethyl)phenyl]amino}methylene)-1,2,3,4-tetrahydroisoquinoline-6-carboxamide;
(4Z)-6-Chloro-4-{[(3-hydroxy-4-methoxybenzyl)amino]methylene}isoquinoline-1,3(2H,4H)-dione;
(4Z)-6-Fluoro-4-{[(3-hydroxy-4-methoxybenzyl)amino)methylene}isoquinoline-1,3(2H,4H-dione;
Acetic acid 3-acetoxy-5-{[(6-bromo-1,3-dioxo-2,3-dihydro-1H-isoquinolin-4-ylidenemethyl)-amino]-methyl}-phenyl ester;
(4Z)-6-Fluoro-4-({[4-(4-methylPiperzin-1-yl)phenyl]amino}methylene)isoquinoline-1,3(2H,4H-dione;
(4Z)-6-Fluoro-4-{[(3-hydroxy-4-methoxybenzyl)amino)methylene}-6-(1H-pyrrol-1-yl)isoquinoline-1,3(2H,4H-dione;
(4Z)-4-({[4-Pyrrolidin-1-ylmethyl)phenyl]amino}methylene)}-6-(1 H-pyrrol-1-yl)isoquinoline-1,3(2H,4H)-dione;
(4Z)-6-Bromo-4-{[(4-{[(4-[(dimethylamino)methyl)methyl}phenyl)amino)methylene}isoquinoline-1,3(2H,4H-dione;
(4Z)-4-({[4-Piperidin-1-ylmethyl)phenyl]amino}methylene)}-6-(1H-pyrrol-1-yl)isoquinoline-1,3(2H,4H)-dione;
(4Z)-6-Bromo-4-{[(4-[(4-hydroxypiperidin-1-yl)methyl}phenyl)amino)methylene}isoquinoline-1,3(2H,4H-dione;
Carbonic acid 5-{[(6-bromo-1,3-dioxo-2,3-dihydro-1H-isoquinolin-4-ylidenemethyl)-amino]-methyl}-2-methoxycarbonyloxy-phenyl ester methyl ester;
5-({[(Z)-(6-Bromo-1,3-dioxo-2,3-dihydroisoquinolin-4(1H)-ylidene)methyl]amino)methyl)-2,3-dimethoxyphenyl acetate;
(4Z)-6-Bromo-4-{[(3-hydroxy-4,5-dimethoxybenzyl)amino)methylene}isoquinoline-1,3(2H,4H-dione;
(4Z)-6-Bromo-4-{[(3,4,5-trihydroxybenzyl)amino)methylene}isoquinoline-1,3(2H,4H-dione;
(4Z)-6-Iodo-4-{[(3-hydroxy-4-methoxybenzyl)amino]methylene}isoquinoline-1,3(2H,4H)-dione;
(4Z)-6-Iodo-4-({[4-(4-methylpiperazin-1-yl)phenyl]amino}methylene)isoquinoline-1,3(2H,4H-dione;
(4Z)-6-Iodo-4-({[4-(piperidin-1-ylmethyl)phenyl]amino}methylene)isoquinoline-1,3(2H,4H-dione;
5-({[(Z)-(6-Bromo-1,3-dioxo-2,3-dihydroisoquinolin-4(1H)-ylidene)methyl]amino}methyl)-2-methoxyphenyl methyl carbonate;
(4Z)-5-Bromo-4-{[(3-hydroxy-4-methoxybenzyl)amino]methylene}isoquinoline-1,3(2H,4H)-dione;
(4Z)-4-{[(3-Hydroxy-4,5-dimethoxybenzyl)amino)methylene}-6-thien-3-ylisoquinoline-1,3(2H,4H-dione;
(4Z)-4-{[(3-Hydroxy-4,5-dimethoxybenzyl)amino)methylene}-6-phenylisoquinoline-1,3(2H,4H)-dione;
(4Z)-6-(3-Furyl)-4-{[(3-hydroxy-4,5-dimethoxybenzyl)amino)methylene}isoquinoline-1,3(2H,4H-dione;
(4Z)-4-{[(3-Hydroxy-4-methoxybenzyl)amino]methylene}-6-thien-3-ylisoquinoline-1,3(2H,4H-dione;
(4Z)-6-Iodo-4-{[(3-hydroxy-4,5-dimethoxybenzyl)amino)methylene}isoquinoline-1,3(2H,4H-dione;

4-[(3-Hydroxy-4-methoxy-benzylamino)-methylene]-6-methoxy-4H-isoquinoline-1,3-dione;
6-Methoxy-4-[(4-piperidin-1-ylmethyl-phenylamino)-methylene]-4H-isoquinoline-1,3-dione;
(4Z)-6-(3-Furyl)-4-{[(3-hydroxy-4-methoxybenzyl)amino)methylene}isoquinoline-1,3(2H,4H-dione;
(4Z)-6-(3-Furyl)-4-({[4-piperidin-1-ylmethyl)phenyl]amino}methylene)}isoquinoline-1,3(2H,4H)-dione;
(4Z)-6-Phenyl-4-({[4-piperidin-1-ylmethyl)phenyl]amino}methylene)}isoquinoline-1,3(2H,4H)-dione;
(4Z)-6-(3-Hydroxyphenyl)-4-({[4-piperidin-1-ylmethyl)phenyl]amino}methylene)}isoquinoline-1,3(2H,4H)-dione;
3-[(4Z)-1,3-Dioxo-4-({[4-piperidin-1-ylmethyl)phenyl]amino}methylene)-1,2,3,4-tetrahydroisoquinoline-6-yl]thiophene-2-carbaldehyde;
(4Z)-4-{[(3-Hydroxy-4-methoxybenzyl)amino]methylene}isoquinoline-1,3(2H,4H)-dione;
5-({[(Z)-(6-Iodo-1,3-dioxo-2,3-dihydroisoquinolin-4(1H)-ylidene)methyl]amino)methyl)-2-methoxyphenyl diethylcarbamate;
(4Z)-6-(4-Phenoxyphenyl)-4-{[(3-hydroxy-4,5-dimethoxybenzyl)amino]methylene}isoquinoline-1,3(2H,4H-dione;
(4Z)-6-(4-Phenoxyphenyl)-4-({[4-piperidin-1-ylmethyl)phenyt]amino}methylene)}isoquinoline-1,3(2H,4H)-dione;
(4Z)-4-({[4-Piperidin-1-ylmethyl)phenyl]amino}methylene)-6-pyridin-3-ylisoquinoline-1,3(2H,4H)-dione;
(4Z)-6-(4-Hydroxyphenyl)-4-({[4-piperidin-1-ylmethyl)phenyl]amino}methylene)}isoquinoline-1,3(2H,4H)-dione;
(4Z)-4-({[4-(Piperidin-1-ylmethyl)phenyl]amino}methylene)-6-thien-3-ylisoquinoline-1,3(2H,4H)-dione;
(4Z)-4-({[4-(4-Methylpiperazin-1-yl)phenyl]amino}methylene)-6-thien-3-ylisoquinoline-1,3(2H,4H)-dione;
(4Z)-4-{[(1,3-Benzodioxol-5-ylmethyl)amino]methylene}-6-bromoisoquinoline-1,3(2H,4H)-dione;
(4Z)-1,3-Dioxo-4-({[4-(piperidin-1-ylmethyl)phenyl]amino}methylene) 1,2,3,4-tetrahydroisoquinoline-6-carbonitrile;
(4Z)-6-(4-Chlorophenyl)-4-({[4-(piperidin-1-ylmethyl)phenyl]amino}methylene)isoquinoline-1,3(2H,4H)-dione;
(4Z)-6-[(1E)-5-Chloropent-1-enyl]-4-({[4-(piperidin-1-ylmethyl)phenyl]amino}methylene)isoquinoline-1,3(2H,4H)-dione;
(4Z)-6-(4-Chlorophenyl)-4-{[(3-hydroxy-4,5-dimethoxybenzyl)amino]methylene}isoquinoline-1,3(2H,4H)-dione;
(4Z)-6-(4-methoxyphenyl)-4-({[4-(4-methylpiperazin-1-yl)phenyl]amino}methylene)-isoquinoline-1,3(2H,4H)-dione
4-[(4Z)-4-({[4-(4-Methylpiperazin-1-yl)phenyl]amino}methylene)-1,3-dioxo-1,2,3,4-tetra-hydroisoquinolin-6-yl]benzaldehyde;
(4Z)-6-(4-Methoxyphenyl)-4-(([4-(piperidin-1-ylmethyl)phenyl]amino}methylene)-isoquinoline-1,3(2H,4H)-dione;
(4Z)-6-(3-Methoxyphenyl)-4-({[4-(piperidin-1-ylmethyl)phenyt]amino}methylene)-isoquinoline-1,3(2H,4H)-dione;
(4Z)-6-Piperidin-1-yl-4-({[4-(piperidin-1-ylmethyl)phenyl]amino}methylene)isoquinoline-1,3(2H,4H)-dione;

(4Z)-6-Piperidin-1-yl-4-({[4-(methylPiperzin-1-yl)phenyl]amino}methylene)isoquinoline-1,3(2H,4H)-dione;
(4Z)-6-Morpholin-4-yl-4-({[4-(piperidin-1-ylmethyl)phenyl]amino}methylene)isoquinoline-1,3(2H,4H)-dione;
(4Z)-6-[(2R)-2-(Methoxymethyl)pyrrolidin-1-yl]-4-({[4-(piperidin-1-ylmethyl)phenyl]amino}methylene)isoquinoline-1,3(2H,4H)-dione;
(4Z)-4-{[(4-Amino-3-hydroxybenzyl)amino]methylene}-6-iodoisoquinoline-1,3(2H,4H)-dione;
(4Z)-6-[(4-Methyl-piperidin-1-yl]-4-({[4-(piperidin-1-ylmethyl)phenyl]amino}methylene)isoquinoline-1,3(2H,4H)-dione;
5-[(4Z)-4-({[4-(4-Methylpiperazin-1-yl)phenyl]amino}methylene)-1,3-dioxo-1,2,3,4-tetradydroisoquinolin-6-yl]-2-furaldehyde;
(4Z)-6-Iodo-4-({[4-(pyrrolidin-1-ylmethyl)phenyl}amino)methylene]isoquinolin-1,3(2H,4H)-dione;
(4Z)-6-(4-Fluorophenyl)-4-({[4-(pyrrolidin-1-ylmethyl)phenyl]amino}methylene)isoquinoline-1,3(2H,4H)-dione;
(4Z)-6-Anilino-4-({[4-(piperidin-1-ylmethyl)phenyl]amino}methylene)isoquinoline-1,3(2H,4H)-dione;
(4Z)-6-Bromo-4-{[(1H-indol-6-ylmethyl)amino]methylene}isoquinoline-1,3(2H,4H)-dione;
(4Z)-6-Bromo-4-{[(3-hydroxy-4-propoxybenzyl)amino]methylene}isoquinoline-1,3(2H,4H)-dione;
(4Z)-4-{[(4-Amino-3-hydroxybenzyl)amino]methylene}-6-(4-fluorophenyl)isoquinoline-1,3(2H,4H)-dione;
(4Z)-7-Bromo-4-{[(3-hydroxy-4-methoxybenzyl)amino]methylene}isoquinoline-1,3(2H,4H)-dione;
(4Z)-4-{[(3-Hydroxy-4-methoxybenzyl)amino]methylene}-6-(1H-pyrazol-4-yl)isoquinoline-1,3(2H,4H)-dione;
(4Z)-6-Bromo-4-{[(3-hydroxy-4-isopropoxybenzyl)amino]methylene}isoquinoline-1,3(2H,4H)-dione;
(4Z)-6-iodo-4-[({4-[(2-methylpyrrolidin-1-yl)methyl]phenyl}amino)methylene]isoquinoline-1,3(2H,4H)-dione;
(4Z)-6-Bromo-4-({[3-hydroxy-4-(2-hydroxyethoxy)benzyl]amino}methylene) isoquinolin-1,3(2H,4H)-dione;
2-(Acetylamino)-5-({[[(Z)-(6-bromo-1,3-dioxo-2,3-dihydroisoquinolin-4(1H)-ylidene)methyl]amino}methyl)phenyl acetate;
N-[4-({[(Z)-(6-Bromo-1,3-dioxo-2,3-dihydroisoquinolin-4(1H)-ylidene)methyl]amino}methyl)-2-hydroxyphenyl]acetamide;
(4Z)-6-Bromo-4-({[3-hydroxy-4-(2-pyrrolidin-1-ylethoxy)benzyl]amino}methylene)isoquinoline-1,3(2H,4H)-dione;
N-[4-({[[(Z)-(1,3-Dioxo-6-thien-3-yl-2,3-dihydroisoquinolin-4(1H)-ylidene)methyl]amino}methyl)-2-hydroxyphenyl]acetamide;
2-(Acetylamino)-5-({[[(Z)-(6-iodo-1,3-dioxo-2,3-dihydroisoquinolin-4(1H)-ylidene)methyl]amino}methyl)phenyl acetate;
(4Z)-4-({[4-(Benzyloxy)-3-hydroxybenzyl]amino}methylene)-6-bromoisoquinoline-1,3(2H,4H)-dione;
(4Z)-6-Bromo-4-{[(4-butoxy-3-hydroxybenzyl)amino]methylene}isoquinoline-1,3(2H,4H)-dione;
(4Z)-4-({[4-(Allyloxy)-3-hydroxybenzyl]amino}methylene)-6-bromoisoquinoline-1,3(2H,4H)-dione;
(4Z)-6-Bromo-4-({[4-(hexyloxy)-3-hydroxybenzyl]amino}methylene)isoquinoline-1,3(2H,4H)-dione;

N-[2-Hydroxy-4-({[[(Z)-(6-iodo-1,3-dioxo-2,3-dihydroisoquinolin-4(1H)-ylidene)methyl]amino}methyl)phenyl]acetamide;
4-(4-{[4-(4-Methyl-piperazin-1-yl)-phenylamino]-methylene}-1,3-dioxo-1,2,3,4-tetrahydro-isoquinolin-6-yl)-benzonitrile;
6-(3-Fluoro-phenyl)-4-{[4-(4-methyl-piperazin-1-yl)-phenylamino]-methylene-4H-isoquinoline-1,3-dione;
4-{[4-(4-Methyl-piperazin-1-yl)-phenylamino]-methylene}-6-(2-morpholin-4-yl-ethoxy)-4H-isoquinoline-1,3-dione;
(4Z)-4-{[(4-Methyl-3-hydroxybenzyl)amino]methylene}-6-iodoisoquinoline-1,3(2H,4H)-dione;
(4Z)-6-Bromo-4-({[3-hydroxy-4-(2-ethoxyethoxy)benzyl]amino}methylene)isoquinoline-1,3(2H,4H)-dione;
(4Z)-4-[({4-[2-(Benzyloxy)ethoxy]-4-hydroxybenzyl}amino)methylene]-6-bromoisoquinoline-1,3(2H,4H)-dione;
(4Z)-4-({[4-(4-Methylpiperazin-1-yl)phenyl]amino}methylene)-6-[3-(tetrahydro-2H-pyran-2-yloxy)prop-1-ynyl]isoquinoline-1,3(2H,4H)-dione;
(4Z)-6-Bromo-4-{[(3-hydroxy-4-methoxybenzyl)(methyl)amino]methylene}isoquinoline-1,3(2H,4H)-dione;
6-Bromo-4-{[4-(1H-imidazol-4-yl)-phenylamino]-methylene}-4H-isoquinolin-1,3-dione;
(4Z)-4-{[(4-Chloro-3-hydroxybenzyl)amino]methylene}-6-iodoisoquinoline-1,3(2H,4H)-dione;
(4Z)-6-Bromo-4-{[(4-ethoxy-3-hydroxybenzyl)amino]methylene}isoquinoline-1,3(2H,4H)-dione;
(4Z)-6-[4-(Piperidin-1-ylmethyl)phenyl]-4-({4-(piperidin-1ylmethyl)phenyl]amino}methylene)isoquinoline-1,3(2H,4H)-dione;
6-Furan-2-yl-4-[(4-pyrrolidin-1-ylmethyl-phenylamino)-methylene]-4H-isoquinoline-1,3-dione;
(4Z)-4-({[4-(4-Methylpiperazin-1-yl)phenyl]amino}methylene)-6-(phenylethynyl)-isoquinoline-1,3(2H,4H)-dione;
(4Z)-6-[(4-Methoxyphenyl)ethynyl]-4-({[4-(4-methylpiperazin-1-yl)phenyl]amino}-methylene)isoquinoline-1,3(2H,4H)-dione;
(4Z)-6-Bromo-4-{[(2,5-dihydroxybenzyl)amino]methylene}isoquinoline-1,3(2H,4H)-dione;
(4Z)-6-Bromo-4-{[(2-hydroxybenzyl)amino]methylene}isoquinoline-1,3(2H,4H)-dione;
(4Z)-6-Bromo-4-{[(2,3,4-trihydroxybenzyl)amino]methylene}isoquinoline-1,3(2H,4H)-dione;
6-Bromo-4-{[4-(2-pyrrolidin-1-yl-ethyl)-phenylamino]-methylene}-4H-isoquinolin-1,3-dione;
(4Z)-6-(3-Methoxyprop-1-ynyl)-4-({[4-(4-methylpiperazin-1-yl)phenyl]amino}-methylene)isoquinoline-1,3(2H,4H)-dione;
(4Z)-4-{[(3-Hydroxy-4-propoxybenzyl)amino]methylene}-6-iodoisoquinoline-1,3(2H,4H)-dione;
(4Z)-4-{[(3-Hydroxy-4-propoxybenzyl)amino]methylene}-6-iodoisoquinoline-1,3(2H,4H)-dione;
(Z)-Diethyl 5-(((6-bromo-1,3-dioxo-2,3-dihydroisoquinolin-4(1H)-ylidene)methylamino)methyl)benzodioxole-2,2-dicarboxyiate;
(4Z)-6-Bromo-4-{[(4-difluoromethoxy-3-hydroxybenzyl)amino)methylene}isoquinoline-1,3(2H,4-dione;
(4Z)-6-Bromo-4-{[(3-fluoro-4-methoxybenzyl)amino]methylene}isoquinoline-1,3(2H,4H)-dione;
(4Z)-6-(2,2-Bithien-5-yl)-4-({[4-(4-methylpiperazin-1-yl)phenyl]amino}methylene)-isoquinoline-1,3(2H,4H)-dione;

(4Z)-4-{[(3-Hydroxy-4-propoxybenzyl)amino]methylene}-6-thiene-3-ylisoquinoline-,3(2H,4H)-dione;
5-({[(Z)-(6-Bromo-1,3-dioxo-2,3-dihydroisoquinolin-4(1H)-ylidene)methyl]amino}methyl)-2-[(methoxycarbonyl)amino]phenyl methyl carbonate;
5-({[(Z)-(6-Bromo-1,3-dioxo-2,3-dihydroisoquinolin-4(1H)-cyclopropanecarboxylate-lidene)methyl]amino}methyl)-2-[(cyclopropylcarbonyl)amino]phenyl;
N-[(4Z)-4-({[4-(4-Methylpiperazin-1-yl)phenyl]amino}methylene)-1,3-dioxo-1,2,3,4-tetrahydroisoquinolin-6-yl]acetamide;
(4Z)-4-({[4-(4-Methylpiperazin-1-yl)phenyl]amino}methylene)-6-(thien-3-ylethynyl)-isoquinoline-1,3(2H,4H)-dione;
1,2,3,4-Tetrahydroisoquinolin-6-yl]benzenesulfonamide-N-[(4Z)-4-({[4-(4-methylpiperazin-1-yl)phenyl]amino}methylene)-1,3-dioxo;
(4Z)-6-Bromo-4-({[1-(3-hydroxy-4-methoxyphenyl)ethyl]amino}methylene)isoquinoline-1,3(2H,4H)-dione;
5-({[(Z)-(6-Bromo-1,3-dioxo-2,3-dihydroisoquinolin-4(1H)-ylidene)methyl]amino}-methyl)-2-propoxyphenyl propionate;
5-({[(Z)-(6-Bromo-1,3-dioxo-2,3-dihydroisoquinolin-4(1H)-ylidene)methyl]amino}-methyl)-2-propoxyphenyl methyl carbonate;
(4Z)-6-(4-Fluorophenyl)-4-{[(3-hydroxy-4-propoxybenzyl)amino]methylene}-isoquinoline-1,3(2H,4H)-dione;
(4Z)-6-(3-Fluorophenyl)-4-{[(3-hydroxy-4-propoxybenzyl)amino]methylene}-isoquinoline-1,3(2H,4H)-dione;
(4Z)-6-(3,4-Difluorophenyl)-4-{](3-hydroxy-4-propoxybenzyl)amino]methylene}-isoquinoline-1,3(2H,4H)-dione;
(4Z)-6-Bromo-4-{[(3-hydroxy-5-propoxybenzyl)amino]methylene}isoquinoline-1,3(2H,4H)-dione;
N-((4Z)-4-{[(3-Hydroxy-4-methoxybenzyl)amino]methylene}-1,3-dioxo-1,2,3,4-tetrahydroisoquinolin-6-yl)benzenesulfonamide;
N-((4Z)-4-{[(3-Hydroxy-4-propoxybenzyl)amino]methylene}-1,3-dioxo-1,2,3,4-1,2,3,4-tetrahydroisoquinolin-6-yl]-2-thien-2-ylacetamide;
1,2,3,4-Tetrahydroisoquinolin-6-yl]-2-thien-2-ylacetamide-N-[(4Z)-4-({[4-(4-methylpiperazin-1-yl)phenyl]amino}methylene)-1,3-dioxo;
(4Z)-4-({[4-(Difluoromethoxy)-3-hydroxybenzyl]amino}methylene)-6-(3-furyl)isoquinoline-1,3(2H,4H)-dione;
(4Z)-4-({[4-(Difluoromethoxy)-3-hydroxybenzyl]amino}methylene)-6-thien-3-ylisoquinoline-1,3(2H,4H)-dione;
(4Z)-6-Bromo-4-({[4-(3,5-dimethylpiperazin-1-yl)phenyl]amino}methylene)isoquinoline-1,3(2H,4H)-dione;
N-(4-Methylpiperazin-1-yl)-N-[(4Z)-4-({[4-(4-methylpiperazin-1-yl)phenyl]amino}methylene)-1,3-dioxo-1,2,3,4-tetrahydroisoquinolin-6-yl]urea;
(4Z)-4-{[(3-Amino-4,5-dihydroxybenzyl)amino]methylene}-6-bromoisoquinoline-1,3(2H,4H)-dione;
(4Z)-4-({[4-(3,5-Dimethylpiperazin-1-yl)phenyl]amino}methylene)-6-(4-fluorophenyl)-isoquinoline-1,3(2H,4H)-dione;
(4Z)-4-({[4-(3,5-Dimethylpiperazin-1-yl)phenyl]amino}methylene)-6-thien-3-ylisoquinoline-1,3(2H,4H)-dione;
(4Z)-4-({[4-(3,5-Dimethylpiperazin-1-yl)phenyl]amino}methylene)-6-(3-furyl)iso-quinoline-1,3(2H,4H)-dione;
(4Z)-6-(4-Fluorophenyl)-4-{[(3-hydroxy-4-methoxybenzyl)amino]methylene}iso-quinoline-1,3(2H,4H)-dione;
(4Z)-6-(3-Fluorophenyl)-4-{[(3-hydroxy-4-methoxybenzyl)amino]methylene}iso-quinoline-1,3(2H,4H)-dione;
(4Z)-6-Bromo-4-{[(3,5-dihydroxy-4-methoxybenzyl)amino]methylene}isoquinoline-1,3(2H,4H)-dione;
(4Z)-6-Bromo-4-{[(3-hydroxy-4,5-dipropoxybenzyl)amino]methylene}isoquinoline-1,3(2H,4H)-dione;
N-[5-({[(Z)-(6-Bromo-1,3-dioxo-2,3-dihydroisoquinolin-4(1H)-ylidene)methylamino)methyl]-2,3-dihydroxyphenyl]acetamide;
(4Z)-6-Bromo-4-[(2,3-dihydro-1H-indol-5-ylamino)methylene]isoquinoline-1,3(2H,4H)-dione;
N-(4-{[(Z)-(6-Bromo-1,3-dioxo-2,3-dihydroisoquinolin-4(1H)-ylidene)methyl]amino}phenyl)-4-methylpiperazine-1-carboxamide;
(4Z)-4-({[4-(3,5-Dimethylpiperazin-1-yl)phenyl]amino}methylene)-6-iodoisoquinoline-1,3(2H,4H)-dione;
N-(4-{[(Z)-(6-Bromo-1,3-dioxo-2,3-dihydroisoquinolin-4(1H)-ylidene)methyl]amino}phenyl)-N-(4-methylpiperazin-1-yl)urea;
N-[4-({[(Z)-(6-Bromo-1,3-dioxo-2,3-dihydroisoquinolin-4(1H)-ylidene)methyl]amino}methyl)-2-hydroxyphenyl]-2,2,2-trifluoroacetamide;
(4Z)-6-Bromo-4-({[4-(cyclopropylmethoxy)-3-hydroxybenzyl]amino}methylene)isoquinoline-1,3(2H,4H)-dione;
(4Z)-6-Bromo-2-(hydroxymethyl)-4-({[4-(4-methylpiperazin-1-yl)phenyl]amino}methylene)isoquinoline-1,3(2H,4H)-dione;
6-Iodo-4-{[4-(5-methyl-2,5-diaza-bicyclo[2.2.1]hept-2-yl)-phenylamino]-methylene}-4H-isoquinoline-1,3-dione;
(4Z)-6-Bromo-4-({[(2-methoxypyridin-4-yl)methyl]amino}methylene)isoquinoline-1,3(2H,4H)-dione;
(4Z) -6-Bromo-4-({[(7-hydroxy-2,2-dimethyl-1,3-benzodioxol-5-yl)methyl]amino}methylene)isoquinoline-1,3(2H,4H)-dione;
(4Z)-6-Bromo-4-({[(2-oxo-1,2-dihydropyridin-4-yl)methyl]amino}methylene)isoquinoline-1,3(2H,4H)-dione;
(4Z)-6-(2,5-Dimethyl-1H-pyrrol-1-yl)-4-({[4-(4-methylpiperazin-1-yl)phenyl]amino}methylene)isoquinoline-1,3(2H,4H)-dione;
(4Z)-4-{[(4-Amino-3-hydroxybenzyl)amino]methylene}-6-bromoisoquinoline-1,3(2H,4H)-dione;
PEG5000thio-acetic acid 5-{[(6-bromo-1,3-dioxo-2,3-dihydro-1H-isoquinolin-4-ylidenemethyl)-amino]-methyl}-2-propoxy-phenyl ester;
(4Z)-6-Bromo-4-{[(4-{[2-(dimethylamino)ethyt]thio}phenyl)amino]methylene}isoquinoline-1,3(2H,4H)dione;
2-Hydroxy-4-[(3-hydroxy-4-propoxy-benzylamino)-methylene]-4H-isoquinoline-1,3-dione;
(4Z)-6-Bromo-4-[({4-[[2-(dimethylamino)ethyl](methyl)amino]phenyl}amino)methylene]isoquinoline-1,3(2H,4H)-dione;
(4Z)-6-Bromo-4-({[4-(4-methyl-1,4-diazepan-1-yl)phenyl]amino}methylene)isoquinoline-1,3(2H,4H)-dione;

(4Z)-6-Iodo-4-[({4-[(2S,5R)-2,4,5-trimethylpiperazin-1-yl]phenyl}amino)methylene]-isoquinoline-1,3(2H,4H)-dione;
(4Z)-6-Iodo-4-[({4-[(3R,5S)-3,4,5-trimethylpiperazin-1-yl]phenyl}amino)methylene]-isoquinoline-1,3(2H,4H)-dione;
(4Z)-4-({[4-(3,5-Dimethylpiperazin-1-yl)phenyl]amino}methylene)-6-nitroisoquinoline-1,3(2H,4H)-dione;
(4Z)-6-(3-Furyl)-4-({[4-(4-methylpiperazin-1-yl)phenyl]amino}methylene)isoquinoline-1,3(2H,4H)-dione;
(4Z)-6-Iodo-4-({[6-(4-methylpiperazin-1-yl)pyridin-3-yl]amino}methylene)isoquinoline-1,3(2H,4H)-dione;
(4Z)-6-Bromo-4-[({4-[(2S,5R)-2,4,5-trimethylpiperazin-1-yl]phenyl}amino)methylene]-isoquinoline-1,3(2H,4H)-dione;
(4Z)-6-Iodo-4-({[4-(1-methylpiperidin-4-yl)phenyl]amino}methylene)isoquinoline-1,3(2H,4H)-dione;
(4Z)-6-Bromo-4-[({4-[(3R,5S)-3,4,5-trimethylpiperazin-1-yl]phenyl}amino)methylene]-isoquinoline-1,3(2H,4H)-dione;
(4Z)-6-(3-Furyl)-4-[({4-[(3R,5S)-3,4,5-trimethylpiperazin-1-yl]phenyi}amino)-methylene]isoquinoline-1,3(2H,4H)-dione;
6-Bromo-7-methoxy-4-{[4-(4-methyl-piperazin-1-yl)-phenylamino]-methylene}-4H-isoquinoline-1,3-dione;
(4Z)-6-Bromo-4-{[(4-{[2-(dimethylamino)ethyl]sulfonyl}phenyl)amino]methylene}isoquinoline-1,3(2H,4H)-dione;
(4Z)-6-Bromo-4-[({4-[(2-hydroxyethyl)(methyl)amino]phenyl}amino)methylene]isoquinoline-1,3(2H,4H)-dione;
(4Z)-6-Bromo-4-[({4-[methyl(1-methylpyrrolidin-3-yl)amino]phenyl}amino)methylene]isoquinoline-1,3(2H,4H)-dione;
6-Bromo-4-[(3-hydroxy-4-propoxy-benzylamino)-methylene]-7-methoxy-4H-isoquinoline-1,3-dione;
(4Z)-6-Iodo-4-({[4-(pyridin-2-ylmethoxy)phenyl]aminomethylene)isoquinoline1,3(2H,4H)-dione;
(4Z)-4-({[4-(3,4-Dimethylpiperazin-1-yl)phenyl]amino}methylene)-6-iodoisoquinoline-1,3(2H,4H)-dione;
(4Z)-6-(3-Furyl)-4-({[6-(4-methylpiperazin-1-yl)pyridin-3-yl]amino}methylene)isoquinoline-1,3(2H,4H)-dione;
(4Z)-6-Bromo-4-({[6-(4-methylpiperazin-1-yl)pyridin-3-yl]amino}methylene)isoquinoline-1,3(2H,4H)-dione;
(4Z)-6-(4-Fluorophenyl)-4-({[4-(piperidin-1-ylmethyl)phenyl]amino}methylene)isoquinoline-1,3(2H,4H)-dione;
6-Bromo-7-methoxy-4-[(4-piperidin-1-ylmethyl-phenylamino)-methylene]-4H-isoquinoline-1,3-dione;
6-(4-Fluoro-phenyl)-7-methoxy-4-[(4-piperidin-1-ylmethyl-phenylamino)-methylene]-4H-isoquinoline-1,3-dione;
6-Furan-3-yl-7-methoxy-4-{[4-(4-methyl-piperazin-1-yl)-phenylamino]-methylene}-4H-isoquinoline-1,3-dione;
(4Z)-6-Bromo-4-[({4-[methyl(2-pyrrolidin-1-ylethyl)amino]phenyl}amino)methyleneisoquinoline-1,3(2H,4H)-dione;
(4Z)-6-Bromo-4-[({4-[methyl(2-piperidin-1-ylethyl)amino]phenyl}amino)methyleneisoquinoline-1,3(2H,4H)-dione;
(4Z)-6-Bromo-4-(({4-[{2-[butyl(methyl)amino]ethyl}(methyl)amino]phenyl}amino)methylene)isoquinoline-1,3(2H,4H)-dione;
(4Z)-6-Bromo-4-[({4-[2-(dimethylamino)ethoxy]phenyt}amino)methylene]isoquinoline-1,3(2H,4H)-dione;
(4Z)-6-Bromo-4-{[(2-methyl-2,3-dihydro-1H-isoindol-5-yl)amino]methylene}isoquinoline-1,3(2H,4H)-dione;
(4Z)-6-Bromo-4-({[4-(1H-imidazol-1-yl)phenyl]amino}methylene)isoquinoline-1,3(2H,4H)-dione;
(4Z)-6-Bromo-4-{[(4-{methyl[2-(4-methylpiperazin-1-yl)ethyl]amino}phenyl)amino]methylene}isoquinoline-1,3(2H,4H)-dione;
(4Z)-6-Bromo-4-[({4-[methyl(2-morpholin-4-ylethyl)amino]phenyl}amino)methylene]isoquinoline-1,3(2H,4H)-dione;
(4Z)-6-(4-Fluorophenyl)-4-({[4-(4-methylpiperazin-1-yl)phenyl]amino}methylene)-isoquinoline-1,3(2H,4H)-dione;
(4Z)-6-Iodo-4-{[(4-{[(3R)-3-methoxypyrrolidin-1-yl]methyl}phenyl)amino]methylene}isoquinoline-1,3(2H,4H)-dione;
(4Z)-6-(4-Fluorophenyl)-4-{[(4-{[(3S)-3-methoxypyrrolidin-1-yl]methyl}phenyl)amino]methylene}isoquinoline-1,3(2H,4H)-dione;
(4Z)-6-Bromo-4-{[(4-{[(3R)-3-methoxypyrrolidin-1-yl]methyl}phenyl)amino]methylene}isoquinoline-1,3(2H,4H)-dione;
(4Z)-6-Iodo-4-{[(4-difluoromethoxy-3-hydroxybenzyl)amino)methylene}isoquinoline-1,3(2H,4-dione);
6-({[(Z)-(6-Bromo-1,3-dioxo-2,3-dihydroisoquinolin-4(1H)-ylidene)methyl]amino}methyl)-2,2-dimethyl-1,3-benzodioxol-4-yl acetate;
6-({[(Z)-(6-Bromo-1,3-dioxo-2,3-dihydroisoquinolin-4(1H)-ylidene)methyl]amino}methyl)-2,2-dimethyl-1,3-benzodioxol-4-yl cyclopropanecarboxylate;
(4Z)-6-Bromo-4-[({4-[3-(dimethylamino)propyl]phenyl}amino)methylene]isoquinoline-1,3(2H,4H)-dione;
(4Z)-6-Bromo-4-[(quinolin-6-ylamino)methylene]isoquinoline-1,3(2H,4H)-dione;
(4Z)-6-Iodo-4-[(quinolin-6-ylamino)methylene]isoquinoline-1,3(2H,4H)-dione;
(4Z)-4-({[4-(1H-Imidazol-1-ylmethyl)phenyl]amino}methylene)-6-iodoisoquinoline-1,3(2H,4H)-dione;
(4Z)-6-Bromo-4-[({4-[3-(methoxyamino)propyl]phenyl}amino)methylene]isoquinoline-1,3(2H,4H)-dione;
(4Z)-6-Bromo-4-[({4-[[3-(dimethylamino)propyl](methyl)amino]phenyl}amino)methylene]isoquinoline-1,3(2H,4H)-dione;
(4Z)-6-Bromo-4-[({4-[(1-methylpyrrolidin-3-yl)oxy]phenyl}amino)methylene]isoquinoline-1,3(2H,4H)-dione;
2-Amino-2-{4-[(6-bromo-1,3-dioxo-2,3-dihydro-1H-isoquinolin-4-ylidenemethyl)-amino]-phenyl}-propionic acid;
4-[(3-Hydroxy-4-propoxy-benzylamino)-methylene]-6-pyrrol-1-yl-4H-isoquinoline-1,3-dione;
4-{[3-(4-Methyl-piperazin-1-yl)-propylamino]-methylene}-6-pyrrol-1-yl-4H-isoquinoline-1,3-dione;
4-{[(Z)-(6-Bromo-1,3-dioxo-2,3-dihydroisoquinolin-4(1H)-ylidene)methyl]amino}-N,N-dimethylbenzohydrazide;
(4Z)-6-Bromo-4-({[4-(1,3-thiazolidin-3-ylmethyl)phenyl]amino}methylene)isoquinoline-1,3(2H,4H)-dione;
(4Z)-4-({[4-(Pyrrolidin-1-ylmethyl)phenyl]amino}methylene)-6-[4-(trifluoromethyl)phenyl]isoquinoline-1,3(2H,4H)-dione;

2-(4-{[(Z)-(6-Bromo-1,3-dioxo-2,3-dihydroisoquinolin-4 (1H)-ylidene)methyl]amino}phenyl)-N,N-dimethylacetohydrazide;
Diethyl[(4Z)-4-({[4-(4-methylpiperazin-1-yl)phenyl] amino}methylene)-1,3-dioxo-1,2,3,4-tetrahydroisoquinolin-6-yl]phosphonate;
(4Z)-6-Iodo-4-{[(4-{[(2S)-2-(methoxymethyl)pyrrolidin-1-yl]methyl}phenyl)amino]methylene}isoquinoline-1, 3(2H,4H)-dione;
(4Z)-6-Bromo-4-({[4-(morpholin-4-ylmethyl)phenyl] amino}methylene)isoquinoline-1,3(2H,4H)-dione;
(4Z)-6-Bromo-4-[({4-[(2-methylpyrrolidin-1-yl)methyl] phenyl}amino)methyl]-isoquinoline-1,3(2H,4H)-dione;
(4Z)-6-Bromo-4-({[3-fluoro-4-(4-methylpiperazin-1-yl) phenyl]amino}methylene)-isoquinoline-1,3(2H,4H)-dione;
(4Z)-6-(4-Fluorophenyl)-4-[({4-[(2-methylpyrrolidin-1-yl)methyl]phenyl}amino)-methylene]isoquinoline-1,3 (2H,4H)-dione;
(4Z)-4-({[3-Fluoro-4-(4-methylpiperazin-1-yl)phenyl] amino}methylene)-6-(4-fluorophenyl)isoquinoline-1,3 (2H,4H)-dione;
(4Z)-6-(3-Furyl)-4-[({4-[(2-methylpyrrolidin-1-yl)methyl]phenyl}amino)methylene]-isoquinoline-1,3(2H, 4H)-dione;
PEG5000thio-acetic acid 5-{[(6-iodo-1,3-dioxo-2,3-dihydro-1H-isoquinolin-4-ylidenemethyl)-amino]-methyl}-2-propoxy-phenyl ester;
5-({[(Z)-(6-Iodo-1,3-dioxo-2,3-dihydroisoquinolin-4 (1H)-ylidene)methyl]amino}methyl)-2-propoxyphenyl chloroacetate;
tert-Butyl 4-(4-{[(Z)-(6-bromo-1,3-dioxo-2,3-dihydroisoquinolin-4(1H)-ylidene)methyl]amino}phenyl)piperazine-1-carboxylate;
(4Z)-4-({[3-Fluoro-4-(4-methylpiperazin-1-yl)phenyl] amino}methylene)-6-iodoisoquinoline-1,3(2H,4H)-dione;
(4Z)-6-Iodo-4-({[4-(morpholin-4-ylmethyl)phenyl] amino}methylene)isoquinoline-1,3(2H,4H)-dione;
(4Z)-4-({[3-Fluoro-4-(4-methylpiperazin-1-yl)phenyl] amino}methylene)-6-(3-furyl)isoquinoline-1,3(2H, 4H)-dione;
(4Z)-4-({[4-(4-Methylpiperazin-1-yl)phenyl] amino}methylene)-6-[4-(trifluoromethoxy)phenyl]isoquinoline-1,3(2H,4H)-dione;
(4Z)-6-(4-Fluorophenyl)-4-{[(4-{[(2S)-2-(methoxymethyl)pyrrolidin-1-yl]methyl}phenyl)amino] methylene}isoquinoline-1,3(2H,4H)-dione;
(4Z)-6-(4-Isopropoxyphenyl)-4-{[(4-{[(2R)-2-(methoxymethyl)pyrrolidin-1-yl]methyl}phenyl)amino] methylene}isoquinoline-1,3(2H,4H)-dione;
N-[4-({[(Z)-(6-Bromo-1,3-dioxo-2,3-dihydroisoquinolin-4(1H)-ylidene)methyl]amino}methyl)-2-hydroxyphenyl]acrylamide;
N-[4-({[(Z)-(6-Bromo-1,3-dioxo-2,3-dihydroisoquinolin-4(1H)-ylidene)methyl]amino}methyl)phenyl]-2,2-dichloroacetamide;
(4Z)-4-[({4-Amino-3-[(triisopropylsilyl)oxy] benzyl}amino)methylene]-6-bromoisoquinoline-1,3 (2H,4H)-dione;
(Z)-6-Bromo-4-((2-(piperazin-1-yl)ethylamino)methylene)isoquinoline-1,3(2H,4H)-dione;
(Z)-6-Bromo-4-((3-(pyrrolidin-1-yl)propylamino)methylene)isoquinoline-1,3(2H,4H)-dione;
(Z)-6-Bromo-4-((3-morpholinopropylamino)methylene) isoquinoline-1,3(2H,4H)-dione;
(Z)-6-Bromo-4-((3-(2-oxopyrrolidin-1-yl)propylamino) methylene)isoquinoline-1,3(2H,4H)-dione;
4-{[(5-Hydroxy-4-oxo-4H-pyran-2-ylmethyl)-amino]-methylene}-6-pyrrol-1-yl-4H-isoquinoline-1,3-dione;
6-Bromo-4-{[(5-hydroxy-4-oxo-4H-pyran-2-ylmethyl)-amino]-methylene}-4H-isoquinoline-1,3-dione;
6-Bromo-4-{[(5-methoxy-4-oxo-4H-pyran-2-ylmethyl)-amino]-methylene}-4H-isoquinoline-1,3-dione;
4-{[(5-Methoxy-4-oxo-4H-pyran-2-ylmethyl)-amino]-methylene}-6-pyrrol-1-yl-4H-isoquinoline-1,3-dione;
(4Z)-6-Bromo-4-[({4-[(3R,5S)-3,5-dimethylpiperazin-1-yl]-3-fluorophenyl}amino)methylene]isoquinoline-1,3 (2H,4H)-dione;
(4Z)-4-[({4-[(3R,5S)-3,5-Dimethylpiperazin-1-yl]-3-fluorophenyl}amino)methylene]-6-iodoisoquinoline-1, 3(2H,4H)-dione;
N-[4-({[(Z)-(6-Bromo-1,3-dioxo-2,3-dihydroisoquinolin-4(1H)-ylidene)methyl]amino}methyl)-2-hydroxyphenyl]-2,2-dichloroacetamide;
N-[4-({[(Z)-(6-Bromo-1,3-dioxo-2,3-dihydroisoquinolin-4(1H)-ylidene)methyl]amino}methyl)phenyl]propanamide;
N-[4-({[(Z)-(6-Bromo-1,3-dioxo-2,3-dihydroisoquinolin-4(1H)-ylidene)methyl]amino}methyl)phenyl]acrylamide;
(4Z)-4-[({4-Amino-3-[(triisopropylsilyl)oxy] benzyl}amino)methylene]-6-iodoisoquinoline-1,3(2H, 4H)-dione;
(4Z)-4-[({4-[(3R,5S)-3,5-Dimethylpiperazin-1-yl]-3-fluorophenyl}amino)methylene]-6-(3-furyl)isoquinoline-1,3(2H,4H)-dione;
(4Z)-4-[({4-[(3R,5S)-3,5-Dimethylpiperazin-1-yl]-3-fluorophenyl}amino)methylene]-6-thien-3-ylisoquinoline-1,3(2H,4H)-dione;
(4Z)-4-[({4-[(3R,5S)-3,5-Dimethylpiperazin-1-yl]-3-fluorophenyl}amino)methylene]-6-(4-fluorophenyl) isoquinoline-1,3(2H,4H)-dione;
(4Z)-4-({[4-(1-Methylpiperidin-4-yl)phenyl] amino}methylene)-6-thien-3-ylisoquinoline-1,3(2H, 4H)-dione;
(4Z)-4-({[3-Fluoro-4-(4-methylpiperazin-1-yl)phenyl] amino}methylene)-6-(1H-pyrrol-1-yl)isoquinoline-1,3 (2H,4H)-dione;
6-Bromo-4-[(4-pyridin-4-yl-phenylamino)-methylene]-4H-isoquinoline-1,3-dione;
(4Z)-6-(3-Furyl)-4-{[(4-{[(2R)-2-(methoxymethyl)pyrrolidin-1-yl]methyl}phenyl)amino] methylene}isoquinoline-1,3(2H,4H)-dione;
(4Z)-4-{[(4-{[(2R)-2-(Methoxymethyl)pyrrolidin-1-yl] methyl}phenyl)amino]methylene}-6-thien-3-ylisoquinoline-1,3(2H,4H)-dione;
6-Bromo-4-{[(4-hydroxy-5-methoxy-pyridin-2-ylmethyl)-amino]-methylene}-4H-isoquinoline-1,3-dione;
4-[(3-Hydroxy-4-methoxy-benzylamino)-methylene]-6-pyrrol-1-yl-4H-isoquinoline-1,3-dione;
N-[2-Hydroxy-4-({[(Z)-(6-iodo-1,3-dioxo-2,3-dihydroisoquinolin-4(1H)-ylidene)methyl]amino}methyl) phenyl]benzamide;
N-[2-Hydroxy-4-({[(Z)-(6-iodo-1,3-dioxo-2,3-dihydroisoquinolin-4(1H)-ylidene)methyl]amino}methyl) phenyl]-2-methylpropanamide;
(2E)-N-[2-Hydroxy-4-({[(Z)-(6-iodo-1,3-dioxo-2,3-dihydroisoquinolin-4(1H)-ylidene)methyl]amino}methyl) phenyl]-2-methylbut-2-enamide;
(2Z)-3-Chloro-N-[2-hydroxy-4-({[(Z)-(6-iodo-1,3-dioxo-2,3-dihydroisoquinolin-4(1H)-ylidene)methyl] amino}methyl)phenyl]acrylamide;

2-[(Dimethylamino)methyl]-N-[2-hydroxy-4-({[(Z)-(6-iodo-1,3-dioxo-2,3-dihydroisoquinolin-4(1H)-ylidene)methyl]amino}methyl)phenyl]acrylamide;

N-[2-Hydroxy-4-({[(Z)-(6-iodo-1,3-dioxo-2,3-dihydroisoquinolin-4(1H)-ylidene)methyl]amino}methyl)phenyl]but-2-ynamide;

N-[2-Hydroxy-4-({[(Z)-(6-iodo-1,3-dioxo-2,3-dihydroisoquinolin-4(1H)-ylidene)methyl]amino}methyl)phenyl]prop-2-ynamide;

N-[2-Hydroxy-4-({[(Z)-(6-iodo-1,3-dioxo-2,3-dihydroisoquinolin-4(1H)-ylidene)methyl]amino}methyl)phenyl]propanamide;

N-[2-Hydroxy-4-({[(Z)-(6-iodo-1,3-dioxo-2,3-dihydroisoquinolin-4(1H)-ylidene)methyl]amino}methyl)phenyl]acrylamide;

2-[(2E)-But-2-enoylamino]-5-({[(Z)-(6-iodo-1,3-dioxo-2,3-dihydroisoquinolin-4(1H)-ylidene)methyl]amino}methyl)phenyl (2E)-but-2-enoate;

(4Z)-6-Bromo-4-({[4-(1-methylpiperidin-4-yl)phenyl]amino}methylene)isoquinoline-1,3(2H,4H)-dione;

(4Z)-4-[({4-[(3R,5S)-3,5-Dimethylpiperazin-1-yl]-3-fluorophenyl}amino)methylene]-6-(4-methoxyphenyl)isoquinoline-1,3(2H,4H)-dione;

(4Z)-4-[({5-[(3R,5S)-3,5-Dimethylpiperazin-1-yl]pyridin-3-yl}amino)methylene]-6-(3-furyl)isoquinoline-1,3(2H,4H)-dione;

(4Z)-4-({[4-(Dimethylamino)-3-hydroxybenzyl]amino}methylene)-6-iodoisoquinoline-1,3(2H,4H)-dione;

6-Bromo-4-{[4-(4-chloro-3,5-dimethyl-pyrazol-1-yl)-phenylamino]-methylene}-4H-isoquinoline-1,3-dione;

6-Bromo-4-[(4-pyridin-3-yl-phenylamino)-methylene]-4H-isoquinoline-1,3-dione;(4Z)-6-bromo-4-{[(3-hydroxy-4propoxybenzyl)amino]methylene}isoquinoline-1,3(2H,4H)-dione;

(4Z)-6-Bromo-4-[({6-[(2R, 6S)-2,6-dimethylpiperidin-4-yl]-5-methylpyridin-3-yl}amino)methylene]isoquinoline-1,3(2H,4H)-dione;

(4Z)-4-({[4-(1-Acetylpiperidin-4-yl)phenyl]amino}methylene)-6-(3-furyl)isoquinoline-1,3(2H,4H)-dione;

5-({[(Z)-(6-Bromo-1,3-dioxo-2,3-dihydroisoquinolin-4(1H)-ylidene)methyl]amino}methyl)-2-propoxybenzoic acid;

5-({[(Z)-(6-Bromo-1,3-dioxo-2,3-dihydroisoquinolin-4(1H)-ylidene)methyl]amino}methyl)-2-propoxybenzamide;

6-Iodo-4-{[4-(1-pyrrolidin-1-yl-ethyl)-phenylamino]-methylene}-4H-isoquinoline-1,3-dione;

(4Z)-4-[({6-[(3R,5S)-3,5-Dimethylpiperazin-1-yl]-5-methylpyridin-3-yl}amino)methylene]-6-(3-furyl)isoquinoline-1,3(2H,4H)-dione;

(4Z)-4-[({6-[(3R,5S)-3,5-Dimethylpiperazin-1-yl]-5-methylpyridin-3-yl}amino)methylene]-6-thien-3-ylisoquinoline-1,3(2H,4H)-dione;

(4Z)-4-[({6-[(3R,5S)-3,5-Dimethylpiperazin-1-yl]-5-methylpyridin-3-yl}amino)methylene]-6-(4-methoxyphenyl)isoquinoline-1,3(2H,4H)-dione;

(4Z)-6-(4-Methoxyphenyl)-4-[({4-[(2-methylpyrrolidin-1-yl)methyl]phenyl}amino)-methylene]-isoquinoline-1,3(2H,4H)-dione;

(2E)-4-(Dimethylamino)-N-[2-hydroxy-4-({[(Z)-(6-iodo-1,3-dioxo-2,3-dihydroisoquinolin-4(1H)-ylidene)methyl]amino}methyl)phenyl]but-2-enamide;

6-Iodo-4-{[4-(4-methyl-piperazin-1-yl)-cyclohexylamino]-methylene}-4H-isoquinoline-1,3-dione;

6-Iodo-4-{[4-(1-methyl-pyrrolidin-2-yl)-phenylamino]-methylene}-4H-isoquinoline-1,3-dione;

6-Iodo-4-{[(4-hydroxy-5-methoxy-pyridin-2-ylmethyl)-aminol-methylene}-4H-isoquinoline-1,3-dione;

4-{[(4-Hydroxy-5-propoxy-pyridin-2-ylmethyl)-amino]-methylene}-6-pyrrol-1-yl-4H-isoquinoline-1,3-dione;

4-{[(4-Hydroxy-5-propoxy-pyridin-2-ylmethyl)-amino]-methylene}-6-iodo-4H-isoquinoline-1,3-dione;

4-([(4-Hydroxy-5-propoxy-pyridin-2-ylmethyl)-amino]-methylene)-6-bromo-4H-isoquinoline-1,3-dione;

(4Z)-4-({[3-Hydroxy-4-(propylamino)benzyl]amino}methylene)-6-iodoisoquinoline-1,3(2H,4H)-dione;

D-1-{4-[(6-Iodo-1,3-dioxo-2,3-dihydro-1H-isoquinolin-4-ylidenemethyl)-amino]-benzyl}-pyrrolidine-2-carboxylic acid methyl ester;

D-4-{[4-(2-Hydroxymethyl-pyrrolidin-1-ylmethyl)-phenylamino]-methylene}-6-iodo-4H-isoquinoline-1,3-dione;

D-4-({4-[2-(1-Hydroxy-1-methyl-ethyl)-pyrrolidin-1-ylmethyl]-phenylamino}-methylene)-6-iodo-4H-isoquinoline-1,3-dione;

(4Z)-6-Bromo-4-[({3,5-difluoro-4-[(8aS)-hexahydropyrrolo[1,2-a]pyrazin-2(1H)-yl]phenyl}amino)methylene]isoquinoline-1,3(2H,4H)-dione;

(4Z)-4-[({3,5-Difluoro-4-[(8aS)-hexahydropyrrolo[1,2-a]pyrazin-2(1H)-yl]phenyl}amino)-methylene]-6-thien-3-ylisoquinoline-1,3(2H,4H)-dione;

(4Z)-6-Bromo-4-({[4-[(3R,5S)-3,5-dimethylpiperazin-1-yl]-3-(trifluoromethyl)phenyl]amino}methylene)isoquinoline-1,3(2H,4H)-dione;

(4Z)-4-[({4-[(3R,5S)-4-(N,N-Dimethylglycyl)-3,5-dimethylpiperazin-1-yl]phenyl}amino)methylene]-6-(3-furyl)isoquinoline-1,3(2H,4H)-dione;

4-({4-[2-(1-Hydroxy-ethyl)-pyrrolidin-1-ylmethyl]-phenylamino}-methylene)-6-iodo-4H-isoquinoline-1,3-dione;

6-Iodo-4-({4-[2-(1-methoxy-ethyl)-pyrrolidin-1-ylmethyl]-phenylamino}-methylene)-4H-isoquinoline-1,3-dione;

L-4-{[4-(2-Hydroxymethyl-pyrrolidin-1-ylmethyl)-phenylamino]-methylene}-6-iodo-4H-isoquinoline-1,3-dione;

tert-Butyl 4-(4-{[(Z)-(6-iodo-1,3-dioxo-2,3-dihydroisoquinolin-4(1H)-ylidene)methyl]amino}phenyl)piperazine-1-carboxylate;

(4Z)-6-Iodo-4-{[(4-piperazin-1-ylphenyl)amino]methylene}isoquinoline-1,3(2H,4H)-dione;

(Z)-5-(((6-bromo-1,3-dioxo-2,3-dihydroisoquinolin-4(1H)-ylidene)methylamino)methyl)-2-propoxyphenyl PEG109-ylcarbamate;

(4Z)-4-[({4-[(3R,5S)-4-(N,N-Dimethylglycyl)-3,5-dimethylpiperazin-1-yl]phenyl}amino)methylene]-6-thien-3-ylisoquinoline-1,3(2H,4H)-dione;

(4Z)-6-Bromo-4-[({4-[(3R,5S)-3,5-dimethylpiperazin-1-yl]-3,5-difluorophenyl}amino)-methylene]isoquinoline-1,3(2H,4H)-dione;

(4Z)-4-[({3-Fluoro-4-[(8aS)-hexahydropyrrolo[1,2-a]pyrazin-2(1H)-yl]phenyl}amino)-methylene]-6-thien-3-ylisoquinoline-1,3(2H,4H)-dione;

(4Z)-4-[({4-[(3R,5S)-3,5-Dimethylpiperazin-1-yl]-3,5-difluorophenyl}amino)methylene]-6-thien-3-ylisoquinoline-1,3(2H,4H)-dione;

N-[(4Z)-4-({[4-(4-Methylpiperazin-1-yl)phenyl]amino}methylene)-1,3-dioxo-1,2,3,4-tetrahydroisoquinolin-6-yl]acrylamide;

(4Z)-6-Iodo-4-({[4-(4-isopropylpiperazin-1-yl)phenyl]amino}methylene)isoquinoline-1,3(2H,4H)-dione;
(4Z)-6-Iodo-4-[({4-[4-(1-methylpiperidin-4-yl)piperazin-1-yl]phenyl}amino)methylene]isoquinoline-1,3(2H,4H)-dione;
(4Z)-6-Iodo-4-({[4-(4-propylpiperazin-1-yl)phenyl]amino}methylene)isoquinoline-1,3(2H,4H)-dione;
(4Z)-4-[({4-{4-(2-Furylmethyl)piperazin-1-yl]phenyl}amino)methylene}-6-iodoisoquinoline-1,3(2H,4H)-dione;
(4Z)-4-[({4-[4-(3-Furylmethyl)piperazin-1-yl]phenyl}amino)methylene]-6-iodoisoquinoline-1,3(2H,4H)-dione;
(4Z)-4-[({4-[4-(Cyolopropy]methyl)piperazin-1-yl]phenyl}amino)methylene]-6-iodoisoquinoline-1,3(2H,4H)-dione;
(4Z)-4-({[4-(4-Cyclobutylpiperazin-1-yl)phenyl]amino}methylene)-6-iodoisoquinoline-1,3(2H,4H)-dione;
(4Z)-4-({[4-(4-Ethylpiperazin-1-yl)phenyl]amino}methylene)-6-iodoisoquinoline-1,3(2H,4H)-dione;
(4Z)-6-Iodo-4-[({4-[(4-methoxypiperidin-1-yl)methyl]phenyl}amino)methylene]isoquinoline-1,3(2H,4H)-dione;
(4Z)-6-(4-Fluorophenyl)-4-[({4-[(4-methoxypiperidin-1-yl)methyl]phenyl}amino)methylene]isoquinoline-1,3(2H,4H)-dione;
(4Z)-4-({[6-(4-Methylpiperazin-1-yl)pyridin-3-yl]amino}methylene)-6-thien-3-ylisoquinoline-1,3(2H,4H)-dione;
(4Z)-6-Bromo-4-[({4-[(4-methoxypiperidin-1-yl)methyl]phenyl}amino)methylene]isoquinoline-1,3(2H,4H)-dione;
(4Z)-4-[({4-[4-(2-Hydroxy-1-methylethyl)piperazin-1-yl]phenyl}amino)methylene]-6-iodoisoquinoline-1,3(2H,4H)-dione;
(4Z)-6-Iodo-4-[({4-[4-(2-methoxy-1-methylethyl)piperazin-1-yl]phenyl}amino)methylene]isoquinoline-1,3(2H,4H)-dione;
(4Z)-4-{[(4-{4-[2-(Dimethylamino)-1-methylethyl]piperazin-1-yl}phenyl)amino]methylene}-6-iodoisoquinoline-1,3(2H,4H)-dione;
(4Z)-4-[({4-[4-(2-Hydroxyethyl)piperazin-1-yl]phenyl}amino)methylene]-6-iodoisoquinoline-1,3(2H,4H)-dione;
4-({4-[1-(4-Dimethylamino-but-2-enoyl)-pyrrolidin-2-yl]-phenylamino}-methylene)-6-iodo-4H-isoquinoline-1,3-dione;
4-{[4-(4,5-Dihydro-3H-pyrrol-2-yl)-phenylamino]-methylene}-6-iodo-4H-isoquinoline-1,3-dione;
4-{[4-(1,2,3,6-Tetrahydro-pyridin-2-yl)-phenylamino]-methylene}-6-thiophen-3-yl-4H-isoquinoline-1,3-dione;
(4Z)-6-Bromo-4-({[3-fluoro-4-(4-pyrrolidin-1-ylpiperidin-1-yl)phenyl]amino}-methylene)-isoquinoline-1,3(2H,4H)-dione;
(4Z)-4-({[3-Fluoro-4-(4-pyrrolidin-1-ylpiperidin-1-yl)phenyl]amino}methylene)-6-thien-3-ylisoquinoline-1,3(2H,4H)-dione;
(4Z)-6-Bromo-4-({[6-(4-pyrrolidin-1-ylpiperidin-1-yl)pyridin-3-yl]amino}methylene)isoquinoline-1,3(2H,4H)-dione;
(4Z)-6-Phenyl-4-({[4-(pyrrolidin-1-ylmethyl)phenyl]amino]methylene)isoquinoline-1,3(2H,4H)-dione;

tert-Butyl 4-(5-{[(Z)-(6-iodo-1,3-dioxo-2,3-dihydroisoquinolin-4(1H)-ylidene)methyl]amino}pyridin-2-yl)piperazine-1-carboxylate;
(4Z)-6-Iodo-4-{[(6-piperazin-1-ylpyridin-3-yl)amino]methylene}isoquinoline-1,3(2H,4H)-dione;
4-{[4-(2-Ethoxymethyl-pyrrolidin-1-ylmethyl)-phenylamino]-methylene}-6-iodo-4H-isoquinoline-1,3-dione;
4-{[4-(2-Dimethylaminomethyl-pyrrolidin-1-yl)-3-fluoro-phenylamino]-methylene}-6-iodo-4H-isoquinoline-1,3-dione;
(4Z)-6-Iodo-4-({[6-(4-isopropylpiperazin-1-yl)pyridin-3-yl]amino}methylene)isoquinoline-1,3(2H,4H)-dione;
(4Z)-4-({[6-(4-Ethylpiperazin-1-yl)pyridin-3-yl]amino}methylene)-6-iodoisoquinoline-1,3(2H,4H)-dione;
(4Z)-4-[({6-[4-(Cyclopropylmethyl)piperazin-1-yl]pyridin-3-yl}amino)methylene]-6-iodoisoquinoline-1,3(2H,4H)-dione;
(4Z)-4-({[6-(4-Ethylpiperazin-1-yl)pyridin-3-yl]amino}methylene)-6-(3-furyl)isoquinoline-1,3(2H,4H)-dione;
(4Z)-4-({[6-(4-Isopropylpiperazin-1-yl)pyridin-3-yl]amino}methylene)-6-(3-thienyl)isoquinoline-1,3(2H,4H)-dione;
(4Z)-4-[({6-[4-(Cyclopropylmethyl)piperazin-1-yl]pyridin-3-yl}amino)methylene]-6-(3-thienyl)isoquinoline-1,3(2H,4H)-dione;
4-{[4-(1-Allyl-pyrrolidin-2-yl)-phenylamino]-methylene}-6-iodo-4H-isoquinoline-1,3-dione;
4-{[4-(1-Allyl-pyrrolidin-2-yl)-phenylamino]-methylene}-6-thiophen-3-yl-4H-isoquinoline-1,3-dione;
4-{[4-(2-Hydroxymethyl-pyrrolidin-1-ylmethyl)-phenylamino]-methylene}-6-thiophen-3-yl-4H-isoquinoline-1,3-dione;
(4Z)-4-{[(4-{[3-(Dimethylamino)pyrrolidin-1-yl]methyl}phenyl)amino]methylene}-6-iodoisoquinoline-1,3(2H,4H)-dione;
(4Z)-4-{[(4-{[3-(Dimethylamino)pyrrolidin-1-yl]methyl}phenyl)amino]methylene}-6-iodoisoquinoline-1,3(2H,4H)-dione;
4-{[(5-Amino-4-hydroxy-pyridin-2-ylmethyl)-aminol-methylene]-6-iodo-4H-isoquinoline-1,3-dione;
(4Z)-4-{[(4-{1-[3-(Dimethylamino)propyl]piperidin-4-yl}phenyl)amino]methylene}-6-iodoisoquinoline-1,3(2H,4H)-dione;
4-{[3-Fluoro-4-(2-hydroxymethyl-pyrrolidin-1-yl)-phenylamino]-methylene}-6-iodo-4H-isoquinoline-1,3-dione;
6-Iodo-4-{[(5-oxo-pyrrolidin-2-ylmethyl)-amino]-methylene}-4H-isoquinoline-1,3-dione;
N-(4-Hydroxy-6-{[(6-iodo-1,3-dioxo-2,3-dihydro-1H-isoquinolin-4-ylidenemethyl)-amino]-methyl}-pyridin-3-yl)-acrylamide;
1-(4-{[(Z)-(6-Iodo-1,3-dioxo-2,3-dihydroisoquinolin-4(1H)-ylidene)methyl]amino}phenyl)-N,N-dimethylpiperidine-4-carboxamide;
1-(4-{[(Z)-(6-Iodo-1,3-dioxo-2,3-dihydroisoquinolin-4(1H)-ylidene)methyl]amino}phenyl)piperidine-4-carboxamide;
1-(4-{[(Z)-(6-Iodo-1,3-dioxo-2,3-dihydroisoquinolin-4(1H)-ylidene)methyl]amino}phenyl)piperidine-4-carboxylic acid;
1-(4-{[(Z)-(6-Iodo-1,3-dioxo-2,3-dihydroisoquinolin-4(1H)-ylidene)methyl]amino}phenyl)-N-methoxy-N-methylpiperidine-4-carboxamide;

N-[2-(Dimethylamino)ethyl]-1-(4-{[(Z)-(6-iodo-1,3-dioxo-2,3-dihydroisoquinolin-4(1H)-ylidene)methyl]amino}phenyl)piperidine-4-carboxamide;

(4Z)-4-[({4-[4-(Hydroxymethyl)piperidin-1-yl]phenyl}amino)methylene]-6-iodoisoquinoline-1,3(2H,4H)-dione;

(4Z)-6-Iodo-4-[({4-[4-(methoxymethyl)piperidin-1-yl]phenyl}amino)methylene]isoquinoline-1,3(2H,4H)-dione;

4-{[4-(2-Ethyl-pyrrolidin-1-ylmethyl)-phenylamino]-methylene}-6-iodo-4H-isoquinoline-1,3-dione;

6-Bromo-4-{[4-(2-hydroxymethyl-pyrrolidin-1-ylmethyl)-phenylamino]-methylene}-4H-isoquinoline-1,3-dione;

4-{[4-(2-Hydroxymethyl-pyrrolidin-1-ylmethyl)-phenylamino]-methylene}-6-thiophen-2-yl-4H-isoquinoline-1,3-dione;

(4Z)-4-{[(4-{[2-(Hydroxymethyl)piperidin-1-yl]methyl}phenyl)amino]methylene}-6-iodoisoquinoline-1,3(2H,4H)-dione;

(4Z)-4-[({4-[(4-Hydroxypiperidin-1-yl)methyl]phenyl}amino)methylene]-6-iodoisoquinoline-1,3(2H,4H)-dione;

6-(5-Chloro-thiophen-2-yl)-4-{[4-(2-hydroxymethyl-pyrrolidin-1-ylmethyl)-phenylamino]-methylene}-4H-isoquinoline-1,3-dione;

(4Z)-6-Bromo-4-({[5-(4-methylpiperazin-1-yl)pyridin-2-yl]amino}methylene)isoquinoline-1,3(2H,4H)-dione;

(4Z)-6-(3-Furyl)-4-({[5-(4-methylpiperazin-1-yl)pyridin-2-yl]amino}methylene)isoquinoline-1,3(2H,4H)-dione;

(Z)-4-((5-Bromopyridin-2-ylamino)methylene)-6-(1H-pyrrol-1-yl)isoquinoline-1,3(2H,4H)-dione;

(4Z)-4-({[2-Fluoro-6-(4-methylpiperazin-1-yl)pyridin-3-yl]amino}methylene)-6-iodoisoquinoline-1,3(2H,4H)-dione;

(4Z)-4-[({4-[4-({[2-(Dimethylamino)ethyl]amino}methyl)piperidin-1-yl]phenyl}amino)methylene]-6-iodoisoquinoline-1,3(2H,4H)-dione;

(4Z)-4-({[2-Hydroxy-6-(4-methylpiperazin-1-yl)pyridin-3-yl]amino}methylene)-6-iodoisoquinoline-1,3(2H,4H)-dione;

4-[(4Z)-4-({[5-(4-Methylpiperazin-1-yl)pyridin-2-yl]amino}methylene)-1,3-dioxo-1,2,3,4-tetrahydroisoquinolin-6-yl]-2-furaldehyde;

(4Z)-4-({[5-(4-Methylpiperazin-1-yl)pyridin-2-yl]amino}methylene)-6-[5-(pyrrolidin-1-ylmethyl)-3-furyl]isoquinoline-1,3(2H,4H)-dione;

4-{[4-(1-Methyl-pyrrolidin-2-yl)-phenylamino]-methylene}-6-thiophen-2-yl-4H-isoquinoline-1,3-dione;

6-Furan-3-yl-4-{[4-(1-methyl-pyrrolidin-2-yl)-phenylamino]-methylene}-4H-isoquinoline-1,3-dione;

(4Z)-6-Iodo-4-({[(1-methyl-2-oxo-1,2-dihydropyridin-4-yl)methyl]amino}methylene)isoquinoline-1,3(2H,4H)-dione;

(4Z)-4-{[(4-{4-[(Dimethylamino)methyl]piperidin-1-yl}phenyl)amino]methylene}-6-iodoisoquinoline-1,3(2H,4H)-dione;

(4Z)-6-Iodo-4-({[4-(4-{[methyl(1-methylpyrrolidin-3-yl)amino]methyl}piperidin-1-yl)phenyl]amino}methylene)isoquinoline-1,3(2H,4H)-dione;

(4Z)-4-{[(4-{4-[(Ethylamino)methyl]piperidin-1-yl}phenyl)amino]methylene}-6-iodoisoquinoline-1,3(2H,4H)-dione;

(4Z)-4-({[2-Fluoro-6-(4-methylpiperazin-1-yl)pyridin-3-yl]amino}methylene)-6-(3-furyl)isoquinoline-1,3(2H,4H)-dione;

(Z)-4-((5-(1-methylpyrrolidin-2-yl)pyridin-2-ylamino)methylene)-6-(1H-pyrrol-1-yl)isoquinoline-1,3(2H,4H)-dione;

(Z)-6-Iodo-4-((5-(1-methylpyrrolidin-2-ylamino)methylene)isoquinoline-1,3(2H,4H)-dione;

2-{4-[(6-Iodo-1,3-dioxo-2,3-dihydro-1H-isoquinolin-4-ylidenemethyl)-amino]-phenyl}-pyrrolidine-1-carboxylic acid tert-butyl ester;

6-Iodo-4-[(4-pyrrolidin-2-yl-phenylamino)-methylene]-4H-isoquinoline-1,3-dione;

6-Furan-3-yl-4-{[4-(2-hydroxymethyl-pyrrolidin-1-ylmethyl)-phenylamino]-methylene}-4H-isoquinoline-1,3-dione;

4-({4-[1-(2-Hydroxy-ethyl)-pyrrolidin-2-yl]-phenylamino}-methylene)-6-iodo-4H-isoquinoline-1,3-dione;

4-{[4-(1-Ethyl-pyrrolidin-2-yl)-phenylamino]-methylene}-6-iodo-4H-isoquinoline-1,3-dione;

6-Furan-2-yl-4-{[4-(2-hydroxymethyl-pyrrolidin-1-ylmethyl)-phenylamino]-methylene}-4H-isoquinoline-1,3-dione;

(4Z)-6-(2-Furyl)-4-{[(4-{[(2S)-2-(methoxymethyl)pyrrolidin-1-yl]methyl}phenyl)amino]methylene}isoquinoline-1,3(2H,4H)-dione;

(4Z)-4-[({5-[(3R,5S)-3,5-Dimethylpiperazin-1-yl]pyridin-2-yl}amino)methylene]-6-(3-furyl)isoquinoline-1,3(2H,4H)-dione;

(4Z)-6-Bromo-4-[({5-[(3R,5S)-3,5-dimethylpiperazin-1-yl]pyridin-2-yl}amino)methylene]isoquinoline-1,3(2H,4H)-dione;

N-(4-Hydroxy-6-{[(6-iodo-1,3-dioxo-2,3-dihydro-1H-isoquinolin-4-ylidenemethyl)-amino]-methyl}-pyridin-3-yl)-propionamide;

6-Iodo-4-{[(1-methyl-4-oxo-5-propoxy-1,4-dihydro-pyridin-2-ylmethyl)-amino]-methylene}-4H-isoquinoline-1,3-dione;

4-{[4-(2-Hydroxymethyl-pyrrolidin-1-ylmethyl)-phenylamino]-methylene}-6-thiazol-2-yl-4H-isoquinoline-1,3-dione;

4-{[4-(1-Ethyl-pyrrolidin-2-yl)-phenylamino]-methylene}-6-furan-3-yl-4H-isoquinoline-1,3-dione;

(4Z)-4-({[6-(4-Methylpiperazin-1-yl)pyridin-3-yl]amino}methylene)-6-(1-methyl-1H-pyrrol-2-yl)isoquinoline-1,3(2H,4H)-dione;

(4Z)-6-Iodo-4-({[2-(4-methylpiperazin-1-yl)pyrimidin-5-yl]amino}methylene)isoquinoline-1,3(2H,4H)-dione;

(4Z)-6-(3-Furyl)-4-({116-(4-methylpiperazin-1-yl)pyridazin-3-yl]amino}methylene)isoquinoline-1,3(2H,4H)-dione;

(4Z)-6-Bromo-4-({[6-(4-methylpiperazin-1-yl)pyridazin-3-yl]amino}methylene)isoquinoline-1,3(2H,4H)-dione;

(4Z)-6-Iodo-4-{[(5-{[(2S)-2-(methoxymethyl)pyrrolidin-1-yl]methyl}pyridin-2-yl)amino]methylene}isoquinoline-1,3(2H,4H)-dione;

4-{[(4-Hydroxy-5-methoxy-pyrimidin-2-ylmethyl)-amino]-methylene}-6-iodo-4H-isoquinoline-1,3-dione;

(4Z)-4-{[(4-{[4-(2-Hydroxyethyl)piperidin-1-yl]methyl}phenyl)amino]methylene}-6-iodoisoquinoline-1,3(2H,4H)-dione;

(4Z)-4-({[5-(4-Ethylpiperazin-1-yl)pyridin-2-yl]amino}methylene)-6-(3-furyl)isoquinoline-1,3(2H,4H)-dione;

(4Z)-6-(4-Fluorophenyl)-4-{[(4-{[4-(2-hydroxyethyl)piperidin-1-yl]methyl}phenyl)amino]methylene}isoquinoline-1,3(2H,4H)-dione;

4-{[4-(1,1-Dioxo-1-thiomorpholin-4-ylmethyl)-phenylamino]-methylene}-6-iodo-4H-isoquinoline-1,3-dione;
(4Z)-6-(3-Furyl)-4-({[2-(4-methylpiperazin-1-yl)pyrimidin-5-yl]amino}methylene)isoquinoline-1,3(2H,4H)-dione;
(4Z)-6-(3-Furyl)-4-{[(3-hydroxy-4-propoxybenzyl)amino]methylene}isoquinoline-1,3(2H,4H)-dione;
(4Z)-6-Bromo-4-({[5-(4-isopropylpiperazin-1-yl)pyridin-2-yl]amino}methylene)isoquinoline-1,3(2H,4H)-dione;
(4Z)-4-[({6-[(3R,5S)-3,5-Dimethylpiperazin-1-yl]pyridin-3-yl}amino)methylene]-6-[5-(hydroxymethyl)-2-furyl]isoquinoline-1,3(2H,4H)-dione;
(4Z)-6-(3-Furyl)-4-({[5-(4-isopropylpiperazin-1-yl)pyridin-2-yl]amino}methylene)isoquinoline-1,3(2H,4H)-dione;
(4Z)-6-Bromo-4-{[(4-{[4-(2-hydroxyethyl)piperidin-1-yl]methyl}phenyl)amino]methylene}isoquinoline-1,3(2H,4H)-dione 4-{[(2-Hydroxy-biphenyl-4-ylmethyl)-amino]-methylene}-6-iodo-4H-isoquinoline-1,3-dione;
(4Z)-6-(3-Furyl)-4-{[(4-{[4-(2-hydroxyethyl)piperidin-1-yl]methyl}phenyl)amino]methylene}isoquinoline-1,3(2H,4H)-dione;
5-[(4Z)-1,3-Dioxo-4-({[4-(piperidin-1-ylmethyl)phenyl]amino}methylene)-1,2,3,4-tetrahydroisoquinolin-6-yl]-2-furaldehyde;
(Z)-4-(((6-Bromo-5-propoxypyridin-2-yl)methylamino)methylene)-6-iodoisoquinoline-1,3(2H,4H)-dione;
6-Furan-3-yl-4-{[(2-hydroxy-biphenyl-4-ylmethyl)-amino]-methylene}-4H-isoquinoline-1,3-dione;
4-[(4-Butyl-3-hydroxy-benzylamino)-methylene]-6-iodo-4H-isoquinoline-1,3-dione;
4-[(5-Hydroxy-2-iodo-benzylamino)-methylene]-6-iodo-4H-isoquinoline-1,3-dione;
(4Z)-4-({[2-Fluoro-6-(4-methylpiperazin-1-yl)pyridin-3-yl]amino}methylene)-6-(3-furyl)isoquinoline-1,3(2H,4H)-dione;
4-[(2-Furan-2-yl-5-hydroxy-benzylamino)-methylene]-6-iodo-4H-isoquinoline-1,3-dione;
4-{[(4'-Fluoro-2-hydroxy-biphenyl-4-ylmethyl)-amino]-methylene}-6-iodo-4H-isoquinoline-1,3-dione;
4-{[(4'-Fluoro-2-hydroxy-biphenyl-4-ylmethyl)-amino]-methylene}-6-furan-2-yl-4H-isoquinoline-1,3-dione;
6-Furan-2-yl-4-{[(4-hydroxy-5-propoxy-pyridin-2-ylmethyl)-amino]-methylene}-4H-isoquinoline-1,3-dione;
6-Furan-2-yl-4-[(5-hydroxy-2-iodo-benzylamino)-methylene]-4H-isoquinoline-1,3-dione;
4-[(3-Hydroxy-4-iodo-benzylamino)-methylene]-6-iodo-4H-isoquinoline-1,3-dione;
4-[(4-Furan-2-yl-3-hydroxy-benzylamino)-methylene]-6-iodo-4H-isoquinoline-1,3-dione;
4-[(4-Furan-3-yl-3-hydroxy-benzylamino)-methylene]-6-iodo-4H-isoquinoline-1,3-dione;
(4Z)-6-Iodo-4-({[5-(4-methylpiperazin-1-yl)pyrazin-2-yl]amino}methylene)isoquinoline-1,3(2H,4H)-dione;
(4Z)-6-(3-Furyl)-4-({[5-(4-methylpiperazin-1-yl)pyrazin-2-yl]amino}methylene)isoquinoline-1,3(2H,4H)-dione;
4-[(3-Hydroxy-4-pyridin-2-yl-benzylamino)-methylene]-6-iodo-4H-isoquinoline-1,3-dione;
4-{[(6-Hydroxy-5-propoxy-pyridin-2-ylmethyl)-amino]-methylene}-6-iodo-4H-isoquinoline-1,3-dione;
4-[(3-Hydroxy-4-pyridin-4-yl-benzylamino)-methylene]-6-iodo-4H-isoquinoline-1,3-dione;
(4Z)-4-{[(4-{[3-(Dimethylamino)pyrrolidin-1-yl]methyl}phenyl)amino]methylene}-6-(4-fluorophenyl)isoquinoline-1,3(2H,4H)-dione;
(4Z)-4-{[(4-{[3-(Dimethylamino)pyrrolidin-1-yl]methyl}phenyl)amino]methylene}-6-(3-furyl)isoquinoline-1,3(2H,4H)-dione;
(4Z)-4-({[3-Hydroxy-4-(1H-pyrrol-1-yl)benzyl]amino}methylene)-6-iodoisoquinoline-1,3(2H,4H)-dione;
4-[(3-Hydroxy-4-pyridin-3-yl-benzylamino)-methylene]-6-iodo-4H-isoquinoline-1,3-dione;
N-[2-Hydroxy-4-({[(Z)-(6-iodo-1,3-dioxo-2,3-dihydroisoquinolin-4(1H)-ylidene)methyl]amino}methyl)phenyl]-2-furamide;
(4Z)-6-Iodo-4-({[(2-oxo-1-phenyl-1,2-dihydropyridin-4-yl)methyl]amino]methylene)isoquinoline-1,3(2H,4H)-dione;
(4Z)-6-Iodo-4-({[(2-oxo-1-phenyl-1,2-dihydropyridin-4-yl)methyl]amino}methylene)isoquinoline-1,3(2H,4H)-dione;
4-{t(3'-Dimethylaminomethyl-2-hydroxy-biphenyl-4-ylmethyl)-amino]-methylene}-6-iodo-4H-isoquinoline-1,3-dione;
4-[(2-Fluoro-4-furan-3-yl-5-hydroxy-benzylamino)-methylene]-6-iodo-4H-isoquinoline-1,3-dione;
(4Z)-4-({[3-Hydroxy-4-(4-methylpiperazin-1-yl)benzyl]amino}methylene)-6-iodoisoquinoline-1,3(2H,4H)-dione;
4-({[4-Hydroxy-5-(2-pyrrolidin-1-yl-ethoxy)-pyridin-2-ylmethyl]-amino}-methylene)-6-iodo-4H-isoquinoline-1,3-dione;
(4Z)-4-[({3-Hydroxy-4-[(2S)-2-(methoxymethyl)pyrrolidin-1-yl]benzyl}amino)methylene]-6-iodoisoquinoline-1,3(2H,4H)-dione;
(4Z)-{[(4-Hydroxy-5-phenyl-pyridin-2-ylmethyl)-amino]-methylene}-6-iodo-4H-isoquinoline-1,3-dione;
(4Z)-4-[({[1-(3-Furyl)-2-oxo-1,2-dihydropyridin-4-yl]methyl}amino)methylene]-6-iodoisoquinoline-1,3(2H,4H)-dione;
$N^1$-[2-Hydroxy-4-({[(Z)-(6-iodo-1,3-dioxo-2,3-dihydroisoquinolin-4(1H)-ylidene)methyl]amino}methyl)phenyl]-$N^2,N^2$-dimethylglycinamide;
(4Z)-{[(5-Furan-3-yl-4-hydroxy-pyridin-2-ylmethyl)-amino]-methylene}-6-iodo-4H-isoquinoline-1,3-dione;
6-tert-Butyl-4-[(2-furan-3-yl-5-hydroxy-benzylamino)-methylene]-4H-isoquinoline-1,3-dione;
6-tert-Butyl-4-[(4-furan-3-yl-3-hydroxy-benzylamino)-methylene]-4H-isoquinoline-1,3-dione;
(4Z)-6-Iodo-4-({[(1-butyl-2-oxo-1,2-dihydropyridin-4-yl)methyl]amino}methylene)isoquinoline-1,3(2H,4H))-dione;
6-tert-Butyl-4-{[(4-hydroxy-5-propoxy-pyridin-2-ylmethyl)-amino]-methylene}-4H-isoquinoline-1,3-dione;
6-tert-Butyl-4-{[(4-hydroxy-5-phenyl-pyridin-2-ylmethyl)-amino]-methylene}-4H-isoquinoline-1,3-dione;
6-tert-Butyl-4-{[(5-furan-3-yl-4-hydroxy-pyridin-2-ylmethyl)-amino]-methylene}-4H-isoquinoline-1,3-dione;
(4Z)-6-tert-Butyl-4-[({[1-(3-furyl)-2-oxo-1,2-dihydropyridin-4-yl]methyl}amino)methylene]isoquinoline-1,3(2H,4H)-dione;
6-tert-Butyl-4-[(2-fluoro-4-furan-3-yl-5-hydroxy-benzylamino)-methylene]-4H-isoquinoline-1,3-dione;
6-tert-Butyl-4-[(4-furan-3-yl-3-hydroxy-benzylamino)-methylene]-4H-isoquinoline-1,3-dione;
6-Cyclopentyl-4-[(4-furan-3-yl-3-hydroxy-benzylamino)-methylene]-4H-isoquinoline-1,3-dione;

6-Cyclopentyl-4-{[(5-furan-3-yl-4-hydroxy-pyridin-2-yl-methyl)-amino]-methylene}-4H-isoquinoline-1,3-dione;
6-Cyclopentyl-4-{[(4-hydroxy-5-propoxy-pyridin-2-ylmethyl)-amino]-methylene}-4H-isoquinoline-1,3-dione;
(4Z)-6-Iodo-4-[({2-oxo-1-(3-thienyl)-1,2-dihydropyridin-4-yl]methyl}amino)methylene]isoquinoline-1,3(2H,4H)-dione;
4-{[(1,3-Dioxo-2,3-dihydro-1H-isoquinolin-4-ylidenemethyl)-amino]-methyl}-benzenesulfonamide;
4-[(2-Trifluoromethoxy-phenylamino)-methylene]-4H-isoquinoline-1,3-dione;
3-[(1,3-Dioxo-2,3-dihydro-1H-isoquinolin-4-ylidenemethyl)-amino]-benzoic acid;
N-(2-Diethylamino-ethyl)-4-[(1,3-dioxo-2,3-dihydro-1H-isoquinolin-4-ylidenemethyl)-amino]-benzamide;
4-{[2-(3,4-Dihydroxy-phenyl)-ethylamino]-methylene}-4H-isoquinoline-1,3-dione;
4-[(4-Amino-phenylamino)-methylene]-4H-isoquinoline-1,3-dione;
N-{4-[(1,3-Dioxo-2,3-dihydro-1H-isoquinolin-4-ylidenemethyl)-amino]-phenyl}-oxalamic acid;
4-[(1,3-Dioxo-2,3-dihydro-1H-isoquinolin-4-ylidenemethyl)-amino]-benzamidine;
(4-[(1,3-Dioxo-2,3-dihydro-1H-isoquinolin-4-ylidenemethyl)-amino]-phenylsulfanyl}-acetic acid;
4-[(1,3-Dioxo-2,3-dihydro-1H-isoquinolin-4-ylidenemethyl)-amino]-N-(5-methyl-[1,3,4]thiadiazol-2-yl)-benzenesulfonamide;
4-[(3,4-Dihydroxy-benzylamino)-methylene]-4H-isoquinoline-1,3-dione;
4-{[2-(1H-Benzoimidazol-2-yl)-phenylamino]-methylene}-4H-isoquinoline-1,3-dione;
3-[N'-(1,3-Dioxo-2,3-dihydro-1H-isoquinolin-4-ylidenemethyl)-hydrazino]-benzoic acid;
N-(4,5-Dimethyl-oxazol-2-yl)-4-[(1,3-dioxo-2,3-dihydro-1H-isoquinolin-4-ylidenemethyl)-amino]-benzenesulfonamide;
N-{4-[(1,3-Dioxo-2,3-dihydro-1H-isoquinolin-4-ylidenemethyl)-amino]-phenyl}-N-methyl-acetamide;
{4-[(1,3-Dioxo-2,3-dihydro-1H-isoquinolin-4-ylidenemethyl)-amino]-phenyl}-acetonitrile;
4-[(1,3-Dioxo-2,3-dihydro-1H-isoquinolin-4-ylidenemethyl)-amino]-N-(5-methyl-isoxazol-3-yl)-benzenesulfonamide;
3-{4-[(1,3-Dioxo-2,3-dihydro-1H-isoquinolin-4-ylidenemethyl)-amino]-phenyl}-acrylic acid;
4-{4-[(1,3-Dioxo-2,3-dihydro-1H-isoquinolin-4-ylidenemethyl)-amino]-phenyl}-butyric acid;
4-[(4-Hydroxy-phenylamino)-methylene]-4H-isoquinoline-1,3-dione;
4-[(1,3-Dioxo-2,3-dihydro-1H-isoquinolin-4-ylidenemethyl)-amino]-2-hydroxy-benzoic acid;
4-[(3-Hydroxy-4-methoxy-phenylamino)-methylene]-4H-isoquinoline-1,3-dione;
2-[(1,3-Dioxo-2,3-dihydro-1H-isoquinolin-4-ylidenemethyl)-amino]-5-hydroxy-benzoic acid;
5-[(1,3-Dioxo-2,3-dihydro-1H-isoquinolin-4-ylidenemethyl)-amino]-2-hydroxy-benzoic acid;
4-{[2-(3,4-Dihydroxy-phenyl)-2-hydroxy-ethylamino]-methylene}-4H-isoquinoline-1,3-dione;
4-[(2,6-Dihydroxy-phenylamino)-methylene]-4H-isoquinoline-1,3-dione;
3-(3,4-Dihydroxy-phenyl)-2-[(1,3-dioxo-2,3-dihydro-1H-isoquinolin-4-ylidenemethyl)-amino]-propionic acid;
3-(3,4-Dihydroxy-phenyl)-2-[(1,3-dioxo-2,3-dihydro-1H-isoquinolin-4-ylidenemethyl)-amino]-propionic acid;
4-[(2,4-Dihydroxy-phenylamino)-methylene]-4H-isoquinoline-1,3-dione;
4-[(8-Hydroxy-quinolin-5-ylamino)-methylene]-4H-isoquinoline-1,3-dione;
4-[(5-Chloro-2-hydroxy-4-nitro-phenylamino)-methylene]-4H-isoquinoline-1,3-dione;
4-({4-[4-(2-Morpholin-4-yl-ethyl)-piperazin-1-yl]-phenylamino}-methylene)-4H-isoquinoline-1,3-dione;
4-({4-[4-(2-Pyrrolidin-1-yl-ethyl)-piperazin-1-yl]-phenylamino}-methylene)-4H-isoquinoline-1,3-dione;
4-[(3-Amino-benzylamino)-methylene]-4H-isoquinoline-1,3-dione;
4-[(4-Diethylaminomethyl-phenylamino)-methylene]-4H-isoquinoline-1,3-dione;
4-({4-[(Cyclopropylmethyl-propyl-amino)-methyl]-phenylamino}-methylene)-4H-isoquinoline-1,3-dione;
4-[(4-Pyrrolidin-1-ylmethyl-phenylamino)-methylene]-4H-isoquinoline-1,3-dione;
4-({4-[(Cyclohexyl-methyl-amino)-methyl]-phenylamino}-methylene)-4H-isoquinoline-1,3-dione;
4-[(3-Aminomethyl-benzylamino)-methylene]-4H-isoquinoline-1,3-dione;
Thiophene-2-sulfonic acid (3-{[(1,3-dioxo-2,3-dihydro-1H-isoquinolin-4-ylidenemethyl)-amino]-methyl}-phenyl)-amide;
Propane-2-sulfonic acid (3-{[(1,3-dioxo-2,3-dihydro-1H-isoquinolin-4-ylidenemethyl)-amino]-methyl}-phenyl)-amide;
N-(3-{[(1,3-Dioxo-2,3-dihydro-1H-isoquinolin-4-ylidenemethyl)-amino]-methyl}-phenyl)-methanesulfonamide;
2,2,2-Trifluoro-ethanesulfonic acid (3-{[(1,3-dioxo-2,3-dihydro-1H-isoquinolin-4-ylidenemethyl)-amino]-methyl}-phenyl)-amide;
Ethanesulfonic acid (3-{[(1,3-dioxo-2,3-dihydro-1H-isoquinolin-4-ylidenemethyl)-amino]-methyl}-phenyl)-amide;
Propane-1-sulfonic acid (3-{[(1,3-dioxo-2,3-dihydro-1H-isoquinolin-4-ylidenemethyl)-amino]-methyl}-phenyl)-amide;
N-(3-{[(1,3-Dioxo-2,3-dihydro-1H-isoquinolin-4-ylidenemethyl)-amino]-methyl}-phenyl)-acetamide;
Cyclopropanecarboxylic acid (3-{[(1,3-dioxo-2,3-dihydro-1H-isoquinolin-4-ylidenemethyl)-amino]-methyl}-phenyl)-amide;
Cyctobutanecarboxylic acid (3-{[(1,3-dioxo-2,3-dihydro-1H-isoquinolin-4-ylidenemethyl)-amino]-methyl}-phenyl)-amide;
Thiophene-2-sulfonic acid (4-{[(1,3-dioxo-2,3-dihydro-1H-isoquinolin-4-ylidenemethyl)-amino]-methyl}-phenyl)-amide;
N-(4{[(1,3-Dioxo-2,3-dihydro-1H-isoquinolin-4-ylidenemethyl)-amino]-methyl}-phenyl)-methanesulfonamide;
N-(4{[(1,3-Dioxo-2,3-dihydro-1H-isoquinolin-4-ylidenemethyl)-amino]-methyl}-phenyl)-C-phenyl-methanesulfonamide;
2,2,2-Trifluoro-ethanesulfonic acid (4{[(1,3-dioxo-2,3-dihydro-1H-isoquinolin-4-ylidenemethyl)-amino]-methyl}-phenyl)-amide;
Propane-1-sulfonic acid (4{[(1,3-dioxo-2,3-dihydro-1H-isoquinolin-4-ylidenemethyl)-amino]-methyl}-phenyl)-amide;

N-(4{[(1,3-Dioxo-2,3-dihydro-1H-isoquinolin-4-ylidenemethyl)-amino]-methyl}-phenyl)-3-methyl-butyramide;
4-[(3,4-Dihydroxy-phenylamino)-methylene]-4H-isoquinoline-1,3-dione;
4-{[4-(4-Ethyl-piperazin-1-yl)-phenylamino]-methylene}-4H-isoquinoline-1,3-dione;
(4-{4-[(1,3-Dioxo-2,3-dihydro-1H-isoquinolin-4-ylidenemethyl)-amino]-phenyt}-piperazin-1-yl)-acetonitrile;
4-{[4-(4-Allyl-piperazin-1-yl)-phenylamino]-methylene}-4H-isoquinoline-1,3-dione;
4-({4-[4-(2-Hydroxy-ethyl)-piperazin-1-yl]-phenylamino}-methylene)-4H-isoquinoline-1,3-dione;
4-({4-[4-(2-Diethylamino-ethyl)-piperazin-1-yl]-phenylamino}-methylene)-4H-isoquinoline-1,3-dione;
4-{[4-(4-Isopropyl-piperazin-1-yl)-phenylamino]-methylene}-4H-isoquinoline-1,3-dione;
4-{[4-(4-Cyclopentyl-piperazin-1-yl)-phenylamino]-methylene}-4H-isoquinoline-1,3-dione;
4-{[4-(4-Cyclobutylmethyl-piperazin-1-yl)-phenylamino]-methylene}-4H-isoquinoline-1,3-dione;
4-{[3-(2,2,2-Trifluoro-ethylamino)-benzylamino]-methylene}-4H-isoquinoline-1,3-dione;
4-[(4-Methylamino-benzylamino)-methylene]-4H-isoquinoline-1,3-dione;
2,2,2-Trifluoro-ethanesulfonic acid 4-[(1,3-dioxo-2,3-dihydro-1H-isoquinolin-4-ylidenemethyl)-amino]-benzylamide;
4-{[(1,3-Dioxo-2,3-dihydro-1H-isoquinolin-4-ylidenemethyl)-amino]-methyi}-N-ethyl-benzenesulfonamide;
4-{[(1,3-Dioxo-2,3-dihydro-1H-isoquinolin-4-ylidenemethyl)-amino]-methyl}-N-pyridin-3-ylmethyl-benzenesulfonamide;
6-Diethylamino-4-[(3,4-dihydroxy-benzylamino)-methylene]-4H-isoquinoline-1,3-dione;
6-(1,3-Dihydro-isoindol-2-yl)-4-[(3,4-dihydroxy-benzylamino)-methylene]-4H-isoquinoline-1,3-dione;
6-[Bis-(3,3,3-triftuoro-propyl)-amino]-4-[(3,4-dihydroxy-benzylamino)-methylene]-4H-isoquinoline-1,3-dione;
N-{4-[(1,3-Dioxo-2,3-dihydro-1H-isoquinolin-4-ylidenemethyl)-amino]-benzyl}-methanesulfonamide;
Ethanesulfonic acid 4-[(1,3-dioxo-2,3-dihydro-1H-isoquinolin-4-ylidenemethyl)-amino]-benzylamide;
4-[(4-Dipropylaminomethyl-phenylamino)-methylene]-4H-isoquinoline-1,3-dione;
4-{[4-(3-Hydroxy-piperidin-1-ylmethyl)-phenylamino]-methylene}-4H-isoquinoline-1,3-dione;
4-[(4-{[(2-Methoxy-ethyl)-methyl-amino]-methyl}-phenylamino)-methylene]-4H-isoquinoline-1,3-dione;
4-{[4-(2-Methyl-pyrrolidin-1-ylmethyl)-phenylamino]-methylene}-4H-isoquinoline-1,3-dione;
4-(Pyridin-4-ylaminomethylene)-4H-isoquinoline-1,3-dione;
4-[(5-Hydroxy-naphthalen-1-ylamino)-methylene]-4H-isoquinoline-1,3-dione;
4-[(3,4-Dihydroxy-benzylamino)-methylene]-6-phenyl-4H-isoquinoline-1,3-dione;
4-((3,4-Dihydroxy-benzylamino)-methylene]-6-furan-2-yl-4H-isoquinoline-1,3-dione;
6-(3-Phenyl-propenyl)-4-[(4-pyrrolidin-1-ylmethyl-phenylamino)-methylene]-4H-isoquinoline-1,3-dione;
{4-[(6-Naphthalen-1-yl-1,3-dioxo-2,3-dihydro-1H-isoquinolin-4-ylidenemethyl)-amino]-phenyl}-acetonitrile;
{4-[(6-Naphthalen-2-yl-1,3-dioxo-2,3-dihydro-1H-isoquinolin-4-ylidenemethyl)-amino]-phenyl}-acetonitrile;
{4-[(1,3-Dioxo-6-quinolin-8-yl-2,3-dihydro-1H-isoquinolin-4-ylidenemethyl)-amino]-phenyl}-acetonitrile;
{4-[(6-Benzofuran-2-yl-1,3-dioxo-2,3-dihydro-1H-isoquinolin-4-ylidenemethyl)-amino]-phenyl}-acetonitrile;
{4-[(6-Benzo[b]thiophen-2-yl-1,3-dioxo-2,3-dihydro-1H-isoquinolin-4-ylidenemethyl)-amino]-phenyl}-acetonitrile;
{4-[(6-Benzo[b]thiophen-3-yl-1,3-dioxo-2,3-dihydro-1H-isoquinolin-4-ylidenemethyl)-amino]-phenyt}-acetonitrile;
(4-{[6-(1H-Indol-5-yl)-1,3-dioxo-2,3-dihydro-1H-isoquinolin-4-ylidenemethyl]-amino}-phenyl)-acetonitrile;
(4-{[1,3-Dioxo-6-(1H-pyrrol-2-yl)-2,3-dihydro-1H-isoquinolin-4-ylidenemethyl]-amino}-phenyl)-acetonitrile;
(4-{[1,3-Dioxo-6-(1H-pyrrol-3-yl)-2,3-dihydro-1H-isoquinolin-4-ylidenemethyl]-amino}-phenyl)-acetonitrile;
4-{[(6—Naphthalen-2-yl-1,3-dioxo-2,3-dihydro-1H-isoquinolin-4-ylidenemethyl)-amino]-methyl}-benzenesulfonamide;
4-{[(1,3-Dioxo-6-quinolin-8-yl-2,3-dihydro-1H-isoquinolin-4-ylidenemethyl)-amino]-methyl}-benzenesulfonamide;
4-{[(6-Benzofuran-2-yl-1,3-dioxo-2,3-dihydro-1H-isoquinolin-4-ylidenemethyl)-amino]-methyl}-benzenesulfonamide;
4-{[(6-Benzo[b]thiophen-2-yl-1,3-dioxo-2,3-dihydro-1H-isoquinolin-4-ylidenemethyl)-amino]-methyl}-benzenesulfonamide;
4-{[(6-Benzo[b]thiophen-3-yl-1,3-dioxo-2,3-dihydro-1H-isoquinolin-4-ylidenemethyl)-amino]-methyl}-benzenesulfonamide;
4-({[6-(1H-Indol-5-yl)-1,3-dioxo-2,3-dihydro-1H-isoquinolin-4-ylidenemethyl]-amino}-methyl)-benzenesulfonamide;
4-({[1,3-Dioxo-6-(1H-pyrrol-2-yl)-2,3-dihydro-1H-isoquinolin-4-ylidenemethyl]-amino}-methyl)-benzenesulfonamide;
4-({[1,3-Dioxo-6-(1H-pyrrol-3-yl)-2,3-dihydro-1H-isoquinolin-4-ylidenemethyl]-amino}-methyl)-benzenesulfonamide;
4-4(3,4-Dihydroxy-benzylamino)-methylene]-6-naphthalen-1-yl-4H-isoquinoline-1,3-dione;
4-[(3,4-Dihydroxy-benzylamino)-methylene]-6-naphthalen-2-yl-4H-isoquinoline-1,3-dione;
4-[(3,4-Dihydroxy-benzylamino)-methylene]-6-quinolin-8-yl-4H-isoquinoline-1,3-dione;
6-Benzofuran-2-yl-4-[(3,4-dihydroxy-benzylamino)-methylene]-4H-isoquinoline-1,3-dione;
6-Benzo[b]thiophen-2-yl-4-[(3,4-dihydroxy-benzylamino)-methylene]-4H-isoquinoline-1,3-dione;
6-Benzo[b]thiophen-3-yl-4-[(3,4-dihydroxy-benzylamino)-methylene]-4H-isoquinoline-1,3-dione;
4-[(3,4-Dihydroxy-benzylamino)-methylene]-6-(1H-indol-5-yl)-4H-isoquinoline-1,3-dione;
4-[(3,4-Dihydroxy-benzylamino)-methylene]-6-(1H-pyrrol-2-yl)-4H-isoquinoline-1,3-dione;
(4-{[1,3-Dioxo-6-(2-pyridin-2-yl-vinyl)-2,3-dihydro-1H-isoquinolin-4-ylidenemethyl]-amino}-phenyl)-acetonitrile;

(4-{[1,3-Dioxo-6-(2-pyridin-4-yl-vinyl)-2,3-dihydro-1H-isoquinolin-4-ylidenemethyl]-amino}-phenyl)-acetonitrile;

{4-[(1,3-Dioxo-6-styryl-2,3-dihydro-1H-isoquinolin-4-ylidenemethyl)-amino]-phenyl}-acetonitrile;

(4-{[6-(2-Imidazol-1-yl-vinyl)-1,3-dioxo-2,3-dihydro-1H-isoquinolin-4-ylidenemethyl]-amino}-phenyl)-acetonitrile;

4-({[1,3-Dioxo-6-(2-pyridin-2-yl-vinyl)-2,3-dihydro-1H-isoquinolin-4-ylidenemethyl]-amino}-methyl)-benzenesulfonamide;

4-({[1,3-Dioxo-6-(2-pyridin-4-yl-vinyl)-2,3-dihydro-1H-isoquinolin-4-ylidenemethyl]-amino}-methyl)-benzenesulfonamide;

4-{[(1,3-Dioxo-6-styryl-2,3-dihydro-1H-isoquinolin-4-ylidenemethyl)-amino]-methyl}-benzenesulfonamide;

4-({[1,3-Dioxo-6-(2-pyrazin-2-yl-vinyl)-2,3-dihydro-1H-isoquinolin-4-ylidenemethyl]-amino}-methyl)-benzenesulfonamide;

4-({[6-(2-Cyclohexyl-vinyl)-1,3-dioxo-2,3-dihydro-1H-isoquinolin-4-ylidenemethyl]-amino}-methyl)-benzenesulfonamide;

4-({[6-(3-Imidazol-1-yl-propenyl)-1,3-dioxo-2,3-dihydro-1H-isoquinolin-4-ylidenemethyl]-amino}-methyl)-benzenesulfonamide;

4-({[6-(2-Imidazol-1-yl-vinyl)-1,3-dioxo-2,3-dihydro-1H-isoquinolin-4-ylidenemethyl]-amino}-methyl)-benzenesulfonamide;

4-[({6-[2-(4-Methyl-thiazol-5-yl)-vinyl]-1,3-dioxo-2,3-dihydro-1H-isoquinolin-4-ylidenemethyl}-amino)-methyl]-benzenesulfonamide;

4-[(3,4-Dihydroxy-benzylamino)-methylene]-6-(3-phenyl-propenyl)-4H-isoquinoline-1,3-dione;

4-[(3,4-Dihydroxy-benzylamino)-methylene]-6-(2-naphthalen-2-yl-vinyl)-4H-isoquinoline-1,3-dione;

4-[(3,4-Dihydroxy-benzylamino)-methylene]-6-(2-pyridin-2-yl-vinyl)-4H-isoquinoline-1,3-dione;

4-[(3,4-Dihydroxy-benzylamino)-methylene]-6-(2-pyridin-4-yl-vinyl)-4H-isoquinoline-1,3-dione;

6-(2-Cyclohexyl-vinyl)-4-[(3,4-dihydroxy-benzylamino)-methylene]-4H-isoquinoline-1,3-dione;

4[(3,4-Dihydroxy-benzylamino)-methylene]-6-(3-imidazol-1-yl-propenyl)-4H-isoquinoline-1,3-dione;

4-[(3,4-Dihydroxy-benzylamino)-methylene]-6-(3-piperazin-1-yl-propenyl)-4H-isoquinoline-1,3-dione;

4-[(3,4-Dihydroxy-benzylamino)-methylene]-6-(2-imidazol-1-yl-vinyl)-4H-isoquinoline-1,3-dione;

4-{[4-(4-Methyl-piperazin-1-yl)-phenylamino]-methylene}-6-naphthalen-2-yl-4H-isoquinoline-1,3-dione;

6-Benzofuran-2-yl-4-{[4-(4-methyl-piperazin-1-yl)-phenylamino]-methylene}-4H-isoquinoline-1,3-dione;

6-Benzo[b]thiophen-2-yl-4-{[4-(4-methyl-piperazin-1-yl)-phenylamino]-methylene}-4H-isoquinoline-1,3-dione;

6-(1H-Indol-5-yl)-4-{[4-(4-methyl-piperazin-1-yl)-phenylamino]-methylene}-4H-isoquinoline-1,3-dione;

4-{[4-(4-Methyl-piperazin-1-yl)-phenylamino]-methylene}-6-(1H-pyrrol-2-yl)-4H-isoquinoline-1,3-dione;

4-{[4-(4-Methyl-piperazin-1-yl)-phenylamino]-methylene}-6-(1H-pyrrol-3-yl)-4H-isoquinoline-1,3-dione;

4-{[4-(4-Methyl-piperazin-1-yl)-phenylamino]-methylene}-6-(2-naphthalen-2-yl-vinyl)-4H-isoquinoline-1,3-dione;

4-{[4-(4-Methyl-piperazin-1-yl)-phenylamino]-methylene}-6-(2-pyridin-2-yl-vinyl)-4H-isoquinoline-1,3-dione;

4-{[4-(4-Methyl-piperazin-1-yl)-phenylamino]-methylene}-6-(2-pyridin-4-yl-vinyl)-4H-isoquinoline-1,3-dione;

4-{[4-(4-Methyl-piperazin-1-yl)-phenylamino]-methylene}-6-styryl-4H-isoquinoline-1,3-dione;

4-{[4-(4-Methyl-piperazin-1-yl)-phenylamino]-methylene}-6-(2-pyrazin-2-yl-vinyl)-4H-isoquinoline-1,3-dione;

6-(3-Imidazol-1-yl-propenyl)-4-{[4-(4-methyl-piperazin-1-yl)-phenylamino]-methylene}-4H-isoquinoline-1,3-dione;

6-(2-Imidazol-1-yl-vinyl)-4-{[4-(4-methyl-piperazin-1-yl)-phenylamino]-methylene}-4H-isoquinoline-1,3-dione;

4-{[4-(4-Methyl-piperazin-1-yl)-phenylamino]-methylene}-6-[2-(4-methyl-thiazol-5-yl)-vinyl]-4H-isoquinoline-1,3-dione;

6-(4-Methoxy-phenyl)-4-{[4-(4-methyl-piperazin-1-yl)-phenylamino]-methylene}-4H-isoquinoline-1,3-dione;

6-(2-Methoxy-phenyl)-4-{[4-(4-methyl-piperazin-1-yl)-phenylamino]-methylene}-4H-isoquinoline-1,3-dione;

6-(2-Fluoro-phenyl)-4-{[4-(4-methyl-piperazin-1-yl)-phenylamino]-methylene}-4H-isoquinoline-1,3-dione;

4-(4-{[4-(4-Methyl-piperazin-1-yl)-phenylamino]-methylene}-1,3-dioxo-1,2,3,4-tetrahydro-isoquinolin-6-yl)-benzoic acid;

3-(4-{[4-(4-Methyl-piperazin-1-yl)-phenylamino]-methylene}-1,3-dioxo-1,2,3,4-tetrahydro-isoquinolin-6-yl)-benzoic acid;

4-{[4-(4-Methyl-piperazin-1-yl)-phenylamino]-methylene}-6-(4-trifluoromethyl-phenyl)-4H-isoquinoline-1,3-dione;

6-(4-Acetyl-phenyl)-4-{[4-(4-methyl-piperazin-1-yl)-phenylamino]-methylene}-4H-isoquinoline-1,3-dione;

6-(4-Chloro-phenyl)-4-{[4-(4-methyl-piperazin-1-yl)-phenylamino]-methylene}-4H-isoquinoline-1,3-dione;

6-(3-Chloro-phenyl)-4-{[4-(4-methyl-piperazin-1-yl)-phenylamino]-methylene}-4H-isoquinoline-1,3-dione;

6-(2-Chloro-phenyl)-4-{[4-(4-methyl-piperazin-1-yl)-phenylamino]-methylene}-4H-isoquinoline-1,3-dione;

4-{[4-(4-Methyl-piperazin-1-yl)-phenylamino]-methylene}-6-p-tolyl-4H-isoquinoline-1,3-dione;

4-{[4-(4-Methyl-piperazin-1-yl)-phenylamino]-methylene}-6-m-tolyl-4H-isoquinoline-1,3-dione;

4-{[4-(4-Methyl-piperazin-1-yl)-phenylamino]-methylene}-6-o-tolyl-4H-isoquinoline-1,3-dione;

3-(4-{[4-(4-Methyl-piperazin-1-yl)-phenylamino]-methylene}-1,3-dioxo-1,2,3,4-tetrahydro-isoquinolin-6-yl)-benzonitrile;

6-Biphenyl-4-yl-4-{[4-(4-methyl-piperazin-1-yl)-phenylamino]-methylene}-4H-isoquinoline-1,3-dione;

6-Biphenyl-3-yl-4-{[4-(4-methyl-piperazin-1-yl)-phenylamino]-methylene}-4H-isoquinoline-1,3-dione;

3-[4-(4-{[4-(4-Methyl-piperazin-1-yl)-phenylamino]-methylene}-1,3-dioxo-1,2,3,4-tetrahydro-isoquinolin-6-yl)-phenyl]-acrylic acid;

3-[3-(4-{(4-(4-Methyl-piperazin-1-yl)-phenylamino]-methylene}-1,3-dioxo-1,2,3,4-tetrahydro-isoquinolin-6-yl)-phenyl]-acrylic acid;

4-{[4-(4-Methyl-piperazin-1-yl)-phenylamino]-methylene}-6-(4-methylsulfanyl-phenyl)-4H-isoquinoline-1,3-dione;

(4-{[6-(4-Methoxy-phenyl)-1,3-dioxo-2,3-dihydro-1H-isoquinolin-4-ylidenemethyl]-amino}-phenyl)-acetonitrile;

(4-{[6-(3-Methoxy-phenyl)-1,3-dioxo-2,3-dihydro-1H-isoquinolin-4-ylidenemethyl]-amino}-phenyl)-acetonitrile;
(4-{[6-(2-Methoxy-phenyl)-1,3-dioxo-2,3-dihydro-1H-isoquinolin-4-ylidenemethyl]-amino}-phenyl)-acetonitrile;
(4-{[6-(4-Fluoro-phenyl)-1,3-dioxo-2,3-dihydro-1H-isoquinolin-4-ylidenemethyl]-amino}-phenyl)-acetonitrile;
(4-{[6-(3-Fluoro-phenyl)-1,3-dioxo-2,3-dihydro-1H-isoquinolin-4-ylidenemethyl]-amino}-phenyl)-acetonitrile;
(4-{[6-(2-Fluoro-phenyl)-1,3-dioxo-2,3-dihydro-1H-isoquinolin-4-ylidenemethyl]-amino}-phenyl)-acetonitrile;
4-{4-[(4-Cyanomethyl-phenylamino)-methylene]-1,3-dioxo-1,2,3,4-tetrahydro-isoquinolin-6-yl}-benzoic acid;
3-{4-[(4-Cyanomethyl-phenylamino)-methylene]-1,3-dioxo-1,2,3,4-tetrahydro-isoquinolin-6-yl}-benzoic acid;
(4-{[1,3-Dioxo-6-(4-trifluoromethyl-phenyl)-2,3-dihydro-1H-isoquinolin-4-ylidenemethyl]-amino}-phenyl)-acetonitrile;
(4-{[6-(4-Acetyl-phenyl)-1,3-dioxo-2,3-dihydro-1H-isoquinolin-4-ylidenemethyl]-amino}-phenyl)-acetonitrile;
(4-{[6-(2-Acetyl-phenyl)-1,3-dioxo-2,3-dihydro-1H-isoquinolin-4-ylidenemethyl]-amino}-phenyl)-acetonitrile;
(4-{[6-(4-Chloro-phenyl)-1,3-dioxo-2,3-dihydro-1H-isoquinolin-4-ylidenemethyl]-amino}-phenyl)-acetonitrile;
(4-{[6-(3-Chloro-phenyl)-1,3-dioxo-2,3-dihydro-1H-isoquinolin-4-ylidenemethyl]-amino}-phenyl)-acetonitrile;
(4-{[6-(2-Chloro-phenyl)-1,3-dioxo-2,3-dihydro-1H-isoquinolin-4-ylidenemethyl]-amino}-phenyl)-acetonitrile;
{4-[(1,3-Dioxo-6-p-tolyl-2,3-dihydro-1H-isoquinolin-4-ylidenemethyl)-amino]-phenyl}-acetonitrile;
{4-[(1,3-Dioxo-6-m-tolyl-2,3-dihydro-1H-isoquinolin-4-ylidenemethyl)-amino]-phenyl}-acetonitrile;
{4-[(1,3-Dioxo-6-o-tolyl-2,3-dihydro-1H-isoquinolin-4-ylidenemethyl)-amino]-phenyl}-acetonitrile;
4-{4-{(4-Cyanomethyl-phenylamino)-methylene]-1,3-dioxo-1,2,3,4-tetrahydro-isoquinolin-6-yl}-benzonitrile;
3-{4-[(4-Cyanomethyl-phenylamino)-methylene]-1,3-dioxo-1,2,3,4-tetrahydro-isoquinolin-6-yl}-benzonitrile;
{4-[(6-Biphenyl-4-yl-1,3-dioxo-2,3-dihydro-1H-isoquinolin-4-ylidenemethyl)-amino]-phenyl}-acetonitrile;
{4-[(6-Biphenyl-3-yl-1,3-dioxo-2,3-dihydro-1H-isoquinolin-4-ylidenemethyl)-amino]-phenyl}-acetonitrile;
(4-{[6-(4-Isopropyl-phenyl)-1,3-dioxo-2,3-dihydro-1H-isoquinolin-4-ylidenemethyl]-amino}-phenyl)-acetonitrile;
(4-{[6-(4-Methylsulfanyl-phenyl)-1,3-dioxo-2,3-dihydro-1H-isoquinolin-4-ylidenemethyl]-amino}-phenyl)-acetonitrile;
6-(3-Hydroxy-propenyl)-4-{[4-(4-methyl-piperazin-1-yl)-phenylamino]-methylene}-4H-isoquinoline-1,3-dione;
6-[2-(4-Amino-phenyl)-vinyl]-4-{[4-(4-methyl-piperazin-1-yl)-phenylamino]-methylene}-4H-isoquinoline-1,3-dione;
6-[2-(4-Chloro-phenyl)-vinyl]-4-{[4-(4-methyl-piperazin-1-yl)-phenylamino]-methylene}-4H-isoquinoline-1,3-dione;
4-[2-(4-{[4-(4-Methyl-piperazin-1-yl)-phenylamino]-methylene}-1,3-dioxo-1,2,3,4-tetrahydro-isoquinolin-6-yl)-vinyl]-benzoic acid;
4-[2-(4-{[4-(4-Methyl-piperazin-1-yl)-phenylamino]-methylene}-1,3-dioxo-1,2,3,4-tetrahydro-isoquinolin-6-yl)-vinyl]-benzenesulfonamide;
4-{[4-(4-Methyl-piperazin-1-yl)-phenylamino]-methylene}-6-[2-(4-trifluoromethyl-phenyl)-vinyl]-4H-isoquinoline-1,3-dione;
6-(3,4-Dihydroxy-but-1-enyl)-4-{[4-(4-methyl-piperazin-1-yl)-phenylamino]-methylene}-4H-isoquinoline-1,3-dione;
6-[2-(4-Fluoro-phenyl)-vinyl]-4-{[4-(4-methyl-piperazin-1-yl)-phenylamino]-methylene}-4H-isoquinoline-1,3-dione;
6-[2-(4-Methoxy-phenyl)-vinyl]-4-{[4-(4-methyl-piperazin-1-yl)-phenylamino]-methylene}-4H-isoquinoline-1,3-dione;
4-[(3-Hydroxy-4-methoxy-benzylamino)-methylene]-6-(2-imidazol-1-yl-vinyl)-4H-isoquinoline-1,3-dione;
4-[(3-Hydroxy-4-methoxy-benzylamino)-methylene]-6-(2-imidazol-1-yl-vinyl)-4H-isoquinoline-1,3-dione;
4-[(3-Hydroxy-4-methoxy-benzylamino)-methylene]-6-(2-pyridin-2-yl-vinyl)-4H-isoquinoline-1,3-dione;
4-[(3,4-Dihydroxy-benzylamino)-methylene]-6-[2-(4-dimethylaminomethyl-phenyl)-vinyl]-4H-isoquinoline-1,3-dione;
4-({[6-(3-Methoxy-phenyl)-1,3-dioxo-2,3-dihydro-1H-isoquinolin-4-ylidenemethyl]-amino}-methyl)-benzenesulfonamide;
4-({[6-(4-Fluoro-phenyl)-1,3-dioxo-2,3-dihydro-1H-isoquinolin-4-ylidenemethyll-amino}-methyl)-benzenesulfonamide;
4-({[6-(3-Fluoro-phenyl)-1,3-dioxo-2,3-dihydro-1H-isoquinolin-4-ylidenemethyl]-amino}-methyl)-benzenesulfonamide;
4-({[6-(2-Fluoro-phenyl)-1,3-dioxo-2,3-dihydro-1H-isoquinolin-4-ylidenemethyl]-amino}-methyl)-benzenesulfonamide;
4-{1,3-Dioxo-4-[(4-sulfamoyl-benzylamino)-methylene]-1,2,3,4-tetrahydro-isoquinolin-6-yl}-benzoic acid;
3-{1,3-Dioxo-4-[(4-sulfamoyl-benzylamino)-methylene]-1,2,3,4-tetrahydro-isoquinolin-6-yl}-benzoic acid;
4-({[1,3-Dioxo-6-(4-trifluoromethyl-phenyl)-2,3-dihydro-1H-isoquinolin-4-ylidenemethyl]-amino}-methyl)-benzenesulfonamide;
4-({[1,3-Dioxo-6-(3-trifluoromethyl-phenyl)-2,3-dihydro-1H-isoquinolin-4-ylidenemethyl]-amino}-methyl)-benzenesulfonamide;
4-({[1,3-Dioxo-6-(2-trifluoromethyl-phenyl)-2,3-dihydro-1H-isoquinolin-4-ylidenemethyl]-amino}-methyl)-benzenesulfonamide;
4-({116-(4-Acetyl-phenyl)-1,3-dioxo-2,3-dihydro-1H-isoquinolin-4-ylidenemethyl]-amino}-methyl)-benzenesulfonamide;
4-({[6-(3-Acetyl-phenyl)-1,3-dioxo-2,3-dihydro-1H-isoquinolin-4-ylidenemethyl]-amino}-methyl)-benzenesulfonamide;
4-({[6-(2-Acetyl-phenyl)-1,3-dioxo-2,3-dihydro-1H-isoquinolin-4-ylidenemethyl]-amino}-methyl)-benzenesulfonamide;

4-({[6-(4-Chloro-phenyl)-1,3-dioxo-2,3-dihydro-1H-isoquinolin-4-ylidenemethyl]-amino}-methyl)-benzenesulfonamide;
4-({[6-(3-Chloro-phenyl)-1,3-dioxo-2,3-dihydro-1H-isoquinolin-4-ylidenemethyl]-amino}-methyl)-benzenesulfonamide;
4-({[6-(2-Chloro-phenyl)-1,3-dioxo-2,3-dihydro-1H-isoquinolin-4-ylidenemethyl]-amino}-methyl)-benzenesulfonamide;
4-{[(1,3-Dioxo-6-p-tolyl-2,3-dihydro-1H-isoquinolin-4-ylidenemethyl)-amino]-methyi}-benzenesulfonamide;
4-{[(1,3-Dioxo-6-m-tolyl-2,3-dihydro-1H-isoquinolin-4-ylidenemethyl)-amino]-methyl}-benzenesulfonamide;
4{(1,3-Dioxo-6-o-tolyl-2,3-dihydro-1H-isoquinolin-4-ylidenemethyl)-amino]-methyl}-benzenesulfonamide;
4-({[6-(4-Cyano-phenyl)-1,3-dioxo-2,3-dihydro-1H-isoquinolin-4-ylidenemethyl]-amino}-methyl)-benzenesulfonamide;
4-({[6-(3-Cyano-phenyl)-1,3-dioxo-2,3-dihydro-1H-isoquinolin-4-ylidenemethyl]-amino}-methyl)-benzenesulfonamide;
4-{[(6-Biphenyl-4-yl-1,3-dioxo-2,3-dihydro-1H-isoquinolin-4-ylidenemethyl)-amino]-methyl}-benzenesulfonamide;
4-{[(6-Biphenyl-3-yl-1,3-dioxo-2,3-dihydro-1H-isoquinolin-4-ylidenemethyl)-amino]-methyl}-benzenesulfonamide;
3-(4-{1,3-Dioxo-4-[(4-sulfamoyl-benzylamino)-methylene]-1,2,3,4-tetrahydro-isoquinolin-6-yl}-phenyl)-acrylic acid;
3-(3-{1,3-Dioxo-4-[(4-sulfamoyl-benzylamino)-methylene]-1,2,3,4-tetrahydro-isoquinolin-6-yl}-phenyl)-acrylic acid;
4-({[6-(4-Isopropyl-phenyl)-1,3-dioxo-2,3-dihydro-1H-isoquinolin-4-ylidenemethyl]-amino}-methyl)-benzenesulfonamide;
4-({[6-(3-Isopropyl-phenyl)-1,3-dioxo-2,3-dihydro-1H-isoquinolin-4-ylidenemethyl]-amino}-methyl)-benzenesulfonamide;
4-({[6-(4-Methylsulfanyl-phenyl)-1,3-dioxo-2,3-dihydro-1H-isoquinolin-4-ylidenemethyl]-amino}-methyl)-benzenesulfonamide;
4-[(3,4-Dihydroxy-benzylamino)-methylene]-6-(4-methoxy-phenyl)-4H-isoquinoline-1,3-dione;
4-[(3,4-Dihydroxy-benzylamino)-methylene]-6-(3-methoxy-phenyl)-4H-isoquinoline-1,3-dione;
4-[(3,4-Dihydroxy-benzylamino)-methylene]-6-(2-methoxy-phenyl)-4H-isoquinoline-1,3-dione;
4-[(3,4-Dihydroxy-benzylamino)-methylene]-6-(4-fluoro-phenyl)-4H-isoquinoline-1,3-dione;
4-[(3,4-Dihydroxy-benzylamino)-methylene]-6-(3-fluoro-phenyl)-4H-isoquinoline-1,3-dione;
4-[(3,4-Dihydroxy-benzylamino)-methylene]-6-(2-fluoro-phenyl)-4H-isoquinoline-1,3-dione;
4-{4-[(3,4-Dihydroxy-benzylamino)-methylene]-1,3-dioxo-1,2,3,4-tetrahydro-isoquinolin-6-yl]-benzoic acid;
3-{4-[(3,4-Dihydroxy-benzylamino)-methylene]-1,3-dioxo-1,2,3,4-tetrahydro-isoquinolin-6-yl]-benzoic acid;
4-[(3,4-Dihydroxy-benzylamino)-methylene]-6-(4-trifluoromethyl-phenyl)-4H-isoquinoline-1,3-dione;
4-[(3,4-Dihydroxy-benzylamino)-methylene]-6-(3-trifluoromethyl-phenyl)-4H-isoquinoline-1,3-dione;
4-[(3,4-Dihydroxy-benzylamino)-methylene]-6-(2-trifluoromethyl-phenyl)-4H-isoquinoline-1,3-dione;
6-(4-Acetyl-phenyl)-4-[(3,4-dihydroxy-benzylamino)-methylene]-4H-isoquinoline-1,3-dione;
6-(3-Acetyl-phenyl)-4-[(3,4-dihydroxy-benzylamino)-methylene]-4H-isoquinoline-1,3-dione;
6-(2-Acetyl-phenyl)-4-[(3,4-dihydroxy-benzylamino)-methylene]-4H-isoquinoline-1,3-dione;
6-(4-Chloro-phenyl)-4-[(3,4-dihydroxy-benzylamino)-methylene]-4H-isoquinoline-1,3-dione;
6-(3-Chloro-phenyl)-4-[(3,4-dihydroxy-benzylamino)-methylene]-4H-isoquinoline-1,3-dione;
6-(2-Chloro-phenyl)-4-[(3,4-dihydroxy-benzylamino)-methylene]-4H-isoquinoline-1,3-dione;
4-[(3,4-Dihydroxy-benzylamino)-methylene]-6-p-tolyl-4H-isoquinoline-1,3-dione;
4-[(3,4-Dihydroxy-benzylamino)-methylene]-6-m-tolyl-4H-isoquinoline-1,3-dione;
4-[(3,4-Dihydroxy-benzylamino)-methylene]-6-o-tolyl-4H-isoquinolin-1,3-dione;
4-{4-[(3,4-Dihydroxy-benzylamino)-methylene]-1,3-dioxo-1,2,3,4-tetrahydro-isoquinolin-6-yl}-benzonitrile;
3-{4-[(3,4-Dihydroxy-benzylamino)-methylene]-1,3-dioxo-1,2,3,4-tetrahydro-isoquinolin-6-yl}-benzonitrile;
6-Biphenyl-4yl-4-[(3,4-dihydroxy-benzylamino)-methylene]-4H-isoquinoline-1,3-dione;
6-Biphenyl-3yl-4-[(3,4-dihydroxy-benzylamino)-methylene]-4H-isoquinoline-1,3-dione;
3-(4-{4-[(3,4-Dihydroxy-benzylamino)-methylene]-1,3-dioxo-1,2,3,4-tetrahydro-isoquinolin-6-yl}-phenyl)-acrylic acid;
3-(3-{4-[(3,4-Dihydroxy-benzylamino)-methylenel]-1,3-dioxo-1,2,3,4-tetrahydro-isoquinolin-6-yl}-phenyl)-acrylic acid;
4-[(3,4-Dihydroxy-benzylamino)-methylene]-6-(4-isopropyl-phenyl)-4H-isoquinoline-1,3-dione;
4-[(3,4-Dihydroxy-benzylamino)-methylene]-6-(3-isopropyl-phenyl)-4H-isoquinoline-1,3-dione;
4-[(3,4-Dihydroxy-benzylamino)-methylene]-6-(4-methylsulfanyl-phenyl)-4H-isoquinoline-1,3-dione;
4[(3,4-Dihydroxy-benzylamino)-methylene]-6-(2-methylsulfanyl-phenyl)-4H-isoquinoline-1,3-dione;
6-[2-(2-Diethylamino-ethoxy)-vinyl]-4-{[4-(4-methyl-piperazin-1-yl)-phenylamino]-methylene}-4H-isoquinoline-1,3-dione;
5-(4-{[4-(4-Methyl-piperazin-1-yl)-phenylamino]-methylene}-1,3-dioxo-1,2,3,4-tetrahydro-isoquinolin-6-yl)-pent-4-enoic acid;
6-(4-Hydroxy-but-1-enyl)-4-{[4-(4-methyl-piperazin-1-yl)-phenylamino]-methylene}-4H-isoquinoline-1,3-dione;
6-(5-Hydroxy-pent-1-enyl)-4-{[4-(4-methyl-piperazin-1-yl)-phenylamino]-methylene}-4H-isoquinoline-1,3-dione;
6-(6-Hydroxy-hex-1-enyl)-4-{[4-(4-methyl-piperazin-1-yl)-phenylamino]-methylene}-4H-isoquinoline-1,3-dione;
6-[3-(2-Hydroxy-ethoxy)-propenyl]-4-{]4-(4-methyl-piperazin-1-yl)-phenylamino]-methylene}-4H-isoquinoline-1,3-dione;
6-[3-(2,4-Dioxo-imidazolidin-1-yl)-propenyl]-4-{[4-(4-methyl-piperazin-1-yl)-phenylamino]-methylene}-4H-isoquinoline-1,3-dione;
6-[3-(2-Hydroxy-phenyl)-propenyl]-4-{[4-(4-methyl-piperazin-1-yl)-phenylamino]-methylene}-4H-isoquinoline-1,3-dione;
2-Methyl-3-(4-{[4-(4-methyl-piperazin-1-yl)-phenylamino]-methylene}-1,3-dioxo-1,2,3,4-tetrahydro-isoquinolin-6-yl)-but-2-enenitrile;

{4-[2-(4-{[4-(4-Methyl-piperazin-1-yl)-phenylamino]-methylene}-1,3-dioxo-1,2,3,4-tetrahydro-isoquinolin-6-yl)-vinyl]-phenyl}-acetonitrile;

4-[(3,4-Dihydroxy-benzylamino)-methylene]-6-[3-(2-hydroxy-3-methoxy-phenyl)-propenyl]-4H-isoquinoline-1,3-dione;

[4-(2-{4-[(3,4-Dihydroxy-benzylamino)-methylene]-1,3-dioxo-1,2,3,4-tetrahydro-isoquinolin-6-yl}-vinyl)-phenyl]-acetonitrile;

6-Benzo[1,3]dioxol-5-yl-4-{[4-(4-methyl-piperazin-1-yl)-phenylamino]-methylene}-4H-isoquinoline-1,3-dione;

6-(4-Dimethylamino-phenyl)-4-{[4-(4-methyl-piperazin-1-yl)-phenylamino]-methylene}-4H-isoquinoline-1,3-dione;

6-(4-Hydroxymethyl-phenyl)-4-{[4-(4-methyl-piperazin-1-yl)-phenylamino]-methylene}-4H-isoquinoline-1,3-dione;

3-[4-(4-{[4-(4-Methyl-piperazin-1-yl)-phenylamino]-methylene}-1,3-dioxo-1,2,3,4-tetrahydro-isoquinolin-6-yl)-phenyl]-propionic acid;

6-(3-Amino-phenyl)-4-{[4-(4-methyl-piperazin-1-yl)-phenylamino]-methylene}-4H-isoquinoline-1,3-dione;

6-(2,4-Dichloro-phenyl)-4-{[4-(4-methyl-piperazin-1-yl)-phenylamino]-methylene}-4H-isoquinoline-1,3-dione;

6-Benzo[1,3]dioxol-5-yl-4-[(3,4-dihydroxy-benzylamino)-methylene]-4H-isoquinoline-1,3-dione;

4-[(3,4-Dihydroxy-benzylamino)-methylene]-6-(3,4-dimethoxy-phenyl)-4H-isoquinoline-1,3-dione;

4-[(3,4-Dihydroxy-benzylamino)-methylene]-6-(2,4-dimethoxy-phenyl)-4H-isoquinoline-1,3-dione;

4-[(3,4-Dihydroxy-benzylamino)-methylene]-6-(3,4,5-trimethoxy-phenyl)-4H-isoquinoline-1,3-dione;

4-[(3,4-Dihydroxy-benzylamino)-methylene]-6-(4-dimethylamino-phenyl)-4H-isoquinoline- 4-[(3,4-Dihydroxy-benzylamino)-methylene]-6-(4-hydroxumethyl-phenyl)-4H-isoquinoline-1,3-dione;

4-[(3,4-Dihydroxy-benzylamino)methylene]-6(4trifluoromethoxy-phenyl)-4H-isoquinoline-1,3-dione;

3-(4-{4-[(3,4-Dihydroxy-benzylamino)-methylene]-1,3-dioxo-1,2,3,4-tetrahydro-isoquinolin-6-yl}-phenyl)-propionic acid;

4[(3,4-Dihydroxy-benzylamino)-methylene]-6-(3-nitrophenyl)-4H-isoquinoline-1,3-dione;

6(3-Amino-phenyl)-4-[(3,4-dihydroxy-benzylamino)-methylene]-4H-isoquinoline-1,3-dione;

N-3-{4-[(3,4-Dihydroxy-benzylamino)-methylene]-1,3-dioxo-1,2,3,4-tetrahydro-isoquinolin-6-yl}-phenyl)-acetamide;

6-(2,4-Dichloro-phenyl)-4-[(3,4-dihydroxy-benzylamino)-methylene]-4H-isoquinoline-1,3-dione;

4-[(3-Hydroxy-4-methoxy-benzylamino)-methylene]-6-(2-pyridin-4-yl-vinyl)-4H-isoquinoline-1,3-dione;

4-[(3-Hydroxy-4-methoxy-benzylamino)-methylene]-6-styryl-4H-isoquinoline-1,3-dione;

6-[3-(2,4-Dioxo-imidazolidin-1-yl)-propenyl]-4-[(3-hydroxy-4-methoxy-benzylamino)-methylene]-4H-isoquinoline-1,3-dione;

4-[(3-Hydroxy-4-methoxy-benzylamino)-methylene]-6-[3-(2-hydroxy-3-methoxy-phenyl)-propenyl]-4H-isoquinoline-1,3-dione;

6-Cyclopentylidenemethyl-4-{[4-(4-methyl-piperazin-1-yl)-phenylamino]-methylene}-4H-isoquinoline-1,3-dione;

4-{[4-(4-Methyl-piperazin-1-yl)-phenylamino]-methylene}-6-[2-(4-nitro-phenyl)-vinyl]-4H-isoquinoline-1,3-dione;

6-Furan-2-yl-4-{[4-(4-methyl-piperazin-1-yl)-phenylamino]-methylene}-4H-isoquinoline-1,3-dione;

4-{[4-(4-Methyl-piperazin-1-yl)-phenylamino]-methylene}-6-phenyl-4H-isoquinoline-1,3-dione;

4-[(3-Hydroxy-4-methoxy-benzylamino)-methylene]-6-phenyl-4H-isoquinoline-1,3-dione;

4-[(3-Hydroxy-4-methoxy-benzylamino)-methylene]-6-(4-methoxy-phenyl)-4H-isoquinoline-1,3-dione;

4-[(3-Hydroxy-4-methoxy-benzylamino)-methylene]-6-naphthalen-2-yl-4H-isoquinoline-1,3-dione;

4-[(3-Hydroxy-4-methoxy-benzylamino)-methylene]-6-(1H-indol-5-yl)-4H-isoquinoline-1,3-dione;

4-[(3-Hydroxy-4-methoxy-benzylamino)-methylene]-6-(1H-pyrrol-2-yl)-4H-isoquinoline-1,3-dione;

6-Furan-2-yl-4-[(3-hydroxy-4-methoxy-benzylamino)-methylene]-4H-isoquinoline-1,3-dione;

4-[(4-Pyrrolidin-1-ylmethyl-phenylamino)-methylene]-6-(1H-pyrrol-2-yl)-4H-isoquinoline-1,3-dione;

4-{1,3-Dioxo-4-[(4-pyrrolidin-1-ylmethyl-phenylamino)-methylene]-1,2,3,4-tetrahydro-isoquinolin-6-yl}-benzonitrile;

6-(4-Hydroxymethyl-phenyl)-4-[4-pyrrolidin-1-ylmethyl-phenylamino)-methylene]-4H-isoquinoline-1,3-dione;

6-[1-(2-Methoxy-ethyl)-1H-pyrrol-3-yl]-4-{[4-(4-methyl-piperazin-1-yl)-phenylamino]-methylene}-4H-isoquinoline-1,3-dione;

2-[5-(4-{[4-(4-Methyl-piperazin-1-yl)-phenylamino]-methylene}-1,3-dioxo-1,2,3,4-tetrahydro-isoquinolin-6-yl)-indol-1-yl]-acetamide;

6-[1-(2-Diethylamino-ethyl)-1H-indol-5-yl]-4-{[4-(4-methyl-piperazin-1-yl)-phenylamino]-methylene}-4H-isoquinoline-1,3-dione;

2-[3-(4-{[4-(4-Methyl-piperazin-1-yl)-phenylamino]-methylene}-1,3-dioxo-1,2,3,4-tetrahydro-isoquinolin-6-yl)-pyrrol-1-yl]-acetamide;

6-[1-(2-Diethylamino-ethyl)-1H-pyrrol-3-yl]-4-{[4-(4-methyl-piperazin-1-yl)-phenylamino]-methylene}-4H-isoquinoline-1,3-dione;

4-[3-(4-{[4-(4-Methyl-piperazin-1-yl)-phenylamino]-methylene}-1,3-dioxo-1,2,3,4-tetrahydro-isoquinolin-6-yl)-pyrrol-1-yl]-butyronitrile;

(4Z)-6-Bromo-4-[({4-[methyl(2-pyrrolidin-1-ylethyl)amino]phenyl}amino)methylene]isoquinoline-1,3(2H,4H)-dione;

(4Z)-B-bromo-4-[({4-[methyl(2-piperidin-1-ylethyl)amino]phenyl}amino)methylene]isoquinoline-1,3(2H,4H)-dione;

(4Z)-6-Bromo-4-[({4-[{2-[butyl(methyl)amino]ethyl}(methyl)amino]phenyl}amino)methylene]isoquinoline-1,3(2H,4H)-dione;

(4Z)6Bromo-4-[({4-[2-(dimethylamino)ethoxy]phenyl}amino)methylene]isoquinoline-1,3(2H,4H)-dione;

(4Z)-6-Bromo-4-{[(2-methyl-2,3-dihydro-1H-isoindol-5-yl)amino]methylene}isoquinoline-1,3(2H,4H)-dione;

(4Z)-6-Bromo-4-({[4-(1H-imidazol-1-yl)phenyl]amino}methylene)isoquinoline-1,3(2H,4H)-dione;

(4Z)-6-Bromo-4-{[(4-{methyl[2-(4-methylpiperazin-1-yl)ethyl]amino}phenyl)amino]methylene}isoquinoline-1,3(2H,4H)-dione;

(4Z)-6-Bromo-4-[({4-[methyl(2-morpholin-4-ylethyl)amino]phenyl}amino)methylene]isoquinoline-1,3(2H,4H)-dione;

6-({[(Z)-(6-Bromo-1,3-dioxo-2,3-dihydroisoquinolin-4 (1H)-ylidene)methyl]amino}methyl)-2,2-dimethyl-1, 3-benzodioxol-4-yl acetate;

6-({[(Z)-(6-Bromo-1,3-dioxo-2,3-dihydroisoquinolin-4 (1H)-ylidene)methyl]amino}methyl)-2,2-dimethyl-1,3-benzodioxol-4-yl cyclopropanecarboxylate;

(4Z)6-Bromo-4-[({4-[3-(dimethylamino)propyl] phenyl}amino)methylene]isoquinoline-1,3(2H,4H)-dione;

(Methoxyamino)propyl]phenyl}amino)methylene]isoquinoline-1,3(2H,4H)-dione;

(4Z)-6-Bromo-4-[({4-[[3-(dimethylamino)propyl](methyl)amino]phenyl}amino)methylene]isoquinoline-1,3 (2H,4H)-dione; and (4Z)-6-Bromo-4-[({4-[(1-methylpyrrolidin-3-yl)oxy] phenyl}amino)methylene]isoquinoline-1,3(2H,4H)-dione;

or a pharmaceutically acceptable salt thereof.

14. A compound according to claim 1 wherein f is 0; $G^2$ is NHaryl; Z is phenyl substituted with $C_{1-6}$ alkylheterocyclyl or a pharmaceutically acceptable salt thereof.

15. The compound according to claim 1, wherein the compound is selected from the group:

(4Z)-6-[(3-aminophenyl)amino]-4-({[4-(piperidin-1-ylmethyl)phenyl]amino}methylene)isoquinoline-1,3(2H, 4H)-dione;

(4Z)-6-[(3-methylphenyl)amino]-4-({[4-(piperidin-1-ylmethyl)phenyl]amino}methylene)isoquinoline-1,3(2H, 4H)-dione;

(4Z)-6-[(3-acetylphenyl)amino]-4-({[4-(piperidin-1-ylmethyl)phenyl]amino}methylene)isoquinoline-1,3(2H, 4H)-dione;

(4Z)-4-({[4-(piperidin-1-ylmethyl)phenyl] amino}methylene)-6-{[3-(trifluoromethyl)phenyl] amino}isoquinoline-1,3(2H,4H)-dione;

(4Z)-6-anilino-4-({[4-(piperidin-1-ylmethyl)phenyl] amino}methylene)isoquinoline-1,3(2H,4H)-dione;

(4Z)-6-{[4-(dimethylamino)phenyl]amino}-4-({[4-(piperidin-1-ylmethyl)phenylamino}methylene)isoquinoline-1,3(2H,4H)-dione;

(4Z)-6-[(4-methylphenyl)amino]-4-({[4-(piperidin-1-ylmethyl)phenyl]amino}methylene)isoquinoline-1,3(2H, 4H)-dione;

(4Z)-6-[(4-chlorophenyl)amino]-4-({[4-(piperidin-1-ylmethyl)phenyl]amino}methylene)isoquinoline-1 3(2H, 4H)-dione;

(4Z)-6-[(2-methoxyphenyl)amino-4-({[4-(piperidin-1-ylmethyl)phenyl]amino}methylene)isoquinoline-1,3(2H, 4H)-dione;

(4Z)-6-[(3-methoxyphenyl)amino]-4-({[4-(piperidin-1-ylmethyl)phenyl]amino}methylene)isoquinoline-1,3 (2H,4H)-dione;

3-{[(4Z)-1,3-dioxo-4-({[4-(piperidin-1-ylmethyl)phenyl] amino}methylene)-1,2,34-tetrahydroisoquinolin-6-yl] amino}benzonitrile;

4-{[(4Z)-1,3-dioxo-4-({[4-(piperidin-1-ylmethyl)phenyl] amino}methylene)-1,2,3,4-tetrahydroisoquinolin-6-yl] amino}benzamide;

(4Z)-6-(2,3-dihydro-1H-inden-5-ylamino)-4-({[4-(piperidin-1-ylmethyl)phenyl]amino}methylene)isoquinoline-1,3(2H,4H)-dione;

(4Z)-6-(1,3-benzodioxol-5-ylamino)-4-({[4-(piperidin-1-ylmethyl)phenyl]amino}methylene)isoquinoline-1,3 (2H,4H)-dione;

4-{[(4Z)-1,3-dioxo-4-({[4-(piperidin-1-ylmethyl)phenyl] amino}methylene)-1,2,3,4-tetrahydroisoquinolin-6-yl] amino}benzonitrile;

(4Z)-6-[(4-methoxyphenyl)amino]-4-({[4-(piperidin-1-ylmethyl)phenyl]amino}methylene)isoquinoline-1,3 (2H,4H)-dione;

(4Z)-6-[(3-fluorophenyl)amino]-4-({[4-(piperidin-1-ylmethyl)phenyl]amino}methylene)isoquinoline-1,3(2H, 4H)-dione;

(4Z)-6-{[3-methoxy-5-(trifluoromethyl)phenyl]amino}-4-({[4-piperidin-1-ylmethyl)phenyl]amino}methylene) isoquinoline-1,3(2H,4H)-dione;

(4Z)-6-[(4-acetylphenyl)amino]-4-({[4-(piperidin-1-ylmethyl)phenyl]amino}methylene)isoquinoline-1,3(2H, 4H)-dione;

2-{[(4Z)-1,3-dioxo-4-({[4-(piperidin-1-ylmethyl)phenyl] amino}methylene)-1,2,3,4-tetrahydroisoquinolin-6-yl] amino}benzonitrile;

ethyl 4-{[(4Z)-1,3-dioxo-4-({[4-(piperidin-1-ylmethyl) phenyl]amino}methylene)-1,2,3,4-tetrahydroisoquinolin-6-yl]amino}benzoate;

(4Z)-6-[(2-chlorophenyl)amino]-4-({[4-(piperidin-1-ylmethyl)phenyl]amino}methylene)isoquinoline-1,3-(2H,4H)-dione;

(4Z)-6-[(3-chlorophenyl)amino]-4-({[4-piperidin-1-ylmethyl)phenyl]amino}methylene)isoquinoline-1,3(2H, 4H)-dione;

(4Z)-6-anilino-4-[({4-[(dimethylamino)methyl] phenyl}amino)methylene]isoquinoline-1,3(2H,4H)-dione;

(4Z)-4-[({4-[(dimethylamino)methyl]phenyl}amino)methylene]-6-[(3-methoxyphenyl)amino]isoquinoline-1,3 (2H,4H)-dione;

(4Z)-4-[({4-[(dimethylamino)methyl]phenyl]amino)methylene]-6-[(4-methoxyphenyl)amino]isoquinoline-1,3 (2H,4H)-dione;

(4Z)-6-[(3-acetylphenyl)amino]-4-[({4-[(dimethylamino) methyl]phenyl}amino)methylene]isoquinoline-1,3(2H, 4H)dione;

(4Z)-6-[(3-acetylphenyl)amino]-4-({[4-(3,5-dimethylpiperazin-1-yl)phenyl]amino}methylene)isoquinoline-1,3 (2H,4H)-dione;

(4Z)-4-[({}4-[(diethylamino)methyl]phenyl}amino)methylene]-6-[(4-methylphenyl)amino]isoquinoline-1,3 (2H,4H)-dione;

(4Z)-6-(1H-indol-5-ylamino)-4-({[4-piperidin-1-ylmethyl)phenyl]amino}methylene)isoquinoline-1,3(2H, 4H)-dione; and (4Z)-4-({[4-(piperidin-1 ylmethyl)phenyl] amino}methylene)-6-(quinolin-5-ylamino)isoquinoline-1,3(2H,4H)-dione.

16. A pharmaceutical composition comprising an effective amount of a compound or a pharmaceutically acceptable salt of the compound of claim 1 and a physiologically acceptable vehicle.

17. A pharmaceutical composition comprising a compound of claim 1 alone or in combination with other therapeutically effective anticancer agent or kinase inhibiting pharmaceutical compositions or chemotherapeutic agents, and a pharmaceutically acceptable carrier.

18. The pharmaceutical composition of claim 17 wherein the kinase inhibiting pharmaceutical compositions or chemotherapeutic agents can be administered concurrently or sequentially with the composition comprising a compound having the Formula (I)

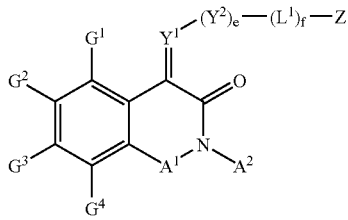

(I)

or a pharmaceutically acceptable salt thereof, $A^1$ is CO;

$A^2$ is H, OH, $CH_2OH$, $C_{1-6}$ alkyl, alkoxy, benzyloxy, arylalkyl, benzyl, aryl, acyl, —C(O)R, —OC(O)O-PEG, —$CH_2$OC(O)O-PEG, —OC(O)N H-PEG, —$CH_2$OC(O)NH-PEG, OC(O)OH, $CH_2$O(C(O)OH, OC(O)halogen, $CH_2$OC(O)halogen, OC(O)$CH_2$halogen, OC(O)$CH_2S(CH_2)_m$O-PEG wherein the aryl or benzyl is optionally substituted with $R_4$;

PEG is —(O$CH_2CH_2)_n$O$CH_3$;

$Y^1$ is $CR_3$;

$Y^2$ is $NR_1$;

$L^1$ is $C(R_7)(R_8)$;

$R_1$ is H, $C_{1-6}$ alkyl, aryl, or benzyl;

$R_3$ is H, aryl, $C_{1-6}$ alkyl, $NR_{10}R_{11}$, or —O—;

$R_4$, is selected from the group consisting of H, aryl, or $C_{1-6}$ alkyl, halogen, —CN, —$OCF_3$, —$NO_2$, —COOH, —$CF_3$, OH, SH, $N_3$, —C(O)H, heteroaryl, $C_{1-6}$alkoxy, heterocycloalkyl, $C_{2-6}$ alkenyl, $C_{2-6}$ alkynyl, —$COR_{100}$, —Oaryl, —$OR_{100}$, —NHaryl, $S(O)_mR_{100}$, —C(O)Q, C(O)$OR_{100}$, —$NR_{100}$aryl, —$OR_{100}$aryl, —$SR_{100}$aryl, —$NHR_{102}$OH, —$NHR_{102}OR_{100}$, —$NHR_{102}NHR_{100}$, —$NR_{100}R_{102}$OH, —$NHR_{102}$Q, —$NR_{100}R_{102}NH_2$, —$NR_{100}R_{102}NHR_{100}$, —$NR_{100}R_{102}OR_{100}$, —$NR_{100}R_{102}$Q, —$OR_{102}$OH, —$OR_{102}OR_{100}$, $OR_{102}NH_2$, —$OR_{102}NHR_{100}$, —$OR_{102}$Q, —$OCOR_{100}$, —$OR_{100}COR_{100}$, —$NHCOR_{100}$, —$NHCONH_2$, —$NHCONHR_{100}$, —$NHR_{100}COR_{100}$, —$NHR_{102}NH_2$, —NHOH, —$NHOR_{100}$, —$CONR_{10}R_{11}$, —$NHSO_2R_{100}$, $NR_{10}$, $R_{11}$, —NHC(O)-heteroaryl,—NHC(O)$R_{102}$-heteroaryl, OC(O)CH2halogen, —OC(O)$CH_2S(CH)_m$O-PEG, OC(O)NH-PEG, —N($R_{10}$)($R_{11}$), —NHC(O)$R_{102}$-aryl, and —NHC(O)NH-heterocycloalkyl that is optionally substituted with up to three $C_{1-3}$ alkyl groups;

wherein said aryl, said heteroaryl, and said heterocycloalkyl are each optionally substituted with up to four independently selected $R_{12}$ groups;

wherein said $C_{2-6}$ alkenyl, said $C_{1-6}$ alkyl, $C_{1-6}$alkoxy, and said $C_{2-6}$ alkynyl are each optionally substituted with up to three independently selected $R_{13}$ groups;

$R_5$ is selected from the group consisting of $C_{1-6}$ alkyl or alkenyl, wherein the alkyl or alkenyl are optionally substituted with OH, OR, $NR_{10}R_{11}$, $C_{1-6}$ alkyl;

$R_7$ and $R_8$ are selected from the group consisting of H, $C_{1-6}$ alkyl, $OR_{100}$, OH, C(O)H or COOH;

$R_{10}$ and $R_{11}$ are selected from the group consisting of H, $C_{1-6}$ alkyl, $C_{2-6}$alkenyl, $C_{1-6}$ acyl, —$S(O)_2$aryl, —C(O)$C_{2-6}$ alkenyl, $C_{2-6}$ alkynyl, aryl or heteroaryl, wherein said $C_{1-6}$ acyl is optionally substituted with a heteroaryl, wherein said $C_{1-6}$ alkyl is optionally substituted with up to three halogen atoms, wherein said aryl and said heteroaryl are optionally substituted with up to three $R_{12}$ groups, wherein $R_{10}$ and $R_{11}$ may be taken together with the N to which they are attached to form a 3-8 membered heterocyclic ring, wherein said heterocyclic ring may contain additional atoms selected from the group N, O, and —$S(O)_m$ and said heterocyclic ring may be additionally substituted with 1 to 4 substituents selected from the group consisting of $C_{1-6}$alkyl, OH, —$OC_{1-6}$alkyl, —$OC_{3-6}$cycloalkyl, —$(CH_2)_n$OH, —$(CH_2)_nOC_{1-6}$ alkyl, —$(CH_2)_nOC_{3-6}$cycloalkyl, —$NR_{10}R_{11}$, —$(CH_2)_n$ $NR_{10}R_{11}$, and =O;

$R_{12}$ is independently selected from the group consisting of aryloxy, halogen, OH, —COOH, —C(O)H, —C(O)R, —$C_{1-3}$ perhaloalkyl, —$OCF_3$, $C_{1-6}$ acyl, —CN, —$NO_2$, aryl, heteroaryl, —S—$C_{1-6}$ alkyl, —$NHCOC_{1-6}$alkyl, —N($R_{15}$)($R_{16}$), $C_{1-3}$ perhaloalkoxy, $C_{1-6}$ alkyl, $C_{2-6}$ alkenyl, —$CONH_2$, —$CF_3$, SH, $N_3$, heterocycloalkyl, —C(O)$R_{100}$, —$OR_{100}$, —NHaryl, —$S(O)_mR_{100}$, —C(O)Q, C(O)$OR_{100}$, —C(O)$NHR_{100}$, —$NR_{100}$aryl, —N($R_{100}$)$R_{102}$aryl, —$OR_{102}$aryl, —$SR_{102}$aryl, —NHS(O)$_2$—$R_{100}$, —$NHR_{102}$OH, —$NHR_{102}OR_{100}$, —$NHR_{102}NHR_{100}$, —N($R_{100}$)$R_{102}$OH, —$NHR_{102}$Q, —N($R_{100}$)$R_{102}NH_2$, —N($R_{100}$)$R_{102}NHR_{100}$, —N($R_{100}$)$R_{102}OR_{100}$, —N($R_{100}$)$R_{102}$Q, —$OR_{102}$OH, —$OR_{102}OR_{100}$, —$OR_{102}NH_2$, —$OR_{102}NHR_{100}$, —$OR_{102}$Q, —OC(O)$R_{100}$, —$OR_{102}$C(O)$R_{100}$, —NHC(O)$R_{100}$, —$NHCONH_2$, —$NHCONHR_{100}$, —$NHR_{102}$C(O)$R_{100}$, —$NHR_{102}NH_2$, —NHS(O)$_2$-aryl, —NHOH, —NHC(O)aryl, —$NHOR_{100}$, —NHC(O)-heteroaryl, —NHC(O)$R_{102}$-heteroaryl, —C(O)N($R_{10}$)($R_{11}$), —N($R_{10}$)($R_{1,}$), NHC(O)$R_{102}$aryl, and NHC(O)NH-heterocycloalkyl that is optionally substituted with up to three $C_{1-3}$ alkyl groups, wherein said $C_{2-6}$ alkenyl, said $C_{1-6}$ alkyl, and said $C_{2-6}$ alkynyl are each optionally substituted with up to three independently selected $R_{13}$ groups and —N($R_{15}$)($R_{16}$);

$R_{13}$ is independently selected from the group consisting of arylalkyl, aryl, heteroaryl, $C_{1-6}$ alkyl, $C_{3-6}$ cycloalkyl, heterocycle, heterocycloalkyl, heterocycloalkyloxy, ON, OH, $C_{1-6}$ alkoxy, halogen and —COOH, —SH, —COH, —$COR_{100}$, —$CONH_2$, —$CONHR_{100}$, —COQ, —$OCOR_{100}$, —$OCONH_2$, —$OCONHR_{100}$, —OCOQ, —$OR_{102}$OH, —$OR_{102}NR_{15}R_{16}$, and

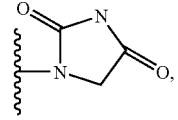

wherein said aryl, heteroaryl, and heterocycloalkyl are optionally substituted with up to three independently selected $R_{18}$ groups;

$R_{15}$ and $R_{16}$ are selected from the group consisting of H, $C_{1-6}$ alkyl, and $C_{1-6}$ acyl; and wherein said $R_{15}$ and $R_{16}$ groups taken together with the nitrogen to which they are attached may form a heterocyclic ring of 3 to 8 atoms with 1 or 2 additional heteroatoms selected from the group N, O, and —$S(O)_m$, the heterocyclic ring may be substituted with groups consisting of OH, —$OC_{3-6}$cycloalkyl, —$OC_{1-6}$ alkyl, —$(CH_2)_n$OH, —$(CH_2)_n$ $OC_{1-6}$alkyl, —$NR_{10}R_{11}$, —$(CH_2)_n$N $R_{10}R_{11}$, and —$(CH_2)_nOC_{3-6}$cycloalkyl;

$R_{18}$ is independently selected from the group consisting of OH, halogen, —$NO_2$, dialkylamino, —N($R_{15}$)($R_{16}$), —COOH, —$S(O)_2NH_2$, $C_{1-3}$ perhaloalkyl, —$OCF_3$, $C_{1-3}$ alkoxy, $C_{1-6}$ alkyl, CN, $C_{1-8}$ cyanoalkyl and $C_{4-6}$ cycloalkenyl, wherein said cycloalkenyl is optionally substituted with up to three groups independently selected from OH and $C_{1-3}$ alkoxy, and wherein said $C_{1-4}$ alkyl is optionally substituted with —$N(R_{15})(R_{16})$;

$R_{20}$ is selected from the group consisting of $C_{1-6}$ alkyl, $C_{3-6}$ cycloalkyl and $C_{2-6}$ alkenyl, wherein said $C_{1-6}$ alkyl is optionally substituted with up to three halogen atoms or a group of formula —$[(CH_2)(Q'')]_k CH_3$;

$R_{21}$ is selected from the group consisting of $C_{1-6}$ alkyl and cycloalkyl;

$R_{22}$ is selected from the group consisting of heteroaryl, aryl, arylalkyl and $C_{1-6}$ alkyl, wherein said $C_{1-6}$ alkyl is optionally substituted up to three halogen atoms;

$R_{23}$ is selected from the group consisting of aryl, heteroaryl and $C_{1-6}$ alkyl, wherein said aryl and said heteroaryl is optionally substituted with up to three $C_{1-3}$ alkyl groups, and said $C_{1-6}$ alkyl is optionally substituted with up to three halogen atoms;

$R_{24}$ is selected from the group consisting of H, —COOH, $C_{3-6}$ cycloalkyl, —$OCHF_2$, —$OCHCl_2$, $C_{1-3}$ perhaloalkyl, $C_{1-6}$ alkoxy, heteroaryl, heterocycloalkyl, $C_{2-6}$ alkynyl, $C_{1-6}$ alkyl, $C_{2-6}$ alkenyl, and aryl, wherein said $C_{1-6}$ alkyl is optionally substituted with up to three groups independently selected from halogen and Ce cycloalkyl, said $C_{2-6}$ alkenyl optionally substituted with up to three groups independently selected from halogen and $N(R_{27})(R_{28})$, said aryl is optionally substituted with up to three OH groups, and said heterocycloalkyl is optionally substituted with up to three independently selected $C_{1-6}$ alkyl groups, —$(CH_2)_m$cycloalkyl, —$(CH_2)_n$OH, —$(CH_2)_n$OR, —$(CH)_2NR_{10}R_{11}$, —$COR_5$, and Q;

$R_{25}$ is OH, or $NR_{10}R_{11}$;

$R_{27}$ and $R_{28}$ are independently selected from the group consisting of $C_{1-6}$ alkyl, $C_{3-6}$ cycloalkyl, heterocycloalkyl, $C_{2-6}$ alkenyl, H, aryl, Q, —C(O) $C_{3-6}$alkyl(cycloalkyl), —COalkyl, —COalkenyl, —COalkynyl, —COaryl, —COheteroaryl, —COcycloalkyl, $C_{1-6}$ acyl, —C(O)C(O)OH, halogen, —$COC_{1-6}$halogen, $C_{1-3}$alkoxy, and arylalkyl, wherein said $C_{1-6}$ alkyl, aryl, acyl, and heterocycloalkyl are optionally substituted with up to three $R_{52}$ groups; or $R_{27}$ and $R_{28}$ together with the nitrogen atom to which they are attached can form a 5 or 6 membered saturated heterocyclic ring that can include one additional O, N, or S ring atom, said saturated heterocyclic ring optionally substituted with a carboxylate or $C_{1-3}$ alkyl groups;

$R_{31}$ is selected from the group consisting of trialkylsilyl, $C_{1-6}$ alkoxycarbonyl, $C_{1-6}$ alkyl, $C_{2-6}$ alkenyl, heteroarylalkyl, heterocycloalkyl and arylalkyl, wherein said $C_{1-6}$ alkyl, said arylalkyl and said heteroarylalkyl are each optionally substituted with up to three independently selected $R_{53}$ groups, and said heterocycloalkyl is optionally substituted with up to three $C_{1-6}$ alkyl groups;

$R_{32}$ is selected from the group consisting of H, $C_{1-6}$ acyl, heteroaryl and $C_{1-6}$ alkyl, wherein said heteroaryl is optionally substituted with up to three $C_{1-3}$ alkyl groups, and said $C_{1-6}$ alkyl is optionally substituted with up to three heteroaryl or $R_{52}$ groups;

$R_{33}$ is selected from the group consisting of heterocloalkyl, aryl, $C_{1-3}$ perhaloalkyl, —$N(R_{27})(R_{28})$ and $C_{1-6}$ alkyl, wherein said aryl, $C_{1-6}$ alkyl, heterocycloalkyl, are optionally substituted with up to three groups selected from halogen, $C_{1-6}$ alkyl, aryl, OH and —$N(R_{27})(R_{28})$;

$R_{34}$ is selected from the group consisting of aryloxy, $C_{1-6}$ alkyl, aryl and alkoxy, wherein said aryl is optionally substituted with COOH, and said alkoxy is optionally substituted with —$N(R_{27})(R_{28})$;

$R_{35}$ is selected from the group consisting of dialkylamino, or $C_{1-6}$ alkyl that is optionally substituted with —COOH or with —$N(R_{27})(R_{28})$;

$R_{41}$ is selected from the group consisting of —$R_{100}$, —$R_{102}R_{100}$, —$R_{102}OR_{100}$, —$R_{102}OH$, and —$R_{102}Q$;

$R_{50}$ is selected from the group consisting of heterocycloalkyl, (N=H), $NH_2$, —$NHOOC_{1-3}$ alkyl, $C_{1-3}$ alkyl, —$NHOOC_{1-3}$ cycloalkyl, —$NHCOC_{1-3}$ heterocycloalkyl, —OH, —ON, —COOH, —$N(R_{27})(R_{28})$, —$SO_2N(R_{27})(R_{28})$, halogen, heteroaryl and aryl, wherein said aryl, heteroaryl, or heterocycloalkyl are optionally substituted with a group selected from $C_{1-3}$ alkyl, C(O)H, $C_{1-4}$ alkoxy, and —$CONHN(R_{21})_2$, and up to three groups selected from halogen, and $NH_2$;

$R_{52}$ is independently selected from the group consisting of COH, OH, CN, $NH_2$, —$NHR_{21}$, —$N(R_{21})_2$, $C_{1-6}$ alkyl, aryl, —COaryl, heterocycloalkyl, halogen, $C_{1-3}$perhaloalkyl, and —$C_{3-6}$ cycloalkyl, wherein the aryl can be substituted with COOH;

$R_{53}$ is selected from the group consisting of OH, $C_{1-6}$ alkyl, arylalkyloxy, heterocycloalkyl, $C_{1-3}$ alkoxy, halogen and $C_{3-6}$ cycloalkyl;

$R_{100}$ is selected from the group consisting of $C_{1-12}$alkyl, $C_{3-6}$ cycloalkyl aryl, heteroaryl, $C_{2-6}$alkenyl, and $C_{2-6}$alkynyl;

$R_{102}$ is a divalent $C_{1-6}$alkyl;

$R_{200}$ is selected from the group consisting of —$(CR_{201}R_{201})_q R_{203}$, $N(R_{201})C(O)(CH_2)_q R_{203}$, $N(R_{201})(CH_2)_q R_{203}$ and —$NHO(O)NH$—$R_{203}$;

$R_{201}$ is selected from the group consisting of H and $C_{1-6}$ alkyl;

$R_{203}$ is selected from the group consisting of dialkylamino and a 5-7 membered heterocycloalkyl ring having up to three ring hetero atoms selected from O, N and S, said heterocycloalkyl ring being optionally substituted with up to three independently selected $R_{204}$ groups;

$R_{204}$ is selected from the group consisting of OH, COOH, $C_{1-6}$ alkyl, alkoxycarbonyl, arylalkyl, heteroarylalkyl, $C_{2-6}$ alkenyl, $C_{3-6}$ cycloalkyl, aryl, $C_{1-6}$ alkoxy, $C_{2-6}$ acyl, heterocycloalkyl, —$C(O)N(R_{300})(R_{300})$, —NHC(O)$R_{300}$, —$N(R_{201})(R201)$, and —$NHC(=O)N(R_{201})(R_{201})$, wherein said $C_{1-6}$ alkyl is optionally substituted with up to three independently selected $R_{207}$ groups, wherein said arylalkyl and said heteroarylalkyl are each optionally substituted with up to three independently selected $R_{206}$ groups, wherein said $C_{2-6}$ acyl may optionally contain one double bond, and may optionally be substituted with —$NR_{10}R_{11}$, wherein said heterocycloalkyl is optionally substituted with up to three independently selected $C_1$ alkyl groups;

$R_{206}$ is independently $C_{1-6}$ alkyl or $C(O)NH_2$;

$R_{207}$ is independently selected from the group consisting of ON, heterocycloalkyl, $C_{1-3}$ alkoxy, OH, $N(R_{27})(R_{28})$ and $C_{3-6}$ cycloalkyl;

$R_{209}$ is $R_{211}$, $R_{212}$—C≡C—, or $(R_{212})_2 C$=$C(R_{212})$—;

$R_{210}$ is $C_{1-6}$ alkyl, or $C_{1-6}$ alkoxy;

$R_{211}$ is aryl and heteroaryl wherein said aryl and said heteroaryl, are each optionally substituted with up to four independently selected $R_{12}$ groups;

$R_{212}$ is $C_{1-6}$ alkyl, aryl, and heteroaryl, wherein said $C_{1-6}$ alkyl is optionally substituted with up to three independently selected $R_{13}$ groups wherein said aryl and said heteroaryl, are each optionally substituted with up to four independently selected $R_{12}$ groups;

$R_{214}$ is $R_{41}$, or $R_{211}$;

$R_{300}$ is selected from the group consisting of H, $C_{1-3}$ alkoxy and $C_{1-6}$ alkyl wherein said $C_{1-6}$ alkyl is optionally substituted with a dialkylamino group;

e is 1 provided that $R_3$ is not $N(C_{1-6}$ alkyl$)_2$, or $N(aryl)_2$, or $N(pyridyl)_2$;

f is 0-5;

k' is 1-6;

m is 0, 1, or 2;

n is 1-4;

q is 1-3;

r is 2-1800;

$G^1, G^2, G^3$ and $G^4$ are each independently selected from the group consisting of H, halogen, —CN, —OCF$_3$, —NO2, —COOH, —CONH$_2$, —CF$_3$, OH, SH, N$_3$, —C(O)H, heteroaryl, $C_{1-6}$alkoxy, heterocycloalkyl, aryl, $C_{3-10}$cycloalkyl, $C_{1-12}$ alkyl, $C_{2-6}$ alkenyl, $C_{2-6}$ alkynyl, —COR$_{100}$, —OC$_{3-10}$cycloalkyl, —Oaryl, —OR$_{100}$, $R_{209}$ $R_{211}$, Q, —OS(O)$_2$NH$_2$, OS(O)$_2$R$_{22}$, —S(O)$_m$ R$_{100}$, —C(O)Q, C(O)OR$_{100}$, —NHR$_{100}$, —NR$_{100}$aryl, —OR$_{102}$aryl, —SR$_{102}$aryl, —NHR$_{102}$OH, —NHR$_{102}$OR$_{100}$, —NHR$_{102}$NHR$_{100}$, —NR$_{100}$R$_{102}$OH, —NHR$_{102}$Q, —NR$_{100}$R$_{102}$NH$_2$, —NR$_{100}$R$_{102}$NHR$_{100}$, —NR$_{100}$R$_{102}$OR$_{100}$, —NR$_{100}$R$_{102}$Q, —OR$_{102}$OH, —OR$_{102}$OR$_{100}$, —OR$_{102}$NH$_2$, —OR$_{102}$NHR$_{100}$, —OR$_{102}$Q, —OCOR$_{100}$, —OR$_{102}$OR$_{100}$, —NHCOR$_{100}$, —NHCONH$_2$, —NHOONHR$_{100}$, —NHR$_{102}$COR$_{100}$, —NHR$_{102}$NH$_2$, —NHOH, —NHOR$_{100}$, —CONR$_{10}$R$_{11}$, —NHSO$_2$R$_{100}$, —NHC(O)-heteroaryl, —NHC(O)R$_{102}$-heteroaryl, OC(O)CH$_2$halogen, OO(O)OH$_2$S(CH)$_m$O-PEG, OC(O)NH-PEG,

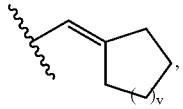

NHC(O)R$_{102}$-aryl, and NHC(O)NH-heterocycloalkyl optionally substituted with up to three $C_{1-3}$ alkyl groups;

wherein said aryl, said heteroaryl, and said heterocycloalkyl are each optionally substituted with up to four independently selected R$_{12}$ groups;

wherein said $C_{2-6}$ alkenyl, said $C_{1-6}$ alkyl, $C_{1-6}$alkoxy, and said $C_{2-6}$ alkynyl are each optionally substituted with up to three independently selected R$_{13}$ groups;

Q is —NR$_{100}$R$_{100}$ optionally the R$_{100}$ groups taken together with the nitrogen to which they are attached form a heterocyclic ring of 3 to 8 atoms with 1 or 2 additional heteroatoms selected from the group N, O, and S, said heterocyclic ring may optionally be substituted with groups consisting of OH, OC$_{1-6}$ alkyl, (COH$_2$)$_n$OH, (CH$_2$)$_n$OC$_{1-6}$alkyl, NR$_{10}$R$_{11}$, (CH$_2$)$_n$ NR$_{10}$R$_{11}$, and C$_{1-6}$ alkyl;

Q" is selected from the group consisting of O, S, and NH;

Z is selected from the group consisting of aryl, heteroaryl, cycloalkyl, heterocycle, pyridone, and pyrone, wherein said aryl, said pyridone, said pyrone, said cycloalkyl, said heteroaryl, and said heterocycle are each optionally substituted with up to five substituents independently selected from the group consisting of R$_{210}$, R$_{41}$, R$_{209}$, R$_{211}$, R$_{214}$, OR$_{41}$, (=O), OH, COOR$_{100}$, C$_{1-6}$ alkyl, C$_{1-6}$ alkoxy, C$_{1-3}$ perhaloalkyl, halogen, C$_{1-3}$ perhaloalkoxy, (=NH), NH$_2$, —NO$_2$, C(O)H, —C(O)OH, —C(O)NH$_2$, CN, Q, heterocycle, heteroaryl, S—C$_{1-3}$ alkyl, S—C$_{13}$ perhaloalkyl, S-heteroaryl, aryl, C$_{2-6}$ alkynyl, C(NH)NH$_2$, heterocloalkyl, C$_{2-6}$ alkenyl, —O—C(O)—R$_{20}$, —O—C(O) OR$_{21}$, —NHS(O)$_2$R$_{22}$, —R$_{102}$NHS(O)$_2$R$_{23}$, —NHC (O)R$_{24}$, —R$_{102}$NHC(O)R$_{24}$, —NHC(O)(CH$_2$)$_m$R$_{25}$, —CH$_2$N(R$_{27}$)(R$_{28}$), —OC(O)N(R$_{27}$)(R$_{28}$), —N(R$_{27}$) (R$_{28}$), —OR$_{31}$, —S(O)$_2$NHR$_{32}$, —S(O)$_2$R$_{33}$, —C(O)R, —CH$_2$C(O)OH, —C(O)NHR$_{35}$, R$_{200}$, —CH$_2$NHS(O)$_2$ R$_{21}$, OC(O)CH$_2$halogen, OC(O)R$_{100}$, OC(O)CH$_2$S (CH$_2$)$_m$O-PEG, —OC(O)NH-PEG, H, —CN, —OCF$_3$, —CF$_3$, SH, N$_3$, —C(O)H, —COR$_{100}$, —OR$_{100}$, —Saryl, —C(O)Q, C(O)OR$_{100}$, —C(O)NHR$_{100}$, —NR$_{100}$aryl, —OR$_{102}$aryl, —SR$_{102}$aryl, —NHS (O)$_2$—R$_{100}$, —NHR$_{102}$OH, —NHR$_{102}$R$_{100}$, —NHR$_{102}$NHR$_{100}$ —NR$_{100}$R$_{102}$OH, —NHR$_{102}$Q, —NR$_{100}$R$_{102}$NH$_2$, —NR$_{100}$R$_{102}$NHR$_{100}$, —NR$_{100}$R$_{102}$OR$_{100}$, —NR$_{100}$R$_{102}$Q, —OR$_{102}$OH, —OR$_{102}$OR$_{100}$, —OR$_{102}$NH$_2$, —OR$_{102}$NHR$_{100}$, —OR$_{102}$Q, —OCOR$_{100}$, —OR$_{102}$COR$_{102}$OR$_{102}$COR$_{100}$, —OR$_{102}$COR$_{102}$OR$_{102}$OR$_{100}$, —NHCOR$_{100}$, —NHCONH$_2$, —NHCONHR$_{100}$, —NHR$_{102}$COR$_{100}$, —NHR$_{102}$NH$_2$, —NHS(O)$_2$-aryl, —NHOH, —NHC (O)aryl, —NHOR$_{100}$, —NHC(O)-heteroaryl, —NHC(O)R$_{102}$-heteroaryl, OC(O)CH$_2$halogen, OC(O)CH$_2$S(CH)$_m$O-PEG, OC(O)NHPEG, OS(O)$_2$ NH$_2$, OS(O)$_2$R$_{22}$, —N(R$_{10}$)(R$_{11}$), NHC(O)R$_{102}$-aryl, and NHC(O)NH-heterocycle that is optionally substituted with up to three $C_{1-3}$ alkyl groups, wherein said $C_{1-6}$ alkenyl, said $C_{1-6}$ alkyl, and said $C_{1-6}$ alkynyl are each optionally substituted with up to three independently selected R$_{13}$ groups, wherein said $C_{1-6}$ alkyl, said —S—C$_{1-6}$ alkyl, and C$_{1-6}$ alkoxy are each optionally substituted with up to three independently selected R$_{50}$ groups, wherein said aryl is optionally substituted with up to three groups independently selected from OH and NH$_2$, wherein said heteroaryl and said S-heteroaryl, heterocycle, and said heterocycloalkyl, are each optionally substituted with up to three independently selected R$_{12}$ groups, wherein said C$_2$ alkenyl is optionally substituted with COOH, wherein any two adjacent carbon atoms of said aryl, heteroaryl or heterocycloalkyl can optionally be joined together by a group of the formula —O—C(Ra)(Rb)—O— wherein R$_a$ and R$_b$ are independently H, C$_{1-3}$ alkyl, phenyl or alkoxycarbonyl; and C$_{1-3}$ alkoxy and C$_{1-3}$ perhaloalkyl, wherein said aryl can be substituted with COOH;

except 4-((2-Phenylaminophenylamino)methylene)2-p-tolylisoquinoline-1,3(2H,4H)-dione, 4-[[(4-methoxyphenyl)amino]methylene]2-(4methylphenyl)-1,3(2H, 4H)-isoquinolinedione, 2-(4-methoxyphenyl)-4-[[(4-methylphenyl)amino]methylene]-1,3(2H,4H)-isoquinolinedione, 2-(4-methoxyphenyl)-4-[[(4-methoxyphenyl)amino]methylene]-1,3(2H,4H)-isoquinolinedione, 2-(4-chlorophenyl)-4-[[(4-nitrophenyl)amino]methylene]-1,3(2H,4H)-isoquinolinedione, 2-(4-chlorophenyl)-4-[[(4-methylphenyl)amino]methylene]-1,3(2H,4H)-isoquinolinedione, 2-phenyl-4-((p-tolylamino) methylene)isoquinoline-1,3(2H,4H)-dione, 6,7-dimethoxy-2-methyl-4-[(phenylamino)methylene]-1,3 (2H,4H)-isoquinolinedione, 4-[(phenylamino) methylene]-2-(phenylmethyl)-1,3(2H,4H)-isoquinolinedione, 2-methyl-4-((phenylamino) methylene]-1,3(2H,4H)-isoquinolinedione, 2-methyl-4-[(methylphenylamino)methylene]1,3(2H,4H)- isoquinolinedione, 4-[(phenylamino)methylene]-1,3 (2H,4H)-isoquinolinedione, 4-[[(4-chlorophenyl)amino]methylene]-1,3(2H,4H)-isoquinolinedione, 4-[[(4-chlorophenyl)amino]methylene]-2methyl-1,3(2H,4H)-isoquinolinedione, 2-(4-methoxyphenyl)-4-[(phenylamino)methylene]1,3(2H,4H)-isoquinolinedione, and 4-[bis(phenylamino)methylene]-2-methyl-1,3(2H,4H)-isoquinolinedione are excluded.

* * * * *